US012577217B2

(12) United States Patent
Seto et al.

(10) Patent No.: US 12,577,217 B2
(45) Date of Patent: Mar. 17, 2026

(54) 15-PGDH INHIBITOR

(71) Applicant: KYORIN Pharmaceutical Co., Ltd., Tokyo (JP)

(72) Inventors: Shigeki Seto, Shimotsuga-gun (JP); Hitomi Yamada, Shimotsuga-gun (JP); Yoshifumi Saito, Shimotsuga-gun (JP); Haruaki Kurasaki, Shimotsuga-gun (JP)

(73) Assignee: KYORIN Pharmaceutical Co., Ltd., Tokyo (JP)

( * ) Notice: Subject to any disclaimer, the term of this patent is extended or adjusted under 35 U.S.C. 154(b) by 1181 days.

(21) Appl. No.: 17/417,201

(22) PCT Filed: Jan. 7, 2020

(86) PCT No.: PCT/JP2020/000115

§ 371 (c)(1),
(2) Date: Jun. 22, 2021

(87) PCT Pub. No.: WO2020/145250

PCT Pub. Date: Jul. 16, 2020

(65) Prior Publication Data

US 2023/0082516 A1 Mar. 16, 2023

(30) Foreign Application Priority Data

Jan. 8, 2019 (JP) ................................ 2019-000915

(51) Int. Cl.

| | |
|---|---|
| ***C07D 265/36*** | (2006.01) |
| ***C07D 267/02*** | (2006.01) |
| ***C07D 267/22*** | (2006.01) |
| ***C07D 279/16*** | (2006.01) |
| ***C07D 281/02*** | (2006.01) |
| ***C07D 471/04*** | (2006.01) |
| ***C07D 498/04*** | (2006.01) |
| ***C07D 519/00*** | (2006.01) |

(52) U.S. Cl.

CPC ......... *C07D 265/36* (2013.01); *C07D 267/02* (2013.01); *C07D 267/22* (2013.01); *C07D 279/16* (2013.01); *C07D 281/02* (2013.01); *C07D 471/04* (2013.01); *C07D 498/04* (2013.01); *C07D 519/00* (2013.01)

(58) Field of Classification Search

CPC .. C07D 215/00; C07D 217/00; C07D 265/36; C07D 267/02; C07D 267/22; C07D 279/16; C07D 281/02; C07D 471/04; C07D 498/04; C07D 519/00

See application file for complete search history.

(56) References Cited

U.S. PATENT DOCUMENTS

| | | | |
|---|---|---|---|
| 6,245,760 | B1 | 6/2001 | He et al. |
| 7,320,967 | B2 | 1/2008 | Michelet et al. |
| 7,705,041 | B2 | 4/2010 | Michelet et al. |
| 8,232,287 | B2 | 7/2012 | Kaneko et al. |
| 8,242,116 | B2 | 8/2012 | Alexander et al. |
| 8,338,592 | B2 | 12/2012 | Alexander et al. |
| 8,710,054 | B2 | 4/2014 | Alexander et al. |
| 8,735,445 | B2 | 5/2014 | Michelet et al. |
| 9,073,902 | B2 | 7/2015 | McCall et al. |
| 9,789,116 | B2 | 10/2017 | Markowitz et al. |
| 9,790,233 | B2 | 10/2017 | Markowitz et al. |
| 9,801,863 | B2 | 10/2017 | Markowitz et al. |
| 10,301,320 | B2 | 5/2019 | Markowitz et al. |
| 10,420,752 | B2 | 9/2019 | Markowitz et al. |
| 10,869,871 | B2 | 12/2020 | Markowitz et al. |
| 10,945,998 | B2 | 3/2021 | Markowitz et al. |
| 2007/0010670 | A1 | 1/2007 | Hirata et al. |
| 2007/0077215 | A1 | 4/2007 | Boulle et al. |
| 2007/0092467 | A1 | 4/2007 | Rozot et al. |
| 2007/0191603 | A1 | 8/2007 | Ackermann et al. |
| 2008/0064871 | A1 | 3/2008 | Hirata et al. |
| 2008/0206320 | A1 | 8/2008 | Michelet et al. |
| 2008/0249117 | A1 | 10/2008 | Michelet et al. |
| 2008/0305169 | A1 | 12/2008 | Miki et al. |
| 2009/0111805 | A1 | 4/2009 | Morris et al. |
| 2009/0131582 | A1 | 5/2009 | Grant et al. |
| 2011/0034440 | A1 | 2/2011 | Nakao et al. |
| 2011/0172217 | A1 | 7/2011 | Fujioka et al. |
| 2013/0324501 | A1 | 12/2013 | Armani et al. |
| 2015/0105373 | A1 | 4/2015 | Mikami et al. |
| 2016/0289196 | A1 | 10/2016 | Choi et al. |
| 2018/0118756 | A1 | 5/2018 | Markowitz et al. |
| 2020/0140453 | A1 | 5/2020 | Markowitz et al. |
| 2020/0147063 | A1 | 5/2020 | Markowitz et al. |
| 2021/0032265 | A1 | 2/2021 | Markowitz et al. |

(Continued)

FOREIGN PATENT DOCUMENTS

| | | | |
|---|---|---|---|
| EP | 0 965 587 | A1 | 12/1999 |
| EP | 2 210 891 | A1 | 7/2010 |
| EP | 3 176 163 | A1 | 6/2017 |

(Continued)

OTHER PUBLICATIONS

Monzavi (Children's Hospital Los Angeles Published Jul. 13, 2015). (Year: 2015).*
Office Action issued Dec. 26, 2023, in corresponding United Arab Emirates Patent Application No. P6001144/2021, 9 pages.
International Search Report issued Mar. 17, 2020 in PCT/JP2020/000115, 5 pages.
International Preliminary Report on Patentability and Written Opinion issued Jul. 22, 2021 in PCT/JP2020/000115, 9 pages.
Duveau, D.Y. et al., "Structure-activity relationship studies and biological characterization of human $NAD^+$-dependent 15-hydroxyprostaglandin dehydrogenase inhibitors", Bioorganic & Medicinal Chemistry Letters, 2014, 24(2), pp. 630-635.
Antczak, M.I. et al., "Inhibitors of 15-Prostaglandin Dehydrogenase To Potentiate Tissue Repair", Journal of Medicinal Chemistry, 2017, 60(9), pp. 3979-4001.

(Continued)

*Primary Examiner* — George W Kosturko
(74) *Attorney, Agent, or Firm* — Oblon, McClelland, Maier & Neustadt, L.L.P.

(57) ABSTRACT

A compound represented by general formula (1) or a pharmacologically acceptable salt thereof for inhibiting 15-PDGH.

24 Claims, No Drawings

(56) References Cited

U.S. PATENT DOCUMENTS

2021/0094968 A1 4/2021 Markowitz et al.
2021/0106587 A1 4/2021 Markowitz et al.

FOREIGN PATENT DOCUMENTS

EP 3 372 601 A1 9/2018
JP 2007-99775 A 4/2007
JP 2008-531542 A 8/2008
JP 2014-505053 A 2/2014
JP 2014-55193 A 3/2014
KR 101734424 B1 * 5/2017 ............. A61P 31/10
WO WO 97/33866 A1 9/1997
WO WO 01/02369 A2 1/2001
WO WO-0117480 A2 * 3/2001 ........... A61K 31/505
WO WO 01/66114 A1 9/2001
WO WO 02/094833 A1 11/2002
WO WO 03/000688 A1 1/2003
WO WO 03/028726 A1 4/2003
WO WO 03/035064 A1 5/2003
WO WO 03/090699 A1 11/2003
WO WO 2004/034963 A2 4/2004
WO WO 2004/089416 A2 10/2004
WO WO 2005/021530 A1 3/2005
WO WO 2006/086255 A2 8/2006
WO WO 2007/005668 A2 1/2007
WO WO 2008/001076 A1 1/2008
WO WO 2008/115719 A1 9/2008
WO WO 2009/017838 A2 2/2009
WO WO 2009/035997 A2 3/2009
WO WO-2009051119 A1 * 4/2009 ........... C07D 401/14
WO WO 2009/098458 A2 8/2009
WO WO-2010124121 A1 * 10/2010 ........... A61K 31/496
WO WO 2011/057757 A1 5/2011
WO WO-2012094462 A2 * 7/2012 ......... A61K 2300/00
WO WO 2012/106343 A2 8/2012
WO WO 2013/003383 A1 1/2013
WO WO 2013/158649 A1 10/2013
WO WO 2013/190123 A1 12/2013
WO WO-2015065716 A1 * 5/2015 ................ A61P 9/12
WO WO 2015/115673 A1 8/2015
WO WO 2016/100184 A1 6/2016
WO WO 2016/137010 A1 9/2016
WO WO 2016/144958 A1 9/2016
WO WO 2016/168472 A1 10/2016
WO WO 2017/075394 A1 5/2017
WO WO 2017/147328 A1 8/2017
WO WO 2018/017582 A1 1/2018
WO WO-2018102552 A1 * 6/2018 ......... A61K 31/4365
WO WO 2018/145080 A1 8/2018
WO WO 2019/183364 A1 9/2019
WO WO 2021/151014 A1 7/2021

OTHER PUBLICATIONS

Niesen, F.H. et al., "High-Affinity Inhibitors of Human NAD$^+$-Dependent 15-Hydroxyprostaglandin Dehydrogenase: Mechanisms of Inhibition and Structure-Activity Relationships", PLos One, 2010, 5(11).

Tai H-H. et al., "Prostaglandin catabolizing enzymes", Prostaglandins Other Lipid Mediat., 2002, vol. 68-69, pp. 483-493.

Takeshi Shimizu, et al., "Recent Understanding of Prostanoids and Leukotrienes in the Pathogenesis of Airway Inflammation", The Oto-rhino-and laryngological clinic, 2007, vol. 100, No. 3, pp. 157-166.

Takahisa Murata et al., "Anti-inflammatory role of $PGD_2$ in acute lung inflammation and therapeutic application of its signal enhancement", PNAS, 2013, vol. 110, No. 13, pp. 5205-5210.

Trista E. North et al., "Prostaglandin E2 regulates vertebrate haematopoietic stem cell Homeostasis", Nature, 2007, vol. 447, No. 7147, 1007-1011.

Paul D. Bozyk et al., "Prostaglandin E2 and the Pathogenesis of Pulmonary Fibrosis", Am J Respir Cell Mol Biol 2011, vol. 45, 445-452.

M. Kinoshita et al., "Roles of Prostaglandins, Nitric Oxide and the Capsaicin-Sensitive Sensory Nerves in Gastroprotection Produced by Ecabet Sodium", J. Pharmacol. Exp. Ther., 1995, vol. 275, No. 1, pp. 494-501.

Makoto Arita et al., The Journal of Japan Rhinologic Society, 2012, vol. 51, No. 1, pp. 60-62.

Zenglin Liao et al., "Resolvin D1 attenuates inflammation in lipopolysaccharide-induced acute lung injury through a process involving the PPARγ/NF-KB pathway", Respiratory Research 2012, vol. 13, pp. 110-121.

Allisson Freire Bento et al., "Omega-3 Fatty Acid-Derived Mediators 17(R)-Hydroxy Docosahexaenoic Acid, Aspirin-Triggered Resolvin D1 and Resolvin D2 Prevent Experimental Colitis in Mice", J. Immunol. 2011, vol. 187, 1957-1969.

Xiahong Chen et al., "Resolvin D1 attenuates $CCl_4$-induced acute liver injury involving up-regulation of HO-1 in mice", Immunopharmacol. Immunotoxicol. 2016, vol. 38, No. 2, 9 pages.

Katherine L. Lee et al., "Discovery of Clinical Candidate 1-{[(2S ,3S ,4S)-3-Ethyl-4-fluoro-5-oxopyrrolidin-2-yl]methoxy}-7-methoxyisoquinoline-6-carboxamide (PF-06650833), a Potent, Selective Inhibitor of Interleukin-1 Receptor Associated Kinase 4 (IRAK4), by Fragment-Based Drug Design", Journal of Medicinal Chemistry, vol. 60, No. 13, Jun. 14, 2017, pp. 5521-5542, XP055554811.

David C. Pryde et al., "Discovery of a Series of Indazole TRPA1 Antagonists", ACS Medicinal Chemistry Letters, vol. 8, No. 6, May 22, 2017, pp. 666-671, XP055688807.

Patcharaporn Khajondetchairit et al., "Design, synthesis, and evaluation of the anticancer activity of 2-amino-aryl-7-aryl-benzoxazole Compounds", Chemical Biology & Drug Design, vol. 90, No. 5, Nov. 1, 2017, pp. 987-994, XP055688815.

Susana Alvarez et al., "Modulation of Retinoic Acid Receptor Subtypes by 5- and 8-Substituted (Naphthalen-2-yl)-based Arotinoids", Chemmedch Em, vol. 10, No. 8, Aug. 1, 2015, pp. 1378-1391, XP055688874.

Landge Sudhir et al., "Discovery of benzothiazoles as antimycobacterial agents: Synthesis, structure-activity relationships and binding studies with *Mycobacterium tuberculosis* decaprenylphosphoryl-[beta]-d-ribose 2'-oxidase", Bioorganic & Medicinal Chemistry, vol. 23, No. 24, Nov. 18, 2015, pp. 7694-7710, XP029342479.

Adel Hamza et al., "Understanding human 15-hydroxyprostaglandin dehydrogenase binding with NAD$^+$ and $PGE_2$ by homology modeling, docking and molecular dynamics simulation", Bioorganic & Medicinal Chemistry 2005, 13, 4544-4551.

Hoon Cho et al., "Role of glutamine 148 of human 15-hydroxyprostaglandin dehydrogenase in catalytic oxidation of prostaglandin $E_2$", Bioorganic & Medicinal Chemistry 2006, 14, 6486-6491.

Ying Wu et al., "Synthesis and SAR of thiazolidinedione derivatives as 15-PGDH inhibitors", Bioorganic & Medicinal Chemistry 2010, 18, 1428-1433.

Dubok Choi et al., "Control of the intracellular levels of prostaglandin $E_2$ through inhibition of the 15-hydroxyprostaglandin dehydrogenase for wound healing", Bioorganic & Medicinal Chemistry 2013, 21, 4477-4484.

Yu Lan Piao et al., "Cell-based biological evaluations of 5-(3-bromo-4-phenethoxybenzylidene)thiazolidine-2,4-dione as promising wound healing agent", Bioorganic & Medicinal Chemistry 2015, 23, 2098-2103.

Dongdong Lu et al., "15-hydroxyprostaglandin Dehydrogenase (15-PGDH)-Derived 15-Kketo-PGE2 Inhibits Cholangiocarcinoma Cell Growth Through Interaction With PPARγ, SMAD2/3 and TAP63", J. Biol. Chem.-2013-Lu-jbc.M113.453886.

Lu Yao et al., "15-hydroxyprostaglandin dehydrogenase (15-PGDH) prevents lipopolysaccharide (LPS)-induced acute liver injury", PLoS ONE 12(4): e0176106. https://doi.org/10.1371/journal.pone.0176106.

Annavarapu Hari Kishore et al., "Prostaglandin dehydrogenase is a target for successful induction of cervical ripening", PNAS 2017 E6427-E6436 www.pnas.org/cgi/doi/10.1073/pnas.1704945114.

Dongdong Lu et al., "15-PGDH inhibits hepatocellular carcinoma growth through 15-keto-$PGE_2$/PPARγ-mediated activation of $p21^{WAF1/Cip1}$", Oncogene. Feb. 27, 2014; 33(9): 1101-1112. doi:10.1038/onc.2013.69.

(56) References Cited

OTHER PUBLICATIONS

A. R. Palla et al., Inhibition of prostaglandin-degrading enzyme 15-PGDH rejuvenates aged muscle mass and strength Science 371, 483 (2021).

Yongyou Zhang et al., "Inhibition of the prostaglandin-degrading enzyme 15-PGDH potentiates tissue regeneration", Science 2015 • vol. 348 Issue 6240 http://dx.doi.org/10.1126/science.aaa2340.

Amar Desai et al., "A second-generation 15-PGDH inhibitor promotes bone marrow transplant recovery independent of age, transplant dose, and G-CSF support", Haematologica 2018 doi:10.3324/haematol.2017.178376.

Stephanie G. Dakin et al., "Increased 15-PGDH expression leads to dysregulated resolution responses in stromal cells from patients with chronic tendinopathy", Scientific Reports | 7: 11009 | DOI:10.1038/s41598-017-11188-y.

Ying Wu et al., "Synthesis and Biological Evaluation of Novel Thiazolidinedione Analogues as 15-Hydroxyprostaglandin Dehydrogenase Inhibitors", J. Med. Chem. 2011, 54, 5260-5264.

Yusuke Watanabe et al., "KAG-308,a newly-identified $EP_4$-selective agonist shows efficacy for treating ulcerative colitis and can bring about lower risk of colorectal carcinogenesis by oral administration", European Journal of Pharmacology 754(2015)179-189.

Kousuke Tani et al., "Development of a Highly Selective EP2-Receptor Agonist. Part 1: Identification of 16-hydroxy-17,17-trimethylene $PGE_2$ Derivatives", Bioorganic & Medicinal Chemistry 10 (2002) 1093-1106.

Kousuke Tani et al., "Development of a Highly Selective EP2-receptor Agonist. Part 2:Identification of 16-Hydroxy-17,17-trimethylene 9β-chloro PGF Derivatives", Bioorganic & Medicinal Chemistry 10 (2002) 1107-1114.

Tohru Kambe et al., "Discovery of novel prostaglandin analogs as potent and selective EP2/EP4 dual agonists", Bioorganic & Medicinal Chemistry 20 (2012) 2235-2251.

Zhong Zhao et al., "Synthesis and evaluation of novel pyrazolidinone analogs of $PGE_2$ as $EP_2$ and $EP_4$ receptors agonists", Bioorganic & Medicinal Chemistry Letters 17 (2007) 6572-6575.

Toru Maruyama et al., "Design and Synthesis of a Selective EP4-Receptor Agonist. Part 2: 3,7-DithiaPGE1 Derivatives with High Selectivity", Bioorganic & Medicinal Chemistry 10 (2002) 989-1008.

Seiji Ogawa et al., "Discovery of G Protein-Biased EP2 Receptor Agonists", ACS Med. Chem. Lett. 2016, 7, 306-311.

Tijana Markovic et al., "Structural features of subtype-selective EP receptor modulators", Drug Discov Today (2016), http://dx.doi.org/10.1016/j.drudis.2016.08.003.

Viktoria Konya et al., "E-type prostanoid receptor 4 (EP4) in disease and therapy", Pharmacology & Therapeutics 138 (2013) 485-502.

Andrew Fensome et al., "Structure-activity relationships of norepinephrine reuptake inhibitors with benzothiadiazine dioxide or dihydrosulfostyril cores", Bioorganic & Medicinal Chemistry Letters 20 (2010) 1555-1558.

Tomoyuki Tanaka et al., "Discovery of benzothiazine derivatives as novel, orally-active anti-epileptic drug candidates with broad anticonvulsant effect", Bioorganic & Medicinal Chemistry Letters 25 (2015) 4518-4521.

Álvaro Gutiérrez-Bonet et al., "Fe-Catalyzed Regiodivergent [1,2]-Shift of α-Aryl Aldehydes", J. Am. Chem. Soc. 2013, 135, 12576-12579.

Yasunari Monguchi et al., "Pd/C-Et3N-mediated catalytic hydrodechlorination of aromatic chlorides under mild conditions", Tetrahedron, 2006 62, 7926-7933.

Nicholas A. Meanwell et al., "Fluorine and Fluorinated Motifs in the Design and Application of Bioisosteres for Drug Design", J. Med. Chem., 2018, 61, 5822-5880.

Corwin Hansch et al., "A Survey of Hammett Substituent Constants and Resonance and Field Parameters", Chem. Rev., 1991, 91, 165-195.

Gang Zhou et al., "Development of Novel Benzomorpholine Class of Diacylglycerol Acyltransferase I Inhibitors", ACS Med. Chem. Lett., 2014, 5, 544-549.

* cited by examiner

15-PGDH INHIBITOR

CROSS-REFERENCE TO RELATED APPLICATIONS

This application is a national stage application of International Application No. PCT/JP2020/000115, filed Jan. 7, 2020, which is based upon and claims the benefit of priority to Japanese Patent Application No. 2019-000915, filed Jan. 8, 2019. The entire contents of these applications are incorporated herein by reference.

TECHNICAL FIELD

The present invention relates to a derivative having 15-PGDH inhibitory activity useful as a pharmaceutical, a pharmacologically acceptable salt thereof, a pharmaceutical composition containing the same, and medical use thereof.

BACKGROUND ART

15-Hydroxyprostaglandin dehydrogenase (15-PGDH) is an enzyme significant in inactivation (for example, conversion into 15-keto-PGE2 by catalyzing an oxidation reaction of the 15-position hydroxyl group of PGE2) of active prostaglandin (PGD2, PGE1, PGE2, PGF2α, PGI2 or the like), hydroxyeicosatetraenoic acid (HETE) and inflammation resolving lipid mediator (RvD1, RvD2, RvE1, MaR1, LXA4 or the like) (which are hereinafter generically designated as substrates of 15-PGDH). A 15-oxo derivative of a substrate of 15-PGDH having been oxidized by 15-PGDH has usually lower biological activity as compared with the 15-hydroxyl molecule. The human enzyme is encoded by the HPGD gene, and consists of a homodimer having subunits of 29 kDa. The enzyme belongs to an evolutionarily conserved superfamily of short-chain dehydrogenase/reductase enzymes (SDRs). Until now, two types of 15-PGDH (SDR36C1), namely, NAD+-dependent type I 15-PGDH and type II NADP-dependent 15-PGDH (CBR1, SDR21C1), have been identified. The affinity of CBR1 for the substrate is low, hence, it is suggested that activity in vivo is mostly attributed to type I 15-PGDH (see Non Patent Literature 1).

Each of these prostaglandins (PGD2, PGE1, PGE2, PGF2α, PGI2 and the like), HETE and inflammation resolving lipid mediators (RvD1, RvD2, RvE1, MaR1, LXA4 and the like) exhibits its function via a specific receptor present on a target cell. Receptors corresponding to the substrates of 15-PGDH are widely distributed differently in a living body, and diversity of types of receptors, diversity of signal transmission and diversity of expression distribution appear as diversity of roles in a living body.

For example, PGE1 works on a blood vessel and a platelet to exhibit a blood flow increasing effect based on vasodilator action and a platelet aggregation inhibiting effect, and hence is known as a useful drug for treatment of chronic arterial occlusion (thromboangiitis obliterans (TAO) or arteriosclerosis obliterans (ASO)), skin ulcer and the like. PGF2a has uterine contraction effect and ocular hypotensive effect (see, for example, Non Patent Literature 2), and its derivative is used as a therapeutic agent for glaucoma. PGD2 is known to inhibit inflammation by enhancing the barrier function of lung blood vessels (see, for example, Non Patent Literature 3). Besides, PGE2 has vasodilator action, and also has a variety of functions including involvement in blood pressure, a pain, bone formation and cell growth, and stem cell differentiation, and antifibrotic and anti-inflammatory effects (see, for example, Non Patent Literatures 2, 4 and 5). PGI2 is known to have an inhibitory effect against platelet activation and relaxant effect for vascular smooth muscle, and its derivative is used as a therapeutic agent for chronic arterial occlusion and primary pulmonary hypertension.

Besides, there is a therapeutic agent for stomach ulcer increasing PGE2 and PGI2 (see, for example, Non Patent Literature 6).

The inflammation resolving lipid mediators (RvD1, RvD2, RvE1, MaR1, LXA4 and the like) inhibit migration/activation of neutrophils, and accelerate apoptosis of neutrophils. Besides, they are important for efficient removal of apoptotic neutrophil/tissue debris remaining in an inflammation site by increasing phagocytic activity of macrophages. These function, promote inflammation and maintain biological homeostasis (see, for example, Non Patent Literature 7).

It has been reported that these inflammation resolving lipid mediators exhibit medicinal efficacy in various types of pathological models (such as a mouse lung inflammation model (see Non Patent Literature 8), a colitis model (see Non Patent Literature 9) and a liver injury model (see Non Patent Literature 10)).

Since 15-PGDH is an enzyme significant in inactivation of the substrates of 15-PGDH involved in such a large number of effects in a living body, a 15-PGDH inhibitor can be used for prevention or treatment of a disease related to 15-PGDH and/or substrate of 15-PGDH, and/or when increase of a substrate level of 15-PGDH is preferable in a subject.

As described above, some substrates of 15-PGDH have antifibrotic effect, anti-inflammatory effect, blood flow improving effect, growth accelerating effect, stem cell increasing effect, smooth muscle contraction/relaxation effect, immunosuppression effect and bone metabolic effect. Therefore, a 15-PGDH inhibitor can be effective for treatment or prevention of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

Currently, as a compound having 15-PGDH inhibitory effect, Patent Literature 1 discloses a compound represented by formula (I) having an amino group and an alkyl-substituted sulfur atom on a double bond:

[Formula 1]

(I)

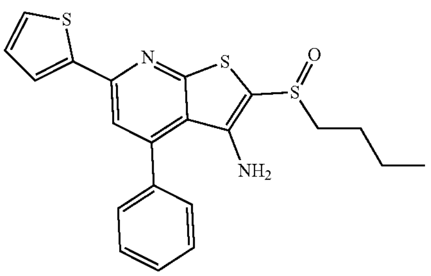

Besides, a tetrazole derivative having a carbonyl methyl group with a substituent (Patent Literature 2) and a thiazolidine-2,4-dione derivative (Patent Literature 3) are disclosed, and Patent Literature 4 discloses a quinazoline derivative, a pyrrole derivative, an oxazolidine derivative, a thiazolidine derivative and the like.

These compounds have, however, basic chemical structural formulas different from that of a present compound. Needless to say, these compounds are not embraced in the appended claims of the present application.

CITATION LIST

Non Patent Literature

[Non Patent Literature 1] TTai H H et al., Prostaglandins Other Lipid Mediat., 2002, vol. 68-69, pp. 483-493

[Non Patent Literature 2] Takeshi Shimizu, et al., The Oto-rhino- and laryngological clinic, 2007, vol. 100, No. 3, pp. 157-166

[Non Patent Literature 3] Takahisa Murata et al., PNAS, 2013, vol. 110, No. 13, pp. 5205-5210

[Non Patent Literature 4] Trista E. North et al., Nature, 2007, vol. 447, No. 7147, 1007-1011

[Non Patent Literature 5] Paul D. Bozyk et al., Am J Respir Cell Mol Biol 2011, vol 45, 445-452

[Non Patent Literature 6] M. Kinoshita et al., J. Pharmacol. Exp. Ther., 1995, vol. 275, No. 1, pp. 494-501

[Non Patent Literature 7] Makoto Arita et al., The Journal of Japan Rhinologic Society, 2012, vol. 51, No. 1, pp. 60-62

[Non Patent Literature 8] Zenglin Liao et al., Respiratory Research 2012, vol. 13, pp. 110-121

[Non Patent Literature 9] Allisson Freire Bento et al., J Immunol. 2011, vol. 187, 1957-1969

[Non Patent Literature 10] Xiahong Chen et al., Immunopharmacol. Immunotoxicol. 2016, vol. 38, No. 2, 61-67

PATENT LITERATURE

[Patent Literature 1] International Publication No. WO2013/158649

[Patent Literature 2] International Publication No. WO2003/090699

[Patent Literature 3] Japanese Patent Laid-Open No. 2007-99775

[Patent Literature 4] Japanese Patent Laid-Open No. 2014-55193

SUMMARY OF INVENTION

Technical Problem

A compound that can be a sufficiently satisfactory pharmaceutical having excellent 15-PGDH inhibitory effect as a preventive and therapeutic agent against the various medical conditions described above has not been found up to the present time.

An object of the present invention is to provide a compound having 15-PGDH inhibitory effect.

Problem to be Solved

As a result of making earnest studies, the present inventors have found that a compound represented by the following general formula (1) (hereinafter sometimes referred to as the compound (1)) has excellent 15-PGDH inhibitory effect, and the present invention was thus accomplished.

Specifically, the present invention provides the following:

[1] A compound represented by the following general formula (1), or a pharmacologically acceptable salt thereof:

[Formula 2]

(1)

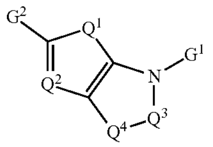

wherein $Q^1$ is $-C(R^1)=C(R^2)-$, $-C(R^3)=N-$, $-N=C(R^3)-$ or a sulfur atom;

$Q^2$ is $C(R^4)$ or a nitrogen atom;

$Q^3$ is $-(CH_2)_m-(CR^5R^6)_n-(CH_2)_p-$;

$Q^4$ is a single bond, a methylene group, an oxygen atom, a sulfur atom, a SO group, a $SO_2$ group, a methyleneoxy group, a difluoromethylene group or a $NR^7$ group;

$G^1$ is a phenyl group, a 5-membered aromatic heterocyclic group, a 6-membered aromatic heterocyclic group, a condensed heterocyclic group having 8 to 10 ring atoms (excluding a 6,7-dihydro-4H-thiazolo[5,4-c]pyridine ring), a $C_3$-$C_8$ cycloalkyl group or a 3- to 8-membered heterocycloalkyl group, each optionally having one or more substituents selected from group A;

$G^2$ is $-C(=O)-NR^8R^9$, $-C(=O)-NR^{10}R^{21}$, $-C(=O)-CHR^{12}R^{13}$, $-CH(OH)-CHR^{12}R^{13}$, $-S-CHR^{12}R^{13}$, $-S(=O)-CHR^{12}R^{13}$ or $-SO_2-CHR^{12}R^{13}$;

$R^1$ and $R^2$ are the same or different, and a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^3$ is a hydrogen atom, or a $C_1$-$C_6$ alkyl group, a $C_1$-$C_6$ alkoxy group or a $C_3$-$C_8$ cycloalkyl group, each optionally having one or more substituents selected from group C;

$R^4$ is a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^5$ and $R^6$ are the same or different, and a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^7$ is a hydrogen atom, or a $C_1$-$C_6$ alkyl group, a $C_3$-$C_0$ cycloalkyl group, a $C_1$-$C_6$ alkylcarbonyl group, a phenyl group, a 5-membered aromatic heterocyclic group or a 6-membered aromatic heterocyclic group, each optionally having one or more substituents selected from group C;

$R^8$ and $R^9$ are the same or different, and a hydrogen atom, or a $C_1$-$C_6$ alkyl group or a C3-C8 cycloalkyl group, each optionally having one or more substituents selected from group B;

when one of $R^8$ and $R^9$ is a hydrogen atom, the other is a $C_1$-$C_6$ alkyl group having one or more substituents selected from a halogen atom, a hydroxy group, a carboxyl group, a $C_1$-$C_6$ alkylcarbonyl group, a $C_1$-$C_6$ alkoxy group and a $C_1$-$C_6$ alkoxycarbonyl group;

$R^{10}$ and $R^{11}$ are, together with the nitrogen atom to which they are attached, a nitrogen-containing heterocycloalkyl group having 3 to 11 ring atoms optionally having one or more substituents selected from group B;

$R^{12}$ and $R^{13}$ are the same or different, and a $C_1$-$C_6$ alkyl group, a $C_3$-$C_8$ cycloalkyl group or a 3- to 8-membered heterocycloalkyl group, each optionally having one or more substituents selected from group B; or $R^{12}$ and $R^{13}$ are, together with the carbon atom to which they are attached, a $C_3$-$C_8$ cycloalkyl group optionally having one or more substituents selected from group B;

group A consists of a halogen atom, a hydroxy group, a carbonyl group, a nitrile group, a carboxyl group, a formyl group, an oxo group (=O); and $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_8$ cycloalkyl group, a $C_3$-$C_8$ cycloalkylcarbonyl group, a $C_3$-$C_8$ cycloalkoxy group, a $C_3$-$C_0$ cycloalkylsulfonyl group, a $C_3$-$C_8$ cycloalkylsulfonylamino group, a 3- to 8-membered heterocycloalkyl group containing an oxygen atom, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A1; an amino group, an aminocarbonyl group and an aminosulfonyl group, each optionally having one or two $C_1$-$C_6$ alkyl groups optionally having, in an amino group, one or more substituents selected from group A1; and a phenyl group, a 5-membered aromatic heterocyclic group and a 6-membered aromatic heterocyclic group, each optionally having one or more substituents selected from group B;

group A1 consists of a halogen atom, a hydroxy group, a carbonyl group, a nitrile group, a carboxyl group, a formyl group, an oxo group (=O); and a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_8$ cycloalkyl group, a 3- to 8-membered heterocycloalkyl group, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A2; an aminocarbonyl group and an amino group, each optionally having one or two $C_1$-$C_6$ alkyl groups optionally having one or more substituents selected from group A2; and a phenyl group, a 5-membered aromatic heterocyclic group and a 6-membered aromatic heterocyclic group, each optionally having one or more substituents selected from group B;

group A2 consists of a halogen atom, a hydroxy group, a nitrile group, a carboxyl group, a formyl group, an oxo group (=O), a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a 5-membered aromatic heterocyclic group, a 6-membered aromatic heterocyclic group, and a 3- to 8-membered heterocycloalkyl group;

group B consists of a halogen atom, a hydroxy group, a nitrile group, a carbonyl group, an oxo group (=O), a carboxyl group, a $C_1$-$C_6$ alkyl group, a $C_1$-$C_6$ alkynyl group, a halo $C_1$-$C_6$ alkyl group, a hydroxy $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkoxy $C_1$-$C_6$ alkyl group, a $C_1$-$C_6$ alkoxycarbonyl $C_1$-$C_6$ alkyl group, a $C_3$-$C_8$ cycloalkyl group, a $C_3$-$C_8$ cycloalkylcarbonyl group, a $C_3$-$C_8$ cycloalkoxy group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group and an amino group optionally having one or two $C_1$-$C_6$ alkyl groups;

group C consists of a halogen atom, a hydroxy group, a nitrile group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, an amino group optionally having one or two $C_1$-$C_6$ alkyl groups, and a 3- to 8-membered heterocycloalkyl group; and each of m, n, and p is 0, 1 or 2, and m+n+p is an integer of 2 to 5.

[2] The compound according to [1], or a pharmacologically acceptable salt thereof, wherein the compound represented by the general formula (1) is a compound represented by a formula selected from the group consisting of the following A1), A2) and A3):

[Formula 3]

A1)

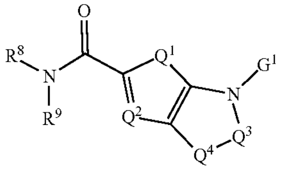

A2)

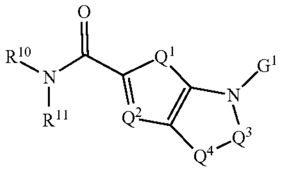

-continued

A3)

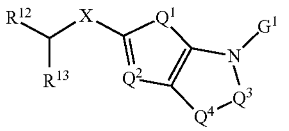

wherein $Q^1$ is $-C(R^1)=C(R^2)-$, $-C(R^3)=N-$, $-N=C(R^3)-$ or a sulfur atom;

$Q^2$ is $C(R^4)$ or a nitrogen atom;

$Q^3$ is $-(CH_2)_m-(CR^5R^6)_n-(CH_2)_p-$;

$Q^4$ is a single bond, a methylene group, an oxygen atom, a sulfur atom, a SO group, a $SO_2$ group, a methyleneoxy group, a difluoromethylene group or a $NR^7$ group;

X is $-C(=O)-$, $-CH(OH)-$, $-S-$, $-SO-$ or $-SO_2-$;

$G^1$ is a phenyl group, a 6-membered aromatic heterocyclic group or a condensed heterocyclic group having 8 to 10 ring atoms (excluding a 6,7-dihydro-4H-thiazolo[5,4-c]pyridine ring) each optionally having one or more substituents selected from group A;

$R^1$ and $R^2$ are the same or different, and a hydrogen atom, a halogen atom, or a $C_1$-$C_3$ alkyl group, a $C_1$-$C_3$ alkoxy group or a $C_3$-$C_8$ cycloalkyl group, each optionally having one or more substituents selected from group C;

$R^3$ is a hydrogen atom, or a $C_1$-$C_3$ alkyl group or a $C_1$-$C_3$ alkoxy group, each optionally having one or more substituents selected from group C;

$R^4$ is a hydrogen atom, a halogen atom, or a $C_1$-$C_3$ alkyl group, a $C_1$-$C_3$ alkoxy group or a $C_3$-$C_8$ cycloalkyl group, each optionally having one or more substituents selected from group C;

$R^5$ and $R^6$ are the same or different, and a hydrogen atom, a halogen atom, or a $C_1$-$C_3$ alkyl group or a $C_1$-$C_3$ alkoxy group, each optionally having one or more substituents selected from group C;

$R^7$ is a hydrogen atom, or a $C_1$-$C_3$ alkyl group optionally having one or more substituents selected from group C;

$R^8$ and $R^9$ are the same or different, and a hydrogen atom, or a $C_1$-$C_6$ alkyl group optionally having one or more substituents selected from group B;

when one of $R^8$ and $R^9$ is a hydrogen atom, the other is a $C_1$-$C_6$ alkyl group having one or more substituents selected from group B;

$R^{10}$ and $R^{11}$ are, together with the nitrogen atom to which they are attached, a nitrogen-containing heterocycloalkyl group having 3 to 11 ring atoms optionally having one or more substituents selected from group B;

the nitrogen-containing heterocycloalkyl group is monocyclic, condensed bicyclic, or bicyclic optionally including a bridged ring or a spiro ring;

the nitrogen-containing heterocycloalkyl group further optionally has one to three heteroatoms selected from a nitrogen atom, an oxygen atom and a sulfur atom;

$R^{12}$ and $R^{13}$ are, together with the carbon atom to which they are attached, a $C_3$-$C_8$ cycloalkyl group optionally having one or more substituents selected from group B;

each of m, n and p is 0, 1 or 2, and m+n+p is an integer of 2 to 5.

[3] The compound according to [2], or a pharmacologically acceptable salt thereof, wherein the compound represented by the general formula (1) is a compound represented by a formula selected from the group consisting of the following A1a), A1b), A2a), A2b), A2c), A2d), A2e), A3a) and A3b):

[Formula 4]

A1a)

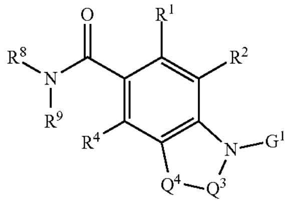

A1b)

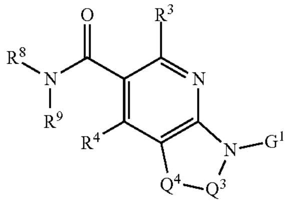

A2a)

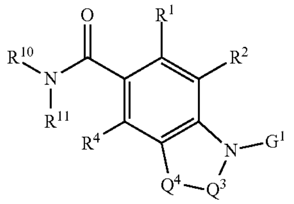

A2b)

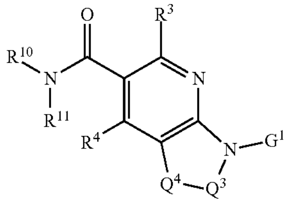

A2c)

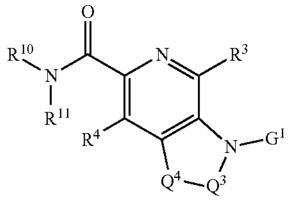

A2d)

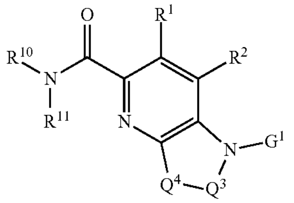

A2e)

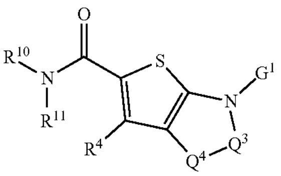

-continued

A3a)

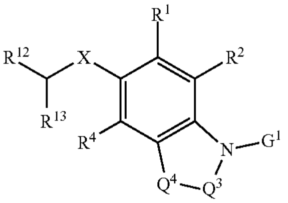

A3b)

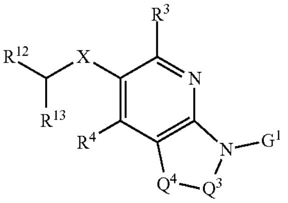

wherein $R^1$ and $R^2$ are the same or different, and a hydrogen atom, a halogen atom, a $C_1$-$C_3$ alkyl group, a $C_1$-$C_3$ alkoxy group or a $C_3$-$C_8$ cycloalkyl group;

$R^3$ is a hydrogen atom, a $C_1$-$C_3$ alkyl group or a $C_1$-$C_3$ alkoxy group;

$R^4$ is a hydrogen atom, a halogen atom, a $C_1$-$C_3$ alkyl group, a $C_1$-$C_3$ alkoxy group or a $C_3$-$C_8$ cycloalkyl group; and $R^7$ is a hydrogen atom or a $C_1$-$C_3$ alkyl group.

[4] The compound according to [3], or a pharmacologically acceptable salt thereof, wherein $NR^{10}R^{11}$ in —$CONR^{10}R^{11}$ of $G^2$ in the general formula (1) is a group selected from the group consisting of the following B1) to B20):

[Formula 5]

B1)

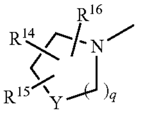

B2)

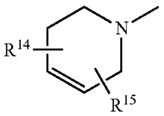

B3)

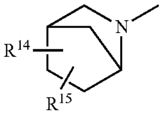

B4)

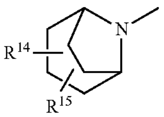

B5)

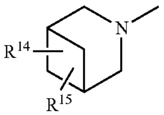

-continued

B6)

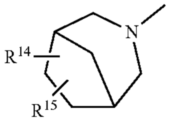

B7)

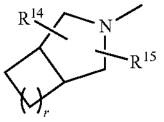

B8)

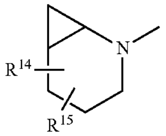

B9)

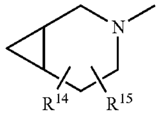

B10)

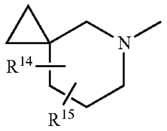

B11)

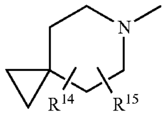

B12)

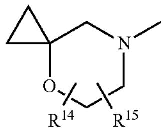

B13)

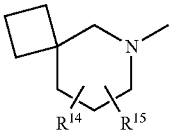

B14)

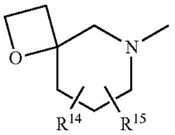

B15)

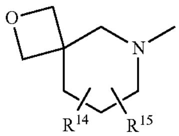

B16)

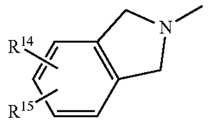

-continued

B17)

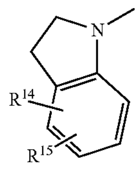

B18)

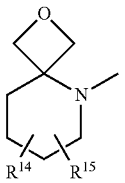

B19)

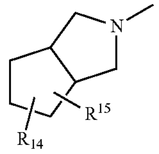

B20)

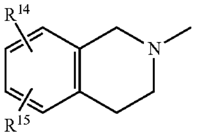

wherein $R^{14}$, $R^{15}$ and $R^{16}$ are the same or different, and a hydrogen atom or a substituent selected from group B1;

$R^{14}$ and $R^{15}$ are substituted optionally in any ring in the formula;

Y is a methylene group, an oxygen atom, a sulfur atom or a N—$R^{17}$ group;

$R^{17}$ is a hydrogen atom or a $C_1$-$C_3$ alkyl group optionally having one or more substituents selected from group D;

group B1 consists of a halogen atom, a hydroxy group, a carbonyl group, a carboxyl group, a $C_1$-$C_6$ alkyl group, a halo $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkylsulfonylamino group, an aminocarbonyl group optionally having one or two $C_1$-$C_6$ alkyl groups, an amino group optionally having one or two $C_1$-$C_6$ alkyl groups, and a 3- to 8-membered heterocycloalkyl group;

group D consists of a halogen atom, a hydroxy group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group, an amino group optionally having one or two $C_1$-$C_6$ alkyl groups, and a 3- to 8-membered heterocycloalkyl group; and each of q and r is 0, 1, 2 or 3, or —$CHR^{12}R^{13}$ of $G^2$ is a group represented by the following C1):

[Formula 6]

C1)

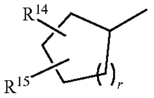

wherein $R^{14}$ and $R^{15}$ are the same or different, and a hydrogen atom or a substituent selected from group B1;

$R^{14}$ and $R^{15}$ are substituted optionally in any ring in the formula; and r is 0, 1, 2 or 3.

[5] The compound according to [4], or a pharmacologically acceptable salt thereof, wherein $G^1$ in the general formula (1) is a group selected from the group consisting of the following G1a), G1b), G1c), G1d), G1e), G1f), G1g), G1h), G1i), G1j), G1k), G1l), G1m), G1n), G1o), G1p), G1q), G1r), G1s), G1t), G1u), G1v), G1w), G1x), G1y), G1z), G1A), G1B), G1C), G1D), G1E), G1F), G1G), G1H), G1I), G1J), G1K), G1L), G1M), G1N), G1O), G1P), G1Q), G1R), G1S) and G1T):

[Formula 7]

G1a)

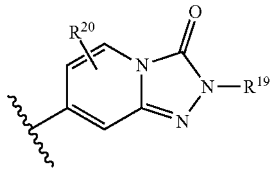

G1b)

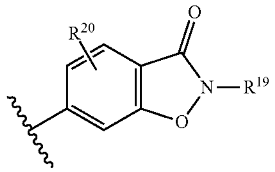

G1c)

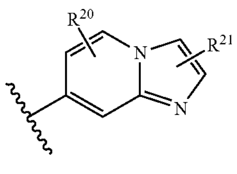

G1d)

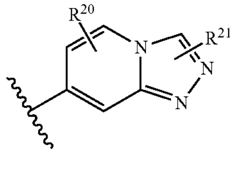

G1e)

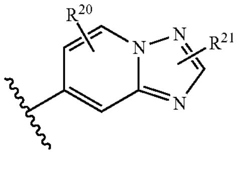

-continued
G1f)
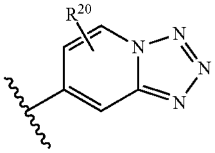
G1g)
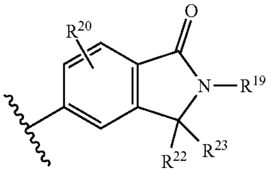
G1h)
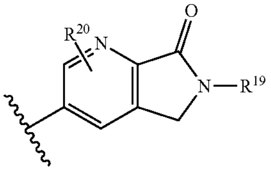
G1i)
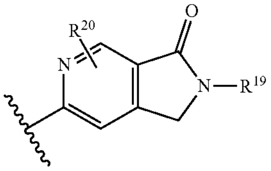
G1j)
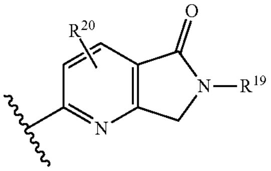
G1k)
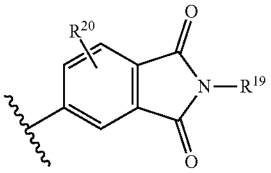
G1l)
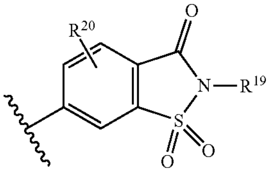
G1m)
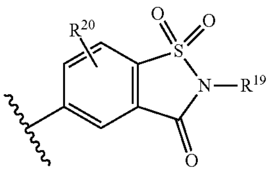
G1n)
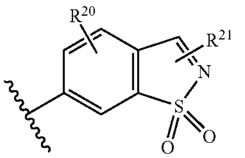
-continued
G1o)
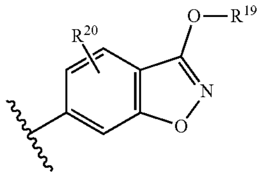
G1p)
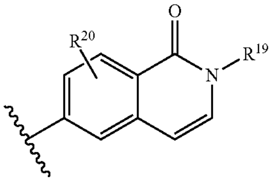
G1q)
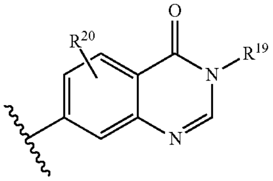
G1r)
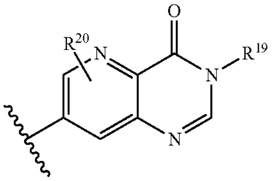
G1s)
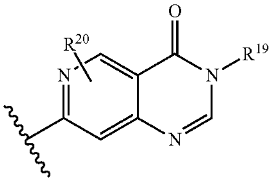
G1t)
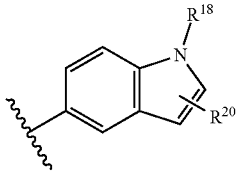
G1u)
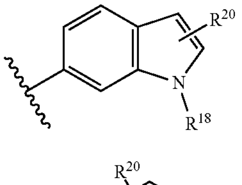
G1v)
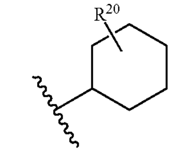
G1w)
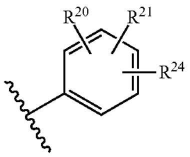

-continued
G1x)
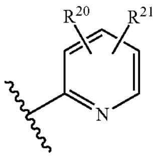
G1y)
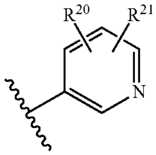
G1z)
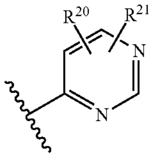
G1A)
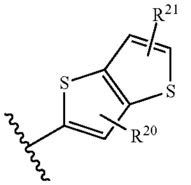
G1B)
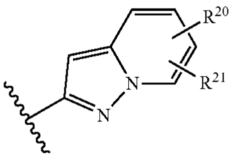
G1C)
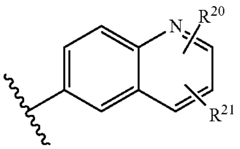
G1D)
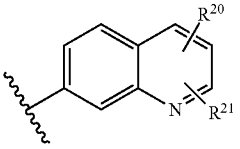
G1E)
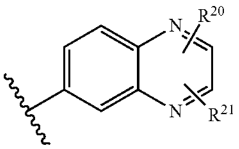
G1F)
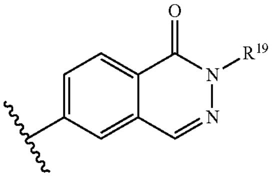
-continued
G1G)
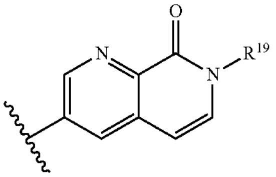
G1H)
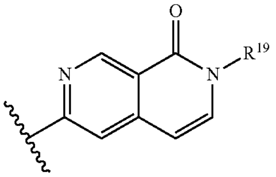
G1I)
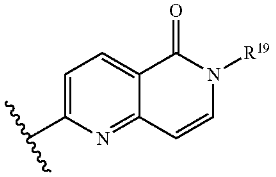
G1J)
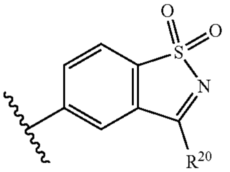
G1K)
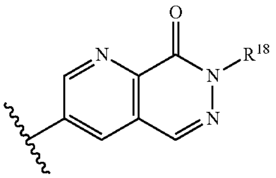
G1L)
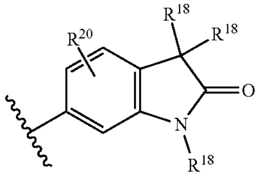
G1M)
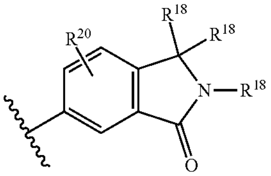
G1N)
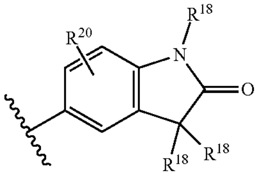

-continued

G1O)

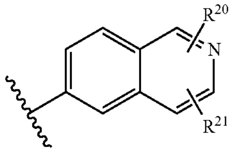

G1P)

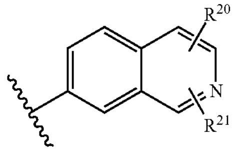

G1Q)

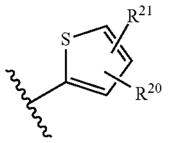

G1R)

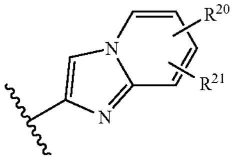

G1S)

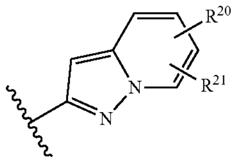

G1T)

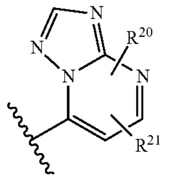

wherein $R^{18}$ is a hydrogen atom or a $C_1$-$C_3$ alkyl group;

$R^{19}$ is a hydrogen atom, a 3- to 8-membered heterocycloalkyl group containing an oxygen atom, or a $C_3$-$C_8$ cycloalkyl group, a hydroxyl $C_1$-$C_6$ alkyl group, a phenyl group, a phenyl $C_1$-$C_3$ alkyl group, a 6-membered aromatic heterocyclic group, a 6-membered aromatic heterocyclic $C_1$-$C_3$ alkyl group, a $C_1$-$C_3$ alkyl group, a halo $C_1$-$C_3$ alkyl group or a $C_1$-$C_3$ alkoxy $C_1$-$C_3$ alkyl group, each optionally having one or more substituents selected from group C;

$R^{20}$ is a hydrogen atom, a halogen atom, a hydroxy group, a nitrile group, a carboxyl group, a formyl group; or $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having one or more substituents selected from group A3; an aminocarbonyl group optionally having one or two $C_1$-$C_6$ alkyl groups optionally having one or more substituents selected from group B1; or a 5-membered aromatic heterocyclic group or a 6-membered aromatic heterocyclic group, each optionally having one or more substituents selected from group B1;

$R^{21}$ is a hydrogen atom, a halogen atom, a hydroxy group, a nitrile group, a carboxyl group, a formyl group; or a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having one or more substituents selected from group B1; an amino group or an aminocarbonyl group, each optionally having one or two $C_1$-$C_6$ alkyl groups optionally having, in an amino group, one or more substituents selected from group A3; or a 5-membered aromatic heterocyclic group or a 6-membered aromatic heterocyclic group, each optionally having one or more substituents selected from group B1;

$R^{20}$ and $R^{21}$ are substituted optionally in any ring in the formula;

$R^{22}$ and $R^{23}$ are the same or different, and a hydrogen atom, a halogen atom or a $C_1$-$C_3$ alkyl group;

$R^{24}$ is a hydrogen atom or a substituent selected from group B1; and group A3 consists of a halogen atom, a hydroxy group, a nitrile group, a carboxyl group, a formyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group and a $C_1$-$C_6$ alkylsulfonylamino group.

[6] The compound according to [5], or a pharmacologically acceptable salt thereof, wherein the compound represented by the general formula (1) is a compound represented by a formula selected from the group consisting of the following A1aa), Alba), A2aa), A2ba), A2ca), A2da), A2ea), A3aa) and A3ba):

[Formula 8]

A1aa)

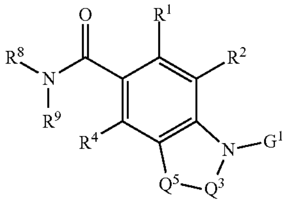

Alba)

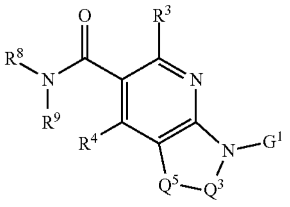

A2aa)

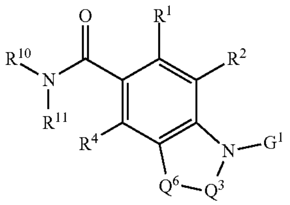

-continued

A2ba)

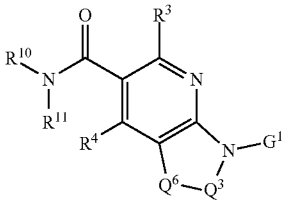

A2ca)

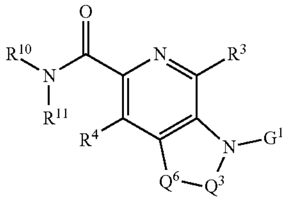

A2da)

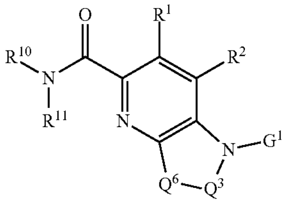

A2ea)

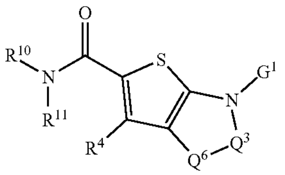

A3aa)

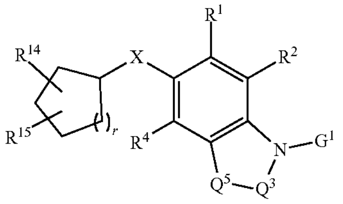

A3ba)

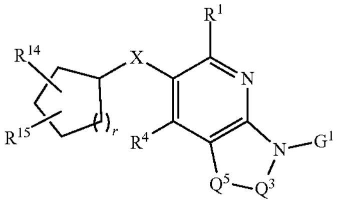

wherein $Q^3$ is $—(CH_2)_m—(CR^5R^6)_n— (CH_2)_p—$;

$Q^5$ is a methylene group, an oxygen atom, a sulfur atom or $NR^7$ group;

$Q^6$ is a single bond, a methylene group, an oxygen atom, a sulfur atom, a SO group, a $SO_2$ group, a methyleneoxy group or $NR^7$ group;

$R^8$ and $R^9$ are the same or different, and a hydrogen atom or a $C_1$-$C_6$ alkyl group optionally having one or more substituents selected from group D1;

when one of $R^8$ and $R^9$ is a hydrogen atom, the other is a $C_1$-$C_6$ alkyl group having one or more substituents selected from group D1;

$R^5$ and $R^6$ are the same or different, and a hydrogen atom, a halogen atom, or a $C_1$-$C_3$ alkyl group or a $C_1$-$C_3$ alkoxy group, each optionally having one or more substituents selected from group D1;

$R^{14}$ and $R^{15}$ are the same or different, and a hydrogen atom, a halogen atom, a hydroxy group, a carbonyl group, a carboxyl group, a $C_1$-$C_6$ alkyl group, a halo $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkylsulfonylamino group, an aminocarbonyl group optionally having one or two $C_1$-$C_6$ alkyl groups, an amino group optionally having one or two $C_1$-$C_6$ alkyl groups, or a 3- to 8-membered heterocycloalkyl group;

each of m, n and p is 0, 1 or 2, and m+n+p is an integer of 2 to 5;

r is 0, 1, 2 or 3; and group D1 consists of a halogen atom, a hydroxy group, a carboxyl group, a $C_1$-$C_6$ alkylcarbonyl group, a $C_1$-$C_6$ alkoxy group and a $C_1$-$C_6$ alkoxycarbonyl group.

[7] The compound according to [6], or a pharmacologically acceptable salt thereof, wherein $G^1$ in the general formula (1) is a group selected from the group consisting of the following G1aa), G1ba), G1ca), G1fa), G1ga), G1ha), G1ia), G1la), G1oa), G1pa), G1qa), G1va), G1wa), G1xa), G1ya) and G1Aa):

[Formula 9]

(G1aa)

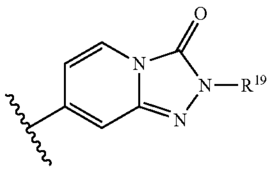

G1ba)

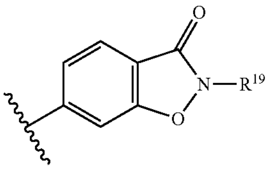

G1ca)

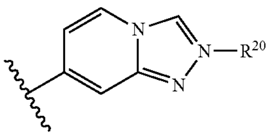

G1fa)

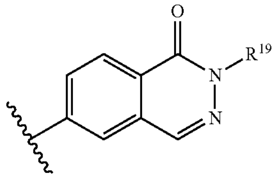

G1ga)

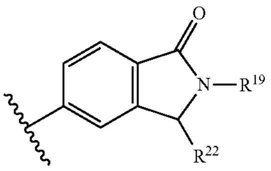

-continued

G1ha)

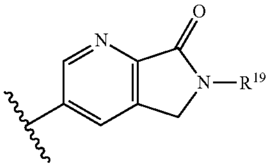

G1ia)

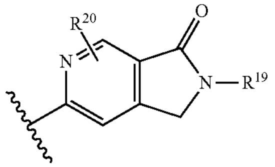

G1la)

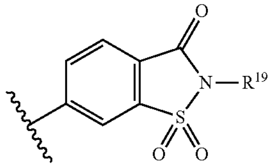

G1oa)

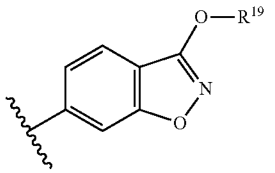

G1pa)

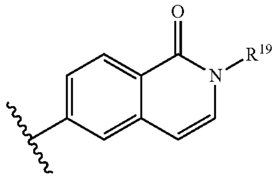

G1qa)

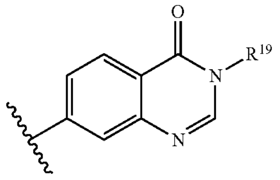

G1va)

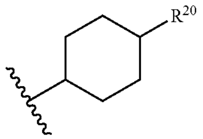

G1wa)

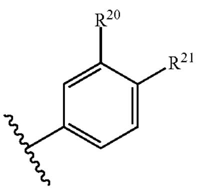

G1xa)

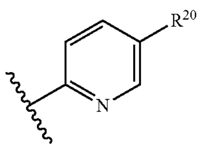

-continued

G1ya)

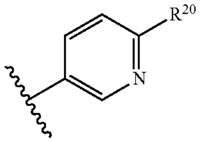

G1Aa)

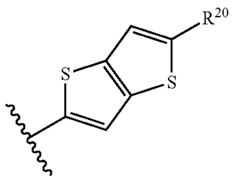

wherein $R^{19}$ is a hydrogen atom, a 3- to 8-membered heterocycloalkyl group containing an oxygen atom, or a $C_3$-$C_0$ cycloalkyl group, a hydroxyl $C_1$-$C_6$ alkyl group, a phenyl group, a phenyl $C_1$-$C_3$ alkyl group, a 6-membered aromatic heterocyclic group, a 6-membered aromatic heterocyclic $C_1$-$C_3$ alkyl group, a $C_1$-$C_3$ alkyl group, a halo $C_1$-$C_3$ alkyl group or a $C_1$-$C_3$ alkoxy $C_1$-$C_3$ alkyl group, each optionally having one or more substituents selected from group C;

$R^{20}$ is a hydrogen atom, a halogen atom, a hydroxy group, a nitrile group, a carboxyl group, a formyl group; or $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having one or more substituents selected from group A3; an aminocarbonyl group optionally having one or two $C_1$-$C_6$ alkyl groups optionally having one or more substituents selected from group B1; or a 5-membered aromatic heterocyclic group or a 6-membered aromatic heterocyclic group, each optionally having one or more substituents selected from group B1;

$R^{21}$ is a hydrogen atom, a halogen atom, a hydroxy group, a nitrile group, a carboxyl group, a formyl group; or a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having one or more substituents selected from group B1; an amino group or an aminocarbonyl group, each optionally having one or two $C_1$-$C_6$ alkyl groups optionally having, in an amino group, one or more substituents selected from group A3; or a 5-membered aromatic heterocyclic group or a 6-membered aromatic heterocyclic group, each optionally having one or more substituents selected from group B1; and $R^{22}$ is a hydrogen atom, a halogen atom or a $C_1$-$C_3$ alkyl group.

[8] The compound according to [7], or a pharmacologically acceptable salt thereof, wherein $NR^{10}R^{11}$ in —$CONR^{10}R^{11}$ of $G^2$ in the general formula (1) is a group selected from the group consisting of the following B1a), B2a), B4a), B5a), B7a), B8a), B9a), B10a), B11a), B13a) and B16a):

[Formula 10]

B1a)

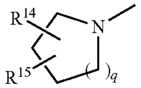

B2a)

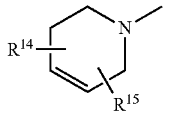

B4a)

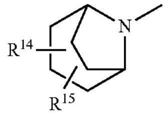

B5a)

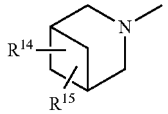

B7a)

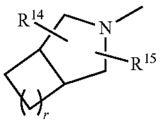

B8a)

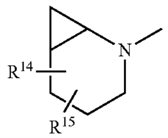

B9a)

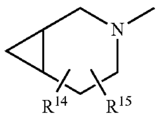

B10a)

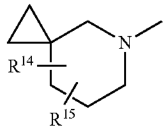

B11a)

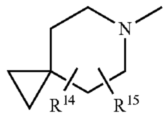

B13a)

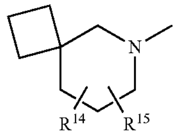

B16a)

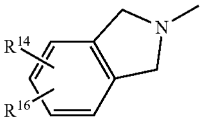

wherein $R^{14}$ and $R^{15}$ are the same or different, and a hydrogen atom, a halogen atom, a hydroxy group, a nitrile group, a carboxyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group or a halo $C_1$-$C_6$ alkyl group;

$R^{14}$ and $R^{15}$ are substituted optionally in any ring in the formula; and each of q and r is 0, 1, 2 or 3, and —$CHR^{12}R^{13}$ of $G^2$ is a group represented by the following C1a):

[Formula 11]

C1a)

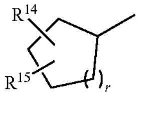

wherein $R^{14}$ and $R^{15}$ are the same or different, and a hydrogen atom, a halogen atom, a hydroxy group, a nitrile group, a carboxyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group or a halo $C_1$-$C_6$ alkyl group;

$R^{14}$ and $R^{15}$ are substituted optionally in any ring in the formula; and r is 0, 1, 2 or 3.

[9] The compound according to [8], or a pharmacologically acceptable salt thereof, wherein the compound represented by the general formula (1) is a compound represented by a formula selected from the group consisting of the following A2aa), A2ba) and A3ba):

[Formula 12]

A2aa)

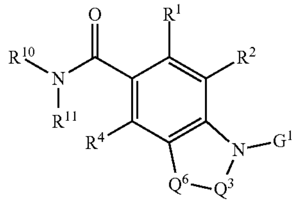

A2ba)

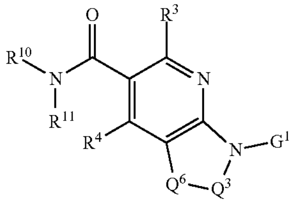

A3ba)

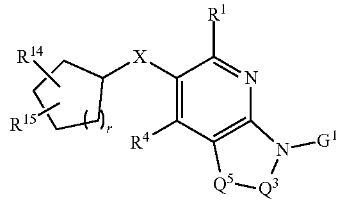

wherein $Q^6$ is a single bond, a methylene group, an oxygen atom, a methyleneoxy group or $NR^7$ group;

$Q^3$ is $—(CH_2)_m—(CR^5R^6)_n—(CH_2)_p—$;

$R^5$ and $R^6$ are the same or different, and a hydrogen atom, a halogen atom, a $C_1$-$C_3$ alkyl group, a $C_1$-$C_3$ alkoxy group or a halo $C_1$-$C_3$ alkyl group; and each of m, n and p is 0, 1 or 2, and m+n+p is an integer of 2 to 5.

[10] The compound according to [9], or a pharmacologically acceptable salt thereof, wherein the compound represented by the general formula (1) is a compound represented by a formula selected from the group consisting of the following A2aaa), A2baa), A2caa) and A2daa):

[Formula 13]

A2aaa)

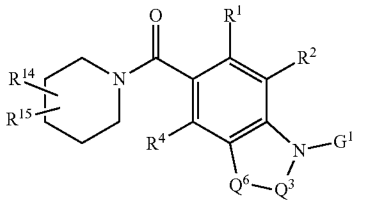

A2baa)

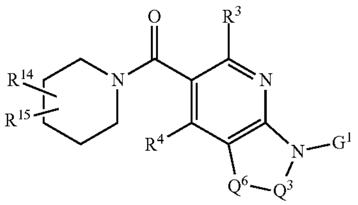

A2caa)

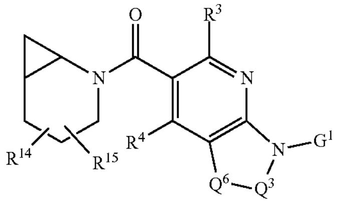

A2daa)

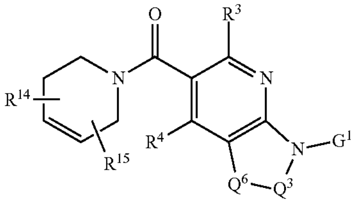

wherein $G^1$ is a group selected from the group consisting of the following G1aa), G1fa), G1ga), G1ia), G1pa), G1qa) and G1ya):

[Formula 14]

G1aa)

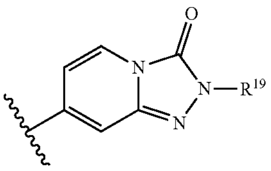

-continued

G1fa)

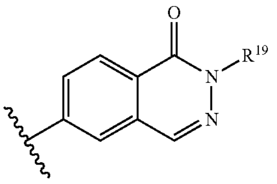

G1ga)

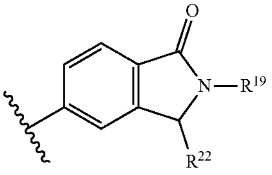

G1ia)

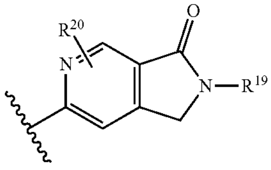

G1pa)

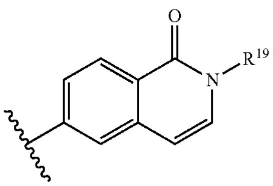

G1qa)

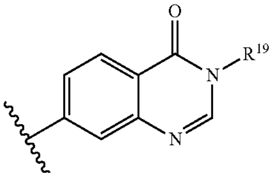

G1ya)

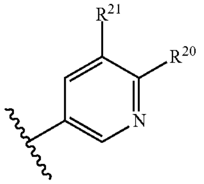

$Q^3$ is $-(CH_2)_m-(CR^5R^6)_n-(CH_2)_p-$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^{19}$ is a hydrogen atom, a $C_1$-$C_3$ alkyl group, a $C_3$-$C_0$ cycloalkyl group, a hydroxyl $C_1$-$C_6$ alkyl group, a $C_1$-$C_6$ alkoxy $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^{22}$ is a hydrogen atom or a $C_1$-$C_3$ alkyl group; and each of m, n and p is 0, 1 or 2, and m+n+p is an integer of 2 to 5.

[11] The compound according to [1], or a pharmacologically acceptable salt thereof, wherein the compound represented by the general formula (1) is a compound having a structure selected from the following structures:

[Formula 15]

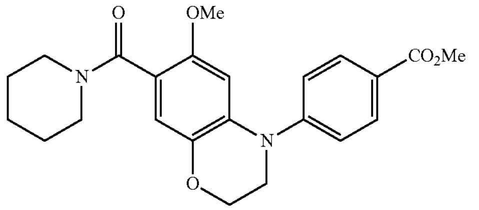

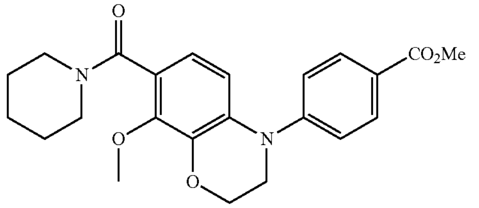

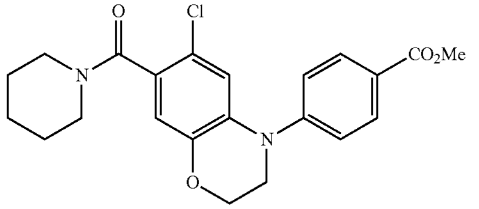

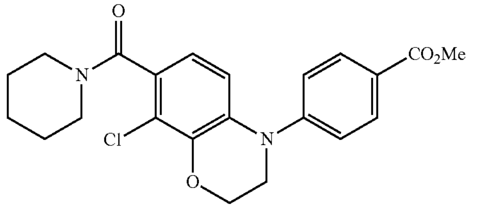

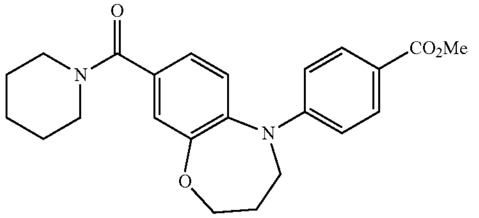

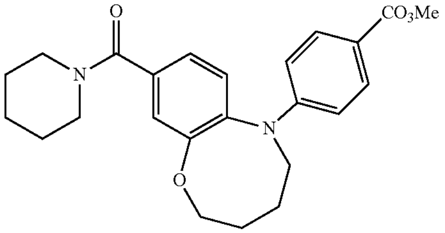

-continued

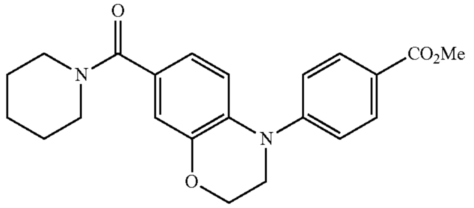

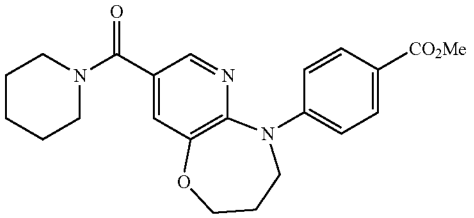

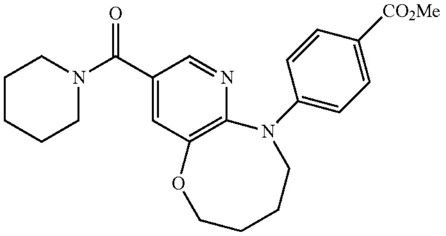

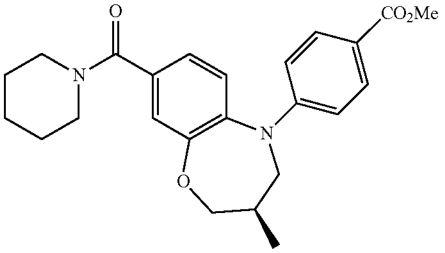

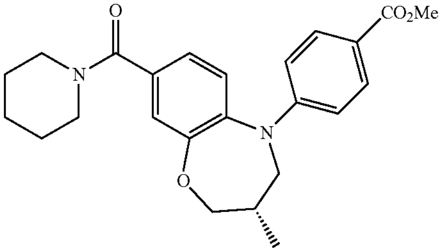

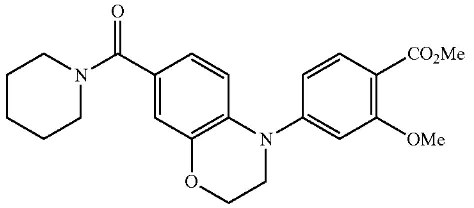

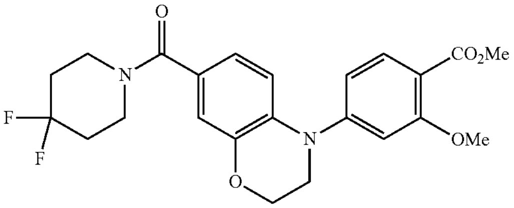

-continued
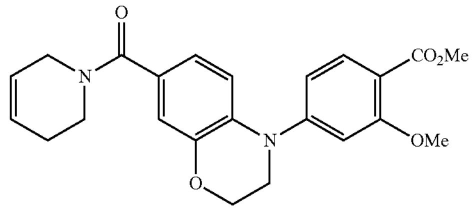
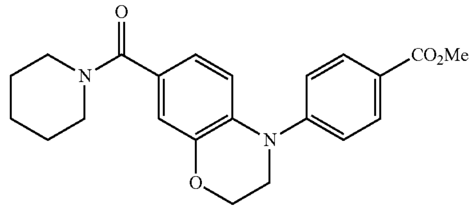
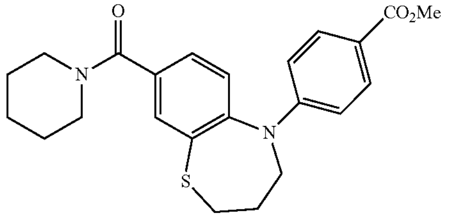
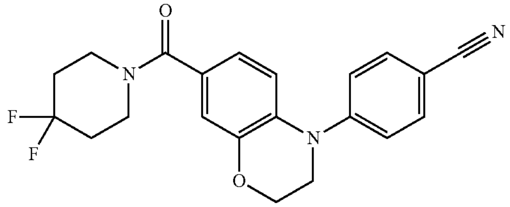
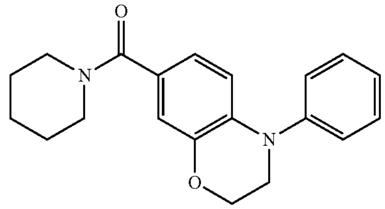
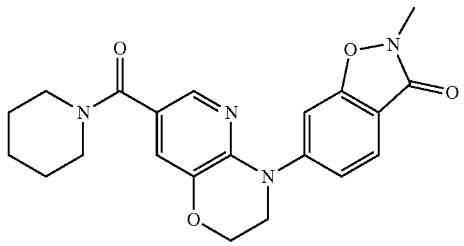
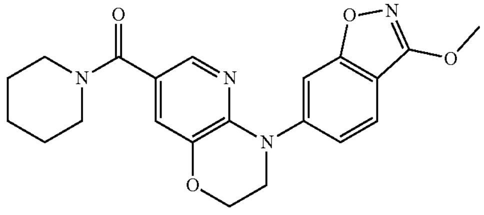
-continued
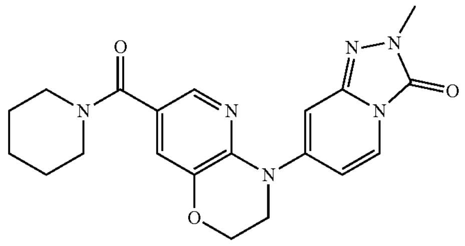
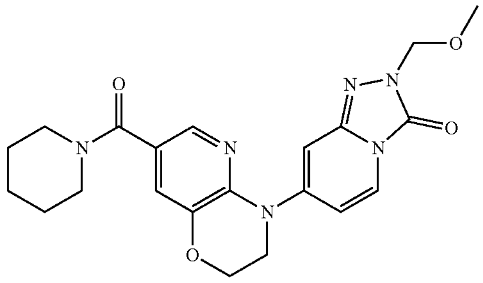
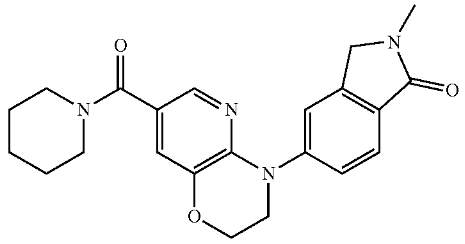
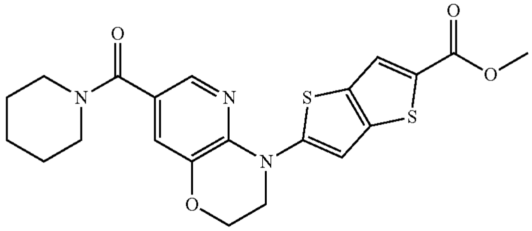
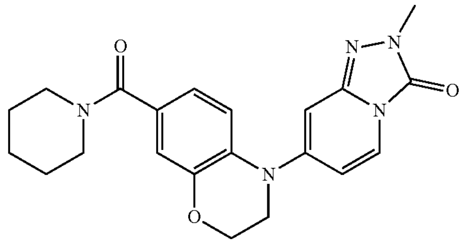
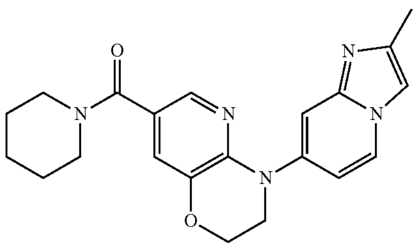

-continued
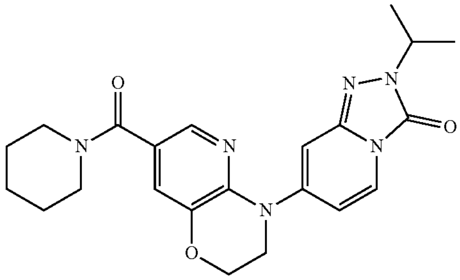
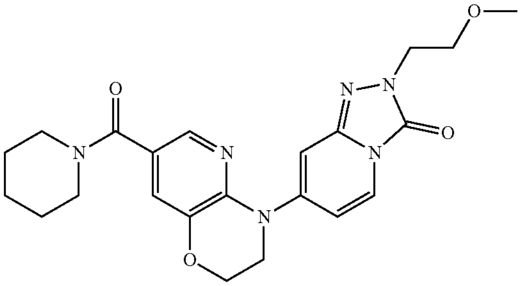
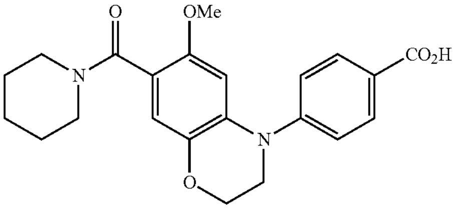
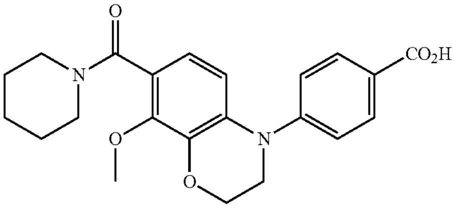
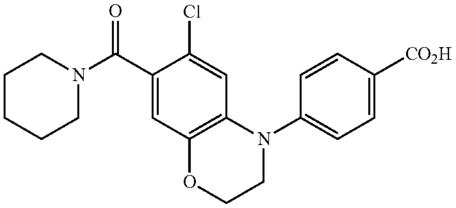
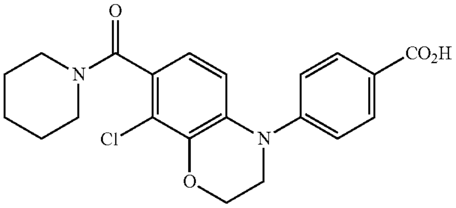
[Formula 16]
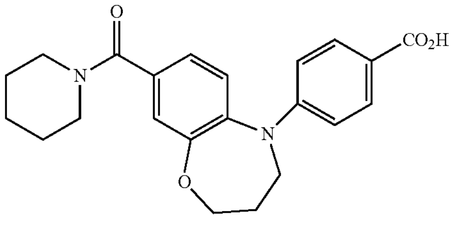
-continued
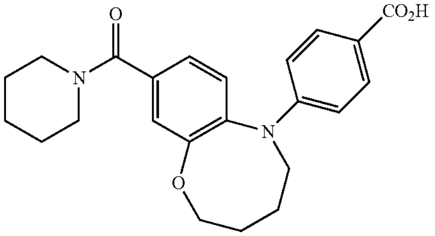
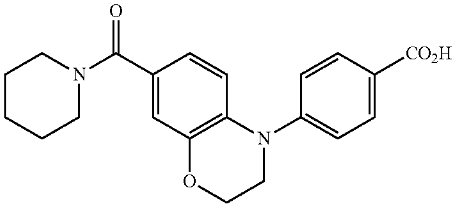
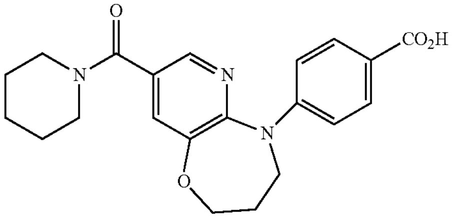
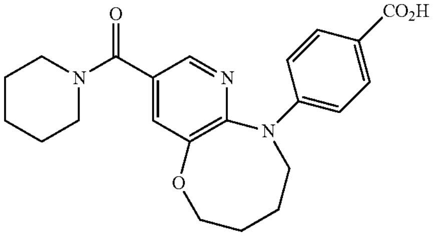
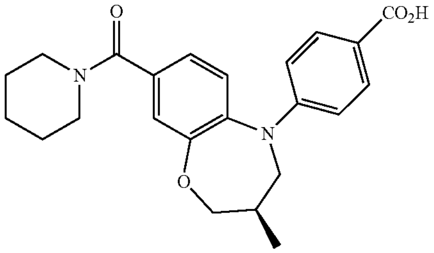
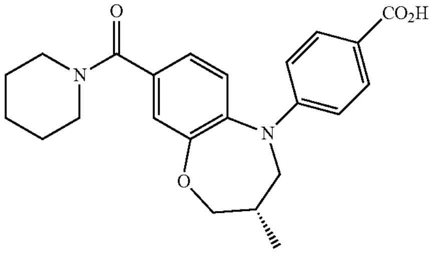
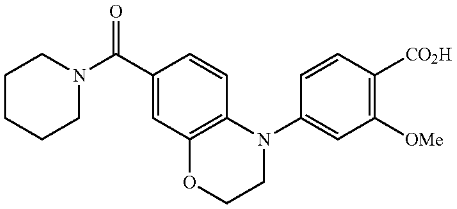

-continued
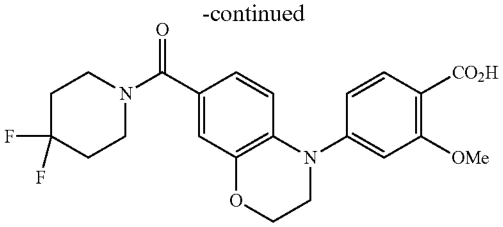
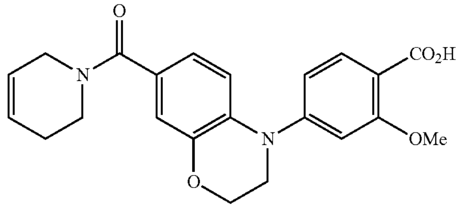
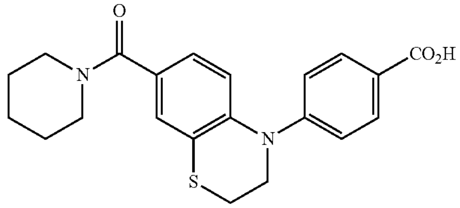
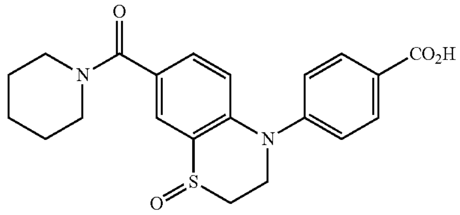
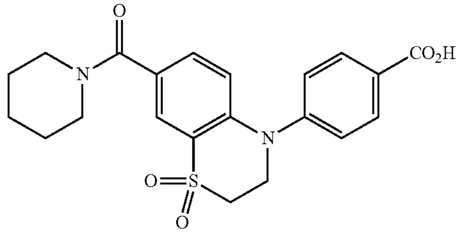
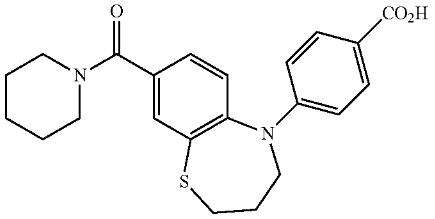
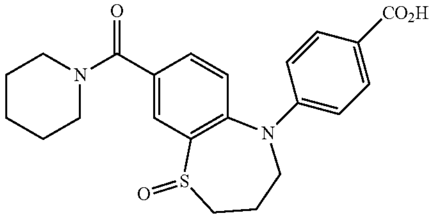
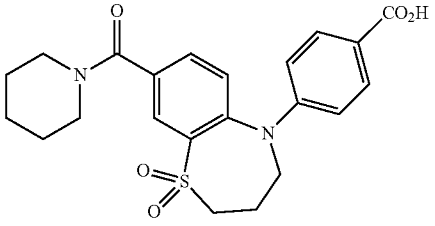
-continued
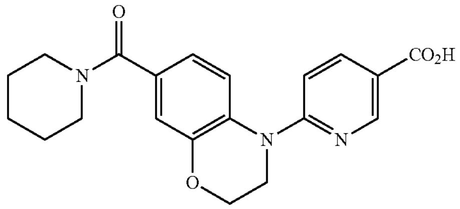
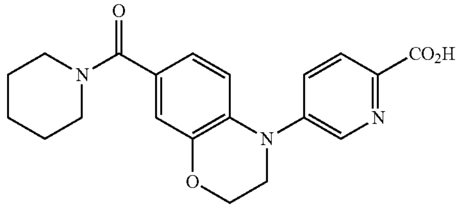
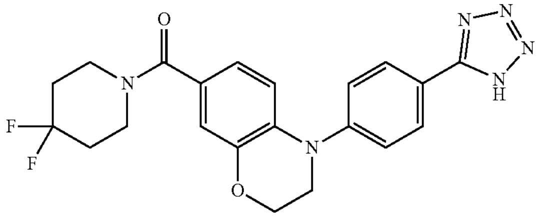
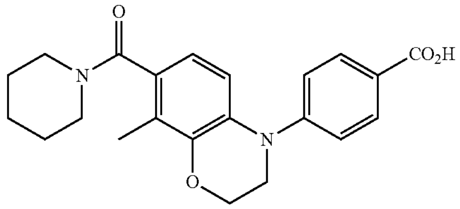
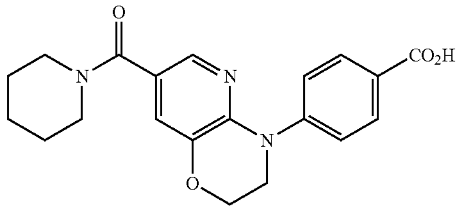
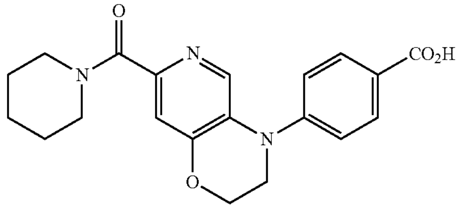
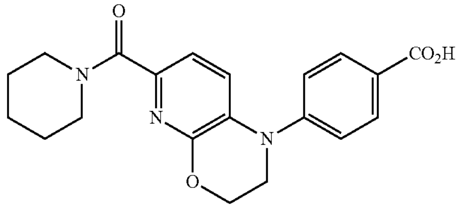
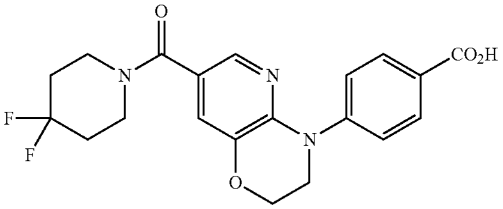

-continued
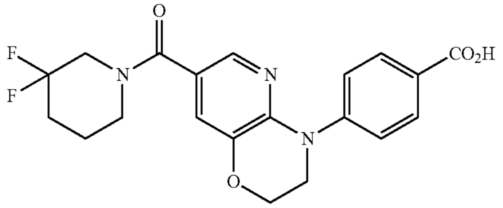
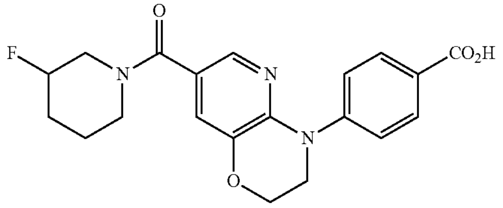
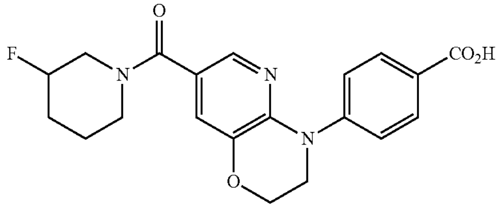
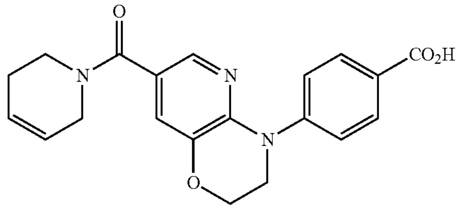
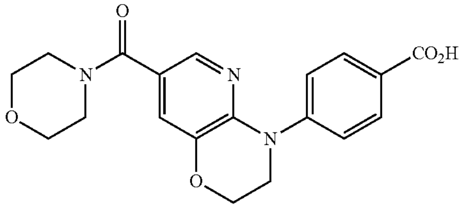
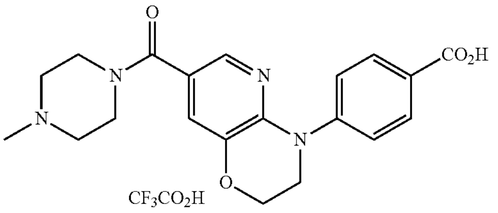
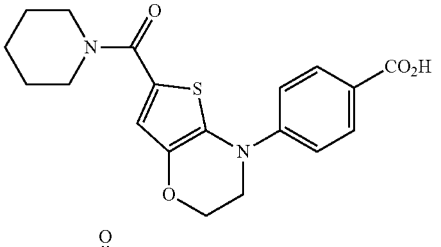
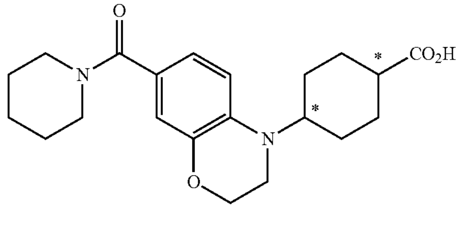
-continued
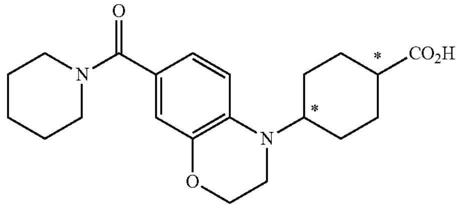
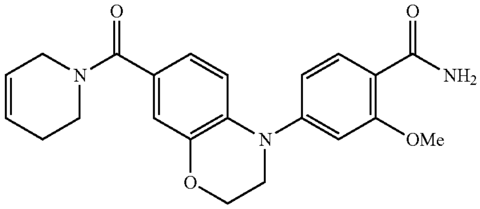
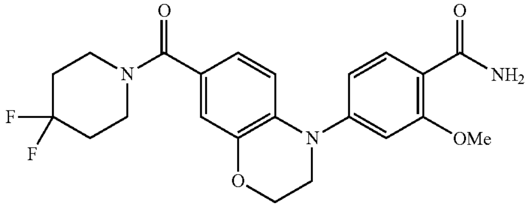
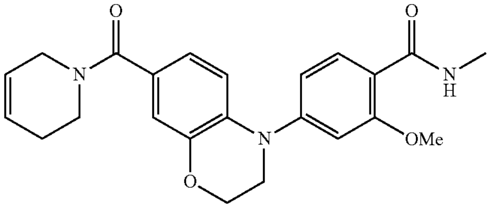
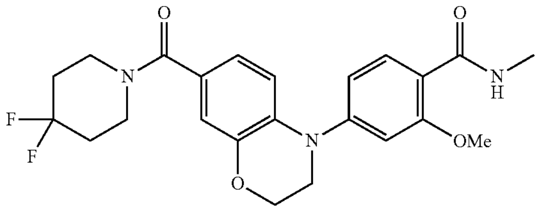
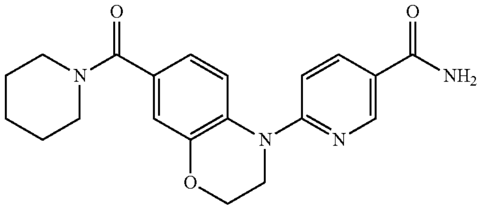
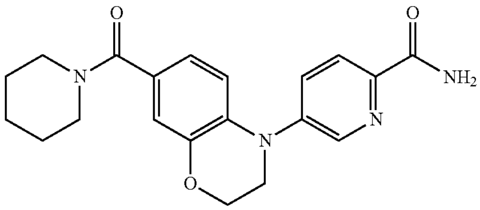
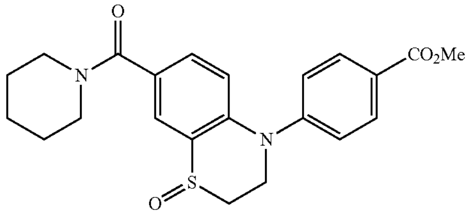

-continued
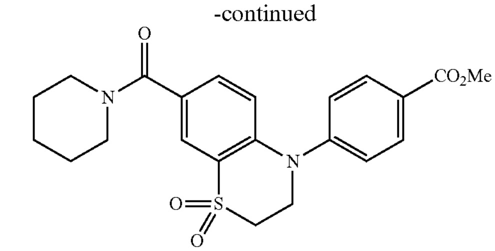
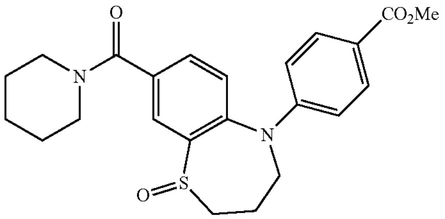
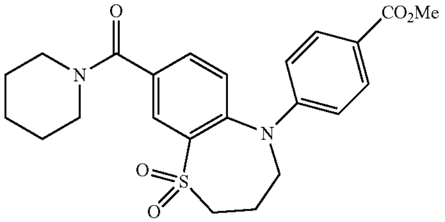
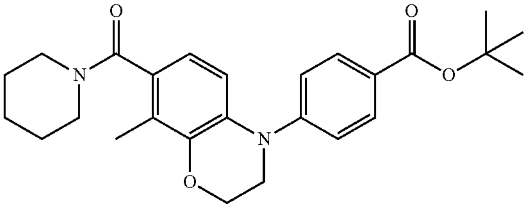
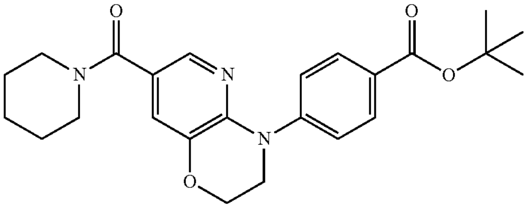
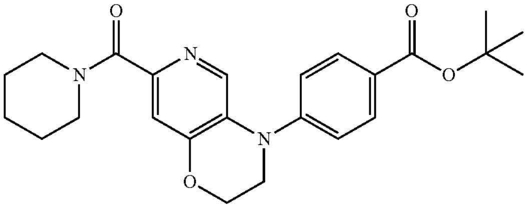
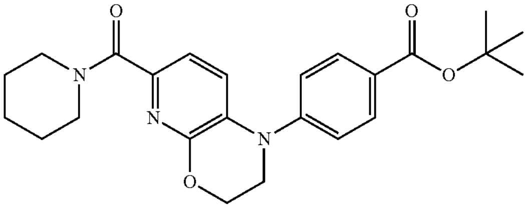
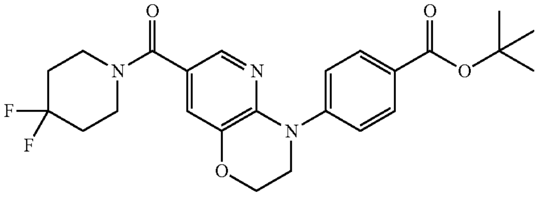
-continued
[Formula 17]
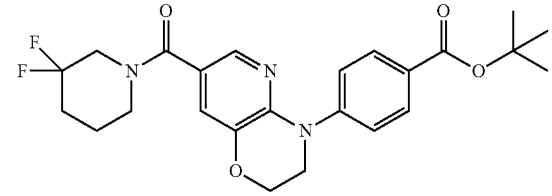
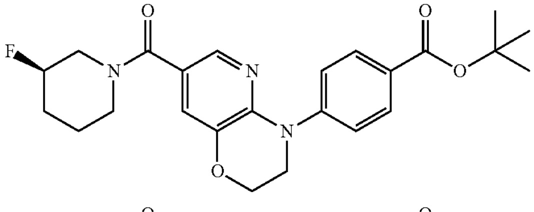
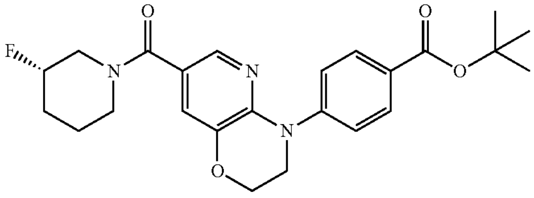
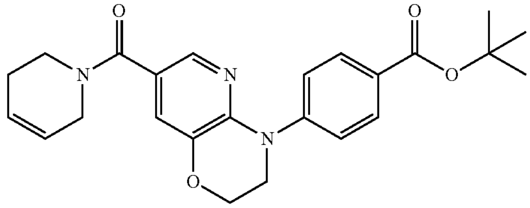
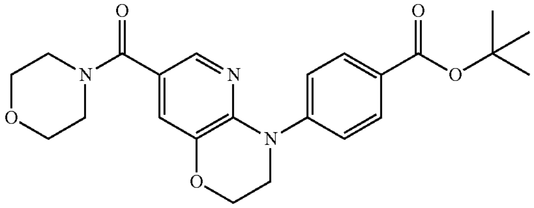
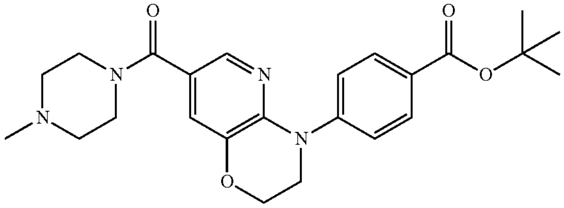
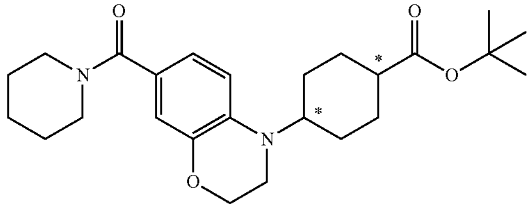
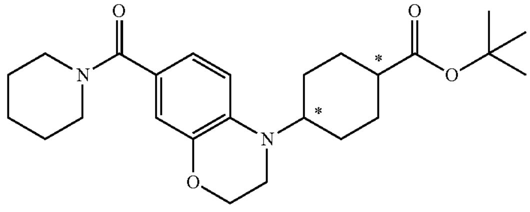

-continued
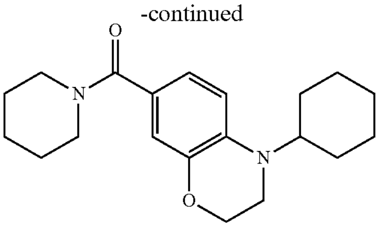
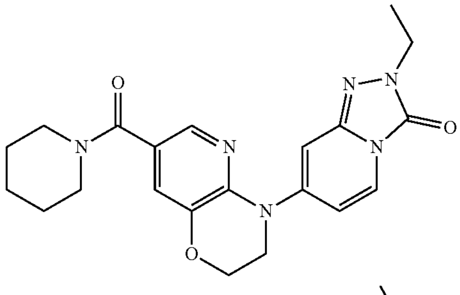
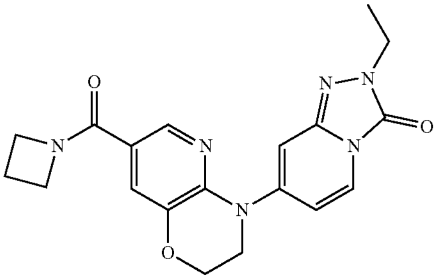
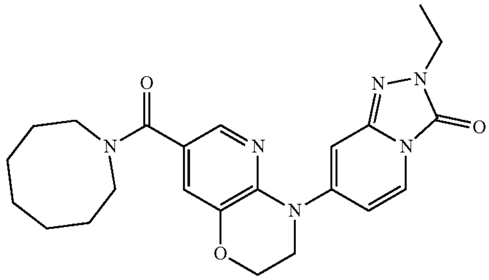
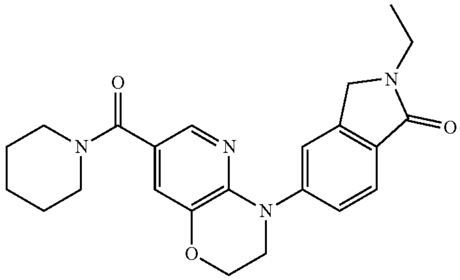
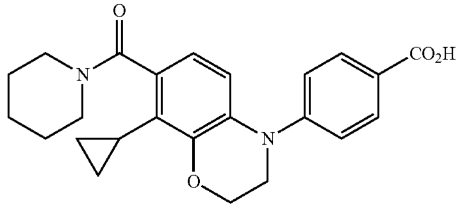
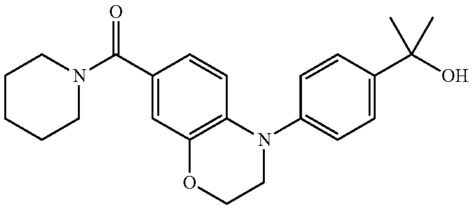
-continued
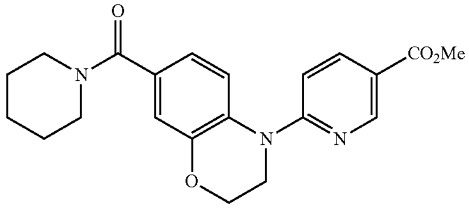
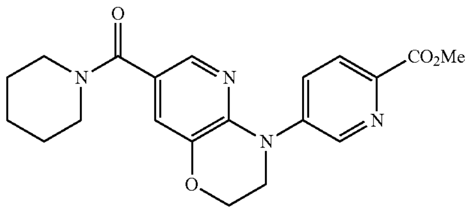
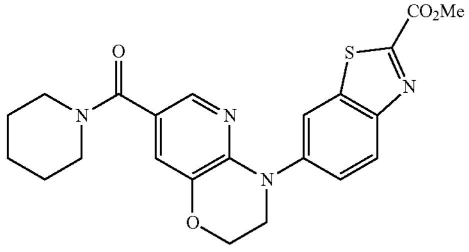
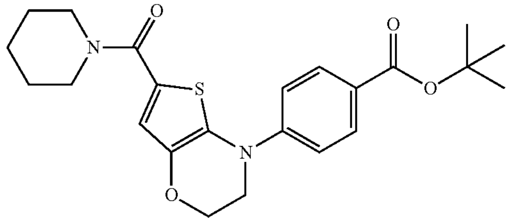
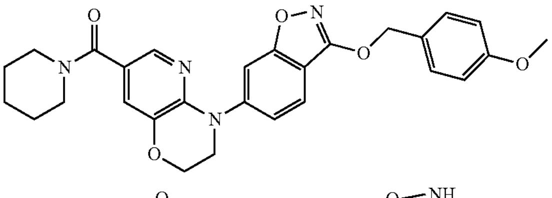
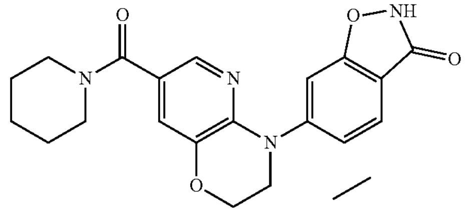
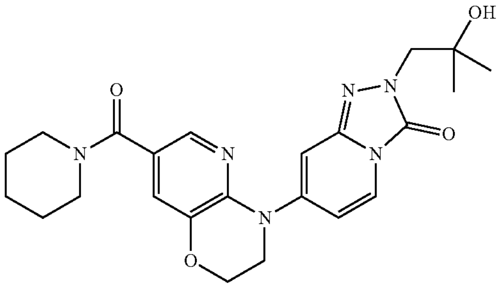

-continued
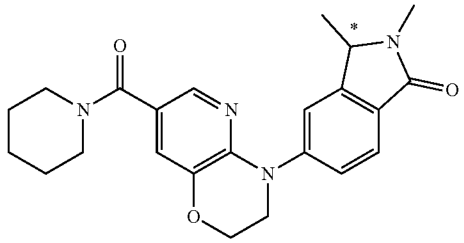
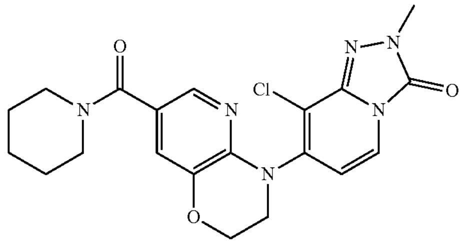
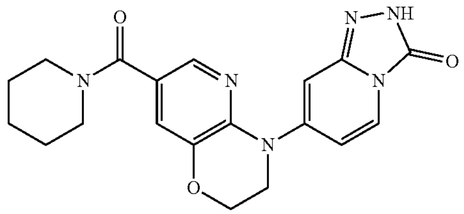
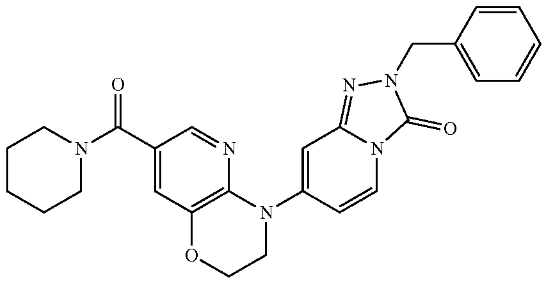
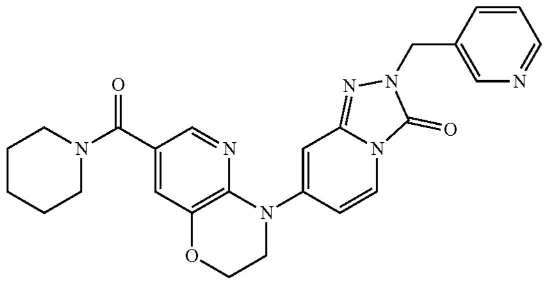
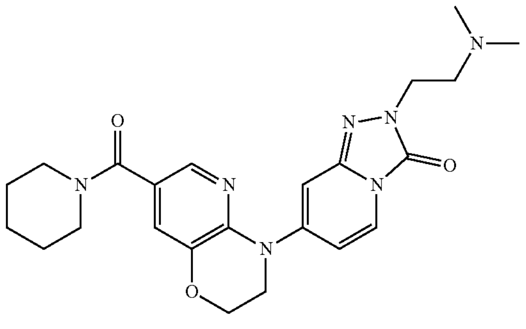
-continued
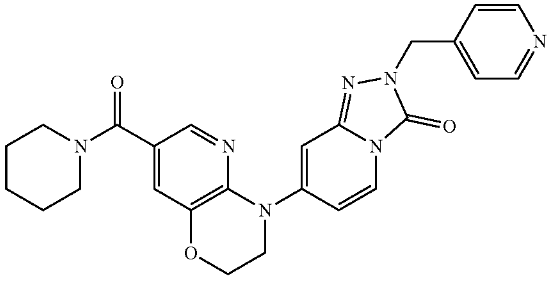
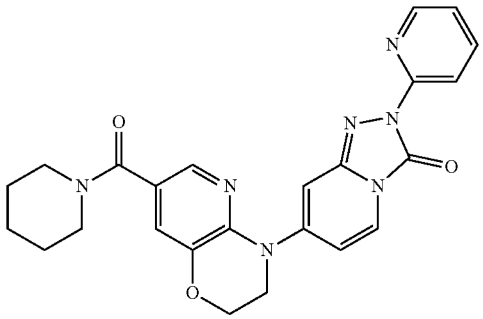
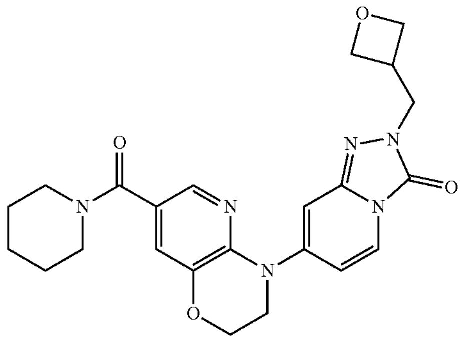
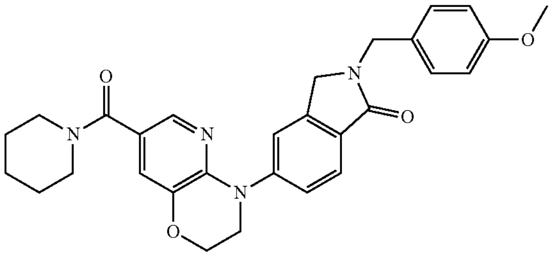
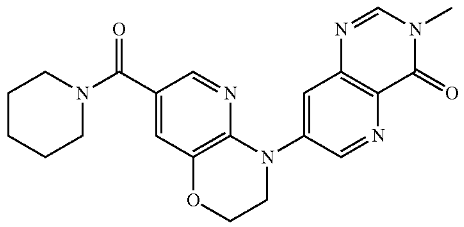
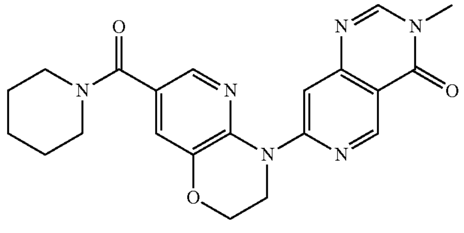

-continued
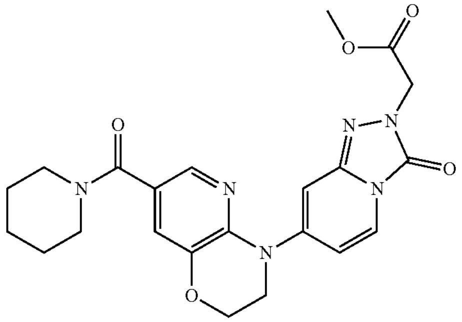
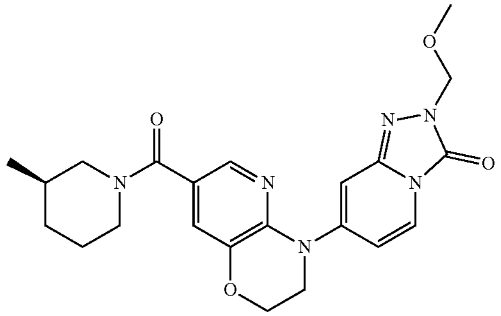
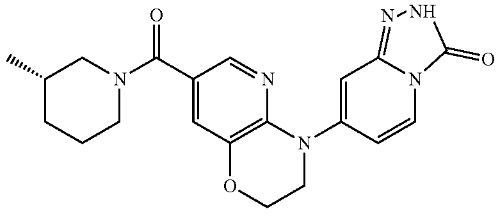
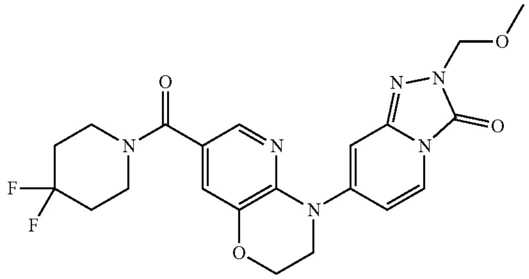
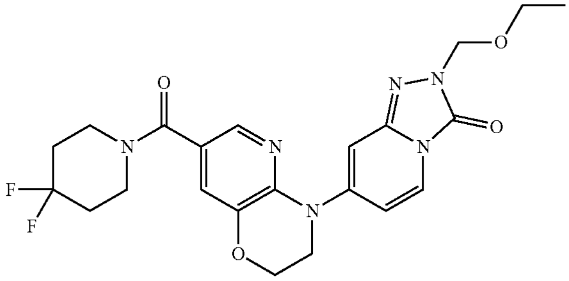
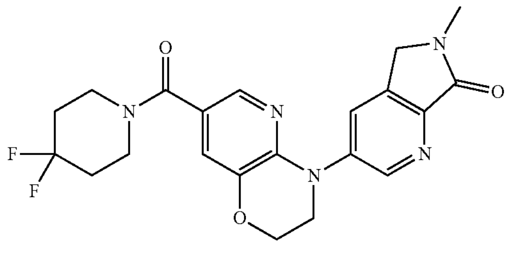
-continued
[Formula 18]
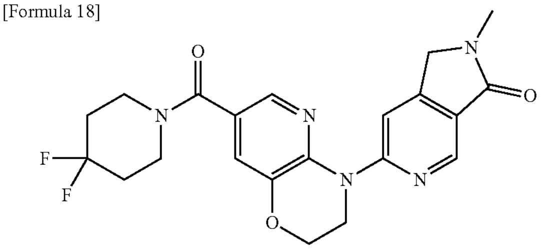
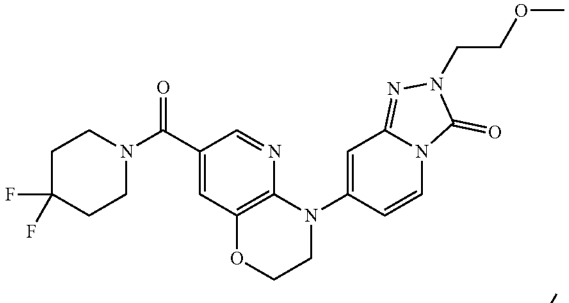
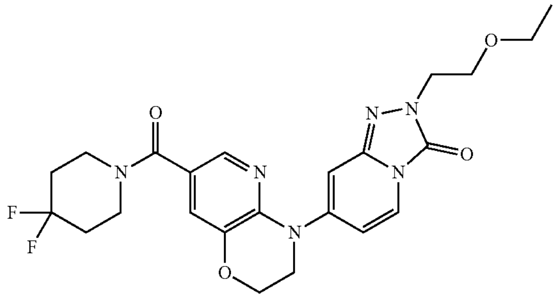
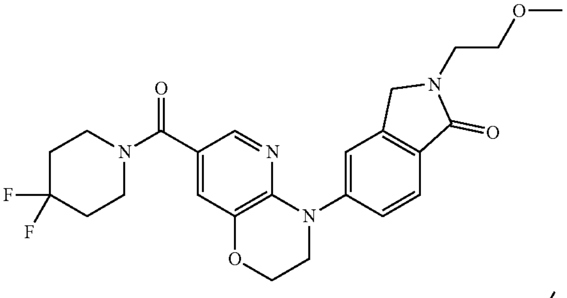
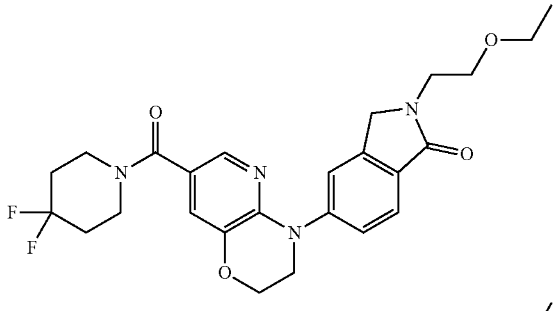
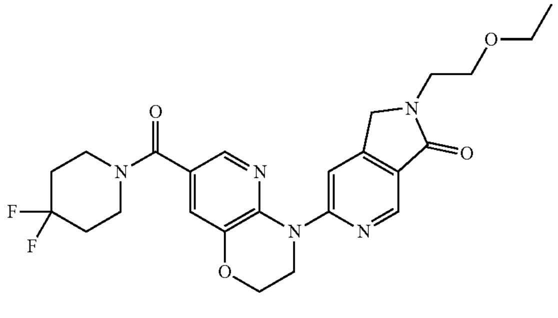

-continued
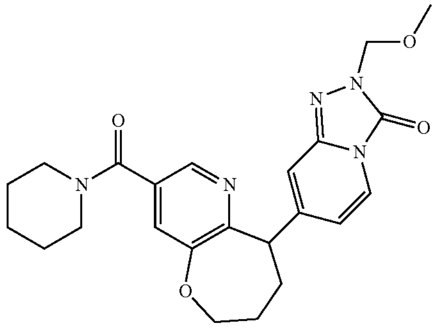
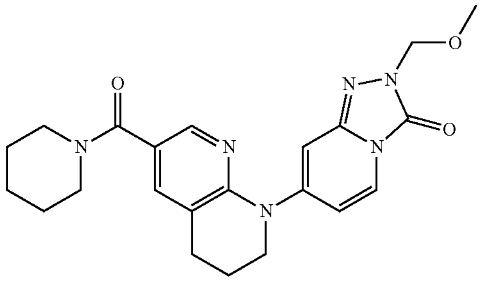
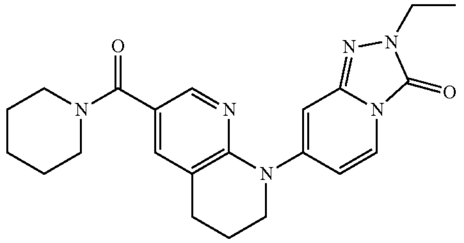
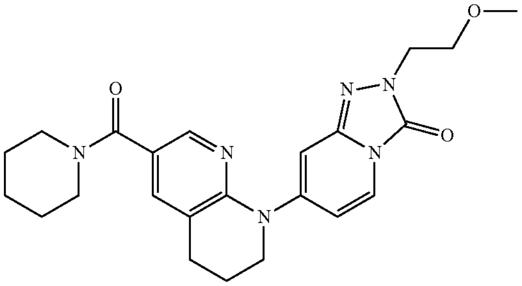
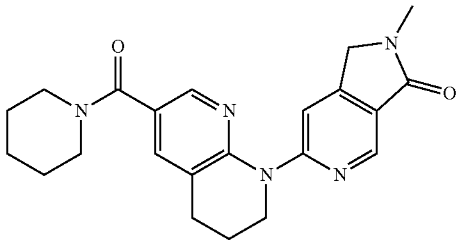
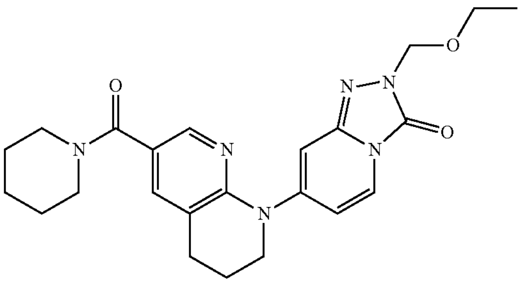
-continued
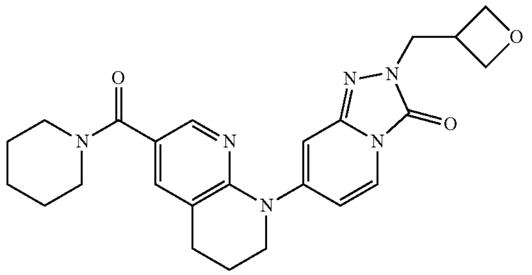
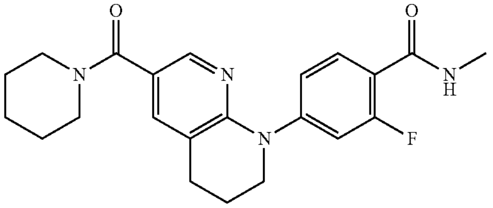
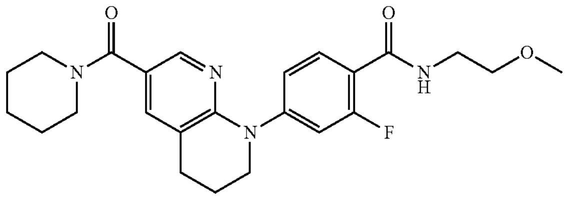
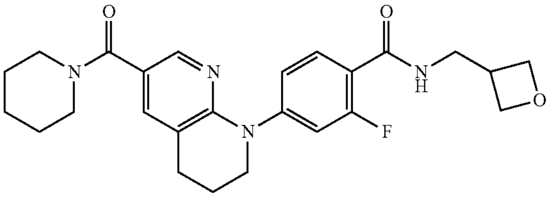
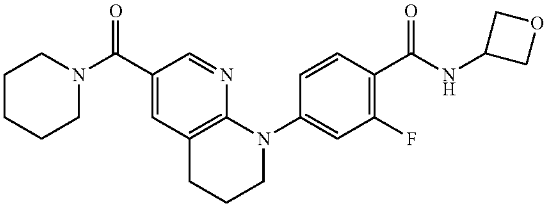
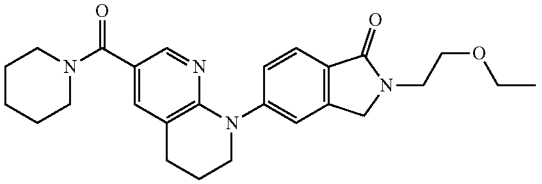
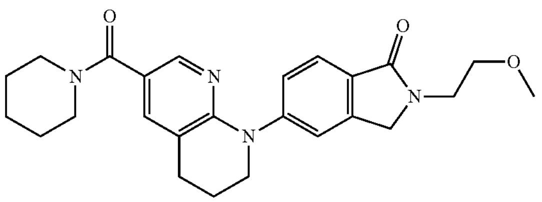
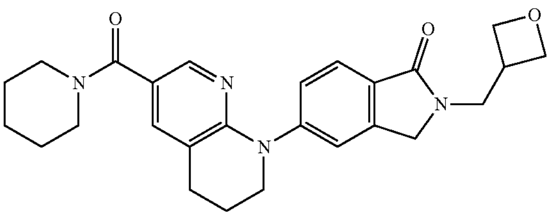

-continued
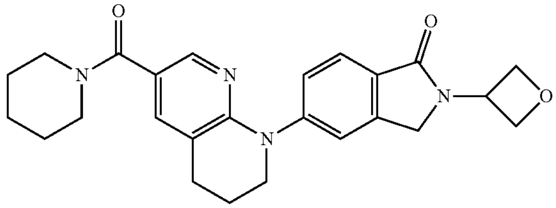
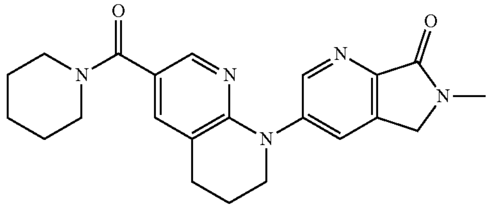
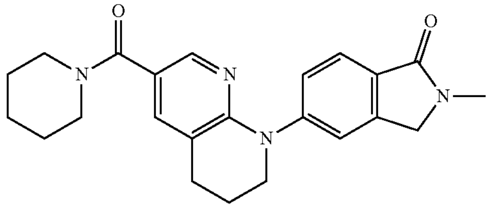
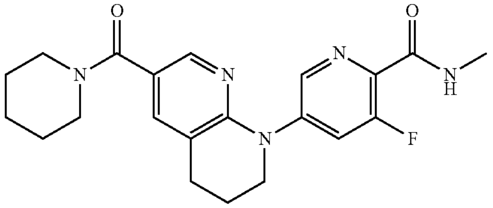
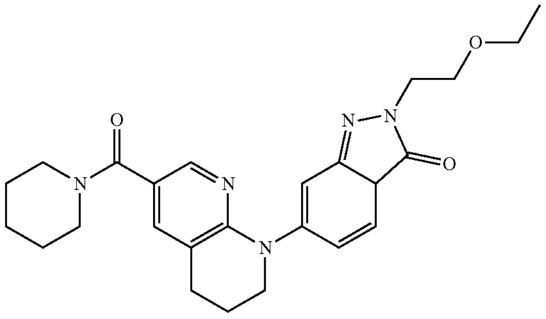
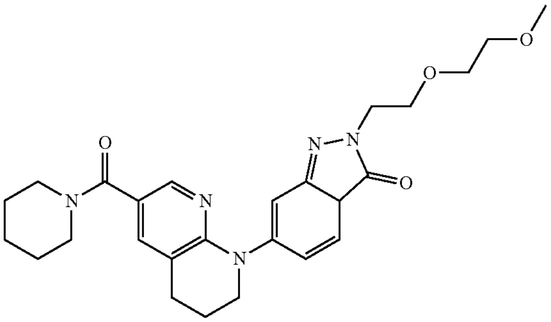
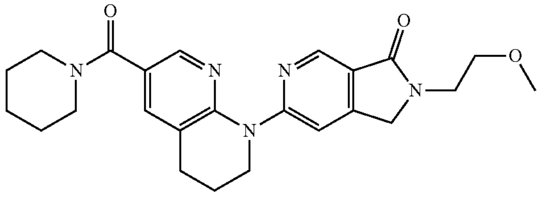
-continued
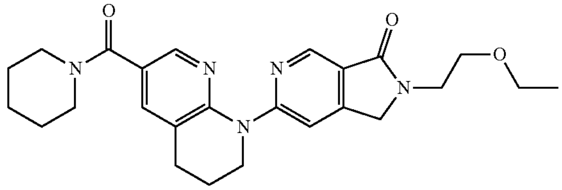
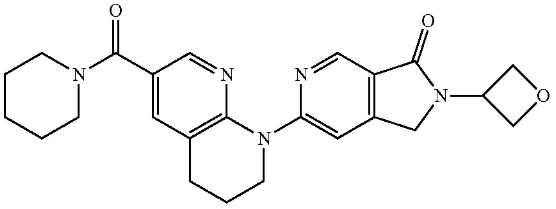
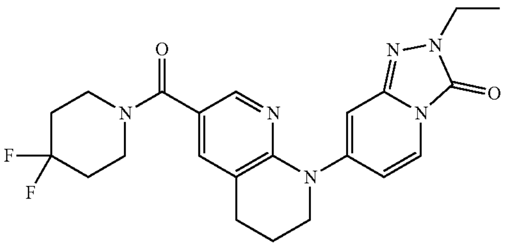
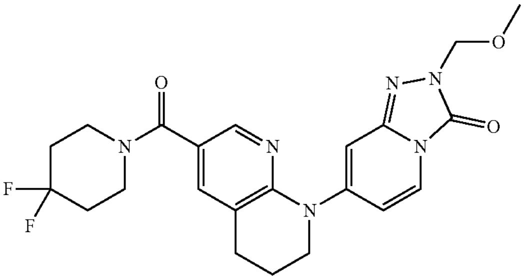
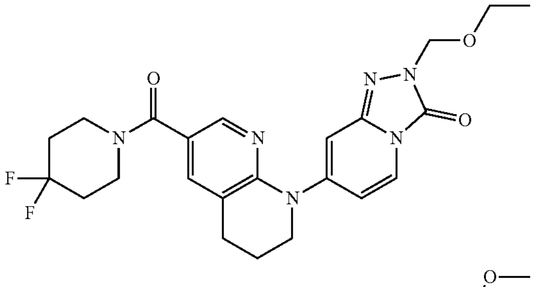
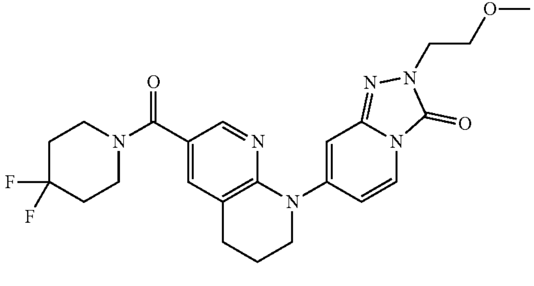

-continued
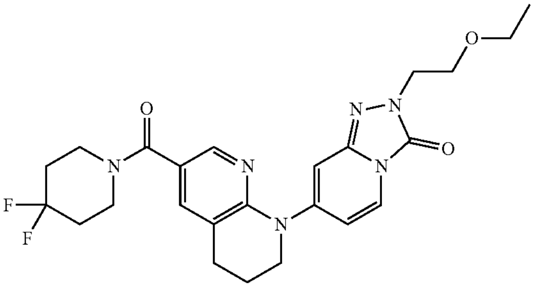
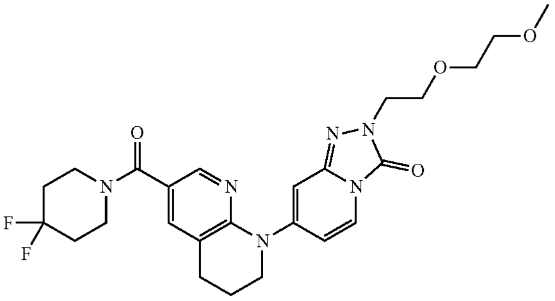
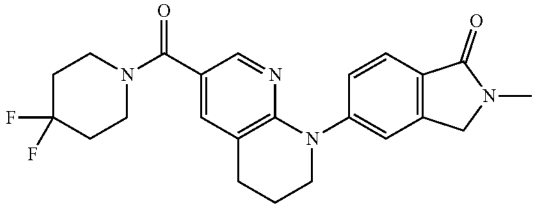
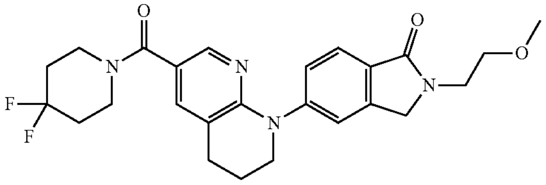
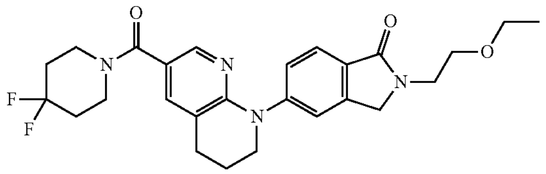
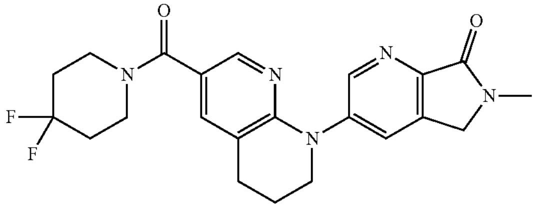
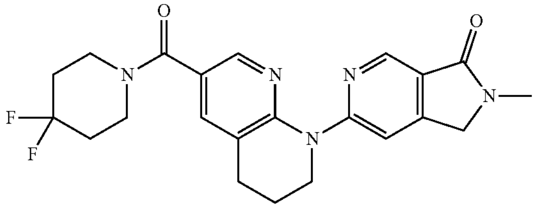
-continued
[Formula 19]
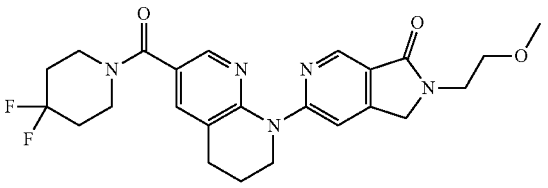
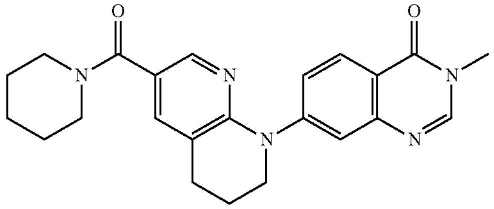
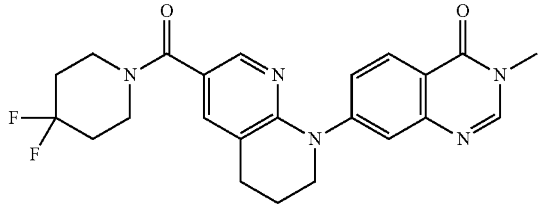
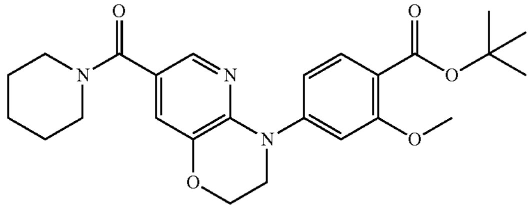
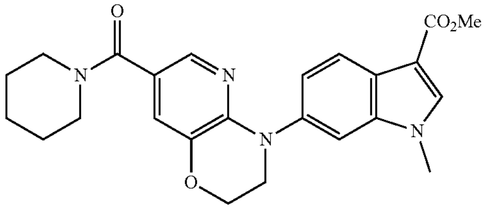
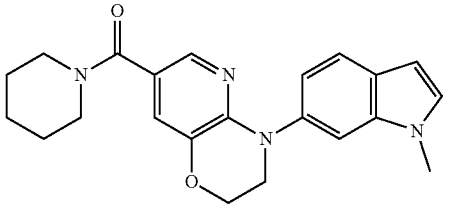
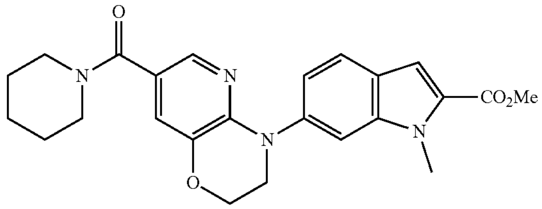
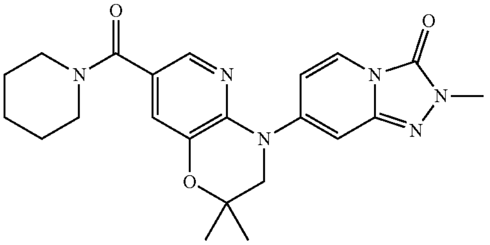

-continued
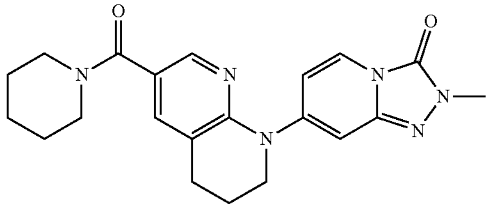
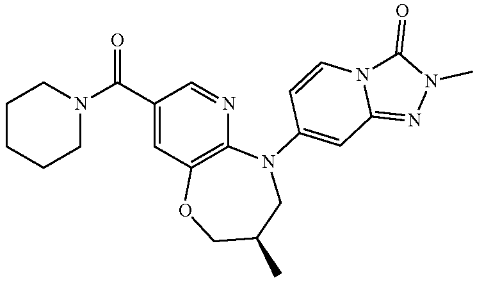
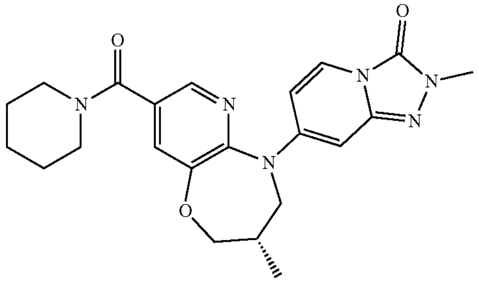
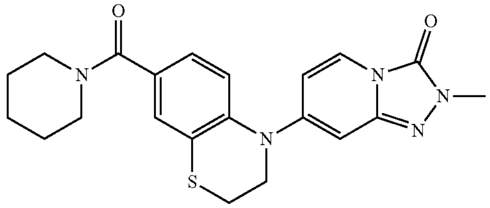
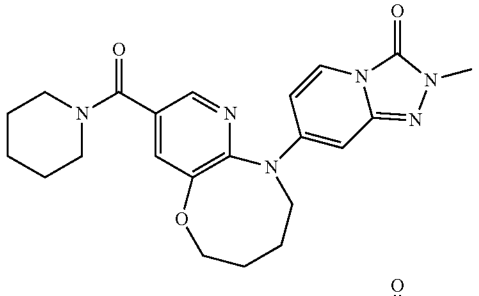
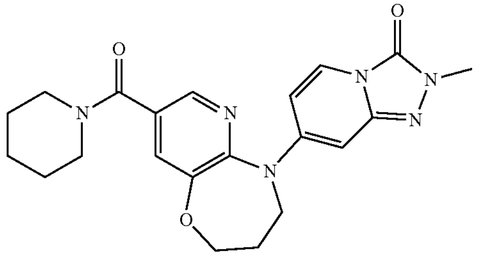
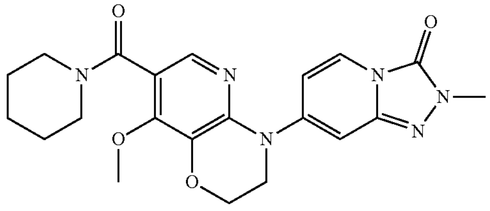
-continued
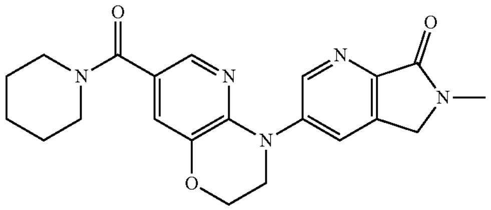
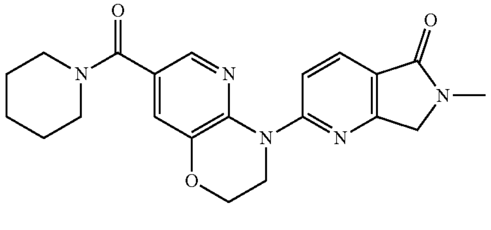
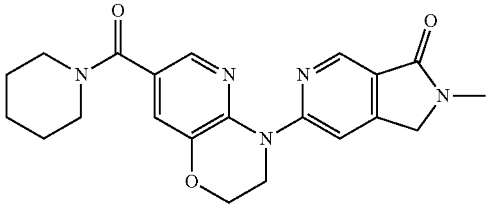
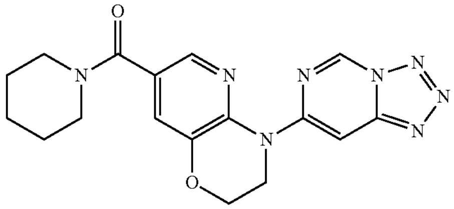
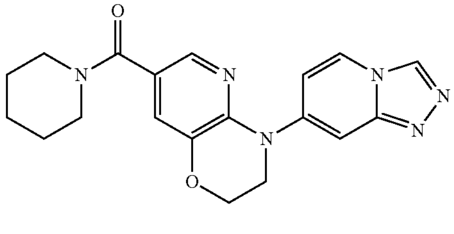
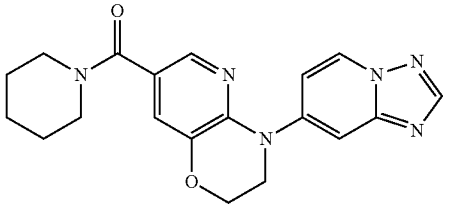
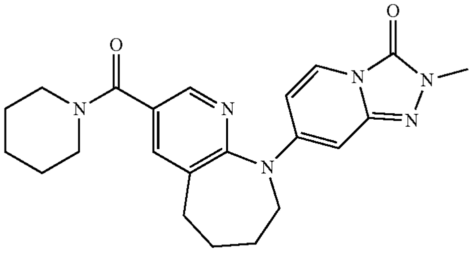

-continued
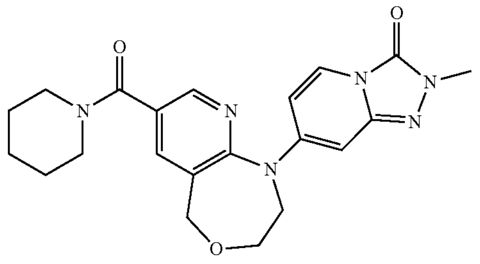
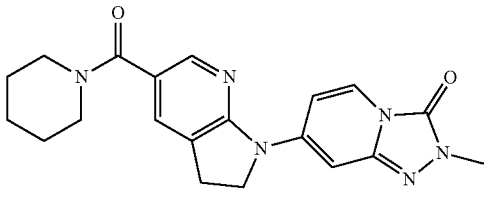
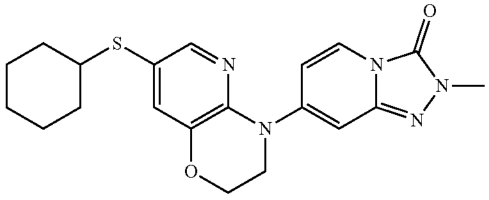
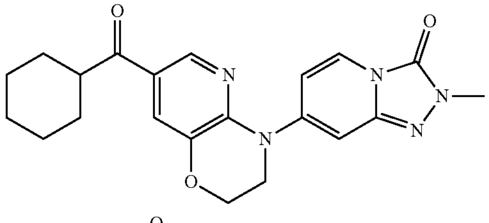
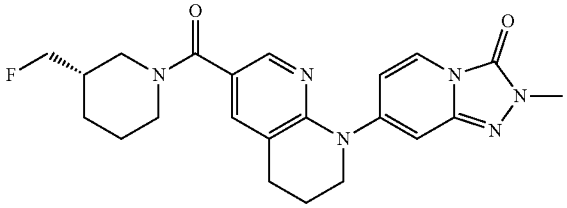
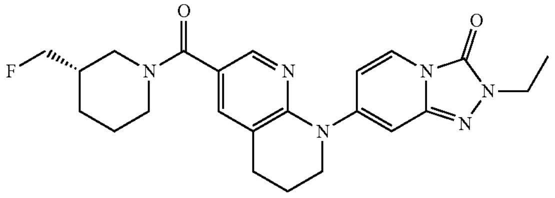
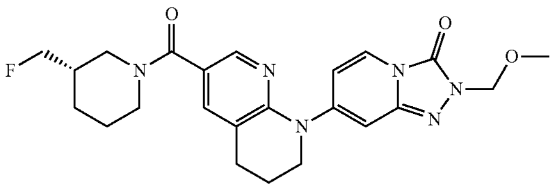
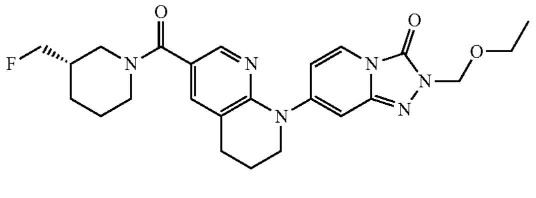
-continued
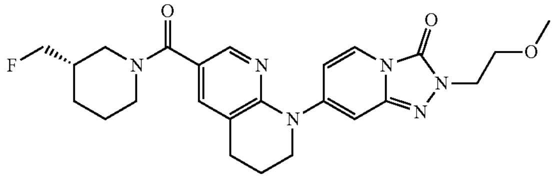
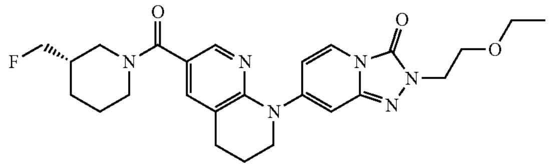
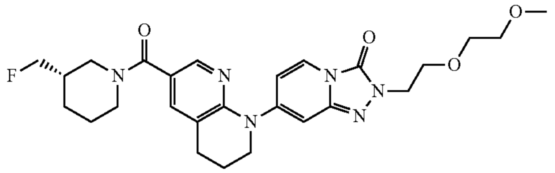
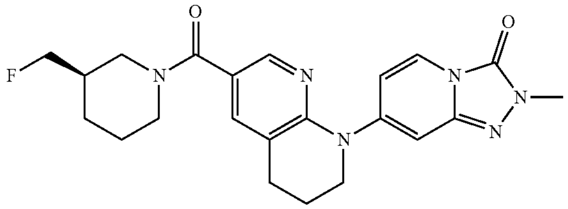
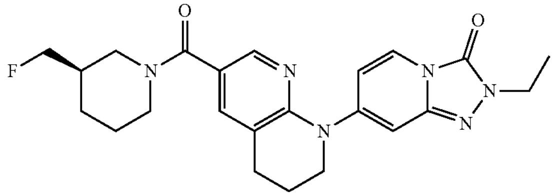
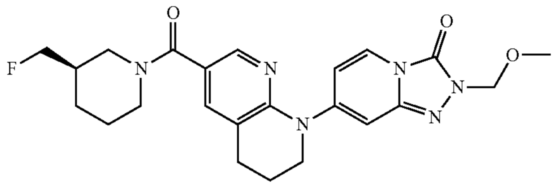
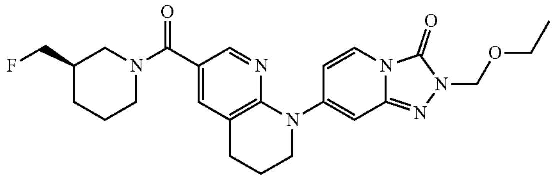
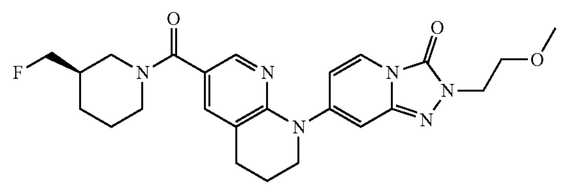
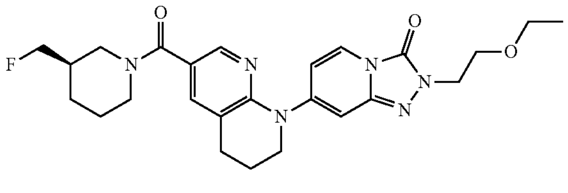

-continued
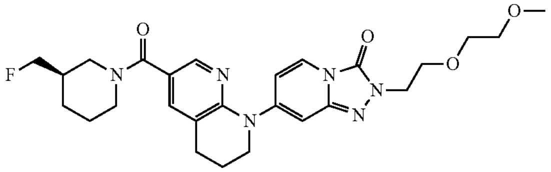
[Formula 20]
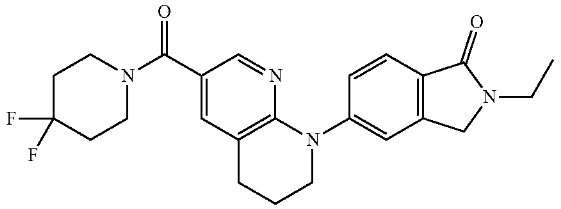
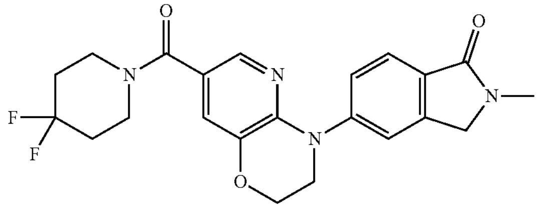
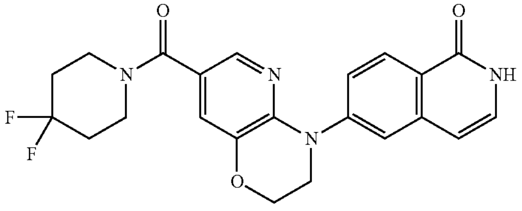
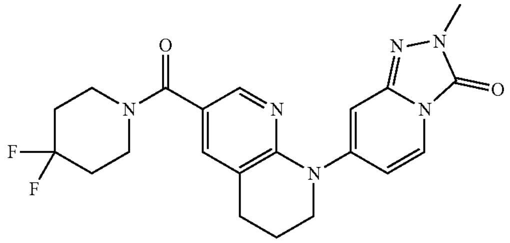
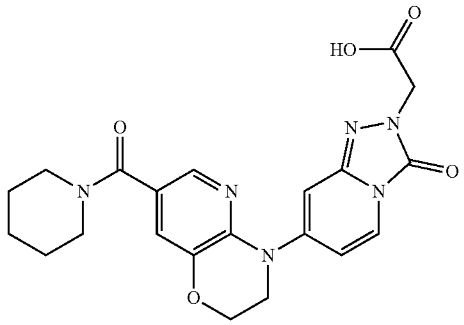
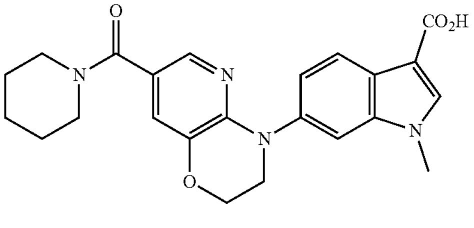
-continued
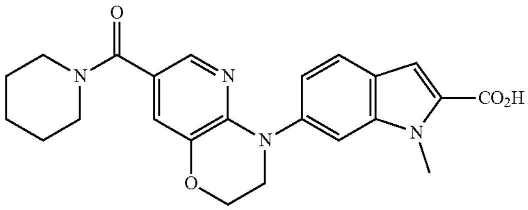
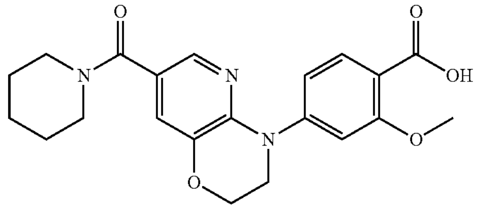
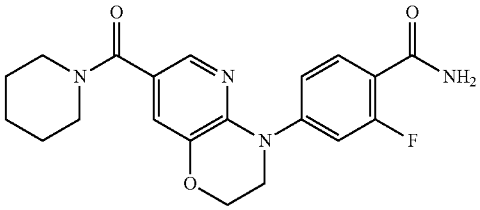
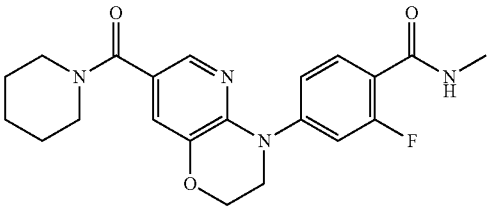
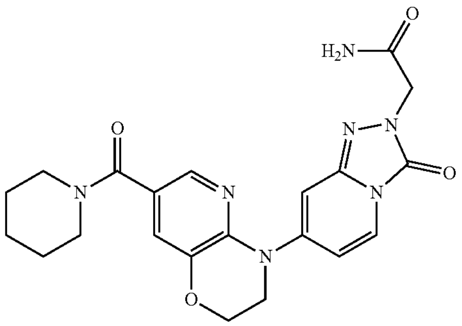
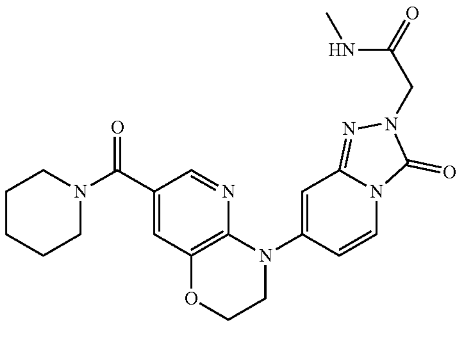

-continued
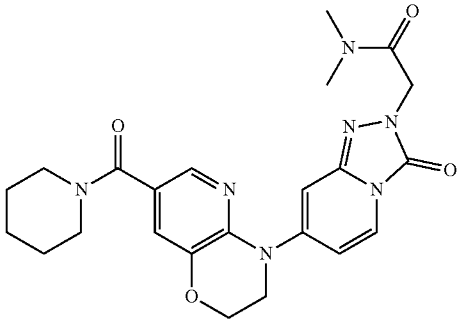
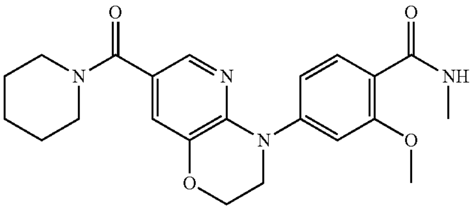
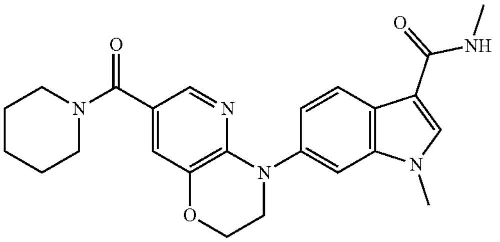
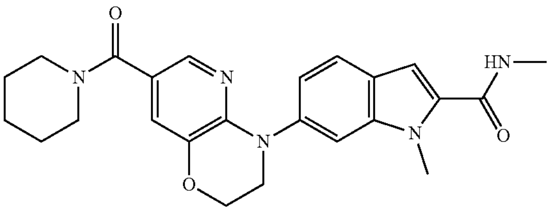
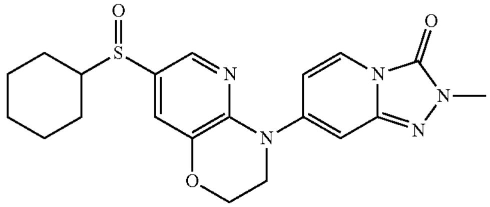
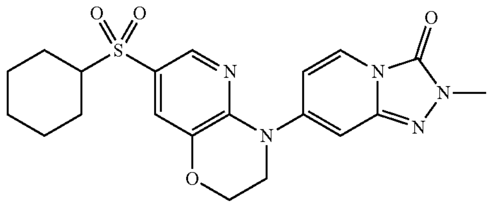
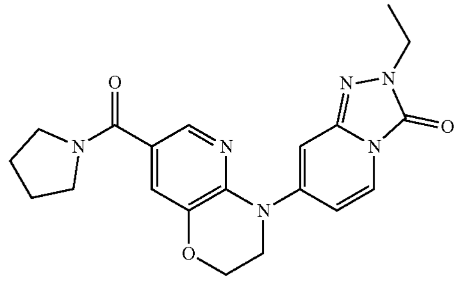
-continued
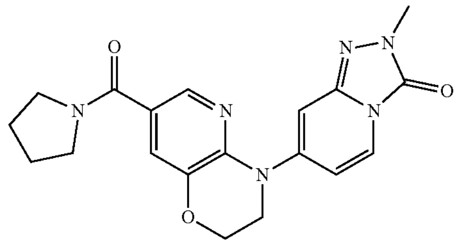
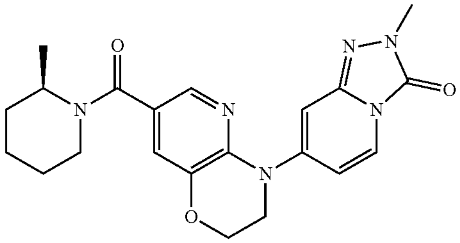
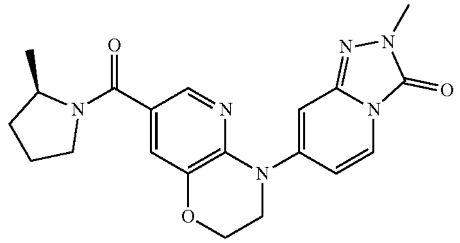
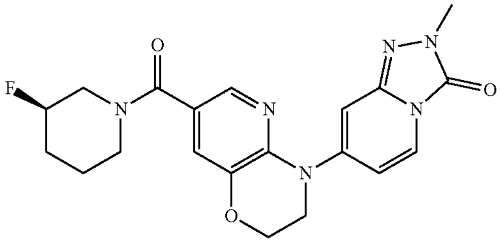
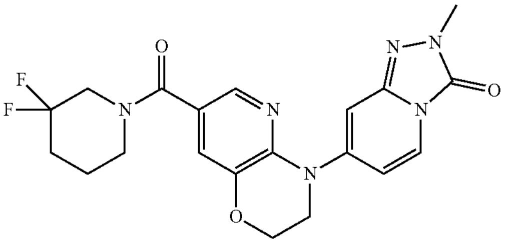
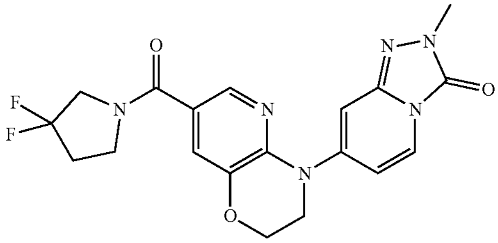
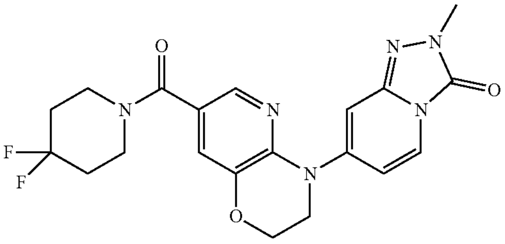

-continued
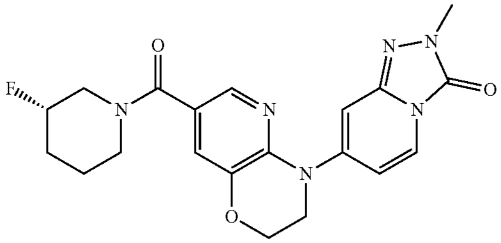
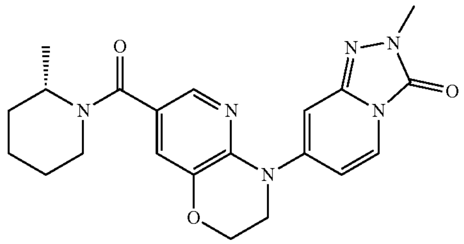
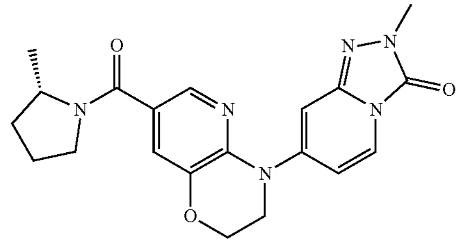
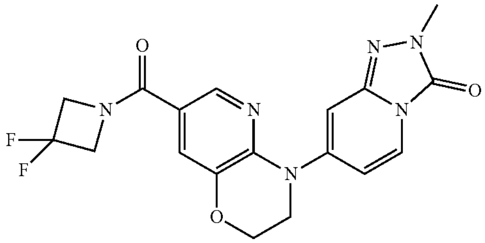
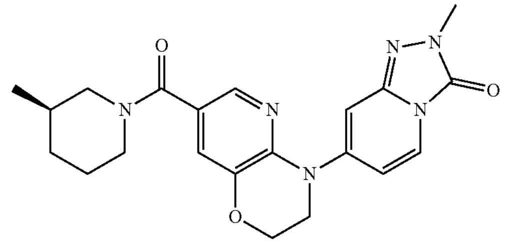
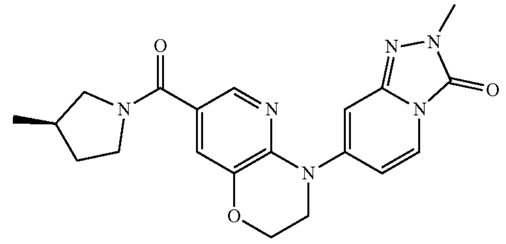
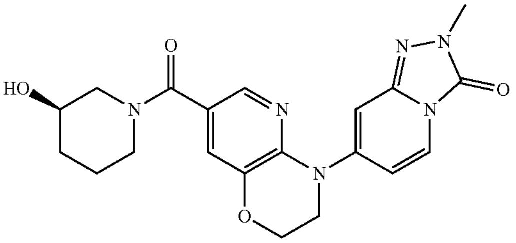
-continued
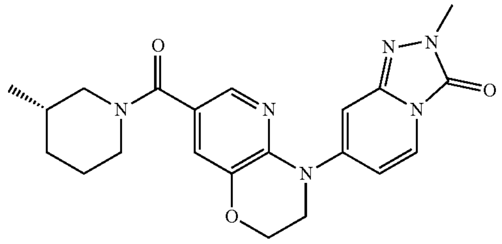
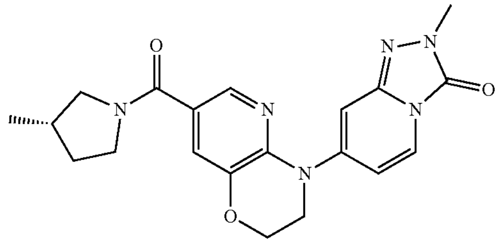
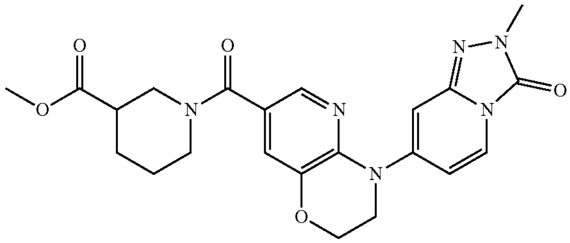
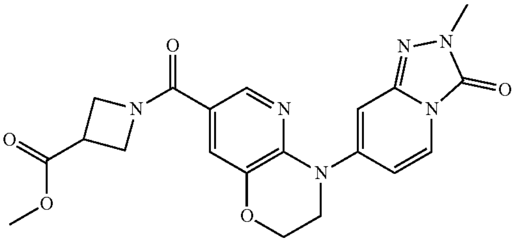
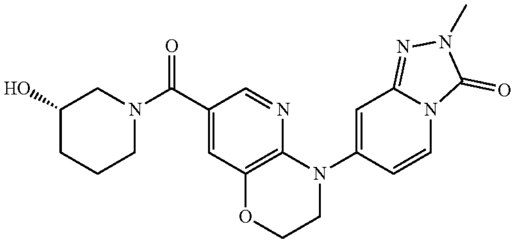
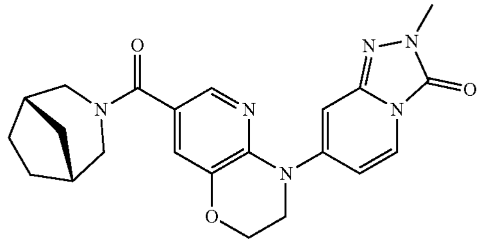
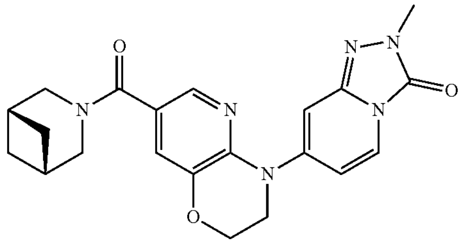

-continued
[Formula 21]
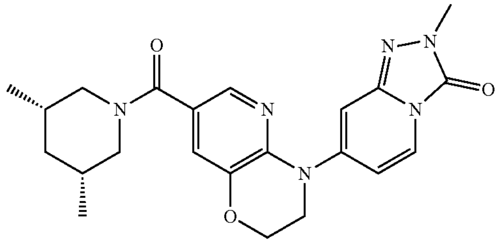
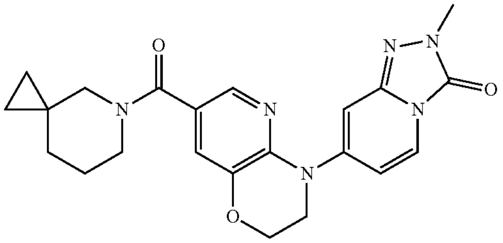
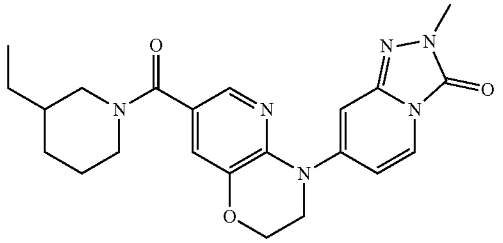
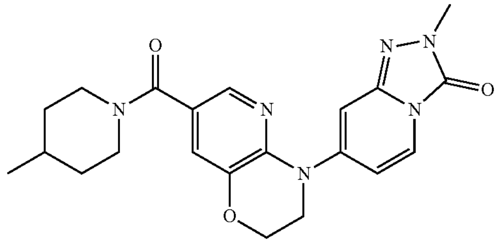
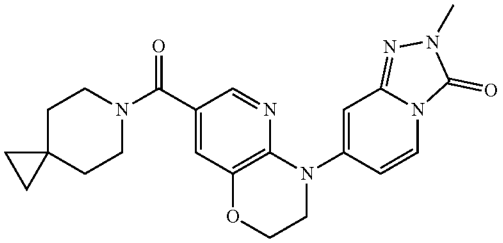
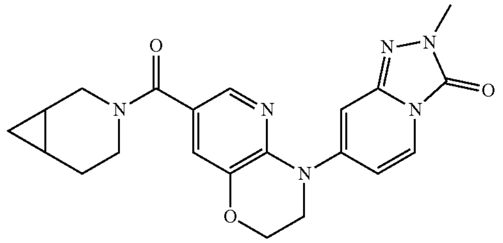
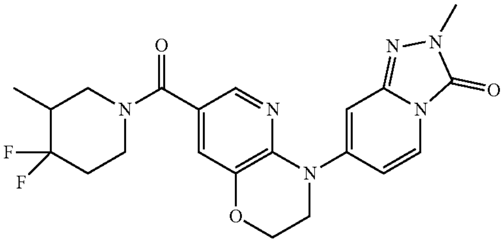
-continued
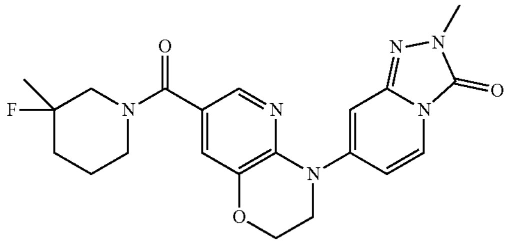
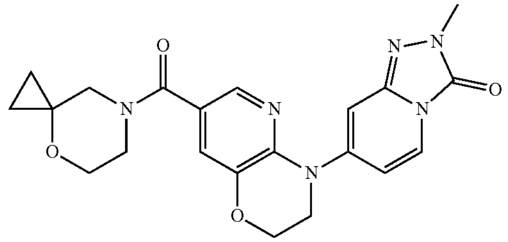
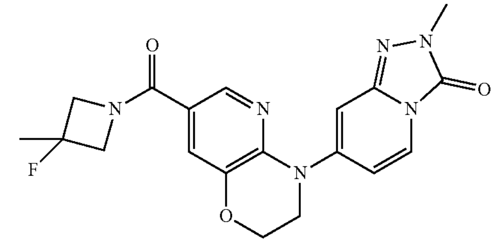
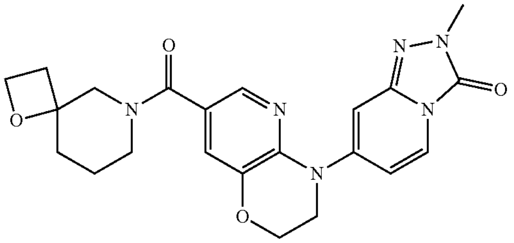
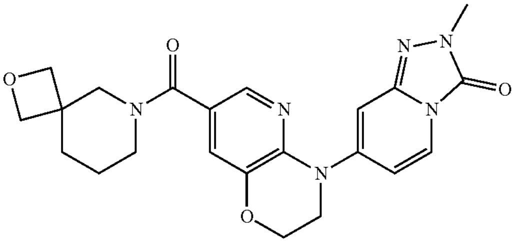
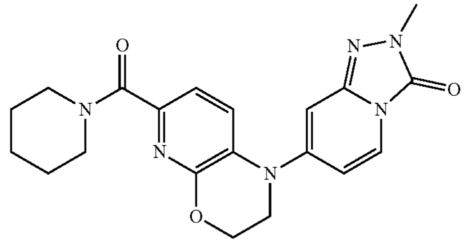
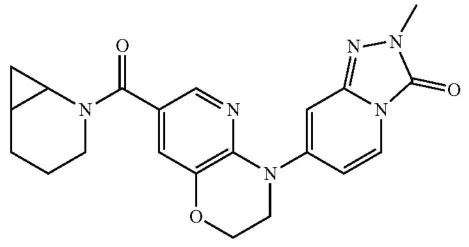

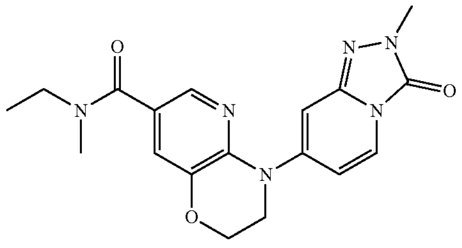
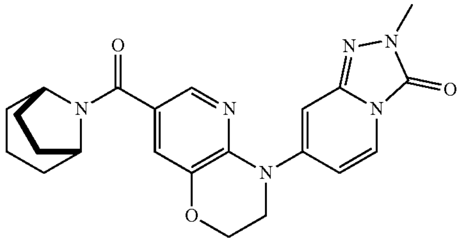
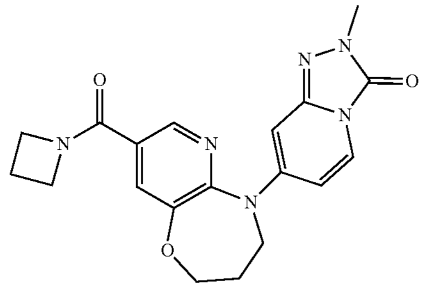
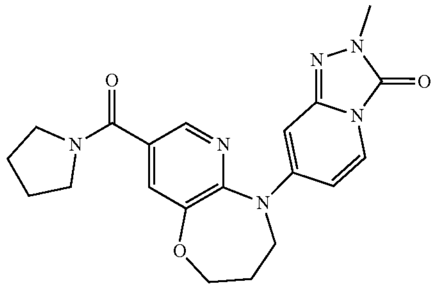
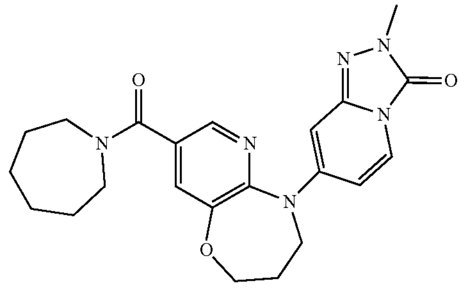
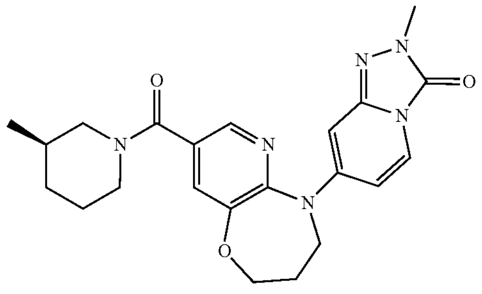
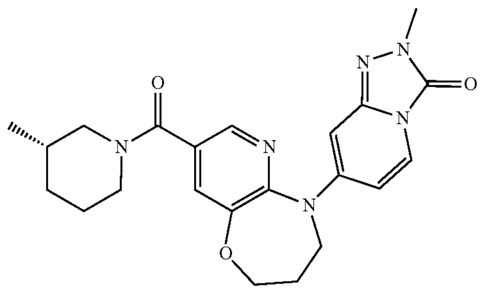
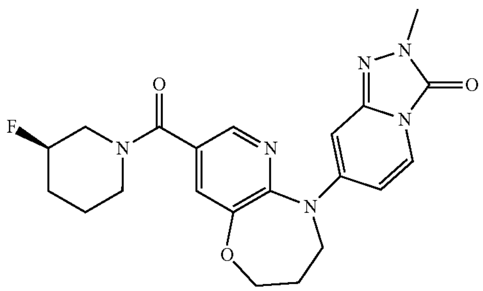
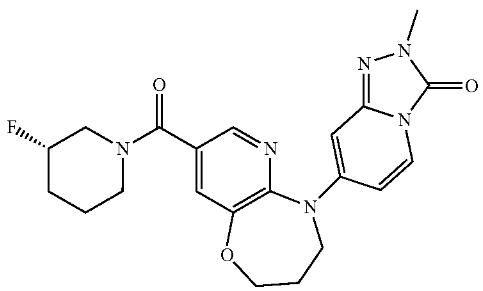
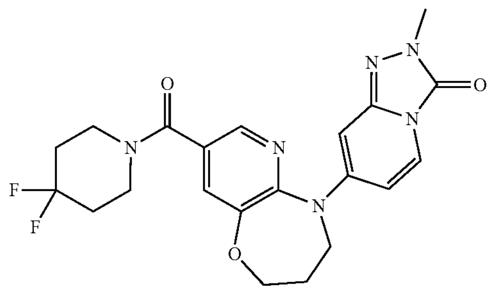
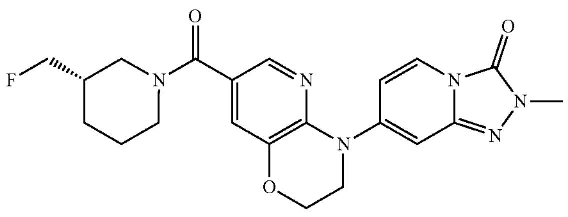
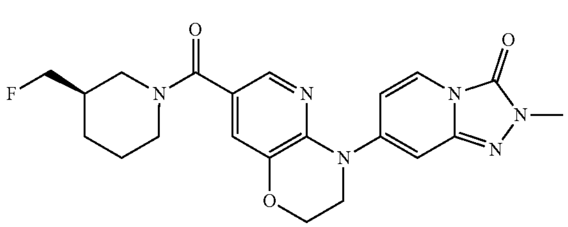

-continued
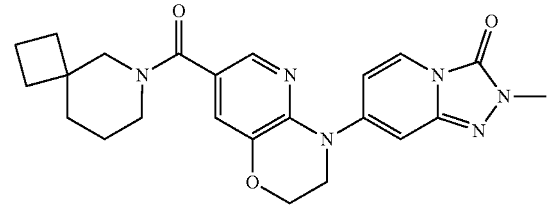
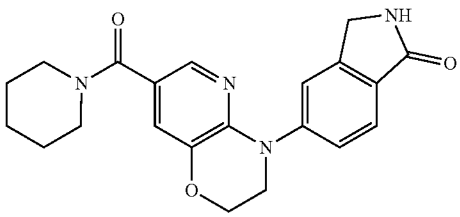
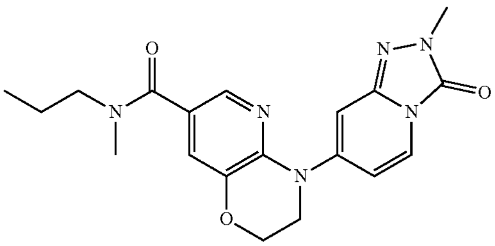
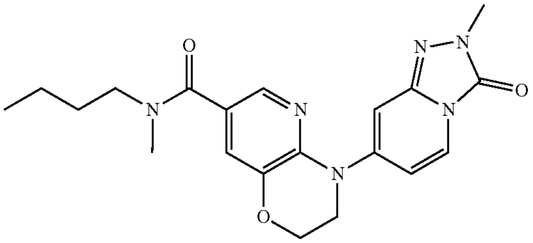
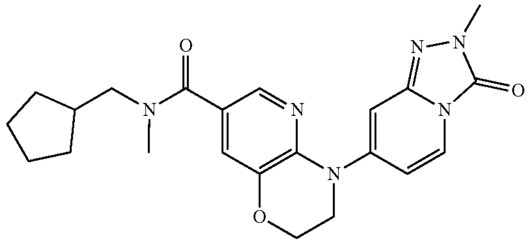
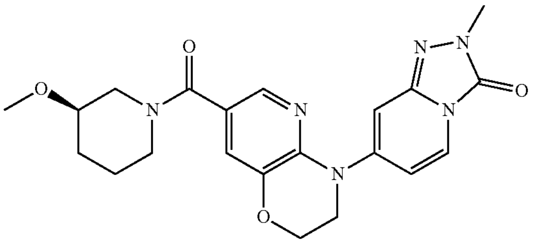
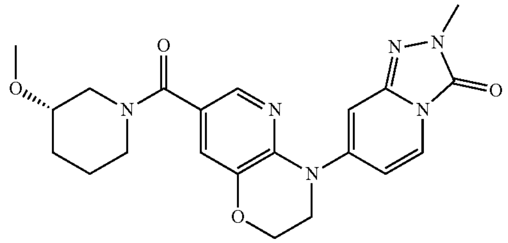
-continued
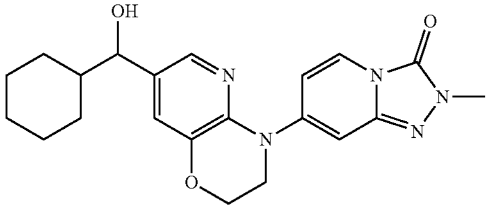
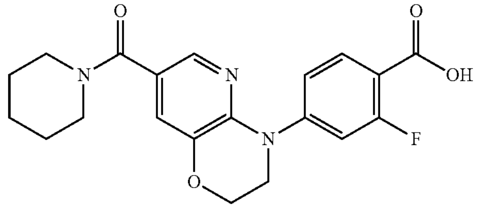
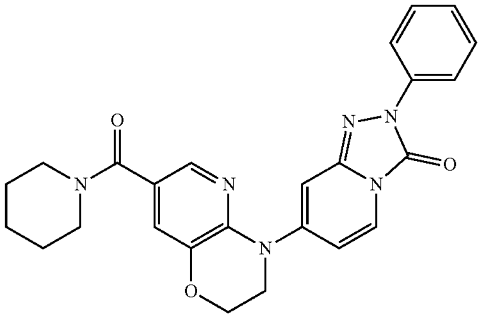
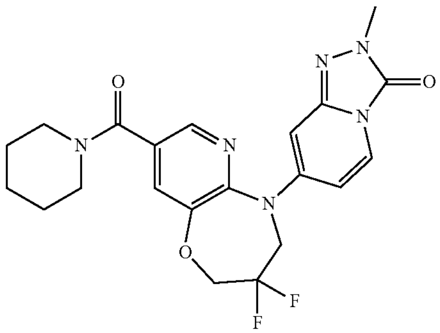
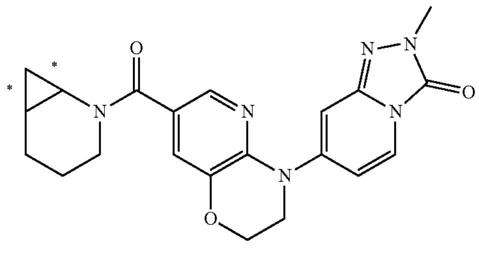
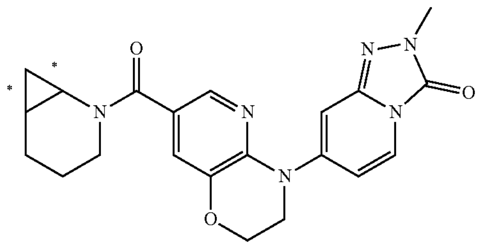

-continued
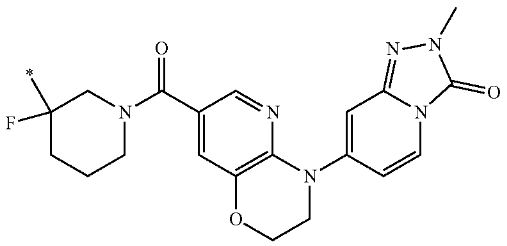
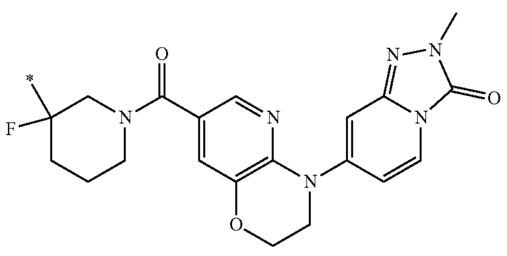
[Formula 22]
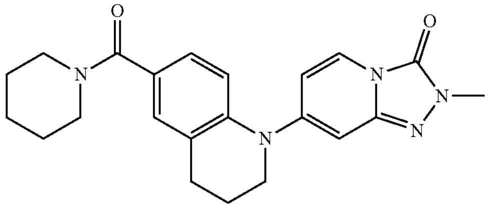
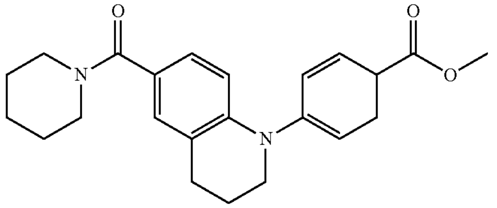
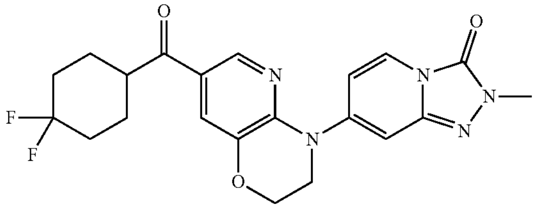
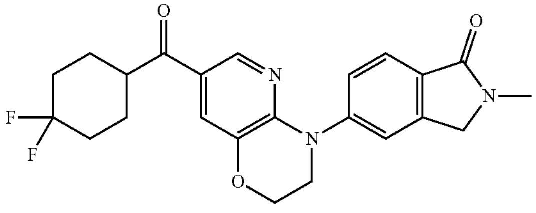
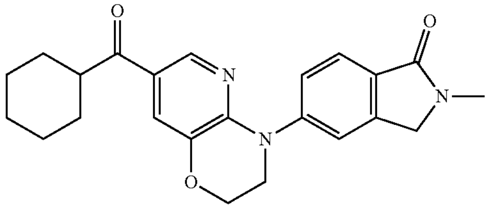
-continued
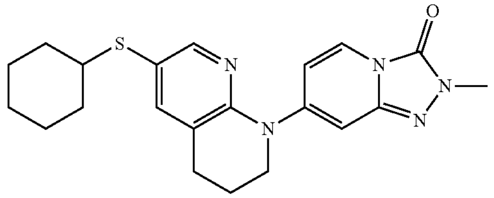
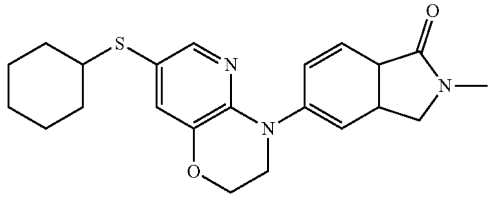
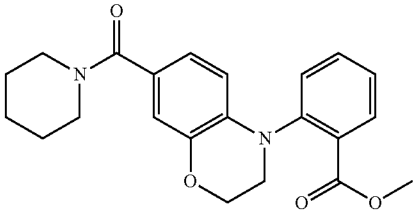
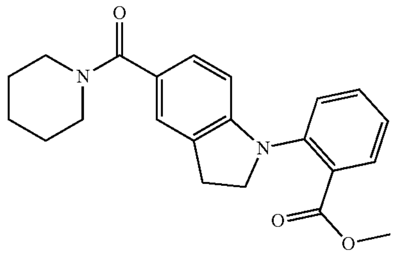
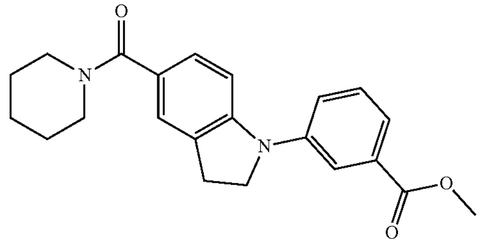
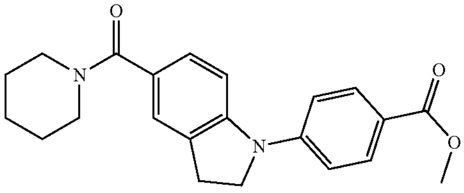
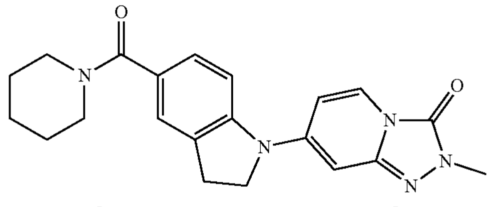
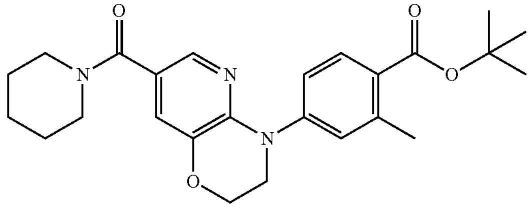

-continued
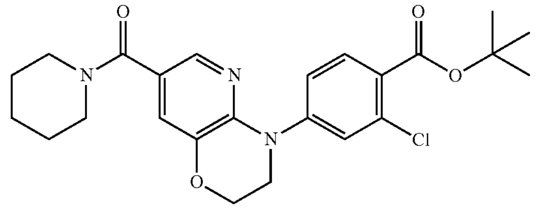
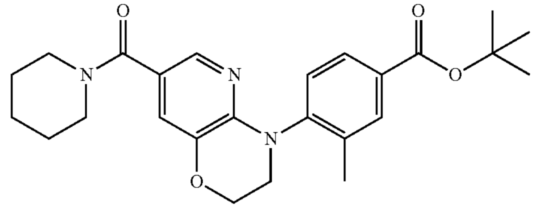
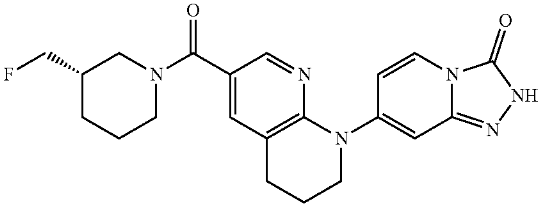
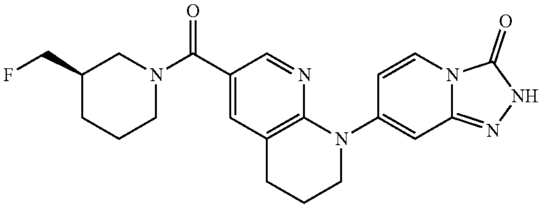
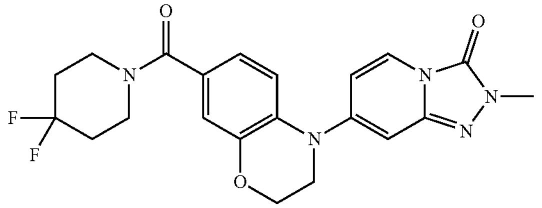
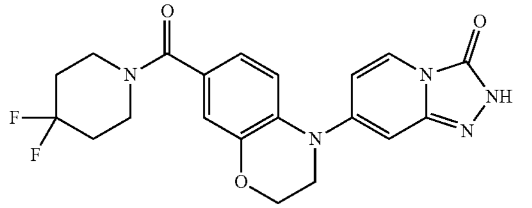
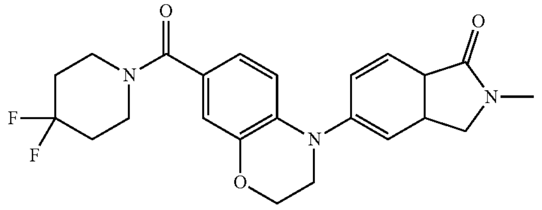
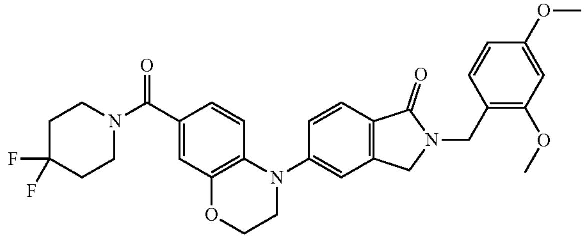
-continued
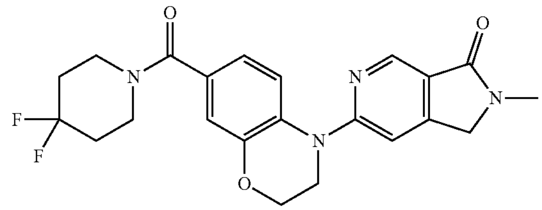
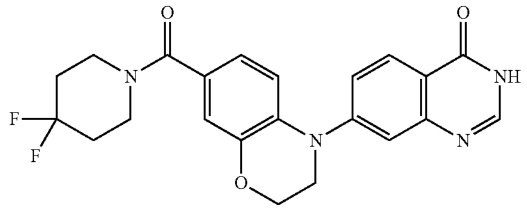
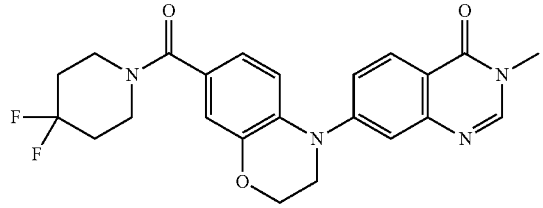
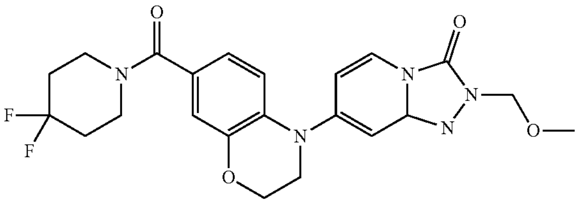
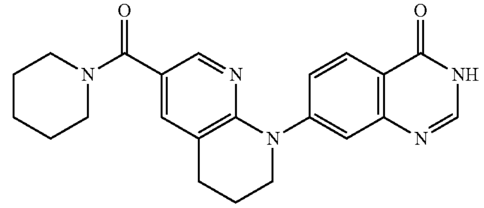
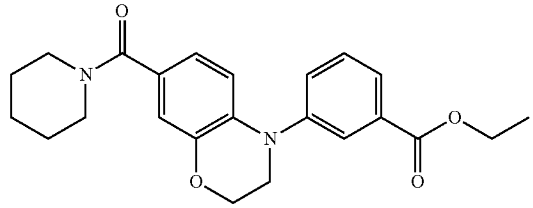
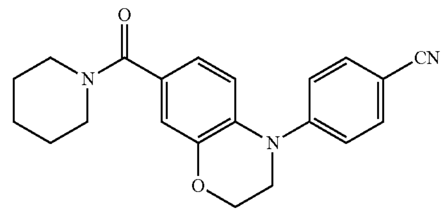
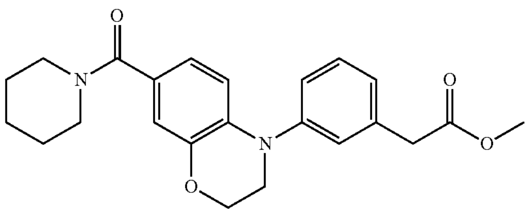

-continued
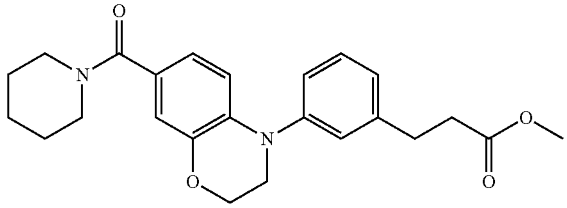
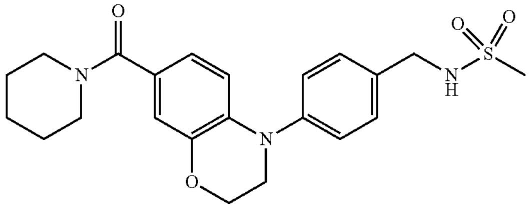
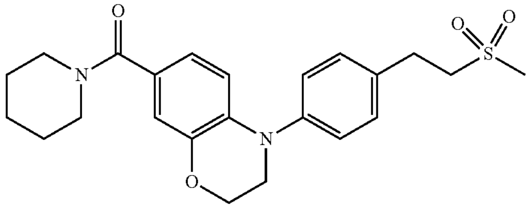
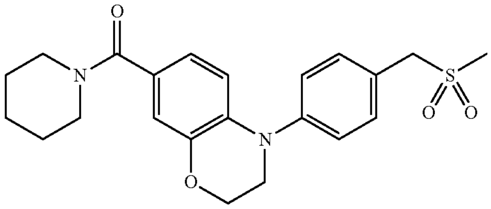
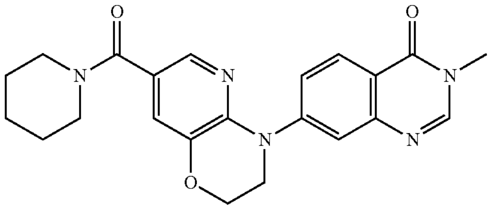
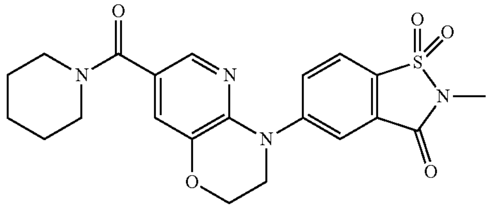
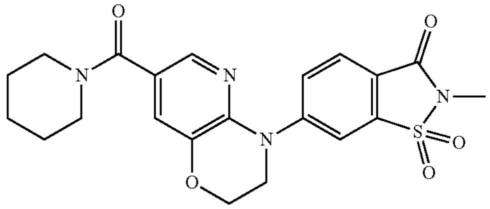
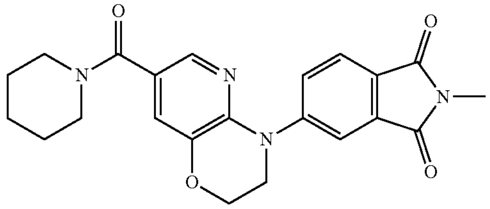
-continued
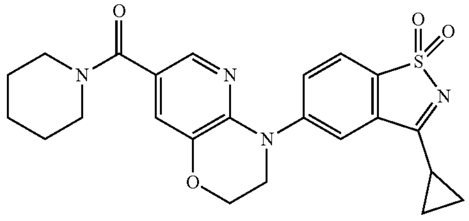
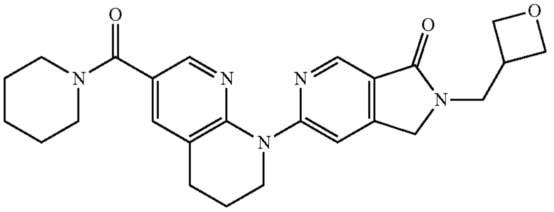
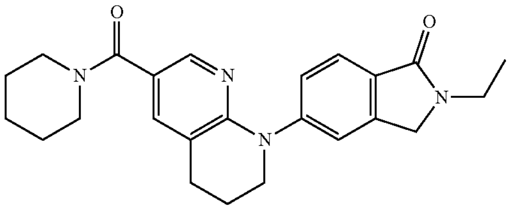
[Formula 23]
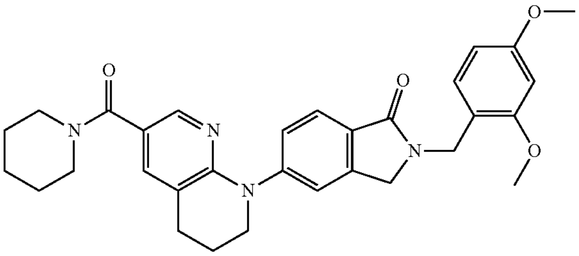
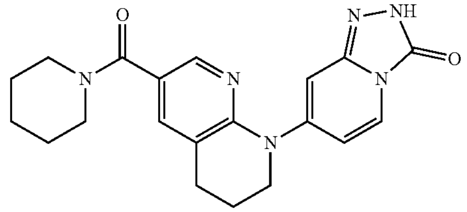
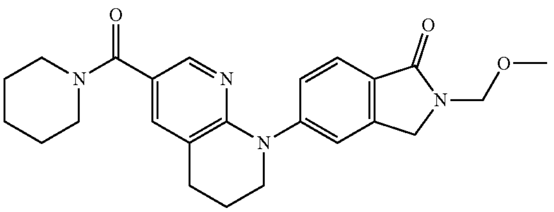
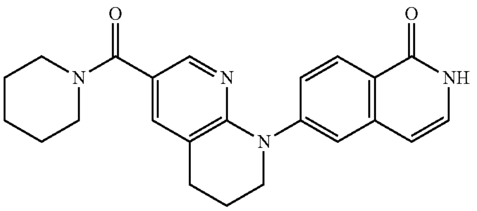

-continued
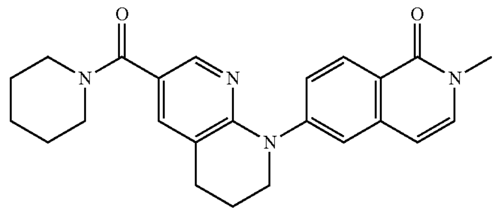
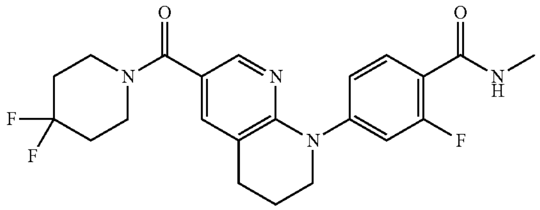
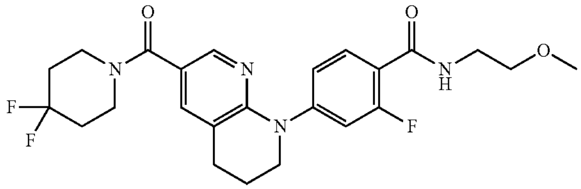
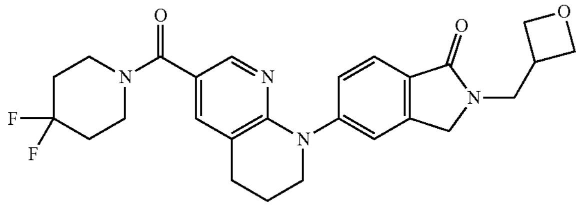
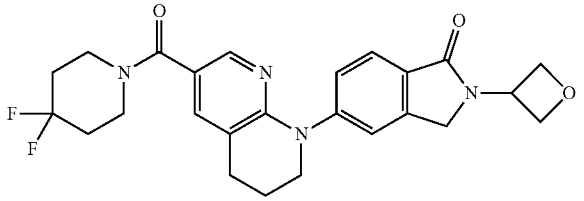
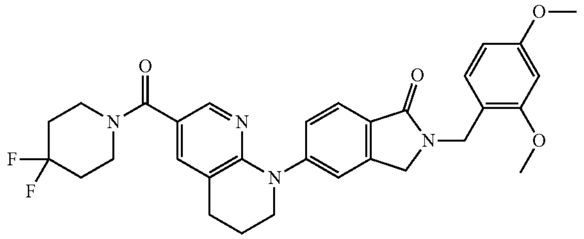
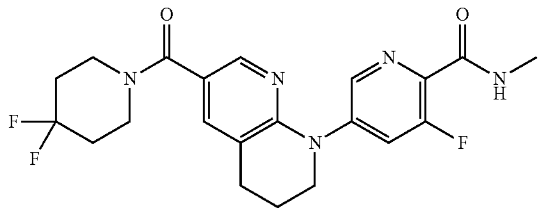
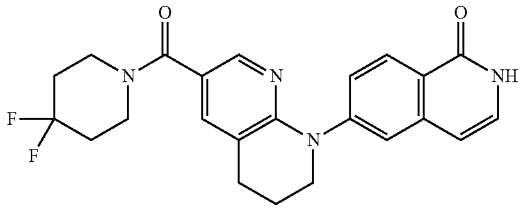
-continued
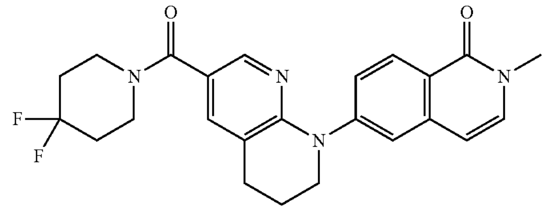
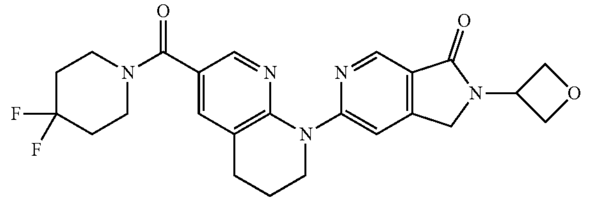
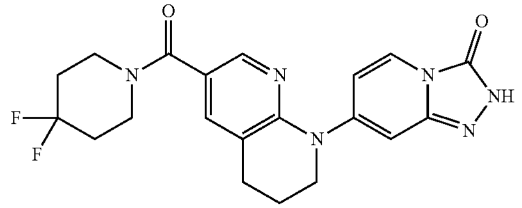
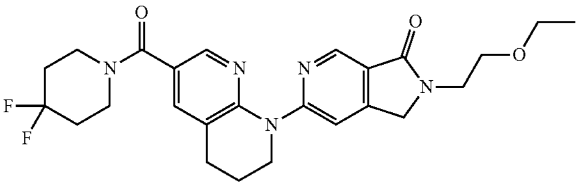
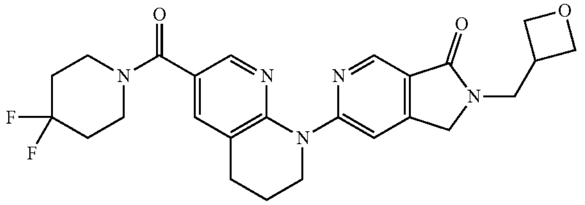
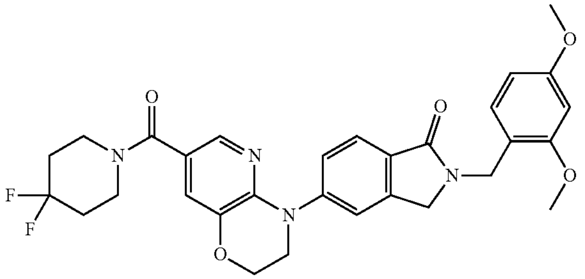
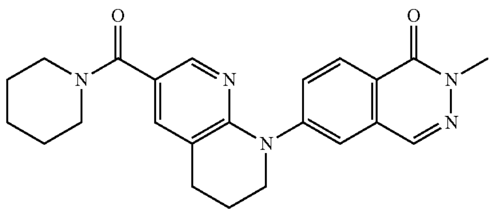
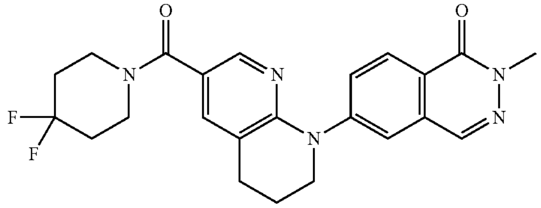

-continued
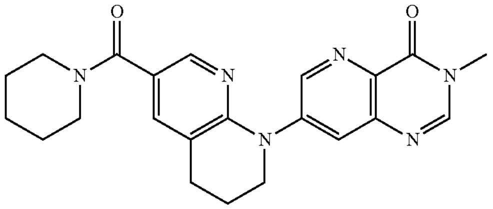
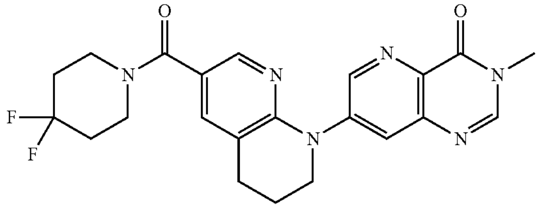
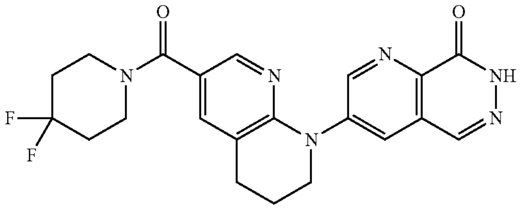
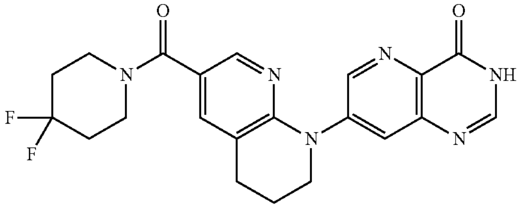
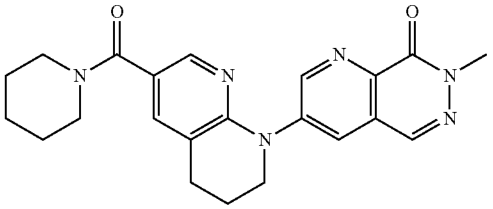
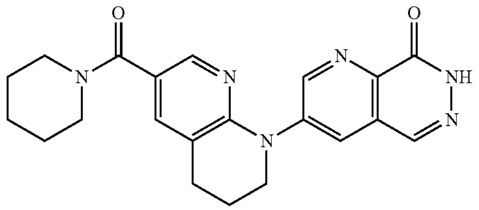
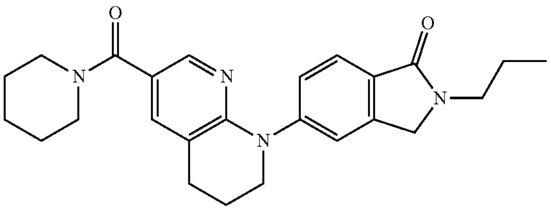
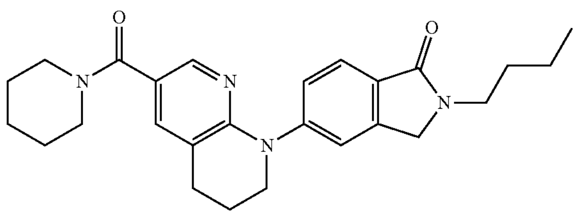
-continued
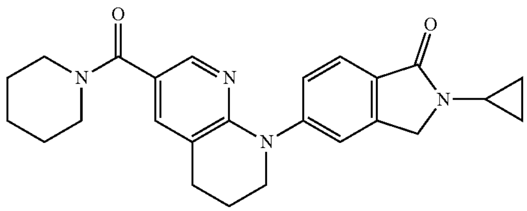
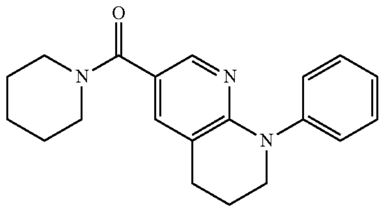
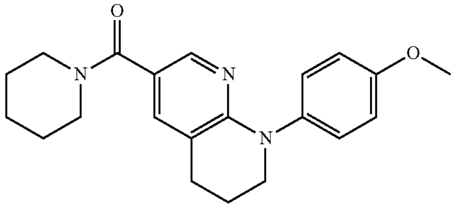
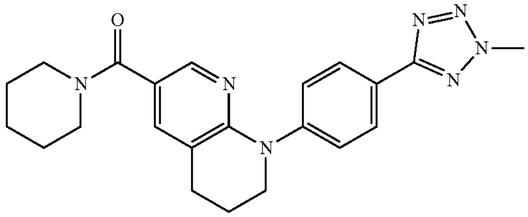
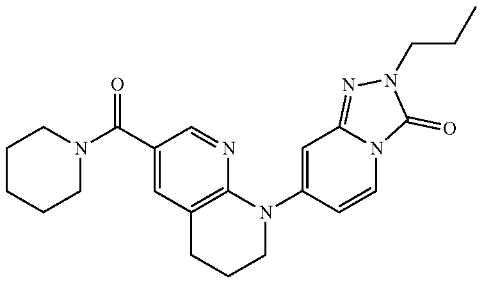
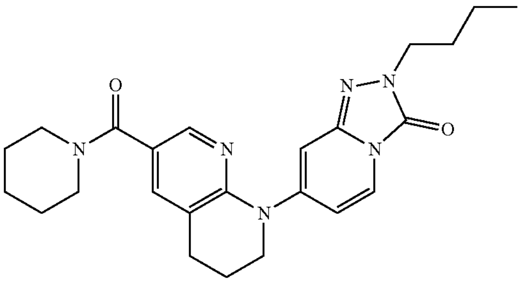
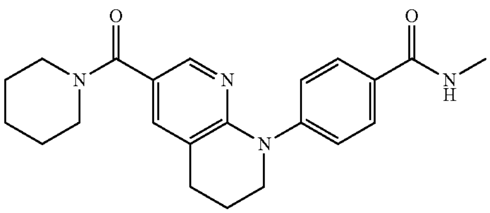

-continued
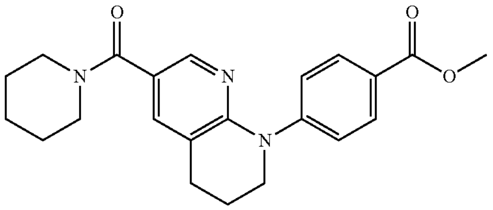
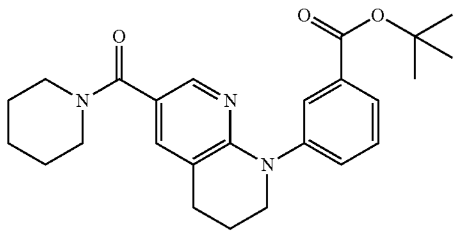
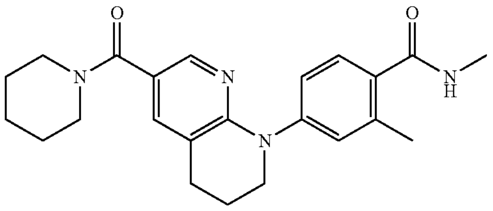
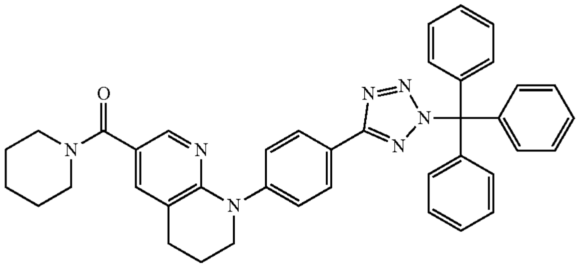
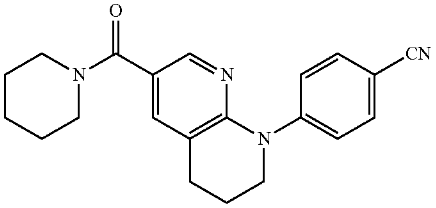
[Formula 24]
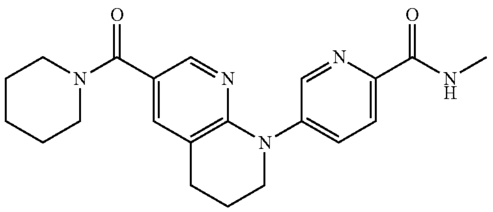
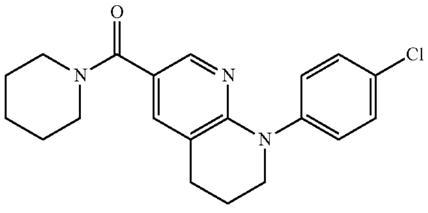
-continued
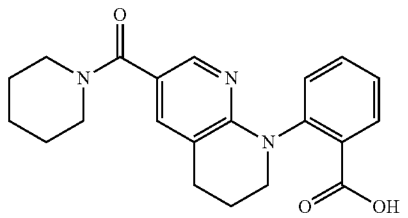
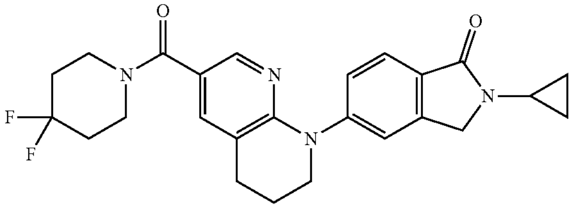
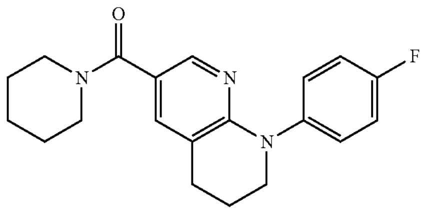
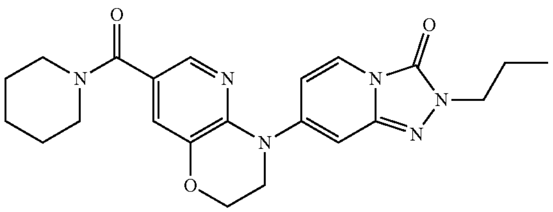
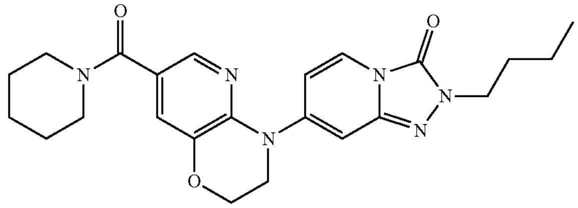
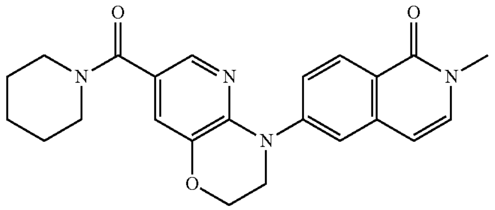
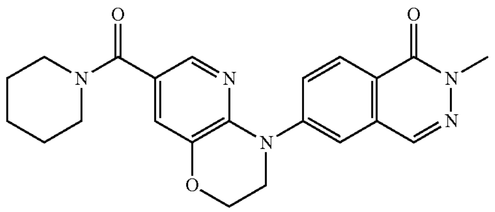
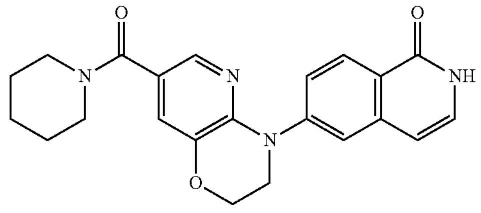

-continued
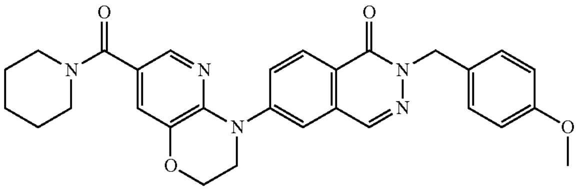
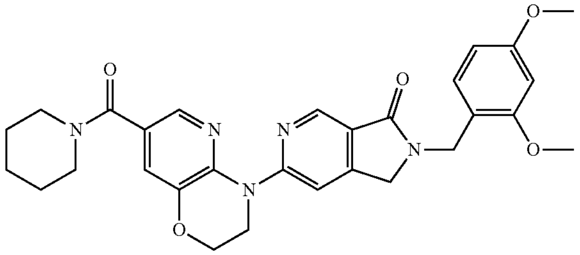
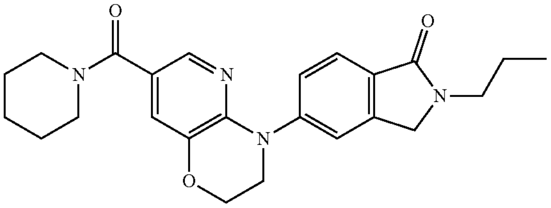
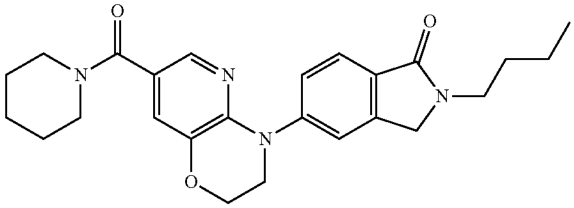
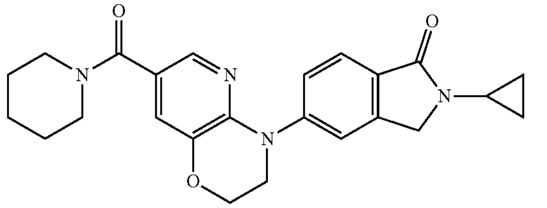
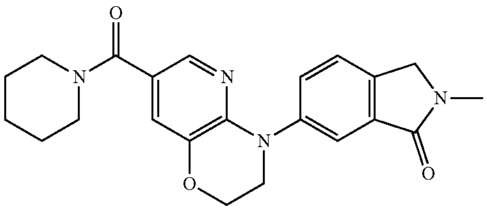
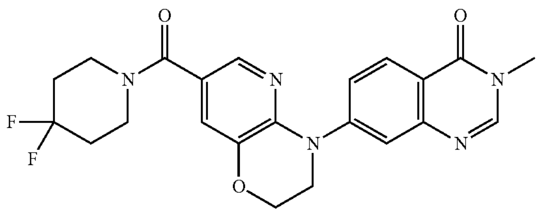
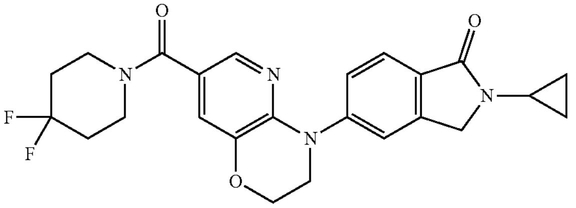
-continued
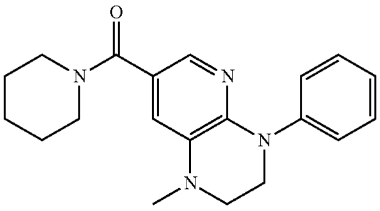
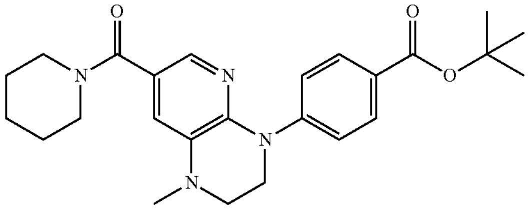
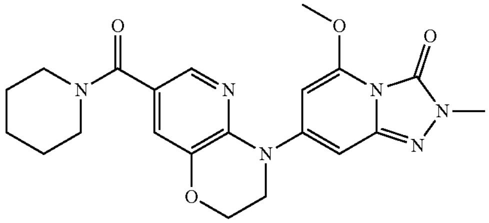
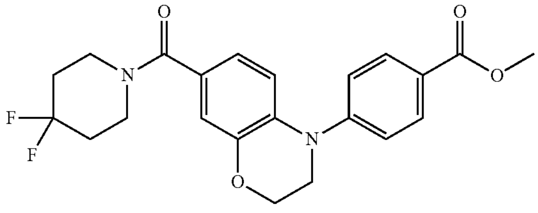
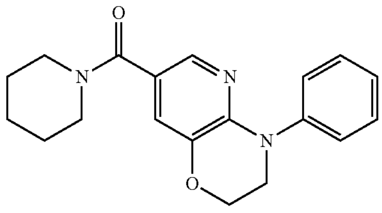
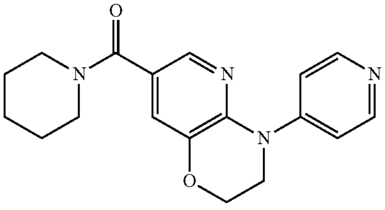
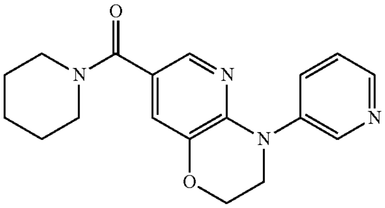
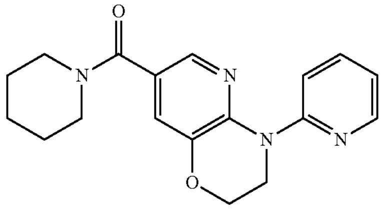

-continued
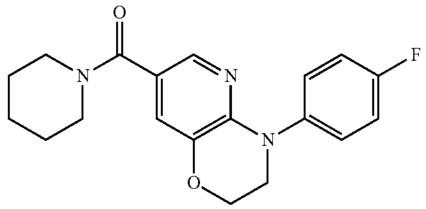
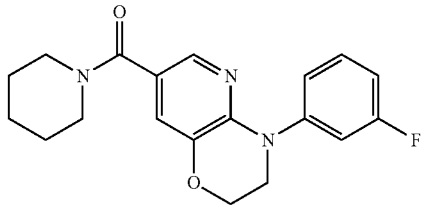
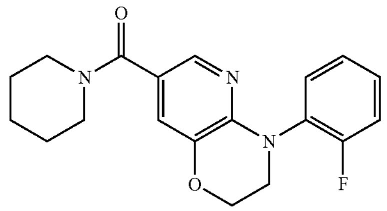
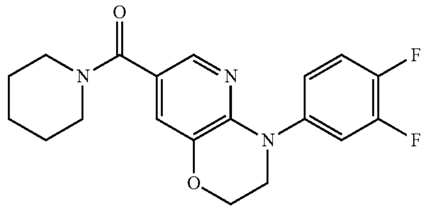
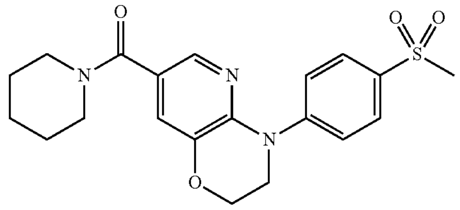
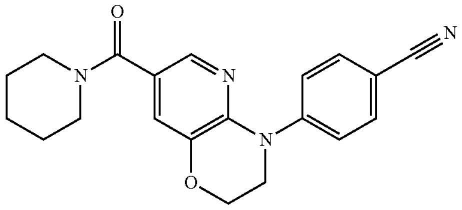
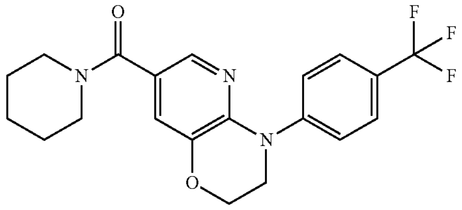
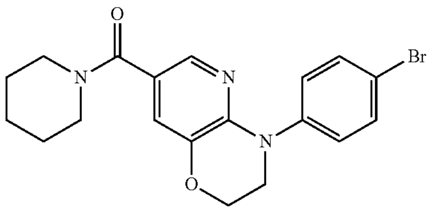
-continued
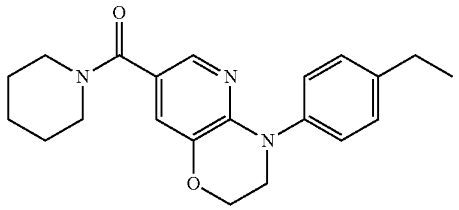
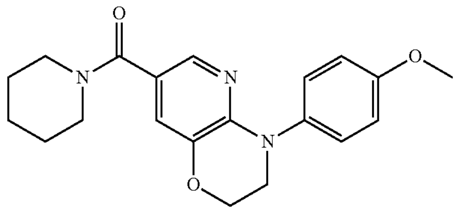
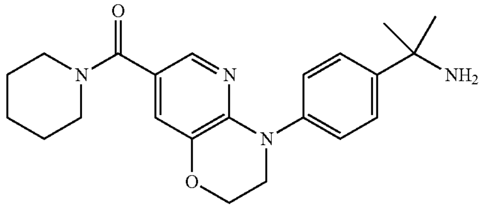
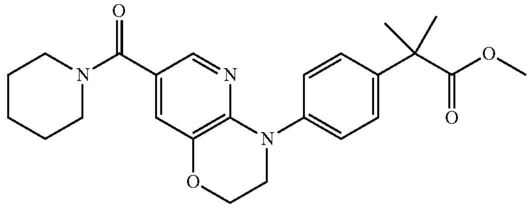
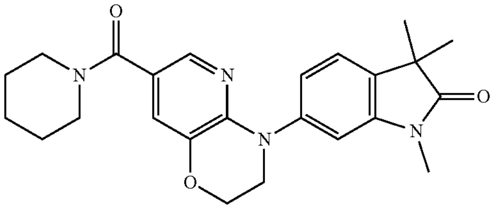
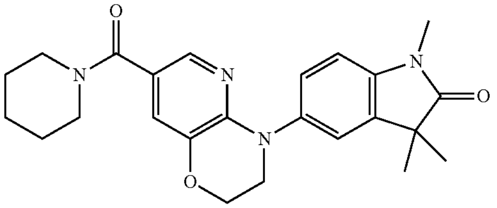
[Formula 25]
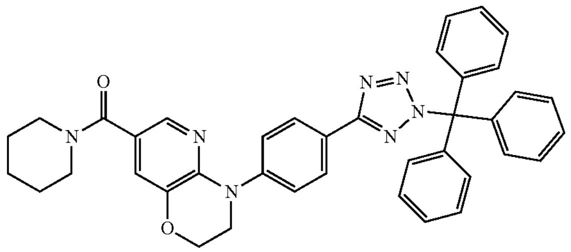

-continued
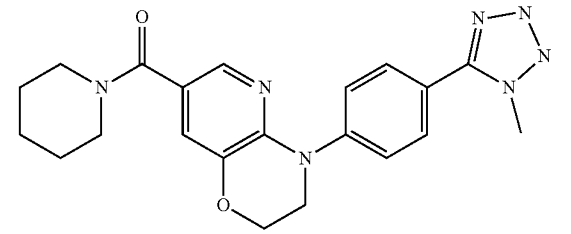
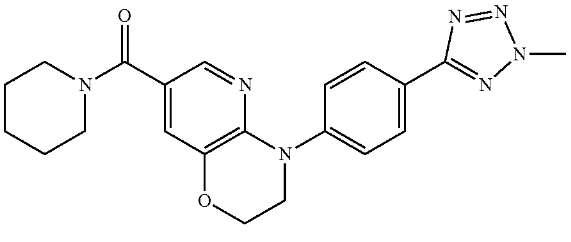
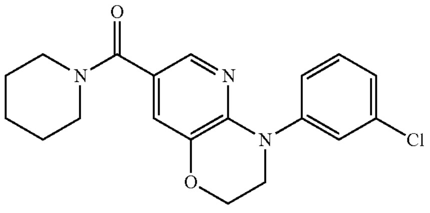
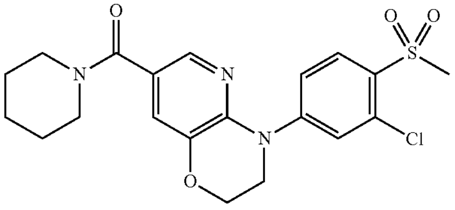
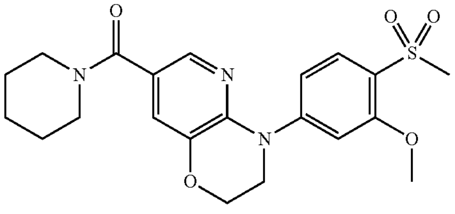
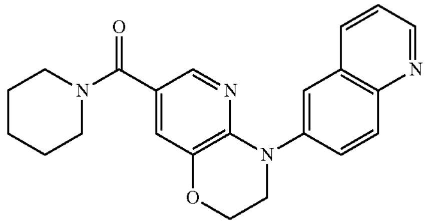
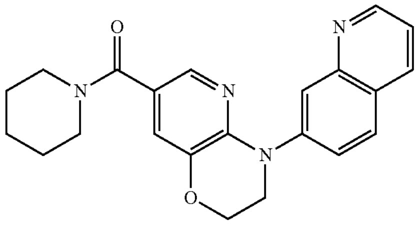
-continued
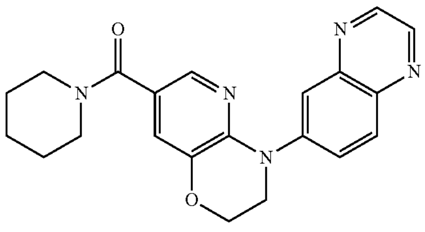
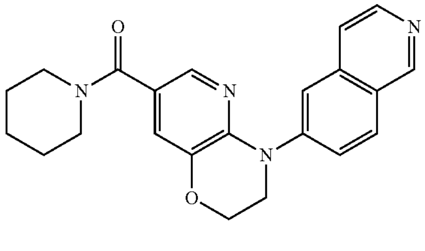
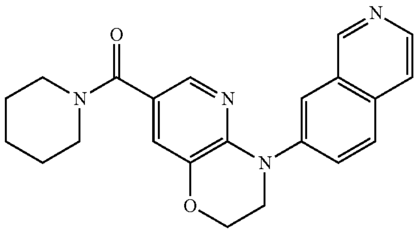
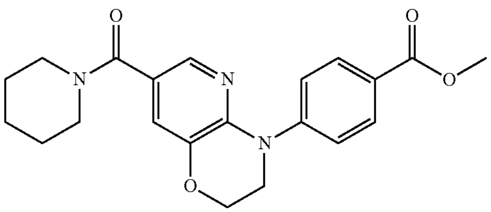
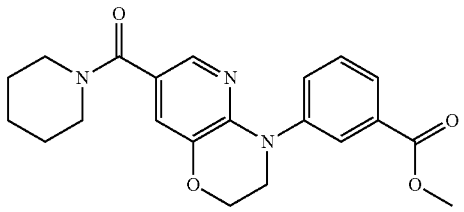
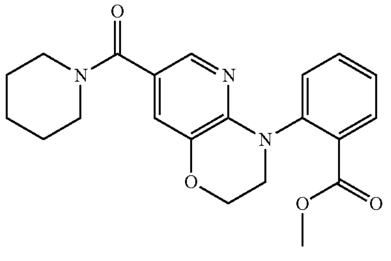
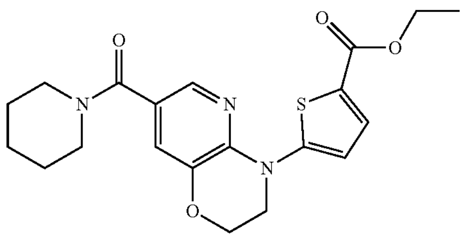

-continued
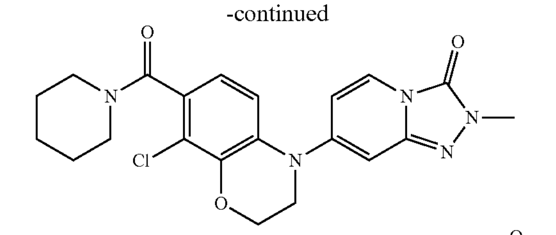
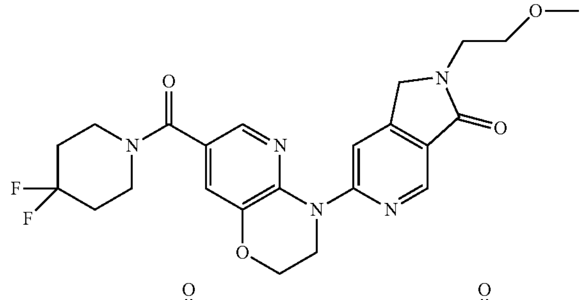
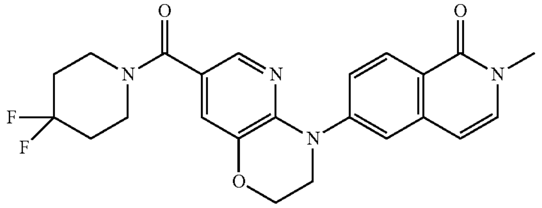
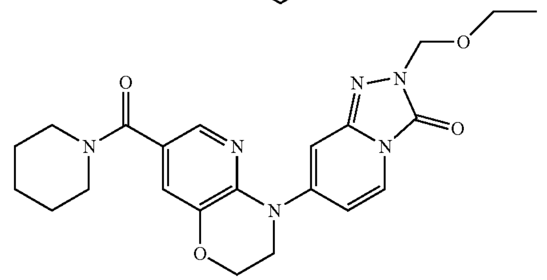
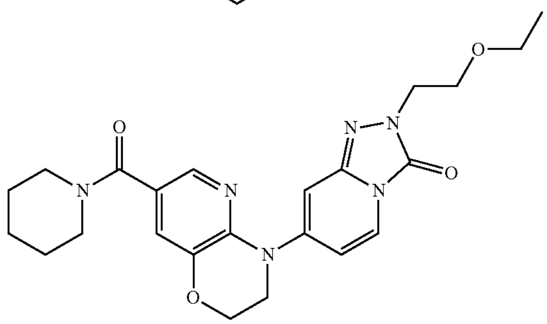
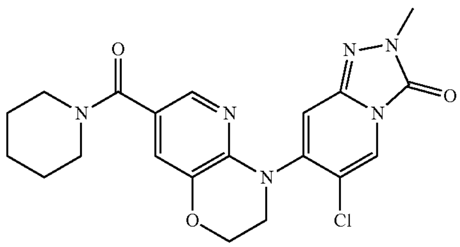
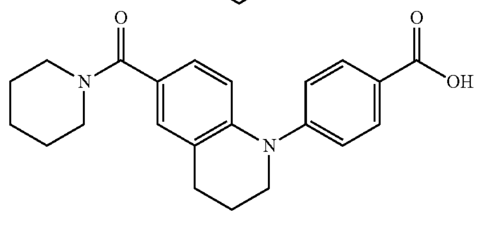
-continued
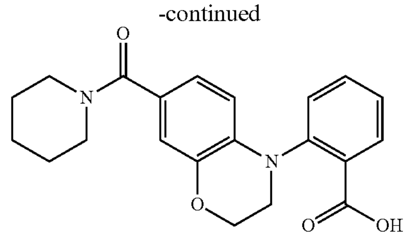
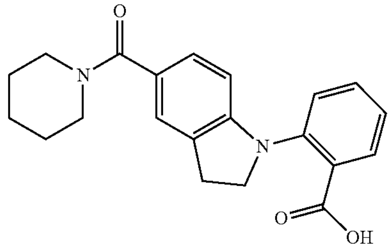
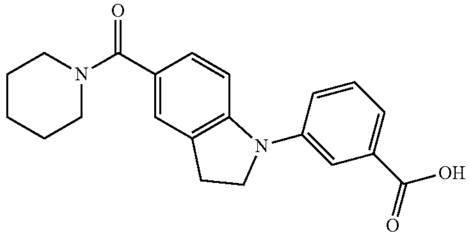
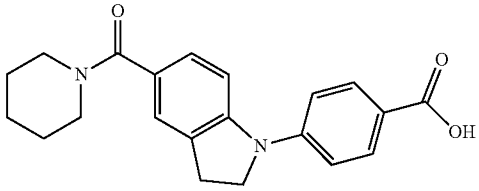
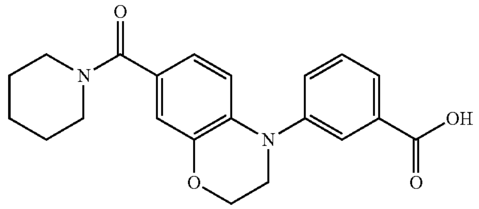
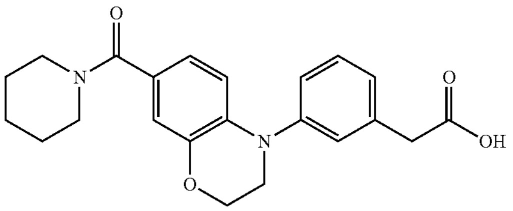
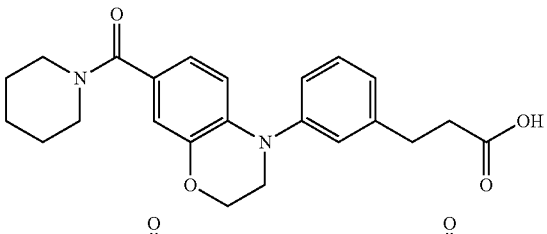
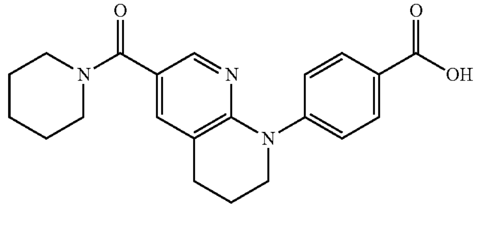

-continued
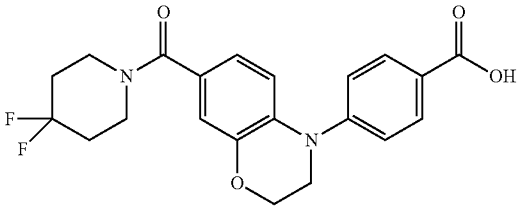
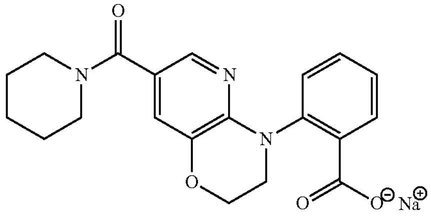
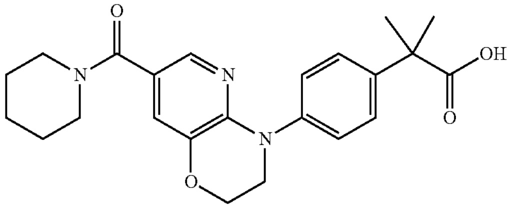
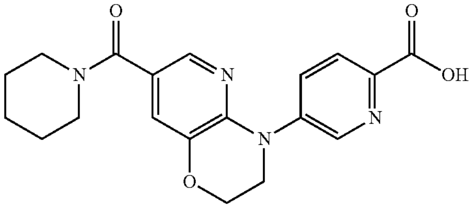
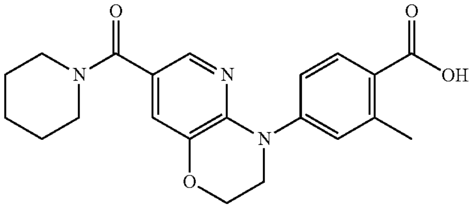
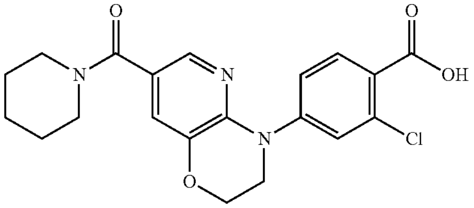
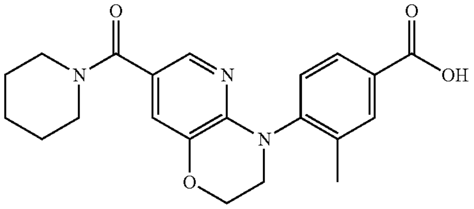
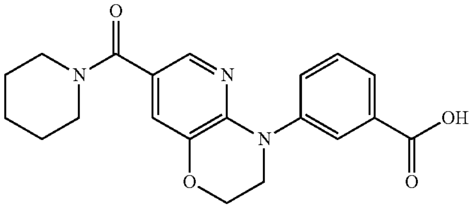
-continued
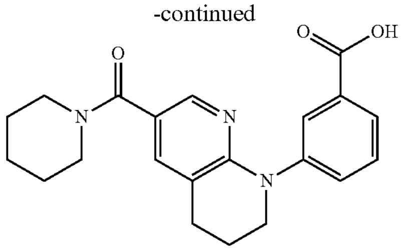
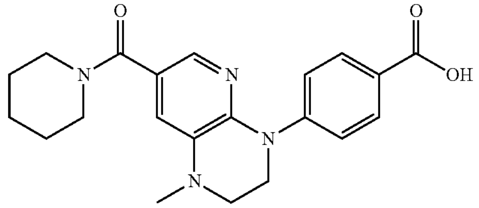
[Formula 26]
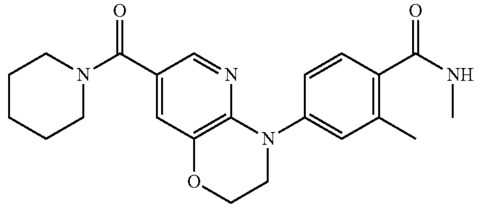
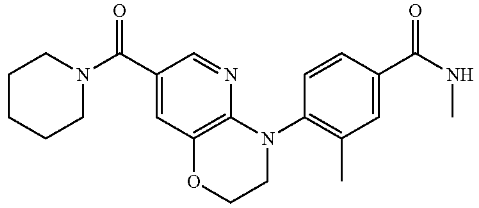
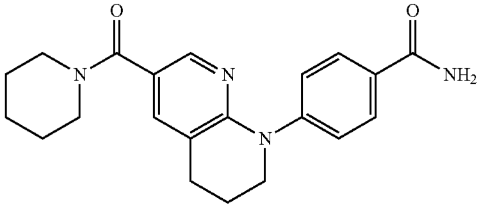
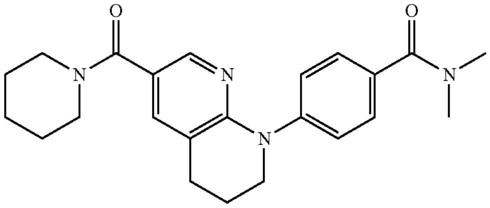
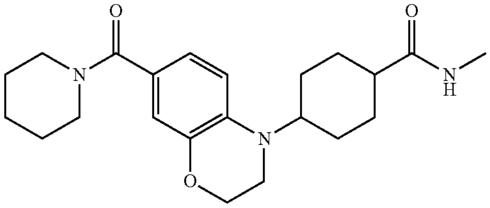
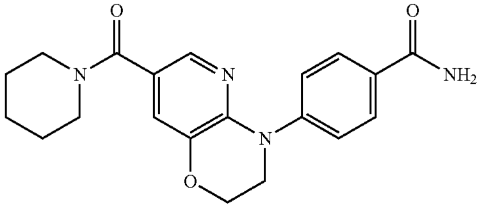

-continued
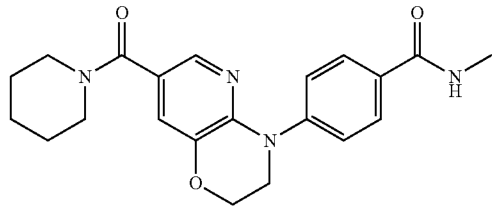
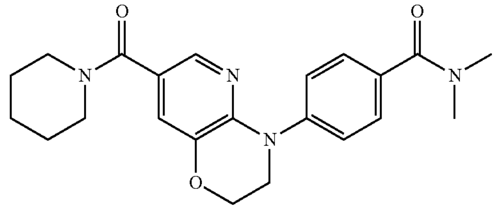
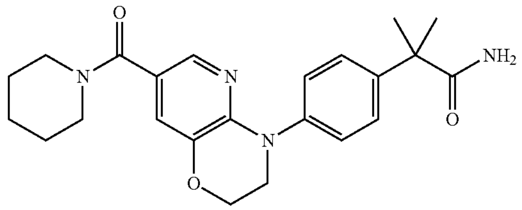
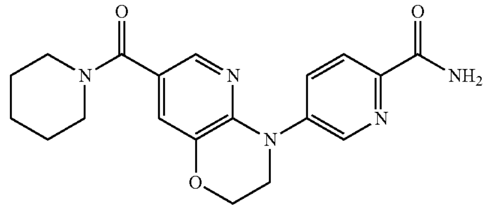
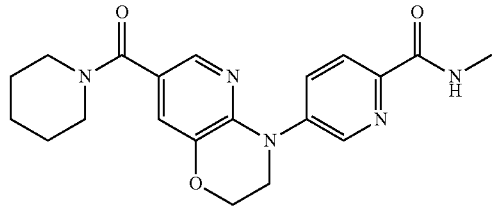
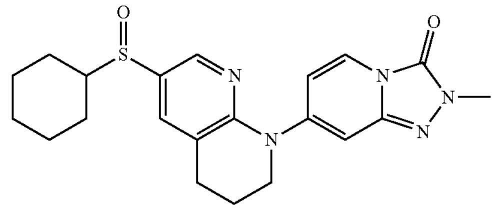
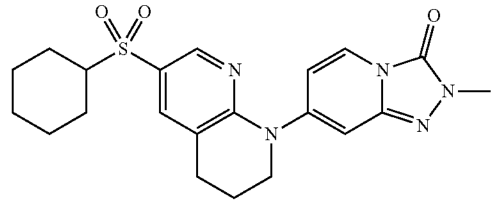
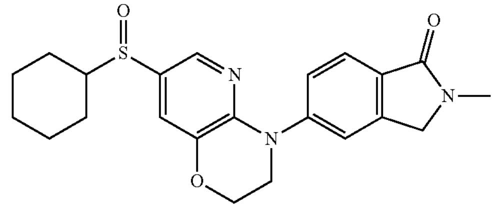
-continued
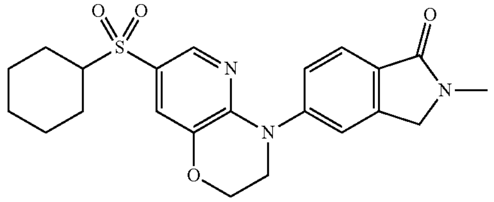
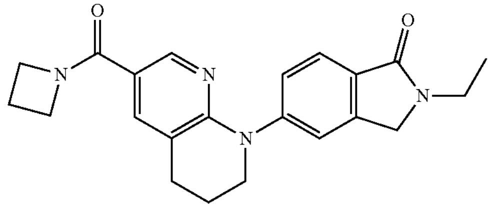
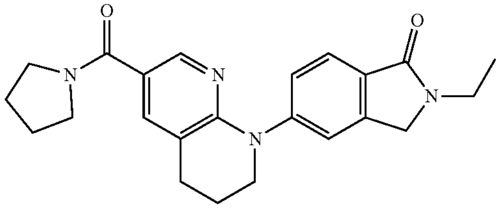
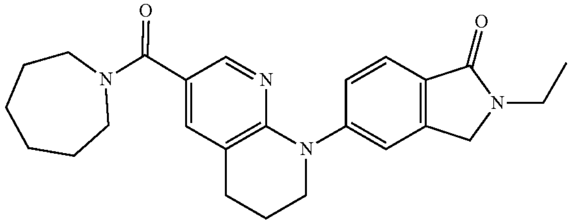
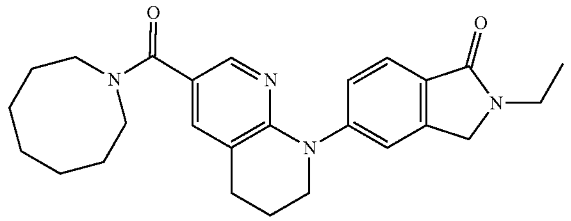
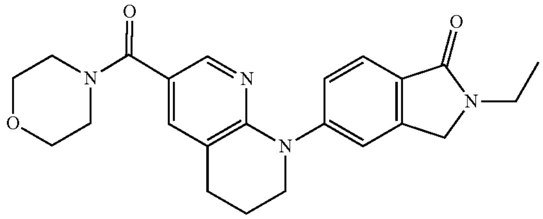
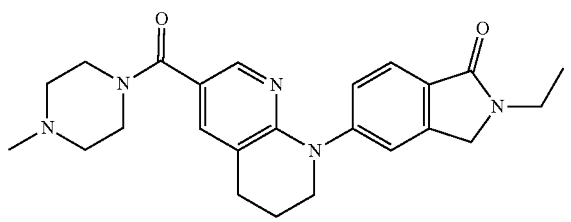
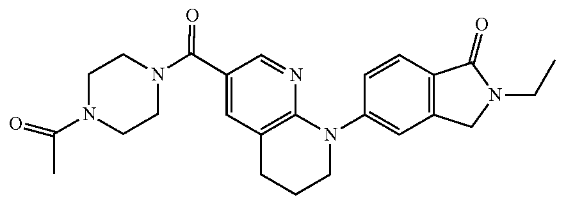

-continued
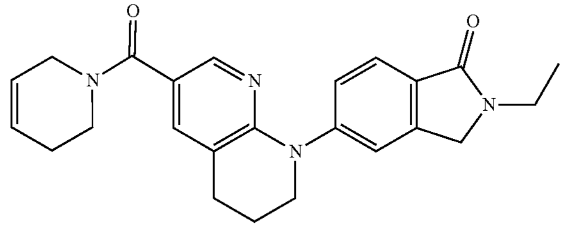
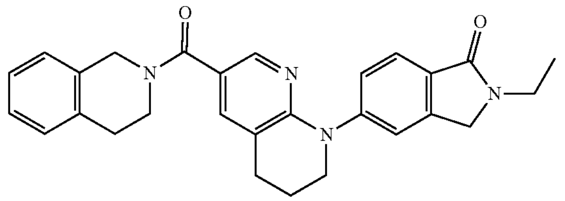
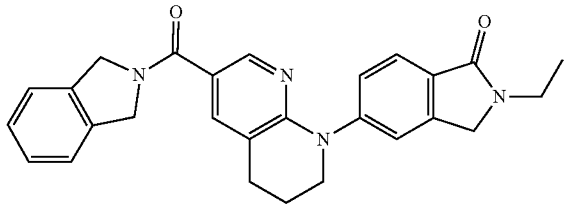
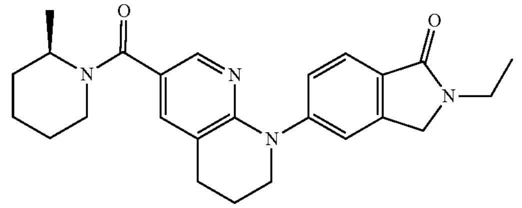
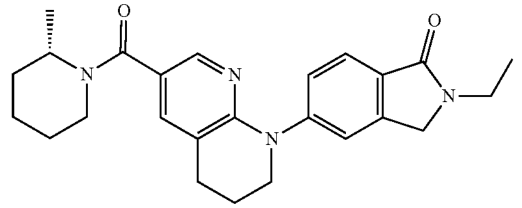
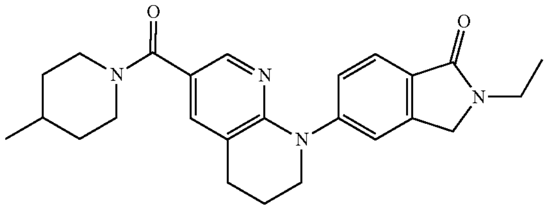
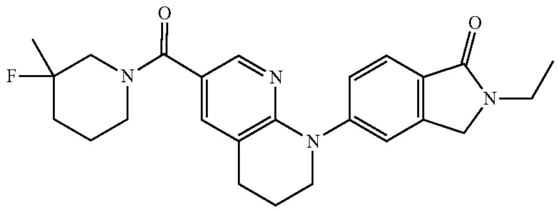
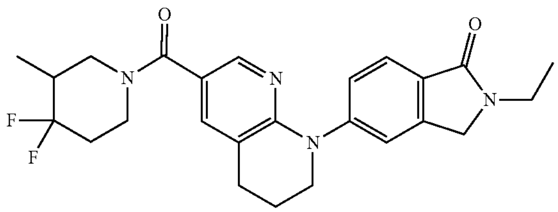
-continued
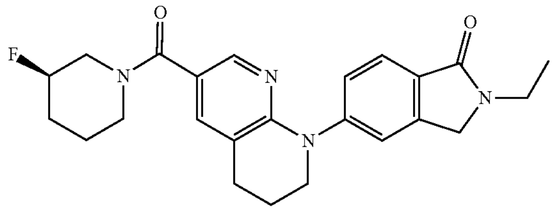
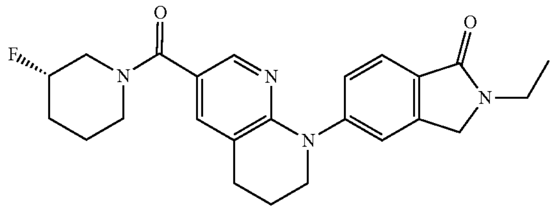
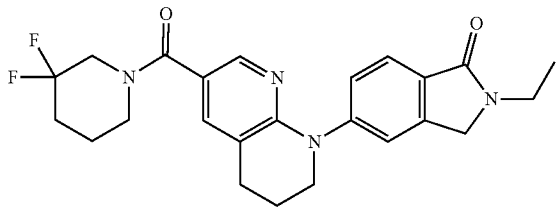
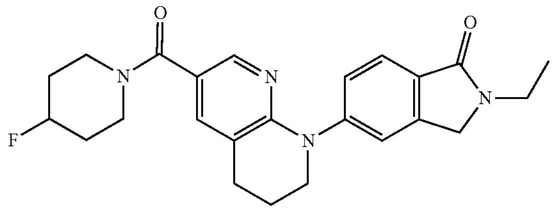
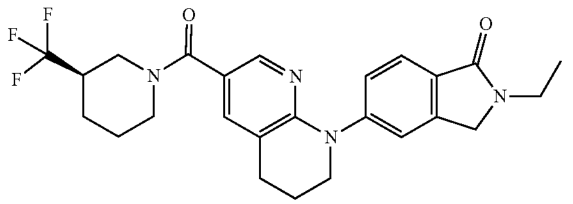
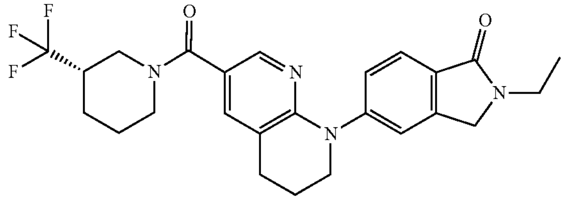
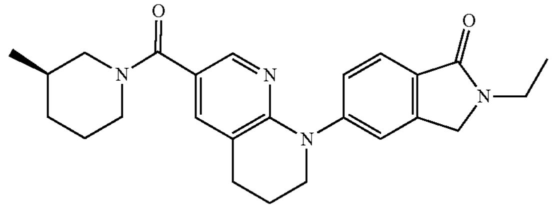
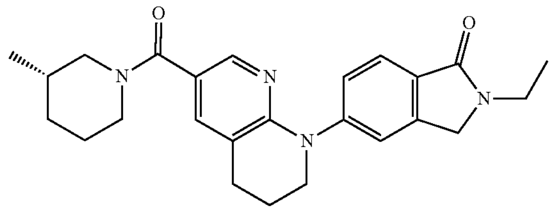

-continued
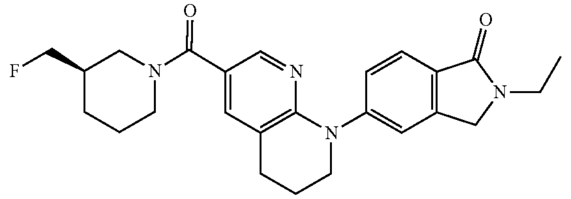
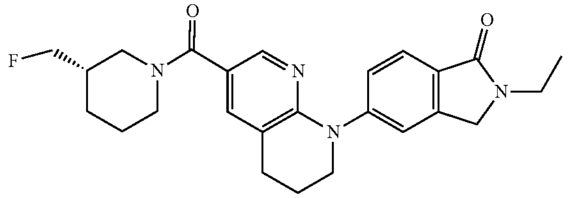
[Formula 27]
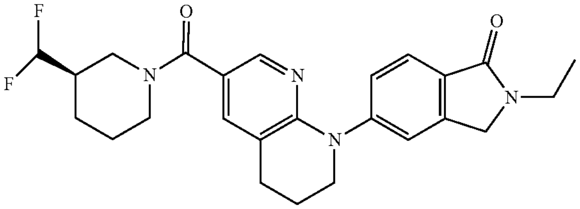
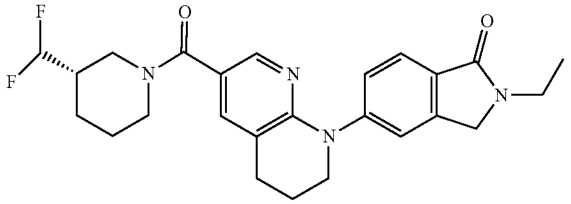
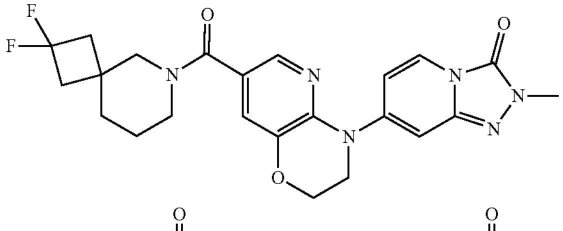
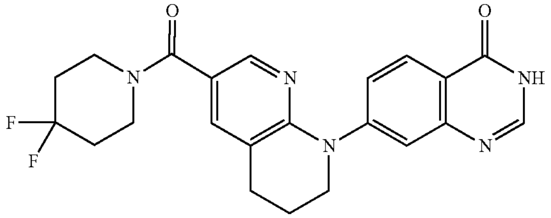
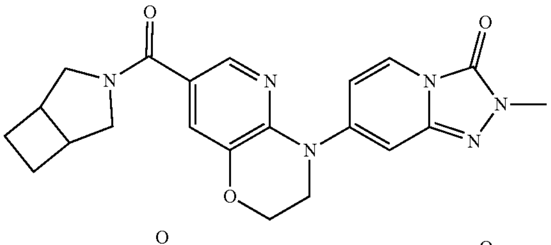
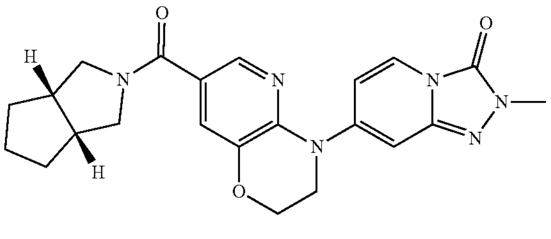
-continued
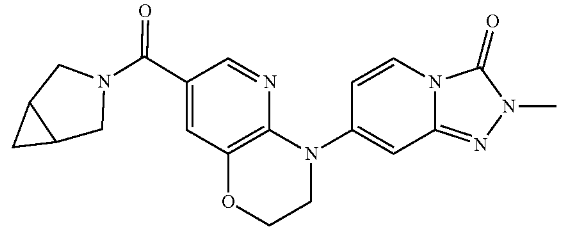
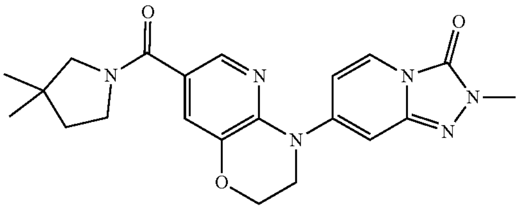
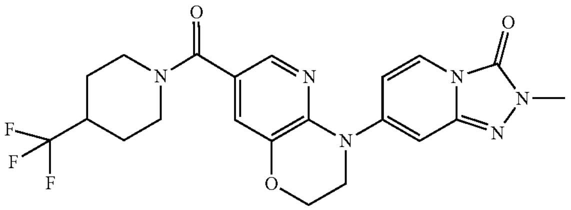
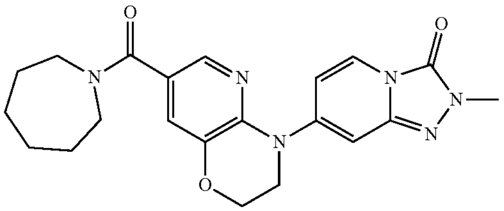
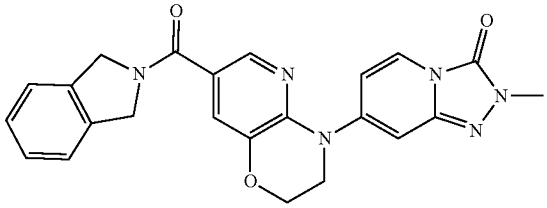
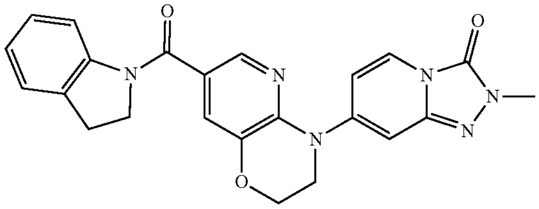
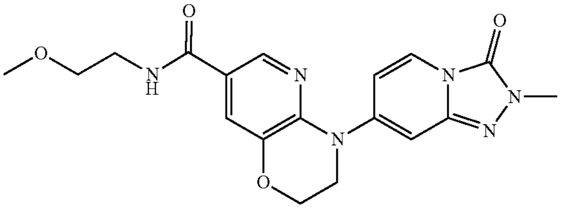
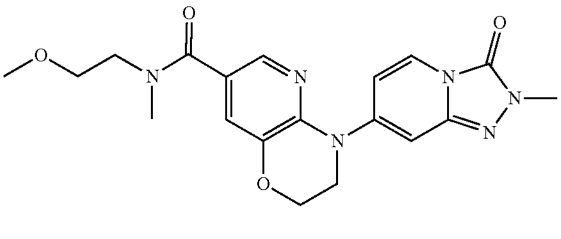

-continued
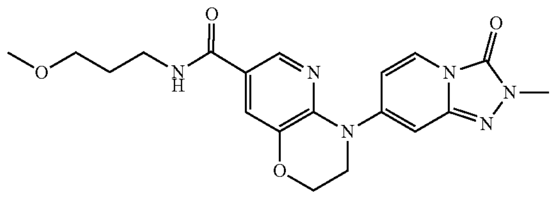
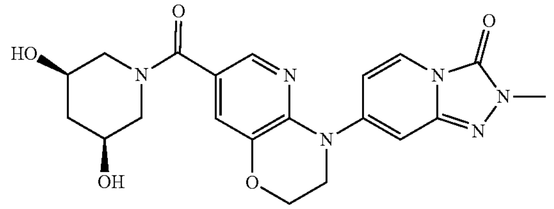
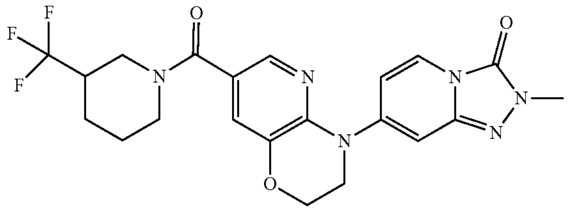
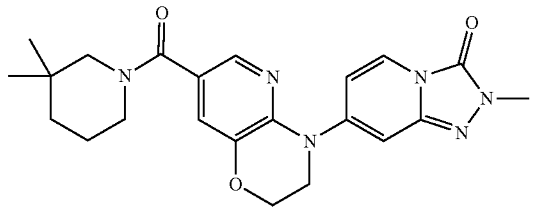
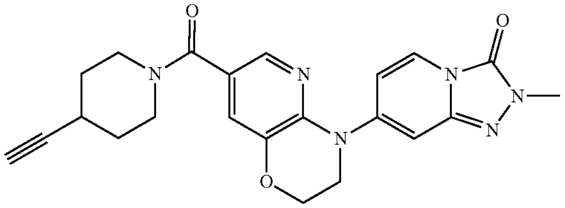
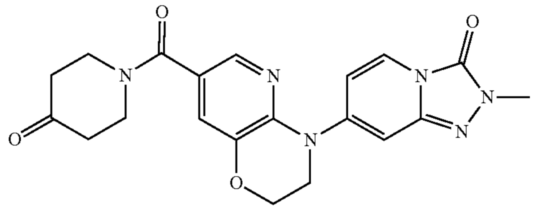
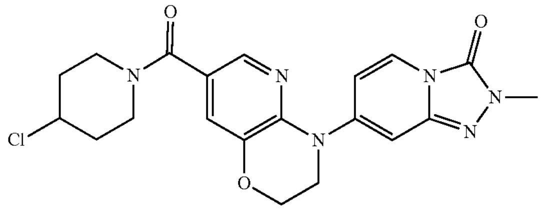
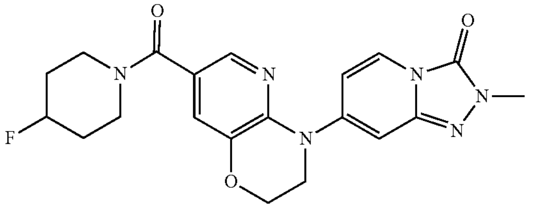
-continued
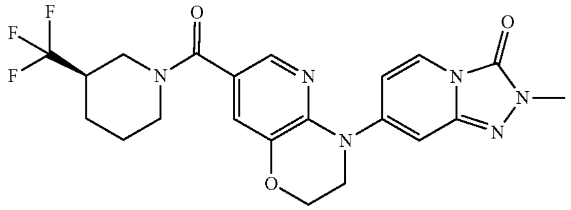
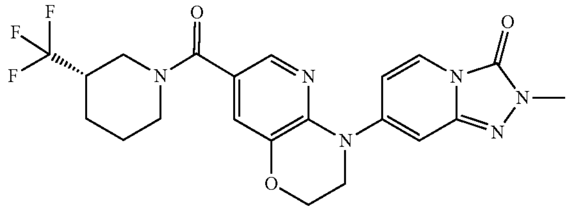
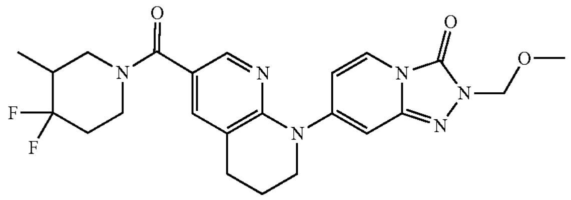
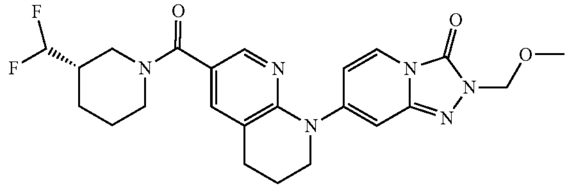
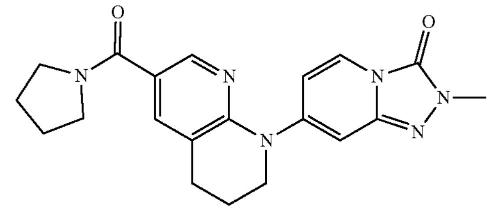
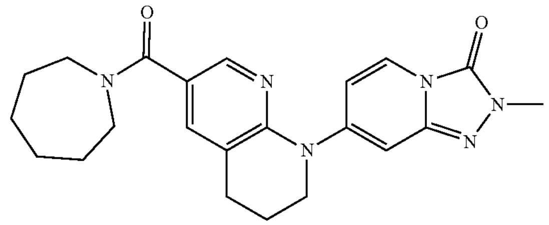
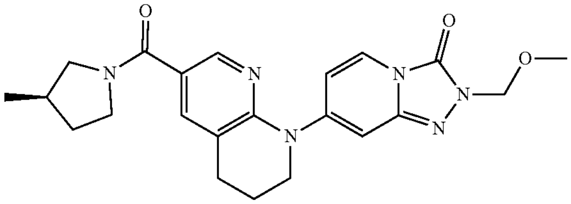
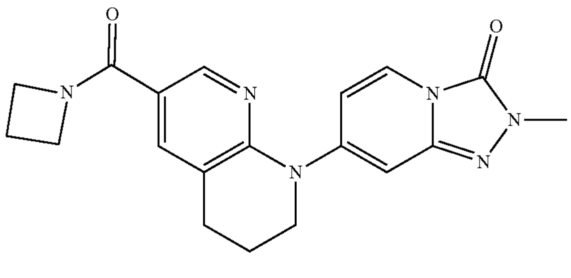

-continued
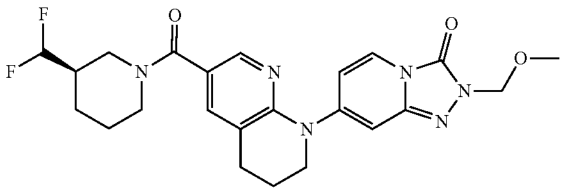
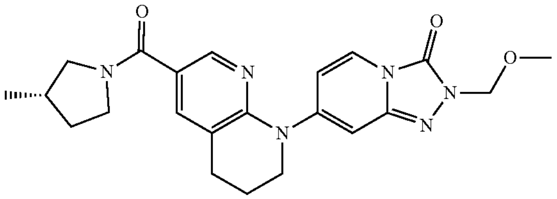
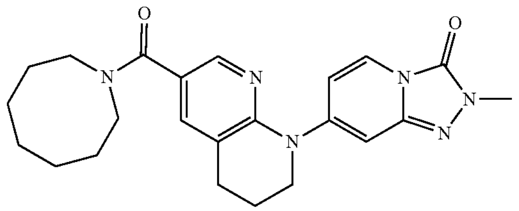
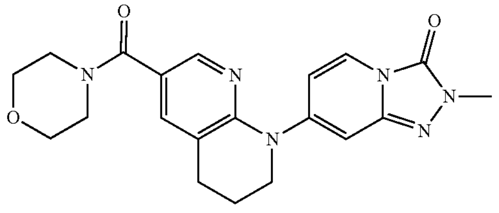
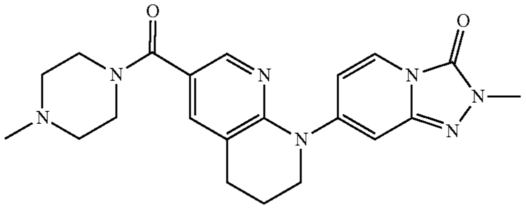
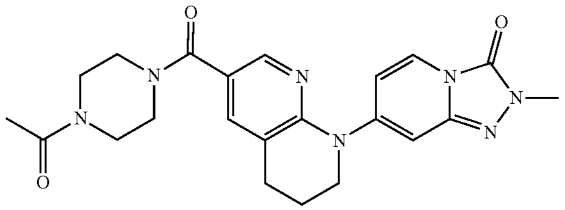
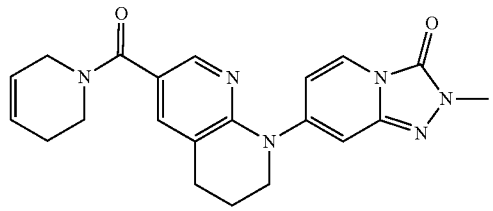
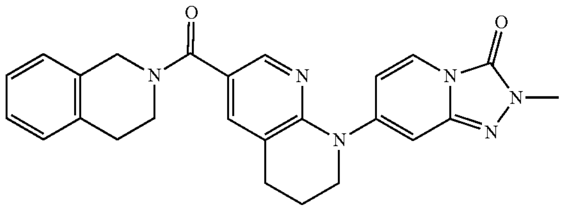
-continued
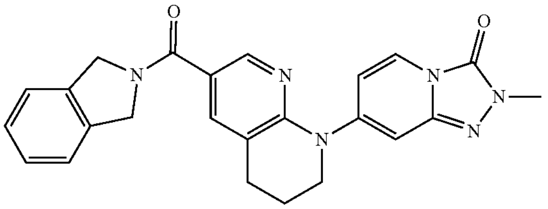
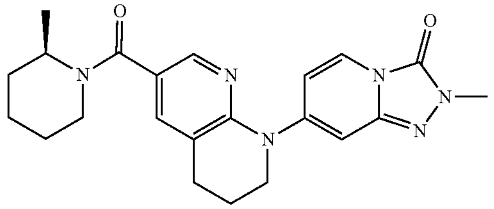
[Formula 28]
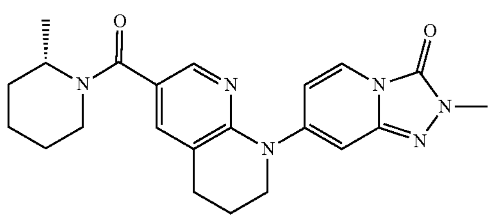
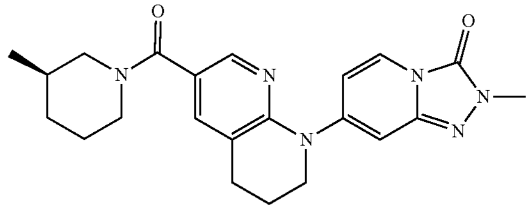
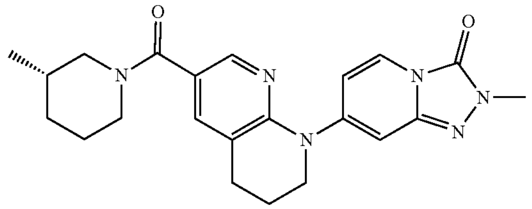
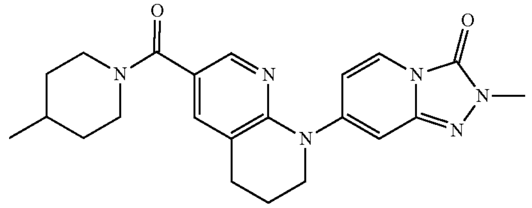
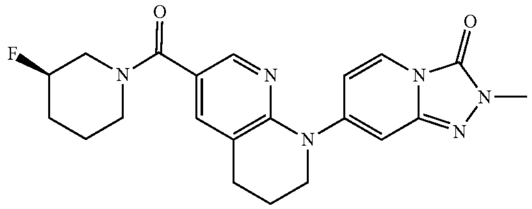
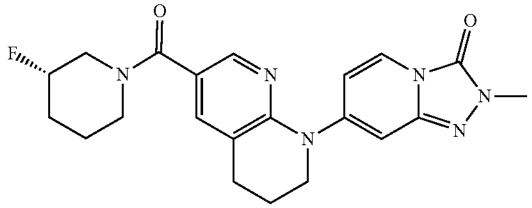

-continued
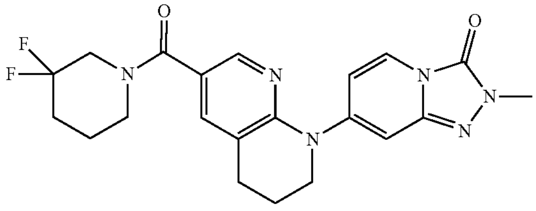
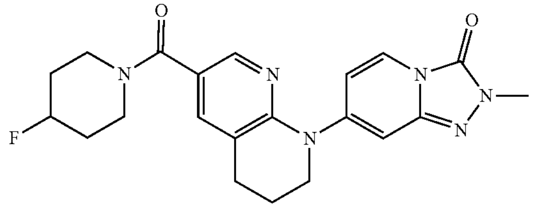
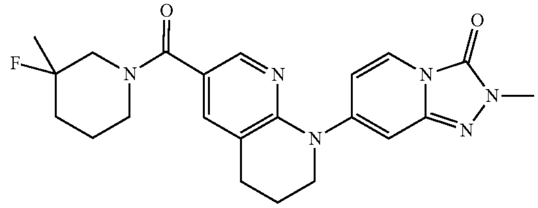
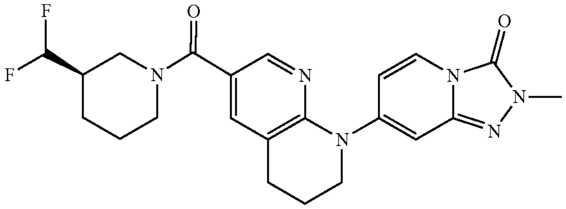
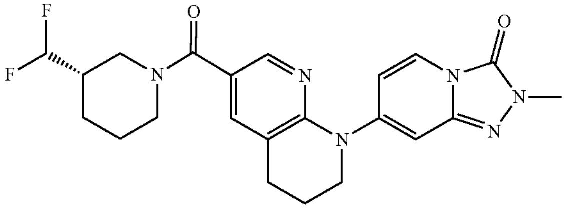
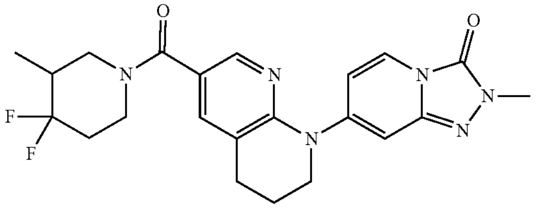
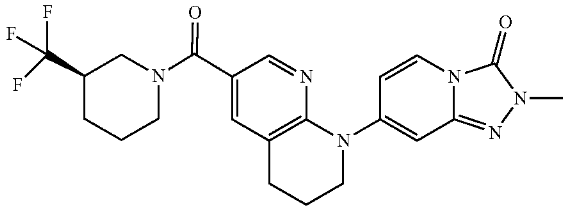
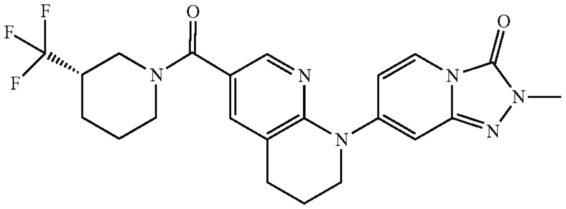
-continued
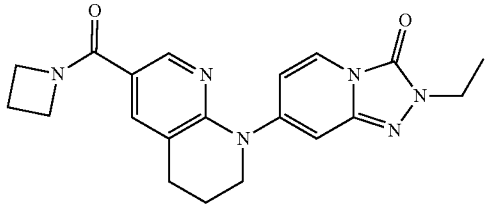
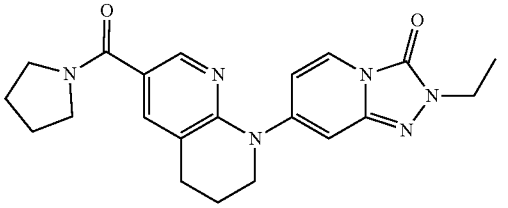
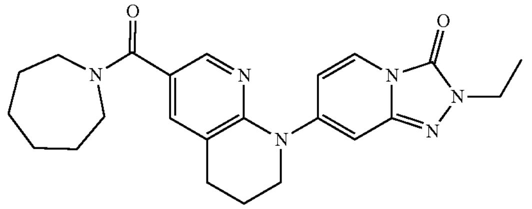
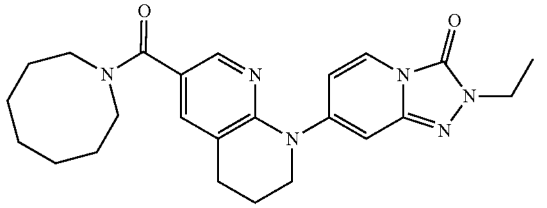
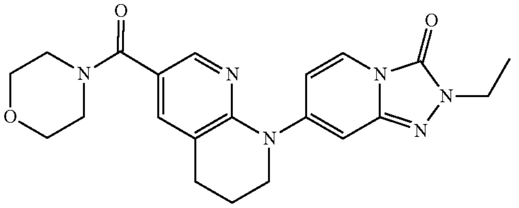
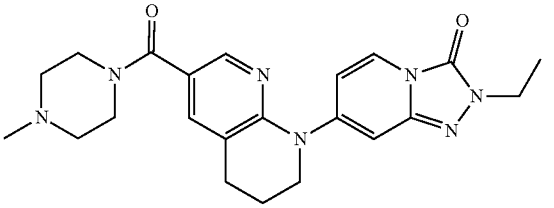
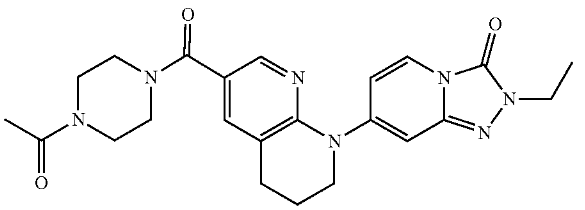
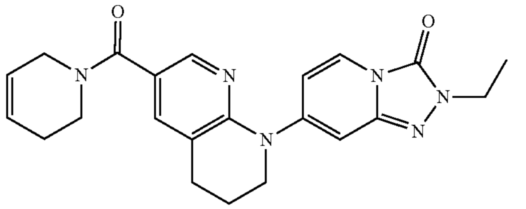

-continued
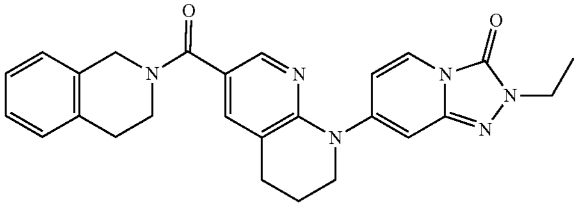
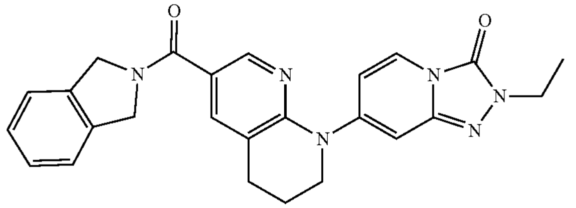
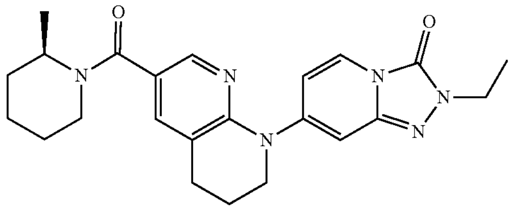
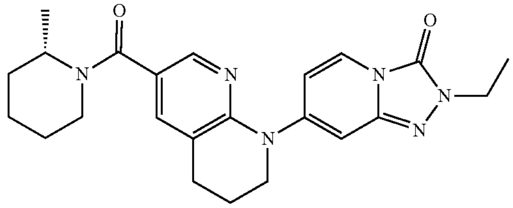
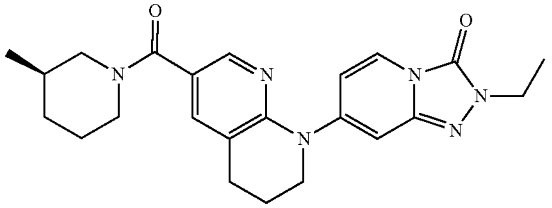
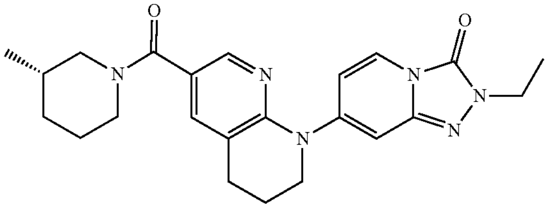
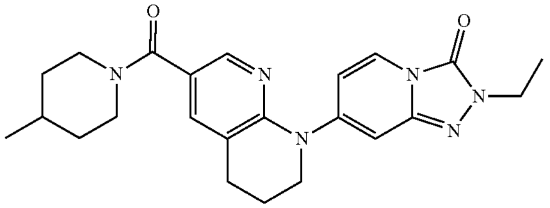
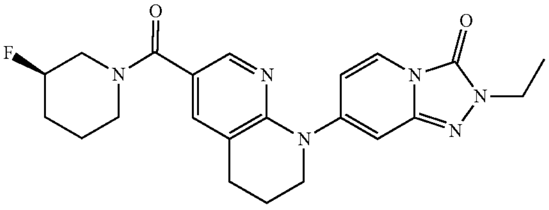
-continued
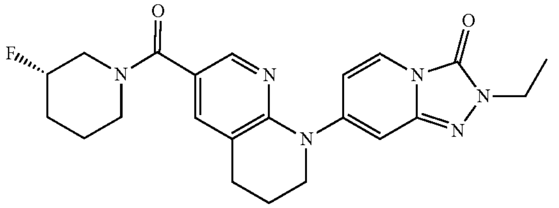
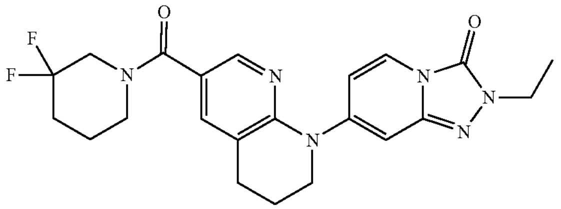
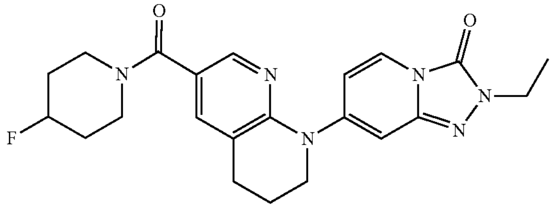
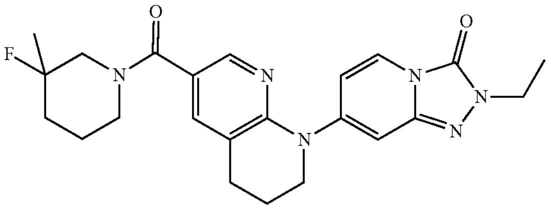
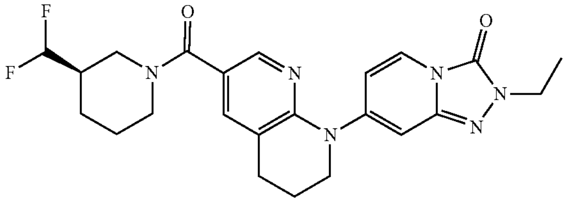
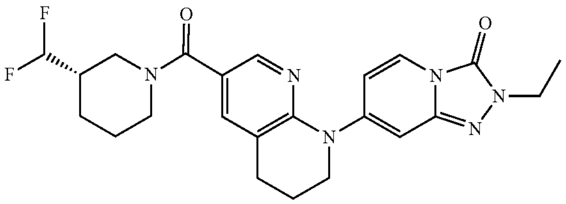
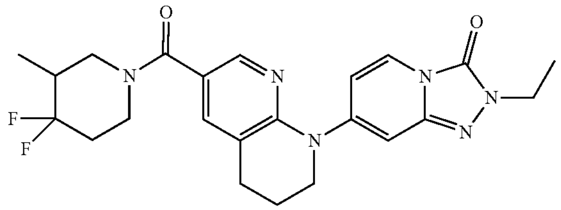
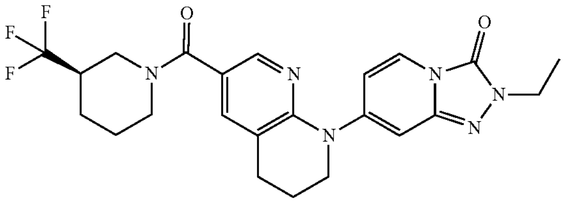

-continued
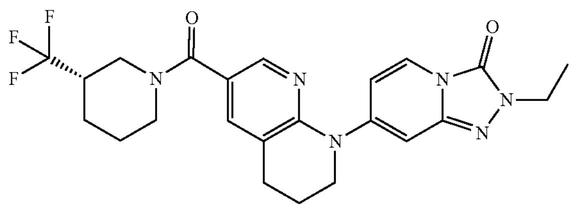
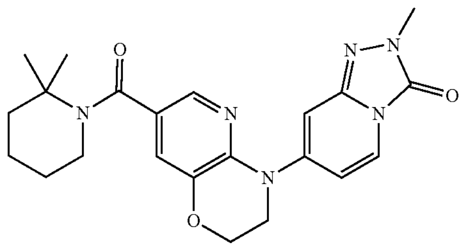
[Formula 29]
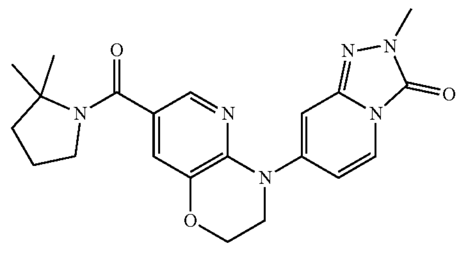
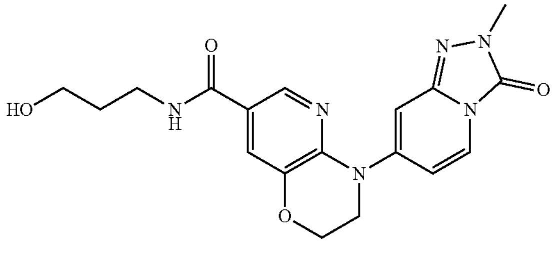
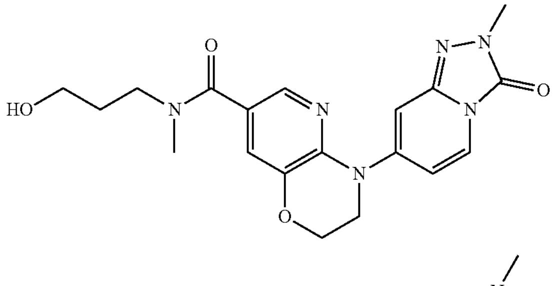
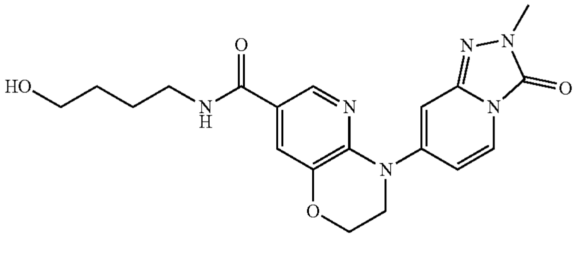
-continued
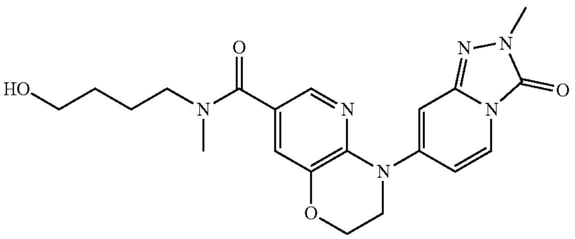
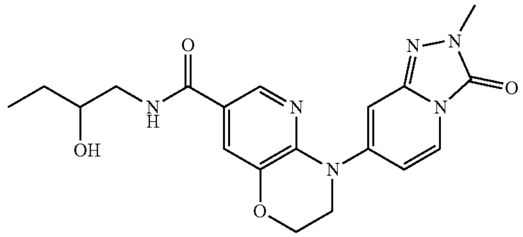
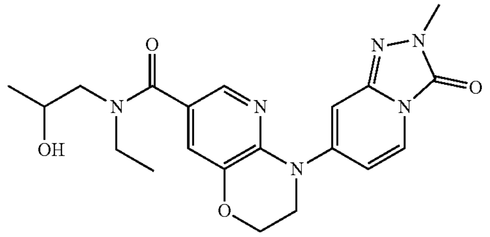
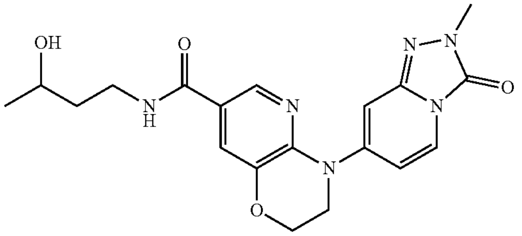
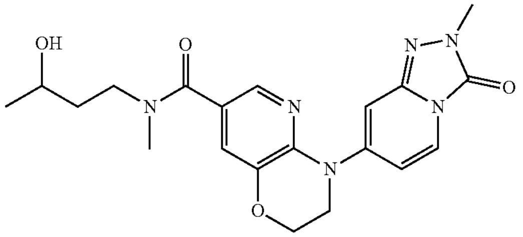
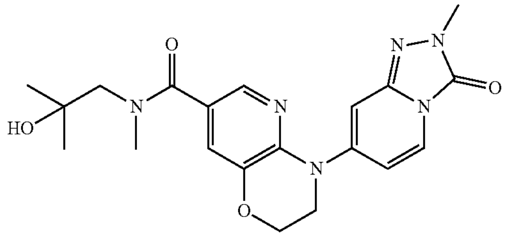
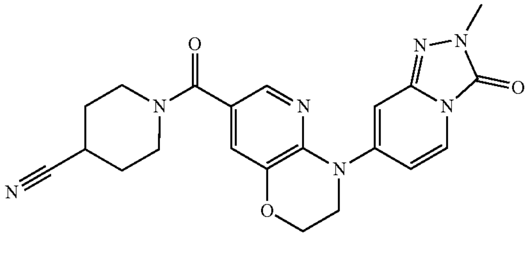

-continued
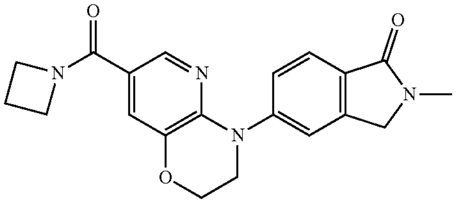
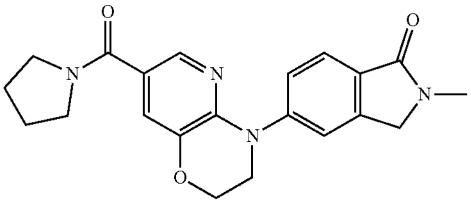
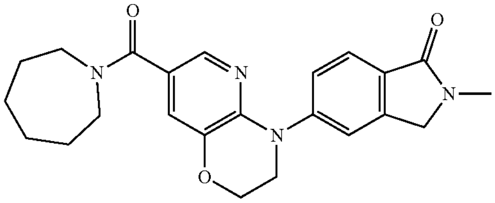
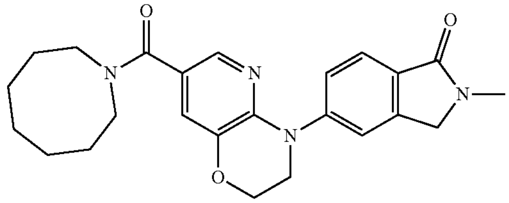
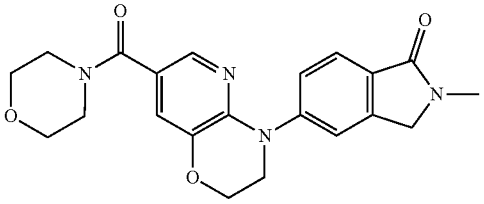
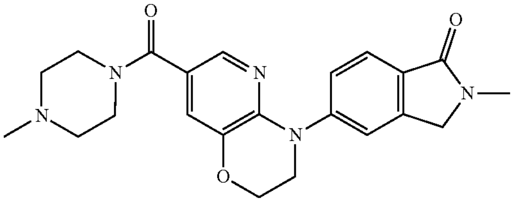
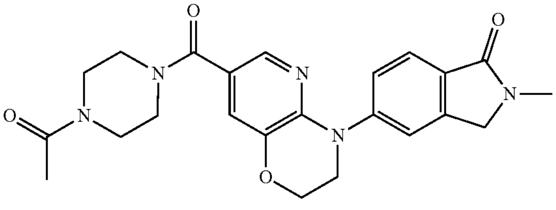
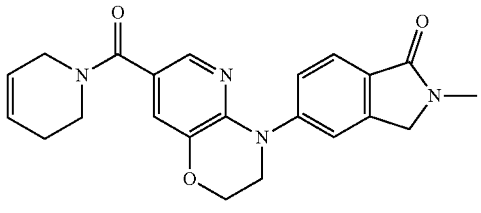
-continued
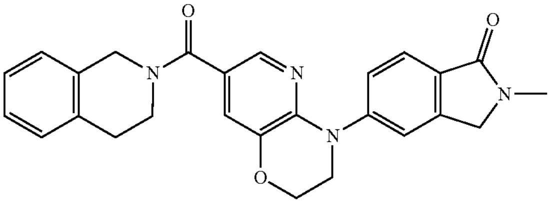
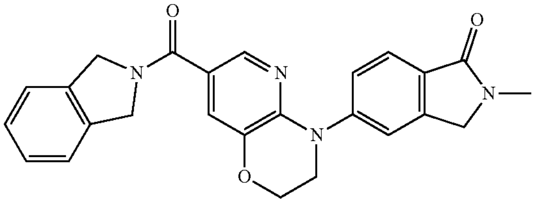
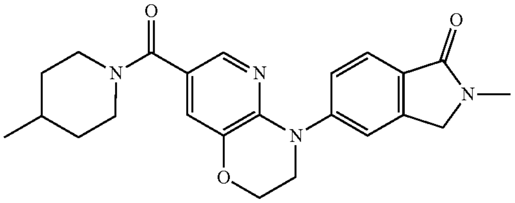
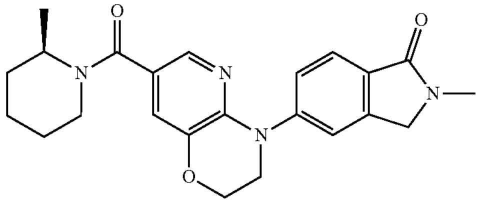
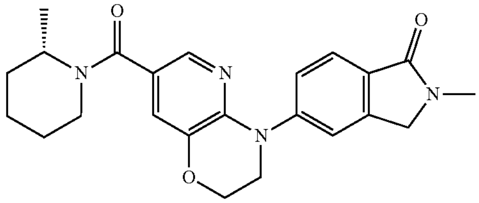
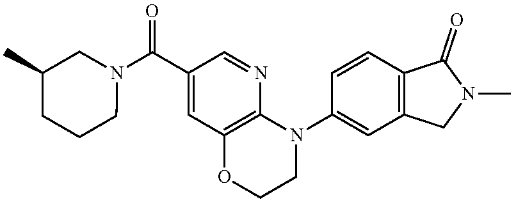
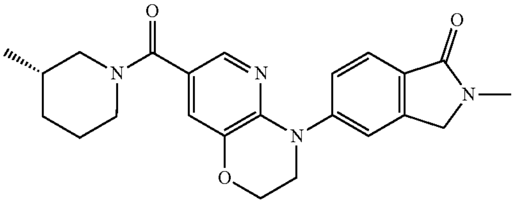
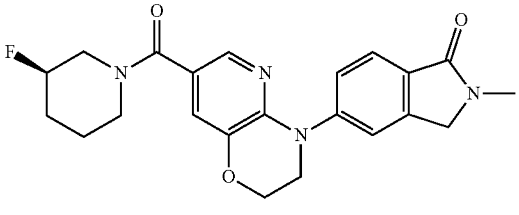

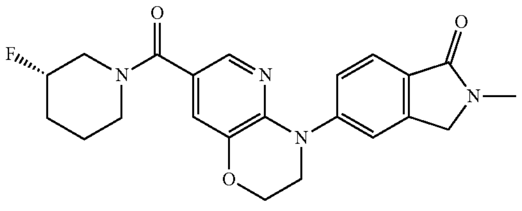
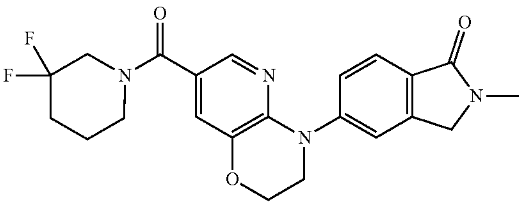
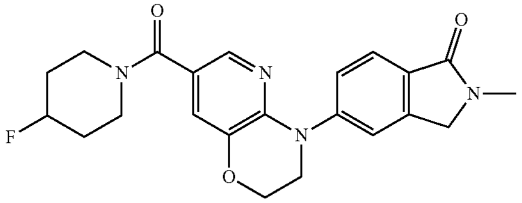
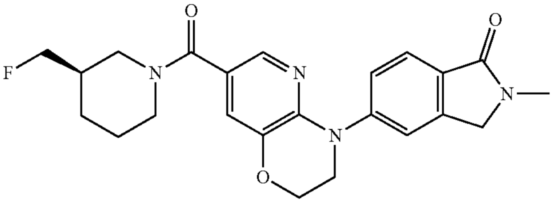
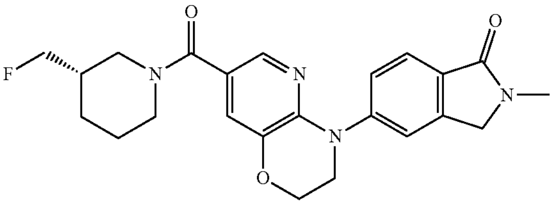
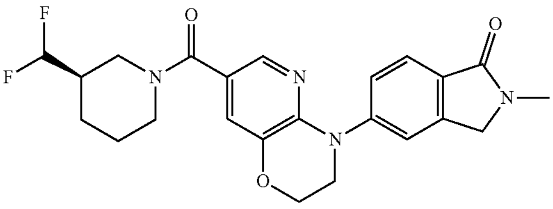
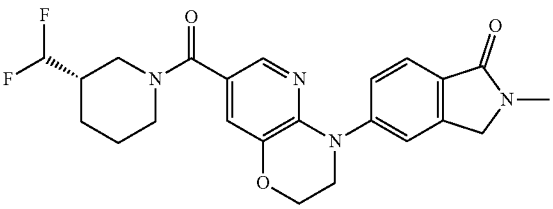
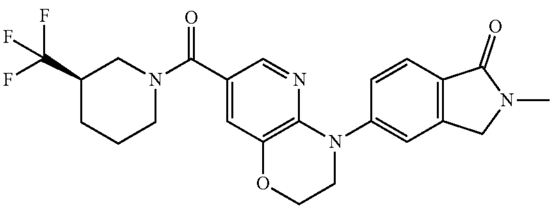
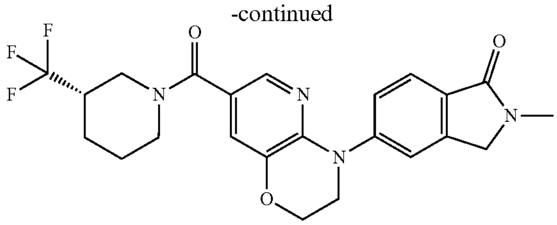
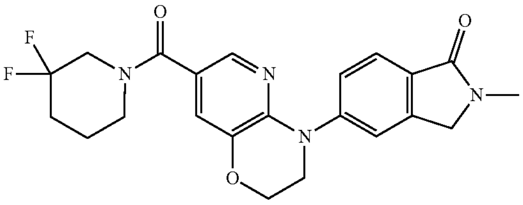
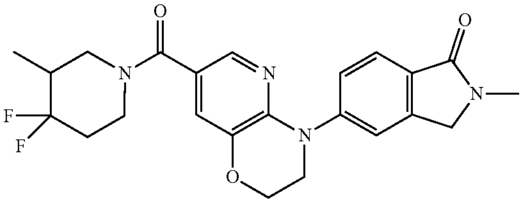
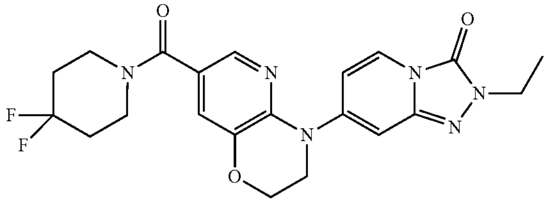
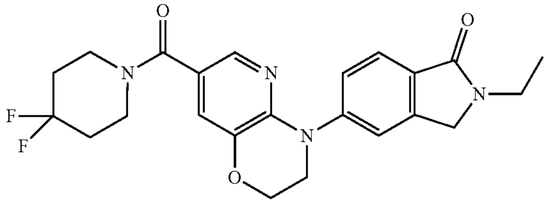
[Formula 30]
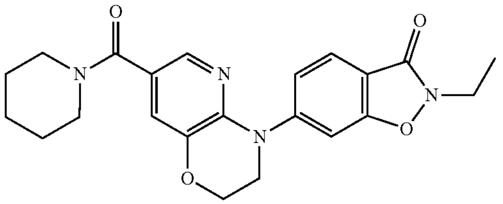
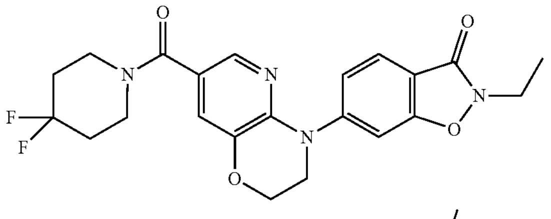
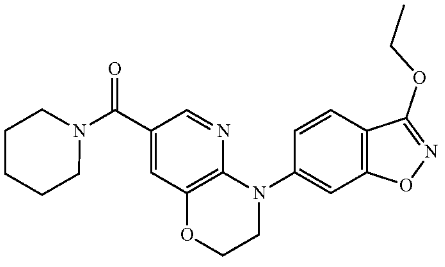

-continued
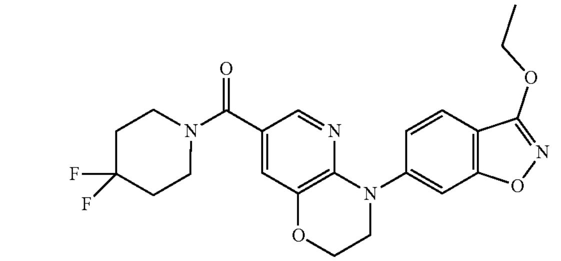
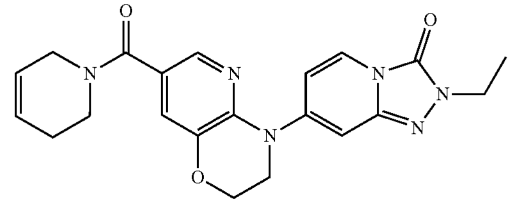
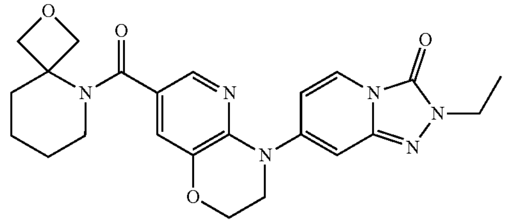
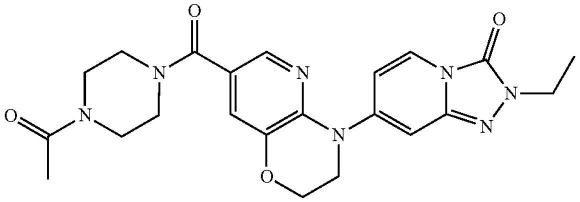
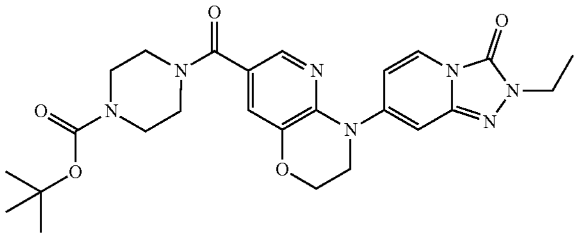
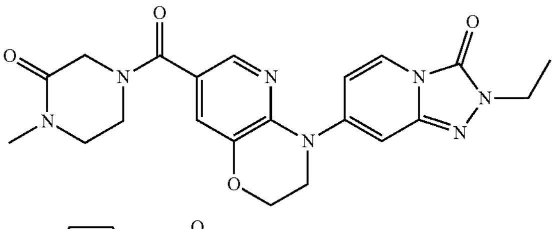
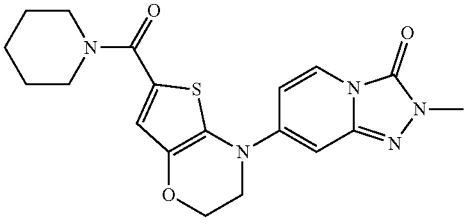
-continued
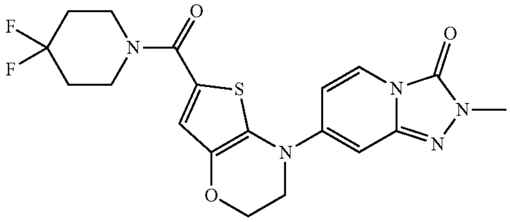
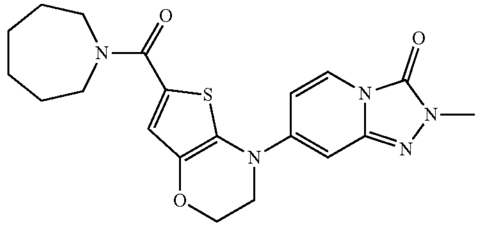
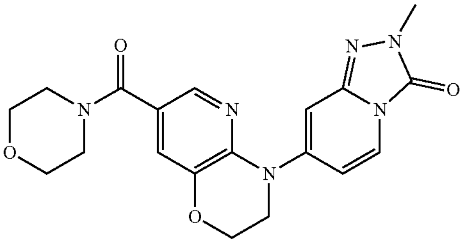
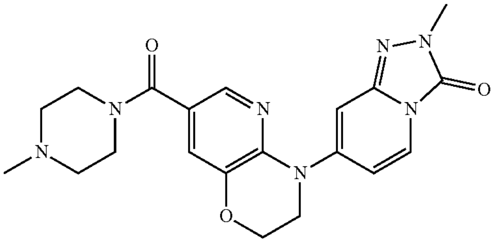
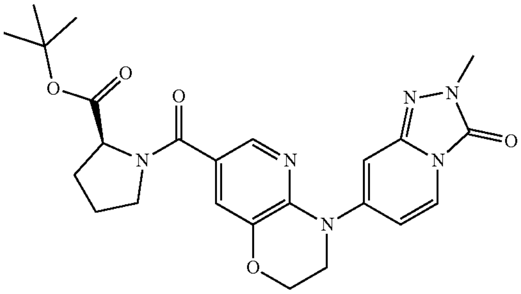
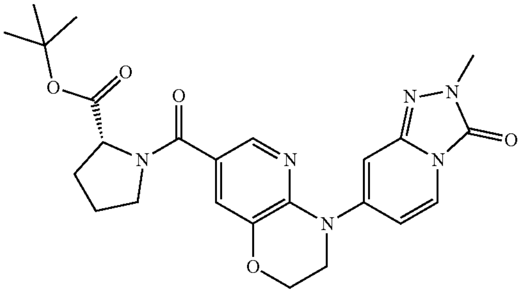
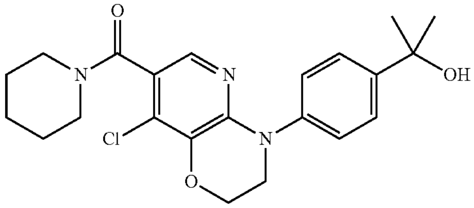

-continued
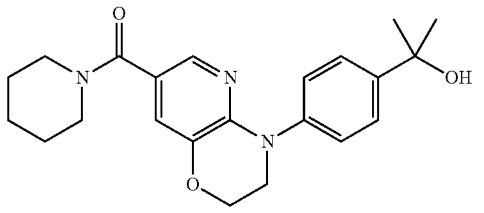
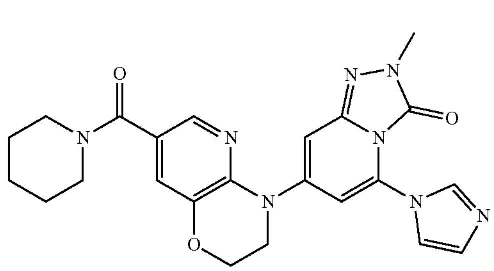
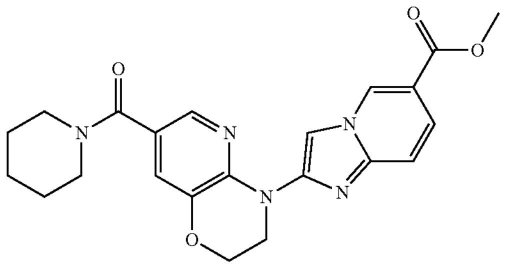
[Formula 31]
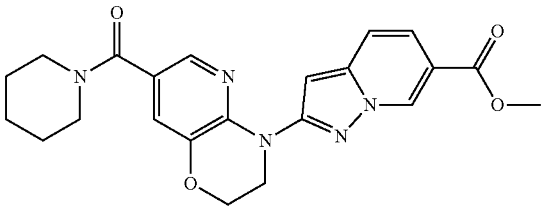
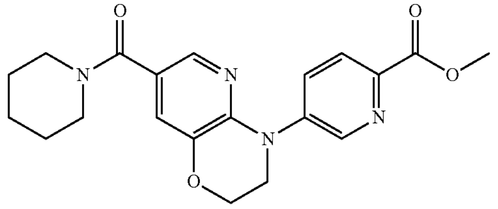
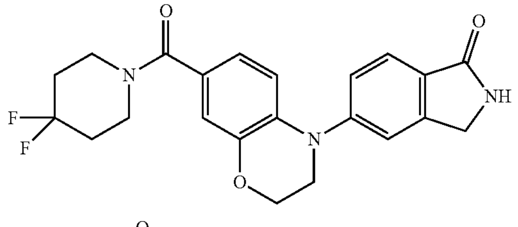
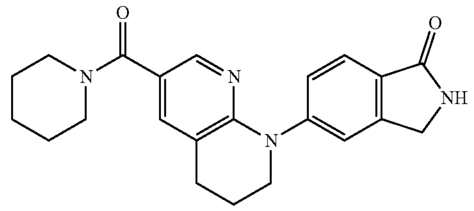
-continued
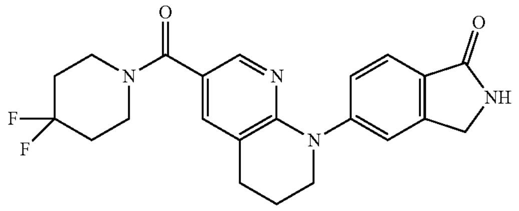
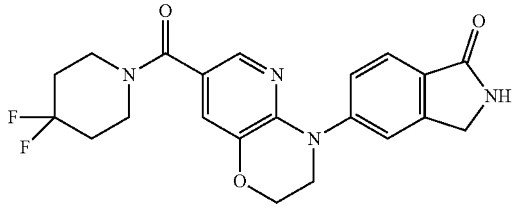
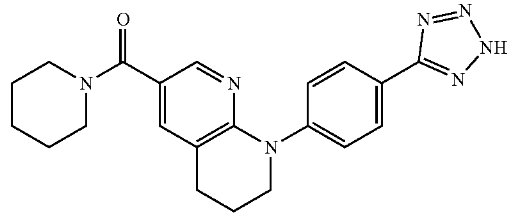
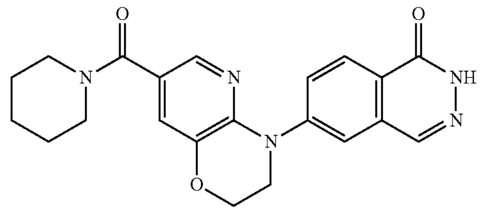
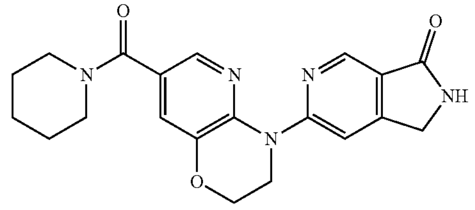
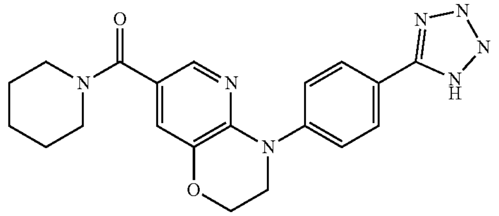
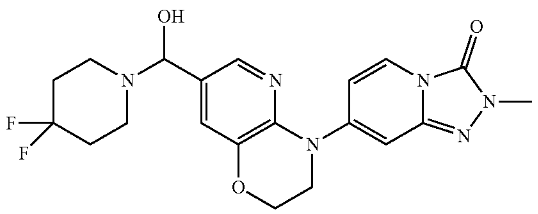
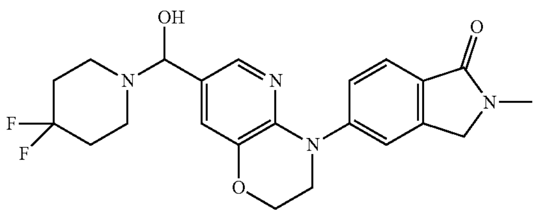

-continued
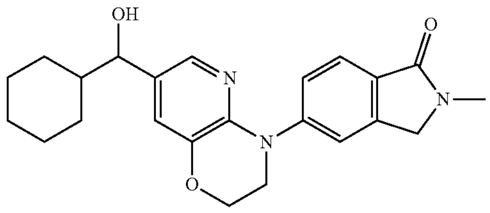
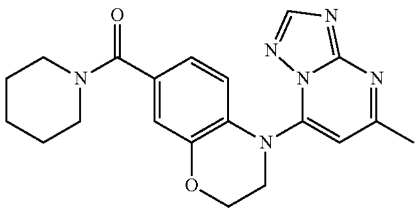
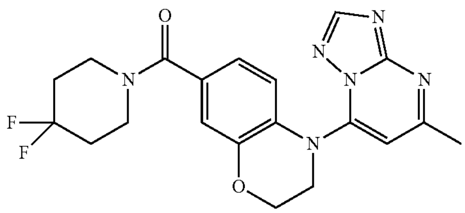
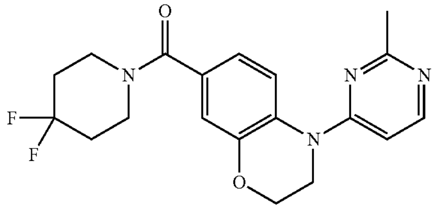
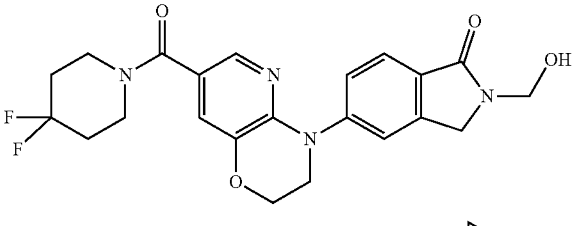
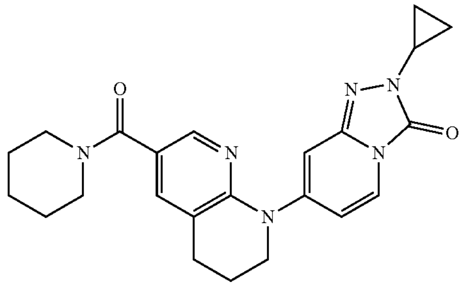
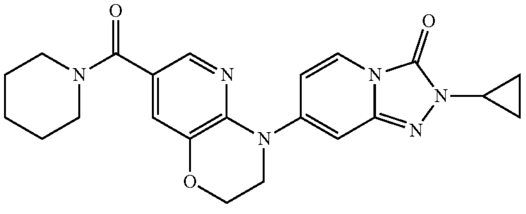
-continued
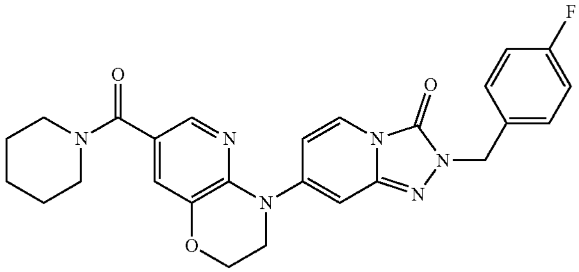
[Formula 32]
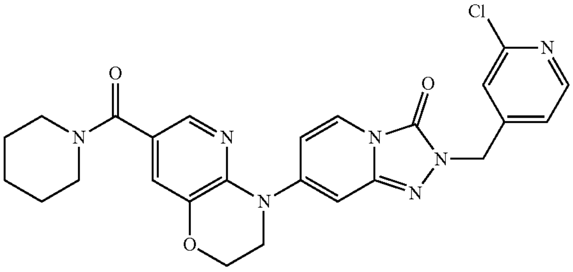
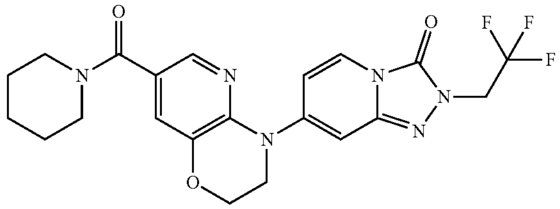
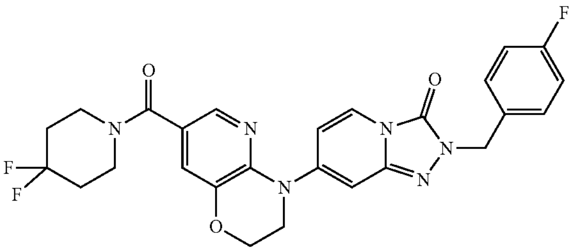
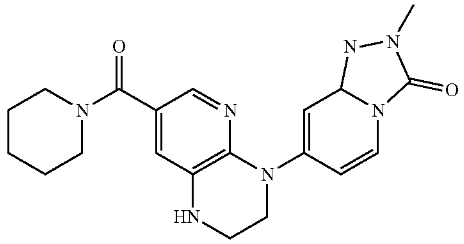
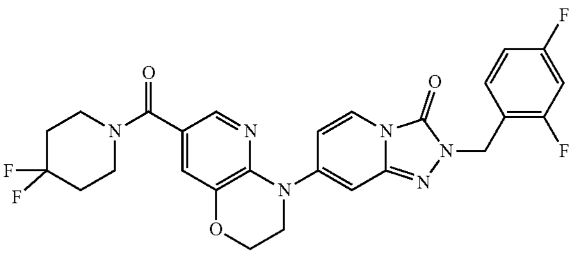

-continued
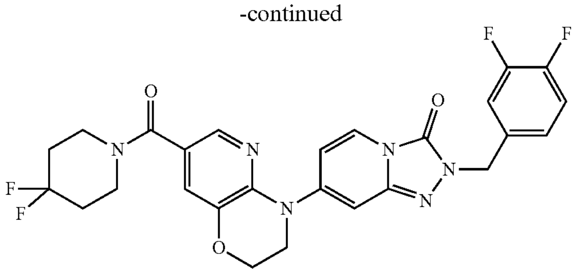
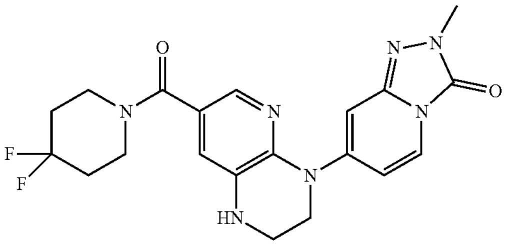
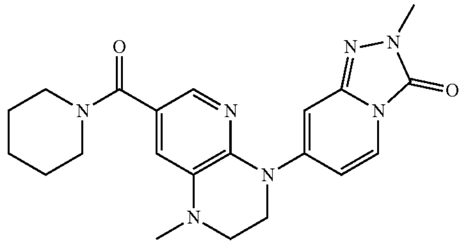
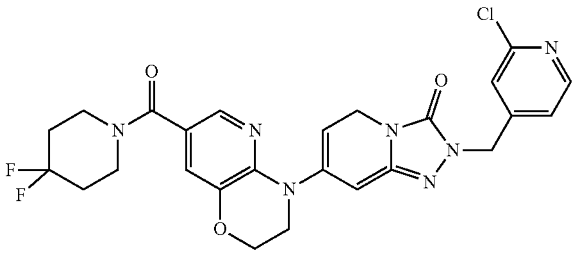
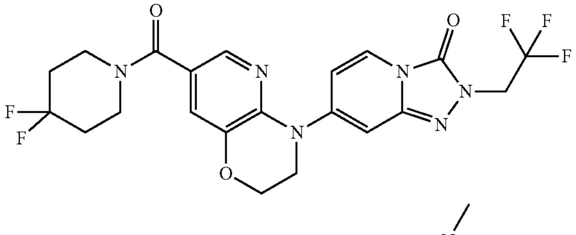
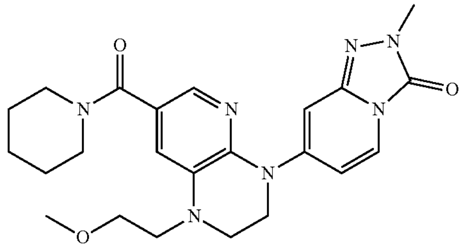
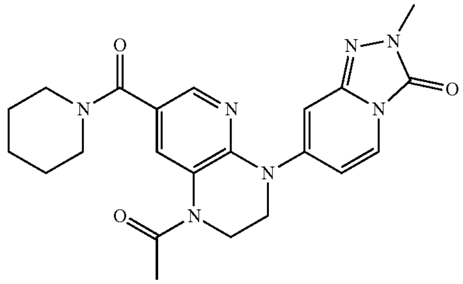
-continued
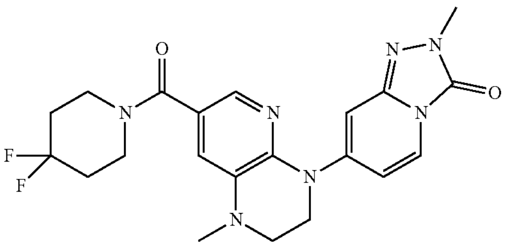
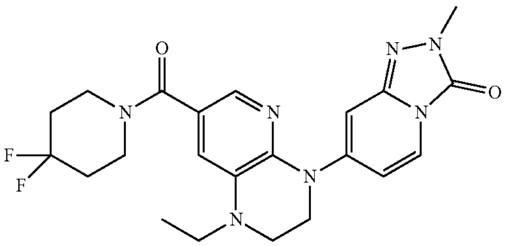
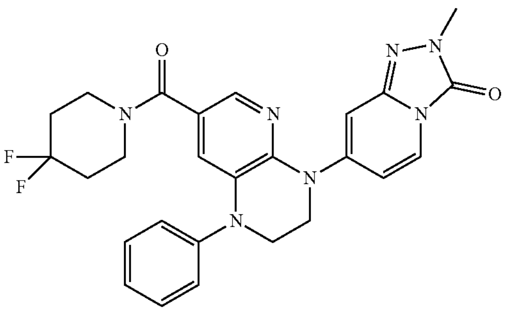
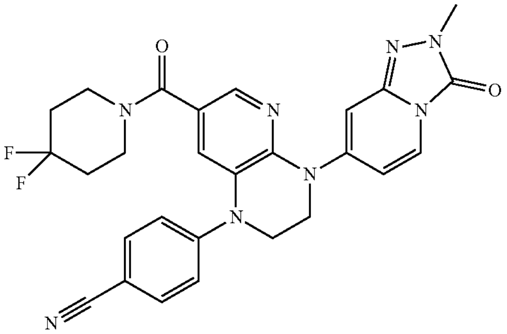
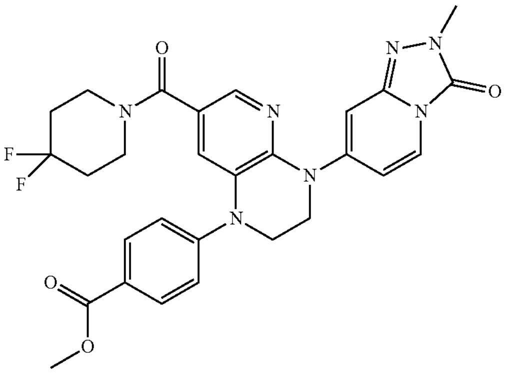

-continued
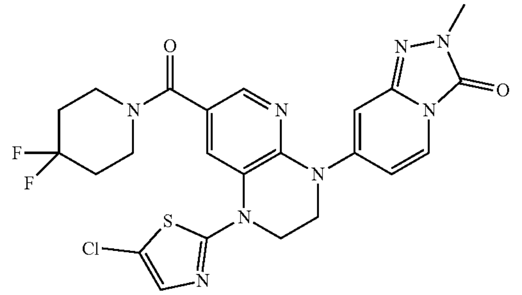
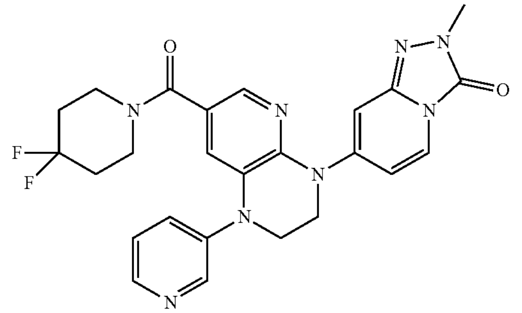
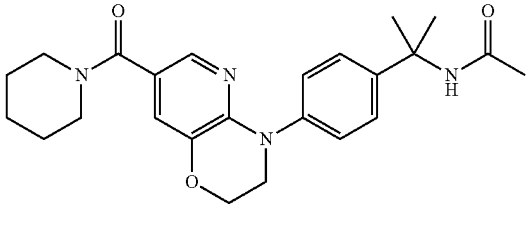
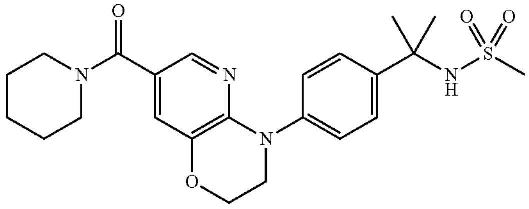
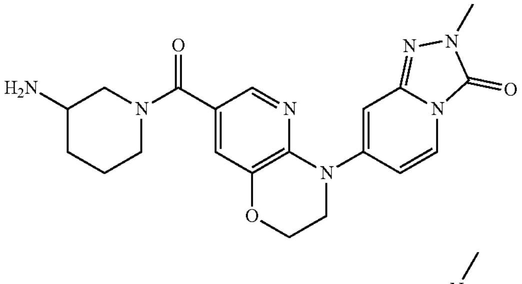
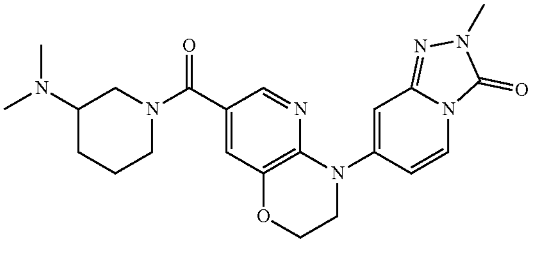
-continued
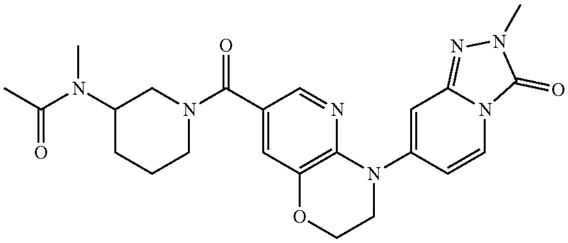
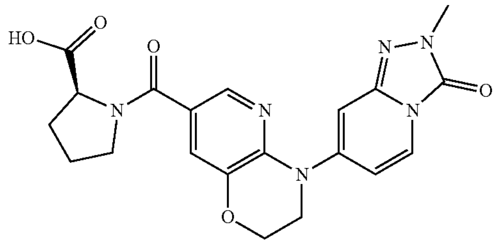
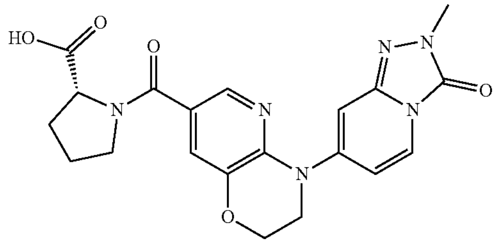
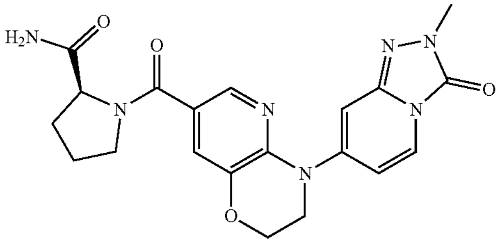
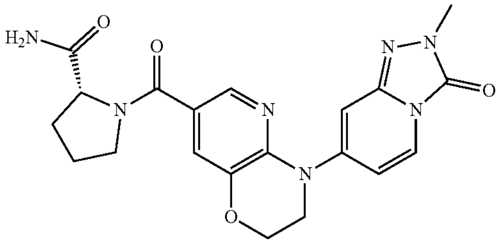
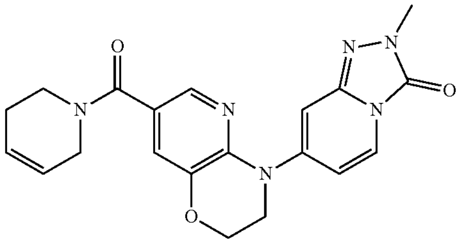
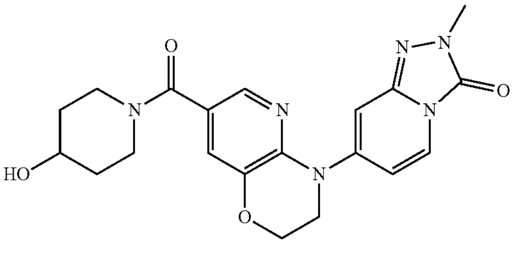

-continued

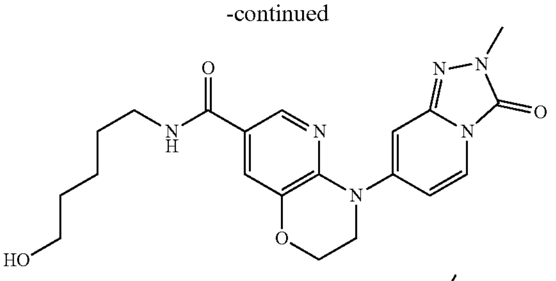

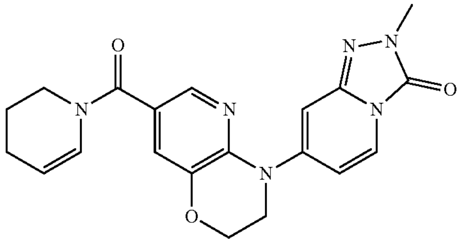

[12] A pharmaceutical comprising, as an active ingredient, the compound according to any one of [1] to [11], or a pharmacologically acceptable salt thereof.

[13] A 15-PGDH inhibitor comprising, as an active ingredient, the compound according to any one of [1] to [11], or a pharmacologically acceptable salt thereof.

[14] A method for treating or preventing one, two or more of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurodegenesis and nerve cell death (such as psycho-neurologic disease, neuropathy, neurotoxic disease, neuropathic pain and neurogenerative disease), muscle regeneration (such as muscular atrophy, muscular dystrophy and muscle damage), and cervical ripening, including administering the compound according to any one of [1] to [11] or a pharmacologically acceptable salt thereof.

[15] Use of the compound according to any one of [1] to [11] or a pharmacologically acceptable salt thereof, for producing a pharmaceutical for treating or preventing one, two or more of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

[16] A pharmaceutical composition containing the compound according to any one of [1] to [11] or a pharmacologically acceptable salt, and a pharmacologically acceptable carrier, for use in treating or preventing one, two or more of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dyseguilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

DESCRIPTION OF EMBODIMENT

Terms herein used will be described.

The term "$C_n$-$C_m$" as used herein means a carbon number of n to m, n and m are respectively independent natural numbers, and m is a larger number than n. For example, "$C_1$-$C_6$" means a carbon number of 1 to 6.

The term "halogen atom" as used herein means a fluorine atom, a chlorine atom, a bromine atom or an iodine atom. Preferably, it is a fluorine atom or a chlorine atom.

The term "5-membered aromatic heterocyclic group" as used herein means a 5-membered aromatic heterocyclic group containing, in the ring, 1 to 4 atoms selected from a sulfur atom, an oxygen atom and a nitrogen atom. Examples of the 5-membered aromatic heterocyclic group include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group and a thiadiazolyl group.

The term "6-membered aromatic heterocyclic group" as used herein means a 6-membered aromatic heterocyclic group containing, in the ring, 1 to 4 nitrogen atoms. Examples of the 6-membered aromatic heterocyclic group include a pyridyl group, a pyridazinyl group, a pyrimidinyl group and a pyrazinyl group.

The term "condensed heterocyclic group having 8 to 10 ring atoms" means a condensed aromatic ring group or non-aromatic ring group that has 8 to 10 atoms constituting the ring, contains 1 to 5 hetero atoms selected from a sulfur atom, an oxygen atom and a nitrogen atom in the atoms constituting the ring, optionally contains 1 to 5 double bonds in the ring, and optionally contains 1 to 3 oxo groups as a ring substituent (excluding a 6,7-dihydro-4H-thiazolo[5,4-c]pyridine ring). Examples of the condensed heterocyclic group having 8 to 10 ring atoms include a thienothiophenyl group, a thienofuranyl group, a thienoimidazolyl group, a benzofuranyl group, an isobenzofuranyl group, a benzoxazolyl group, a benzoisoxazolyl group, a benzothiazolyl group, a benzoisothiazolyl group, a benzoimidazolyl group, a benzothiophenyl group, an indolinyl group, an isoindolinyl group, an indazolyl group, a thiazolopyridyl group, an oxazolopyrazinyl group, a tetrahydrobenzothiophenyl group, a tetrahydrobenzofuranyl group, a dihydrobenzoxazolyl group, an imidazo[1,2-a]pyridinyl group, a 3-oxo-2,3-dihydro[1,2,4]triazolo[4,3-a]pyridinyl group, a 3-oxo-2,3-dihydrobenzo[d]isoxazolyl group, a [1,2,4]triazolo[4,3-a]pyridinyl group, a [1,2,4]triazolo[1,5-a]pyridinyl group, a triazolo[1,5-a]pyridinyl group, a 7-oxo-6,7-dihydro-5H-pyrrolo[3,4-b]pyridinyl group, a 3-oxo-2,3-dihydro-1H-pyrrolo[3,4-c]pyridinyl group, a 1-oxoisoindolinyl group, a 1,3-dioxoisoindolynyl group, a 1,1-dioxide-3-oxo-2,3-dihydrobenzo[d]isothiazolyl group, a 1,1-dioxide-3-oxo-2,3-dihydrobenzo[b]thiophenyl group, a 1,1-dioxidebenzo[d]isothiazolyl group, a benzo[d]isoxazolyl group, a 1-oxo-1,2-dihydroisoquinolinyl group, a 4-oxo-3,4-dihydroquinazolinyl group, a 4-oxo-3,4-dihydropyrido[3,2-d]pyrimidinyl group, a 4-oxo-3,4-dihydropyrido[4,3-d]pyrimidinyl group, a 8-oxo-7,8-dihydro-1,7-naphthyridinyl group, a 8-oxo-7,8-dihydro-2,7-naphthyridinyl group, a 5-oxo-5,6-dihydro-1,6-naphthyridinyl group, a 1-oxo-1,2-dihydrophthaladinyl group, a 1-oxo-1,2,3,4-tetrahydroisoquinolinyl group, a thieno[3,2-b]thiophenyl group, a pyrazolo[1,5-a]pyridinyl group, a quinolinyl group, a quinoxalinyl group, a naphthyridinyl group, a 8-oxopyrido[2,3-d]pyridazinyl group, a 2-oxoindolinyl group and an isoquinolinyl group.

The term "methylene group" as used herein means a $CH_2$ group.

The term "carbonyl group" as used herein means a C═O group.

The term "oxo group" as used herein means an ═O group.

The term "formyl group" as used herein means a —CHO group.

The term "$C_1$-$C_6$ alkyl group" as used herein means a linear or branched alkyl group having 1 to 6 carbon atoms. Examples include a methyl group, an ethyl group, a propyl group, an isopropyl group, a butyl group, an isobutyl group, a sec-butyl group, a tert-butyl group, a pentyl group, an isopentyl group, a neopentyl group, a 1-methylbutyl group, a 2-methylbutyl group, a 1,2-dimethylpropyl group, a hexyl group and an isohexyl group.

The term "$C_1$-$C_6$ alkynyl group" as used herein means a linear or branched alkynyl group having at least one triple bond and 1 to 6 carbon atoms. Examples include an ethynyl group, a 2-propynyl group, a butynyl group, a 5-pentynyl group and a hexenyl group.

The term "$C_1$-$C_6$ alkylcarbonyl group" as used herein is an alkylcarbonyl group derived from linear or branched aliphatic carboxylic acid having 1 to 6 carbon atoms, and means a $C_1$-$C_6$ alkyl-C(═O)— group. Examples of the $C_1$-$C_6$ alkylcarbonyl group include a methylcarbonyl group, an ethylcarbonyl group, a propylcarbonyl group, an isopropylcarbonyl group, a butylcarbonyl group, an isobutylcarbonyl group, a sec-butylcarbonyl group, a t-butylcarbonyl group, a pentylcarbonyl group, an isopentylcarbonyl group, a neopentylcarbonyl group, a 1-methylbutylcarbonyl group, a 2-methylbutylcarbonyl group, a 1,2-dimethypropylcarbonyl group, a hexylcarbonyl group and an isohexylcarbonyl group.

The term "$C_1$-$C_6$ alkoxy group" as used herein is a linear or branched alkoxy group having 1 to 6 carbon atom, and means a $C_1$-$C_6$ alkyl-O— group. Examples include a methoxy group, an ethoxy group, a propoxy group, an isopropoxy group, an isobutoxy group, a butoxy group, a sec-butoxy group, a tert-butoxy group, a pentyloxy group and a hexyloxy group.

The term "$C_1$-$C_6$ alkoxycarbonyl group" as used herein is a linear or branched alkoxycarbonyl group having 1 to 6 carbon atoms, and means a $C_1$-$C_6$ alkyl-O—C(═O)— group. Examples include a methoxycarbonyl group, an ethoxycarbonyl group, a propoxycarbonyl group, an isopropoxycarbonyl group, an isobutoxycarbonyl group, a butoxycarbonyl group, a sec-butoxycarbonyl group, a tert-butoxycarbonyl group, a pentyloxycarbonyl group and a hexyloxycarbonyl group.

The term "$C_1$-$C_6$ alkylsulfonyl group" as used herein is a linear or branched alkylsulfonyl group having 1 to 6 carbon atoms, and means a $C_1$-$C_6$ alkyl-$SO_2$— group. Examples include a methylsulfonyl group, an ethylsulfonyl group, a propylsulfonyl group, an isopropylsulfonyl group, a butylsulfonyl group, an isobutylsulfonyl group, a sec-butylsulfonyl group and a tert-butylsulfonyl group.

The term "$C_1$-$C_6$ alkylsulfonylamino group" as used herein is an amino group having one hydrogen atom thereof substituted with a $C_1$-$C_6$ alkylsulfonyl group, and means a $C_1$-$C_6$ alkyl-$SO_2NH$— group. Examples include a methylsulfonylamino group, an ethylsulfonylamino group, a propylsulfonylamino group, an isopropylsulfonylamino group, a butylsulfonylamino group, an isobutylsulfonylamino group, a sec-butylsulfonylamino group and a tert-butylsulfonylamino group.

The term "$C_3$-$C_8$ cycloalkyl group" as used herein means a monocyclic saturated alicyclic hydrocarbon group having 3 to 8 carbon atoms. Examples include a cyclopropyl group, a cyclobutyl group, a cyclopentyl group, a cyclohexyl group, a cycloheptyl group and a cyclooctyl group.

The term "$C_3$-$C_8$ cycloalkylcarbonyl group" as used herein is a cycloalkylcarbonyl group derived from a monocyclic saturated alicyclic hydrocarbon carboxylic acid having 3 to 8 carbon atoms, and means a $C_3$-$C_8$ cycloalkyl —C(═O)— group. Examples of the $C_3$-$C_8$ cycloalkylcarbonyl group include a cyclopropylcarbonyl group, a cyclobutylcarbonyl group, a cyclopentylcarbonyl group, a cyclohexylcarbonyl group, a cycloheptylcarbonyl group and a cyclooctylcarbonyl group.

The term "$C_3$-$C_8$ cycloalkylsulfonyl group" as used herein means a cycloalkyl —$SO_2$— group having 3 to 8 carbon atoms. Examples include a cyclopropylsulfonyl group, a cyclobutylsulfonyl group, a cyclopentylsulfonyl group, a cyclohexylsulfonyl group, a cycloheptylsulfonyl group and a cyclooctylsulfonyl group.

The term "$C_3$-$C_8$ cycloalkylsulfonylamino group" as used herein is an amino group having one hydrogen atom thereof substituted with a $C_3$-$C_0$ cycloalkylsulfonyl group, and means a $C_3$-$C_0$ cycloalkyl —$SO_2NH$— group. Examples include a cyclopropylsulfonylamino group, a cyclobutylsulfonylamino group, a cyclopentylsulfonylamino group, a cyclohexysulfonylamino group, a cycloheptylsulfonylamino group and a cyclooctylsulfonylamino group.

The term "nitrogen-containing heterocycloalkyl group having 3 to 11 ring atoms" as used herein means a saturated or non-aromatic unsaturated monocyclic, bicyclic or tricyclic heterocycloalkyl group having 3, 4, 5, 6, 7, 8, 9 or 10 ring members that contains one or more nitrogen atoms in its ring structure, and optionally contains an oxygen atom or a sulfur atom.

The nitrogen-containing heterocycloalkyl group having 3 to 11 ring atoms may be condensed further with a 6-membered aromatic hydrocarbon ring or a 6-membered aromatic heterocycle. Besides, the nitrogen-containing heterocycloalkyl group having 3 to 11 ring atoms can be a bridged or spiro ring group. Examples of the nitrogen-containing heterocycloalkyl group having 3 to 11 ring atoms include an aziridinyl group, an azetidinyl group, a pyrrolidinyl group, a piperidinyl group, an azepanyl group, an azocanyl group, a dihydropyrrolyl group, a tetrahydropyridinyl group, a piperazinyl group, a morpholinyl group, a thiomorpholinyl group, a 1-oxidethiomorpholinyl group, a 1,1-dioxidethiomorpholinyl group, an oxazepinyl group, a thiazepanyl group, a 1-oxide-1,4-thiazepanyl group, a 1,1-dioxide-1,4-thiazepanyl group, a 1,4-dithiazepanyl group, a 1,4-oxazocanyl group, a 1,5-oxazocanyl group, an octahydroindolinyl group, an octahydroisoindolinyl group, an octahydrocyclopenta[c]pyrrolyl group, a 3-azabicyclo[3,2,0]heptanyl group, a 3-azabicyclo[3,1,0]hexanyl group, a 5-azabicyclo[2,1,1]hexanyl group, a 2-azabicyclo[2,1,1]hexanyl group, a 2-azabicyclo[4,1,0]heptanyl group, a 3-azabicyclo[4,1,0]heptanyl group, a 2-azabicyclo[4,2,0]octanyl group, a 3-azabicyclo[4,2,0]octanyl group, an octahydro-1H-cyclopenta[c]pyridinyl group, a 3-azabicyclo[3,1,1]heptanyl group, a 2-azabicyclo[2,2,1]heptanyl group, a 6-azabicyclo[3,1,1]heptanyl group, a 8-azabicyclo[3,2,1]octanyl group, a 3-azabicyclo[3,2,1]octanyl group, a 6-azabicyclo[3,2,1]octanyl group, a 4-azaspiro[2,4]heptanyl group, a 5-azaspiro[2,4]heptanyl group, a 1-oxo-5-azaspiro[2,4]heptanyl group, a 5-azaspiro[3,4]octanyl group, a 6-azaspiro[3,4]octanyl group, a 2-oxo-6-azaspiro[3,4]octanyl group, a 1-oxo-6-azaspiro[3,4]octanyl group, a 1-azaspiro[4,4]nonanyl group, a 2-azaspiro[4,4]nonanyl group, a 2-oxa-7-azaspiro[4,4]nonanyl group, a 1-oxa-7-azaspiro[4,4]nonanyl group, a 2-azaspiro[4,5]decanyl group, a 8-oxa-2-azaspiro[4,5]decanyl group, a 7-oxa-2-azaspiro[4,5]decanyl group, a 6-oxa-2-azaspiro[4,5]decanyl group, a 2-azaspiro[4,6]undecanyl group, a 4-azaspiro[2,5]octanyl group, a 5-azaspiro[2,5]octanyl group, a 6-azaspiro[2,5]octanyl group, a 1-oxa-5-azaspiro[2,5]octanyl group, a 4-oxa-7-azaspiro[2,5]octanyl group, a 1-oxa-6-azaspiro[2,5]octanyl group, a 5-azaspiro[3,5]nonanyl group, a 6-azaspiro[3,5]nonanyl group, a 7-azaspiro[3,5]nonanyl group, a 1-oxa-6-azaspiro[3,5]nonanyl group, a 2-oxa-6-azaspiro[3,5]nonanyl group, a 2-oxa-5-azaspiro[3,5]nonanyl group, a 2-oxa-7-azaspiro[3,5]nonanyl group, a 7-azaspiro[4,5]decanyl group, a 8-azaspiro[4,5]decanyl group, a 2-azaspiro[5,5]undecanyl group and a 3-azaspiro[5,5]undecanyl group. Examples of the nitrogen-containing heterocycloalkyl group having 3 to 11 ring atoms with which a 6-membered aromatic hydrocarbon ring or a 6-membered aromatic heterocycle is condensed include an indolinyl group, an isoindolinyl group, a 1,2,3,4-tetrahydroquinolyl group, a 1,2,3,4-tetrahydroisoquinolyl group, a 2,3,4,5-tetrahydro-1H-benzo[b]azepinyl group, a 2,3,4,5-tetrahydro-1H-benzo[c]azepinyl group, a 2,3,4,5-tetrahydro-1H-benzo[d]azepinyl group, a 2,3-dihydro-1H-pyrrolo[2,3-b]pyridinyl group, a 2,3-dihydro-1H-pyrrolo[2,3-c]pyridinyl group, a 2,3-dihydro-1H-pyrrolo[3,2-c]pyridinyl group, a 2,3-dihydro-1H-pyrrolo[3,2-b]pyridinyl group, a 6,7-dihydro-5H-pyrrolo[3,4-b]pyridinyl group, a 2,3-dihydro-1H-pyrrolo[3,4-c]pyridinyl group, a 1,2,3,4-tetrahydro-1,8-naphthyridinyl group, a 1,2,3,4-tetrahydro-1,7-naphthyridinyl group, a 1,2,3,4-tetrahydro-1,6-naphthyridinyl group, a 1,2,3,4-tetrahydro-1,5-naphthyridinyl group, a 5,6,7,8-tetrahydro-1,6-naphthyridinyl group, a 1,2,3,4-tetrahydro-2,6-naphthyridinyl group, a 1,2,3,4-tetrahydro-2,7-naphthyridinyl group, a 5,6,7,8-tetrahydro-1,7-naphthyridinyl group, a 3,4-dihydro-2H-benzo[b][1,4]oxadinyl group, a 2,3,4,5-tetrahydrobenzo[b][1,4]oxazepinyl group, a 2,3,4,5-tetrahydrobenzo[b][1,4]thiazepinyl group and a 2,3,4,5-tetrahydrobenzo[f][1,4]oxazepinyl group.

The term "3- to 8-membered heterocycloalkyl group" as used herein means a monocyclic, bicyclic or tricyclic heterocycloalkyl group having 3, 4, 5, 6, 7 or 8 ring members that contains 1 to 4 endocyclic hetero atoms independently selected from the group consisting of N, N-oxide, O, S, SO and $SO_2$, optionally has 1 to 3 carbonyls, and optionally has one double bond in the ring.

The 3- to 8-membered heterocycloalkyl group may be condensed further with a 6-membered aromatic hydrocarbon ring or a 6-membered aromatic heterocycle. Besides, the 3- to 8-membered heterocycloalkyl group can be a bridged or spiro ring group. Examples of the 3- to 8-membered heterocycloalkyl group include an aziridinyl group, an azetidinyl group, an oxiranyl group, an oxetanyl group, a tetrahydro-2H-pyranyl group, a dihydropyranyl group, a pyranyl group, a tetrahydrofuranyl group, an imidazolyl group, a dihydropyrazolyl group, a dihydroimidazolyl group, a dihydrooxadiazolyl group, a thiazolidyl group, a pyrrolidinyl group, a piperidinyl group, an azepanyl group, an azocanyl group, a dihydropyrrolyl group, a tetrahydropyridinyl group, a piperazinyl group, a morpholinyl group, a thiomorpholinyl group, a 1-oxide thiomorphlinyl group, a 1,1-dioxide thiomorpholinyl group, an oxazepinyl group, a thiazepanyl group, a 1-oxide-1,4-thiazepanyl group, a 1,1-dioxide-1,4-thiazepanyl group, a 1,4-diazepanyl group, a 1,4-oxazocanyl group, a 1,5-oxazocanyl group, an octahydrocyclopenta[c]pyrrolyl group, a 3-azabicyclo[3,2,0]heptanyl group, a 3-azabicyclo[3,1,0]hexanyl group, a 5-azabicyclo[2,1,1]hexanyl group, a 2-azabicyclo[2,1,1]hexanyl group, a 2-azabicyclo[4,1,0]heptanyl group, a 3-azabicyclo[4,1,0]heptanyl group, a 2-azabicyclo[4,2,0]octanyl group, a 3-azabicyclo[4,2,0]octanyl group, a 3-azabicyclo[3,1,1]heptanyl group, a 2-azabicyclo[2,2,1]heptanyl group, a 6-azabicyclo[3,1,1]heptanyl group, a 8-azabicyclo[3,2,1]octanyl group, a 3-azabicyclo[3,2,1]octanyl group, a 6-azabicyclo[3,2,1]octanyl group, a 4-azaspiro[2,4]heptanyl group, a 5-azaspiro[2,4]heptanyl group, a 1-oxo-5-azaspiro[2,4]heptanyl group, a 5-azaspiro[3,4]octanyl group, a 6-azaspiro[3,4]octanyl group, a 2-oxo-6-azaspiro[3,4]octanyl group, a 1-oxo-6-azaspiro[3,4]octanyl group, a 4-azaspiro[2,5]octanyl group, a 5-azaspiro[2,5]octanyl group, a 6-azaspiro[2,5]octanyl group, a 1-oxa-5-azaspiro[2,5]octanyl group, a 4-oxa-7-azaspiro[2,5]octanyl group and a 1-oxa-6-azaspiro[2,5]octanyl group. Examples of the 3- to 8-membered heterocycloalkyl group with which a 6-membered aromatic hydrocarbon ring or 6-membered aromatic heterocycle is condensed include an indolinyl group, an isoindolinyl group, a 1,2,3,4-tetrahydroquinolyl group, a 1,2,3,4-tetrahydroisoquinolyl group, a 2,3,4,5-tetrahydro-1H-benzo[b]azepinyl group, a 2,3,4,5-tetrahydro-1H-benzo[c]azepinyl group, a 2,3,4,5-tetrahydro-1H-benzo[d]azepinyl group, a 2,3-dihydro-1H-pyrrolo[2,3-b]pyridinyl group, a 2,3-dihydro-1H-pyrrolo[2,3-c]pyridinyl group, a 2,3-dihydro-1H-pyrrolo[3,2-c]pyridinyl group, a 2,3-dihydro-1H-pyrrolo[3,2-b]pyridinyl group, a 6,7-dihydro-5H-pyrrolo[3,4-b]pyridinyl group, a 2,3-dihydro-1H-pyrrolo[3,4-c]pyridinyl group, a 1,2,3,4-tetrahydro-1,8-naphthyridinyl group, a 1,2,3,4-tetrahydro-1,7-naphthyridinyl group, a 1,2,3,4-tetrahydro-1,6-naphthyridinyl group, a 1,2,3,4-tetrahydro-1,5-naphthrydinyl group, a 5,6,7,8-tetrahydro-1,6-napthyridinyl group, a 1,2,3,4-tetrahydro-2,6-napthyridinyl group, a 1,2,3,4-tetrahydro-2,7-naphthyridinyl group, a 5,6,7,8-tetrahydro-1,7-naphthyridinyl group, a 3,4-dihydro-2H-benzo[b][1,4]oxadinyl group, a 2,3,4,5-tetrahydrobenzo[b][1,4]oxazepinyl group, a 2,3,4,5-tetrahydrobenzo[b][1,4]thiazepinyl group and a 2,3,4,5-tetrahydrobenzo[f][1,4]oxazepinyl group.

The term "3- to 8-membered heterocycloalkyl group containing an oxygen atom" as used herein means a 3- to 8-membered heterocycloalkyl group containing one or more endocyclic oxygen atoms. Examples of the 3- to 8-membered heterocycloalkyl group containing an oxygen atom include an oxiranyl group, an oxetanyl group, a tetrahydro-2H-pyranyl group, a dihydropyranyl group, a pyranyl group, a tetrahydrofuranyl group, a dihydrooxadiazolyl group, a morpholinyl group, an oxazepinyl group, a 1,4-oxazocanyl group, a 1,5-oxazocanyl group, a 3,4-dihydro-2H-benzo[b][1,4]oxadinyl group, a 2,3,4,5-tetrahydrobenzo[b][1,4]oxazepinyl group and a 2,3,4,5-tetrahydrobenzo[f][1,4]oxazepinyl group.

The term "3- to 8-membered heterocycloalkylcarbonyl group" as used herein means a 3- to 8-membered heterocycloalkyl —C(═O)— group. Examples of the 3- to 8-membered heterocycloalkylcarbonyl group include an aziridinylcarbonyl group, an azetidinylcarbonyl group, an oxetanylcarbonyl group, an imidazolidylcarbonyl group, a thiazolidylcarbonyl group, a pyrrolidinylcarbonyl group, a piperidinylcarbonyl group, a piperazinylcarbonyl group, a morpholinylcarbonyl group, a thiomorpholinylcarbonyl group, a dihydropyrazolylcarbonyl group, a dihydropyrrolylcarbonyl group, a dihydroimidazolylcarbonyl group, a dihydrooxadiazolylcarbonyl group, a dihydropyranylcarbonyl group, a pyranylcarbonyl group, a tetrahydropyrazinylcarbonyl group, an azepanylcarbonyl group, a diazepanylcarbonyl group, an oxazepanylcarbonyl group, a thiazepanylcarbonyl group and a tetrahydrodiazepinylcarbonyl group.

The term "3- to 8-membered heterocycloalkylamino group" as used herein means a 3- to 8-membered heterocycloalkyl —NH— group. Examples of the 3- to 8-membered heterocycloalkylamino group include an aziridinylamino group, an azetidinylamino group, an oxetanylamino group, an imidazolidylamino group, a thiazolidylamino group, a pyrrolidinylamino group, a piperidinylamino group, a piperazinylamino group, a morpholinylamino group, a thiomorpholinylamino group, a dihydropyrazolylamino group, a dihydropyrrolylamino group, a dihydroimidazolylamino group, a dihydrooxadiazolylamino group, a dihydropyranylamino group, a pyranylamino group, a tetrahydropyrazinylamino group, an azepanylamino group, a diazepanylamino group, an oxazepanylamino group, a thiazepanylamino group and a tetrahydrodiazepinylamino group.

The term "3- to 8-membered heterocycloalkylaminocarbonyl group" as used herein means a 3- to 8-membered heterocycloalkyl —NHC(═O)— group. Examples of the 3- to 8-membered heterocycloalkylaminocarbonyl group include an aziridinylaminocarbonyl group, an azetidinylaminocarbonyl group, an oxetanylaminocarbonyl group, an imidazolidylaminocarbonyl group, a thiazolidylaminocarbonyl group, a pyrrolidinylaminocarbonyl group, a piperidinylaminocarbonyl group, a piperazinylaminocarbonyl group, a morpholinylaminocarbonyl group, a thiomorpholinylaminocarbonyl group, a dihydropyrazolylaminocarbonyl group, a dihydropyrrolylaminocarbonyl group, a dihydroimidazolylaminocarbonyl group, a dihydrooxadiazolylaminocarbonyl group, a dihydropyranylaminocarbonyl group, a pyranylaminocarbonyl group, a tetrahydropyrazinylaminocarbonyl group, an azepanylaminocarbonyl group, a diazepanylaminocarbonyl group, an oxazepanylaminocarbonyl group, a thiazepanylaminocarbonyl group and a tetrahydrodiazepinylaminocarbonyl group.

The term "$C_3$-$C_0$ cycloalkoxy group" as used herein is a monocyclic saturated alicyclic hydrocarbon ring alkoxy group having 3 to 8 carbon atoms, and means a $C_3$-$C_8$ cycloalkyl-O— group. Examples include a cyclopropyloxy group, a cyclobutyloxy group, a cyclopentyloxy group, a cyclohexyloxy group, a cycloheptyloxy group and a cyclooctyloxy group.

The term "halo $C_1$-$C_6$ alkyl group" as used herein means a $C_1$-$C_6$ alkyl group substituted with 1 to 5 same or different halogen atoms. Examples of the halo $C_1$-$C_6$ alkyl group include a fluoromethyl group, a difluoromethyl group, a trifluoromethyl group, a 2-fluoroethyl group, a 2-chloroethyl group, a 2,2-difluoroethyl group, a 1,1-difluoroethyl group, a 1,2-difluoroethyl group, a 2,2,2-trifluoroethyl group, a 1,1,2,2,2-pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 4-fluorobutyl group, a 5-fluoropentyl group and a 6-fluorohexyl group.

The term "halo $C_1$-$C_6$ alkoxy group" as used herein means a $C_1$-$C_6$ alkoxy group substituted with 1 to 5 same or different halogen atoms. Examples of the halo $C_1$-$C_6$ alkoxy group include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentoxy group and a 6-fluorohexyloxy group.

The term "hydroxy $C_1$-$C_6$ alkyl group" as used herein means a $C_1$-$C_6$ alkyl group substituted with a hydroxyl group. Examples of the hydroxy $C_1$-$C_6$ alkyl group include a 2-hydroxyethyl group, a 1-hydroxyethyl group, a 3-hydroxypropyl group, a 2-hydroxypropyl group, a 1-hydroxypropyl group, a 4-hydroxybutyl group, a 3-hydroxybutyl group, a 2-hydroxybutyl group, a 1-hydroxybutyl group, a 5-hydroxypentyl group and a 6-hydroxyhexyl group.

The term "$C_7$-$C_{10}$ aralkyl group" as used herein means a $C_1$-$C_4$ alkyl group substituted with a phenyl group. Examples of the $C_7$-$C_{10}$ aralkyl group include a benzyl group, a 2-phenylethyl group, a 1-phenylethyl group, a 3-phenylpropyl group, a 1-phenylpropyl group and a 4-phenylbutyl group.

The term "amino group optionally having one or two $C_1$-$C_6$ alkyl groups" as used herein means an amino group in which one or two hydrogen atoms thereof are optionally substituted with a linear alkyl group or branched alkyl group having 1 to 6 carbon atoms. Examples include an amino group, a methylamino group, an ethylamino group, a propylamino group, an isopropylamino group, a butylamino group, an isobutylamino group, a sec-butylamino group, a tert-butylamino group, a pentylamino group, an isopentylamino group, a neopentylamino group, a 1-methylbutylamino group, a 2-methylbutylamino group, a 1,2-dimethylpropylamino group, a hexylamino group, an isohexylamino group, a dimethylamino group, a diethylamino group, a N-ethyl-N-methylamino group and a N-ethyl-N-propylamino group.

The term "aminocarbonyl group optionally having one or two $C_1$-$C_6$ alkyl groups" as used herein means an aminocarbonyl group in which one or two hydrogen atoms of an amino group are optionally substituted with a linear alkyl group or branched alkyl group having 1 to 6 carbon atoms. Examples include an aminocarbonyl group, a methylaminocarbonyl group, an ethylaminocarbonyl group, a propylaminocarbonyl group, an isopropylaminocarbonyl group, a butylaminocarbonyl group, an isobutylaminocarbonyl group, a sec-butylaminocarbonyl group, a tert-butylaminocarbonyl group, a pentylaminocarbonyl group, an isopentylaminocarbonyl group, a neopentylaminocarbonyl group, a 1-methylbutylaminocarbonyl group, a 2-methylbutylaminocarbonyl group, a 1,2-dimethylpropylaminocarbonyl group, a hexylaminocarbonyl group, an isohexylaminocarbonyl group, a dimethylaminocarbonyl group, a diethylaminocarbonyl group, a N-ethyl-N-methylaminocarbonyl group and a N-ethyl-N-propylaminocarbonyl group.

The term "aminosulfonyl group optionally having one or two $C_1$-$C_6$ alkyl groups" as used herein means an aminosulfonyl group in which one or two hydrogen atoms of an amino group are optionally substituted with a linear alkyl group or branched alkyl group having 1 to 6 carbon atoms. Examples include an aminosulfonyl group, a methylaminosulfonyl group, an ethylaminosulfonyl group, a propylaminosulfonyl group, an isopropylaminosulfonyl group, a butylaminosulfonyl group, an isobutylaminosulfonyl group, a sec-butylaminosulfonyl group, a tert-butylaminosulfonyl group, a pentylaminosulfonyl group, an isopentylaminosulfonyl group, a neopentylaminosulfonyl group, a 1-methylbutylaminosulfonyl group, a 2-methylbutylaminosulfonyl group, a 1,2-dimethylpropylaminosulfonyl group, a hexylaminosulfonyl group, an isohexylaminosulfonyl group, a dimethylaminosulfonyl group, a diethylaminosulfonyl group, a N-ethyl-N-methylaminosulfonyl group and a N-ethyl-N-propylaminosulfonyl group.

Now, the present embodiment will be described in more detail.

In the following description, definition of each functional group included in a general formula may be sometimes omitted by referring to definition already given. Referred definition corresponds to definition mentioned in the following description of the embodiment.

The present embodiment relates to a compound represented by the following general formula (1) or a pharmacologically acceptable salt thereof.

[Formula 33]

(1)

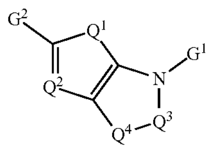

In the general formula (1), $Q^1$ is —C(R$^1$)═C(R$^2$)—, —C(R$^3$)═N— or a sulfur atom;

$Q^2$ is C(R$^4$) or a nitrogen atom;

$Q^3$ is $—(CH_2)_m—(CR^5R^6)_n— (CH_2)_p—$;

$Q^4$ is a single bond, a methylene group, an oxygen atom, a sulfur atom, a SO group, a $SO_2$ group, a methyleneoxy group, a difluoromethylene group or a NR$^7$ group;

$G^1$ is a phenyl group, a 5-membered aromatic heterocyclic group, a 6-membered aromatic heterocyclic group, a condensed heterocyclic group having 8 to 10 ring atoms (excluding a 6,7-dihydro-4H-thiazolo[5,4-c]pyridine ring), a $C_3$-$C_8$ cycloalkyl group or a 3- to 8-membered heterocycloalkyl group, each optionally having one or more substituents selected from group A;

$G^2$ is —C(═O)—NR$^8$R$^9$, —C(═O)—NR$^{10}$R$^{11}$, —C(═O)—CHR$^{12}$R$^{13}$, —CH(OH)—CHR$^{12}$R$^{13}$, —S—CHR$^{12}$R$^{13}$, —S(═O)—CHR$^{12}$R$^{13}$ or —SO$_2$—CHR$^{12}$R$^{13}$;

$R^1$ and $R^2$ are the same or different, and a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^3$ is a hydrogen atom, or a $C_2$-$C_6$ alkyl group, a $C_1$-$C_6$ alkoxy group or a $C_3$-$C_8$ cycloalkyl group, each optionally having one or more substituents selected from group C;

$R^4$ is a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^5$ and $R^6$ are the same or different, and a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^7$ is a hydrogen atom, or a $C_1$-$C_6$ alkyl group, a $C_3$-$C_8$ cycloalkyl group, a $C_1$-$C_6$ alkylcarbonyl group, a phenyl group, a 5-membered aromatic heterocyclic group or a 6-membered aromatic heterocyclic group, each optionally having one or more substituents selected from group C;

$R^8$ and $R^9$ are the same or different, and a hydrogen atom, or a $C_1$-$C_6$ alkyl group or a $C_3$-$C_8$ cycloalkyl group, each optionally having one or more substituents selected from group B;

when one of $R^8$ and $R^9$ is a hydrogen atom, the other is a $C_1$-$C_6$ alkyl group having one or more substituents selected from a halogen atom, a hydroxy group, a carboxyl group, a $C_1$-$C_6$ alkylcarbonyl group, a $C_1$-$C_6$ alkoxy group and a $C_1$-$C_6$ alkoxycarbonyl group;

$R^{10}$ and $R^{11}$ are, together with the nitrogen atom to which they are attached, a nitrogen-containing heterocycloalkyl group having 3 to 11 ring atoms optionally having one or more substituents selected from group B;

$R^{12}$ and $R^{13}$ are the same or different, and a $C_1$-$C_6$ alkyl group, a $C_3$-$C_8$ cycloalkyl group or a 3- to 8-membered heterocycloalkyl group, each optionally having one or more substituents selected from group B; or $R^{12}$ and $R^{13}$ are, together with the carbon atom to which they are attached, a $C_3$-$C_5$ cycloalkyl group optionally having one or more substituents selected from group B;

group A consists of a halogen atom, a hydroxy group, a carbonyl group, a nitrile group, a carboxyl group, a formyl group, an oxo group (=O); and $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_8$ cycloalkyl group, a $C_3$-$C_8$ cycloalkylcarbonyl group, a $C_3$-$C_8$ cycloalkoxy group, a $C_3$-$C_8$ cycloalkylsulfonyl group, a $C_3$-$C_8$ cycloalkylsulfonylamino group, a 3- to 8-membered heterocycloalkyl group containing an oxygen atom, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A1; an amino group, an aminocarbonyl group and an aminosulfonyl group, each optionally having one or two $C_1$-$C_6$ alkyl groups optionally having, in an amino group, one or more substituents selected from group A1; and a phenyl group, a 5-membered aromatic heterocyclic group and a 6-membered aromatic heterocyclic group, each optionally having one or more substituents selected from group B;

group A1 consists of a halogen atom, a hydroxy group, a carbonyl group, a nitrile group, a carboxyl group, a formyl group, an oxo group (=O); and a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_8$ cycloalkyl group, a 3- to 8-membered heterocycloalkyl group, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A2; an aminocarbonyl group and an amino group, each optionally having one or two $C_1$-$C_6$ alkyl groups optionally having one or more substituents selected from group A2; and a phenyl group, a 5-membered aromatic heterocyclic group and a 6-membered aromatic heterocyclic group, each optionally having one or more substituents selected from group B;

group A2 consists of a halogen atom, a hydroxy group, a nitrile group, a carboxyl group, a formyl group, an oxo group (=O), a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a 5-membered aromatic heterocyclic group, a 6-membered aromatic heterocyclic group, and a 3- to 8-membered heterocycloalkyl group;

group B consists of a halogen atom, a hydroxy group, a nitrile group, a carbonyl group, an oxo group (=O), a carboxyl group, a $C_1$-$C_6$ alkyl group, a $C_1$-$C_6$ alkynyl group, a halo $C_1$-$C_6$ alkyl group, a hydroxy $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkoxy $C_1$-$C_6$ alkyl group, a $C_1$-$C_6$ alkoxycarbonyl $C_1$-$C_6$ alkyl group, a $C_3$-$C_0$ cycloalkyl group, a $C_3$-$C_0$ cycloalkylcarbonyl group, a $C_3$-$C_8$ cycloalkoxy group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group and an amino group optionally having one or two $C_1$-$C_6$ alkyl groups;

group C consists of a halogen atom, a hydroxy group, a nitrile group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, an amino group optionally having one or two $C_1$-$C_6$ alkyl groups, and a 3- to 8-membered heterocycloalkyl group; and each of m, n, p is 0, 1 or 2, and m+n+p is an integer of 2 to 5.

With regard to the compound (1) of the present embodiment or a pharmacologically acceptable salt thereof, preferred compounds are as follows.

The compound represented by the general formula (1) is preferably a compound represented by a formula selected from the group consisting of the following A1a), A1b), A2a), A2b), A2c), A2d), A2e), A3a) and A3b):

[Formula 34]

A1a)

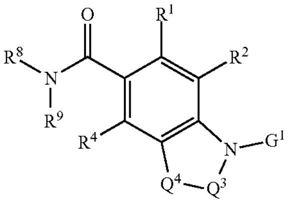

A1b)

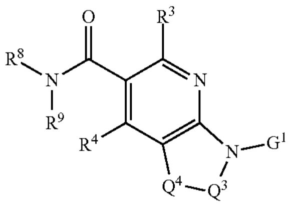

A2a)

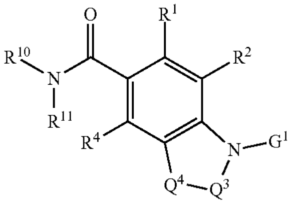

-continued
A2b)
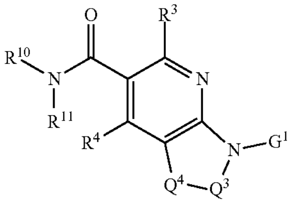
A2c)
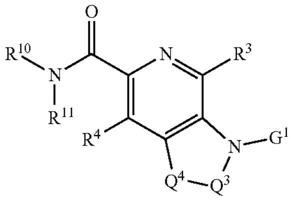
A2d)
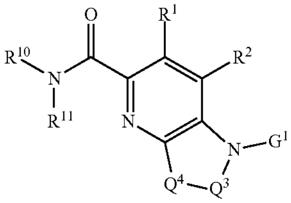
A2e)
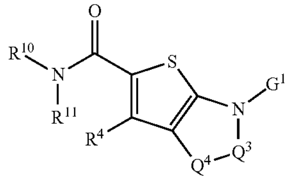
A3a)
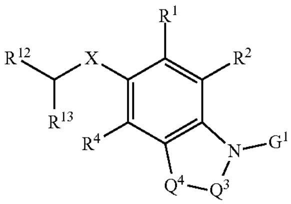
A3b)
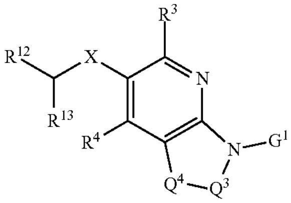
In the general formula (1), preferably, $NR^{10}R^{11}$ in —$CONR^{10}R^{11}$ of $G^2$ is a group selected from the group consisting of the following B1) to B20), or —$CHR^{12}R^{13}$ of $G^2$ is a group represented by the following $C_1$):
[Formula 35]
B1)
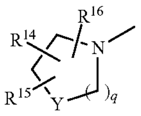
-continued
B2)
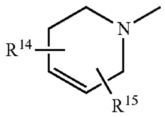
B3)
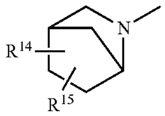
B4)
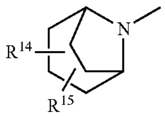
B5)
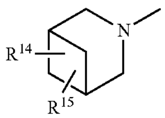
B6)
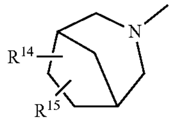
B7)
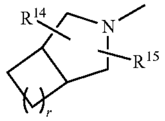
B8)
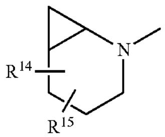
B9)
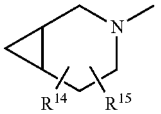
B10)
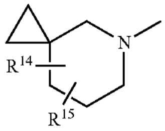
B11)
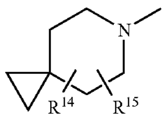
B12)
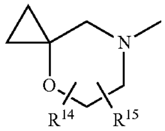
B13)
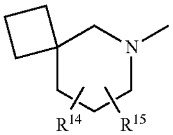

-continued
B14)
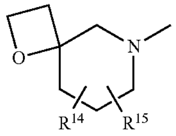
B15)
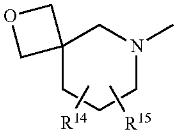
B16)
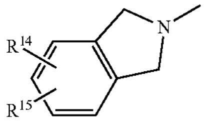
B17)
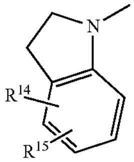
B18)
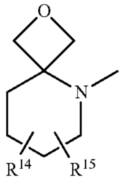
B19)
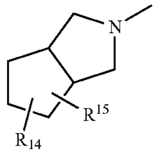
B20)
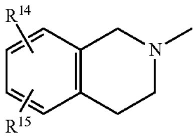
C1)
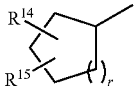
The compound represented by the general formula (1) is more preferably a compound represented by a formula selected from the group consisting of the following A1aa), A1ba), A2aa), A2ba), A2ca), A2da), A2ea), A3aa) and A3ba):
[Formula 36]
A1aa)
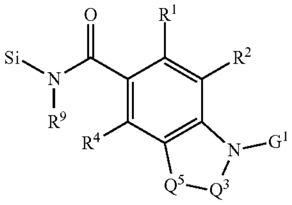
-continued
A1ba)
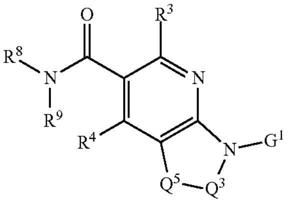
A2aa)
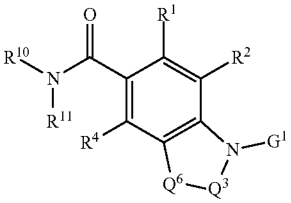
A2ba)
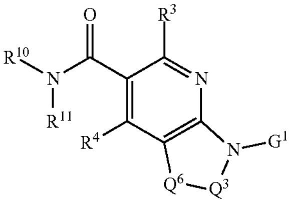
A2ca)
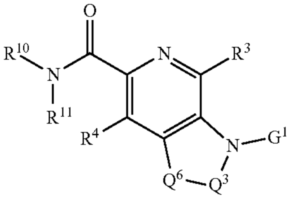
A2da)
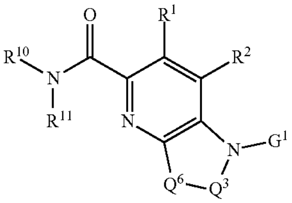
A2ea)
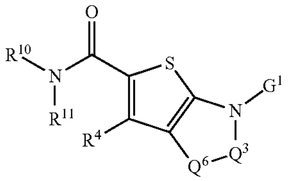
A3aa)
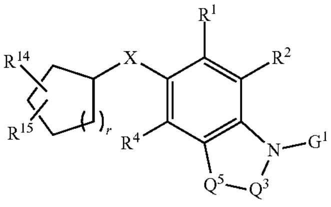

-continued
A3ba)
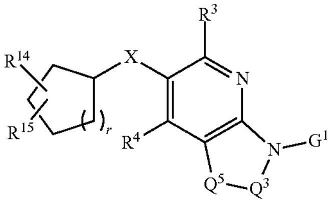
In the general formula (1), $G^1$ is preferably a group selected from the following G1a), G1b), G1c), G1d), G1e), G1f), G1g), G1h), G1i), G1j), G1k), G1l), G1m), G1n), G1o), G1p), G1q), G1r), G1s), G1t), G1u), G1v), G1w), G1x), G1y), G1z), G1A), G1B), G1C), G1D), G1E), G1F), G1G), G1H), G1I), G1J), G1K), G1L), G1M), G1N), G1O), G1P), G1Q), G1R), G1S) and G1T):
[Formula 37]
G1a)
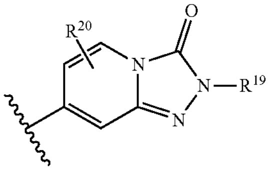
G1b)
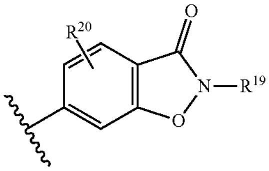
G1c)
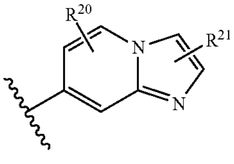
G1d)
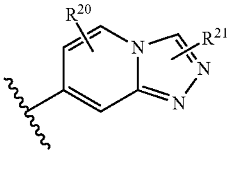
G1e)
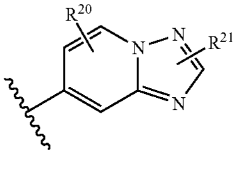
G1f)
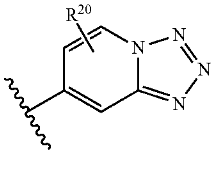
-continued
G1g)
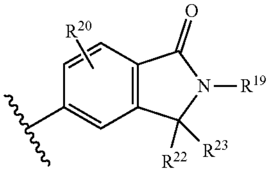
G1h)
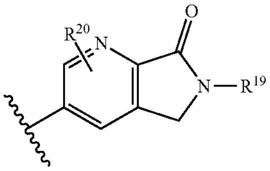
G1i)
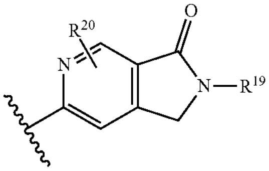
G1j)
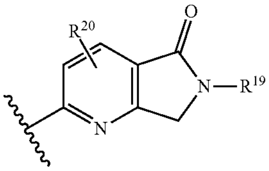
G1k)
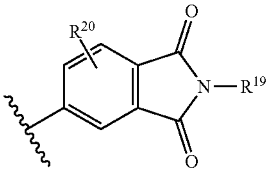
G1l)
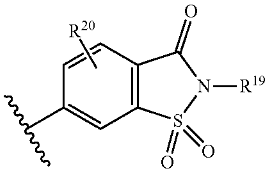
G1m)
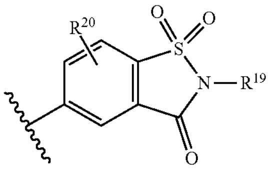
G1n)
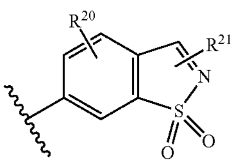
G1o)
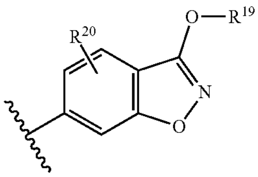

G1p)
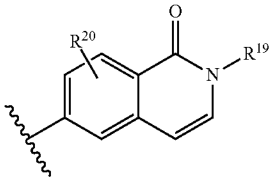
G1q)
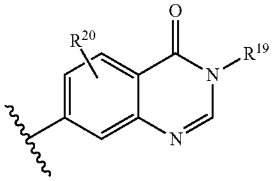
G1r)
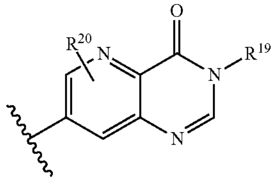
G1s)
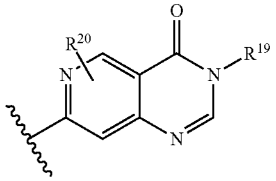
G1t)
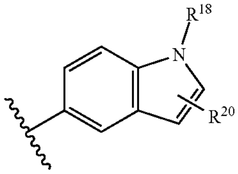
G1u)
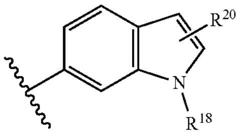
G1v)
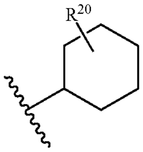
G1w)
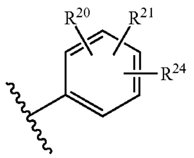
G1x)
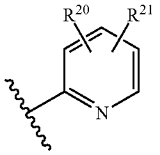
G1y)
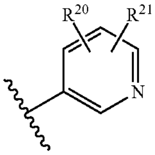
G1z)
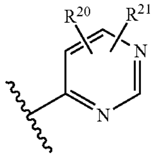
G1A)
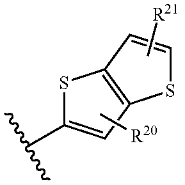
G1B)
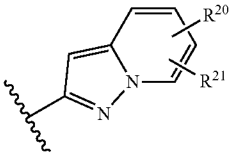
G1C)
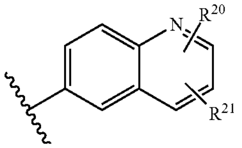
G1D)
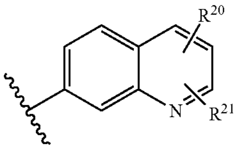
G1E)
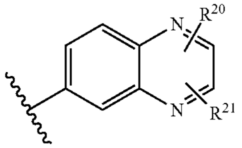
G1F)
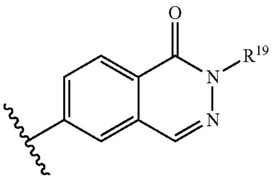
G1G)
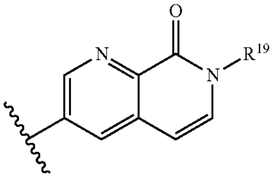

-continued
G1H)
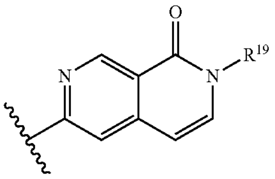
G1I)
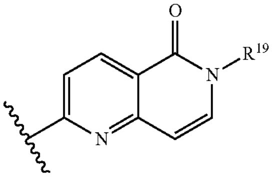
G1J)
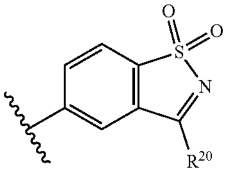
G1K)
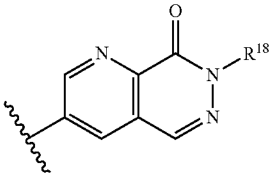
G1L)
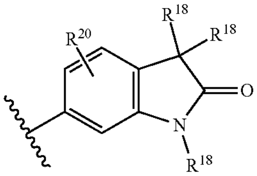
G1M)
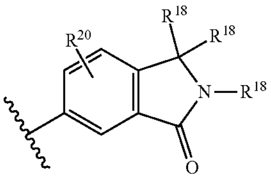
G1N)
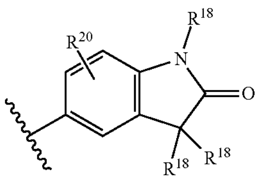
G1O)
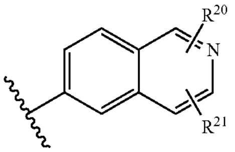
-continued
G1P)
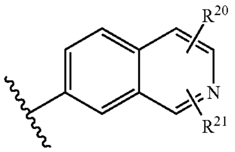
G1Q)
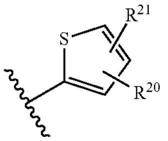
G1R)
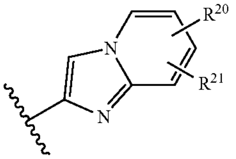
G1S)
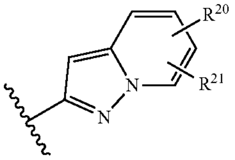
G1T)
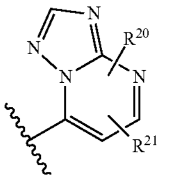
In the general formula (1), $G^1$ is more preferably a group selected from the following G1aa), G1ba), G1ca), G1fa), G1ga), G1ha), G1ia), G1la), G1oa), G1pa), G1qa), G1va), G1wa), G1xa), G1ya) and G1Aa):
[Formula 9]
(G1aa)
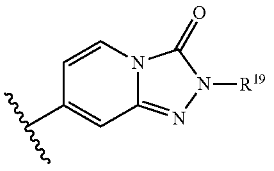
G1ba)
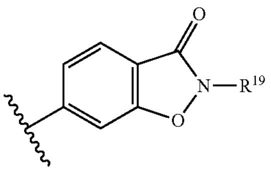
G1ca)
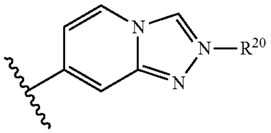

-continued

G1fa)

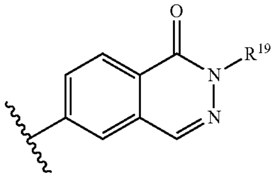

G1ga)

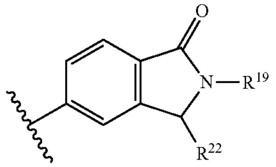

G1ha)

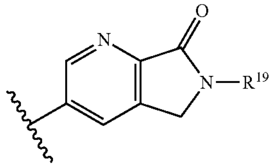

G1ia)

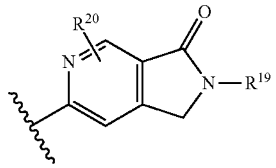

G1la)

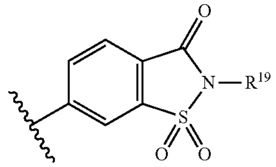

G1oa)

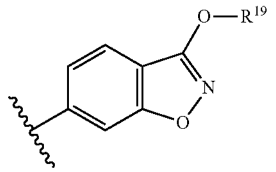

G1pa)

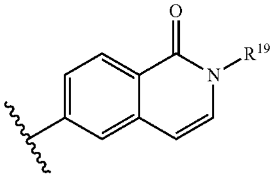

G1qa)

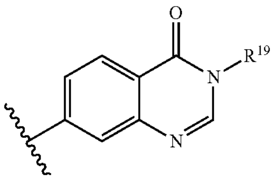

G1va)

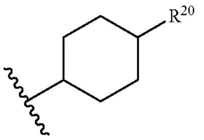

-continued

G1wa)

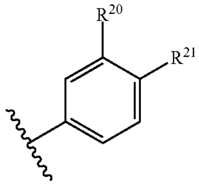

G1xa)

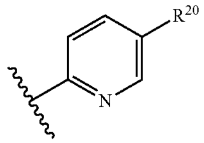

G1ya)

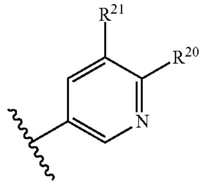

G1Aa)

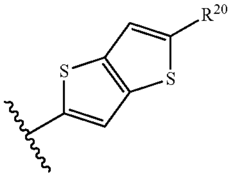

$R^1$ and $R^2$ are preferably the same or different, and a hydrogen atom, a halogen atom, or a $C_1$-$C_3$ alkyl group, a $C_1$-$C_3$ alkoxy group or a $C_3$-$C_8$ cycloalkyl group, each optionally having one or more substituents selected from group C;

$R^1$ and $R^2$ are more preferably the same or different, and a hydrogen atom, a halogen atom, a $C_1$-$C_3$ alkyl group, a $C_1$-$C_3$ alkoxy group or a $C_3$-$C_8$ cycloalkyl group;

$R^3$ is preferably a hydrogen atom, or a $C_1$-$C_3$ alkyl group or a $C_1$-$C_3$ alkoxy group optionally having one or more substituents selected from group C;

$R^3$ is more preferably a hydrogen atom, a $C_1$-$C_3$ alkyl group or a $C_1$-$C_3$ alkoxy group;

$R^4$ is preferably a hydrogen atom, a halogen atom, or a $C_1$-$C_3$ alkyl group, a $C_1$-$C_3$ alkoxy group or a $C_3$-$C_8$ cycloalkyl group, each optionally having one or more substituents selected from group C;

$R^4$ is more preferably a hydrogen atom, a halogen atom, a $C_1$-$C_3$ alkyl group, a $C_1$-$C_3$ alkoxy group or a $C_3$-$C_8$ cycloalkyl group;

$R^5$ and $R^6$ are preferably the same or different, and a hydrogen atom, a halogen atom, or a $C_1$-$C_6$ alkyl group, a $C_1$-$C_6$ alkoxy group or a $C_3$-$C_8$ cycloalkyl group, each optionally having one or more substituents selected from group C;

$R^5$ and $R^6$ are more preferably the same or different, and a hydrogen atom, a halogen atom, or a $C_1$-$C_3$ alkyl group or a $C_1$-$C_3$ alkoxy group, each optionally having one or more substituents selected from group C;

$R^7$ is preferably a hydrogen atom, or a $C_1$-$C_6$ alkyl group or a $C_3$-$C_8$ cycloalkyl group, each optionally having one or more substituents selected from group C;

$R^7$ is more preferably a hydrogen atom, or a $C_1$-$C_3$ alkyl group optionally having one or more substituents selected from group C; and $R^7$ is most preferably a hydrogen atom, or a $C_1$-$C_3$ alkyl group.

$R^8$ and $R^9$ are preferably the same or different, and a hydrogen atom, or a $C_1$-$C_6$ alkyl group optionally having one or more substituents selected from group B;

when one of $R^8$ and $R^9$ is a hydrogen atom, the other is a $C_1$-$C_6$ alkyl group having one or more substituents selected from group B;

$R^8$ and $R^9$ are more preferably the same or different, and a hydrogen atom, or a $C_1$-$C_6$ alkyl group optionally having one or more substituents selected from group D1;

when one of $R^8$ and $R^9$ is a hydrogen atom, the other is a $C_1$-$C_6$ alkyl group having one or more substituents selected from group D1;

$R^{10}$ and $R^{11}$ preferably represent, together with the nitrogen atom to which they are attached, a nitrogen-containing heterocycloalkyl group optionally having one or more substituents selected from group B and having 3 to 11 ring atoms;

the nitrogen-containing heterocycloalkyl group is monocyclic, condensed bicyclic, or bicyclic optionally containing a bridged or spiro ring;

the nitrogen-containing heterocycloalkyl group optionally further contains one to three hetero atoms selected from a nitrogen atom, an oxygen atom and a sulfur atom;

$R^{12}$ and $R^{13}$ preferably represent, together with the carbon atom to which they are attached, a $C_3$-$C_8$ cycloalkyl group optionally having one or more substituents selected from group B;

$R^{14}$ and $R^{15}$ are preferably the same or different, and a hydrogen atom, a halogen atom, a hydroxy group, a nitrile group, a carboxyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group or a halo $C_1$-$C_6$ alkyl group;

$R^{14}$ and $R^{15}$ are optionally substituted in any ring in the formula;

$R^{16}$ is a hydrogen atom, or a $C_1$-$C_3$ alkyl group optionally having one or more substituents selected from group D;

$R^{17}$ and $R^{18}$ are preferably the same or different, and a hydrogen atom, a halogen atom, or a $C_1$-$C_3$ alkyl group or a $C_1$-$C_3$ alkoxy group, each optionally having one or more substituents selected from group D1;

$R^{17}$ and $R^{18}$ are preferably the same or different, and a hydrogen atom, a halogen atom, a $C_1$-$C_3$ alkyl group, a $C_1$-$C_3$ alkoxy group or a halo $C_1$-$C_3$ alkyl group;

$R^{19}$ is preferably a hydrogen atom, a 3- to 8-membered heterocycloalkyl group containing an oxygen atom, or a $C_3$-$C_8$ cycloalkyl group, a hydroxy $C_1$-$C_3$ alkyl group, a phenyl group, a phenyl $C_1$-$C_3$ alkyl group, a 6-membered aromatic heterocyclic group, a 6-membered aromatic heterocyclic $C_1$-$C_3$ alkyl group, a $C_1$-$C_3$ alkyl group or a $C_1$-$C_3$ alkoxy $C_1$-$C_3$ alkyl group, each optionally having one or more substituents selected from group C;

$R^{20}$ is preferably a hydrogen atom, a halogen atom, a hydroxy group, a nitrile group, a carboxyl group, a formyl group, or $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group, or a 3- to 8-membered heterocycloalkylaminocarbonyl group, each optionally having one or more substituents selected from group A3, or an aminocarbonyl group optionally having one or two $C_1$-$C_6$ alkyl groups optionally having one or more substituents selected from group B1, or a 5-membered aromatic heterocyclic group or a 6-membered aromatic heterocyclic group, each optionally having one or more substituents selected from group B1;

$R^{21}$ is preferably a hydrogen atom, a halogen atom, a hydroxy group, a nitrile group, a carboxyl group, a formyl group; or a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having one or more substituents selected from group B1; an amino group or an aminocarbonyl group, each optionally having one or two $C_1$-$C_6$ alkyl groups optionally having, in an amino group, one or more substituents selected from group A3; or a 5-membered aromatic heterocyclic group or a 6-membered aromatic heterocyclic group, each optionally having one or more substituents selected from group B1;

$R^{20}$ and $R^{21}$ are optionally substituted in any ring in the formula;

$R^{22}$ and $R^{23}$ are preferably the same or different, and a hydrogen atom, a halogen atom or a $C_1$-$C_3$ alkyl group;

$R^{24}$ is a hydrogen atom, or one or more substituents selected from group B1;

Y is preferably a methylene group, an oxygen atom, a sulfur atom or a N—$R^{16}$ group;

$Q^5$ is preferably a methylene group, an oxygen atom or a sulfur atom;

$Q^6$ is preferably a single bond, a methylene group, an oxygen atom, a sulfur atom, a SO group, a $SO_2$ group, a methyleneoxy group, a difluoromethylene group or $NR^7$, and more preferably a single bond, a methylene group, an oxygen atom or a methyleneoxy group.

each of m, n and p is 0, 1 or 2, and m+n+p is an integer of 2 to 5.

q and r are preferably 0, 1, 2 or 3.

Group A consists of a halogen atom, a hydroxy group, a carbonyl group, a nitrile group, a carboxyl group, a formyl group, an oxo group (═O); and a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_8$ cycloalkyl group, a $C_3$-$C_8$ cycloalkylcarbonyl group, a $C_3$-$C_8$ cycloalkoxy group, a $C_3$-$C_8$ cycloalkylsulfonyl group, a $C_3$-$C_8$ cycloalkylsulfonylamino group, a 3- to 8-membered heterocycloalkyl group containing an oxygen atom, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A1; an amino group, an aminocarbonyl group and an aminosulfonyl group, each optionally having one or two $C_1$-$C_6$ alkyl groups optionally having, in an amino group, one or more substituents selected from group A1; and a phenyl group, a 5-membered aromatic heterocyclic group and a 6-membered aromatic heterocyclic group, each optionally having one or more substituents selected from group B.

Group A1 consists of a halogen atom, a hydroxy group, a carbonyl group, a nitrile group, a carboxyl group, a formyl group, an oxo group (═O); and a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonyl group, a $C_1$-$C_6$ alkylsulfonylamino group, a $C_3$-$C_0$ cycloalkyl group, a 3- to 8-membered heterocycloalkyl group, a 3- to 8-membered heterocycloalkylcarbonyl group, a 3- to 8-membered heterocycloalkylamino group and a 3- to 8-membered heterocycloalkylaminocarbonyl group, each optionally having one or more substituents selected from group A2; an aminocarbonyl group and an amino group, each optionally having one or two $C_1$-$C_6$ alkyl groups optionally having one or more substituents selected from group A2; and a phenyl group, a 5-membered aromatic heterocyclic group and a 6-membered aromatic heterocyclic group, each optionally having one or more substituents selected from group B.

Group A2 consists of a halogen atom, a hydroxy group, a nitrile group, a carboxyl group, a formyl group, an oxo group (=O), a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a 5-membered aromatic heterocyclic group, a 6-membered aromatic heterocyclic group, and a 3- to 8-membered heterocycloalkyl group.

Group A3 consists of a halogen atom, a hydroxy group, a nitrile group, a carboxyl group, an oxo group (=O), a formyl group, a $C_1$-$C_6$ alkyl group, a $C_1$-$C_6$ alkynyl group, a $C_1$-$C_6$ alkylcarbonyl group, a $C_1$-$C_6$ alkoxy group, a $C_1$-$C_6$ alkoxycarbonyl group and a $C_1$-$C_6$ alkylsulfonylamino group.

Group B consists of a halogen atom, a hydroxy group, a nitrile group, a carbonyl group, a carboxyl group, a $C_1$-$C_6$ alkyl group, a halo $C_1$-$C_6$ alkyl group, a hydroxy $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkoxy $C_1$-$C_6$ alkyl group, a $C_1$-$C_6$ alkoxycarbonyl $C_1$-$C_6$ alkyl group, a $C_3$-$C_8$ cycloalkyl group, a $C_3$-$C_8$ cycloalkylcarbonyl group, a $C_3$-$C_8$ cycloalkoxy group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group, and an amino group optionally having one or two $C_1$-$C_6$ alkyl groups.

Group B1 consists of a halogen atom, a hydroxy group, a nitrile group, a carbonyl group, a carboxyl group, a $C_1$-$C_6$ alkyl group, a halo $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkylsulfonylamino group, an aminocarbonyl group optionally having one or two $C_1$-$C_6$ alkyl groups, an amino group optionally having one or two $C_1$-$C_6$ alkyl groups, and a 3- to 8-membered heterocycloalkyl group.

Group C consists of a halogen atom, a hydroxy group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, an amino group optionally having one or two $C_1$-$C_6$ alkyl groups and a 3- to 8-membered heterocycloalkyl group.

Group D consists of a halogen atom, a hydroxy group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group, an amino group optionally having one or two $C_1$-$C_6$ alkyl groups and a 3- to 8-membered heterocycloalkyl group.

Group D1 consists of a halogen atom, a hydroxy group, a carboxyl group, a $C_1$-$C_6$ alkylcarbonyl group, a $C_1$-$C_6$ alkoxy group and a $C_1$-$C_6$ alkoxycarbonyl group.

Examples of a preferable compound of the present embodiment include the following compounds:

[Formula 39]

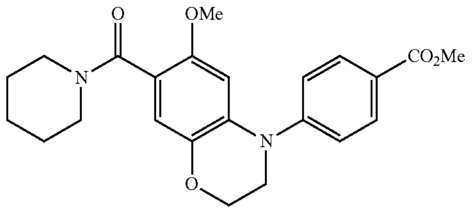

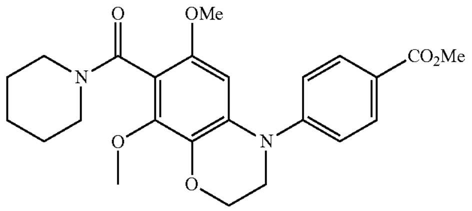

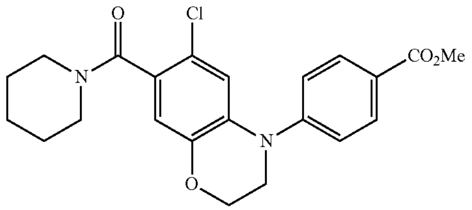

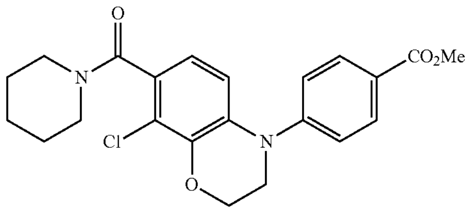

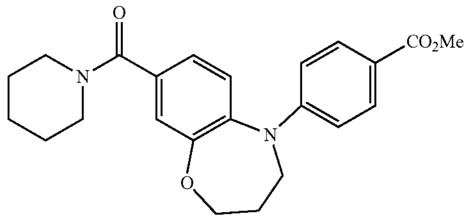

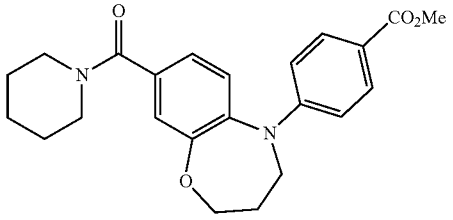

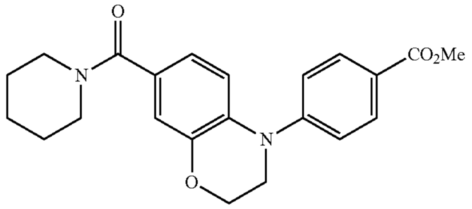

-continued
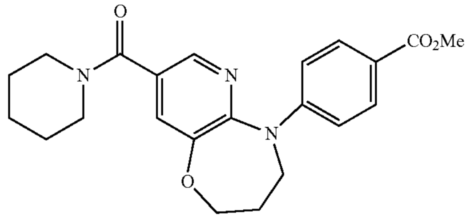
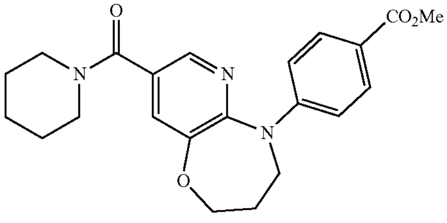
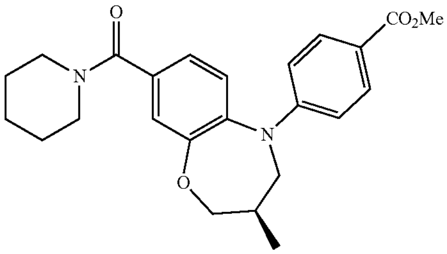
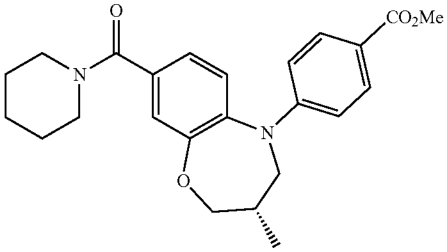
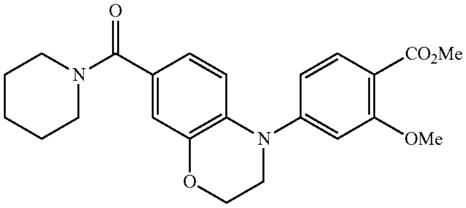
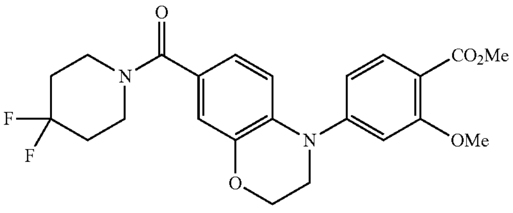
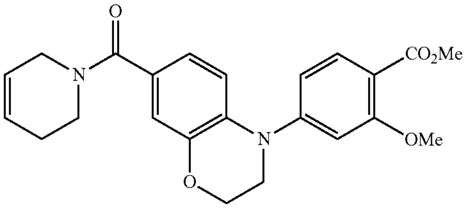
-continued
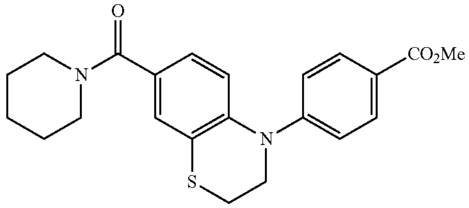
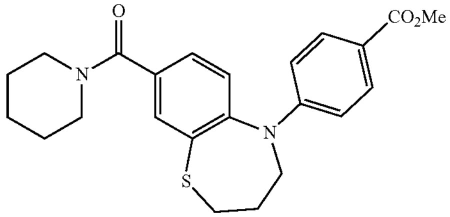
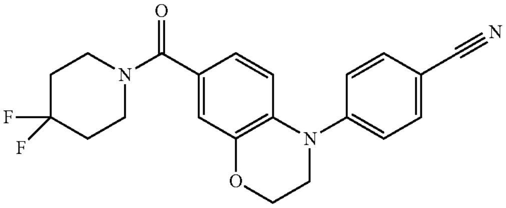
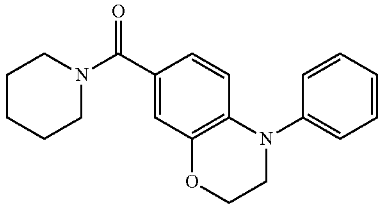
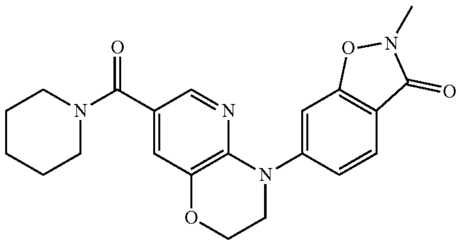
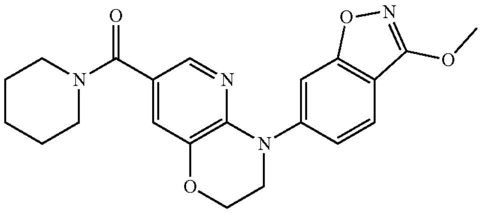
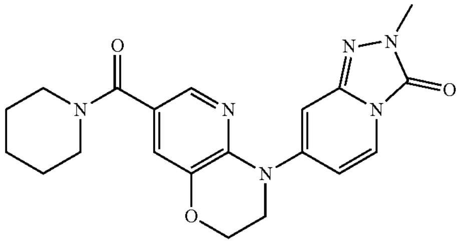

-continued
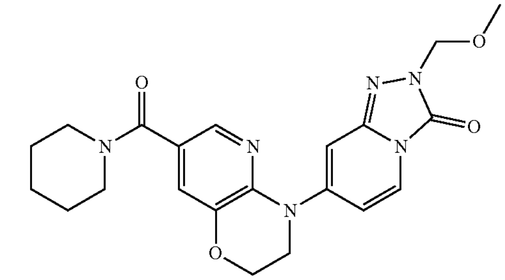
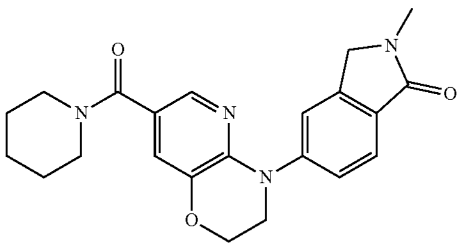
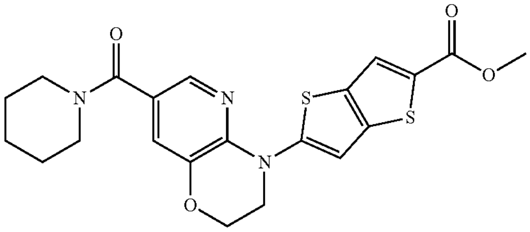
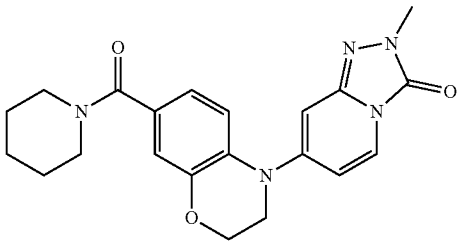
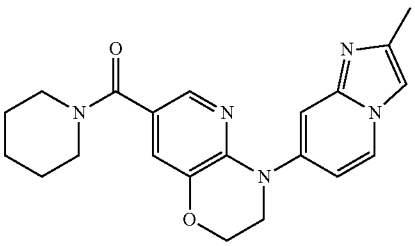
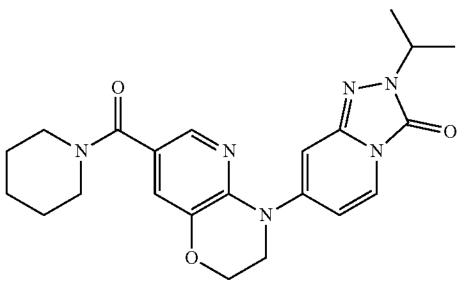
-continued
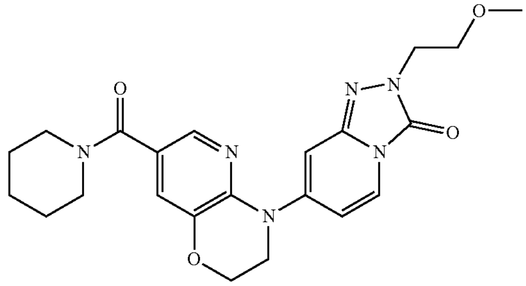
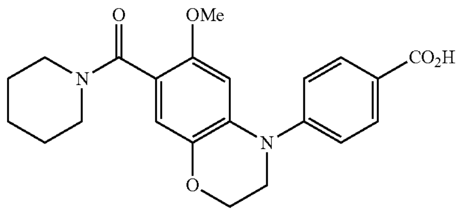
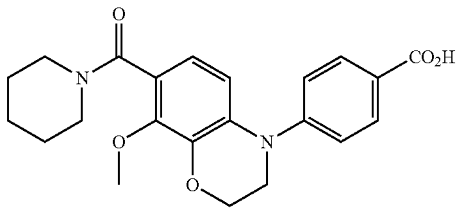
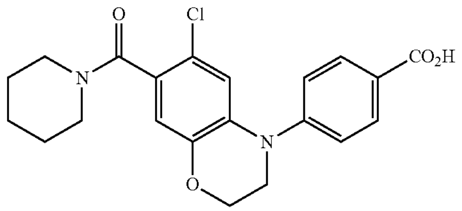
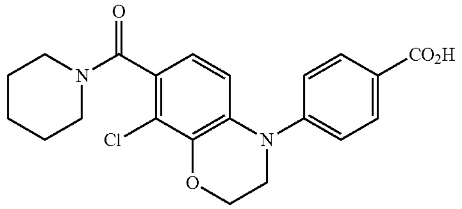
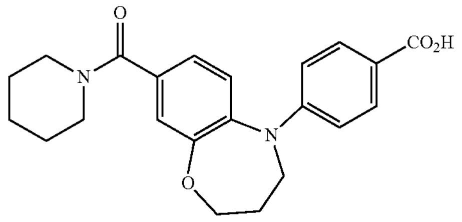
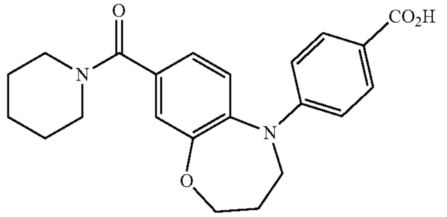

-continued
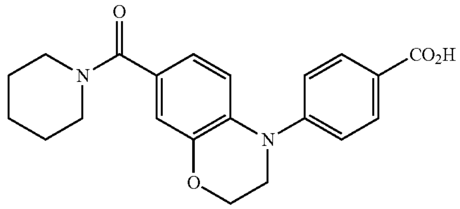
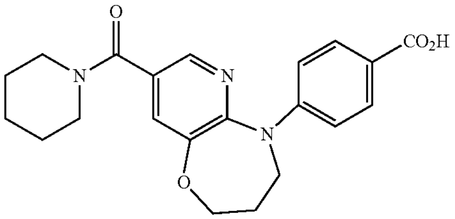
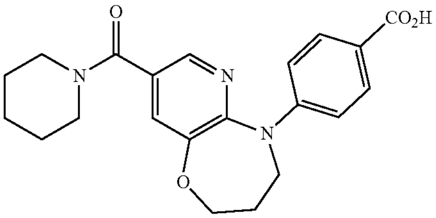
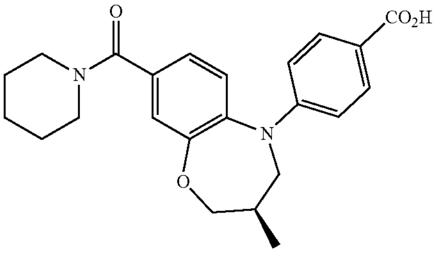
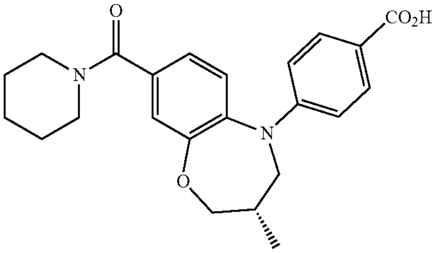
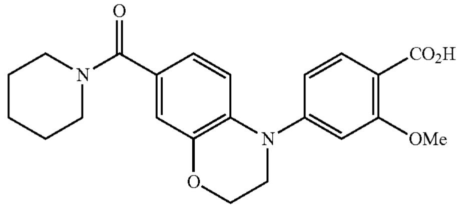
[Formula 40]
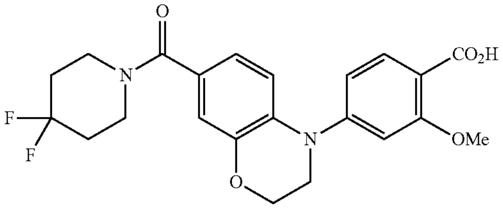
-continued
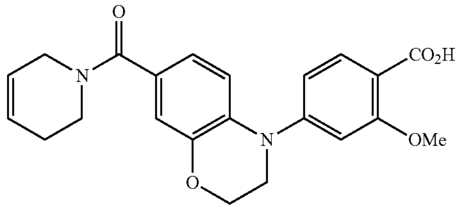
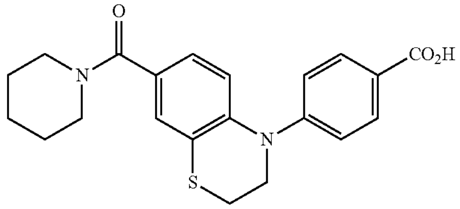
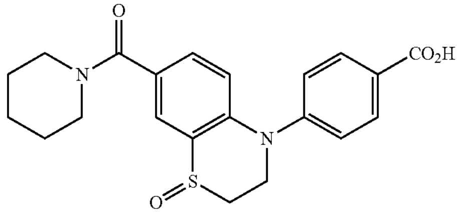
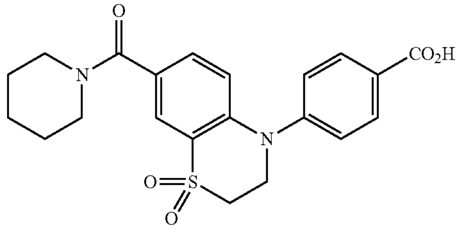
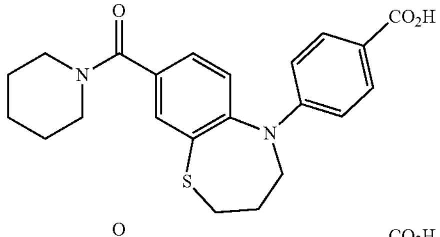
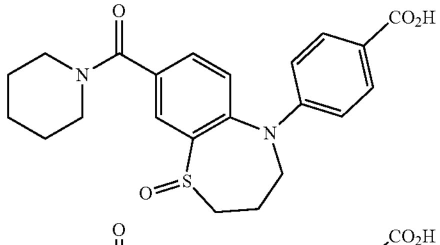
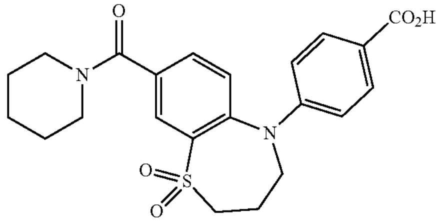
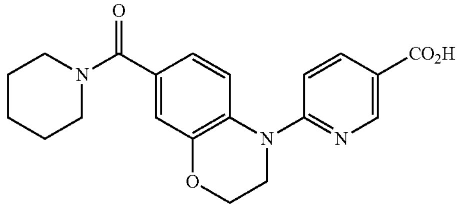

-continued
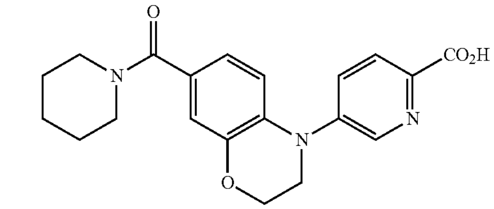
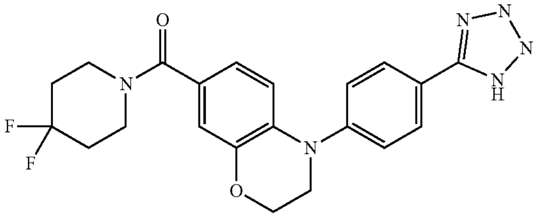
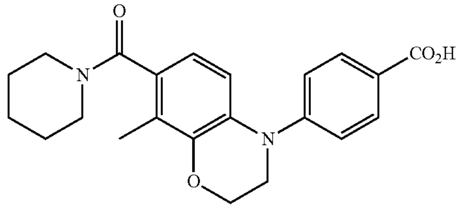
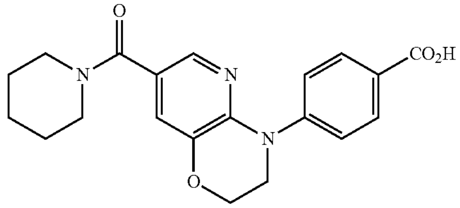
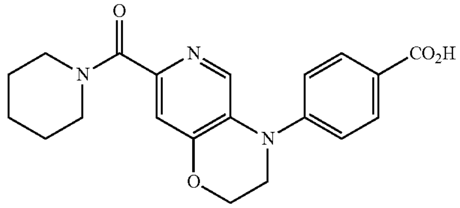
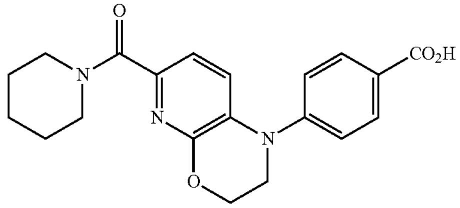
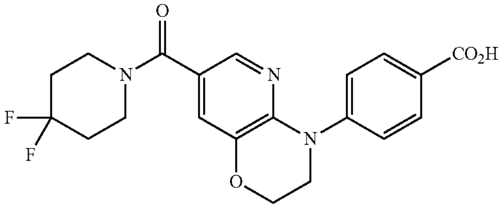
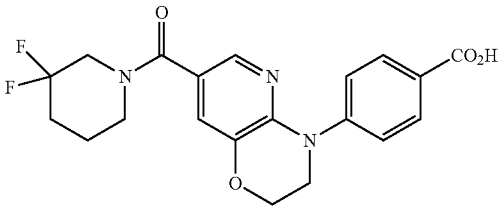
-continued
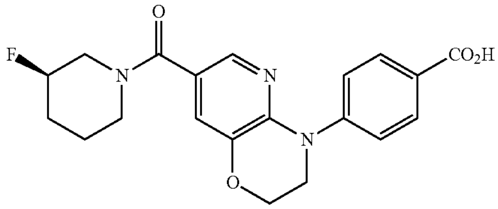
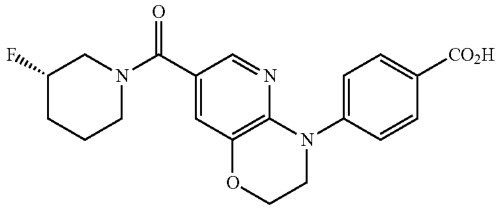
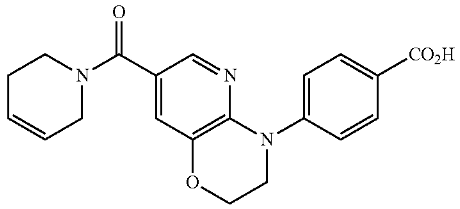
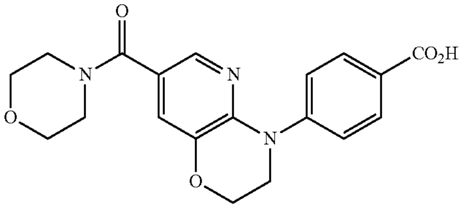
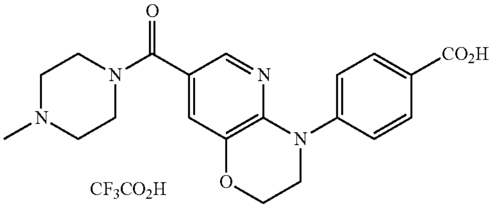
$CF_3CO_2H$
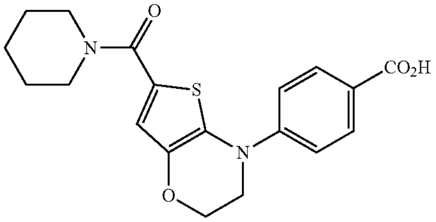
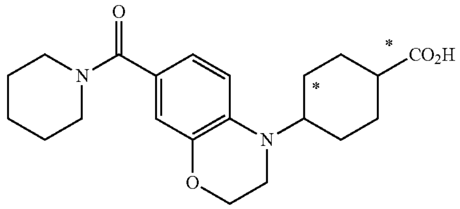
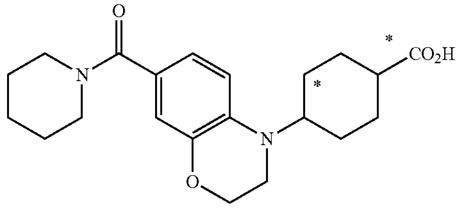

-continued
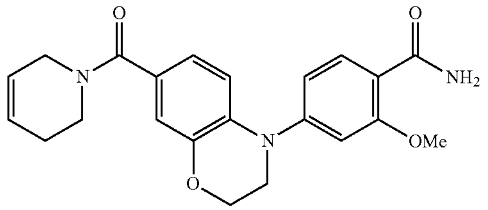
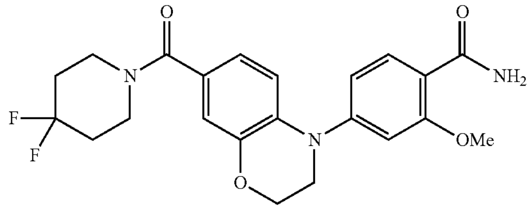
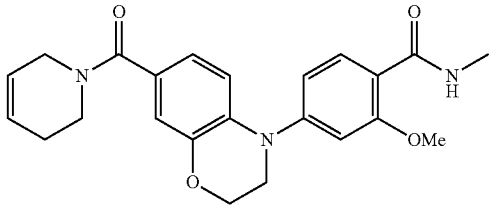
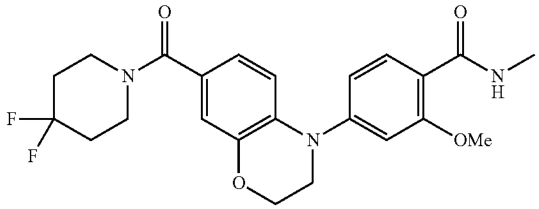
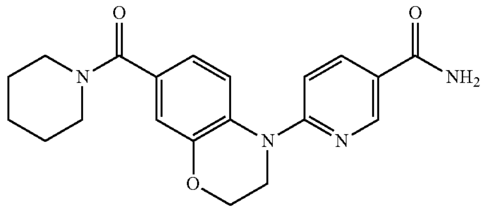
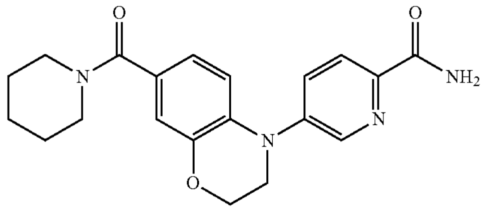
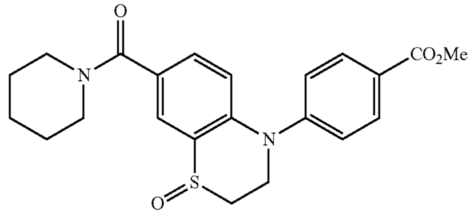
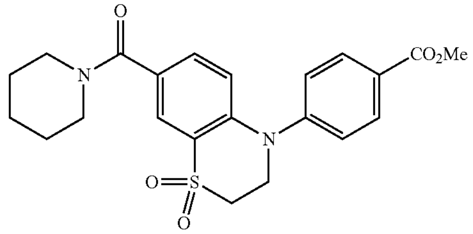
-continued
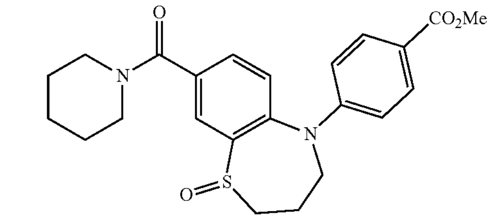
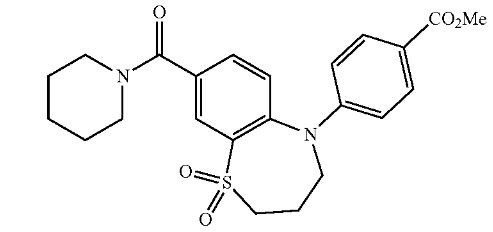
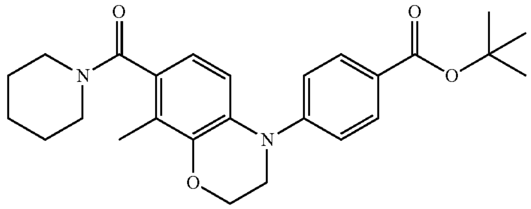
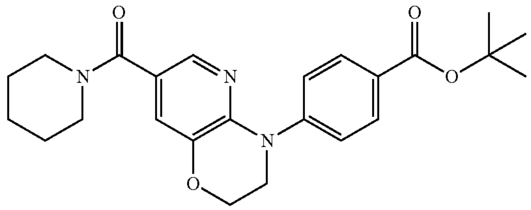
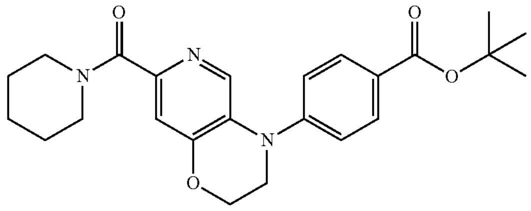
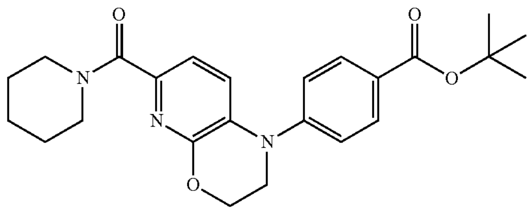
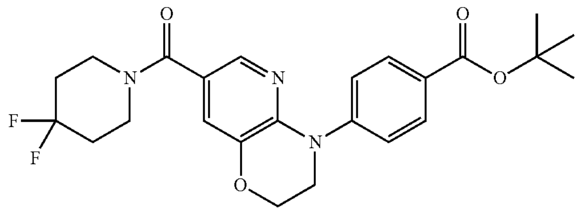
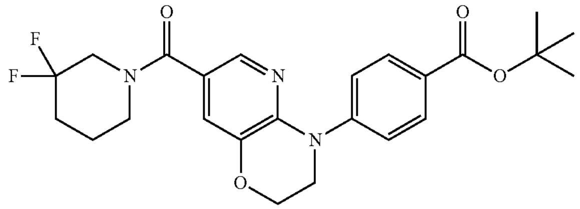

-continued
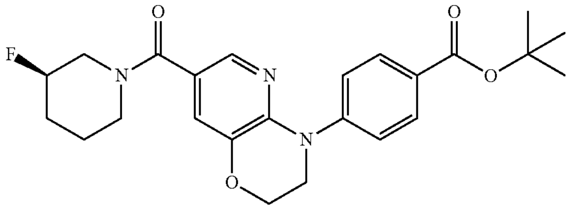
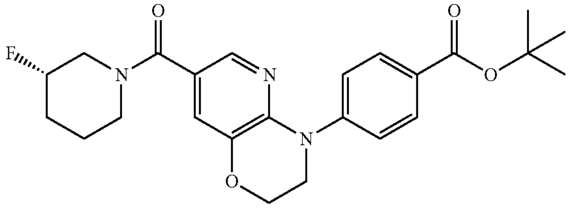
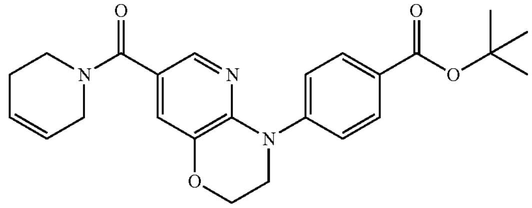
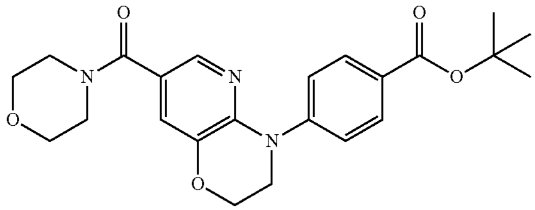
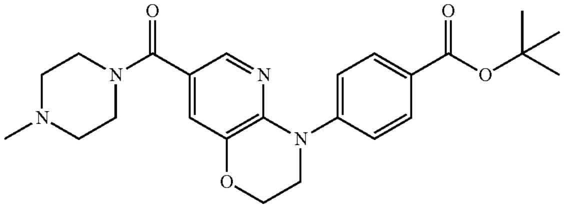
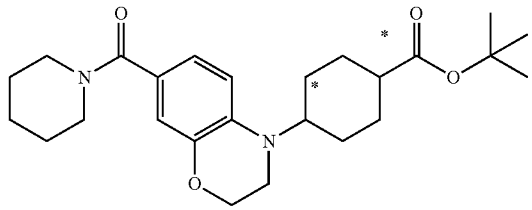
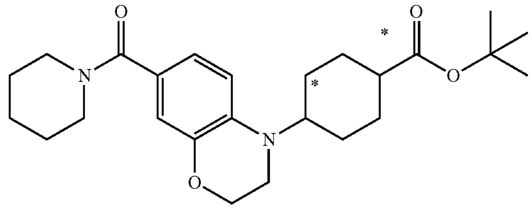
[Formula 41]
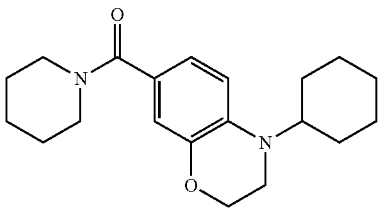
-continued
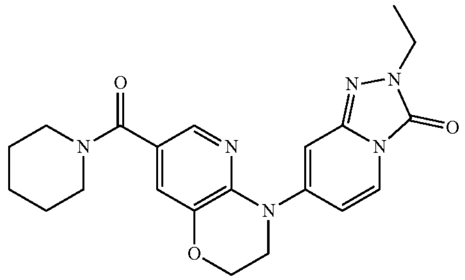
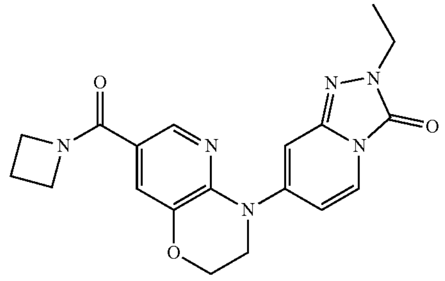
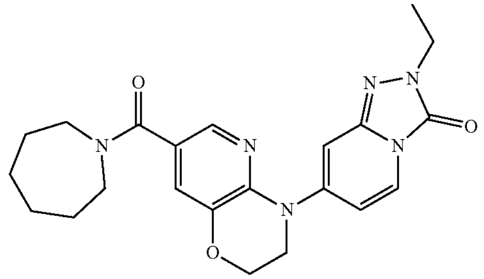
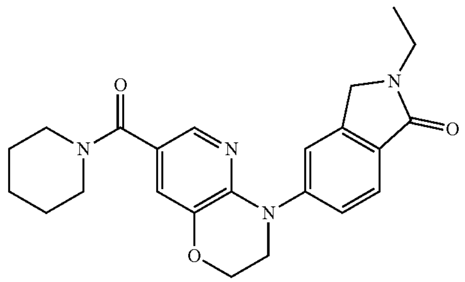
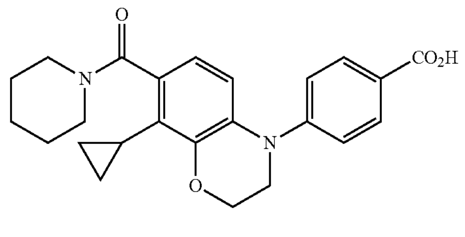
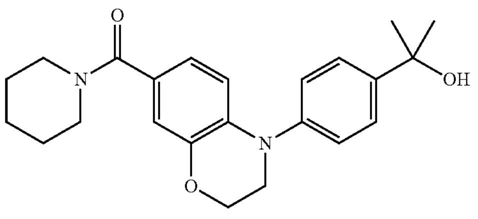

-continued
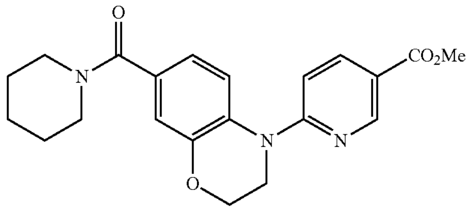
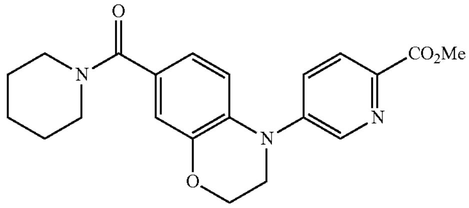
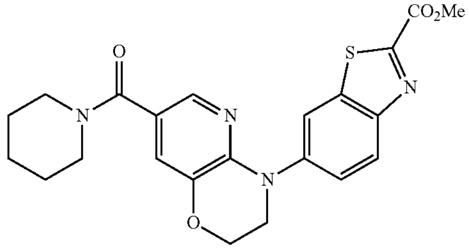
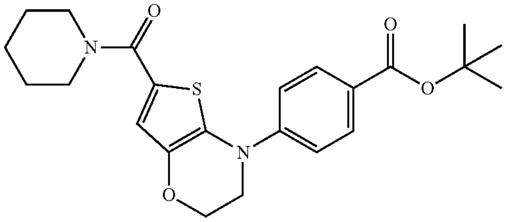
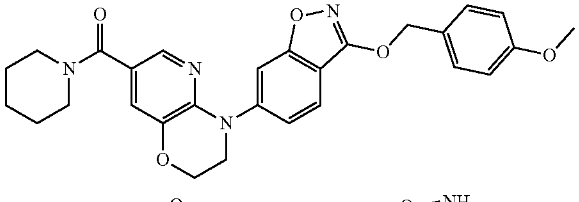
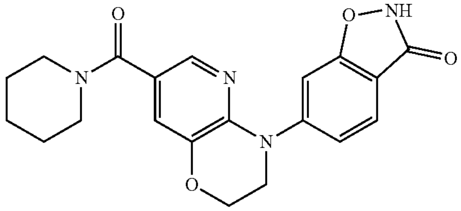
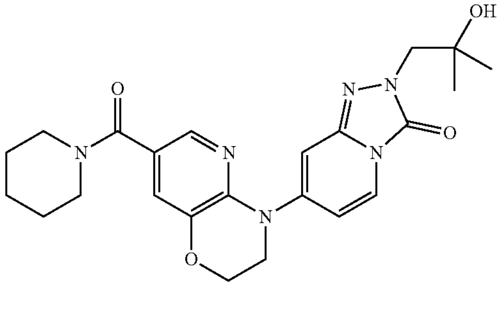
-continued
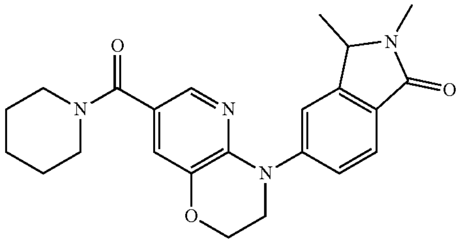
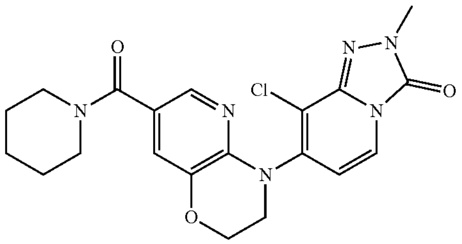
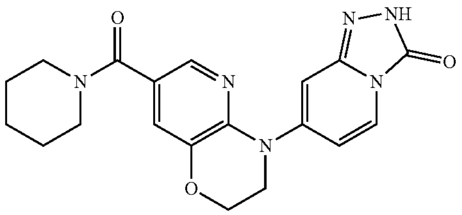
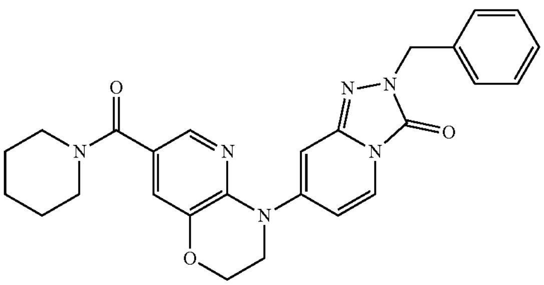
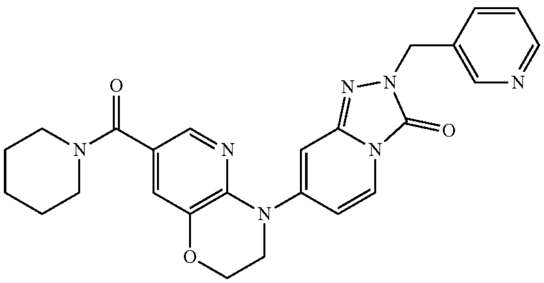
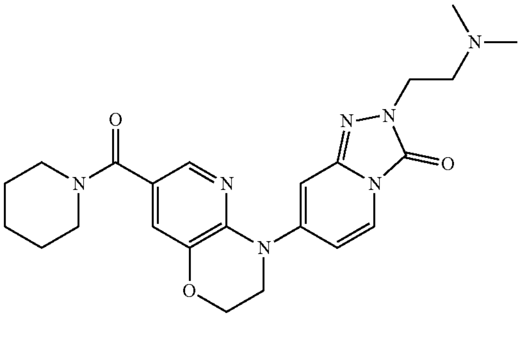

-continued
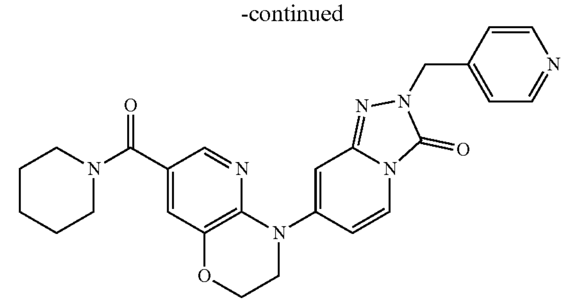
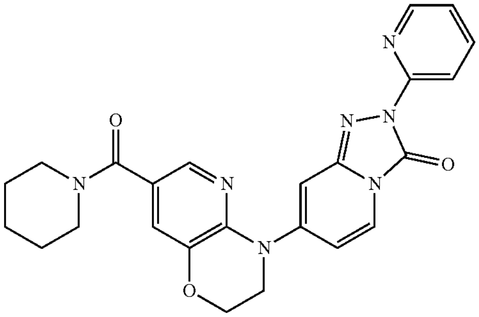
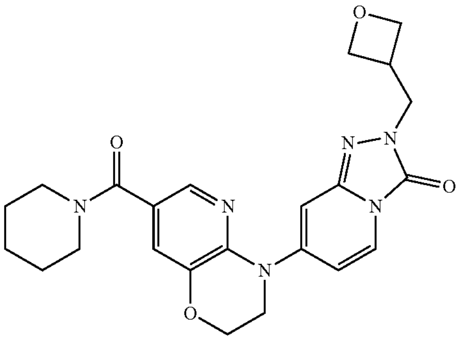
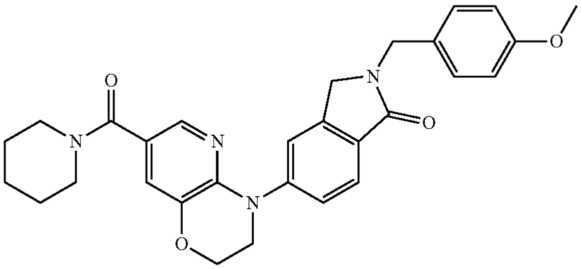
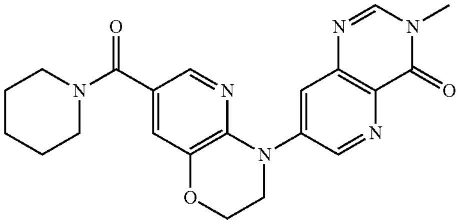
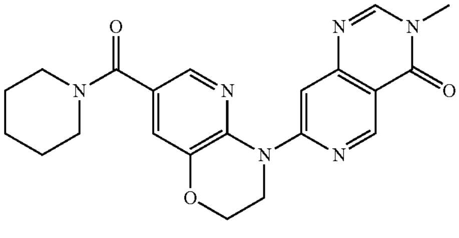
-continued
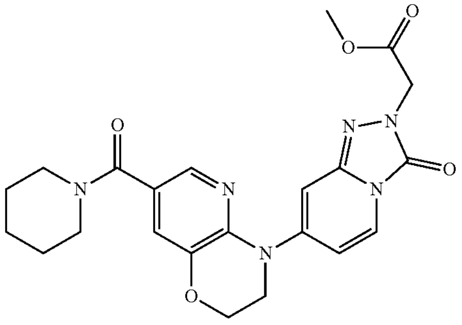
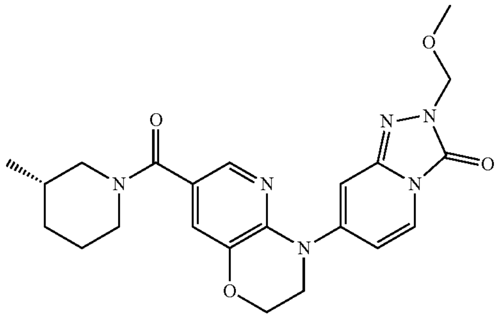
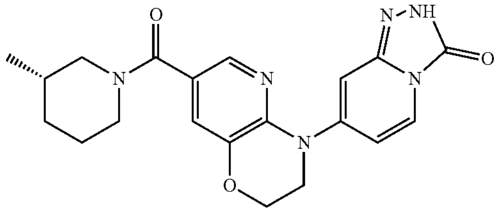
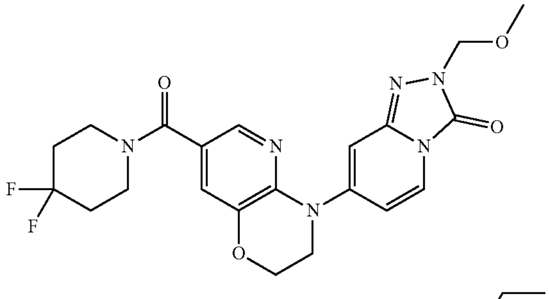
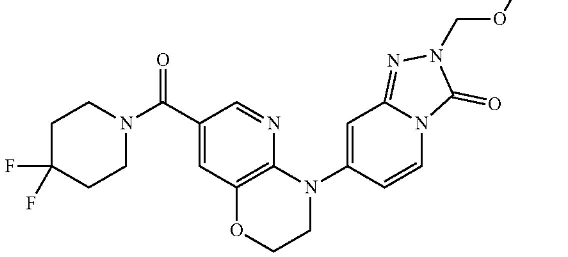
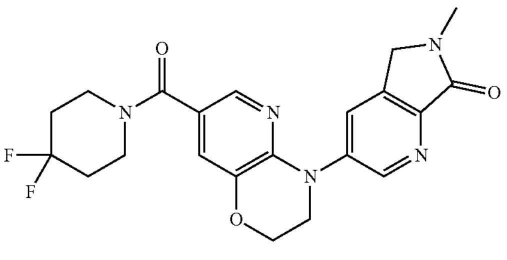

-continued
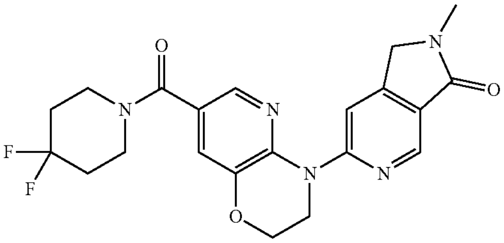
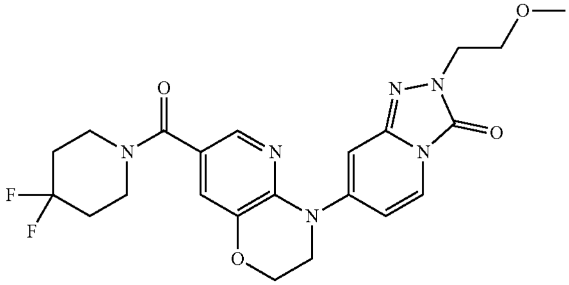
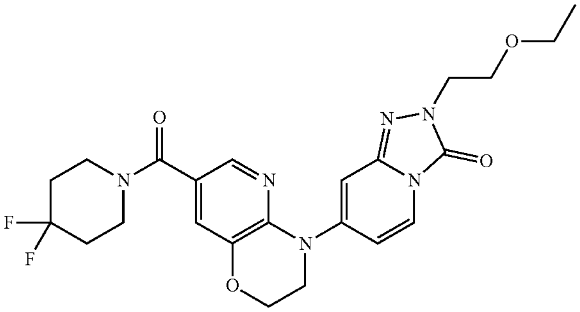
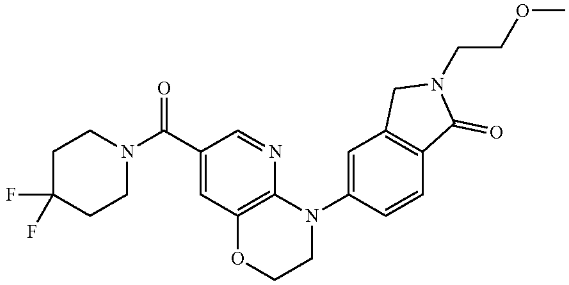
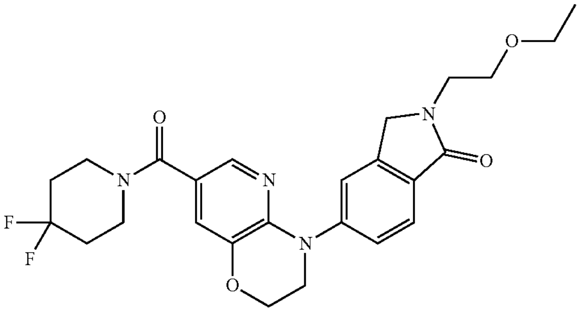
-continued
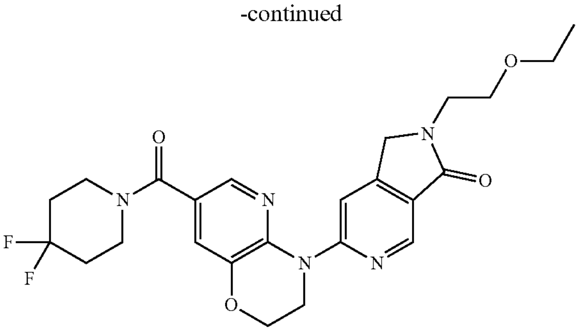
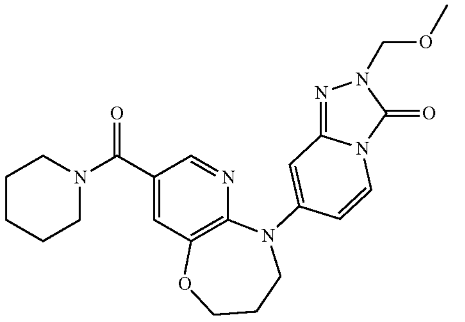
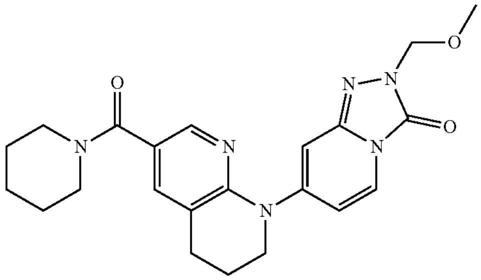
[Formula 42]
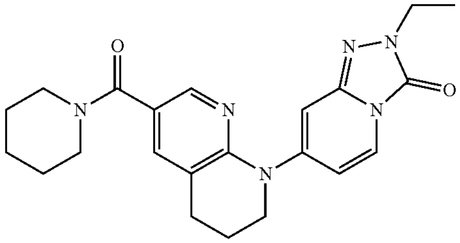
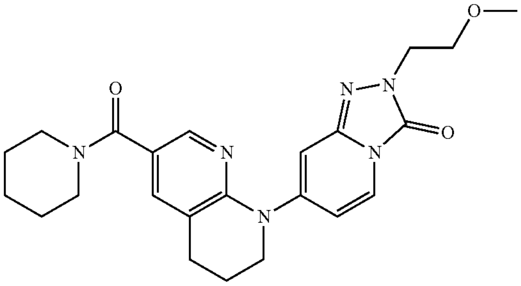
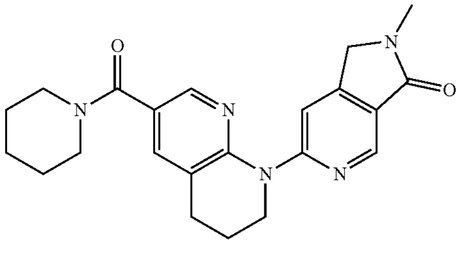

-continued
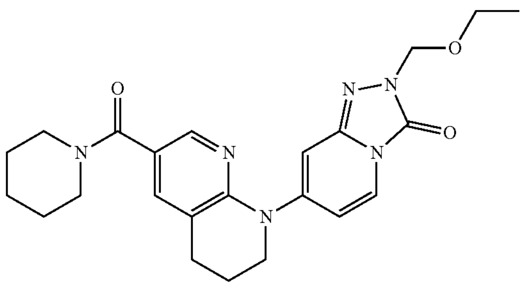
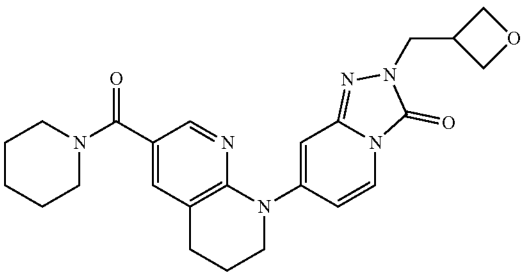
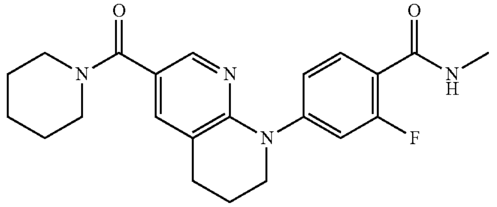
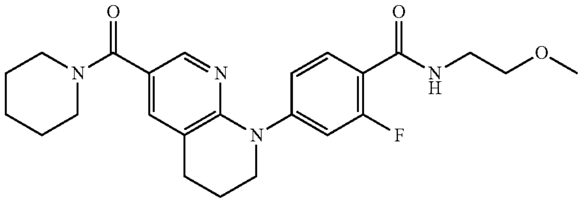
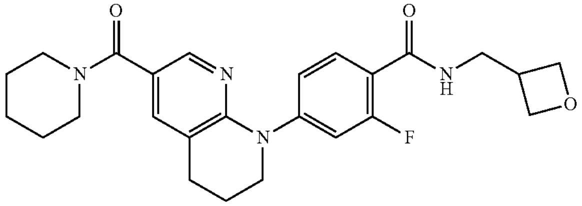
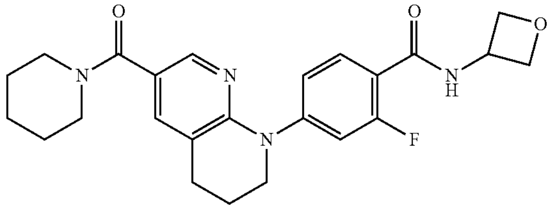
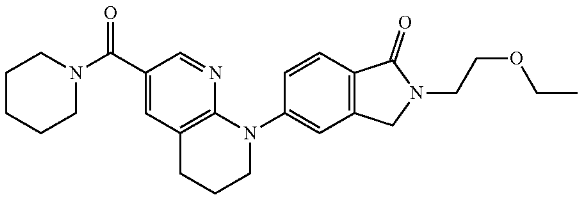
-continued
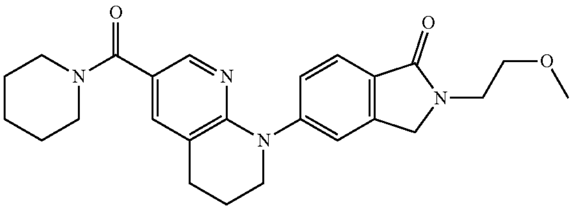
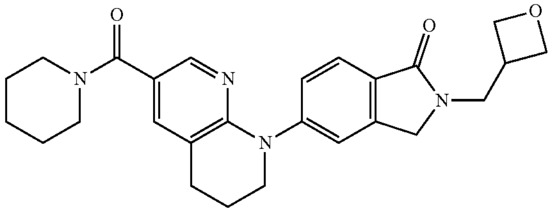
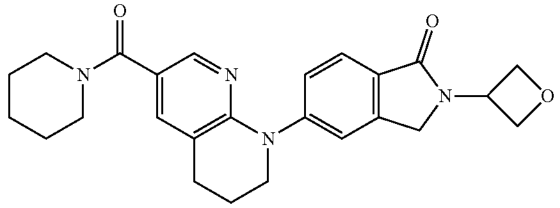
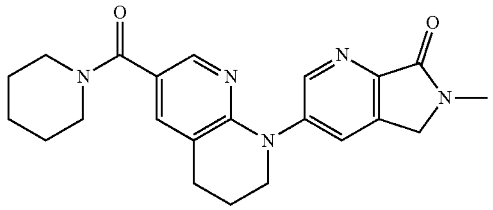
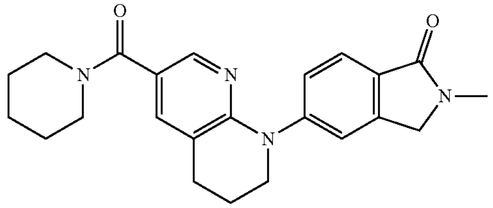
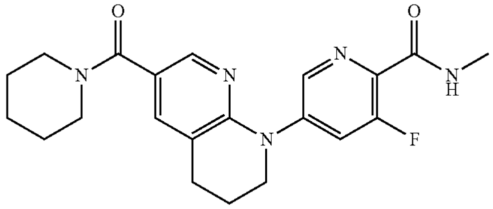
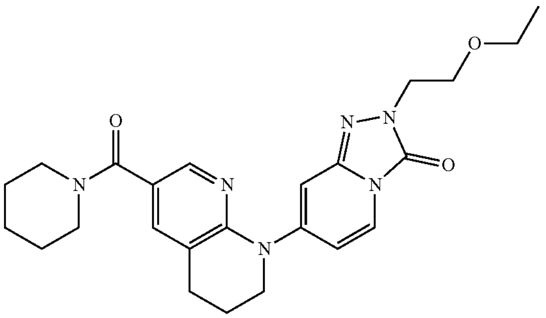

-continued
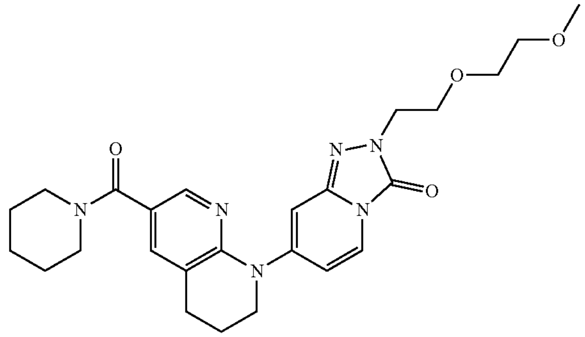
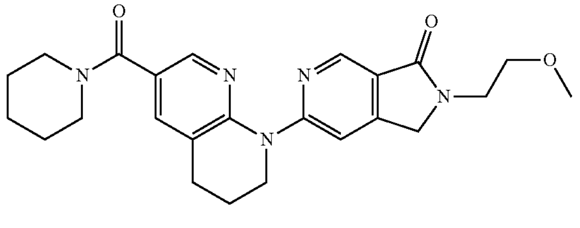
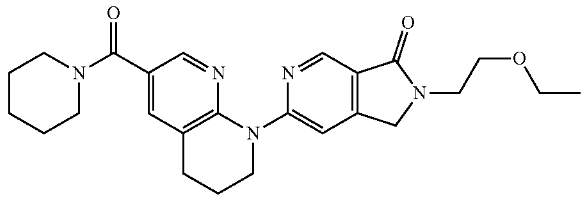
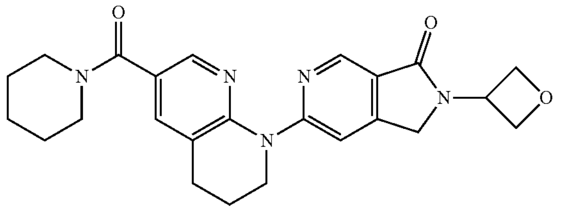
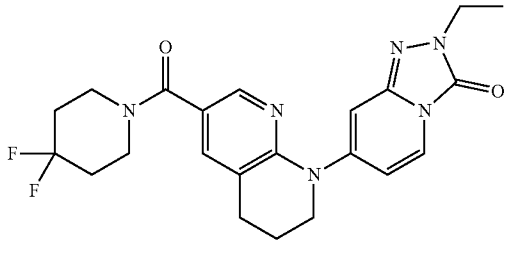
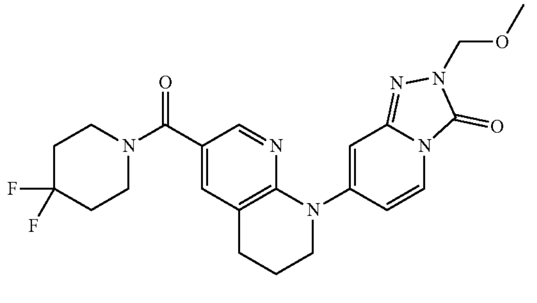
-continued
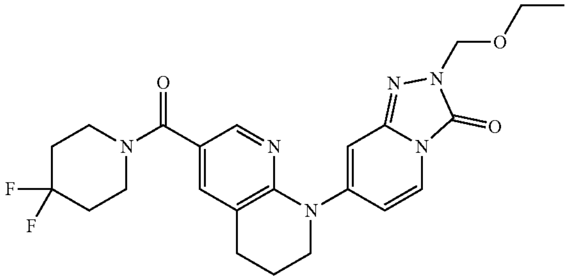
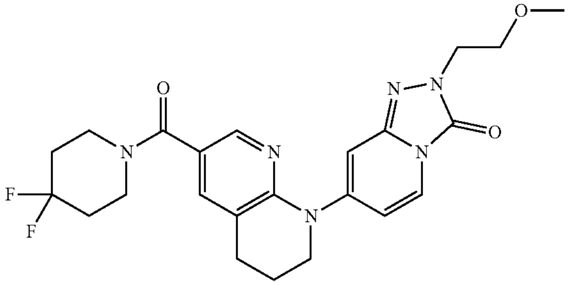
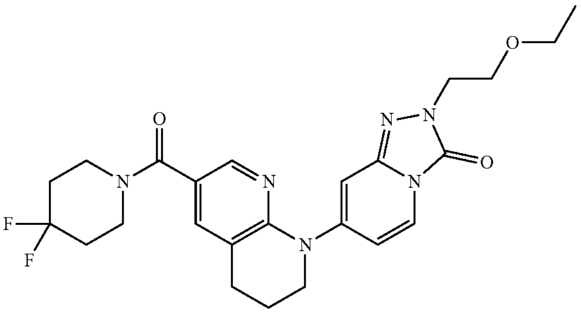
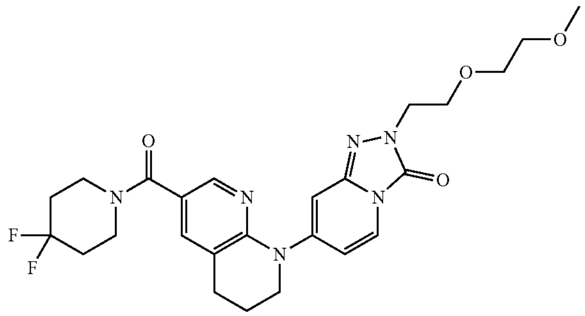
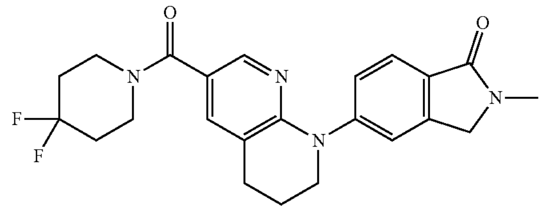
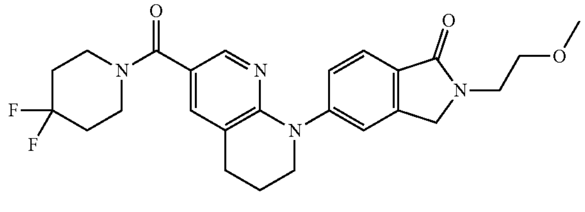

-continued
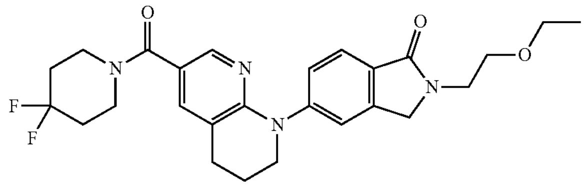
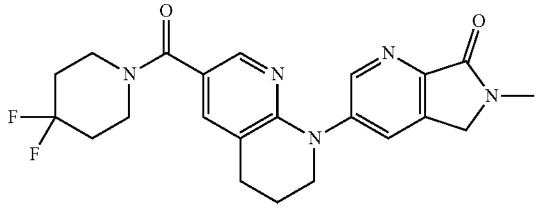
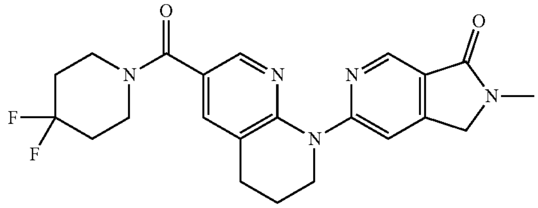
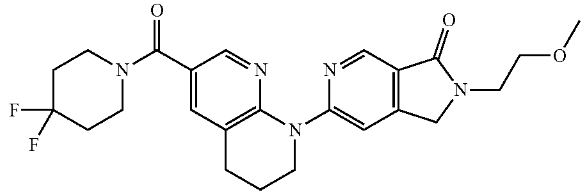
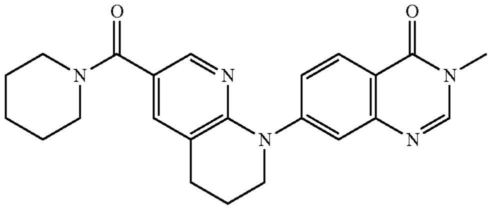
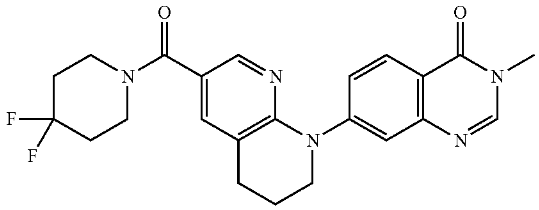
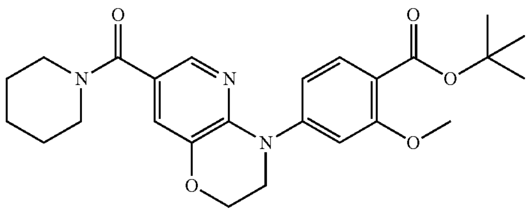
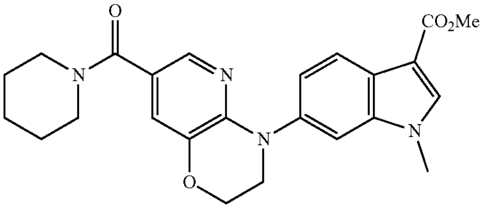
-continued
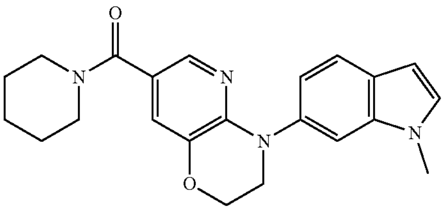
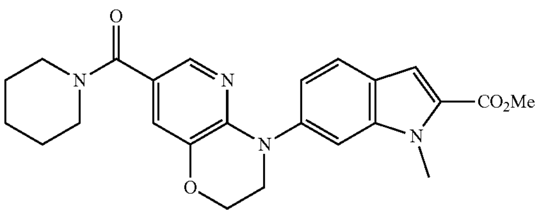
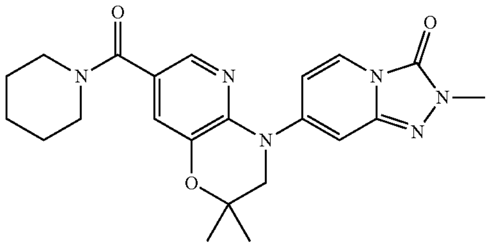
[Formula 43]
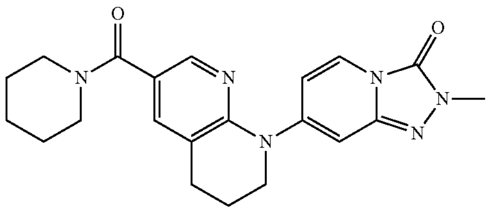
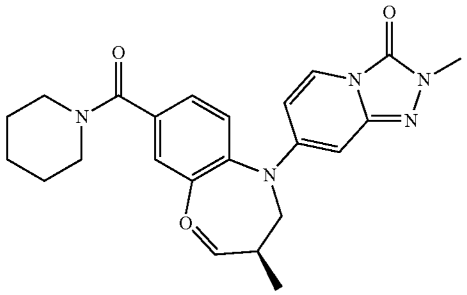
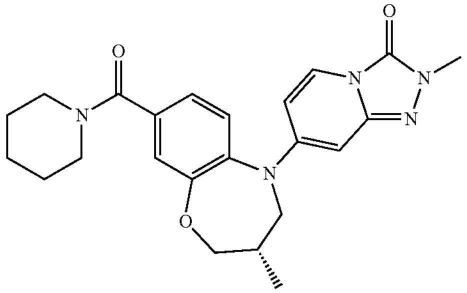

-continued
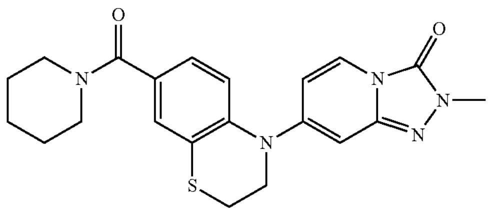
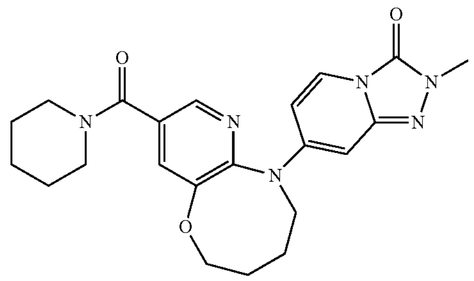
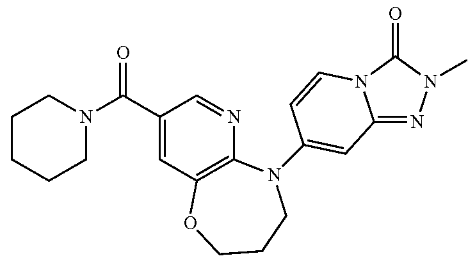
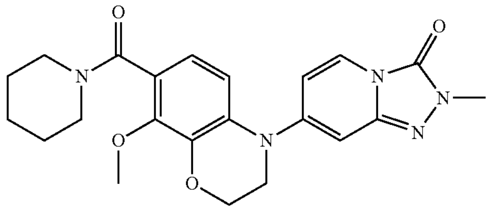
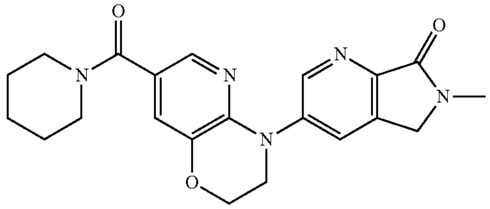
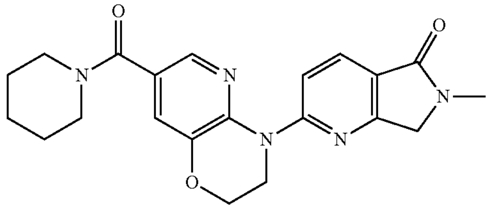
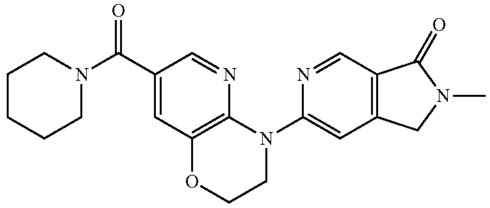
-continued
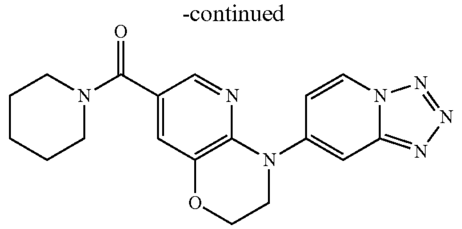
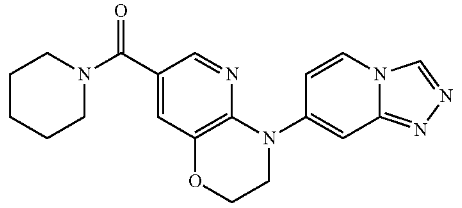
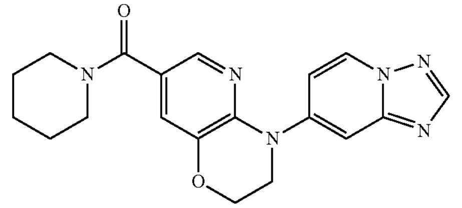
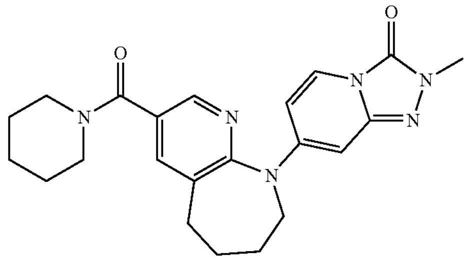
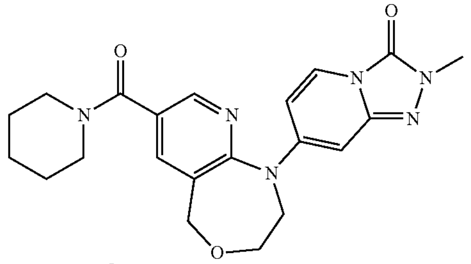
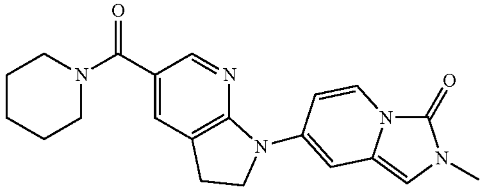
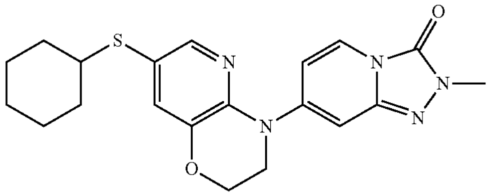
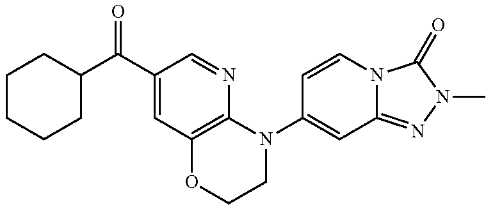

-continued
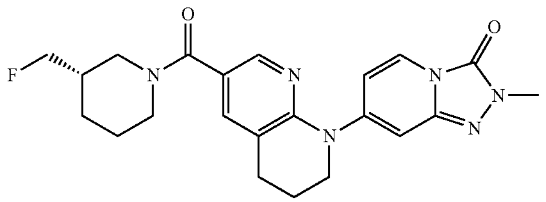
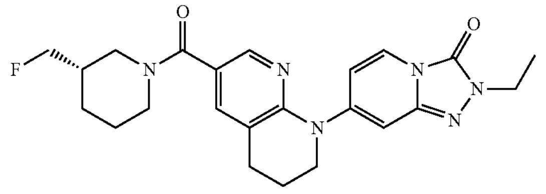
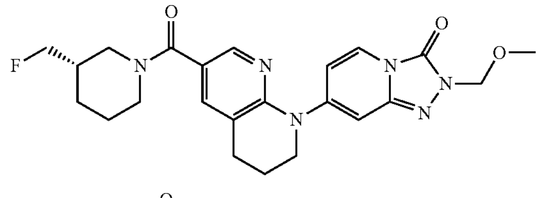
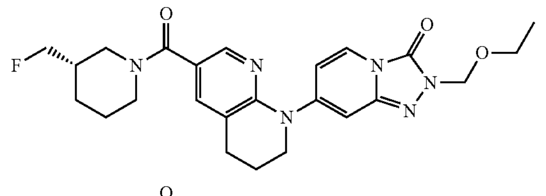
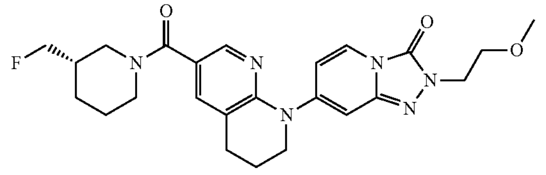
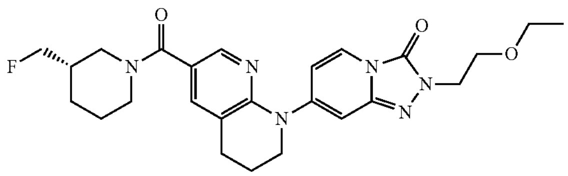
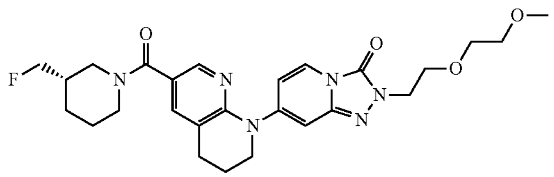
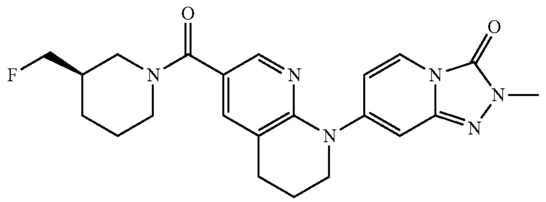
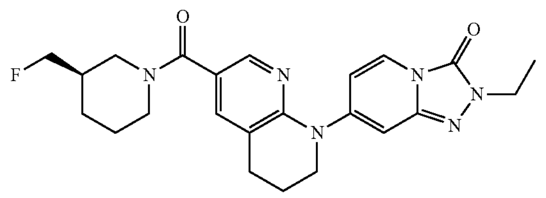
-continued
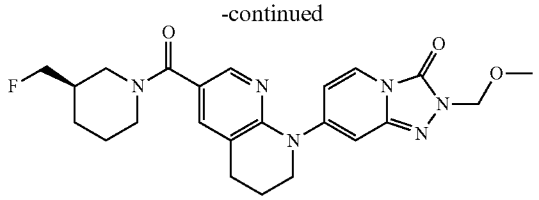
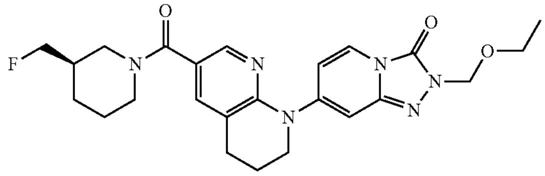
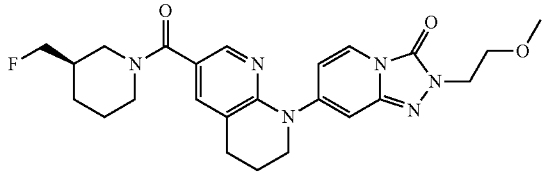
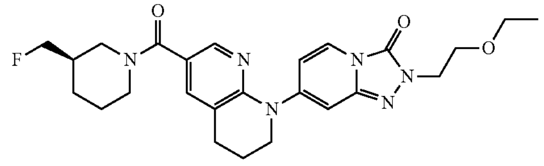
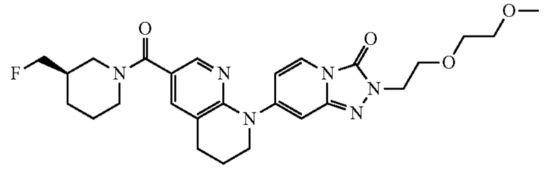
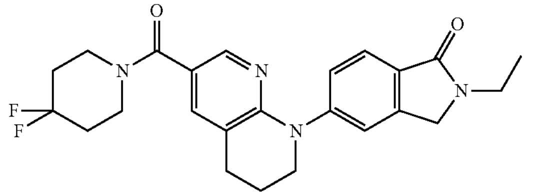
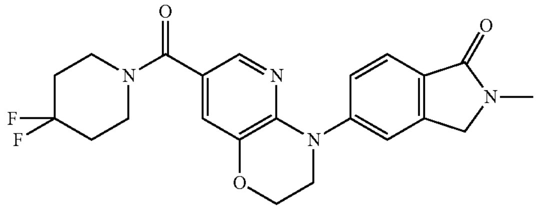
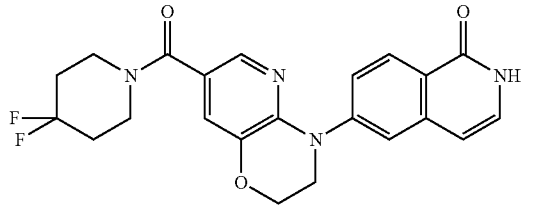
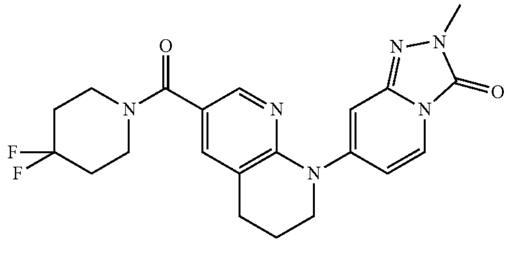

-continued
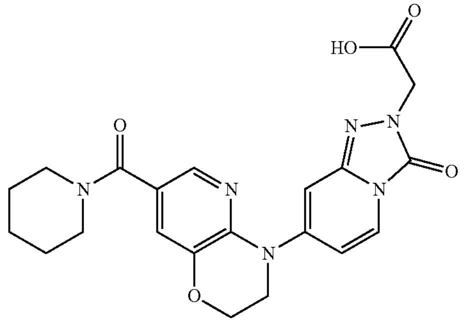
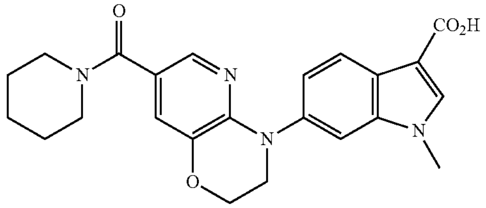
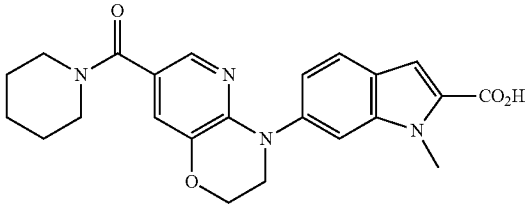
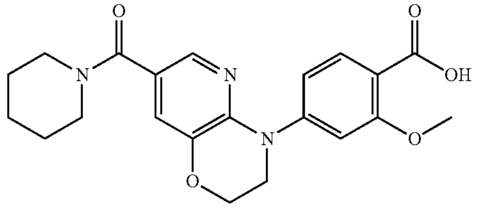
[Formula 44]
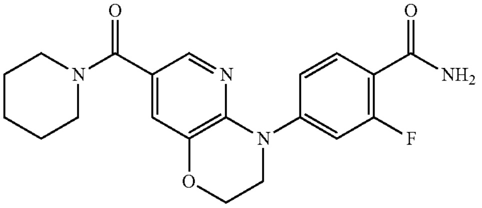
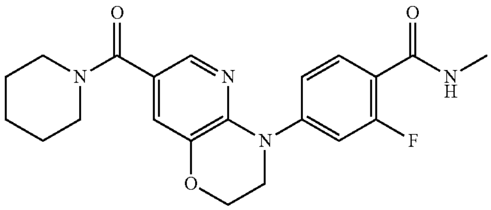
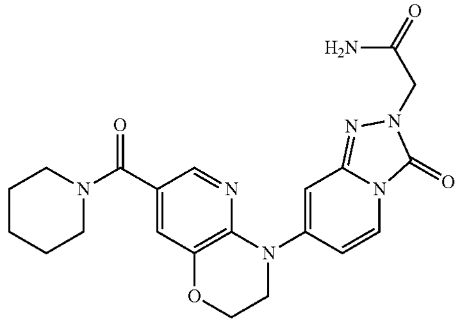
-continued
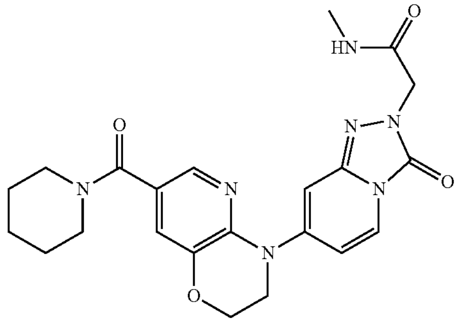
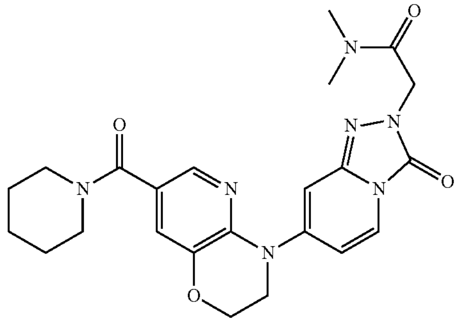
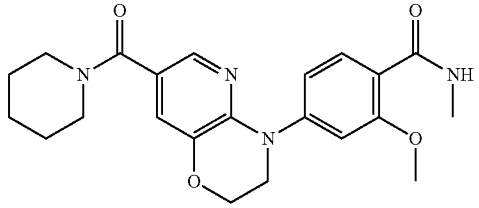
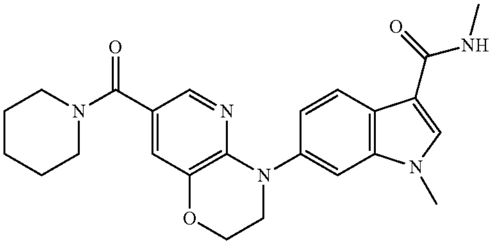
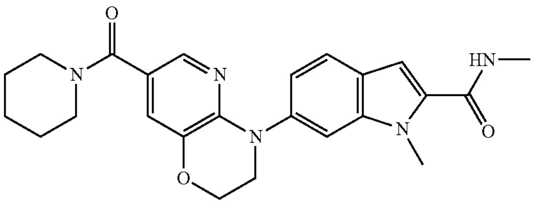
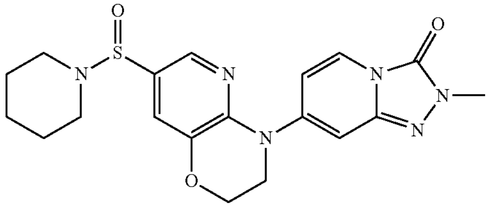
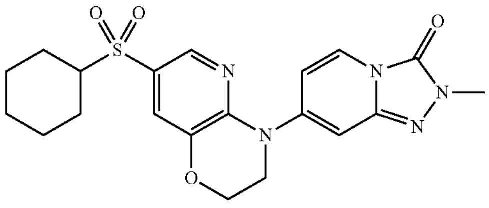

-continued
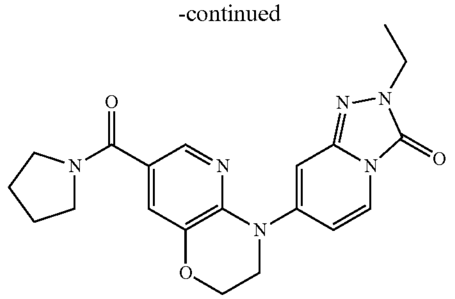
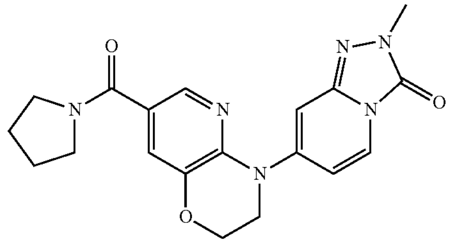
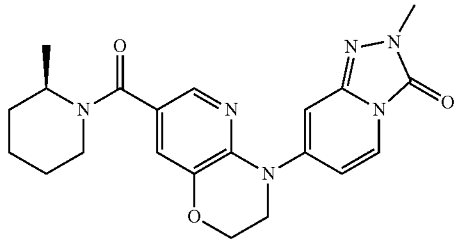
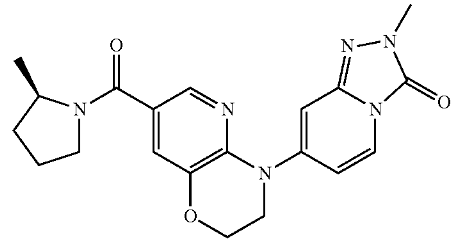
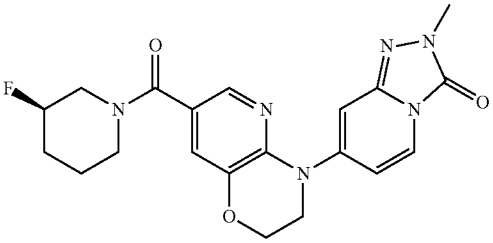
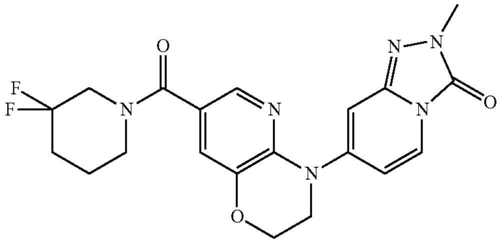
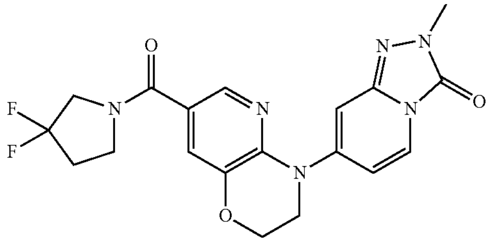
-continued
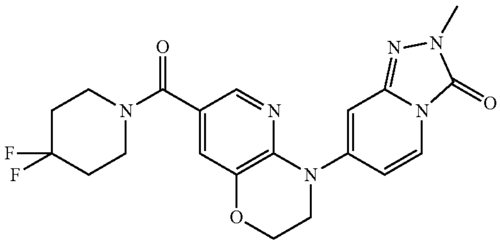
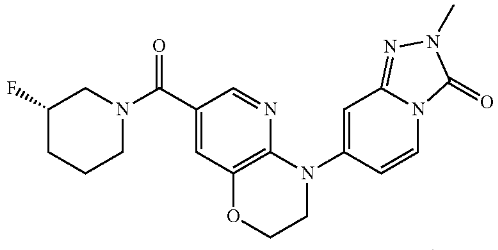
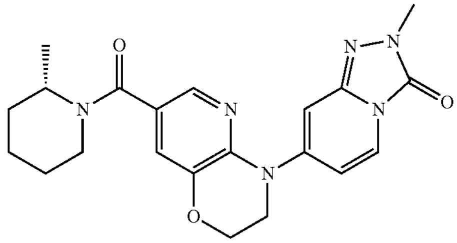
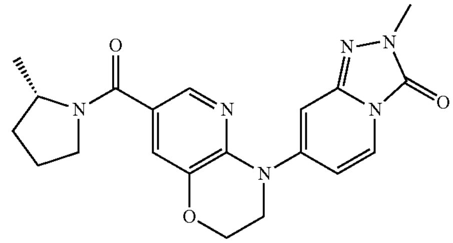
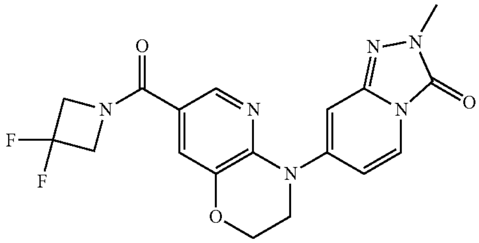
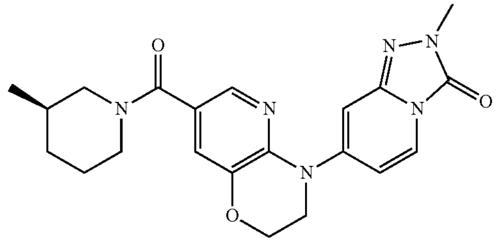
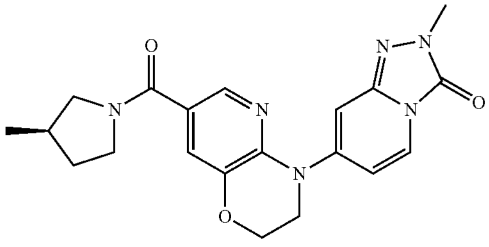

-continued
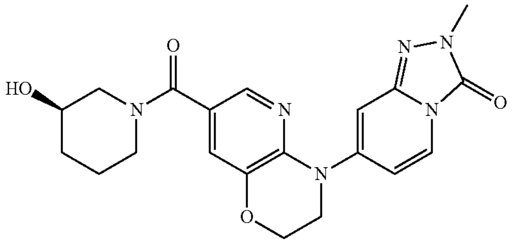
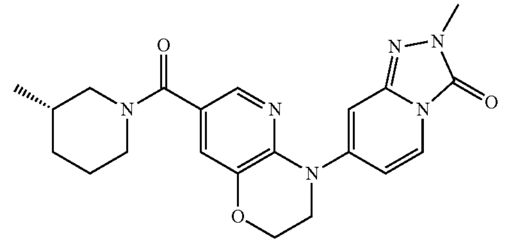
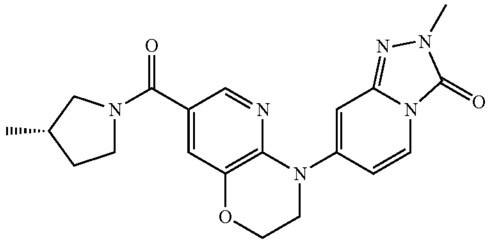
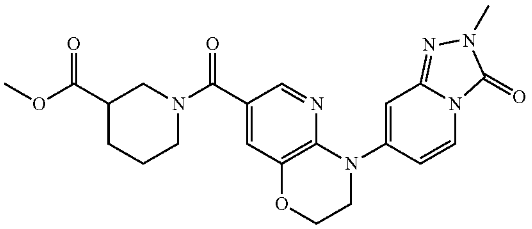
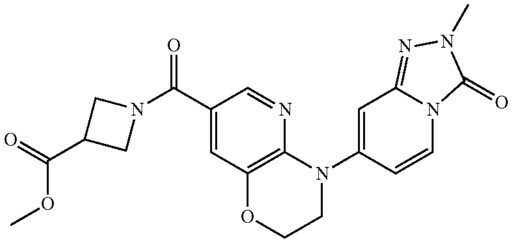
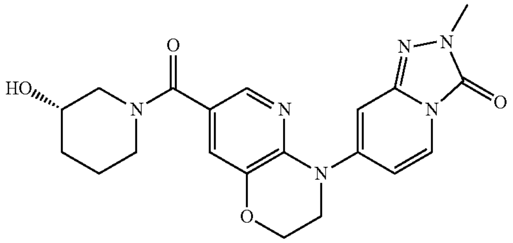
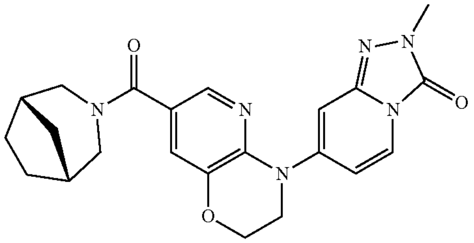
-continued
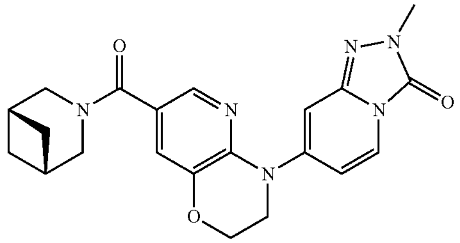
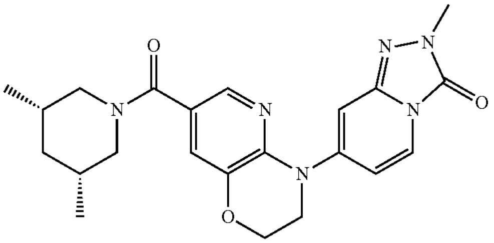
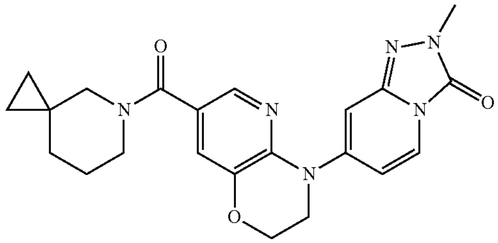
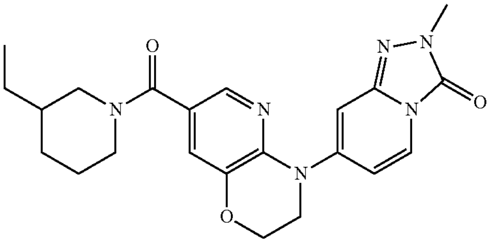
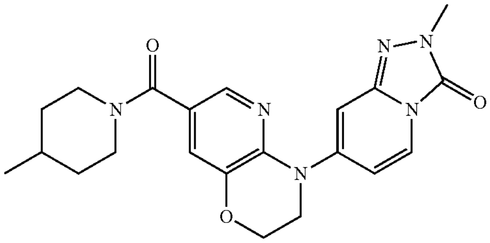
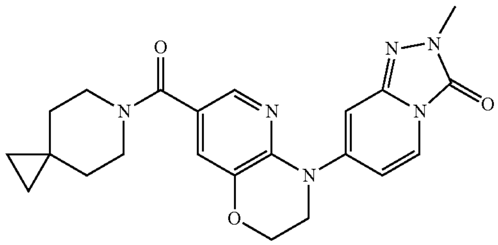
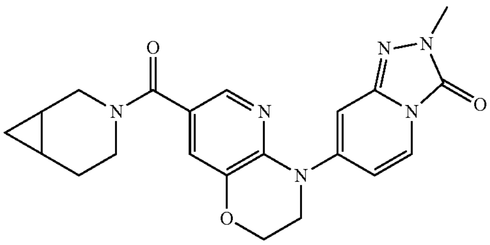

-continued
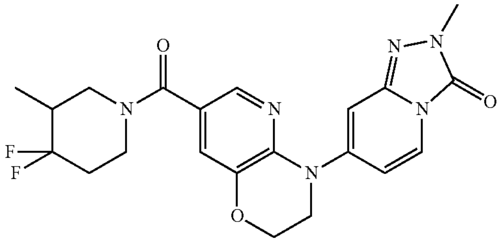
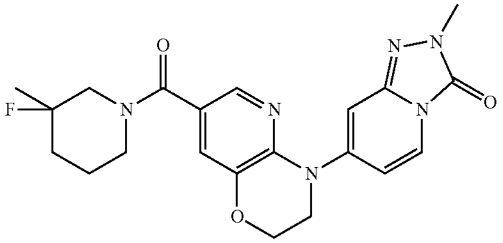
[Formula 45]
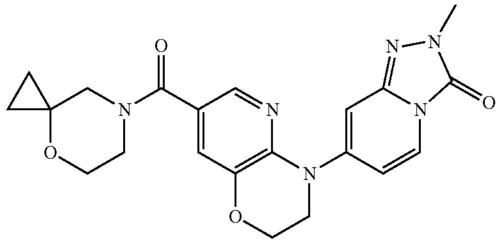
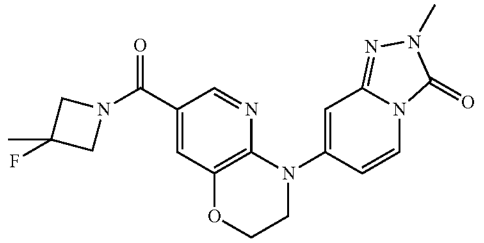
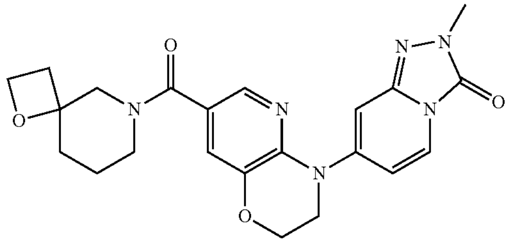
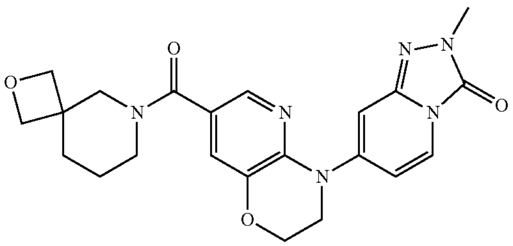
-continued
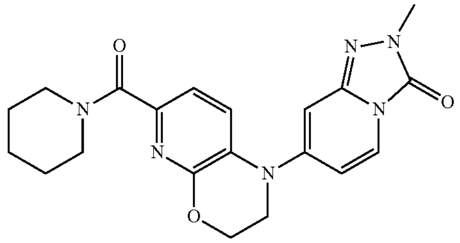
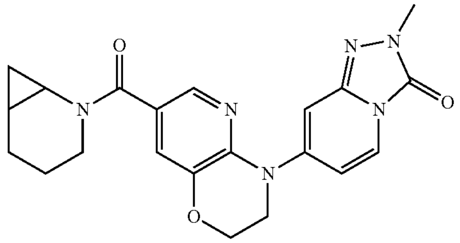
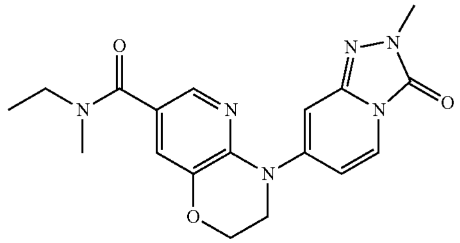
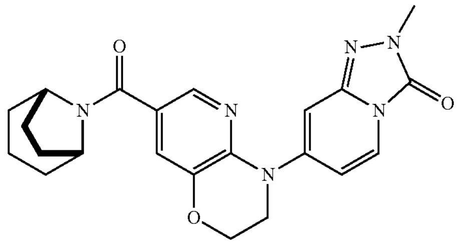
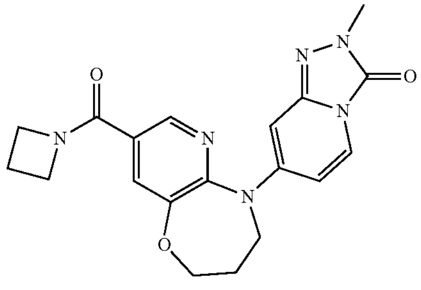
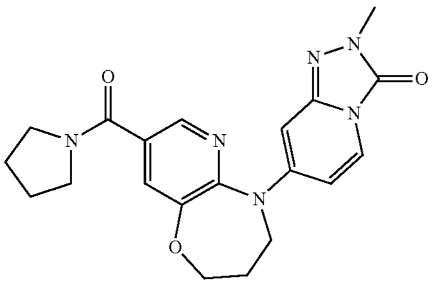

-continued
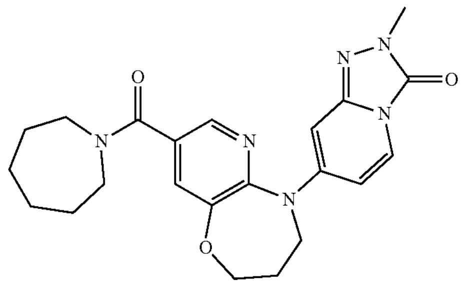
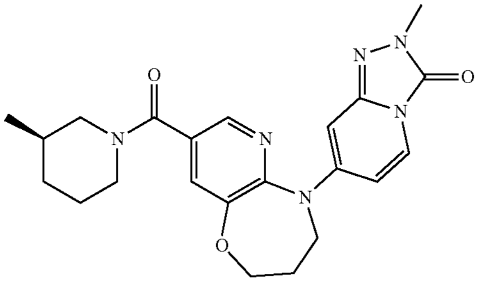
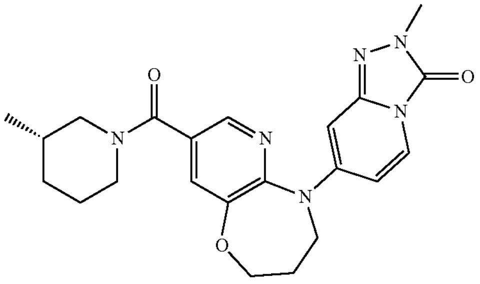
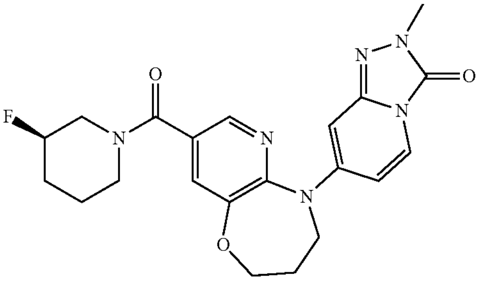
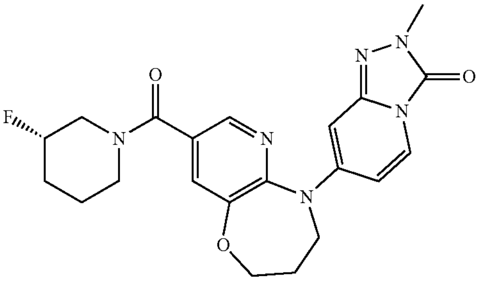
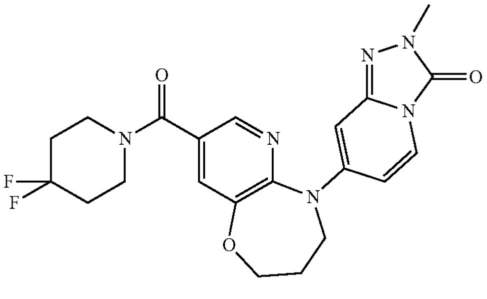
-continued
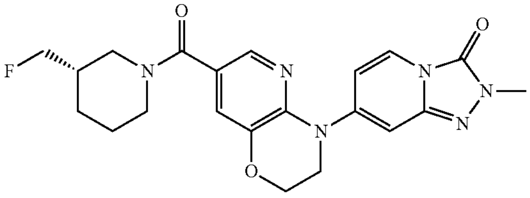
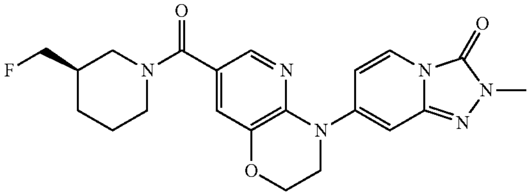
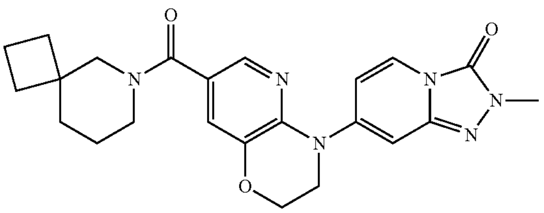
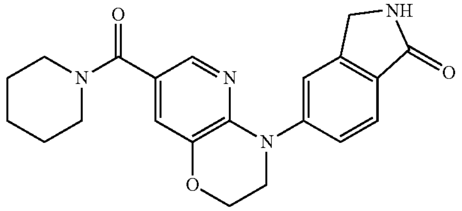
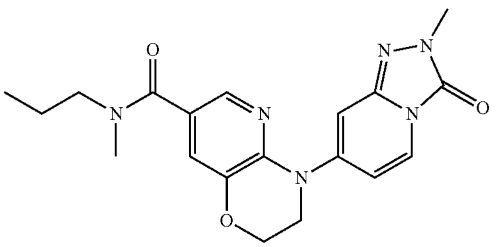
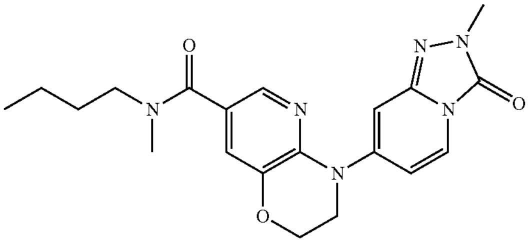
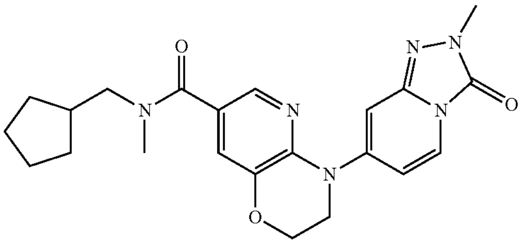

-continued
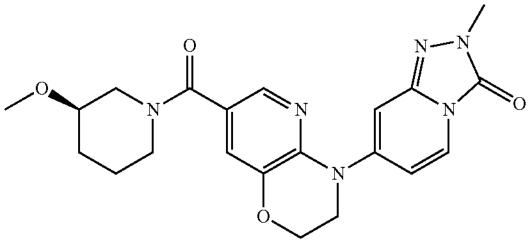
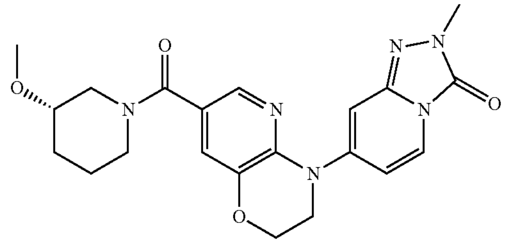
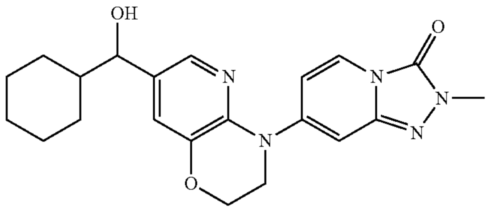
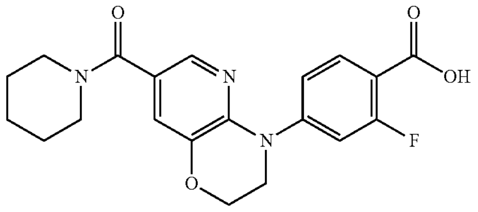
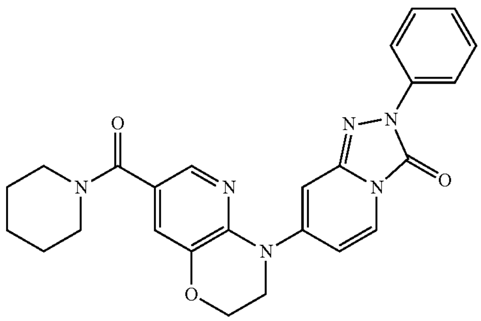
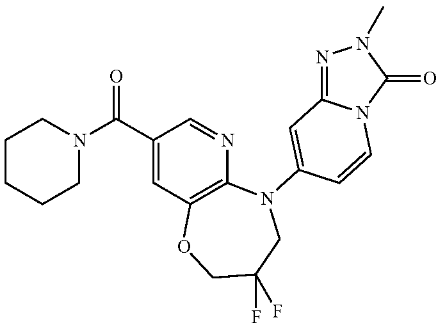
-continued
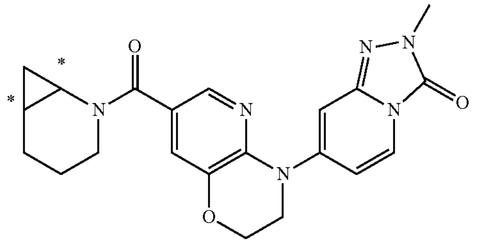
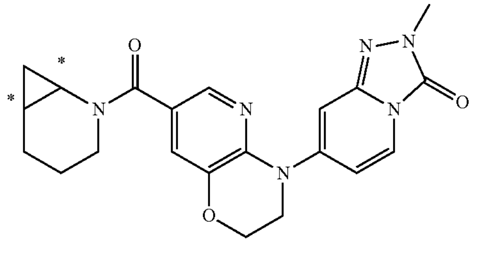
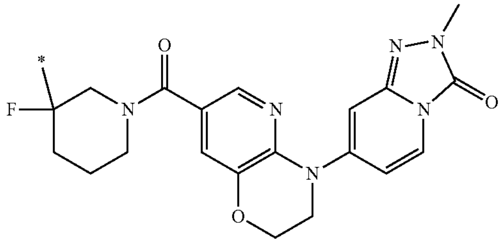
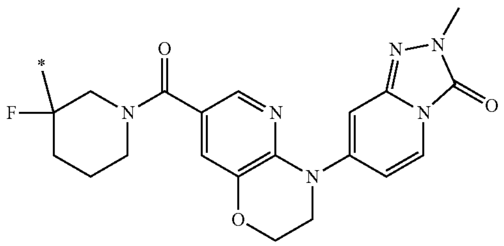
[Formula 46]
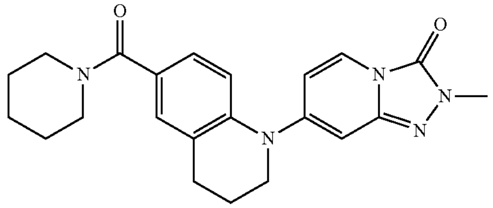
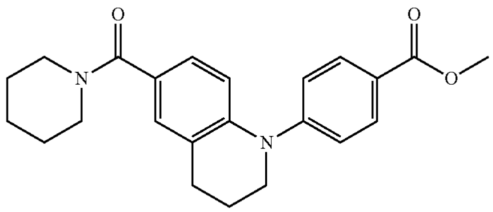
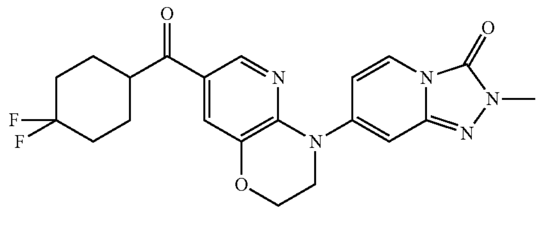

-continued
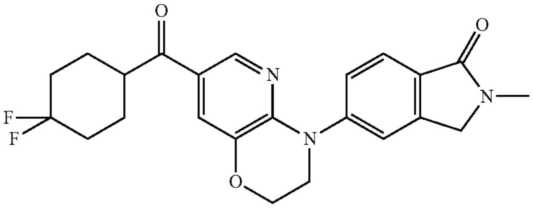
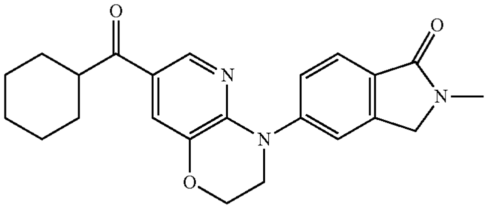
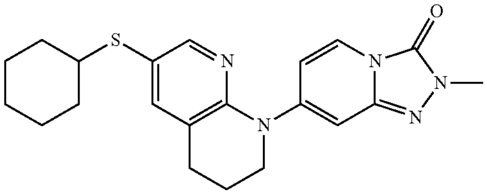
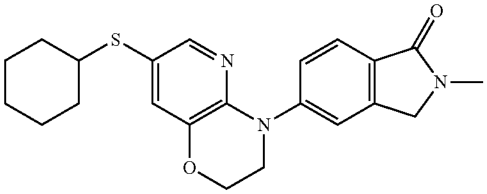
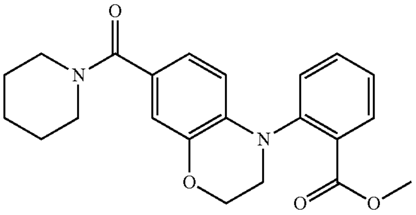
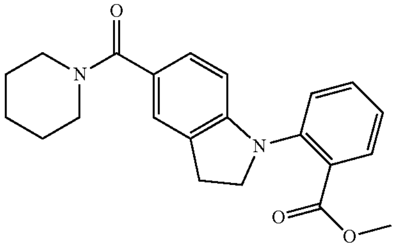
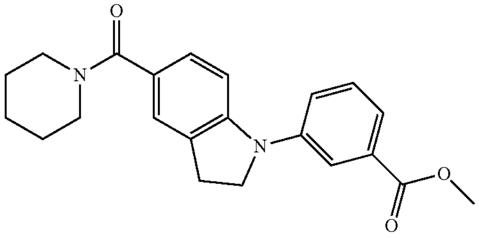
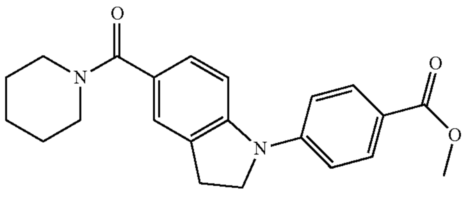
-continued
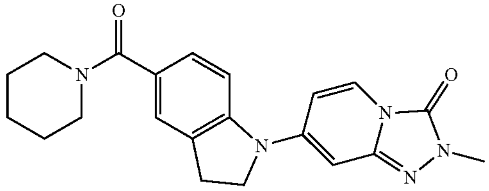
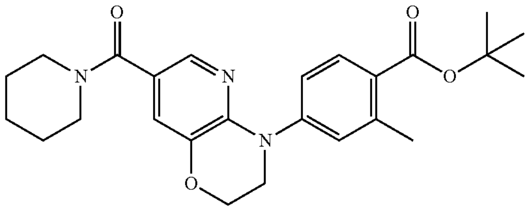
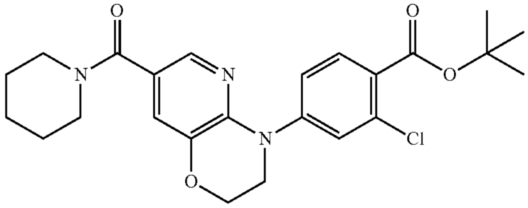
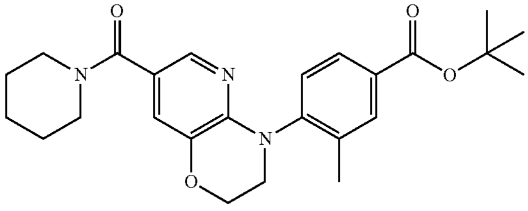
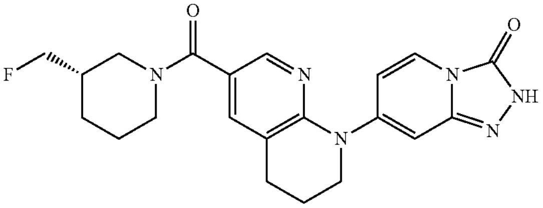
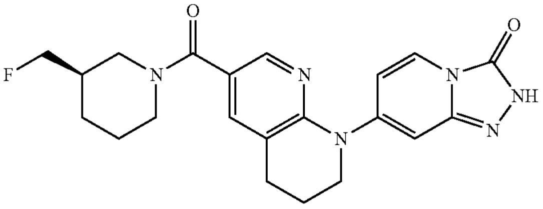
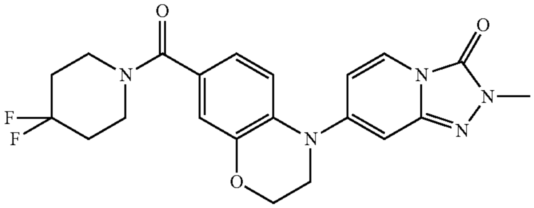
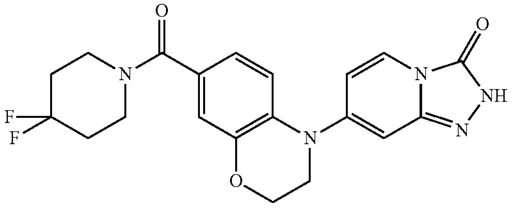

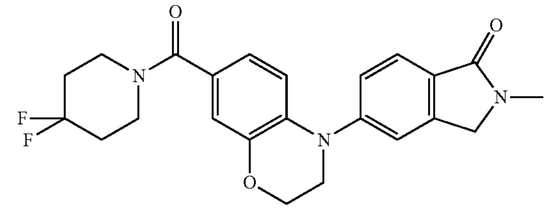
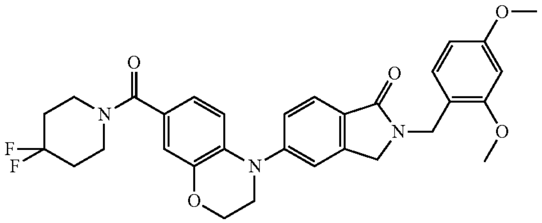
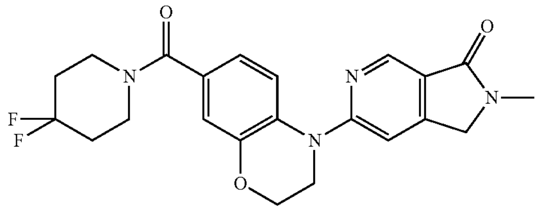
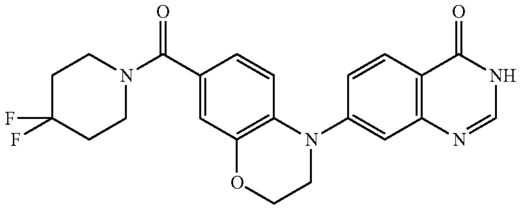
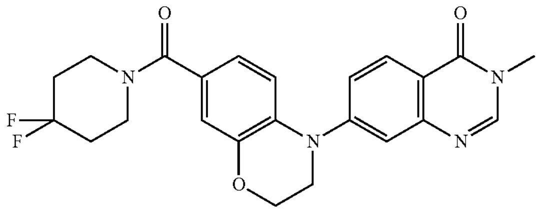
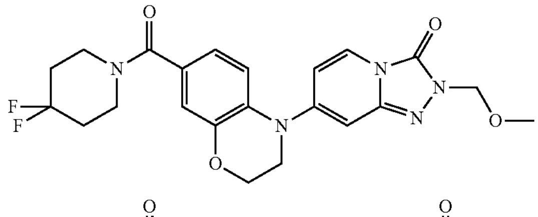
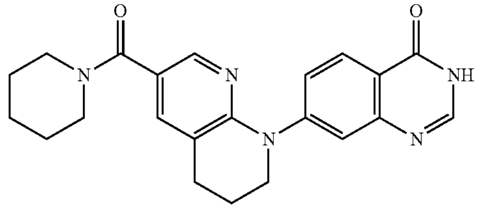
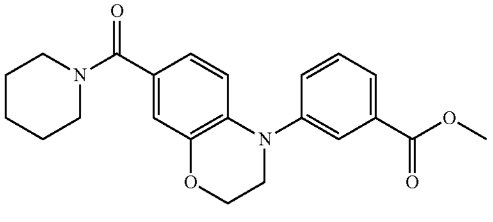
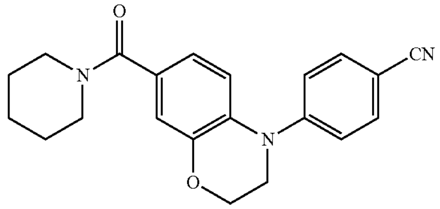
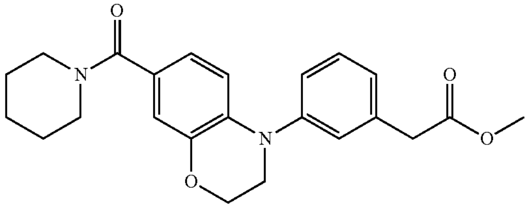
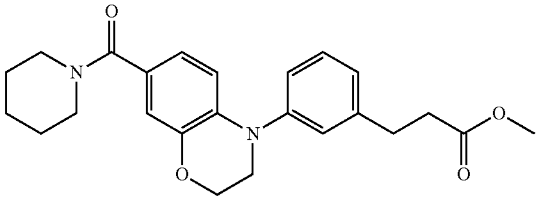
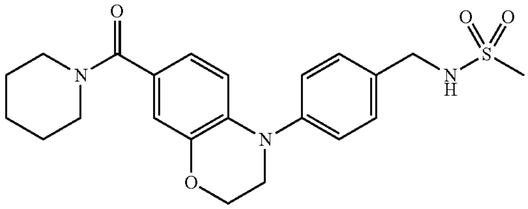
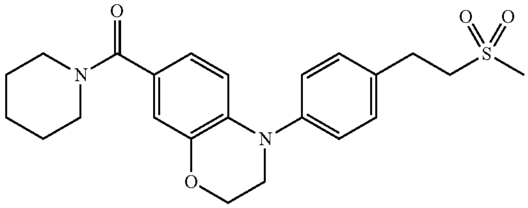
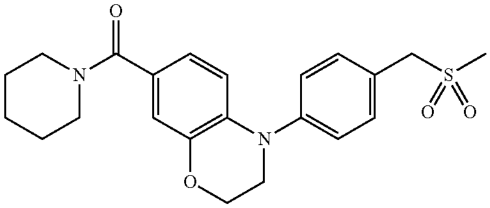
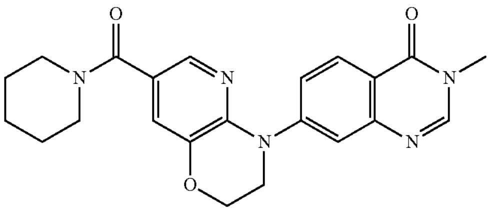
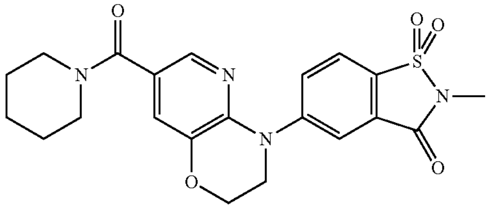

-continued
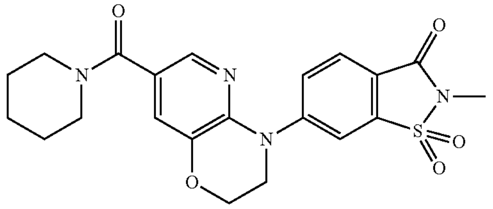
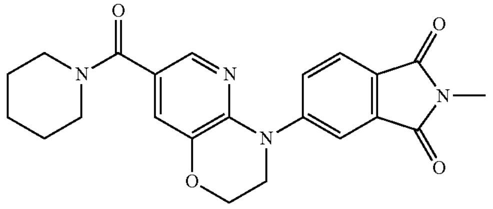
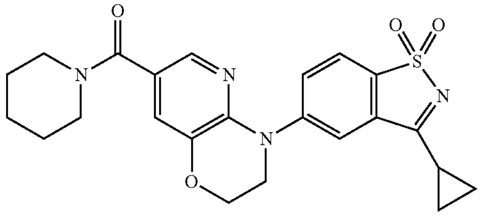
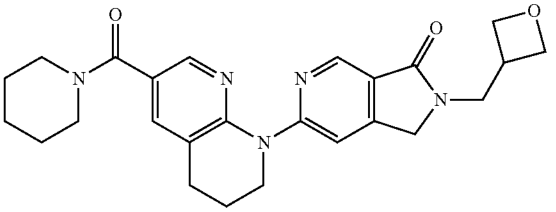
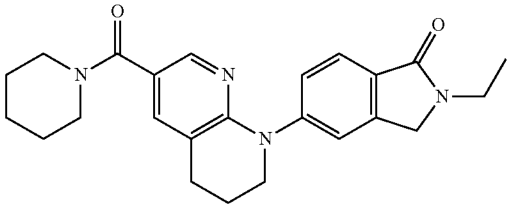
[Formula 47]
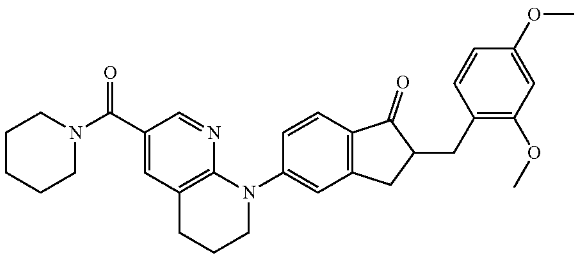
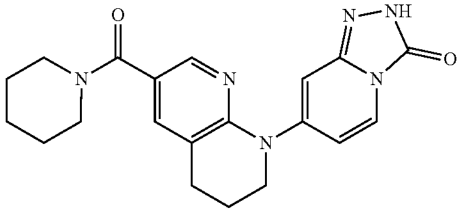
-continued
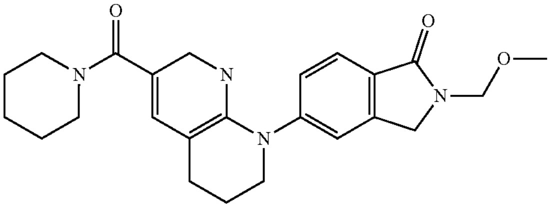
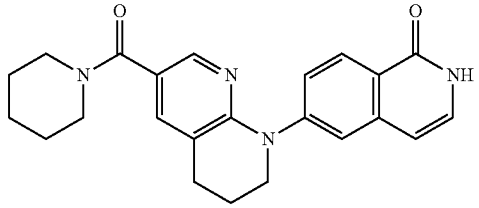
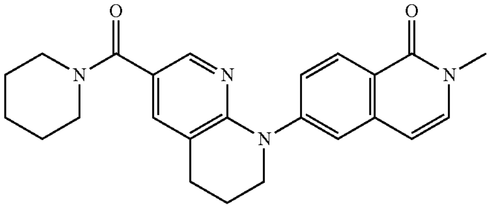
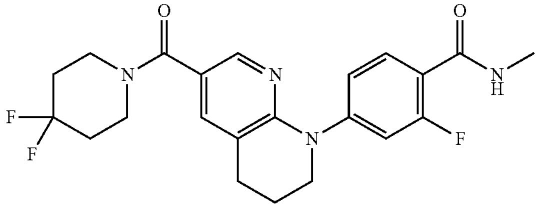
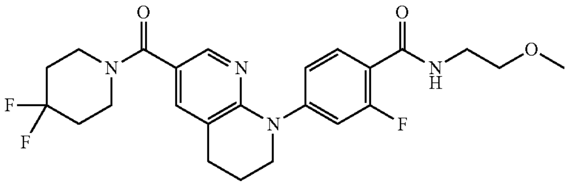
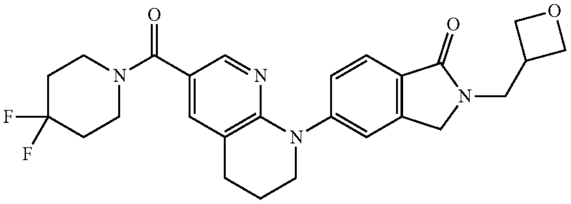
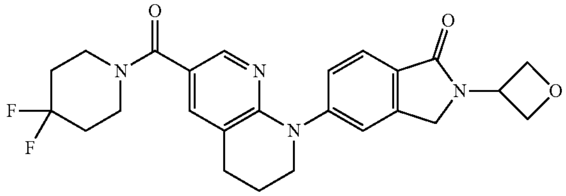
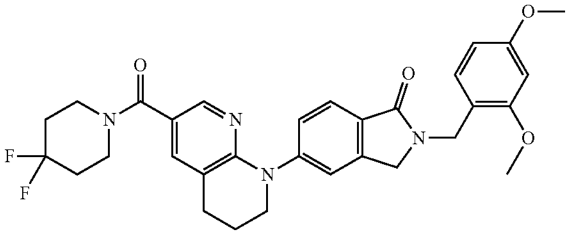

-continued
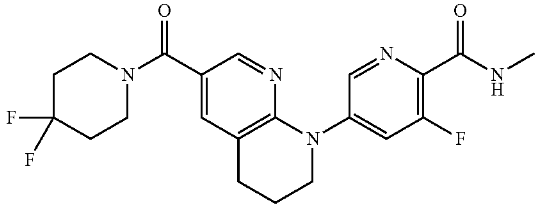
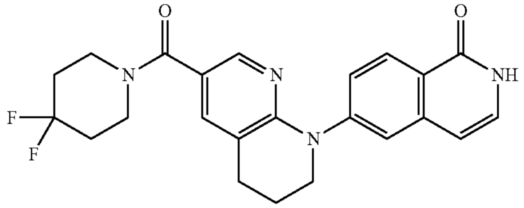
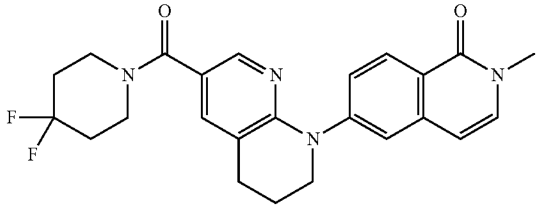
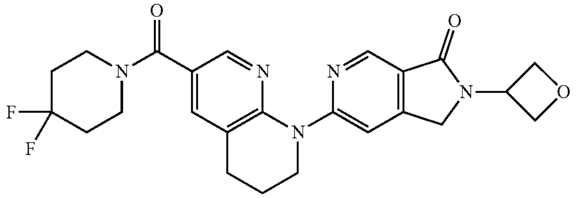
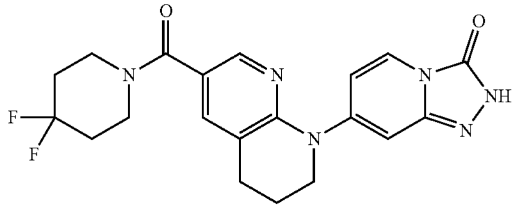
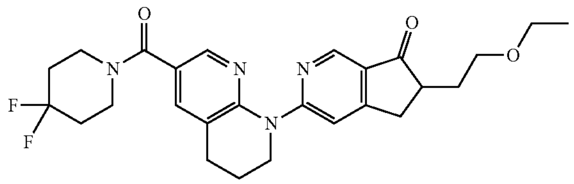
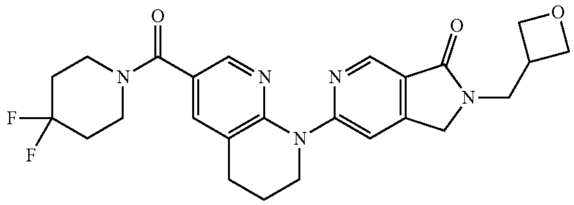
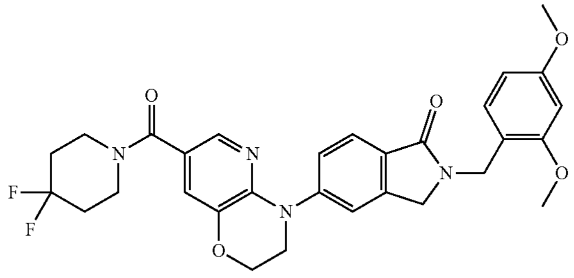
-continued
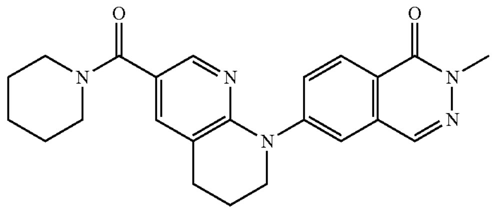
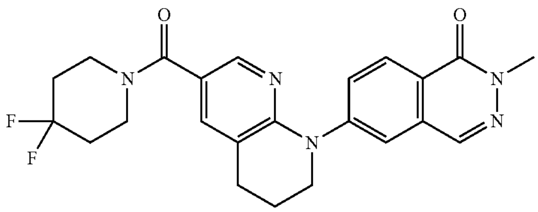
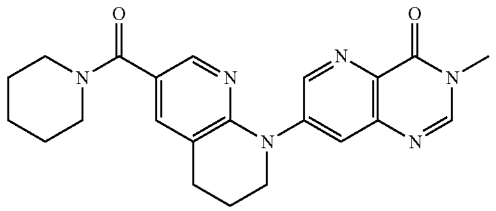
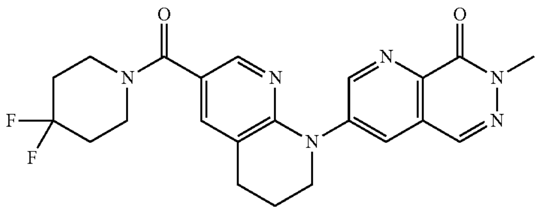
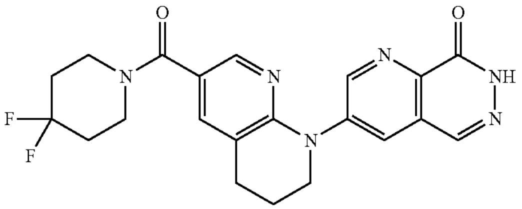
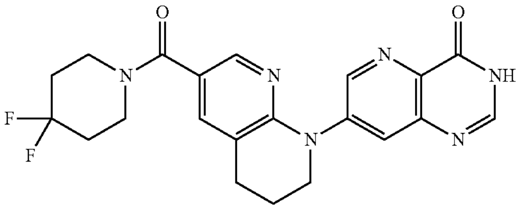
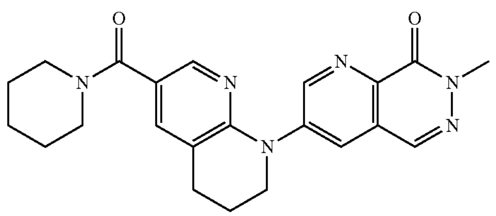
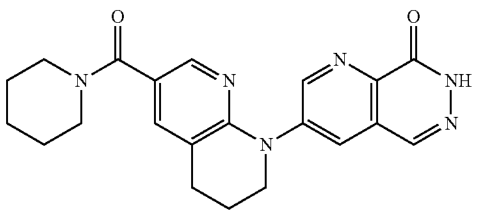

-continued
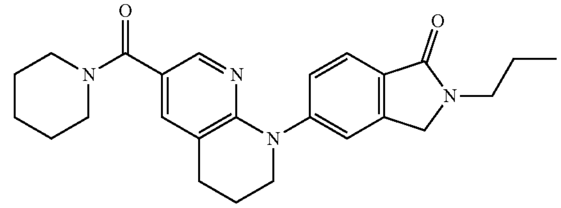
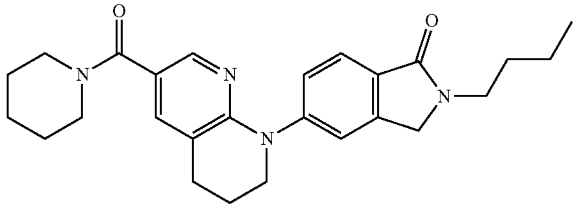
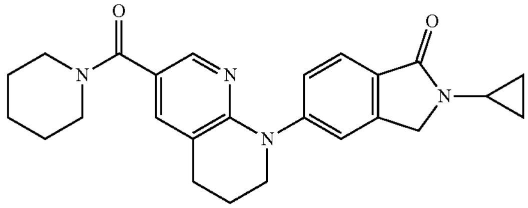
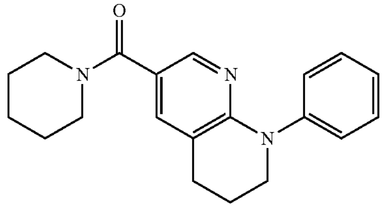
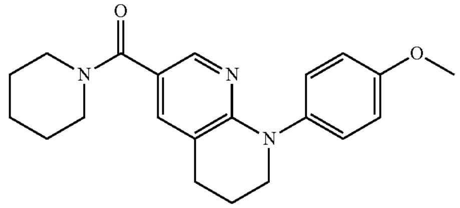
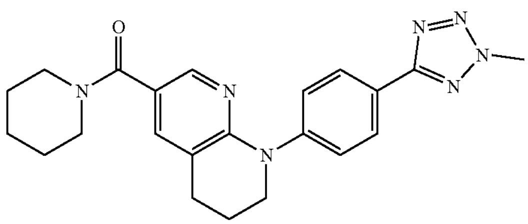
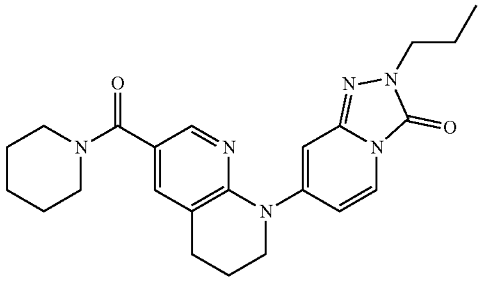
-continued
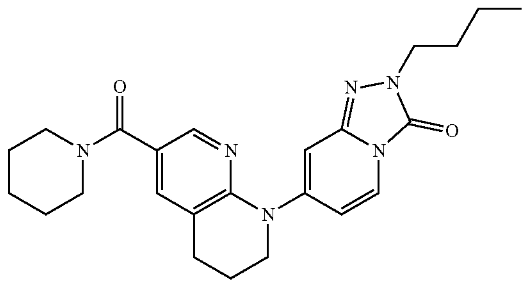
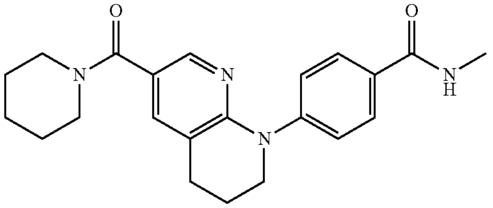
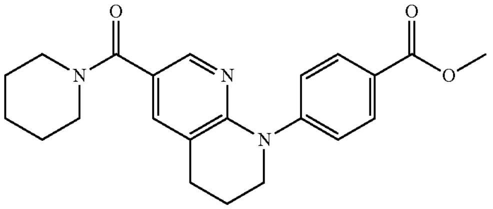
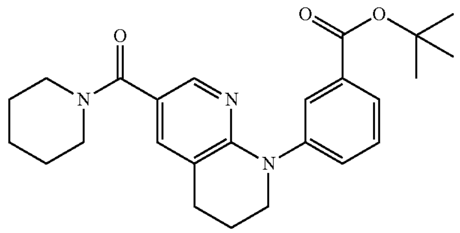
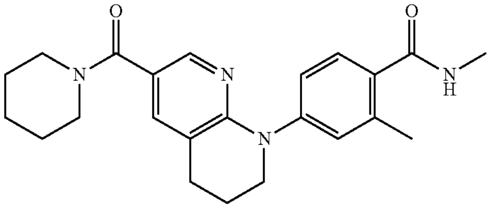
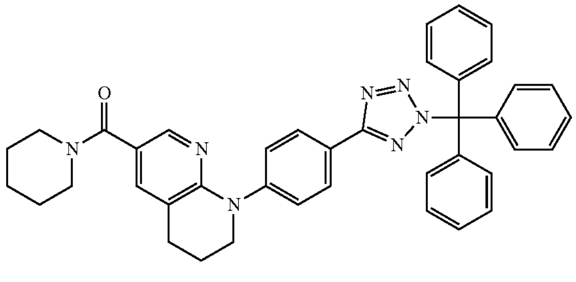
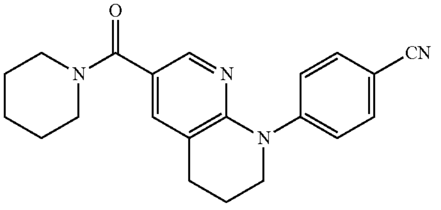 [SMILES: N#Cc1ccc(N2CCCc3cc(C(=O)N4CCCCC4)cnc32)cc1]

[Formula 48]
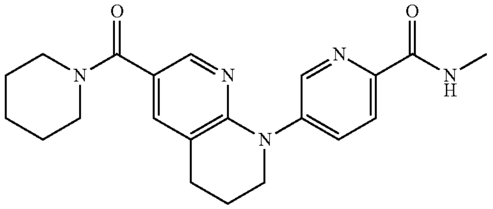
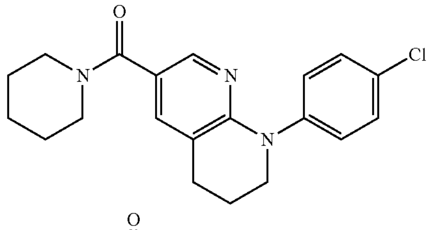
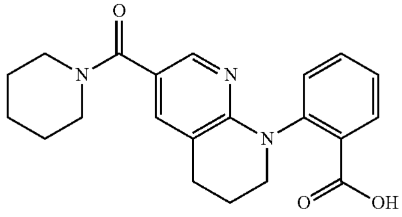
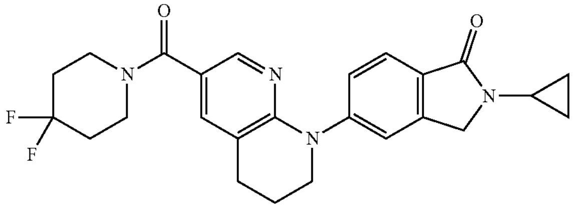
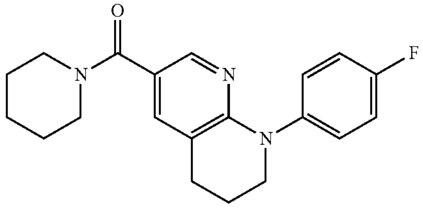
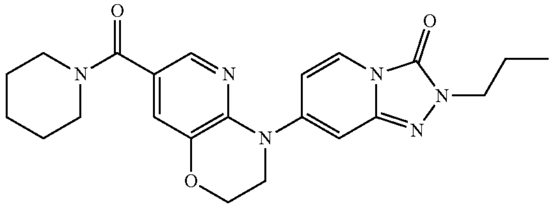
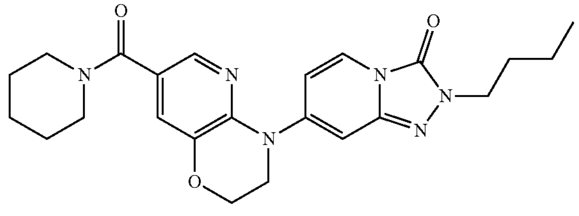
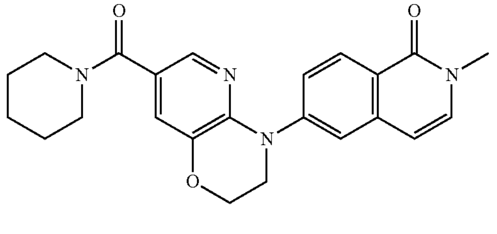
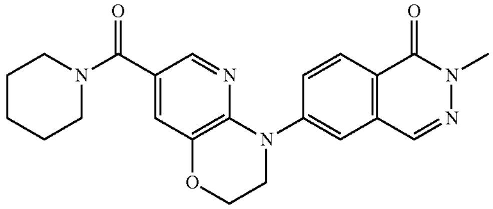
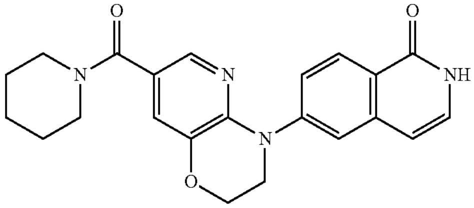
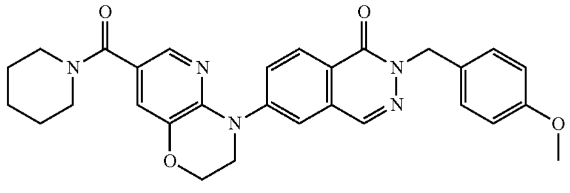
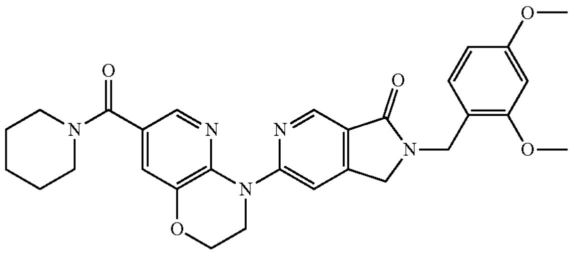
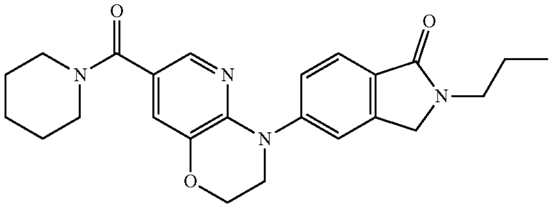
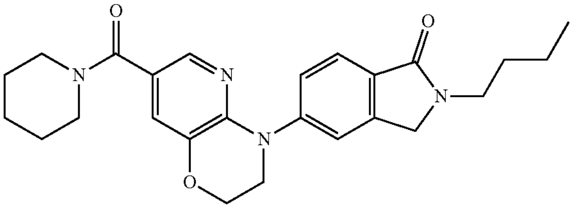
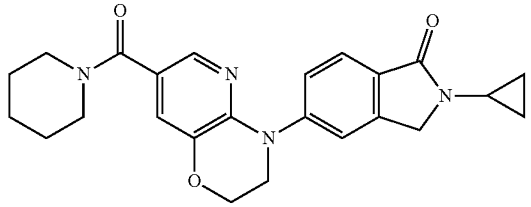
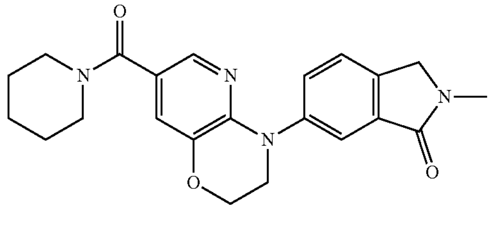

-continued
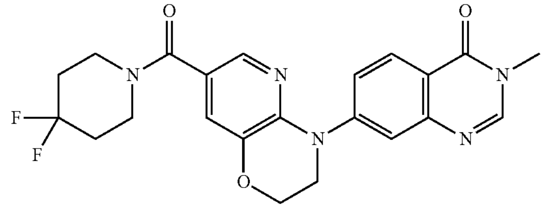
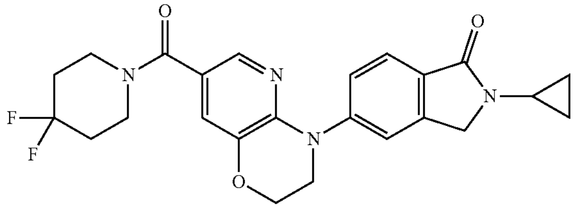
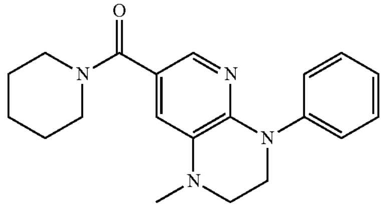
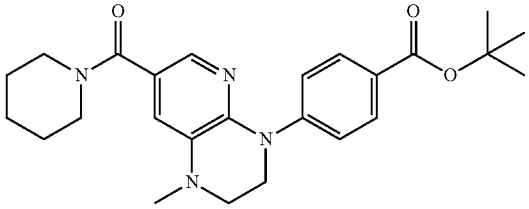
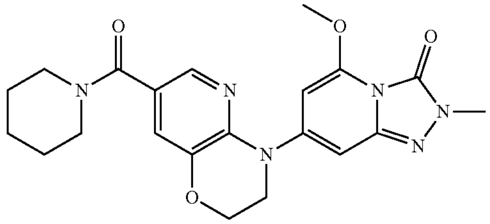
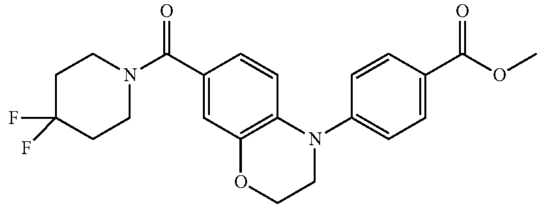
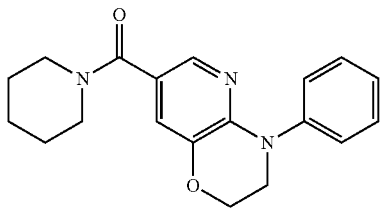
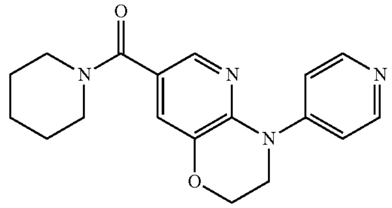
-continued
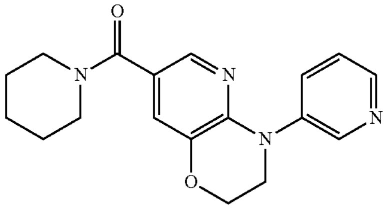
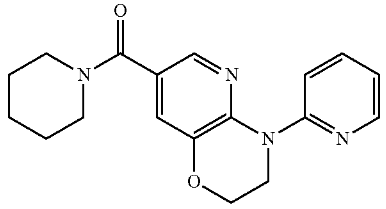
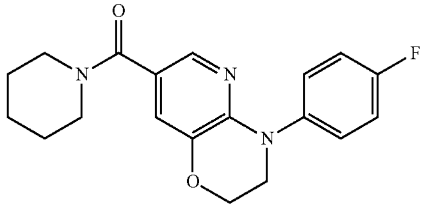
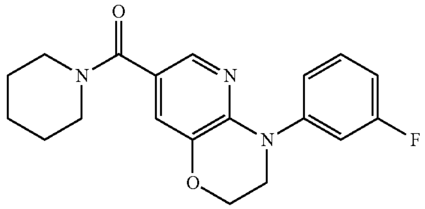
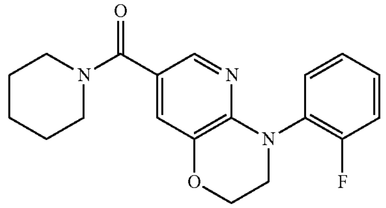
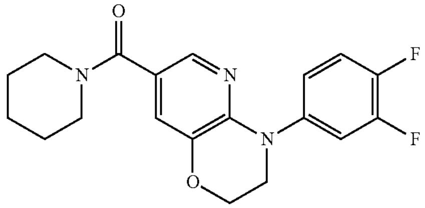
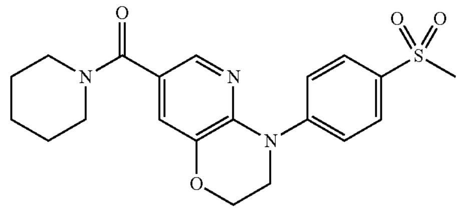
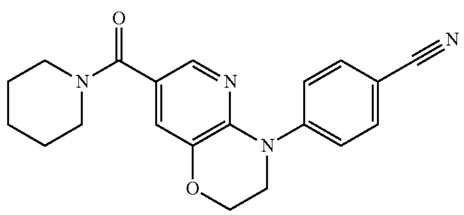

-continued
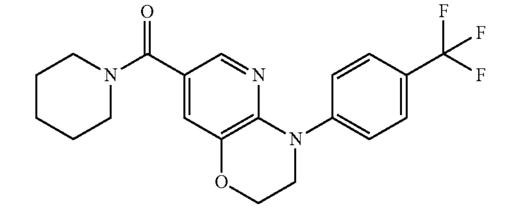
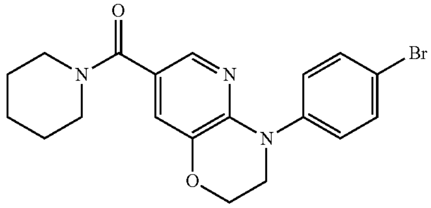
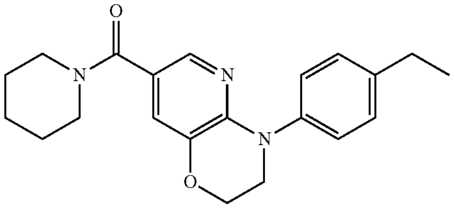
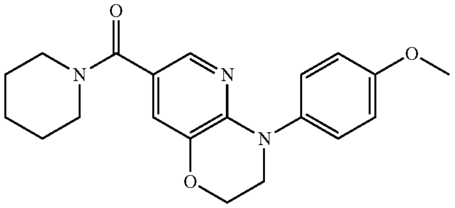
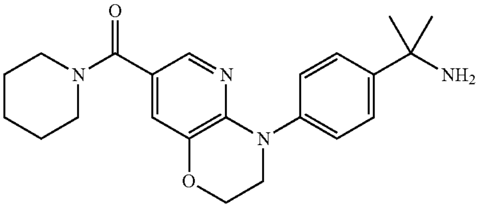
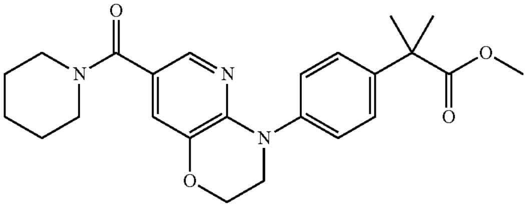
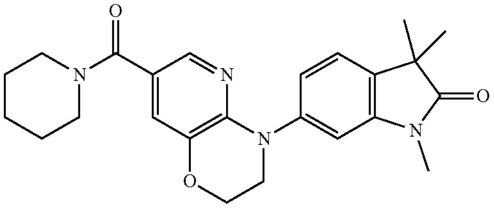
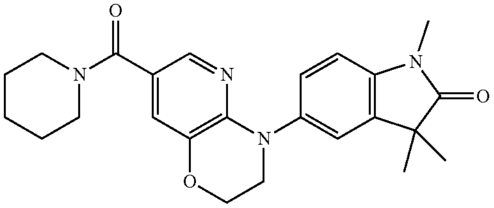
-continued
[Formula 49]
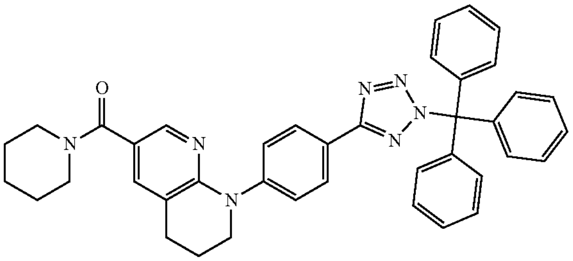
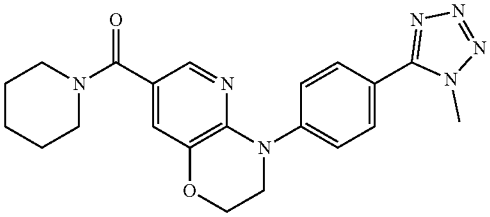
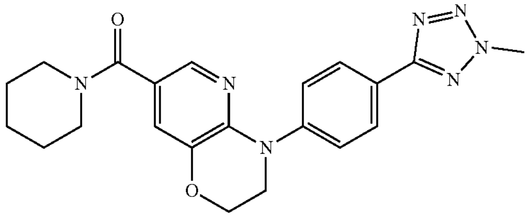
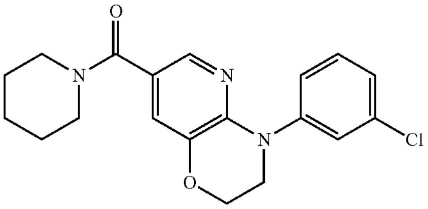
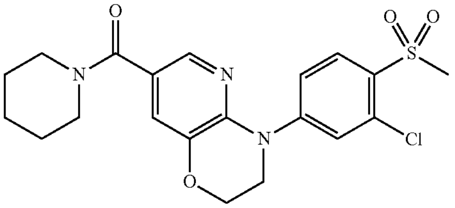
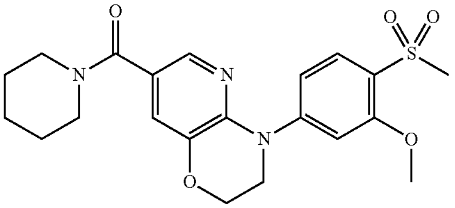
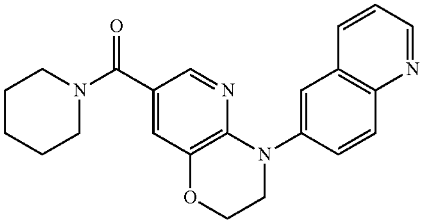

-continued
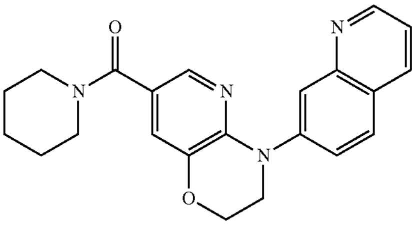
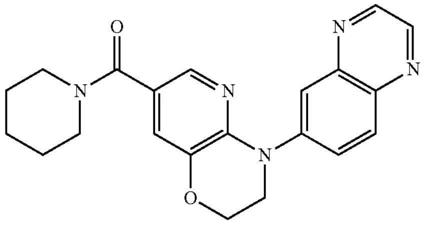
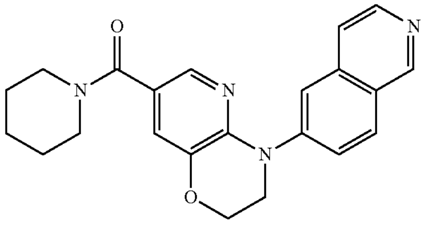
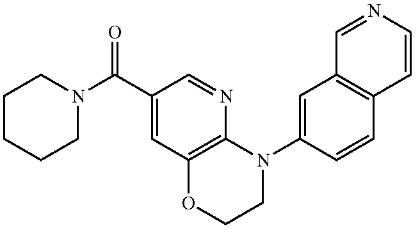
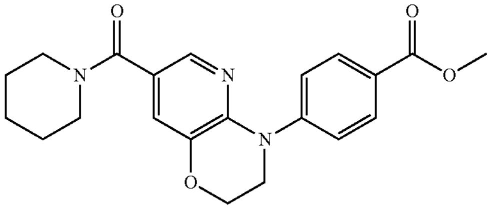
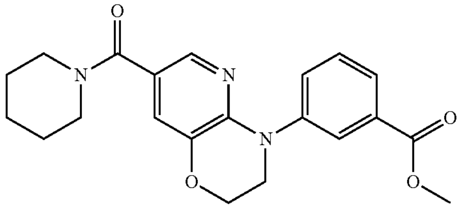
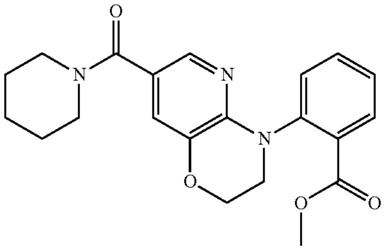
-continued
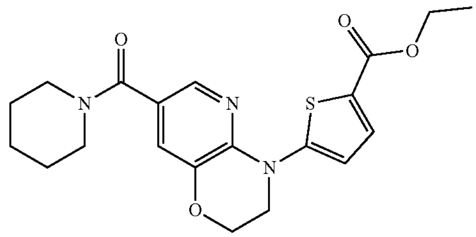
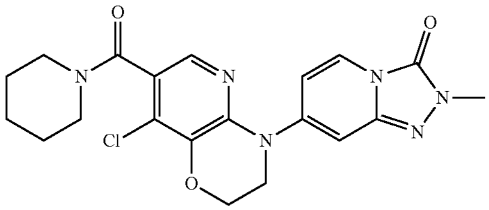
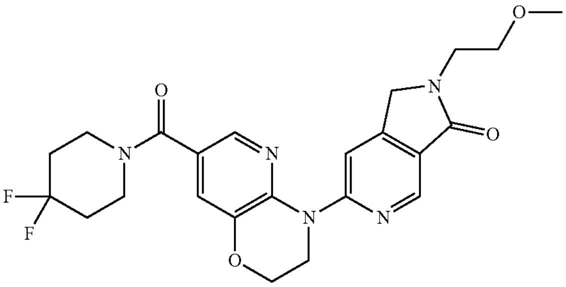
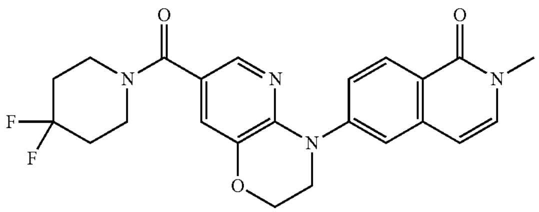
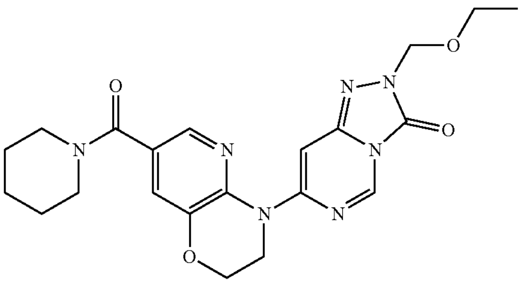
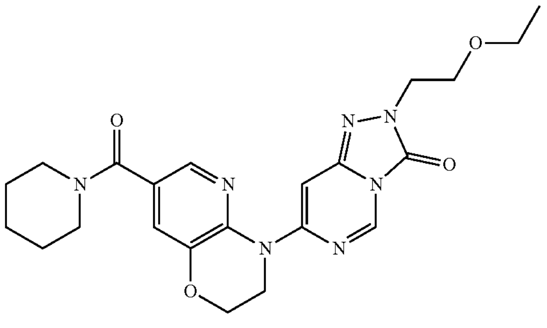

-continued
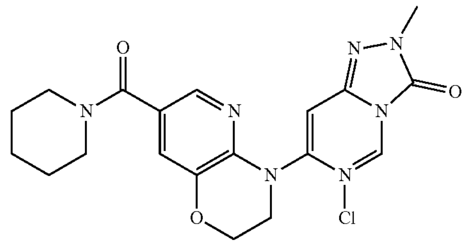
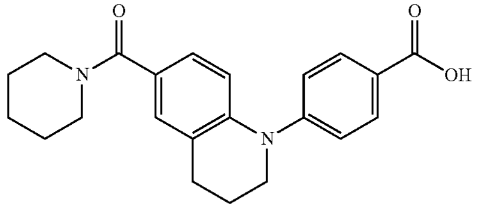
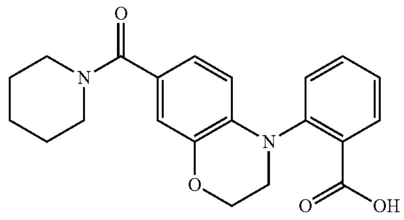
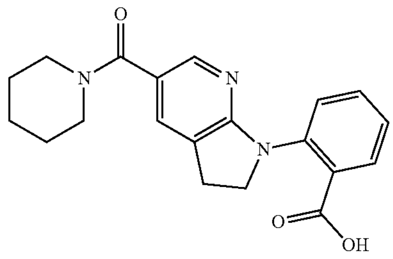
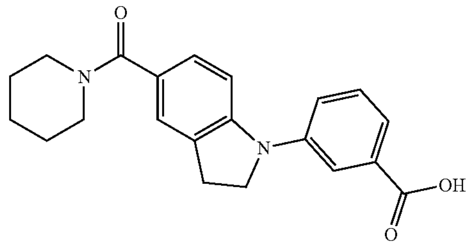
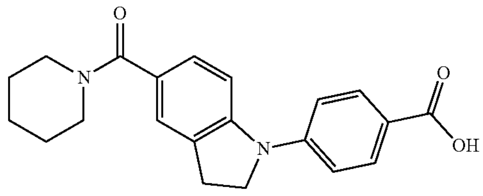
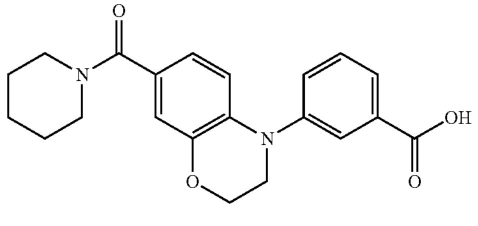
-continued
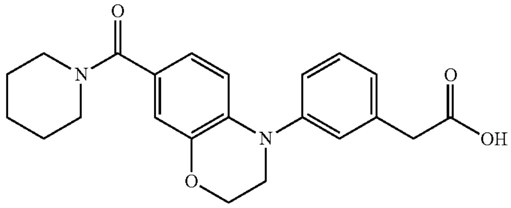
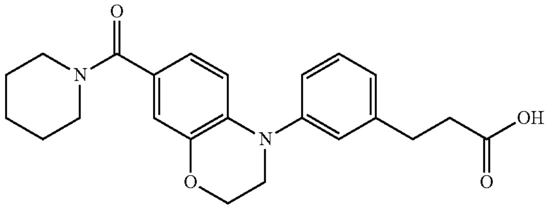
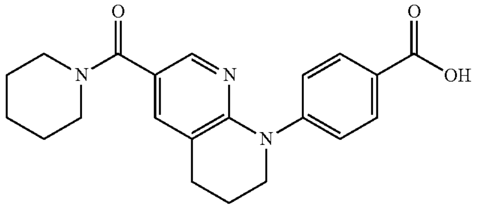
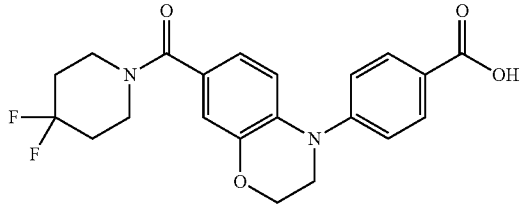
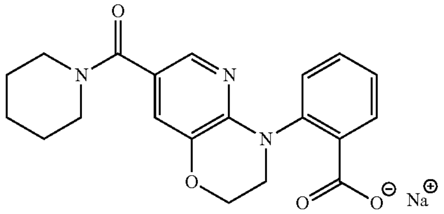
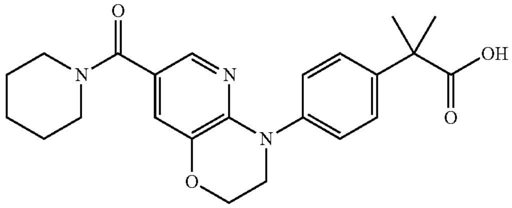
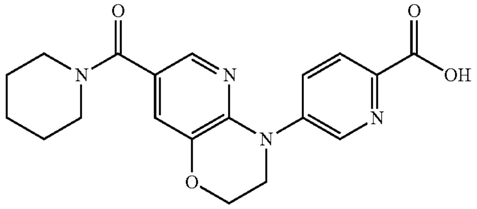
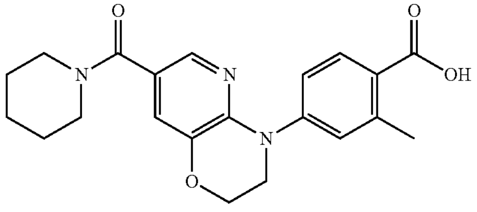

-continued
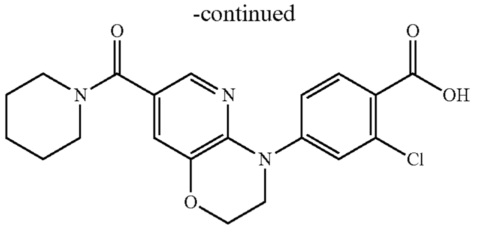
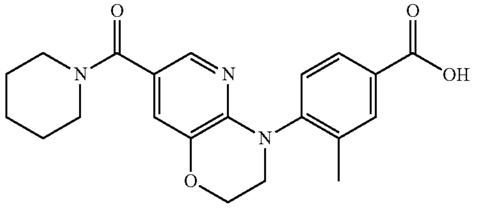
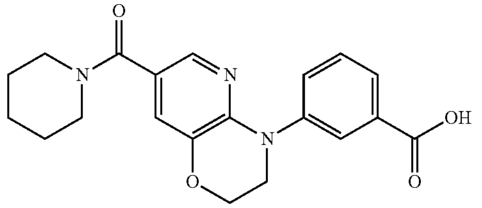
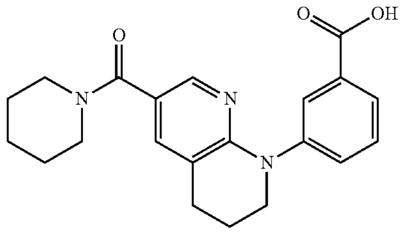
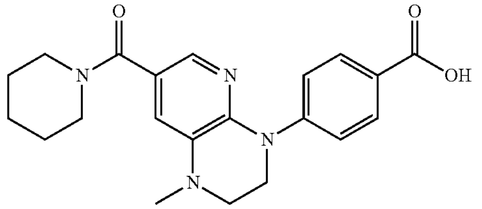
[Formula 50]
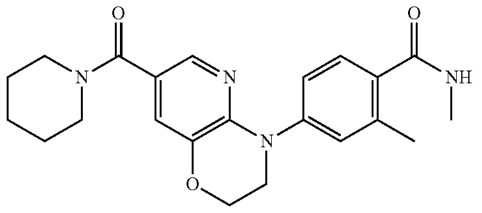
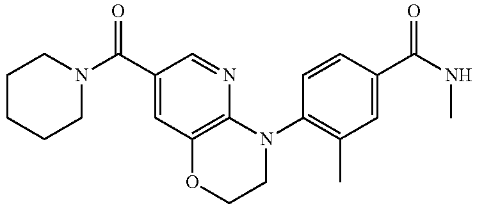
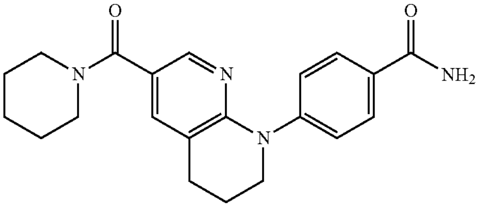
-continued
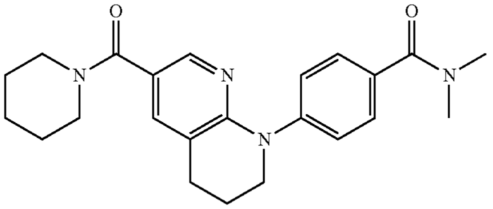
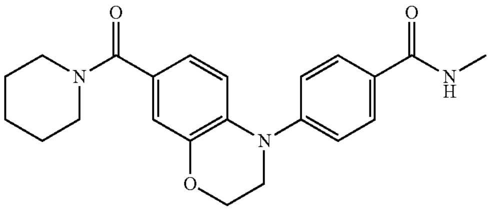
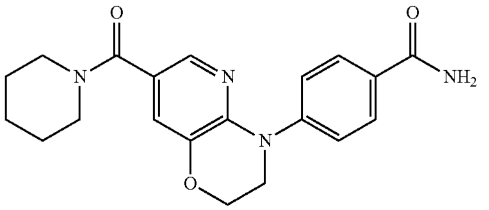
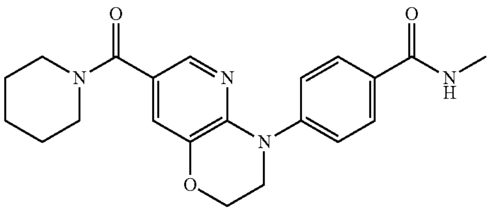
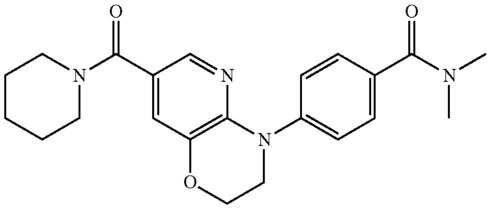
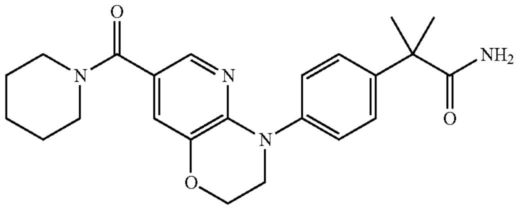
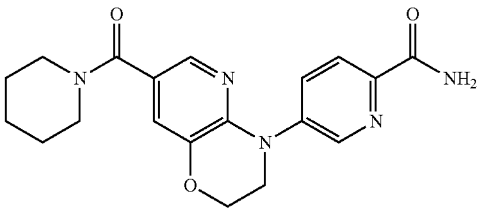
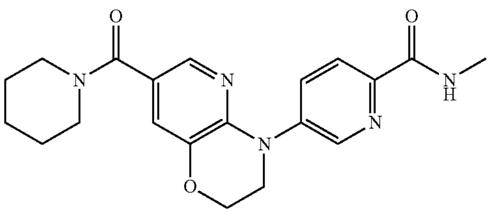

-continued
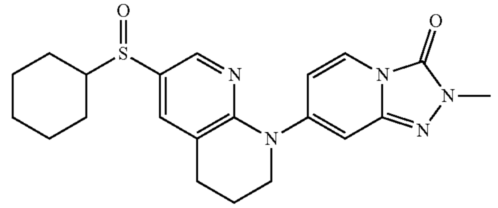
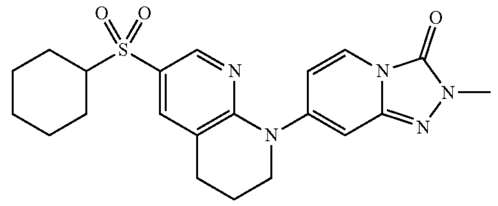
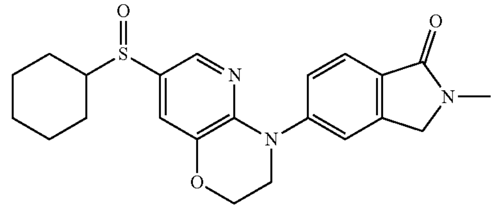
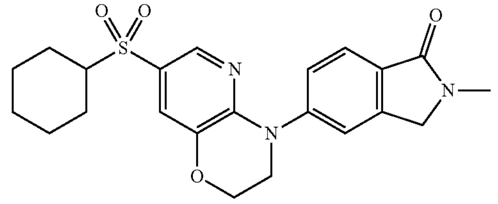
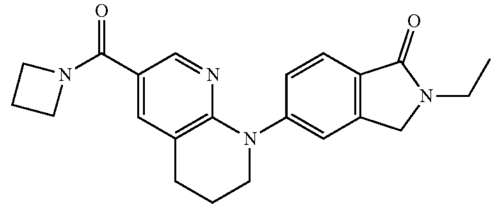
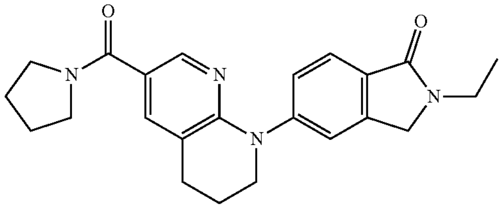
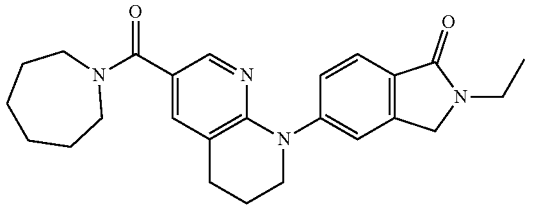
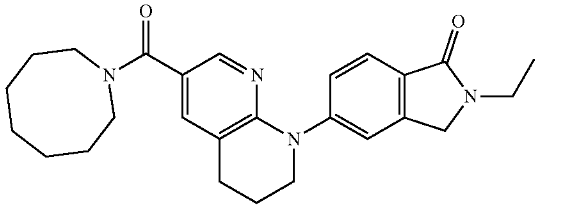
-continued
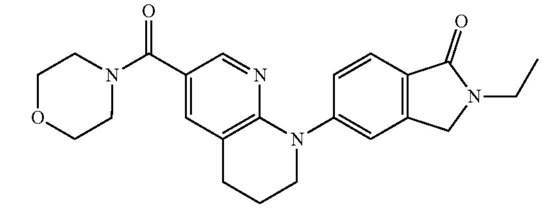
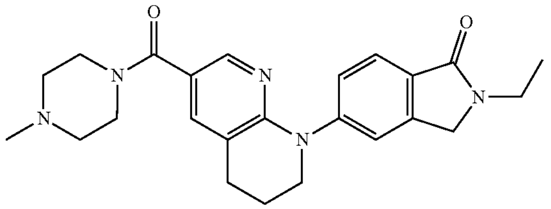
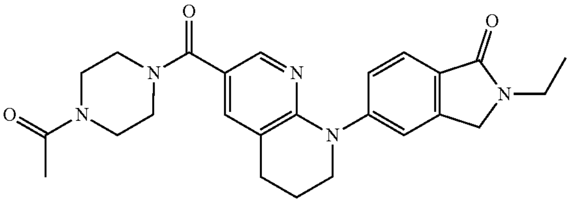
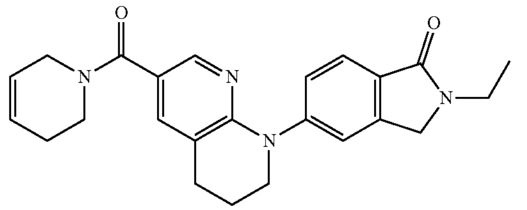
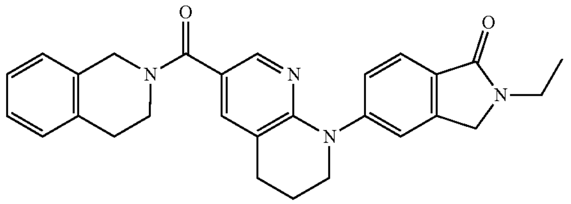
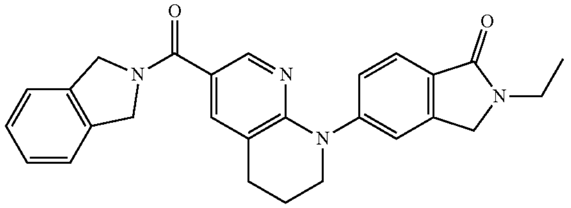
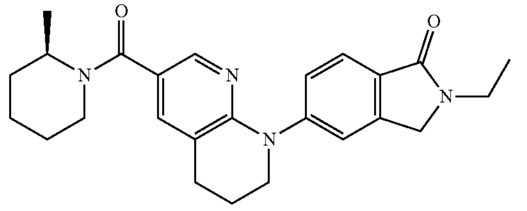
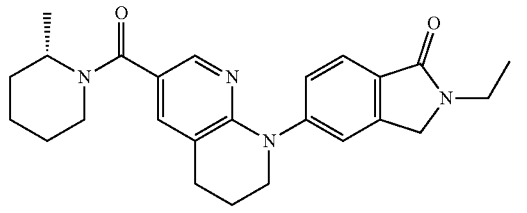

-continued
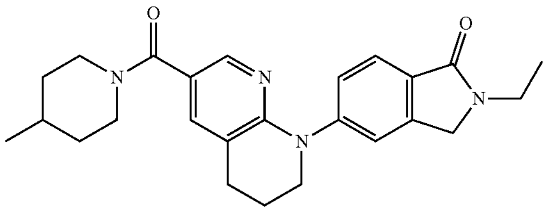
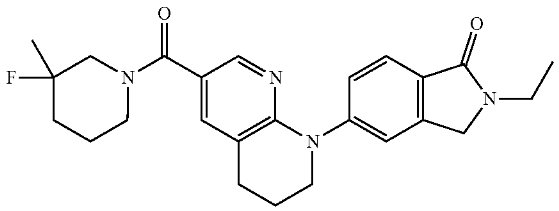
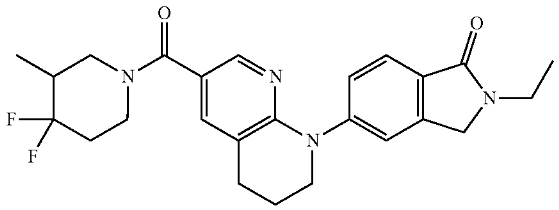
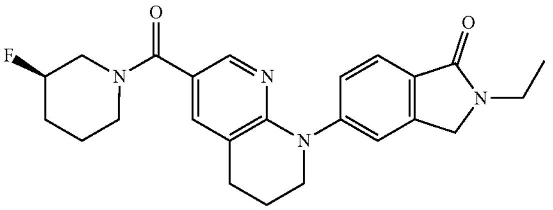
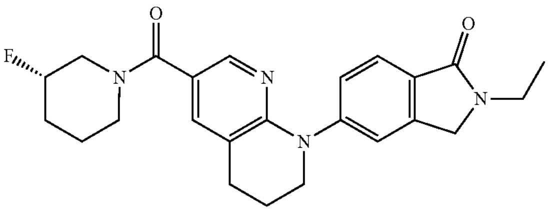
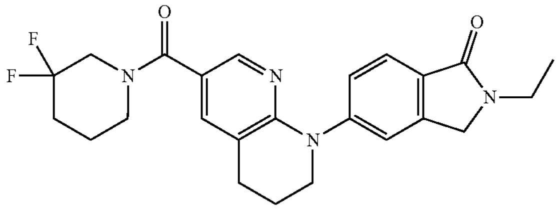
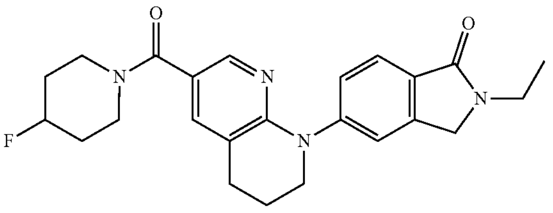
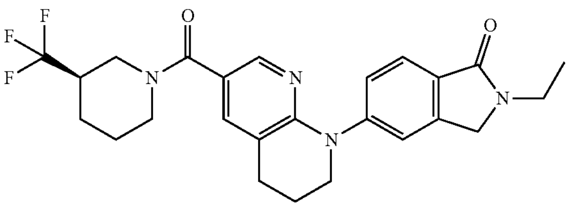
-continued
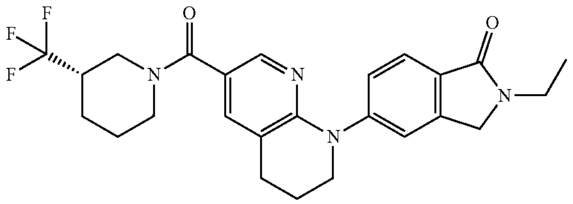
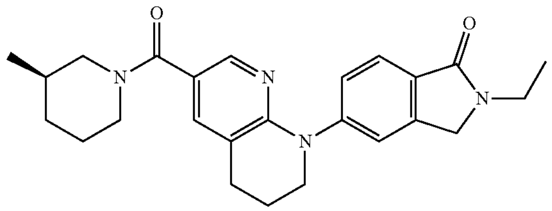
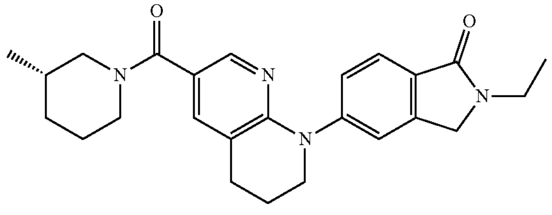
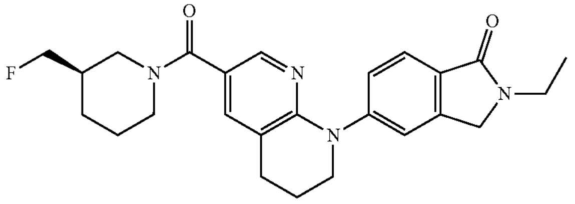
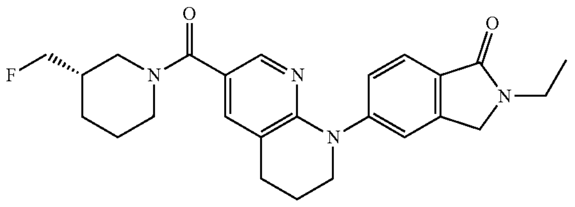
[Formula 51]
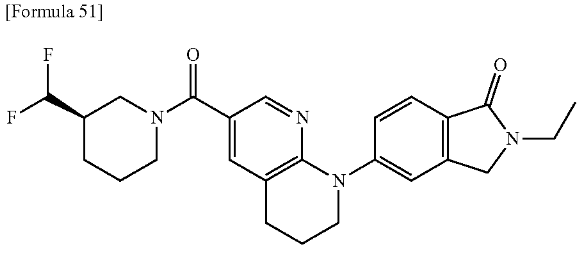
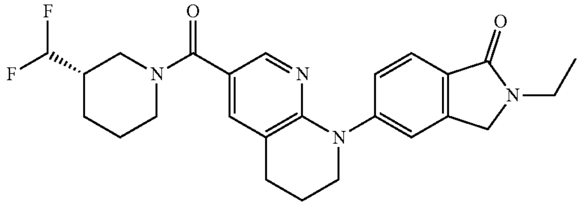

-continued
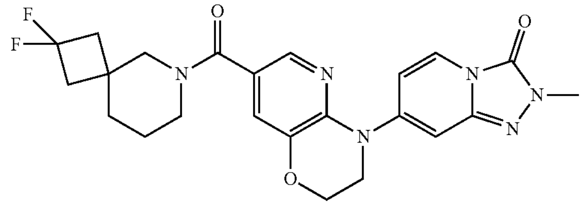
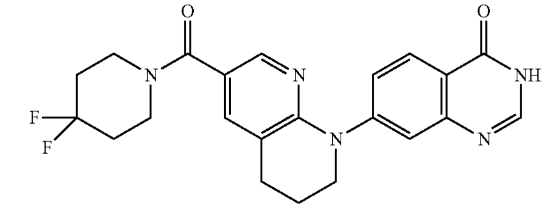
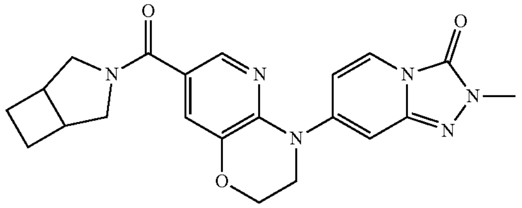
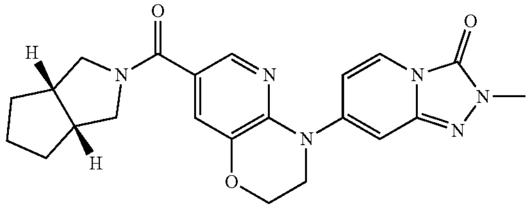
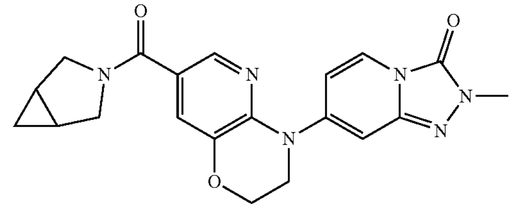
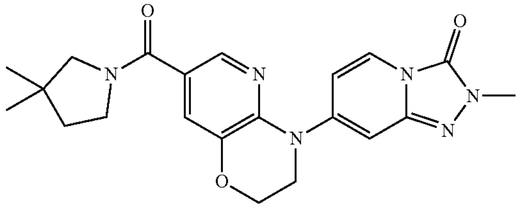
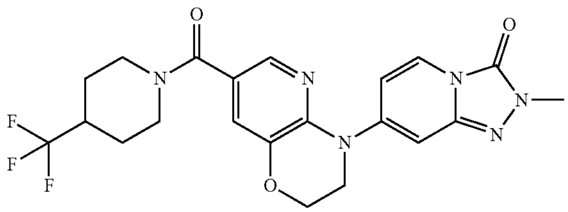
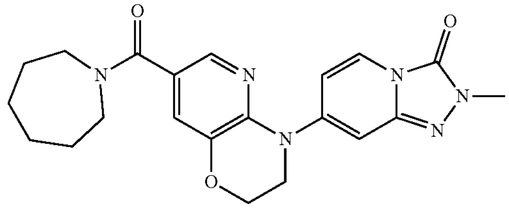
-continued
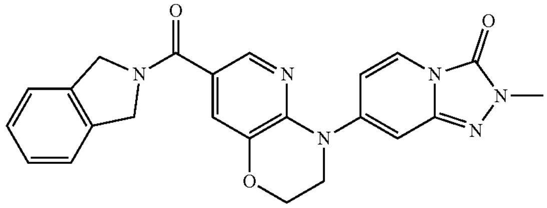
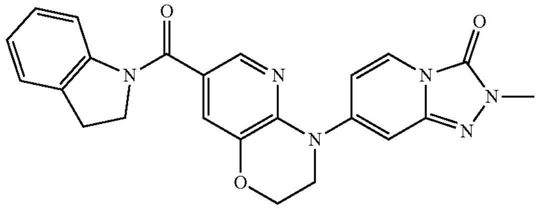
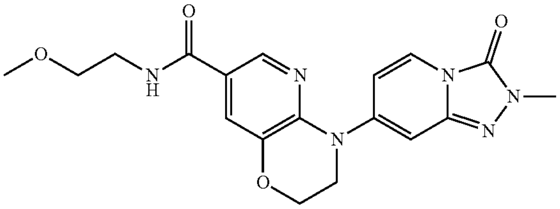
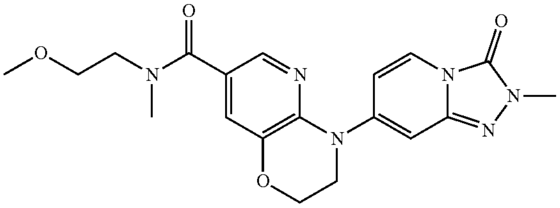
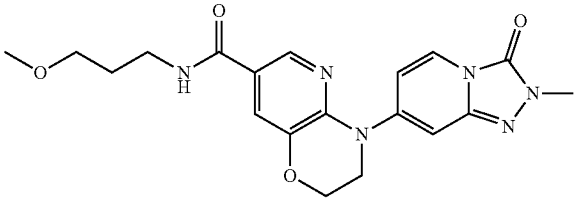
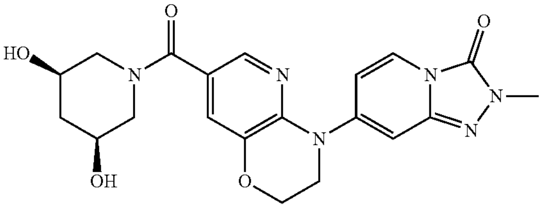
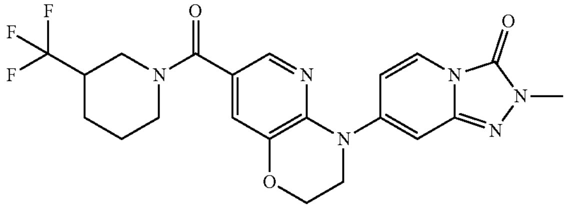
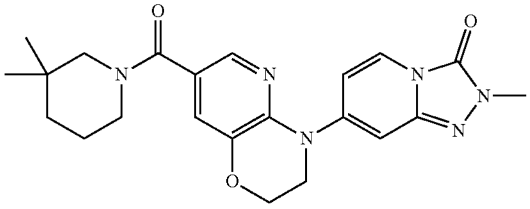

-continued
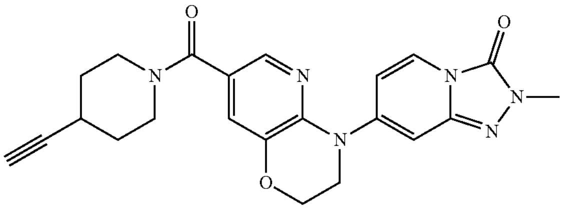
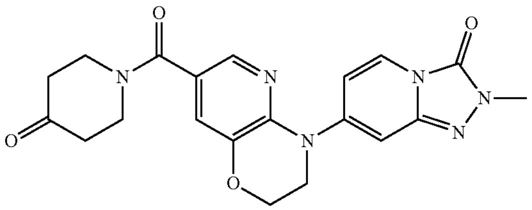
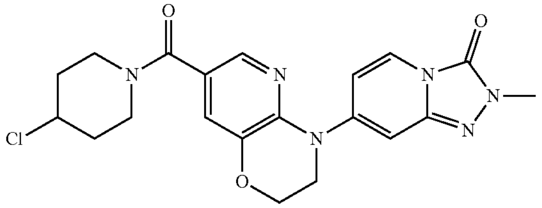
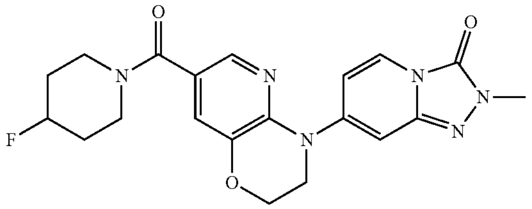
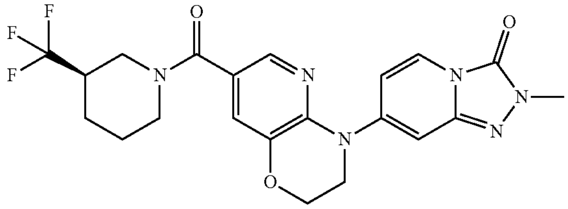
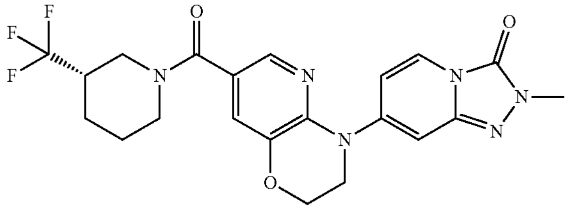
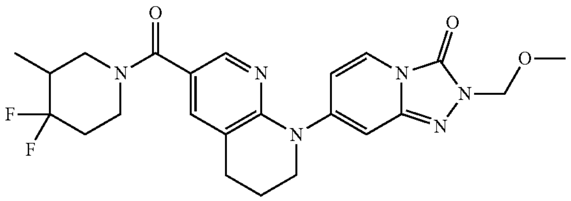
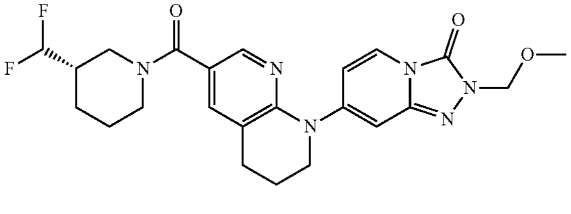
-continued
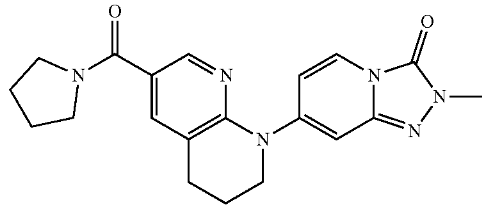
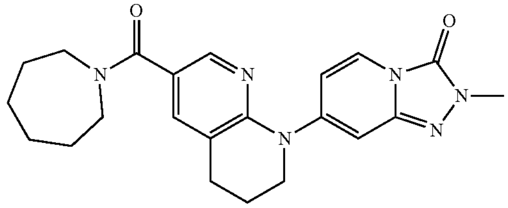
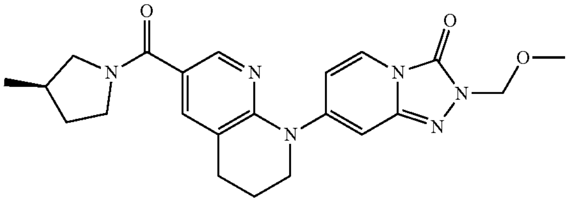
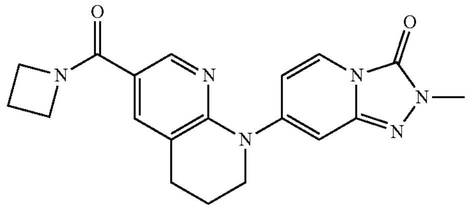
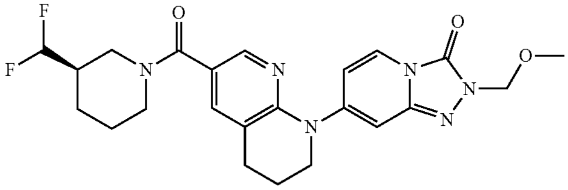
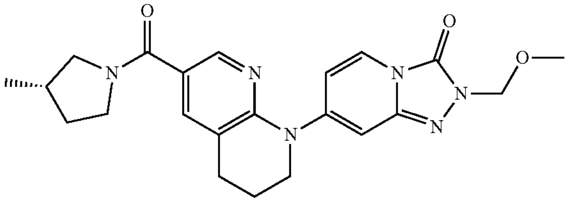
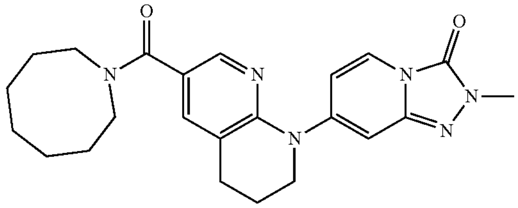
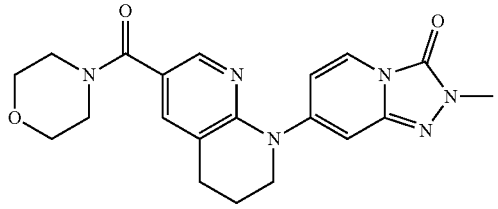

-continued
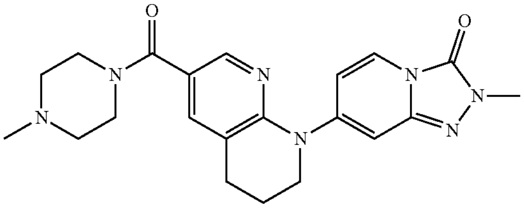
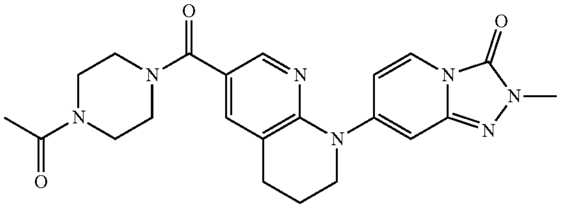
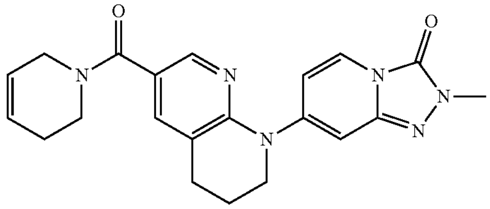
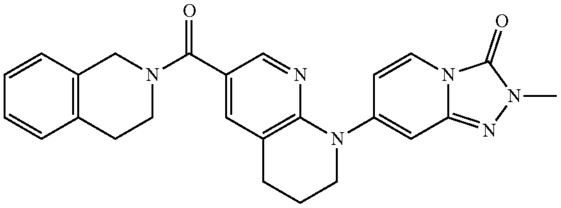
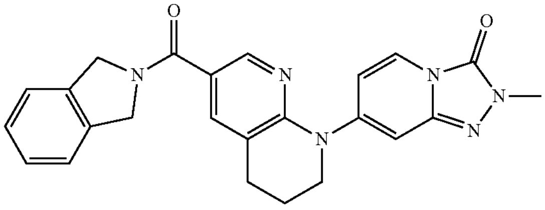
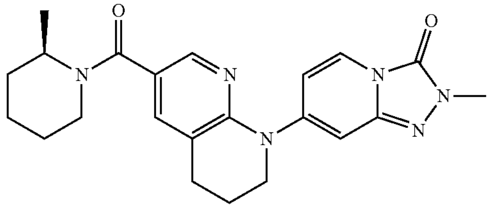
[Formula 52]
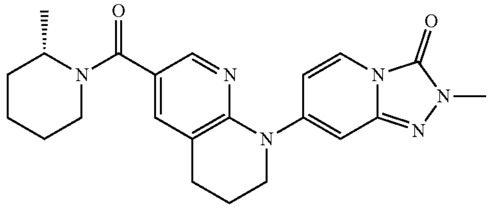
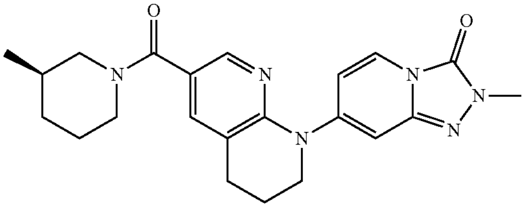
-continued
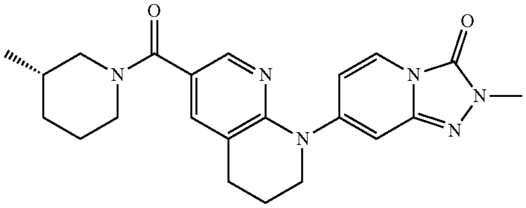
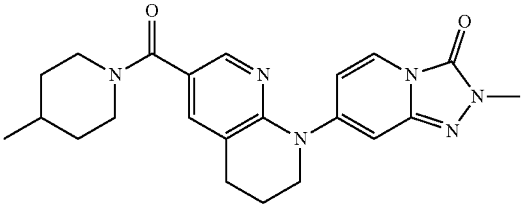
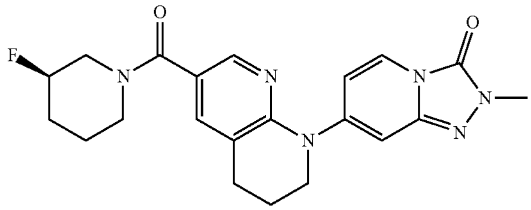
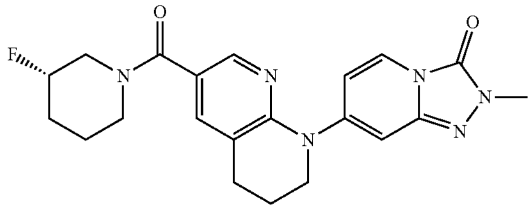
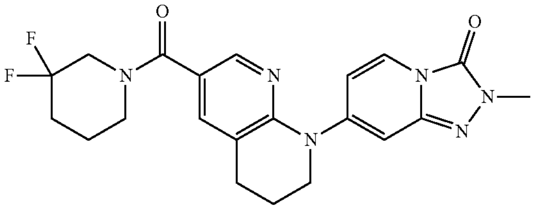
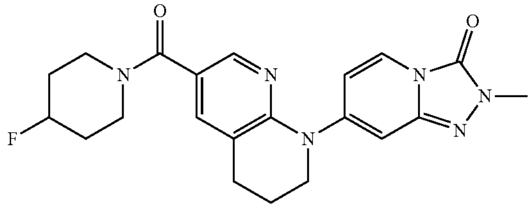
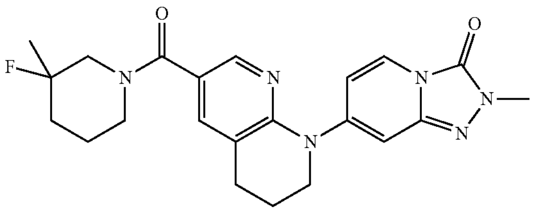
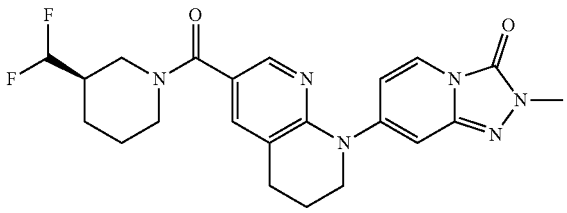

-continued
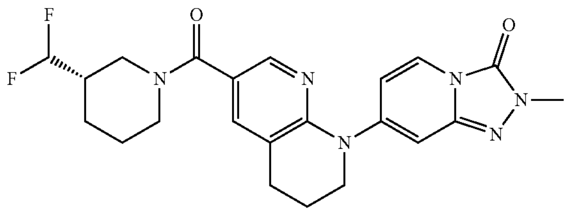
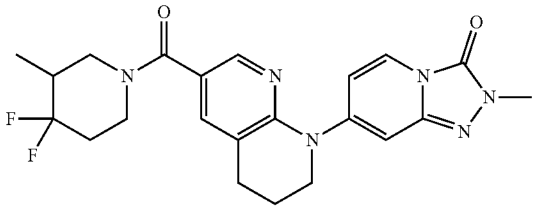
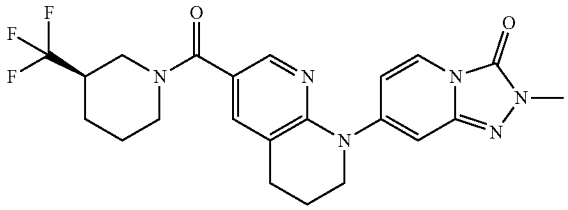
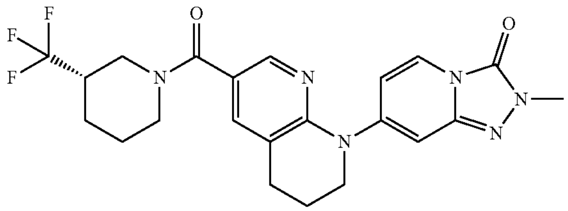
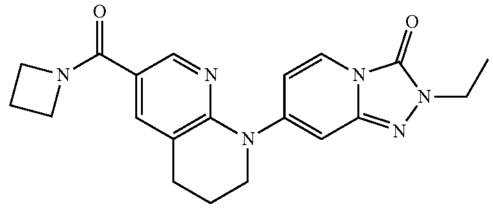
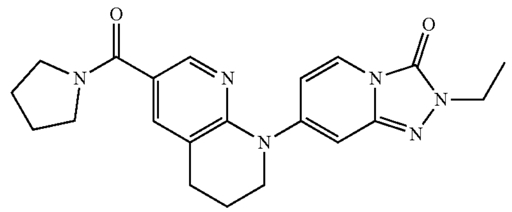
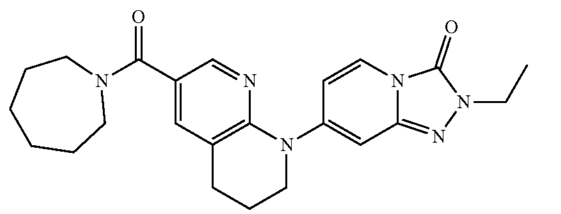
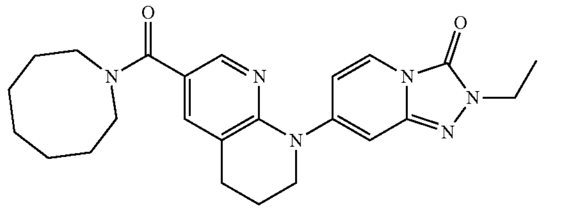
-continued
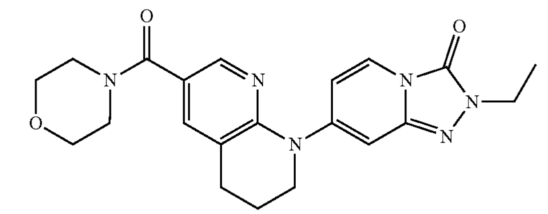
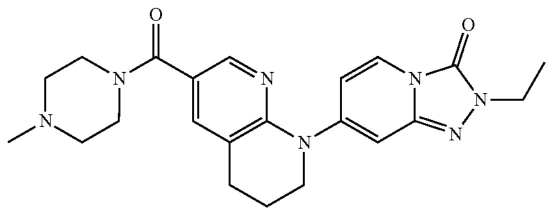
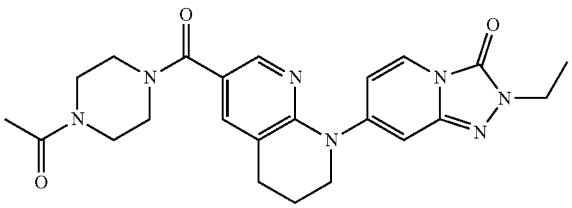
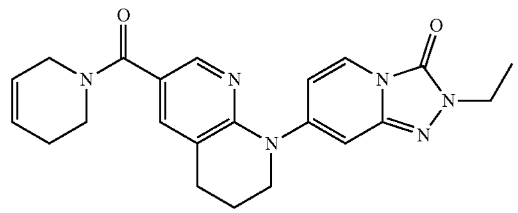
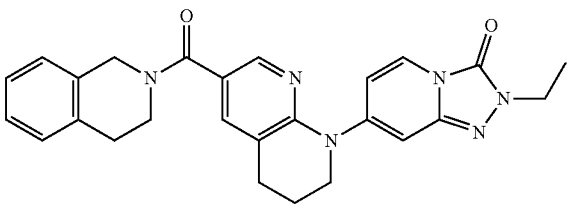
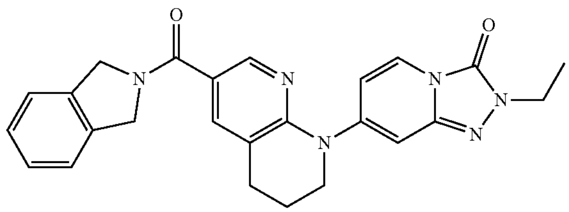
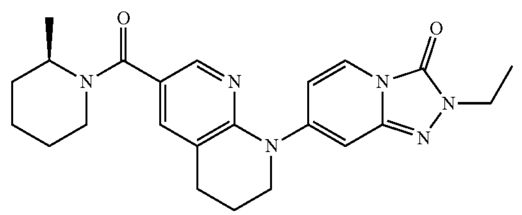
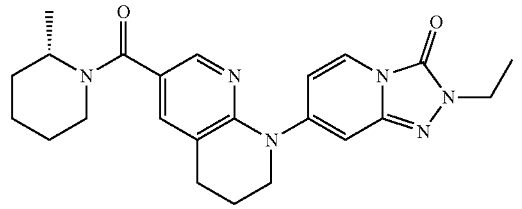

-continued
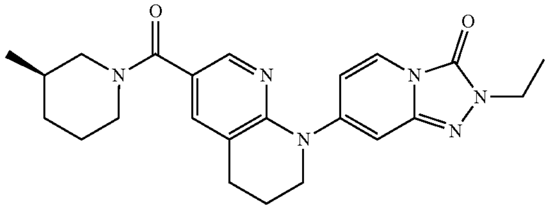
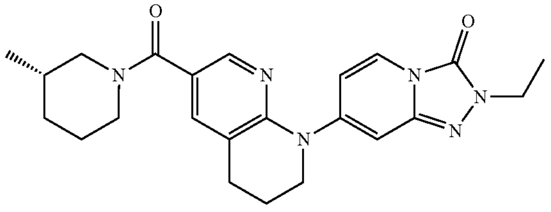
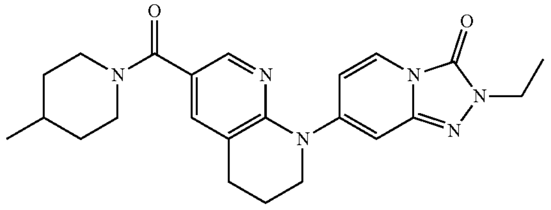
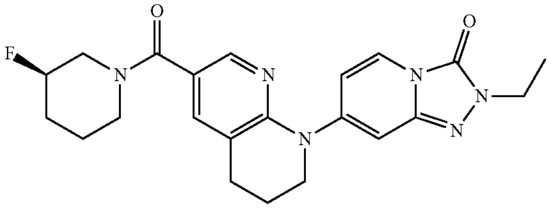
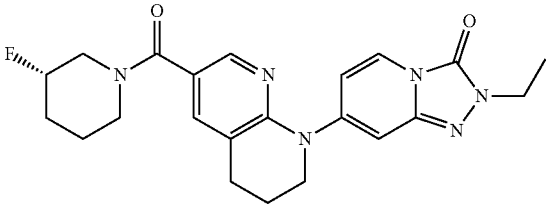
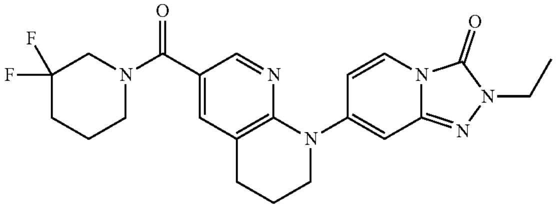
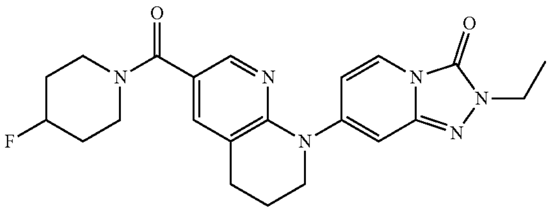
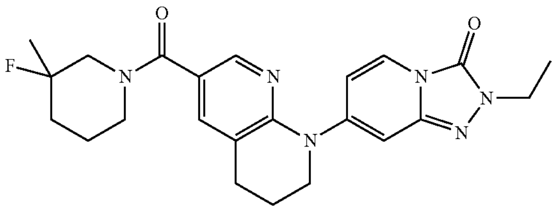
-continued
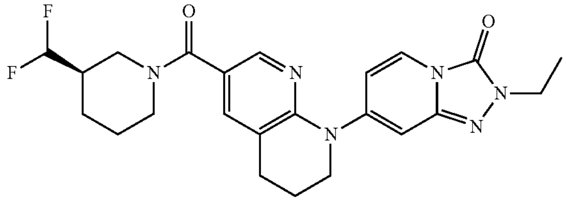
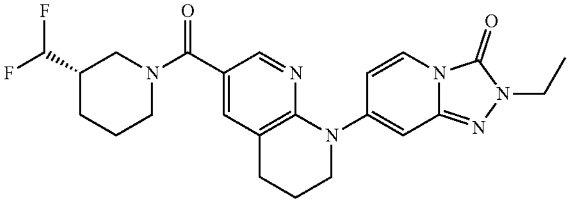
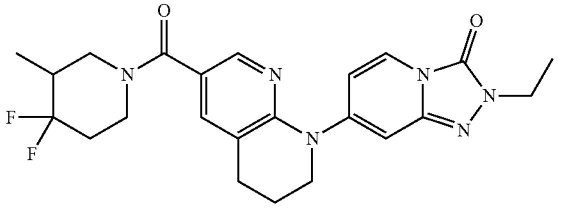
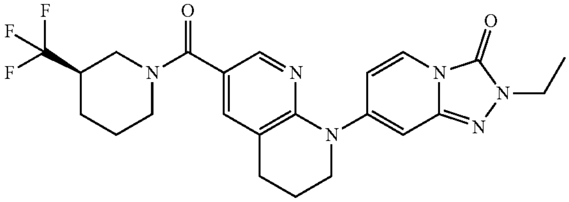
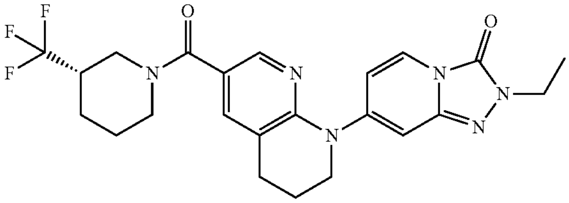
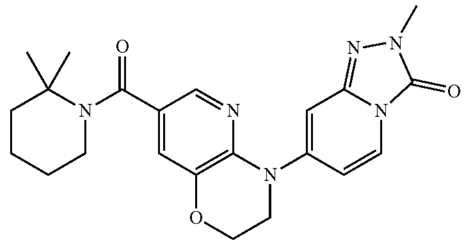
[Formula 53]
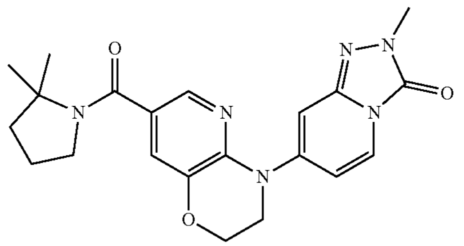

-continued
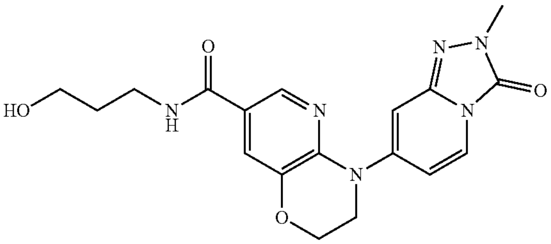
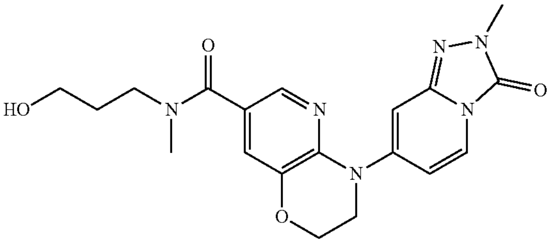
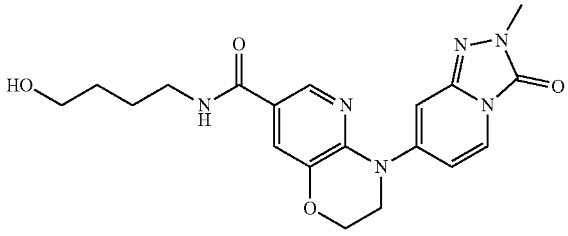
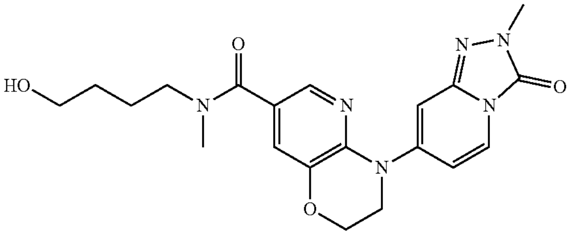
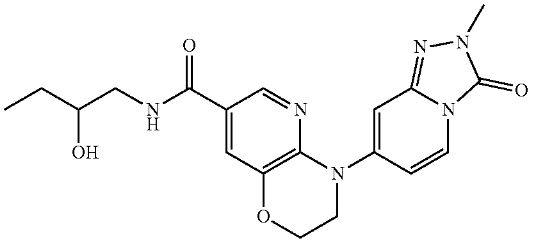
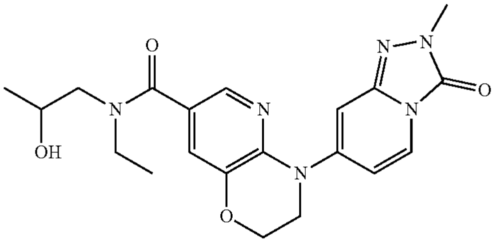
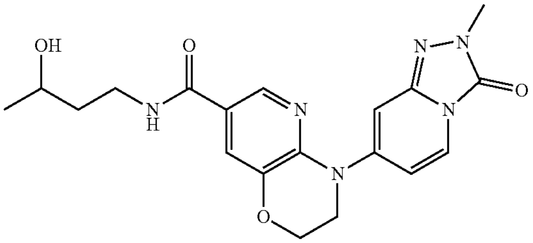
-continued
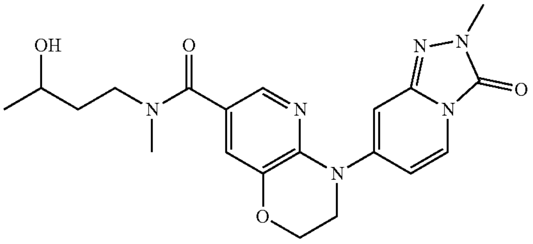
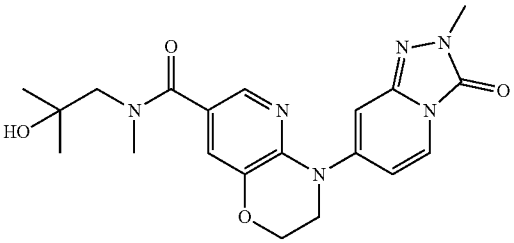
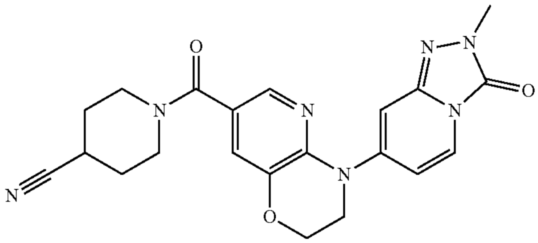
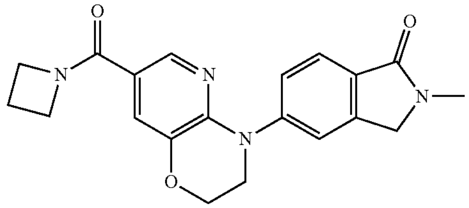
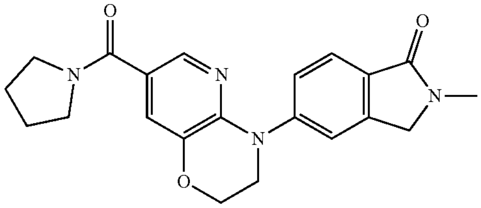
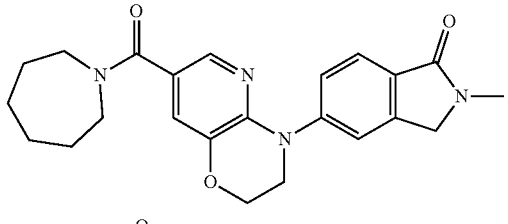
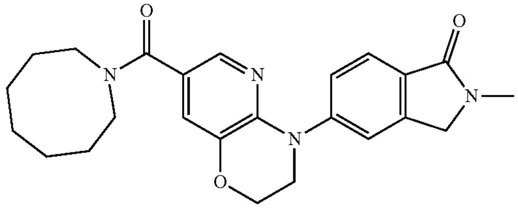

-continued
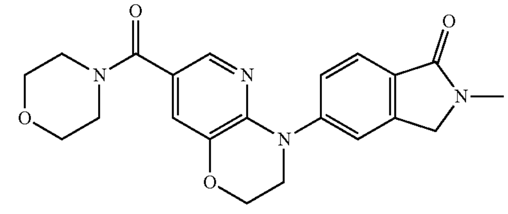
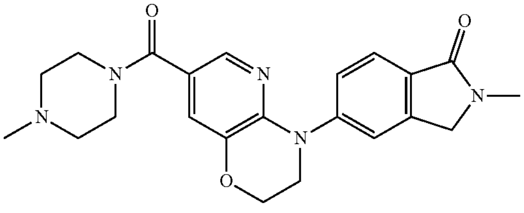
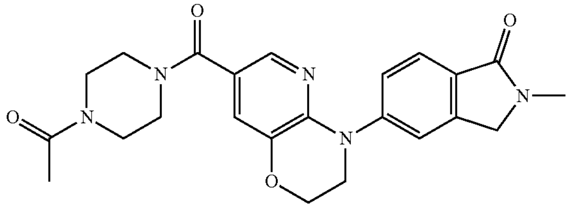
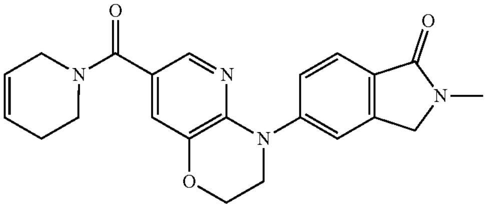
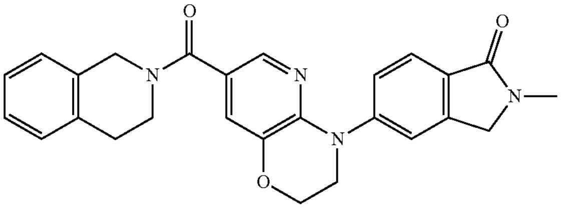
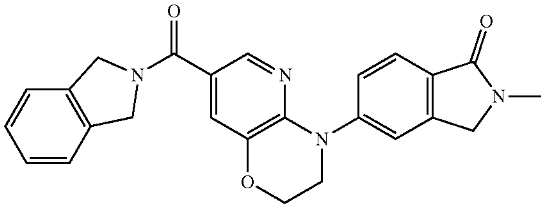
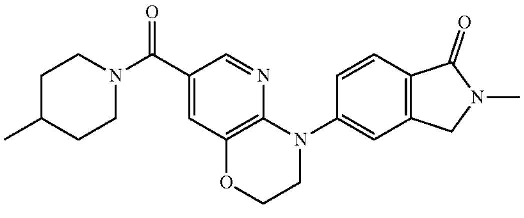
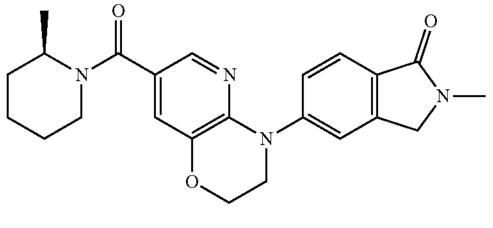
-continued
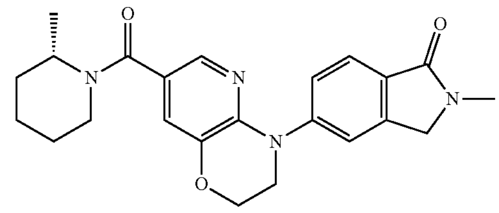
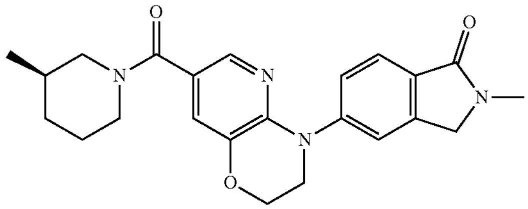
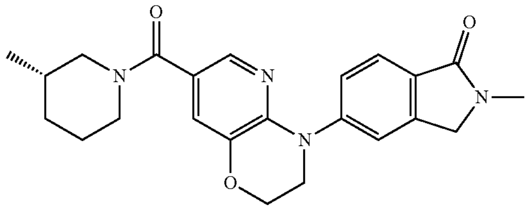
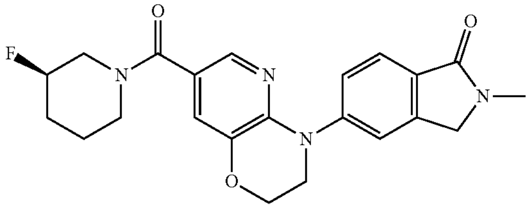
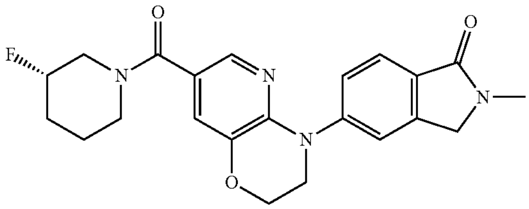
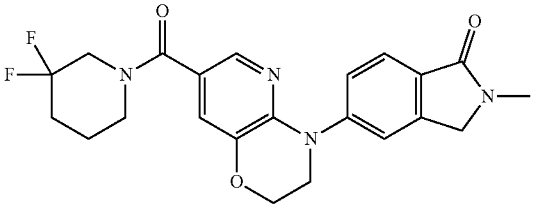
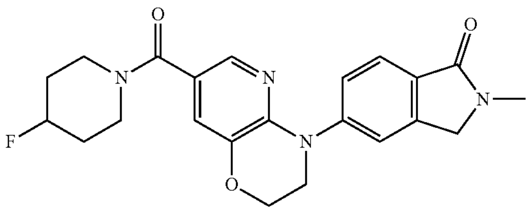
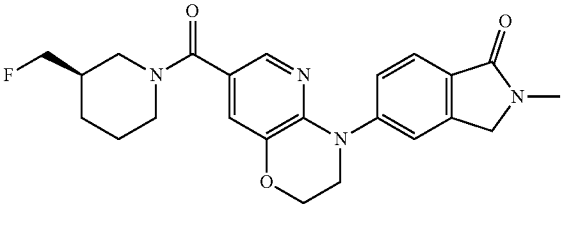

-continued
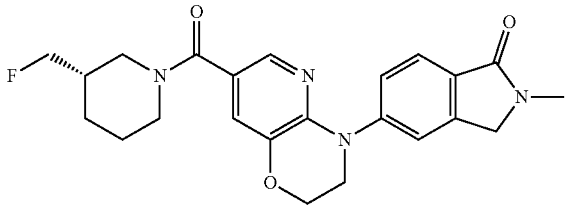
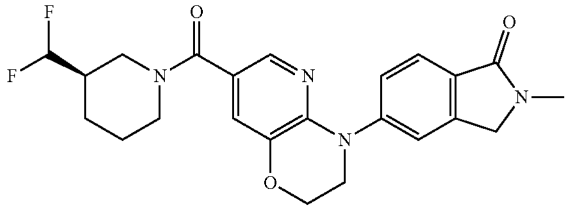
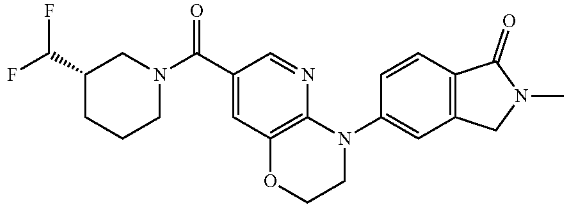
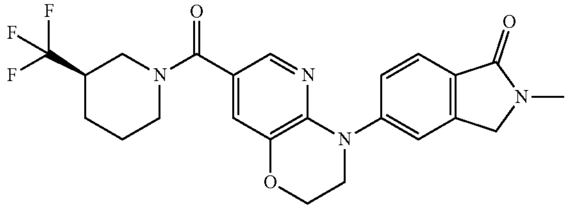
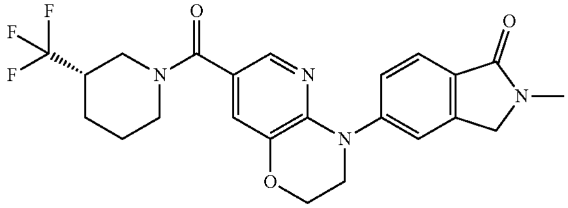
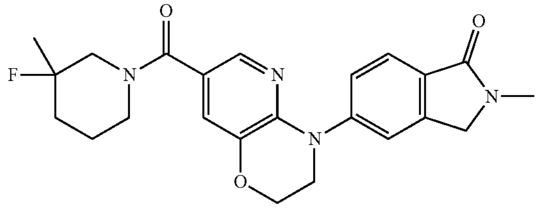
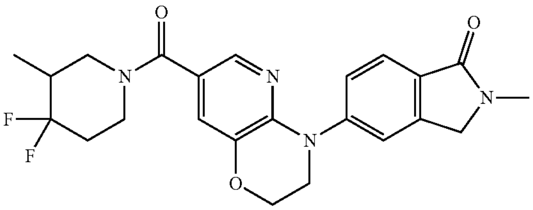
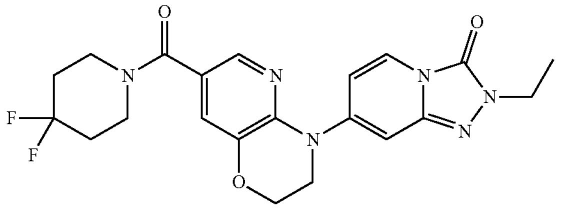
-continued
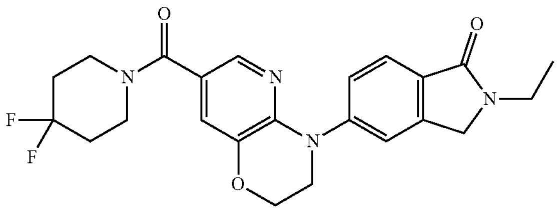
[Formula 54]
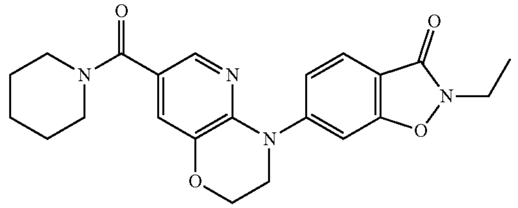
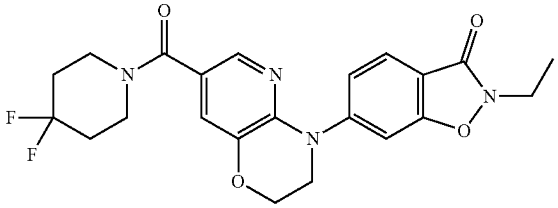
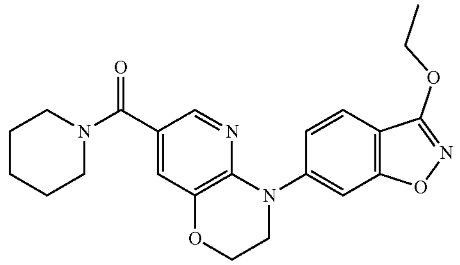
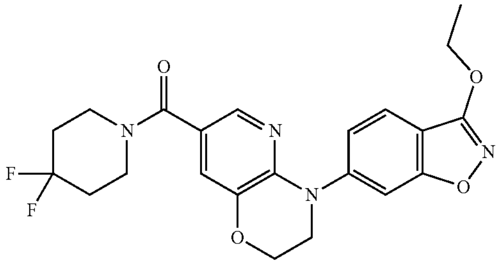
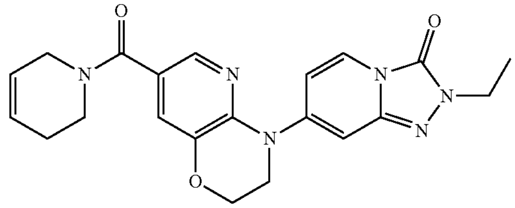
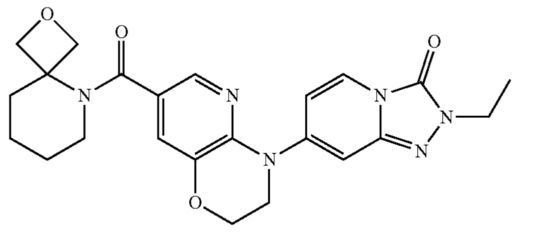

-continued
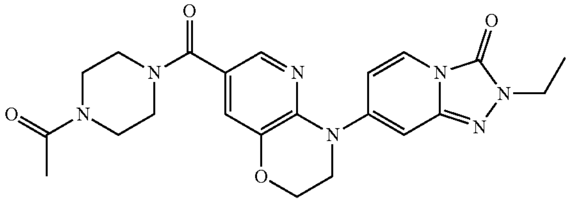
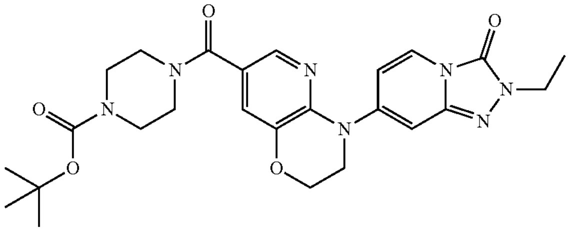
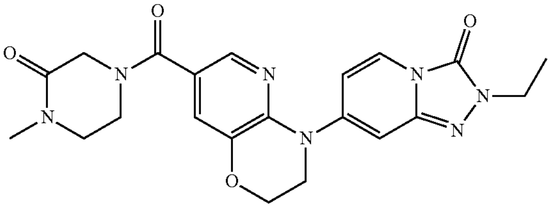
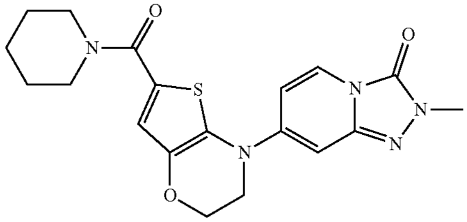
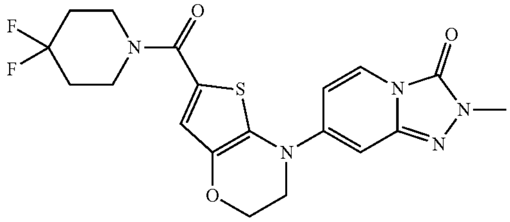
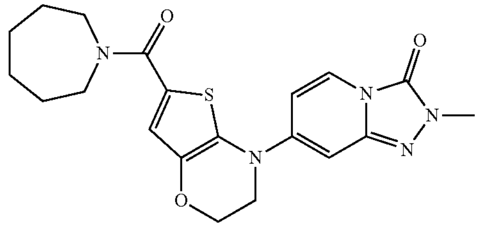
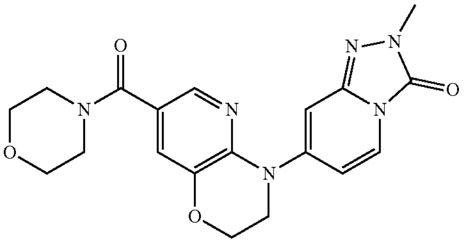
-continued
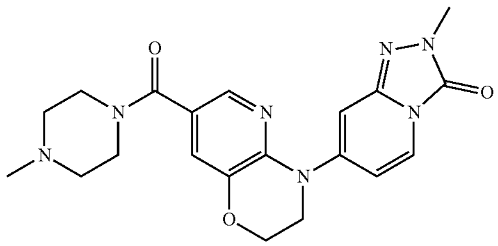
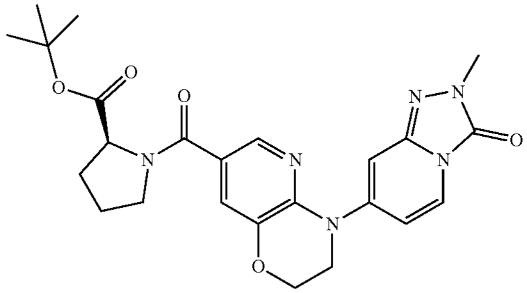
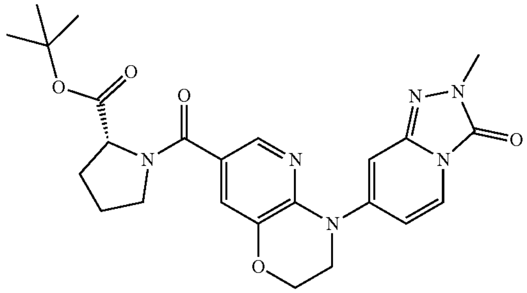
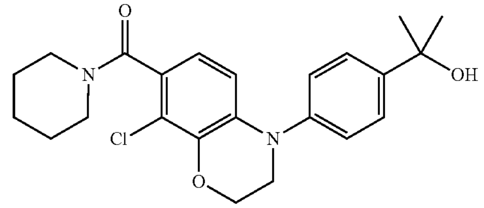
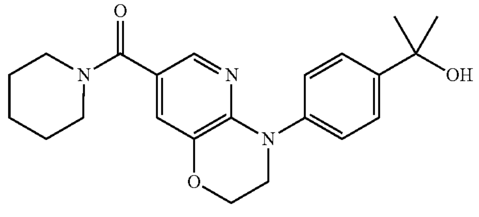
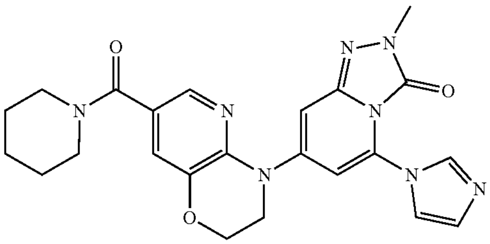

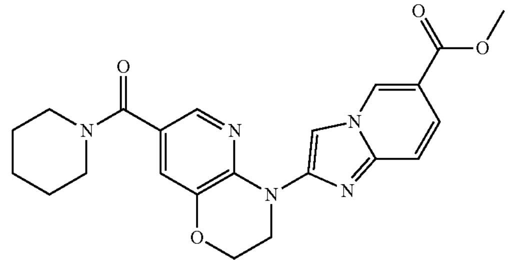
[Formula 55]
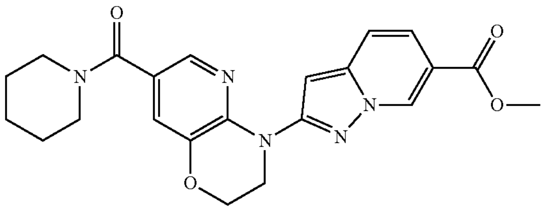
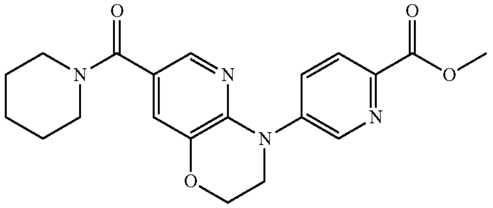
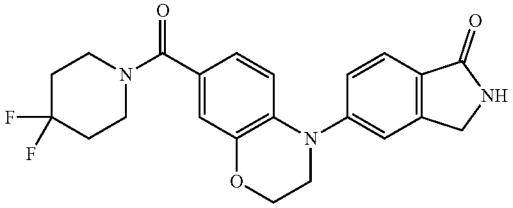
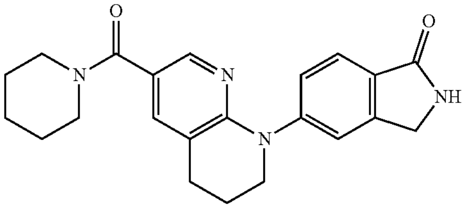
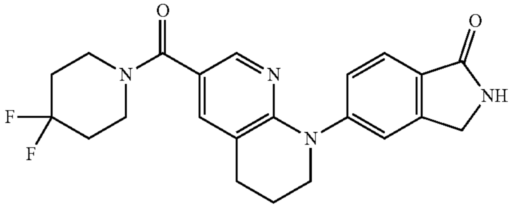
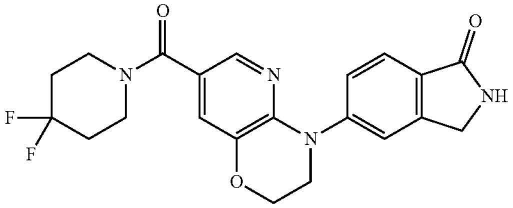
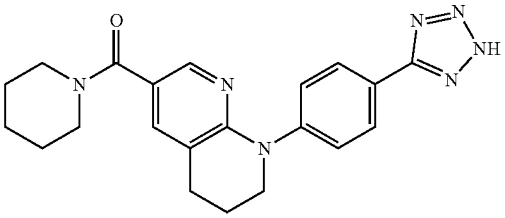
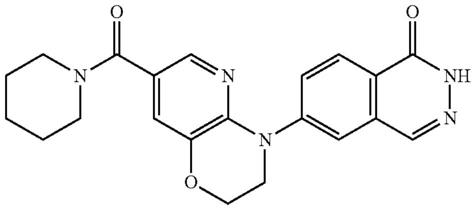
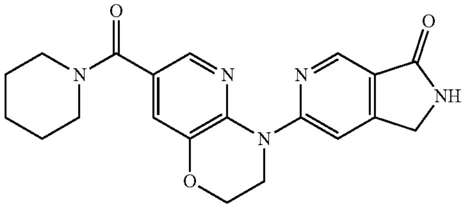
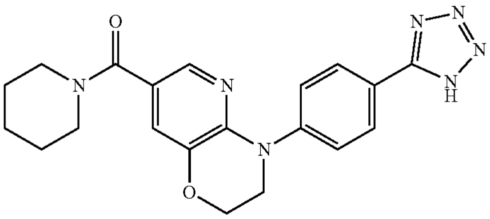
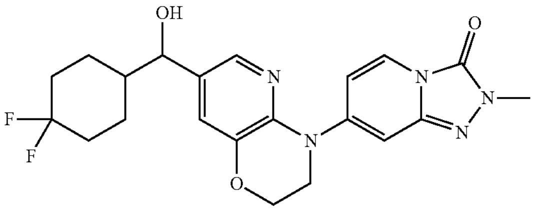
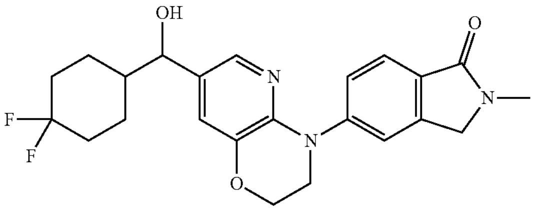
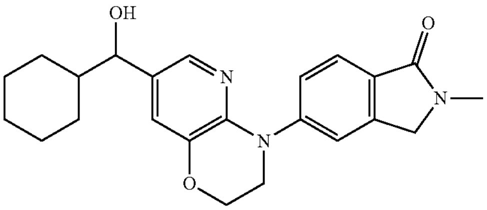
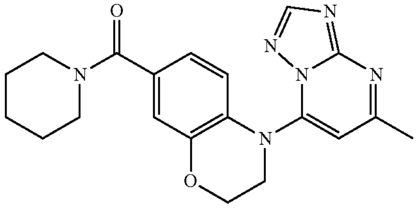

-continued
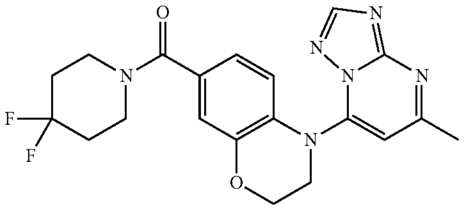
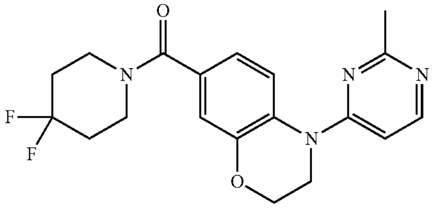
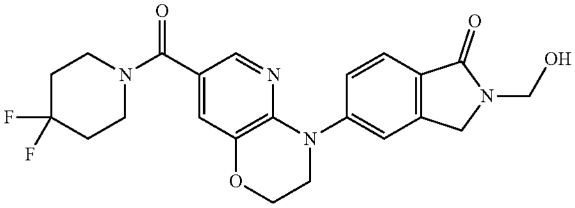
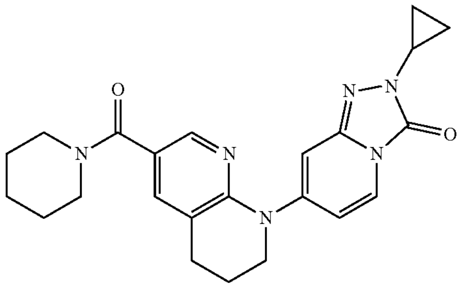
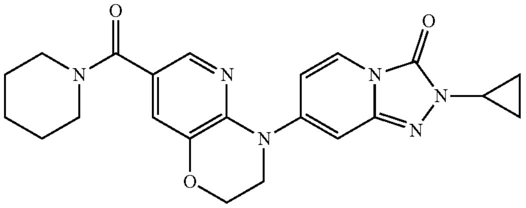
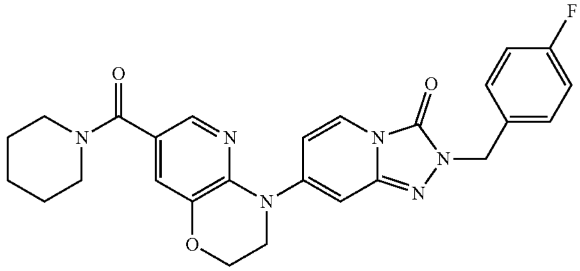
[Formula 56]
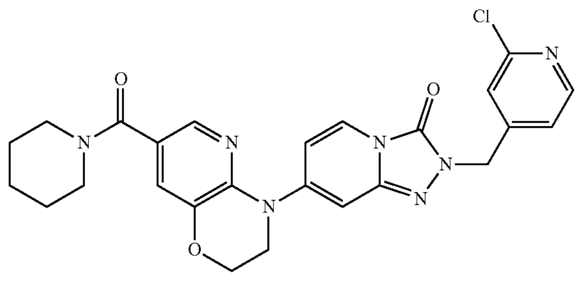
-continued
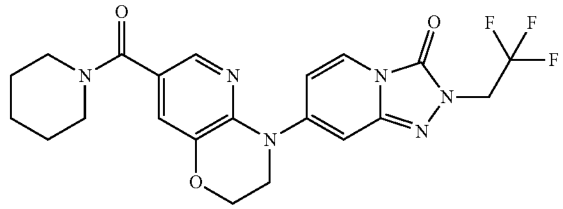
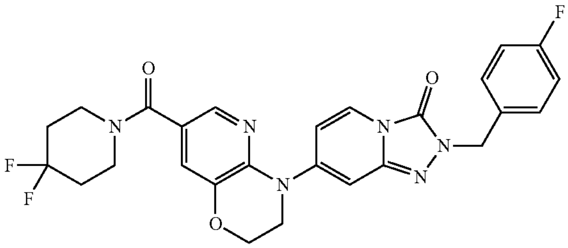
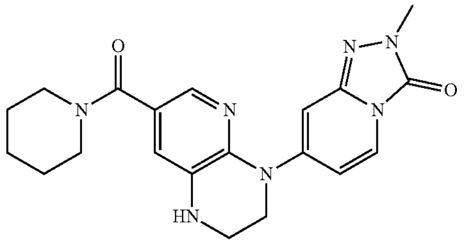
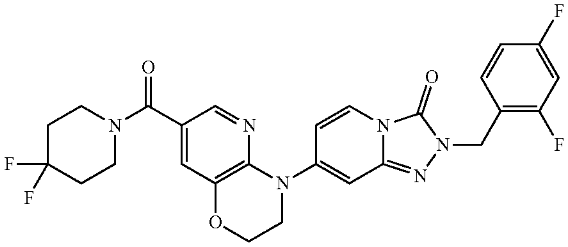
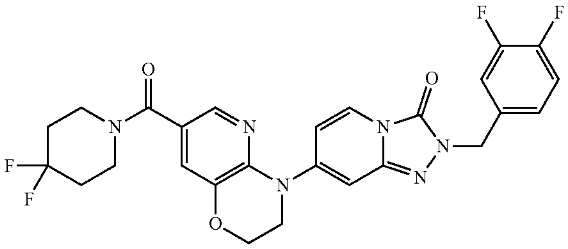
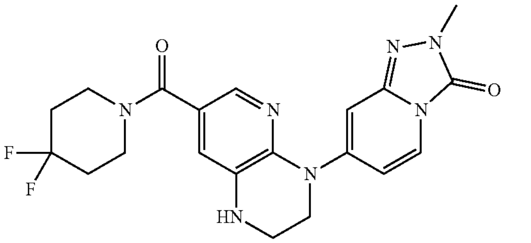
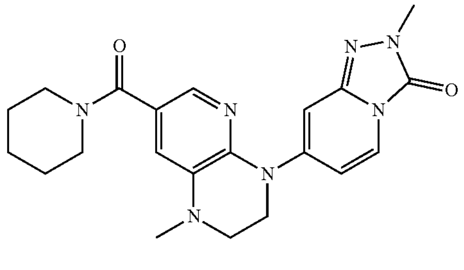

-continued
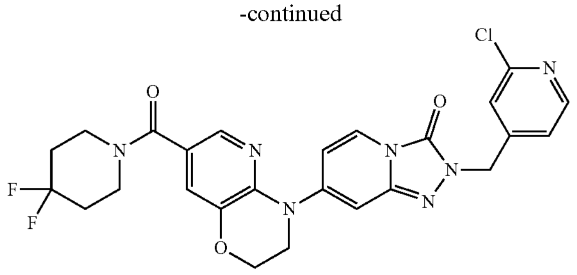
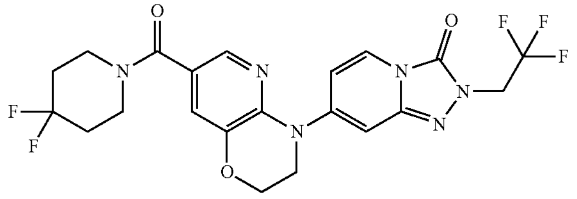
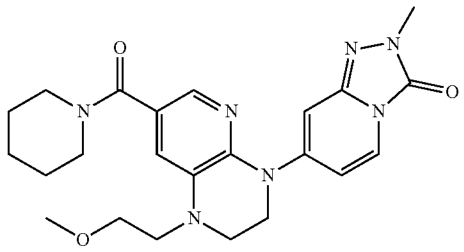
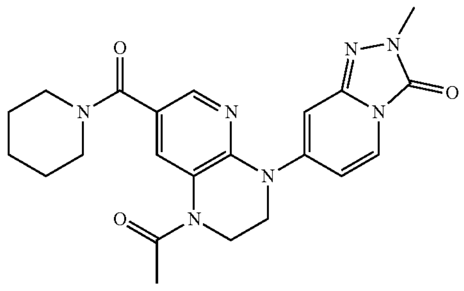
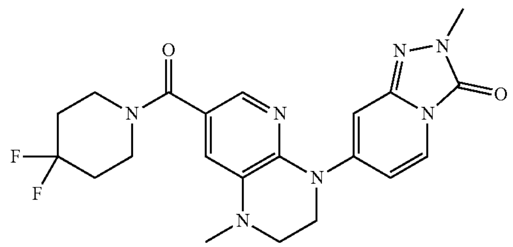
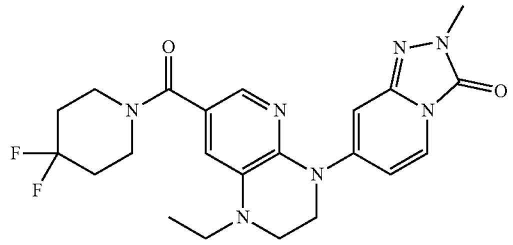
-continued
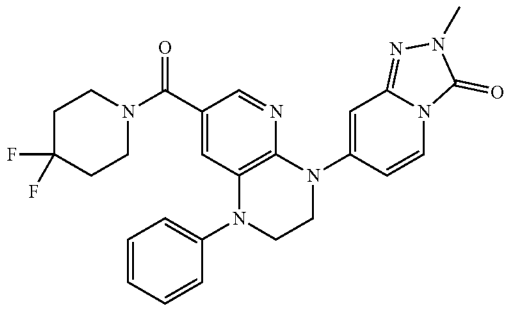
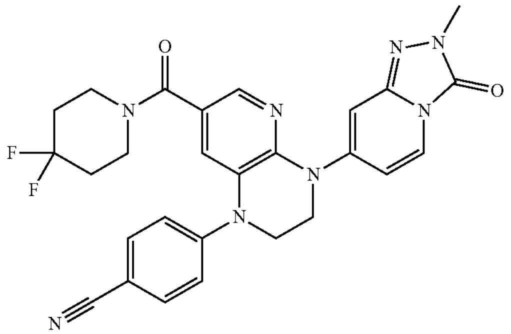
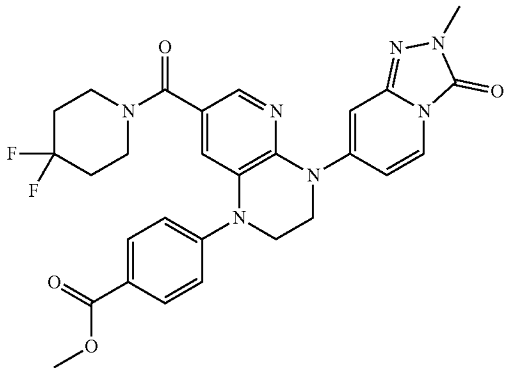
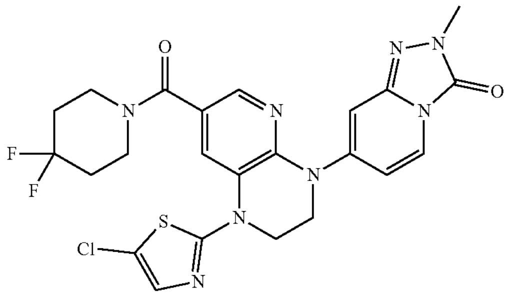
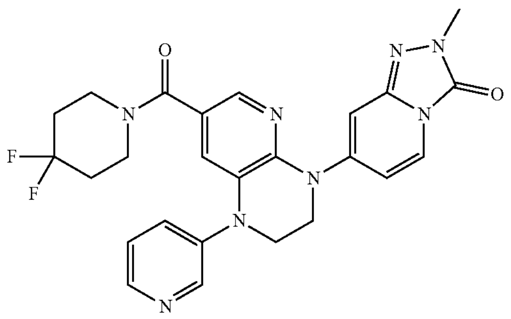

-continued

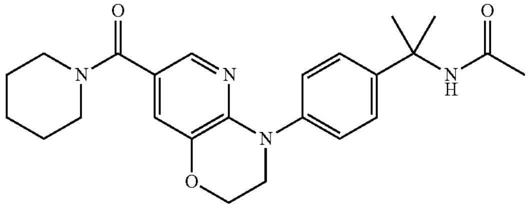

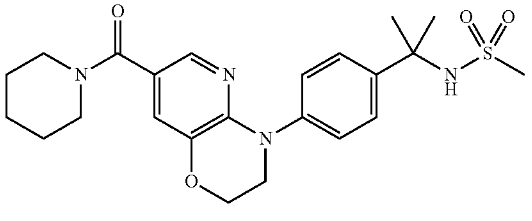

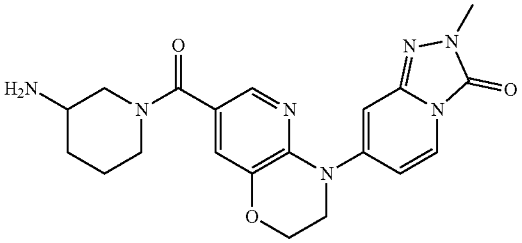

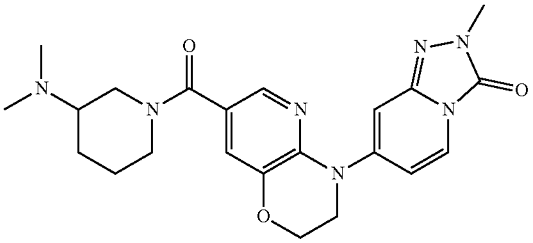

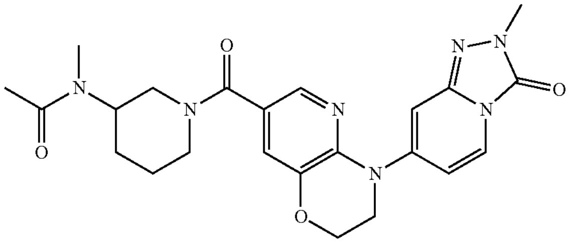

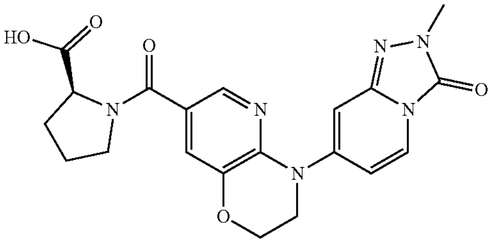

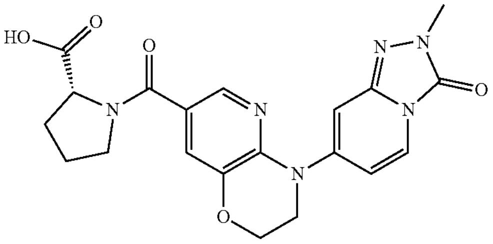

-continued

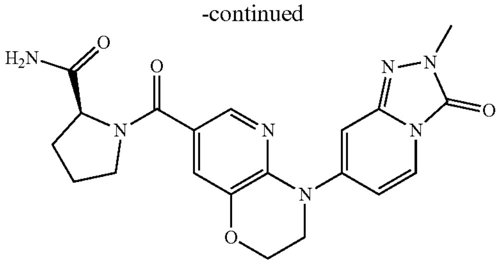

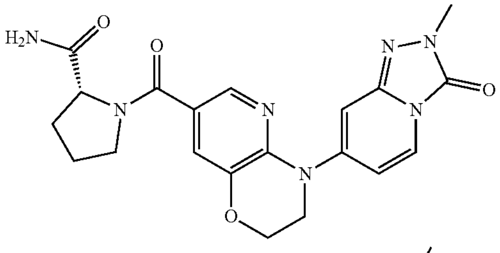

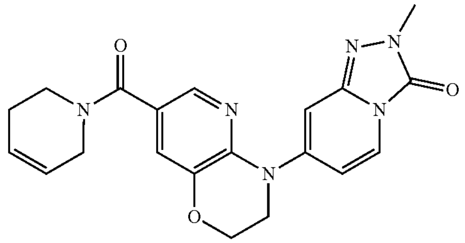

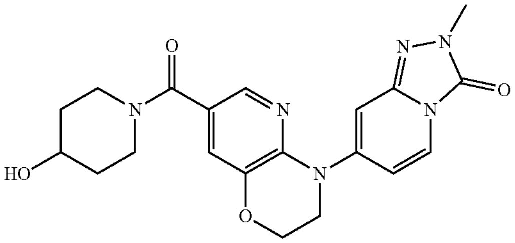

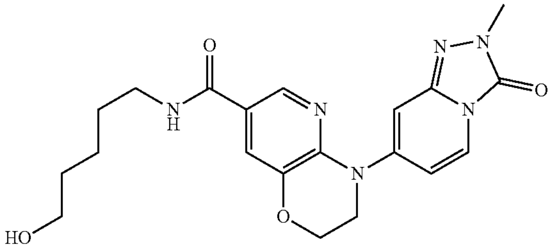

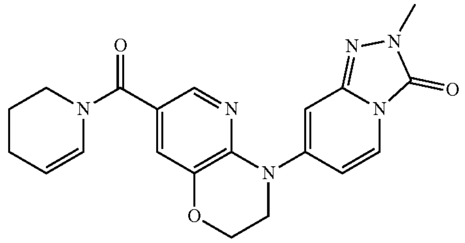 [SMILES: Cn1nc2cc(N3CCOc4cc(C(=O)N5C=CCCC5)cnc43)ccn2c1=O]

The compound (1) of the present embodiment can be formed into a pharmacologically acceptable salt thereof by a normal method if necessary. A pharmacologically acceptable salt means a salt with a pharmacologically acceptable non-toxic base or acid (for example, an inorganic or organic base, or an inorganic or organic acid).

Examples of a salt derived from a pharmacologically acceptable non-toxic base include salts with inorganic bases such as a sodium salt, a potassium salt, a calcium salt and a magnesium salt, and salts with organic bases such as piperidine, morpholine, pyrrolidine, arginine and lysine.

Examples of a salt derived from a pharmacologically acceptable non-toxic acid include acid addition salts with mineral acids such as hydrochloric acid, hydrobromic acid, sulfuric acid and nitric acid, and acid addition salts with organic acids such as formic acid, acetic acid, trifluoroacetic acid, maleic acid, fumaric acid, succinic acid, lactic acid, malic acid, tartaric acid, citric acid, methanesulfonic acid, p-toluenesulfonic acid, salicylic acid, stearic acid and palmitic acid.

Besides, the compound (1) of the present embodiment or a pharmacologically acceptable salt thereof may be present as a hydrate or a solvate in some cases. Not only the preferable compounds specifically described above but also arbitrary hydrates and solvates formed by a derivative represented by the general formula (1) or a salt thereof are all embraced in the scope of the present invention. Examples of a solvent capable of forming a solvate include methanol, ethanol, 2-propanol, acetone, ethyl acetate, dichloromethane and diisopropyl ether.

The compound (1) of the present embodiment or a pharmacologically acceptable salt thereof embraces not only a racemic body but also an optically active substance, a stereoisomer and a rotamer.

When the compound (1) of the present embodiment is an optical isomer having one or more asymmetric carbon atoms, the compound (1) of the present embodiment may have either the R configuration or the S configuration as the configuration of each asymmetric carbon atom. Besides, any optical isomers are embraced in the present invention, and a mixture of such optical isomers is also embraced therein. Furthermore, with respect to a mixture of optically active substances, a racemic body composed of an equivalent amount of optical isomers is also embraced in the scope of the present invention. When the compound (1) of the present embodiment is a solid or crystal of a racemic body, the racemic body, a racemic mixture and a solid solution of the racemic body are also embraced in the scope of the present invention.

When the compound (1) of the present embodiment has geometric isomers, the present invention embraces all the geometric isomers.

When the compound (1) of the present embodiment has tautomers, the present invention embraces all the tautomers.

Besides, a pharmacologically acceptable salt thereof embraces a proton tautomer.

A compound obtained by labeling the compound (1) of the present embodiment or a pharmacologically acceptable salt thereof with an isotope (such as $^{3}H$, $^{14}C$ or $^{35}S$) is also embraced in the compound of the present invention.

Besides, a deuterated compound obtained by substituting $^{1}H$ with $^{2}H$ (D) is also embraced in the compound of the present invention.

Each compound name of the compound (1) of the present embodiment was created by using ChemDraw Professional, version 15.0.0.106 (PerkinElmer Informatics, Inc. (registered trademark)).

The term "15-PGDH inhibitory effect" as used in the present embodiment refers to an effect to inhibit 15-hydroxyprostaglandin dehydrogenase (15-PGDH), that is, an enzyme significant in inactivation (for example, conversion into 15-keto-PGE2 by catalyzing an oxidation reaction of the 15-position hydroxyl group of PGE2) of active prostaglandin (PGD2, PGE1, PGE2, PGF2α, PGI2 or the like), hydroxyeicosatetraenoic acid (HETE) and inflammation resolving lipid mediator (RvD1, RvD2, RvE1, MaR1, LXA4 or the like) (which are hereinafter generically designated as substrates of 15-PGDH).

The compound (1) of the present embodiment or a pharmacologically acceptable salt thereof inhibits, for example, decomposition of PGE2 by inhibiting 15-PGDH. As a result, the compound (1) of the present embodiment or a pharmacologically acceptable salt thereof is applicable to a disease in which inactivation of a substrate of 15-PGDH is involved. A 15-PGDH inhibitor is useful as a therapeutic agent or a preventive agent against one, two or more of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

Production Method for Compound (1) of Present Embodiment

The compound (1) of the present embodiment or a pharmacologically acceptable salt thereof can be produced by any of methods described in detail as Schemes 1 to 31 described below or any equivalent methods, methods described in other literatures or any equivalent methods.

The compound (1) of the present embodiment can be produced by any of various synthesis methods. Next, representative production methods for the compound (1) of the present invention will be described. The production intermediate may be produced as a salt according to a conventional method as necessary. In some cases, microwaves irradiation are used for heating.

Scheme 1

[Formula 57]

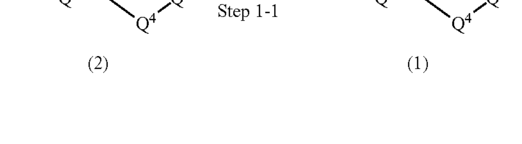

(2) (1)

wherein $Q^1$, $Q^2$, $Q^3$, $Q^4$, $G^1$ and $G^2$ have the same meaning as defined above; and $L^1$ is a fluorine atom, a chlorine atom, a bromine atom, an iodine atom, a boronic acid derivative or the like.

Step 1-1

This step is a step of producing the compound (1) by reacting a compound (2) and a compound (3).

For example, when $L^1$ of the compound (3) is a bromine atom or an iodine atom, the compound (1) can be produced by reacting the compound (2) and the compound (3) under normal Buchwald-Hartwig cross-coupling reaction conditions, for example, in a solvent in the presence of a palladium reagent and a base. Examples of the solvent to be used include tetrahydrofuran, 1,4-dioxane, benzene, toluene, xylene, methanol, ethanol, propanol, N,N-dimethylformamide, dimethylsulfoxide, water and a mixed solvent of any of these. Examples of the palladium reagent to be used include tris(dibenzylideneacetone)dipalladium (0), palladium (II) acetate and bis(tri-tert-butylphosphine)dipalladium (0). Examples of the base to be used include sodium tert-butoxide, potassium tert-butoxide, sodium methoxide, potassium methoxide, sodium ethoxide, potassium ethoxide, cesium carbonate, sodium carbonate, potassium carbonate and potassium phosphate. It is noted that this step can be performed, if necessary, under addition of a ligand such as 4,5-bis(diphenylphosphino)-9,9-dimethylxanthene (Xantphos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2',4',6'-triisopropylbiphenyl (XPhos) or tri-tert-butylphosphine. The reaction temperature is usually room temperature to a solvent reflux temperature. The reaction time varies depending on a starting material and a solvent to be used, the reaction temperature and the like, and is usually 30 minutes to 3 days.

Alternatively, for example, when $L^1$ of the compound (3) is a boronic acid derivative, the compound (1) can be produced by reacting the compound (2) and the compound (3) under normal Chan-Lam-Evans coupling reaction conditions, for example, in a solvent in the presence of a copper reagent and in the presence or absence of a base. Examples of the solvent to be used include dichloromethane, chloroform, 1,2-dichloroethane, acetonitrile, tetrahydrofuran, 1,4-dioxane, benzene, toluene and a mixed solvent of any of these. An example of the copper reagent to be used includes copper (II) acetate. Examples of the base to be used include triethylamine, pyridine and diisopropylethylamine. It is noted that this step can be performed, if necessary, under addition of a desiccant such as molecular sieves 4A. The reaction temperature is usually room temperature to a solvent reflux temperature. The reaction time varies depending on a starting material and a solvent to be used, the reaction temperature and the like, and is usually 30 minutes to 3 days.

Alternatively, for example, when $L^1$ is an iodine atom or a bromine atom, the compound (1) can be produced by reacting the compound (2) and the compound (3) under normal Goldberg amination reaction conditions, for example, in a solvent in the presence of a copper reagent and a base and in the presence or absence of a ligand. Examples of the solvent to be used include 1,4-dioxane, N,N-dimethylformamide, N,N-dimethylacetamide and a mixed solvent of any of these. Examples of the copper reagent to be used include copper (I) iodide, copper (I) bromide and copper. Examples of the base to be used include potassium phosphate, sodium phosphate, cesium carbonate, potassium carbonate and sodium carbonate. Examples of the ligand to be used include N,N'-dimethylethylenediamine and tetramethylethylenediamine. The reaction temperature is usually room temperature to a solvent reflux temperature. The reaction time varies depending on a starting material and a solvent to be used, the reaction temperature and the like, and is usually 30 minutes to 3 days.

Besides, the compound (1) can be produced, for example, through a nucleophilic substitution reaction using $L^1$ as a leaving group. Examples of the leaving group include a fluorine atom and a chlorine atom. This reaction can be performed by reacting the compound (2) and the compound (3) in a solvent or without using a solvent in the presence or absence of an acid or a base. Examples of the solvent to be used include N,N-dimethylformamide, dimethylsulfoxide, water, tetrahydrofuran, 1,4-dioxane, ethanol and a mixed solvent of any of these. Examples of the acid to be used include hydrogen chloride, p-toluenesulfonic acid and methanesulfonic acid. Examples of the base to be used include triethylamine, diisopropylethylamine, pyridine, 2,6-dimethylpyridine, 2,4,6-trimethylpyridine, potassium carbonate and cesium carbonate. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Here, when the compound (2) is represented as a compound (2a), the compound (2a) can be produced by a method shown in Scheme 2 or any equivalent method, or a method described in any literature or any equivalent method.

Scheme 2

[Formula 58]

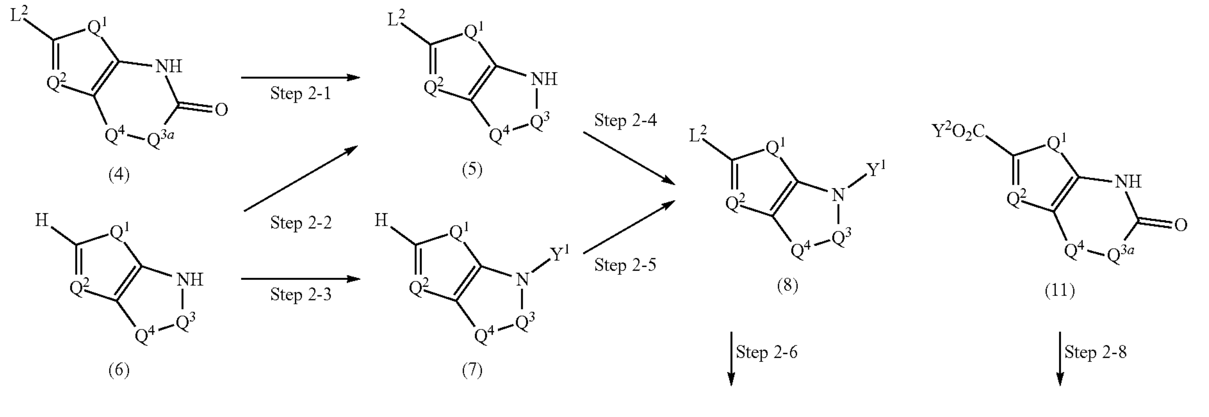

-continued

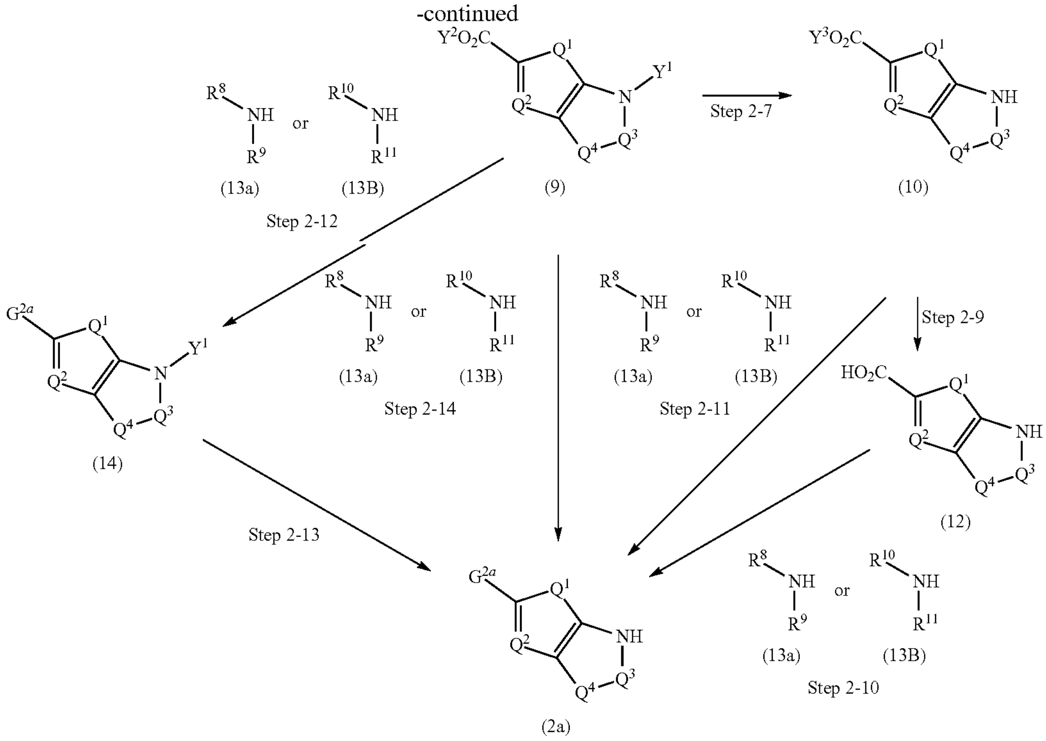

wherein $Q^1$, $Q^2$, $Q^3$, $Q^4$, $R^5$, $R^6$, $R^8$, $R^9$, $R^{10}$ and $R^{11}$ have the same meaning as defined above; $Q^{3a}$ is $—(CH_2)_m—(CR^5R^6)_n—(CH_2)_{p1}—$; each of m, n and p1 is 0, 1 or 2, and m+n+p1 is an integer of 2 to 4; $G^{2a}$ is $—C(=O)—NR^8R^9$ or $—C(=O)—NR^{10}R^{21}$; $L^2$ is a chlorine atom, a bromine atom or an iodine atom; $Y^1$ is a $C_1$-$C_6$ acyl group or a $C_1$-$C_6$ alkoxycarbonyl group; and $Y^2$ is a $C_1$-$C_6$ alkyl group or a phenyl group optionally having one or more halogen atoms.

Step 2-1

This step is a step of producing a compound (5) by reducing secondary amide of a compound (4) to secondary amine. The compound (5) can be produced, for example, by performing, in a solvent, a reduction reaction of the compound (4) using a borane-tetrahydrofuran complex, a borane-dimethylsulfide complex or the like. Examples of the solvent to be used include tetrahydrofuran and 1,4-dioxane. With respect to the reaction temperature, the reaction can be performed usually at −20° C. to a solvent reflux temperature, and is preferably performed at 0° C. to room temperature. The reaction time varies depending on a starting material and a solvent to be used, the reaction temperature and the like, and is usually 30 minutes to 3 days.

Step 2-2

This step is a step of producing the compound (5) by introducing a halogen atom into a compound (6). The compound (5) can be produced, for example, by reacting the compound (6) in a solvent in the presence of a halogenating agent. Examples of the solvent to be used include acetonitrile, carbon tetrachloride, chloroform, dichloromethane, 1,4-dioxane, tetrahydrofuran and a mixed solvent of any of these. Examples of the halogenating agent to be used include, as for, for example, a brominating agent, N-bromosuccinimide and bromine. With respect to the reaction temperature, the reaction can be performed usually at −20° C. to a solvent reflux temperature. The reaction time varies depending on a starting material and a solvent to be used, the reaction temperature and the like, and is usually 30 minutes to 3 days.

Step 2-3

This step is a step of producing a compound (7) by introducing an alkoxycarbonyl group or an acyl group into an amino group of the compound (6). The compound (7) can be produced by, for example, reacting the compound (6) with an alkoxycarbonylating agent or an acylating agent in a solvent or without using a solvent in the presence or absence of a base. An example of the alkoxycarbonylating agent to be used includes di-tert-butyldicarbonate. Examples of the acylating agent to be used include acetic anhydride and acetyl chloride. Examples of the solvent to be used for the reaction include dichloromethane, tetrahydrofuran, 1,4-dioxane and a mixed solvent of any of these. Besides, when a base is used in this reaction, triethylamine, diisopropylethylamine, pyridine, N,N-dimethyl-4-aminopyridine or the like can be used. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 2-4

This step is a step of producing a compound (8) by introducing an alkoxycarbonyl group or an acyl group into an amino group of the compound (5). This step can be performed in the same manner as in Step 2-3 described above.

Step 2-5

This step is a step of producing the compound (8) by introducing a halogen atom into the compound (7). This step can be performed in the same manner as in Step 2-2 described above.

Step 2-6

This step is a step of producing a compound (9) by converting $L^2$ of the compound (8) into an alkoxycarbonyl group or a phenoxycarbonyl group optionally having one or more halogen atoms.

When $Y^2$ is a $C_1$-$C_6$ alkyl group, the compound (9) can be produced by reacting, in a solvent, the compound (8) in the presence of a palladium reagent and a base under carbon monoxide atmosphere. Examples of the solvent to be used include alcohols such as methanol, ethanol and propanol, and in addition, a mixture of any of these alcohols with N,N-dimethylformamide, N,N-dimethylacetamide, dimethylsulfoxide, water or the like can be used. An example of the palladium reagent to be used includes a [1,1-bis(diphenylphosphino)ferrocene]palladium (II) dichloride dichloromethane adduct. Examples of the base to be used include triethylamine and diisopropylethylamine. The reaction temperature is usually room temperature to a solvent reflux temperature. The reaction time varies depending on a starting material and a solvent to be used, the reaction temperature and the like, and is usually 30 minutes to 3 days.

Alternatively, when $Y^2$ is a phenyl group optionally having one or more halogen atoms, the compound (9) can be produced by reacting, in a solvent, a phenyl formate derivative and the compound (8) in the presence of a palladium reagent and a base. Examples of the phenyl formate derivative to be used include phenyl formate and 2,4,6-trichlorophenyl formate. Examples of the solvent to be used include toluene, benzene and 1,4-dioxane, and in addition, a mixture of any of these with N,N-dimethylformamide, N,N-dimethylacetamide, dimethylsulfoxide or the like can be used. An example of the palladium reagent to be used includes palladium (II) acetate. Examples of the base to be used include triethylamine and diisopropylethylamine. It is noted that this step can be performed, if necessary, under addition of a ligand such as 4,5-bis(diphenylphosphino)-9,9-dimethylxanthene (Xantphos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2',4',6'-triisopropylbiphenyl (XPhos) or tri-tert-butylphosphine. The reaction temperature is usually room temperature to a solvent reflux temperature. The reaction time varies depending on a starting material and a solvent to be used, the reaction temperature and the like, and is usually 30 minutes to 3 days.

Step 2-7

This step is a step of producing a compound (10) by removing an alkoxycarbonyl group or an acyl group from the compound (9).

The compound (10) can be produced by, for example, treating the compound (9) with an acid in a solvent or without using a solvent. Examples of the solvent to be used for the reaction include dichloromethane, 1,4-dioxane, tetrahydrofuran, methanol, ethanol, water and a mixed solvent of any of these. Examples of the acid to be used include trifluoroacetic acid and hydrogen chloride. With respect to the reaction temperature, the reaction can be performed usually at −20° C. to a solvent reflux temperature. The reaction time varies depending on a starting material and a solvent to be used, the reaction temperature and the like, and is usually 30 minutes to 3 days.

Alternatively, the compound (10) can be produced by, for example, treating the compound (9) with a base in a solvent. Examples of the solvent for the reaction to be used include methanol, ethanol, water, tetrahydrofuran and a mixed solvent of any of these. Examples of the base to be used include sodium methoxide, potassium methoxide, sodium ethoxide, potassium ethoxide, sodium hydroxide and potassium hydroxide. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days. It is noted that this step may accompany a transesterification reaction in some cases depending on the solvent or the base to be used. For example, when methanol is used as the solvent and sodium methoxide is used as the base, a compound in which all or part of the compound (10) to be produced has been converted into $CO_2Me$ can be obtained.

Step 2-8

This step is a step of producing the compound (10) by reducing secondary amide of a compound (11) to secondary amine. This step can be performed in the same manner as in Step 2-1 described above.

Step 2-9

This step is a step of producing a compound (12) by hydrolyzing an ester moiety of the compound (10).

The compound (12) can be produced by, for example, reacting, in a solvent, the compound (10) in the presence of a base under usual ester hydrolysis conditions. Examples of the solvent to be used include water, methanol, ethanol, propanol, isopropyl alcohol, butanol, tetrahydrofuran, 1,4-dioxane and a mixed solvent of any of these. Examples of the base to be used include alkali metal salts such as lithium hydroxide, sodium hydroxide and potassium hydroxide. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Alternatively, for example, when $Y^2$ of the compound (10) is a tert-butyl group or the like, the compound (12) can be produced through a reaction in the presence of an acid. Examples of a solvent to be used include water, tetrahydrofuran, 1,4-dioxane, methylene chloride, and a mixed solvent of any of these. Examples of the acid to be used include trifluoroacetic acid and hydrogen chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 2-10

This step is a step of producing a compound (2a) through a condensation reaction of the compound (12) and a compound (13a) or a compound (13b).

The compound (2a) can be produced by, for example, reacting the compound (12) and the compound (13a) or the compound (13b) in a solvent in the presence of a condensing agent and in the presence or absence of a base. Examples of the solvent to be used include N,N-dimethylformamide, N,N-dimethylacetamide, N-methylpyrrolidone, dichloromethane, 1,4-dioxane, tetrahydrofuran and a mixed solvent of any of these. Examples of the condensing agent to be used include 1-[bis(dimethylamino)methylene]-1H-1,2,3-triazolo[4,5-b]pyridinium 3-oxide hexafluorophosphate (HATU), 1-ethyl-3-(3-dimethylaminopropyl)carbodiimide (EDCI) and dicyclohexylcarbodiimide (DCC). Examples of the base to be used include triethylamine and diisopropylethylamine. Besides, N,N-dimethyl-4-aminopyridine, pyridine, 1-hydroxybenzotriazole (HOBT) or the like can be added as a reaction accelerator if necessary. With respect to the reaction temperature, the reaction can be performed usually at 0° C. to a solvent reflux temperature and is preferably performed at 0° C. to 30° C. The reaction time varies depending on a starting material and a solvent to be used, the reaction temperature and the like, and is usually 30 minutes to 3 days. Alternatively, the compound (2a) can be produced by, for example, reacting the compound (12) with thionyl chloride or the like in the presence or absence of a solvent to obtain acid chloride, and reacting the resultant with the compound (13a) or the compound (13b) in a solvent in the presence or absence of a base. Examples of the solvent to be used for producing the acid chloride include methylene chloride, toluene and tetrahydrofuran. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days. Examples of the solvent to be used in the reaction between the acid chloride and the compound (13a) or the compound (13b) include methylene chloride, toluene, tetrahydrofuran and 1,4-dioxane. Examples of the base to be used include triethylamine, diisopropylethylamine, pyridine, 2,6-dimethylpyridine and 2,4,6-trimethylpyridine. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 2-11

This step is a step of producing the compound (2a) by reacting the compound (10) and the compound (13a) or the compound (13b).

The compound (2a) can be produced by, for example, reacting the compound (10) and the compound (13a) or the compound (13b) in a solvent in the presence or absence of a base. Examples of the solvent to be used include toluene, xylene, 1,4-dioxane, tetrahydrofuran, N,N-dimethylformamide, N,N-dimethylacetamide, N-methylpyrrolidone, dichloromethane and a mixed solvent of any of these. Examples of the base to be used include triethylamine, diisopropylethylamine, pyridine, 2,6-dimethylpyridine and 2,4,6-trimethylpyridine. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Alternatively, in this step, the compound can be produced by hydrolyzing an ester moiety of the compound (10) followed by a condensation reaction with the compound (13a) or the compound (13b). The compound (2a) can be produced by continuously performing Step 2-9 and Step 2-10 described above.

Step 2-12

This step is a step of producing a compound (14) by reacting the compound (9) and the compound (13a) or the compound (13b). This step can be performed in the same manner as in Step 2-11 described above.

Step 2-13

This step is a step of producing the compound (2a) by removing an alkoxycarbonyl group or an acyl group from the compound (14). This step can be performed in the same manner as in Step 2-7 described above.

Step 2-14

This step is a step of producing the compound (2a) by reacting the compound (9) and the compound (13a) or the compound (13b) followed by removal of an alkoxycarbonyl group or an acyl group. The compound (2a) can be produced by continuously performing Step 2-12 and Step 2-13 described above.

Here, when the compound (2) is represented as a compound (2b) or a compound (2c), the compound (2b) or the compound (2c) can be produced by a method shown in Scheme 3 or any equivalent method, or a method described in any literature or any equivalent method.

Scheme 3

[Formula 59]

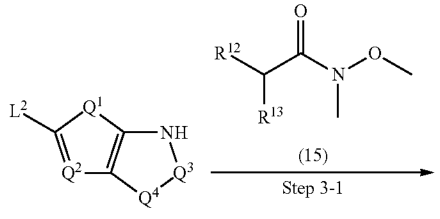

(5)

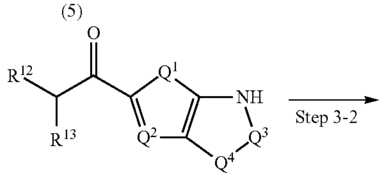

(2b)

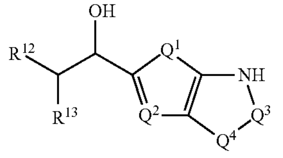

(2c)

wherein $Q^1$, $Q^3$, $Q^3$, $Q^4$, $R^{12}$, $R^{13}$ and $L^2$ have the same meaning as defined above.

Step 3-1

This step is a step of producing the compound (2b) by reacting the compound (5) and a compound (15). The compound (2b) can be produced by, for example, lithiating the compound (5) in a solvent with an alkyllithium salt or the like, followed by a reaction with the compound (15). Examples of the solvent to be used include tetrahydrofuran, diethylether, 1,2-dimethoxyethane, 1,4-dioxane and a mixed solvent of any of these. Examples of the alkyllithium salt to be used include n-butyllithium and sec-butyllithium. With respect to the reaction temperature, the reaction can be performed usually at −78° C. to 50° C., and is performed preferably at −78° C. to 20° C. The reaction time varies depending on a starting material and a solvent to be used, the reaction temperature and the like, and is usually 30 minutes to 3 days.

Step 3-2

This step is a step of producing the compound (2c) having a hydroxy group by reducing a ketone moiety of the compound (2b). The compound (2c) can be produced by, for example, allowing a reducing agent such as a metal hydride to act on the compound (2b) in a solvent. An example of the metal hydride to be used includes sodium borohydride. As the solvent, an alcohol-based solvent such as methanol or ethanol can be singly used, or a mixed solvent of such a solvent with dichloromethane, chloroform, tetrahydrofuran, 1,4-dioxane or the like can be used. With respect to the reaction temperature, the reaction can be performed usually at −78° C. to a solvent reflux temperature, and is performed preferably at −20° C. to 20° C. The reaction time varies depending on a starting material and a solvent to be used, the reaction temperature and the like, and is usually 30 minutes to 3 days.

Here, when the compound (2) is represented as a compound (2d), the compound (2d) can be produced by a method shown in Scheme 4 or any equivalent method, or a method described in any literature or any equivalent method.

Scheme 4

[Formula 60]

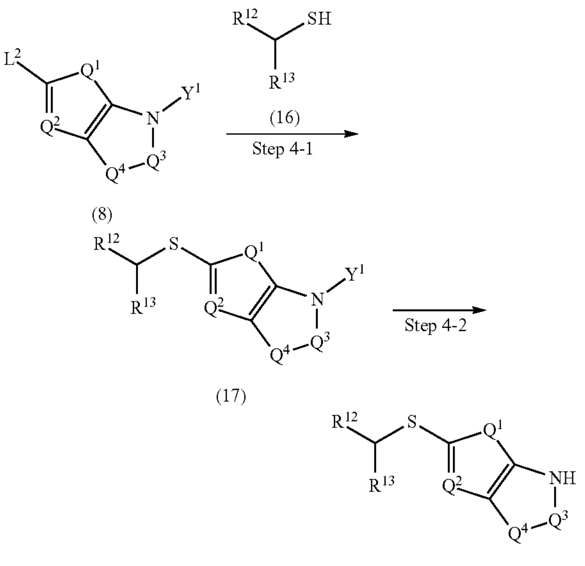

(8) (16) (17) (2d)

wherein $Q^1$, $Q^2$, $Q^3$, $Q^4$, $R^{12}$, $R^{13}$, $L^2$ and $Y^1$ have the same meaning as defined above.

Step 4-1

This step is a step of producing a compound (17) by reacting the compound (8) and a compound (16).

For example, when $L^2$ of the compound (8) is a bromine atom or an iodine atom, the compound (17) can be produced by reacting, in a solvent, the compound (8) and the compound (16) in the presence of a palladium reagent and a base. Examples of the solvent to be used include tetrahydrofuran, 1,4-dioxane, benzene, toluene, xylene, N,N-dimethylformamide, dimethylsulfoxide and a mixed solvent of any of these. Examples of the palladium reagent to be used include tris(dibenzylideneacetone)dipalladium (0), palladium (II) acetate and bis(tri-tert-butylphosphine)dipalladium (0). Examples of the base to be used include triethylamine and diisopropylethylamine. Examples of the ligand to be used include 4,5-bis(diphenylphosphino)-9,9-dimethylxanthene (Xantphos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2',4',6'-triisopropylbiphenyl (XPhos) and tri-tert-butylphosphine. The reaction temperature is usually room temperature to a solvent reflux temperature. The reaction time varies depending on a starting material and a solvent to be used, the reaction temperature and the like, and is usually 30 minutes to 3 days.

Step 4-2

This step is a step of producing the compound (2d) by removing an alkoxycarbonyl group or an acyl group from the compound (17). This step can be performed in the same manner as in Step 2-7 described above.

Here, when the compound (9) is represented as a compound (9a), the compound (9a) can be produced by a method shown in Scheme 5 or any equivalent method, or a method described in any literature or any equivalent method.

Scheme 5

[Formula 61]

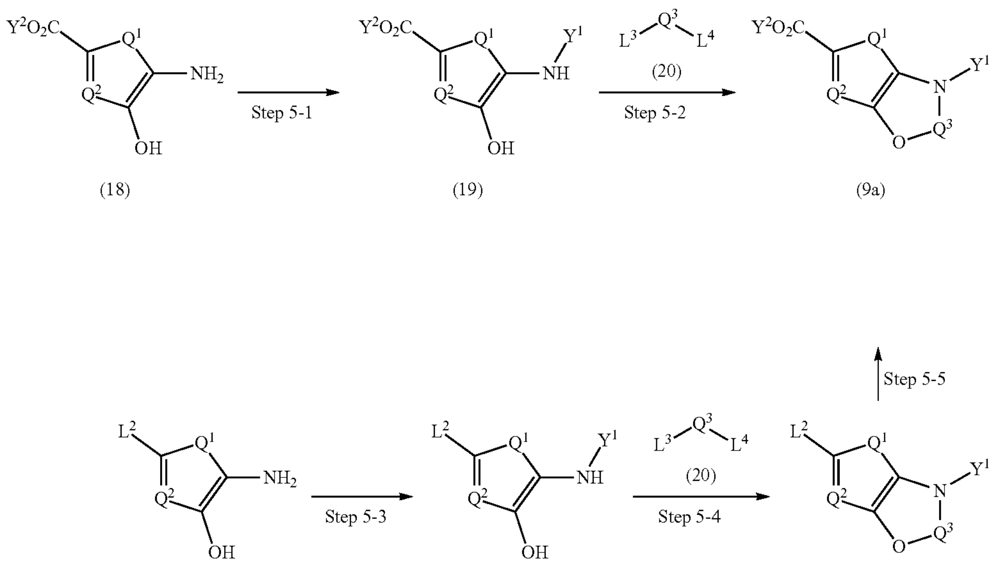

(18) (19) (20) (9a) (21) (22) (20) (9a)

wherein $Q^1$, $Q^2$, $Q^3$, $L^2$, $Y^1$ and $Y^3$ have the same meaning as defined above; and $L^3$ and $L^4$ are the same or different, and a chlorine atom, a bromine atom, an iodine atom or a methanesulfonyloxy group.

Step 5-1

This step is a step of producing a compound (19) by introducing an alkoxycarbonyl group or an acyl group into an amino group of a compound (18). This step can be performed in the same manner as in Step 2-3 described above.

Step 5-5

This step is a step of producing the compound (9a) by converting $L^2$ of the compound (8a) into an alkoxycarbonyl group or an aryloxycarbonyl group. This step can be performed in the same manner as in Step 2-6 described above.

Here, when the compound (10) is represented as a compound (10a), the compound (10a) can be produced by a method shown in Scheme 6 or any equivalent method, or a method described in any literature or any equivalent method.

Scheme 6

[Formula 62]

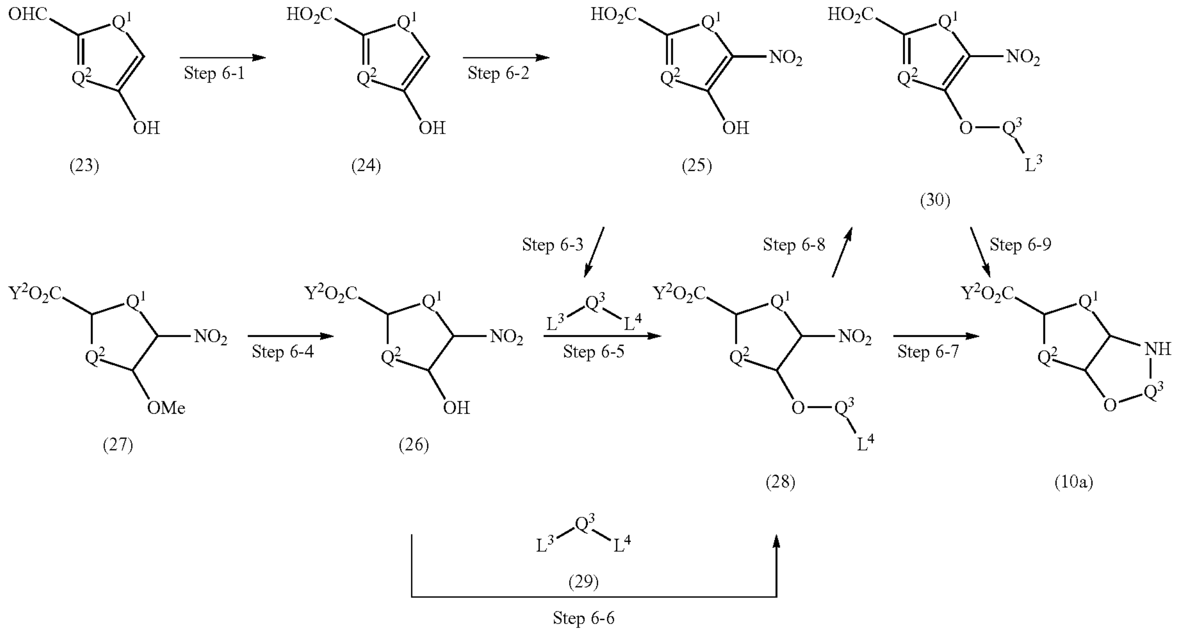

Step 5-2

This step is a step of producing a compound (9a) by reacting the compound (19) and a compound (20). The compound (9a) can be produced by reacting the compound (19) and the compound (20) in a solvent in the presence of a base. Examples of the solvent to be used include acetonitrile, N,N-dimethylformamide, N,N-dimethylacetamide, N-methylpyrrolidone, 1,4-dixane, tetrahydrofuran, dimethylsulfoxide and a mixed solvent of any of these. Examples of the base to be used include sodium carbonate, potassium carbonate, cesium carbonate and potassium phosphate. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Step 5-3

This step is a step of producing a compound (22) by introducing an alkoxycarbonyl group or an acyl group into an amino group of a compound (21). This step can be performed in the same manner as in Step 2-3 described above.

Step 5-4

This step is a step of producing a compound (8a) by reacting the compound (22) and the compound (20). This step can be performed in the same manner as in Step 5-2 described above.

wherein $Q^1$, $Q^2$, $Q^3$, $L^3$, $L^4$ and $Y^2$ have the same meaning as defined above.

Step 6-1

This step is a step of producing a compound (24) by oxidizing an aldehyde group of a compound (23). The compound (24) can be produced by, for example, reacting sulfamic acid and sodium hypochlorite with the compound (23) in a solvent. Examples of the solvent to be used include tetrahydrofuran, 1,4-dioxane, dimethylsulfoxide, water and a mixed solvent of any of these. With respect to the reaction temperature, the reaction can be performed usually at −20° C. to a solvent reflux temperature. The reaction time varies depending on a starting material and a solvent to be used, the reaction temperature and the like, and is usually 30 minutes to 3 days.

Step 6-2

This step is a step of producing a compound (25) by nitrating the compound (24). The compound (25) can be produced by, for example, reacting a nitric acid aqueous solution having an appropriate concentration and the compound (24) with acetic acid used as a solvent. The concentration of the nitric acid aqueous solution to be used is usually 50 to 80%. With respect to the reaction temperature, the reaction can be performed usually at −20° C. to a solvent reflux temperature, and is performed preferably at 0° C. to 30° C. The reaction time varies depending on a starting material material and a solvent to be used, the reaction temperature and the like, and is usually 30 minutes to 3 days.

Step 6-3

This step is a step of producing a compound (26) through an esterification reaction of the compound (25). The compound (26) can be produced by reacting the compound (25) in an alcohol solvent in the presence of hydrogen chloride or thionyl chloride. Examples of the alcohol solvent to be used include methanol, ethanol and propanol. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 6-4

This step is a step of producing the compound (26) through a demethylation reaction of a compound (27). The compound (26) can be produced by, for example, allowing lithium iodide to act with pyridine used as a solvent. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Step 6-5

This step is a step of producing a compound (28) by reacting the compound (26) and the compound (20). The compound (28) can be produced by reacting the compound (26) and the compound (20) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate and sodium hydride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 6-6

This step is a step of producing the compound (28) by reacting the compound (26) and a compound (29). The compound (28) can be produced by, for example, reacting the compound (26) with the compound (29) in a solvent in the presence of a reagent used for Mitsunobu reaction. An example of the solvent to be used includes tetrahydrofuran. Examples of the reagent used for Mitsunobu reaction include diisopropyl azodicarboxylate, diethyl azodicarboxylate, bis(2-methoxyethyl) azodicarboxylate, triphenylphosphine and tributylphosphine. With respect to the reaction temperature, the reaction can be performed usually at −78° C. to a solvent reflux temperature, and is performed preferably at 0° C. to 30° C. The reaction time varies depending on a starting material and a solvent to be used, the reaction temperature and the like, and is usually 30 minutes to 3 days.

Step 6-7

This step is a step of producing the compound (10a) by reducing a nitro group of the compound (28) into an amino group, followed by a ring closure reaction accompanying elimination of $L^3$. The compound (10a) can be produced by, for example, reacting reduced iron and the compound (28) in a solvent in the presence of an acid. Examples of the solvent to be used include tetrahydrofuran and 1,4-dioxane. An example of the acid to be used includes acetic acid, and acetic acid can be used also as the solvent. With respect to the reaction temperature, the reaction can be performed usually at room temperature to a solvent reflux temperature. It is noted that a temperature of 60° C. to 150° C. is usually necessary for completing the ring closure reaction accompanying the elimination of $L^3$. The reaction time varies depending on a starting material and a solvent to be used, the reaction temperature and the like, and is usually 30 minutes to 3 days.

Step 6-8

This step is a step of producing a compound (30) by reducing a nitro group of the compound (28) into an amino group.

The compound (30) can be produced by, for example, reacting reduced iron, zinc or the like with the compound (28) in a solvent in the presence or absence of an acid. Examples of the solvent to be used include tetrahydrofuran, 1,4-dioxane, N,N-dimethylformamide, N,N-dimethylacetamide, methanol, ethanol, propanol, butanol, water and a mixed solvent of any of these. Examples of the acid to be used include acetic acid, ammonium chloride, ammonium formate and hydrogen chloride, and acetic acid can be used also as the solvent. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Alternatively, the compound (30) can be produced by, for example, reacting tin (II) chloride and the compound (28) in a solvent. Examples of the solvent to be used include ethanol, methanol, water, tetrahydrofuran and 1,4-dioxane. It is noted that this step can be performed under addition of an acid such as hydrogen chloride if necessary. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Alternatively, the compound (30) can be produced by, for example, reacting the compound (28) by using palladium carbon or the like in a solvent in the presence of a hydrogen source. Examples of the solvent to be used include tetrahydrofuran, 1,4-dioxane, N,N-dimethylformamide, N,N-dimethylacetamide, methanol, ethanol, propanol, butanol, water and a mixed solvent of any of these. Examples of the hydrogen source to be used include hydrogen and ammonium formate. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Step 6-9

This step is a step of producing the compound (10a) from the compound (30) through a ring closure reaction accompanying elimination of $L^3$. The compound (10a) can be produced from the compound (30) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, sodium hydroxide, potassium hydroxide, triethylamine, diisopropylethylamine, pyridine and 1,8-diazabicyclo[5,4,0]-7-undecene. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Here, when the compound (11) is represented as a compound (11a), the compound (11a) can be produced by a method shown in Scheme 7 or any equivalent method, or a method described in any literature or any equivalent method.

Scheme 7

[Formula 63]

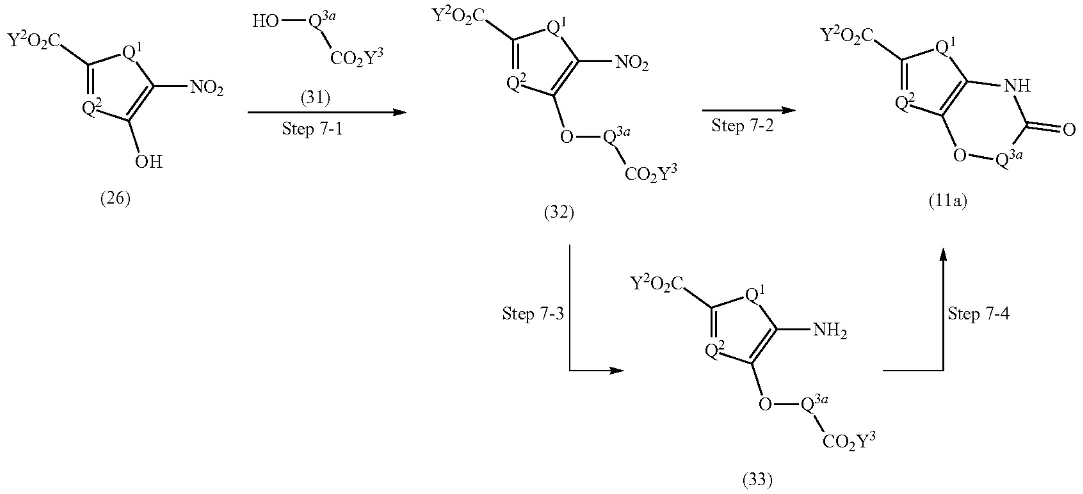

wherein $Q^1$, $Q^2$, $Q^{3a}$ and $Y^2$ have the same meaning as defined above; and $Y^3$ is a $C_1$-$C_6$ alkyl group.

Step 7-1

This step is a step of producing a compound (32) by reacting the compound (26) and a compound (31). This step can be performed in the same manner as in Step 6-6 described above.

Step 7-2

This step is a step of producing the compound (11a) by reducing a nitro group of the compound (32) into an amino group, followed by a ring closure reaction. In this step, a procedure of reducing a nitro group into an amino group can be performed in the same manner as in Step 6-8 described above. Besides, the ring closure reaction may proceed rapidly under conditions for converting a nitro group into an amino group, but usually requires further heating. The heating temperature is usually 50° C. to a solvent reflux temperature. The reaction time varies depending on a starting material and a solvent to be used, the reaction temperature and the like, and is usually 30 minutes to 3 days.

Step 7-3

This step is a step of producing a compound (33) by reducing a nitro group of the compound (32) into an amino group. This step can be performed in the same manner as in Step 6-8 described above.

Step 7-4

This step is a step of producing the compound (11a) through an intramolecular condensation reaction of the compound (33).

The compound (11a) can be produced, for example, from the compound (33) in a solvent in the presence of an acid. Examples of the solvent to be used include toluene, xylene, 1,4-dioxane, tetrahydrofuran and a mixed solvent of any of these. Examples of the acid to be used include p-toluenesulfonic acid and acetic acid. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Alternatively, the compound (11a) can be produced from the compound (33) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Here, when the compound (11) is represented as a compound (lib), the compound (lib) can be produced by a method shown in Scheme 8 or any equivalent method, or a method described in any literature or any equivalent method.

Scheme 8

[Formula 64]

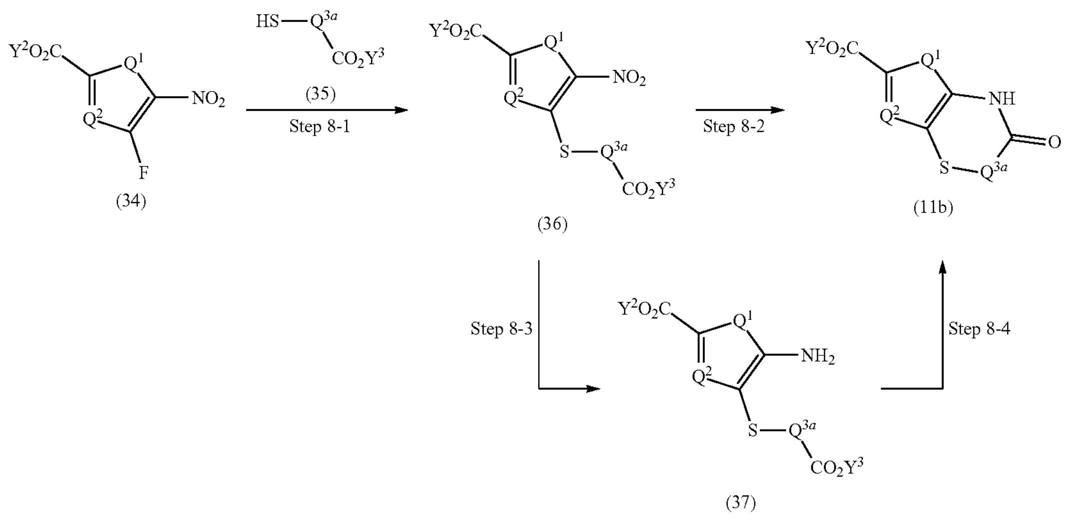

(34) (35) (36) (11b) (37)

wherein $Q^1$, $Q^2$, $Q^{3a}$, $Y^2$ and $Y^3$ have the same meaning as defined above.

Step 8-1

This step is a step of producing a compound (36) by performing a nucleophilic substitution reaction of a fluorine atom of a compound (34) with a compound (35). The compound (36) can be produced from the compound (34) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 8-2

This step is a step of producing the compound (lib) by reducing a nitro group of the compound (36) into an amino group, followed by a ring closure reaction. This step can be performed in the same manner as in Step 7-2 described above.

Step 8-3

This step is a step of producing a compound (37) by reducing a nitro group of the compound (36) into an amino group. This step can be performed in the same manner as in Step 6-8 described above.

Step 8-4

This step is a step of producing the compound (lib) through an intramolecular condensation reaction of the compound (37). This step can be performed in the same manner as in Step 7-4.

Here, when the compound (2) is represented as a compound (2aa), the compound (2aa) can be produced by a method shown in Scheme 9 or any equivalent method, or a method described in any literature or any equivalent method.

Scheme 9

[Formula 65]

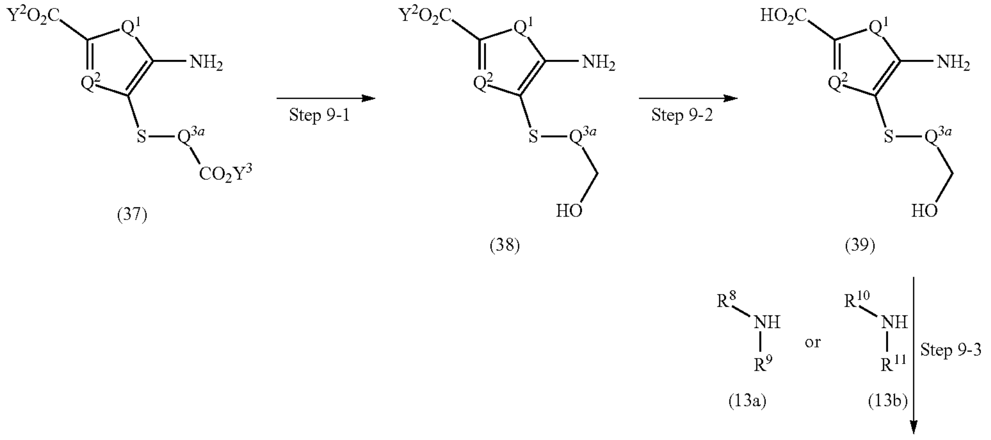

(37) (38) (39) (13a) (13b)

-continued

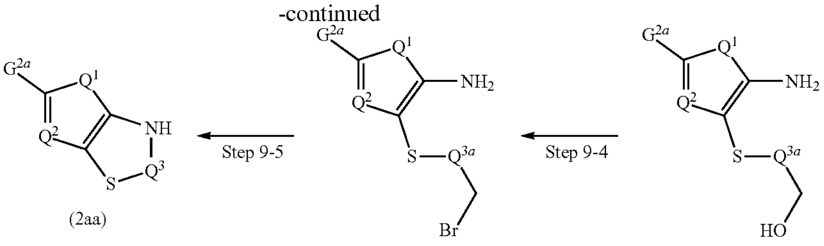

(2aa) (41) (40)

wherein $Q^1$, $Q^2$, $Q^3$, $R^8$, $R^9$, $R^{10}$, $R^{11}$, $Q^{3a}$, $G^{2a}$, $Y^2$ and $Y^3$ have the same meaning as defined above.

Step 9-1

This step is a step of producing a compound (38) from the compound (37). The compound (38) can be produced by, for example, performing a reduction reaction of the compound (37) in a solvent by using a borane-tetrahydrofuran complex, a borane-dimethylsulfide complex or the like. Examples of the solvent to be used include tetrahydrofuran and 1,4-dioxane. With respect to the reaction temperature, the reaction can be performed usually at −20° C. to a solvent reflux temperature, and is performed preferably at 0° C. to room temperature. The reaction time varies depending on a starting material and a solvent to be used, the reaction temperature and the like, and is usually 30 minutes to 3 days.

Step 9-2

This step is a step of producing a compound (39) by hydrolyzing an ester moiety of the compound (38). This step can be performed in the same manner as in Step 2-9 described above.

Step 9-3

This step is a step of producing a compound (40) through a condensation reaction of the compound (39) and the compound (13a) or the compound (13b). This step can be performed in the same manner as in Step 2-10 described above.

Step 9-4

This step is a step of producing a compound (41) by replacing a hydroxy group of the compound (40) with a bromine atom. The compound (41) can be produced by, for example, allowing phosphorus tribromide to act in a solvent or without using a solvent. Examples of the solvent to be used include chloroform and tetrahydrofuran. With respect to the reaction temperature, the reaction can be performed usually at −78° C. to a solvent reflux temperature, and is performed preferably at 0° C. to 80° C. The reaction time varies depending on a starting material and a solvent to be used, the reaction temperature and the like, and is usually 30 minutes to 3 days.

Step 9-5

This step is a step of producing the compound (2aa) from the compound (41) through a ring closure reaction accompanying elimination of a bromine atom. This step can be performed in the same manner as in Step 6-9 described above.

Here, when the compound (1) is represented as a compound (1a), the compound (1a) can be produced by a method shown in Scheme 10 or any equivalent method, or a method described in any literature or any equivalent method.

[Formula 66]
Scheme 10
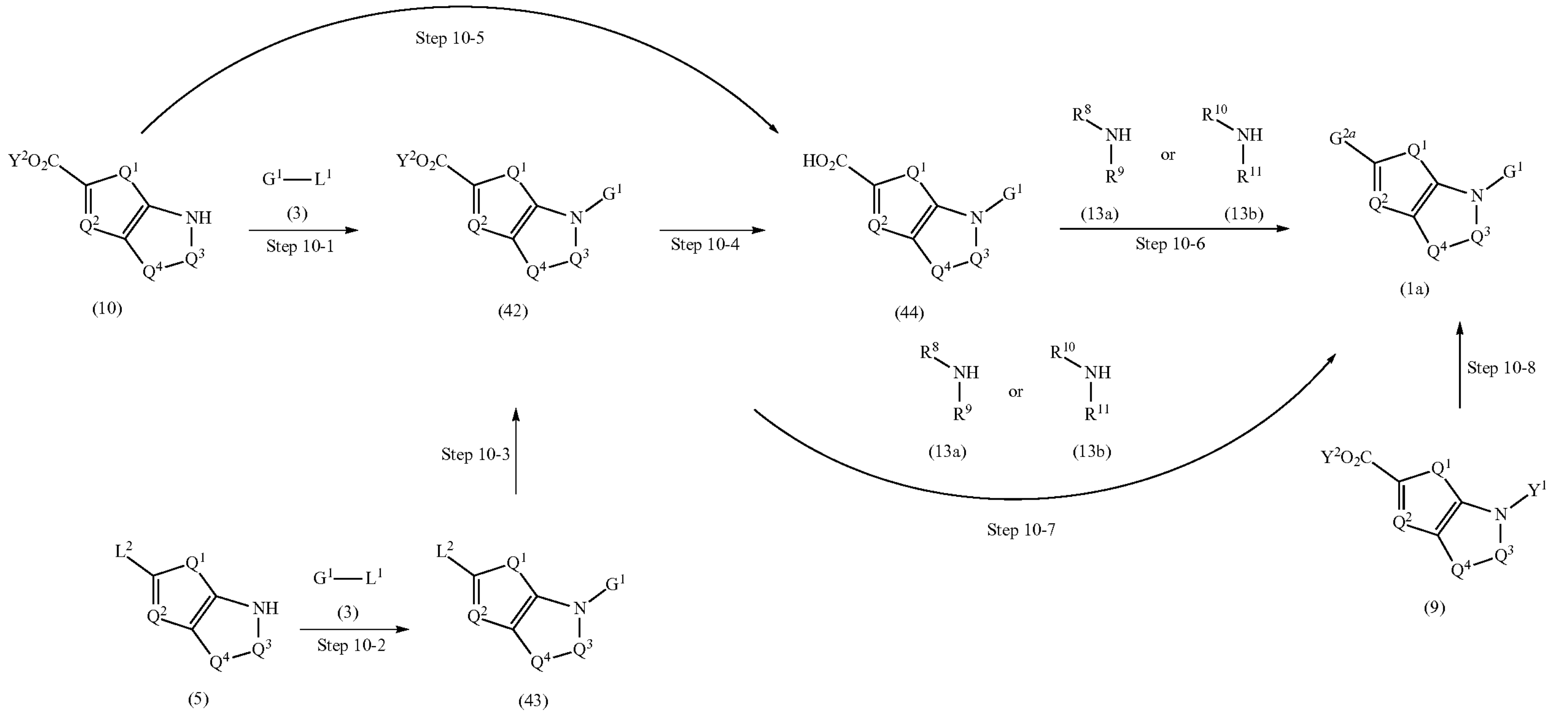

wherein $Q^1$, $Q^2$, $Q^3$, $Q^4$, $R^8$, $R^9$, $R^{10}$, $R^{11}$, $G^1$, $G^{2a}$, $L^1$, $L^2$, $Y^1$ and $Y^2$ have the same meaning as defined above.

Step 10-1

This step is a step of producing a compound (42) by reacting the compound (10) and the compound (3). This step can be performed in the same manner as in Step 1-1 described above.

Step 10-2

This step is a step of producing a compound (43) by reacting the compound (5) and the compound (3). This step can be performed in the same manner as in Step 1-1 described above.

Step 10-3

This step is a step of producing the compound (42) by converting $L^2$ of the compound (43) into an alkoxycarbonyl group or an aryloxycarbonyl group. This step can be performed in the same manner as in Step 2-6 described above.

Step 10-4

This step is a step of producing a compound (44) by hydrolyzing an ester moiety of the compound (42). This step can be performed in the same manner as in Step 2-9 described above.

Step 10-5

This step is a step of producing the compound (44) by reacting the compound (10) and the compound (3), followed by hydrolysis of an ester moiety of the resultant compound (42). In this step, the compound can be produced by continuously performing Step 10-1 and Step 10-4 described above.

Step 10-6

This step is a step of producing the compound (1a) through a condensation reaction of the compound (44) and the compound (13a) or the compound (13b). This step can be performed in the same manner as in Step 2-10 described above.

Step 10-7

This step is a step of producing the compound (1a) by reacting the compound (42) and the compound (13a) or the compound (13b). This step can be performed in the same manner as in Step 2-11 described above.

Step 10-8

This step is a step of producing the compound (1a) from the compound (9) by continuously performing the series of reactions of Step 2-12, Step 2-13 and Step 1-1 described above.

Here, when the compound (42) is represented as a compound (42a), the compound (42a) can be produced by a method shown in Scheme 11 or any equivalent method, or a method described in any literature or any equivalent method.

Scheme 11

[Formula 67]

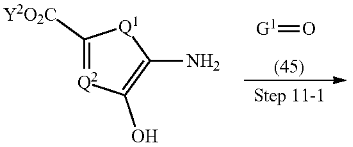

(18)

-continued

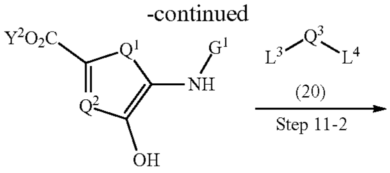

(46)

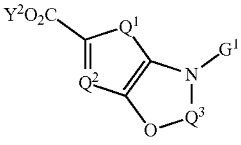

(42a)

wherein $Q^1$, $Q^2$, $Q^3$, $G^1$, $L^3$, $L^4$ and $Y^2$ have the same meaning as defined above.

Step 11-1

This step is a step of producing a compound (46) through a reductive amination reaction of the compound (18) and a compound (45). The compound (46) can be produced by, for example, allowing a reducing agent to act in a solvent in the presence or absence of an acid. Examples of the solvent to be used include tetrahydrofuran, 1,2-dimethoxyethane and 1,4-dioxane. Examples of the reducing agent to be used include sodium triacetoxyborohydride, sodium cyanoborohydride and sodium borohydride. An example of the acid to be used includes acetic acid. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 11-2

This step is a step of producing the compound (42a) by reacting the compound (46) and the compound (20). This step can be performed in the same manner as in Step 5-2 described above.

Here, when the compound (42) is represented as a compound (42c), the compound (42c) can be produced by a method shown in Scheme 12 or any equivalent method, or a method described in any literature or any equivalent method.

Scheme 12

[Formula 68]

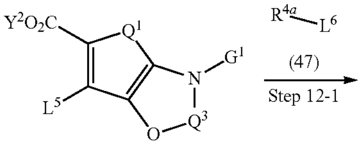

(42b)

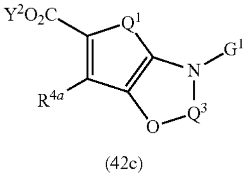

(42c)

wherein $Q^1$, $Q^2$, $Q^3$, $G^1$ and $Y^2$ have the same meaning as defined above; $R^{4a}$ is a $C_1$-$C_6$ alkyl group or a $C_3$-$C_8$ cycloalkyl group; $L^5$ is a chlorine atom, a bromine atom, an iodine atom or a methanesulfonyloxy group; and $L^6$ is a boronic acid derivative.

Step 12-1

This step is a step of producing the compound (42c) through a reaction of a compound (42b) and a compound (47). The compound (42c) can be produced by reacting the compound (42b) and the compound (47) under usual Suzuki coupling reaction conditions, for example, in a solvent in the presence of a palladium reagent and a base. Examples of the solvent to be used include tetrahydrofuran, 1,4-dioxane, benzene, toluene, ethanol, propanol, N,N-dimethylformamide, dimethylsulfoxide, water and a mixed solvent of any of these. Examples of the palladium reagent to be used include dichlorobis(triphenylphosphine)palladium and tetrakis(triphenylphosphine)palladium. Examples of the base to be used include sodium carbonate, potassium carbonate, sodium bicarbonate, potassium bicarbonate, cesium carbonate, sodium phosphate and potassium phosphate. Besides, a ligand such as (2-biphenyl)di-tert-butylphosphine (JohnPhos), 2-dicyclohexylphosphino-2',6'-dimethoxybiphenyl (SPhos) or 2-dicyclohexylphosphino-2',4',6'-triisopropylbiphenyl (XPhos) can be added if necessary. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Here, when the compound (3) is represented as a compound (3a), a compound (3b), a compound (3c) or a compound (3d), the compound (3a), the compound (3b), the compound (3c) or the compound (3d) can be produced by a method shown in Scheme 13 or any equivalent method, or a method described in any literature or any equivalent method.

$M^2$ is a $C_1$-$C_6$ alkyl group, a $C_3$-$C_0$ cycloalkyl group, a phenyl group, a 5-membered aromatic heterocyclic group, a 6-membered aromatic heterocyclic group or a heterocyclic group; and group E consists of a halogen atom, a $C_1$-$C_6$ alkyl group, a $C_3$-$C_8$ cycloalkyl group, a $C_1$-$C_6$ alkoxy group, a $C_1$-$C_6$ alkoxycarbonyl group, a 3- to 8-membered heterocycloalkyl group, an aminocarbonyl group optionally having two $C_1$-$C_6$ alkyl groups, an amino group optionally having two $C_1$-$C_6$ alkyl groups, a phenyl group optionally having one or more halogen atoms or $C_1$-$C_6$ alkoxy groups, a 5-membered aromatic heterocyclic group, and a 6-membered aromatic heterocyclic group.

Step 13-1

This step is a step of producing a compound (49) by reacting a compound (48) with hydrazine. The compound (49) can be produced by reacting the compound (48) with hydrazine or a hydrate thereof in a solvent in the presence of a base. Examples of the solvent to be used include ethanol, propanol, isopropyl alcohol, butanol, methanol, acetonitrile, N,N-dimethylformamide, N,N-dimethylacetamide, N-methylpyrrolidone, 1,4-dioxane, tetrahydrofuran, dimethylsulfoxide and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 13-2

This step is a step of producing the compound (3a) through cyclization by introducing a carbonyl group into the compound (49). The compound (3a) can be produced by reacting the compound (49) and a compound corresponding to a carbonyl source in a solvent in the presence or absence Scheme 13

[Formula 69]

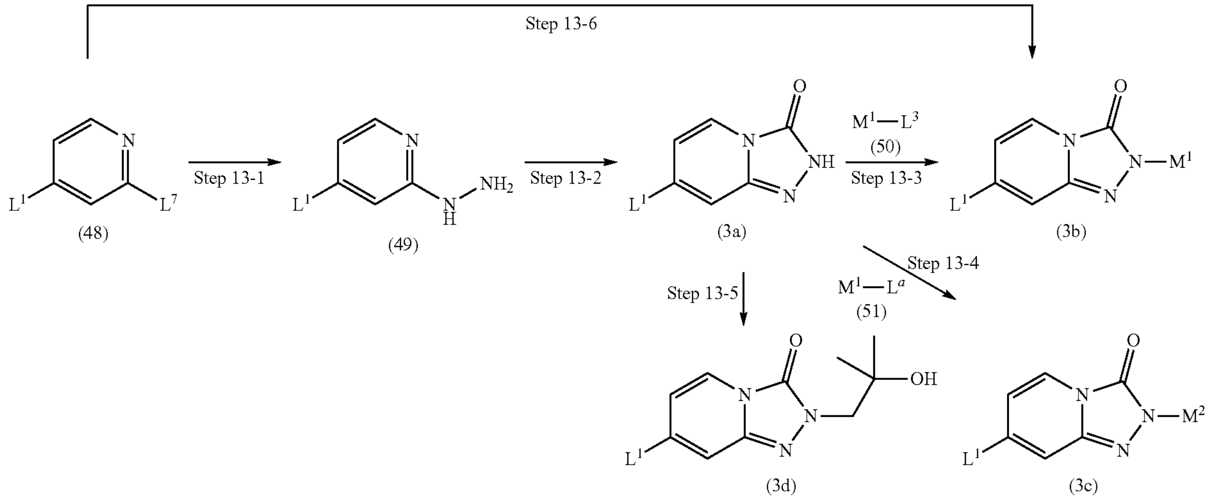

wherein $L^1$, $L^3$ and $L^6$ have the same meaning as defined above; $L^7$ is a fluorine atom or a chlorine atom; $M^1$ is a $C_1$-$C_6$ alkyl group, a $C_3$-$C_8$ cycloalkyl group or a 3- to 8-membered heterocycloalkyl group containing an oxygen atom each optionally having one or more substituents selected from group E described below;

of a base. Examples of the carbonyl source to be used include 1,1'-carbonyldiimidazole, triphosgene and a phosgene dimer. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include triethylamine, diisopropylethylamine and pyridine. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

When 1,1'-carbonyldiimidazole is used as the carbonyl source and the compound (3a) has an atom easily nucleophilically reacted, such as a fluorine atom, the compound (3a) in which an imidazolyl group is substituted may be obtained as a side reaction of this step in some cases.

Step 13-3

This step is a step of producing the compound (3b) by reacting the compound (3a) and a compound (50). The compound (3b) can be produced by reacting the compound (3a) and the compound (50) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium hydride, sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 13-4

This step is a step of producing the compound (3c) by reacting the compound (3a) and a compound (51). The compound (3c) can be produced by reacting the compound (51) and the compound (3a) under usual Chan-Lam-Evans coupling reaction conditions, for example, in a solvent in the presence of a copper reagent and in the presence or absence of a base. Examples of the solvent to be used include dichloromethane, chloroform, 1,2-dichloroethane, acetonitrile, tetrahydrofuran, 1,4-dioxane, benzene, toluene and a mixed solvent of any of these. An example of the copper reagent to be used includes copper (II) acetate. Examples of the base to be used include triethylamine, pyridine and diisopropylethylamine. It is noted that this step can be performed under addition of a desiccant such as molecular sieves 4A if necessary. The reaction temperature is usually room temperature to a solvent reflux temperature. The reaction time varies depending on a starting material and a solvent to be used, the reaction temperature and the like, and is usually 30 minutes to 3 days.

Step 13-5

This step is a step of producing the compound (3d) through an alkylation reaction of the compound (3a). The compound (3d) can be produced by reacting the compound (3a) and 2,2-dimethyloxirane in a solvent in the presence of a base. Examples of the solvent to be used include N,N-dimethylformamide, N,N-dimethylacetamide, N-methylpyrrolidone, acetonitrile, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Step 13-6

This step is a step of producing the compound (3b) from the compound (48) by continuously performing the series of reactions of Step 13-1, Step 13-2 and Step 13-3 described above.

Here, when the compound (1) is represented as a compound (1ba) or a compound (1bb), the compound (1ba) or the compound (1bb) can be produced by a method shown in Scheme 14 or any equivalent method, or a method described in any literature or any equivalent method.

Scheme 14

[Formula 70]

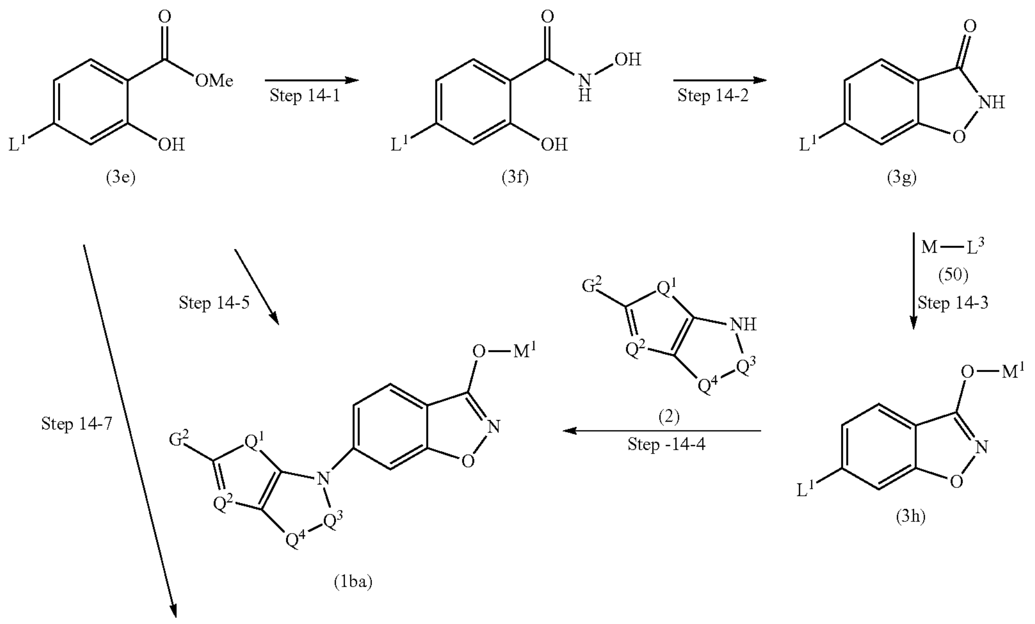

-continued

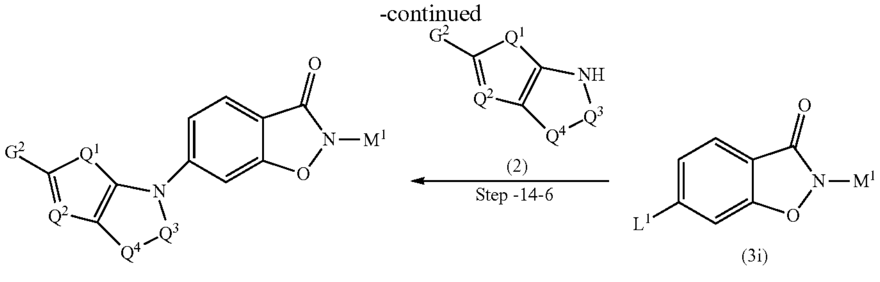

(1bb) (3i)

wherein $Q^1$, $Q^2$, $Q^3$, $Q^4$, $G^2$, $L^1$, $L^3$ and $M^1$ have the same meaning as defined above.

Step 14-1

This step is a step of producing a compound (3f) from a compound (3e). The compound (3f) can be produced by reacting hydroxylamine and the compound (3e) in a solvent. Examples of the solvent to be used include 1,4-dioxane, tetrahydrofuran, N,N-dimethylformamide, N,N-dimethylacetamide, dimethylsulfoxide and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 14-2

This step is a step of producing a compound (3g) through an intramolecular condensation reaction of the compound (3f). The compound (3g) can be produced by, for example, reacting the compound (3f) in a solvent in the presence of 1,1'-carbodiimidazole or thionyl chloride. Examples of the solvent to be used include 1,4-dioxane, tetrahydrofuran, dichloromethane and a mixed solvent of any of these. Besides, triethylamine or the like can be added if necessary. With respect to the reaction temperature, the reaction can be performed usually at room temperature to a solvent reflux temperature. The reaction time varies depending on a starting material and a solvent to be used, the reaction temperature and the like, and is usually 30 minutes to 3 days.

Step 14-3

This step is a step of producing either one of a compound (3h) and a compound (3i) or both of the compound (3h) and the compound (3i) by reacting the compound (3g) and the compound (50). This step can be performed in the same manner as in Step 13-3 described above.

Step 14-4

This step is a step of producing the compound (1ba) by reacting the compound (3h) and the compound (2). This step can be performed in the same manner as in Step 1-1 described above.

Step 14-5

This step is a step of producing the compound (1ba) from the compound (3a) by continuously performing the series of reactions of Step 14-1, Step 14-2, Step 14-3 and Step 14-4 described above.

Step 14-6

This step is a step of producing the compound (1bb) by reacting the compound (3i) and the compound (2). This step can be performed in the same manner as in Step 1-1 described above.

Step 14-7

This step is a step of producing the compound (1bb) from the compound (3a) by continuously performing the series of reactions of Step 14-1, Step 14-2, Step 14-3 and Step 14-6 described above.

Here, when the compound (23) is represented as a compound (23a) or a compound (23b), the compound (23a) or the compound (23b) can be produced by a method shown in Scheme 15 or any equivalent method, or a method described in any literature or any equivalent method.

Scheme 15

[Formula 71]

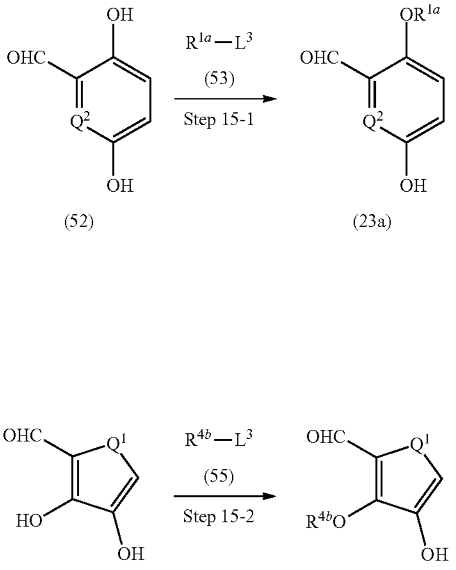

(52) (23a)

(54) (23b)

wherein $Q^1$, $Q^2$ and $L^3$ have the same meaning as defined above; $R^{1a}$ is a $C_1$-$C_6$ alkyl group; and $R^{4b}$ is a $C_1$-$C_6$ alkyl group.

Step 15-1

This step is a step of producing the compound (23a) by reacting a compound (52) and a compound (53). This step can be performed in the same manner as in Step 13-3 described above.

Step 15-2

This step is a step of producing the compound (23b) by reacting a compound (54) and a compound (55). This step can be performed in the same manner as in Step 13-3 described above.

Here, when the compound (8) is represented as a compound (8d), the compound (8d) can be produced by a method shown in Scheme 16 or any equivalent method, or a method described in any literature or any equivalent method.

Scheme 16

[Formula 72]

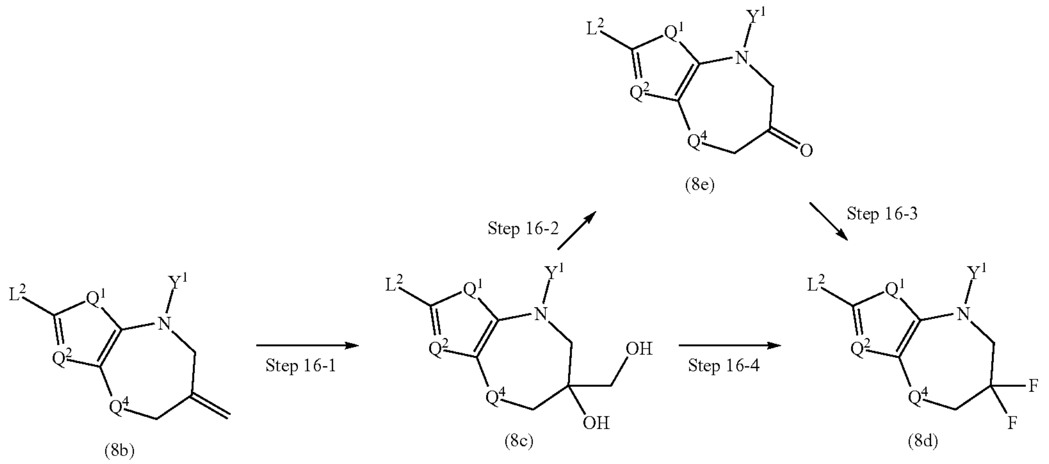

(8e) (8b) (8c) (8d)

wherein $Q^1$, $Q^2$, $Q^4$, $L^2$ and $Y^1$ have the same meaning as defined above.

Step 16-1

This step is a step of producing a compound (8c) from a compound (8b). The compound (8c) can be produced by reacting osmium tetroxide and the compound (8b) in a solvent in the presence or absence of a reoxidant. Examples of the solvent to be used include acetone, water, tert-butanol and a mixed solvent of any of these. Examples of the reoxidant to be used include N-methylmorpholine oxide, trimethylamine oxide, tert-butylhydroxy peroxide and potassium ferricyanide. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 16-2

This step is a step of producing a compound (8e) from the compound (8c). The compound (8e) can be produced by reacting sodium periodate or periodic acid with the compound (8c) in a solvent. Examples of the solvent to be used include water, 1,4-dioxane, tetrahydrofuran and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 16-3

This step is a step of producing the compound (8d) from the compound (8e). The compound (8d) can be produced by reacting a fluorinating agent and the compound (8e) in a solvent. Examples of the fluorinating agent to be used include N,N-dimethylaminosulfur trifluoride, Deoxo-Fluor and Pheno-Fluor. Examples of the solvent to be used include toluene and benzene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 16-4

This step is a step of producing the compound (8d) from the compound (8c) by continuously performing the series of reactions of Step 16-2 and Step 16-3 described above.

Here, when the compound (8) is represented as a compound (8f), the compound (8f) can be produced by a method shown in Scheme 17 or any equivalent method, or a method described in any literature or any equivalent method.

Scheme 17

[Formula 73]

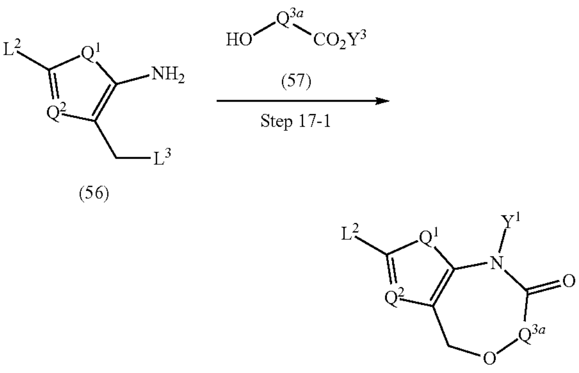

(57) (56) (8f)

wherein $Q^1$, $Q^2$, $Q^{3a}$, $L^2$, $L^3$, $Y^1$ and $Y^3$ have the same meaning as defined above.

Step 17-1

This step is a step of producing the compound (8f) from a compound (56) and a compound (57). The compound (8f) can be produced by reacting the compound (56) and the compound (57) in a solvent in the presence of a base. Examples of the solvent to be used include N,N-dimethylformamide, acetonitrile, tetrahydrofuran and a mixed solvent of any of these. Examples of the base to be used include sodium hydride, potassium carbonate and cesium carbonate. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, when the compound (3) is represented as a compound (3k), the compound (3k) can be produced by a method shown in Scheme 18 or any equivalent method, or a method described in any literature or any equivalent method.

Scheme 18

[Formula 74]

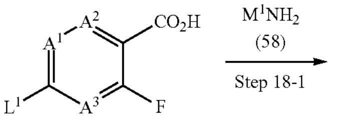

(3j)

-continued

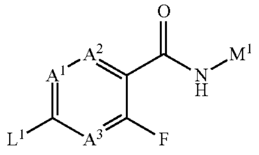

(3k)

wherein $L^1$ and $M^1$ have the same meaning as defined above; $A^1$ is a carbon atom or a nitrogen atom; $A^2$ is a carbon atom or a nitrogen atom; and $A^3$ is a carbon atom or a nitrogen atom.

Step 18-1

This step is a step of producing the compound (3k) through a condensation reaction of a compound (3j) and a compound (58). The compound (3k) can be produced by, for example, reacting the compound (3j) and the compound (58) in a solvent in the presence of a condensing agent and in the presence or absence of a base. Examples of the solvent to be used include N,N-dimethylformamide, N,N-dimethylacetamide, N-methylpyrrolidone, dichloromethane, 1,4-dioxane, tetrahydrofuran and a mixed solvent of any of these. Examples of the condensing agent to be used include 1-[bis(dimethylamino)methylene]-1H-1,2,3-triazolo[4,5-b]pyridinium 3-oxide hexafluorophosphate (HATU), 1-ethyl-3-(3-dimethylaminopropyl)carbodiimide (EDCI) and dicyclohexylcarbodiimide (DCC). Examples of the base to be used include triethylamine and diisopropylethylamine. Besides, N,N-dimethyl-4-aminopyridine, pyridine, 1-hydroxybenzotriazole (HOBT) or the like can be added as a reaction accelerator if necessary. With respect to the reaction temperature, the reaction can be performed usually at 0° C. to a solvent reflux temperature, and is performed preferably at 0° C. to 30° C. The reaction time varies depending on a starting material and a solvent to be used, the reaction temperature and the like, and is usually 30 minutes to 3 days.

Here, when the compound (3) is represented as a compound (3m), the compound (3m) can be produced by a method shown in Scheme 19 or any equivalent method, or a method described in any literature or any equivalent method.

Scheme 19

[Formula 75]

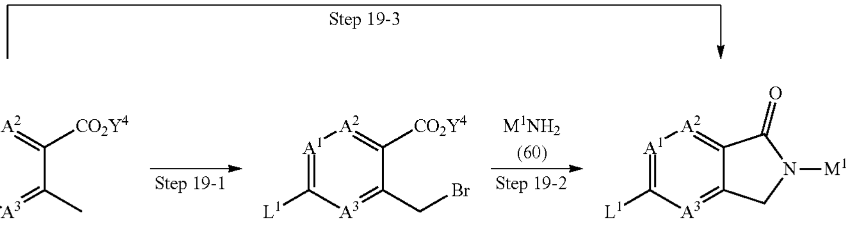

(3l) (59) (3m)

wherein $L^1$, $A^1$, $A^2$, $A^3$ and $M^1$ have the same meaning as defined above; and $Y^4$ is a $C_1$-$C_6$ alkyl group or an aryl group.

Step 19-1

This step is a step of producing a compound (59) through a bromination reaction of the compound (3l). The compound (59) can be produced by, for example, reacting the compound (3l) in a solvent in the presence of a brominating agent and in the presence or absence of a radical initiator. Examples of the solvent to be used include carbon tetrachloride, chloroform, dichloromethane and a mixed solvent of any of these. Examples of the brominating agent to be used include N-bromosuccinimide and bromine. Examples of the radical initiator to be used include azoisobutyronitrile and 1,1'-azobis(cyclohexanecarbonitrile). With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 19-2

This step is a step of producing the compound (3m) from the compound (59) and a compound (60) through a ring closure reaction accompanying elimination of a bromine atom and $Y^4OH$. The compound (3m) can be produced from the compound (59) and the compound (60) in a solvent in the presence of a base. Examples of the solvent to be used include tetrahydrofuran, 1,4-dioxane, toluene, acetonitrile, N,N-dimethylformamide, N,N-dimethylacetamide, N-methylpyrrolidone, dimethylsulfoxide and a mixed solvent of any of these. Examples of the base to be used include triethylamine, diisopropylethylamine, pyridine, 1,8-diazabicyclo[5,4,0]-7-undecene, sodium carbonate, potassium carbonate and cesium carbonate. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 19-3

This step is a step of producing the compound (3m) from the compound (31) by continuously performing the series of reactions of Step 19-1 and Step 19-2 described above.

Here, when the compound (13) is represented as a compound (13ba), the compound (13ba) can be produced by a method shown in Scheme 20 or any equivalent method, or a method described in any literature or any equivalent method.

Scheme 20

[Formula 76]

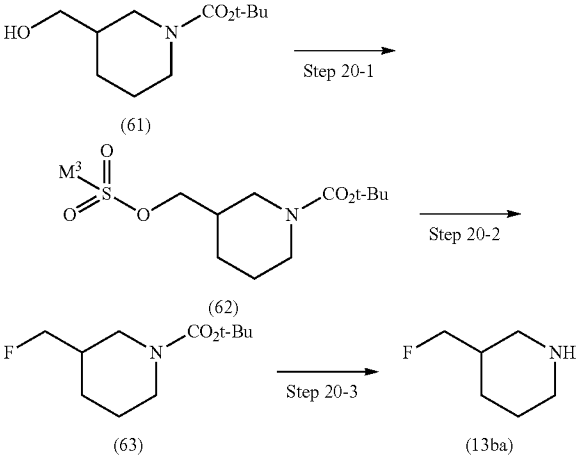

(61)

(62)

(63)

(13ba)

wherein $M^3$ is a $C_1$-$C_6$ alkyl group.

Step 20-1

This step is a step of producing a compound (62) through an alkylsulfonylation reaction of a compound (61). The compound (62) can be produced by reacting the compound (61) with an alkylsulfonylation agent in a solvent in the presence of a base. Examples of the solvent to be used include dichloromethane, chloroform, toluene, tetrahydrofuran and a mixed solvent of any of these. Examples of the base to be used include triethylamine, diisopropylethylamine and pyridine. Examples of the alkylsulfonylation agent to be used include methanesulfonyl chloride and ethanesulfonyl chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 20-2

This step is a step of producing a compound (63) by substituting an alkylsulfonyl group of the compound (62) with a fluorine atom. The compound (63) can be produced by reacting with the compound (62) in a solvent in the presence of tetrabutylammonium fluoride. Examples of the solvent to be used include tetrahydrofuran, 1,4-dioxane and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 20-3

This step is a step of producing the compound (13ba) by removing a tert-butoxycarbonyl group of the compound (63). The compound (13ba) can be produced by, for example, treating the compound (63) with an acid in a solvent or without using a solvent. Examples of the solvent to be used for the reaction include dichloromethane, 1,4-dioxane, tetrahydrofuran, methanol, ethanol, water and a mixed solvent of any of these. Examples of the acid to be used include trifluoroacetic acid and hydrogen chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, when the compound (1) is represented as a compound (1e) or a compound (1f), the compound (1e) or the compound (1f) can be produced by a method shown in Scheme 21 or any equivalent method, or a method described in any literature or any equivalent method.

Scheme 21

[Formula 77]

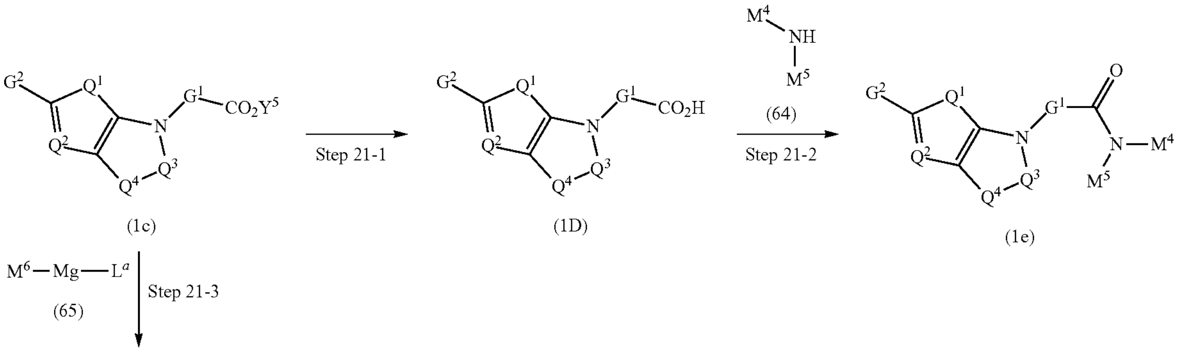

(1c)

(1D)

(64)

(1e)

(65)

-continued

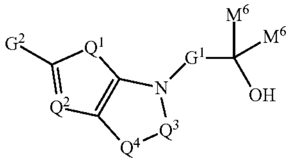

(1f)

wherein $Q^1$, $Q^2$, $Q^3$, $Q^4$, $G^1$ and $G^2$ have the same meaning as defined above; $L^8$ is a chlorine atom or a bromine atom; $Y^5$ is a $C_1$-$C_6$ alkyl group or an aryl group; $M^4$ is a hydrogen atom or a $C_1$-$C_6$ alkyl group; $M^5$ is a hydrogen atom or a $C_1$-$C_6$ alkyl group; and $M^6$ is a $C_1$-$C_6$ alkyl group.

Step 21-1

This step is a step of producing a compound (1d) by hydrolyzing an ester moiety of a compound (1c). This step varies depending on a starting material and a solvent to be used, the reaction temperature and the like, and is usually 30 minutes to 3 days.

Here, when the compound (1) is represented as a compound (1da), the compound (1da) can be produced by a method shown in Scheme 22 or any equivalent method, or a method described in any literature or any equivalent method.

Scheme 22

[Formula 78]

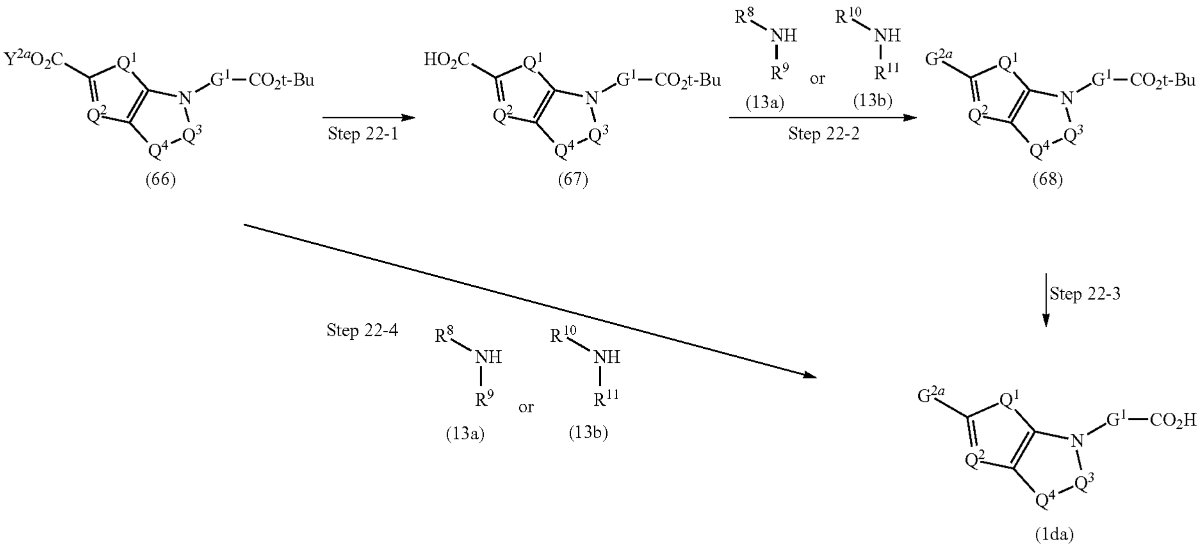

(66) (67) (68) (1da)

(13a) or (13b)

can be performed in the same manner as in Step 2-9 described above.

Step 21-2

This step is a step of producing the compound (1e) through a condensation reaction of the compound (1d) and a compound (64). This step can be performed in the same manner as in Step 2-10 described above.

Step 21-3

This step is a step of producing the compound (1f) from the compound (1c). The compound (1f) can be produced by reacting the compound (1c) and a compound (65) in a solvent. Examples of the solvent to be used include diethyl ether, tetrahydrofuran, 1,2-dimethoxyethane, 1,4-dioxane and a mixed solvent of any of these. With respect to the reaction temperature, the reaction can be performed usually at −80° C. to a solvent reflux temperature. The reaction time wherein $Q^1$, $Q^2$, $Q^3$, $Q^4$, $R^8$, $R^9$, $R^{10}$, $R^{11}$, $G^1$ and $G^{2a}$ have the same meaning as defined above; and $Y^{2a}$ is a $C_1$-$C_6$ alkyl group.

Step 22-1

This step is a step of producing a compound (67) by hydrolyzing an alkyl ester moiety of a compound (66).

The compound (67) can be produced by, for example, reacting the compound (66) in a solvent in the presence of a base. Examples of the solvent to be used include water, methanol, ethanol, propanol, isopropyl alcohol, butanol, tetrahydrofuran, 1,4-dioxane and a mixed solvent of any of these. Examples of the base to be used include alkali metal salts such as lithium hydroxide, sodium hydroxide and potassium hydroxide. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 22-2

This step is a step of producing a compound (68) through a condensation reaction of the compound (67) and the compound (13a) or the compound (13b). This step can be performed in the same manner as in Step 2-10 described above.

Step 22-3

This step is a step of producing the compound (1da) by hydrolyzing a tert-butyl ester moiety of the compound (68). The compound (1da) can be produced by reacting the compound (68) in the presence or absence of a solvent and in the presence of an acid. Examples of the solvent to be used include water, tetrahydrofuran, 1,4-dioxane, methylene chloride and a mixed solvent of any of these. Examples of the acid to be used include trifluoroacetic acid and hydrogen chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 22-4

This step is a step of producing the compound (1da) from the compound (66) by continuously performing the series of reactions of Step 22-1, Step 22-2 and Step 22-3 described above.

Here, when the compound (1) is represented as a compound (1ga) or a compound (1gb), the compound (1ga) or the compound (1gb) can be produced by a method shown in Scheme 23 or any equivalent method, or a method described in any literature or any equivalent method.

Scheme 23

[Formula 79]

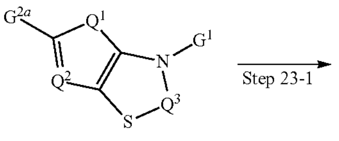

(1g)

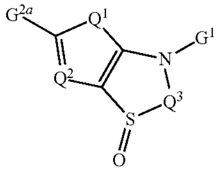

or

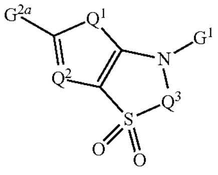

(1ga) (1gb)

wherein $Q^1$, $Q^2$, $Q^3$, $G^1$ and $G^{2a}$ have the same meaning as defined above.

Step 23-1

This step is a step of producing the compound (1ga) or the compound (1gb) by oxidizing a sulfur atom of a compound (1g). The compound (1ga) or the compound (1gb) can be produced by reacting the compound (1g) with a peroxide in a solvent. Examples of the solvent to be used include dichloromethane, ethyl acetate, water and a mixed solvent of any of these. Examples of the peroxide to be used include 3-chloroperbenzoate and a hydrogen peroxide solution. With respect to the reaction temperature, the reaction can be performed usually at 0° C. to a solvent reflux temperature, and is performed preferably at 0° C. to room temperature. The reaction time varies depending on a starting material and a solvent to be used, the reaction temperature and the like, and is usually 30 minutes to 3 days.

Here, when the compound (1) is represented as a compound (1ha) or a compound (1hb), the compound (1ha) or the compound (1hb) can be produced by a method shown in Scheme 24 or any equivalent method, or a method described in any literature or any equivalent method.

Scheme 24

[Formula 80]

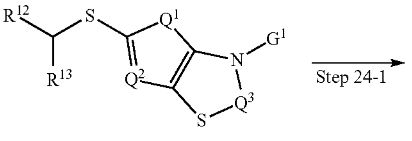

(1h)

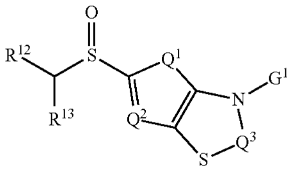

(1ha)

or

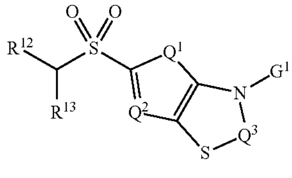

(1hb)

wherein $Q^1$, $Q^2$, $Q^3$, $Q^4$, $G^1$, $R^{12}$ and $R^{13}$ have the same meaning as defined above.

Step 24-1

This step is a step of producing the compound (1ha) or the compound (1hb) by oxidizing a sulfur atom of a compound (1h). This step can be performed in the same manner as in Step 23-1 described above.

Here, when the compound (1) is represented as a compound (1j), the compound (1j) can be produced by a method shown in Scheme 25 or any equivalent method, or a method described in any literature or any equivalent method.

Scheme 25

[Formula 81]

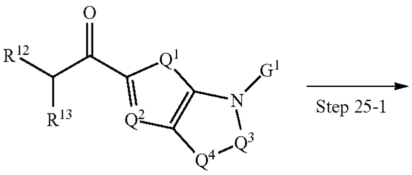

(1i)

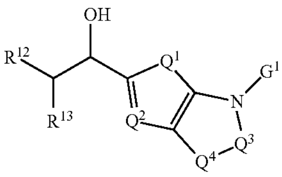

(1j)

wherein $Q^1$, $Q^2$, $Q^3$, $Q^4$, $G^1$, $R^{12}$ and $R^{13}$ have the same meaning as defined above.

Step 25-1

This step is a step of producing the compound (1j) having a hydroxy group by reducing a ketone moiety of a compound (1i). This step can be performed in the same manner as in Step 3-2 described above.

Here, when the compound (1) is represented as a compound (1ka), the compound (1ka) can be produced by a method shown in Scheme 26 or any equivalent method, or a method described in any literature or any equivalent method.

Scheme 26

[Formula 82]

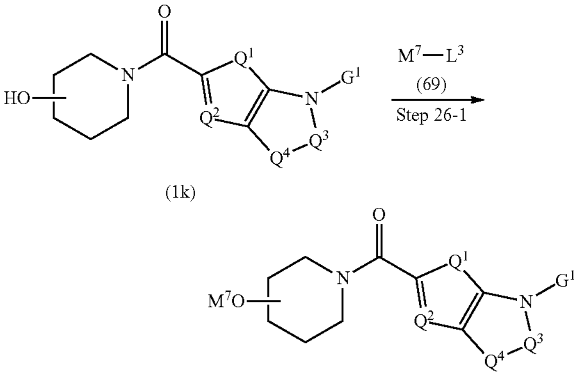

(1k)

(1ka)

wherein $Q^1$, $Q^2$, $Q^3$, $Q^4$, $G^1$ and $L^3$ have the same meaning as defined above; and $M^7$ is a $C_1$-$C_6$ alkyl group.

Step 26-1

This step is a step of producing the compound (1ka) by reacting a compound (1k) and a compound (69). The compound (1ka) can be produced by reacting the compound (1k) and the compound (69) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium hydride, sodium carbonate, potassium carbonate, cesium carbonate and potassium phosphate. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, when the compound (1) is represented as a compound (1m), the compound (1m) can be produced by a method shown in Scheme 27 or any equivalent method, or a method described in any literature or any equivalent method.

Scheme 27

[Formula 83]

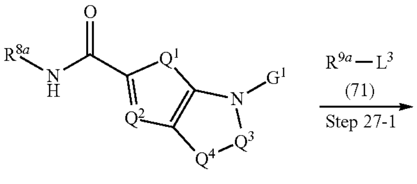

(70)

-continued

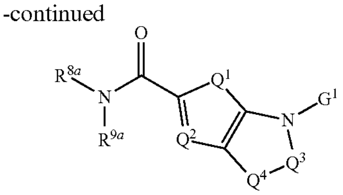

(1m)

wherein $Q^1$, $Q^2$, $Q^3$, $Q^4$, $G^1$ and $L^3$ have the same meaning as defined above; $R^{8a}$ is a $C_1$-$C_6$ alkyl group or a $C_3$-$C_8$ cycloalkyl group; and $R^{9a}$ is a $C_1$-$C_6$ alkyl group.

Step 27-1

This step is a step of producing the compound (1m) by reacting a compound (70) and a compound (71). The compound (1m) can be produced by reacting the compound (70) and the compound (71) in a solvent in the presence of a base. Examples of the solvent to be used include acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium hydride, sodium carbonate, potassium carbonate, cesium carbonate and potassium phosphate. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, the compound (1) can be produced by a method shown in Scheme 28 or any equivalent method, or a method described in any literature or any equivalent method.

Scheme 28

[Formula 84]

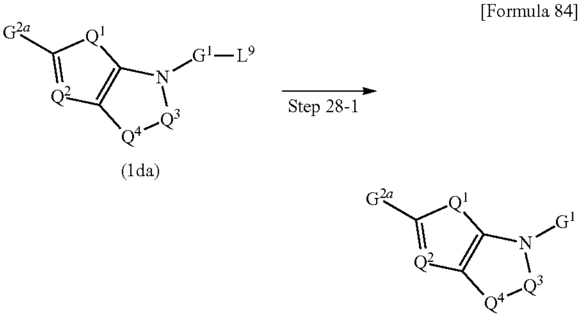

(1da)

(1)

wherein $Q^1$, $Q^2$, $Q^3$, $Q^4$, $G^1$ and $G^2$ have the same meaning as defined above; and $L^9$ is a $C_7$-$C_{10}$ aralkyl group.

Step 28-1

This step is a step of producing the compound (1) by removing $L^9$ from a compound (1n). The compound (1) can be produced by, for example, reacting the compound (1n) in the presence or absence of a solvent and in the presence of an acid. Examples of the solvent to be used include water, tetrahydrofuran, 1,4-dioxane, methylene chloride and a mixed solvent of any of these. Examples of the acid to be used include trifluoroacetic acid and hydrogen chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, when the compound (1) is represented as a compound (1p) or a compound (1q), the compound (1p) or the compound (1q) can be produced by a method shown in Scheme 29 or any equivalent method, or a method described in any literature or any equivalent method.

Step 30-1

This step is a step of producing the compound (1d) by reacting the compound (2) and a compound (3n), followed by a hydrolysis reaction of an ester moiety.

The reaction between the compound (2) and the compound (3n) can be performed in a solvent or without using a solvent in the presence or absence of an acid or a base.

Scheme 29

[Formula 85]

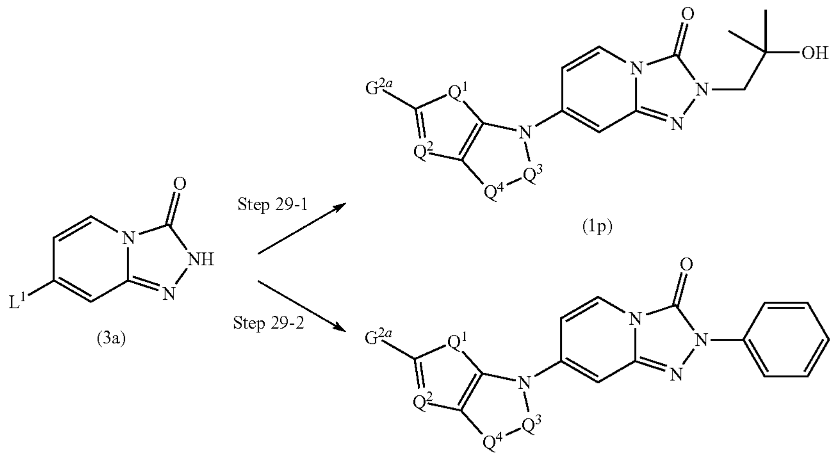

(3a) (1p) (1q)

wherein $Q^1$, $Q^2$, $Q^3$, $Q^4$, $G^2$ and $L^1$ have the same meaning as defined above.

Step 29-1

This step is a step of producing the compound (1p) from the compound (3a) by continuously performing the series of reactions of Step 13-5 and Step 1-1 described above.

Step 29-2

This step is a step of producing the compound (1q) from the compound (3a) by continuously performing the series of reactions of Step 13-4 and Step 1-1 described above.

Here, when the compound (1) is represented as a compound (1d), the compound (1d) can be produced by a method shown in Scheme 30 or any equivalent method, or a method described in any literature or any equivalent method.

Scheme 30

[Formula 86]

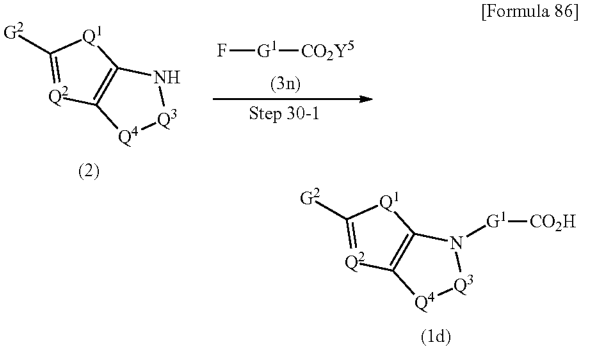

(2) (1d)

wherein $Q^1$, $Q^2$, $Q^3$, $Q^4$, $G^1$, $G^2$ and $Y^5$ have the same meaning as defined above.

Examples of the solvent to be used include N,N-dimethylformamide, dimethylsulfoxide, water, tetrahydrofuran, 1,4-dioxane, ethanol and a mixed solvent of any of these. Examples of the acid to be used include hydrogen chloride, p-toluenesulfonic acid and methanesulfonic acid. Examples of the base to be used include triethylamine, diisopropylethylamine, pyridine, 2,6-dimethylpyridine, 2,4,6-trimethylpyridine, potassium carbonate and cesium carbonate. With respect to the reaction temperature, the reaction can be performed usually at room temperature to a solvent reflux temperature. The reaction time varies depending on a starting material and a solvent to be used, the reaction temperature and the like, and is usually 30 minutes to 3 days. Besides, the hydrolysis reaction of an ester moiety subsequently performed can be performed in the same manner as in Step 2-9 described above.

Here, when the compound (1) is represented as a compound (1ra), the compound (1ra) can be produced by a method shown in Scheme 31 or any equivalent method, or a method described in any literature or any equivalent method.

Scheme 31

[Formula 87]

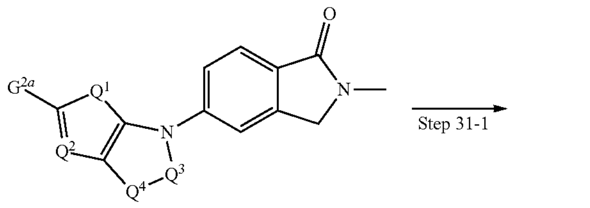

(1q)

-continued

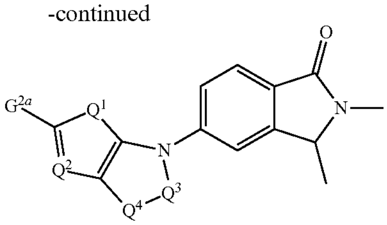

(1ra)

wherein $Q^1$, $Q^2$, $Q^3$, $Q^4$ and $G^2$ have the same meaning as defined above.

Step 31-1

This step is a step of producing the compound (1ra) by a methylation reaction of a compound (1r). The compound (1ra) can be produced by, for example, reacting the compound (1r) in a solvent in the presence of a base and a methylating agent. Examples of the solvent to be used include tetrahydrofuran, 1,4-dioxane, 1,2-dimethoxyethane and a mixed solvent of any of these. An example of the base to be used includes sodium bis(trimethylsilyl)amide. Examples of the methylating agent to be used include methyl iodide and dimethyl sulfate. With respect to the reaction temperature, the reaction can be performed usually at −78° C. to room temperature. The reaction time varies depending on a starting material and a solvent to be used, the reaction temperature and the like, and is usually 30 minutes to 3 days.

Here, when the compound (3) is represented as a compound (3pa), a compound (3qa), a compound (3ra), a compound (3sa), a compound (3ta) or a compound (3tb), the compound (3pa), the compound (3qa), the compound (3ra), the compound (3sa), the compound (3ta) or the compound (3tb) can be produced by a method shown in Scheme 32 or any equivalent method, or a method described in any literature or any equivalent method.

Scheme 32

[Formula 88]

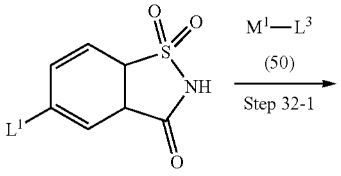

(3p)

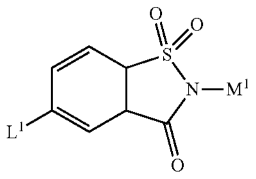

(3pa)

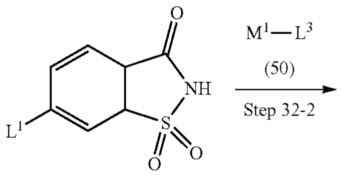

(3q)

-continued

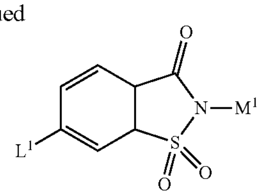

(3qa)

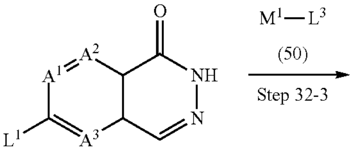

(3r)

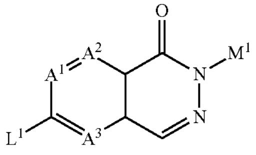

(3ra)

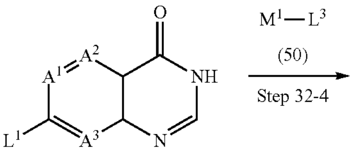

(3s)

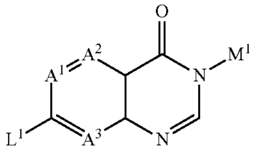

(3sa)

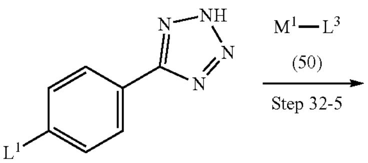

(3t)

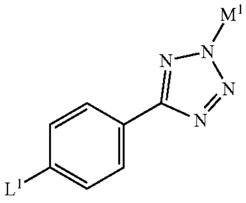

(3ta)

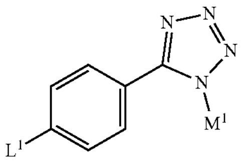

(3tb)

wherein $A^1$, $A^2$, $A^3$, $L^1$, $L^3$ and $M^1$ have the same meaning as defined above.

Step 32-1

This step is a step of producing the compound (3pa) by reacting a compound (3p) and the compound (50). This step can be performed in the same manner as in Step 13-3 described above.

Step 32-2

This step is a step of producing the compound (3qa) by reacting a compound (3q) and the compound (50). This step can be performed in the same manner as in Step 13-3 described above.

Step 32-3

This step is a step of producing the compound (3ra) by reacting a compound (3r) and the compound (50). This step can be performed in the same manner as in Step 13-3 described above.

Step 32-4

This step is a step of producing the compound (3sa) by reacting a compound (3s) and the compound (50). This step can be performed in the same manner as in Step 13-3 described above.

Step 32-5

This step is a step of producing either of the compound (3ta) and a compound (3tb) or both of the compound (3ta) and the compound (3tb) by reacting a compound (3t) and the compound (50). This step can be performed in the same manner as in Step 13-3 described above.

Here, when the compound (1) is represented as a compound (1sa), a compound (1sb), a compound (1sc) or a compound (1sd), the compound (1sa), the compound (1sb), the compound (1sc) or the compound (1sd) can be produced by a method shown in Scheme 33 or any equivalent method, or a method described in any literature or any equivalent method.

Step 33-1

This step is a step of producing the compound (1sa) by reacting a compound (1s) and the compound (50). This step can be performed in the same manner as in Step 13-3 described above.

Step 33-2

This step is a step of producing the compound (1sb) by reacting the compound (1s) and the compound (51). This step can be performed in the same manner as in Step 13-4 described above.

Step 33-3

This step is a step of producing the compound (1sc) through a hydroxymethylation reaction of the compound (1s). The compound (1sc) can be produced by, for example, reacting the compound (1s) with formaldehyde in a solvent in the presence or absence of a base. Examples of the solvent to be used include tetrahydrofuran, 1,4-dioxane, 1,2-dimethoxyethane, acetone, methanol, ethanol, water and a mixed solvent of any of these. Examples of the base to be used include potassium hydroxide, sodium hydroxide, potassium carbonate and sodium carbonate. With respect to the reaction temperature, the reaction can be performed usually at 0° C. to room temperature. The reaction time varies depending on Scheme 33

[Formula 89]

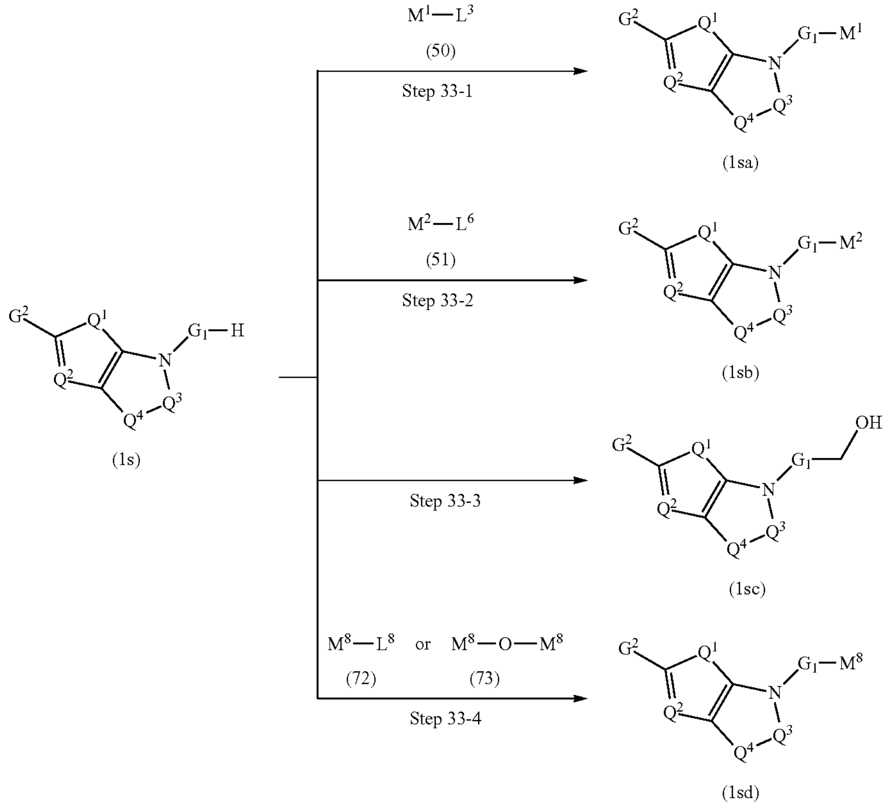

wherein $G^1$, $G^2$, $L^3$, $L^6$, $L^8$, $M^1$, $M^2$, $Q^1$, $Q^2$, $Q^3$ and $Q^4$ have the same meaning as defined above; and $M^8$ is a $C_1$-$C_6$ alkylcarbonyl group, a $C_1$-$C_6$ alkylsulfonyl group, a $C_3$-$C_8$ cycloalkylcarbonyl group or a $C_3$-$C_8$ cycloalkylsulfonyl group.

a starting material and a solvent to be used, the reaction temperature and the like, and is usually 30 minutes to 3 days.

Step 33-4

This step is a step of producing the compound (1sd) through an acylation or sulfonylation reaction of the compound (1s).

The compound (1sd) can be produced by, for example, reacting the compound (1s) and a compound (72) or a compound (73) in a solvent in the presence of a base. Examples of the solvent to be used include dichloromethane, chloroform, acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Here, when the compound (1) is represented as a compound (1ta), a compound (1tb), a compound (1tc), a compound (1ua) or a compound (1ub), the compound (1ta), the compound (1tb), the compound (1tc), the compound (1ua) or the compound (1ub) can be produced by a method shown in Scheme 34 or any equivalent method, or a method described in any literature or any equivalent method.

Scheme 34

[Formula 90]

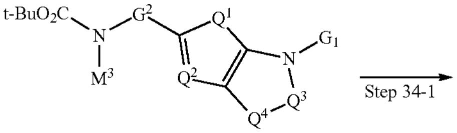

(1t)

$M^8-L^8$
(72)
or

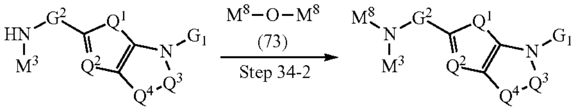

(1ta) (1tb)

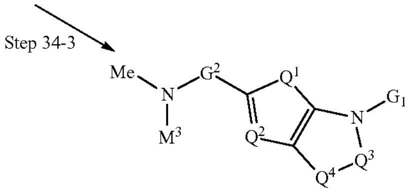

(1tc)

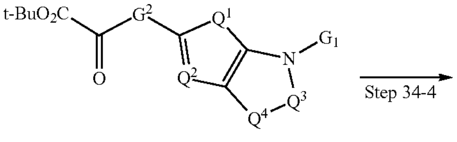

(1u)

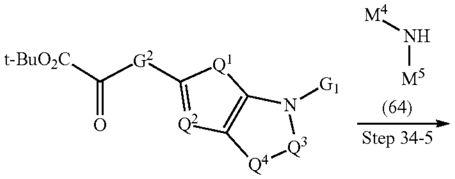

(1ua)

-continued

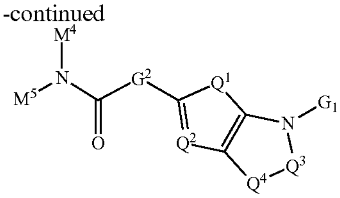

(1ub)

wherein $G^1$, $G^2$, $L^8$, $M^3$, $M^4$, $M^5$, $M^8$, $Q^1$, $Q^7$, $Q^3$ and $Q^4$ have the same meaning as defined above.

Step 34-1

This step is a step of producing the compound (1ta) by removing a tert-butoxycarbonyl group from a compound (1t). The compound (1ta) can be produced by reacting the compound (1t) in the presence or absence of a solvent and in the presence of an acid. Examples of the solvent to be used include water, tetrahydrofuran, 1,4-dioxane, methylene chloride and a mixed solvent of any of these. Examples of the acid to be used include trifluoroacetic acid and hydrogen chloride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 34-2

This step is a step of producing the compound (1tb) through an acylation or sulfonylation reaction of the compound (1ta). This step can be performed in the same manner as in Step 33-4 described above.

Step 34-3

This step is a step of producing the compound (1tc) through a reductive methylation reaction of the compound (1ta). The compound (1tc) can be produced by reacting the compound (1ta) with formaldehyde in the presence or absence of a solvent and in the presence of acetic acid or acetic anhydride, and then allowing a reducing agent to act on the resultant. Examples of the solvent to be used include tetrahydrofuran, 1,4-dioxane, methylene chloride and a mixed solvent of any of these. Examples of the reducing agent to be used include sodium triacetoxyborohydride, sodium cyanoborohydride and sodium borohydride. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 34-4

This step is a step of producing the compound (1ua) by hydrolyzing a tert-butyl ester moiety of a compound (1u). This step can be performed in the same manner as in Step 22-3 described above.

Step 34-5

This step is a step of producing the compound (1ub) through a condensation reaction of the compound (1ua) and the compound (64). This step can be performed in the same manner as in Step 2-10 described above.

Here, when the compound (10) is represented as a compound (10ba), the compound (10ba) can be produced by a method shown in Scheme 35 or any equivalent method, or a method described in any literature or any equivalent method.

Scheme 35

[Formula 91]

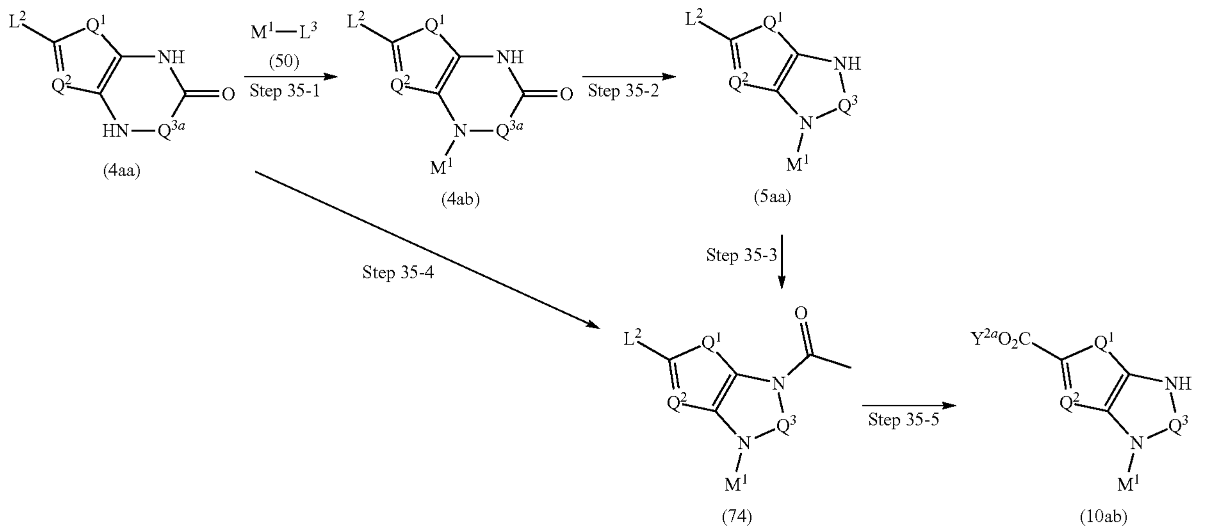

(4aa) (4ab) (5aa) (74) (10ab)

wherein $L^2$, $L^3$, $M^1$, $Q^1$, $Q^2$, $Q^3$, $Q^{3a}$ and $Y^{2a}$ have the same meaning as defined above.

Step 35-1

This step is a step of producing the compound (4ab) by reacting a compound (4aa) and the compound (50). This step can be performed in the same manner as in Step 13-3 described above.

Step 35-2

This step is a step of producing a compound (5aa) by reducing secondary amide of the compound (4ab) into secondary amine. This step can be performed in the same manner as in Step 2-1 described above.

Step 35-3

This step is a step of producing a compound (74) through an acetylation reaction of the compound (5aa). The compound (74) can be produced by, for example, reacting the compound (5aa) with acetic anhydride or acetyl chloride in a solvent in the presence of a base. Examples of the solvent to be used include dichloromethane, chloroform, acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 35-4

This step is a step of producing the compound (74) from the compound (4aa). The compound (74) can be produced by continuously performing Step 35-1, Step 35-2 and Step 35-3 described above.

Step 35-5

This step is a step of producing the compound (10ba) by converting $L^2$ of the compound (74) into an alkoxycarbonyl group and removing an acetyl group substituted with a nitrogen atom.

The compound (10ba) can be produced by reacting the compound (74) in a solvent in the presence of a palladium reagent and a base under carbon monoxide atmosphere. Examples of the solvent to be used include alcohols such as methanol, ethanol and propanol, and alternatively, a mixture of any of these alcohols with N,N-dimethylformamide, N,N-dimethylacetamide, dimethylsulfoxide, water or the like can be used. An example of the palladium reagent to be used includes a [1,1-bis(diphenylphosphino)ferrocene]palladium (II) dichloride dichloromethane adduct. Examples of the base to be used include triethylamine and diisopropylethylamine. The reaction temperature is usually room temperature to a solvent reflux temperature. The reaction time varies depending on a starting material and a solvent to be used, the reaction temperature and the like, and is usually 30 minutes to 3 days.

Here, when the compound (1) is represented as a compound (1va), a compound (1vb), a compound (1vc) or a compound (1vd), the compound (1va), the compound (1vb), the compound (1vc) or the compound (1vd) can be produced by a method shown in Scheme 36 or any equivalent method, or a method described in any literature or any equivalent method.

[Formula 92]

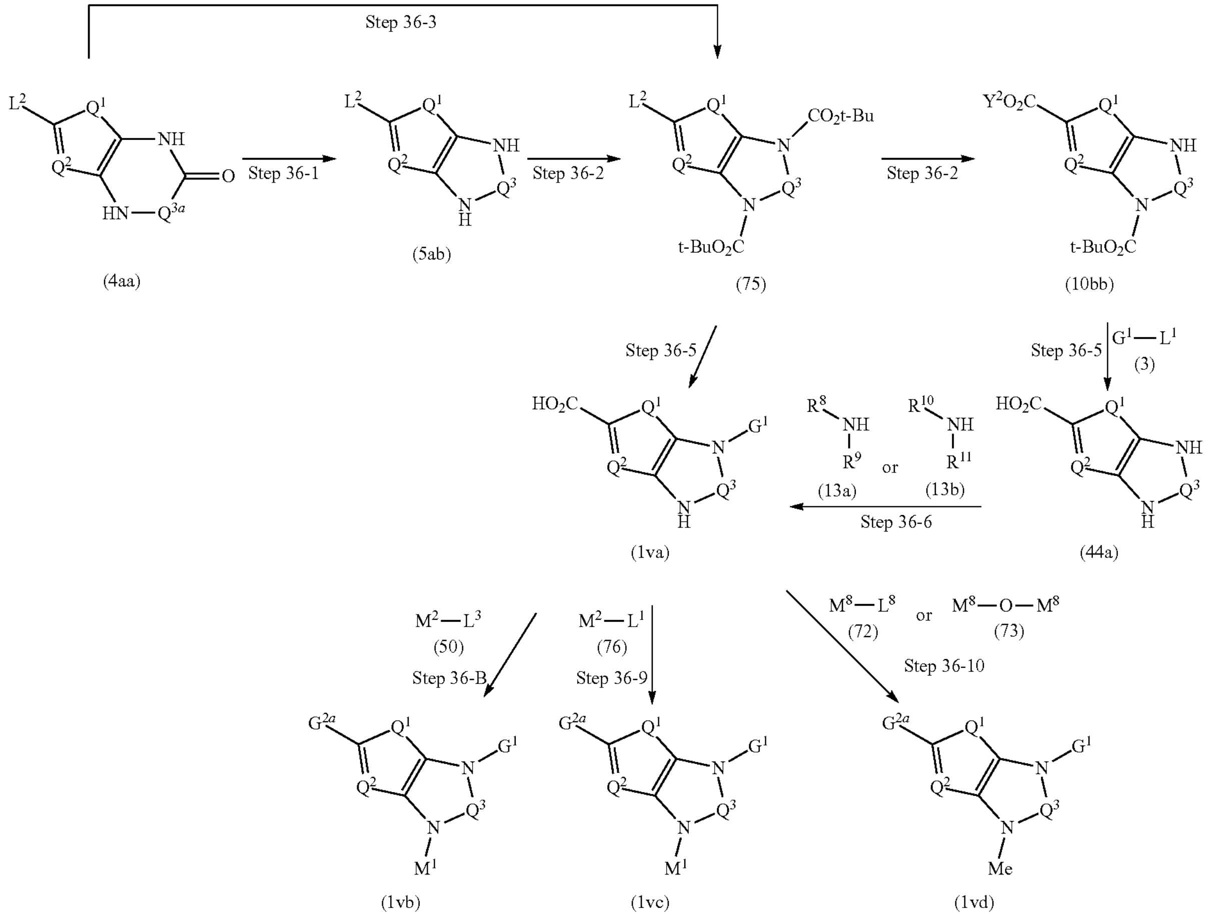

wherein $L^1$, $L^2$, $L^3$, $L^8$, $M^1$, $M^2$, $M^8$, $G^1$, $G^{2a}$, $Q^1$, $Q^2$, $Q^3$, $Q^{3a}$, $R^8$, $R^9$, $R^{10}$, $R^{11}$ and $Y^2$ have the same meaning as defined above.

Step 36-1

This step is a step of producing a compound (5ab) by reducing secondary amide of the compound (4aa) into secondary amine. This step can be performed in the same manner as in Step 2-1 described above.

Step 36-2

This step is a step of producing a compound (75) by introducing a tert-butoxycarbonyl group into the compound (5ab). The compound (75) can be produced by, for example, reacting the compound (5ab) with di-tert-butyl dicarbonate in a solvent in the presence of a base. Examples of the solvent to be used include dichloromethane, chloroform, acetonitrile, N,N-dimethylformamide, N,N-dimethylacetamide, N-methylpyrrolidone, 1,4-dioxane, tetrahydrofuran, dimethylsulfoxide and a mixed solvent of any of these. Examples of the base to be used include sodium carbonate, potassium carbonate, cesium carbonate, potassium phosphate, triethylamine, diisopropylethylamine, pyridine and 1,8-diazabicyclo[5,4,0]-7-undecene. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 36-3

This step is a step of producing the compound (75) by reducing secondary amide of the compound (4aa) into secondary amine to obtain the compound (5ab), followed by an introduction reaction of a tert-butoxycarbonyl group thereinto. The compound (75) can be produced by continuously performing Step 36-1 and Step 36-2 described above.

Step 36-4

This step is a step of producing a compound (10bb) through an elimination reaction, occurring as a side reaction, of a tert-butoxy group substituted with one nitrogen atom, that is, a reaction to convert $L^2$ of the compound (75) into an alkoxycarbonyl group. This step can be performed in the same manner as in Step 2-1 described above.

Step 36-5

This step is for causing a coupling reaction between the compound (10bb) and the compound (3), and is a step of producing a compound (44a) through a hydrolysis reaction of an ester group of the compound (10bb) under conditions of this reaction and an elimination reaction, occurring as a side reaction, of a tert-butoxy group. This step can be performed in the same manner as in Step 1-1 described above.

Step 36-6

This step is a step of producing the compound (1va) through a condensation reaction of the compound (44a) and the compound (13a) or the compound (13b). This step can be performed in the same manner as in Step 2-10 described above.

Step 36-7

This step is a step of producing the compound (1va) by continuously performing an alkoxycarbonylation reaction involving a tert-butoxycarbonyl group of the compound (75), a hydrolysis reaction of an ester group of the resultant compound (10bb) and a coupling reaction with the compound (3) accompanying an elimination reaction of a tert-butoxy group, and a condensation reaction of the resultant compound (44a) and the compound (13a) or the compound (13b). The compound (1va) can be produced by continuously performing Step 36-4, Step 36-5 and Step 36-6 described above.

Step 36-8

This step is a step of producing the compound (1vb) by reacting the compound (1va) and the compound (50). This step can be performed in the same manner as in Step 13-3 described above.

Step 36-9

This step is a step of producing the compound (1vc) by reacting the compound (1va) and a compound (76). This step can be performed in the same manner as in Step 1-1 described above.

Step 36-10

This step is a step of producing the compound (1vd) through an acylation or sulfonylation reaction of the compound (1va). This step can be performed in the same manner as in Step 33-4 described above.

Here, when the compound (13) is represented as a compound (13bb), the compound (13bb) can be produced by a method shown in Scheme 37 or any equivalent method, or a method described in any literature or any equivalent method.

Scheme 37

[Formula 93]

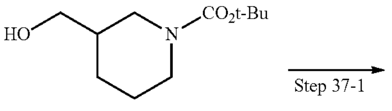

(61)

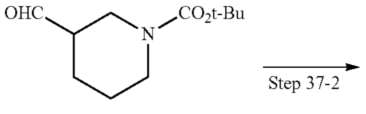

(77)

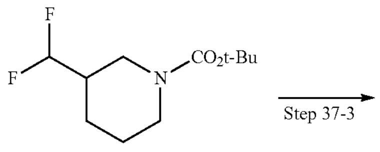

(78)

-continued

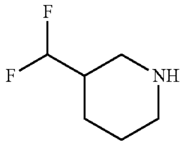

(13bb)

Step 37-1

This step is a step of producing a compound (77) through oxidation of primary alcohol of the compound (61). The compound (77) can be produced from the compound (61) in a solvent under usual oxidation conditions from alcohol to aldehyde, for example, trough Dess-Martin oxidation, pyridinium chlorochromate (PCC) oxidation, pyridinium dichromate (PDC) oxidation, Swern oxidation, 2,2,6,6-tetramethylpiperidine-1-oxy radical (TEMPO) oxidation, tetrapropylammonium perruthenate (TPAP) oxidation, Parikh-Doering oxidation or the like. Examples of the solvent to be used include dichloromethane, chloroform and a mixed solvent of any of these. Examples of an oxidant to be used include a Dess-Martin periodinane (DMP), pyridinium chlorochromate (PCC), pyridinium dichromate (PDC), oxalyl chloride and dimethylsulfoxide, 2,2,6,6-tetramethylpiperidine-1-oxy radical (TEMPO), tetrapropylammonium perruthenate (TPAP), and a sulfur trioxide pyridine complex and dimethylsulfoxide. Besides, a base such as triethylamine can be added if necessary. Furthermore, iodo benzene diacetate, sodium hypochlorite or the like can be added as a reoxidant. With respect to the reaction temperature, the reaction can be performed usually at −78° C. to a solvent reflux temperature. The reaction time varies depending on a starting material and a solvent to be used, the reaction temperature and the like, and is usually 30 minutes to 3 days.

Step 37-2

This step is a step of producing a compound (78) by substituting an aldehyde group of the compound (77) with two fluorine atoms. The compound (78) can be produced by reacting with the compound (77) in a solvent in the presence of N,N-diethylaminosulfur trifluoride (DAST). Examples of the solvent to be used include dichloromethane and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

Step 37-3

This step is a step of producing the compound (13bb) by removing a tert-butoxycarbonyl group from the compound (78). This step can be performed in the same manner as in Step 20-3 described above.

Here, when the compound (1) is represented as a compound (1wb), the compound (1wb) can be produced by a method shown in Scheme 38 or any equivalent method, or a method described in any literature or any equivalent method.

[Formula 94]

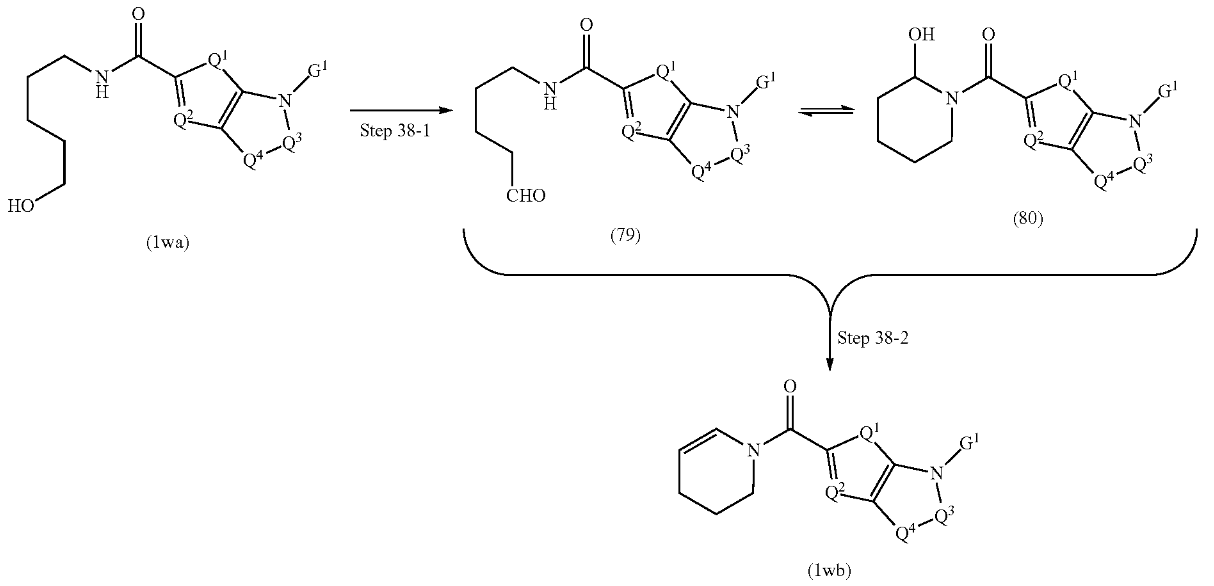

(1wa) (79) (80) (1wb)

Step 38-1

This step is a step of producing either or both of a compound (79) and a compound (80) by oxidizing primary alcohol of a compound (1wa). This step can be performed in the same manner as in Step 37-1 described above.

Step 38-2

This step is a step of producing the compound (1wb) through a dehydration reaction of the compound (79) or the compound (80). The compound (1wb) can be produced by reacting the compound (79) or the compound (80) in a solvent in the presence of an acid catalyst. Examples of the acid catalyst to be used include trifluoroacetic acid, hydrogen chloride and sulfuric acid. Examples of the solvent to be used include dichloromethane, 1,2-dichloroethane, chloroform, benzene, toluene and a mixed solvent of any of these. With respect to the reaction temperature, the reaction can be performed usually at 0° C. to a solvent reflux temperature. The reaction time varies depending on a starting material and a solvent to be used, the reaction temperature and the like, and is usually 30 minutes to 3 days.

A pharmacologically acceptable salt of the compound (1) of the present embodiment can be produced by a usual method using the compound (1) of the present embodiment.

The above-described schemes are merely examples to be employed for producing the compound (1) of the present embodiment or production intermediates thereof. These schemes can be modified into various schemes easily understood by those skilled in the art.

Besides, when a protecting group is necessary depending on the type of functional group, it can be used by appropriately combining introduction and elimination operations by an ordinary method. With respect to the type, introduction and elimination of protecting group, for example, methods described in "Greene's Protective Groups in Organic Synthesis" edited by Theodra W. Green & Peter G. M. Wuts, fourth edition, Wiley-Interscience, 2006 can be employed.

An intermediate used for producing the compound (1) of the present embodiment or a pharmacologically acceptable salt thereof can be isolated/purified, if necessary, by isolation/purification methods known to those skilled in the art, such as solvent extraction, crystallization, recrystallization, chromatography and preparative high-performance liquid chromatography.

The term "15-PGDH inhibitory effect" as used in the present embodiment means exhibition of inhibitory activity by acting on 15-PGDH.

The compound (1) of the present embodiment or a pharmacologically acceptable salt thereof exhibits potent inhibitory activity in, for example, a 15-PGDH enzyme inhibition test or a 15-PGDH inhibitory activity evaluation test in mouse lung tissue. Accordingly, the compound (1) of the present embodiment or a pharmacologically acceptable salt thereof is useful as a therapeutic agent or a preventive agent against fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

Besides, it can be used for producing a pharmaceutical for treatment or prevention of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dyseguilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening.

Furthermore, a pharmaceutical containing the compound (1) of the present embodiment as an active ingredient can be used as a preventive agent or a therapeutic agent against, for example, various medical conditions in which 15-PGDH involves (for example, fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurogenesis and nerve cell death (such as psycho-neurologic disease, neuropathy, neurotoxic disease, neuropathic pain and neurodegenerative disease), muscle regeneration (such as muscular atrophy, muscular dystrophy and muscle damage), and cervical ripening).

Pharmaceutical Containing Compound (1) of Present Embodiment or Pharmacologically Acceptable Salt Thereof A pharmaceutical containing, as an active ingredient, the compound (1) of the present embodiment or a pharmacologically acceptable salt thereof can be in various dosage forms depending on usage. Examples of such dosage forms include a powder, a granule, a fine granule, a dry syrup, a tablet, a capsule, an injection, a liquid, an ointment, a suppository, a patch and a sublingual tablet, which are orally or parenterally administered.

Such a pharmaceutical can be constituted, by any known method according with the dosage form, as a pharmaceutical composition containing the compound (1) of the present invention or a pharmacologically acceptable salt thereof as an active ingredient, and a pharmacologically acceptable additive. Examples of the additive to be contained in the pharmaceutical composition include an excipient, a disintegrating agent, a binder, a lubricant, a diluent, a buffer, a tonicity agent, a preservative, a wetting agent, an emulsifier, a dispersant, a stabilizer and a dissolution assisting agent. The pharmaceutical composition can be prepared by appropriately mixing the compound (1) of the present invention or a pharmacologically acceptable salt thereof, or diluting/dissolving, with/in an additive, the compound (1) or a pharmacologically acceptable salt thereof. Besides, when used in combination with an agent different from the 15-PGDH inhibitor, it can be produced by formulating active ingredients of the respective agents simultaneously or separately in the same manner as described above.

The pharmaceutical of the present embodiment can be administered systemically or locally, and orally or parenterally (nasally, pulmonarilly, intravenously, ractally, subcutaneously, intramuscularly or transdermally).

When a pharmaceutical composition containing the compound (1) of the present embodiment or a pharmacologically acceptable salt thereof as an active ingredient is used in actual treatment, a dose of the compound (1) of the present embodiment or the pharmacologically acceptable salt thereof corresponding to the active ingredient is appropriately determined in accordance with the age, sex and weight of a patient, the extent of disease and treatment, and the like. For example, for oral administration, it can be appropriately administered at the range of a dose of about 0.03 to 1000 mg/body once or several times a day for an adult (assumed to have a weight of 60 kg). A dose per day as an oral agent is preferably 0.06 to 540 mg/body, and more preferably 0.18 to 180 mg/body. For parenteral administration, it can be appropriately administered at the range of a dose of about 0.01 to 300 mg once or several times a day for an adult. A dose per day as a parenteral agent is preferably 0.01 to 100 mg/body, and more preferably 0.06 to 60 mg/body. Besides, a dose of the compound (1) of the present embodiment or a pharmacologically acceptable salt thereof can be reduced in accordance with a dose of an agent different from the 15-PGDH inhibitor.

EXAMPLES

Now, the present invention will be described in more detail based on test examples, examples and reference examples. Also, since raw material compounds used in the production of the compound (1) include a novel compound, a production example of the raw material compounds will be described as reference examples. It is noted that the present invention is not limited to compounds described in the following examples but may be modified without departing from the scope of the present invention.

In signs used in each reference example, each example and each table, $^1$H NMR means a hydrogen nuclear magnetic resonance spectrum, $CDCl_3$ means chloroform-d, and DMSO-$d_6$ means dimethylsulfoxide-de. LRMS(ESI), LRMS (EI), LRMS(CI), LRMS (FI) mean low resolution mass spectrometry spectrum data measured by an electrospray ionization method, electron ionization method, chemical ionization method, field ionization method, respectively.

A solid line and broken line wedge used in a structural formula do not correspond to absolute configuration but correspond to relative configuration in an optical active substance. A thick solid line and broken line correspond to relative configuration in a racemic body or an optical active substance obtained by racemic resolution.

Reference Example 1-1

[Formula 95]

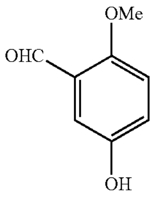

5-Hydroxy-2-methoxybenzaldehyde

To a solution, in N,N-dimethylformamide (36.2 ml), of 2,5-dihydroxybenzaldehyde (2.50 g) and iodo methane (1.24 mL), potassium carbonate (8.26 g) was added under ice cooling, followed by stirring at room temperature for 5 hours. To the resultant reaction solution, water and 6 mol/L hydrogen chloride aqueous solution were successively added to adjust pH to 1, followed by extraction with ethyl acetate. The thus obtained extract was dried over anhydrous sodium sulfate, and concentrated under reduced pressure. The thus obtained residue was purified by silica gel column chromatography (hexane:ethyl acetate=2:1) to obtain the title compound (1.57 g).

$^1$H NMR (400 MHz, $CDCl_3$) δ 3.89 (3H, s), 4.93 (1H, s), 6.91 (1H, d, J=8.5 Hz), 7.09 (1H, dd, J=8.5, 3.6 Hz), 7.29 (1H, d, J=3.6 Hz), 10.42 (1H, s).

LRMS ($ESI^+$) 153 $[M+H]^+$.

Reference Example 1-2

[Formula 96]

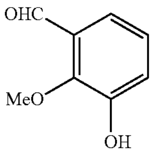

3-Hydroxy-2-methoxybenzaldehyde

The title compound was synthesized in the same manner as in Reference Example 1-1 by using corresponding hydroxybenzaldehyde derivative and reactant.

$^1$H NMR (400 MHz, $CDCl_3$) δ 3.98 (3H, s), 5.80 (1H, s), 7.16 (1H, t, J=7.9 Hz), 7.23 (1H, dd, J=7.9, 1.8 Hz), 7.38 (1H, dd, J=7.9, 1.8 Hz), 10.27 (1H, s).

LRMS ($ESI^-$) 151 $[M-H]^-$.

Reference Example 2-1

[Formula 97]

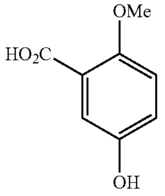

5-Hydroxy-2-methoxybenzoic Acid

Water (250 mL), tetrahydrofuran (125 mL) and dimethylsulfoxide (12.5 mL) were added to 5-hydroxy-2-methoxybenzaldehyde (1.96 g) for allowing it to be dissolved therein, and to the resultant, an aqueous solution (50 mL) of sulfamic acid (4.41 g) and an aqueous solution (50 mL) of sodium hypochlorite (3.80 g) were successively added at 0° C., followed by stirring for 1 hour. The resultant reaction solution was extracted with diethyl ether, and the resultant extract was dried over anhydrous sodium sulfate, and concentrated under reduced pressure. The thus obtained residue was purified by silica gel column chromatography (ethyl acetate) to obtain the title compound (2.06 g).

$^1$H NMR (400 MHz, DMSO-$d_6$) δ 3.72 (3H, s), 6.88 (1H, dd, J=9.1, 3.0 Hz), 6.94 (1H, d, J=9.1 Hz), 7.04 (1H, d, J=3.0 Hz), 9.21 (1H, s), 12.50 (1H, brs).

LRMS ($ESI^+$) 169 $[M+H]^+$.

Reference Example 2-2

[Formula 98]

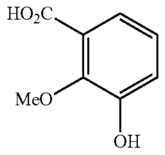

3-Hydroxy-2-methoxybenzoic Acid

The title compound was synthesized in the same manner as in Reference Example 2-1 by using corresponding benzaldehyde derivative and reactant.

Methyl 5-Hydroxy-2-methoxy-4-nitrobenzoate

To a solution of 5-hydroxy-2-methoxy benzoic acid (2.05 g) in acetic acid (50 mL), a 70% nitric acid aqueous solution (0.80 mL) was added at room temperature over 5 minutes, followed by stirring at room temperature for 12 hours. The resultant reaction solution was concentrated under reduced pressure, the thus obtained residue was diluted with methanol (60 mL), and thionyl chloride (1.80 mL) was added thereto at 0° C. over 5 minutes, followed by stirring at room temperature for 12 hours. The resultant reaction solution was concentrated under reduced pressure, and the thus obtained residue was purified by silica gel column chromatography (hexane:ethyl acetate=3:1) to obtain the title compound (698 mg).

$^1$H NMR (400 MHz, $CDCl_3$) δ 3.91 (3H, s), 3.93 (3H, s), 7.51 (1H, s), 7.60 (1H, s), 10.14 (1H, s).

LRMS ($ESI^-$) 226 $[M-H]^-$.

Compounds of the following Reference Examples 3-2 to 3-4 were obtained in the same manner as in Reference Example 3-1 by using corresponding starting materials and reactants. Their structures and spectrum data are shown in the following table.

TABLE 1

| Reference Example No. | Chemical Structural Formula | Spectrum Data |
|---|---|---|
| 3-2 | 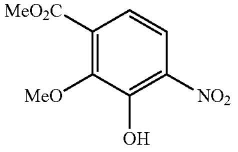 [SMILES: COC(=O)c1ccc([N+](=O)[O-])c(O)c1OC] | $^1$H NMR (400 MHz, $CDCl_3$) δ 3.96 (3H, s), 4.02 (3H, s), 7.26 (1H, d, J = 9.1 Hz), 7.89 (1H, d, J = 9.1 Hz), 10.73 (1H, s). LRMS ($ESI^-$) 226 $[M - H]^-$. |
| 3-3 | 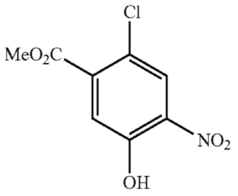 [SMILES: COC(=O)c1cc(O)c([N+](=O)[O-])cc1Cl] | $^1$H NMR (400 MHz, $CDCl_3$) δ 3.98 (3H, s), 7.58 (1H, s), 8.21 (1H, s), 10.34 (1H, s). LRMS ($EI^+$) 231 $[M]^+$. |
| 3-4 | 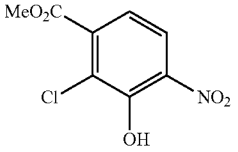 [SMILES: COC(=O)c1ccc([N+](=O)[O-])c(O)c1Cl] | $^1$H NMR (400 MHz, $CDCl_3$) δ 3.99 (3H, s), 7.32 (1H, d, J = 8.6 Hz), 8.10 (1H, d, J = 8.6 Hz), 11.16 (1H, s). LRMS ($EI^+$) 231 $[M]^+$. |

$^1$H NMR (400 MHz, DMSO-$d_6$) δ 3.74 (3H, s), 6.96 (1H, t, J=7.9 Hz), 7.00 (1H, dd, J=7.9, 2.4 Hz), 7.05 (1H, dd, J=7.9, 2.4 Hz), 9.55 (1H, s), 12.71 (1H, brs).

LRMS ($ESI^-$) 167 $[M-H]^-$.

Reference Example 3-1

[Formula 99]

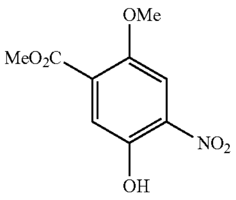

Reference Example 4-1

[Formula 100]

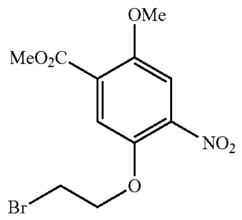

Methyl 5-(2-Bromoethoxy)-2-methoxy-4-nitrobenzoate

A suspension, in acetonitrile (31 mL), of methyl 5-hydroxy-2-methoxy-4-nitrobenzoic acid (692 mg), 1,2-dibromoethane (1.10 mL) and potassium carbonate (2.11 g) was heated to reflux for 8 hours. To the resultant reaction solution, water and 1 mol/L hydrogen chloride aqueous solution were successively added to adjust pH to 1, followed by extraction with ethyl acetate. The resultant extract was dried over anhydrous sodium sulfate, and concentrated under reduced pressure. The thus obtained residue was purified by silica gel column chromatography (hexane:ethyl acetate=7:3) to obtain the title compound (748 mg).

$^1$H NMR (400 MHz, $CDCl_3$) δ 3.66 (2H, t, J=6.7 Hz), 3.92 (3H, s), 3.94 (3H, s), 4.41 (2H, t, J=6.7 Hz), 7.43 (1H, s), 7.54 (1H, s).

LRMS (ESI$^+$) 334 [M+H]$^+$.

Compounds of the following Reference Examples 4-2 to 4-4 were obtained in the same manner as in Reference Example 4-1 by using corresponding starting materials and reactants. Their structures and spectrum data are shown in the following table.

TABLE 2

| Reference Example No. | Chemical Structural Formula | Spectrum Data |
|---|---|---|
| 4-2 | 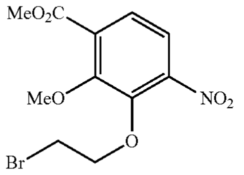 [SMILES: COC(=O)c1ccc([N+](=O)[O-])c(OCCBr)c1OC] | $^1$H NMR (400 MHz, $CDCl_3$) δ 3.68 (2H, t, J = 6.1 Hz), 3.96 (3H, s), 3.99 (3H, s), 4.49 (2H, t, J = 6.1 Hz), 7.54 (1H, d, J = 8.6 Hz), 7.61 (1H, d, J = 8.6 Hz). LRMS (EI$^+$) 333 [M]$^+$. |
| 4-3 | 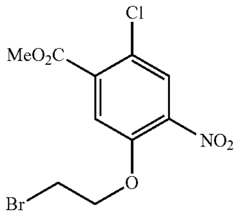 [SMILES: COC(=O)c1cc(OCCBr)c([N+](=O)[O-])cc1Cl] | $^1$H NMR (400 MHz, $CDCl_3$) δ 3.68 (2H, t, J = 6.1 Hz), 3.99 (3H, s), 4.45 (2H, t, J = 6.1 Hz), 7.53 (1H, s), 7.91 (1H, s). LRMS (EI$^+$) 337 [M]$^+$. |
| 4-4 | 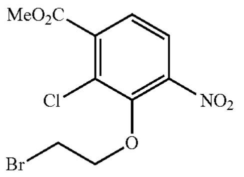 [SMILES: COC(=O)c1ccc([N+](=O)[O-])c(OCCBr)c1Cl] | $^1$H NMR (400 MHz, $CDCl_3$) δ 3.72 (2H, t, J = 6.7 Hz), 3.99 (3H, s), 4.49 (2H, t, J = 6.7 Hz), 7.64 (1H, d, J = 8.6 Hz), 7.74 (1H, d, J = 8.6 Hz). LRMS (EI$^+$) 337 [M]$^+$. |

Reference Example 5-1

[Formula 101]

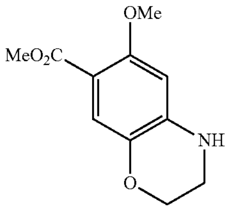 [SMILES: COC(=O)c1cc2c(cc1Cl)NCCO2]

Methyl 6-Methoxy-3,4-dihydro-2H-benzo[b][1,4]oxazine-7-carboxylate

Methyl 5-(2-bromoethoxy)-2-methoxy-4-nitrobenzoic acid (734 mg) and reduced iron (615 mg) were suspended in tetrahydrofuran (3.7 ml) and acetic acid (1.5 mL), followed by stirring under heating at 70° C. for 3 hours. The resultant reaction solution was filtered through celite, and the thus obtained solid was washed with hot ethyl acetate and ethanol. To the resultant filtrate, a saturated sodium bicarbonate aqueous solution was added to adjust pH to 10, followed by extraction with ethyl acetate. The resultant extract was dried over anhydrous sodium sulfate, and concentrated under reduced pressure. The thus obtained residue was dissolved in N,N-dimethylformamide (11 mL), and potassium carbonate (1.21 g) was added thereto, followed by stirring under heating at 100° C. for 2 hours. The resultant reaction solution was filtered through celite, and the resultant filtrate was concentrated under reduced pressure. The thus obtained residue was purified by silica gel column chromatography (hexane:ethyl acetate=1:1) to obtain the title compound (428 mg).

$^1$H NMR (400 MHz, $CDCl_3$) δ 3.45-3.49 (2H, m), 3.81 (3H, s), 3.82 (3H, s), 4.18 (2H, t, J=4.3 Hz), 4.23 (1H, brs), 6.12 (1H, s), 7.36 (1H, s).

LRMS (ESI$^+$) 224 [M+H]$^+$.

Compounds of the following Reference Examples 5-2 to 5-4 were obtained in the same manner as in Reference Example 5-1 by using corresponding starting materials and reactants. Their structures and spectrum data are shown in the following table.

TABLE 3

| Reference Example No. | Chemical Structural Formula | Spectrum Data |
|---|---|---|
| 5-2 | 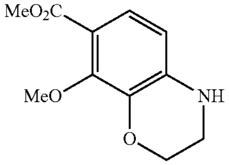 | $^1$H NMR (400 MHz, $CDCl_3$) δ 3.48 (2H, t, J = 4.3 Hz), 3.85 (3H, s), 3.90 (3H, s), 4.28 (2H, t, J = 4.3 Hz), 6.32 (1H, d, J = 8.6 Hz), 7.33 (1H, d, J = 8.6 Hz). (NH proton signal is missing) LRMS (ESI$^+$) 224 [M + H]$^+$. |
| 5-3 | 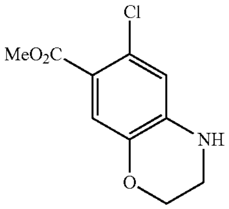 | $^1$H NMR (400 MHz, $CDCl_3$) δ 3.44-3.49 (2H, m), 3.85 (3H, s), 4.19-4.25 (3H, m), 6.58 (1H, s), 7.40 (1H, s). LRMS (EI$^+$) 227 [M]$^+$. |
| 5-4 | 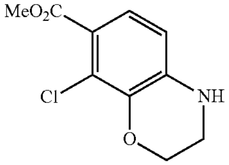 | $^1$H NMR (400 MHz, $CDCl_3$) δ 3.48-3.52 (2H, m), 3.86 (3H, s), 4.25 (1H, brs), 4.34 (2H, t, J = 4.9 Hz), 6.45 (1H, d, J = 8.5 Hz), 7.41 (1H, d, J = 8.5 Hz). LRMS (ESI$^+$) 228 [M + H]$^+$. |

Reference Example 6-1

[Formula 102]

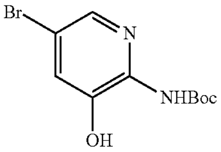

tert-Butyl (5-Bromo-3-hydroxypyridin-2-yl)carbamate

To a suspension, in dichloromethane (26 mL), of 2-amino-5-bromopyridin-3-ol (5.00 g) and di-tert-butyl dicarbonate (7.05 g), triethylamine (4.50 mL) was added at room temperature. The resultant reaction solution was stirred at room temperature for 8 hours, and then concentrated under reduced pressure. The thus obtained residue was purified by silica gel column chromatography (hexane:ethyl acetate=4:1) to obtain the title compound (6.99 g).

$^1$H NMR (400 MHz, $CDCl_3$) δ 1.56 (9H, s), 4.63 (2H, brs), 7.58 (1H, d, J=2.4 Hz), 7.98 (1H, d, J=2.4 Hz).

LRMS (ESI$^+$) 289 [M+H]$^+$.

Reference Example 7-1

[Formula 103]

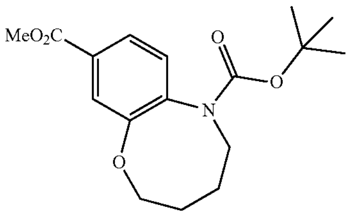

5-(tert-Butyl) 8-Methyl 3,4-Dihydrobenzo[b] [1,4] oxazepine-5,8(2H)-dicarboxylate To a solution of methyl 4-((tert-butoxycarbonyl)amino)-3-hydroxybenzoate (1.00 g) in dimethylsulfoxide (19 mL), potassium carbonate (2.59 g) and 1,3-dibromopropane (1.53 mL) were added at room temperature, followed by stirring at 100° C. for 3 hours. The resultant reaction solution was purified by silica gel column chromatography (hexane:ethyl acetate=3:1) to obtain the title compound (398 mg).

$^1$H NMR (400 MHz, $CDCl_3$) δ 1.45 (9H, s), 2.03-2.12 (2H, m), 3.68-3.81 (2H, m), 3.89 (3H, s), 4.10-4.20 (2H, m), 7.30-7.40 (1H, m), 7.60-7.70 (2H, m).

LRMS (ESI$^+$) 308 [M+H]$^+$.

Compounds of the following Reference Examples 7-2 to 7-9 were obtained in the same manner as in Reference Example 7-1 by using corresponding starting materials and reactants. Their structures and spectrum data are shown in the following tables.

TABLE 4

| Reference Example No. | Chemical Structural Formula | Spectrum Data |
|---|---|---|
| 7-2 | 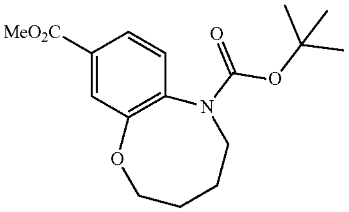 [SMILES: COC(=O)c1ccc2c(c1)OCCCCN2C(=O)OC(C)(C)C] | $^1$H NMR (400 MHz, $CDCl_3$) δ 1.38 (9H, s), 1.65-1.74 (2H, m), 1.75-1.84 (2H, m), 3.62 (2H, t, J = 5.5 Hz), 3.91 (3H, s), 4.18 (2H, t, J = 5.5 Hz), 7.21 (1H, d, J = 9.2 Hz), 7.74 (1H, dd, J = 9.2, 1.8 Hz), 7.75 (1H, d, J = 1.8 Hz). LRMS (ESI$^+$) 322 [M + H]$^+$. |
| 7-3 | 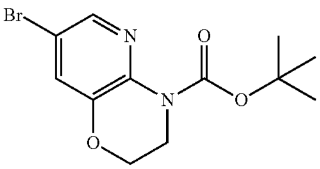 [SMILES: CC(C)(C)OC(=O)N1CCOc2cc(Br)cnc21] | $^1$H NMR (400 MHz, $CDCl_3$) δ 1.54 (9H, s), 3.91 (2H, t, J = 4.9 Hz), 4.24 (2H, t, J = 4.9 Hz), 7.33 (1H, d, J = 2.4 Hz), 8.11 (1H, d, J = 2.4 Hz). LRMS (ESI$^+$) 315 [M + H]$^+$. |
| 7-4 | 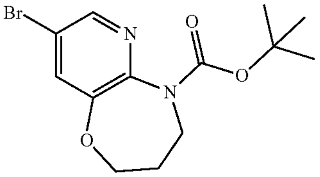 [SMILES: CC(C)(C)OC(=O)N1CCCOc2cc(Br)cnc21] | $^1$H NMR (400 MHz, $CDCl_3$) δ 1.46 (9H, s), 2.03-2.13 (2H, m), 3.70-3.80 (2H, m), 4.18 (2H, t, J = 5.5 Hz), 7.49 (1H, d, J = 1.8 Hz), 8.22 (1H, d, J = 1.8 Hz). LRMS (ESI$^+$) 329 [M + H]$^+$. |
| 7-5 | 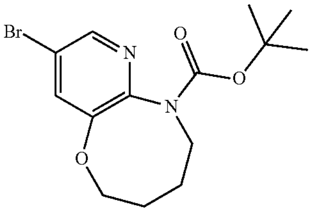 [SMILES: CC(C)(C)OC(=O)N1CCCCOc2cc(Br)cnc21] | $^1$H NMR (400 MHz, $CDCl_3$) δ 1.39 (9H, s), 1.72-1.82 (4H, m), 3.65-3.72 (2H, m), 4.23-4.28 (2H, m), 7.56 (1H, d, J = 2.4 Hz), 8.28 (1H, d, J = 2.4 Hz). LRMS (ESI$^+$) 343 [M + H]$^+$. |

TABLE 5

| Reference Example No. | Chemical Structural Formula | Spectrum Data |
|---|---|---|
| 7-6 Isomer A | 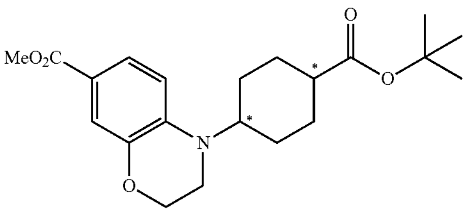 [SMILES: COC(=O)c1ccc2c(c1)OCCN2C1CCC(C(=O)OC(C)(C)C)CC1] | $^1$H NMR (400 MHz, $CDCl_3$) δ 1.48 (9H, s), 1.53-1.74 (6H, m) 2.22-2.30 (2H, m), 2.56-2.63 (1H, m), 3.32 (2H, t, J = 4.5 Hz), 3.61-3.71 (1H, m), 3.84 (3H, s), 4.16 (2H, t, J = 4.5 Hz), 6.67 (1H, d, J = 9.1 Hz), 7.43 (1H, d, J = 2.4 Hz), 7.54 (1H, dd, J = 8.5, 2.4 Hz). LRMS (ESI$^+$) 376 [M + H]$^+$. |

TABLE 5-continued

| Reference Example No. | Chemical Structural Formula | Spectrum Data |
| --- | --- | --- |
| 7-6 Isomer B | 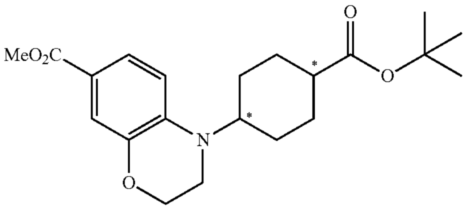 [SMILES: COC(=O)c1ccc2c(c1)OCCN2C1CCC(C(=O)OC(C)(C)C)CC1] | $^1$H NMR (400 MHz, $CDCl_3$) δ: 1.42-1.66 (13H, m), 1.90 (2H, d, J = 11.5 Hz), 2.07-2.22 (3H, m), 3.33 (2H, t, J = 4.5 Hz), 3.62-3.72 (1H, m), 3.84 (3H, s), 4.18 (2H, t, J = 4.5 Hz), 6.67 (1H, d, J = 8.5 Hz), 7.43 (1H, d, J = 1.8 Hz), 7.55 (1H, dd, J = 8.8, 2.1 Hz). LRMS (ESI$^+$) 276 [M + H]$^+$. |
| 7-7 | 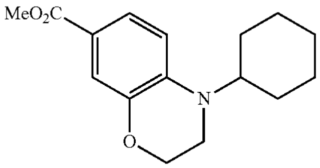 [SMILES: COC(=O)c1ccc2c(c1)OCCN2C1CCCCC1] | $^1$H NMR (400 MHz, $CDCl_3$) δ: 109-122 (1H, m), 1.33-1.50 (4H, m), 1.69-1.95 (5H, m), 3.35 (2H, t, J = 4.5 Hz), 3.60-3.69 (1H, m), 3.84 (3H, s), 4.17 (2H, t, J = 4.5 Hz), 6.68 (1H, d, J = 9.1 Hz), 7.43 (1H, d, J = 2.4 Hz), 7.55 (1H, dd, J = 8.5, 1.8 Hz). LRMS (ESI$^+$) 276 [M + H]$^+$. |
| 7-8 | 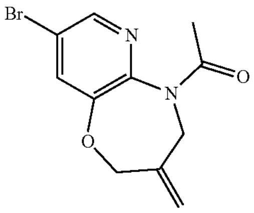 [SMILES: C=C1COc2cc(Br)cnc2N(C(C)=O)C1] | $^1$H NMR (400 MHz, $CDCl_3$) δ 2.09 (3H, s), 4.53 (2H, s), 4.66 (2H, s), 5.24 (2H, d, J = 16.5 Hz), 7.51 (1H, d, J = 2.4 Hz), 8.18 (1H, d, J = 2.4 Hz). LRMS (ESI$^+$) 283 [M + H]$^+$. |
| 7-9 | 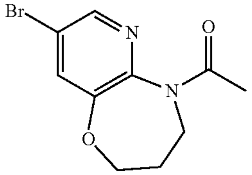 | $^1$H NMR (400 MHz, DMSO-$d_6$) δ 1.89-1.99 (5H, m), 3.77 (2H, t, J = 5.4 Hz), 4.18 (2H, t, J = 5.4 Hz), 7.85 (1H, d, J = 2.4 Hz), 8.28 (1H, d, J = 1.8 Hz). LRMS (ESI$^+$) 271 [M + H]$^+$. |

Reference Example 8-1

[Formula 104]

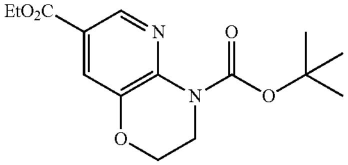

4-(tert-Butyl) 7-Ethyl 2,3-Dihydro-4H-pyrido[3,2-b][1,4]oxazine-4,7-dicarboxylate To tert-butyl 7-bromo-2,3-dihydro-4H-pyrido[3,2-b] [1,4] oxazine-4-carboxylate (20.0 g), [1,1'-bis(diphenylphosphino)ferrocene]palladium (II) dichloride dichloromethane adduct (5.19 g), triethylamine (17.7 ml), ethanol (320 mL) and N,N-dimethylformamide (32 mL) were added at room temperature, followed by stirring the resultant mixture under carbon monoxide atmosphere at 70° C. for 12 hours. The resultant reaction solution was filtered through celite, and the resultant filtrate was concentrated under reduced pressure. The thus obtained residue was purified by silica gel column chromatography (hexane:ethyl acetate=3:1) to obtain the title compound (17.2 g).

$^1$H NMR (400 MHz, $CDCl_3$) δ 1.39 (3H, t, J=7.3 Hz), 1.56 (9H, s), 3.95 (2H, t, J=4.2 Hz), 4.28 (2H, t, J=4.2 Hz), 4.37 (2H, q, J=7.3 Hz), 7.74 (1H, d, J=1.8 Hz), 8.68 (1H, d, J=1.8 Hz).

LRMS (ESI$^+$) 309 [M+H]$^+$.

Compounds of the following Reference Examples 8-2 to 8-12 were obtained in the same manner as in Reference Example 8-1 by using corresponding starting materials and reactants. Their structures and spectrum data are shown in the following tables.

TABLE 6

| Reference Example No. | Chemical Structural Formula | Spectrum Data |
| --- | --- | --- |
| 8-2 | 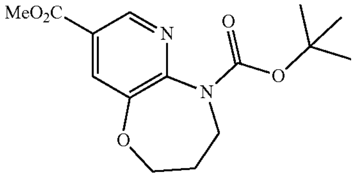 [SMILES: COC(=O)c1cnc2c(c1)OCCCN2C(=O)OC(C)(C)C] | $^1$H NMR (400 MHz, $CDCl_3$) δ 1.47 (9H, s), 2.07-2.15 (2H, m), 3.81 (2H, t, J = 5.5 Hz), 3.94 (3H, s), 4.21 (2H, t, J = 5.5 Hz), 7.90 (1H, d, J = 1.8 Hz), 8.76 (1H, d, J = 1.8 Hz). LRMS (ESI$^+$) 309 $[M + H]^+$. |
| 8-3 | 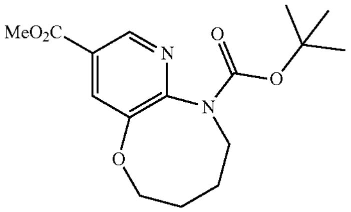 [SMILES: COC(=O)c1cnc2c(c1)OCCCCN2C(=O)OC(C)(C)C] | $^1$H NMR (400 MHz, $CDCl_3$) δ 1.39 (9H, s), 1.71-1.85 (4H, m), 3.71 (2H, t, J = 5.5 Hz), 3.96 (3H, s), 4.25 (2H, t, J = 5.5 Hz), 7.99 (1H, d, J = 1.8 Hz), 8.83 (1H, d, J = 1.8 Hz). LRMS (ESI$^+$) 323 $[M + H]^+$. |
| 8-4 | 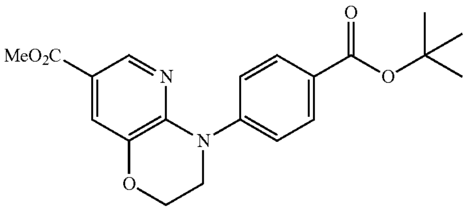 [SMILES: COC(=O)c1cnc2c(c1)OCCN2c1ccc(C(=O)OC(C)(C)C)cc1] | $^1$H NMR (400 MHz, $CDCl_3$) δ 1.59 (9H, s), 3.88 (3H, s), 3.97 (2H, t, J = 4.2 Hz), 4.38 (2H, t, J = 4.5 Hz), 7.42-7.47 (2H, m), 7.65 (1H, d, J = 1.8 Hz), 8.00-8.05 (2H, m), 8.41 (1H, d, J = 1.8 Hz). LRMS (ESI$^+$) 371 $[M + H]^+$. |
| 8-5 | 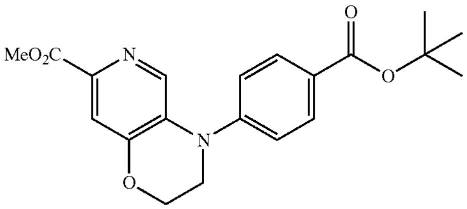 [SMILES: COC(=O)c1cc2c(cn1)N(c1ccc(C(=O)OC(C)(C)C)cc1)CCO2] | $^1$H NMR (400 MHz, $CDCl_3$) δ 1.60 (9H, s), 3.82 (2H, t, J = 4.2 Hz), 3.96 (3H, s), 4.40 (2H, t, J = 4.2 Hz), 7.23-7.28 (2H, m), 7.68 (1H, s), 7.97-8.02 (2H, m), 8.39 (1H, s). LRMS (ESI$^+$) 371 $[M + H]^+$. |
| 8-6 | 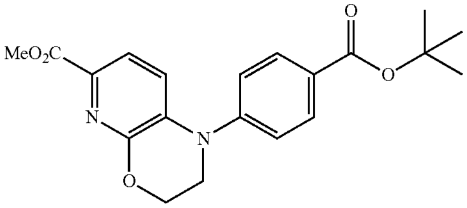 [SMILES: COC(=O)c1ccc2c(n1)OCCN2c1ccc(C(=O)OC(C)(C)C)cc1] | $^1$H NMR (400 MHz, $CDCl_3$) δ 1.61 (9H, s), 3.82 (2H, t, J = 4.6 Hz), 3.93 (3H, s), 4.53 (2H, t, J = 4.6 Hz), 7.25-7.30 (3H, m), 7.64 (1H, d, J = 7.9 Hz), 8.03-8.06 (2H, m). LRMS (ESI$^+$) 371 $[M + H]^+$. |

TABLE 7

| Reference Example No. | Chemical Structural Formula | Spectrum Data |
| --- | --- | --- |
| 8-7 | 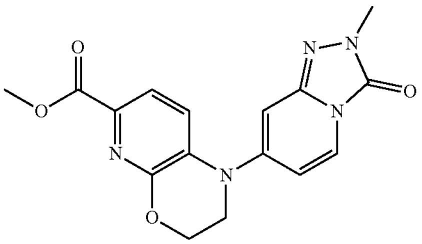 [SMILES: COC(=O)c1ccc2c(n1)OCCN2c1ccn2c(=O)n(C)nc2c1] | $^1$H NMR (400 MHz, $CDCl_3$) δ 3.65 (3H, s), 3.78-3.83 (2H, m), 3.95 (3H, s), 4.53-4.57 (2H, m), 6.51 (1H, dd, J = 7.6, 2.1 Hz), 6.64-6.66 (1H, m), 7.35 (1H, d, J = 7.9 Hz), 7.73 (1H, d, J = 8.6 Hz), 7.77 (1H, d, J = 8.6 Hz). LRMS (ESI$^+$) 342 $[M + H]^+$. |

TABLE 7-continued

| Reference Example No. | Chemical Structural Formula | Spectrum Data |
|---|---|---|
| 8-8 | 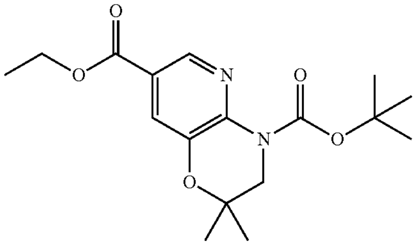 [SMILES: CCOC(=O)c1cnc2c(c1)OC(C)(C)CN2C(=O)OC(C)(C)C] | $^1$H NMR (400 MHz, $CDCl_3$) δ 1.35-1.41 (9H, m), 1.55 (9H, s), 3.70 (2H, s), 4.37 (2H, q, J = 7.3 Hz), 7.72 (1H, d, J = 1.8 Hz), 8.68 (1H, d, J = 1.8 Hz).<br>LRMS (ESI$^+$) 337 [M + H]$^+$. |
| 8-9 | 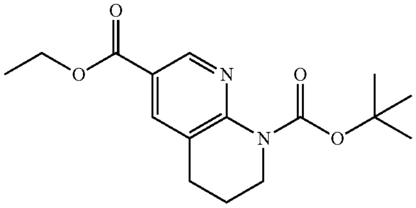 [SMILES: CCOC(=O)c1cnc2c(c1)CCCN2C(=O)OC(C)(C)C] | $^1$H NMR (400 MHz, $CDCl_3$) δ 1.39 (3H, t, J = 7.0 Hz), 1.55 (9H, s), 1.91-1.99 (2H, m), 2.80 (2H, t, J = 6.4 Hz), 3.80 (2H, t, J = 6.1 Hz), 4.37 (2H, q, J = 7.1 Hz), 7.97-7.98 (1H, m), 8.92 (1H, d, J = 2.4 Hz).<br>LRMS (ESI$^+$) 307 [M + H]$^+$. |
| 8-10 | 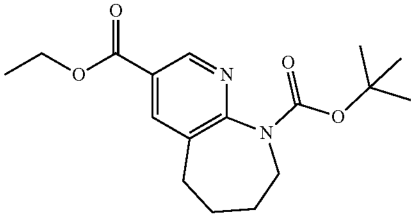 [SMILES: CCOC(=O)c1cnc2c(c1)CCCCN2C(=O)OC(C)(C)C] | $^1$H NMR (400 MHz, $CDCl_3$) δ 1.41 (3H, t, J = 7.3 Hz), 1.43 (9H, s), 1.65-1.76 (2H, m), 1.82-1.90 (2H, m), 2.79 (2H, t, J = 5.8 Hz), 3.37-3.77 (2H, m), 4.41 (2H, q, J = 7.3 Hz), 8.15 (1H, d, J = 2.4 Hz), 8.95 (1H, d, J = 2.4 Hz).<br>LRMS (ESI$^+$) 321 [M + H]$^+$. |
| 8-11 | 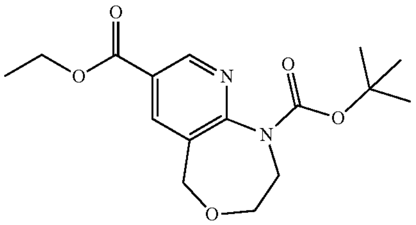 [SMILES: CCOC(=O)c1cnc2c(c1)COCCN2C(=O)OC(C)(C)C] | $^1$H NMR (400 MHz, $CDCl_3$) δ 1.41 (3H, t, J = 7.3 Hz), 1.46 (9H, s), 3.37-3.99 (4H, m), 4.42 (2H, q, J = 7.3 Hz), 4.64 (2H, br s), 8.23 (1H, d, J = 2.4 Hz), 9.04 (1H, d, J = 1.8 Hz).<br>LRMS (ESI$^+$) 323 [M + H]$^+$. |
| 8-12 | 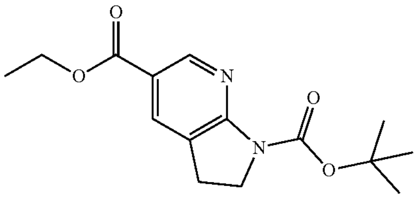 [SMILES: CCOC(=O)c1cnc2c(c1)CCN2C(=O)OC(C)(C)C] | $^1$H NMR (400 MHz, $CDCl_3$) δ 1.38 (3H, t, J = 7.3 Hz), 1.57 (9H, s), 3.09 (2H, t, J = 8.6 Hz), 4.07 (2H, t, J = 8.6 Hz), 4.36 (2H, q, J = 7.3 Hz), 7.97 (1H, d, J = 1.8 Hz), 8.88 (1H, d, J = 1.8 Hz).<br>LRMS (ESI$^+$) 293 [M + H]$^+$. |

Reference Example 9-1

[Formula 105]

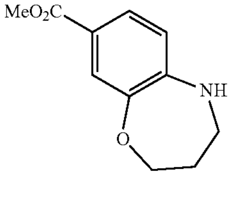

Methyl 2,3,4,5-Tetrahydrobenzo[b][1,4]oxazepine-8-carboxylate

To a solution of 5-(tert-butyl) 8-methyl 3,4-dihydrobenzo[b][1,4]oxazepine-5,8 (2H)-dicarboxylate (390 mg) in dichloromethane (1.3 mL), trifluoroacetic acid (0.60 ml) was added at room temperature. The resultant reaction solution was stirred at room temperature for 24 hours, and then concentrated under reduced pressure. The thus obtained residue was purified by silica gel column chromatography (hexane:ethyl acetate=3:1) to obtain the title compound (266 mg).

$^1H$ NMR (400 MHz, $CDCl_3$) δ 2.00-2.09 (2H, m), 3.37 (2H, t, J=5.5 Hz), 3.85 (3H, s), 4.06 (1H, brs), 4.16 (2H, t, J=5.5 Hz), 6.64 (1H, d, J=8.6 Hz), 7.54 (1H, dd, J=8.6, 1.8 Hz), 7.60 (1H, d, J=1.8 Hz).

LRMS ($ESI^+$) 208 $[M+H]^+$.

Compounds of the following Reference Examples 9-2 to 9-10 were obtained in the same manner as in Reference Example 9-1 by using corresponding starting materials and reactants. Their structures and spectrum data are shown in the following tables.

TABLE 8

| Reference Example No. | Chemical Structural Formula | Spectrum Data |
|---|---|---|
| 9-2 | 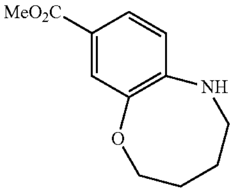 [SMILES: COC(=O)c1ccc2c(c1)OCCCCN2] | $^1H$ NMR (400 MHz, $CDCl_3$) δ 1.70-1.78 (2H, m), 1.82-1.90 (2H, m), 3.74 (2H, t, J = 5.5 Hz), 3.83 (3H, s), 4.15 (2H, t, J = 5.5 Hz), 4.29 (1H, brs), 6.47 (1H, d, J = 7.9 Hz), 7.56 (1H, dd, J = 7.9, 1.8 Hz), 7.59 (1H, d, J = 1.8 Hz). LRMS ($ESI^+$) 222 $[M + H]^+$. |
| 9-3 | 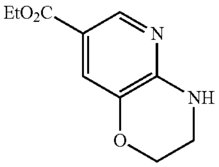 | $^1H$ NMR (400 MHz, $CDCl_3$) δ 1.36 (3H, t, J = 7.3 Hz), 3.59-3.65 (2H, m), 4.22 (2H, t, J = 4.3 Hz), 4.32 (2H, q, J = 7.3 Hz), 5.34 (1H, brs), 7.53 (1H, d, J = 1.8 Hz), 8.37 (1H, d, J = 1.8 Hz). LRMS ($FI^+$) 208 $[M]^+$ |
| 9-4 | 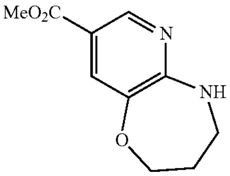 [SMILES: COC(=O)c1cnc2c(c1)OCCCN2] | $^1H$ NMR (400 MHz, $CDCl_3$) δ 2.06-2.15 (2H, m), 3.48-3.55 (2H, m), 3.87 (3H, s), 4.22 (2H, t, J = 5.5 Hz), 5.16 (1H, br s), 7.67 (1H, d, J = 1.8 Hz), 8.43 (1H, d, J = 1.8 Hz). LRMS ($ESI^+$) 209 $[M + H]^+$. |
| 9-5 | 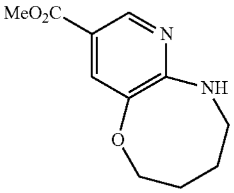 [SMILES: COC(=O)c1cnc2c(c1)OCCCCN2] | $^1H$ NMR (400 MHz, $CDCl_3$) δ 1.71-1.80 (2H, m), 1.85-1.94 (2H, m), 3.75-3.85 (2H, m), 3.86 (3H, s), 4.16 (2H, t, J = 5.5 Hz), 5.37-5.47 (1H, m), 7.69 (1H, d, J = 1.8 Hz), 8.45 (1H, d, J = 1.8 Hz). LRMS ($ESI^+$) 223 $[M + H]^+$. |

TABLE 9

| Reference Example No. | Chemical Structural Formula | Spectrum Data |
|---|---|---|
| 9-6 | 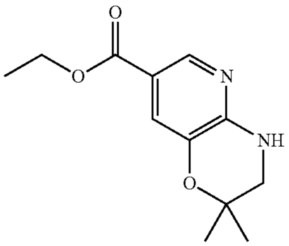 [SMILES: CCOC(=O)c1cnc2c(c1)OC(C)(C)CN2] | $^1H$ NMR (400 MHz, $CDCl_3$) δ 1.36 (3H, t, J = 7.3 Hz), 1.36 (6H, s), 3.32 (2H, d, J = 2.4 Hz), 4.32 (2H, q, J = 7.3 Hz), 5.44 (1H, br s), 7.52 (1H, d, J = 1.8 Hz), 8.38 (1H, d, J = 1.8 Hz). LRMS ($ESI^+$) 237 $[M + H]^+$. |
| 9-7 | 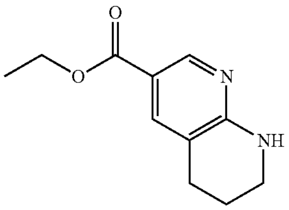 | $^1H$ NMR (400 MHz, $CDCl_3$) δ 1.36 (3H, t, J = 6.7 Hz), 1.89-1.97 (2H, m), 2.76 (2H, t, J = 6.1 Hz), 3.45-3.50 (2H, m), 4.32 (2H, q, J = 6.7 Hz), 5.47 (1H, br s), 7.71-7.74 (1H, m), 8.54 (1H, d, J = 1.8 Hz). LRMS ($ESI^+$) 207 $[M + H]^+$. |

TABLE 9-continued

| Reference Example No. | Chemical Structural Formula | Spectrum Data |
|---|---|---|
| 9-8 | 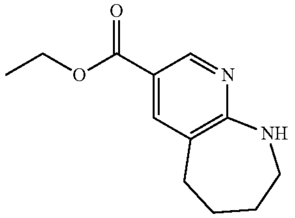 [SMILES: CCOC(=O)c1cnc2c(c1)CCCCN2] | $^1$H NMR (400 MHz, $CDCl_3$) δ 1.37 (3H, t, J = 7.3 Hz), 1.77-1.91 (4H, m), 2.75-2.80 (2H, m), 3.26-3.33 (2H, m), 4.34 (2H, q, J = 7.3 Hz), 5.20 (1H, br s), 7.87 (1H, d, J = 1.2 Hz), 8.57 (1H, d, J = 1.8 Hz).<br>LRMS ($ESI^+$) 221 $[M + H]^+$. |
| 9-9 | 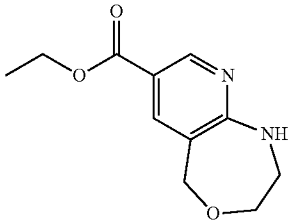 [SMILES: CCOC(=O)c1cnc2c(c1)COCCN2] | $^1$H NMR (400 MHz, $CDCl_3$) δ 1.38 (3H, t, J = 7.3 Hz), 3.33-3.38 (2H, m), 3.85-3.90 (2H, m), 4.35 (2H, q, J = 7.3 Hz), 4.60 (2H, s), 5.42 (1H, br s), 7.97 (1H, d, J = 1.2 Hz), 8.70 (1H, d, J = 2.4 Hz).<br>LRMS ($ESI^+$) 223 $[M + H]^+$. |
| 9-10 | 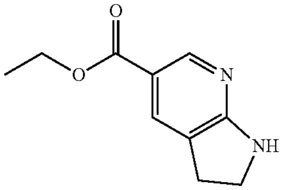 | $^1$H NMR (400 MHz, $CDCl_3$) δ 1.36 (3H, t, J = 7.3 Hz), 3.11 (2H, t, J = 8 6 Hz), 3.72 (2H, t, J = 8.6 Hz), 4.32 (2H, q, J = 7.3 Hz), 5.00 (1H, br s), 7.78 (1H, d, J = 1.8 Hz), 8.54 (1H, d, J = 1.8 Hz).<br>LRMS ($ESI^+$) 193 $[M + H]^+$. |

Reference Example 10-1

[Formula 106]

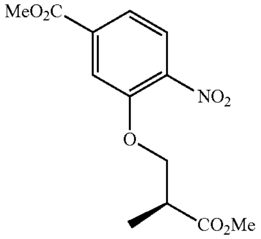

Methyl (S)-3-(3-Methoxy-2-methyl-3-oxopropoxy)-4-nitrobenzoate

To a solution, in tetrahydrofuran (40 mL), of methyl 3-hydroxy-4-nitrobenzoate (2.00 g), methyl (S)-3-hydroxy-2-methylpropionate (1.70 mL) and triphenylphosphine (4.04 g), diisopropyl azodicarboxylate (3.10 mL) was added at room temperature. The resultant reaction mixture was stirred at room temperature for 6 hours, diluted with ethyl acetate, and washed successively with a saturated sodium bicarbonate aqueous solution and saturated saline. The resultant organic layer was dried by adding anhydrous sodium sulfate thereto, and filtered, and the resultant filtrate was concentrated under reduced pressure. The thus obtained residue was purified by silica gel column chromatography (hexane:ethyl acetate=3:1) to obtain the title compound (2.57 g).

$^1$H NMR (400 MHz, $CDCl_3$) δ 1.34 (3H, d, J=7.3 Hz), 2.97-3.09 (1H, m), 3.75 (3H, s), 3.97 (3H, s), 4.21 (1H, dd, J=8.5, 6.7 Hz), 4.37 (1H, dd, J=8.5, 6.7 Hz), 7.70 (1H, d, J=8.5 Hz), 7.76 (1H, s), 7.83 (1H, d, J=8.5 Hz).

LRMS ($ESI^+$) 298 $[M+H]^+$.

Compounds of the following Reference Examples 10-2 to 10-4 were obtained in the same manner as in Reference Example 10-1 by using corresponding starting materials and reactants. Their structures and spectrum data are shown in the following table.

TABLE 10

| Reference Example No. | Chemical Structural Formula | Spectrum Data |
|---|---|---|
| 10-2 | 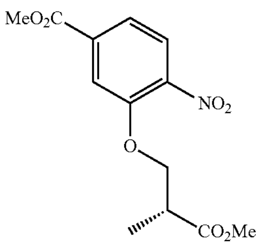 [SMILES: COC(=O)c1ccc([N+](=O)[O-])c(OC[C@@H](C)C(=O)OC)c1] | $^1$H NMR (400 MHz, $CDCl_3$) δ 1.34 (3H, d, J = 7.3 Hz), 2.98-3.09 (1H, m), 3.75 (3H, s), 3.97 (3H, s), 4.21 (1H, dd, J = 8.6, 6.7 Hz), 4.37 (1H, dd, J = 8.6, 6.7 Hz), 7.70 (1H, dd, J = 8.5, 1.8 Hz), 7.76 (1H, d, J = 1.8 Hz), 7.83 (1H, d, J = 8.5 Hz). LRMS (ESI$^+$) 298 [M + H]$^+$. |
| 10-3 | 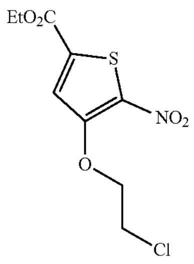 [SMILES: CCOC(=O)c1cc(OCCCl)c([N+](=O)[O-])s1] | $^1$H NMR (400 MHz, $CDCl_3$) δ 1.41 (3H, t, J = 7.0 Hz), 3.89 (2H, t, J = 5.8 Hz), 4.41 (2H, q, J = 7.1 Hz), 4.49 (2H, t, J = 6.1 Hz), 7.47 (1H, s). |
| 10-4 | 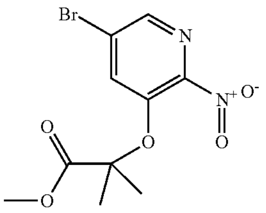 | $^1$H NMR (400 MHz, $CDCl_3$) δ 1.67 (6H, s), 3.83 (3H, s), 7.61 (1H, d, J = 1.8 Hz), 8.20 (1H, d, J = 1.8 Hz). LRMS (CI$^+$) 319 [M + H]$^+$. |

Reference Example 11-1

[Formula 107]

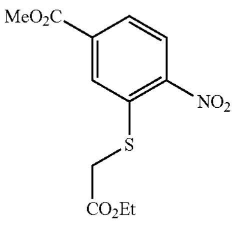

Methyl 3-((2-Ethoxy-2-oxoethyl)thio)-4-nitrobenzoate

To a suspension of methyl 3-fluoro-4-nitrobenzoate (4.00 g) and potassium carbonate (3.34 g) in N,N-dimethylformamide (100 mL), ethyl 2-mercaptoacetate (2.20 g) was added at 0° C. The resultant reaction solution was heated to room temperature, followed by stirring for 3 hours. The resultant reaction solution was filtered through celite, and the resultant filtrate was concentrated under reduced pressure. The thus obtained residue was purified by silica gel column chromatography (hexane:ethyl acetate=7:3) to obtain the title compound (5.61 g).

$^1$H NMR (400 MHz, $CDCl_3$) δ 1.29 (3H, t, J=7.3 Hz), 3.82 (2H, s), 3.98 (3H, s), 4.24 (2H, q, J=7.3 Hz), 7.91 (1H, dd, J=8.5, 1.8 Hz), 8.20 (1H, d, J=1.8 Hz), 8.26 (1H, d, J=8.5 Hz).

LRMS (ESI$^+$) 300 [M+H]$^+$.

Reference Example 11-2

[Formula 108]

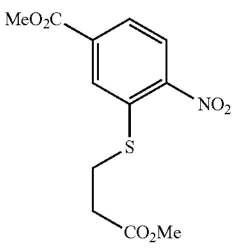

Methyl 3-((3-Methoxy-3-oxopropyl)thio)-4-nitrobenzoate

The title compound was synthesized in the same manner as in Reference Example 11-1 by using corresponding starting material and reactant.

$^1$H NMR (400 MHz, $CDCl_3$) δ 2.76 (2H, t, J=7.3 Hz), 3.33 (2H, t, J=7.3 Hz), 3.74 (3H, s), 3.99 (3H, s), 7.89 (1H, dd, J=9.1, 1.8 Hz), 8.10 (1H, d, J=1.8 Hz), 8.23 (1H, d, J=9.1 Hz).

LRMS (ESI$^+$) 300 [M+H]$^+$.

Reference Example 12-1

[Formula 109]

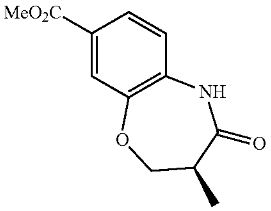

Methyl (S)-3-Methyl-4-oxo-2,3,4,5-tetrahydrobenzo[b][1,4]oxazepine-8-carboxylate To methyl (S)-3-(3-methoxy-2-methyl-3-oxopropoxy)-4-nitrobenzoate (3.60 g), reduced iron (3.38 g), 1,4-dioxane (20 mL) and acetic acid (8.0 mL) were added at room temperature to obtain a suspension, followed by stirring under heating at 120° C. for 6 hours. The resultant reaction solution was cooled to room temperature, a saturated sodium bicarbonate aqueous solution was added thereto to adjust pH to 10, and then the resultant was filtered through celite, and the resultant solid was washed with hot ethyl acetate. The resultant extract was dried over anhydrous sodium sulfate, and concentrated under reduced pressure. The thus obtained residue was purified by silica gel column chromatography (hexane:ethyl acetate=1:1) to obtain the title compound (417 mg).

$^1$H NMR (400 MHz, $CDCl_3$) δ 1.22 (3H, d, J=6.7 Hz), 2.95-3.06 (1H, m), 3.91 (3H, s), 4.25 (1H, dd, J=11.5, 9.7 Hz), 4.35 (1H, dd, J=11.5, 4.9 Hz), 6.95 (1H, d, J=8.5 Hz), 7.71 (1H, dd, J=8.5, 1.8 Hz), 7.74 (1H, d, J=1.8 Hz), 7.88 (1H, brs).

LRMS ($ESI^+$) 236 $[M+H]^+$.

Compounds of the following Reference Examples 12-2 to 12-5 were obtained in the same manner as in Reference Example 12-1 by using corresponding starting materials and reactants. Their structures and spectrum data are shown in the following table.

TABLE 11

| Reference Example No. | Chemical Structural Formula | Spectrum Data |
|---|---|---|
| 12-2 | 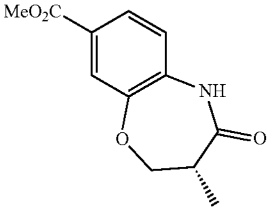 [SMILES: COC(=O)c1ccc2c(c1)OC[C@@H](C)C(=O)N2] | $^1$H NMR (400 MHz, $CDCl_3$) δ 1.22 (3H, d, J = 7.3 Hz), 2.95-3.05 (1H, m), 3.91 (3H, s), 4.25 (1H, dd, J = 11.5, 9.7 Hz), 4.35 (1H, dd, J = 11.5, 4.9 Hz), 6.92 (1H, d, J - 8.5 Hz), 7.57 (1H, brs), 7.71 (1H, dd, J = 8.5, 1.8 Hz), 7.74 (1H, d, J = 1.8 Hz). LRMS ($ESI^+$) 236 $[M + H]^+$. |
| 12-3 | 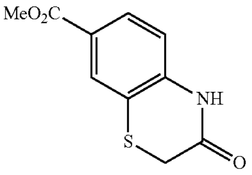 | $^1$H NMR (400 MHz, $CDCl_3$) δ 3.47 (2H, s), 3.91 (3H, s), 6.88 (1H, d, J = 8.5 Hz), 7.85 (1H, dd, J = 8.5, 1.8 Hz), 8.03 (1H, d, J = 1.8 Hz), 8.45 (1H, brs). LRMS ($ESI^+$) 224 $[M + H]^+$. |
| 12-4 | 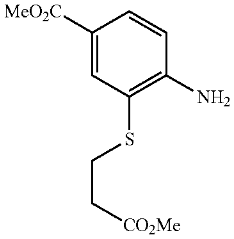 [SMILES: COC(=O)CCSc1cc(C(=O)OC)ccc1N] | $^1$H NMR (400 MHz, $CDCl_3$) δ 2.57 (2H, t, J = 7.3 Hz), 2.99 (2H, t, J = 7.3 Hz), 3.68 (3H, s), 3.86 (3H,s), 4.86 (2H, s), 6.69 (1H, d, J = 8.5 Hz), 7.80 (1H, dd, J = 8.5, 1.8 Hz), 8.08 (1H, d, J = 1.8 Hz). LRMS ($ESI^+$) 270 $[M + H]^+$. |
| 12-5 | 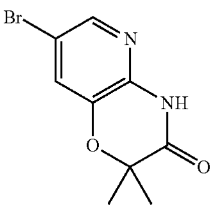 | $^1$H NMR (400 MHz, $CDCl_3$) δ 1.56 (6H, s), 7.40 (1H, d, J = 3.1 Hz), 8.04 (1H, d, J = 1.8 Hz), 8.91 (1H, br s). LRMS ($ESI^+$) 257 $[M + H]^+$. |

Reference Example 13-1

[Formula 110]

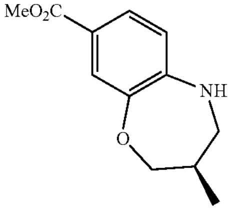

Methyl (R)-3-Methyl-2,3,4,5-tetrahydrobenzo[b][1,4]oxazepine-8-carboxylate

To a solution of methyl (S)-3-methyl-4-oxo-2,3,4,5-tetrahydrobenzo[b][1,4]oxazepine-8-carboxylate (2.09 g) in tetrahydrofuran (18 mL), borane-tetrahydrofuran complex (27 mL, 1 mol/L tetrahydrofuran solution) was added at 0° C. The resultant reaction mixture was stirred at room temperature for 2 hours, and the reaction was stopped by adding water thereto. The resultant was extracted with ethyl acetate, the resultant organic layer was dried over anhydrous sodium sulfate and filtered, and the resultant filtrate was concentrated under reduced pressure. The thus obtained residue was purified by silica gel column chromatography (hexane:ethyl acetate=3:1) to obtain the title compound (1.53 g).

$^1$H NMR (400 MHz, $CDCl_3$) δ 0.99 (3H, d, J=7.3 Hz), 2.20-2.32 (1H, m), 3.00 (1H, dd, J=12.7, 6.7 Hz), 3.49 (1H, dd, J=12.7, 4.9 Hz), 3.73 (1H, dd, J=11.5, 7.9 Hz), 3.85 (3H, s), 3.99 (1H, brs), 4.27 (1H, dd, J=11.5, 4.9 Hz), 6.60 (1H, d, J=8.5 Hz), 7.52 (1H, dd, J=8.5, 2.4 Hz), 7.55 (1H, d, J=2.4 Hz).

LRMS (EI$^+$) 221 [M]$^+$.

Compounds of the following Reference Examples 13-2 to 13-7 were obtained in the same manner as in Reference Example 13-1 by using corresponding starting materials and reactants. Their structures and spectrum data are shown in the following table.

TABLE 12

| Reference Example No. | Chemical Structural Formula | Spectrum Data |
|---|---|---|
| 13-2 | 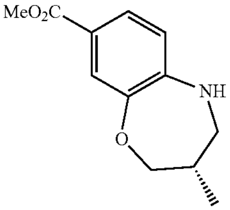 [SMILES: COC(=O)c1ccc2c(c1)OC[C@@H](C)CN2] | $^1$H NMR (400 MHz, $CDCl_3$) δ 0.99 (3H, d, J = 6.7 Hz), 2.20-2.32 (1H, m), 3.00 (1H, dd, J = 13.3, 6.7 Hz), 3.49 (1H, d, J = 12.7, 4.2 Hz), 3.72 (1H, dd, J = 12.1, 7.3 Hz), 3.84 (3H, s), 3.99 (1H, brs), 4.27 (1H, dd, J = 12.1, 4.9 Hz), 6.60 (1H, d, J = 8.5 Hz), 7.52 (1H, dd, J = 8.5, 1.8 Hz), 7.55 (1H, d, J = 1.8 Hz). LRMS (ESI$^+$) 222 [M + H]$^+$. |
| 13-3 | 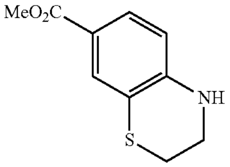 [SMILES: COC(=O)c1ccc2c(c1)SCCN2] | $^1$H NMR (400 MHz, $CDCl_3$) δ 3.00-3.05 (2H, m), 3.69-3.74 (2H, m), 3.84 (3H, s), 4.44 (1H, brs), 6.42 (1H, d, J = 8.5 Hz), 7.57 (1H, dd, J = 8.5, 2.4 Hz), 7.72 (1H, d, J = 2.4 Hz). LRMS (ESI$^+$) 210 [M + H]$^+$. |
| 13-4 | 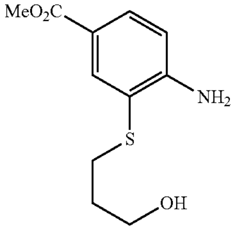 [SMILES: COC(=O)c1ccc(N)c(SCCCO)c1] | $^1$H NMR (400 MHz, $CDCl_3$) δ 1.43 (1H, brs), 1.77-1.85 (2H, m), 2.87 (2H, t, J = 7.3 Hz), 3.75 (2H, t, J = 6.1 Hz), 3.86 (3H, s), 4.80 (2H, s), 6.69 (1H, d, J = 8.5 Hz), 7.79 (1H, dd, J = 8.5, 1.8 Hz), 8.08 (1H, d, J = 1.8 Hz). LRMS (ESI$^+$) 242 [M + H]$^+$. |
| 13-5 | 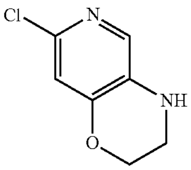 [SMILES: Clc1cc2c(cn1)NCCO2] | $^1$H NMR (400 MHz, $CDCl_3$) δ 3.40-3.46 (2H, m), 3.82 (1H, br s), 4.31 (2H, t, J = 3.9 Hz), 6.72 (1H, s), 7.66 (1H, s). LRMS (ESI$^+$) 171 [M + H]$^+$. |
| 13-6 | 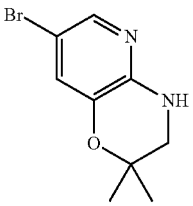 | $^1$H NMR (400 MHz, $CDCl_3$) δ 1.35 (6H, s), 3.24 (2H, d, J = 2.4 Hz), 4.85 (1H, br s), 7.08 (1H, d, J = 1.8 Hz), 7.71 (1H, d, J = 1.8 Hz). LRMS (FI+) 242 [M]$^+$. |

TABLE 12-continued

| Reference Example No. | Chemical Structural Formula | Spectrum Data |
|---|---|---|
| 13-7 | 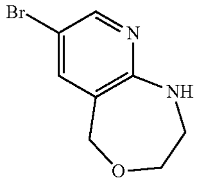 [SMILES: Brc1cnc2c(c1)COCCN2] | $^1$H NMR (400 MHz, $CDCl_3$) δ 3.53 (2H, dd, J = 9.2, 4.3 Hz), 3.92 (2H, t, J = 4.3 Hz), 4.60 (2H, s), 6.70 (1H, br s), 7.60 (1H, d, J = 1.8 Hz), 8.35 (1H, d, J = 1.8 Hz). LRMS ($ESI^+$) 229 $[M + H]^+$. |

Reference Example 14-1

[Formula 111]

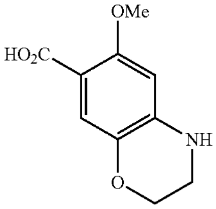

6-Methoxy-3,4-dihydro-2H-benzo[b][1,4]oxazine-7-carboxylic Acid

Methyl 6-methoxy-3,4-dihydro-2H-benzo[b][1,4]oxazine-7-carboxylate (200 mg) was dissolved in tetrahydrofuran (3.6 mL) and methanol (3.6 mL), and 1 mol/L lithium hydroxide aqueous solution (3.6 mL) was added thereto at room temperature, followed by stirring at 70° C. for 3 hours. The resultant reaction solution was concentrated under reduced pressure, and 6 mol/L hydrogen chloride aqueous solution was added to the resultant residue to adjust pH to 4. The thus precipitated product was collected by filtration to obtain the title compound (151 mg).

$^1$H NMR (400 MHz, DMSO-$d_6$) δ3.10-3.50 (2H, m), 3.69 (3H, s), 4.04 (2H, t, J=4.3 Hz), 6.21 (1H, s), 6.65 (1H, brs), 7.06 (1H, s), 11.53 (1H, brs).

LRMS ($ESI^+$) 210 $[M+H]^+$.

Compounds of the following Reference Examples 14-2 to 14-35 were obtained in the same manner as in Reference Example 14-1 by using corresponding starting materials and reactants. Their structures and spectrum data are shown in the following tables.

TABLE 13

| Reference Example No. | Chemical Structural Formula | Spectrum Data |
|---|---|---|
| 14-2 | 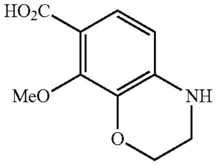 [SMILES: COc1c(C(=O)O)ccc2c1OCCN2] | $^1$H NMR (400 MHz, DMSO-$d_6$) δ 3.20-3.50 (2H, m), 3.71 (3H, s), 4.11 (2H, t, J = 4.9 Hz), 6.32 (1H, d, J = 8.6 Hz), 6.56 (1H, brs), 7.15 (1H, d, J = 8.6 Hz), 11.85 (1H, brs). LRMS ($ESI^+$) 210 $[M + H]^+$. |
| 14-3 | 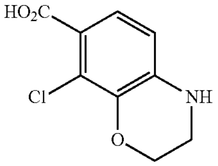 [SMILES: O=C(O)c1ccc2c(c1Cl)OCCN2] | $^1$H NMR (400 MHz, DMSO-$d_6$) δ 3.20-3.50 (2H, m), 4.18 (2H, t, J = 4.9 Hz), 6.50 (1H, d, J = 8.6 Hz), 6.81 (1H, brs), 7.30 (1H, d, J = 8.6 Hz), 12.35 (1H, brs). LRMS ($ESI^+$) 214 $[M + H]^+$. |
| 14-4 | 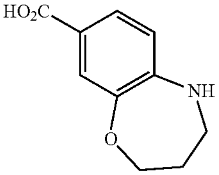 [SMILES: O=C(O)c1ccc2c(c1)OCCCN2] | $^1$H NMR (400 MHz, DMSO-$d_6$) δ 1.86-1.95 (2H, m), 3.18-3.25 (2H, m), 4.06 (2H, t, J = 5.5 Hz), 6.10 (1H, brs), 6.74 (1H, d, J = 8.6 Hz), 7.29 (1H, d, J = 1.8 Hz), 7.36 (1H, dd, J = 8.6, 1.8 Hz), 12.26 (1H, brs). LRMS ($ESI^+$) 194 $[M + H]^+$. |

TABLE 14

| Reference Example No. | Chemical Structural Formula | Spectrum Data |
|---|---|---|
| 14-5 | 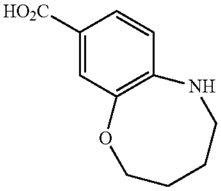 [SMILES: O=C(O)c1ccc2c(c1)OCCCCN2] | $^1H$ NMR (400 MHz, DMSO-$d_6$) δ 1.56-1.66 (2H, m), 1.71-1.81 (2H, m), 3.51-3.61 (2H, m), 4.04 (2H, t, J = 5.5 Hz), 6.50 (1H, t, J = 6.1 Hz), 6.56 (1H, d, J = 8.5 Hz), 7.30 (1H, d, J = 1.8 Hz), 7.37 (1H, dd, J = 8.5, 1.8 Hz), 12.02 (1H, br s). LRMS (ESI$^+$) 208 $[M + H]^+$. |
| 14-6 | 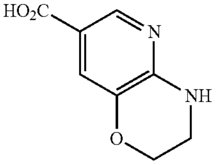 [SMILES: O=C(O)c1cnc2c(c1)OCCN2] | $^1H$ NMR (400 MHz, DMSO-$d_6$) δ 3.42-3.47 (2H, m), 4.11 (2H, t, J = 4.2 Hz), 7.24 (1H, d, J = 1.8 Hz), 7.62 (1H, brs), 8.16 (1H, d, J = 1.8 Hz), 12.43 (1H, brs). LRMS (ESI$^+$) 181 $[M + H]^+$. |
| 14-7 | 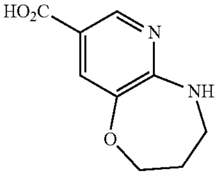 [SMILES: O=C(O)c1cnc2c(c1)OCCCN2] | $^1H$ NMR (400 MHz, DMSO-$d_6$) δ 1.93-2.03 (2H, m), 3.30-3.50 (2H, m), 4.14 (2H, t, J = 6.1 Hz), 6.98 (1H, brs), 7.39 (1H, d, J = 1.8 Hz), 8.24 (1H, d, J = 1.8 Hz), 12.52 (1H, br s). LRMS (ESI$^+$) 195 $[M + H]^+$. |
| 14-8 | 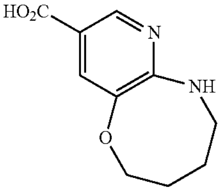 [SMILES: O=C(O)c1cnc2c(c1)OCCCCN2] | $^1H$ NMR (400 MHz, DMSO-$d_6$) δ 1.57-1.66 (2H, m), 1.73-1.83 (2H, m), 3.55-3.67 (2H, m), 4.05-4.15 (2H, m), 7.20-7.30 (1H, m), 7.47 (1H, d, J = 1.8 Hz), 8.26 (1H, d, J = 1.8 Hz), 12.33 (1H, brs). LRMS (ESI$^+$) 209 $[M + H]^+$. |
| 14-9 | 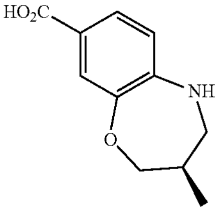 | $^1H$ NMR (400 MHz, DMSO-$d_6$) δ 0.91 (3H, d, J = 6.7 Hz), 2.08-2.20 (1H, m), 2.83-2.92 (1H, m), 3.30-3.40 (1H, m), 3.64 (1H, dd, J = 11.5, 7.3 Hz), 4.18 (1H, dd, J = 11.5, 4.9 Hz), 6.08 (1H, brs), 6.70 (1H, d, J = 7.9 Hz), 7.25 (1H, d, J = 2.4 Hz), 7.34 (1H, dd, J = 7.9, 2.4 Hz), 12.23 (1H, brs). LRMS (EI$^+$) 207 $[M]^+$. |
| 14-10 | 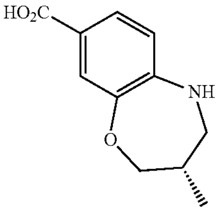 | $^1H$ NMR (400 MHz, DMSO-$d_6$) δ 0.91 (3H, d, J = 6.7 Hz), 2.08-2.20 (1H, m), 2.83-2.92 (1H, m), 3.37-3.40 (1H, m), 3.65 (1H, dd, J = 12.2, 7.3 Hz), 4.18 (1H, dd, J – 12.2, 4.9 Hz), 6.07 (1H, brs), 6.70 (1H, d, J = 8.6 Hz), 7.25 (1H, d, J = 1.8 Hz), 7.35 (1H, dd, J = 8.6, 1.8 Hz), 12.23 (1H, brs). LRMS (ESI$^+$) 208 $[M + H]^+$. |

TABLE 15

| Reference Example No. | Chemical Structural Formula | Spectrum Data |
|---|---|---|
| 14-11 | 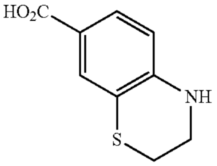 [SMILES: O=C(O)c1ccc2c(c1)SCCN2] | $^1H$ NMR (400 MHz, DMSO-$d_6$) δ 2.92-3.00 (2H, m), 3.52-3.60 (2H, m), 6.50 (1H, d, J = 8.5 Hz), 6.88 (1H, brs), 7.39 (1H, dd, J = 8.5, 1.8 Hz), 7.43 (1H, d, J = 1.8 Hz), 12.12 (1H, brs). LRMS (ESI$^+$) 196 $[M + H]^+$. |

TABLE 15-continued

| Reference Example No. | Chemical Structural Formula | Spectrum Data |
|---|---|---|
| 14-12 | 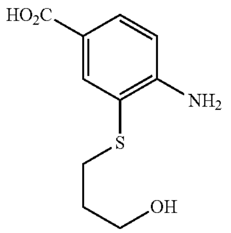 [SMILES: Nc1ccc(C(=O)O)cc1SCCCO] | $^1H$ NMR (400 MHz, DMSO-$d_6$) δ 1.55-1.65 (2H, m), 2.75 (2H, t, J = 7.3 Hz), 3.46 (2H, t, J = 6.7 Hz), 4.52 (1H, brs), 6.07 (2H, s), 6.70 (1H, d, J = 8.5 Hz), 7.59 (1H, dd, J = 8.5, 2.4 Hz), 7.80 (1H, d, J = 2.4 Hz), 12.19 (1H, brs). LRMS (ESI$^+$) 228 [M + H]$^+$. |
| 14-13 | 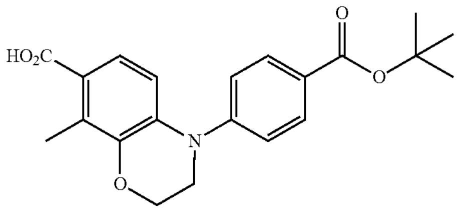 | $^1H$ NMR (400 MHz, $CDCl_3$) δ 1.60 (9H, s), 2.55 (3H, s), 3.78 (2H, t, J = 4.3 Hz), 4.37 (2H, t, J = 4.6 Hz), 6.87 (1H, d, J = 8.6 Hz), 7.24-7.28 (2H, m), 7.48 (1H, d, J = 8.6 Hz), 7.97-8.01 (2H, m). (COOH peak missing) LRMS (ESI$^+$) 370 [M + H]$^+$. |
| 14-14 | 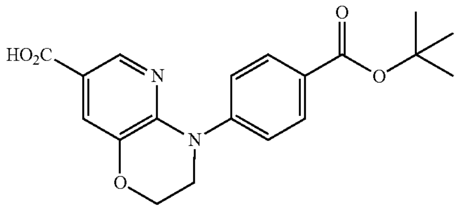 | $^1H$ NMR (400 MHz, DMSO-$d_6$) δ 1.54 (9H, s), 3.98 (2H, t, J = 4.2 Hz), 4.35 (2H, t, J = 4.2 Hz), 7.48 (1H, d, J = 1.8 Hz), 7.52-7.58 (2H, m), 7.86-7.91 (2H, m), 8.19 (1H, d, J = 1.8 Hz), 12.81 (1H, br s). LRMS (ESI$^+$) 357 [M + H]$^+$. |
| 14-15 | 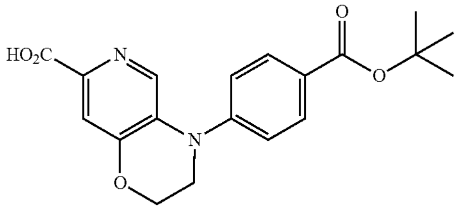 | $^1H$ NMR (400 MHz, DMSO-$d_6$) δ 1.54 (9H, s), 3.84 (2H, t, J = 4.2 Hz), 4.39 (2H, t, J = 4.2 Hz), 7.41 (2H, d, J = 9.1 Hz), 7.47 (1H, s), 7.90 (2H, d, J = 8.5 Hz), 8.27 (1H, s). (COOH peak missing) LRMS (ESI$^+$) 357 [M + H]$^+$. |
| 14-16 | 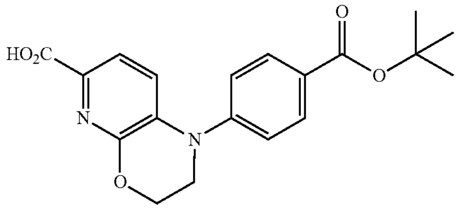 | $^1H$ NMR (400 MHz, DMSO-$d_6$) δ 1.41 (9H, s), 3.69 (2H, t, J = 4.6 Hz), 4.33 (2H, t, J = 4.6 Hz), 7.22 (1H, d, J = 8.6 Hz), 7.27-7.31 (2H, m), 7.39 (1H, d, J = 8.6 Hz), 7.78-7.82 (2H, m), 12.4 (1H, br s). LRMS (ESI$^+$) 357 [M + H]$^+$. |

TABLE 16

| Reference Example No. | Chemical Structural Formula | Spectrum Data |
|---|---|---|
| 14-17 | 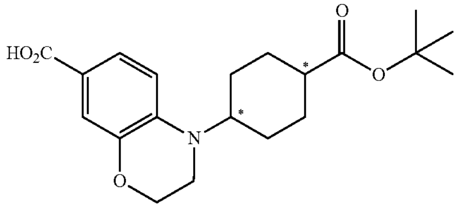 | $^1H$ NMR (400 MHz, $CDCl_3$) δ: 1.43-1.74 (15H, m), 2.23-2.30 (2H, m), 2.58-2.63 (1H, m), 3.34 (2H, t, J = 4.5 Hz), 3.61-3.74 (1H, m), 4.17 (2H, t, J = 4.5 Hz), 6.69 (1H, d, J = 8.5 Hz), 7.47 (1H, d, J = 2.4 Hz), 7.59 (1H, dd, J = 8.8, 2.1 Hz). (COOH peak missing) LRMS (ESI$^+$) 362 [M + H]$^+$. |

TABLE 16-continued

| Reference Example No. | Chemical Structural Formula | Spectrum Data |
|---|---|---|
| 14-18 | 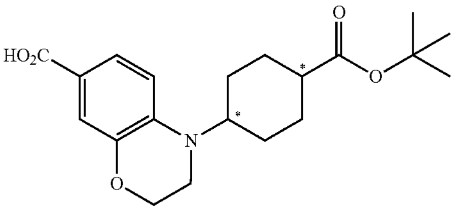 | $^1$H NMR (400 MHz, $CDCl_3$) δ: 1.39-1.70 (13H, m), 1.91 (2H, d, J = 11.5 Hz), 2.12 (2H, d, J = 15.1 Hz), 2.16-2.22 (1H, m), 3.35 (2H, t, J = 4.5 Hz), 3.63-3.76 (1H, m), 4.19 (2H, t, J = 4.5 Hz), 6.69 (1H, d, J = 9.1 Hz), 7.47 (1H, d, J = 1.8 Hz), 7.60 (1H, dd, J = 8.8, 2.1 Hz). (COOH peak missing)<br>LRMS (ESI$^+$) 362 [M + H]$^+$. |
| 14-19 | 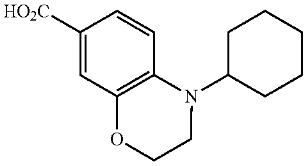 | $^1$H NMR (400 MHz, $CDCl_3$) δ: 1.12-1.25 (1H, m), 1.36-1.95 (9H, m), 3.40 (2H, t, J = 4.5 Hz), 3.64-3.74 (1H, m), 4.21 (2H, t, J = 4.5 Hz), 6.72 (1H, d, J = 9.1 Hz), 7.50 (1H, d, J = 1.8 Hz), 7.63 (1H, dd, J = 8.5, 1.8 Hz). (COOH peak missing)<br>LRMS (ESI$^+$) 262 [M + H]$^+$. |
| 14-20 | 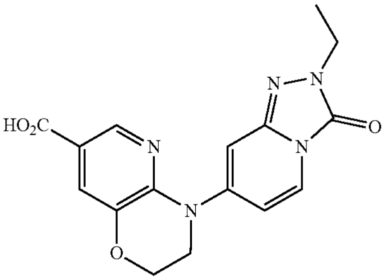 | $^1$H NMR (400 MHz, DMSO-$d_6$) δ: 1.28 (3H, t, J = 7.3 Hz), 3.88 (2H, q, J = 7.3 Hz), 3.96 (2H, t, J = 4.3 Hz), 4.37 (2H, t, J = 4.6 Hz), 6.93 (1H, dd, J = 7.6, 2.1 Hz), 6.99 (1H, d, J = 1.2 Hz), 7.52 (1H, d, J = 1.8 Hz), 7.77 (1H, d, J = 6.7 Hz), 8.26 (1H, d, J = 1.8 Hz), 12.94 (1H, s).<br>LRMS (ESI$^+$) 342 [M + H]$^+$. |
| 14-21 | 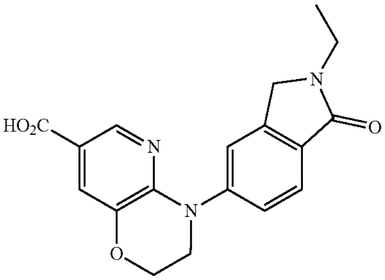 | $^1$H NMR (400 MHz, DMSO-$d_6$) δ: 1.16 (3H, t, J = 7.0 Hz), 3.53 (2H, q, J = 7.1 Hz), 3.98 (2H, t, J = 4.3 Hz), 4.36 (2H, t, J = 4.3 Hz), 4.46 (2H, s), 7.46 (1H, d, J = 2.4 Hz), 7.51 (1H, dd, J = 8.6, 1.8 Hz), 7.61-7.68 (2H, m), 8.17 (1H, d, J = 1.8 Hz), 12.79 (1H, s).<br>LRMS (ESI$^+$) 340 [M + H]$^+$. |
| 14-22 | 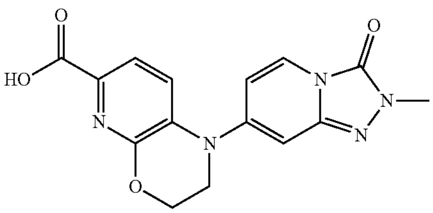 | $^1$H NMR (400 MHz, DMSO-$d_6$) δ 3.49 (3H, s), 3.82 (2H, t, J = 4.3 Hz), 4.47 (2H, t, J = 4.3 Hz), 6.60 (1H, dd, J = 7.9, 1.8 Hz), 6.91 (1H, d, J = 1.2 Hz), 7.39 (1H, d, J = 8.6 Hz), 7.58 (1H, d, J = 7.9 Hz), 7.84 (1H, d, J = 7.9 Hz), 12.70 (1H, br s).<br>LRMS (ESI$^+$) 328 [M + H]$^+$. |

TABLE 17

| Reference Example No. | Chemical Structural Formula | Spectrum Data |
|---|---|---|
| 14-23 | 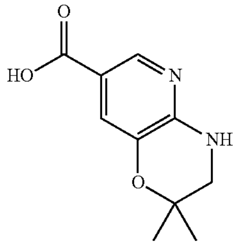 | $^{1}$H NMR (400 MHz, DMSO-$d_6$) δ 1.26 (6H, s), 3.22 (2H, d, J = 2.4 Hz), 7.22 (1H, d, J = 1.8 Hz), 7.63 (1H, s), 8.17 (1H, d, J = 1.8 Hz), 12.42 (1H, s).<br>LRMS (ESI$^+$) 209 [M + H]$^+$. |
| 14-24 | 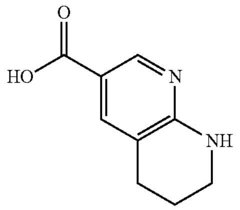 [SMILES: O=C(O)c1cnc2c(c1)CCCN2] | $^{1}$H NMR (400 MHz, DMSO-$d_6$) δ 1.72-1.82 (2H, m), 2.68 (2H, t, J = 6.1 Hz), 3.26-3.39 (2H, m), 7.30 (1H, br s), 7.56-7.59 (1H, m), 8.32 (1H, d, J = 1.8 Hz), 12.22 (1H, s).<br>LRMS (ESI$^+$) 179 [M + H]$^+$. |
| 14-25 | 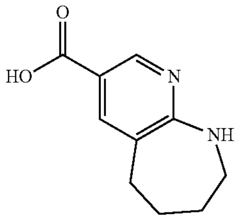 [SMILES: O=C(O)c1cnc2c(c1)CCCCN2] | $^{1}$H NMR (400 MHz, DMSO-$d_6$) δ 1.72-1.80 (4H, m), 2.70-2.77 (2H, m), 3.21-3.27 (2H, m), 6.79 (1H, t, J = 4.3 Hz), 7.70 (1H, d, J = 1.8 Hz), 8.36 (1H, d, J = 2.4 Hz), 12.42 (1H, br s).<br>LRMS (ESI$^+$) 193 [M + H]$^+$. |
| 14-26 | 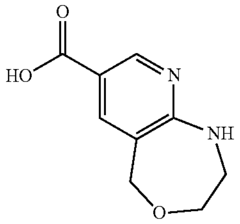 [SMILES: O=C(O)c1cnc2c(c1)COCCN2] | $^{1}$H NMR (400 MHz, DMSO-$d_6$) δ 3.26 (2H, dd, J = 8.6, 4.3 Hz), 3.75 (2H, t, J = 4.3 Hz), 4.55 (2H, s), 7.11-7.16 (1H, m), 7.87 (1H, d, J = 1.8 Hz), 8.48 (1H, d, J = 2.4 Hz), 12.59 (1H, br s).<br>LRMS (ESI$^+$) 195 [M + H]$^+$. |
| 14-27 | 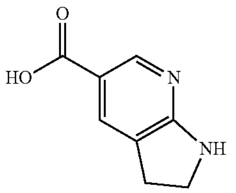 [SMILES: O=C(O)c1cnc2c(c1)CCN2] | $^{1}$H NMR (400 MHz, DMSO-$d_6$) δ 3.01 (2H, t, J = 8.6 Hz), 3.56 (2H, t, J = 8.6 Hz), 7.27 (1H, br s), 7.59 (1H, d, J = 1.8 Hz), 8.30 (1H, d, J = 1.8 Hz), 12.26 (1H, br s).<br>LRMS (ESI$^+$) 165 [M + H]$^+$. |

TABLE 18

| Reference Example No. | Chemical Structural Formula | Spectrum Data |
|---|---|---|
| 14-28 | 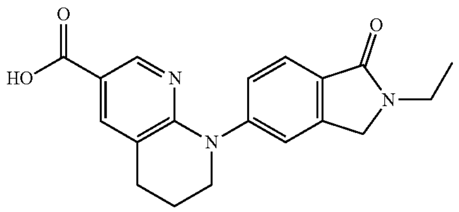 [SMILES: CCN1Cc2cc(N3CCCc4cc(C(=O)O)cnc43)ccc2C1=O] | $^{1}$H NMR (400 MHz, DMSO-$d_6$) δ 1.17 (3H, t, J = 7.3 Hz), 1.97-2.07 (2H, m), 2.89 (2H, t, J = 6.1 Hz), 3.54 (2H, q, J = 7.3 Hz), 3.82 (2H, t, J = 5.5 Hz), 4.46 (2H, s), 7.42 (1H, dd, J = 7.9, 1.2 Hz), 7.54 (1H, s), 7.65 (1H, d, J = 7.9 Hz), 7.79 (1H, d, J = 1.2 Hz), 8.31 (1H, d, J = 1.8 Hz), 12.53 (1H, br s).<br>LRMS (ESI$^+$) 338 [M + H]$^+$. |

TABLE 18-continued

| Reference Example No. | Chemical Structural Formula | Spectrum Data |
|---|---|---|
| 14-29 | 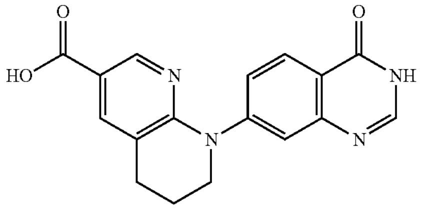 [SMILES: O=C(O)c1cnc2c(c1)CCCN2c1ccc2c(=O)[nH]cnc2c1] | $^1$H NMR (400 MHz, DMSO-$d_6$) δ 1.98-2.08 (2H, m), 2.89 (2H, t, J = 6.1 Hz), 3.90 (2H, t, J = 6.1 Hz), 7.55 (1H, dd, J = 8.6, 1.8 Hz), 7.57 (1H, t, J = 2.1 Hz), 7.84 (1H, d, J = 2.4 Hz), 8.03-8.09 (2H, m), 8.37 (1H, d, J = 1.8 Hz), 12.16 (1H, br s), 12.62 (1H, br s). LRMS (FD$^+$) 322 [M]$^+$. |
| 14-30 | 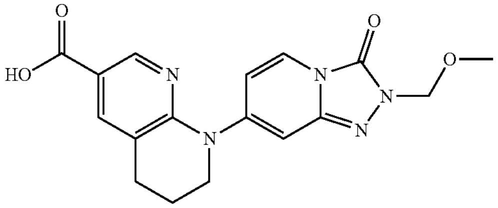 [SMILES: COCn1nc2cc(N3CCCc4cc(C(=O)O)cnc43)ccn2c1=O] | $^1$H NMR (400 MHz, DMSO-$d_6$) δ 1.95-2.06 (2H, m), 2.86 (2H, t, J – 6.4 Hz), 3.31 (3H, s), 3.84 (2H, t, J – 5.8 Hz), 5.18 (2H, s), 6.74 (1H, dd, J = 7.6, 2.1 Hz), 6.99 (1H, d, J = 1.8 Hz), 7.74 (1H, d, J = 7.9 Hz), 7.88 (1H, d, J = 1.8 Hz), 8.46 (1H, d, J = 1.8 Hz), 12.81 (1H, br s). LRMS (ESI$^+$) 356 [M + H]$^+$. |
| 14-31 | 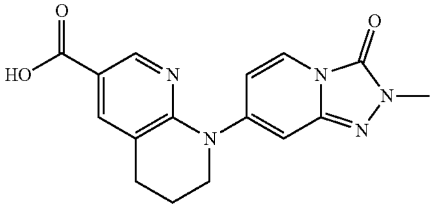 [SMILES: Cn1nc2cc(N3CCCc4cc(C(=O)O)cnc43)ccn2c1=O] | $^1$H NMR (400 MHz, DMSO-$d_6$) δ 1.94-2.07 (2H, m), 2.86 (2H, t, J – 6.4 Hz), 3.51 (3H, s), 3.83 (2H, t, J – 5.8 Hz), 6.72 (1H, dd, J = 7.6, 2.1 Hz), 6.99 (1H, d, J = 1.8 Hz), 7.72 (1H, d, J = 7.9 Hz), 7.83-7.90 (1H, m), 8.45 (1H, d, J = 2.4 Hz), 12.75 (1H, s). LRMS (ESI$^-$) 324 [M – H]$^-$. |

TABLE 19

| Reference Example No. | Chemical Structural Formula | Spectrum Data |
|---|---|---|
| 14-32 | 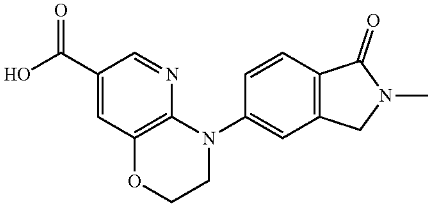 [SMILES: CN1Cc2cc(N3CCOc4cc(C(=O)O)cnc43)ccc2C1=O] | $^1$H NMR (400 MHz, DMSO-$d_6$) δ 3.06 (3H, s), 3.98 (2H, t, J = 4.2 Hz), 4.36 (2H, t, J = 4.5 Hz), 4.45 (2H, s), 7.46 (1H, d, J = 1.8 Hz), 7.52 (1H, dd, J = 8.5, 1.8 Hz), 7.61-7.68 (2H, m), 8.18 (1H, d, J = 1.8 Hz), 2.76 (1H s). LRMS (ESI$^+$) 326 [M + H]$^+$. |
| 14-33 | 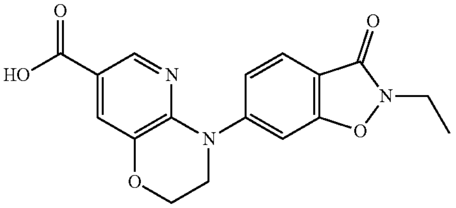 [SMILES: CCn1oc2cc(N3CCOc4cc(C(=O)O)cnc43)ccc2c1=O] | $^1$H NMR (400 MHz, DMSO-$d_6$) δ 1.26 (3H, t, J = 7.3 Hz), 3.93-4.05 (4H, m), 4.37 (2H, t, J = 4.3 Hz), 7.44 (1H, dd, J = 8.6, 1.8 Hz), 7.50 (1H, d, J = 1.8 Hz), 7.55 (1H, d, J = 1.8 Hz), 7.73 (1H, d, J = 8.6 Hz), 8.23 (1H, d, J = 1.8 Hz), 12.86 (1H, s). LRMS (ESI$^+$) 342 [M + H]$^+$. |
| 14-34 | 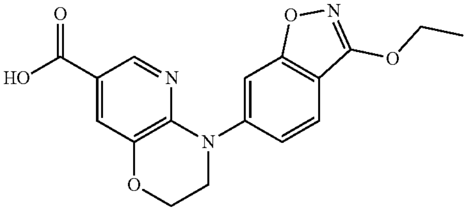 [SMILES: CCOc1noc2cc(N3CCOc4cc(C(=O)O)cnc43)ccc12] | $^1$H NMR (400 MHz, DMSO-$d_6$) δ 1.45 (3H, t, J = 7.0 Hz), 4.02 (2H, t, J = 4.3 Hz), 4.37 (2H, t, J = 4.6 Hz), 4.45 (2H q, J = 6.9 Hz), 7.43-7.52 (2H, m), 7.64-7.71 (2H, m), 8.20 (1H, d, J = 1.8 Hz), 12.81 (1H, s). LRMS (ESI$^+$) 342 [M + H]$^+$. |

TABLE 19-continued

| Reference Example No. | Chemical Structural Formula | Spectrum Data |
|---|---|---|
| 14-35 | 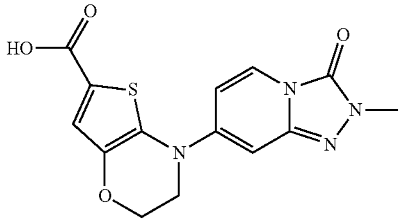 | $^1$H NMR (400 MHz, DMSO-$d_6$) δ 3.47 (3H, s), 3.81 (2H, t, J = 4.0 Hz), 4.30 (2H, t, J = 4.0 Hz), 6.77 (1H, d, J = 1.2 Hz), 6.84 (1H, dd, J = 7.3, 2.4 Hz), 7.24 (1H, s), 7.86 (1H, d, J = 7.3 Hz), 12.89 (1H, s). LRMS (ESI$^+$) 333 [M + H]$^+$. |

Reference Example 15-1

[Formula 112]

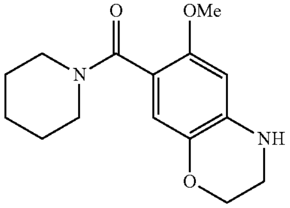

(6-Methoxy-3,4-dihydro-2H-benzo[b][1,4]oxazin-7-yl)(piperidin-1-yl)methanone

A mixture of 6-methoxy-3,4-dihydro-2H-benzo[b][1,4]oxazine-7-carboxylic acid (50.0 mg) and thionyl chloride (0.40 ml) was stirred under heating at 70° C. for 30 minutes. The resultant reaction mixture was concentrated under reduced pressure, the thus obtained residue was dissolved in tetrahydrofuran (1 mL), and the resultant was added to a solution of piperidine (1.00 mL) in tetrahydrofuran (1 mL) under ice cooling. Thereafter, the resultant reaction solution was stirred at room temperature for 3 hours, and then concentrated under reduced pressure. The thus obtained residue was purified by silica gel column chromatography (ethyl acetate) to obtain the title compound (68.1 mg).

$^1$H NMR (400 MHz, $CDCl_3$) δ 1.37-1.70 (6H, m), 3.24 (2H, t, J=4.2 Hz), 3.42 (2H, t, J=4.2 Hz), 3.55-3.65 (1H, m), 3.71 (3H, s), 3.72-3.82 (1H, m), 3.82-3.90 (1H, m), 4.10-4.25 (2H, m), 6.13 (1H, s), 6.68 (1H, s).

LRMS (ESI$^+$) 277 [M+H]$^+$.

Reference Example 15-2

[Formula 113]

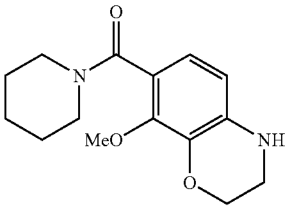

(8-Methoxy-3,4-dihydro-2H-benzo[b][1,4]oxazin-7-yl)(piperidin-1-yl)methanone

The title compound was synthesized in the same manner as in Reference Example 15-1 by using corresponding carboxylic acid derivative and reactant.

$^1$H NMR (400 MHz, $CDCl_3$) δ 1.38-1.50 (1H, m), 1.50-1.72 (5H, m), 3.15-3.35 (2H, m), 3.41-3.46 (2H, m), 3.65-3.75 (2H, m), 3.84 (3H, s), 3.85-3.90 (1H, m), 4.25-4.35 (2H, m), 6.35 (1H, d, J=8.5 Hz), 6.64 (1H, d, J=8.5 Hz).

LRMS (ESI$^+$) 277 [M+H]$^+$.

Reference Example 16-1

[Formula 114]

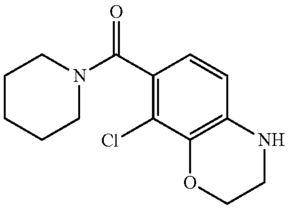

(8-Chloro-3,4-dihydro-2H-benzo[b][1,4]oxazin-7-yl)(piperidin-1-yl)methanone

To a solution of 8-chloro-3,4-dihydro-2H-benzo[b][1,4]oxazine-7-carboxylic acid (60.0 mg) in N,N-dimethylformamide (1.4 mL), piperidine (56.0 μL), 1-[bis (dimethylamino)methylene]-1H-1,2,3-triazolo[4,5-b]pyridinium 3-oxide hexafluorophosphate (130 mg) and diisopropylethylamine (100 μL) were added at room temperature, followed by stirring at room temperature for 12 hours. The resultant reaction mixture was concentrated under reduced pressure, and the thus obtained residue was purified by silica gel column chromatography (hexane:ethyl acetate=4:1) to obtain the title compound (78.8 mg).

$^1$H NMR (400 MHz, $CDCl_3$) δ 1.39-1.49 (1H, m), 1.53-1.73 (5H, m), 3.15-3.30 (2H, m), 3.42-3.48 (2H, m), 3.65-3.80 (2H, m), 3.92-4.00 (1H, m), 4.28-4.42 (2H, m), 6.50 (1H, d, J=8.6 Hz), 6.66 (1H, d, J=8.6 Hz).

LRMS (ESI$^+$) 281 [M+H]$^+$.

Compounds of the following Reference Examples 16-2 to 16-26 were obtained in the same manner as in Reference Example 16-1 by using corresponding starting materials and reactants. Their structures and spectrum data are shown in the following tables.

TABLE 20

| Reference Example No. | Chemical Structural Formula | Spectrum Data |
|---|---|---|
| 16-2 | 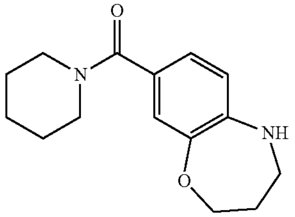 [SMILES: O=C(c1ccc2c(c1)OCCCN2)N1CCCCC1] | $^1$H NMR (400 MHz, $CDCl_3$) δ 1.50-1.63 (4H, m), 1.63-1.70 (2H, m), 1.98-2.05 (2H, m), 3.28 (2H, t, J = 5.5 Hz), 3.35-3.70 (4H, m), 4.11 (2H, t, J = 5.5 Hz), 6.67 (1H, d, J = 7.9 Hz), 6.92 (1H, dd, J = 7.9, 1.8 Hz), 7.00 (1H, d, J = 1.8 Hz). (NH proton signal is missing) LRMS (ESI$^+$) 261 [M + H]$^+$. |
| 16-3 | 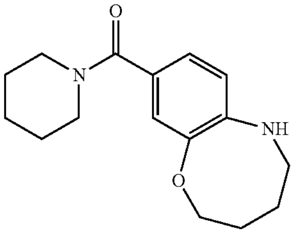 [SMILES: O=C(c1ccc2c(c1)OCCCCN2)N1CCCCC1] | $^1$H NMR (400 MHz, DMSO-$d_6$) δ 1.43-1.52 (4H, m), 1.56-1.68 (4H, m), 1.72-1.80 (2H, m), 3.40-3.45 (4H, m), 3.52 (2H, q, J = 6.1 Hz), 4.00-4.07 (2H, m), 6.11 (1H, t, J = 6.1 Hz), 6.55 (1H, d, J – 8.5 Hz), 6.81 (1H, d, J = 1.8 Hz), 6.86 (1H, dd, J = 8.5, 1.8 Hz). LRMS (ESI$^+$) 275 [M + H]$^+$. |
| 16-4 | 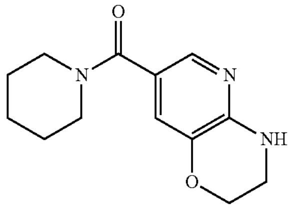 [SMILES: O=C(c1cnc2c(c1)OCCN2)N1CCCCC1] | $^1$H NMR (400 MHz, $CDCl_3$) δ 1.52-1.72 (6H, m), 3.45-3.65 (6H, m), 4.23 (2H, t, J = 4.2 Hz), 5.07 (1H, brs), 7.07 (1H, d, J = 1.8 Hz), 7.78 (1H, d, J = 1.8 Hz). LRMS (ESI$^+$) 248 [M + H]$^+$. |
| 16-5 | 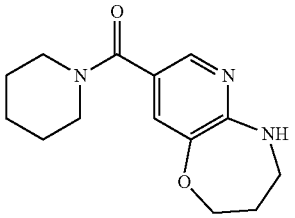 [SMILES: O=C(c1cnc2c(c1)OCCCN2)N1CCCCC1] | $^1$H NMR (400 MHz, $CDCl_3$) δ 1.55-1.73 (6H, m), 2.02-2.12 (2H, m), 3.40-3.40 (2H, m), 3.46-3.06 (4H, m), 4.20 (2H, t, J = 5.5 Hz), 4.91 (1H, brs), 7.23 (1H, d, J = 1.8 Hz), 7.87 (1H, d, J = 1.8 Hz). LRMS (ESI$^+$) 262 [M + H]$^+$. |
| 16-6 | 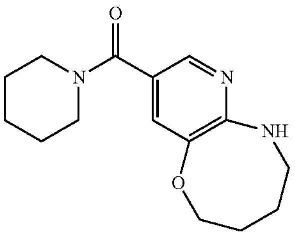 [SMILES: O=C(c1cnc2c(c1)OCCCCN2)N1CCCCC1] | $^1$H NMR (400 MHz, $CDCl_3$) δ 1.55-1.72 (6H, m), 1.72-1.80 (2H, m), 1.85-1.93 (2H, m), 3.45-3.65 (4H, m), 3.76 (2H, q, J = 6.1 Hz), 4.16 (2H, t, J = 5.5 Hz), 5.17 (1H, t, J = 7.3 Hz), 7.26 (1H, d, J = 2.4 Hz), 7.90 (1H, d, J = 2.4 Hz). LRMS (ESI$^+$) 276 [M + H]$^+$. |
| 16-7 | 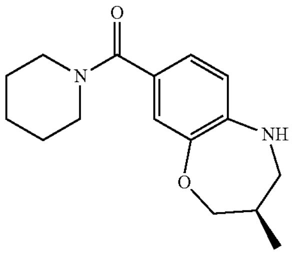 [SMILES: C[C@@H]1CNc2ccc(C(=O)N3CCCCC3)cc2OC1] | $^1$H NMR (400 MHz, $CDCl_3$) δ 0.98 (3H, d, J = 6.7 Hz), 1.50-1.70 (6H, m), 2.15-2.30 (1H, m), 2.90 (1H, dd, J = 12.7, 7.3 Hz), 3.41 (1H, dd, J = 12.7, 4.2 Hz), 3.37-3.65 (4H, m), 3.69 (1H, dd, J = 12.1, 7.3 Hz), 3.79 (1H, brs), 4.24 (1H, d, d, J = 12.1, 4.2 Hz), 6.63 (1H, d, J = 7.9 Hz), 6.91 (1H, dd J = 7.9, 2.4 Hz), 6.97 (1H, d, J = 2.4 Hz). LRMS (EI$^+$) 274 [M]$^+$. |

TABLE 21

| Reference Example No. | Chemical Structural Formula | Spectrum Data |
|---|---|---|
| 16-8 | 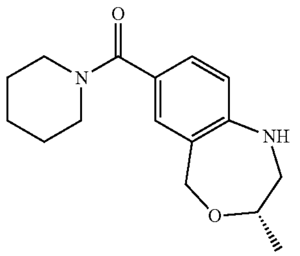 [SMILES: C[C@H]1CNc2ccc(C(=O)N3CCCCC3)cc2CO1] | $^1$H NMR (400 MHz, $CDCl_3$) δ 0.98 (3H, d, J = 6.7 Hz), 1.50-1.72 (6H, m), 2.15-2.30 (1H, m), 2.90 (1H, dd, J = 12.8, 7.3 Hz), 3.41 (1H, dd, J = 12.8, 4.9 Hz), 3.40-3.65 (4H, m), 3.69 (1H, dd, J = 11.6, 7.3 Hz), 3.79 (1H, brs), 4.24 (1H, d d, J =11.6, 4.9 Hz), 6.63 (1H, d, J = 7.9 Hz), 6.91 (1H, dd, J = 7.9, 1.8 Hz), 6.97 (1H, d, J = 1.8 Hz). LRMS (ESI$^+$) 275 [M + H]$^+$. |
| 16-9 | 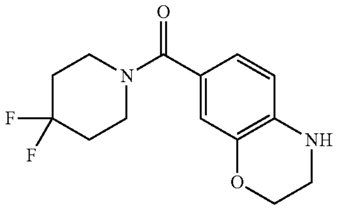 [SMILES: O=C(c1ccc2c(c1)OCCN2)N1CCC(F)(F)CC1] | $^1$H NMR (400 MHz, $CDCl_3$) δ 1.90-2.08 (4H, m), 3.46 (2H, t, J = 4.2 Hz), 3.68-3.78 (4H, m), 4.03 (1H, brs), 4.24 (2H, I, J = 4.2 Hz), 6.56 (1H, d, J = 8.5 Hz), 6.85-6.90 (2H, m). LRMS (EI$^+$) 282 [M]$^+$. |
| 16-10 | 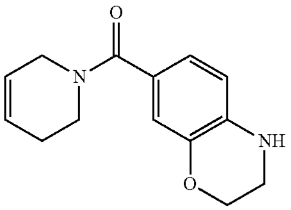 [SMILES: O=C(c1ccc2c(c1)OCCN2)N1CC=CCC1] | $^1$H NMR (400 MHz, $CDCl_3$) δ 2.16-2.25 (2H, m), 3.45 (2H, t, J = 4.3 Hz), 3.55-3.73 (2H, m), 3.95-4.15 (3H, m), 4.24 (2H, t, J = 4.3 Hz), 5.65-5.78 (1H, m), 5.82-5.90 (1H, m), 6.55 (1H, d, J = 8.5 Hz), 6.86-6.92 (2H, m). LRMS (EI$^+$) 244 [M]$^+$. |
| 16-11 | 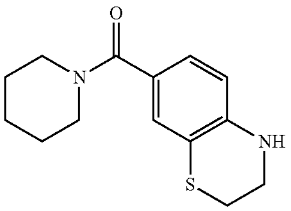 [SMILES: O=C(c1ccc2c(c1)SCCN2)N1CCCCC1] | $^1$H NMR (400 MHz, $CDCl_3$) δ 1.50-1.70 (6H, m), 3.00-3.05 (2H, m), 3.45-3.60 (4H, m), 3.67 (2H, t, J = 4.9 Hz), 4.20 (1H, brs), 6.42 (1H, d, J = 8.5 Hz), 6.97 (1H, dd, J = 8.5, 1.8 Hz), 7.08 (1H, d, J = 1.8 Hz). LRMS (ESI$^+$) 263 [M + H]$^+$. |
| 16-12 | 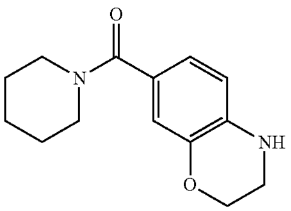 [SMILES: O=C(c1ccc2c(c1)OCCN2)N1CCCCC1] | $^1$H NMR (400 MHz, $CDCl_3$) δ 1.47-1.74 (6H, m), 3.35-3.68 (6H, m), 3.94 (1H, s), 4.24 (2H, t, J = 4.3 Hz), 6.53-6.58 (1H, m), 6.82-6.89 (2H, m). LRMS (ESI$^+$) 247 [M + H]$^+$. |
| 16-13 | 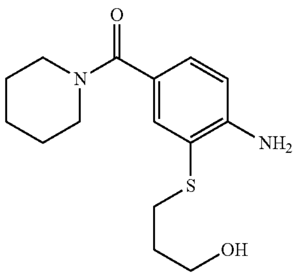 [SMILES: Nc1ccc(C(=O)N2CCCCC2)cc1SCCCO] | $^1$H NMR (400 MHz, $CDCl_3$) δ 1.50-1.75 (6H, m), 1.75-1.85 (2H,m), 2.88 (2H, t, J = 7.3 Hz), 2.98 (2H, d, J = 5.5 Hz), 3.42-3.65 (4H, m), 3.73 (2H, t, J = 6.1 Hz), 4.40-4.70 (1H, m), 6.69 (1H, d, J = 7.9 Hz), 7.19 (1H, dd. J = 7.9, 1.8 Hz), 7.46 (1H, d, J = 1.8 Hz). LRMS (ESI$^+$) 295 [M + H]$^+$. |

TABLE 22

| Reference Example No. | Chemical Structural Formula | Spectrum Data |
|---|---|---|
| 16-14 | 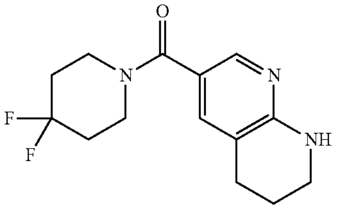 [SMILES: O=C(c1cnc2c(c1)CCCN2)N1CCC(F)(F)CC1] | $^1$H NMR (400 MHz, $CDCl_3$) δ 1.85-2.11 (6H, m), 2.75 (2H, t, J = 6.4 Hz), 3.41-3.50 (2H, m), 3.75 (4H, t, J = 5.4 Hz), 5.17 (1H, br s), 7.29-7.33 (1H, m), 7.98 (1H, d, J = 2.4 Hz). LRMS (ESI$^+$) 282 [M + H]$^+$. |
| 16-15 | 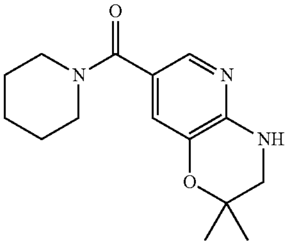 [SMILES: CC1(C)CNc2ncc(C(=O)N3CCCCC3)cc2O1] | $^1$H NMR (400 MHz, $CDCl_3$) δ 1.36 (6H, s), 1.41-1.76 (6H, m), 3.28 (2H, s), 3.46-3.64 (4H, m), 5.11 (1H, br s), 7.04 (1H, d, J = 1.8 Hz), 7.78 (1H, d, J = 2.4 Hz). LRMS (ESI$^+$) 276 [M + H]$^+$. |
| 16-16 | 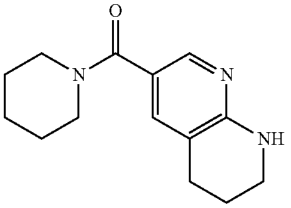 [SMILES: O=C(c1cnc2c(c1)CCCN2)N1CCCCC1] | $^1$H NMR (400 MHz, $CDCl_3$) δ 1.54-1.77 (6H, m), 1.89-1.95 (2H, m), 2.74 (2H, t, J = 6.1 Hz), 3.45 (2H, t, J = 4.8 Hz), 3.50-3.64 (4H, m), 5.14 (1H, br s), 7.30 (1H, d, J = 1.2 Hz), 7.94 (1H, d, J = 1.8 Hz). LRMS (ESI$^+$) 246 [M + H]$^+$. |
| 16-17 | 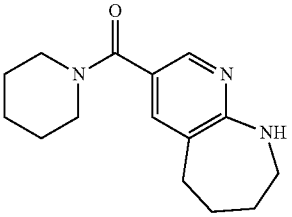 [SMILES: O=C(c1cnc2c(c1)CCCCN2)N1CCCCC1] | $^1$H NMR (400 MHz, $CDCl_3$) δ 1.54-1.72 (6H, m), 1.72-1.80 (2H, m), 1.80-1.87 (2H, m), 2.71-2.76 (2H, m), 3.19-3.24 (2H, m), 3.40-3.71 (4H, m), 4.91-4.98 (1H, m), 7.44 (1H, d, J = 2.4 Hz), 8.01 (1H, d, J = 2.4 Hz). LRMS (ESI$^+$) 260 [M + H]$^+$. |
| 16-18 | 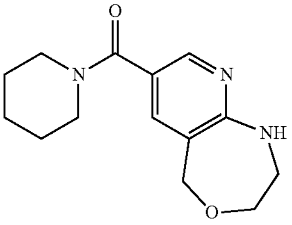 [SMILES: O=C(c1cnc2c(c1)COCCN2)N1CCCCC1] | $^1$H NMR (400 MHz, $CDCl_3$) δ 1.53-1.73 (6H, m), 3.27-3.33 (2H, m), 3.36-3.76 (4H, m), 3.84-3.89 (2H, m), 4.56 (2H, s), 5.19 (1H, br s), 7.51 (1H, d, J = 1.8 Hz), 8.15 (1H, d, J = 2.4 Hz). LRMS (ESI$^+$) 262 [M + H]$^+$. |
| 16-19 | 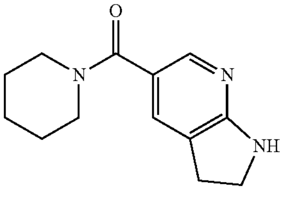 [SMILES: O=C(c1cnc2c(c1)CCN2)N1CCCCC1] | $^1$H NMR (400 MHz, $CDCl_3$) δ 1.54-1.76 (6H, m), 3.10 (2H, t, J = 8.6 Hz), 3.50-3.62 (4H, m), 3.68 (2H, t, J = 8.6 Hz), 4.73 (1H, br s), 7.35-7.37 (1H, m), 7.88-7.91 (1H, m). LRMS (ESI$^+$) 232 [M + H]$^+$. |
| 16-20 | 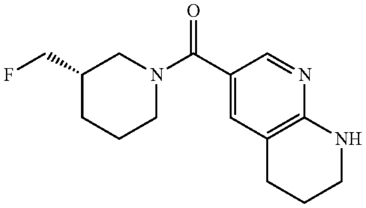 [SMILES: O=C(c1cnc2c(c1)CCCN2)N1CCC[C@H](CF)C1] | $^1$H NMR (400 MHz, $CDCl_3$) δ 1.35-1.62 (2H, m), 1.72-1.82 (1H, m), 1.83-2.03 (4H, m), 2.74 (2H, t, J = 6.1 Hz), 2.80-3.07 (2H, m), 3.41-3.49 (2H, m), 3.99-4.47 (4H, m), 5.12 (1H, s), 7.30 (1H, d, J = 1.8 Hz), 7.96 (1H, d, J = 1.8 Hz.). LRMS (ESI$^+$) 278 [M + H]$^+$. |

TABLE 23

| Reference Example No. | Chemical Structural Formula | Spectrum Data |
|---|---|---|
| 16-21 | 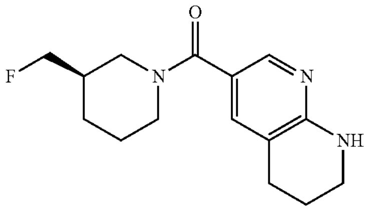 [SMILES: O=C(c1cnc2c(c1)CCCN2)N1CCC[C@@H](CF)C1] | $^1$H NMR (400 MHz, $CDCl_3$) δ 1.33-1.64 (2H, m), 1.70-1.81 (1H, m), 1.82-2.05 (4H, m), 2.74 (2H, t, J = 6.1 Hz), 2.79-3.08 (2H, m), 3.45 (2H, t, J = 5.5 Hz), 3.85-4.54 (4H, m), 5.22 (1H, s), 7.30 (1H, d, J = 2.4 Hz), 7.95 (1H, d, J = 2.4 Hz). LRMS ($FD^+$) 277 $[M]^+$. |
| 16-22 | 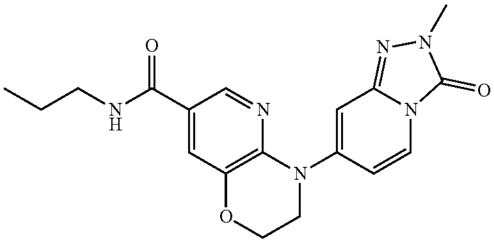 [SMILES: CCCNC(=O)c1cnc2c(c1)OCCN2c1ccn2c(=O)n(C)nc2c1] | $^1$H NMR (400 MHz, DMSO-$d_6$) δ 0.86 (3H, t, J = 7.3 Hz), 1.44-1.56 (2H, m), 3.13-3.22 (2H, m), 3.49 (3H, s), 3.94 (2H, t, J = 4.6 Hz), 4.36 (2H, t, J = 4.3 Hz), 6.91 (1H, d, J = 1.2 Hz), 6.96 (1H, dd, J = 7.3, 1.8 Hz), 7.60 (1H, d, J = 2.4 Hz), 7.76 (1H, d, J = 7.3 Hz), 8.24 (1H, d, J = 2.4 Hz), 8.37 (1H, t, J = 5.5 Hz). LRMS ($ESI^+$) 369 $[M + H]^+$. |
| 16-23 | 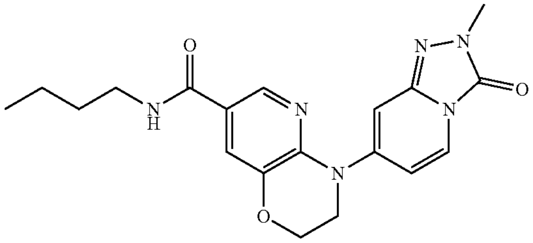 [SMILES: CCCCNC(=O)c1cnc2c(c1)OCCN2c1ccn2c(=O)n(C)nc2c1] | $^1$H NMR (400 MHz, DMSO-$d_6$) δ 0.88 (3H, t, J = 7.3 Hz), 1.25-1.34 (2H, m), 1.44-1.51 (2H, m), 3.22 (2H, q, J = 6.7 Hz), 3.49 (3H, s), 3.94 (2H, t, J = 4.3 Hz), 4.36 (2H, t, J = 4.3 Hz), 6.91 (1H, s), 6.96 (1H, dd, J = 7.6, 2.1 Hz), 7.60 (1H, d, J = 1.8 Hz), 7.76 (1H, d, J = 7.9 Hz), 8.23 (1H, d, J = 1.8 Hz), 8.35 (1H, t, J = 5.8 Hz). LRMS ($ESI^+$) 383 $[M + H]^+$. |
| 16-24 | 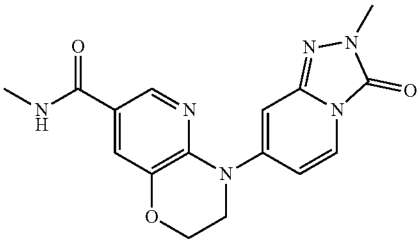 [SMILES: CNC(=O)c1cnc2c(c1)OCCN2c1ccn2c(=O)n(C)nc2c1] | $^1$H NMR (400 MHz, DMSO-$d_6$) δ 3.01 (3H, d, J = 4.9 Hz), 3.65 (3H, s), 3.91 (2H, t, J = 4.6 Hz), 4.41 (2H, t, J = 4.6 Hz), 5.96-6.04 (1H, m), 6.66 (1H, d, J = 1.2 Hz), 6.95 (1H, dd, J = 7.6, 2.1 Hz), 7.58 (1H, d, J = 2.4 Hz), 7.69 (1H, d, J = 7.9 Hz), 8.17 (1H, d, J = 1.8 Hz). LRMS ($ESI^+$) 341 $[M + H]^+$. |

TABLE 24

| Reference Example No. | Chemical Structural Formula | Spectrum Data |
|---|---|---|
| 16-25 | 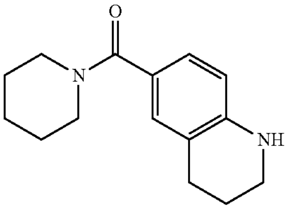 [SMILES: O=C(c1ccc2c(c1)CCCN2)N1CCCCC1] | $^1$H NMR (400 MHz, $CDCl_3$) δ 1.52-1.62 (4H, m), 1.63-1.71 (2H, m), 1.88-1.98 (2H, m), 2.75 (2H, t, J = 6.1 Hz), 3.32 (2H, t, J = 5.5 Hz), 3.46-3.64 (4H, m), 4.03 (1H, s), 6.40 (1H, d, J = 8.6 Hz), 7.02 (1H, dd, J = 8.6, 1.8 Hz), 7.07 (1H, d, J = 1.2 Hz). LRMS ($ESI^+$) 245 $[M+H]^+$. |

TABLE 24-continued

| Reference Example No. | Chemical Structural Formula | Spectrum Data |
|---|---|---|
| 16-26 | 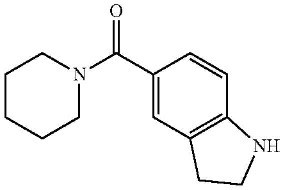 [SMILES: O=C(c1ccc2c(c1)CCN2)N1CCCCC1] | $^1$H NMR (400 MHz, $CDCl_3$) δ 1.52-1.71 (6H, m), 3.04 (2H, t, J = 8.5 Hz), 3.45-3.64 (6H, m), 3.92 (1H, br s), 6.56 (1H, d, J = 7.9 Hz), 7.08 (1H, dd, J = 7.9, 1.8 Hz), 7.20 (1H, d, J = 1.2 Hz). LRMS (ESI$^+$) 231 [M + H]$^+$. |

Reference Example 17-1

[Formula 115]

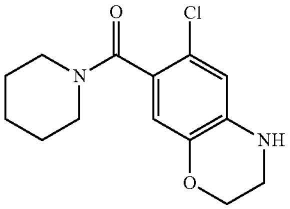

(6-Chloro-3,4-dihydro-2H-benzo[b][1,4]oxazin-7-yl)(piperidin-1-yl)methanone

Methyl 6-chloro-3,4-dihydro-2H-benzo[b][1,4]oxazine-7-carboxylate (56.0 mg) was dissolved in tetrahydrofuran (1.0 mL) and methanol (1.0 mL), and 1 mol/L lithium hydroxide aqueous solution (1.0 mL) was added thereto at room temperature, followed by stirring at room temperature for 12 hours and subsequently at 60° C. for 2 hours. 6 mol/L hydrogen chloride aqueous solution was added to the resultant reaction solution to adjust pH to 4, and the resultant was concentrated under reduced pressure. The thus obtained residue was dissolved in N,N-dimethylformamide (1.2 mL), and piperidine (49.0 μL), 1-[bis(dimethylamino)methylene]-1H-1,2,3-triazolo[4,5-b]pyridinium 3-oxide hexafluorophosphate (113 mg) and diisopropylethylamine (85.0 μm) were added thereto at room temperature, followed by stirring at room temperature for 12 hours. The resultant reaction mixture was concentrated under reduced pressure and the thus obtained residue was purified by silica gel column chromatography (hexane:ethyl acetate=1:4) to obtain the title compound (61.5 mg).

$^1$H NMR (400 MHz, $CDCl_3$) δ 1.40-1.70 (6H, m), 3.18-3.32 (2H, m), 3.39-3.45 (2H, m), 3.59-3.70 (1H, m), 3.70-3.81 (1H, m), 3.94 (1H, brs), 4.15-4.28 (2H, m), 6.56 (1H, s), 6.67 (1H, s).

LRMS (ESI$^+$) 281 [M+H]$^+$.

A compound of the following Reference Example 17-2 was obtained in the same manner as in Reference Example 17-1 by using corresponding starting material and reactant. Its structure and spectrum data are shown in the following table.

TABLE 25

| Reference Example No. | Chemical Structural Formula | Spectrum Data |
|---|---|---|
| 17-2 | 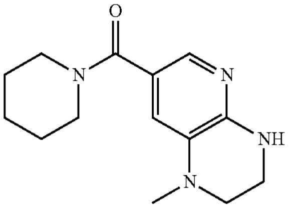 [SMILES: CN1CCNc2ncc(C(=O)N3CCCCC3)cc21] | $^1$H NMR (400 MHz, $CDCl_3$) δ 1.51-1.74 (6H, m), 2.86 (3H, s), 3.20-3.27 (2H, m), 3.50-3.69 (6H, m), 6.73 (1H, d, J = 1.8 Hz), 7.53 (1H, d, J = 1.8 Hz). (NH peak missing) LRMS (ESI$^+$) 261 [M + H]$^+$. |

Reference Example 18-1

[Formula 116]

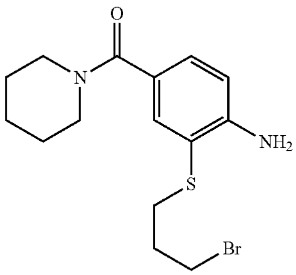

(4-Amino-3-((3-bromopropyl)thio)phenyl)(piperidin-1-yl)methanone

To a solution of (4-amino-3-((3-hydroxypropyl)thio)phenyl)(piperidin-1-yl)methanone (1.26 g) in chloroform (8.5 ml), phosphorus tribromide (1.22 mL) was added at 0° C., followed by stirring at room temperature for 1 hour and subsequently at 60° C. for 2 hours. The resultant reaction solution was poured into ice water, and a saturated sodium bicarbonate aqueous solution was added thereto to adjust pH to 10, followed by extraction with ethyl acetate. The resultant organic layer was dried over anhydrous sodium sulfate and filtered, and the resultant filtrate was concentrated under reduced pressure. The thus obtained residue was purified by silica gel column chromatography (hexane:ethyl acetate=1:1) to obtain the title compound (1.10 g).

$^1$H NMR (400 MHz, $CDCl_3$) δ 1.50-1.72 (6H, m), 2.02-2.10 (2H, m), 2.89 (2H, t, J=6.7 Hz), 3.50 (2H, t, J=6.7 Hz), 3.42-3.65 (4H, m), 4.54 (2H, brs), 6.70 (1H, d, J=7.9 Hz), 7.22 (1H, dd, J=7.9, 1.8 Hz), 7.45 (1H, d, J=1.8 Hz).

LRMS ($ESI^+$) 357 $[M+H]^+$.

Reference Example 19-1

[Formula 117]

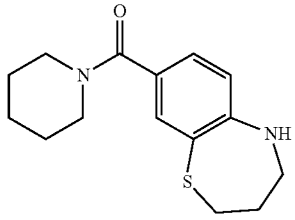

Piperidin-1-yl(2,3,4,5-tetrahydrobenzo[b][1,4]thiazepin-8-yl)methanone

To a solution of (4-amino-3-((3-bromopropyl)thio)phenyl)(piperidin-1-yl)methanone (914 mg) in dimethylsulfoxide (5 mL), potassium hydroxide (215 mg) was added, followed by stirring at 100° C. for 5 hours. The resultant reaction solution was concentrated under reduced pressure, and the thus obtained residue was purified by silica gel column chromatography (hexane:ethyl acetate=1:1) to obtain the title compound (410 mg).

$^1$H NMR (400 MHz, $CDCl_3$) δ 1.50-1.70 (6H, m), 2.03-2.12 (2H, m), 2.93 (2H, t, J=6.1 Hz), 3.38 (2H, t, J=5.5 Hz), 3.35-3.70 (4H, m), 4.06 (1H, brs), 6.66 (1H, d, J=7.9 Hz), 7.09 (1H, dd, J=7.9, 1.8 Hz), 7.40 (1H, d, J=1.8 Hz).

LRMS ($ESI^+$) 277 $[M+H]^+$.

Reference Example 20-1

[Formula 118]

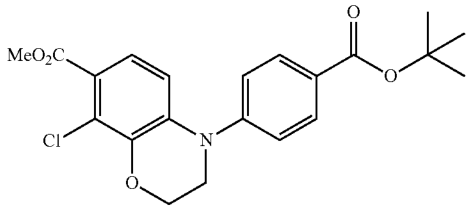

Methyl 4-(4-tert-Butoxycarbonyl)phenyl)-8-chloro-3,4-dihydro-2H-benzo[b][1,4]oxazine-7-carboxylate A solution, in toluene (15 mL), of methyl 8-chloro-3,4-dihydro-2H-benzo[b][1,4]oxazine-7-carboxylate (341 mg), tert-butyl 4-iodobenzoate (684 mg), tris(dibenzylideneacetone) dipalladium (0) (68.6 mg), 4,5-bis(diphenylphosphino)-9,9-dimethylxanthene (Xantphos) (86.8 mg) and sodium tert-butoxide (288 mg) was stirred at 85° C. for 2 hours, and the resultant reaction solution was then filtered, and the resultant filtrate was concentrated under reduced pressure. The thus obtained residue was purified by silica gel column chromatography (ethyl acetate:hexane=5:95 to 20:80) to obtain the title compound (394 mg).

$^1$H NMR (400 MHz, $CDCl_3$) δ: 1.60 (9H, s), 3.80 (2H, t, J=4.3 Hz), 3.89 (3H, s), 4.45 (2H, t, J=4.3 Hz), 6.88 (1H, d, J=9.2 Hz), 7.23-7.28 (2H, m), 7.34 (1H, d, J=9.2 Hz), 7.98-8.03 (2H, m).

LRMS ($ESI^+$) 404 $[M+H]^+$.

Compounds of the following Reference Examples 20-2 to 20-10 were obtained in the same manner as in Reference Example 20-1 by using corresponding starting materials and reactants. Their structures and spectrum data are shown in the following tables.

TABLE 26

| Reference Example No. | Chemical Structural Formula | Spectrum Data |
|---|---|---|
| 20-2 | 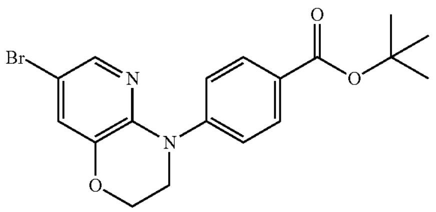 [SMILES: CC(C)(C)OC(=O)c1ccc(N2CCOc3cc(Br)cnc32)cc1] | $^1$H NMR (400 MHz, $CDCl_3$) δ 1.59 (9H, s), 3.91 (2H, t, J = 4.5 Hz), 4.35 (2H, t, J = 4.5 Hz), 7.24-7.27 (1H, m), 7.37-7.42 (2H, m), 7.80 (1H, d, J = 1.8 Hz), 7.97-8.02 (2H, m). LRMS ($ESI^+$) 391 $[M + H]^+$. |

TABLE 27

| Reference Example No. | Chemical Structural Formula | Spectrum Data |
|---|---|---|
| 20-3 | 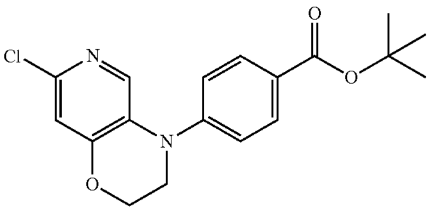 [SMILES: CC(C)(C)OC(=O)c1ccc(N2CCOc3cc(Cl)ncc32)cc1] | $^1$H NMR (400 MHz, $CDCl_3$) δ 1.59 (9H, s), 3.76 (2H, t, J = 4.2 Hz), 4.35 (2H, t, J = 4.2 Hz), 6.86 (1H, s), 7.17-7.22 (2H, m), 7.95-7.99 (2H, m), 8.09 (1H, s). LRMS (ESI$^+$) 347 [M + H]$^+$. |
| 20-4 | 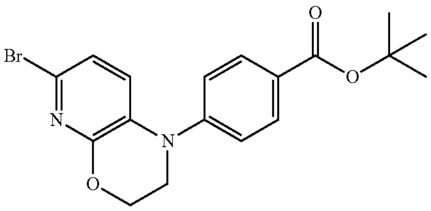 [SMILES: CC(C)(C)OC(=O)c1ccc(N2CCOc3nc(Br)ccc32)cc1] | $^1$H NMR (400 MHz, $CDCl_3$) δ 1.60 (9H, s), 3.75 (2H, t, J = 4.2 Hz), 4.48 (2H, t, J = 4.2 Hz), 6.93 (1H, d, J = 8.5 Hz), 7.17-7.21 (2H, m), 7.23 (1H, d, J = 8.5 Hz), 7.97-8.01 (2H, m). LRMS (ESI$^+$) 391 [M + H]$^+$. |
| 20-5 | 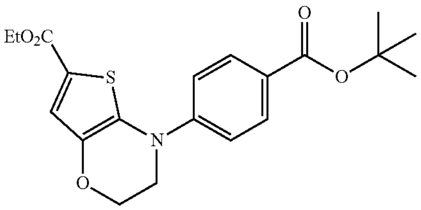 [SMILES: CCOC(=O)c1cc2c(s1)N(c1ccc(C(=O)OC(C)(C)C)cc1)CCO2] | $^1$H NMR (400 MHz, $CDCl_3$) δ 1.33 (3H, t, J = 7.0 Hz), 1.59 (9H, s), 3.80 (2H, t, J = 4.3 Hz), 4.29 (2H, q, J = 7.1 Hz), 4.35 (2H, t, J = 4.3 Hz), 7.31-7.35 (3H, m), 7.96-8.00 (2H, m). LRMS (ESI$^+$) 390 [M + H]$^+$. |
| 20-6 | 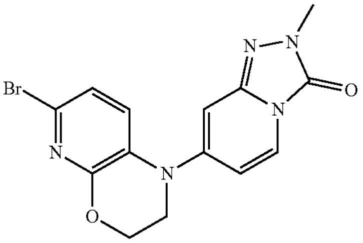 [SMILES: Cn1nc2cc(N3CCOc4nc(Br)ccc43)ccn2c1=O] | $^1$H NMR (400 MHz, $CDCl_3$) δ 3.63 (3H, s), 3.72-3.77 (2H, m), 4.48-4.52 (2H, m), 6.47 (1H, dd, J = 7.6, 2.1 Hz), 6.51 (1H, d, J = 1.8 Hz), 7.03 (1H, d, J = 7.9 Hz), 7.22 (1H, d, J = 8.6 Hz), 7.73 (1H, d, J = 8.6 Hz). LRMS (ESI$^+$) 362 [M + H]$^+$. |

TABLE 28

| Reference Example No. | Chemical Structural Formula | Spectrum Data |
|---|---|---|
| 20-7 | 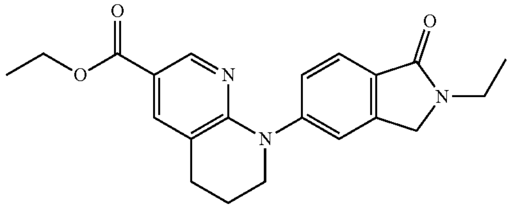 [SMILES: CCOC(=O)c1cnc2c(c1)CCCN2c1ccc2c(c1)CN(CC)C2=O] | $^1$H NMR (400 MHz, $CDCl_3$) δ 1.26 (3H, t, J = 7.3 Hz), 1.35 (3H, t, J = 7.3 Hz), 2.08-2.16 (2H, m), 2.92 (2H, t, J = 6.1 Hz), 3.68 (2H, q, J = 7.3 Hz), 3.86 (2H, t, J = 6.1 Hz), 4.32 (2H, q, J - 7.3 Hz), 4.39 (2H, s), 7.37 (1H, dd, J = 7.9, 1.8 Hz), 7.44 (1H, d, J = 1.2 Hz), 7.83-7.89 (2H, m), 8.56 (1H, d, J = 2.4 Hz). LRMS (ESI$^+$) 366 [M + H]$^+$. |
| 20-8 | 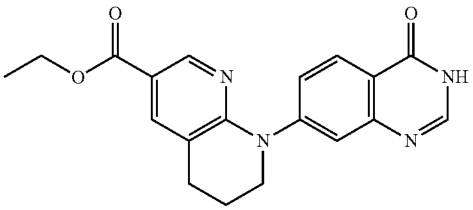 [SMILES: CCOC(=O)c1cnc2c(c1)CCCN2c1ccc2c(=O)[nH]cnc2c1] | $^1$H NMR (400 MHz, $CDCl_3$) δ 1.36 (3H, t, J = 7.3 Hz), 2.10-2.19 (2H, m), 2.94 (2H, t, J = 6.1 Hz), 3.95 (2H, t, J = 6.1 Hz), 4.34 (2H, q, J = 7.3 Hz), 7.60-7.65 (2H, m), 7.90-7.92 (1H, m), 8.00 (1H, br s), 8.24 (1H, d, J = 9.2 Hz), 8.61 (1H, d, J = 2.4 Hz), 9.70-9.87 (1H, m). LRMS (FD$^+$) 350 [M]$^+$. |

TABLE 28-continued

| Reference Example No. | Chemical Structural Formula | Spectrum Data |
|---|---|---|
| 20-9 | 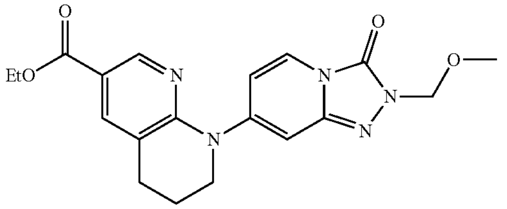 | $^1$H NMR (400 MHz, $CDCl_3$) δ 1.38 (3H, t, J = 7.0 Hz), 2.09-2.21 (2H, m), 2.91 (2H, t, J – 6.4 Hz), 3.44 (3H, s), 3.85 (2H, t, J = 5.8 Hz), 4.36 (2H, q, J = 7.1 Hz), 5.31 (2H, s), 6.68-6.79 (2H, m), 7.64 (1H, d, J = 7.3 Hz), 7.94 (1H, t, J = 1.2 Hz), 8.66 (1H, d, J = 2.4 Hz). LRMS (ESI$^+$) 384 [M + H]$^+$. |
| 20-10 | 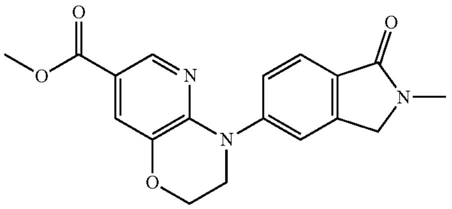 | $^1$H NMR (400 MHz, $CDCl_3$) δ 3.22 (3H, s), 3.90 (3H, s), 3.98-4.03 (2H, m), 4.37-4.44 (4H, m), 7.43 (1H, dd J = 8.6, 1.8 Hz), 7.56-7.58 (1H, m), 7.68 (1H, d J = 1.8 Hz), 7.89 (1H, d J = 8.6 Hz), 8.42 (1H, d J = 1.8 Hz). LRMS (ESI$^+$) 340 [M + H]$^+$. |

Reference Example 21-1

[Formula 119]

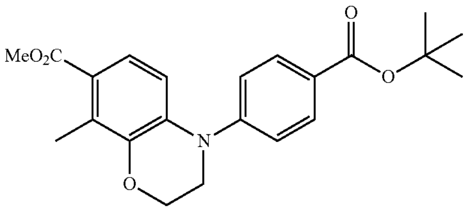

Methyl 4-(4-(tert-Butoxycarbonyl)phenyl)-8-methyl-3,4-dihydro-2H-benzo[b][1,4]oxazine-7-carboxylate A solution, in 1,4-dioxane (2.0 mL), of methyl 4-(4-tert-butoxycarbonyl)phenyl)-8-chloro-3,4-dihydro-2H-benzo[b][1,4]oxazine-7-carboxylate (80.0 mg), trimethylboroxine (49.7 mg), tetrakis(triphenylphosphine)palladium (0) (45.8 mg) and potassium carbonate (109 mg) was heated to reflux for 7.5 hours, and 1,4-dioxane (4 mL) was then added thereto. To the resultant reaction solution, trimethylboroxine (49.7 mg), tetrakis(triphenylphosphine)palladium (0) (45.8 mg) and potassium carbonate (109 mg) were added, the resultant was heated to reflux for 9.5 hours, and the resultant reaction solution was then concentrated under reduced pressure. The thus obtained residue was purified by silica gel column chromatography (ethyl acetate:hexane=5:95 to 20:80) to obtain the title compound (53.1 mg).

$^1$H NMR (400 MHz, $CDCl_3$) δ: 1.59 (9H, s), 2.50 (3H, s), 3.77 (2H, t, J=4.6 Hz), 3.85 (3H, s), 4.35 (2H, t, J=4.3 Hz), 6.87 (1H, d, J=8.6 Hz), 7.22-7.28 (2H, m), 7.36 (1H, d, J=9.2 Hz), 7.95-7.99 (2H, m).

LRMS (ESI$^+$) 384 [M+H]$^+$.

Reference Example 21-2

[Formula 120]

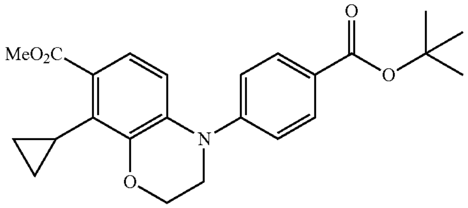

Methyl 4-(4-(tert-Butoxycarbonyl)phenyl)-8-cyclopropyl-3,4-dihydro-2H-benzo[b][1,4]oxazine-7-carboxylate The title compound was synthesized in the same manner as in Reference Example 21-1 by using corresponding starting material and reactant.

$^1$H NMR (400 MHz, $CDCl_3$) δ: 0.53 (2H, g, J=5.5 Hz), 0.92-0.98 (2H, m), 1.59 (9H, s), 1.92-2.01 (1H, m), 3.77 (2H, t, J=4.3 Hz), 3.88 (3H, s), 4.35 (2H, t, J=4.3 Hz), 6.90 (1H, d, J=8.6 Hz), 7.09 (1H, d, J=8.6 Hz), 7.20-7.25 (2H, m), 7.94-7.98 (2H, m).

LRMS (ESI$^+$) 410 [M+H]$^+$.

Reference Example 22-1

[Formula 121]

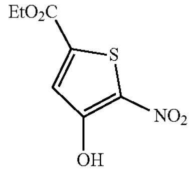

Ethyl 4-Hydroxy-5-nitrothiophene-2-carboxylate

To a solution of ethyl 4-methoxy-5-nitrothiophene-2-carboxylate (701 mg; known compound described in literature, US 20130324501) in pyridine (30.3 mL), lithium iodide (4.05 g) was added. The resultant was stirred at 100° C. for 2.5 hours, and the resultant reaction solution was added to 1 mol/L hydrogen chloride aqueous solution (100 mL). The resultant was extracted with dichloromethane (10 mL×5), and the resultant organic layers were combined, washed with 4 mol/L hydrogen chloride aqueous solution (35 mL×3) and saturated saline, and dried over sodium sulfate. After filtration, the resultant filtrate was concentrated under reduced pressure to obtain the title compound in the form of a reddish brown solid (505 mg).

$^1$H NMR (400 MHz, $CDCl_3$) δ 1.40 (3H, t, J=7.3 Hz), 4.41 (2H, q, J=7.1 Hz), 7.39 (1H, s), 9.83 (1H, s).

LRMS (ESI−) 216 $[M-H]^-$.

Reference Example 23-1

[Formula 122]

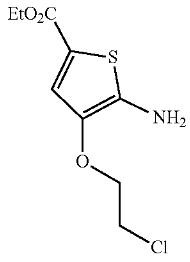

Ethyl 5-Amino-4-(2-chloroethoxy)thiophene-2-carboxylate

A solution, in acetic acid (44 mL), of ethyl 4-(2-chloroethoxy)-5-nitrothiophene-2-carboxylate (617 mg) and reduced iron (614 mg) was stirred at 60° C. for 40 minutes, and the resultant reaction solution was filtered through celite. The resultant filtrate was concentrated under reduced pressure, and the thus obtained residue was purified by silica gel column chromatography (ethyl acetate:hexane=10:90 to 50:50) to obtain the title compound (507 mg).

$^1$H NMR (400 MHz, $CDCl_3$) δ 1.33 (3H, t, J=7.3 Hz), 3.75 (2H, t, J=5.5 Hz), 4.08-4.22 (4H, m), 4.28 (2H, q, J=7.3 Hz), 7.37 (1H, s).

Reference Example 24-1

[Formula 123]

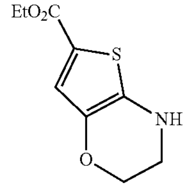

Ethyl 3,4-Dihydro-2H-thieno[3,2-b][1,4]oxazine-6-carboxylate

To a solution of ethyl 5-amino-4-(2-chloroethoxy)thiophene-2-carboxylate (481 mg) in N,N-dimethylacetamide (38 mL), potassium carbonate (530 mg) was added. The resultant reaction solution was stirred at 100° C. for 1 hour, and the resultant reaction solution was added to a 0.2 mol/L hydrogen chloride aqueous solution under ice cooling. The resultant was extracted with ethyl acetate, and the resultant organic layers were combined and dried over sodium sulfate. After filtering, the resultant filtrate was concentrated under reduced pressure, and the thus obtained residue was purified by silica gel column chromatography (ethyl acetate: hexane=5:95 to 35:65) to obtain the title compound (266 mg).

$^1$H NMR (400 MHz, $CDCl_3$) δ 1.33 (3H, t, J=7.0 Hz), 3.44 (2H, t, J=4.3 Hz), 3.94 (1H, s), 4.17 (2H, t, J=4.3 Hz), 4.28 (2H, q, J=7.1 Hz), 7.24 (1H, s).

LRMS ($ESI^+$) 214 $[M+H]^+$.

Reference Example 25-1

[Formula 124]

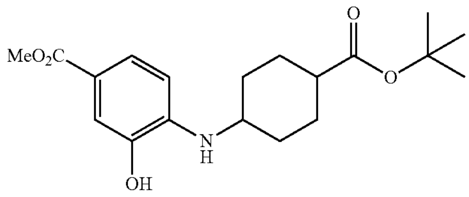

Methyl 4-((4-(tert-Butoxycarbonyl)cyclohexyl)amino)-3-hydroxybenzoate

To a solution, in tetrahydrofuran (50 mL), of methyl 4-amino-3-hydroxybenzoate (1.00 g) and tert-butyl 4-oxocyclohexane-1-carboxylate (991 mg), acetic acid (2.8 mL) was added. The resultant was stirred at 65° C. for 1.5 hours, sodium triacetoxyborohydride (1.59 g) was added to the resultant reaction solution at room temperature, followed by stirring at 65° C. for 4 hours. The reaction solution was added to a saturated sodium bicarbonate aqueous solution (200 mL), the resultant was extracted with ethyl acetate (50 mL×2), and the resultant organic layers were combined and dried over sodium sulfate. The resultant was filtered, the obtained filtrate was concentrated under reduced pressure, and the thus obtained residue was purified by silica gel column chromatography (ethyl acetate:hexane=10:90 to 40:60) to obtain the title compound (1.12 g).

$^1$H NMR (400 MHz, $CDCl_3$) δ: 1.14-2.49 (18H, m), 3.25-3.60 (1H, m), 3.85 (3H, d, J=1.8 Hz), 4.37-4.74 (1H, m), 5.19-5.64 (1H, m), 6.55 (1H, t, J=7.0 Hz), 7.35-7.49 (1H, m), 7.57 (1H, d, J=8.5 Hz).

LRMS ($ESI^+$) 350 $[M+H]^+$.

Reference Example 25-2

[Formula 125]

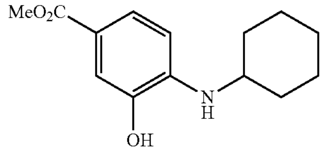

Methyl 4-(Cyclohexylamino)-3-hydroxybenzoate

The title compound was synthesized in the same manner as in Reference Example 25-1 by using corresponding starting material and reactant.

$^{1}$H NMR (400 MHz, $CDCl_3$) δ: 1.17-1.32 (3H, m), 1.33-1.46 (2H, m), 1.62-1.71 (1H, m), 1.72-1.85 (2H, m), 1.99-2.13 (2H, m), 3.26-3.41 (1H, m), 3.85 (3H, s), 4.53 (1H, s), 5.09-5.51 (1H, m), 6.56 (1H, d, J=8.5 Hz), 7.38-7.50 (1H, m), 7.57 (1H, d, J=7.9 Hz).

LRMS ($ESI^+$) 250 $[M+H]^+$.

Reference Example 26-1

[Formula 126]

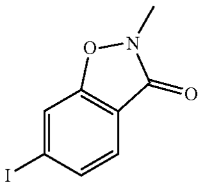

Isomer A

[Formula 127]

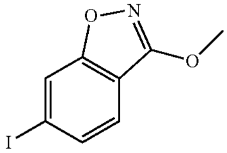

Isomer B

Isomer A: 6-iodo-2-methylbenzo[d]isoxazol-3 (2H)-one

Isomer B: 6-iodo-3-methoxybenzo[d]isoxazole

To a solution of methyl 2-hydroxy-4-iodobenzoate (7.75 g; commercially available product) in 1,4-dioxane (200 mL), hydroxylamine (50 mL) was added at room temperature. The resultant was stirred at room temperature for 3 days, water and ethyl acetate were added to the resultant reaction solution, and the organic layer and the aqueous layer were separated. The aqueous layer was prepared to be acidic by using concentrated hydrochloric acid. The resultant was extracted with ethyl acetate, washed with saturated saline, and dried over sodium sulfate. The resultant was filtered, the thus obtained filtrate was concentrated under reduced pressure to obtain a crude product containing N, 2-dihydroxy-4-iodobenzamide (11.8 g).

To a solution, in tetrahydrofuran (200 mL), of the crude product (11.8 g) containing N,2-dihydroxy-4-iodobenzamide, 1,1'-carbonyldiimidazole (13.6 g) was added. The resultant reaction solution was heated to reflux for 1.5 hours, water and ethyl acetate were added thereto, and the organic layer and the aqueous layer were separated. The aqueous layer was prepared to be acidic by using concentrated hydrochloric acid. The resultant was extracted with ethyl acetate, washed with water and saturated saline, and dried over magnesium sulfate. The resultant was filtered, and the thus obtained filtrate was concentrated under reduced pressure to obtain a crude product containing 6-iodobenzo[d]isoxazol-3 (2H)-one (4.08 g).

To a solution, in N,N-dimethylformamide (5.9 mL), of the crude product (461 mg) containing 6-iodobenzo[d]isoxazol-3 (2H)-one, methyl iodide (219 μL) was added. To the resultant reaction solution, potassium carbonate (486 mg) was added at room temperature, followed by stirring at room temperature for 5 hours. The resultant was filtered, the thus obtained filtrate was concentrated under reduced pressure, and the thus obtained residue was purified by silica gel column chromatography (ethyl acetate:hexane=5:95 to 100:0) to obtain 6-iodo-2-methylbenzo[d]isoxazol-3 (2H)-one (104 mg) and 6-iodo-3-methoxybenzo[d]isoxazole (111 mg).

6-Iodo-2-methylbenzo[d]isoxazol-3 (2H)-one $^{1}$H NMR (400 MHz, $CDCl_3$) δ: 3.65 (3H, s), 7.55 (1H, d, J=7.9 Hz), 7.61 (1H, dd, J=7.9, 1.2 Hz), 7.65 (1H, d, J=1.2 Hz).

LRMS ($ESI^+$) 276 $[M+H]^+$.

6-Iodo-3-methoxybenzo[d]isoxazole $^{1}$H NMR (400 MHz, $CDCl_3$) δ: 4.16 (3H, s), 7.36 (1H, d, J=7.9 Hz), 7.59 (1H, dd, J=7.9, 1.2 Hz), 7.86 (1H, s).

LRMS ($ESI^+$) 276 $[M+H]^+$.

Compounds of the following Reference Example 26-2 (an isomer A and an isomer B) were obtained in the same manner as in Reference Example 26-1 by using corresponding starting materials and reactants. Their structures and spectrum data are shown in the following table.

TABLE 29

| Reference Example No. | Chemical Structural Formula | Spectrum Data |
|---|---|---|
| 26-2 Isomer A | 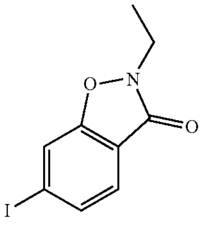 | $^{1}$H NMR (400 MHz, $CDCl_3$) δ 1.38 (3H, t, J = 7.0 Hz), 4.08 (2H, q, J = 7.1 Hz), 7.55 (1H, d, J = 8.6 Hz), 7.61 (1H, dd, J = 7.9, 1.2 Hz), 7.66 (1H, d, J = 1.2 Hz). LRMS ($ESI^+$) 290 $[M + H]^+$. |

TABLE 29-continued

| Reference Example No. | Chemical Structural Formula | Spectrum Data |
|---|---|---|
| 26-2 Isomer B | 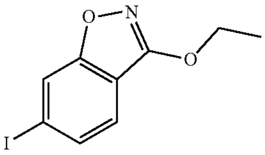 | $^1$H NMR (400 MHz, $CDCl_3$) δ 1.51 (3H, t, J = 7.0 Hz), 4.49 (2H, q, J = 6.9 Hz), 7.37 (1H, d, J = 8.6 Hz), 7.58 (1H, dd, J = 7.9, 1.2 Hz), 7.85 (1H, s). LRMS (ESI$^+$) 290 [M + H]$^+$. |

Reference Example 27-1

[Formula 128]

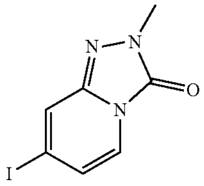

7-Iodo-2-methyl-[1,2,4]triazolo[4,3-a]pyridin-3(2H)-one

To a solution of 7-iodo-[1,2,4]triazolo[4,3-a]pyridin-3(2H)-one (203 mg; known compound described in literature, WO2011057757A1) in N,N-dimethylformamide (2.6 mL), methyl iodide (96 μL) was added. To the resultant reaction solution, potassium carbonate (214 mg) was added at room temperature, followed by stirring at room temperature for 2 hours. A solid precipitated by adding water to the resultant reaction mixture was collected by filtration, dissolved in dichloromethane (5 mL) and dried over sodium sulfate. The resultant was filtered, the thus obtained filtrate was concentrated under reduced pressure, and the thus obtained residue was purified by silica gel column chromatography (ethyl acetate:hexane=10:90 to 65:35) to obtain the title compound (122 mg).

$^1$H NMR (400 MHz, $CDCl_3$) δ: 3.64 (3H, s), 6.71 (1H, dd, J=7.3, 1.8 Hz), 7.50 (1H, d, J=7.3 Hz), 7.56 (1H, d, J=1.2 Hz).

LRMS (ESI$^+$) 276 [M+H]$^+$.

Compounds of the following Reference Examples 27-2 to 27-32 were obtained in the same manner as in Reference Example 27-1 by using corresponding starting materials and reactants. Their structures and spectrum data are shown in the following tables.

TABLE 30

| Reference Example No. | Chemical Structural Formula | Spectrum Data |
|---|---|---|
| 27-2 | 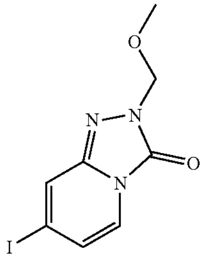 | $^1$H NMR (400 MHz, $CDCl_3$) δ: 3.28 (3H, s), 5.17 (2H, s), 6.81 (1H, dd, J = 7.3, 1.2 Hz), 7.65 (1H, dd, J = 7.3, 1.2 Hz), 7.82 (1H, s). LRMS (ESI$^+$) 306 [M + H]$^+$. |
| 27-3 | 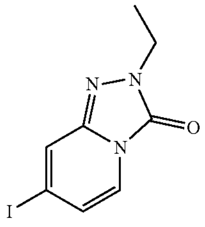 | $^1$H NMR (400 MHz, $CDCl_3$) δ: 1.41 (3H, t, J = 7.0 Hz), 4.03 (2H, q, J = 7.1 Hz), 6.70 (1H, dd, J = 7.3, 1.8 Hz), 7.50 (1H, d, J = 7.3 Hz), 7.57 (1H, t, J = 1.2 Hz). LRMS (CI$^+$) 290 [M + H]$^+$. |
| 27-4 | 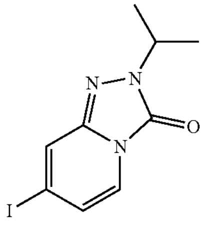 | $^1$H NMR (400 MHz, $CDCl_3$) δ: 1.44 (6H, d, J = 6.7 Hz), 4.64-4.71 (1H, m), 6.69 (1H, dd, J = 7.3, 1.2 Hz), 7.50 (1H, d, J = 7.3 Hz), 7.59 (1H, s). LRMS (ESI$^+$) 304 [M + H]$^+$. |

TABLE 30-continued

| Reference Example No. | Chemical Structural Formula | Spectrum Data |
|---|---|---|
| 27-5 | 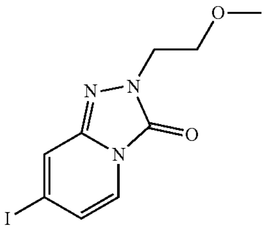 | $^1$H NMR (400 MHz, $CDCl_3$) δ: 3.36 (3H, s), 3.76 (2H, t, J = 5.5 Hz), 4.16 (2H, t, J = 5.5 Hz), 6.70 (1H, dd, J = 7.3, 1.2 Hz), 7.50 (1H, d, J = 7.3 Hz), 7.57 (1H, s). LRMS (ESI$^+$) 320 [M + H]$^+$. |
| 27-6 | 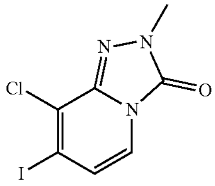 | $^1$H NMR (400 MHz, $CDCl_3$) δ 3.70 (3H, s), 6.86 (1H, d, J = 7.3 Hz), 7.47 (1H, d, J = 7.3 Hz). LRMS (ESI+) 310 [M + H]$^+$. |
| 27-7 | 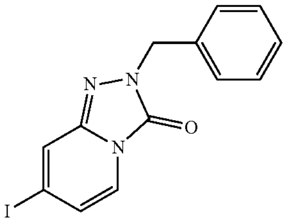 [SMILES: O=c1n(Cc2ccccc2)nc2cc(I)ccn12] | $^1$H NMR (400 MHz, $CDCl_3$) δ 5.13 (2H, s), 6.70 (1H, dd, J = 7.3, 1.8 Hz), 7.27-7.41 (5H, m), 7.51 (1H, dd, J = 7.3, 1.2 Hz), 7.54 (1H, d, J = 1.2 Hz). LRMS (ESI$^+$) 352 [M + H]$^+$. |

TABLE 31

| Reference Example No. | Chemical Structural Formula | Spectrum Data |
|---|---|---|
| 27-8 | 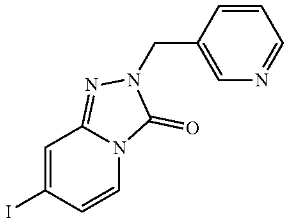 [SMILES: O=c1n(Cc2cccnc2)nc2cc(I)ccn12] | $^1$H NMR (400 MHz, $CDCl_3$) δ 5.14 (2H, s), 6.72 (1H, dd, J = 7.3, 1.2 Hz), 7.24-7.32 (1H, m), 7.51 (1H, d, J = 7.3 Hz), 7.55 (1H, t, J = 1.2 Hz), 7.72 (1H, dt, J = 7.9, 1.8 Hz), 8.57 (1H, dd, J = 4.6, 1.5 Hz), 8.67 (1H, d, J = 2.4 Hz). LRMS (ESI$^+$) 342 [M + H]$^+$. |
| 27-9 | 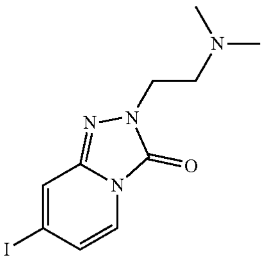 [SMILES: CN(C)CCn1nc2cc(I)ccn2c1=O] | $^1$H NMR (400 MHz, $CDCl_3$) δ 2.30 (6H, s), 2.74 (2H, t, J = 6.4 Hz), 4.07 (2H, t, J = 6.4 Hz), 6.69 (1H, dd, J = 7.3, 1.8 Hz), 7.49 (1H, dd, J = 7.3, 1.2 Hz), 7.56 (1H, t, J = 1.2 Hz). LRMS (ESI$^+$) 333 [M + H]$^+$. |
| 27-10 | 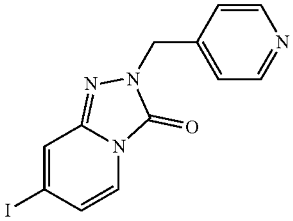 [SMILES: O=c1n(Cc2ccncc2)nc2cc(I)ccn12] | $^1$H NMR (400 MHz, $CDCl_3$) δ 5.13 (2H, s), 6.75 (1H, dd, J = 7.3, 1.8 Hz), 7.22-7.30 (2H, m), 7.52 (1H, d, J = 7.3 Hz), 7.56-7.59 (1H, m), 8.57-8.61 (2H, m). LRMS (ESI$^+$) 353 [M + H]$^+$. |

TABLE 31-continued

| Reference Example No. | Chemical Structural Formula | Spectrum Data |
|---|---|---|
| 27-11 | 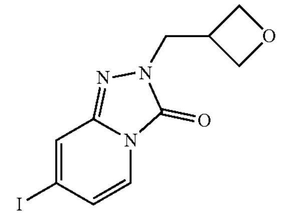 [SMILES: O=c1n(CC2COC2)nc2cc(I)ccn12] | $^1$H NMR (400 MHz, $CDCl_3$) δ 3.42-3.56 (1H, m), 4.27 (2H, d, J = 7.3 Hz), 4.61 (2H, t, J = 6.1 Hz), 4.82 (2H, dd, J = 7.9, 6.7 Hz), 6.72 (1H, dd, J = 7.3, 1.2 Hz), 7.49 (1H, d, J = 7.3 Hz), 7.56 (1H, t, J = 1.2 Hz).<br>LRMS ($ESI^+$) 332 $[M + H]^+$. |
| 27-12 | 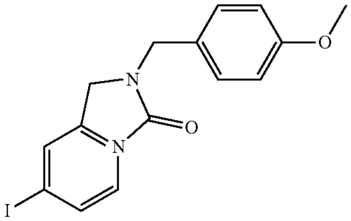 | $^1$H NMR (400 MHz, $CDCl_3$) δ 3.79 (3H, s), 4.22 (2H, s), 4.72 (2H, s), 6.83-6.90 (2H, m), 7.20-7.25 (2H, m), 7.53 (1H, d, J = 1.2 Hz), 7.58-7.62 (1H, m), 7.74 (1H, d, J = 7.9 Hz).<br>LRMS ($ESI^+$) 342 $[M + H]^+$. |
| 27-13 | 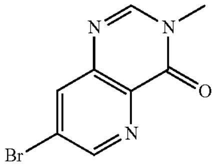 | $^1$H NMR (400 MHz, $CDCl_3$) δ 3.67 (3H, s), 8.12 (1H, s), 8.24 (1H, d, J = 1.8 Hz), 8.90 (1H, d, J = 1.8 Hz).<br>LRMS ($ESI^+$) 240 $[M + H]^+$. |
| 27-14 | 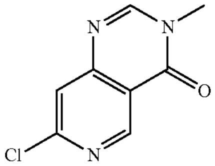 | $^1$H NMR (400 MHz, DMSO-$d_6$) 5 3.48 (3H, s), 7.75 (1H, s), 8.60 (1H, s), 9.14 (1H, s).<br>LRMS ($ESI^+$) 196 $[M + H]^+$. |

TABLE 32

| Reference Example No. | Chemical Structural Formula | Spectrum Data |
|---|---|---|
| 27-15 | 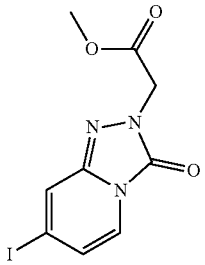 [SMILES: COC(=O)Cn1nc2cc(I)ccn2c1=O] | $^1$H NMR (400 MHz, $CDCl_3$) δ 3.79 (3H, s), 4.75 (2H, s), 6.73 (1H, dd, J = 7.3, 1.2 Hz), 7.50 (1H, d, J = 7.3 Hz), 7.57 (1H, d, J = 1.2 Hz).<br>LRMS ($ESI^+$) 334 $[M + H]^+$. |
| 27-16 | 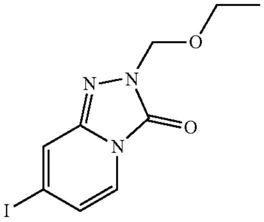 | $^1$H NMR (400 MHz, $CDCl_3$) δ 1.22 (3H, t, J = 7.0 Hz), 3.65 (2H, q, J = 7.1 Hz), 5.34 (2H, s), 6.71 (1H, dd. J = 7.3, 1.8 Hz), 7.50 (1H, dd, J = 7.3, 1.2 Hz), 7.56-7.61 (1H, m).<br>LRMS ($ESI^+$) 320 $[M + H]^+$. |

TABLE 32-continued

| Reference Example No. | Chemical Structural Formula | Spectrum Data |
|---|---|---|
| 27-17 | 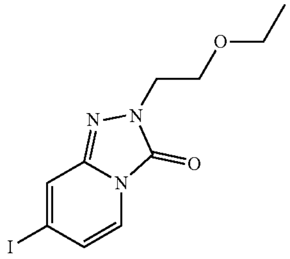 [SMILES: CCOCCn1nc2cc(I)ccn2c1=O] | $^1$H NMR (400 MHz, $CDCl_3$) δ 1.16 (3H, t, J = 7.0 Hz), 3.53 (2H, q, J = 7.1 Hz), 3.80 (2H, t, J = 5.8 Hz), 4.15 (2H, t, J = 5.8 Hz), 6.69 (1H, dd, J = 7.3, 1.2 Hz), 7.50 (1H, d, J = 7.3 Hz), 7.57 (1H, d, J = 1.2 Hz). LRMS (ESI$^+$) 334 [M + H]$^+$. |
| 27-18 | 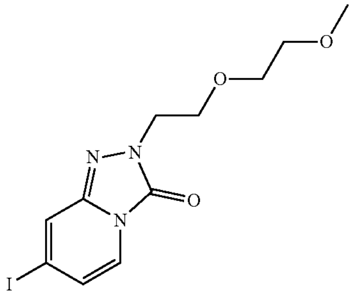 [SMILES: COCCOCCn1nc2cc(I)ccn2c1=O] | $^1$H NMR (400 MHz, $CDCl_3$) δ 3.34 (3H, s), 3.49-3.54 (2H, m), 3.61-3.67 (2H, m), 3.88 (2H, t, J = 6.1 Hz), 4.16 (2H, t, J = 5.8 Hz), 6.69 (1H, dd, J = 7.3, 1.2 Hz), 7.49 (1H, dd, J = 7.3, 1.2 Hz), 7.56 (1H, d, J = 1.2 Hz). LRMS (ESI$^+$) 364 [M + H]$^+$. |

TABLE 33

| Reference Example No. | Chemical Structural Formula | Spectrum Data |
|---|---|---|
| 27-19 | 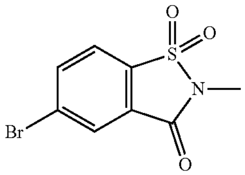 | $^1$H NMR (400 MHz, $CDCl_3$) δ 3.27 (3H, s), 7.80 (1H, d, 8.2 Hz), 8.00 (1H, dd, J = 8.2, 1.8 Hz), 8.20 (1H, d, J = 1.8 Hz). LRMS (ESI$^+$): 276 [M + H]$^+$. |
| 27-20 | 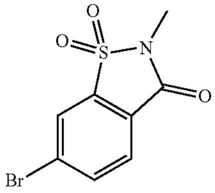 | $^1$H NMR (400 MHz, $CDCl_3$) δ 3.26 (3H, s), 7.92 (1H, d, 8.5 Hz), 7.96 (1H, dd, J = 8.5, 1.8 Hz), 8.07 (1H, d, J = 1.8 Hz). LRMS (ESI$^+$): 276 [M + H]$^+$. |
| 27-21 | 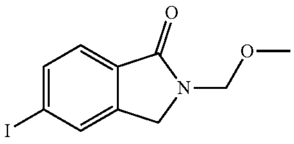 | $^1$H NMR (400 MHz, $CDCl_3$) δ 3.32 (3H, s), 4.46 (2H, s), 5.01 (2H, s), 7.62 (1H, d, J = 7.9 Hz), 7.84 (1H, d, J = 9.7 Hz), 7.88 (1H, s). LRMS (ESI$^+$) 304 [M + H]$^+$. |
| 27-23 | 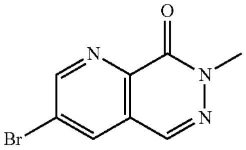 | $^1$H NMR (400 MHz, $CDCl_3$) δ 3.92 (3H, s), 8.09 (1H, s), 8.22 (1H, d, J = 1.8 Hz), 9.12 (1H, d, J = 2.4 Hz). LRMS (ESI$^+$) 240 [M + H]$^+$. |

TABLE 33-continued

| Reference Example No. | Chemical Structural Formula | Spectrum Data |
|---|---|---|
| 27-24 | 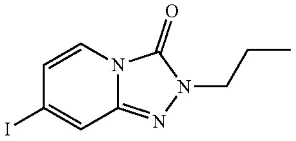 | $^1H$ NMR (400 MHz, $CDCl_3$) δ 0.96 (3H, t, J = 7.3 Hz), 1.79-1.92 (2H, m), 3.93 (2H, t, J = 7.3 Hz), 6.70 (1H, dd, J = 7.3, 1.2 Hz), 7.48-7.53 (1H, m), 7.55-7.59 (1H, m). LRMS ($EI^+$) 303 $[M]^+$. |
| 27-25 | 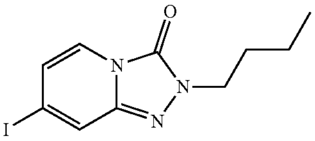 | $^1H$ NMR (400 MHz, $CDCl_3$) δ 0.95 (3H, t, J = 7.3 Hz), 1.31-1.43 (2H, m), 1.75-1.87 (2H, m), 3.96 (2H, t, J = 7.3 Hz), 6.70 (1H, dd, J = 7.3, 1.2 Hz), 7.48-7.52 (1H, m), 7.55-7.58 (1H, m). LRMS ($EI^+$) 317 $[M]^+$. |
| 27-26 | 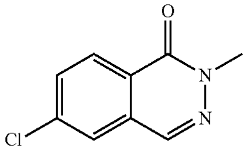 | $^1H$ NMR (400 MHz, $CDCl_3$) δ 3.70 (3H, s), 7.88 (1H, dd, J = 8.6, 2.4 Hz), 8.09 (1H, d, J = 1.8 Hz), 8.23 (1H, d, J = 8.6 Hz), 8.37 (1H, s). LRMS ($ESI^+$) 195 $[M + H]^+$. |

TABLE 34

| Reference Example No. | Chemical Structural Formula | Spectrum Data |
|---|---|---|
| 27-27 | 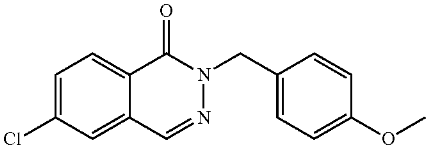 [SMILES: COc1ccc(Cn2ncc3cc(Cl)ccc3c2=O)cc1] | $^1H$ NMR (400 MHz, $CDCl_3$) δ 3.77 (3H, s), 5.32 (2H, s), 6.83-6.88 (2H, m), 7.40-7.45 (2H, m), 7.65 (1H, d, J = 1.8 Hz), 7.69 (1H, dd, J = 8.3, 2.1 Hz), 8.09 (1H, s), 8.36 (1H, d, J = 8.6 Hz). LRMS ($ESI^+$) 301 $[M + H]^+$. |
| 27-28 | 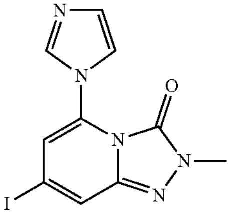 [SMILES: Cn1nc2cc(I)cc(-n3ccnc3)n2c1=O] | $^1H$ NMR (400 MHz, $CDCl_3$) δ 3.57 (3H, s), 6.58 (1H, d, J = 12 Hz), 7.19-7.23 (2H, m), 7.59 (1H, d, J = 1.8 Hz), 7.75 (1H, s). LRMS ($ESI^+$) 342 $[M + H]^+$. |
| 27-29 | 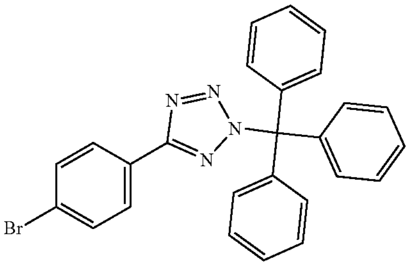 | $^1H$ NMR (400 MHz, $CDCl_3$) δ 7.09-7.20 (6H, m), 7.29-7.45 (9H, m), 7.56-7.61 (2H, m), 7.99-8.04 (2H, m). MS (not detected) |
| 27-30 | 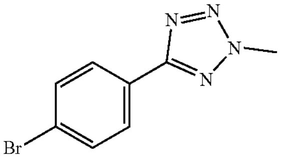 | $^1H$ NMR (400 MHz, $CDCl_3$) δ 4.40 (3H, s), 7.61-7.65 (2H, m), 7.99-8.03 (2H, m). LRMS ($ESI^+$) 239 $[M + H]^+$. |

TABLE 34-continued

| Reference Example No. | Chemical Structural Formula | Spectrum Data |
|---|---|---|
| 27-31 | 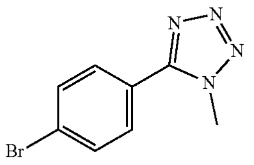 | $^{1}$H NMR (400 MHz, $CDCl_3$) δ 4.18 (3H, s), 7.62-7.65 (2H, m), 7.71-7.75 (2H, m). LRMS (ESI$^+$) 239 [M + H]$^+$. |
| 27-32 | 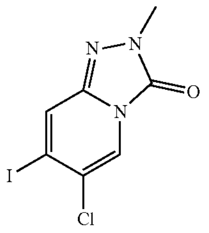 | $^{1}$H NMR (400 MHz, $CDCl_3$) δ 3.65 (3H, s), 7.76 (1H, s), 7.88 (1H, s). LRMS (ESI$^+$) 310 [M + H]$^+$. |

[Formula 129]

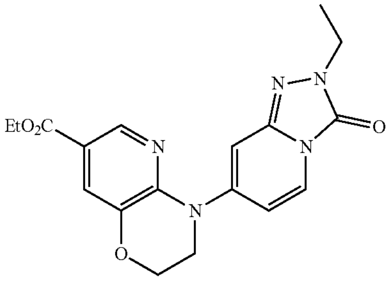

Ethyl 4-(2-Ethyl-3-oxo-2,3-dihydro-[1,2,4]triazolo[4,3-a]pyridin-7-yl)-3,4-dihydro-2H-pyrido[3,2-b][1,4]oxazine-7-carboxylate A solution, in toluene (16 mL), of ethyl 3,4-dihydro-2H-pyrido[3,2-b][1,4]oxazine-7-carboxylate (339 mg), 2-ethyl-7-iodo-[1,2,4]triazolo[4,3-a]pyridin-3(2H)-one (474 mg), palladium (II) acetate (18.3 mg), 2-dicyclohexylphosphino-2',4',6'-triisopropylbiphenyl (58.1 mg) and cesium carbonate (1.59 g) was stirred for 3 hours under heating to reflux, the resultant reaction solution was filtered, and the thus obtained filtrate was concentrated under reduced pressure. The thus obtained residue was purified by silica gel column chromatography (ethyl acetate:hexane=10:90 to 100:0) to obtain the title compound (498 mg).

$^{1}$H NMR (400 MHz, DMSO-$d_6$) δ: 1.25-1.31 (6H, m), 3.89 (2H, q, J=7.1 Hz), 3.97 (2H, t, J=4.2 Hz), 4.27 (2H, q, J=7.5 Hz), 4.37 (2H, t, J=4.2 Hz), 6.92 (1H, dd, J=7.6, 2.1 Hz), 7.01 (1H, d, J=1.2 Hz), 7.53 (1H, d, J=1.8 Hz), 7.78 (1H, d, J=7.3 Hz), 8.29 (1H, d, J=1.8 Hz).

LRMS (ESI$^+$) 370 [M+H]$^+$.

Compounds of the following Reference Examples 28-2 to 28-6 were obtained in the same manner as in Reference Example 28-1 by using corresponding starting materials and reactants. Their structures and spectrum data are shown in the following tables.

TABLE 35

| Reference Example No. | Chemical Structural Formula | Spectrum Data |
|---|---|---|
| 28-2 | 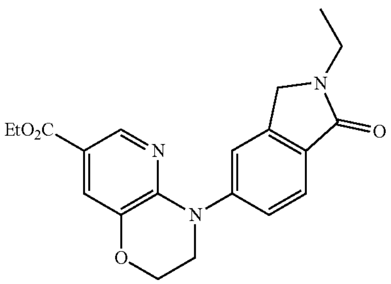 | $^{1}$H NMR (400 MHz, $CDCl_3$) δ: 1.27 (3H, t, J = 7.3 Hz), 1.36 (3H, t, J = 7.3 Hz), 3.68 (2H, q, J = 7.3 Hz), 3.98 (2H, t, J = 4.3 Hz), 4.31-4.42 (6H, m), 7.40 (1H, dd, J = 7.9, 1.8 Hz), 7.56 (1H, d, J = 1.2 Hz), 7.66 (1H, d, J = 1.8 Hz), 7.87 (1H, d, J = 7.9 Hz), 8.41 (1H, d, J = 1.8 Hz). LRMS (ESI$^+$) 368 [M + H]$^+$. |

TABLE 36

| Reference Example No. | Chemical Structural Formula | Spectrum Data |
|---|---|---|
| 28-3 | 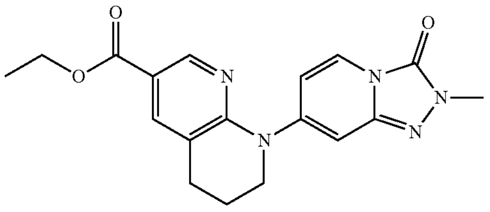 [SMILES: CCOC(=O)c1cnc2c(c1)CCCN2c1ccn2c(=O)n(C)nc2c1] | $^1H$ NMR (400 MHz, $CDCl_3$) δ 1.37 (3H, t, J = 7.0 Hz), 2.08-2.18 (2H, m), 2.90 (2H, t, J = 6.7 Hz), 3.64 (3H, s), 3.84 (2H, t, J = 5.8 Hz), 4.35 (2H, q, J = 7.1 Hz), 6.70-6.76 (2H, m), 7.61-7.68 (1H, m), 7.90-7.95 (1H, m), 8.63-8.68 (1H, m). LRMS ($ESI^+$) 354 $[M + H]^+$. |
| 28-4 | 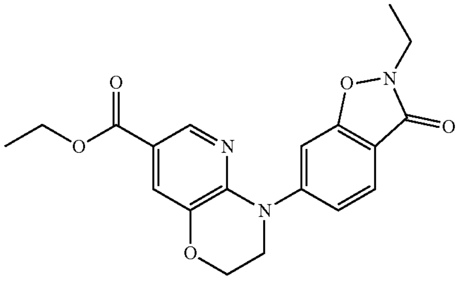 [SMILES: CCOC(=O)c1cnc2c(c1)OCCN2c1ccc2c(=O)n(CC)oc2c1] | $^1H$ NMR (400 MHz, $CDCl_3$) δ 1.33-1.42 (6H, m), 4.00 (2H, t, J = 4.6 Hz), 4.08 (2H, q, J = 7.1 Hz), 4.31-4.42 (4H, m), 7.29 (1H, dd, J = 8.6, 1.8 Hz), 7.33 (1H, d, J = 1.8 Hz), 7.70 (1H, d, J = 1.8 Hz), 7.82 (1H, d, J = 8.6 Hz), 8.45 (1H, d, J = 1.8 Hz). LRMS ($ESI^+$) 370 $[M + H]^+$. |
| 28-5 | 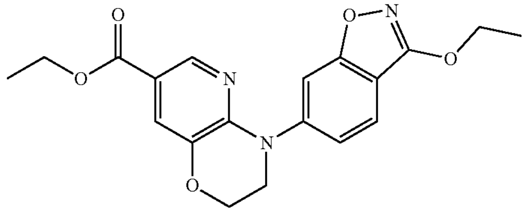 [SMILES: CCOC(=O)c1cnc2c(c1)OCCN2c1ccc2c(OCC)noc2c1] | $^1H$ NMR (400 MHz, $CDCl_3$) δ 1.36 (3H, t, J = 7.3 Hz), 1.52 (3H, t, J = 7.0 Hz), 4.00 (2H, t, J = 4.6 Hz), 4.34 (2H, q, J = 7.1 Hz), 4.40 (2H, t, J = 4.6 Hz), 4.50 (2H, q, J = 7.1 Hz), 7.37 (1H, dd, J = 8.6, 1.8 Hz), 7.41 (1H, d, J = 1.2 Hz), 7.62 (1H, d, J = 8.6 Hz), 7.67 (1H, d, J = 2.4 Hz), 8.42 (1H, d, J = 1.8 Hz). LRMS ($ESI^+$) 370 $[M + H]^+$. |
| 28-6 | 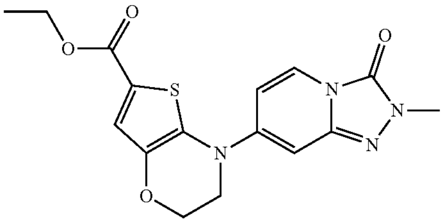 [SMILES: CCOC(=O)c1cc2c(s1)N(c1ccn3c(=O)n(C)nc3c1)CCO2] | $^1H$ NMR (400 MHz, $CDCl_3$) δ 1.25 (3H, t, J = 7.0 Hz), 3.47 (3H, s), 3.83 (2H, t, J = 4.3 Hz), 4.22 (2H, q, J = 7.1 Hz), 4.33 (2H, t, J = 4.0 Hz), 6.81 (1H, d, J = 2.4 Hz), 6.85 (1H, dd, J = 7.6, 2.1 Hz), 7.37 (1H, s), 7.88 (1H, d, J = 6.7 Hz). LRMS ($ESI^+$) 361 $[M + H]^+$. |

Reference Example 29-1

[Formula 130]

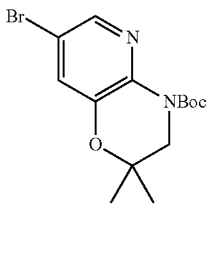

tert-Butyl 7-Bromo-2,2-dimethyl-2,3-dihydro-4H-pyrido[3,2-b] [1,4]oxazine-4-carboxylate A mixture of 7-bromo-2,2-dimethyl-3,4-dihydro-2H-pyrido[3,2-b][1,4]oxazine (633 mg) and di-tert-butyl dicarbonate (2.84 g) was stirred at 80° C. for 5 hours. The resultant reaction mixture was purified by silica gel column chromatography (ethyl acetate:hexane=1:5) to obtain the title compound (925 mg).

$^1H$ NMR (400 MHz, $CDCl_3$) δ 1.34 (6H, s), 1.54 (9H, s), 3.67 (2H, s), 7.29 (1H, d, J=1.8 Hz), 8.10 (1H, d, J=1.8 Hz).

LRMS ($ESI^+$) 343 $[M+H]^+$.

Compounds of the following Reference Examples 29-2 to 29-4 were obtained in the same manner as in Reference Example 29-1 by using corresponding starting materials and reactants. Their structures and spectrum data are shown in the following table.

TABLE 37

| Reference Example No. | Chemical Structural Formula | Spectrum Data |
|---|---|---|
| 29-2 | 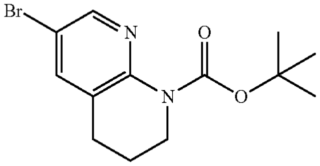 | $^1$H NMR (400 MHz, $CDCl_3$) δ 1.53 (9H, s), 1.88-1.96 (2H, m), 2.75 (2H, t, J = 6.7 Hz), 3.76 (2H, t, J = 6.1 Hz), 7.52 (1H, d, J = 2.4 Hz), 8.35 (1H, d, J = 2.4 Hz).<br>LRMS (ESI$^+$) 254 [M + H]$^+$. |
| 29-3 | 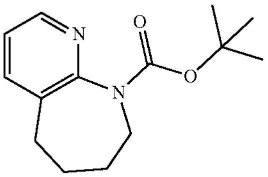 | $^1$H NMR (400 MHz, $CDCl_3$) δ 1.43 (9H, s), 1.55-1.79 (4H, m), 1.80-1.91 (2H, m), 2.73 (2H, t, J = 5.4 Hz), 7.11 (1H, d d, J = 7.3, 4.8 Hz), 7.54 (1H, dd, J = 7.3, 1.8 Hz), 8.35 (1H, d, J = 3.6 Hz).<br>LRMS (ESI$^+$) 254 [M + H]$^+$. |
| 29-4 | 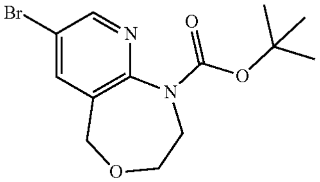 | $^1$H NMR (400 MHz, $CDCl_3$) δ 1.46 (9H, s), 3.29-4.22 (4H, m), 4.54 (2H, s), 7.76 (1H, d, J = 2.4 Hz), 8.49 (1H, d, J = 1.8 Hz).<br>LRMS (ESI$^+$) 254 [M + H]$^+$. |

Reference Example 30-1

[Formula 131]

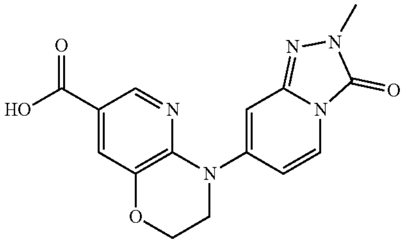

4-(2-Methyl-3-oxo-2,3-dihydro-[1,2,4]triazolo[4,3-a]pyridin-7-yl)-3,4-dihydro-2H-pyrido[3,2-b][1,4]oxazine-7-carboxylic Acid A solution, in toluene (49 mL), of ethyl 3,4-dihydro-2H-pyrido[3,2-b] [1,4]oxazine-7-carboxylate (1.02 g), 7-iodo-2-methyl-[1,2,4]triazolo[4,3-a]pyridin-3(2H)-one (1.48 g), palladium (II) acetate (55.0 mg), 2-dicyclohexylphosphino-2',4',6'-triisopropylbiphenyl (175 mg) and cesium carbonate (4.79 g) was heated to reflux for 3 hours. The resultant reaction solution was filtered through celite, and to the thus obtained filtrate, activated carbon (55 mg) and QuadraPure™ MPA (26 mg) were added, followed by heating to reflux for 1 hour. The resultant mixture was filtered through celite, and the thus obtained filtrate was concentrated under reduced pressure to obtain a crude product of ethyl 4-(2-methyl-3-oxo-2,3-dihydro-[1,2,4]triazolo[4,3-a]pyridin-7-yl)-3,4-dihydro-2H-pyrido[3,2-b][1,4] oxazine-7-carboxylate (2.09 g).

To a mixed solution, in tetrahydrofuran (80 mL) and methanol (20 mL), of the obtained crude product (2.09 g) of ethyl 4-(2-methyl-3-oxo-2,3-dihydro-[1,2,4]triazolo[4,3-a]pyridin-7-yl)-3,4-dihydro-2H-pyrido[3,2-b][1,4]oxazine-7-carboxylate, a 1 mol/L lithium hydroxide aqueous solution (4.9 mL) was added at room temperature. The resultant reaction solution was stirred at 45° C. for 4 hours, and then at room temperature for 13.7 hours. To the resultant reaction solution, a 1 mol/L lithium hydroxide aqueous solution (490 μL) was added at room temperature. The resultant reaction solution was stirred at 45° C. for 2.5 hours, and a 1 mol/L hydrogen chloride aqueous solution (5.4 mL) was then added to the reaction solution at room temperature. The resultant reaction solution was concentrated under reduced pressure, and the resultant was washed with water and then with ethyl acetate to obtain the title compound (1.59 g).

$^1$H NMR (400 MHz, DMSO-$d_6$) δ3.50 (3H, s), 3.96 (2H, t, J=4.6 Hz), 4.37 (2H, t, J=4.6 Hz), 6.94 (1H, dd, J=7.6, 2.1 Hz), 6.97 (1H, s), 7.52 (1H, d, J=1.8 Hz), 7.77 (1H, d, J=7.3 Hz), 8.27 (1H, d, J=1.8 Hz), 12.93 (1H, s).

LRMS (ESI$^+$) 328 [M+H]$^+$.

Compounds of the following Reference Examples 30-2 to 30-3 were obtained in the same manner as in Reference Example 30-1 by using corresponding starting materials and reactants. Their structures and spectrum data are shown in the following tables.

TABLE 38

| Reference Example No. | Chemical Structural Formula | Spectrum Data |
|---|---|---|
| 30-2 | 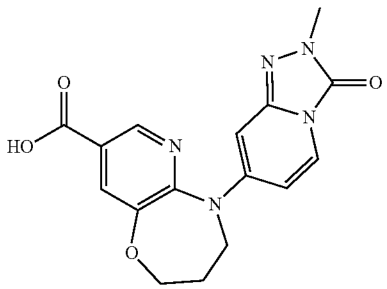 [SMILES: Cn1nc2cc(N3CCCOc4cc(C(=O)O)cnc43)ccn2c1=O] | $^1$H NMR (400 MHz, DMSO-d$_6$) δ 2.02-2.10 (2H, m), 3.47 (3H, s), 3.99 (2H, t, J = 6.1 Hz), 4.24 (2H, t, J = 5 8 Hz), 6.46 (1H, dd, J = 7.9, 1.8 Hz), 6.75 (1H, d, J = 1.8 Hz), 7.66 (1H, d, J = 7.9 Hz), 7.73 (1H, d, J = 2.4 Hz), 8.48 (1H, d, J = 1.8 Hz), 13.26 (1H, s). LRMS (ESI$^-$) 340 [M − H]$^-$. |

TABLE 39

| Reference Example No. | Chemical Structural Formula | Spectrum Data |
|---|---|---|
| 30-3 | 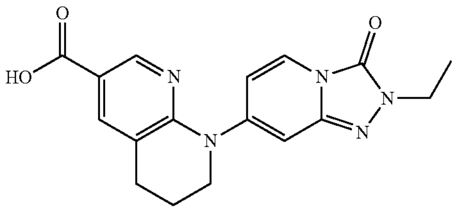 [SMILES: CCn1nc2cc(N3CCCc4cc(C(=O)O)cnc43)ccn2c1=O] | $^1$H NMR (400 MHz, CDCl$_3$) δ 1.29 (3H, t, J = 7.0 Hz), 1.95-2.06 (2H, m), 2.86 (2H, t, J = 6.4 Hz), 3.78-3.94 (4H, m), 6.72 (1H, dd, J = 7.9, 1.8 Hz), 7.01 (1H, d, J = 1.8 Hz), 7.72 (1H, d, J = 6.7 Hz), 7.84-7.89 (1H, m), 8.45 (1H, d, J = 1.8 Hz), 12.75 (1H, br s). LRMS (ESI$^-$) 338 [M − H]$^-$. |

Reference Example 31-1

[Formula 132]

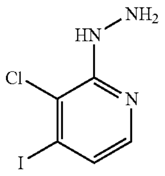

3-Chloro-2-hydrazinyl-4-iodopyridine

To a solution of 3-chloro-3-fluoro-4-iodopyridine (257 mg) in ethanol (2.6 mL), hydrazine monohydrate (514 μL) was added. The resultant was stirred under heating at room temperature for 0.5 hours and at 50° C. for 1 hour, ice water was added to the resultant reaction solution, and the thus precipitated solid was collected by filtration to obtain the title compound (245 mg).

$^1$H NMR (400 MHz, CDCl$_3$) δ 3.98 (2H, br s), 6.34 (1H, br s), 7.14 (1H, d, J=5.5 Hz), 7.72 (1H, d, J=5.5 Hz).

LRMS (ESI$^+$) 270 [M+H]$^+$.

Compounds of the following Reference Examples 31-2 to 31-3 were obtained in the same manner as in Reference Example 31-1 by using corresponding starting materials and reactants. Their structures and spectrum data are shown in the following table.

TABLE 40

| Reference Example No. | Chemical Structural Formula | Spectrum Data |
|---|---|---|
| 31-2 | 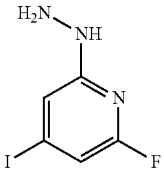 | $^1$H NMR (400 MHz, CDCl$_3$) δ 3.76 (2H, s), 5.86 (1H, s), 6.62 (1H, d, J = 1.8 Hz), 7.01 (1H, s). LRMS (ESI$^+$) 254 [M + H]$^+$. |

TABLE 40-continued

| Reference Example No. | Chemical Structural Formula | Spectrum Data |
|---|---|---|
| 31-3 | 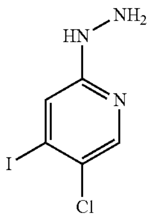 | $^1$H NMR (400 MHz, $CDCl_3$) δ 3.77 (2H, br s), 5.81 (1H, br s), 7.36 (1H, s), 8.04 (1H, s). LRMS ($ESI^+$) 270 $[M + H]^+$. |

Reference Example 32-1

[Formula 133]

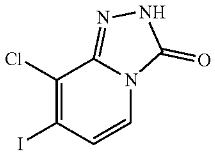

8-Chloro-7-iodo-[1,2,4]triazolo[4,3-a]pyridin-3(2H)-one

To a solution of 3-chloro-2-hydrazinyl-4-iodopyridine (240 mg) in acetonitrile (4.8 mL), 1,1'-carbonyldiimidazole (173 mg) was added, followed by stirring at room temperature for 8.3 hours. Ice water was added to the resultant reaction solution, and the thus precipitated solid was collected by filtration to obtain the title compound (242 mg).

$^1$H NMR (400 MHz, DMSO-$d_6$) δ6.91 (1H, d, J=7.3 Hz), 7.60 (1H, d, J=7.3 Hz), 12.70 (1H, s).

LRMS (ESI−) 294 $[M-H]^-$.

A compound of the following Reference Example 32-2 was obtained in the same manner as in Reference Example 32-1 by using corresponding starting material and reactant. Its structure and spectrum data are shown in the following table.

TABLE 41

| Reference Example No. | Chemical Structural Formula | Spectrum Data |
|---|---|---|
| 32-2 | 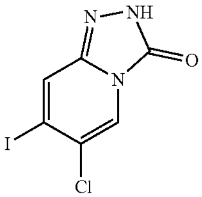 [SMILES: O=c1[nH]nc2cc(I)c(Cl)cn12] | $^1$H NMR (400 MHz, DMSO-$d_6$) δ 8.03 (1H, s), 8.13 (1H, d, J = 1.2 Hz), 12.63 (1H, s). LRMS ($ESI^-$) 294 $[M - H]^-$. |

Reference Example 33-1

[Formula 134]

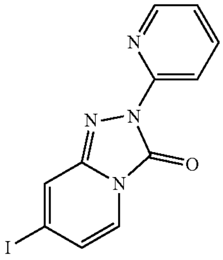

7-Iodo-2-(pyridin-2-yl)-[1,2,4]triazolo[4,3-a]pyridin-3(2H)-one

To a mixed solution, in dichloromethane (20 mL) and methanol (4 mL), of 7-iodo-[1,2,4]triazolo[4,3-a]pyridin-3(2H)-one (131 mg), triethylamine (209 μL) and pyridin-2-yl boronic acid (92.3 mg) were added. To the resultant reaction solution, copper (II) acetate (136 mg) was added at room temperature, followed by heating to reflux for 13.5 hours. The resultant reaction solution was concentrated under reduced pressure, and the thus obtained residue was purified by silica gel column chromatography (ethyl acetate:hexane=5:95 to 100:0, subsequently methanol:ethyl acetate=0:100 to 20:80) to obtain the title compound (8.4 mg).

$^1$H NMR (400 MHz, $CDCl_3$) δ 6.75-6.78 (1H, m), 7.19-7.32 (1H, m), 7.58 (1H, d, J=7.3 Hz), 7.69-7.71 (1H, m), 7.84-7.90 (1H, m), 8.28-8.33 (1H, m), 8.60-8.64 (1H, m).

LRMS ($ESI^+$) 339 $[M+H]^+$.

Reference Example 34-1

[Formula 135]

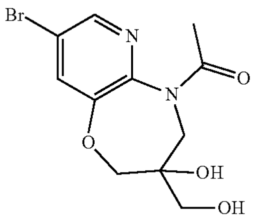

1-(8-Bromo-3-hydroxy-3-(hydroxymethyl)-3,4-dihydropyrido[3,2-b][1,4]oxazepin-5(2H)-yl)ethan-1-one To a mixture, with acetone (3.6 mL) and water (0.4 mL), of 1-(8-bromo-3-methylene-3,4-dihydropyrido[3,2-b][1,4]oxazepin-5(2H)-yl)ethan-1-one (111 mg), osmium tetroxide (2.5 wt % tert-butanol solution, 160 μL) and N-methylmorpholine oxide (68.9 mg) were added at room temperature. The resultant was stirred at 60° C. for 3 hours, and an aqueous solution (30 mL) of sodium hydrogen sulfite (40 mg) was added to the resultant reaction solution. After extraction with dichloromethane, the resultant organic layers were combined, washed with saturated saline, and dried over anhydrous sodium sulfate. The resultant was filtered, the obtained filtrate was concentrated under reduced pressure, and the thus obtained residue was purified by silica gel column chromatography (ethyl acetate:hexane=10:90 to 100:0, subsequently methanol/ethyl acetate=0:100 to 20:80)) to obtain the title compound (115 mg).

$^1$H NMR (400 MHz, $CDCl_3$) δ 1.53-1.66 (1H, m), 2.22 (3H, s), 2.91-3.08 (1H, m), 3.48-3.83 (4H, m), 3.88 (1H, d, J=12.2 Hz), 3.99-4.20 (1H, m), 7.59 (1H, d, J=1.8 Hz), 8.23 (1H, d, J=2.4 Hz).

LRMS (ESI$^+$) 317 [M+H]$^+$.

Reference Example 35-1

[Formula 136]

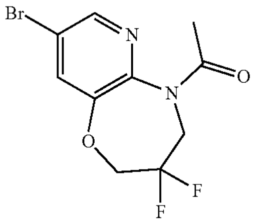

1-(8-Bromo-3,3-di fluoro-3,4-dihydropyrido[3,2-b][1,4]oxazepin-5(2H)-yl)ethan-1-one To a mixed solution, in acetone (13.5 mL) and water (4.5 mL), of 1-(8-bromo-3-hydroxy-3-(hydroxymethyl)-3,4-dihydropyrido[3,2-b][1,4]oxazepin-5(2H)-yl)ethan-1-one (114 mg), sodium periodate (385 mg) was added. The resultant was stirred at room temperature for 5 hours, and water was added to the resultant reaction solution. After extraction with a mixed solvent of dichloromethane and methanol, the resultant organic layers were combined, washed with saturated saline, and dried over anhydrous sodium sulfate. The resultant was filtered, the obtained filtrate was concentrated under reduced pressure, and the thus obtained residue was purified by silica gel column chromatography (ethyl acetate:hexane=10:90 to 100:0) to obtain a crude product of 5-acetyl-8-bromo-4,5-dihydropyrido[3,2-b][1,4]oxazepin-3(2H)-one (118 mg). To a solution, in dichloromethane (12 mL), of the thus obtained crude product (71.1 mg) of 5-acetyl-8-bromo-4,5-dihydropyrido[3,2-b][1,4]oxazepin-3(2H)-one, N,N-diethylaminosulfur trifluoride (131 μL) was added at room temperature. The resultant was stirred at room temperature for 2.5 hours, and a saturated sodium bicarbonate aqueous solution was added to the resultant reaction solution. After extraction with dichloromethane, the resultant organic layers were combined, washed with saturated saline, and dried over anhydrous sodium sulfate. The resultant was filtered, the obtained filtrate was concentrated under reduced pressure, and the thus obtained residue was purified by silica gel column chromatography (ethyl acetate:hexane=0:100 to 100:0) to obtain the title compound (39.3 mg).

$^1$H NMR (400 MHz, $CDCl_3$) δ 2.22 (3H, s), 4.18-4.41 (4H, m), 7.63 (1H, d, J=1.8 Hz), 8.26 (1H, d, J=1.8 Hz).

LRMS (FI$^+$) 306 [M]$^+$.

Reference Example 36-1

[Formula 137]

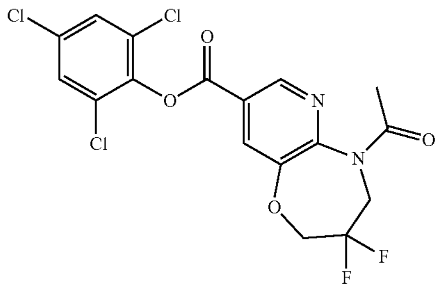

2,4,6-Trichlorophenyl 5-Acetyl-3,3-difluoro-2,3,4,5-tetrahydropyrido[3,2-b][1,4]oxazepine-8-carboxylate To a solution, in toluene (2.6 mL), of 1-(8-bromo-3,3-di fluoro-3,4-dihydropyrido[3,2-b] [1,4]oxazepin-5(2H)-yl) ethan-1-one (38.3 mg), palladium acetate (2.8 mg), 4,5-bis (diphenylphosphino)-9,9-dimethylxanthene (Xantphos) (14.5 mg) and diisopropylethylamine (63.8 μL), a solution of 2,4,6-trichlorophenyl formate (56.4 mg) in toluene (1.3 mL) was added at 85° C. in a dropwise manner over 1 hour, and the resultant was stirred at 85° C. for 1.5 hours. To the resultant reaction solution, diisopropylethylamine (63.8 μL) was added, and a solution of 2,4,6-trichlorophenyl formate (56.4 mg) in toluene (1.3 mL) was added thereto in a dropwise manner over 1 hour. The resultant was stirred at 85° C. for 0.5 hours, the resultant reaction solution was concentrated under reduced pressure, and the thus obtained residue was purified by silica gel column chromatography (ethyl acetate:hexane=5:95 to 50:50) to obtain the title compound (47.4 mg).

$^1$H NMR (400 MHz, $CDCl_3$) δ 2.39 (3H, s), 4.37 (2H, t, J=10.7 Hz), 4.45 (2H, t, J=11.6 Hz), 7.45 (2H, s), 8.18 (1H, d, J=2.4 Hz), 8.96 (1H, d, J=2.4 Hz).

LRMS (ESI$^+$) 451 [M+H]$^+$.

Compounds of the following Reference Examples 36-2 to 36-3 were obtained in the same manner as in Reference Example 36-1 by using corresponding starting materials and reactants. Their structures and spectrum data are shown in the following table.

TABLE 42

| Reference Example No. | Chemical Structural Formula | Spectrum Data |
|---|---|---|
| 36-2 | 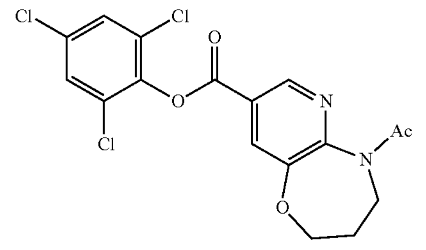 [SMILES: CC(=O)N1CCCOc2cc(C(=O)Oc3c(Cl)cc(Cl)cc3Cl)cnc21] | $^1$H NMR (400 MHz, DMSO-$d_6$) δ 1.96-2.04 (2H, m), 2.16 (3H, s), 3.90 (2H, t, J = 6.1 Hz), 4.29 (2H, t, J = 5.8 Hz), 7.95 (2H, s), 8.09 (1H, d, J = 1.8 Hz), 8.87 (1H, d, J = 2.4 Hz). LRMS (ESI$^+$) 415 [M + H]$^+$. |
| 36-3 | 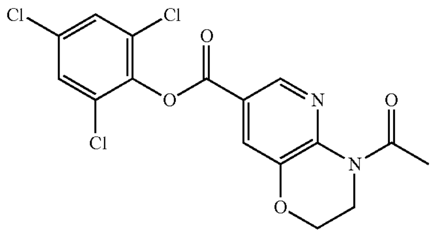 [SMILES: CC(=O)N1CCOc2cc(C(=O)Oc3c(Cl)cc(Cl)cc3Cl)cnc21] | $^1$H NMR (400 MHz, $CDCl_3$) δ 2.71 (3H, s), 4.12 (2H, t, J = 4.9 Hz), 4.33 (2H, t, J = 4.9 Hz), 7.44 (2H, s), 7.94 (1H, J = 2.4 Hz), 8.79 (1H, d, J = 1.8 Hz). LRMS (ESI$^+$) 401 [M + H]$^+$. |

Reference Example 37-1

[Formula 138]

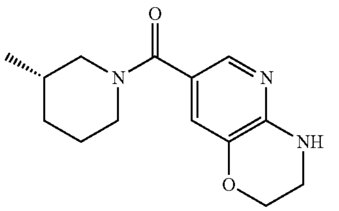

(S)-(3,4-Dihydro-2H-pyrido[3,2-b] [1,4]oxazin-7-yl)(3-methylpiperidin-1-yl)methanone To a solution of (S)-3-methylpiperidine hydrochloride (814 mg) in tetrahydrofuran (10 ml), triethylamine (2.79 mL), N,N-dimethyl-4-aminopyridine (30.5 mg) and 2,4,6-trichlorophenyl 4-acetyl-3,4-dihydro-2H-pyrido[3,2-b][1,4]oxazine-7-carboxylate (2.01 g) were added. After stirring at 45° C. for 8.3 hours, triethylamine (1.4 mL) was added to the resultant reaction solution. After stirring at 45° C. for 1.5 hours, methanol (6 mL) and an aqueous solution (6 mL) of potassium hydroxide (701 mg) was added to the reaction solution. After stirring at room temperature for 7.3 hours, an aqueous solution (6 mL) of potassium hydroxide (420 mg) was added to the reaction solution. After stirring at room temperature for 16 hours, 1 mol/L hydrogen chloride aqueous solution (12.5 mL) was added to the reaction solution. After extraction with ethyl acetate, the resultant organic layers were combined, washed with saturated saline and dried over anhydrous sodium sulfate. The resultant was filtered, and the obtained filtrate was concentrated under reduced pressure, and the thus obtained residue was purified by silica gel column chromatography (ethyl acetate: hexane=20:80 to 100:0) to obtain the title compound (1.28 g).

$^1$H NMR (400 MHz, $CDCl_3$) δ 0.78-0.99 (3H, m), 1.10-1.22 (1H, m), 1.42-1.76 (3H, m), 1.82-1.90 (1H, m), 2.37-3.03 (2H, m), 3.56-3.61 (2H, m), 3.63-4.71 (4H, m), 5.07 (1H, s), 7.07 (1H, d, J=1.2 Hz), 7.78 (1H, d, J=1.8 Hz).

LRMS (ESI$^+$) 262 [M+H]$^+$.

Compounds of the following Reference Examples 37-2 to 37-3 were obtained in the same manner as in Reference Example 37-1 by using corresponding starting materials and reactants. Their structures and spectrum data are shown in the following table.

TABLE 43

| Reference Example No. | Chemical Structural Formula | Spectrum Data |
|---|---|---|
| 37-2 | 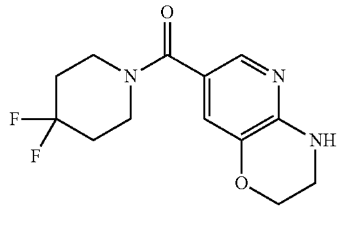 [SMILES: O=C(c1cnc2c(c1)OCCN2)N1CCC(F)(F)CC1] | $^1$H NMR (400 MHz, DMSO-$d_6$) δ 1.92-2.08 (4H, m), 3.38-3.45 (2H, m), 3.57 (4H, t, J = 5.5 Hz), 4.11 (2H, t, J = 4.6 Hz), 6.99 (1H, d, J = 1.8 Hz), 7.23 (1H, s), 7.70 (1H, d, J = 1.8 Hz). LRMS (ESI$^+$) 284 [M + H]$^+$. |

TABLE 43-continued

| Reference Example No. | Chemical Structural Formula | Spectrum Data |
|---|---|---|
| 37-3 | 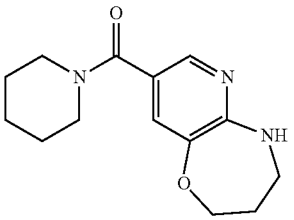 [SMILES: O=C(c1cnc2c(c1)OCCCN2)N1CCCCC1] | $^1$H NMR (400 MHz, $CDCl_3$) δ 1.55-1.73 (6H, m), 2.02-2.12 (2H, m), 3.40-3.46 (2H, m), 3.46-3.66 (4H, m), 4.20 (2H, t, J = 5.5 Hz), 4.91 (1H, brs), 7.23 (1H, d, J = 1.8 Hz), 7.87 (1H, d, J = 1.8 Hz).<br>LRMS ($ESI^+$) 262 $[M + H]^+$. |

Reference Example 38-1

[Formula 139]

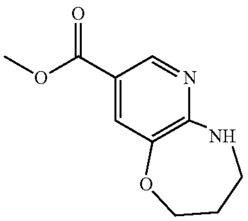

Methyl 2,3,4,5-Tetrahydropyrido[3,2-b][1,4]oxazepine-8-carboxylate

To a suspension of 2,4,6-trichlorophenyl 5-acetyl-2,3,4,5-tetrahydropyrido[3,2-b][1,4]oxazepine-8-carboxylate (1.10 g) in methanol (13.2 mL), a 5 mol/L sodium methoxide methanol solution (1.06 mL) was added in a dropwise manner, followed by stirring at 40° C. for 17.5 hours. To the resultant reaction solution, a 3 mol/L hydrogen chloride aqueous solution was added under ice cooling, and the resultant was washed with dichloromethane. The resultant organic layer was extracted with a 1 mol/L hydrogen chloride aqueous solution, and the extracted aqueous layers were combined. To the resultant aqueous layers, a 2 mol/L sodium hydroxide aqueous solution was added to adjust pH to 10 to 12, followed by extraction with dichloromethane. The thus extracted organic layers were combined, and dried over anhydrous sodium sulfate. The resultant was concentrated under reduced pressure to obtain the title compound (446 mg).

$^1$H NMR (400 MHz, $CDCl_3$) δ 2.06-2.15 (2H, m), 3.48-3.55 (2H, m), 3.87 (3H, s), 4.22 (2H, t, J=5.5 Hz), 5.16 (1H, brs), 7.67 (1H, d, J=1.8 Hz), 8.43 (1H, d, J=1.8 Hz).

LRMS ($ESI^+$) 209 $[M+H]^+$.

Reference Example 39-1

[Formula 140]

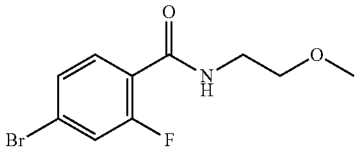

4-Bromo-2-fluoro-N-(2-methoxyethyl)benzamide

To a solution of 4-bromo-2-fluorobenzoic acid (500 mg) in N,N-dimethylformamide (22.9 mL), 2-methoxyethane-1-amine (236 μL), diisopropylethylamine (1.94 mL), and 1-[bis(dimethylamino)methylene]-1H-1,2,3-triazolo[4,5-b]pyridinium 3-oxide hexafluorophosphate (1.04 g) were added, followed by stirring at room temperature for 6 hours. The resultant reaction solution was concentrated under reduced pressure and purified by silica gel column chromatography (ethyl acetate:hexane=20:80 to 100:0) to obtain the title compound (599 mg).

$^1$H NMR (400 MHz, $CDCl_3$) δ 3.40 (3H, s), 3.57 (2H, t, J=5.1 Hz), 3.63-3.70 (2H, m), 6.99 (1H, br s), 7.32 (1H, dd, J=10.9, 1.8 Hz), 7.41 (1H, dd, J=8.5, 1.8 Hz), 7.98 (1H, t, J=8.2 Hz).

LRMS ($ESI^+$) 276 $[M+H]^+$.

Compounds of the following Reference Examples 39-2 to 39-5 were obtained in the same manner as in Reference Example 39-1 by using corresponding starting materials and reactants. Their structures and spectrum data are shown in the following tables.

TABLE 44

| Reference Example No. | Chemical Structural Formula | Spectrum Data |
|---|---|---|
| 39-2 | 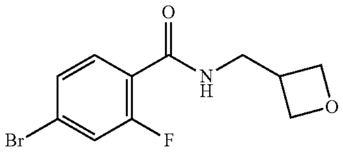 [SMILES: O=C(NCC1COC1)c1ccc(Br)cc1F] | $^1$H NMR (400 MHz, $CDCl_3$) δ 3.23-3.39 (1H, m), 3.74-3.81 (2H, m), 4.48 (2H, t, J = 6.1 Hz), 4.84 (2H, dd, J = 7.6, 6.4 Hz), 6.85 (1H, br s), 7.33 (1H, dd, J = 10.9, 1.8 Hz), 7.43 (1H, dd, J = 8.5, 1.8 Hz), 7.98 (1H, t, J = 8.5 Hz).<br>LRMS ($ESI^+$) 288 $[M + H]^+$. |

TABLE 44-continued

| Reference Example No. | Chemical Structural Formula | Spectrum Data |
|---|---|---|
| 39-3 | 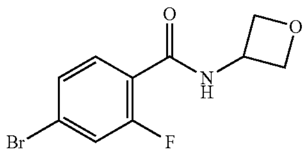 [SMILES: O=C(NC1COC1)c1ccc(Br)cc1F] | $^1$H NMR (400 MHz, $CDCl_3$) δ 4.61 (2H, t, J = 6.7 Hz), 5.02 (2H, t, J = 7.3 Hz), 5.19-5.30 (1H, m), 7.14 (1H, br s), 7.37 (1H, dd, J = 11.5, 1.8 Hz), 7.44 (1H, dd, J = 8.5, 1.8 Hz), 7.97 (1H, t, J = 8.5 Hz). LRMS (ESI$^+$) 274 [M + H]$^+$. |
| 39-4 | 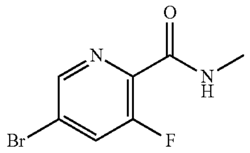 | $^1$H NMR (400 MHz, $CDCl_3$) δ 3.01 (3H, d, J = 4.8 Hz), 7.55-7.80 (2H, m), 8.41-8.46 (1H, m). LRMS (ESI$^+$) 233 [M + H]$^+$. |

TABLE 45

| Reference Example No. | Chemical Structural Formula | Spectrum Data |
|---|---|---|
| 39-5 | 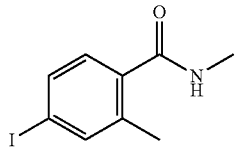 | $^1$H NMR (400 MHz, $CDCl_3$) δ 2.40 (3H, s), 2.99 (3H, d, J = 4.8 Hz), 5.62-5.85 (1H, m), 7.07 (1H, d, J = 8.5 Hz), 7.4 (1H, dd, J = 7.9, 1.2 Hz), 7.58-7.63 (1H, m). LRMS (ESI$^+$) 276 [M + H]$^+$. |

Reference Example 40-1

[Formula 141]

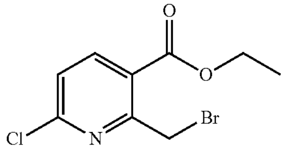

Ethyl 2-(Bromomethyl)-6-chloronicotinate

To a solution of ethyl 6-chloro-2-methylnicotinate (500 mg) in carbon tetrachloride (5 mL), N-bromosuccinimide (490 mg) and azobisisobutyronitrile (4.2 mg) were added at room temperature, and the resultant reaction mixture was heated to reflux for 4 hours. The resultant reaction solution was cooled to room temperature and concentrated under reduced pressure. The thus obtained residue was purified by silica gel column chromatography (hexane:ethyl acetate=9:1) to obtain the title compound (713 mg).

$^1$H NMR (400 MHz, $CDCl_3$) δ 1.44 (3H, t, J=7.3 Hz), 4.44 (2H, q, J=7.3 Hz), 4.97 (2H, s), 7.36 (1H, d, J=8.6 Hz), 8.24 (1H, d, J=7.9 Hz).

LRMS (ESI$^+$) 278 [M+H]$^+$.

A compound of the following Reference Example 40-2 was obtained in the same manner as in Reference Example 40-1 by using corresponding starting material and reactant. Its structure and spectrum data are shown in the following table.

TABLE 46

| Reference Example No. | Chemical Structural Formula | Spectrum Data |
|---|---|---|
| 40-2 | 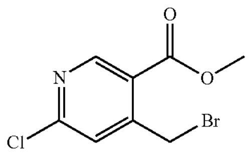 | $^1$H NMR (400 MHz, $CDCl_3$) δ 3.98 (3H, s), 4.86 (2H, s), 7.50 (1H, s), 8.94 (1H, s). LRMS (ESI$^+$) 264 [M + H]$^+$. |

Reference Example 41-1

[Formula 142]

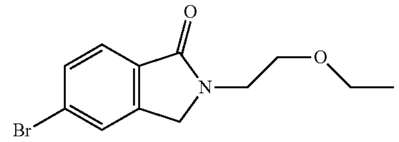

5-Bromo-2-(2-ethoxyethyl)isoindolin-1-one

To a solution of methyl 4-bromo-2-(bromomethyl) benzoate (500 mg) in tetrahydrofuran (8.1 mL), 2-ethoxyethane-1-amine (341 μL) and diisopropylethylamine (827 μL) were added, followed by stirring at room temperature for 21 hours. The resultant reaction solution was concentrated under reduced pressure, and the thus obtained residue was purified by silica gel column chromatography (ethyl acetate: hexane=20:80 to 80:20) to obtain the title compound (431 mg).

$^1$H NMR (400 MHz, $CDCl_3$) δ 1.19 (3H, t, J=7.0 Hz), 3.49 (2H, q, J=6.9 Hz), 3.66 (2H, t, J=4.8 Hz), 3.78 (2H, t, J=4.8 Hz), 4.53 (2H, s), 7.57-7.63 (2H, m), 7.71 (1H, d, J=8.5 Hz).

LRMS ($ESI^+$) 284 $[M+H]^+$.

Compounds of the following Reference Examples 41-2 to 41-15 were obtained in the same manner as in Reference Example 41-1 by using corresponding starting materials and reactants. Their structures and spectrum data are shown in the following tables.

TABLE 47

| Reference Example No. | Chemical Structural Formula | Spectrum Data |
|---|---|---|
| 41-2 | 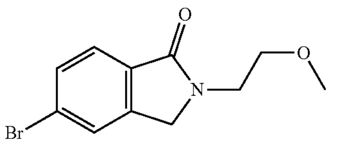 | $^1$H NMR (400 MHz, $CDCl_3$) δ 3.35 (3H, s), 3.63 (2H, t, J = 4.8 Hz), 3.79 (2H, t, J = 4.8 Hz), 4.51 (2H, s), 7.57-7.62 (2H, m), 7.71 (1H, d, J = 9.1 Hz). LRMS ($ESI^+$) 270 $[M + H]^+$. |
| 41-3 | 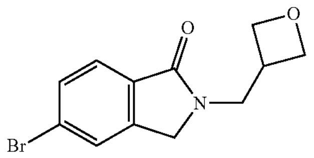 [SMILES: O=C1c2ccc(Br)cc2CN1CC1COC1] | $^1$H NMR (400 MHz, $CDCl_3$) δ 3.32-3.42 (1H, m), 3.94 (2H, d, J = 7.3 Hz), 4.35 (2H, s), 4.56 (2H, t, J = 6.4 Hz), 4.84 (2H, dd, J = 7.9, 6.7 Hz), 7.59-7.64 (2H, m), 7.71 (1H, dd, J = 7.0, 2.1 Hz). LRMS ($ESI^+$) 282 $[M + H]^+$. |
| 41-4 | 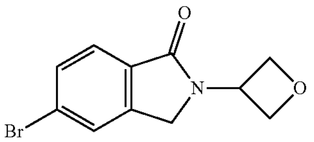 | $^1$H NMR (400 MHz, $CDCl_3$) δ 4.69 (2H, s), 4.86 (2H, t, J = 6.7 Hz), 5.00 (2H, t, J = 7.3 Hz), 5.59-5.69 (1H, m), 7.61-7.65 (1H, m), 7.68-7.73 (2H, m). LRMS ($ESI^+$) 268 $[M + H]^+$. |
| 41-5 | 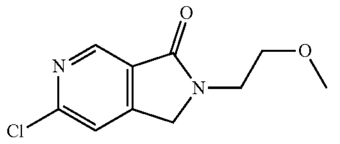 | $^1$H NMR (400 MHz, $CDCl_3$) δ 3.35 (3H, s), 3.63 (2H, t, J = 4.8 Hz), 3.79 (2H, t, J = 5.1 Hz), 4.58 (2H, s), 7.45 (1H,), 8.86 (1H, s). LRMS ($ESI^+$) 227 $[M + H]^+$. |
| 41-6 | 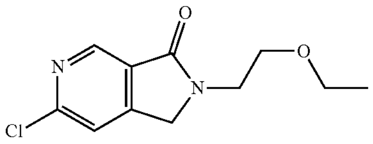 [SMILES: CCOCCN1Cc2cc(Cl)ncc2C1=O] | $^1$H NMR (400 MHz, $CDCl_3$) δ 1.19 (3H, t, J = 7.0 Hz), 3.49 (2H, q, J = 6.9 Hz), 3.66 (2H, t, J = 4.8 Hz), 3.79 (2H, t, J = 5.1 Hz), 4.60 (2H, s), 7.46 (1H, s), 8.86 (1H, s). LRMS ($ESI^+$) 241 $[M + H]^+$. |
| 41-7 | 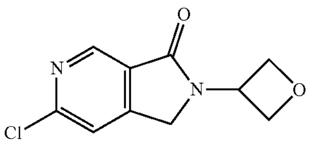 [SMILES: O=C1c2cnc(Cl)cc2CN1C1COC1] | $^1$H NMR (400 MHz, $CDCl_3$) δ 4.75 (2H, s), 4.84 (2H, t, J = 6.7 Hz), 5.01 (2H, t, J = 7.6 Hz), 5.58-5.67 (1H, m), 7.55 (1H, d, J = 1.2 Hz), 8.87 (1H, s). LRMS ($ESI^+$) 225 $[M + H]^+$. |

TABLE 47-continued

| Reference Example No. | Chemical Structural Formula | Spectrum Data |
|---|---|---|
| 41-8 | 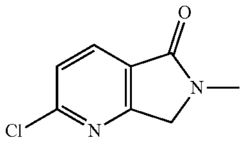 | $^{1}H$ NMR (400 MHz, $CDCl_3$) δ 3.23 (3H, s), 4.43 (2H, s), 7.43 (1H, d, J = 7.9 Hz), 8.05 (1H, d, J = 7.9 Hz). LRMS ($ESI^+$) 183 $[M + H]^+$. |

TABLE 48

| Reference Example No. | Chemical Structural Formula | Spectrum Data |
|---|---|---|
| 41-9 | 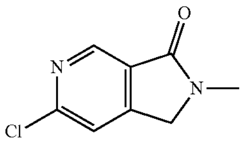 | $^{1}H$ NMR (400 MHz, $CDCl_3$) δ 3.20 (3H, s), 4.42 (2H, s), 7.46 (1H, s), 8.85 (1H, s). LRMS ($ESI^+$) 183 $[M + H]^+$. |

TABLE 49

| Reference Example No. | Chemical Structural Formula | Spectrum Data |
|---|---|---|
| 41-10 | 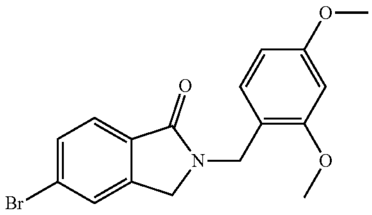 [SMILES: COc1ccc(CN2Cc3cc(Br)ccc3C2=O)c(OC)c1] | $^{1}H$ NMR (400 MHz, $CDCl_3$) δ 3.79 (3H, s), 3.84 (3H, s), 4.26 (2H, s), 4.73 (2H, s), 6.44 (1H, dd, J = 8.6, 2.4 Hz), 6.47 (1H, d, J = 2.4 Hz), 7.20 (1H, d, J = 7.9 Hz), 7.53 (1H, d, J = 1.2 Hz), 7.58 (1H, dd, J = 7.9, 1.2 Hz), 7.71 (1H, d, J = 8.6 Hz). LRMS ($FD^+$) 361 $[M]^+$. |
| 41-11 | 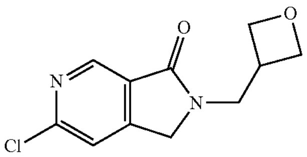 [SMILES: O=C1c2cnc(Cl)cc2CN1CC1COC1] | $^{1}H$ NMR (400 MHz, $CDCl_3$) δ 3.29-3.43 (1H, m), 3.95 (2H, d, J = 7.3 Hz), 4.41 (2H, s), 4.54 (2H, t, J = 6.4 Hz), 4.81-4.88 (2H, m), 7.46 (1H, s), 8.86 (1H, s). LRMS ($ESI^+$) 239 $[M + H]^+$. |
| 41-12 | 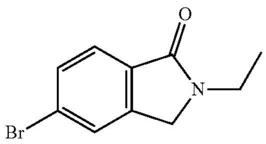 | $^{1}H$ NMR (400 MHz, $CDCl_3$) δ 1.27 (3H, t, J = 7.3 Hz), 3.67 (2H, q, J = 7.3 Hz), 4.37 (2H, s), 7.58-7.63 (2H, m), 7.70 (1H, d, J = 7.9 Hz) .LRMS ($ESI^+$) 240 $[M + H]^+$. |
| 41-13 | 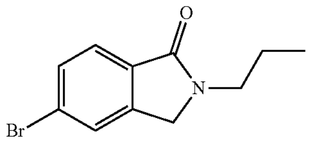 | $^{1}H$ NMR (400 MHz, $CDCl_3$) δ 0.96 (3H, t, J = 7.6 Hz), 1.63-1.76 (2H, m), 3.57 (2H, t, J = 7.3 Hz), 4.36 (2H, s), 7.58-7.62 (2H, m), 7.69-7.73 (1H, m). LRMS ($ESI^+$) 254 $[M + H]^+$. |
| 41-14 | 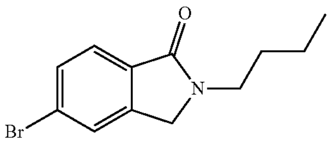 | $^{1}H$ NMR (400 MHz, $CDCl_3$) δ 0.96 (3H, t J = 7.6 Hz), 1.32-1.43 (2H, m), 1.60-1.69 (2H, m), 3.61 (2H, t, J = 7.3 Hz), 4.35 (2H, s), 7.56-7.63 (2H, m), 7.67-7.73 (1H, m). LRMS ($ESI^+$) 268 $[M + H]^+$. |

TABLE 49-continued

| Reference Example No. | Chemical Structural Formula | Spectrum Data |
|---|---|---|
| 41-15 | 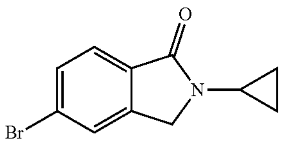 [SMILES: O=C1c2ccc(Br)cc2CN1C1CC1] | $^1$H NMR (400 MHz, $CDCl_3$) δ 0.80-0.98 (4H, m), 2.87-2.95 (1H, m), 4.30 (2H, s), 7.56-7.63 (2H, m), 7.66-7.73 (1H, m). LRMS ($ESI^+$) 252 [M + H]$^+$. |

Reference Example 42-1

[Formula 143]

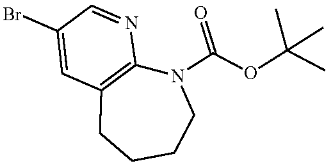

tert-Butyl 3-Bromo-5,6,7,8-tetrahydro-9H-pyrido[2,3-b]azepine-9-carboxylate

To a solution of tert-butyl 5,6,7,8-tetrahydro-9H-pyrido[2,3-b]azepine-9-carboxylate (749 mg) in acetonitrile (6 mL), N-bromosuccinimide (644 mg) was added at room temperature. The resultant reaction solution was stirred at 40° C. for 3 hours, and subsequently at 80° C. for 8 hours. The resultant reaction solution was concentrated under reduced pressure. The thus obtained residue was purified by silica gel column chromatography (hexane:ethyl acetate=3:1) to obtain the title compound (534 mg).

$^1$H NMR (400 MHz, $CDCl_3$) δ 1.43 (9H, s), 1.62-1.76 (2H, m), 1.79-1.89 (2H, m), 2.65-2.74 (2H, m), 3.11-4.03 (2H, m), 7.69 (1H, d, J=2.4 Hz), 8.39 (1H, d, J=2.4 Hz).

LRMS ($ESI^+$) 327 [M+H]$^+$.

Reference Example 43-1

[Formula 144]

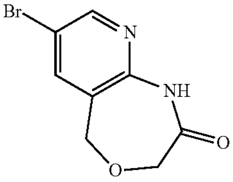

7-Bromo-1,5-dihydropyrido[2,3-e] [1,4]oxazepin-2(3H)-one

To a solution of ethyl 2-hydroxyacetate (5.50 mL) in N,N-dimethylformamide (200 mL), sodium hydride (60% oil suspension, 2.30 g) was added at 0° C. The resultant reaction solution was stirred at 0° C. for 0.5 hours, and 5-bromo-3-(bromomethyl)pyridine-2-amine hydrochloride (10.0 g) was added thereto over 10 minutes, followed by stirring at 0° C. for 0.5 hours, and subsequently at room temperature for 3 hours. Water was added to the resultant reaction solution. The thus precipitated solid was collected by filtration to obtain the title compound (2.06 g).

$^1$H NMR (400 MHz, DMSO-$d_6$) δ4.51 (2H, s), 4.74 (2H, s), 7.90 (1H, d, J=1.2 Hz), 8.34 (1H, d, J=2.4 Hz), 10.56 (1H, s).

LRMS ($ESI^+$) 243 [M+H]$^+$.

Reference Example 44-1

[Formula 145]

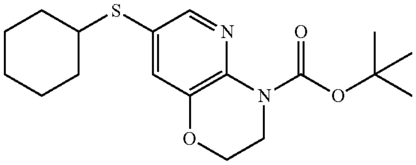

tert-Butyl 7-(Cyclohexylthio)-2,3-dihydro-4H-pyrido[3,2-b] [1,4]oxazine-4-carboxylate To a solution of tert-butyl 7-bromo-2,3-dihydro-4H-pyrido[3,2-b][1,4]oxazine-4-carboxylate (765 mg) in 1,4-dioxane (24 mL), cyclohexanethiol (0.36 mL), tris(dibenzylideneacetone) dipalladium (0) (111 mg), 4,5-bis(diphenylphosphino)-9,9-dimethylxanthene (Xantphos) (140 mg) and diisopropylethylamine (0.85 mL) were added at room temperature, followed by stirring at 90° C. for 5 hours. The resultant reaction solution was cooled to room temperature, and then concentrated under reduced pressure. The thus obtained residue was purified by silica gel column chromatography (hexane:ethyl acetate=5:1) to obtain the title compound (984 mg).

$^1$H NMR (400 MHz, $CDCl_3$) δ 1.16-1.40 (6H, m), 1.55 (9H, s), 1.70-1.81 (2H, m), 1.91-2.00 (2H, m), 2.92-3.03 (1H, m), 3.92 (2H, t, J=4.6 Hz), 4.24 (2H, t, J=4.6 Hz), 7.24 (1H, d, J=2.4 Hz), 8.11 (1H, d, J=1.8 Hz).

LRMS ($ESI^+$) 351 [M+H]$^+$.

A compound of the following Reference Example 44-2 was obtained in the same manner as in Reference Example 44-1 by using corresponding starting material and reactant. Its structure and spectrum data are shown in the following table.

TABLE 50

| Reference Example No. | Chemical Structural Formula | Spectrum Data |
|---|---|---|
| 44-2 | 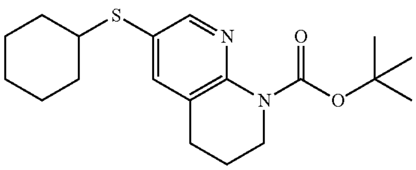 | $^1$H NMR (400 MHz, $CDCl_3$) δ 1.15-1.40 (6H, m), 1.54 (9H, s), 1.71-1.80 (2H, m), 1.88-1.99 (4H, m), 2.74 (2H, t, J = 6.7 Hz), 2.88-2.98 (1H, m), 3.77 (2H, t, J = 6.1 Hz), 7.44-7.47 (1H, m), 8.37 (1H, d, J = 2.4 Hz). LRMS (ESI$^+$) 349 [M + H]$^+$. |

Reference Example 45-1

[Formula 146]

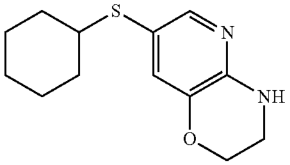

7-(Cyclohexylthio)-3,4-dihydro-2H-pyrido[3,2-b][1,4]oxazine

A mixture of tert-butyl 7-(cyclohexylthio)-2,3-dihydro-4H-pyrido[3,2-b][1,4]oxazine-4-carboxylate (300 mg) and a 4 mol/L solution (2.0 mL) of hydrogen chloride in 1,4-dioxane was stirred at room temperature for 3 hours. The resultant reaction solution was concentrated under reduced pressure, and the thus obtained residue was purified by silica gel column chromatography (hexane:ethyl acetate=1:1) to obtain the title compound (219 mg).

$^1$H NMR (400 MHz, $CDCl_3$) δ 1.13-1.36 (6H, m), 1.70-1.81 (2H, m), 1.86-1.96 (2H, m), 2.74-2.84 (1H, m), 3.54-3.59 (2H, m), 4.22 (2H, t, J=4.3 Hz), 4.92 (1H, br s), 7.10 (1H, d, J=1.8 Hz), 7.77 (1H, d, J=1.8 Hz).

LRMS (ESI$^+$) 251 [M+H]$^+$.

A compound of the following Reference Example 45-2 was obtained in the same manner as in Reference Example 45-1 by using corresponding starting material and reactant. Its structure and spectrum data are shown in the following table.

Reference Example 46-1

[Formula 147]

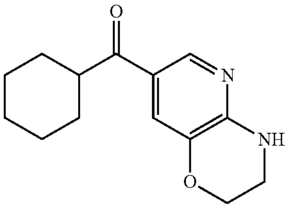

Cyclohexyl (3,4-Dihydro-2H-pyrido[3,2-b] [1,4] oxazin-7-yl)methanone

To a solution of 7-bromo-3,4-dihydro-2H-pyrido[3,2-b][1,4]oxazine (2.15 g) in tetrahydrofuran (20 mL), n-butyllithium (2.6 mol/L tetrahydrofuran solution, 10.0 mL) was added at −78° C. in a dropwise manner over 30 minutes, followed by stirring for 1 hour. To the resultant solution, N-ethoxy-N-methylcyclohexanecarboxamide (4.50 g) was added at −78° C. over 10 minutes. The resultant reaction solution was slowly heated to 0° C., followed by stirring at 0° C. for 0.5 hours. To the reaction solution, water and a 6 mol/L hydrogen chloride aqueous solution were added to adjust pH to 4. The resultant was extracted with ethyl acetate and dried over anhydrous sodium sulfate. The resultant reaction solution was concentrated under reduced pressure, and the thus obtained residue was purified by silica gel column chromatography (hexane:ethyl acetate=1:1) to obtain the title compound (1.41 g).

$^1$H NMR (400 MHz, $CDCl_3$) δ 1.19-1.31 (1H, m), 1.31-1.43 (2H, m), 1.44-1.56 (2H, m), 1.68-1.77 (1H, m), 1.79-1.89 (4H, m), 3.05-3.15 (1H, m), 3.59-3.66 (2H, m), 4.22 (2H, t, J=4.6 Hz), 5.43 (1H, br s), 7.52 (1H, d, J=1.8 Hz), 8.34 (1H, d, J=1.8 Hz).

LRMS (ESI$^+$) 247 [M+H]$^+$.

TABLE 51

| Reference Example No. | Chemical Structural Formula | Spectrum Data |
|---|---|---|
| 45-2 | 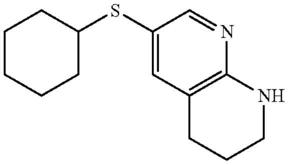 [SMILES: c1nc2c(cc1SC1CCCCC1)CCCN2] | $^1$H NMR (400 MHz, $CDCl_3$) δ 1.10-1.34 (6H, m), 1.69-1.80 (2H, m), 1.86-1.98 (4H, m), 2.72 (3H, t, J = 6.4 Hz), 3.39-3.46 (2H, m), 4.91 (1H, s), 7.25 (1H, d, J = 1.2 Hz), 7.95 (1H, d, J = 1.8 Hz). LRMS (ESI$^+$) 249 [M + H]$^+$. |

A compound of the following Reference Example 46-2 was obtained in the same manner as in Reference Example 46-1 by using corresponding starting material and reactant. Its structure and spectrum data are shown in the following table.

TABLE 52

| Reference Example No. | Chemical Structural Formula | Spectrum Data |
|---|---|---|
| 46-2 | 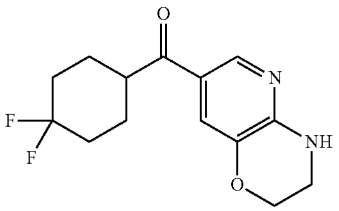 | $^1$H NMR (400 MHz, $CDCl_3$) δ 1.75-2.00 (6H, m), 2.14-2.28 (2H, m), 3.13-3.25 (1H, m), 3.60-3.69 (2H, m), 4.23 (2H, t, J = 4.9 Hz), 5.49 (1H, s), 7.50 (1H, d, J = 1.2 Hz), 8.32 (1H, d, J = 1.8 Hz).<br>LRMS (ESI$^+$) 283 [M + H]$^+$. |

Reference Example 47-1

[Formula 148]

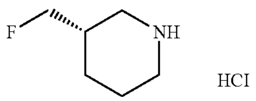

(S)-3-(Fluoromethyl)piperidine Hydrochloride

To a solution of tert-butyl (S)-3-(hydroxymethyl)piperidine-1-carboxylate (3.23 g) in dichloromethane (30 mL), triethylamine (4.20 mL) and ethanesulfonyl chloride (2.14 mL) were added under ice cooling. The resultant reaction solution was slowly heated to room temperature over 3 hours. The resultant reaction solution was diluted with chloroform, washed successively with a 10% citric acid aqueous solution, a saturated sodium bicarbonate aqueous solution and saturated saline, and then dried over anhydrous sodium sulfate. The resultant reaction solution was concentrated under reduced pressure, and the thus obtained residue was purified by silica gel column chromatography (hexane:ethyl acetate=1:1) to obtain tert-butyl (S)-3-(((ethylsulfonyl)oxy)methyl)piperidine-1-carboxylate (5.95 g).

$^1$H NMR (400 MHz, $CDCl_3$) δ 1.23-1.36 (1H, m), 1.44 (3H, t, J=7.3 Hz), 1.46 (9H, s), 1.48-1.54 (1H, m), 1.63-1.71 (1H, m), 1.78-1.87 (1H, m), 1.89-2.01 (1H, m), 2.64-2.84 (1H, m), 2.84-2.93 (1H, m), 3.15 (2H, q, J=7.3 Hz), 3.79-3.89 (1H, m), 3.90-4.03 (1H, m), 4.03-4.15 (2H, m).

LRMS (ESI$^+$) 308 [M+H]$^+$.

A mixture of tert-butyl (S)-3-(((ethylsulfonyl)oxy)methyl)piperidine-1-carboxylate (1.50 g) and tetrabutylammonium fluoride (1 mol/L tetrahydrofuran solution, 26.0 mL) was stirred at 80° C. for 12 hours. The resultant reaction solution was diluted with chloroform, washed successively with a 10% citric acid aqueous solution and saturated saline, and then dried over anhydrous sodium sulfate. The resultant reaction solution was concentrated under reduced pressure, and the thus obtained residue was purified by silica gel column chromatography (hexane:ethyl acetate=3:1) to obtain tert-butyl (S)-3-(fluoromethyl)piperidine-1-carboxylate (914 mg).

$^1$H NMR (400 MHz, $CDCl_3$) δ 1.22-1.35 (1H, m), 1.41-1.54 (10H, m), 1.61-1.71 (1H, m), 1.74-1.82 (1H, m), 1.83-1.96 (1H, m), 2.60-2.88 (2H, m), 3.85-4.14 (2H, m), 4.20-4.29 (1H, m), 4.31-4.41 (1H, m).

LRMS (ESI$^+$) 218 [M+H]$^+$.

A mixture of tert-butyl (S)-3-(fluoromethyl)piperidine-1-carboxylate (903 mg) and 4 mol/L solution (11.0 mL) of hydrogen chloride in 1,4-dioxane was stirred at room temperature for 12 hours. The resultant reaction solution was concentrated under reduced pressure to obtain the title compound (655 mg).

$^1$H NMR (400 MHz, DMSO-$d_6$) δ1.20-1.35 (1H, m), 1.61-1.84 (3H, m), 2.06-2.25 (1H, m), 2.61-2.81 (2H, m), 3.16-3.29 (2H, m), 4.25-4.50 (2H, m), 8.92-9.23 (2H, m).

LRMS (ESI$^+$) 118 [M+H]$^+$.

A compound of the following Reference Example 47-2 was obtained in the same manner as in Reference Example 47-1 by using corresponding starting material and reactant. Its structure and spectrum data are shown in the following table.

TABLE 53

| Reference Example No. | Chemical Structural Formula | Spectrum Data |
|---|---|---|
| 47-2 | 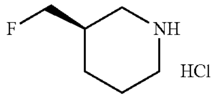 | $^1$H NMR (400 MHz, DMSO-$d_6$) δ 1.20-1.35 (1H. m), 1.61-1.84 (3H, m), 2.07-2.24 (1H, m), 2.61-2.81 (2H, m), 3.15-3.29 (2H, m), 4.24-4.50 (2H, m), 8.92-9.27 (2H, m).<br>LRMS (ESI$^+$) 118 [M + H]$^+$. |

Reference Example 48-1

[Formula 149]

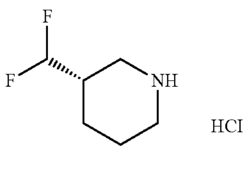

(S)-3-(Difluoromethyl)piperidine Hydrochloride tert-Butyl (S)-3-(hydroxymethyl)piperidine-1-caboxylate (3.23 g) was dissolved in dichloromethane (125 mL). To the resultant, Dess-Martin periodinane (DMP) (7.00 g) was added, followed by stirring at room temperature for 1.5 hours. To the resultant reaction solution, a 10% sodium thiosulfate aqueous solution (125 mL) and a saturated sodium bicarbonate aqueous solution (125 mL) were added, and the resultant was stirred for 30 minutes, followed by extraction with dichloromethane. The resultant organic layers were combined, washed with a saturated sodium bicarbonate aqueous solution and saturated saline, and dried over anhydrous sodium sulfate. The solvent was distilled off to obtain tert-butyl (S)-3-formylpiperidine-1-carboxylate (2.91 g).

$^1$H NMR (400 MHz, $CDCl_3$) δ 1.37-1.55 (10H, m), 1.63-1.76 (2H, m), 1.90-2.02 (1H, m), 2.36-2.50 (1H, m), 3.03-3.15 (1H, m), 3.32 (1H, dd, J=13.6, 8.2 Hz), 3.56-3.72 (1H, m), 3.92 (1H, br s), 9.70 (1H, s).

A reaction vessel was charged with dichloromethane (53.5 mL), and diethylaminosulfur trifluoride (LAST) (4.00 mL) was added dropwise thereto at −20° C. Subsequently, a solution of tert-butyl (S)-3-(hydroxymethyl)piperidine-1-carboxylate (2.67 g) in dichloromethane (9.00 mL) was added thereto, followed by stirring for 5 hours. The resultant reaction solution was added to an ice cooled saturated sodium bicarbonate aqueous solution, and extracted with dichloromethane. The resultant organic layers were combined, washed with a saturated sodium bicarbonate aqueous solution and saturated saline, and dried over anhydrous sodium sulfate. The resultant reaction solution was concentrated under reduced pressure, and the thus obtained residue was purified by silica gel column chromatography (ethyl acetate:hexane=10:90 to 50:50) to obtain tert-butyl (S)-3-(difluoromethyl)piperidine-1-carboxylate (1.27 g).

$^1$H NMR (400 MHz, $CDCl_3$) δ 1.35-1.52 (11H, m), 1.68-1.77 (1H, m), 1.82-2.08 (2H, m), 2.56-3.10 (2H, m), 3.72-4.37 (2H, m), 5.64 (1H, td, J=56.2, 4.6 Hz).

LRMS (ESI$^+$) 236 [M+H]$^+$.

To a solution of tert-butyl (S)-3-(difluoromethyl)piperidine-1-carboxylate (1.26 g) in 1,4-dioxane (26.8 mL), a 4 mol/L solution (26.8 mL) of hydrogen chloride in 1,4-dioxane was added, followed by stirring at room temperature for 4 hours. The resultant reaction solution was subjected to distillation under reduced pressure to obtain the title compound (919 mg).

$^1$H NMR (400 MHz, $CDCl_3$) δ 1.29-1.45 (1H, m), 1.53-1.71 (1H, m), 1.75-1.88 (2H, m), 2.17-2.39 (1H, m), 2.72-2.86 (2H, m), 3.15-3.45 (2H, m), 6.03 (1H, td, J=55.7, 4.2 Hz), 8.74 (2H, s).

LRMS (ESI$^+$) 136 [M+H]$^+$.

A compound of the following Reference Example 48-2 was obtained in the same manner as in Reference Example 48-1 by using corresponding starting material and reactant. Its structure and spectrum data are shown in the following table.

TABLE 54

| Reference Example No. | Chemical Structural Formula | Spectrum Data |
|---|---|---|
| 48-2 | 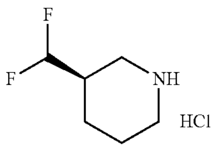 | $^1$H NMR (DMSO, 400 MHz) δ 1.30-1.45 (1H, m), 1.60-1.75 (1H, m), 1.77-1.88 (2H, m), 2.22-2.44 (1H, m), 2.70-2.86 (2H, m), 3.18-3.31 (2H, m), 6.05 (1H, td, J = 56.0, 4.0 Hz), 9.12 (2H, br s). LRMS (ESI$^+$) 136 [M + H]$^+$. |

Reference Example 49-1

[Formula 150]

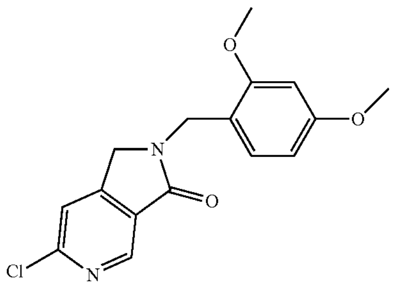

6-Chloro-2-(2,4-dimethoxybenzyl)-1,2-dihydro-3H-pyrrolo[3,4-c]pyridin-3-one

To a solution of methyl 6-chloro-4-methylnicotinate (1.86 g) in carbon tetrachloride (74 mL), N-bromosuccinimide (NBS) (2.14 g) and benzoyl peroxide (129 mg) were added at room temperature, followed by stirring at 85° C. for 6 hours. The resultant reaction solution was concentrated under reduced pressure, and the thus obtained residue was purified by silica gel column chromatography (ethyl acetate: hexane=0:100 to 20:80) to obtain a mixture containing methyl 4-(bromomethyl)-6-chloronicotinate (582 mg).

To a solution, in methanol (20 mL), of the mixture (580 mg) containing methyl 4-(bromomethyl)-6-chloronicotinate, diisopropylethylamine (701 μL) and (2,4-dimethoxyphenyl) methanamine (310 (μL) were successively added at room temperature. After stirring at room temperature for 7.5 hours, the resultant reaction solution was concentrated under reduced pressure, and the thus obtained residue was purified by silica gel column chromatography (ethyl acetate: hexane=10:90 to 80:20) to obtain the title compound (378 mg).

$^1$H NMR (400 MHz, $CDCl_3$) δ 3.80 (3H, s), 3.84 (3H, s), 4.31 (2H, s), 4.73 (2H, s), 6.43-6.49 (2H, m), 7.23 (1H, d, J=7.9 Hz), 7.38 (1H, s), 8.85 (1H, s).

LRMS (ESI$^+$) 319 [M+H]$^+$.

Reference Example 50-1

[Formula 151]

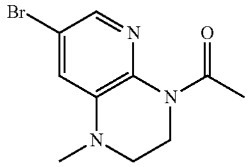

1-(7-Bromo-1-methyl-2,3-dihydropyrido[2,3-b]pyrazin-4(1H)-yl)ethan-1-one

To a solution of 7-bromo-3,4-dihydropyrido[2,3-b]pyrazin-2(1H)-one (228 mg) in N,N-dimethylformamide (5.0 mL), sodium hydride (22 mg) was added at room temperature. After stirring at room temperature for 3 hours, methyl iodide (31 μL) was added thereto. After stirring at room temperature for 2 hours, N,N-dimethylformamide (15.0 mL) was added thereto. After stirring at room temperature for 17.5 hours, sodium hydride (22 mg) was added thereto. After stirring at room temperature for 20 minutes, methyl iodide (31 μL) was added thereto. After stirring at room temperature for 7.5 hours, a saturated ammonium chloride aqueous solution was added to the resultant reaction solution, the resultant was extracted with ethyl acetate, and the resultant organic layers were combined, washed with saturate saline, and dried over anhydrous sodium sulfate. The resultant reaction solution was concentrated under reduced pressure to obtain a mixture containing 7-bromo-1-methyl-3,4-dihydropyrido[2,3-b]pyrazin-2(1H)-one (174 mg).

To a solution, in tetrahydrofuran (7.2 mL), of the mixture (174 mg) containing 7-bromo-1-methyl-3,4-dihydropyrido[2,3-b]pyrazin-2 (1H)-one, a borane-dimethylsulfide complex (720 μL) was added at room temperature. After stirring at room temperature for 22.5 hours, the resultant was stirred for 5 hours under heating to reflux. After adding methanol, the resultant reaction solution was concentrated under reduced pressure to obtain a mixture containing 7-bromo-1-methyl-1,2,3,4-tetrahydropyrido[2,3-b]pyrazine (173 mg).

To the mixture (173 mg) containing 7-bromo-1-methyl-1,2,3,4-tetrahydropyrido[2,3-b]pyrazine, pyridine (1 mL) and acetic anhydride (1 mL) were added. After stirring at room temperature for 2.5 hours, the resultant reaction solution was concentrated under reduced pressure, and the thus obtained residue was purified by silica gel column chromatography (ethyl acetate:hexane=10:90 to 100:0) to obtain the title compound (43.0 mg).

$^1$H NMR (400 MHz, $CDCl_3$) δ 2.43 (3H, s), 2.96 (3H, s), 3.36 (2H, t, J=5.2 Hz), 3.98 (2H, t, J=5.2 Hz), 6.97 (1H, d, J=1.8 Hz), 7.71 (1H, d, J=1.8 Hz).

LRMS (ESI$^+$) 270 [M+H]$^+$.

Reference Example 51-1

[Formula 152]

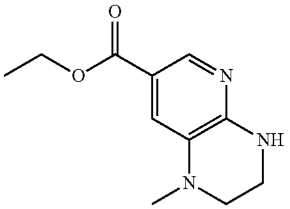

Ethyl 1-Methyl-1,2,3,4-tetrahydropyrido[2,3-b]pyrazine-7-carboxylate

To a solution of 1-(7-bromo-1-methyl-2,3-dihydropyrido[2,3-b]pyrazin-4(1H)-yl)ethan-1-one (115 mg) in ethanol (4.3 mL), diisopropylethylamine (289 μL) and [1,1-bis(diphenylphosphino)ferrocene]palladium (II) dichloride dichloromethane adduct (34.7 mg) were added. The resultant mixture was stirred under carbon monoxide atmosphere at 85° C. for 9 hours. The resultant reaction solution was concentrated under reduced pressure, and the thus obtained residue was purified by silica gel column chromatography (ethyl acetate:hexane=5:95 to 100:0) to obtain the title compound (68.0 mg).

$^1$H NMR (400 MHz, $CDCl_3$) δ 1.37 (3H, t, J=7.0 Hz), 2.89 (3H, s), 3.19-3.23 (2H, m), 3.62-3.67 (2H, m), 4.33 (2H, q, J=7.1 Hz), 5.22 (1H, s), 7.15 (1H, d, J=1.2 Hz), 8.18 (1H, d, J=1.8 Hz).

LRMS (ESI$^+$) 222 [M+H]$^+$.

Reference Example 52-1

[Formula 153]

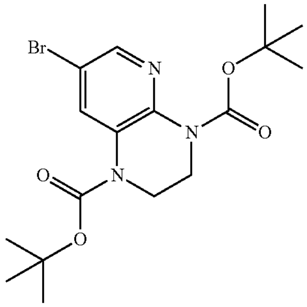

Di-tert-butyl 7-Bromo-2,3-dihydropyrido[2,3-b]pyrazine-1,4-dicarboxylate

To a solution of 7-bromo-3,4-dihydropyrido[2,3-b]pyrazin-2(1H)-one (3.08 g) in tetrahydrofuran (135 mL), borane-dimethylsulfide complex (3.8 mL) was added at room temperature. After stirring under heating to reflux for 2 hours, ethanol (20 mL) and a 1 mol/L sodium hydroxide aqueous solution (80 mL) were added to the resultant reaction solution. After stirring at 85° C. for 2 hours, the resultant was filtered through celite. The thus obtained filtrate was extracted with ethyl acetate, and the resultant organic layers were combined and dried over anhydrous sodium sulfate. The resultant reaction solution was concentrated under reduced pressure, and to a solution of the thus obtained residue in dichloromethane (100 mL), di-tert-butyl dicarbonate (5.89 g) and N,N-dimethyl-4-aminopyridine (82.5 mg) were added at room temperature. After stirring at room temperature for 14.5 hours, the resultant reaction solution was concentrated under reduced pressure, and the thus obtained residue was purified by silica gel column chromatography (ethyl acetate:hexane=0:100 to 50:50) to obtain the title compound (2.69 g).

$^1$H NMR (400 MHz, $CDCl_3$) δ 1.53 (9H, s), 1.55 (9H, s), 3.76-3.87 (4H, m), 8.18 (1H, d, J=1.8 Hz), 8.41-8.56 (1H, m).

LRMS ($ESI^+$) 414 $[M+H]^+$.

Reference Example 53-1

[Formula 154]

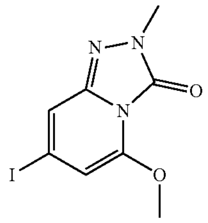

7-Iodo-5-methoxy-2-methyl-[1,2,4]triazolo[4,3-a]pyridin-3(2H)-one

To a solution of 2-fluoro-4-iodo-6-methoxypyridine (228 mg) in ethanol (2.3 mL), hydrazine monohydrate (456 μL) was added at room temperature. After stirring at 50° C. for 8 hours, a solid precipitated by adding ice water to the resultant reaction mixture was collected by filtration to obtain a mixture containing 2-hydrazinyl-4-iodo-6-methoxypyridine (111 mg).

To a solution, in acetonitrile (2.5 mL), of the mixture (111 mg) containing 2-hydrazinyl-4-iodo-6-methoxypyridine, 1,1'-carbonyldiimidazole (81.2 mg) was added. After stirring at room temperature for 2.6 days, a solid precipitated by adding ice water to the resultant reaction mixture was collected by filtration to obtain a mixture containing 7-iodo-5-methoxy-[1,2,4]triazolo[4,3-b]pyridin-3(2H)-one (93.3 mg).

To a solution, in N,N-dimethylformamide (1.2 mL), of the mixture (93.3 mg) containing 7-iodo-5-methoxy-[1,2,4]triazolo[4,3-a]pyridin-3(2H)-one, potassium carbonate (88.5 mg) and methyl iodide (40 μL) were added at room temperature. After stirring at room temperature for 1 hour, N,N-dimethylformamide (1.2 mL) was added to the resultant reaction solution. After stirring at room temperature for 17 hours, tetrahydrofuran (1.0 mL) was added to the resultant reaction solution, followed by stirring under heating to reflux for 40 minutes. A solid precipitated by adding ice water to the resultant reaction solution was collected by filtration to obtain the title compound (70.9 mg).

$^1$H NMR (400 MHz, DMSO-$d_6$) δ3.37 (3H, s), 3.89 (3H, s), 5.99 (1H, s), 7.19 (1H, s).

LRMS ($ESI^+$) 306 $[M+H]^+$.

Reference Example 54-1

[Formula 155]

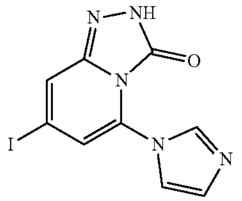

5-(1H-Imidazole-1-yl)-7-iodo-[1,2,4]triazolo[4,3-a]pyridin-3(2H)-one

To a solution of 2-fluoro-6-hydrazinyl-4-iodopyridine (225 mg) in acetonitrile (4.5 mL), 1,1'-carbonyldiimidazole (174 mg) was added. After stirring at room temperature for 1.6 days, a solid precipitated by adding ice water to the resultant reaction solution was collected by filtration to obtain the title compound (141 mg).

$^1$H NMR (400 MHz, DMSO-$d_6$) δ6.76 (1H, d, J=1.2 Hz), 6.98 (1H, t, J=1.2 Hz), 7.48 (1H, t, J=1.5 Hz), 7.80 (1H, d, J=1.8 Hz), 7.93 (1H, d, J=1.2 Hz), 12.51 (1H, s).

LRMS ($ESI^+$) 328 $[M+H]^+$.

Example 1-1

[Formula 156]

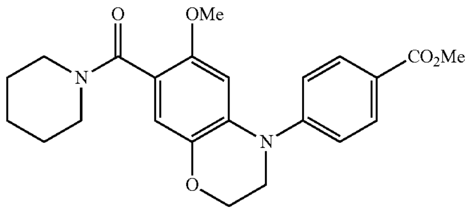

Methyl 4-(6-Methoxy-7-(piperidine-1-carbonyl)-2,3-dihydro-4H-benzo[b][1,4]oxazin-4-yl)benzoate To a solution of (6-methoxy-3,4-dihydro-2H-benzo[b][1,4]oxazin-7-yl)(piperidin-1-yl)methanone (62.0 mg) in toluene (1.2 mL), methyl 4-iodobenzoate (89.0 mg), tris(dibenzylideneacetone)dipalladium (0) (11.0 mg), 4,5-bis(diphenylphosphino)-9,9-dimethylxanthene (Xantphos) (13.0 mg) and sodium tert-butoxide (43.1 mg) were added at room temperature, followed by stirring under heating at 90° C. for 3 hours. The resultant reaction mixture was cooled to room temperature, an insoluble matter was filtered off, and the resultant filtrate was concentrated under reduced pressure. The thus obtained residue was purified by silica gel column chromatography (hexane:ethyl acetate=1:1) to obtain the title compound (67.7 mg).

$^1$H NMR (400 MHz, $CDCl_3$) δ 1.40-1.70 (6H, m), 3.26 (2H, t, J=5.5 Hz), 3.60-3.85 (4H, m), 3.61 (3H, s), 3.91 (3H, s), 4.20-4.30 (2H, m), 6.63 (1H, s), 6.82 (1H, s), 7.27 (2H, d, J=9.1 Hz), 8.01 (2H, d, J=9.1 Hz).

LRMS ($ESI^+$) 411 $[M+H]^+$.

Compounds of the following Examples 1-2 to 1-270 were obtained in the same manner as in Example 1-1 by using corresponding starting materials and reactants. Their structures and spectrum data are shown in the following tables.

TABLE 55

| Reference Example No. | Chemical Structural Formula | Spectrum Data |
|---|---|---|
| 1-2 | 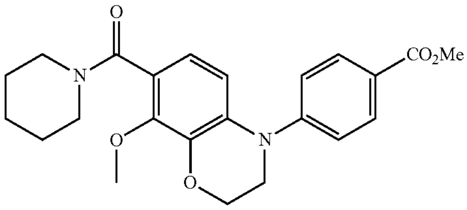 [SMILES: COC(=O)c1ccc(N2CCOc3c2ccc(C(=O)N2CCCCC2)c3OC)cc1] | $^1$H NMR (400 MHz, $CDCl_3$) δ 1.40-1.70 (6H, m), 3.18-3.38 (2H, m), 3.65-3.77 (2H. m), 3.79 (2H, t. J = 4.8 Hz), 3.89 (3H, s), 3.90 (3H, s), 4.29-4.43 (2H, m), 6.66 (1H, d, J = 8.5 Hz), 6.88 (1H, d, J = 8.5 Hz), 7.24 (2H, d, J = 8.5 Hz), 8.00 (2H, d, J = 8.5 Hz).<br>LRMS ($ESI^+$) 411 $[M + H]^+$. |
| 1-3 | 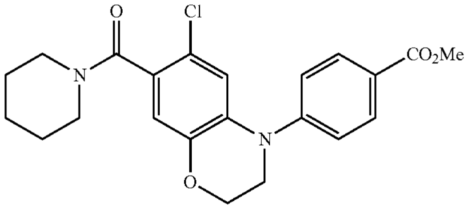 [SMILES: COC(=O)c1ccc(N2CCOc3cc(C(=O)N4CCCCC4)c(Cl)cc32)cc1] | $^1$H NMR (400 MHz, $CDCl_3$) δ 1.42-1.72 (6H, m), 3.20-3.33 (2H, m), 3.62-3.81 (4H, m), 3.92 (3H, s), 4.24-4.36 (2H, m), 6.82 (1H, s), 7.06 (1H, s), 7.27 (2H, d, J = 8.6 Hz), 8.04 (2H, d, J = 8.6 Hz).<br>LRMS ($ESI^+$) 415 $[M + H]^+$. |
| 1-4 | 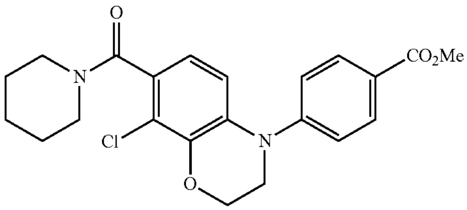 [SMILES: COC(=O)c1ccc(N2CCOc3c2ccc(C(=O)N2CCCCC2)c3Cl)cc1] | $^1$H NMR (400 MHz, $CDCl_3$) δ 1.40-1.75 (6H, m), 3.17-3.35 (2H, m), 3.70-3.77 (2H, m), 3.77-3.82 (2H, m), 3.91 (3H, s), 4.34-4 49 (2H, m), 6.69 (1H, d, J = 8 6 Hz), 7.01 (1H, d, J = 8.6 Hz), 7.23 (2H, d, J = 8.6 Hz), 8.01 (2H, d, J = 8.6 Hz).<br>LRMS ($ESI^+$) 415 $[M + H]^+$. |
| 1-5 | 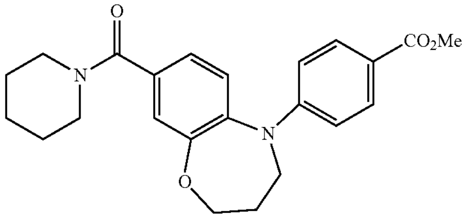 | $^1$H NMR (400 MHz, $CDCl_3$) δ 1.55-1.75 (6H, m), 2.07-2.17 (2H, m), 3.35-3.77 (4H, m), 3.86 (3H, s), 3.96 (2H, t, J = 6.1 Hz), 4.11 (2H, t, J = 5.5 Hz), 6.89 (2H, d, J = 9.2 Hz), 7.01 (1H, dd, J = 7.9, 1.8 Hz), 7.09 (1H, d, J = 1.8 Hz), 7.18 (1H, d, J = 7.9 Hz), 7.89 (2H, d, J = 9.2 Hz).<br>LRMS ($ESI^+$) 395 $[M + H]^+$. |
| 1-6 | 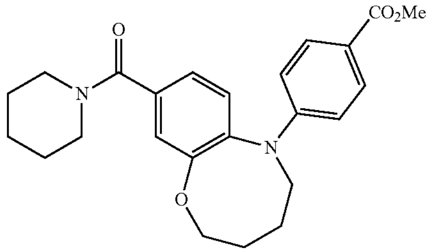 [SMILES: COC(=O)c1ccc(N2CCCCOc3cc(C(=O)N4CCCCC4)ccc32)cc1] | $^1$H NMR (400 MHz, $CDCl_3$) δ 1.50-1.75 (6H, m), 1.80-1.90 (4H, m), 3.35-3.76 (4H, m), 3.80-3.85 (2H, m), 3.86 (3H, s), 4.18 (2H, t, J = 5.5 Hz), 6.73 (2H, d, J = 9.1 Hz), 7.05 (1H, dd, J = 7.9, 1.8 Hz), 7.14 (1H, d, J = 1.8 Hz), 7.15 (1H, d, J = 7.9 Hz), 7.87 (2H, d, J = 9.1 Hz).<br>LRMS ($ESI^+$) 409 $[M + H]^+$. |

TABLE 56

| Reference Example No. | Chemical Structural Formula | Spectrum Data |
|---|---|---|
| 1-7 | 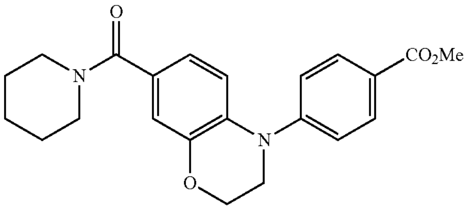 [SMILES: COC(=O)c1ccc(N2CCOc3cc(C(=O)N4CCCCC4)ccc32)cc1] | $^1$H NMR (400 MHz, $CDCl_3$) δ 1.52-1.72 (6H, m), 3.45-3.65 (4H, m), 3.78 (2H, t, J = 4.2 Hz), 3.90 (3H, s), 4.30 (2H, t, J = 4.2 Hz), 6.85 (1H, dd, J = 8.5, 2.4 Hz), 6.98 (1H, d, J = 2.4 Hz), 7.10 (1H, d, J - 8.5 Hz), 7.24 (2H, d, J = 9.1 Hz), 8.00 (2H, d, J = 9.1 Hz).<br>LRMS ($ESI^+$) 381 $[M + H]^+$. |

TABLE 56-continued

| Reference Example No. | Chemical Structural Formula | Spectrum Data |
|---|---|---|
| 1-8 | 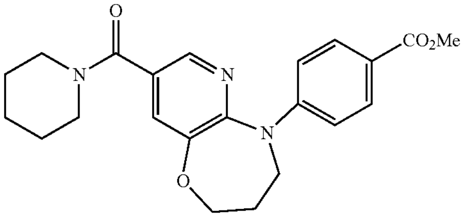 [SMILES: COC(=O)c1ccc(N2CCCOc3cc(C(=O)N4CCCCC4)cnc32)cc1] | $^1$H NMR (400 MHz, $CDCl_3$) δ 1.50-1.75 (6H, m), 2.09-2.18 (2H, m), 3.35-3.78 (4H, m), 3.88 (3H, s), 4.09 (2H, t, J = 6.1 Hz), 4.23 (2H, t, J = 6.1 Hz), 7.14 (2H, d, J = 9.2 Hz), 7.37 (1H, d, J = 1.8 Hz), 7.96 (2H, d, J = 9.2 Hz), 8.06 (1H, d, J = 1.8 Hz).<br>LRMS (ESI$^+$) 396 [M + H]$^+$. |
| 1-9 | 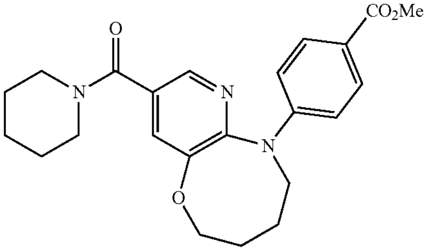 | $^1$H NMR (400 MHz, $CDCl_3$) δ 1.51-1.74 (6H, m), 1.82-1.95 (4H, m), 3.35-3.80 (4H, m), 3.88 (3H, s), 4.10 (2H, t, J = 5.5 Hz), 4.23 (2H, t, J = 5.5 Hz), 7.07 (2H, d, J = 9.1 Hz), 7.44 (1H, d, J = 2.4 Hz), 7.97 (2H, d, J = 9.1 Hz), 8.04 (1H, d, J = 2.4 Hz).<br>LRMS (ESI$^+$) 410 [M + H]$^+$. |
| 1-10 | 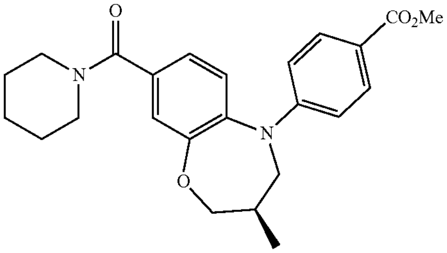 [SMILES: COC(=O)c1ccc(N2C[C@@H](C)COc3cc(C(=O)N4CCCCC4)ccc32)cc1] | $^1$H NMR (400 MHz, $CDCl_3$) δ 1.02 (3H, d. J = 6.7 Hz), 1.50-1.75 (6H, m), 2.35-2.45 (1H, m), 3.33 (1H, dd, J = 14.5, 9.7 Hz), 3.35-3.75 (4H, m), 3.76 (1H, dd, J = 12.1, 4.8 Hz), 3.86 (3H, s), 4.12-4.20 (2H, m), 6.90 (2H, d, J = 8.5 Hz), 7.00 (1H, dd, J = 8.5, 1.8 Hz), 7.09 (1H, d, J = 1.8 Hz), 7.16 (1H, d, J = 8.5 Hz), 7.88 (2H, d, J = 8.5 Hz).<br>LRMS (EI$^+$) 408 [M]$^+$. |
| 1-11 | 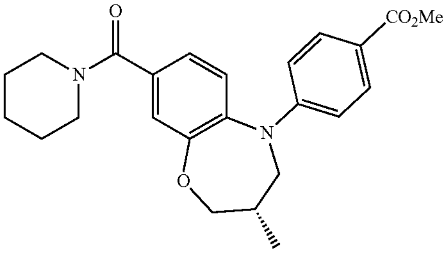 [SMILES: COC(=O)c1ccc(N2C[C@H](C)COc3cc(C(=O)N4CCCCC4)ccc32)cc1] | $^1$H NMR (400 MHz, $CDCl_3$) δ 1.02 (3H, d, J = 6.7 Hz), 1.50-1.75 (6H, m), 2.35-2.45 (1H, m), 3.33 (1H, dd, J = 15.1, 10.3 Hz), 3.35-3.80 (4H, m), 3.76 (1H, dd, J = 12.1, 4.9 Hz), 3.86 (3H, s), 4.12-4.20 (2H, m), 6.90 (2H, d, J = 9.1 Hz), 7.00 (1H, dd, J = 8.5, 1.8 Hz), 7.09 (1H, d, J = 1.8 Hz), 7.16 (1H, d, J = 8.5 Hz), 7.87 (2H, d, J = 9.1 Hz).<br>LRMS (ESI$^+$) 409 [M + H]$^+$. |
| 1-12 | 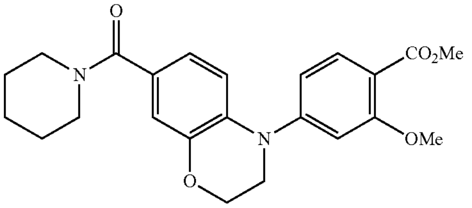 [SMILES: COC(=O)c1ccc(N2CCOc3cc(C(=O)N4CCCCC4)ccc32)cc1OC] | $^1$H NMR (400 MHz, $CDCl_3$) δ 1.50-1.72 (6H, m), 3.40-3.75 (4H, m), 3.78 (2H, t, J = 4.2 Hz), 3.86 (3H, s), 3.88 (3H, s), 4.31 (2H, t, J = 4.2 Hz), 6.78 (1H, dd, J = 8.5, 2.4 Hz), 6.81 (1H, d, J = 2.4 Hz), 6.86 (1H, dd, J = 8.5, 2.4 Hz), 6.98 (1H, d, J = 2.4 Hz), 7.12 (1H, d, J = 8.5 Hz), 7.84 (1H, d, J = 8.5 Hz).<br>LRMS (EI$^+$) 410 [M]$^+$. |

TABLE 57

| Example No. | Chemical Structural Formula | Spectrum Data |
|---|---|---|
| 1-13 | 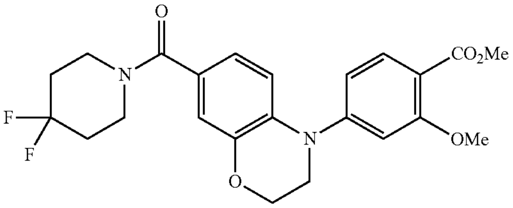 [SMILES: COC(=O)c1ccc(N2CCOc3cc(C(=O)N4CCC(F)(F)CC4)ccc32)cc1OC] | $^1$H NMR (400 MHz, $CDCl_3$) δ 1.93-2.10 (4H, m), 3.70-3.78 (4H, m), 3.79 (2H, t, J = 4.2 Hz), 3.87 (3H, s), 3.88 (3H, s), 4.33 (2H, t, J = 4.2 Hz), 6.80 (1H, dd, J = 8.5, 2.4 Hz), 6.81 (1H, d, J = 2.4 Hz), 6.88 (1H, dd, J = 8.5, 2.4 Hz), 7.00 (1H, d, J = 2.4 Hz), 7.12 (1H, d, J = 8.5 Hz), 7.85 (1H, d, J = 8.5 Hz).<br>LRMS (EI$^+$) 446 [M]$^+$. |

TABLE 57-continued

| Example No. | Chemical Structural Formula | Spectrum Data |
|---|---|---|
| 1-14 | 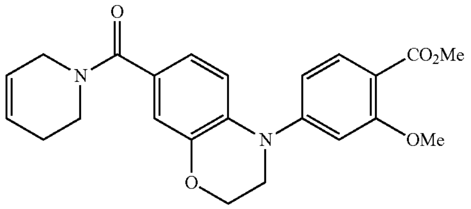 | $^1H$ NMR (400 MHz, $CDCl_3$) δ 2.15-2.27 (2H, m), 3.50-3.70 (2H, m), 3.78 (2H, t, J = 4.3 Hz), 3.86 (3H, s), 3.88 (3H, s), 4.00-4.20 (2H, m), 4.32 (2H, t, J = 4.3 Hz), 5.50-5.80 (1H, m), 5.84-5.92 (1H, m), 6.78 (1H, dd, J = 8.6, 2.4 Hz), 6.82 (1H, d, J = 1.8 Hz), 6.90 (1H, dd, J = 7.9, 1.8 Hz), 7.01 (1 H, d, J = 1.8 Hz), 7.13 (1H, d, J = 8.6 Hz), 7.84 (1H, d, J = 7.9 Hz). LRMS ($EI^+$) 408 $[M]^+$. |
| 1-15 | 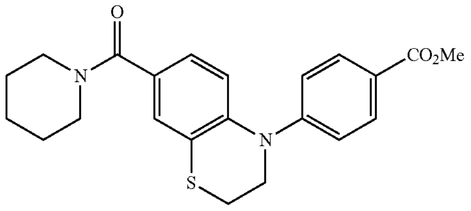 | $^1H$ NMR (400 MHz, $CDCl_3$) δ 1.52-1.65 (4H, m), 1.65-1.72 (2H, m), 3.10-3.15 (2H, m), 3.35-3.75 (4H, m), 3.90 (3H, s), 3.96-4.02 (2H, m), 6.99 (2H, d, J = 1.2 Hz), 7.14 (2H, d, J = 8.5 Hz), 7.23-7.28 (1H, m), 7.96 (2H, d, J = 8.5 Hz). LRMS ($ESI^+$) 397 $[M + H]^+$. |
| 1-16 | 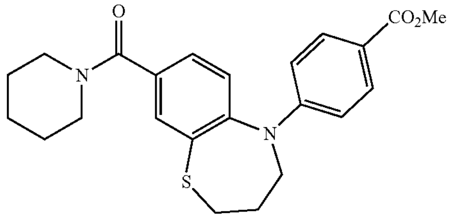 [SMILES: COC(=O)c1ccc(N2CCCSc3cc(C(=O)N4CCCCC4)ccc32)cc1] | $^1H$ NMR (400 MHz, $CDCl_3$) δ 1.52-1.75 (6H, m), 2.16-2.24 (2H, m), 2.85 (2H, t, J = 5.5 Hz), 3.35-3.80 (4H, m), 3.85 (3 s), 3.88-3.96 (211, m), 6.67 (2H, d, J = 9.1 Hz), 7.21-7.29 (2H, m), 7.59 (1H, d, J = 1.8 Hz), 7.86 (2H, d, J = 9.1 Hz). LRMS ($ESI^+$) 411 $[M + H]^+$. |
| 1-17 | 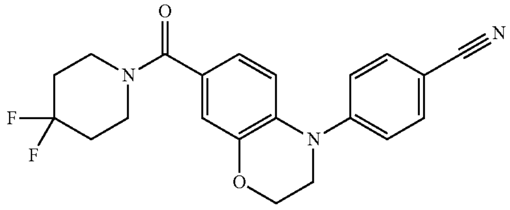 [SMILES: N#Cc1ccc(N2CCOc3cc(C(=O)N4CCC(F)(F)CC4)ccc32)cc1] | $^1H$ NMR (400 MHz, DMSO-$d_6$) δ 1.94-2.07 (4H, m), 3.50-3.64 (4H, m), 3.81 (2H, t, J = 4.5 Hz), 4.27 (2H, t, J = 4.2 Hz), 6.88 (1H, dd, J = 8.5, 1.8 Hz), 6.98 (1H, d, J = 2.4 Hz), 7.13 (1H, d, J = 8.5 Hz), 7.38-7.42 (2H, m), 7.75-7.79 (2 H, m). LRMS ($ESI^+$ 384 $[M + H]^+$. |
| 1-18 | 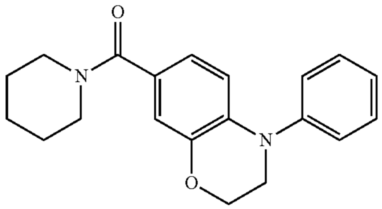 [SMILES: O=C(c1ccc2c(c1)OCCN2c1ccccc1)N1CCCCC1] | $^1H$ NMR (400 MHz, DMSO-$d_6$) δ: 1.40-1.51 (4H, m), 1.55-1.64 (2H, m), 3.37-3.48 (4H, m), 3.71 (2H, t, J = 4.5 Hz), 4.28 (2H, t, J = 4.5 Hz), 6.71-6.77 (2H, m), 6.80-6.82 (1H, m), 7.12-7.17 (1H, m), 7.26-7.31 (2H, m), 7.37-7.43 (2H, m). LRMS ($ESI^+$) 323 $[M + H]^+$. |

TABLE 58

| Example No. | Chemical Structural Formula | Spectrum Data |
|---|---|---|
| 1-19 | 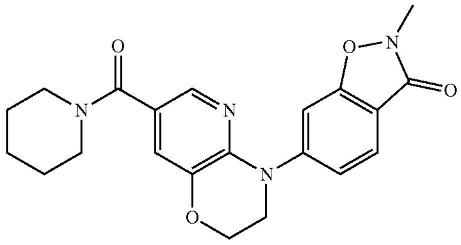 [SMILES: Cn1oc2cc(N3CCOc4cc(C(=O)N5CCCCC5)cnc43)ccc2c1=O] | $^1H$ NMR (400 MHz, DMSO-$d_6$) δ 1.41-1.66 (6H, m), 3.35-3.53 (4H, m), 3.54 (3H, s), 3.99 (2H, t, J = 4.3 Hz), 4.36 (2H t, J = 4.6 Hz), 7.19 (1H, d, J = 2.4 Hz), 7.45 (1H, dd, J = 8.6, 1.8 Hz), 7.50 (1H, d, J = 1.8 Hz), 7.70 (1H, d, J = 8.6 Hz), 7.74 (1H, d, J = 1.8 Hz). LRMS ($ESI^+$) 395 $[M + H]^+$. |

TABLE 58-continued

| Example No. | Chemical Structural Formula | Spectrum Data |
|---|---|---|
| 1-20 | 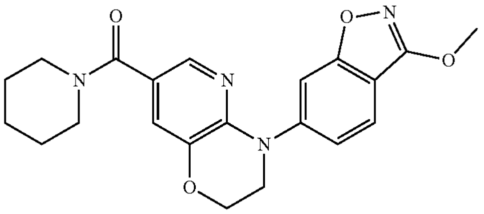 [SMILES: COc1noc2cc(N3CCOc4cc(C(=O)N5CCCCC5)cnc43)ccc12] | $^1$H NMR (400 MHz, DMSO-$d_6$) δ: 1.40-1.66 (6H, m), 3.37-3.53 (4H, m), 3.99 (2H, t, J = 4.3 Hz), 4.09 (3H, s), 4.36 (2H t, J = 4.3 Hz), 7.17 (1H, d, J = 1.8 Hz), 7.50 (1H, dd, J = 8.6, 1.8 Hz), 7.62 (1H, d, J = 1.2 Hz), 7.65 (1H, d, J = 8.6 Hz), 7.71 (1H, d, J = 1.8 Hz).<br>LRMS (ESI$^+$) 395 [M + H]$^+$. |
| 1-21 | 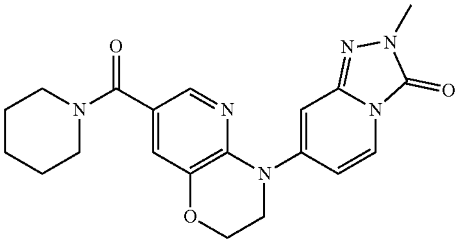 [SMILES: Cn1nc2cc(N3CCOc4cc(C(=O)N5CCCCC5)cnc43)ccn2c1=O] | $^1$H NMR (400 MHz, DMSO-$d_6$) δ: 1.41-1.66 (6H, m), 3.23-3.64 (7H, m), 3.93 (2H, t, J = 4.3 Hz), 4.36 (2H, t, J = 4.3 Hz), 6.88 (1H, d, J = 1.8 Hz), 6.98 (1H, dd, J = 7.6, 2.1 Hz), 7.21 (1H, d, J = 1.8 Hz), 7.75 (1H, d, J = 6.7 Hz), 7.77 (1H, d, J = 2.4 Hz).<br>LRMS (ESI$^+$) 395 [M + H]$^+$. |
| 1-22 | 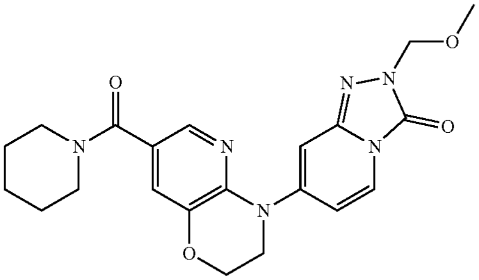 | $^1$H NMR (400 MHz, DMSO-$d_6$) δ: 1.42-1.66 (6H, m), 3.29 (3H, s), 3.30-3.60 (4H, m), 3.94 (2H, t, J = 4.3 Hz), 4.37 (2 H, t, J = 4.3 Hz), 5.16 (2H, s), 6.89 (1H, d, J = 1.8 Hz), 7.00 (1H, dd, J = 7.6, 2.1 Hz), 7.22 (1H, d, J = 1.8 Hz), 7.75-7.80 (2H, m).<br>LRMS (ESI$^+$) 425 [M + H]$^+$. |
| 1-23 | 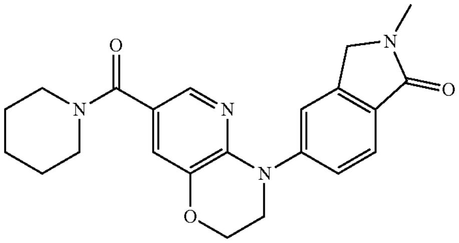 | $^1$H NMR (400 MHz, DMSO-$d_6$) δ: 1.40-1.66 (6H, m), 3.06 (3H, s), 3.35-3.55 (4H, m), 3.96 (2H, t, J = 4.3 Hz), 4.35 (2 H, t, J = 4.3 Hz), 4.44 (2H, s), 7.15 (1H, d, J = 1.8 Hz), 7.51 (1H, dd, J = 8.3, 2.1 Hz), 7.59-7.66 (2H, m), 7.69 (1H, d, J = 1.8 Hz).<br>LRMS (ESI$^+$) 393 [M + H]$^+$. |
| 1-24 | 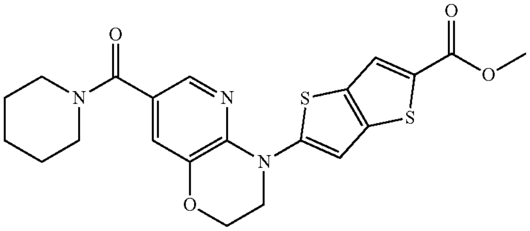 [SMILES: COC(=O)c1cc2sc(N3CCOc4cc(C(=O)N5CCCCC5)cnc43)cc2s1] | $^1$H NMR (400 MHz, DMSO-$d_6$) δ: 1.43-1.66 (6H, m), 3.34-3.60 (4H, m), 3.81 (3H, s), 4.16 (2H, t, J = 4.9 Hz), 4.44 (2H, t, J = 4.6 Hz), 7.13 (1H, s), 7.28 (1H, d, J = 1.8 Hz), 7.97 (1H, d, J = 1.8 Hz), 8.07 (1H, s).<br>LRMS (ESI$^+$) 444 [M + H]$^+$. |

TABLE 59

| Example No. | Chemical Structural Formula | Spectrum Data |
|---|---|---|
| 1-25 | 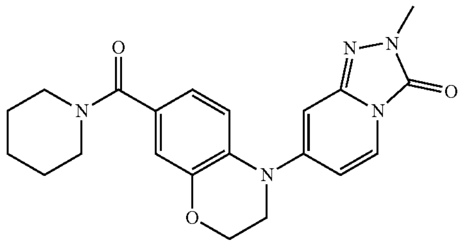 [SMILES: Cn1nc2cc(N3CCOc4cc(C(=O)N5CCCCC5)ccc43)ccn2c1=O] | $^1$H NMR (400 MHz, DMSO-$d_6$) δ: 1.40-1.65 (6H, m), 3.36-3.57 (7H, m), 3.77 (2H, t, J = 4.3 Hz), 4.29 (2H, t, J = 4.3 Hz), 6.64-6.70 (2H, m), 6.83 (1H, dd, J = 8.3, 2.1 Hz), 6.87 (1H, d, J = 1.8 Hz), 7.05 (1H, d, J = 8.6 Hz), 7.75-7.81 (1 H, m). LRMS (ESI$^+$) 394 [M + H]$^+$. |
| 1-26 | 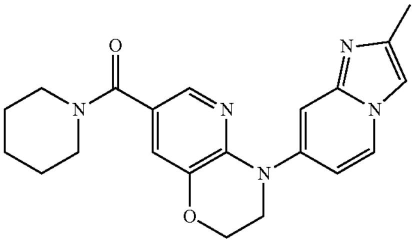 [SMILES: Cc1cn2ccc(N3CCOc4cc(C(=O)N5CCCCC5)cnc43)cc2n1] | $^1$H NMR (400 MHz, DMSO-$d_6$) δ: 1.40-1.64 (6H, m), 2.29 (3H, s), 3.37-3.53 (4H, m), 3.95 (2H, t, J = 4.2 Hz), 4.36 (2 H, t, J = 4.2 Hz), 7.07 (1H, dd, J = 7.3, 1.8 Hz), 7.14 (1H, d, J = 2.4 Hz), 7.27 (1H, d, J = 1.8 Hz), 7.56 (1H, s), 7.70 (1H, d, J = 1.8 Hz), 8.33 (1H, d, J = 7.3 Hz). LRMS (ESI$^+$) 378 [M + H]$^+$. |
| 1-27 | 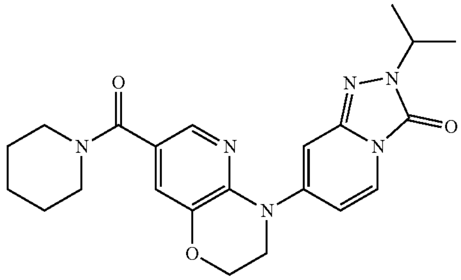 [SMILES: CC(C)n1nc2cc(N3CCOc4cc(C(=O)N5CCCCC5)cnc43)ccn2c1=O] | $^1$H NMR (400 MHz, DMSO-$d_6$) δ: 1.33 (6H, d, J = 6.7 Hz), 1.40-1.66 (6H, m), 3.34-3.57 (4H, m), 3.92 (2H, t, J = 4.6 Hz), 4.36 (2H, t, J = 4.6 Hz), 4.45-4.55 (1H, m), 6.92-7.00 (2 H, m), 7.20 (1H, d, J = 1.8 Hz), 7.72-7.81 (2H, m). LRMS (ESI$^+$) 423 [M + H]$^+$. |
| 1-28 | 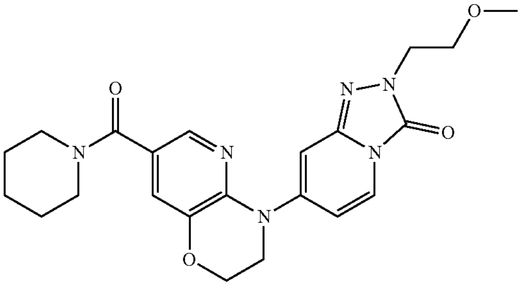 [SMILES: COCCn1nc2cc(N3CCOc4cc(C(=O)N5CCCCC5)cnc43)ccn2c1=O] | $^1$H NMR (400 MHz, DMSO-$d_6$) δ: 1.42-1.64 (6H, m), 3.22 (3H, s), 3.25-3.59 (4H, m), 3.66 (2H, t, J = 5.5 Hz), 3.93 (2 H, t, J = 4.3 Hz), 4.00 (2H, t, J = 5.5 Hz), 4.36 (2H, t, J = 4.3 Hz), 6.91 (1H, d, J = 1.8 Hz), 6.98 (1H, dd, J = 7.9, 1.8 Hz), 7.21 (1H, d, J = 1.8 Hz), 7.73-7.79 (2H, m). LRMS (ESI$^+$) 439 [M + H]$^+$. |
| 1-29 | 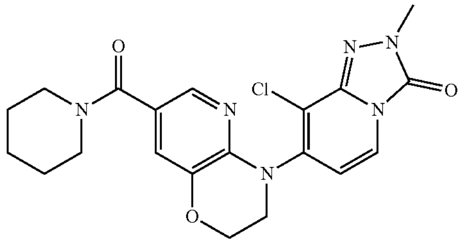 [SMILES: Cn1nc2c(Cl)c(N3CCOc4cc(C(=O)N5CCCCC5)cnc43)ccn2c1=O] | $^1$H NMR (400 MHz, DMSO-$d_6$) δ 1.40-1.64 (6H, m), 3.25-3.61 (7H, m), 3.87 (2H, t, J = 4.6 Hz), 4.35 (2H, t, J = 4.3 Hz), 6.73 (1H, d, J = 7.3 Hz), 7.19 (1H, d, J = 1.8 Hz), 7.70 (1H, d, J = 2.4 Hz), 7.90 (1H, d, J = 7.3 Hz). LRMS (ESI$^+$) 429 [M + H]$^+$. |
| 1-30 | 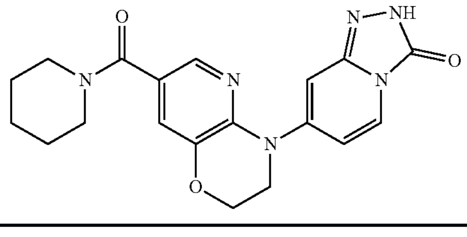 | $^1$H NMR (400 MHz, DMSO-$d_6$) δ 1.40-1.64 (6H, m), 3.27-3.65 (4H, m), 3.92 (2H, t, J = 4.6 Hz), 4.36 (2H, t, J = 4.3 Hz), 6.88 (1H, d, J = 2.4 Hz), 6.93 (1H, dd, J = 7.9, 1.8 Hz), 7.20 (1H, d, J = 1.8 Hz), 7.71 (1H, d, J = 6.7 Hz), 7.77 (1H, d, J = 1.8 Hz), 12.22 (1H, s). LRMS (ESI$^+$) 381 [M + H]$^+$. |

TABLE 60

| Example No. | Chemical Structural Formula | Spectrum Data |
|---|---|---|
| 1-31 | 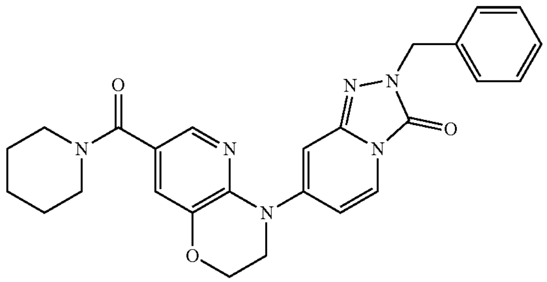 [SMILES: O=C(c1cnc2c(c1)OCCN2c1ccn2c(=O)n(Cc3ccccc3)nc2c1)N1CCCCC1] | $^{1}H$ NMR (400 MHz, DMSO-$d_6$) δ 1.41-1.65 (6H, m), 3.25-3.57 (4H, m), 3.92 (2H, t, J = 4.3 Hz), 4.35 (2H, t, J = 4.3 Hz), 5.06 (2H, s), 6.88 (1H, d, J = 1.2 Hz), 7.00 (1H, dd, J = 7.6, 2.1 Hz), 7.20 (1H, d, J = 1.8 Hz), 7.25-7.37 (5H, m), 7.76-7.81 (2H, m). LRMS (ESI$^{+}$) 471 [M + H]$^{+}$. |
| 1-32 | 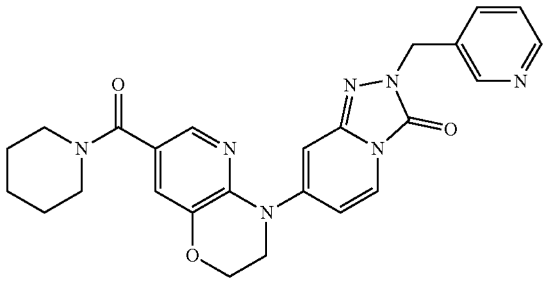 [SMILES: O=C(c1cnc2c(c1)OCCN2c1ccn2c(=O)n(Cc3cccnc3)nc2c1)N1CCCCC1] | $^{1}H$ NMR (400 MHz, DMSO-$d_6$) δ 1.40-1.67 (611, m), 3.21-3.65 (4H, m), 3.91 (2H, t, J = 4.3 Hz), 4.35 (2H, t, J = 4.6 Hz), 5.12 (2H, s), 6.89 (1H, d, J = 1.8 Hz), 7.00 (1H, dd, J = 7.9, 1.8 Hz), 7.21 (1H, d, J = 1.8 Hz), 7.33-7.41 (1H, m), 7.67-7.72 (1H, m), 7.75-7.81 (2H, m), 8.50 (1H, dd, J = 4.9, 1.8 Hz), 8.55 (1H, d, J = 1.8 Hz). LRMS (ESI$^{+}$) 472 [M + H]$^{+}$. |
| 1-33 | 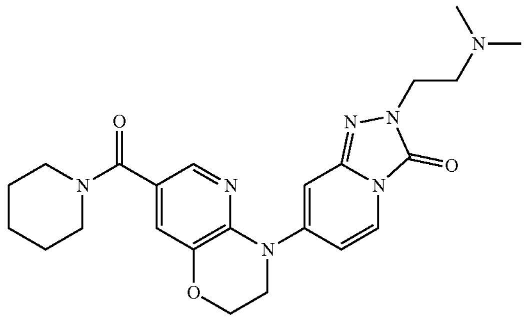 [SMILES: CN(C)CCn1nc2cc(N3CCOc4cc(C(=O)N5CCCCC5)cnc43)ccn2c1=O] | $^{1}H$ NMR (400 MHz, DMSO-$d_6$) δ 1.39-1.67 (6H, m), 2.15 (6 H, s), 2.59 (2H, t, J = 6.1 Hz), 3.22-3.65 (4H, m), 3.87-3.97 (4H, m), 4.36 (2H, t, J = 4.3 Hz Hz), 6.91 (1H, d, J = 1.8 Hz), 6.97 (1H, dd, J = 7.9, 1.8), 7.21 (1H, d, J = 1.8 Hz), 7.72-7.79 (2H, m). LRMS (ESI$^{+}$) 452 [M + H]$^{+}$. |
| 1-34 | 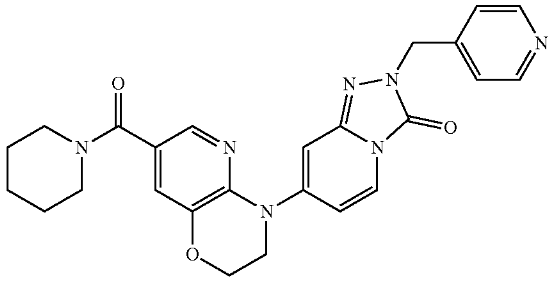 [SMILES: O=C(c1cnc2c(c1)OCCN2c1ccn2c(=O)n(Cc3ccncc3)nc2c1)N1CCCCC1] | $^{1}H$ NMR (400 MHz, DMSO-$d_6$) δ 1.38-1.68 (6H, m), 3.21-3.64 (4H, m), 3.93 (2H, t, J = 4.6 Hz), 4.36 (2H, t, J = 4.3 Hz), 5.12 (2H, s), 6.90 (1H, d, J = 1.8 Hz), 7.02 (1H, dd, J = 7.6, 2.1 Hz), 7.21 (1H, d, J = 1.8 Hz), 7.22-7.26 (2H, m), 7.78 (1H, d, J = 1.8 Hz), 7.81 (1H, d, J = 8.6 Hz), 8.49-8.55 (2H, m). LRMS (ESI$^{+}$) 472 [M + H]$^{+}$. |
| 1-35 | 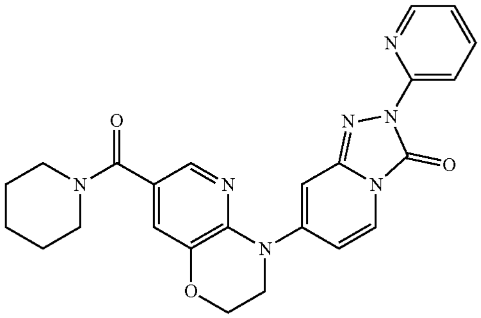 [SMILES: O=C(c1cnc2c(c1)OCCN2c1ccn2c(=O)n(-c3ccccn3)nc2c1)N1CCCCC1] | $^{1}H$ NMR (400 MHz, DMSO-$d_6$) δ 1.41-1.66 (6H, m), 3.25-3.62 (4H, m), 3.98 (2H, t, J = 4.6 Hz), 4.39 (2H, t, J = 4.3 Hz), 6.94 (1H, d, J = 1.2 Hz), 7.06 (1H, dd, J = 7.6, 2.1 Hz), 7.24 (1H, d, J = 2.4 Hz), 7.32-7.37 (1H, m),, 7.81 (1H, d, J = 2.4 Hz), 7.85 (1H, d, J = 7.9 Hz), 7.95-8.05 (2H, m), 8.51-8.55 (1H, m). LRMS (ESI$^{+}$) 458 [M + H]$^{+}$. |

TABLE 60-continued

| Example No. | Chemical Structural Formula | Spectrum Data |
|---|---|---|
| 1-36 | 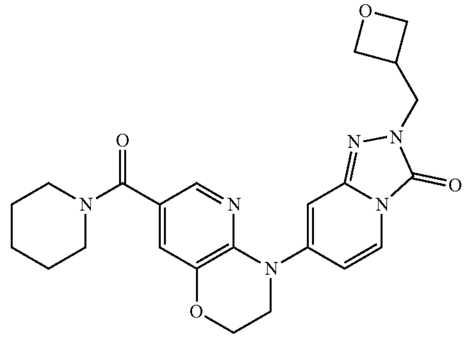 [SMILES: O=C(c1cnc2c(c1)OCCN2c1ccn2c(=O)n(CC3COC3)nc2c1)N1CCCCC1] | $^1$H NMR (400 MHz, DMSO-d$_6$) δ 1.39-1.66 (6H, m), 3.24-3.64 (5H, m), 3.92 (2H, t, J = 4.3 Hz), 4.15 (2H, d, J = 6.7 Hz), 4.36 (2H, t, J = 4.3 Hz), 4.44 (2H, dd, J = 6.1, 6.1 Hz), 4.65 (2H, dd, J = 7.9, 6.1 Hz), 6.91 (1H, d, J = 1.8 Hz), 6.99 (1H, dd, J = 7.9, 1.8 Hz), 7.21 (1H, d, J = 1.8 Hz), 7.74-7.79 (2H, m). LRMS (ESI$^+$) 451 [M + H]$^+$. |

TABLE 61

| Example No. | Chemical Structural Formula | Spectrum Data |
|---|---|---|
| 1-37 | 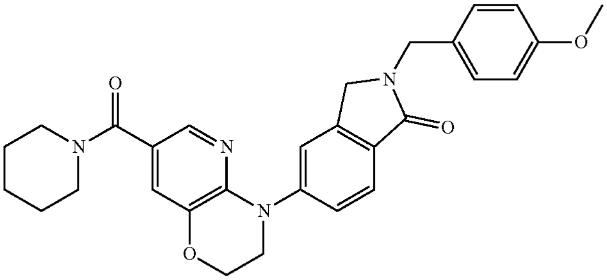 [SMILES: COc1ccc(CN2Cc3cc(N4CCOc5cc(C(=O)N6CCCCC6)cnc54)ccc3C2=O)cc1] | $^1$H NMR (400 MHz, CDCl$_3$) δ 1.46-1.77 (6H, m), 3.34-3.73 (4H, m), 3.79 (3H, s), 3.93 (2H, t, J = 4.3 Hz), 4.24 (2H, s), 4.36 (2H, t, J = 4.3 Hz), 4.73 (2H, s), 6.83-6.89 (2H, m), 7.19-7.28 (3H, m), 7.39 (1H, dd, J = 7.9, 1.8 Hz), 7.48 (1H, d, J = 1.2 Hz), 7.80 (1H, d, J = 1.8 Hz), 7.89 (1H, d, J = 8.6 Hz). LRMS (ESI$^+$) 499 [M + H]$^+$. |
| 1-38 | 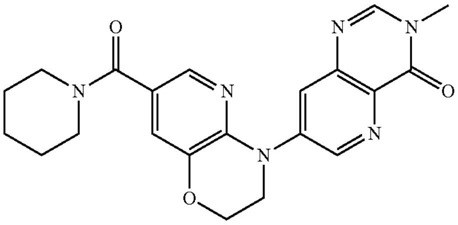 [SMILES: Cn1cnc2cc(N3CCOc4cc(C(=O)N5CCCCC5)cnc43)cnc2c1=O] | $^1$H NMR (400 MHz, DMSO-d$_6$) δ 1.43-1.64 (6H, m), 3.37-3.56 (7H, m), 4.05-4.11 (2H, m), 4.39-4.44 (2H, m), 7.24 (1H, d, J = 1.8 Hz), 7.76 (1H, d, J = 1.8 Hz), 7.93 (1H, d, J = 2.4 Hz), 8.42 (1H, s), 9.07 (1H, d, J = 2.4 Hz). LRMS (ESI$^+$) 407 [M + H]$^+$. |
| 1-39 | 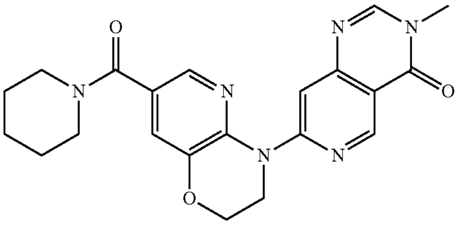 [SMILES: Cn1cnc2cc(N3CCOc4cc(C(=O)N5CCCCC5)cnc43)ncc2c1=O] | $^1$H NMR (400 MHz, DMSO-d$_6$) δ 1.42-1.67 (6H, m), 3.26-3.68 (7H, m), 4.29-4.42 (4H, m), 7.31 (1H, d, J = 2.4 Hz), 7.94 (1H, d, J = 1.8 Hz), 8.29 (1H, s), 8.44 (1H, s), 9.12 (1H, s). LRMS (ESI$^+$) 407 [M + H]$^+$. |

TABLE 61-continued

| Example No. | Chemical Structural Formula | Spectrum Data |
| --- | --- | --- |
| 1-40 | 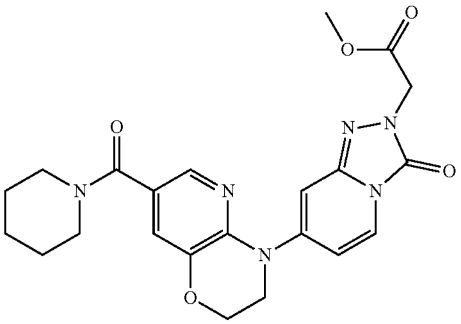 [SMILES: COC(=O)Cn1nc2cc(N3CCOc4cc(C(=O)N5CCCCC5)cnc43)ccn2c1=O] | $^{1}H$ NMR (400 MHz, DMSO-$d_6$) δ 1.41-1.66 (6H, m), 3.26-3.63 (4H, m), 3.69 (3H, s), 3.94 (2H, t, J = 4.3 Hz), 4.37 (2H, t, J = 4.3 Hz), 4.77 (2H, s), 6.88 (1H, d, J = 1.2 Hz), 7.01 (1H, dd, J = 7.6, 2.1 Hz), 7.22 (1H, d, J = 1.8 Hz), 7.77-7.81 (2H, m). LRMS (ESI$^+$) 453 [M + H]$^+$. |
| 1-41 | 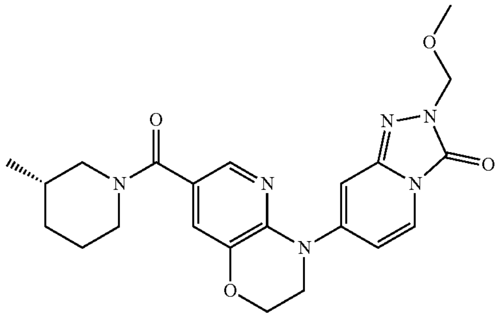 [SMILES: COCn1nc2cc(N3CCOc4cc(C(=O)N5CCC[C@H](C)C5)cnc43)ccn2c1=O] | $^{1}H$ NMR (400 MHz, DMSO-$d_6$) δ 0.74-1.04 (3H, m), 1.07-1.33 (1H, m), 1.39-1.55 (1H, m), 1.56-1.77 (2H, m), 1.78-1.94 (1H, m), 2.64-3.17 (2H, m), 3.37 (3H, s), 3.56-3.87 (1H, m), 4.01 (2H, t, J = 4.3 Hz), 4.13-4.54 (3H, m), 5.24 (2H, s), 6.96 (1H, d, J = 1.2 Hz), 7.08 (1H, dd, J = 7.6, 2.1 Hz), 7.29 (1H, d, J = 1.8 Hz), 7.82-7.90 (2H, m). LRMS (ESI$^+$) 439 [M + H]$^+$. |
| 1-42 | 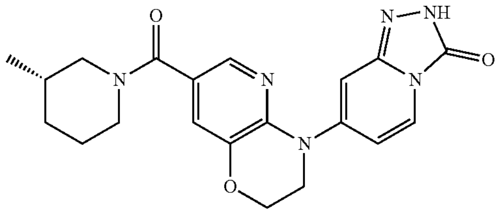 [SMILES: C[C@H]1CCCN(C(=O)c2cnc3c(c2)OCCN3c2ccn3c(=O)[nH]nc3c2)C1] | $^{1}H$ NMR (400 MHz, DMSO-$d_6$) δ 0.73-0.93 (3H, m), 1.07-1.19 (1H, m), 1.34-1.46 (1H, m), 1.49-1.67 (2H, m), 1.71-1.81 (1H, m), 2.61-3.13 (2H, m), 3.40-3.83 (1H, m), 3.92 (2H, t, J = 4.3 Hz), 4.00-4.45 (3H, m), 6.88 (1H, d, J = 1.2 Hz), 6.94 (1H, dd, J = 7.9, 1.8 Hz), 7.19 (1H, d, J = 1.8 Hz), 7.71 (1H, d, J = 8.6 Hz), 7.77 (1H, d, J = 1.8 Hz), 12.22 (1H, s). LRMS (ESI$^+$) 395 [M + H]$^+$. |

TABLE 62

| Example No. | Chemical Structural Formula | Spectrum Data |
| --- | --- | --- |
| 1-43 | 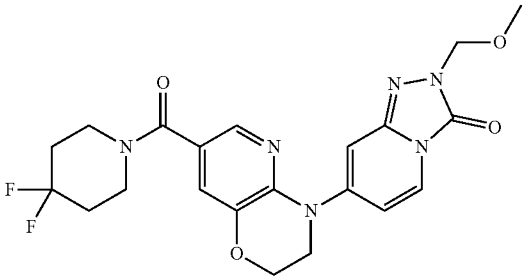 [SMILES: COCn1nc2cc(N3CCOc4cc(C(=O)N5CCC(F)(F)CC5)cnc43)ccn2c1=O] | $^{1}H$ NMR (400 MHz, DMSO-$d_6$) δ 1.93-2.12 (4H, m), 3.29 (3H, s), 3.43-3.77 (4H, m), 3.94 (2H, t, J = 4.3 Hz), 4.37 (2H, t, J = 4.3 Hz), 5.16 (2H, s), 6.90 (1H, d, J = 1.2 Hz), 7.00 (1H, dd, J = 7.6, 2.1 Hz), 7.31 (1H, d, J = 1.8 Hz), 7.79 (1H, d, J = 8.6 Hz), 7.86 (1H, d, J = 1.8 Hz). LRMS (ESI$^+$) 461 [M + H]$^+$. |

TABLE 62-continued

| Example No. | Chemical Structural Formula | Spectrum Data |
|---|---|---|
| 1-44 | 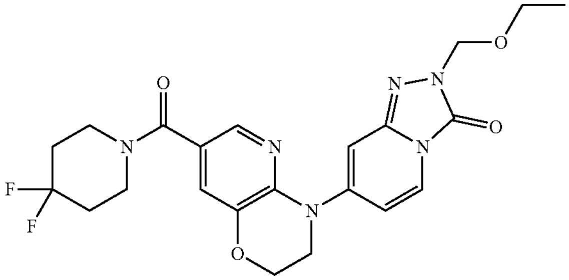 [SMILES: CCOCn1nc2cc(N3CCOc4cc(C(=O)N5CCC(F)(F)CC5)cnc43)ccn2c1=O] | $^1$H NMR (400 MHz, DMSO-$d_6$) δ 1.09 (3H, t, J = 7.0 Hz), 1.95-2.11 (4H, m), 3.45-3.70 (6H, m), 3.94 (2H, t, J = 4.3 Hz), 4.37 (2H, t, J = 4.3 Hz), 5.20 (2H, s), 6.90 (1H, d, J = 1.8 Hz), 6.99 (1H, dd, J = 7.9, 1.8 Hz), 7.31 (1H, d, J = 1.8 Hz), 7.78 (1H, d, J = 7.3 Hz), 7.86 (1H, d, J = 1.8 Hz). LRMS (ESI$^+$) 475 [M + H]$^+$. |
| 1-45 | 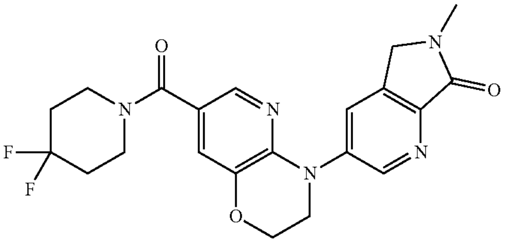 [SMILES: CN1Cc2cc(N3CCOc4cc(C(=O)N5CCC(F)(F)CC5)cnc43)cnc2C1=O] | $^1$H NMR (400 MHz, DMSO-$d_6$) δ 1.95-2.09 (4H, m), 3.10 (3H, s), 3.51-3.66 (4H, m), 3.99-4.05 (2H, m), 4.36-4.42 (2H, m), 4.47 (2H, s), 7.28 (1H, d, J = 1.8 Hz), 7.78 (1H, d, J = 2.4 Hz), 8.06 (1H, d, J = 2.4 Hz), 8.82 (1H, d, J = 2.4 Hz). LRMS (ESI$^+$) 430 [M + H]$^+$. |
| 1-46 | 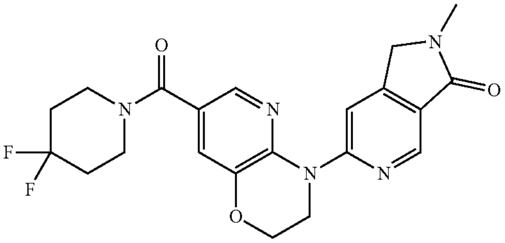 [SMILES: CN1Cc2cc(N3CCOc4cc(C(=O)N5CCC(F)(F)CC5)cnc43)ncc2C1=O] | $^1$H NMR (400 MHz, DMSO-$d_6$) δ 1.95-2.12 (4H, m), 3.03 (3H, s), 3.49-3.74 (4H, m), 4.27 (2H, t, J = 4.0 Hz), 4.36 (2H, t, J = 4.3 Hz), 4.50 (2H, s), 7.37 (1H, d, J = 1.8 Hz), 7.96 (1H, d, J = 2.4 Hz), 8.28 (1H, s), 8.63 (1H, s). LRMS (ESI$^+$) 430 [M + H]$^+$. |
| 1-47 | 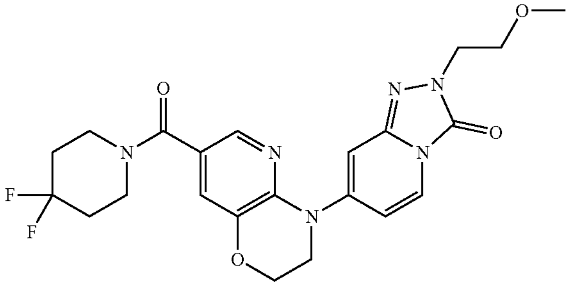 [SMILES: COCCn1nc2cc(N3CCOc4cc(C(=O)N5CCC(F)(F)CC5)cnc43)ccn2c1=O] | $^1$H NMR (400 MHz, DMSO-$d_6$) δ 1.95-2.10 (4H, m), 3.22 (3H, s), 3.47-3.71 (6H, m), 3.94 (2H, t, J = 4.3 Hz), 4.00 (2H, t, J = 5.5 Hz), 4.37 (2H, 1, 5 = 4.3 Hz), 6.92 (1H, d, J = 1.8 Hz), 6.98 (1H, dd, J = 7.9, 1.8 Hz), 7.30 (1H, d, J = 1.8 Hz), 7.76 (1H, d, J = 6.7 Hz), 7.86 (1H, d, J = 1.8 Hz). LRMS (ESI$^+$) 475 [M + H]$^+$. |
| 1-48 | 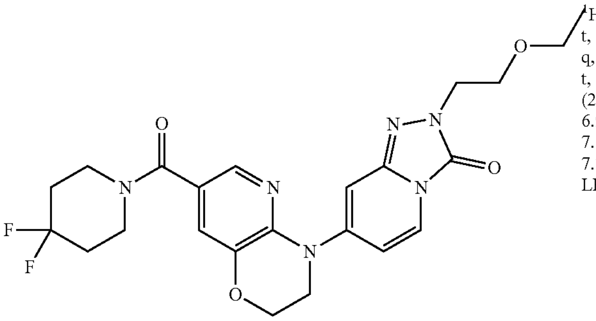 | $^1$H NMR (400 MHz, DMSO-$d_6$) δ 1.04 (3H, t, J = 6.7 Hz), 1.95-2.11 (4H, m), 3.42 (2H, q, J = 7.1 Hz), 3.51-3.65 (4H, m), 3.70 (2H, t, J = 5.5 Hz), 3.94 (2H, t, J = 4.3 Hz), 3.99 (2H, t, J = 5.5 Hz), 4.37 (2H, t, J = 4.3 Hz), 6.92 (1H, d, J = 1.2 Hz), 6.98 (1H, dd, J = 7.6, 2.1 Hz), 7.30 (11-1, d, J = 1.8 Hz), 7.77 (1H, d, J = 7.9 Hz), 7.85 (1H, d, J = 1.8 Hz). LRMS (ESI$^+$) 489 [M + H]$^+$. |

TABLE 63

| Example No. | Chemical Structural Formula | Spectrum Data |
|---|---|---|
| 1-49 | 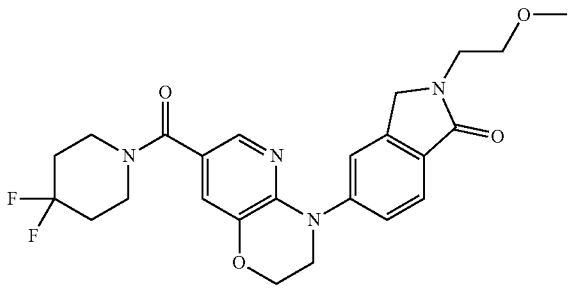 [SMILES: COCCN1Cc2cc(N3CCOc4cc(C(=O)N5CCC(F)(F)CC5)cnc43)ccc2C1=O] | $^1$H NMR (400 MHz, DMSO-$d_6$) δ 1.94-2.09 (4H, m), 3.26 (3H, s), 3.52-3.63 (6H, m), 3.67 (2H, t, J = 5.2 Hz), 3.96 (2H, t, J = 4.3 Hz), 4.36 (2H, t, J = 4.3 Hz), 4.50 (2H, s), 7.24 Hz (1H, d, J = 1.8 ), 7.52 (1H, dd, J = 8.3, 2.1 Hz), 7.60-7.67 (2H, m), 7.76 (1H, d, J = 1.8 Hz). LRMS (ESI$^+$) 473 [M + H]$^+$. |
| 1-50 | 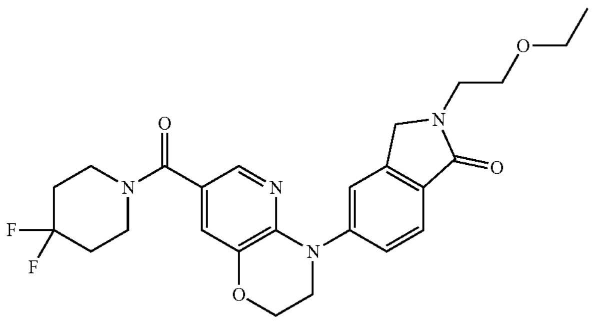 [SMILES: CCOCCN1Cc2cc(N3CCOc4cc(C(=O)N5CCC(F)(F)CC5)cnc43)ccc2C1=O] | $^1$H NMR (400 MHz, DMSO-$d_6$) δ 1.09 (3H, t, J = 6.7 Hz), 1.95-2.08 (4H, m), 3.45 2H, q, J = 6.9 Hz), 3.51-3.69 (8H, m), 3.96 (2H, t, J = 4.6 Hz), 4.36 (2H, t, J = 4.3 Hz), 4.51 (2H, s), 7.24 (1H, d, J = 1.8 Hz), 7.52 (1H, dd, J = 7.9, 1.8 Hz), 7.61-7.67 (2H, m), 7.76 (1H, d, J = 1.8 Hz). LRMS (ESI$^+$) 487 [M + H]$^+$. |
| 1-51 | 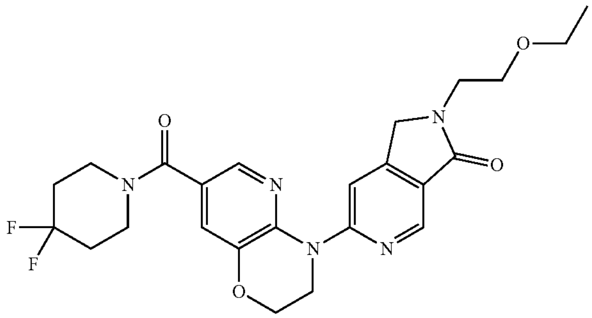 [SMILES: CCOCCN1Cc2cc(N3CCOc4cc(C(=O)N5CCC(F)(F)CC5)cnc43)ncc2C1=O] | $^1$H NMR (400 MHz, DMSO-$d_6$) δ 1.09 (3H, t, J = 7.0 Hz), 1.96-2.12 (4H, m), 3.44 (2H, q, J = 6.9 Hz), 3.49-3.74 (8H, m), 4.24-4.29 (2H, m), 4.34-4.40 (2H, m), 4.57 (2H, s), 7.38 (1H, d, J = 1.8 Hz), 7.95 (1H, d, J = 1.8 Hz), 8.29 (1H, s), 8.66 (1H, d, J = 1.2 Hz). LRMS (ESI$^+$) 488 [M + H]$^+$. |
| 1-52 | 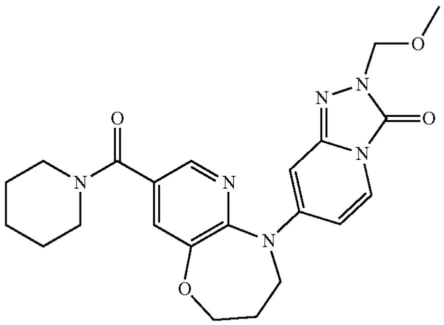 [SMILES: COCn1nc2cc(N3CCCOc4cc(C(=O)N5CCCCC5)cnc43)ccn2c1=O] | $^1$H NMR (400 MHz, DMSO-$d_6$) δ 1.41-1.69 (6H, m), 2.02-2.14 (2H, m), 3.15-3.70 (7H, m), 3.96 (2H, t, J = 6.1 Hz), 4.22 (2H, t, J = 5.8 Hz), 5.13 (2H, s), 6.49 (1H, dd, J = 7.9, 2.4 Hz), 6.63 (1H, d, J = 1.8 Hz), 7.42 (1H, d, J = 1.8 Hz), 7.68 (1H, d, J = 7.9 Hz), 8.04 (1H, d, J = 2.4 Hz). LRMS (ESI$^+$) 439 [M + H]$^+$. |
| 1-53 | 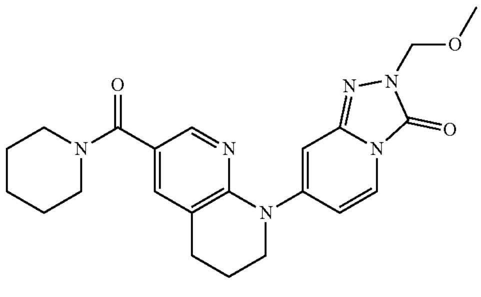 | $^1$H NMR (400 MHz, DMSO-$d_6$) δ 1.43-1.67 (6H, m), 1.95-2.06 (2H, m), 2.83 (2H, t, J = 6.4 Hz), 3.33 (3H, s), 3.36-3.59 (4H, m), 3.81 (2H, t, J = 5.8 Hz), 5.17 (2H, s), 6.80 (1H, dd, J = 7.9, 1.8 Hz), 6.89 (111, d, J = 1.2 Hz), 7.51 (1H, d, J = 1.8 Hz), 7.71 (1H, d, J = 7.9 Hz), 8.00 (1H, d, J = 2.4 Hz). LRMS (ESI$^+$) 423 [M + H]$^+$. |

TABLE 63-continued

| Example No. | Chemical Structural Formula | Spectrum Data |
|---|---|---|
| 1-54 | 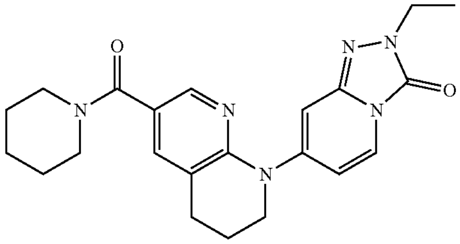 [SMILES: CCn1nc2cc(N3CCCc4cc(C(=O)N5CCCCC5)cnc43)ccn2c1=O] | $^1$H NMR (400 MHz, DMSO-$d_6$) δ 1.29 (3H, t, J = 7.0 Hz), 1.43-1.68 (6H, m), 1.94-2.05 (2H, m), 2.83 (2H, t, J = 6.4 Hz), 3.39-3.57 (4H, m), 3.80 (2H, t, J = 5.8 Hz), 3.88 (2H, q, J = 7.3 Hz), 6.77 (1H, dd, J = 7.9, 1.8 Hz), 6.91 (1H, d, J = 1.2 Hz), 7.49 (1H, d, J = 1.8 Hz), 7.69 (1H, d, J = 7.9 Hz), 7.99 (1H, d, J = 2.4 Hz). LRMS (ESI$^+$) 407 [M + H]$^+$. |

TABLE 64

| Example No. | Chemical Structural Formula | Spectrum Data |
|---|---|---|
| 1-55 | 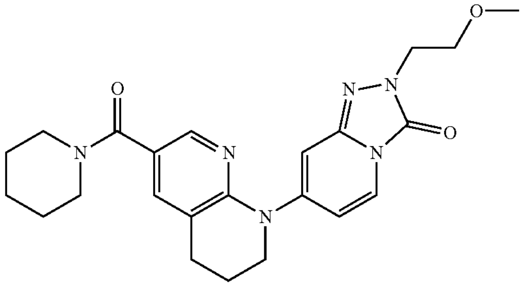 [SMILES: COCCn1nc2cc(N3CCCc4cc(C(=O)N5CCCCC5)cnc43)ccn2c1=O] | $^1$H NMR (400 MHz, DMSO-$d_6$) δ 1.44-1.67 (6H, m), 1.95-2.05 (2H, m), 2.83 (2H, t, J = 6.4 Hz), 3.23 (3H, s), 3.38-3.57 (4H, m), 3.67 (2H, t, J = 5.4 Hz), 3.80 (2H, t, J = 5.8 Hz), 4.00 (2H, t, J = 5.4 Hz), 6.78 (1H, dd, J = 7.9, 1.8 Hz), 6.91 (1H, d, J = 1.2 Hz), 7.49 (1H, d, J = 2.4 Hz), 7.69 (1H, d, J = 7.9 Hz), 7.99 (1H, d, J = 2.4 Hz). LRMS (ESI$^+$) 437 [M + H]$^+$. |
| 1-56 | 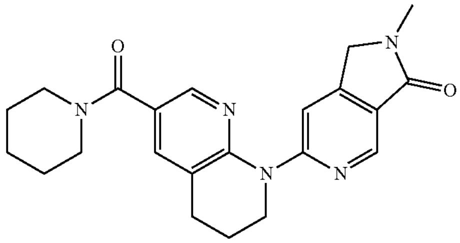 [SMILES: CN1Cc2cc(N3CCCc4cc(C(=O)N5CCCCC5)cnc43)ncc2C1=O] | $^1$H NMR (400 MHz, DMSO-$d_6$) δ 1.43-1.68 (6H, m), 1.93-2.03 (2H, m), 2.86 (2H, t, J = 6.4 Hz), 3.03 (3H, s), 3.40-3.57 (4H, m), 4.03-4.11 (2H, m), 4.47 (2H, s), 7.56 (1H, d, J = 2.4 Hz), 7.97 (1H, s), 8.06 (1H, d, J = 1.8 Hz), 8.63 (1H, s). LRMS (ESI$^+$) 392 [M + H]$^+$. |
| 1-57 | 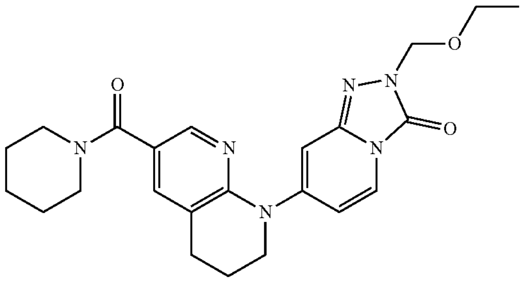 | $^1$H NMR (400 MHz, DMSO-$d_6$) δ 1.11 (3H, t, J = 7.0 Hz), 1.40-1.67 (6H, m), 1.95-2.05 (2H, m), 2.83 (2H, t, J = 6.4 Hz), 3.38-3.61 (6H, m), 3.81 (2H, t, J = 5.8 Hz), 5.21 (2H, s), 6.79 (1H, dd, J = 7.6, 2.1 Hz), 6.89 (1H, d, J = 1.8 Hz), 7.50 (1H, d, J = 1.8 Hz), 7.70 (1H, d, J = 7.9 Hz), 8.00 (1H, d, J = 1.8 Hz). LRMS (ESI$^+$) 437 [M + H]$^+$. |
| 1-58 | 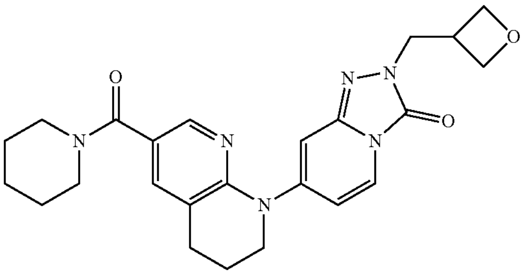 [SMILES: O=C(c1cnc2c(c1)CCCN2c1ccn2c(=O)n(CC3COC3)nc2c1)N1CCCCC1] | $^1$H NMR (400 MHz, DMSO-$d_6$) δ 1.43-1.67 (6H, m), 1.94-2.05 (2H, m), 2.83 (2H, t, J = 6.4 Hz), 3.27-3.37 (1H, m), 3.38-3.57 (4H, m), 3.79 (2H, t, J = 6.1 Hz), 4.16 (2H, d, J = 7.3 Hz), 4.45 (2H, 1, J = 6.1 Hz), 4.66 (2H, dd, J = 7.6, 6.4 Hz), 6.78 (1H, dd, J = 7.9, 1.8 Hz), 6.91 (1H, d, J = 1.8 Hz), 7.49 (1H, d, J = 1.8 Hz), 7.70 (1H, d, J = 7.3 Hz), 7.98 (1H, d, J = 2.4 Hz). LRMS (ESI$^+$) 449 [M + H]$^+$. |

TABLE 64-continued

| Example No. | Chemical Structural Formula | Spectrum Data |
|---|---|---|
| 1-59 | 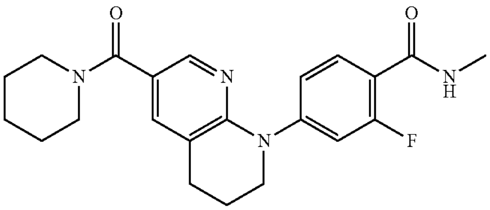 [SMILES: CNC(=O)c1ccc(N2CCCc3cc(C(=O)N4CCCCC4)cnc32)cc1F] | $^1H$ NMR (400 MHz, DMSO-$d_6$) δ 1.43-1.67 (6H, m), 1.93-2.06 (2H, m), 2.78 (3H, d, J = 4.8 Hz), 2.84 (2H, t, J = 6.1 Hz), 3.37-3.55 (4H, m), 3.79 (2H, t, J = 5.4 Hz), 7.26 (1H, dd, J = 8.5, 2.4 Hz), 7.32 (1H, dd, J = 13.0, 2.1 Hz), 7.44 (1H, d, J = 2.4 Hz), 7.61 (1H, t, J = 8.5 Hz), 7.91 (1H, d, J = 1.8 Hz), 8.08-8.17 (1H, m) LRMS (ESI$^+$) 397 $[M + H]^+$. |

TABLE 65

| Example No. | Chemical Structural Formula | Spectrum Data |
|---|---|---|
| 1-60 | 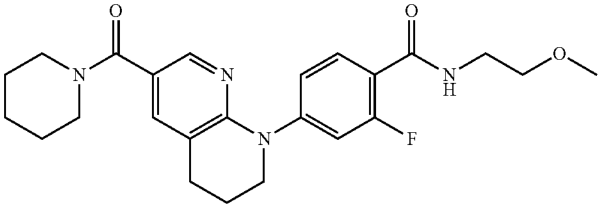 [SMILES: COCCNC(=O)c1ccc(N2CCCc3cc(C(=O)N4CCCCC4)cnc32)cc1F] | $^1H$ NMR (400 MHz, DMSO-$d_6$) δ 1.42-1.67 (6H, m), 1.94-2.05 (2H, m), 2.85 (2H, t, J = 6.4 Hz), 3.21-3.53 (11H, m), 3.80 (2H, t, J = 5.4 Hz), 7.26 (1H, dd, J = 8.5, 2.4 Hz), 7.32 (1H, dd, J = 13.3, 1.8 Hz), 7.44 (1H, d, J = 1.8 Hz), 7.61 (1H, t, J = 8.5 Hz), 7.90 (1H, d, J = 2.4 Hz), 8.13-8.21 (1H, m). LRMS (ESI$^+$) 441 $[M + H]^+$. |
| 1-61 | 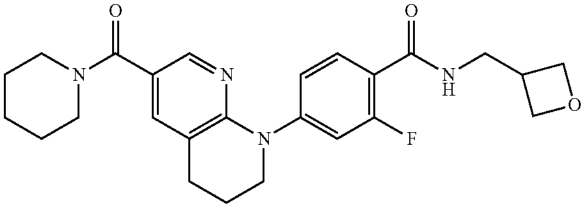 [SMILES: O=C(NCC1COC1)c1ccc(N2CCCc3cc(C(=O)N4CCCCC4)cnc32)cc1F] | $^1H$ NMR (400 MHz, DMSO-$d_6$) δ 1.42-1.68 (6H, m), 1.95-2.06 (2H, m), 2.85 (2H, t, J = 6.4 Hz), 3.10-3.22 (1H, m), 3.38-3.57 (6H, m), 3.79 (2H, t, J = 5.4 Hz), 4.35 (2H, t, J = 6.1 Hz), 4.62 (2H, dd, J = 7.9, 6.1 Hz), 7.26 (1H, dd, J = 8.5, 2.4 Hz), 7.32 (1H, dd, J = 12.7, 1.8 Hz), 7.43 (1H, d, J = 2.4 Hz.), 7.57 (1H, t, J = 8.5 Hz.), 7.89 (1H, d, J = 2.4 Hz), 8.34-8.43 (1H, m). LRMS (ESI$^+$) 453 $[M + H]^+$. |
| 1-62 | 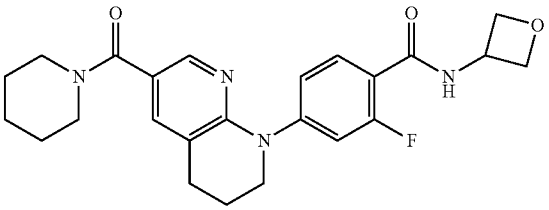 [SMILES: O=C(NC1COC1)c1ccc(N2CCCc3cc(C(=O)N4CCCCC4)cnc32)cc1F] | $^1H$ NMR (400 MHz, DMSO-$d_6$) δ 1.42-1.68 (6H, m), 1.95-2.06 (2H, m), 2.85 (2H, t, J = 6.4 Hz), 3.37-3.56 (4H, m), 3.80 (2H, t, J = 5.4 Hz), 4.56 (2H, t, J = 6.7 Hz), 4.76 (2H, t, J = 7.0 Hz), 4.93-5.05 (1H, m), 7.27 (1H, dd, J = 8.5, 2.4 Hz), 7.34 (1H, dd, J = 13.0, 2.1 Hz), 7.44 (1H, d, J = 1.8 Hz), 7.58 (HI, t, J = 8.5 Hz), 7.90 (1H, d, J = 1.8 Hz), 8.94 (1H, d, J = 5.4 Hz). LRMS (ESI$^+$) 439 $[M + H]^+$. |
| 1-63 | 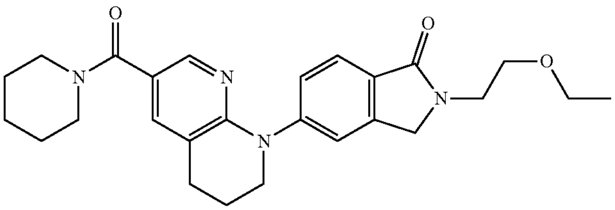 [SMILES: CCOCCN1Cc2cc(N3CCCc4cc(C(=O)N5CCCCC5)cnc43)ccc2C1=O] | $^1H$ NMR (400 MHz, DMSO-$d_6$) δ 1.10 (3H, t, J = 7.0 Hz), 1.39-1.67 (6H, m), 1.97-2.06 (2H, m), 2.87 (2H, t, J = 6.4 Hz), 3.40-3.51 (6H, m), 3.59 (2H, t, J = 5.1 Hz), 3.67 (2H, t, J = 5.4 Hz), 3.81 (2H, t, J = 5.4 Hz), 4.51 (2H, s), 7.39-7.46 (2H, m), 7.52-7.56 (1H, m), 7.64 (1H, d, J = 8.5 Hz), 7.84 (1H, d, J = 2.4 Hz). LRMS (ESI$^+$) 449 $[M + H]^+$. |
| 1-64 | 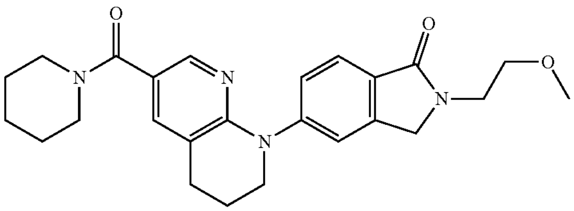 [SMILES: COCCN1Cc2cc(N3CCCc4cc(C(=O)N5CCCCC5)cnc43)ccc2C1=O] | $^1H$ NMR (400 MHz, DMSO-$d_6$) δ 1.43-1.67 (6H, m), 1.97-2.06 (2H, m), 2.87 (2H, t, J = 6.1 Hz), 3.27 (3H, s), 3.40-3.51 (4H, m), 3.56 (2H, t, J = 5.1 Hz), 3.67 (2H, t, J = 5.4 Hz), 3.80 (2H, t, J = 5.8 Hz), 4.49 (2H, s), 7.40-7.45 (2H, m), 7.54 (1H, d, J = 1.2 Hz), 7.64 (1H, d, J = 8.5 Hz), 7.84 (1H, d, J = 2.4 Hz). LRMS (ESI$^+$) 435 $[M+ H]^+$. |

TABLE 66

| Example No. | Chemical Structural Formula | Spectrum Data |
|---|---|---|
| 1-65 | 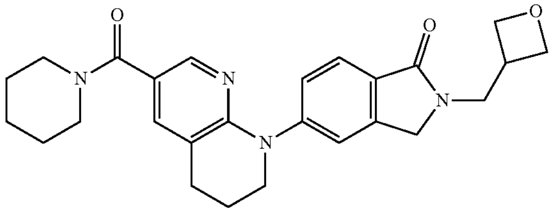 [SMILES: O=C(c1cnc2c(c1)CCCN2c1ccc2c(c1)CN(CC1COC1)C2=O)N1CCCCC1] | $^1$H NMR (400 MHz, DMSO-$d_6$) δ 1.41-1.66 (6H, m), 1.95-2.07 (2H, m), 2.86 (2H, t, J = 6.4 Hz), 3.26-3.36 (1H, m), 3.37-3.56 (4H, m), 3.76-3.87 (4H, m), 4.35-4.44 (4H, m), 4.67 (2H, dd, J = 7.9, 6.1 Hz), 7.39-7.45 (2H, m), 7.52 (1H, s), 7.64 (1H, d, J = 8.5 Hz), 7.83 (1H, d, J = 2.4 Hz). LRMS (ESI$^+$) 447 [M + H]$^+$. |
| 1-66 | 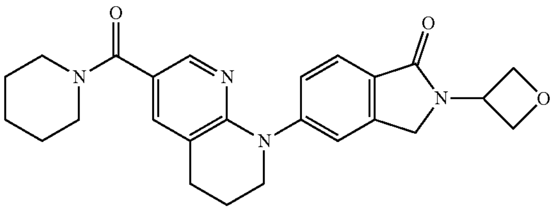 [SMILES: O=C(c1cnc2c(c1)CCCN2c1ccc2c(c1)CN(C1COC1)C2=O)N1CCCCC1] | $^1$H NMR (400 MIIz, DMSO-$d_6$) δ 1.42-1.69 (6H, m), 1.97-2.08 (2H, m), 2.87 (2H, t, J = 6.4 Hz), 3.38-3.57 (4H, m), 3.82 (2H, t, J = 5.4 Hz), 4.75-4.91 (6H, m), 5.37-5.47 (1H, m), 7.40-7.47 (2H, m), 7.59-7.62 (1H, m), 7.65 (1H, d, J = 7.9 Hz), 7.85 (1H, d, J = 2.4 Hz). LRMS (ESI$^+$) 433 [M + H]$^+$. |
| 1-67 | 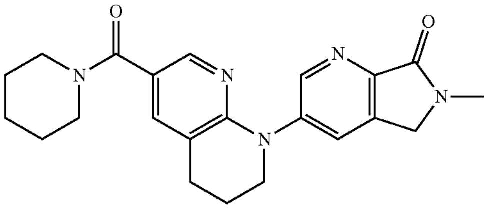 [SMILES: CN1Cc2cc(N3CCCc4cc(C(=O)N5CCCCC5)cnc43)cnc2C1=O] | $^1$H NMR (400 MHz, DMSO-$d_6$) δ 1.43-1.66 (6H, m), 2.00-2.09 (2H, m), 2.89 (2H, t, J = 6.4 Hz), 3.10 (3H, s), 3.39-3.54 (4H, m), 3.86 (2H, t, J = 5.4 Hz), 4.46 (2H, s), 7.45 (1H, d, J = 2.4 Hz), 7.87 (1H, d, J = 2.4 Hz), 8.00 (1H, d, J = 2.4 Hz), 8.72 (1H, d, J = 2.4 Hz). LRMS (ESI$^+$) 392 [M + H]$^+$. |
| 1-68 | 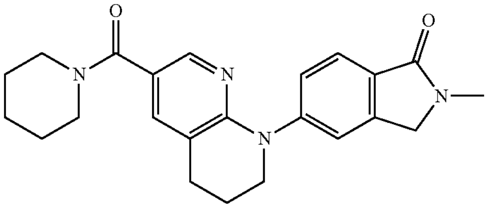 [SMILES: CN1Cc2cc(N3CCCc4cc(C(=O)N5CCCCC5)cnc43)ccc2C1=O] | $^1$H NMR (400 MHz, DMSO-$d_6$) δ 1.40-1.67 (6H, m), 1.94-2.07 (2H, m), 2.86 (2H, t, J = 6.1 Hz), 3.07 (3H, s), 3.37-3.55 (4H, m), 3.80 (2H, t, J = 5.4 Hz), 4.43 (2H, s), 7.39-7.44 (2H, m), 7.52-7.54 (1H, m), 7.62 (1H, d, J = 7.9 Hz), 7.84 (1H, d, J = 2.4 Hz). LRMS (ESI$^+$) 391 [M + H]$^+$. |
| 1-69 | 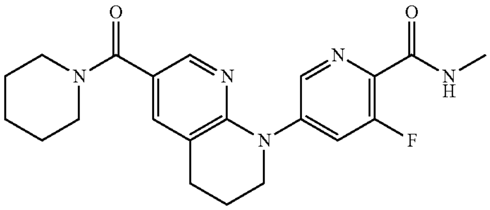 [SMILES: CNC(=O)c1ncc(N2CCCc3cc(C(=O)N4CCCCC4)cnc32)cc1F] | $^1$H NMR (400 MHz, DMSO-$d_6$) δ 1.42-1.68 (6H, m), 1.98-2.07 (2H, m), 2.78 (3H, d, J = 4.8 Hz), 2.87 (2H, t, J = 6.4 Hz), 3.38-3.56 (4H, m), 3.87 (2H, t, J = 5.4 Hz), 7.50 (1H, J = 2.4 Hz), 7.85 (1H, dd, J = 13.3, 1.8 Hz), 7.95 (1H, d, J = 2.4 Hz), 8.50-8.58 (1H, m), 8.59-8.63 (1H, m) LRMS (ESI$^+$) 398 [M + H]$^+$. |
| 1-70 | 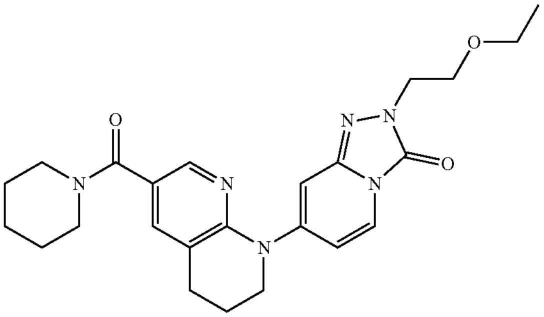 [SMILES: CCOCCn1nc2cc(N3CCCc4cc(C(=O)N5CCCCC5)cnc43)ccn2c1=O] | $^1$H NMR (400 MHz, DMSO-$d_6$) δ 1.05 (3H, t, J = 7.0 Hz), 1.41-1.67 (6H, m), 1.95-2.05 (2H, m), 2.83 (2H, t, J = 6.4 Hz), 3.38-3.57 (6H, m), 3.71 (2H, t, J = 5.4 Hz), 3.80 (2H, t, J = 5.8 Hz), 3.99 (2H, t, J = 5.8 Hz), 6.78 (1H, dd, J = 7.6, 2.1 Hz), 6.91 (1H, d, J = 1.2 Hz), 7.49 (1H, t, J = 1.2 Hz), 7.70 (1H, d, J = 6.7 Hz), 7.99 (1H, d, J = 2.4 Hz). LRMS (ESI$^+$) 451 [M + H]$^+$. |

TABLE 67

| Example No. | Chemical Structural Formula | Spectrum Data |
| --- | --- | --- |
| 1-71 | 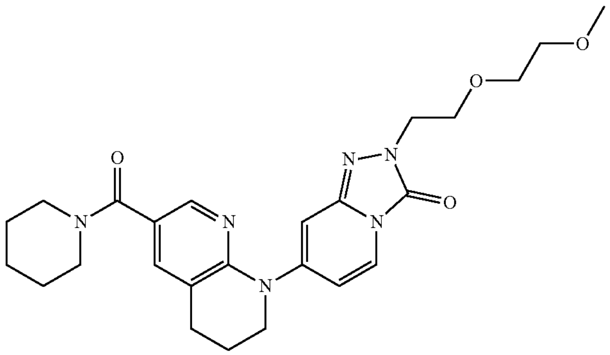 [SMILES: COCCOCCn1nc2cc(N3CCCc4cc(C(=O)N5CCCCC5)cnc43)ccn2c1=O] | $^{1}$H NMR (400 MHz, DMSO-$d_6$) δ 1.42-1.68 (6H, m), 1.94-2.06 (2H, m), 2.83 (2H, t, J = 6.4 Hz), 3.20 (3H, s), 3.26-3.55 (8H, m), 3.72-3.85 (4H, m), 4.00 (2H, t, J = 5.8 Hz), 6.78 (1H, dd, J = 7.9, 1.8 Hz), 6.91 (1H, d, J = 1.8 Hz), 7.49 (1H, d, J = 1.8 Hz), 7.70 (1H, d, J = 7.3 Hz), 7.99 (1H, d, J = 2.4 Hz). LRMS (ESI$^+$) 481 [M + H]$^+$. |
| 1-72 | 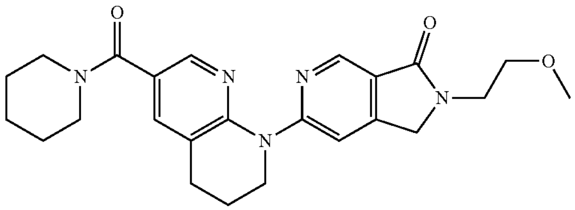 [SMILES: COCCN1Cc2cc(N3CCCc4cc(C(=O)N5CCCCC5)cnc43)ncc2C1=O] | $^{1}$H NMR (400 MHz, DMSO-$d_6$) δ 1.45-1.68 (6H, m), 1.91-2.03 (2H, m), 2.87 (2H, t, J = 6.4 Hz), 3.26 (3H, s), 3.39-3.59 (6H, m), 3.65 (2H, t, J = 5.1 Hz), 4.07 (2H, t, J = 5.8 Hz), 4.53 (2H, s), 7.56 (1H, d, J = 2.4 Hz), 7.97 (1H, s), 8.06 (1H, d, J = 2.4 Hz), 8.65 (1H, d, J = 1.2 Hz). LRMS (ESI$^+$) 436 [M + H]$^+$. |
| 1-73 | 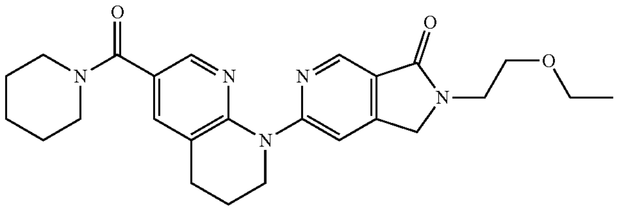 [SMILES: CCOCCN1Cc2cc(N3CCCc4cc(C(=O)N5CCCCC5)cnc43)ncc2C1=O] | $^{1}$H NMR (400 MHz, DMSO-$d_6$) δ 1.10 (3H, t, J = 7.0 Hz), 1.44-1.68 (6H, m), 1.92-2.02 (2H, m), 2.87 (2H, t, J = 6.4 Hz), 3.40-3.61 (8H, m), 3.64 (2H, t, J = 5.1 Hz), 4.07 (2H, t, J = 5.8 Hz), 4.54 (2H, s), 7.56 (1H, d, J = 2.4 Hz), 7.98 (1 H, s), 8.06 (1H, d, J = 2.4 Hz), 8.65 (1H, s). LRMS (ESI$^+$) 450 [M + H]$^+$. |
| 1-74 | 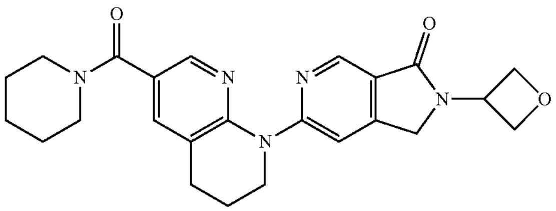 [SMILES: O=C(c1cnc2c(c1)CCCN2c1cc2c(cn1)C(=O)N(C1COC1)C2)N1CCCCC1] | $^{1}$H NMR (400 MHz, DMSO-$d_6$) δ 1.45-1.69 (6H, m), 1.93-2.03 (2H, m), 2.87 (2H, t, J = 6.4 Hz), 3.39-3.64 (4H, m), 4.08 (2H, t, J = 5.8 Hz), 4.73-4.90 (6H, m), 5.34-5.45 (1H, m), 7.58 (1H, d, J = 1.8 Hz), 8.02-8.08 (2H, m), 8.67 (1H, d, J = 1.2 Hz). LRMS (ESI$^+$) 434 [M + H]$^+$. |
| 1-75 | 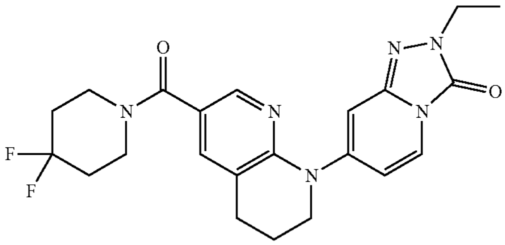 [SMILES: CCn1nc2cc(N3CCCc4cc(C(=O)N5CCC(F)(F)CC5)cnc43)ccn2c1=O] | $^{1}$H NMR (400 MHz, DMSO-$d_6$) δ 1.29 (3H, t, J = 7.3 Hz), 1.94-2.12 (6H, m), 2.84 (2H, t, J = 6.4 Hz), 3.53-3.67 (4H, m), 3.81 (2H, t, J = 5.8 Hz), 3.88 (2H, q, J = 7.1 Hz), 6.77 (1H, dd, J = 7.6, 2.1 Hz), 6.93 (1H, d, J = 1.2 Hz), 7.56 (1H, d, J = 2.4 Hz), 7.71 (1H, d, J = 8.5 Hz), 8.07 (1H, d, J = 2.4 Hz). LRMS (ESI$^+$) 443 [M + H]$^+$. |
| 1-76 | 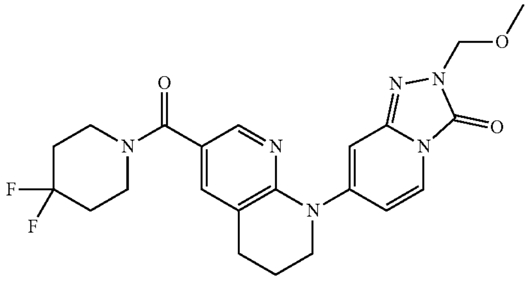 | $^{1}$H NMR (400 MHz, DMSO-$d_6$) δ 1.95-2.13 (6H, m), 2.84 (2H, t, J = 6.4 Hz), 3.31 (3H, s), 3.52-3.69 (4H, m), 3.82 (2H, t, 5 = 5.8 Hz), 5.17 (2H, s), 6.79 (1H, dd, J = 7.9, 1.8 Hz), 6.91 (1H, d, J = 2.4 Hz), 7.58 (1H, d, J = 2.4 Hz), 7.73 (1H, d, J = 8.5 Hz), 8.08 (1H, d, J = 2.4 Hz). LRMS (ESI$^+$) 459 [M + H]$^+$. |

TABLE 68

| Example No. | Chemical Structural Formula | Spectrum Data |
|---|---|---|
| 1-77 | 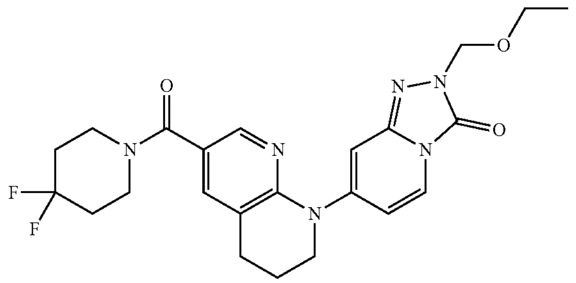 | $^1$H NMR (400 MHz, DMSO-$d_6$) δ 1.11 (3H, t, J = 7.0 Hz), 1.95-2.12 (6H, m), 2.84 (2H, t, J = 6.4 Hz), 3.51-3.68 (6H, m), 3.82 (2H, t, J = 5.8 Hz), 5.21 (2H, s), 6.79 (1H, dd, J = 7.9, 1.8 Hz), 6.91 (1H, d, J = 1.2 Hz), 7.58 (1H, d, J = 2.4 Hz), 7.72 (1H, d, J = 8.5 Hz), 8.08 (1H, d, J = 2.4 Hz). LRMS (ESI$^+$) 473 [M + H]$^+$. |
| 1-78 | 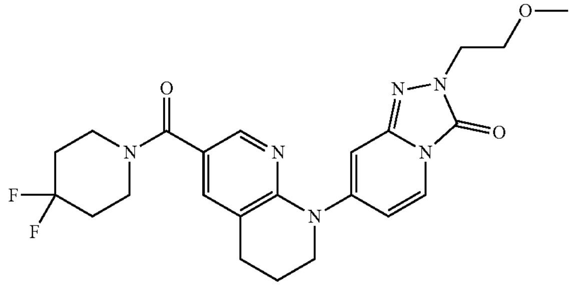 [SMILES: COCCn1nc2cc(N3CCCc4cc(C(=O)N5CCC(F)(F)CC5)cnc43)ccn2c1=O] | $^1$H NMR (400 MHz, DMSO-$d_6$) δ 1.96-2.11 (6H, m), 2.84 (2H, t, J = 6.4 Hz), 3.23 (3H, s), 3.55-3.71 (6H, m), 3.81 (2H, t, J = 5.8 Hz), 4.01 (2H, t, J = 5.4 Hz), 6.77 (1H, dd, J = 7.9, 1.8 Hz), 6.93 (1H, d, J = 1.2 Hz), 7.56 (1H, d, J = 2.4 Hz), 7.71 (1H, d, J = 8.5 Hz), 8.07 (1H, d, J = 2.4 Hz). LRMS (ESI$^+$) 473 [M + H]$^+$. |
| 1-79 | 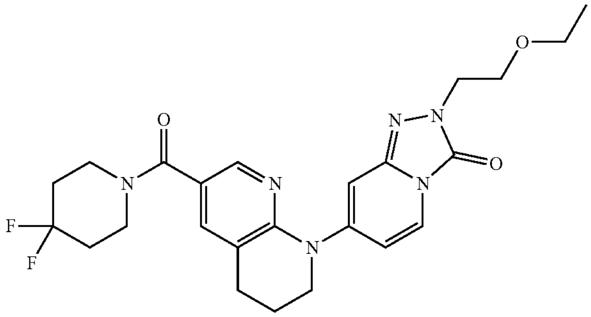 | $^1$H NMR (400 MHz, DMSO-$d_6$) δ 1.05 (3H, t, J = 7.0 Hz), 1.94-2.12 (6H, m), 2.84 (2H, t, J = 6.4 Hz), 3.43 (2H, q, J = 7.1 Hz), 3.52-3.66 (4H, m), 3.71 (2H, t, J = 5.8 Hz), 3.81 (2H, t, J = 5.8 Hz), 3.99 (2H, t, J = 5.8 Hz), 6.77 (1H, dd, J = 7.9, 1.8 Hz), 6.94 (1H, d, J = 1.2 Hz), 7.56 (1H, d, J = 2.4 Hz), 7.71 (1H, d, J = 7.9 Hz), 8.07 (1H, d, J = 2.4 Hz). LRMS (ESI$^+$) 487 [M + H]$^+$. |
| 1-80 | 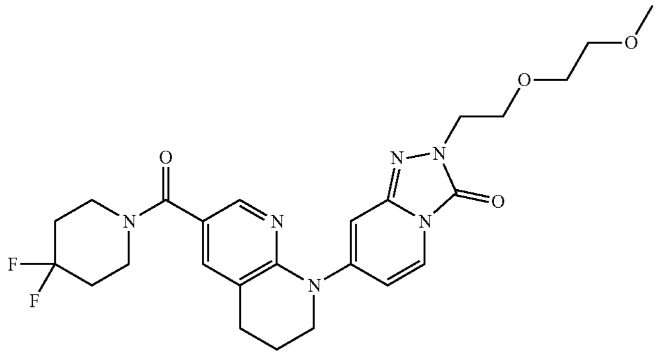 [SMILES: COCCOCCn1nc2cc(N3CCCc4cc(C(=O)N5CCC(F)(F)CC5)cnc43)ccn2c1=O] | $^1$H NMR (400 MHz, DMSO-$d_6$) δ 1.95-2.12 (6H, m), 2.84 (2H, t, J = 6.4 Hz), 3.20 (3H, s), 3.36-3.42 (2H, m), 3.49-3.55 (2H, m), 3.56-3.68 (4H, m), 3.72-3.85 (4H, m), 4.00 (2H, t, J = 5.4 Hz), 6.77 (1H, dd, J = 7.6, 2.1 Hz), 6.94 (1H, d, J = 1.8 Hz), 7.56 (1H, d, J = 2.4 Hz), 7.71 (1H, d, J = 7.9 Hz), 8.07 (1H, d, J = 2.4 Hz). LRMS (ESI$^+$) 517 [M + H]$^+$. |
| 1-81 | 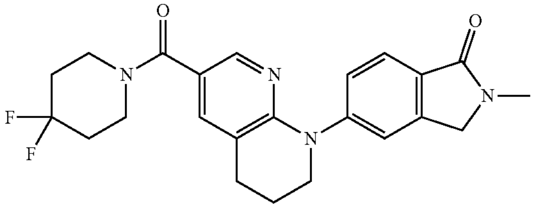 [SMILES: CN1Cc2cc(N3CCCc4cc(C(=O)N5CCC(F)(F)CC5)cnc43)ccc2C1=O] | $^1$H NMR (400 MHz, DMSO-$d_6$) δ 1.94-2.09 (6H, m), 2.87 (2H, t, J = 6.1 Hz), 3.07 (3H, s), 3.55-3.64 (4H, m), 3.81 (2H, t, J = 5.4 Hz), 4.44 (2H, s), 7.42 (1H, dd, J = 8.5, 1.8 Hz), 7.48 (1H, d, J = 2.4 Hz), 7.53 (1H, d, J = 1.2 Hz), 7.63 (1H, d, J = 8.5 Hz), 7.93 (1H, d, J = 2.4 Hz). LRMS (ESI$^+$) 427 [M + H]$^+$. |

TABLE 69

| Example No. | Chemical Structural Formula | Spectrum Data |
|---|---|---|
| 1-82 | 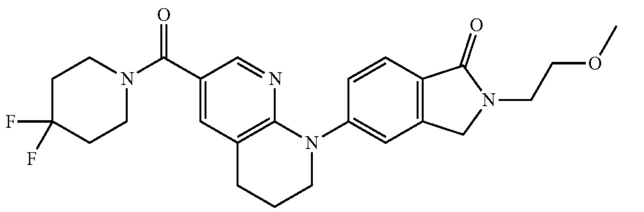 [SMILES: COCCN1Cc2cc(N3CCCc4cc(C(=O)N5CCC(F)(F)CC5)cnc43)ccc2C1=O] | $^1$H NMR (400 MHz, DMSO-d$_6$) δ 1.94-2.10 (6H, m), 2.87 (2H, t, J = 6.4 Hz), 3.27 (3H, s), 3.53-3.63 (6H, m), 3.68 (2H, t, J = 5.4 Hz), 3.81 (2H, t, J = 5.8 Hz), 4.50 (2H, s), 7.43 (1H, dd, J = 8.5, 1.8 Hz), 7.48 (1H, d, J = 2.4 Hz), 7.54 (1H, d, J = 1.2 Hz), 7.64 (1H, d, J = 8.5 Hz), 7.92 (1H, d, J = 2.4 Hz). LRMS (ESI$^+$) 471 [M + H]$^+$. |
| 1-83 | 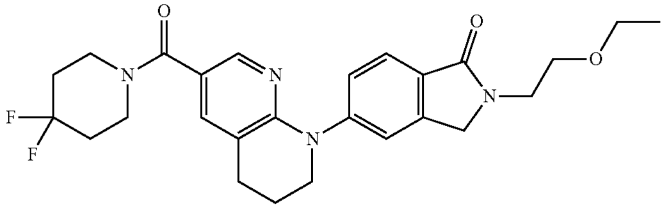 [SMILES: CCOCCN1Cc2cc(N3CCCc4cc(C(=O)N5CCC(F)(F)CC5)cnc43)ccc2C1=O] | $^1$H NMR (400 MHz, DMSO-d$_6$) δ 1.10 (3H, t, J = 7.0 Hz), 1.91-2.12 (6H, m), 2.87 (2H, t, J = 6.1 Hz), 3.46 (2H, q, J = 7.1 Hz), 3.56-3.63 (6H, m), 3.67 (2H, t, J = 5.1 Hz), 3.81 (2H, t, J = 5.4 Hz), 4.51 (2H, s), 7.43 (1H, dd, J = 8.5, 1.8 Hz), 7.48 (1H, d, J = 2.4 Hz), 7.55 (1H, d, J = 1.2 Hz), 7.65 (1H, d, J = 7.9 Hz), 7.92 (1H, d, J = 2.4 Hz). LRMS (ESI$^+$) 485 [M + H]$^+$. |
| 1-84 | 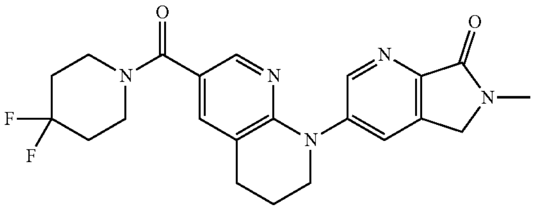 [SMILES: CN1Cc2cc(N3CCCc4cc(C(=O)N5CCC(F)(F)CC5)cnc43)cnc2C1=O] | $^1$H NMR (400 MHz, DMSO-d$_6$) δ 1.93-2.12 (6H, m), 2.89 (2H, t, J = 6.4 Hz), 3.11 (3H, s), 3.52-3.67 (4H, m), 3.86 (2H, t, J = 5.4 Hz), 4.47 (2H, s), 7.53 (1H, d, J = 2.4 Hz), 7.95 (1H, d, J = 2.4 Hz), 8.00 (1H, d, J = 2.4 Hz), 8.72 (1H, d, J = 2.4 Hz). LRMS (ESI$^+$) 428 [M + H]$^+$. |
| 1-85 | 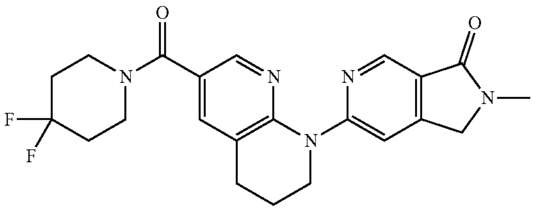 [SMILES: CN1Cc2cc(N3CCCc4cc(C(=O)N5CCC(F)(F)CC5)cnc43)ncc2C1=O] | $^1$H NMR (400 MHz, DMSO-d$_6$) δ 1.91-2.13 (6H, m), 2.87 (2H, t, J = 6.4 Hz), 3.04 (3H, s), 3.53-3.71 (4H, m), 4.07 (2H, t, J = 5.8 Hz), 4.47 (2H, s), 7.63 (1H, d, J = 2.4 Hz), 7.97 (1H, d, J = 1.2 Hz), 8.14 (1H, d, J = 2.4 Hz), 8.64 (1H, s) LRMS (ESI$^+$) 428 [M + H]$^+$. |
| 1-86 | 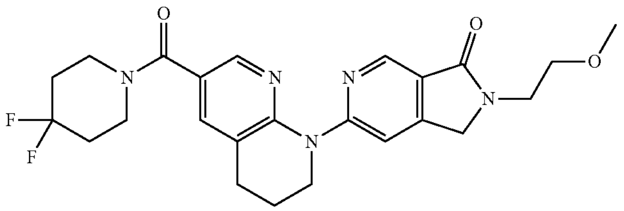 [SMILES: COCCN1Cc2cc(N3CCCc4cc(C(=O)N5CCC(F)(F)CC5)cnc43)ncc2C1=O] | $^1$H NMR (400 MHz, DMSO-d$_6$) δ 1.92-2.14 (6H, m), 2.87 (2H, t, J = 6.1 Hz), 3.26 (3H, s), 3.51-3.72 (8H, m), 4.08 (2H, t, J = 5.8 Hz), 4.53 (2H, s), 7.63 (1H, d, J = 2.4 Hz), 7.97 (1H, s), 8.13 (1H, d, J = 2.4 Hz), 8.66 (1H, s). LRMS (ESI$^+$) 472 [M + H]$^+$. |
| 1-87 | 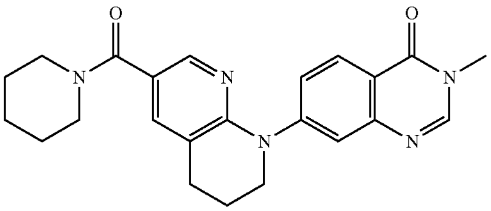 [SMILES: Cn1cnc2cc(N3CCCc4cc(C(=O)N5CCCCC5)cnc43)ccc2c1=O] | $^1$H NMR (400 MHz, DMSO-d$_6$) δ 1.43-1.67 (6H, m), 1.97-2.09 (2H, m), 2.87 (2H, t, J = 6.4 Hz), 3.40-3.54 (7H, m), 3.88 (2H, t, J = 5.8 Hz), 7.46 (1H, d, J = 2.4 Hz), 7.55 (1H, d, J = 2.4 Hz), 7.59 (1H, dd, J = 8.8, 2.1 Hz), 7.92 (1H, d, J = 2.4 Hz), 8.05 (1H, d, J = 8.5 Hz), 8.33 (1H, s). LRMS (ESI$^+$) 404 [M + H]$^+$. |

TABLE 70

| Example No. | Chemical Structural Formula | Spectrum Data |
|---|---|---|
| 1-88 | 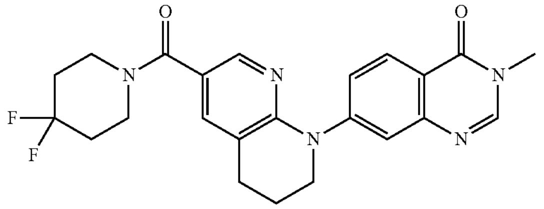 [SMILES: Cn1cnc2cc(N3CCCc4cc(C(=O)N5CCC(F)(F)CC5)cnc43)ccc2c1=O] | $^1$H NMR (400 MHz, DMSO-$d_6$) δ 1.94-2.12 (6H, m), 2.88 (2 H, t, J = 6.4 Hz), 3.49 (3H, s), 3.54-3.68 (4H, m), 3.89 (2H, t, J = 5.4 Hz), 7.53 (1H, d, J = 2.4 Hz), 7.56 (1H, d, J = 1.8 Hz), 7.59 (1H, dd, J = 8.5, 1.8 Hz), 8.00 (1H, d, J = 1.8 Hz), 8.06 (1H, d, J = 8.5 Hz), 8.34 (1H, s). LRMS (ESI$^+$) 440 [M + H]$^+$. |
| 1-89 | 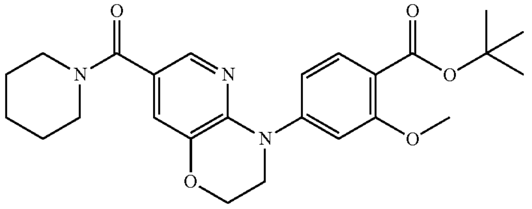 [SMILES: COc1cc(N2CCOc3cc(C(=O)N4CCCCC4)cnc32)ccc1C(=O)OC(C)(C)C] | $^1$H NMR (400 MHz, $CDCl_3$) δ 1.50-1.72 (15H, m), 3.36-3.76 (4H, m), 3.89 (3H, s), 3.93 (2H, t, J = 4.3 Hz), 4.36 (2H, t, J = 4.3 Hz), 6.92 (1H, dd, J = 8.6, 1.8 Hz), 7.08 (1H, d, J = 1.8 Hz), 7.21 (1H, d, J = 1.8 Hz), 7.82 (1H, d, J = 7.9 Hz), 7.86 (1H, d, J = 1.8 Hz). LRMS (ESI$^+$) 454 [M + H]$^+$. |
| 1-90 | 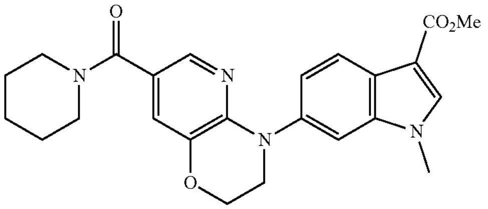 [SMILES: COC(=O)c1cn(C)c2cc(N3CCOc4cc(C(=O)N5CCCCC5)cnc43)ccc12] | $^1$H NMR (400 MHz, $CDCl_3$) δ 1.50-1.71 (6H, m), 3.45-3.66 (4H, m), 3.81 (3H, s), 3.91 (3H, s), 3.97 (2H, t, J = 4.3 Hz), 4.39 (2H, t, J = 4.3 Hz), 7.19 (1H, d, J = 1.8 Hz), 7.23 (1 H, dd, J = 8.6, 1.8 Hz), 7.37 (1H, d, J = 1.8 Hz), 7.78 (1H, s), 7.81 (1H, d, J = 1.8 Hz), 8.18 (1H, d, J = 8.6 Hz). LRMS (ESI$^+$) 435 [M + H]$^+$. |
| 1-91 | 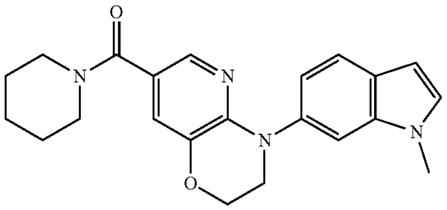 [SMILES: Cn1ccc2ccc(N3CCOc4cc(C(=O)N5CCCCC5)cnc43)cc21] | $^1$H NMR (400 MHz, $CDCl_3$) δ 1.48-1.70 (6H, m), 3.43-3.68 (4H, m), 3.77 (3H, s), 3.95 (2H, t, J = 4.3 Hz), 4.38 (2H, t, J = 4.3 Hz), 6.47 (1H, d, J = 2.4 Hz), 7.03-7.08 (2H, m), 7.18 (1H, d, J = 1.8 Hz), 7.29 (1H, s), 7.64 (1H, d, J = 7.9 Hz), 7.81 (1H, d, J = 1.8 Hz). LRMS (ESI$^+$) 377 [M + H]$^+$. |
| 1-92 | 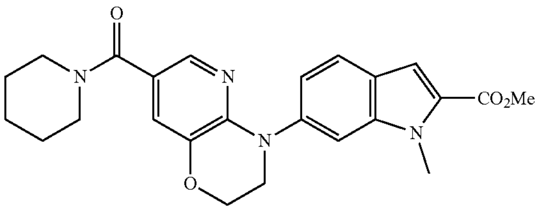 [SMILES: COC(=O)c1cc2ccc(N3CCOc4cc(C(=O)N5CCCCC5)cnc43)cc2n1C] | $^1$H NMR (400 MHz, $CDCl_3$) δ 1.48-1.71 (6H, m), 3.40-3.71 (4H, m), 3.91 (3H, s), 3.98 (2H, t, J = 4.3 Hz), 4.05 (3H, s), 4.39 (2H, t, J = 4.6 Hz), 7.16 (1H, dd, J = 8.6, 1.8 Hz), 7.20 (1H, d, J = 1.8 Hz), 7.27 (1H, s), 7.33 (1H, s), 7.68 (1H, d, J = 8.6 Hz), 7.82 (1H, d, J = 1.8 Hz). LRMS (ESI$^+$) 435 [M + H]$^+$. |
| 1-93 | 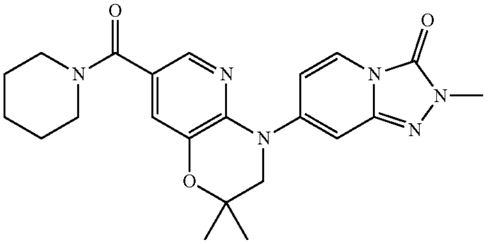 [SMILES: Cn1nc2cc(N3CC(C)(C)Oc4cc(C(=O)N5CCCCC5)cnc43)ccn2c1=O] | $^1$H NMR (400 MHz, $CDCl_3$) δ 1.41 (6H, s), 1.47-1.74 (6H, m), 3.35-3.78 (4H, m), 3.62 (2H, s), 3.64 (3H, s), 6.59 (1H, d, J = 1.8 Hz), 6.93 (1H, dd, J = 7.9, 1.8 Hz), 7.22 (1H, d, J = 1.8 Hz), 7.68 (1H, d, J = 6.7 Hz), 7.89 (1H, d, J = 1.8 Hz). LRMS (ESI$^+$) 423 [M + H]$^+$. |

TABLE 71

| Example No. | Chemical Structural Formula | Spectrum Data |
|---|---|---|
| 1-94 | 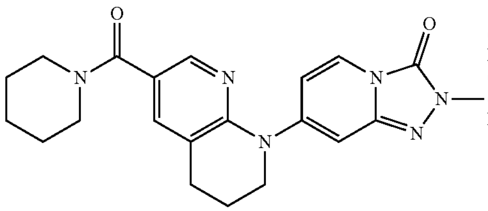 | $^1$H NMR (400 MHz, $CDCl_3$) δ 1.51-1.76 (6H, m), 2.08-2.16 (2H, m), 2.88 (2H, t, J = 6.4 Hz), 3.41-3.73 (4H, m), 3.64 (3 H, s), 3.81 (2H, t, J = 6.1 Hz), 6.67 (1H, d, J = 1.2 Hz), 6.76 (1H, dd, J = 7.9, 1.8 Hz), 7.50 (1H, t, J = 1.2 Hz), 7.63 (1H, d, J = 6.7 Hz), 8.09 (1H, d, J = 2.4 Hz). LRMS (ESI$^+$) 393 [M + H]$^+$. |
| 1-95 | 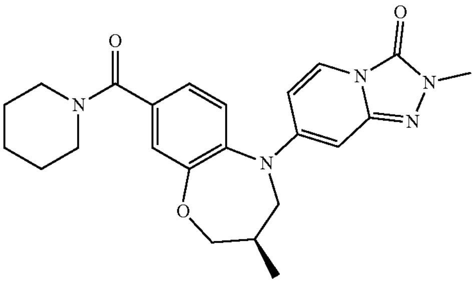 [SMILES: C[C@H]1COc2cc(C(=O)N3CCCCC3)ccc2N(c2ccn3c(=O)n(C)nc3c2)C1] | $^1$H NMR (400 MHz, $CDCl_3$) δ 1.02 (3H, d, J = 6.7 Hz), 1.50-1.75 (6H, m), 2.35-2.51 (1H, m), 3.24 (1H, dd, J = 14.7, 10 Hz), 3.34-3.49 (2H, m), 3.58 (3H, s), 3.64-3.78 (3H, m), 4.00 (1H, dd, J = 14.7, 4.9 Hz), 4.19 (1H, dd, J = 11.6, 3.7 Hz), 6.15 (1H, d, J = 1.8 Hz), 6.27 (1H, dd, J = 7.9, 2.4 Hz), 7.05 (1H, dd, J = 7.9, 1.8 Hz), 7.11-7.14 (2H, m), 7.58 ( 1H, d, J = 7.9 Hz). LRMS (ESI$^+$) 422 [M + H]$^+$. |
| 1-96 | 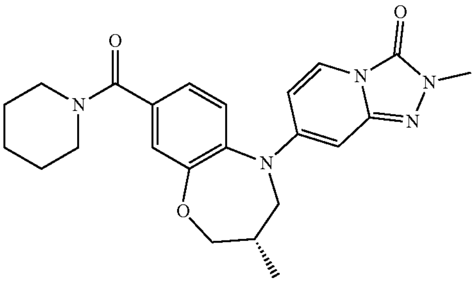 [SMILES: C[C@@H]1COc2cc(C(=O)N3CCCCC3)ccc2N(c2ccn3c(=O)n(C)nc3c2)C1] | $^1$H NMR (400 MHz, $CDCl_3$) δ 1.02 (3H, d, J = 7.3 Hz), 1.51-1.75 (6H, m), 2.36-2.50 (1H, m), 3.24 (1H, dd, J = 14.1, 10.4 Hz), 3.33-3.48 (2H, m), 3.58 (3H, s), 3.64-3.78 (3H, m), 4.00 (1H, dd, J = 14.7, 4.9 Hz), 4.19 (1H, dd, J = 11.6, 4.3 Hz), 6.15 (1H, d, J = 1.8 Hz), 6.27 (1H, dd, J = 7.3, 2.4 Hz), 7.05 (1H, dd, J = 8.6 1.8 Hz), 7.10-7.15 (2H, m), 7.58 (1H, d, J = 7.9 Hz). LRMS (ESI$^+$) 422 [M + H]$^+$. |
| 1-97 | 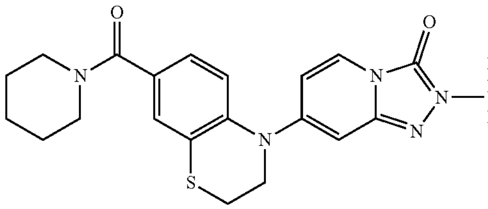 | $^1$H NMR (400 MHz, $CDCl_3$) δ 1.50-1.75 (6H, m), 3.13-3.18 (2H, m), 3.32-3.56 (2H, m), 3.62 (3H, s), 3.63-3.77 (2H, m), 3.91-3.97 (2H, m), 6.37-6.42 (2H, m), 7.01 (1H, d, J = 7.9 Hz), 7.10 (1H, dd, J = 7.9, 1.8 Hz), 7.31 (1H, d, J = 1.8 Hz), 7.61 (1H, d, J = 7.3 Hz). LRMS (ESI$^+$) 410 [M + H]$^+$. |
| 1-98 | 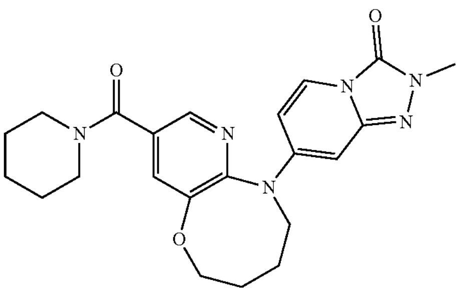 [SMILES: Cn1nc2cc(N3CCCCOc4cc(C(=O)N5CCCCC5)cnc43)ccn2c1=O] | $^1$H NMR (400 MHz, $CDCl_3$) δ 1.55-1.75 (6H, m), 1.86-2.00 (4H, m), 3.35-3.50 (2H, m), 3.62 (3H, s), 3.65-3.78 (2H, m), 3.94 (2H, t, J = 4.9 Hz), 4.28 (2H, t, I = 4.9 Hz), 6.18 (1H, dd, J = 7.9, 2.4 Hz), 6.44 (1H, d, J = 1.8 Hz), 7.45 (1H, d, J = 1.8 Hz), 7.58 (1H, d, J = 7.3 Hz), 8.10 (1H, d, J = 1.8 Hz). LRMS (ESI$^+$) 423 [M + H]$^+$. |

TABLE 72

| Example No. | Chemical Structural Formula | Spectrum Data |
|---|---|---|
| 1-99 | 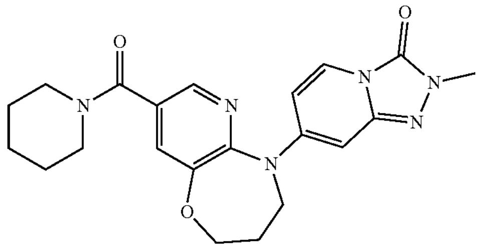 [SMILES: Cn1nc2cc(N3CCCOc4cc(C(=O)N5CCCCC5)cnc43)ccn2c1=O] | $^1$H NMR (400 MHz, $CDCl_3$) δ 1.55-1.76 (6H, m), 2.15-2.24 (2H, m), 3.35-3.50 (2H, m), 3.61 (3H, s), 3.65-3.77 (2H, m), 3.96 (2H, t, J = 6.1 Hz), 4.26 (2H, t, J = 6.1 Hz), 6.42-6.46 (2H, m), 7.40 (1H, d, J = 1.8 Hz), 7.60 (1H, dd, J = 6.7, 2.4 Hz), 8.10 (1H, d, J = 2.4 Hz). LRMS (ESI$^+$) 409 [M + H]$^+$. |
| 1-100 | 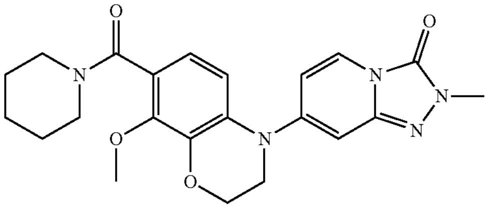 [SMILES: COc1c(C(=O)N2CCCCC2)ccc2c1OCCN2c1ccn2c(=O)n(C)nc2c1] | $^1$H NMR (400 MHz, $CDCl_3$) δ 1.40-1.71 (6H, m), 3.17-3.35 (2H, m), 3.62 (3H, s), 3.68-3.80 (4H, m), 3.89 (3H, s), 4.36-1.43 (2H, m), 6.51 (1H, d, J = 2.4 Hz), 6.57 (1H, dd, J = 7.9, 2.4 Hz), 6.72 (1H, d, J = 8.6 Hz), 6.82 (1H, d, J = 8.6 Hz), 7.69 (1H, d, J = 8.6 Hz). LRMS (ESI$^+$) 424 [M + H]$^+$. |
| 1-101 | 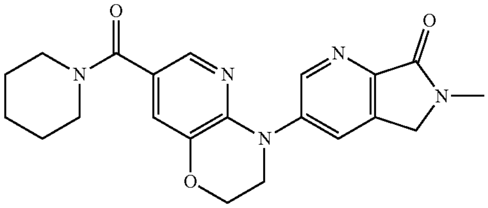 [SMILES: CN1Cc2cc(N3CCOc4cc(C(=O)N5CCCCC5)cnc43)cnc2C1=O] | $^1$H NMR (400 MHz, $CDCl_3$) δ 1.51-1.72 (6H, m), 3.27 (3H, s), 3.36-3.76 (4H, m), 4.03 (2H, t, J = 4.3 Hz), 4.39-4.43 (4H, m), 7.25 (1H, d, J = 1.8 IIz), 7.83 (1H, d, J = 1.8 Hz), 8.02 (1H, d, J = 1.8 Hz), 8.73 (1H, d, J = 2.4 Hz). LRMS (ESI$^+$) 394 [M + H]$^+$. |
| 1-102 | 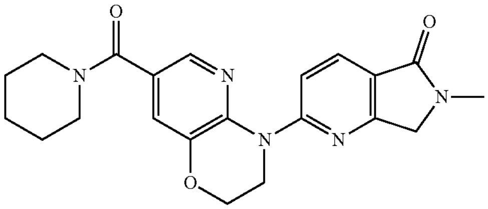 [SMILES: CN1Cc2nc(N3CCOc4cc(C(=O)N5CCCCC5)cnc43)ccc2C1=O] | $^1$H NMR (400 MHz, $CDCl_3$) δ 1.53-1.74 (6H, m), 3.21 (3H, s), 3.37-3.78 (4H, m), 4.31-4.41 (6H, m), 7.29 (1H, d, J = 1.8 Hz), 7.97 (1H, d, J = 1.8 Hz), 7.99 (1H, d, J = 9.2 Hz), 8.24 (1H, d, J = 9.2 Hz). LRMS (ESI$^+$) 394 [M + H]$^+$. |
| 1-103 | 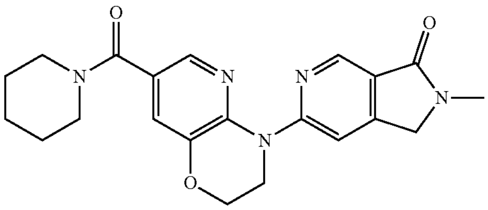 [SMILES: CN1Cc2cc(N3CCOc4cc(C(=O)N5CCCCC5)cnc43)ncc2C1=O] | $^1$H NMR (400 MHz, $CDCl_3$) δ 1.51-1.74 (6H, m), 3.18 (3H, s), 3.38-3.76 (4H, m), 4.34-4.43 (6H, m), 7.27 (1H, d, J = 2.4 Hz), 7.96 (1H, d, J = 2.4 Hz), 8.29 (1H, d, J = 1.2 Hz), 8.79 (1H, s). LRMS (ESI$^+$) 394 [M + H]$^+$. |
| 1-104 | 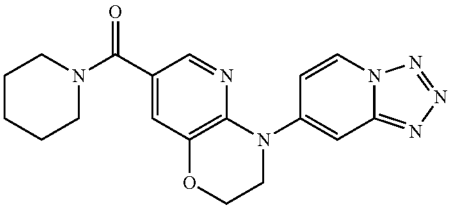 [SMILES: O=C(c1cnc2c(c1)OCCN2c1ccn2nnnc2c1)N1CCCCC1] | $^1$H NMR (400 MHz, $CDCl_3$) δ 1.51-1.75 (6H, m), 3.32-3.77 (4H, m), 4.03 (2H, t, J = 4.5 Hz), 4.47 (2H, t, J = 4.5 Hz), 7.31 (1H, d, J = 1.8 Hz), 7.53 (1H, d, J = 1.8 Hz), 7.80 (1H, dd, J = 7.9, 2.4 Hz), 7.89 (1H, d, J = 2.4 Hz), 8.67 (1H, d, J = 7.3 Hz). LRMS (ESI$^+$) 366 [M + H]$^+$. |

TABLE 73

| Example No. | Chemical Structural Formula | Spectrum Data |
|---|---|---|
| 1-105 | 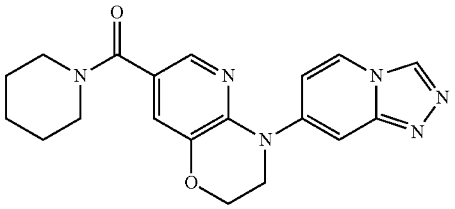 [SMILES: O=C(c1cnc2c(c1)OCCN2c1ccn2cnnc2c1)N1CCCCC1] | $^1$H NMR (400 MHz, $CDCl_3$) δ 1.48-1.79 (6H, m), 3.31-3.78 (4H, m), 3.99 (2H, t, J = 4.5 Hz), 4.44 (2H, t, J = 4.5 Hz), 7.26 (1H, d, J = 1.8 Hz), 7.33 (1H, d, J = 1.8 Hz), 7.41 (1H, dd, J = 7.3, 1.8 Hz), 7.87 (1H, d, J = 1.8 Hz), 8.01 (1H, d, J = 6.7 Hz), 8.72 (1H, s). LRMS (ESI$^+$) 365 [M + H]$^+$. |
| 1-106 | 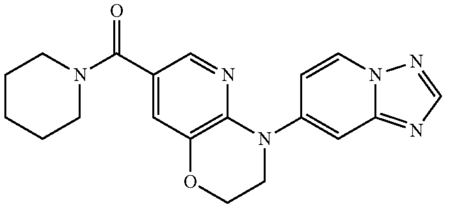 [SMILES: O=C(c1cnc2c(c1)OCCN2c1ccn2ncnc2c1)N1CCCCC1] | $^1$H NMR (400 MHz, $CDCl_3$) δ 1.50-1.74 (6H, m), 3.34-3.76 (4H, m), 4.00 (2H, t, J = 4.5 Hz), 4.44 (2H, t, J = 4.5 Hz), 7.28 (1H, d, J = 1.8 Hz). 7.42 (1H, d, J = 2.4 Hz), 7.50 (1 H, dd, J = 7.9, 2.4 Hz), 7.88 (1H, d, J = 1.8 Hz), 8.27 (1H, s), 8.48 (1H, d, J = 7.3 Hz). LRMS (ESI$^+$) 365 [M + H]$^+$. |
| 1-107 | 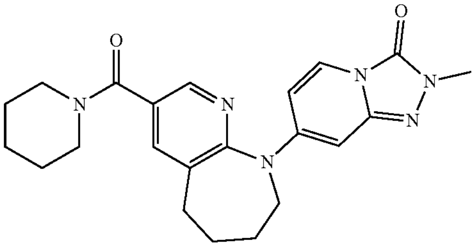 [SMILES: Cn1nc2cc(N3CCCCc4cc(C(=O)N5CCCCC5)cnc43)ccn2c1=O] | $^1$H NMR (400 MHz, $CDCl_3$) δ 1.53-1.76 (6H, m), 1.77-1.91 (4H, m), 2.80 (2H, t, J = 6.1 Hz), 3.36-3.53 (2H, m), 3.59 (3H, s), 3.64-3.79 (4H, m), 6.08 (1H, dd, J – 7.9, 1.8 Hz), 6.23 (1H, d, J = 1.8 Hz), 7.52 (1H, d, J = 7.9 Hz), 7.71 (1H, d, J – 2.4 Hz), 8.36 (1H, d, J = 2.4 Hz). LRMS (ESI$^+$) 407 [M + H]$^+$. |
| 1-108 | 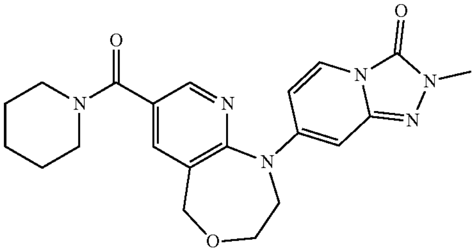 [SMILES: Cn1nc2cc(N3CCOCc4cc(C(=O)N5CCCCC5)cnc43)ccn2c1=O] | $^1$H NMR (400 MHz, $CDCl_3$) δ 1.52-1.76 (6H, m), 3.34-3.52 (2H, m), 3.62 (3H, s), 3.65-3.78 (2H, m), 3.80-3.85 (2H, m), 3.93-3.98 (2H, m), 4.67 (2H, s), 6.17 (1H, dd, J = 7.9, 2.4 Hz), 6.45 (1H, d, J = 1.8 Hz), 7.57 (1H, d, J = 8.6 Hz), 7.7 4 (1H, d, J = 2.4 Hz), 8.36 (1H, d, J = 2.4 Hz). LRMS (ESI$^+$) 409 [M + H]$^+$. |
| 1-109 | 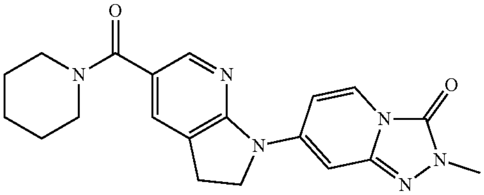 [SMILES: Cn1nc2cc(N3CCc4cc(C(=O)N5CCCCC5)cnc43)ccn2c1=O] | $^1$H NMR (400 MHz, $CDCl_3$) δ 1.54-1.75 (6H, m), 3.23 (2H, t, J = 8.6 IIz), 3.43-3.75 (4H, m), 3.64 (3H, s), 4.08 (2H, t, J = 8.6 Hz), 6.68 (1H, d, J = 1.2 Hz), 7.51-7.55 (1H, m), 7.72 (1H, d, J = 7.9 Hz), 8.09-8.14 (2H, m). LRMS (ESI$^+$) 379 [M + H]$^+$. |
| 1-110 | 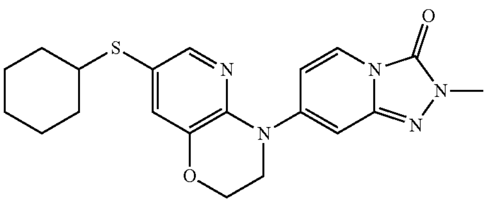 [SMILES: Cn1nc2cc(N3CCOc4cc(SC5CCCCC5)cnc43)ccn2c1=O] | $^1$H NMR (400 MHz, $CDCl_3$) δ 1.15-1.39 (6H, m), 1.70-1.83 (2H, m), 1.87-2.01 (2H, m), 2.86-2.97 (1H, m), 3.64 (3H, s), 3.87 (2H, t, J = 4.6 Hz), 4.39 (2H, t, J = 4.6 Iiz), 6.59 (1H, d, J = 1.2 Hz), 7.01 (1H, dd, J = 7.9, 1.8 Hz), 7.26 (1H, d, J = 1.8 Hz), 7.67 (1H, d, J = 7.9 Hz), 7.88 (1H, d, J = 2.4 Hz). LRMS (ESI$^+$) 398 [M + H]$^+$. |

TABLE 74

| Example No. | Chemical Structural Formula | Spectrum Data |
|---|---|---|
| 1-111 | 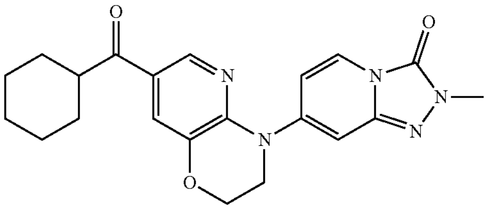 | $^1$H NMR (400 MHz, $CDCl_3$) δ 1.20-1.54 (5H, m), 1.69-1.77 (1H, m), 1.80-1.91 (4H, m), 3.07-3.16 (1H, m), 3.65 (3H, s), 3.93 (2H, t, J = 4.3 Hz), 4.42 (2H, t, J = 4.3 Hz), 6.69 (1H, d, J = 1.2 Hz), 6.97 (1H, dd, J = 7.3, 1.8 Hz), 7.68 (1H, d, J = 1.8 Hz), 7.70 (1H, d, J = 8.6 Hz), 8.43 (1H, d, J = 1.8 Hz).<br>LRMS (ESI$^+$) 394 [M + H]$^+$. |
| 1-112 | 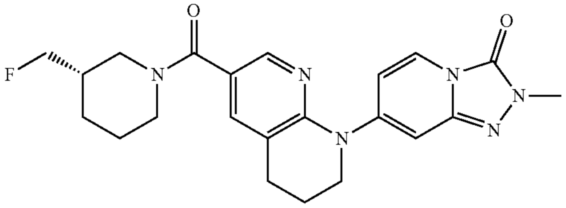 [SMILES: Cn1nc2cc(N3CCCc4cc(C(=O)N5CCC[C@H](CF)C5)cnc43)ccn2c1=O] | $^1$H NMR (400 MHz, $CDCl_3$) δ 1.33-2.06 (6H, m), 2.09-2.17 (2H, m), 2.77-3.10 (4H, m), 3.64 (3H, s), 3.82 (2H, t, J = 5.5 Hz), 4.15-4.51 (3H, m), 6.68 (1H, d, J = 1.2 Hz), 6.76 (1H, dd, J = 7.3, 1.8 Hz), 7.47-7.51 (1H, m), 7.64 (1H, d, J = 6.7 Hz), 8.09 (1H, d, J = 1.8 Hz).<br>LRMS (ESI$^+$) 425 [M + H]$^+$. |
| 1-113 | 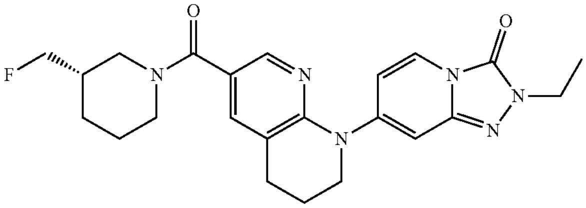 [SMILES: CCn1nc2cc(N3CCCc4cc(C(=O)N5CCC[C@H](CF)C5)cnc43)ccn2c1=O] | $^1$H NMR (400 MHz, $CDCl_3$) δ 1.34-2.06 (6H, m), 1.41 (3H, t, J = 7.3 Hz), 2.09-2.17 (2H, m), 2.76-3.10 (4H, m), 3.82 (2H, t, J = 5.5 Hz), 4.02 (2H, q, J = 7.3 Hz), 4.16-4.53 (3H, m), 6.71 (1H, d, J = 1.2 Hz), 6.74 (1H, dd, J = 7.3, 1.8 Hz), 7.47-7.51 (1H, m), 7.64 (1H, d, J = 6.7 Hz), 8.08 (1H, d, J = 2.4 Hz).<br>LRMS (ESI$^+$) 439 [M + H]$^+$. |
| 1-114 | 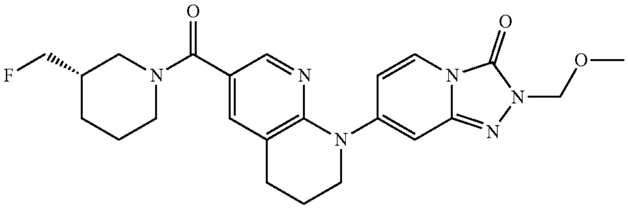 [SMILES: COCn1nc2cc(N3CCCc4cc(C(=O)N5CCC[C@H](CF)C5)cnc43)ccn2c1=O] | $^1$H NMR (400 MHz, $CDCl_3$) δ 1.33-2.06 (6H, m), 2.09-2.19 (2H, m), 2.72-3.14 (4H, m), 3.43 (3H, s), 3.82 (2H, t, J = 5.5 Hz), 4.12-4.67 (3H, m), 5.30 (2H, s), 6.67 (1H, d, J = 1.2 Hz), 6.77 (1H, dd, J = 7.3, 1.8 Hz), 7.48-7.52 (1H, m), 7.63 (1H, d, J = 8.6 Hz), 8.10 (1H, d, J = 2.4 Hz).<br>LRMS (ESI$^+$) 455 [M + H]$^+$. |
| 1-115 | 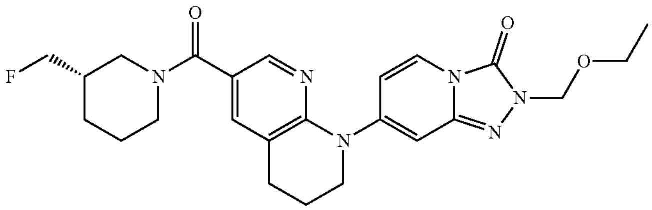 [SMILES: CCOCn1nc2cc(N3CCCc4cc(C(=O)N5CCC[C@H](CF)C5)cnc43)ccn2c1=O] | $^1$H NMR (400 MHz, $CDCl_3$) δ 1.22 (3H, t, J = 7.3 Hz), 1.34-2.05 (6H, m), 2.09-2.18 (2H, m), 2.71-3.13 (4H, m), 3.65 (2H, q, J = 7.3 Hz), 3.82 (2H, t, J = 5.5 Hz), 4.06-4.64 (3H, m), 5.34 (2H, s), 6.65-6.69 (1H, m), 6.76 (1H, dd, J = 7.3, 1.8 Hz), 7.48-7.52 (1H, m), 7.63 (1H, d, J = 8.6 Hz), 8.09 (1H, d, J = 2.4 Hz).<br>LRMS (ESI$^+$) 469 [M + H]$^+$. |

TABLE 75

| Example No. | Chemical Structural Formula | Spectrum Data |
|---|---|---|
| 1-116 | 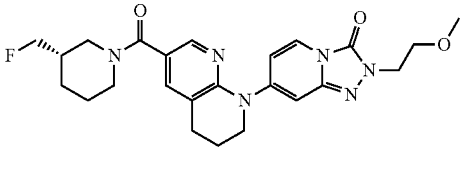 [SMILES: COCCn1nc2cc(N3CCCc4cc(C(=O)N5CCC[C@H](CF)C5)cnc43)ccn2c1=O] | $^1$H NMR (400 MHz, $CDCl_3$) δ 1.34-2.06 (6H, m), 2.08-2.16 (2H, m), 2.69-3.14 (4H, m), 3.37 (3H, s), 3.77 (2H, t, J = 5.5 Hz), 3.81 (2H, t, J = 5.5 Hz), 4.15 (2H, t, J = 5.5 Hz), 4.20-4.60 (3H, m), 6.69-6.71 (1H, m), 6.73 (1H, dd, J = 7.9, 1.8 Hz), 7.49 (1H, d, J = 1.8 Hz), 7.62-7.66 (1H, m), 8.08 (1H, d, J = 2.4 Hz).<br>LRMS (ESI$^+$) 469 [M + H]$^+$. |

TABLE 75-continued

| Example No. | Chemical Structural Formula | Spectrum Data |
|---|---|---|
| 1-117 | 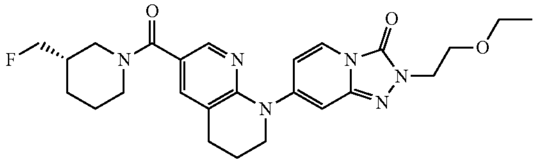 [SMILES: CCOCCn1nc2cc(N3CCCc4cc(C(=O)N5CCC[C@H](CF)C5)cnc43)ccn2c1=O] | $^1$H NMR (400 MHz, $CDCl_3$) δ 1.18 (3H, t, J = 7.3 Hz), 1.32-2.06 (6H, m), 2.08-2.18 (2H, m), 2.70-3.15 (4H, m), 3.53 (2H, q, J = 7.3 Hz), 3.78-3.84 (4H, m), 4.15 (2H, t, J = 5.5 Hz), 4.20-4.58 (3H, m), 6.70 (1H, d, J = 1.2 Hz), 6.73 (1H, dd, J = 7.3, 1.8 Hz), 7.49 (1H, d, J = 2.4 Hz), 7.64 (1H, d, J = 6.7 Hz), 8.08 (1H, d, J = 2.4 Hz). LRMS (ESI$^+$) 483 [M + H]$^+$. |
| 1-118 | 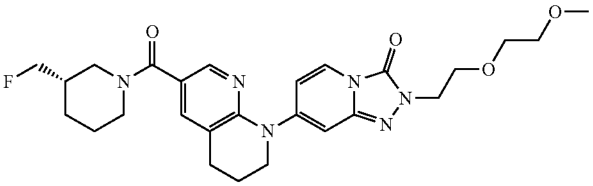 [SMILES: COCCOCCn1nc2cc(N3CCCc4cc(C(=O)N5CCC[C@H](CF)C5)cnc43)ccn2c1=O] | $^1$H NMR (400 MHz, $CDCl_3$) δ 1.34-2.05 (6H, m), 2.08-2.17 (2H, m), 2.75-3.14 (4H, m), 3.36 (3H, s), 3.50-3.55 (2H, m), 3.62-3.67 (2H, m), 3.81 (2H, t, J = 5.8 Hz), 3.88 (2H, t, J = 5.8 Hz), 4.16 (2H, t, J = 5.8 Hz), 4.21-4.49 (3H, m), 6.69 (1H, d, J = 1.2 Hz), 6.73 (1H, dd, J = 7.9, 1.8 Hz), 7.47-7.51 (1H, m), 7.63 (1H, dd, J = 7.9, 1.2 Hz), 8.08 (1H, d, J = 2.4 Hz). LRMS (ESI$^+$) 513 [M + H]$^+$. |
| 1-119 | 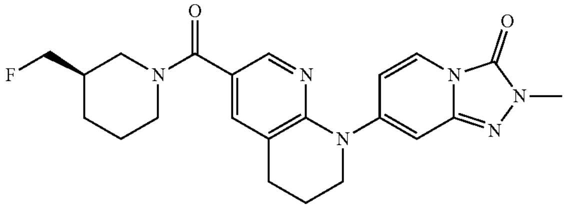 [SMILES: Cn1nc2cc(N3CCCc4cc(C(=O)N5CCC[C@@H](CF)C5)cnc43)ccn2c1=O] | $^1$H NMR (400 MHz, $CDCl_3$) δ 1.34-2.05 (6H, m), 2.08-2.19 (2H, m), 2.69-3.12 (4H, m), 3.64 (3H, s), 3.82 (2H, t, J = 5.5 Hz), 4.16-4.62 (3H, m), 6.68 (1H, d, J = 1.2 Hz), 6.76 (1H, dd, J = 7.9, 1.2 Hz), 7.49 (1H, d, J = 1.8 Hz), 7.64 (1H, d, J = 8.6 Hz), 8.09 (1H, d, J = 2.4 Hz). LRMS (ESI$^+$) 425 [M + H]$^+$. |
| 1-120 | 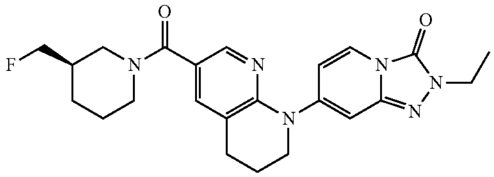 [SMILES: CCn1nc2cc(N3CCCc4cc(C(=O)N5CCC[C@@H](CF)C5)cnc43)ccn2c1=O] | $^1$H NMR (400 MHz, $CDCl_3$) δ 1.34-2.06 (6H, m), 1.41 (3H, t, J = 7.3 Hz), 2.08-2.18 (2H, m), 2.72-3.14 (4H, m), 3.82 (2H, t, J = 5.5 Hz), 4.02 (2H, q, J = 7.3 Hz), 4.17-4.63 (3H, m), 6.71 (1H, d, J = 1.2 Hz), 6.74 (1H, dd, J = 7.9, 1.8 Hz), 7.49 (1H, d, J = 1.8 Hz), 7.64 (1H, dd, J = 7.3, 1.2 Hz), 8.08 (1H, d, J = 2.4 Hz). LRMS (ESI$^+$) 439 [M + H]$^+$. |

TABLE 76

| Example No. | Chemical Structural Formula | Spectrum Data |
|---|---|---|
| 1-121 | 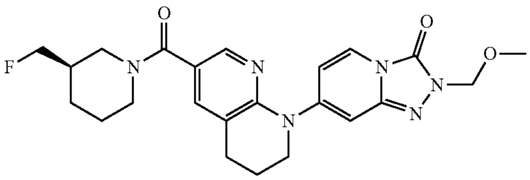 [SMILES: COCn1nc2cc(N3CCCc4cc(C(=O)N5CCC[C@@H](CF)C5)cnc43)ccn2c1=O] | $^1$H NMR (400 MHz, $CDCl_3$) δ 1.33-2.06 (6H, m), 2.09-2.20 (2H, m), 2.67-3.14 (4H, m), 3.43 (3H, s), 3.83 (2H, t, J = 5.5 Hz), 4.17-4.67 (3H, m), 5.30 (2H, s), 6.67 (1H, d, J = 1.8 Hz), 6.77 (1H, dd, J = 7.3, 1.8 Hz), 7.50 (1H, d, J = 1.8 Hz), 7.64 (1H, d, J = 7.3 Hz), 8.10 (1H, d, J = 2.4 Hz). LRMS (ESI$^+$) 455 [M + H]$^+$. |
| 1-122 | 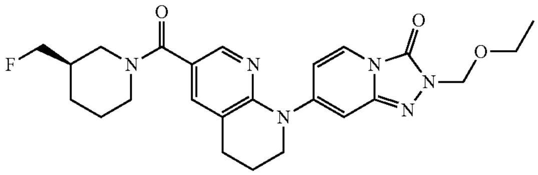 | $^1$H NMR (400 MHz, $CDCl_3$) δ 1.22 (3H, t, J = 7.3 IIz), 1.33-2.06 (6H, m), 2.08-2.19 (2H, m), 2.70-3.15 (4H, m), 3.65 (2H, q, J = 7.3 Hz), 3.82 (2H, t, J = 5.5 Hz), 4.17-4.62 (3H, m), 5.34 (2H, s), 6.67 (1H, d, J = 1.2 Hz), 6.76 (1H, dd, J = 7.9, 1.8 Hz), 7.50 (1H, d, J = 1.8 Hz), 7.63 (1H, d, J = 7.3 Hz), 8.09 (1H, d, J = 1.8 Hz). LRMS (ESI$^+$) 469 [M + H]$^+$. |
| 1-123 | 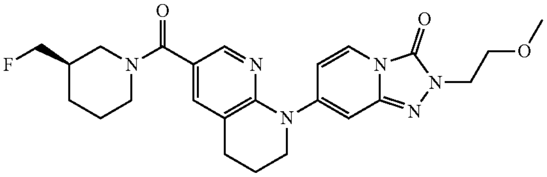 [SMILES: COCCn1nc2cc(N3CCCc4cc(C(=O)N5CCC[C@@H](CF)C5)cnc43)ccn2c1=O] | $^1$H NMR (400 MHz, $CDCl_3$) δ 1.34-2.06 (6H, m), 2.08-2.18 (2H, m), 2.69-3.13 (4H, m), 3.37 (3H, s), 3.77 (2H, t, J = 5.5 Hz), 3.81 (2H, t, J = 5.5 Hz), 4.16 (2H, t, J = 5.5 Hz), 4.20-4.65 (3H, m), 6.71 (1H, d, J = 1.2 Hz), 6.73 (1H, dd, J = 7.3, 1.8 Hz), 7.49 (1H, d, J = 1.2 Hz), 7.64 (1H, d, J = 8.6 Hz), 8.08 (1H, d, J = 1.8 Hz). LRMS (ESI$^+$) 469 [M + H]$^+$. |

TABLE 76-continued

| Example No. | Chemical Structural Formula | Spectrum Data |
|---|---|---|
| 1-124 | 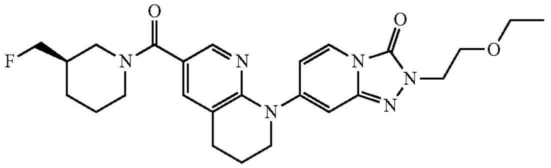 [SMILES: CCOCCn1nc2cc(N3CCCc4cc(C(=O)N5CCC[C@@H](CF)C5)cnc43)ccn2c1=O] | $^1H$ NMR (400 MHz, $CDCl_3$) δ 1.17 (3H, t, J = 7.3 Hz), 1.34-2.06 (11H, m), 2.08-2.17 (2H, m), 2.73-3.12 (4H, m), 3.53 (2H, q, J = 7.3 Hz), 3.77-3.85 (4H, m), 4.14 (2H, t, J = 5.5 Hz), 4.19-4.59 (3H, m), 6.70 (1H, d, J = 1.8 Hz), 6.73 (1H, dd, J = 7.9, 1.8 Hz), 7.49 (1H, d, J = 1.2 Hz), 7.64 (1H, dd, J = 7.3, 1.2 Hz), 8.08 (1H, d, J = 2.4 Hz). LRMS ($ESI^+$) 483 $[M + H]^+$. |
| 1-125 | 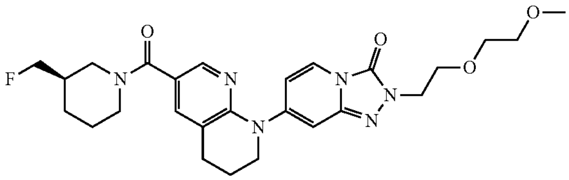 [SMILES: COCCOCCn1nc2cc(N3CCCc4cc(C(=O)N5CCC[C@@H](CF)C5)cnc43)ccn2c1=O] | $^1H$ NMR (400 MHz, $CDCl_3$) δ 1.33-2.06 (6H, m), 2.08-2.17 (2H, m), 2.70-3.14 (4H, m), 3.36 (3H, s), 3.50-3.55 (2H, m), 3.63-3.68 (2H, m), 3.81 (2H, t, J = 5.5 Hz), 3.88 (2H, t, J = 5.5 Hz), 4.16 (2H, t, J = 5.5 Hz), 4.20-4.64 (3H, m), 6.69 (1H, d, J = 1.2 Hz), 6.74 (1H, dd, J = 7.9, 1.8 Hz), 7.49 (1H, d, J = 2.4 Hz), 7.63 (1H, d, J = 6.7 Hz), 8.08 (1H, d, J = 2.4 Hz). LRMS ($ESI^+$) 513 $[M + H]^+$. |

TABLE 77

| Reference Example No. | Chemical Structural Formula | Spectrum Data |
|---|---|---|
| 1-126 | 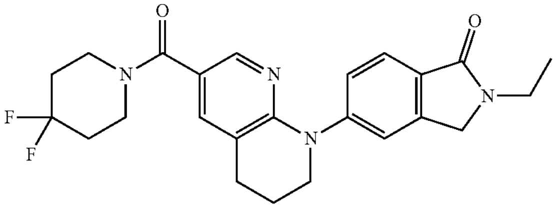 [SMILES: CCN1Cc2cc(N3CCCc4cc(C(=O)N5CCC(F)(F)CC5)cnc43)ccc2C1=O] | $^1H$ NMR (400 MHz, $CDCl_3$) δ 1.17 (3H, t, J = 7.3 Hz), 1.93-2.11 (6H, m), 2.87 (2H, t, J = 6.4 Hz), 3.47-3.68 (6H, m), 3.81 (2H, t, J = 5.4 Hz), 4.45 (2H, s), 7.42 (1H, dd, J = 8.5, 1.8 Hz), 7.48 (1H, d, J = 2.4 Hz), 7.54 (1H, d, J = 1.2 Hz), 7.63 (1H, d, J = 7.9 Hz), 7.92 (1H, d, J = 1.8 Hz). LRMS ($ESI^+$) 441 $[M + H]^+$. |
| 1-127 | 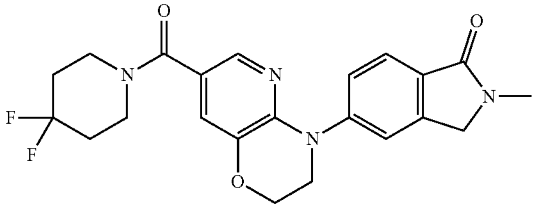 | $^1H$ NMR (400 MHz, $CDCl_3$) δ 1.94-2.10 (4H, m), 3.06 (3H, s), 3.48-3.69 (4H, m), 3.96 (2H, t, J = 4.3 Hz), 4.36 (2H, t, J = 4.3 Hz), 4.44 (2H, s), 7.24 (1H, d, J = 1.8 Hz), 7.51 (1H, dd, J = 7.9, 1.8 Hz), 7.60-7.66 (2H, m), 7.76 (1H, d, J = 1.8 Hz). LRMS ($ESI^+$) 429 $[M + H]^+$. |
| 1-128 | 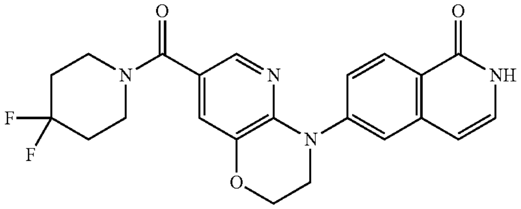 [SMILES: O=C(c1cnc2c(c1)OCCN2c1ccc2c(=O)[nH]ccc2c1)N1CCC(F)(F)CC1] | $^1H$ NMR (400 MHz, $CDCl_3$) δ 1.95-2.09 (4H, m), 3.48-3.68 (4H, m), 4.01 (2H, t, J = 4.3 Hz), 4.37 (2H, t, J = 4.3 Hz), 6.48 (1H, d, J = 6.7 Hz), 7.13 (1H, dd, J = 7.0, 5.8 Hz), 7.26 (1H, d, J = 1.8 Hz), 7.58 (1H, d, J = 1.8 Hz), 7.62 (1H, dd, J = 8.9, 2.1 Hz), 7.80 (1H, d, J = 2.4 Hz), 8.11 (1H, d, J = 8.6 Hz), 11.08-11.15 (1H, m). LRMS ($ESI^+$) 427 $[M + H]^+$. |
| 1-129 | 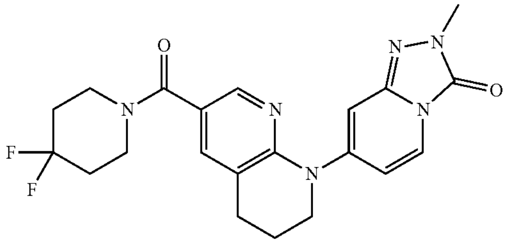 [SMILES: Cn1nc2cc(N3CCCc4cc(C(=O)N5CCC(F)(F)CC5)cnc43)ccn2c1=O] | $^1H$ NMR (400 MHz, $CDCl_3$) δ 1.94-2.08 (4H, m), 2.10-2.17 (2H, m), 2.89 (2H, t, J = 6.4 Hz), 3.64 (3H, s), 3.69-3.80 (4H, m), 3.83 (2H, t, J = 5.8 Hz), 6.70 (1H, d, J = 1.2 Hz), 6.74 (1H, dd, J = 7.6, 2.1 Hz), 7.51 (1H, d, J = 1.8 Hz), 7.65 (1H, d, J = 8.6 Hz), 8.10 (1H, cl, J = 2.4 Hz). LRMS ($ESI^+$) 429 $[M + H]^+$. |

TABLE 78

| Example No. | Chemical Structural Formula | Spectrum Data |
|---|---|---|
| 1-130 | 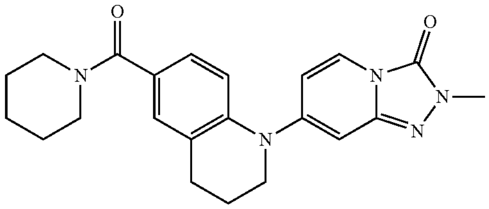 [SMILES: Cn1nc2cc(N3CCCc4cc(C(=O)N5CCCCC5)ccc43)ccn2c1=O] | $^1$H NMR (400 MHz, $CDCl_3$) δ 1.51-1.75 (6H, m), 2.01-2.11 (2H, m), 2.76 (2H, t, J = 6.1 Hz), 3.36-3.78 (9H, m), 6.42 (1H, d, J = 1.8 Hz), 6.54 (1H, dd, J = 7.9, 1.8 Hz), 6.98 (1H, d, J = 7.9 Hz), 7.15 (1H, dd, J = 8.6, 1.8 Hz), 7.24 (1H, d, J = 1.8 Hz), 7.59 (1H, d, J = 7.9 Hz). LRMS (ESI$^+$) 392 [M + H]$^+$. |
| 1-131 | 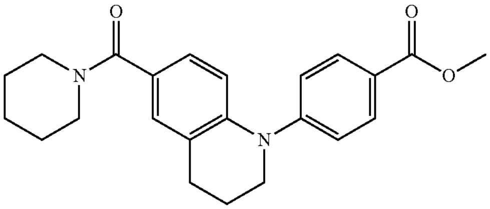 [SMILES: COC(=O)c1ccc(N2CCCc3cc(C(=O)N4CCCCC4)ccc32)cc1] | $^1$H NMR (400 MHz, $CDCl_3$) δ 1.51-1.73 (6H, m), 1.99-2.09 (2H, m), 2.81 (2H, t, J =6.1 Hz), 3.36-3.66 (4H, m), 3.69 (2H, t, J = 6.1 Hz), 3.90 (3H, s), 7.01 (1H, d, J = 8.6 Hz), 7.04 (1H, dd, J = 8.6, 1.8 Hz), 7.20 (1H, d, J = 1.2 Hz), 7.24 (2H, d, J = 8.6 Hz), 7.97 (2H, d, J = 9.2 Hz). LRMS (ESI$^+$) 379 [M + H]$^+$. |
| 1-132 | 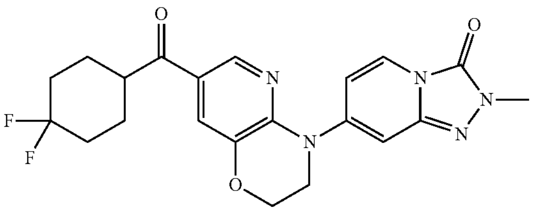 [SMILES: Cn1nc2cc(N3CCOc4cc(C(=O)C5CCC(F)(F)CC5)cnc43)ccn2c1=O] | $^1$H NMR (400 MHz, $CDCl_3$) δ 1.75-2.01 (6H, m), 2.14-2.27 (2H, m), 3.15-3.25 (1H, m), 3.66 (3H, s), 3.94 (2H, t, J = 4.3 Hz), 4.43 (2H, t, J = 4.3 Hz), 6.72 (1H, d, J = 1.2 Hz), 6.94 (1H, dd, J = 7.9, 1.8 Hz), 7.67 (1H, d, J = 2.4 Hz), 7.71 (1H, dd, J = 7.9, 1.2 Hz), 8.41 (1H, d, J = 1.8 Hz). LRMS (ESI$^+$) 430 [M + H]$^+$. |
| 1-133 | 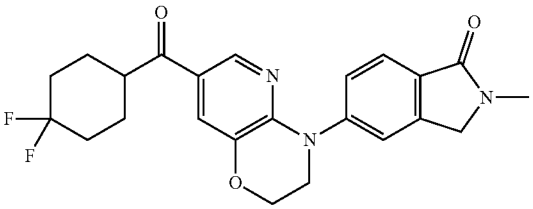 [SMILES: CN1Cc2cc(N3CCOc4cc(C(=O)C5CCC(F)(F)CC5)cnc43)ccc2C1=O] | $^1$H NMR (400 MHz, $CDCl_3$) δ 1.72-2.00 (6H, m), 2.13-2.26 (2H, m), 3.12-3.24 (4H, m), 4.00 (2H, t, J = 4.9 Hz), 4.37-4.44 (4H, m), 7.44 (1H, dd, J = 7.9, 1.8 Hz), 7.53 (1H, d, J = 1.2 Hz), 7.63 (1H, d, J = 1.8 Hz), 7.89 (1H, d, J = 8.6 Hz), 8.35 (1H, d, J = 2.4 Hz). LRMS (ESI$^+$) 428 [M + H]$^+$. |
| 1-134 | 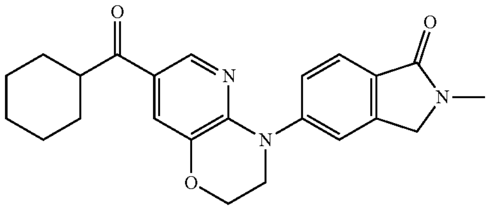 [SMILES: CN1Cc2cc(N3CCOc4cc(C(=O)C5CCCCC5)cnc43)ccc2C1=O] | $^1$H NMR (400 MHz, $CDCl_3$) δ 1.19-1.41 (3H, m), 1.43-1.56 (2H, m), 1.67-1.76 (1H, m), 1.78-1.93 (4H, m), 3.02-3.15 (1H, m), 3.21 (3H, s), 3.99 (2H, t, J = 4.3 Hz), 4.33-4.47 (4H, m), 7.43 (1H, dd, J = 8.6, 1.8 Hz), 7.54 (1H, s), 7.65 (1H, d, J = 1.8 Hz), 7.88 (1H, d, J = 7.9 Hz), 8.38 (1H, d, J = 1.8 Hz). LRMS (ESI$^+$) 392 [M + H]$^+$. |
| 1-135 | 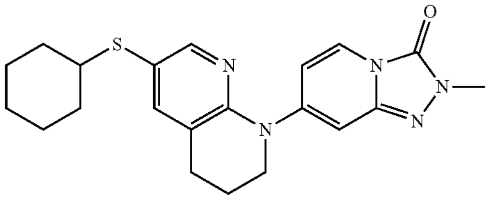 [SMILES: Cn1nc2cc(N3CCCc4cc(SC5CCCCC5)cnc43)ccn2c1=O] | $^1$H NMR (400 MHz, $CDCl_3$) δ 1.15-1.39 (6H, m), 1.71-1.82 (2H, m), 1.88-1.99 (2H, m), 2.06-2.15 (2H, m), 2.80-2.91 (3H, m), 3.63 (3H, s), 3.79 (2H, t, J = 6.1 Hz), 6.61 (1H, d, J = 1.2 Hz), 6.80 (1H, dd, J = 7.9, 1.8 Hz), 7.43-7.47 (1H, m), 7.61 (1H, d, J = 7.3 Hz), 8.10 (1H, d, J = 2.4 Hz). LRMS (ESI$^+$) 396 [M + H]$^+$. |

TABLE 79

| Example No. | Chemical Structural Formula | Spectrum Data |
|---|---|---|
| 1-136 | 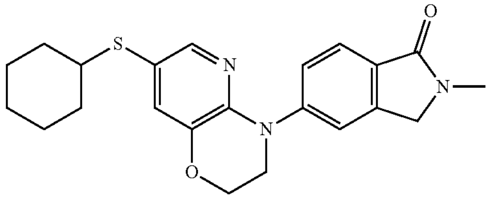 [SMILES: CN1Cc2cc(N3CCOc4cc(SC5CCCCC5)cnc43)ccc2C1=O] | $^1$H NMR (400 MHz, $CDCl_3$) δ 1.13-1.38 (6H, m), 1.69-1.80 (2H, m), 1.89-1.98 (2H, m), 2.81-2.90 (1H, m), 3.19 (3H, s), 3.94 (2H, t, J = 4.3 Hz), 4.33-4.39 (4H, m), 7.23 (1H, d, J = 1.8 Hz), 7.38 (1H, dd, J = 7.9, 1.8 Hz), 7.55 (1H, d, J = 1.2 Hz), 7.80-7.86 (2H, m).<br>LRMS (ESI$^+$) 396 [M + H]$^+$. |
| 1-137 | 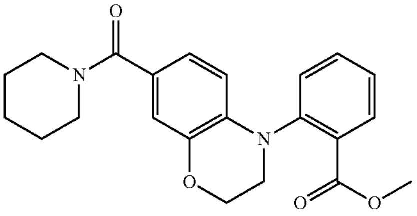 [SMILES: COC(=O)c1ccccc1N1CCOc2cc(C(=O)N3CCCCC3)ccc21] | $^1$H NMR (400 MHz, $CDCl_3$) δ 1.49-1.70 (6H, m), 3.35-3.83 (9H, m), 4.25-4.44 (2H, m), 6.35 (1H, d, J = 7.9 Hz), 6.75 (1H, dd, J = 8.5, 1.8 Hz), 6.95 (1H, d, J = 1.8 Hz), 7.29-7.37 (2H, m), 7.56 (1H, td, J = 7.3, 1.8 Hz), 7.88 (1H, dd, J = 7.9, 1.2 Hz).<br>LRMS (ESI$^+$) 381 [M + H]$^+$. |
| 1-138 | 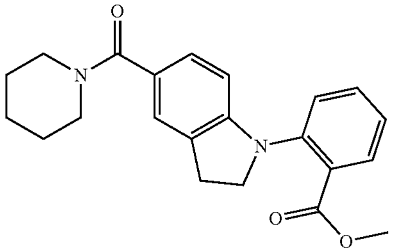 [SMILES: COC(=O)c1ccccc1N1CCc2cc(C(=O)N3CCCCC3)ccc21] | $^1$H NMR (400 MHz, $CDCl_3$) δ 1.51-1.71 (6H, m), 3.17 (2H, t, J = 8.5 Hz), 3.46-3.63 (4H, m), 3.69 (3H, s), 3.98 (2H, t, J – 8.5 Hz), 6.40 (1H, d, J – 8.5 Hz), 7.05 (1H, dd, J = 7.9, 1.8 Hz), 7.21 (1H, td, J = 7.3, 1.2 Hz), 7.25 (1H, d, J = 1.2 Hz), 7.37 (1H, dd, J = 7.9, 1.2 Hz), 7.51 (1H, td, J = 7.3, 1.8 Hz), 7.83 (1H, dd, J = 7.9, 1.8 Hz).<br>LRMS (ESI$^+$) 365 [M + H]$^+$. |
| 1-139 | 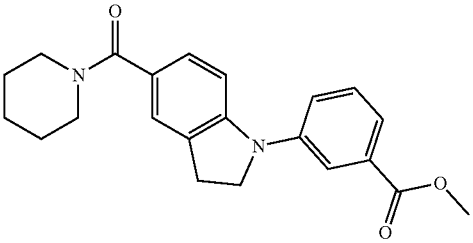 [SMILES: COC(=O)c1cccc(N2CCc3cc(C(=O)N4CCCCC4)ccc32)c1] | $^1$H NMR (400 MHz, $CDCl_3$) δ 1.51-1.73 (6H, m), 3.17 (2H, t, J = 8.5 Hz), 3.44-3.70 (4H, m), 3.93 (3H, s), 4.04 (2H, t, J = 8.5 Hz), 7.09 (1H, d, J = 7.9 Hz), 7.17 (1H, dd, J = 7.9, 1.2 Hz), 7.29 (1H, d, J = 1.2 Hz), 7.38-7.46 (2H, m), 7.65 (1H, td, J = 6.7, 1.8 Hz), 7.88 (1H, s).<br>LRMS (ESI$^+$) 365 [M + H]$^+$. |
| 1-140 | 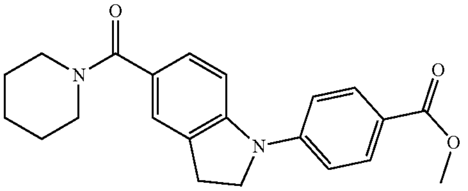 [SMILES: COC(=O)c1ccc(N2CCc3cc(C(=O)N4CCCCC4)ccc32)cc1] | $^1$H NMR (400 MHz, $CDCl_3$) δ 1.52-1.73 (6H, m), 3.18 (2H, t, J = 8.5 Hz), 3.41-3.73 (4H, m), 3.90 (3H, s), 4.06 (2H, t, J = 8.5 Hz), 7.16-7.25 (4H, m), 7.30 (1H, s), 7.99-8.05 (2H, 1H).<br>LRMS (ESI$^+$) 365 [M + H]$^+$. |
| 1-141 | 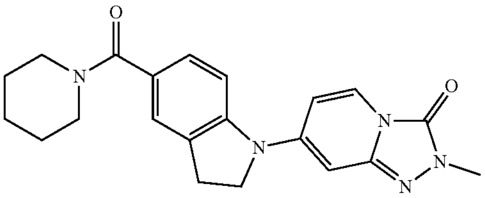 [SMILES: Cn1nc2cc(N3CCc4cc(C(=O)N5CCCCC5)ccc43)ccn2c1=O] | $^1$H NMR (400 MHz, $CDCl_3$) δ 1.51-1.74 (6H, m), 3.19 (2H, t, J = 8.3 Hz), 3.39-3.73 (7H, m), 4.02 (2H, t, J = 8.3 Hz), 6.41 (1H, d, J = 1.2 Hz), 6.75 (1H, dd, J = 7.9, 1.8 Hz), 7.12 (1H, d, J = 7.9 Hz), 7.20 (1H, dd, J = 8.6, 1.8 Hz), 7.31 (1H, d, J = 1.2 Hz), 7.71 (1H, d, J = 7.9 Hz).<br>LRMS (ESI$^+$) 378 [M + H]$^+$. |

TABLE 80

| Example No. | Chemical Structural Formula | Spectrum Data |
| --- | --- | --- |
| 1-142 | 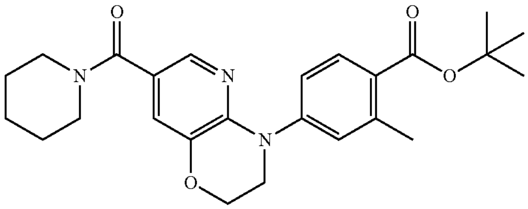 [SMILES: Cc1cc(N2CCOc3cc(C(=O)N4CCCCC4)cnc32)ccc1C(=O)OC(C)(C)C] | $^1H$ NMR (400 MHz, $CDCl_3$) δ 1.56-1.58 (4H, m), 1.58 (9H, s), 1.64-1.73 (2H, m), 2.59 (3H, s), 3.37-3.75 (4H, m), 3.89-3.94 (2H, m), 4.32-4.37 (2H, m), 7.21 (2H, d, J = 1.8 Hz), 7.24-7.28 (1H, m), 7.84 (1H, d, J = 1.8 Hz), 7.90 (1H, d, J = 8.6 Hz). LRMS ($ESI^+$) 438 $[M + H]^+$. |
| 1-143 | 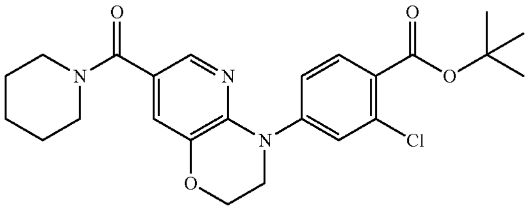 [SMILES: CC(C)(C)OC(=O)c1ccc(N2CCOc3cc(C(=O)N4CCCCC4)cnc32)cc1Cl] | $^1H$ NMR (400 MHz, $CDCl_3$) δ 1.50-1.58 (4H, m), 1.60 (9H, s), 1.65-1.73 (2H, m), 3.34-3.76 (4H, m), 3.91 (2H, t, J = 4.6 Hz), 4.36 (2H, t, J = 4.6 Hz), 7.23 (1H, d, J = 1.8 Hz), 7.38 (1H, dd, J = 8.6, 2.4 Hz), 7.46 (1H, d, J = 2.4 Hz), 7.82 (1H, d, J = 8.6 Hz), 7.85 (1H, d, J = 1.8 Hz). LRMS ($ESI^+$) 458 $[M + H]^+$. |
| 1-144 | 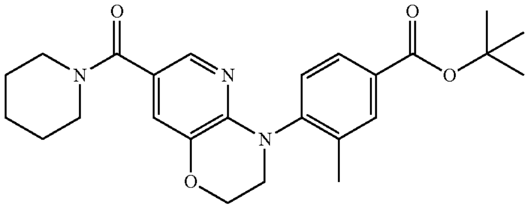 [SMILES: Cc1cc(C(=O)OC(C)(C)C)ccc1N1CCOc2cc(C(=O)N3CCCCC3)cnc21] | $^1H$ NMR (400 MHz, $CDCl_3$) δ 1.50-1.58 (414, m), 1.59 (9H, s), 1.62-1.71 (2H, m), 2.22 (3H, s), 3.39-3.99 (6H, m), 4.34-4.43 (2H, m), 7.18 (1H, d, J = 1.8 Hz), 7.24 (1H, d, J = 8.6 Hz), 7.77 (1H, d, J = 1.8 Hz), 7.90 (1H, dd, J = 7.9, 1.8 Hz), 7.94 (1H, d, J = 1.8 Hz). LRMS ($ESI^+$) 438 $[M + H]^+$. |
| 1-145 | 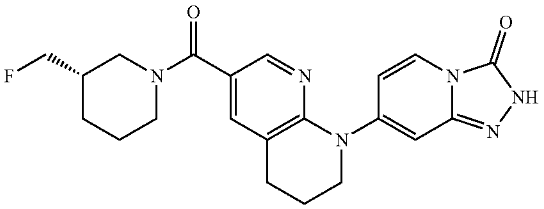 [SMILES: O=C(c1cnc2c(c1)CCCN2c1ccn2c(=O)[nH]nc2c1)N1CCC[C@H](CF)C1] | $^1H$ NMR (400 MHz, $CDCl_3$) δ 1.34-2.06 (6H, m), 2.08-2.19 (2H, m), 2.71-3.14 (4H, m), 3.83 (2H, t, J = 5.5 Hz), 4.14-4.63 (3H, m), 6.70 (1H, d, J = 1.2 Hz), 6.77 (1H, dd, J = 7.9, 1.8 Hz), 7.48-7.52 (1H, m), 7.64 (1H, d, J = 6.7 Hz), 8.10 (1H, d, J = 2.4 Hz), 9.22 (1H, br s). LRMS ($ESI^+$) 411 $[M + H]^+$. |
| 1-146 | 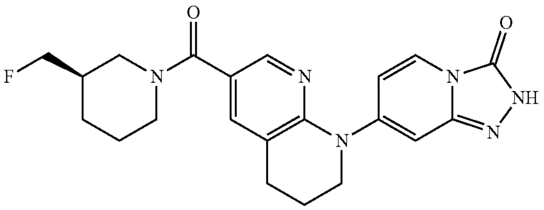 [SMILES: O=C(c1cnc2c(c1)CCCN2c1ccn2c(=O)[nH]nc2c1)N1CCC[C@@H](CF)C1] | $^1H$ NMR (400 MHz, $CDCl_3$) δ 1.35-2.06 (6H, m), 2.09-2.18 (2H, m), 2.75-3.14 (4H, m), 3.83 (2H, t, J = 5.5 Hz), 4.12-4.68 (3H, m), 6.70 (1H, d, J = 1.2 Hz), 6.77 (1H, dd, J = 7.9, 1.8 Hz), 7.48-7.52 (1H, m), 7.64 (1H, d, J = 6.7 Hz), 8.10 (1H, d, J = 2.4 Hz), 9.21 (1H, br s). LRMS ($ESI^+$) 411 $[M + H]^+$. |
| 1-147 | 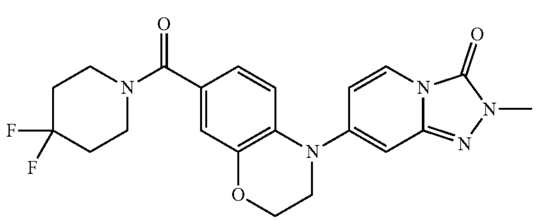 [SMILES: Cn1nc2cc(N3CCOc4cc(C(=O)N5CCC(F)(F)CC5)ccc43)ccn2c1=O] | $^1H$ NMR (400 MHz, $CDCl_3$) δ 1.93-2.11 (4H, m), 3.63 (3H, s), 3.66-3.87 (6H, m), 4.35 (2H, t, J = 4.3 Hz), 6.53-6.59 (2H, m), 6.91 (1H, dd, J = 8.6, 1.8 Hz), 7.02 (1H, d, J = 1.8 Hz), 7.06 (1H, d, J = 8.6 Hz), 7.71 (1H, dd, J = 7.3, 1.2 Hz). LRMS ($ESI^+$) 430 $[M + H]^+$. |

TABLE 81

| Example No. | Chemical Structural Formula | Spectrum Data |
|---|---|---|
| 1-148 | 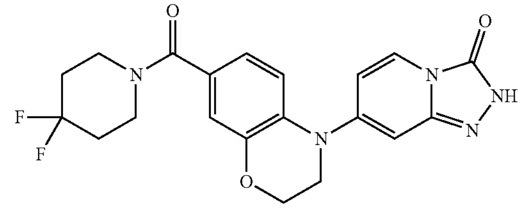 [SMILES: O=C(c1ccc2c(c1)OCCN2c1ccn2c(=O)[nH]nc2c1)N1CCC(F)(F)CC1] | $^1$H NMR (400 MHz, $CDCl_3$) δ 1.90-2.14 (4H, m), 3.46-3.95 (6H, m), 4.35 (2H, t, J = 4.3 Hz), 6.55-6.61 (2H, m), 6.93 (1H, dd, J = 7.9, 1.8 Hz), 7.02 (1H, d, J = 1.8 Hz), 7.07 (1H, d, J = 8.6 Hz), 7.72 (1H, dd, J = 7.3, 1.2 Hz), 9.36 (1H, br s). LRMS (ESI$^+$) 416 [M + H]$^+$. |
| 1-149 | 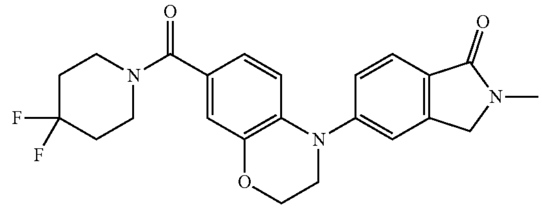 [SMILES: CN1Cc2cc(N3CCOc4cc(C(=O)N5CCC(F)(F)CC5)ccc43)ccc2C1=O] | $^1$H NMR (400 MHz, $CDCl_3$) δ 1.91-2.11 (4H, m), 3.20 (3H, s), 3.64-3.85 (6H, m), 4.33 (2H, t, J = 4.3 Hz), 4.35 (2H, s), 6.86 (1H, dd, J = 8.6, 1.8 Hz), 7.00 (2H, dd, J = 5.5, 3.1 Hz), 7.28-7.32 (2H, m), 7.82 (1H, d, J = 8.6 Hz). LRMS (ESI$^+$) 428 [M + H]$^+$. |
| 1-150 | 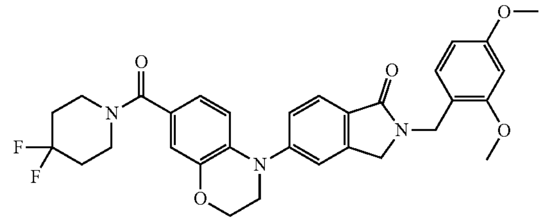 [SMILES: COc1ccc(CN2Cc3cc(N4CCOc5cc(C(=O)N6CCC(F)(F)CC6)ccc54)ccc3C2=O)c(OC)c1] | $^1$H NMR (400 MHz, $CDCl_3$) δ 1.91-2.08 (4H, m), 3.67-3.79 (6H, m), 3.79 (3H, s), 3.84 (3H, s), 4.26 (2H, s), 4.31 (2H, t, J = 4.2 Hz), 4.75 (2H, s), 6.44 (1H, dd, J = 8.5, 2.4 Hz), 6.47 (1H, d, J = 2.4 Hz), 6.83 (1H, dd, J = 8.5, 1.8 Hz), 6.95-7.00 (2H, m), 7.20-7.24 (2H, m), 7.28 (1H, dd, J = 7.9, 1.8 Hz), 7.83 (1H, d, J = 7.9 Hz). LRMS (ESI$^+$) 564 [M + H]$^+$. |
| 1-151 | 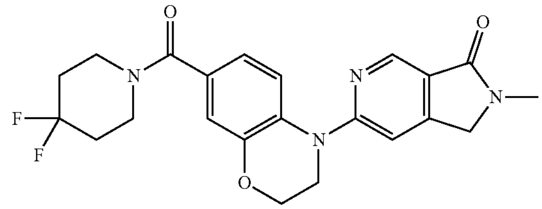 [SMILES: CN1Cc2cc(N3CCOc4cc(C(=O)N5CCC(F)(F)CC5)ccc43)ncc2C1=O] | $^1$H NMR (400 MHz, $CDCl_3$) δ 1.94-2.12 (4H, m), 3.16 (3H, s), 3.63-3.88 (4H, m), 4.22 (2H, t, J = 4.9 Hz), 4.29-4.34 (4H, m), 6.96 (1H, dd, J = 8.6, 1.8 Hz), 7.02 (1H, d, J = 1.8 Hz), 7.28 (1H, d, J = 1.2 Hz), 7.42 (1H, d, J = 7.9 Hz), 8.76 (1H, d, J = 1.2 Hz). LRMS (ESI$^+$) 429 [M + H]$^+$. |
| 1-152 | 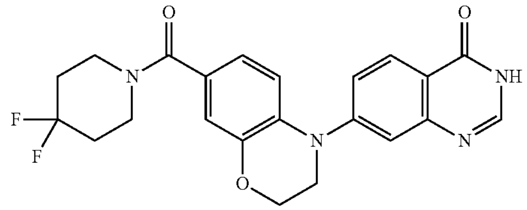 [SMILES: O=C(c1ccc2c(c1)OCCN2c1ccc2c(=O)[nH]cnc2c1)N1CCC(F)(F)CC1] | $^1$H NMR (400 MHz, $CDCl_3$) δ 1.94-2.11 (4H, m), 3.64-3.84 (4H, m), 3.87 (2H, t, J = 4.3 Hz), 4.35 (2H, t, J = 4.3 Hz), 6.89 (1H, dd, J = 8.6, 1.8 Hz), 7.04 (1H, d, J = 2.4 Hz), 7.24 (1H, d, J = 8.6 Hz), 7.41-7.47 (2H, m), 8.00 (1H, d, J = 3.7 Hz), 8.23 (1H, d, J = 8.6 Hz), 9.72 (1H, br s). LRMS (ESI$^+$) 427 [M + H]$^+$. |
| 1-153 | 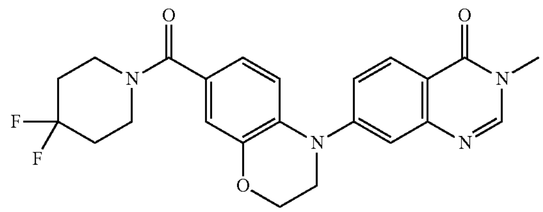 [SMILES: Cn1cnc2cc(N3CCOc4cc(C(=O)N5CCC(F)(F)CC5)ccc43)ccc2c1=O] | $^1$H NMR (400 MHz, $CDCl_3$) δ 1.93-2.12 (4H, m), 3.59 (3H, s), 3.66-3.83 (4H, m), 3.86 (2H, t, J = 4.3 Hz), 4.35 (2H, t, J = 4.3 Hz), 6.88 (1H, dd, J = 8.6, 1.8 Hz), 7.03 (1H, d, J = 1.8 Hz), 7.21 (1H, d, J = 7.9 Hz), 7.38-7.43 (2H, m), 8.02 (1H, s), 8.22-8.28 (1H, m). LRMS (ESI$^+$) 441 [M + H]$^+$. |

TABLE 82

| Example No. | Chemical Structural Formula | Spectrum Data |
|---|---|---|
| 1-154 | 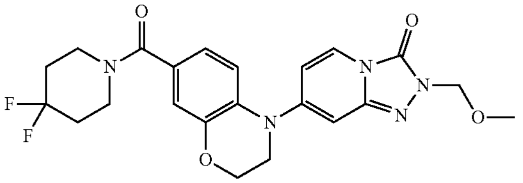 [SMILES: COCn1nc2cc(N3CCOc4cc(C(=O)N5CCC(F)(F)CC5)ccc43)ccn2c1=O] | $^1$H NMR (400 MHz, $CDCl_3$) δ 1.92-2.12 (4H, m), 3.46 (3H, s), 3.61-3.88 (6H, m), 4.35 (2H, t, J = 4.3 Hz), 5.28 (2H, s), 6.54 (1H, t, J = 1.2 Hz), 6.58 (1H, dd, J = 7.9, 1.8 Hz), 6.92 (1H, dd, J = 8.6, 1.8 Hz), 7.02 (1H, d, J = 1.8 Hz), 7.07 (1H, d, J = 8.6 Hz), 7.71 (1H, dd, J = 7.9, 1.2 Hz). LRMS (ESI$^+$) 460 [M + H]$^+$. |
| 1-155 | 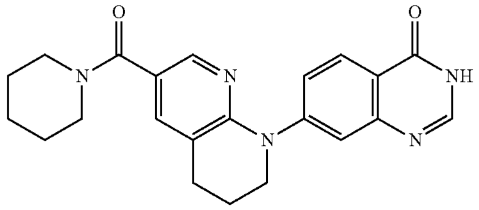 [SMILES: O=C(c1cnc2c(c1)CCCN2c1ccc2c(=O)[nH]cnc2c1)N1CCCCC1] | $^1$H NMR (400 MHz, $CDCl_3$) δ 1.49-1.73 (6H, m), 2.09-2.19 (2H, m), 2.92 (2H, t, J = 6.1 Hz), 3.41-3.75 (4H, m), 3.93 (2H, t, J = 6.1 Hz), 7.51 (1H, d, J = 1.8 Hz), 7.60-7.67 (2H, m), 8.02 (1H, d, J = 2.4 Hz), 8.05 (1H, d, J = 2.4 Hz), 8.23 (1H, d, J = 8.6 Hz), 10.43 (1H, br s). LRMS (ESI$^+$) 390 [M + H]$^+$. |
| 1-156 | 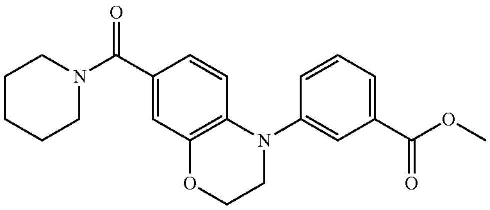 [SMILES: COC(=O)c1cccc(N2CCOc3cc(C(=O)N4CCCCC4)ccc32)c1] | $^1$H NMR (400 MHz, $CDCl_3$) δ 1.59 (4H, s), 1.67 (2H, s), 3.45-3.65 (4H, m), 3.75 (2H, t, J = 4.2 Hz), 3.92 (3H, s), 4.32 (2H, t, J = 4.2 Hz), 6.84 (2H, dt, J = 15.3, 6.4 Hz), 6.97 (1H, d, J = 1.8 Hz), 7.44 (2H, t, J = 3.0 Hz), 7.78 (1H, t, J = 3.3 Hz), 7.90 (1H, s). LRMS (ESI$^+$) 381 [M + H]$^+$. |
| 1-157 | 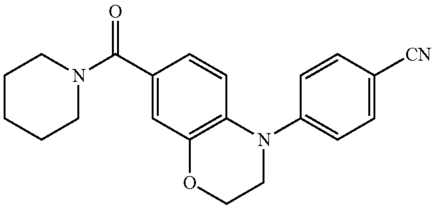 [SMILES: N#Cc1ccc(N2CCOc3cc(C(=O)N4CCCCC4)ccc32)cc1] | $^1$H NMR (400 MHz, $CDCl_3$) δ 1.43-1.53 (4H, m), 1.55-1.64 (2H, m), 3.35-3.50 (4H, m), 3.81 (2H, t, J = 4.5 Hz), 4.26 (2H, t, J = 4.5 Hz), 6.80 (1H, dd, J = 8.5, 1.8 Hz), 6.88 (1H, d, J = 1.8 Hz), 7.13 (1H, d, J = 8.5 Hz), 7.39 (2H, dd, J = 7.0, 2.1 Hz), 7.76 (2H, dd, J = 11.5, 2.4 Hz). LRMS (ESI$^+$) 348 [M + H]$^+$. |
| 1-158 | 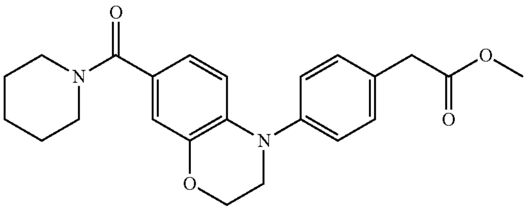 [SMILES: COC(=O)Cc1ccc(N2CCOc3cc(C(=O)N4CCCCC4)ccc32)cc1] | $^1$H NMR (400 MHz, $CDCl_3$) δ 1.64-1.70 (6H, m), 3.43-3.60 (4H, m), 3.62 (2H, s), 3.70 (2H, t, J = 3.6 Hz), 3.72 (3H, s), 4.30 (2H, t, J = 4.5 Hz), 6.80 (1H, dd, J = 8.5, 1.8 Hz), 6.86 (1H, d, J = 8.5 Hz), 6.95 (1H, d, J = 1.8 Hz), 7.19 (2H, d, J = 8.5 Hz), 7.28 (2H, d, J = 8.5 Hz). LRMS (ESI$^+$) 395 [M + H]$^+$. |
| 1-159 | 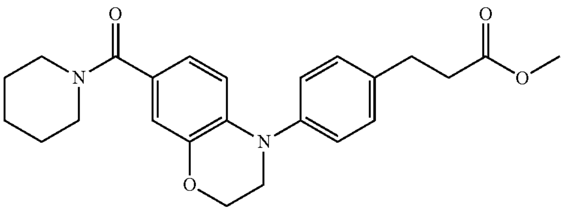 [SMILES: COC(=O)CCc1ccc(N2CCOc3cc(C(=O)N4CCCCC4)ccc32)cc1] | $^1$H NMR (400 MHz, $CDCl_3$) δ 1.57-1.71 (6H, m), 2.65 (2H, t, J = 7.9 Hz), 2.95 (2H, t, J = 7.9 Hz), 3.45-3.65 (4H, m), 3.69 (3H, s), 3.71 (2H, s), 4.31 (2H, t, J = 4.3 Hz), 6.80 (2H, s), 6.94 (1H, s), 7.16 (2H, d, J = 7.9 Hz), 7.21 (2H, d, J = 8.6 Hz). LRMS (ESI$^+$) 409 [M + H]$^+$. |

TABLE 83

| Example No. | Chemical Structural Formula | Spectrum Data |
|---|---|---|
| 1-160 | 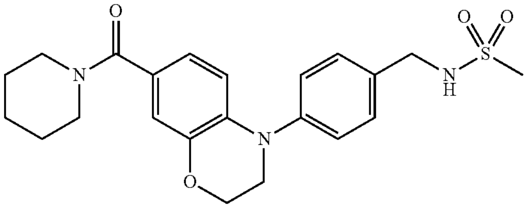 [SMILES: CS(=O)(=O)NCc1ccc(N2CCOc3cc(C(=O)N4CCCCC4)ccc32)cc1] | $^1$H NMR (400 MHz, $CDCl_3$) δ 1.58-1.70 (6H, m), 2.95 (3H, s), 3.40-3.68 (4H, m), 3.72 (2H, t, J = 4.3 Hz), 4.29-4.34 (4H, m), 4.55 (1H, t, J = 5.8 Hz), 6.81 (1H, dd, J = 8.6, 1.8 Hz), 6.86 (1H, d, J − 7.9 Hz), 6.96 (1H, d, J = 1.8 Hz), 7.23 (2H, d, J = 8.6 Hz), 7.35 (2H, d, J = 8.6 Hz). LRMS (ESI$^+$) 430 [M + H]$^+$. |
| 1-161 | 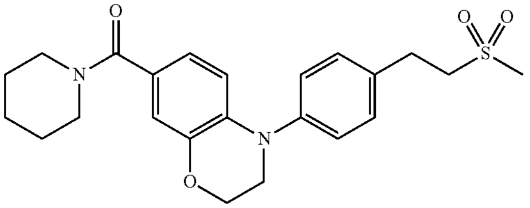 [SMILES: CS(=O)(=O)CCc1ccc(N2CCOc3cc(C(=O)N4CCCCC4)ccc32)cc1] | $^1$H NMR (400 MHz, $CDCl_3$) δ 1.51-1.70 (6H, m), 2.89 (3H, s), 3.14-3.19 (2H, m), 3.29-3.34 (2H, m), 3.39-3.67 (4H, m), 3.70 (2H, t, J = 4.3 Hz), 4.30 (2H, t, J = 4.3 Hz), 6.79-6.84 (2H, m), 6.95 (1H, d, J = 1.2 Hz), 7.19-7.25 (4H, m). LRMS (ESI$^+$) 429 [M + H]$^+$. |
| 1-162 | 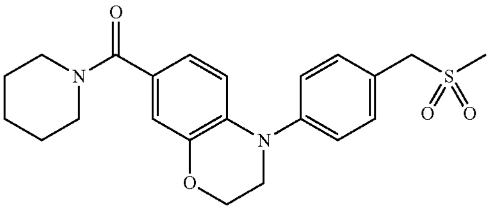 [SMILES: CS(=O)(=O)Cc1ccc(N2CCOc3cc(C(=O)N4CCCCC4)ccc32)cc1] | $^1$H NMR (400 MHz, $CDCl_3$) δ 1.59-1.72 (6H, m), 2.83 (3H, s), 3.40-3.65 (4H, m), 3.74 (2H, t, J = 4.3 Hz), 4.23 (2H, s), 4.30 (2H, t, J = 4.3 Hz), 6.83 (1H, dd, J = 8.3, 2.1 Hz), 6.97 (2H, dd, J = 4.9, 3.1 Hz), 7.27-7.28 (2H, m), 7.39 (2H, d, J = 8.6 Hz). LRMS (ESI$^+$) 415 [M + H]$^+$. |
| 1-163 | 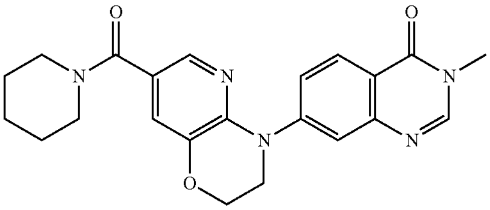 [SMILES: Cn1cnc2cc(N3CCOc4cc(C(=O)N5CCCCC5)cnc43)ccc2c1=O] | $^1$H NMR (400 MHz, $CDCl_3$) δ 1.62-1.73 (6H, m), 3.40-3.77 (7H, m), 4.02 (2H, dd, J = 5.5, 3.1 Hz), 4.40 (2H, dd, J − 5.8, 3.4 Hz), 7.26 (1H, s), 7.59 (1H, d, J = 2.4 Hz), 7.73 (1H, dd, J = 8.6, 2.4 Hz), 7.87 (1H, d, J = 2.4 Hz), 8.03 (1H, s), 8.28 (1H, d, J = 8.6 Hz). LRMS (ESI$^+$): 406 (M + H$^+$). |
| 1-164 | 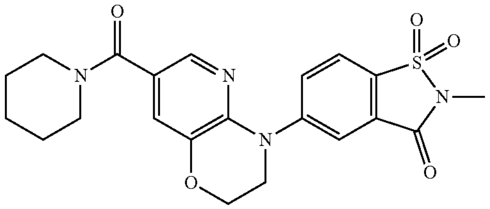 [SMILES: CN1C(=O)c2cc(N3CCOc4cc(C(=O)N5CCCCC5)cnc43)ccc2S1(=O)=O] | $^1$H NMR (400 MHz, $CDCl_3$) δ 1.54-1.73 (6H, m), 3.27 (3H, s), 3.36-3.80 (4H, m), 4.00 (2H, t, J = 4.3 Hz), 4.42 (2H, t, J = 4.3 Hz), 7.29 (1H, d, J − 1.8 Hz), 7.86 (1H, d, J = 1.8 Hz), 7.88 (1H, d, J = 8.6 Hz), 7.98 (1H, dd, J = 8.6, 1.8 Hz), 8.02 (1H, d, J = 1.8 Hz). LRMS (ESI$^+$): 443 (M + H$^+$). |
| 1-165 | 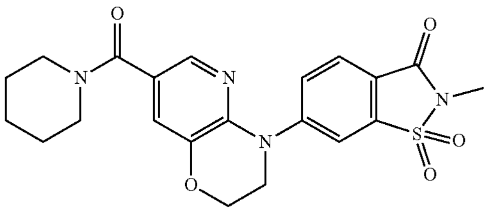 [SMILES: CN1C(=O)c2ccc(N3CCOc4cc(C(=O)N5CCCCC5)cnc43)cc2S1(=O)=O] | $^1$H NMR (400 MHz, $CDCl_3$) δ 1.56-1.74 (6H, m), 3.26 (3H, s), 3.38-3.82 (4H, m), 4.00-4.02 (2H, m), 4.41-1.43 (2H, m), 7.30 (1H, d, J = 1.8 Hz), 7.82 (1H, dd, J = 8.6, 1.8 Hz), 7.89 (1H, d, J = 1.8 Hz), 8.00 (1H, d, J = 8.6 Hz), 8.07 (1H, d, J = 1.8 Hz). LRMS (ESI$^+$): 443 (M + H$^+$). |

TABLE 84

| Example No. | Chemical Structural Formula | Spectrum Data |
|---|---|---|
| 1-166 | 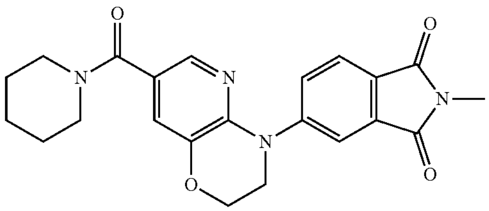 [SMILES: CN1C(=O)c2ccc(N3CCOc4cc(C(=O)N5CCCCC5)cnc43)cc2C1=O] | $^1$H NMR (400 MHz, $CDCl_3$) δ 1.59-1.76 (6H, m), 3.18 (3H, s), 3.35-3.79 (4H, m), 3.99 (2H, t, J = 4.3 Hz), 4.40 (2H, t, J = 4.6 Hz), 7.27 (1H, d, J = 1.8 Hz), 7.71 (1H, dd, J = 8.3, 2.1 Hz), 7.83 (1H, d, J = 7.9 Hz), 7.86 (1H, d, J = 1.8 Hz), 7.92 (1H, d, J = 1.8 Hz). LRMS (ESI$^+$): 407 (M + H$^+$). |
| 1-167 | 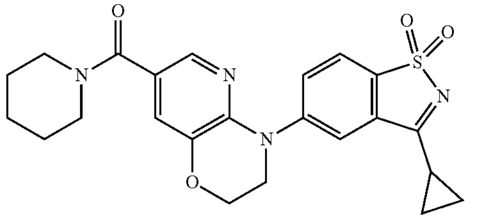 [SMILES: O=C(c1cnc2c(c1)OCCN2c1ccc2c(c1)C(C1CC1)=NS2(=O)=O)N1CCCCC1] | $^1$H NMR (400 MHz, $CDCl_3$) δ 1.39-1.44 (2H, m), 1.58-1.74 (8H, m), 2.22-2.29 (1H, m), 3.40-3.74 (4H, m), 3.99 (2H, t, J = 4.5 Hz), 4.41 (2H, t, J = 4.5 Hz), 7.26 (1H, s), 7.57 (1H, dd, J = 8.5, 1.8 Hz), 7.86 (1H, d, J = 6.1 Hz), 7.88 (1H, s), 8.05 (1H, d, J = 1.8 Hz). LRMS (ESI$^+$): 453 (M + H$^+$). |
| 1-168 | 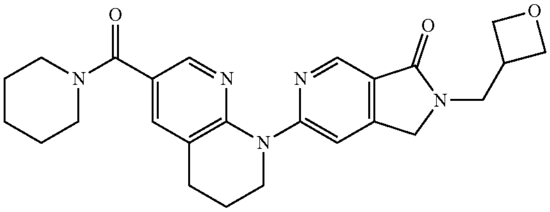 [SMILES: O=C(c1cnc2c(c1)CCCN2c1cc2c(cn1)C(=O)N(CC1COC1)C2)N1CCCCC1] | $^1$H NMR (400 MHz, $CDCl_3$) δ 1.44-1.68 (6H, m), 1.90-2.03 (2H, m), 2.86 (2H, t, J = 6.4 Hz), 3.22-3.37 (1H, m), 3.40-3.59 (4H, m), 3.80 (2H, d, J − 7.3 Hz), 4.07 (2H, t, J − 5.8 Hz), 4.37 (2H, t, J = 6.1 Hz), 4.45 (2H, s), 4.66 (2H, dd, J = 7.9, 6.1 Hz), 7.56 (1H, d, J = 2.4 Hz), 7.96 (1H, s), 8.04 (1H, d, J = 2.4 Hz), 8.65 (1H, d, J = 1.2 Hz). LRMS (ESI$^+$) 448 [M + H]$^+$. |
| 1-169 | 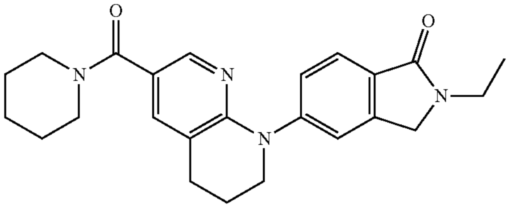 [SMILES: CCN1Cc2cc(N3CCCc4cc(C(=O)N5CCCCC5)cnc43)ccc2C1=O] | $^1$H NMR (400 MHz, $CDCl_3$) δ 1.17 (3H, t, J = 7.3 Hz), 1.41-1.67 (6H, m), 1.95-2.07 (2H, m), 2.87 (2H, t, J − 6.4 Hz), 3.39-3.60 (6H, m), 3.80 (2H, t, J = 5.8 Hz), 4.45 (2H, s), 7.39-7.45 (2H, m), 7.53 (1H, s), 7.63 (1H, d, J = 7.9 Hz), 7.84 (1H, d, J = 2.4 Hz). LRMS (ESI$^+$) 405 [M + H]$^+$. |
| 1-170 | 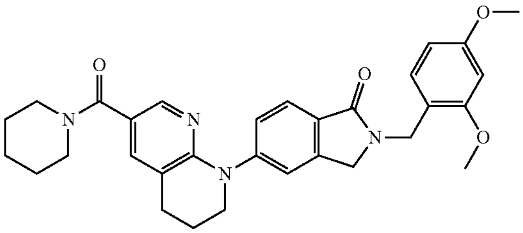 [SMILES: COc1ccc(CN2Cc3cc(N4CCCc5cc(C(=O)N6CCCCC6)cnc54)ccc3C2=O)c(OC)c1] | $^1$H NMR (400 MHz, $CDCl_3$) δ 1.45-1.77 (6H, m), 2.02-2.15 (2H, m), 2.89 (2H, t, J = 6.4 Hz), 3.43-3.67 (4H, m), 3.72-3.89 (8H, m), 4.26 (2H, s), 4.74 (2H, s), 6.41-6.48 (2H, m), 7.18 (1H, d, J = 7.9 Hz), 7.32-7.38 (2H, m), 7.41-7.44 (1H, m), 7.86 (1H, d, J = 8.5 Hz), 7.96 (1H, d, J = 2.4 Hz).. LRMS (ESI$^+$) 527 [M + H]$^+$. |
| 1-171 | 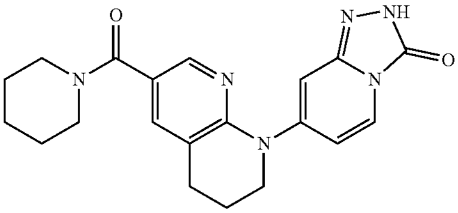 [SMILES: O=C(c1cnc2c(c1)CCCN2c1ccn2c(=O)[nH]nc2c1)N1CCCCC1] | $^1$H NMR (400 MHz, $CDCl_3$) δ 1.46-1.76 (6H, m), 2.08-2.19 (2H, m), 2.88 (2H, t, J = 6.4 Hz), 3.22-3.76 (4H, m), 3.82 (2H, t, J = 5.8 Hz), 6.69 (1H, d, J = 1.2 Hz), 6.78 (1H, dd, J = 7.9, 1.8 Hz), 7.49-7.52 (1H, m), 7.64 (1H, d, J = 8.5 Hz), 8.10 (1H, d, J = 1.8 Hz), 9.05 (1H, br s). LRMS (ESI$^+$) 379 [M + H]$^+$. |

TABLE 85

| Example No. | Chemical Structural Formula | Spectrum Data |
|---|---|---|
| 1-172 | 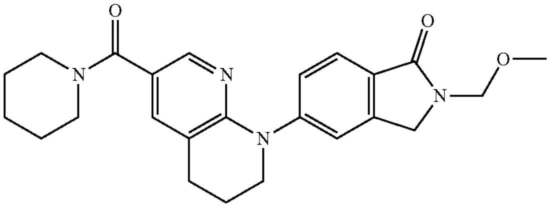 [SMILES: COCN1Cc2cc(N3CCCc4cc(C(=O)N5CCCCC5)cnc43)ccc2C1=O] | $^1$H NMR (400 MHz, $CDCl_3$) δ 1.42-1.68 (6H, m), 1.97-2.07 (2H, m), 2.87 (2H, t, J = 6.4 Hz), 3.21 (3H, s), 3.38-3.55 (4H, m), 3.82 (2H, t, J = 5.8 Hz), 4.52 (2H, s), 4.91 (2H, s), 7.42 (1H, d, J – 1.8 Hz), 7.47 (1H, dd, J – 7.9, 1.8 Hz), 7.58 (1H, d, J = 1.2 Hz), 7.70 (1H, d, J = 8.5 Hz), 7.86 (1H, d, J = 2.4 Hz). LRMS (ESI$^+$) 421 [M + H]$^+$. |
| 1-173 | 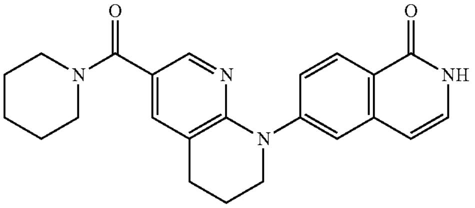 [SMILES: O=C(c1cnc2c(c1)CCCN2c1ccc2c(=O)[nH]ccc2c1)N1CCCCC1] | $^1$H NMR (400 MHz, $CDCl_3$) δ 1.42-1.67 (6H, m), 1.97-2.08 (2H, m), 2.87 (2H, t, J = 6.4 Hz), 3.37-3.59 (4H, m), 3.85 (2H, t, J = 5.4 Hz), 6.48 (1H, d, J = 7.3 Hz), 7.10-7.16 (1H, m), 7.44 (1H, d, J = 1.8 Hz), 7.49 (1H, dd, J = 8.8, 2.1 Hz), 7.54 (1H, d, J = 2.4 Hz), 7.88 (1H, d, J = 2.4 Hz), 8.10 (1H, d, J = 8.5 Hz), 11.11 (1H, d, J = 4.8 Hz). LRMS (ESI$^+$) 389 [M + H]$^+$. |
| 1-174 | 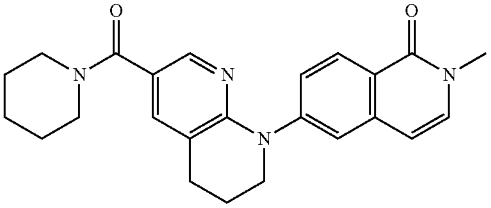 [SMILES: Cn1ccc2cc(N3CCCc4cc(C(=O)N5CCCCC5)cnc43)ccc2c1=O] | $^1$H NMR (400 MHz, $CDCl_3$) δ 1.44-1.67 (6H, m), 1.97-2.08 (2H, m), 2.87 (2H, t, J = 6.4 Hz), 3.39-3.57 (7H, m), 3.85 (2H, t, J = 5.4 Hz), 6.54 (1H, d, J = 7.9 Hz), 7.40-7.46 (2H, m), 7.49-7.56 (2H, m), 7 86-7.90 (1H, m), 8.13 (1H, d, J = 8.5 Hz). I,RMS (ESI$^+$) 403 [M + H]$^+$. |
| 1-175 | 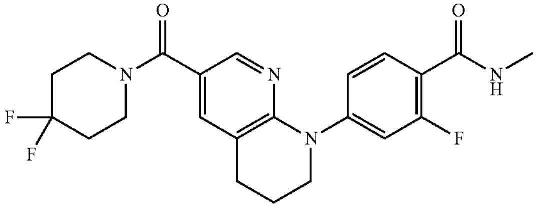 [SMILES: CNC(=O)c1ccc(N2CCCc3cc(C(=O)N4CCC(F)(F)CC4)cnc32)cc1F] | $^1$H NMR (400 MHz, $CDCl_3$) δ 1.91-2.12 (6H, m), 2.78 (3H, d, J = 4.8 Hz), 2.85 (2H, t, J = 6.1 Hz), 3.51-3.68 (4H, m), 3.80 (2H, t, J = 5.8 Hz), 7.26 (1H, dd, J = 8.5, 2.4 Hz), 7.33 (1H, dd, J = 13.0, 2.1 Hz), 7.51 (1H, d, J = 2.4 Hz), 7.61 (1H, t, J = 8.5 Hz), 7.98 (1H, d, J = 2.4 Hz), 8.08-8.18 (1H, m). LRMS (ESI$^+$) 433 [M + H]$^+$. |
| 1-176 | 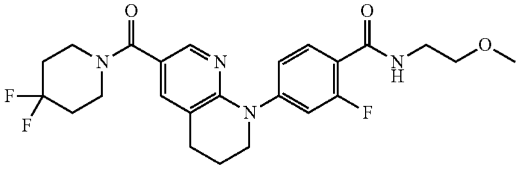 [SMILES: COCCNC(=O)c1ccc(N2CCCc3cc(C(=O)N4CCC(F)(F)CC4)cnc32)cc1F] | $^1$H NMR (400 MHz, $CDCl_3$) δ 1.93-2.12 (6H, m), 2.85 (2H, t, J = 6.4 Hz), 3.28 (3H, s), 3.38-3.50 (4H, m), 3.52-3.69 (4H, m), 3.80 (2H, t, J = 5.8 Hz), 7.27 (1H, dd, J = 8.5, 2.4 Hz), 7.33 (1H, dd, J = 13.3, 1.8 Hz), 7.51 (1H, d, J = 2.4 Hz), 7.61 (1H, t, J = 8.5 Hz), 7.98 (1H, d, J = 2.4 Hz), 8.18 (1H, t, J = 4.2 Hz). LRMS (ESI$^+$) 477 [M + H]$^+$. |
| 1-177 | 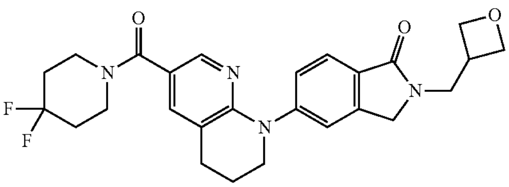 [SMILES: O=C(c1cnc2c(c1)CCCN2c1ccc2c(c1)CN(CC1COC1)C2=O)N1CCC(F)(F)CC1] | $^1$H NMR (400 MHz, $CDCl_3$) δ 1.90-2.13 (6H, m), 2.87 (2H, t, J = 6.4 Hz), 3.27-3.35 (1H, m), 3.52-3.68 (4H, m), 3.76-3.87 (4H, m), 4.35-4.45 (4H, m), 4.64-4.71 (2H, m), 7.43 (1H, dd, J = 7.9, 1.8 Hz), 7.48 (1H, d, J = 1.8 Hz), 7.53 (1H, d, J – 1.2 Hz), 7.65 (1H, d, J – 8.5 Hz), 7.91 (1H, d, J – 2.4 Hz). LRMS (ESI$^+$) 483 [M + H]$^+$. |

TABLE 86

| Example No. | Chemical Structural Formula | Spectrum Data |
|---|---|---|
| 1-178 | 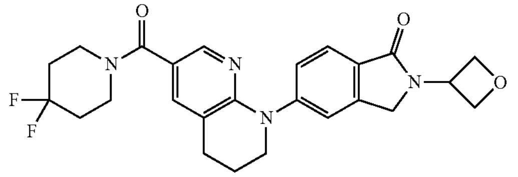 [SMILES: O=C(c1cnc2c(c1)CCCN2c1ccc2c(c1)CN(C1COC1)C2=O)N1CCC(F)(F)CC1] | $^1$H NMR (400 MHz, $CDCl_3$) δ 1.94-2.11 (6H, m), 2.88 (2H, t, J = 6.4 Hz), 3.52-3.66 (4H, m), 3.82 (2H, t, J = 5.4 Hz), 4.75-4.90 (6H, m), 5.36-5.49 (1H, m), 7.45 (1H, dd, J = 8.2, 2.1 Hz), 7.49 (1H, d, J – 2.4 Hz), 7.61 (1H, s), 7.66 (1H, d, J = 8.5 Hz), 7.93 (1H, d, J = 1.8 Hz). LRMS (ESI$^+$) 469 [M + H]$^+$.. |
| 1-179 | 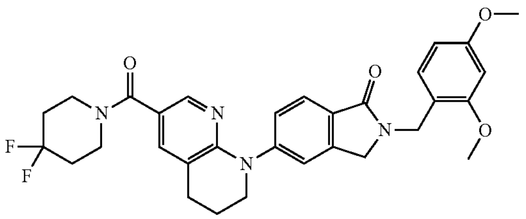 [SMILES: COc1ccc(CN2Cc3cc(N4CCCc5cc(C(=O)N6CCC(F)(F)CC6)cnc54)ccc3C2=O)c(OC)c1] | $^1$H NMR (400 MHz, $CDCl_3$) δ 1.83-2.18 (6H, m), 2.90 (2H, t, J = 6.4 Hz), 3.61-3.91 (12H, m), 4.27 (2H, s), 4.74 (2H, s), 6.39-6.49 (2H, m), 7.16-7.21 (1H, m), 7.32-7.37 (2H, m), 7.43-7.47 (in, m), 7.86 (1H, d, J – 8.5 Hz), 7.95-7.99 (1H, m). .LRMS (ESI$^+$) 563 [M + H]$^+$. |
| 1-180 | 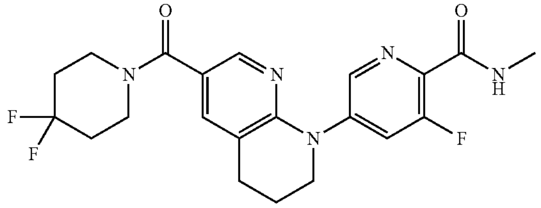 [SMILES: CNC(=O)c1ncc(N2CCCc3cc(C(=O)N4CCC(F)(F)CC4)cnc32)cc1F] | $^1$H NMR (400 MHz, $CDCl_3$) δ 1.93-2.12 (6H, m), 2.78 (3H, d, J = 4.8 Hz), 2.88 (2H, t, J = 6.4 Hz), 3.52-3.71 (4H, m), 3.87 (2H, t, J – 5.4 Hz), 7.57 (1H, d, J – 2.4 Hz), 7.86 (1H, dd, J = 13.0, 2.1 Hz), 8.03 (1H, d, J = 1.8 Hz), 8.51-8.58 (1H, m), 8.61 (1H, t, J = 1.5 Hz). .LRMS (ESI$^+$) 434 [M + H]$^+$. |
| 1-181 | 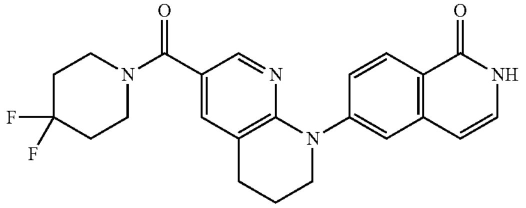 [SMILES: O=C(c1cnc2c(c1)CCCN2c1ccc2c(=O)[nH]ccc2c1)N1CCC(F)(F)CC1] | $^1$H NMR (400 MHz, $CDCl_3$) δ 1.94-2.12 (6H, m), 2.88 (2H, t, J = 6.4 Hz), 3.52-3.67 (4H, m), 3.86 (2H, t, J = 5.4 Hz), 6.48 (1H, d, J – 7.3 Hz), 7.11-7.17 (1H, m), 7.46-7.52 (2H, m), 7.55 (1H, d, J = 1.8 Hz), 7.96 (1H, d, J = 2.4 Hz), 8.10 (1H, d, J = 9.1 Hz), 11.12 (1H, d, J = 4.8 Hz). .LRMS (ESI$^+$) 425 [M + H]$^+$. |
| 1-182 | 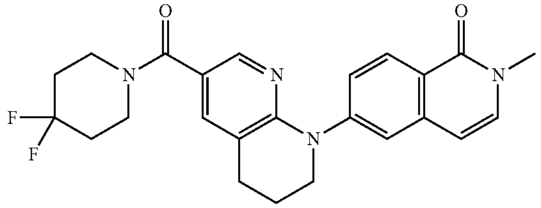 [SMILES: Cn1ccc2cc(N3CCCc4cc(C(=O)N5CCC(F)(F)CC5)cnc43)ccc2c1=O] | $^1$H NMR (400 MHz, $CDCl_3$) δ 1.95-2.11 (6H, m), 2.88 (2H, t, J – 6.4 Hz), 3.50 (3H, s), 3.54-3.69 (4H, m), 3.86 (2H, t, J = 5.4 Hz), 6.54 (1H, d, J = 7.3 Hz), 7.44 (1H, d, J = 7.3 Hz), 7.48-7.56 (3H, m), 7.96 (1H, d, J = 1.8 Hz), 8.14 (1H, d, J = 9.1 Hz). .LRMS (ESI$^+$) 439 [M + H]$^+$. |
| 1-183 | 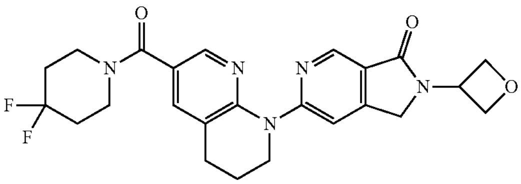 [SMILES: O=C(c1cnc2c(c1)CCCN2c1cc2c(cn1)C(=O)N(C1COC1)C2)N1CCC(F)(F)CC1] | $^1$H NMR (400 MHz, $CDCl_3$) δ 1.92-2.16 (6H, m), 2.88 (2H, t, J – 6.4 Hz), 3.49-3.76 (4H, m), 4.09 (2H, t, J – 5.4 Hz), 4.74-4.90 (6H, m), 5.34-5.45 (1H, m), 7.63-7.67 (1H, m), 8.03-8.06 (1H, m), 8.14 (1H, d, J = 2.4 Hz), 8.68 (1H, d, J = 1.2 Hz). LRMS (ESI$^+$) 470 [M + H]$^+$. |

TABLE 87

| Example No. | Chemical Structural Formula | Spectrum Data |
|---|---|---|
| 1-184 | 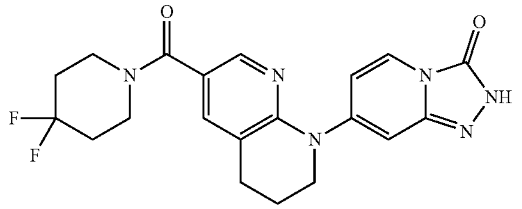 [SMILES: O=C(c1cnc2c(c1)CCCN2c1ccn2c(=O)[nH]nc2c1)N1CCC(F)(F)CC1] | $^1H$ NMR (400 MHz, $CDCl_3$) δ 1.92-2.09 (4H, m), 2.10-2.19 (2H, m), 2.90 (2H, t, J = 6.7 Hz), 3.67-3.88 (6H, m), 6.70-6.78 (2H, m), 7.52 (1H, d, J = 1.8 Hz), 7.65 (1H, d, J = 7.3 Hz), 8.11 (1H, d, J = 2.4 IIz), 8.98 (1H, br s). .LRMS ($ESI^+$) 415 $[M + H]^+$. |
| 1-185 | 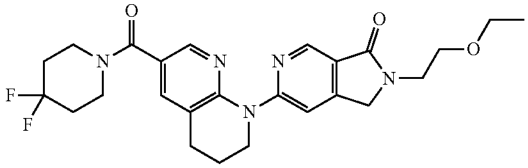 [SMILES: CCOCCN1Cc2cc(N3CCCc4cc(C(=O)N5CCC(F)(F)CC5)cnc43)ncc2C1=O] | $^1H$ NMR (400 MHz, $CDCl_3$) δ 1.10 (3H, t, J – 7.0 Hz), 1.90-2.13 (6H, m), 2.87 (2H, t, J = 6.4 Hz), 3.45 (2H, q, J = 6.9 Hz), 3.53-3.69 (8H, m), 4.08 (2H, t, J = 5.8 Hz), 4.54 (2H, s), 7.63 (1H, d, J = 1.8 Hz), 7.98 (1H, s), 8.13 (1H, d, J = 2.4 Hz), 8.66 (1H, s). LRMS ($ESI^+$) 486 $[M + H]^+$. |
| 1-186 | 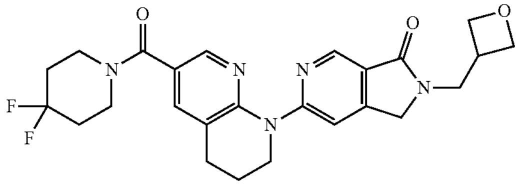 [SMILES: O=C(c1cnc2c(c1)CCCN2c1cc2c(cn1)C(=O)N(CC1COC1)C2)N1CCC(F)(F)CC1] | $^1H$ NMR (400 MHz, $CDCl_3$) δ 1.93-2.14 (6H, m), 2.91 (2H, t, J = 6.4 Hz), 3.29-3.44 (1H, m), 3.66-3.87 (4H, m), 3.93 (2H, d, J = 7.3 Hz), 4.19 (2H, t, J = 5.8 Hz), 4.38 (2H, s), 4.55 (2H, t, J = 6.1 Hz), 4.80-4.87 (2H, m), 7.51-7.55 (1H, m), 7.91-7.95 (1H, m), 8.12 (1H, d, J = 2.4 Hz), 8.83-8.87 (1H, m). .LRMS ($ESI^+$) 484 $[M + H]^+$. |
| 1-187 | 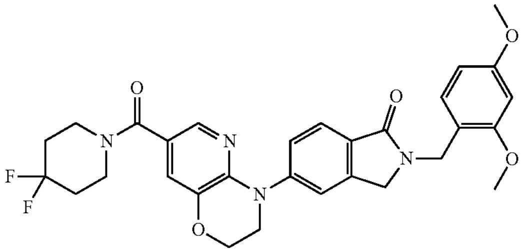 [SMILES: COc1ccc(CN2Cc3cc(N4CCOc5cc(C(=O)N6CCC(F)(F)CC6)cnc54)ccc3C2=O)c(OC)c1] | $^1H$ NMR (400 MHz, $CDCl_3$) δ 1.92-2.09 (4H, m), 3.66-3.77 (4H, m), 3.80 (3H, s), 3.84 (3H, s), 3.95 (2H, t, J = 4.3 Hz), 4.28 (2H, s), 4.37 (2H, t, J = 4.3 Hz), 4.75 (2H, s), 6.44 (1H, dd, J = 7.9, 1.8 Hz), 6.47 (1H, d, J = 1.8 Hz), 7.19 (1H, d, J = 7.9 Hz), 7.22 (1H, d, J = 1.8 Hz), 7.37 (1H, dd, J = 7.9, 1.8 Hz), 7.47 (1H, d, J = 1.2 Hz), 7.81 (1H, d, J = 2.4 Hz), 7.88 (1H, d, J = 7.9 Hz). LRMS ($ESI^+$) 565 $[M + H]^+$. |
| 1-188 | 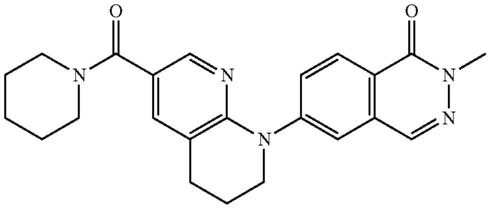 | $^1H$ NMR (400 MHz, DMSO-$d_6$) δ 1.42-1.69 (6H, m), 1.98-2.10 (2H, m), 2.89 (2H, t, J = 6.4 Hz), 3.36-3.57 (4H, m), 3.71 (3H, s), 3.90 (2H, t, J = 5.4 Hz), 7.47-7.51 (1H, m), 7.84 (1H, d, J – 1.8 Hz), 7.88-7.94 (2H, m), 8.16 (1H, d, J – 8.5 Hz), 8.33 (1H, s). LRMS ($ESI^+$) 404 $[M + H]^+$. |
| 1-189 | 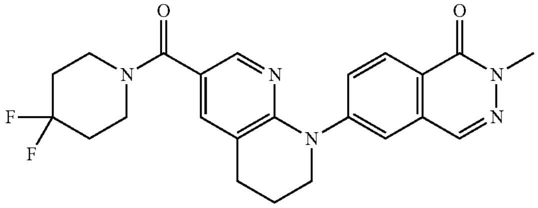 [SMILES: Cn1ncc2cc(N3CCCc4cc(C(=O)N5CCC(F)(F)CC5)cnc43)ccc2c1=O] | $^1H$ NMR (400 MHz, DMSO-$d_6$) δ 1.93-2.15 (6H, m), 2.90 (2H, t, J = 6.1 Hz), 3.51-3.66 (4H, m), 3.71 (3H, s), 3.91 (2H, t, J = 5.1 Hz), 7.53-7.59 (1H, m), 7.82-7.86 (1H, m), 7.88-7.94 (1H, m), 7.98-8.03 (1H, m), 8.17 (1H, d, J = 8.5 Hz), 8.33 (1H, s). LRMS ($ESI^+$) 440 $[M + H]^+$. |

TABLE 88

| Example No. | Chemical Structural Formula | Spectrum Data |
|---|---|---|
| 1-190 | 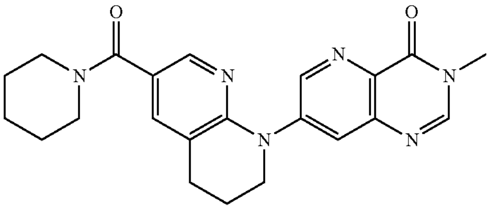 | $^1$H NMR (400 MHz, DMSO-$d_6$) δ 1.45-1.67 (6H, m), 2.01-2.11 (2H, m), 2.89 (2H, t, J = 6.4 Hz), 3.39-3.57 (7H, m), 3.93 (2H, t, J = 5.4 Hz), 7.49-7.53 (1H, m), 7.89 (1H, d, J = 2.4 Hz), 7.95 (1H, d, J = 2.4 Hz), 8.42 (1H, s), 8.95 (1H, d, J = 2.4 Hz). LRMS (ESI$^+$) 405 [M + H]$^+$. |
| 1-191 | 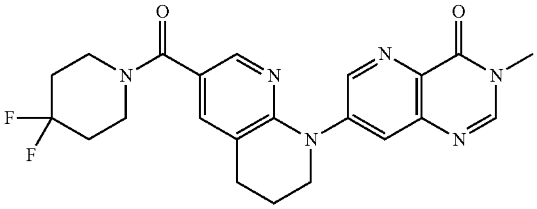 | $^1$H NMR (400 MHz, DMSO-$d_6$) δ 1.97-2.12 (6H, m), 2.90 (2H, t, J = 6.4 Hz), 3.52 (3H, s), 3.56-3.68 (4H, m), 3.94 (2H, t, J = 5.4 Hz), 7.58 (1H, d, J = 1.8 Hz), 7.91 (1H, d, J = 2.4 Hz), 8.03 (1H, d, J = 1.8 Hz), 8.43 (1H, s), 8.95 (1H, d, J = 2.4 Hz). LRMS (ESI$^+$) 441 [M + H]$^+$. |
| 1-192 | 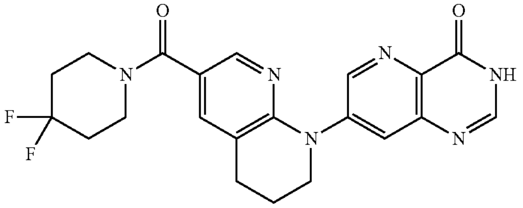 | $^1$H NMR (400 MHz, DMSO-$d_6$) δ 1.95-2.15 (6H, m), 2.92 (2H, t, J = 6.4 Hz), 3.56-3.67 (4H, m), 3.94 (2H, t, J = 5.4 Hz), 7.58-7.63 (1H, m), 8.03 (1H, d, J – 1.8 Hz), 8.19 (1H, d, J = 2.4 Hz), 8.32 (1H, s), 9.20 (1H, d, J = 2.4 Hz), 12.79 (1H, s). LRMS (ESI$^+$) 427 [M + H]$^+$. |
| 1-193 | 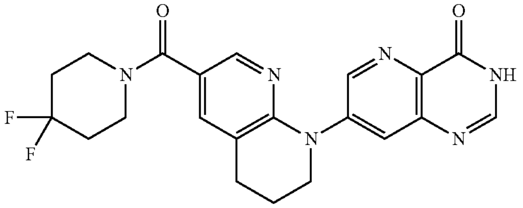 | $^1$H NMR (400 MHz, DMSO-$d_6$) δ 1.95-2.13 (6H, m), 2.90 (2H, t, J = 6.4 Hz), 3.49-3.72 (4H, m), 3.93 (2H, t, J = 5.8 Hz), 7.56-7.60 (1H, m), 7.89 (1H, d, J – 2.4 Hz), 8.02 (1H, d, J = 2.4 Hz), 8.11 (1H, s), 8.91 (1H, d, J = 2.4 Hz), 12.37 (1H, br s). LRMS (ESI$^+$) 427 [M + H]$^+$. |
| 1-194 | 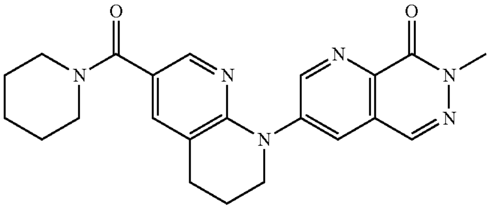 | $^1$H NMR (400 MHz, DMSO-$d_6$) δ 1.44-1.68 (6H, m), 2.02-2.13 (2H, m), 2.91 (2H, t, J = 6.4 Hz), 3.39-3.58 (4H, m), 3.74 (3H, s), 3.94 (2H, t, J = 5.8 Hz), 7.51-7.56 (1H, m), 7.95 (1H, d, J = 1.8 Hz), 8.19 (1H, d, J = 2.4 Hz), 8.36 (1H, s), 9.22 (1H, d, J = 2.4 Hz). LRMS (ESI$^+$) 405 [M + H]$^+$. |
| 1-195 | 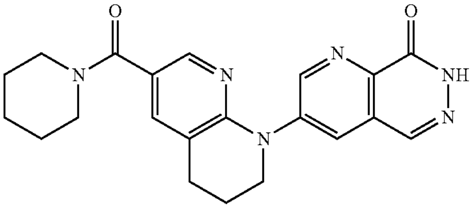 | $^1$H NMR (400 MHz, DMSO-$d_6$) δ 1.43-1.67 (6H, m), 2.03-2.12 (2H, m), 2.91 (2H, t, J – 7.0 Hz), 3.38-3.55 (4H, m), 3.94 (2H, t, J = 5.8 Hz), 7.51-7.55 (1H, m), 7.93-7.97 (1H, m), 8.18 (1H, d, J = 2.4 Hz), 8.32 (1H, s), 9.20 (1H, d, J = 2.4 Hz), 12.78 (1H, s). LRMS (ESI$^+$) 391 [M + H]$^+$. |
| 1-196 | 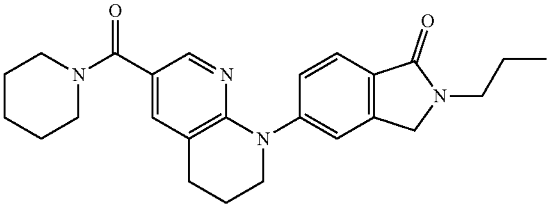 [SMILES: CCCN1Cc2cc(N3CCCc4cc(C(=O)N5CCCCC5)cnc43)ccc2C1=O] | $^1$H NMR (400 MHz, DMSO-$d_6$) δ 0.87 (3H, t, J = 7.6 Hz), 1.41-1.69 (8H, m), 1.96-2.07 (2H, m), 2.87 (2H, t, J = 6.4 Hz), 3.36-3.57 (6H, m), 3.80 (2H, t, J = 5.4 Hz), 4.44 (2H, s), 7.38-7.45 (2H, m), 7.51-7.55 (1H, m), 7.63 (1H, d, J = 7.9 Hz), 7.84 (1H, d, J = 2.4 Hz). LRMS (ESI$^+$) 419 [M + H]$^+$. |

TABLE 89

| Example No. | Chemical Structural Formula | Spectrum Data |
|---|---|---|
| 1-197 | 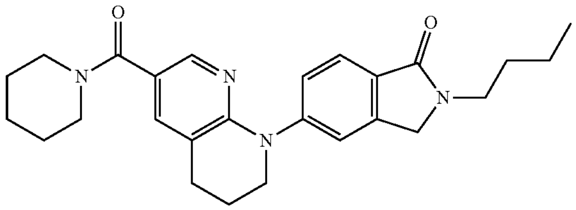 | $^1$H NMR (400 MHz, DMSO-$d_6$) δ 0.91 (3H, t, J = 7.6 Hz), 1.23-1.36 (2H, m), 1.43-1.66 (8H, m), 1.96-2.08 (2H, m), 2.87 (2H, t, J = 6.4 Hz), 3.39-3.55 (6H, m), 3.80 (2H, t, J = 5.4 Hz), 4.44 (2H, s), 7.39-7.44 (2H, m), 7.53 (1H, d, J = 1.2 Hz), 7.63 (1H, d, J = 7.9 Hz), 7.84 (1H, d, J = 1.8 Hz). LRMS (ESI$^+$) 433 [M + H]$^+$. |
| 1-198 | 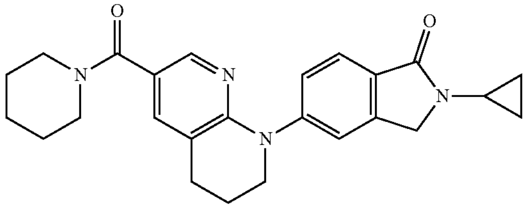 [SMILES: O=C(c1cnc2c(c1)CCCN2c1ccc2c(c1)CN(C1CC1)C2=O)N1CCCCC1] | $^1$H NMR (400 MHz, DMSO-$d_6$) δ 0.76-0.86 (4H, m), 1.41-1.68 (6H, m), 1.96-2.06 (2H, m), 2.80-2.97 (3H, m), 3.36-3.57 (4H, m), 3.79 (2H, t, J = 5.4 Hz), 4.37 (2H, s), 7.38-7.44 (2H, m), 7.47-7.51 (1H, m), 7.61 (1H, d, J – 7.9 Hz), 7.83 (1H, d, J = 2.4 Hz). LRMS (ESI$^+$) 417 [M + H]$^+$. |
| 1-199 | 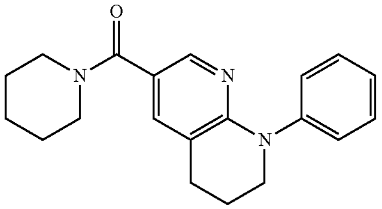 [SMILES: O=C(c1cnc2c(c1)CCCN2c1ccccc1)N1CCCCC1] | $^1$H NMR (400 MHz, DMSO-$d_6$) δ 1.42-1.67 (6H, m), 1.94-2.06 (2H, m), 2.85 (2H, t, J = 6.1 Hz), 3.38-3.53 (4H, m), 3.74 (2H, t, J = 5.4 Hz), 7.13-7.20 (1H, m), 7.28-7.41 (5H, m), 7.80 (1H, d, J = 2.4 Hz). LRMS (ESI$^+$) 322 [M + H]$^+$. |
| 1-200 | 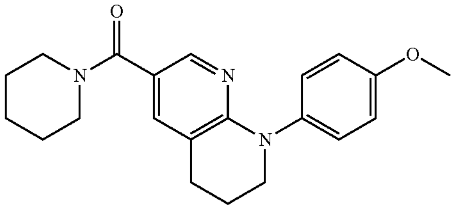 [SMILES: COc1ccc(N2CCCc3cc(C(=O)N4CCCCC4)cnc32)cc1] | $^1$H NMR (400 MHz, DMSO-$d_6$) δ 1.41-1.65 (6H, m), 1.93-2.04 (2H, m), 2.83 (2H, t, J = 6.4 Hz), 3.38-3.50 (4H, m), 3.68 (2H, t, J = 5.4 Hz), 3.76 (3H, s), 6.90-6.96 (2H, m), 7.17-7.23 (2H, m), 7.30-7.33 (1H, m), 7.77 (1H, d, J = 2.4 Hz). LRMS (ESI$^+$) 352 [M + H]$^+$. |
| 1-201 | 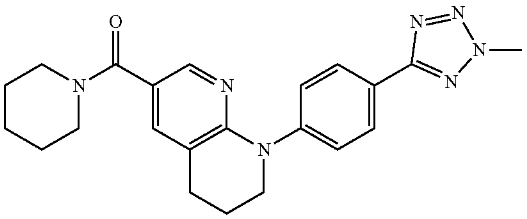 [SMILES: Cn1nnc(-c2ccc(N3CCCc4cc(C(=O)N5CCCCC5)cnc43)cc2)n1] | $^1$H NMR (400 MHz, DMSO-$d_6$) δ 1.43-1.69 (6H, m), 1.97-2.08 (2H, m), 2.87 (2H, t, J = 6.4 Hz), 3.39-3.56 (4H, m), 3.82 (2H, t, J = 5.4 Hz), 4.43 (3H, s), 7.39-7.44 (1H, m), 7.50-7.56 (2H, m), 7.87 (1H, d, J = 2.4 Hz), 7.99-8.06 (2H, m). LRMS (ESI$^+$) 404 [M + H]$^+$. |
| 1-202 | 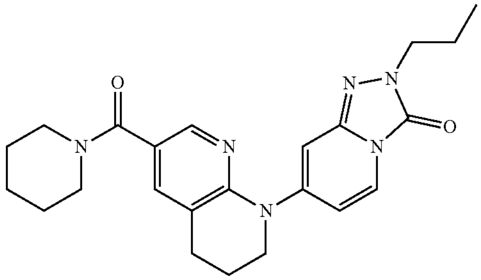 [SMILES: CCCn1nc2cc(N3CCCc4cc(C(=O)N5CCCCC5)cnc43)ccn2c1=O] | $^1$H NMR (400 MHz, DMSO-$d_6$) δ 0.86 (3H, t, J = 7.6 Hz), 1.41-1.67 (6H, m), 1.69-1.81 (2H, m), 1.95-2.06 (2H, m), 2.83 (2H, t, J = 6.4 Hz), 3.36-3.65 (4H, m), 3.75-3.86 (4H, m), 6.77 (1H, dd, J = 7.6, 2.1 Hz), 6.91 (1H, d, J = 1.2 Hz), 7.49 (1H, d, J = 1.8 Hz), 7.70 (1H, d, J = 6.7 Hz), 7.99 (1H, d, J = 2.4 Hz). LRMS (ESI$^+$) 421 [M + H]$^+$. |

TABLE 89-continued

| Example No. | Chemical Structural Formula | Spectrum Data |
|---|---|---|
| 1-203 | 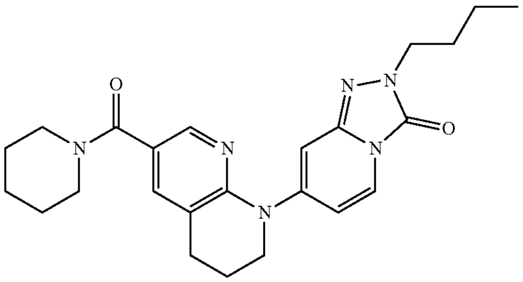 [SMILES: CCCCn1nc2cc(N3CCCc4cc(C(=O)N5CCCCC5)cnc43)ccn2c1=O] | $^1$H NMR (400 MHz, DMSO-$d_6$) δ 0.90 (3H, t, J = 7.6 Hz), 1.23-1.35 (2H, m), 1.40-1.78 (8H, m), 1.95-2.06 (2H, m), 2.83 (2H, t, J = 6.4 Hz), 3.36-3.62 (4H, m), 3.75-3.91 (4H, m), 6.77 (1H, dd, J = 7.9, 1.8 Hz), 6.91 (1H, d. J = 1.2 Hz), 7.47-7.51 (1H, m), 7.69 (1H, d, J = 7.3 Hz), 7.99 (1H, d, J = 2.4 Hz).<br>LRMS (ESI$^+$) 435 [M + H]$^+$. |

TABLE 90

| Example No. | Chemical Structural Formula | Spectrum Data |
|---|---|---|
| 1-204 | 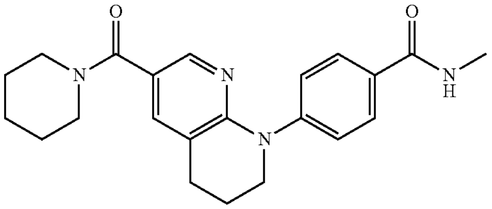 [SMILES: CNC(=O)c1ccc(N2CCCc3cc(C(=O)N4CCCCC4)cnc32)cc1] | $^1$H NMR (400 MHz, DMSO-$d_6$) δ 1.42-1.68 (6H, m), 1.94-2.06 (2H, m), 2.78 (3H, d, J = 4.2 Hz), 2.85 (2H, t, J = 6.4 Hz), 3.36-3.59 (4H, m), 3.79 (2H, t, J = 5.8 Hz), 7.37-7.45 (3H, m), 7.77-7.83 (2H, m), 7.85 (1H, d, J – 2.4 Hz), 8.31-8.40 (1H, m).<br>LRMS (ESI$^+$) 379 [M + H]$^+$. |
| 1-205 | 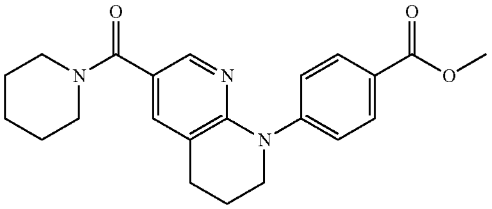 [SMILES: COC(=O)c1ccc(N2CCCc3cc(C(=O)N4CCCCC4)cnc32)cc1] | $^1$H NMR (400 MHz, $CDCl_3$) δ 1.48-1.75 (6H, m), 2.06-2.14 (2H, m), 2.89 (2H, t, J = 6.4 Hz), 3.39-3.73 (4H, m), 3.84 (2H, t, J = 5.8 Hz), 3.90 (3H, s), 7.38-7.48 (3H, m), 7.99-8.08 (3H, m).<br>LRMS (ESI$^+$) 380 [M + H]$^+$. |
| 1-206 | 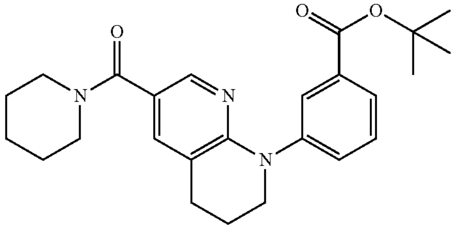 [SMILES: CC(C)(C)OC(=O)c1cccc(N2CCCc3cc(C(=O)N4CCCCC4)cnc32)c1] | $^1$H NMR (400 MHz, $CDCl_3$) δ 1.51-1.71 (15H, m), 2.06-2.15 (2H, m), 2.89 (2H, t, J = 6.4 Hz), 3.42-3.70 (4H, m), 3.81 (2H, t, J = 5.4 Hz), 7.40-7.45 (2H, m), 7.48-7.52 (1H, m), 7.79-7.83 (1H, m), 7.91 (1H, t, J = 1.8 Hz), 7.97 (1H, d, J = 2.4 Hz).<br>LRMS (ESI$^+$) 422 [M + H]$^+$. |
| 1-207 | 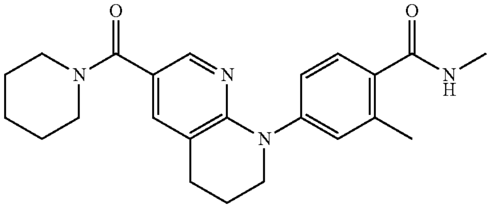 [SMILES: CNC(=O)c1ccc(N2CCCc3cc(C(=O)N4CCCCC4)cnc32)cc1C] | $^1$H NMR (400 MHz, DMSO-$d_6$) δ 1.42-1.65 (6H, m), 1.93-2.05 (2H, m), 2.32 (3H, s), 2.74 (3H, d, J = 4.2 Hz), 2.84 (2H, t, J = 6.1), 3.37-3.55 (4H, m), 3.73 (2H, t, J = 5.4 Hz), 7.13-7.19 (2H, m), 7.31 (1H, d, J = 8.5 Hz), 7.36 (1H, d, J = 1.8 Hz), 7.82 (1H, d, J = 1.8 Hz), 8.11-8.20 (1H, m).<br>LRMS (ESI$^+$) 393 [M + H]$^+$. |

TABLE 90-continued

| Example No. | Chemical Structural Formula | Spectrum Data |
|---|---|---|
| 1-208 | 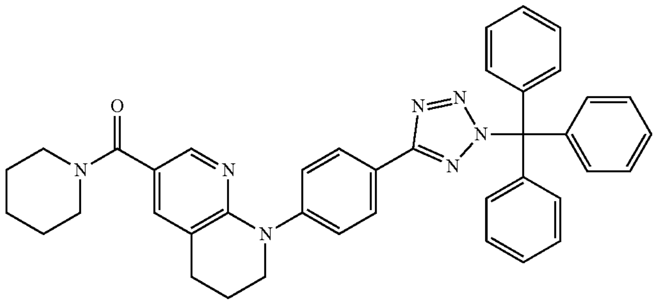 [SMILES: O=C(c1cnc2c(c1)CCCN2c1ccc(-c2nnn(C(c3ccccc3)(c3ccccc3)c3ccccc3)n2)cc1)N1CCCCC1] | $^1$H NMR (400 MHz, DMSO-$d_6$) δ 1.43-1.66 (6H, m), 1.96-2.07 (2H, m), 2.86 (2H, t, J = 6.4 Hz), 3.39-3.52 (4H, m), 3.81 (2H, t, J = 5.4 Hz), 7.07-7.14 (6H, m), 7.39-7.47 (10H, m), 7.49-7.54 (2H, m), 7.85 (1H, d, J = 1.8 Hz), 7.96-8.01 (2H, m). LRMS ESI$^+$) 632 [M + H]$^+$. |
| 1-209 | 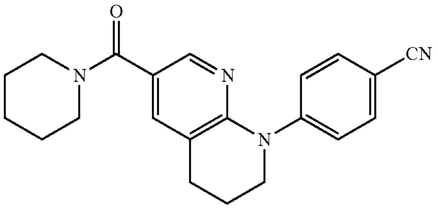 [SMILES: N#Cc1ccc(N2CCCc3cc(C(=O)N4CCCCC4)cnc32)cc1] | $^1$H NMR (400 MHz, DMSO-$d_6$) δ 1.42-1.67 (6H, m), 1.94-2.06 (2H, m), 2.85 (2H, t, J - 6.4 Hz), 3.38-3.57 (4H, m), 3.82 (2H, t, J = 5.4 Hz), 7.45-7.48 (1H, m), 7.54-7.58 (2H, m), 7.74-7.79 (2H, m), 7.90-7.93 (1H, m). LRMS (ESI$^+$) 347 [M + H]$^+$. |
| 1-210 | 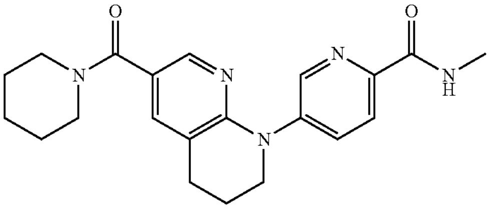 | $^1$H NMR (400 MHz, DMSO-$d_6$) δ 1.43-1.66 (6H, m), 1.98-2.08 (2H, m), 2.82 (3H, d, J = 4.8 Hz), 2.88 (2H, t, J = 6.1 Hz), 3.38-3.54 (4H, m), 3.86 (2H, t, J = 5.4 Hz), 7.43-7.48 (1H, m), 7.86-7.93 (2H, m), 8.00 (1H, d, J = 8.5 Hz), 8.62-8.73 (2H, m). LRMS (ESI$^+$) 380 [M + H]$^+$. |

TABLE 91

| Example No. | Chemical Structural Formula | Spectrum Data |
|---|---|---|
| 1-211 | 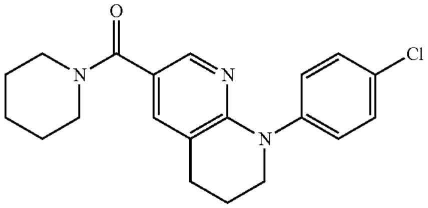 [SMILES: O=C(c1cnc2c(c1)CCCN2c1ccc(Cl)cc1)N1CCCCC1] | $^1$H NMR (400 MHz, DMSO-$d_6$) δ 1.41-1.67 (6H, m), 1.94-2.06 (2H, m), 2.84 (2H, t, J = 6.4 Hz), 3.36-3.55 (4H, m), 3.74 (2H, t, J = 5.8 Hz), 7.31-7.45 (5H, m), 7.82 (1H, d, J = 1.8 Hz). LRMS (ESI$^+$) 356 [M + H]$^+$. |
| 1-212 | 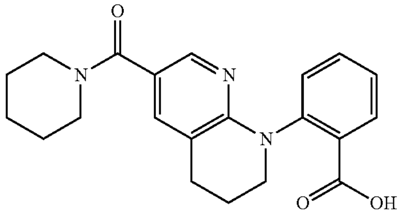 [SMILES: O=C(O)c1ccccc1N1CCCc2cc(C(=O)N3CCCCC3)cnc21] | $^1$H NMR (400 MHz, DMSO-$d_6$) δ 1.38-1.67 (6H, m), 1.91-2.11 (2H, m), 2.73-2.88 (2H, m), 3.38-3.50 (4H, m), 3.54-3.88 (2H, m), 7.30 (1H, d, J = 2.4 Hz), 7.32-7.38 (2H, m), 7.58-7.63 (1H, m), 7.69 (1H, d, J = 2.4 Hz), 7.79 (1H, d, J = 7.3 Hz), 12.58 (1H, br s). LRMS (ESI$^+$) 366 [M + H]$^+$. |
| 1-213 | 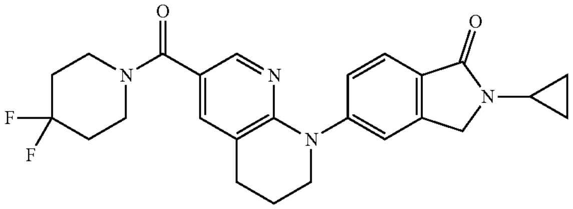 [SMILES: O=C(c1cnc2c(c1)CCCN2c1ccc2c(c1)CN(C1CC1)C2=O)N1CCC(F)(F)CC1] | $^1$H NMR (400 MHz, DMSO-$d_6$) δ 0.75-0.89 (4H, m), 1.93-2.11 (6H, m), 2.82-2.98 (3H, m), 3.53-3.66 (4H, m), 3.80 (2H, t, J = 5.8 Hz), 4.37 (2H, s), 7.41 (1H, dd, J = 8.5, 1.8 Hz), 7.45-7.51 (2H, m), 7.61 (1H, d, J = 7.9 Hz), 7.91 (1H, d, J = 1.8 Hz). LRMS (ESI$^+$) 453 [M + H]$^+$. |

TABLE 91-continued

| Example No. | Chemical Structural Formula | Spectrum Data |
|---|---|---|
| 1-214 | 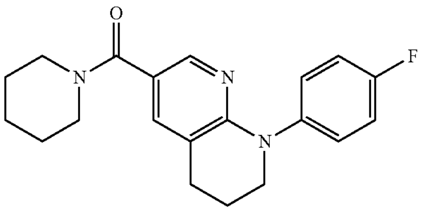 [SMILES: O=C(c1cnc2c(c1)CCCN2c1ccc(F)cc1)N1CCCCC1] | $^1$H NMR (400 MHz, DMSO-d$_6$) δ 1.41-1.69 (6H, m), 1.93-2.07 (2H, m), 2.84 (2H, t, J = 6.1 Hz), 3.39-3.55 (4H, m), 3.72 (2H, t, J = 5.4 Hz), 7.15-7.24 (2H, m), 7.30-7.38 (3H, m), 7.80 (1H, d, J = 2.4 Hz). LRMS (ESI$^+$) 340 [M + H]$^+$. |
| 1-215 | 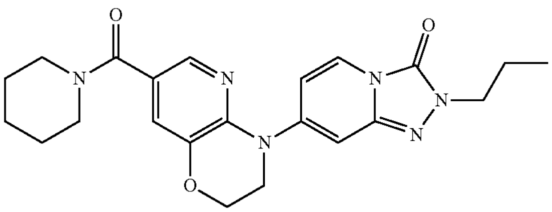 [SMILES: CCCn1nc2cc(N3CCOc4cc(C(=O)N5CCCCC5)cnc43)ccn2c1=O] | $^1$H NMR (400 MHz, DMSO-d$_6$) δ 0.85 (3H, t, J = 7.3 Hz), 1.41-1.64 (6H, m), 1.67-1.80 (2H, m), 3.28-3.58 (4H, m), 3.80 (2H, t, J = 6.7 Hz), 3.93 (2H, t , J = 4.6 Hz), 4.36 (2H, t, J = 4.6 Hz), 6.90 (1H, d, J = 1.2 Hz), 6.98 (1H, dd, J = 7.6, 2.1 Hz), 7.21 (1H, d, J = 1.8 Hz), 7.73-7.79 (2H, m). LRMS (ESI$^+$) 423 [M + H]$^+$. |
| 1-216 | 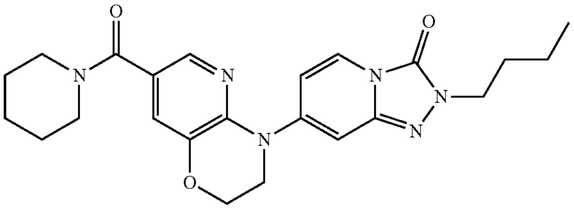 [SMILES: CCCCn1nc2cc(N3CCOc4cc(C(=O)N5CCCCC5)cnc43)ccn2c1=O] | $^1$H NMR (400 MHz, DMSO-d$_6$) δ 0.87 (3H, t, J = 7.3 Hz), 1.19-1.32 (2H, m), 1.40-1.62 (6H, m), 1.63-1.74 (2H, m), 3.33-3.57 (4H, m), 3.83 (2H, t, J = 7.0 Hz), 3.92 (2H, t, J = 4.5 Hz), 4.35 (2H, t, J = 4.2 Hz), 6.89 (1H, d, J = 1.8 Hz), 6.96 (1H, dd, J = 7.6, 2.1 Hz), 7.19 (1H, d, J = 1.8 Hz), 7.71-7.78 (2H, m). LRMS (ESI$^+$) 437 [M + H]$^+$. |

TABLE 92

| Example No. | Chemical Structural Formula | Spectrum Data |
|---|---|---|
| 1-217 | 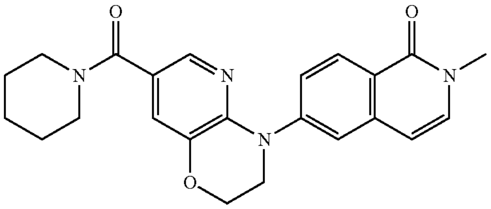 [SMILES: Cn1ccc2cc(N3CCOc4cc(C(=O)N5CCCCC5)cnc43)ccc2c1=O] | $^1$H NMR (400 MHz, DMSO-d$_6$) δ 1.41-1.66 (6H, m), 3.34-3.58 (7H, m), 4.00 (2H, t, J = 3.7 Hz), 4.37 (2H, t, J = 4.3 Hz), 6.54 (1H, d, J = 7.3 Hz), 7.17 (1H, d, J = 1.8 Hz), 7.43 (1H, d, J = 7.3 Hz), 7.57 (1H, d, J = 1.8 Hz), 7.64 (1H, dd, J = 8.6, 2.4 Hz), 7.72 (1H, d, J = 1.8 Hz), 8.14 (1H, d, J = 8.6 Hz). LRMS (ESI$^+$) 405 [M + H]$^+$. |
| 1-218 | 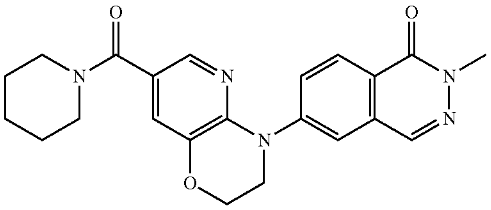 [SMILES: Cn1ncc2cc(N3CCOc4cc(C(=O)N5CCCCC5)cnc43)ccc2c1=O] | $^1$H NMR (400 MHz, DMSO-d$_6$) δ 1.43-1.65 (6H, m), 3.35-3.55 (4H, m), 3.70 (3H, s), 3.98-4.12 (2H, m), 4.39 (2H, t, J = 4.5 Hz), 7.22 (1H, d, J = 1.8 Hz), 7.75 (1H, d, J = 2.4 Hz), 7.87 (1H, d, J = 1.8 Hz), 8.01 (1H, dd, J = 8.5, 2.4 Hz), 8.18 (1H, d, J = 8.5 Hz), 8.34 (1H, s). LRMS (ESI$^+$) 406 [M + H]$^+$. |
| 1-219 | 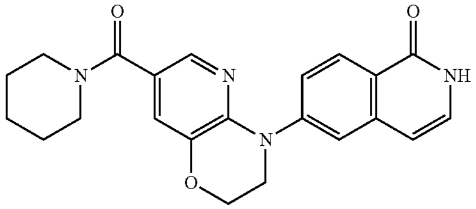 [SMILES: O=C(c1cnc2c(c1)OCCN2c1ccc2c(=O)[nH]ccc2c1)N1CCCCC1] | $^1$H NMR (400 MHz, DMSO-d$_6$) δ 1.42-1.64 (6H, m), 3.35-3.56 (4H, m), 4.00 (2H, t, J = 4.3 Hz), 4.37 (2H, t, J = 4.3 Hz), 6.48 (1H, d, J = 6.7 Hz), 7.12 (1H, dd, J = 7.0, 5.8 Hz), 7.17 (1H, d, J = 1.8 Hz), 7.57 (1H, d, J = 1.8 Hz), 7.62 (1H, dd, J = 8.6, 2.4 Hz), 7.72 (1H, d, J = 1.8 Hz), 8.10 (1H, d, J = 9.2 Hz), 11.08-11.13 (1H, m). LRMS (ESI$^+$) 391 [M + H]$^+$. |

TABLE 92-continued

| Example No. | Chemical Structural Formula | Spectrum Data |
|---|---|---|
| 1-220 | 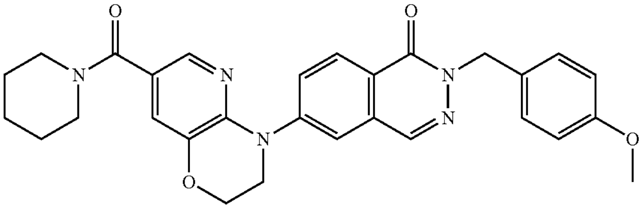 [SMILES: COc1ccc(Cn2ncc3cc(N4CCOc5cc(C(=O)N6CCCCC6)cnc54)ccc3c2=O)cc1] | $^1$H NMR (400 MHz, $CDCl_3$) δ 1.42-1.73 (6H, m), 3.33-3.87 (7H, m), 4.00 (2H, t, J = 4.2 Hz), 4.40 (2H, t, J = 4.2 Hz), 5.34 (2H, s), 6.82-6.88 (2H, m), 7.26 (1H, d, J = 1.8 Hz), 7.37-7.43 (2H, m), 7.65 (1H, d, J = 1.81 Hz), 7.79-7.87 (2H, m), 8.10 (1H, s), 8.41 (1H, d, J = 9.1 Hz). LRMS (ESI$^+$) 512 [M + H]$^+$. |
| 1-221 | 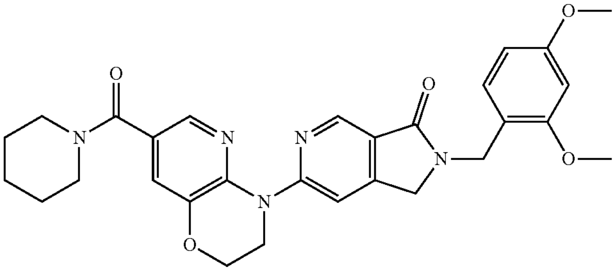 [SMILES: COc1ccc(CN2Cc3cc(N4CCOc5cc(C(=O)N6CCCCC6)cnc54)ncc3C2=O)c(OC)c1] | $^1$H NMR (400 MHz, $CDCl_3$) δ 1.47-1.79 (6H, m), 3.31-3.75 (4H, m), 3.80 (3H, s), 3.84 (3H, s), 4.28-4.32 (2H, m), 4.33-4.39 (4H, m), 4.71-4.75 (2H, m), 6.42-6.49 (2H, m), 7.20 (1H, d, J = 7.9 Hz), 7.24-7.28 (1H, m), 7.92 (1H, d, J = 1.8 Hz), 8.20 (1H, s), 8.80 (1H, s). LRMS (ESI$^+$) 530 [M + H]$^+$. |
| 1-222 | 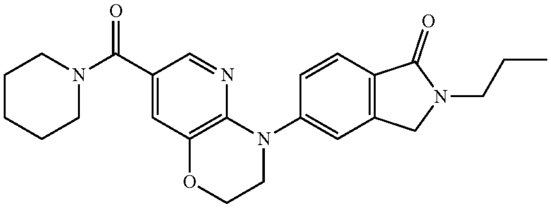 | $^1$H NMR (400 MHz, DMSO-$d_6$) δ 0.86 (3H, t, J = 7.6 Hz), 1.43-1.66 (8H, m), 3.35-3.52 (6H, m), 3.96 (2H, t, J = 4.3 Hz), 4.35 (2H, t, J = 4.6 Hz), 4.44 (2H, s), 7.15 (1H, d, J = 2.4 Hz), 7.51 (1H, dd, J = 8.6, 1.8 Hz), 7.60-7.65 (2H, m), 7.68 (1H, d, J = 1.8 Hz). LRMS (ESI$^+$) 421 [M + H]$^+$. |
| 1-223 | 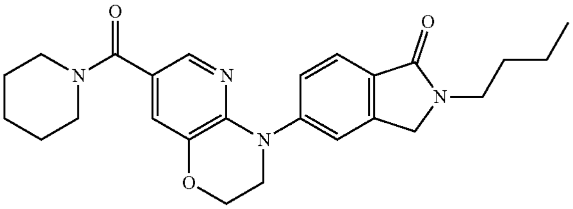 [SMILES: CCCCN1Cc2cc(N3CCOc4cc(C(=O)N5CCCCC5)cnc43)ccc2C1=O] | $^1$H NMR (400 MHz, DMSO-$d_6$) δ 0.90 (3H, t, J = 7.3 Hz), 1.22-1.34 (2H, m), 1.43-1.64 (8H, m), 3.35-3.55 (6H, m), 3.96 (2H, t, J = 4.6 Hz), 4.35 (2H, t, J = 4.3 Hz), 4.44 (2H, s), 7.15 (1H, d, J = 1.8 Hz), 7.50 (1H, dd, J = 8.6, 1.8 Hz), 7.60-7.65 (2H, m), 7.68 (1H, d, J = 1.8 Hz). LRMS (ESI$^+$) 435 [M + H]$^+$. |

TABLE 93

| Example No. | Chemical Structural Formula | Spectrum Data |
|---|---|---|
| 1-224 | 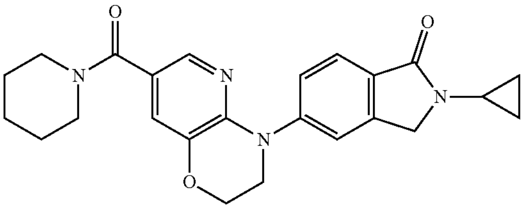 | $^1$H NMR (400 MHz, DMSO-$d_6$) δ 0.72-0.87 (4H, m), 1.42-1.64 (6H, m), 2.87-2.95 (1H, m), 3.34-3.54 (4H, m), 3.94 (2H, t, J = 4.2 Hz), 4.32-4.39 (4H, m), 7.14 (1H, d, J = 2.4 Hz), 7.50 (1H, dd, J = 8.5, 1.8 Hz), 7.57 (1H, d, J = 1.2 Hz), 7.61 (1H, d, J = 8.5 Hz), 7.67 (1H, d, J = 2.4 Hz). LRMS (ESI$^+$) 419 [M + H]$^+$. |
| 1-225 | 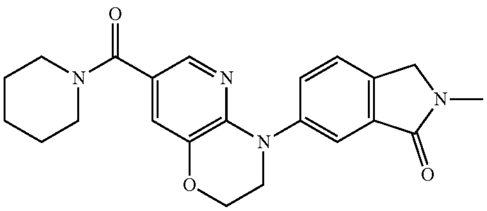 [SMILES: CN1Cc2ccc(N3CCOc4cc(C(=O)N5CCCCC5)cnc43)cc2C1=O] | $^1$H NMR (400 MHz, DMSO-$d_6$) δ 1.42-1.63 (6H, m), 3.08 (3H, s), 3.36-3.51 (4H, m), 3.95 (2H, t, J = 4.3 Hz), 4.35 (2H, t, J = 4.3 Hz), 4.44 (2H, s), 7.11 (1H, d, J = 2.4 Hz), 7.53-7.58 (1H, m), 7.60-7.66 (3H, m). LRNIS (ESI$^+$) 393 [M + H]$^+$. |

TABLE 93-continued

| Example No. | Chemical Structural Formula | Spectrum Data |
|---|---|---|
| 1-226 | 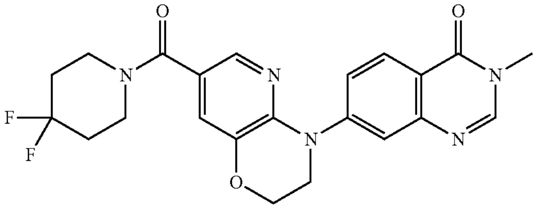 [SMILES: Cn1cnc2cc(N3CCOc4cc(C(=O)N5CCC(F)(F)CC5)cnc43)ccc2c1=O] | $^1$H NMR (400 MHz, DMSO-d$_6$) δ 1.95-2.10 (4H, m), 3.48 (3H, s), 3.50-3.69 (4H, m), 4.04 (2H, t, J = 4.6 Hz), 4.38 (2H, t, J = 4.3 Hz), 7.28 (1H, d, J = 1.8 Hz), 7.61 (1H, d, J = 1.8 Hz), 7.71 (1H, dd, J = 8.9, 2.1 Hz), 7.82 (1H, d, J = 2.4 Hz), 8.08 (1H, d, J = 8.6 Hz), 8.34 (1H, s). LRMS (ESI$^+$) 442 [M + H]$^+$. |
| 1-227 | 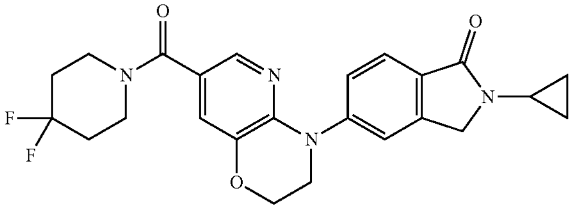 [SMILES: O=C(c1cnc2c(c1)OCCN2c1ccc2c(c1)CN(C1CC1)C2=O)N1CCC(F)(F)CC1] | $^1$H NMR (400 MHz, DMSO-d$_6$) δ 0.74-0.87 (4H, m), 1.95-2.09 (4H, m), 2.90-2.93 (1H, m), 3.51-3.66 (4H m), 3.95 (2H, t, J = 4.2 Hz), 4.33-4.40 (4H, m), 7.23 (1H, d, J = 1.8 Hz), 7.50 (1H, dd, J = 8.5, 1.8 Hz), 7.56-7.59 (1H, m), 7.62 (1H, d, J = 8.5 Hz), 7.75 (1H, d, J = 2.4 Hz). LRMS (ESI$^+$) 455 [M + H]$^+$. |
| 1-228 | 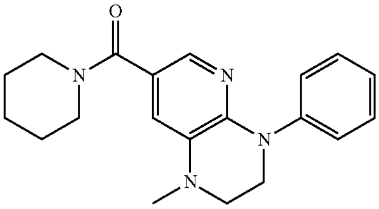 [SMILES: CN1CCN(c2ccccc2)c2ncc(C(=O)N3CCCCC3)cc21] | $^1$H NMR (400 MHz, DMSO-d$_6$) δ 1.40-1.65 (6H, m), 2.86 (3H, s), 3.33-3.39 (2H, m), 3.40-3.52 (4H, m), 3.83-3.90 (2H, m), 6.71 (1H, d, J = 1.8 Hz), 7.08-7.15 (1H, m), 7.28-7.38 (5H, m). LRMS (ESI$^+$) 337 [M + H]$^+$. |
| 1-229 | 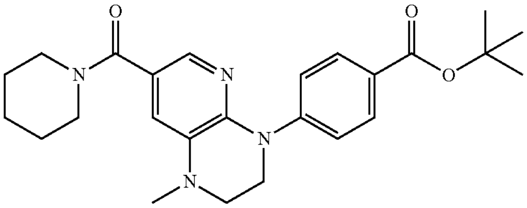 [SMILES: CN1CCN(c2ccc(C(=O)OC(C)(C)C)cc2)c2ncc(C(=O)N3CCCCC3)cc21] | $^1$H NMR (400 MHz, CDCl$_3$) δ 1.47-1.75 (15H, m), 2.95 (3H, s), 3.38-3.45 (2H, m), 3.45-3.73 (4H, m), 3.92-3.99 (2H, m), 6.88 (1H, d, J = 1.8 Hz), 7.34-7.40 (2H, m), 7.57 (1H, d, J = 1.8 Hz), 7.96-8.01 (2H, m). LRMS (ESI$^+$) 437 [M + H]$^+$. |
| 1-230 | 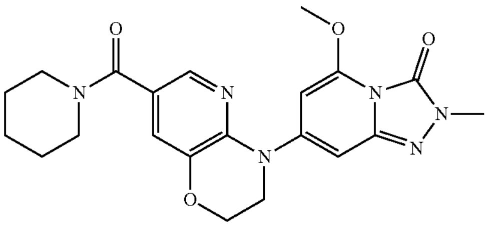 [SMILES: COc1cc(N2CCOc3cc(C(=O)N4CCCCC4)cnc32)cc2nn(C)c(=O)n12] | $^1$H NMR (400 MHz, DMSO-d$_6$) δ 1.43-1.64 (6H, m), 3.25-3.58 (7H, m), 3.83-3.94 (5H, m), 4.30-4.37 (2H, m), 6.13 (1H, d, J = 1.8 Hz), 6.48 (1H, d, J = 1.8 Hz), 7.19 (1H, d, J = 1.8 Hz), 7.80 (1H, d, J = 1.8 Hz). LRMS (ESI$^+$) 425 [M + H]$^+$. |

TABLE 94

| Example No. | Chemical Structural Formula | Spectrum Data |
|---|---|---|
| 1-231 | 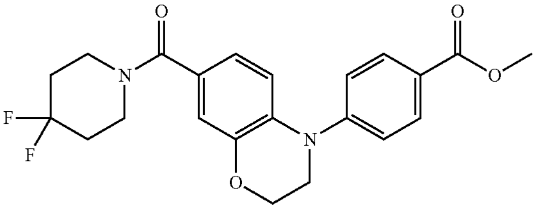 [SMILES: COC(=O)c1ccc(N2CCOc3cc(C(=O)N4CCC(F)(F)CC4)ccc32)cc1] | $^1$H NMR (400 MHz, DMSO-d$_6$) δ 1.94-2.09 (4H, m), 3.50-3.65 (4H, m), 3.78-3.84 (5H, m), 4.28 (2H, t, J = 4.5 Hz), 6.87 (1H, dd, J = 8.5, 1.8 Hz), 6.97 (1H, d, J = 1.8 Hz), 7.10 (1H, d, J = 8.5 Hz), 7.34-7.39 (2H, m), 7.90-7.95 (2H, m). LRMS (ESI$^+$) 417 [M + H]$^+$. |

TABLE 94-continued

| Example No. | Chemical Structural Formula | Spectrum Data |
|---|---|---|
| 1-232 | 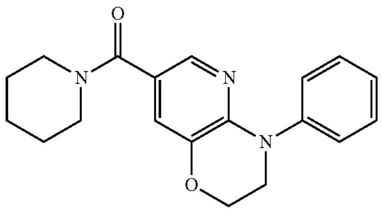 | $^{1}H$ NMR (400 MHz, DMSO-$d_6$) δ 1.40-1.64 (6H, m), 3.35-3.53 (4H, m) 3.89 (2H, t, J = 4.5 Hz), 4.33 (2H, t, J = 4.5 Hz), 7.09 (1H, d, J = 1.8 Hz), 7.11-7.17 (1H, m), 7.33-7.43 (4H, m), 7.64 (1H, d, J = 1.8 Hz). LRMS (ESI$^+$) 324 [M + H]$^+$. |
| 1-233 | 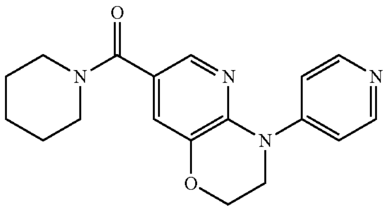 [SMILES: O=C(c1cnc2c(c1)OCCN2c1ccncc1)N1CCCCC1] | $^{1}H$ NMR (400 MHz, DMSO-$d_6$) δ 1.41-1.64 (6H, m), 3.34-3.58 (4H, m), 3.96 (2H, t, J = 4.3 Hz), 4.34 (2H, t, J = 4.6 Hz), 7.22 (1H, d, J = 2.4 Hz), 7.48-7.51 (2H, m), 7.79 (1H, d, J = 1.8 Hz), 8.41-8.44 (2H, m). LRMS (ESI$^+$) 325 [M + H]$^+$. |
| 1-234 | 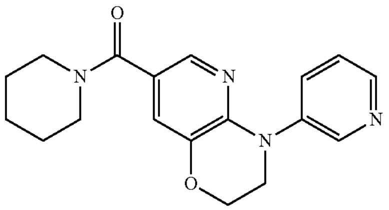 [SMILES: O=C(c1cnc2c(c1)OCCN2c1cccnc1)N1CCCCC1] | $^{1}H$ NMR (400 MHz, DMSO-$d_6$) δ 1.41-1.64 (6H, m), 3.36-3.51 (4H, m), 3.95 (2H, t, J = 4.3 Hz), 4.36 (2H, t, J = 4.6 Hz), 7.14 (1H, d, J = 1.8 Hz), 7.40 (1H, dd, J = 8.3, 4.6 Hz), 7.67 (1H, d, J = 1.8 Hz), 7.81-7.85 (1H, m), 8.31 (1H, dd, J = 4.6, 1.5 Hz), 8.69 (1H, d, J = 2.4 Hz). LRMS (ESI$^+$) 325 [M + H]$^+$. |
| 1-235 | 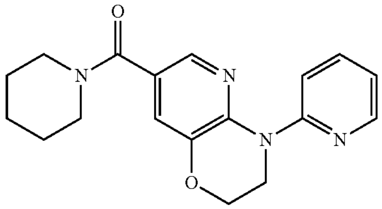 [SMILES: O=C(c1cnc2c(c1)OCCN2c1ccccn1)N1CCCCC1] | $^{1}H$ NMR (400 MHz, $CDCl_3$) δ 1.44-1.76 (6H, m), 3.33-3.79 (4H, m), 4.24-4.29 (2H, m), 4.33-4.38 (2H, m), 6.92-6.98 (1H, m), 7.24 (1H, d, J = 1.8 Hz), 7.61-7.68 (1H, m), 7.92 (1H, d, J = 2.4 Hz), 8.08 (1H, d, J = 8.6 Hz), 8.35-8.38 (1H, m). LRMS (ESI$^+$) 325 [M + H]$^+$. |
| 1-236 | 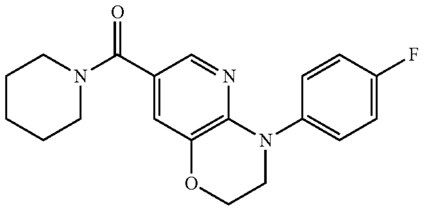 [SMILES: O=C(c1cnc2c(c1)OCCN2c1ccc(F)cc1)N1CCCCC1] | $^{1}H$ NMR (400 MHz, $CDCl_3$) δ 1.46-1.72 (6H, m), 3.45-3.66 (4H, m), 3.86-3.89 (2H, m), 4.33-4.37 (2H, m), 7.07-7.12 (2H, m), 7.18 (1H, d, J = 2.4 Hz), 7.28-7.34 (2H, m), 7.80 (1H, d, J = 2.4 Hz). LRMS (ESI$^+$) 342 [M + H]$^+$. |
| 1-237 | 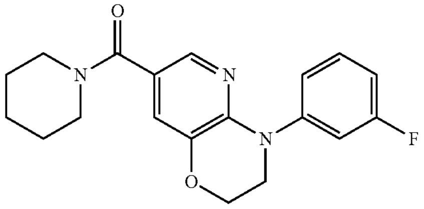 [SMILES: O=C(c1cnc2c(c1)OCCN2c1cccc(F)c1)N1CCCCC1] | $^{1}H$ NMR (400 MHz, $CDCl_3$) δ 1.50-1.73 (6H, m), 3.37-3.72 (4H, m), 3.90 (2H, t, J = 4.3 Hz), 4.35 (2H, t, J = 4.3 Hz), 6.83-6.89 (1H, m), 7.13-7.18 (2H, m), 7.21 (1H, d, J = 1.8 Hz), 7.30-7.38 (1H, m), 7.84 (1H, d, J = 1.8 Hz). LRMS (ESI$^+$) 342 [M + H]$^+$. |

TABLE 95

| Example No. | Chemical Structural Formula | Spectrum Data |
|---|---|---|
| 1-238 | 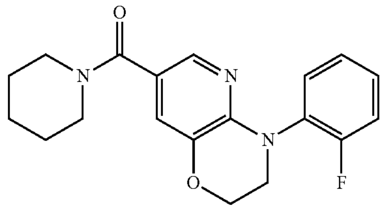 [SMILES: O=C(c1cnc2c(c1)OCCN2c1ccccc1F)N1CCCCC1] | $^1H$ NMR (400 MHz, $CDCl_3$) δ 1.49-1.72 (6H, m), 3.40-3.70 (4H, m), 3.86 (2H, t, J = 4.6 Hz), 4.37 (2H, t, J = 4.6 Hz), 7.14-7.30 (4H, m), 7.34-7.41 (1H, m), 7.79 (1H, d, J = 1.8 Hz). LRMS ($ESI^+$) 342 $[M + H]^+$. |
| 1-239 | 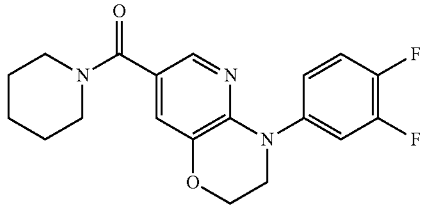 [SMILES: O=C(c1cnc2c(c1)OCCN2c1ccc(F)c(F)c1)N1CCCCC1] | $^1H$ NMR (400 MHz, $CDCl_3$) δ 1.50-1.66 (6H, m), 3.38-3.72 (4H, m), 3.87 (2H, t, J = 4.5 Hz), 4.35 (2H, t, J = 4.5 Hz), 7.04-7.10 (1H, m), 7.13-7.22 (2H, m), 7.23-7.30 (1H, m), 7.81 (1H, d, J = 1.8 Hz). LRMS ($ESI^+$) 360 $[M + H]^+$. |
| 1-240 | 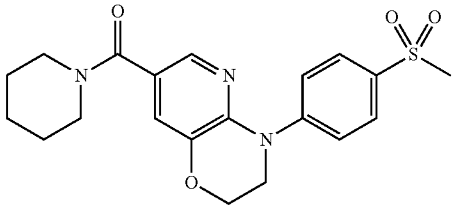 [SMILES: CS(=O)(=O)c1ccc(N2CCOc3cc(C(=O)N4CCCCC4)cnc32)cc1] | $^1H$ NMR (400 MHz, DMSO-$d_6$) δ 1.41-1.66 (6H, m), 3.20 (3H, s), 3.34-3.54 (4H, m), 3.98 (2H, t, J = 4.3 Hz), 4.36 (2H, t, J = 4.3 Hz), 7.19 (1H, d, J = 1.8 Hz), 7.65-7.70 (2H, m), 7.72 (1H, d, J = 1.8 Hz), 7.85-7.89 (2H, m). LRMS ($ESI^+$) 402 $[M + H]^+$. |
| 1-241 | 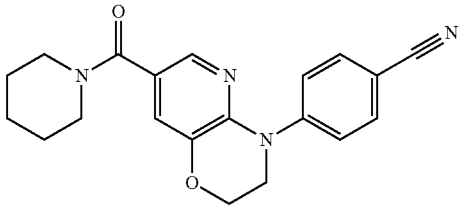 [SMILES: N#Cc1ccc(N2CCOc3cc(C(=O)N4CCCCC4)cnc32)cc1] | $^1H$ NMR (400 MHz, DMSO-$d_6$) δ 1.40-1.65 (6H, m), 3.35-3.53 (4H, m), 3.96 (2H, t, J = 4.3 Hz), 4.35 (2H, t, J = 4.3 Hz), 7.20 (1H, d, J = 1.8 Hz), 7.61-7.66 (2H, m), 7.73 (1H, d, J = 1.8 Hz), 7.76-7.82 (2H, m). LRMS ($ESI^+$) 349 $[M + H]^+$. |
| 1-242 | 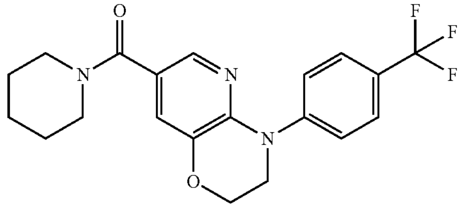 [SMILES: O=C(c1cnc2c(c1)OCCN2c1ccc(C(F)(F)F)cc1)N1CCCCC1] | $^1H$ NMR (400 MHz, DMSO-$d_6$) δ 1.43-1.63 (6H, m), 3.34-3.53 (4H, m), 3.96 (2H, t, J = 4.6 Hz), 4.35 (2H, t, J = 4.3 Hz), 7.17 (1H, d, J = 1.8 Hz), 7.61-7.67 (2H, m), 7.68-7.72 (3H, m). LRMS ($ESI^+$) 392 $[M + H]^+$. |
| 1-243 | 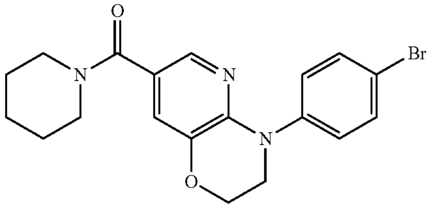 [SMILES: O=C(c1cnc2c(c1)OCCN2c1ccc(Br)cc1)N1CCCCC1] | $^1H$ NMR (400 MHz, DMSO-$d_6$) δ 1.41-1.63 (6H, m), 3.35-3.50 (4H, m), 3.89 (2H, t, J = 4.6 Hz), 4.33 (2H, t, J = 4.3 Hz), 7.11 (1H, d, J = 2.4 Hz), 7.35-7.42 (2H, m), 7.51-7.56 (2H, m), 7.65 (1H, d, J = 1.8 Hz). LRMS ($ESI^+$) 402 [M + H]+. |
| 1-244 | 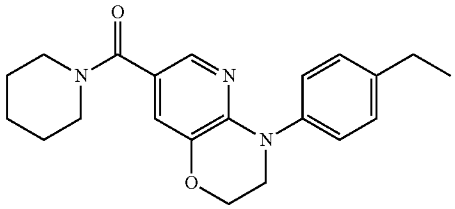 [SMILES: CCc1ccc(N2CCOc3cc(C(=O)N4CCCCC4)cnc32)cc1] | $^1H$ NMR (400 MHz, DMSO-$d_6$) δ 1.18 (3H, t, J = 7.6 Hz), 1.42-1.63 (6H, m), 2.59 (2H, q, J = 7.5 Hz), 3.38-3.48 (4H, m), 3.86 (2H, t, J = 4.6 Hz), 4.32 (2H, t, J = 4.6 Hz), 7.07 (1H, d, J = 1.8 Hz), 7.17-7.22 (2H, m), 7.26-7.31 (2H, m), 7.62 (1H, d, J = 1.8 Hz). LRMS ($ESI^+$) 352 $[M + H]^+$. |

TABLE 96

| Example No. | Chemical Structural Formula | Spectrum Data |
|---|---|---|
| 1-245 | 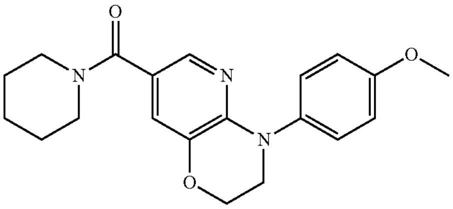 [SMILES: COc1ccc(N2CCOc3cc(C(=O)N4CCCCC4)cnc32)cc1] | $^1$H NMR (400 MHz, $CDCl_3$) δ 1.47-1.70 (6H, m), 3.40-3.70 (4H, m), 3.82 (3H, s), 3.86 (2H, t, J = 4.2 Hz), 4.34 (2H, t, J = 4.5 Hz), 6.92-6.97 (2H, m), 7.16 (1H, d, J = 1.8 Hz), 7.23-7.29 (2H, m), 7.80 (1H, d, J = 1.8 Hz). LRMS (ESI$^+$) 354 [M + H]$^+$. |
| 1-246 | 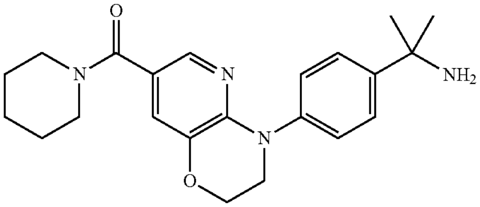 [SMILES: CC(C)(N)c1ccc(N2CCOc3cc(C(=O)N4CCCCC4)cnc32)cc1] | $^1$H NMR (400 MHz, DMSO-$d_6$) δ 1.37 (6H, s), 1.41-1.64 (6H, m), 1.85 (2H, s), 3.37-3.51 (4H, m), 3.87 (2H, t, J = 4.3 Hz), 4.32 (2H, t, J = 4.3 Hz), 7.07 (1H, d, J = 1.8 Hz), 7.26-7.31 (2H, m), 7.48-7.53 (2H, m), 7.62 (1H, d, J = 2.4 Hz). LRMS (ESI$^+$) 381 [M + H]$^+$. |
| 1-247 | 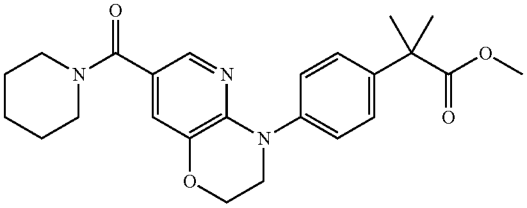 [SMILES: COC(=O)C(C)(C)c1ccc(N2CCOc3cc(C(=O)N4CCCCC4)cnc32)cc1] | $^1$H NMR (400 MHz, $CDCl_3$) δ 1.49-1.71 (12H, m), 3.47-3.64 (4H, m), 3.66 (3H, s), 3.90 (2H, t, J = 4.3 Hz), 4.32 (2H, t, J = 4.3 Hz), 7.19 (1H, d, J = 1.8 Hz), 7.32-7.38 (4H, m), 7.83 (1H, d, J = 1.8 Hz). LRMS (ESI$^+$) 424 [M + H]$^+$. |
| 1-248 | 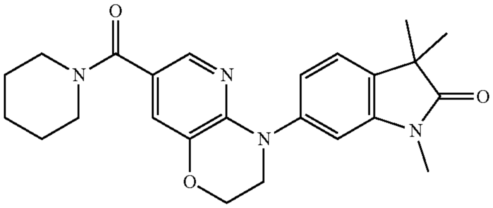 [SMILES: CN1C(=O)C(C)(C)c2ccc(N3CCOc4cc(C(=O)N5CCCCC5)cnc43)cc21] | $^1$H NMR (400 MHz, DMSO-$d_6$) δ 1.27 (6H, s), 1.43-1.63 (6H, m), 3.10 (3H, s), 3.36-3.50 (4H, m), 3.90 (2H, t, J = 4.3 Hz), 4.33 (2H, t, J = 4.3 Hz), 7.02 (1H, dd, J = 7.9, 1.8 Hz), 7.06-7.11 (2H, m), 7.33 (1H, d, J = 7.9 Hz), 7.65 (1H, d, J = 2.4 Hz). LRMS (ESI$^+$) 421 [M + H]$^+$. |
| 1-249 | 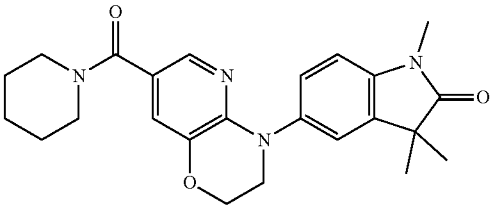 [SMILES: CN1C(=O)C(C)(C)c2cc(N3CCOc4cc(C(=O)N5CCCCC5)cnc43)ccc21] | $^1$H NMR (400 MHz, DMSO-$d_6$) δ 1.27 (6H, s), 1.40-1.64 (6H, m), 3.14 (3H, s), 3.37-3.49 (4H, m), 3.86 (2H, t, J = 4.3 Hz), 4.33 (2H, t, J = 4.3 Hz), 7.00 (1H, d, J = 8.6 Hz), 7.06 (1H, d, J = 1.8 Hz), 7.26 (1H, dd, J = 8.3, 2.1 Hz), 7.38 (1H, d, J = 2.4 Hz), 7.60 (1H, d, J = 2.4 Hz). LRMS (ESI$^+$) 421 [M + H]$^+$. |
| 1-250 | 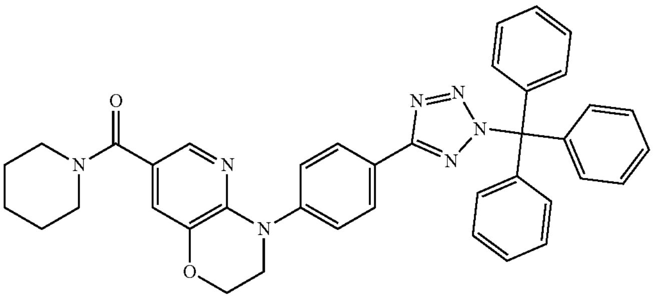 [SMILES: O=C(c1cnc2c(c1)OCCN2c1ccc(-c2nnn(C(c3ccccc3)(c3ccccc3)c3ccccc3)n2)cc1)N1CCCCC1] | $^1$H NMR (400 MHz, $CDCl_3$) δ 1.45-1.73 (6H, m), 3.39-3.69 (4H, m), 3.95 (2H, t, J = 4.3 Hz), 4.37 (2H, t, J = 4.3 Hz), 7.14-7.19 (6H, m) 7.21 (1H, d, J = 2.4 Hz), 7.29-7.41 (9H, m), 7.45-7.51 (2H, m), 7.83 (1H, d, J = 1.8 Hz), 8.14-8.21 (2H, m). LRMS (ESI$^+$) 634 [M + H]$^+$. |

TABLE 97

| Example No. | Chemical Structural Formula | Spectrum Data |
|---|---|---|
| 1-251 | 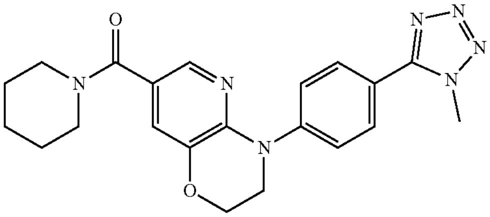 [SMILES: Cn1nnnc1-c1ccc(N2CCOc3cc(C(=O)N4CCCCC4)cnc32)cc1] | $^1$H NMR (400 MHz, DMSO-$d_6$) δ 1.43-1.64 (6H, m), 3.37-3.52 (4H, m), 3.97 (2H, t, J = 4.3 Hz), 4.36 (2H, t, J = 4.3 Hz), 4.42 (3H, s), 7.15 (1H, d, J = 1.8 Hz), 7.59-7.64 (2H, m), 7.71 (1H, d, J = 2.4 Hz), 8.01-8.05 (2H, m). LRMS (ESI$^+$) 406 [M + H]$^+$. |
| 1-252 | 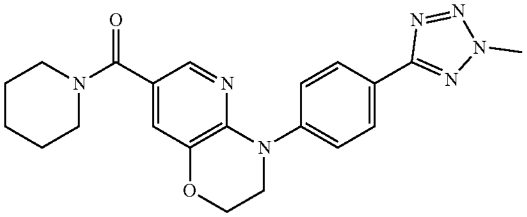 [SMILES: Cn1nnc(-c2ccc(N3CCOc4cc(C(=O)N5CCCCC5)cnc43)cc2)n1] | $^1$H NMR (400 MHz, DMSO-$d_6$) δ 1.44-1.64 (6H, m), 3.38-3.52 (4H, m), 4.00 (2H, t, J = 4.6 Hz), 4.19 (3H, s), 4.37 (2H, t, J = 4.3 Hz), 7.18 (1H, d, J = 1.8 Hz), 7.65-7.70 (2H, m), 7.72 (1H, d, J = 1.8 Hz), 7.83-7.88 (2H, m). LRMS (ESI$^+$) 406 [M + H]$^+$. |
| 1-253 | 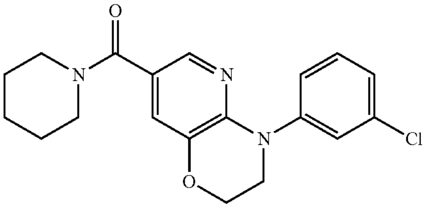 [SMILES: O=C(c1cnc2c(c1)OCCN2c1cccc(Cl)c1)N1CCCCC1] | $^1$H NMR (400 MHz, $CDCl_3$) δ 1.46-1.78 (6H, m), 3.40-3.70 (4H, m), 3.89 (2H, t, J = 4.6 Hz), 4.35 (2H, t, J = 4.3 Hz), 7.14 (1H, dt, J = 7.0, 1.8 Hz), 7.21 (1H, d, J = 1.8 Hz), 7.25-7.35 (2H, m), 7.39 (1H, t, J = 1.8 Hz), 7.83 (1H, d, J = 1.8 Hz). LRMS (ESI$^+$) 358 [M + H]$^+$. |
| 1-254 | 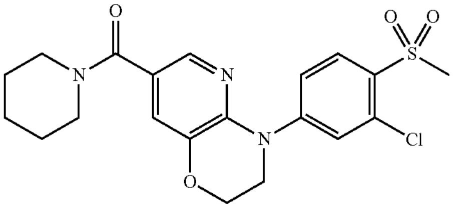 [SMILES: CS(=O)(=O)c1ccc(N2CCOc3cc(C(=O)N4CCCCC4)cnc32)cc1Cl] | $^1$H NMR (400 MHz, DMSO-$d_6$) δ 1.43-1.65 (6H, m), 3.31 (3H, s), 3.35-3.56 (4H, m), 3.99 (2H, t, J = 4.5 Hz), 4.36 (2H, t, J = 4.2 Hz), 7.23 (1H, d, J = 1.8 Hz), 7.63 (1H, dd, J = 8.8, 2.1 Hz), 7.77 (1H, d, J = 1.8 Hz), 7.84 (1H, d, J = 2.4 Hz), 7.97 (1H, d, J = 9.1 Hz). LRMS (ESI$^+$) 436 [M + H]$^+$. |
| 1-255 | 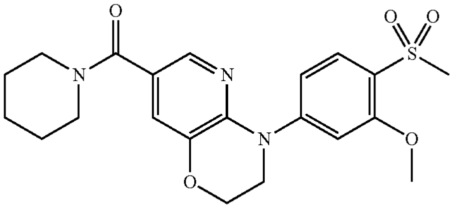 [SMILES: COc1cc(N2CCOc3cc(C(=O)N4CCCCC4)cnc32)ccc1S(C)(=O)=O] | $^1$H NMR (400 MHz, DMSO-$d_6$) δ 1.43-1.64 (6H, m), 3.21 (3H, s), 3.33-3.56 (4H, m), 3.92 (3H, s), 3.99 (2H, t, J = 4.2 Hz), 4.36 (2H, t, J = 4.5 Hz), 7.15-7.21 (2H, m), 7.35 (1H, d, J = 1.8 Hz), 7.72 (1H, d, J = 9.1 Hz), 7.75 (1H, d, J = 1.8 Hz). LRMS (ESI$^+$) 432 [M + H]$^+$. |
| 1-256 | 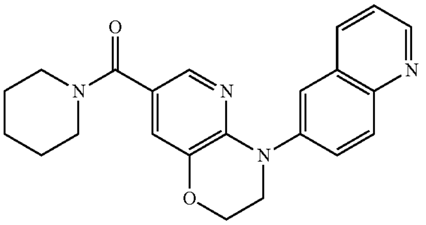 [SMILES: O=C(c1cnc2c(c1)OCCN2c1ccc2ncccc2c1)N1CCCCC1] | $^1$H NMR (400 MHz, $CDCl_3$) δ 1.40-1.72 (6H, m), 3.40-3.70 (4H, m), 4.04 (2H, t, J = 4.2 Hz), 4.42 (2H, t, J = 4.2 Hz), 7.21-7.28 (1H, m), 7.39 (1H, dd, J = 8.5, 4.2 Hz), 7.65 (1H, d, J = 2.4 Hz), 7.84 (1H, d, J = 1.8 Hz), 7.89 (1H, dd, J = 9.1, 2.4 Hz), 8.08-8.13 (2H, m), 8.86 (1H, d, J = 4.2 Hz). LRMS (ESI$^+$) 375 [M + H]$^+$. |

TABLE 98

| Example No. | Chemical Structural Formula | Spectrum Data |
| --- | --- | --- |
| 1-257 | 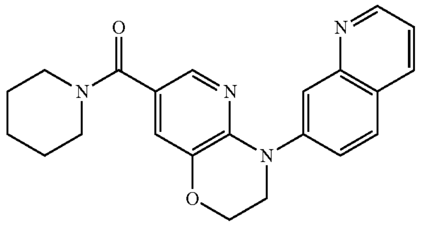 [SMILES: O=C(c1cnc2c(c1)OCCN2c1ccc2cccnc2c1)N1CCCCC1] | $^1$H NMR (400 MHz, $CDCl_3$) δ 1.47-1.78 (6H, m), 3.35-3.75 (4H, m), 4.08 (2H, t, J = 4.3 Hz), 4.43 (2H, t, J = 4.6 Hz), 7.24 (1H, d, J = 1.8 Hz), 7.34 (1H, dd, J = 8.6, 4.3 Hz), 7.79 (1H, d, J = 8.6 Hz), 7.82-7.90 (3H, m), 8.12 (1H, dd, J = 8.3, 1.5 Hz), 8.86 (1H, dd, J = 4.3, 1.8 Hz). LRMS (ESI$^+$) 375 $[M + H]^+$. |
| 1-258 | 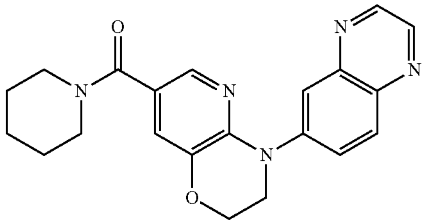 [SMILES: O=C(c1cnc2c(c1)OCCN2c1ccc2nccnc2c1)N1CCCCC1] | $^1$H NMR (400 MHz, $CDCl_3$) δ 1.49-1.78 (6H, m), 3.30-3.80 (4H, m), 4.09 (2H, t, J = 4.5 Hz), 4.45 (2H, t, J = 4.5 Hz), 7.27 (1H, t, J = 2.1 Hz), 7.84 (2H, dd, J = 12.4, 2.1 Hz), 8.07 (1H, d, J = 9.1 Hz), 8.13 (1H, dd, J = 9.1, 2.4 Hz), 8.78 (2H, dd, J = 9.1, 1.8 Hz). LRMS (ESI$^+$) 376 $[M + H]^+$. |
| 1-259 | 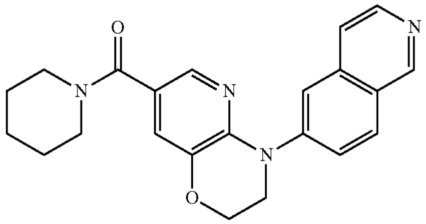 [SMILES: O=C(c1cnc2c(c1)OCCN2c1ccc2cnccc2c1)N1CCCCC1] | $^1$H NMR (400 MHz, DMSO-$d_6$) δ 1.37-1.66 (6H, m), 3.35-3.55 (4H, m), 4.06 (2H, t, J = 4.2 Hz), 4.40 (2H, t, J = 4.2 Hz), 7.19 (1H, d, J = 1.8 Hz), 7.70-7.75 (2H, m), 7.77 (1H, d, J = 2.4 Hz), 7.91 (1H, dd, J = 8.8, 2.1 Hz), 8.04 (1H, d, J = 9.1 Hz), 8.42 (1H, d, J = 5.4 Hz), 9.20 (1H, s). LRMS (ESI$^+$) 375 $[M + H]^+$. |
| 1-260 | 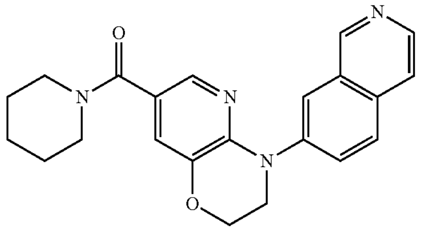 [SMILES: O=C(c1cnc2c(c1)OCCN2c1ccc2ccncc2c1)N1CCCCC1] | $^1$H NMR (400 MHz, DMSO-$d_6$) δ 1.39-1.65 (6H, m), 3.36-3.53 (4H, m), 4.05 (2H, t, J = 3.6 Hz), 4.41 (2H, t, J = 3.9 Hz), 7.17 (1H, d, J = 1.8 Hz), 7.68 (1H, d, J = 1.2 Hz), 7.77 (1H, d, J = 6.1 Hz), 7.88-8.02 (3H, m), 8.43 (1H, d, J = 5.4 Hz), 9.23 (1H, s). LRMS (ESI$^+$) 375 $[M + H]^+$. |
| 1-261 | 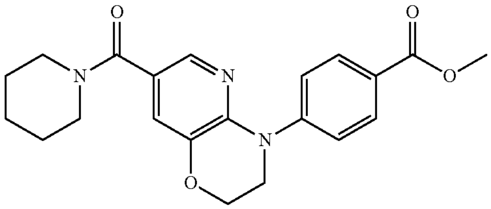 [SMILES: COC(=O)c1ccc(N2CCOc3cc(C(=O)N4CCCCC4)cnc32)cc1] | $^1$H NMR (400 MHz, DMSO-$d_6$) δ 1.39-1.65 (6H, m), 3.34-3.61 (4H, m), 3.83 (3H, s), 3.96 (2H, t, J = 4.5 Hz), 4.35 (2H, t, J = 4.2 Hz), 7.18 (1H, d, J = 1.8 Hz), 7.55-7.60 (2H, m), 7.72 (1H, d, J = 1.8 Hz), 7.91-7.96 (2H, m). LRMS (ESI$^+$) 382 $[M + H]^+$. |
| 1-262 | 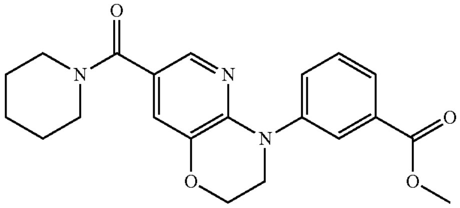 [SMILES: COC(=O)c1cccc(N2CCOc3cc(C(=O)N4CCCCC4)cnc32)c1] | $^1$H NMR (400 MHz, DMSO-$d_6$) δ 1.38-1.68 (6H, m), 3.34-3.59 (4H, m), 3.85 (3H, s), 3.91-3.98 (2H, m), 4.284.41 (2H, m), 7.13 (1H, d, J = 1.8 Hz), 7.52 (1H, t, J = 7.9 Hz), 7.66 (1H, d, J = 1.8 Hz), 7.68-7.75 (2H, m), 7.95-7.99 (1H, m). LRMS (ESI$^+$) 382 $[M + H]^+$. |

TABLE 99

| Example No. | Chemical Structural Formula | Spectrum Data |
| --- | --- | --- |
| 1-263 | 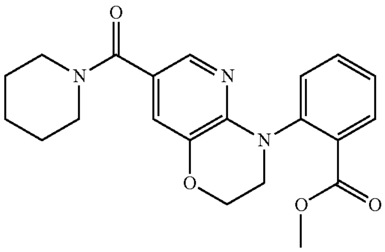 [SMILES: COC(=O)c1ccccc1N1CCOc2cc(C(=O)N3CCCCC3)cnc21] | $^1$H NMR (400 MHz, DMSO-$d_6$) δ 1.38-1.66 (6H, m), 3.34-3.46 (4H, m), 3.48 (3H, s), 3.77-4.05 (2H, m), 4.24-4.44 (2H, m), 7.07 (1H, d, J = 1.8 Hz), 7.32-7.38 (1H, m), 7.41-7.45 (1H, m), 7.49 (1H, d, J = 1.8 Hz), 7.62-7.68 (1H, m), 7.75 (1H, dd, J = 7.6, 1.5 Hz). LRMS (ESI$^+$) 382 [M + H]$^+$. |
| 1-264 | 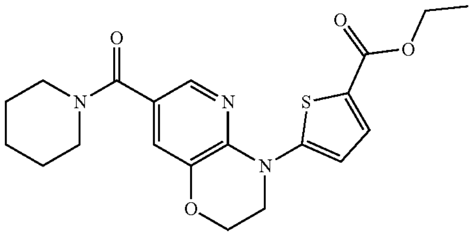 [SMILES: CCOC(=O)c1ccc(N2CCOc3cc(C(=O)N4CCCCC4)cnc32)s1] | $^1$H NMR (400 MHz, DMSO-$d_6$) δ 1.28 (3H, t, J = 7.0 Hz), 1.40-1.68 (6H, m), 3.24-3.66 (6H, m), 4.15 (2H, t, J = 4.6 Hz), 4.24 (2H, q, J = 7.1 Hz), 4.42 (2H, t, J = 4.6 Hz), 6.77 (1H, d, J = 4.9 Hz), 7.28 (1H, d, J = 1.8 Hz), 7.65 (1H, d, J = 4.3 Hz), 8.03 (1H, d, J = 1.8 Hz). LRMS (ESI$^+$) 402 [M + H]$^+$. |
| 1-265 | 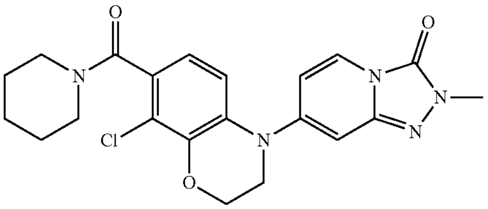 [SMILES: Cn1nc2cc(N3CCOc4c3ccc(C(=O)N3CCCCC3)c4Cl)ccn2c1=O] | $^1$H NMR (400 MHz, DMSO-$d_6$) δ 1.34-1.67 (6H, m), 3.09-3.18 (2H, m), 3.47 (3H, s), 3.57 (2H, t, J = 5.2 Hz), 3.74-3.85 (2H, m), 4.39 (2H, t, J = 4.6 Hz), 6.65 (1H, dd, J = 7.6, 2.1 Hz), 6.72 (1H, d, J = 1.8 Hz), 6.75 (1H, d, J = 8.6 Hz), 7.01 (1H, d, J = 8.6 Hz), 7.80 (1H, d, J = 7.3 Hz). LRMS (ESI$^+$) 428 [M + H]$^+$. |
| 1-266 | 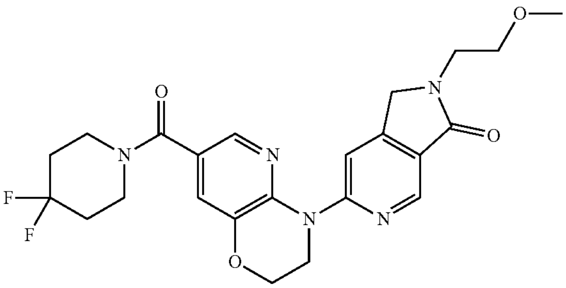 [SMILES: COCCN1Cc2cc(N3CCOc4cc(C(=O)N5CCC(F)(F)CC5)cnc43)ncc2C1=O] | $^1$H NMR (400 MHz, DMSO-$d_6$) δ 1.97-2.12 (4H, m), 3.25 (3H, s), 3.46-3.74 (8H, m), 4.27 (2H, t, J = 4.3 Hz), 4.36 (2H, t, J = 4.3 Hz), 4.56 (2H, s), 7.38 (1H, d, J = 1.8 Hz), 7.95 (1H, d, J = 1.8 Hz), 8.28 (1H, s), 8.65 (1H, s). LRMS (ESI$^+$) 474 [M + H]$^+$. |
| 1-267 | 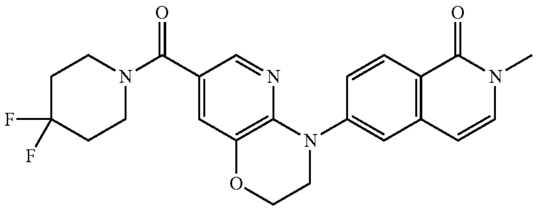 [SMILES: Cn1ccc2cc(N3CCOc4cc(C(=O)N5CCC(F)(F)CC5)cnc43)ccc2c1=O] | $^1$H NMR (400 MHz, DMSO-$d_6$) δ 1.95-2.10 (4H, m), 3.48 (3H, s), 3.51-3.71 (4H, m), 4.01 (2H, t, J = 4.6 Hz), 4.37 (2H, t, J = 4.3 Hz), 6.54 (1H, d, J = 7.9 Hz), 7.26 (1H, d, J = 2.4 Hz), 7.43 (1H, d, J = 7.3 Hz), 7.58 (1H, d, J = 1.8 Hz), 7.64 (1H, dd, J = 8.9, 2.1 Hz), 7.80 (1H, d, J = 2.4 Hz), 8.14 (1H, d, J = 8.6 Hz). LRMS (ESI$^+$) 441 [M + H]$^+$. |
| 1-268 | 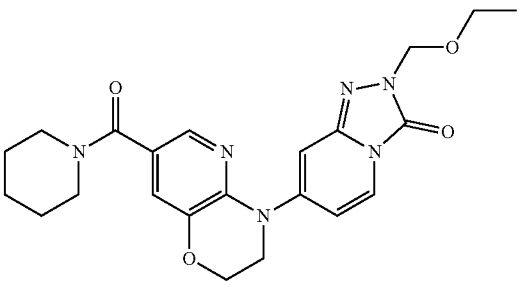 | $^1$H NMR (400 MHz, DMSO-$d_6$) δ 1.09 (3H, t, J = 7.0 Hz), 1.42-1.64 (6H, m), 3.26-3.60 (6H, m), 3.94 (2H, t, J = 4.6 Hz), 4.37 (2H, t, J = 4.3 Hz), 5.20 (2H, s), 6.88 (1H, d, J = 1.8 Hz), 7.00 (1H, dd, J = 7.6, 2.1 Hz), 7.22 (1H, d, J = 1.8 Hz), 7.75-7.80 (2H, m). LRMS (ESI$^+$) 439 [M + H]$^+$. |

TABLE 100

| Example No. | Chemical Structural Formula | Spectrum Data |
|---|---|---|
| 1-269 | 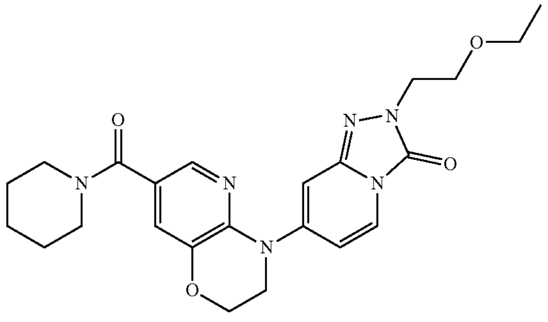 [SMILES: CCOCCn1nc2cc(N3CCOc4cc(C(=O)N5CCCCC5)cnc43)ccn2c1=O] | $^1$H NMR (400 MHz, DMSO-$d_6$) δ 1.04 (3H, t, J = 6.7 Hz), 1.44-1.65 (6H, m), 3.34-3.57 (6H, m), 3.70 (2H, t, J = 5.5 Hz), 3.93 (2H, t, J = 4.6 Hz), 3.98 (2H, t, J = 5.5 Hz), 4.36 (2H, t, J = 4.3 Hz), 6.91 (1H, d, J = 1.2 Hz), 6.98 (1H, dd, J = 7.9, 1.8 Hz), 7.21 (1H, d, J = 1.8 Hz), 7.74-7.79 (2H, m). LRMS (ESI+) 453 [M + H]$^+$. |
| 1-270 | 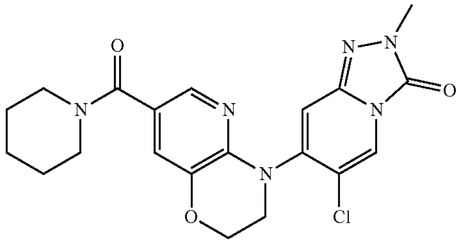 [SMILES: Cn1nc2cc(N3CCOc4cc(C(=O)N5CCCCC5)cnc43)c(Cl)cn2c1=O] | $^1$H NMR (400 MHz, DMSO-$d_6$) δ 1.42-1.64 (6H, m), 3.36-3.57 (7H, m), 3.75-3.98 (2H, m), 4.31-4.46 (2H, m), 7.16 (1H, d, J = 1.8 Hz), 7.44 (1H, s), 7.68 (1H, d, J = 2.4 Hz), 8.19 (1H, s). LRMS (ESI$^+$) 429 [M + H]$^+$. |

Example 2-1

[Formula 157]

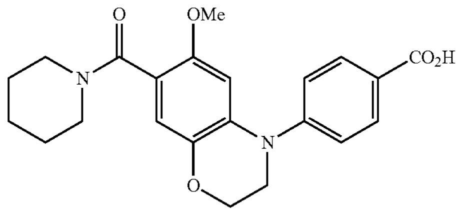

4-(6-Methoxy-7-(piperidine-1-carbonyl)-2,3-dihydro-4H-benzo[b] [1,4]oxazin-4-yl)benzoic Acid To a solution of methyl 4-(6-methoxy-7-(piperidine-1-carbonyl)-2,3-dihydro-4H-benzo[b][1,4]oxazin-4-yl)benzoate (61.9 mg) in methanol (1.5 mL), a 2 mol/L sodium hydroxide aqueous solution (0.45 mL) was added at room temperature, followed by stirring at 50° C. for 3 hours. The resultant reaction solution was concentrated under reduced pressure, and a 1 mol/L hydrogen chloride aqueous solution was added to the thus obtained residue to adjust pH to 2. The thus precipitated product was collected by filtration to obtain the title compound (51.9 mg).

$^1$H NMR (400 MHz, DMSO-$d_6$) δ1.33-1.54 (4H, m), 1.54-1.63 (2H, m), 3.12-3.18 (2H, m), 3.40-3.52 (2H, m), 3.57 (3H, s), 3.75-3.82 (2H, m), 4.18-4.23 (2H, m), 6.67 (2H, s), 7.36 (2H, d, J=8.6 Hz), 7.91 (2H, d, J=8.6 Hz), 12.60 (1H, brs).

LRMS (ESI$^+$) 397 [M+H]$^+$.

Compounds of the following Examples 2-2 to 2-38 were obtained in the same manner as in Example 2-1 by using corresponding starting materials and reactants. Their structures and spectrum data are shown in the following tables.

TABLE 101

| Example No. | Chemical Structural Formula | Spectrum Data |
|---|---|---|
| 2-2 | 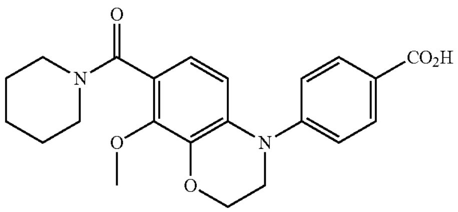 [SMILES: COc1c(C(=O)N2CCCCC2)ccc2c1OCCN2c1ccc(C(=O)O)cc1] | $^1$H NMR (400 MHz, DMSO-$d_6$) δ 1.33-1.55 (4H, m), 1.55-1.63 (2H, m), 3.13-3.21 (2H, m), 3.45-3.65 (2H, m), 3.74 (3H, s), 3.80 (2H, t, J = 4.3 Hz), 4.31 (2H, t, J = 4.3 Hz), 6.56 (1H, d, J = 8.6 Hz), 6.82 (1H, d, J = 8.6 Hz), 7.32 (2H, d, J = 8.6 Hz), 7.90 (2H, d, J = 8.6 Hz), 12.68 (1H, brs). LRMS (ESI$^+$) 397 [M + H]$^+$. |

TABLE 101-continued

| Example No. | Chemical Structural Formula | Spectrum Data |
|---|---|---|
| 2-3 | 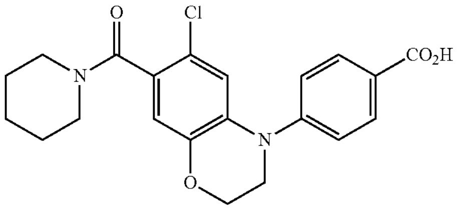 | $^1$H NMR (400 MHz, DMSO-$d_6$) δ 1.38-1.65 (6H, m), 3.17 (2H, t, J = 5.5 Hz), 3.45-3.65 (2H, m), 3.78-3.82 (2H, m), 4.30 (2H, t, J = 4.3 Hz), 6.82 (1H, s), 6.99 (1H, s), 7.38 (2H, d, J = 8.6 Hz), 7.95 (2H, d, J = 8.6 Hz), 12.77 (1H, brs). LRMS (ESI$^+$) 401 [M + H]$^+$. |
| 2-4 | 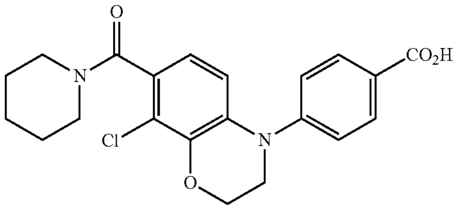 [SMILES: O=C(O)c1ccc(N2CCOc3c2ccc(C(=O)N2CCCCC2)c3Cl)cc1] | $^1$H NMR (400 MHz, DMSO-$d_6$) δ 1.35-1.65 (6H, m), 3.10-3.20 (2H, m), 3.55-3.62 (2H, m), 3.80-3.85 (2H, m), 4.34-4.42 (2H, m), 6.69 (1H, d, J = 8.6 Hz), 7.02 (1H, d, J = 8.6 Hz), 7.34 (2H, d, J = 8.6 Hz), 7.92 (2H, d, J = 8.6 Hz), 12.73 (1H, brs). LRMS (ESI$^+$) 401 [M + H]$^+$. |
| 2-5 | 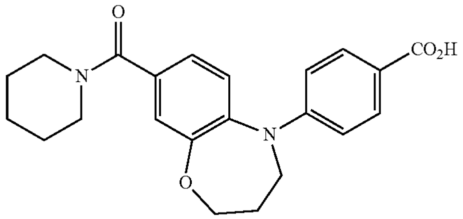 [SMILES: O=C(O)c1ccc(N2CCCOc3cc(C(=O)N4CCCCC4)ccc32)cc1] | $^1$H NMR (400 MHz, DMSO-$d_6$) δ 1.45-1.58 (4H, m), 1.58-1.67 (2H, m), 1.97-2.06 (2H, m), 3.25-3.65 (4H, m), 3.93 (2H, t, J = 5.5 Hz), 4.05 (2H, t, J = 5.5 Hz), 6.90 (2H, d, J = 9.2 Hz), 7.00-7.06 (2H, m), 7.22 (1H, d, J = 8.6 Hz), 7.76 (2 H, d, J = 9.2 Hz), 12.36 (1H, brs). LRMS (ESI$^+$) 381 [M + H]$^+$. |
| 2-6 | 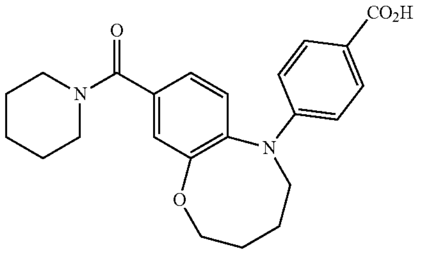 | $^1$H NMR (400 MHz, DMSO-$d_6$) δ 1.45-1.57 (4H, m), 1.57-1.67 (2H, m), 1.67-1.80 (4H, m), 3.25-3.65 (4H, m), 3.73-3.80 (2H, m), 4.10 (2H, t, J = 5.5 Hz), 6.65 (2H, d, J = 8.5 Hz), 7.11 (1H, dd, J = 7.9, 1.8 Hz), 7.15 (1H, d, J = 1.8 Hz), 7.20 (1H, d, J = 7.9 Hz), 7.73 (2H, d, J = 8.5 Hz), 12.24 (1H, brs). LRMS (ESI$^+$) 395 [M + H]$^+$. |

TABLE 102

| Example No. | Chemical Structural Formula | Spectrum Data |
|---|---|---|
| 2-7 | 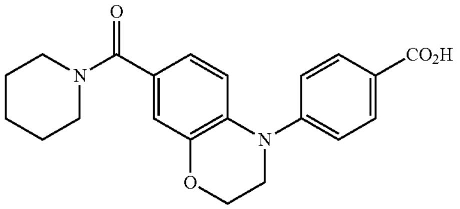 | $^1$H NMR (400 MHz, DMSO-$d_6$) δ 1.42-1.65 (6H, m), 3.35-3.55 (4H, m), 3.80 (2H, t, J = 4.8 Hz), 4.28 (2H, t, J = 4.8 Hz), 6.79 (1H, dd, J = 8.5, 1.8 Hz), 6.86 (1H, d, J = 2.4 Hz), 7.06 (1H, d, J = 8.5 Hz), 7.33 (2H, d, J = 8.5 Hz), 7.91 (2H, d, J = 8.5 Hz), 12.77 (1H, brs). LRMS (ESI$^+$) 367 [M + H]$^+$. |
| 2-8 | 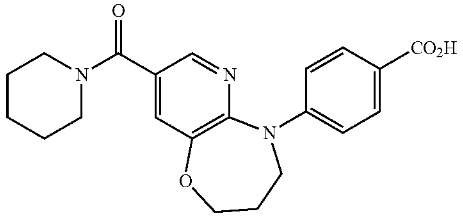 [SMILES: O=C(O)c1ccc(N2CCCOc3cc(C(=O)N4CCCCC4)cnc32)cc1] | $^1$H NMR (400 MHz, DMSO-$d_6$) δ 1.40-1.70 (6H, m), 1.95-2.12 (2H, m), 3.15-3.70 (4H, m), 3.97-4.09 (2H, m), 4.12-4.22 (2H, m), 7.19 (2H, d, J = 8.6 Hz), 7.38 (1H, s), 7.81 (2H, d, J = 8.6 Hz), 7.99 (1H, s), 12.51 (1H, brs) LRMS (ESI$^+$) 382 [M + H]$^+$. |

TABLE 102-continued

| Example No. | Chemical Structural Formula | Spectrum Data |
|---|---|---|
| 2-9 | 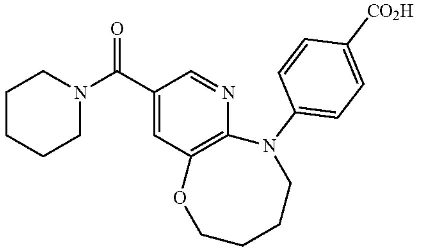 [SMILES: O=C(O)c1ccc(N2CCCCOc3cc(C(=O)N4CCCCC4)cnc32)cc1] | $^1$H NMR (400 MHz, DMSO-$d_6$) δ 1.47-1.66 (6H, m), 1.71-1.85 (4H, m), 3.35-3.60 (4H, m), 3.97-4.05 (2H, m), 4.15-4.24 (2H, m), 7.08 (2H, d, J = 8.5 Hz), 7.44 (1H, d, J = 2.4 Hz), 7.82 (2H, d, J = 8.5 Hz), 7.95 (1H, d, J = 2.4 Hz), 12.53 (1H, brs). LRMS (ESI$^+$) 396 [M + H]$^+$. |
| 2-10 | 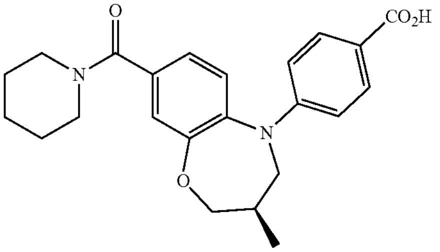 [SMILES: C[C@H]1COc2cc(C(=O)N3CCCCC3)ccc2N(c2ccc(C(=O)O)cc2)C1] | $^1$H NMR (400 MHz, DMSO-$d_6$) δ 0.93 (3H, d, J = 6.7 Hz), 1.42-1.68 (6H, m), 2.25-2.35 (1H, m), 3.20-3.65 (5H, m), 3.71 (1H, dd, J = 12.1, 6.1 Hz), 4.09 (1H, dd, J = 12.1, 4.2 Hz), 4.25 (1H, dd, J = 15.1, 4.2 Hz), 6.92 (2H, d, J = 8.5 Hz), 7.00-7.06 (2H, m), 7.20 (1H, d, J = 7.9 Hz), 7.76 (2H, d, J = 8.5 Hz), 12.36 (1H, brs). LRMS (ESI$^+$) 395 [M + H]$^+$. |
| 2-11 | 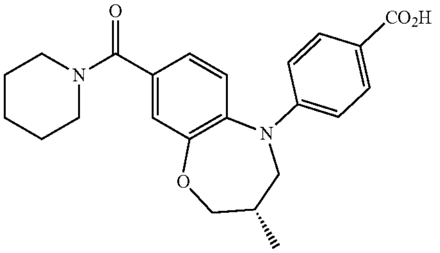 [SMILES: C[C@@H]1COc2cc(C(=O)N3CCCCC3)ccc2N(c2ccc(C(=O)O)cc2)C1] | $^1$H NMR (400 MHz, DMSO-$d_6$) δ 0.93 (3H, d, J = 7.3 Hz), 1.42-1.67 (6H, m), 2.25-2.35 (1H, m), 3.20-3.65 (5H, m), 3.71 (1H, dd, J = 12.2, 5.5 Hz), 4.09 (1H, dd, J = 12.2, 4.3 Hz), 4.24 (1H, dd, J = 15.3, 4.3 Hz), 6.92 (2H, d, J = 8.6 Hz), 7.02 (1H, dd, J = 7.9, 1.8 Hz), 7.04 (1H, d, J = 1.8 Hz), 7.20 (1H, d, J = 7.9 Hz), 7.76 (2H, d, J = 8.6 Hz), 12.35 (1H, brs). LRMS (ESI$^+$) 395 [M + H]$^+$. |

TABLE 103

| Example No. | Chemical Structural Formula | Spectrum Data |
|---|---|---|
| 2-12 | 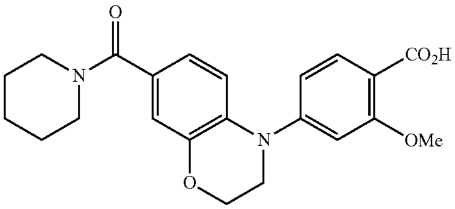 [SMILES: COc1cc(N2CCOc3cc(C(=O)N4CCCCC4)ccc32)ccc1C(=O)O] | $^1$H NMR (400 MHz, DMSO-$d_6$) δ 1.43-1.65 (6H, m), 3.40-3.55 (4H, m), 3.81 (3H, s), 3.72-3.85 (2H, m), 4.29 (2H, t, J = 4.9 Hz), 6.80 (1H, dd, J = 8.6, 1.8 Hz), 6.85-6.90 (2H, m), 6.92 (1H, d, J = 1.8 Hz), 7.10 (1H, d, J = 8.6 Hz), 7.69 (1H, d, J = 8.6 Hz), 12.30 (1H, brs). LRMS (ESI$^+$) 397 [M + H]$^+$. |
| 2-13 | 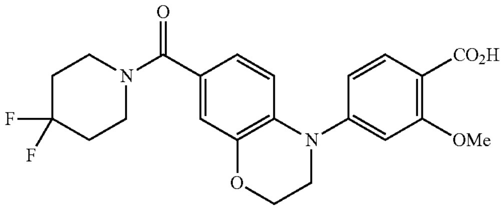 [SMILES: COc1cc(N2CCOc3cc(C(=O)N4CCC(F)(F)CC4)ccc32)ccc1C(=O)O] | $^1$H NMR (400 MHz, DMSO-$d_6$) δ 1.94-2.10 (4H, m), 3.52-3.65 (4H, m), 3.77-3.87 (2H, m), 3.81 (3H, s), 4.30 (2H, t, J = 4.9 Hz), 6.88 (2H, dd, J = 8.6, 1.8 Hz), 6.93 (1H, d, J = 1.8 Hz), 6.97 (1H, d, J = 1.8 Hz), 7.10 (1H, d, J = 8.6 Hz), 7.70 (1H, d, J = 8.6 Hz), 12.31 (1H, brs). LRMS (ESI$^+$) 433 [M + H]$^+$. |

TABLE 103-continued

| Example No. | Chemical Structural Formula | Spectrum Data |
|---|---|---|
| 2-14 | 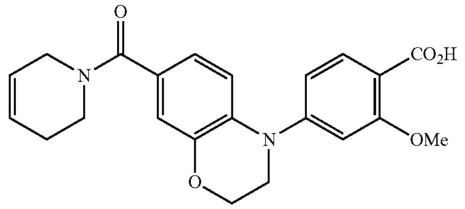 [SMILES: COc1cc(N2CCOc3cc(C(=O)N4CC=CCC4)ccc32)ccc1C(=O)O] | $^1$H NMR (400 MHz, DMSO-$d_6$) δ 2.10-2.18 (2H, m), 3.45-3.60 (2H, m), 3.78-3.85 (2H, m), 3.81 (3H, s), 3.95-4.03 (2H, m), 4.29 (2H, t, J = 4.9 Hz), 5.60-5.80 (1H, m), 5.80-5.90 (1, H, m), 6.84 (1H, dd, J = 8.6, 1.8 Hz), 6.88 (1H, dd, J = 8.6, 1.8 Hz), 6.91 (1H, d, J = 1.8 Hz), 6.93 (1H, d, J = 1.8 Hz), 7.10 (1H, d, J = 8.6 Hz), 7.69 (1H, d, J = 8.6 Hz), 12.37 (1H, brs). LRMS (ESI$^+$) 395 [M + H]$^+$. |
| 2-15 | 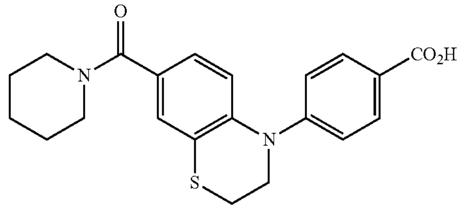 [SMILES: O=C(O)c1ccc(N2CCSc3cc(C(=O)N4CCCCC4)ccc32)cc1] | $^1$H NMR (400 MHz, DMSO-$d_6$) δ 1.43-1.53 (4H, m), 1.56-1.65 (2H, m), 3.13-3.20 (2H, m), 3.35-3.50 (4H, m), 3.95-4.00 (2H, m), 6.97 (2H, s), 7.17 (1H, s), 7.23 (2H, d, J = 9.1 Hz), 7.87 (2H, d, J = 9.1 Hz), 12.66 (1H, brs). LRMS (ESI$^-$) 381 [M − H]$^-$. |
| 2-16 | 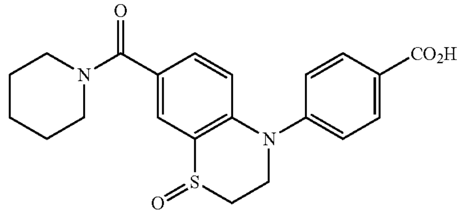 [SMILES: O=C(O)c1ccc(N2CCS(=O)c3cc(C(=O)N4CCCCC4)ccc32)cc1] | $^1$H NMR (400 MHz, DMSO-$d_6$) δ 1.43-1.56 (4H, m), 1.56-1.66 (2H, m), 3.12-3.30 (2H, m), 3.40-3.55 (4H, m), 3.90-4.00 (1H, m), 4.08-4.20 (1H, m), 6.80 (1H, d, J = 8.5 Hz), 7.32 (1H, dd, J = 8.5, 1.8 Hz), 7.49 (2H, d, J = 8.5 Hz), 7.63 ( 1H, d, J = 1.8 Hz), 8.03 (2H, d, J = 8.5 Hz), 13.01 (1H, brs) LRMS (ESI$^-$) 397 [M + H]$^-$. |
| 2-17 | 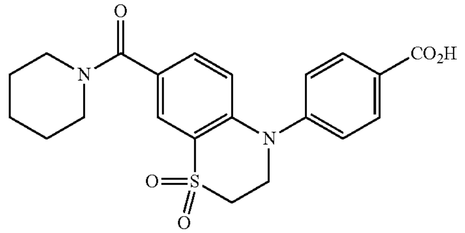 [SMILES: O=C(O)c1ccc(N2CCS(=O)(=O)c3cc(C(=O)N4CCCCC4)ccc32)cc1] | $^1$H NMR (400 MHz, DMSO-$d_6$) δ 1.44-1.55 (4H, m), 1.55-1.65 (2H, m), 3.35-3.50 (4H, m), 3.73-3.82 (2H, m), 4.20-4.28 (2H, m), 6.63 (1H, d, J = 8.5 Hz), 7.34 (1H, dd, J = 8.5, 1.8 Hz), 7.51 (2H, d, J = 8.5 Hz), 7.68 (1H, d, J = 1.8 Hz), 8.04 (2H, d, J = 8.5 Hz), 13.08 (1H, brs). LRMS (ESI$^-$) 413 [M + H]$^-$. |

TABLE 104

| Example No. | Chemical Structural Formula | Spectrum Data |
|---|---|---|
| 2-18 | 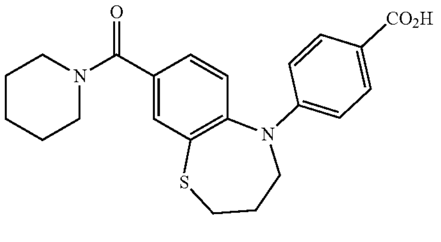 [SMILES: O=C(O)c1ccc(N2CCCSc3cc(C(=O)N4CCCCC4)ccc32)cc1] | $^1$H NMR (400 MHz, DMSO-$d_6$) δ 1.42-1.66 (6H, m), 2.05-2.12 (2H, m), 2.82-2.90 (2H, m), 3.20-3.45 (2H, m), 3.45-3.65 (2H, m), 3.83-3.95 (2H, m), 6.64 (2H, d, J = 8.5 Hz), 7.28-7.35 (2H, m), 7.54 (1H, d, J = 1.2 Hz), 7.73 (2H, d, J = 8.5 Hz), 12.26 (1H, brs). LRMS (ESI$^+$) 397 [M + H]$^+$. |
| 2-19 | 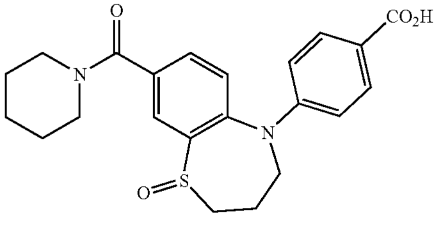 [SMILES: O=C(O)c1ccc(N2CCCS(=O)c3cc(C(=O)N4CCCCC4)ccc32)cc1] | $^1$H NMR (400 MHz, DMSO-$d_6$) δ 1.45-1.70 (6H, m), 1.90-2.00 (1H, m), 2.30-2.45 (1H, m), 2.95-3.06 (1H, m), 3.09-3.20 (1H, m), 3.25-3.45 (3H, m), 3.50-3.75 (2H, m), 4.14-4.25 (1H, m), 6.69 (2H, d, J = 9.1 Hz), 7.40 (1H, d, J = 8.5 Hz), 7.62 (1H, dd, J = 8.5, 1.8 Hz), 7.67 (1H, d, J = 1.8 Hz), 7.76 (2H, d, J = 9.1 Hz), 12.36 (1H, brs). LRMS (ESI$^+$) 413 [M + H]$^+$. |

TABLE 104-continued

| Example No. | Chemical Structural Formula | Spectrum Data |
| --- | --- | --- |
| 2-20 | 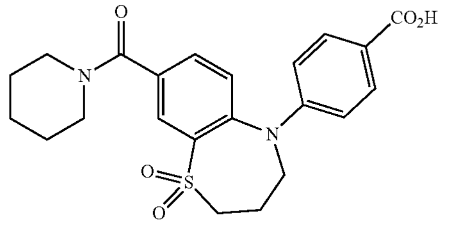 [SMILES: O=C(O)c1ccc(N2CCCS(=O)(=O)c3cc(C(=O)N4CCCCC4)ccc32)cc1] | $^1$H NMR (400 MHz, DMSO-$d_6$) δ 1.45-1.70 (6H, m), 2.00-2.17 (2H, m), 3.25-4.00 (8H, m), 6.71 (2H, d, J = 8.5 Hz), 7.55 (1H, d, J = 7.9 Hz), 7.71-7.83 (3H, m), 7.95 (1H, d, J = 1.8 Hz), 12.31 (1H, brs). LRMS (ESI$^+$) 429 [M + H]$^+$. |
| 2-21 | 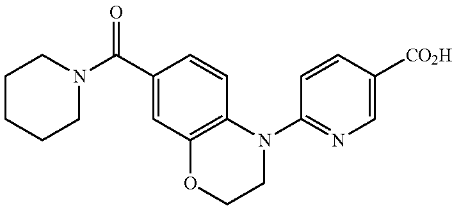 [SMILES: O=C(O)c1ccc(N2CCOc3cc(C(=O)N4CCCCC4)ccc32)nc1] | $^1$H NMR (400 MHz, DMSO-$d_6$) δ 1.39-1.65 (6H, in), 3.18-3.61 (4H, m), 4.09 (2H, t, J = 3.9 Hz), 4.27 (2H, t, J = 4.2 Hz), 6.86 (1H, dd, J = 8.5, 1.8 Hz), 6.90 (1H, d, J = 2.4 Hz), 7.28 (1H, d., J = 9.1 Hz), 7.50 (1H, d, J = 7.9 Hz), 8.07 (1H, dd, J = 8.8, 2.1 Hz), 8.76 (1H, d, J = 2.4 Hz). (COO H peak missing) LRMS (ESI$^+$) 368 [M + H]$^+$. |
| 2-22 | 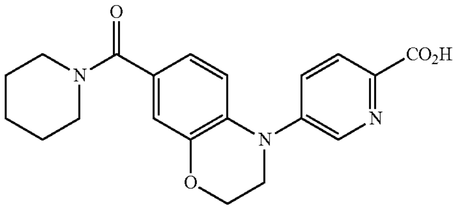 [SMILES: O=C(O)c1ccc(N2CCOc3cc(C(=O)N4CCCCC4)ccc32)cn1] | $^1$H NMR (400 MHz, DMSO-$d_6$) δ 1.42-1.53 (4H, m), 1.56-1.64 (2H, m), 3.28-3.54 (4H, mbrs), 3.84 (2H, t, J = 4.3 Hz), 4.29 (2H, t, J = 4.6 Hz), 6.80 (1H, dd, J = 8.6, 1.8 Hz), 6.88 (1H, d, J = 1.8 Hz), 7.06-7.12 (1H, m), 7.75 (1H, dd, J = 8.6, 2.4 Hz), 7.98 (1H, d, J = 8.6 Hz), 8.60 (1H, d, J = 2.4 Hz). (COOH peak missing) LRMS (ESI$^+$) 368 [M + H]$^+$. |

TABLE 105

| Example No. | Chemical Structural Formula | Spectrum Data |
| --- | --- | --- |
| 2-23 | 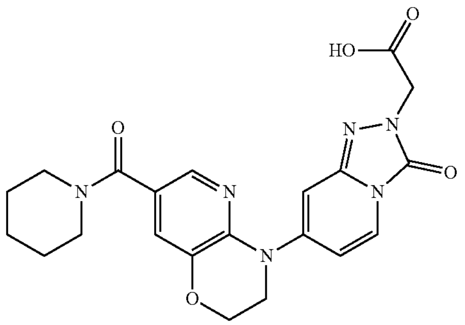 [SMILES: O=C(O)Cn1nc2cc(N3CCOc4cc(C(=O)N5CCCCC5)cnc43)ccn2c1=O] | $^1$H NMR (400 MHz, DMSO-$d_6$) δ 1.44-1.64 (6H, m), 3.27-3.55 (4H, m), 3.94 (2H, t, J = 4.3 Hz), 4.37 (2H, t, J = 4.6 Hz), 4.62 (2H, s), 6.89 (1H, d, J = 1.8 Hz), 7.00 (1H, dd, J = 7.6, 2.1 Hz), 7.21 (1H, d, J = 2.4 Hz), 7.76-7.80 (2H, m), 13.20 (1H, s). LRMS (ESI$^+$) 439 [M + H]$^+$. |
| 2-24 | 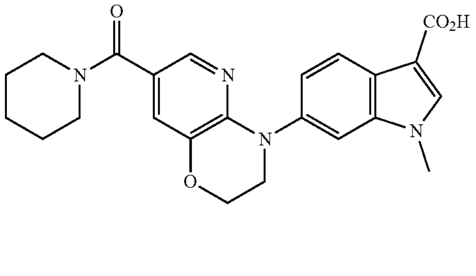 [SMILES: Cn1cc(C(=O)O)c2ccc(N3CCOc4cc(C(=O)N5CCCCC5)cnc43)cc21] | $^1$H NMR (400 MHz, DMSO-$d_6$) δ 1.43-1.65 (6H, m), 3.40-3.50 (4H, m), 3.82 (3H, s), 3.92-4.02 (2H, m), 4.38 (2H, t, J = 4.3 Hz), 7.09 (1H, d, J = 1.8 Hz), 7.21-7.27 (1H, m), 7.53 (1H, d, J = 1.8 Hz), 7.61 (1H, d, J = 2.4 Hz), 7.97 (1H, d, J = 7.9 Hz), 8.04 (1H, d, J = 7.9 Hz), 12.02 (1H, br s). LRMS (ESI$^+$) 421 [M + H]$^+$. |

TABLE 105-continued

| Example No. | Chemical Structural Formula | Spectrum Data |
| --- | --- | --- |
| 2-25 | 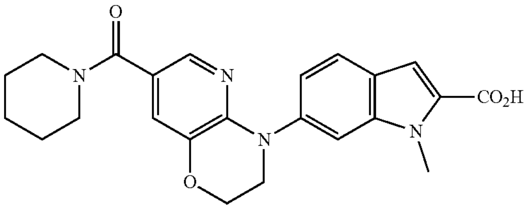 [SMILES: Cn1c(C(=O)O)cc2ccc(N3CCOc4cc(C(=O)N5CCCCC5)cnc43)cc21] | $^1$H NMR (400 MHz, DMSO-d$_6$) δ 1.42-1.65 (6H, m), 3.39-3.55 (4H, m), 3.95-4.03 (5H, m), 4.38 (2H, t, J = 4.3 Hz), 7.11 (1H, d, J = 2.4 Hz), 7.18-7.23 (2H, m), 7.54 (1H, s), 7.61-7.66 (2H, m), 12.86 (1H, br s).<br>LRMS (ESI$^+$) 421 [M + H]$^+$. |

TABLE 106

| Example No. | Chemical Structural Formula | Spectrum Data |
| --- | --- | --- |
| 2-26 | 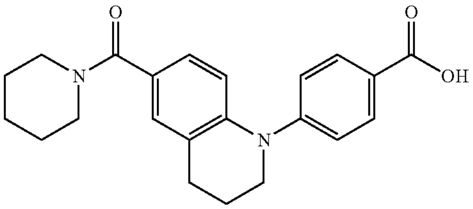 [SMILES: O=C(O)c1ccc(N2CCCc3cc(C(=O)N4CCCCC4)ccc32)cc1] | $^1$H NMR (400 MHz, DMSO-d$_6$) δ 1.42-1.55 (4H, m), 1.57-1.66 (2H, m), 1.91-2.01 (2H, m), 2.78 (2H, t, J = 6.1 Hz), 3.39-3.53 (4H, m), 3.67 (2H, t, J = 6.1 Hz), 6.93 (1H, d, J = 8.6 Hz), 7.02 (1H, dd, J = 8.6, 1.8 Hz), 7.14 (1H, d, J = 1.8 Hz), 7.31 (2H, d, J = 9.2 Hz), 7.89 (2H, d, J = 8.6 Hz), 12.67 (1H, br s).<br>LRMS (ESI$^+$) 365 [M + H]$^+$. |
| 2-27 | 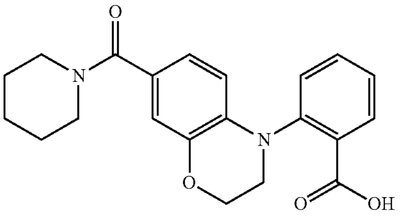 [SMILES: O=C(O)c1ccccc1N1CCOc2cc(C(=O)N3CCCCC3)ccc21] | $^1$H NMR (400 MHz, DMSO-d$_6$) δ 1.39-1.65 (6H, m), 3.38-3.47 (4H, m), 3.62-3.72 (2H, m), 4.29 (2H, t, J = 4.6 Hz), 6.18 (1 H, d, J = 7.9 Hz), 6.67 (1H, dd, J = 7.9, 1.8 Hz), 6.78 (1H, d, J = 1.8 Hz), 7.36-7.46 (2H, in), 7.64 (1H, t, J = 7.3 Hz), 7.82 (1H, d, J = 7.9 Hz), 12.94 (1H, br s).<br>LRMS (ESI$^+$) 367 [M + H]$^+$. |
| 2-28 | 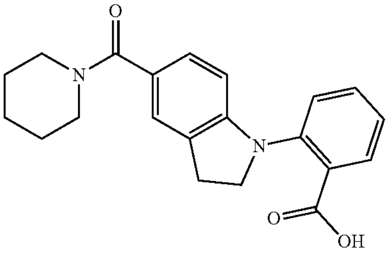 [SMILES: O=C(O)c1ccccc1N1CCc2cc(C(=O)N3CCCCC3)ccc21] | $^1$H NMR (400 MHz, DMSO-d$_6$) δ 1.42-1.67 (6H, m), 3.11 (2H, t, J = 8.6 Hz), 3.40-3.52 (4H, m), 3.95 (2H, t, J = 8.6 Hz), 6.32 (1H, d, J = 8.6 Hz), 7.00 (1H, dd, J = 8.6, 1.2 Hz), 7.16 (1H, d, J = 1.2 Hz), 7.25 (1H, td, J = 7.3, 1.2 Hz), 7.44 (1H, dd, J = 7.9, 1.2 Hz), 7.56 (1H, Id, J = 7.3, 1.8 Hz), 7.75 (1H, dd, J = 7.9, 1.8 Hz), 12.87 (1H, br s).<br>LRMS (ESI$^+$) 351 [M + H]$^+$. |

TABLE 107

| Example No. | Chemical Structural Formula | Spectrum Data |
| --- | --- | --- |
| 2-29 | 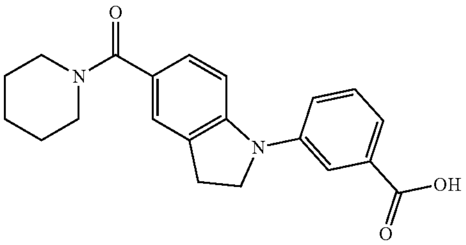 [SMILES: O=C(O)c1cccc(N2CCc3cc(C(=O)N4CCCCC4)ccc32)c1] | $^1$H NMR (400 MHz, DMSO-d$_6$) δ 1.42-1.67 (6H, m), 3.14 (2H, t, J = 8.6 Hz), 3.41-3.54 (4H, m), 4.03 (2H, t, J = 8.6 Hz), 7.08 (1H, d, J = 8.6 Hz), 7.14 (1H, dd, J = 8.6, 1.8 Hz), 7.23 (1H, s), 7.45-7.58 (3H, m), 7.79 (1H, s), 13.07 (1H, br s)<br>LRMS (ESI$^+$) 351 [M + H]$^+$. |

TABLE 107-continued

| Example No. | Chemical Structural Formula | Spectrum Data |
|---|---|---|
| 2-30 | 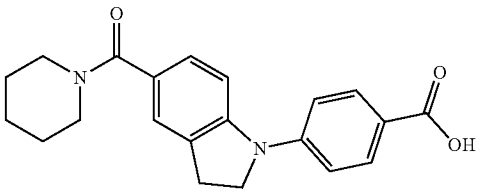 [SMILES: O=C(O)c1ccc(N2CCc3cc(C(=O)N4CCCCC4)ccc32)cc1] | $^1$H NMR (400 MHz, DMSO-d$_6$) δ 1.43-1.68 (6H, m), 3.15 (2H, t, J = 8.6 Hz), 3.40-3.55 (4H, m), 4.06 (2H, t, J = 8.6 Hz), 7.16 (1H, dd, J = 8.6, 1.8 Hz), 7.25 (1H, d, J = 1.2 Hz), 7.28 (1H, d, J = 7.9 Hz), 7.32 (2H, d, J = 9.2 Hz), 7.92 (2H, d, J = 8.6 Hz), 12.56 (1H, br s). LRMS (ESI$^+$) 351 [M + H]$^+$. |
| 2-31 | 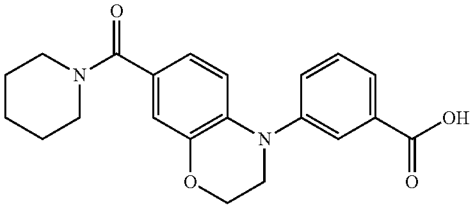 [SMILES: O=C(O)c1cccc(N2CCOc3cc(C(=O)N4CCCCC4)ccc32)c1] | $^1$H NMR (400 MHz, DMSO-d$_6$) δ 1.42-1.52 (4H, m), 1.55-1.63 (2H, m), 3.38-3.48 (4H, m), 3.75 (2H, t, J = 4.3 Hz), 4.28 (2 H, t, J = 4.3 Hz), 6.75 (1H, dd, J = 8.6, 1.8 Hz), 6.80-6.84 (2H, m), 7.48-7.55 (2H, m), 7.65-7.69 (1H, m), 7.79 (1H, d, J = 1.8 Hz), 13.11 (1H, s). LRMS (ESI$^+$) 367 [M + H]$^+$. |
| 2-32 | 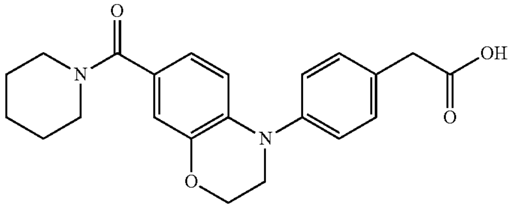 [SMILES: O=C(O)Cc1ccc(N2CCOc3cc(C(=O)N4CCCCC4)ccc32)cc1] | $^1$H NMR (400 MHz, DMSO-d$_6$) δ 1.42-1.51 (4H, m), 1.54-1.63 (2H, m), 3.37-3.48 (4H, m), 3.55 (2H, s), 3.69 (2H, t, J = 4.3 Hz), 4.27 (2H, t, J = 4.3 Hz), 6.72 (2H, s), 6.80 (1H, s), 7.21-7.24 (2H, m), 7.28 (2H, d, J = 8.6 Hz), 12.26 (1H, s). LRMS (ESI$^+$) 381 [M + H]$^+$. |
| 2-33 | 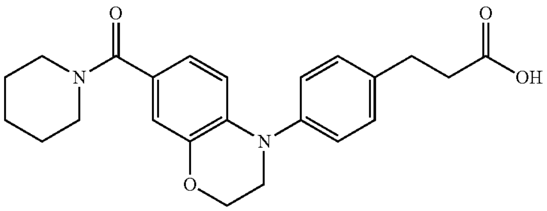 [SMILES: O=C(O)CCc1ccc(N2CCOc3cc(C(=O)N4CCCCC4)ccc32)cc1] | $^1$H NMR (400 MHz, DMSO-d$_6$) δ 1.42-1.51 (4H, m), 1.54-1.63 (2H, m), 2.54 (2H, t, J = 7.6 Hz), 2.81 (2H, t, J = 7.6 Hz), 3.38-3.48 (4H, m), 3.67 (2H, t, J = 4.2 Hz), 4.27 (2H, t, J = 4.2 Hz), 6.67 (1H, d, J = 8.5 Hz), 6.72 (1H, dd, J = 8.5, 1.8 Hz), 6.79 (1H, d, J = 1.8 Hz), 7.19 (2H, d, J = 8.5 Hz), 7.26 (2H, d, J = 8.5 Hz), 12.13 (1H, s). LRMS (ESI$^+$) 395 [M + H]$^+$. |
| 2-34 | 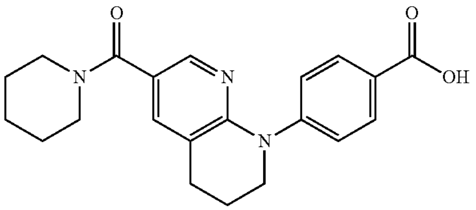 [SMILES: O=C(O)c1ccc(N2CCCc3cc(C(=O)N4CCCCC4)cnc32)cc1] | $^1$H NMR (400 MHz, DMSO-d$_6$) δ 1.41-1.69 (6H, m), 1.94-2.07 (2H, m), 2.85 (2H, t, J = 6.4 Hz), 3.22-3.60 (4H, m), 3.81 (2 H, t, J = 5.4 Hz), 7.37-7.53 (3H, m), 7.85-7.97 (3H, m), 12.58-12.92 (1H, m). LRMS (ESI$^+$) 366 [M + H]$^+$. |

TABLE 108

| Example No. | Chemical Structural Formula | Spectrum Data |
|---|---|---|
| 2-35 | 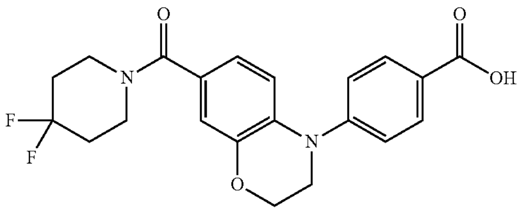 [SMILES: O=C(O)c1ccc(N2CCOc3cc(C(=O)N4CCC(F)(F)CC4)ccc32)cc1] | $^1$H NMR (400 MHz, DMSO-d$_6$) δ 1.94-2.07 (4H, m), 3.51-3.63 (4H, m), 3.79 (2H, t, J = 4.2 Hz), 4.28 (2H, t, J = 4.2 Hz), 6.86 (1H, dd, J = 8.5, 1.8 Hz), 6.96 (1H, d, J = 1.8 Hz), 7.07 (1H, d, J = 8.5 Hz), 7.31-7.36 (2H, m), 7.89-7.93 (2H, m), 12.59-12.92 (1H, m). LRMS (ESI$^+$) 403 [M + H]$^+$. |

TABLE 108-continued

| Example No. | Chemical Structural Formula | Spectrum Data |
|---|---|---|
| 2-36 | 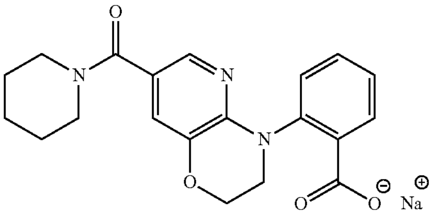 [SMILES: O=C([O-])c1ccccc1N1CCOc2cc(C(=O)N3CCCCC3)cnc21 ; [Na+]] | $^1H$ NMR (400 MHz, DMSO-$d_6$) δ 1.40-1.64 (6H, m), 3.39-3.48 (4H, m), 3.77-3.89 (2H, m), 4.27 (2H, t, J = 4.3 Hz), 6.92 (1H, d, J = 1.8 Hz), 7.09-7.22 (3H, m), 7.48 (1H, d, J = 2.4 Hz), 7.57 (1H, dd, J = 7.6, 2.1 Hz). LRMS (ESI$^+$) 368 [M + H]$^+$. |
| 2-37 | 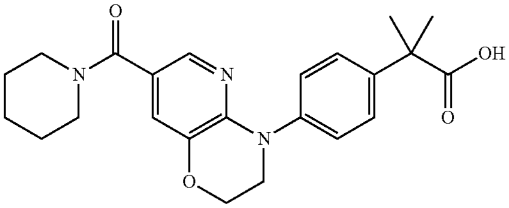 [SMILES: CC(C)(C(=O)O)c1ccc(N2CCOc3cc(C(=O)N4CCCCC4)cnc32)cc1] | $^1H$ NMR (400 MHz, DMSO-$d_6$) δ 1.26-1.70 (12H, m), 3.00-3.65 (4H, m), 3.85 (2H, t, J = 4.3 Hz), 4.31 (2H, t, J = 4.3 Hz), 7.05 (1H, d, J = 1.8 Hz), 7.17-7.22 (2H, m), 7.32-7.37 (2H, m), 7.62 (1H, d, J = 1.8 Hz). (COOH peak missing) LRMS (ESI$^+$) 410 [M + H]$^+$. |
| 2-38 | 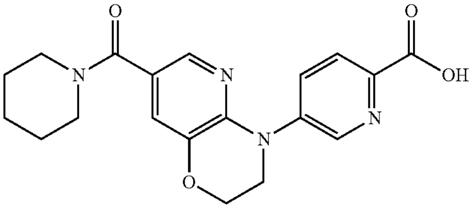 [SMILES: O=C(O)c1ccc(N2CCOc3cc(C(=O)N4CCCCC4)cnc32)cn1] | $^1H$ NMR (400 MHz, DMSO-$d_6$) δ 1.36-1.68 (6H, m), 3.09-3.67 (4H, m), 3.92-4.00 (2H, m), 4.32-4.40 (2H, m), 7.15 (1H, s), 7.67 (1H, s), 7.85 (1H, d, J = 8.6 Hz), 7.95 (1H, d, J = 8.6 Hz), 8.60 (1H, s). (COOH peak missing) LRMS (ESI$^+$) 369 [M + H]$^+$. |

Example 3-1

[Formula 158]

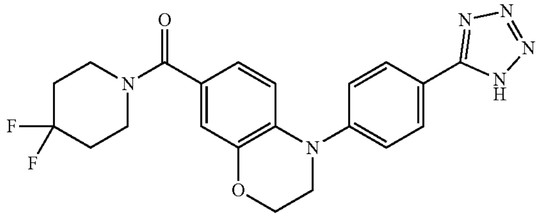

(4-(4-(1H-Tetrazol-5-yl)phenyl)-3,4-dihydro-2H-benzo[b][1,4]oxazin-7-yl)(4,4-difluoropiperidin-1-yl)methanone To a solution of (4,4-difluoropiperidin-1-yl)(3,4-dihydro-2H-benzo[b][1,4]oxazin-7-yl)methanone (56.5 mg) in toluene (2 mL), 5-(4-bromophenyl)-1H-tetrazole (67.6 mg), bis(tri-tert-butylphosphine)palladium (0) (10.5 mg) and sodium tert-butoxide (58.0 mg) were added at room temperature, followed by stirring under heating at 100° C. for 3 hours. The resultant reaction mixture was cooled to room temperature, and a 6 mol/L hydrogen chloride aqueous solution was added to the resultant reaction solution to adjust pH to 4. The resultant mixture was concentrated under reduced pressure, and the thus obtained residue was purified by silica gel column chromatography (chloroform:methanol=9:1) to obtain the title compound (22.0 mg).

$^1H$ NMR (400 MHz, $CDCl_3$) δ 1.85-2.10 (4H, m), 3.40-3.90 (7H, m), 4.05-4.20 (2H, m), 6.65-7.05 (5H, m), 7.75-7.90 (2H, m).

LRMS (ESI$^-$) 425 [M−H]$^-$.

Example 4-1

[Formula 159]

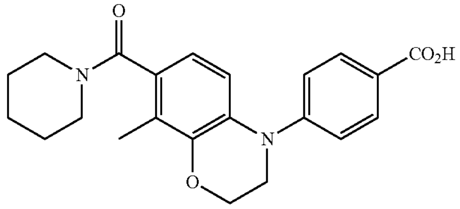

4-(8-Methyl-7-(piperidine-1-carbonyl)-2,3-dihydro-4H-benzo[b][1,4]oxazin-4-yl)benzoic Acid To a solution of tert-butyl 4-(8-methyl-7-(piperidine-1-carbonyl)-2,3-dihydro-4H-benzo[b][1,4]oxazin-4-yl)benzoate (30.1 mg) in dichloromethane (1.0 mL), trifluoroacetic acid (0.5 ml) was added. After stirring at room temperature for 4 hours, the resultant reaction solution was concentrated under reduced pressure to obtain the title compound (23.9 mg).

$^1H$ NMR (400 MHz, DMSO-$d_6$) δ: 1.30-1.45 (2H, m), 1.47-1.62 (4H, m), 2.03 (3H, s), 3.30-3.63 (4H, m), 3.74-3.81 (2H, m), 4.29 (2H, t, J=4.3 Hz), 6.55 (1H, d, J=8.6 Hz), 6.94 (1H, d, J=7.9 Hz), 7.26-7.31 (2H, m), 7.85-7.91 (2H, m), 12.61 (1H, s).

LRMS (ESI$^+$) 381 [M+H]$^+$.

Compounds of the following Examples 4-2 to 4-21 were obtained in the same manner as in Example 4-1 by using corresponding starting materials and reactants. Their structures and spectrum data are shown in the following tables.

TABLE 109

| Reference Example No. | Chemical Structural Formula | Spectrum Data |
|---|---|---|
| 4-2 | 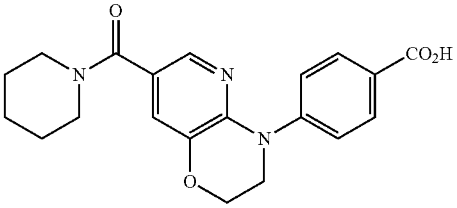 [SMILES: O=C(O)c1ccc(N2CCOc3cc(C(=O)N4CCCCC4)cnc32)cc1] | $^1$H NMR (400 MHz, $CDCl_3$) δ 1.40-1.65 (6H, m), 3.27-3.56 (4H, m), 3.96 (2H, t, J = 4.2 Hz), 4.35 (2H, t, J = 4.5 Hz), 7.17 (1H, d, J = 2.4 Hz), 7.52-7.57 (2H, m), 7.71 (1H, d, J = 1.8 Hz), 7.89-7.93 (2H, m), 12.71 (1H, brs). LRMS (ESI$^+$) 368 [M + H]$^+$. |
| 4-3 | 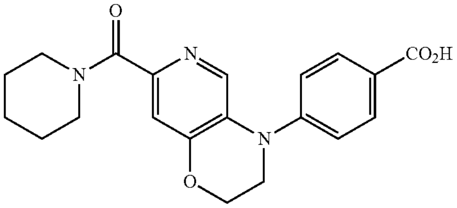 [SMILES: O=C(O)c1ccc(N2CCOc3cc(C(=O)N4CCCCC4)ncc32)cc1] | $^1$H NMR (400 MHz, $CDCl_3$) δ 1.40-1.63 (6H, m), 3.40-3.47 (2H, m), 3.51-3.57 (2H, m), 3.81 (2H, t, J = 4.2 Hz), 4.36 (2H, t, J = 4.2 Hz), 7.03 (1H, s), 7.32 (2H, d, J = 8.5 Hz), 7.91 (2H, d, J = 8.5 Hz), 8.15 (1H, s). (COOH peak missing) LRMS (ESI$^+$) 366 [M + H]$^+$. |
| 4-4 | 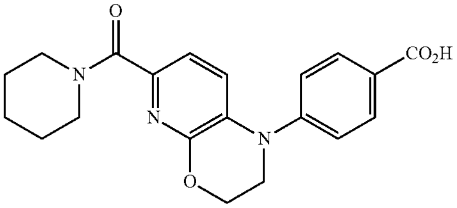 [SMILES: O=C(O)c1ccc(N2CCOc3nc(C(=O)N4CCCCC4)ccc32)cc1] | $^1$H NMR (400 MHz, $CDCl_3$) δ 1.41-1.65 (6H, m), 3.42-3.59 (4H, m), 3.81 (2H, t, J = 4.3 Hz), 4.43 (2H, t, J = 4.3 Hz), 7.04 (1H, d, J = 7.9 Hz), 7.37 (2H, d, J = 8.6 Hz), 7.44 (1H, d, J = 7.9 Hz), 7.94 (2H, d, J = 8.6 Hz), 12.79 (1H, brs). LRMS (ESI$^+$) 368 [M + H]$^+$. |

TABLE 110

| Example No. | Chemical Structural Formula | Spectrum Data |
|---|---|---|
| 4-5 | 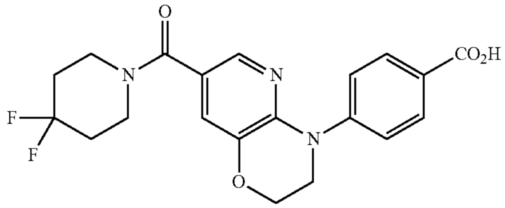 [SMILES: O=C(O)c1ccc(N2CCOc3cc(C(=O)N4CCC(F)(F)CC4)cnc32)cc1] | $^1$H NMR (400 MHz, DMSO-$d_6$) δ: 1.96-2.08 (4H, m), 3.52-3.65 (4H, m), 3.96 (2H, t, J = 4.3 Hz), 4.35 (2H, t, J = 4.6 Hz), 7.25 (1H, d, J = 1.8 Hz), 7.51-7.56 (2H, m), 7.79 (1H, d, J = 1.8 Hz), 7.89-7.94 (2H, m), 12.74 (1H, s). LRMS (ESI$^+$) 404 [M + H]$^+$. |
| 4-6 | 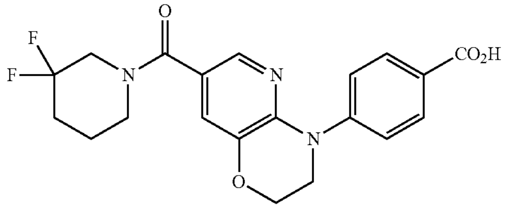 [SMILES: O=C(O)c1ccc(N2CCOc3cc(C(=O)N4CCCC(F)(F)C4)cnc32)cc1] | $^1$H NMR (400 MHz, DMSO-$d_6$) δ: 1.64-1.73 (2H, m), 2.01-2.14 (2H, m), 3.45-3.60 (2H, m), 3.82 (2H, t, J = 11.3 Hz), 3.97 (2H, t, J = 4.3 Hz), 4.36 (2H, t, J = 4.0 Hz), 7.17 (1H, d, J = 2.4 Hz), 7.55 (2H, d, J = 8.6 Hz), 7.73 (1H, d, J = 1.8 Hz), 7.92 (2H, d, J = 8.6 Hz), 12.76 (1H, s). LRMS (ESI$^+$) 404 [M + H]$^+$. |
| 4-7 | 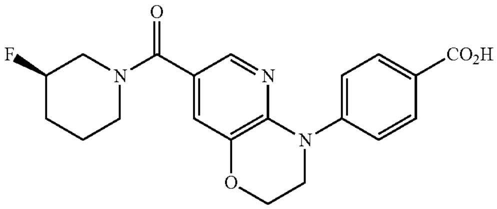 [SMILES: O=C(O)c1ccc(N2CCOc3cc(C(=O)N4CCC[C@@H](F)C4)cnc32)cc1] | $^1$H NMR (400 MHz, DMSO-$d_6$) δ: 1.43-1.94 (4H, m), 3.00-3.58 (3H, m), 3.84 (1H, s), 3.96 (2H, t, J = 4.3 Hz), 4.35 (2H, t, J = 4.3 Hz), 4.75 (1H, d, J = 47.1 Hz), 7.16 (1H, d, J = 1.8 Hz), 7.53 (2H, d, J = 8.6 Hz), 7.72 (1H, d, J = 2.4 Hz), 7.91 (2H, d, J = 8.6 Hz), 12.77 (1H, s). LRMS (ESI$^+$) 386 [M + H]$^+$. |

TABLE 110-continued

| Example No. | Chemical Structural Formula | Spectrum Data |
|---|---|---|
| 4-8 | 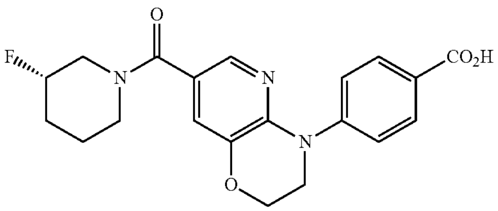 | $^1$H NMR (400 MHz, DMSO-$d_6$) δ: 1.42-1.97 (4H, m), 3.00-3.58 (3H, m), 3.72-4.03 (3H, m), 4.35 (2H, t, J = 4.6 Hz), 4.75 (1H, d, J = 47.7 Hz), 7.16 (1H, d, J = 1.8 Hz), 7.88-7.94 (2H, m), 7.72 (1H, d, J = 1.8 Hz), 7.90-7.92 (2H, m), 12.77 (1H, s).<br>LRMS (ESI$^+$) 386 [M + H]$^+$. |
| 4-9 | 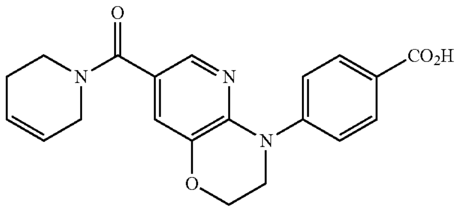 [SMILES: O=C(O)c1ccc(N2CCOc3cc(C(=O)N4CC=CCC4)cnc32)cc1] | $^1$H NMR (400 MHz, DMSO-$d_6$) δ: 2.10-2.18 (2H, m), 3.42-3.65 (2H, m), 3.93-4.04 (4H, m), 4.35 (2H, t, J = 4.2 Hz), 5.62-5.76 (1H, m), 5.80-5.88 (1H, m), 7.20 (1H, d, J = 1.8 Hz), 7.54 (2H, d, J = 8.5 Hz), 7.76 (1H, d, J = 1.8 Hz), 7.91 (2 H, d, J = 8.5 Hz), 12.76 (1H, s).<br>LRMS (ESI$^+$) 366 [M + H]$^+$. |
| 4-10 | 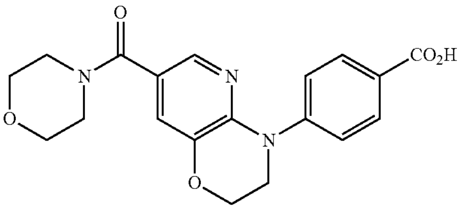 [SMILES: O=C(O)c1ccc(N2CCOc3cc(C(=O)N4CCOCC4)cnc32)cc1] | $^1$H NMR (400 MHz, DMSO-$d_6$) δ: 3.40-3.56 (8H, m), 3.90 (2H, t, J = 4.6 Hz), 4.29 (2H, t, J = 4.3 Hz), 7.16 (1H, d, J = 2.4 Hz), 7.46-7.51 (2H, m), 7.70 (1H, d, J = 1.8 Hz), 7.83-7.88 (2H, m). (COOH peak missing)<br>LRMS (ESI$^+$) 370 [M + H]$^+$. |

TABLE 111

| Example No. | Chemical Structural Formula | Spectrum Data |
|---|---|---|
| 4-11 | 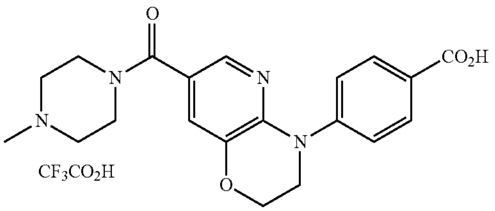 [SMILES: "CF3CO2H" ; CN1CCN(C(=O)c2cnc3c(c2)OCCN3c2ccc(C(=O)O)cc2)CC1]<br>$CF_3CO_2H$ | $^1$H NMR (400 MHz, DMSO-$d_6$) δ: 2.77 (3H, s), 2.91-3.64 (8 H, m), 3.97 (2H, t, J = 4.3 Hz), 4.36 (2H, t, J = 4.3 Hz), 7.25 (1H, d, J = 2.4 Hz), 7.53-7.59 (2H, m), 7.81 (1H, d, J = 1.8 Hz), 7.90-7.96 (2H, in), 9.83 (1H, s), 12.75 (1H, s).<br>LRMS (ESI$^+$) 383 [M + H]$^+$. |
| 4-12 | 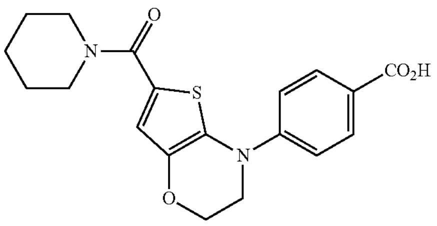 [SMILES: O=C(O)c1ccc(N2CCOc3cc(C(=O)N4CCCCC4)sc32)cc1] | $^1$H NMR (400 MHz, DMSO-$d_6$) δ 1.45-1.65 (6H, m), 3.55-3.62 (4H, m), 3.83 (2H, t, J = 4.0 Hz), 4.30 (2H, t, J = 4.3 Hz), 7.05 (1H, s), 7.38-7.43 (2H, m), 7.89-7.94 (2H, m). (CO OH peak missing)<br>LRMS (ESI$^+$) 373 [M + H]$^+$. |
| 4-13 | 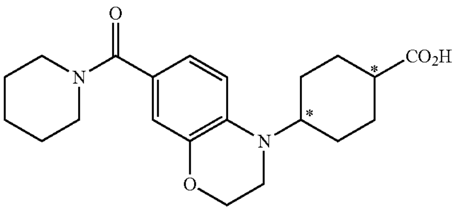 [SMILES: O=C(O)C1CCC(N2CCOc3cc(C(=O)N4CCCCC4)ccc32)CC1] | $^1$H NMR (400 MHz, DMSO-$d_6$) δ: 1.40-1.67 (12H, m), 2.06-2.16 (2H, m), 2.56-2.62 (1H, m), 3.19 (2H, t, J = 4.2 Hz), 3.34-3.56 (4H, m), 3.62-3.72 (1H, m), 4.10 (2H, t, J = 4.5), 6.67 (1H, d, J = 1.8 Hz), 6.75-6.84 (2H, m), 12.18 (1H, s)<br>LRMS (ESI$^+$) 373 [M + H]$^+$. |

TABLE 111-continued

| Example No. | Chemical Structural Formula | Spectrum Data |
|---|---|---|
| 4-14 | 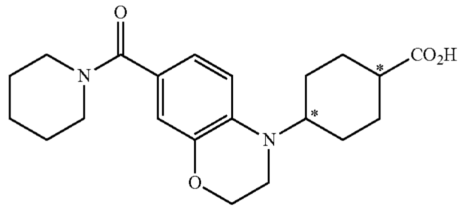 [SMILES: O=C(O)C1CCC(N2CCOc3cc(C(=O)N4CCCCC4)ccc32)CC1] | $^1$H NMR (400 MHz, DMSO-$d_6$) δ: 1.41-1.63 (10H, m), 1.64-1.77 (2H, m), 1.91-2.02 (2H, m), 2.13-2.23 (1H, m), 3.25 (2 H, t, J = 4.2 Hz), 3.30-3.53 (4H, m), 3.60-3.70 (1H, m), 4.11 (2H, t, J = 4.2 Hz), 6.67 (1H, s), 6.80 (2H, s), 12.07 (1H, s). LRMS (ESI$^+$) 373 [M + H]$^+$. |
| 4-15 | 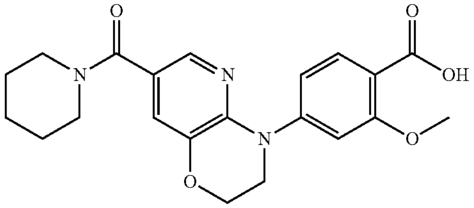 [SMILES: COc1cc(N2CCOc3cc(C(=O)N4CCCCC4)cnc32)ccc1C(=O)O] | $^1$H NMR (400 MHz, DMSO-$d_6$) δ 1.42-1.65 (6H, m), 3.42-3.58 (4H, m), 3.81 (3H, s), 3.98 (2H, t, J = 4.3 Hz), 4.36 (2H t, J = 4.3 Hz), 7.07 (1H, dd, J = 8.3, 2.1 Hz), 7.17 (1H, d, J = 1.8 Hz), 7.20 (1H, d, J = 1.8 Hz), 7.69 (1H, d, J = 8.6 Hz), 7.74 (1H, d, J = 1.8 Hz), 12.35 (1H, br s). LRMS (ESI$^+$) 398 [M + H]$^+$. |

TABLE 112

| Example No. | Chemical Structural Formula | Spectrum Data |
|---|---|---|
| 4-16 | 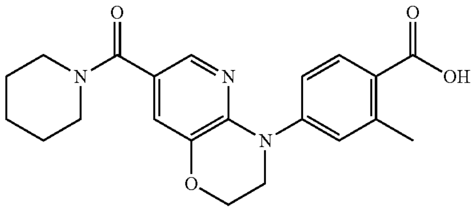 [SMILES: Cc1cc(N2CCOc3cc(C(=O)N4CCCCC4)cnc32)ccc1C(=O)O] | $^1$H NMR (400 MHz, DMSO-$d_6$) δ 1.42-1.66 (6H, m), 2.54 (3H, s), 3.41-3.62 (4H, m), 3.94 (2H, t, J = 4.3 Hz), 4.34 (2H, t, J = 4.6 Hz), 7.16 (1H, d, J = 1.8 Hz), 7.32-7.39 (2H, m), 7.72 (1H, d, J = 1.8 Hz), 7.85 (1H, d, J = 7.9 Hz), 12.60 (1H, br s). LRMS (ESI$^+$) 382 [M + H]$^+$. |
| 4-17 | 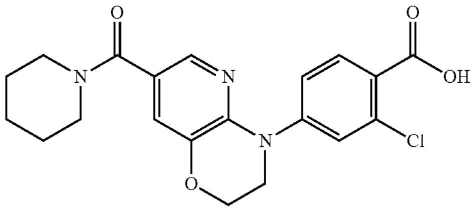 [SMILES: O=C(O)c1ccc(N2CCOc3cc(C(=O)N4CCCCC4)cnc32)cc1Cl] | $^1$H NMR (400 MHz, DMSO-$d_6$) δ 1.43-1.67 (6H, m), 3.41-3.65 (4H, m), 3.97 (2H, t, J = 4.3 Hz), 4.35 (2H, t, J = 4.3 Hz), 7.20 (1H, d, J = 1.8 Hz), 7.50 (1H, dd, J = 8.6, 1.8 Hz), 7.65 (1H, d, J = 2.4 Hz), 7.76 (1H, d, J = 1.8 Hz), 7.85 (1H, d, J = 8.6 Hz), 13.12 (1H, br s). LRMS (ESI$^+$) 402 [M + H]$^+$. |
| 4-18 | 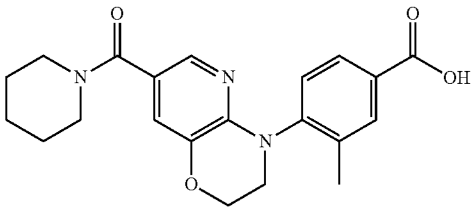 [SMILES: Cc1cc(C(=O)O)ccc1N1CCOc2cc(C(=O)N3CCCCC3)cnc21] | $^1$H NMR (400 MHz, DMSO-$d_6$) δ 1.41-1.64 (6H, m), 2.17 (3H, s), 3.37-3.53 (4H, m), 3.60-4.05 (2H, m), 4.30-4.48 (2H, m), 7.10 (1H, d, J = 1.8 Hz), 7.39 (1H, d, J = 7.9 Hz), 7.60 (1H, d, J = 1.8 Hz), 7.82 (1H, dd, J = 8.3, 2.1 Hz), 7.87 (1H, d, J = 1.8 Hz), 12.89 (1H, br s). LRMS (ESI$^+$) 382 [M + H]$^+$. |
| 4-19 | 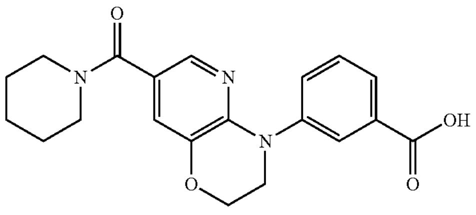 [SMILES: O=C(O)c1cccc(N2CCOc3cc(C(=O)N4CCCCC4)cnc32)c1] | $^1$H NMR (400 MHz, DMSO-$d_6$) δ 1.44-1.54 (4H, m), 1.55-1.63 (2H, m), 3.37-3.50 (4H, m), 3.94 (2H, t, J = 4.3 Hz), 4.35 (2 H, t, J = 4.3 Hz), 7.12 (1H, d, J = 1.8 Hz), 7.48 (1H, t, J = 7.6 Hz), 7.67 (2H, dd, J = 6.4, 1.5 Hz), 7.70 (1H, dt, J = 7.7, 1.4 Hz), 7.94 (1H, t, J = 1.8 Hz), 13.01 (1H, s). LRMS (ESI$^+$) 368 [M + H]$^+$. |

TABLE 112-continued

| Example No. | Chemical Structural Formula | Spectrum Data |
|---|---|---|
| 4-20 | 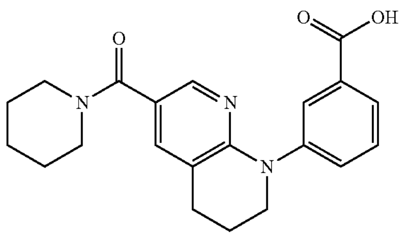 [SMILES: O=C(O)c1cccc(N2CCCc3cc(C(=O)N4CCCCC4)cnc32)c1] | $^1$H NMR (400 MHz, DMSO-$d_6$) δ 1.41-1.67 (6H, m), 1.96-2.08 (2H, m), 2.86 (2H, t, J = 6.1 Hz), 3.39-3.57 (4H, m), 3.78 (2 H, t, J = 5.4 Hz), 7.38 (1H, d, J = 2.4 Hz), 7.48 (1H, t, J = 7.9 Hz), 7.54-7.60 (1H, m), 7.70-7.75 (1H, m), 7.81-7.87 (2H, m), 13.04 (1H, br s). LRMS (ESI$^+$) 366 [M + H]$^+$. |
| 4-21 | 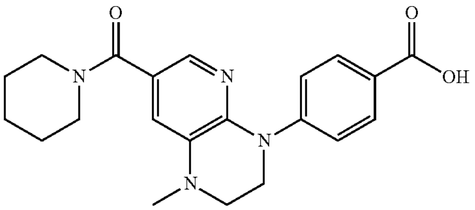 [SMILES: CN1CCN(c2ccc(C(=O)O)cc2)c2ncc(C(=O)N3CCCCC3)cc21] | $^1$H NMR (400 MHz, DMSO-$d_6$) δ 1.42-1.65 (6H, m), 2.89 (3 H, s), 3.35-3.52 (6H, m), 3.89-3.94 (2H, m), 6.79 (1H, d, J = 1.8 Hz), 7.39 (1H, d, J = 1.8 Hz), 7.42-7.47 (2H, m), 7.85-7.90 (2H, m), 12.67 (1H, s). LRMS (ESI$^+$) 381 [M + H]$^+$. |

Example 5-1

[Formula 160]

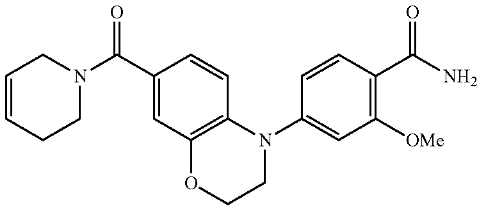

2-Methoxy-4-(7-(1,2,3,6-tetrahydropyridine-1-carbonyl)-2,3-dihydro-4H-benzo[b][1,4]oxazin-4-yl) benzamide A mixture of 2-methoxy-4-(7-(1,2,3,6-tetrahydropyridine-1-carbonyl)-2,3-dihydro-4H-benzo[b][1,4]oxazin-4-yl)benzoic acid (50.0 mg) and thionyl chloride (0.5 mL) was stirred at room temperature for 12 hours. The resultant reaction solution was concentrated under reduced pressure, and to the thus obtained residue, tetrahydrofuran (1 mL) was added, and then a 7 mol/L methanol solution (2 mL) of ammonia was added at room temperature. The resultant mixture was stirred at room temperature for 5 hours, the resultant was concentrated under reduced pressure, and the thus obtained residue was purified by silica gel column chromatography (ethyl acetate/methanol=10:1) to obtain the title compound (11.2 mg).

$^1$H NMR (400 MHz, $CDCl_3$) δ 2.17-2.27 (2H, m), 3.50-3.75 (2H, m), 3.79 (2H, t, J=4.3 Hz), 3.92 (3H, s), 4.00-4.25 (2H, m), 4.32 (2H, t, J=4.3 Hz), 5.60-5.80 (2H, m), 5.83-5.91 (1H, m), 6.83-6.94 (3H, m), 7.01 (1H, d, J=1.8 Hz), 7.14 (1H, d, J=8.5 Hz), 7.62 (1H, brs), 8.20 (1H, d, J=8.5 Hz).

LRMS (ESI$^+$) 394 [M+H]$^+$.

Compounds of the following Examples 5-2 to 5-3 were obtained in the same manner as in Example 5-1 by using corresponding starting materials and reactants. Their structures and spectrum data are shown in the following tables.

TABLE 113

| Example No. | Chemical Structural Formula | Spectrum Data |
|---|---|---|
| 5-2 | 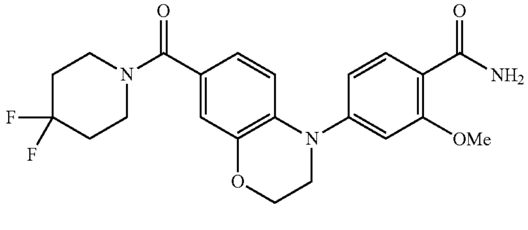 [SMILES: COc1cc(N2CCOc3cc(C(=O)N4CCC(F)(F)CC4)ccc32)ccc1C(N)=O] | $^1$H NMR (400 MHz, $CDCl_3$) δ 1.94-2.10 (4H, m), 3.65-3.80 (4H, m), 3.79 (2H, t, J = 4.9 Hz), 3.93 (3H, s), 4.33 (2H, t, J = 4.9 Hz), 5.73 (1H, brs), 6.85 (1H, d, J = 1.2 Hz), 6.86-6.93 (2H, m), 7.00 (1H, d, J = 1.2 Hz), 7.13 (1H, d, J = 8.6 Hz), 7.62 (1H, brs), 8.21 (1H, d, J = 8.6 Hz). LRMS (ESI$^+$) 432 [M + H]$^+$. |

TABLE 113-continued

| Example No. | Chemical Structural Formula | Spectrum Data |
|---|---|---|
| 5-3 | 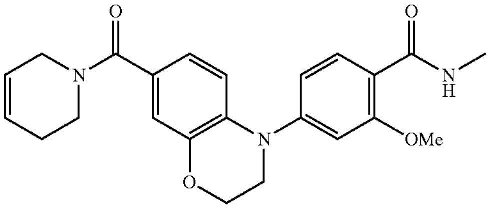 [SMILES: CNC(=O)c1ccc(N2CCOc3cc(C(=O)N4CC=CCC4)ccc32)cc1OC] | $^1$H NMR (400 MHz, $CDCl_3$) δ 2.16-2.28 (2H, m), 3.10 (3H, d, J = 4.3 Hz), 3.50-3.75 (2H, m), 3.78 (2H, t, J = 4.3 Hz), 3.91 (3H, s), 4.00-4.25 (2H, m), 4.32 (2H, t, J = 4.2 Hz), 5.55-5.80 (1H, m), 5.84-5.91 (1H, m), 6.83 (1H, d, J = 1.8 Hz), 6.85-6.92 (2H, m), 7.01 (1H, d, J = 1.8 Hz), 7.10 (1H, d, J = 8.6 Hz), 7.70-7.78 (1H, m), 8.21 (1H, d, J = 8.6 Hz). LRMS (ESI$^+$) 408 [M + H]$^+$. |

Example 6-1

[Formula 161]

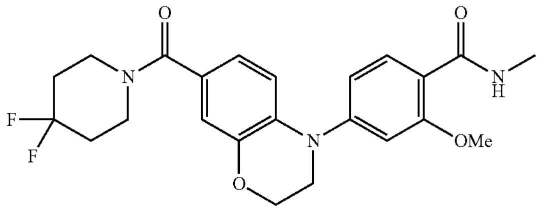

4-(7-(4,4-Difluoropiperidine-1-carbonyl)-2,3-dihydro-4H-benzo[b][1,4]oxazin-4-yl)-2-methoxy-N-methylbenzamide To a suspension, in tetrahydrofuran (0.5 mL), of 4-(7-(4,4-di fluoropiperidine-1-carbonyl)-2,3-dihydro-4H-benzo[b][1,4]oxazin-4-yl)-2-methoxybenzoic acid (30.0 mg) and a 2 mol/L tetrahydrofuran solution (1 mL) of methylamine, 1-[bis(dimethylamino)methylene]-1H-1,2,3-triazolo[4,5-b]pyridinium 3-oxide hexafluorophosphate (32.0 mg) and diisopropylethylamine (24.0 μL) were added at room temperature, followed by stirring at room temperature for 2 hours. The resultant reaction mixture was concentrated under reduced pressure, and the thus obtained residue was purified by silica gel column chromatography (ethyl acetate: methanol=20:1) to obtain the title compound (12.8 mg).

$^1$H NMR (400 MHz, $CDCl_3$) δ 1.94-2.08 (4H, m), 3.01 (3H, d, J=4.8 Hz), 3.68-3.80 (4H, m), 3.78 (2H, t, J=4.2 Hz), 3.92 (3H, s), 4.33 (2H, t, J=4.2 Hz), 6.83 (1H, d, J=1.8 Hz), 6.87 (1H, dd, J=8.5, 1.8 Hz), 6.90 (1H, dd, J=8.5, 1.8 Hz), 6.99 (1H, d, J=1.8 Hz), 7.09 (1H, d, J=8.5 Hz), 7.68-7.75 (1H, m), 8.22 (1H, d, J=8.5 Hz).

LRMS (ESI$^+$) 446 [M+H]$^+$.

Compounds of the following Examples 6-2 to 6-22 were obtained in the same manner as in Example 6-1 by using corresponding starting materials and reactants. Their structures and spectrum data are shown in the following tables.

TABLE 114

| Example No. | Chemical Structural Formula | Spectrum Data |
|---|---|---|
| 6-2 | 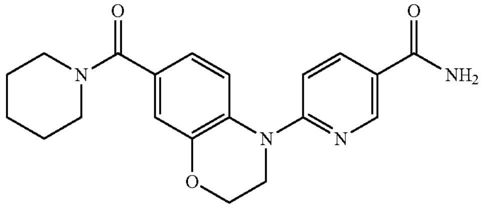 [SMILES: NC(=O)c1ccc(N2CCOc3cc(C(=O)N4CCCCC4)ccc32)nc1] | $^1$H NMR (400 MHz, DMSO-$d_6$) δ 1.39-1.66 (6H, m), 3.27-3.62 (4H, m), 4.07 (2H, t, J = 4.2 Hz), 4.27 (2H, t, J = 4.5 Hz), 6.86 (1H, dd, J = 8.5, 1.8 Hz), 6.89 (1H, d, J = 1.8 Hz), 7.28 (1H, d., J = 9.1 Hz), 7.34 (1H, s), 7.49 (1H, d, J = 8.5 Hz), 7.93 (1H, s), 8.08 (1H, dd, J = 9.1, 2.4 Hz), 8.77 (1H, d, J = 1.8 Hz). LRMS (ESI$^+$) 367 [M + H]$^+$. |
| 6-3 | 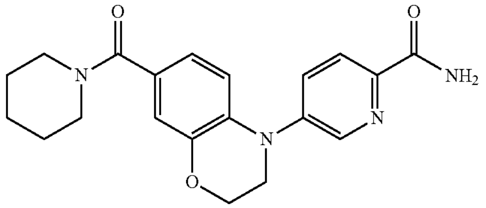 [SMILES: NC(=O)c1ccc(N2CCOc3cc(C(=O)N4CCCCC4)ccc32)cn1] | $^1$H NMR (400 MHz, DMSO-$d_6$) δ 1.40-1.66 (6H, m), 3.29-3.58 (4H, m), 3.83 (2H, t, J = 4.5 Hz), 4.29 (2H, t, J = 4.5 Hz), 6.79 (1H, dd, J = 8.5, 1.8 Hz), 6.87 (1H, d, J = 2.4 Hz), 7.05 (1H, d., J = 7.9 Hz), 7.48-7.54 (1H, m), 7.80 (1H, d d, J = 8.8, 2.7Hz), 7.94-8.02 (2H, m), 8.54 (1H, d, J = 2.4 Hz). LRMS (ESI$^+$) 367 [M + H]$^+$. |
| 6-4 | 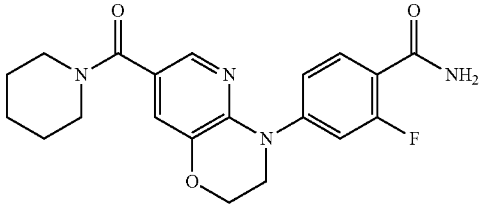 [SMILES: NC(=O)c1ccc(N2CCOc3cc(C(=O)N4CCCCC4)cnc32)cc1F] | $^1$H NMR (400 MHz, DMSO-$d_6$) δ 1.39-1.67 (6H, m), 3.34-3.61 (4H, m), 3.94 (2H, t, J = 4.6 Hz), 4.34 (2H, t, J = 4.3 Hz), 7.18 (1H, d, J = 2.4 Hz), 7.33 (1H, dd, J = 8.6, 2.4 Hz), 7.41 (1H, dd, J = 13.4, 1.8 Hz), 7.55 (2H, br s), 7.67 (1 H, t, J = 8.9 Hz), 7.74 (1H, d, J = 2.4 Hz). LRMS (ESI$^+$) 385 [M + H]$^+$. |

TABLE 114-continued

| Example No. | Chemical Structural Formula | Spectrum Data |
| --- | --- | --- |
| 6-5 | 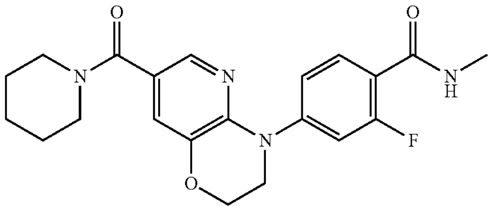 [SMILES: CNC(=O)c1ccc(N2CCOc3cc(C(=O)N4CCCCC4)cnc32)cc1F] | $^1$H NMR (400 MHz, DMSO-$d_6$) δ 1.39-1.66 (6H, m), 2.77 (3H, d, J = 4.3 Hz), 3.34-3.58 (4H, m), 3.94 (2H, t, J = 4.3 Hz), 4.34 (2H, t, J = 4.3 Hz), 7.17 (1H, d, J = 1.8 Hz), 7.33 (1H, dd, J = 8.6, 1.8), 7.42 (1H, dd, J = 13.1, 2.1 Hz), 7.63 (1H, t, J = 8.9 Hz), 7.73 (1H, d, J = 1.8 Hz), 8.05-8.16 (1H, m).<br>LRMS (ESI$^+$) 399 [M + H]$^+$. |

TABLE 115

| Example No. | Chemical Structural Formula | Spectrum Data |
| --- | --- | --- |
| 6-6 | 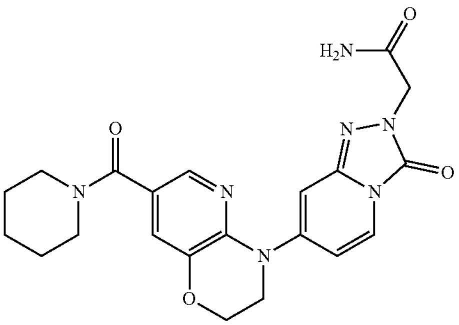 [SMILES: NC(=O)Cn1nc2cc(N3CCOc4cc(C(=O)N5CCCCC5)cnc43)ccn2c1=O] | $^1$H NMR (400 MHz, DMSO-$d_6$) δ 1.41-1.64 (6H, m), 3.26-3.62 (4H, m), 3.93 (2H, t, J = 4.3 Hz), 4.37 (2H, t, J = 4.6 t, Hz), 4.42 (2H, s), 6.88 (1H, d, J = 1.2 Hz), 6.97 (1H, dd, J = 7.6, 2.1 Hz), 7.21 (1H, d, J = 2.4 Hz), 7.24-7.31 (1H, m), 7.47-7.53 (1H, m), 7.74-7.79 (2H, m).<br>LRMS (ESI$^+$) 438 [M + H]$^+$. |
| 6-7 | 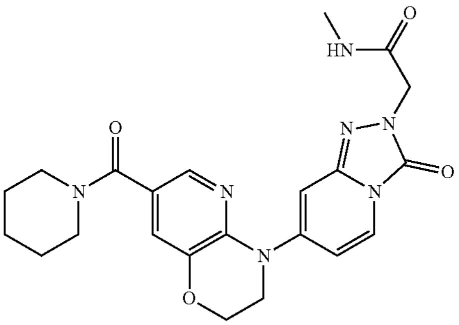 [SMILES: CNC(=O)Cn1nc2cc(N3CCOc4cc(C(=O)N5CCCCC5)cnc43)ccn2c1=O] | $^1$H NMR (400 MHz, DMSO-$d_6$) δ 1.38-1.66 (6H, m), 2.59 (3 H, d, J = 4.3 Hz), 3.22-3.65 (4H, m), 3.93 (2H, t, J = 4.6 Hz), 4.37 (2H, t, J = 4.3 Hz), 4.44 (2H, s), 6.88 (1H, d, J = 1.2 Hz), 6.98 (1H, dd, J = 7.9, 1.8 Hz), 7.21 (1H, d, J = 1.8 Hz), 7.75-7.80 (2H, m), 7.92 (1H, q, J = 4.5 Hz).<br>LRMS (ESI$^+$) 452 [M + H]$^+$. |
| 6-8 | 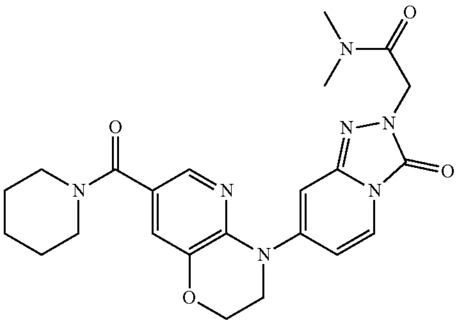 [SMILES: CN(C)C(=O)Cn1nc2cc(N3CCOc4cc(C(=O)N5CCCCC5)cnc43)ccn2c1=O] | $^1$H NMR (400 MHz, DMSO-$d_6$) δ 1.43-1.64 (6H, m), 2.83 (3 H, s), 3.03 (3H, s), 3.27-3.58 (4H, m), 3.94 (2H, t, J = 4.3 Hz), 4.37 (2H, t, J = 4.3 Hz), 4.79 (2H, s), 6.86 (1H, d, J = 1.2 Hz), 6.97 (1H, dd, J = 7.6, 2.1 Hz), 7.21 (1H, d, J = 1.8 Hz), 7.75-7.79 (2H, m).<br>LRMS (ESI$^+$) 466 [M + H]$^+$. |

TABLE 115-continued

| Example No. | Chemical Structural Formula | Spectrum Data |
|---|---|---|
| 6-9 | 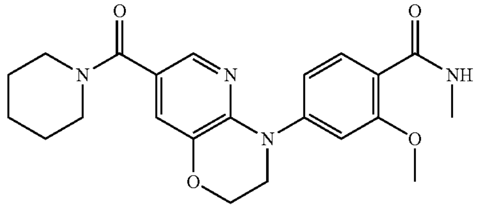 [SMILES: CNC(=O)c1ccc(N2CCOc3cc(C(=O)N4CCCCC4)cnc32)cc1OC] | $^1H$ NMR (400 MHz, DMSO-$d_6$) δ 1.20-1.30 (2H, m), 1.42-1.56 (2H, m), 1.56-1.65 (2H, m), 2.73-2.89 (3H, m), 3.38-3.55 (4H, m), 3.88 (3H, s), 3.96 (2H, t, J = 4.2 Hz), 4.35 (2H, t, J = 4.2 Hz), 7.08 (1H, dd, J = 8.5, 1.8 Hz), 7.16 (1H, d, J = 1.8 Hz), 7.21 (1H, d, J = 2.4 Hz), 7.72 (1H, d, J = 1.8 Hz), 7.79 (1H, d, J = 8.5 Hz), 8.06-8.12 (1H, m). LRMS (ESI$^+$) 411 [M + H]$^+$. |
| 6-10 | 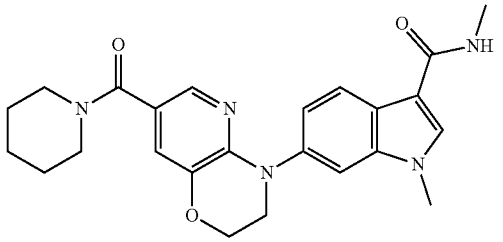 [SMILES: CNC(=O)c1cn(C)c2cc(N3CCOc4cc(C(=O)N5CCCCC5)cnc43)ccc12] | $^1H$ NMR (400 MHz, DMSO-$d_6$) δ 1.42-1.67 (6H, m), 2.77 (3 H, d, J = 4.9 Hz), 3.40-3.50 (4H, m), 3.79 (3H, s), 3.95 (2H, t, J = 4.3 Hz), 4.37 (2H, t, J = 4.0 Hz), 7.08 (1H, d, J = 1.8 Hz), 7.18 (1H, dd, J = 8.6, 1.2 Hz), 7.48 (1H, s), 7.61 (1H, d, J = 1.8 Hz), 7.80-7.86 (1H, m), 7.90 (1H, s), 8.10 (1 H, d, J = 8.6 Hz). LRMS (ESI$^+$) 434 [M + H]$^+$. |
| 6-11 | 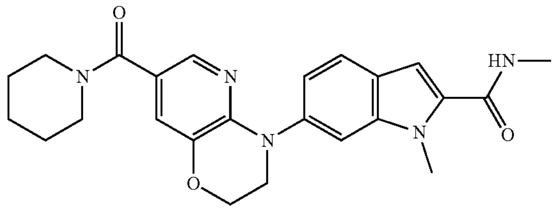 [SMILES: CNC(=O)c1cc2ccc(N3CCOc4cc(C(=O)N5CCCCC5)cnc43)cc2n1C] | $^1H$ NMR (400 MHz, DMSO-$d_6$) δ 1.42-1.65 (6H, m), 2.79 (3 H, d, J = 4.3 Hz), 3.34-3.57 (4H, m), 3.92-4.04 (5H, m), 4.40 (2H, t, J = 4.3 Hz), 7.05 (1H, s), 7.14-7.21 (2H, m), 7.52-7.61 (2H, m), 7.65 (1H, d, J = 8.6 Hz), 8.43-8.51 (1H, m). LRMS (ESI$^+$) 434 [M + H]$^+$. |

TABLE 116

| Example No. | Chemical Structural Formula | Spectrum Data |
|---|---|---|
| 6-12 | 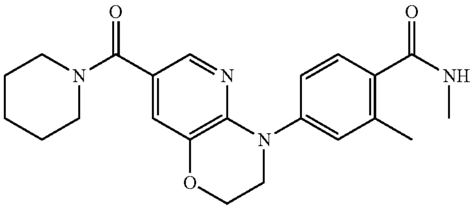 [SMILES: CNC(=O)c1ccc(N2CCOc3cc(C(=O)N4CCCCC4)cnc32)cc1C] | $^1H$ NMR (400 MHz, DMSO-$d_6$) δ 1.43-1.66 (6H, m), 2.34 (3H, s), 2.74 (3H, d, J = 4.9 Hz), 3.40-3.58 (4H, m), 3.85-3.95 (2 H, m), 4.29-4.39 (2H, m), 7.12 (1H, d, J = 1.8 Hz), 7.24-7.29 (2H, m), 7.33 (1H, d, J = 7.9 Hz), 7.66 (1H, d, J = 1.8 Hz), 8.11-8.19 (1H, m). LRMS (ESI$^+$) 395 [M + H]$^+$. |
| 6-13 | 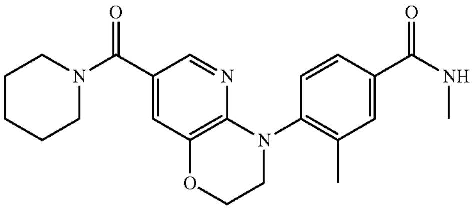 [SMILES: CNC(=O)c1ccc(N2CCOc3cc(C(=O)N4CCCCC4)cnc32)c(C)c1] | $^1H$ NMR (400 MHz, DMSO-$d_6$) δ 1.42-1.63 (6H, m), 2.16 (3H, s), 2.79 (3H, d, J = 4.9 Hz), 3.39-3.52 (4H, m), 3.56-4.00 (2H, H, m), 4.31-4.45 (2H, m), 7.09 (1H, d, J = 1.8 Hz), 7.35 (1H, d, J = 7.9 Hz), 7.59 (1H, d, J = 1.8 Hz), 7.69 (1H, dd, J = 7.9, 1.8 Hz), 7.75 (1H, d, J = 1.2 Hz), 8.37-8.45 (1H, m) LRMS (ESI$^+$) 395 [M + H]$^+$. |
| 6-14 | 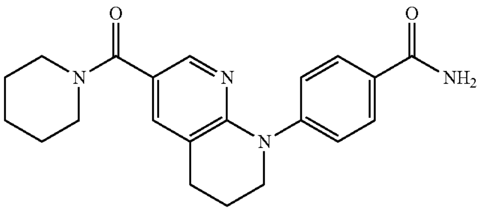 [SMILES: NC(=O)c1ccc(N2CCCc3cc(C(=O)N4CCCCC4)cnc32)cc1] | $^1H$ NMR (400 MHz, DMSO-$d_6$) δ 1.41-1.68 (6H, m), 1.94-2.06 (2H, m), 2.85 (2H, t, J = 6.1 Hz), 3.38-3.56 (4H, m), 3.79 (2H, t, J = 5.4 Hz), 7.23-7.31 (1H, m), 7.36-7.43 (3H, m), 7.80-7.95 (4H, m). LRMS (ESI$^+$) 365 [M + H]$^+$. |

TABLE 116-continued

| Example No. | Chemical Structural Formula | Spectrum Data |
|---|---|---|
| 6-15 | 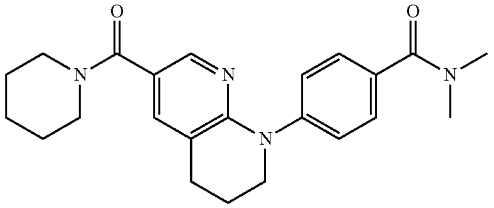 [SMILES: CN(C)C(=O)c1ccc(N2CCCc3cc(C(=O)N4CCCCC4)cnc32)cc1] | $^1$H NMR (400 MHz, DMSO-$d_6$) δ 1.41-1.68 (6H, m), 1.95-2.06 (2H, m), 2.85 (2H, t, J = 6.1 Hz), 2.98 (6H, s), 3.36-3.56 (4H, m), 3.78 (2H, t, J = 5.4 Hz), 7.35-7.44 (5H, m), 7.85 (1 H, d, J = 1.8 Hz).<br>LRMS (ESI$^+$) 393 [M + H]$^+$. |
| 6-16 | 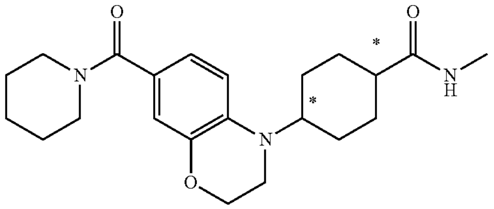 [SMILES: CNC(=O)C1CCC(N2CCOc3cc(C(=O)N4CCCCC4)ccc32)CC1] | $^1$H NMR (400 MHz, DMSO-$d_6$) δ 1.36-1.63 (10H, m), 1.66-1.84 (4H, m), 2.00-2.10 (1H, m), 2.55 (3H, (1, J = 4.9 Hz), 3.26 (2H, t, J = 4.3 Hz), 3.58-3.68 (4H, m), 3.61-3.66 (1H, m), 4.11 (2H, t, J = 4.3 Hz), 6.67 (1H, d, J = 12 Hz), 6.76-6.84 (2H, m), 7.63-7.72 (1H, m).<br>LRMS (ESI$^+$) 386 [M + H]$^+$. |
| 6-17 | 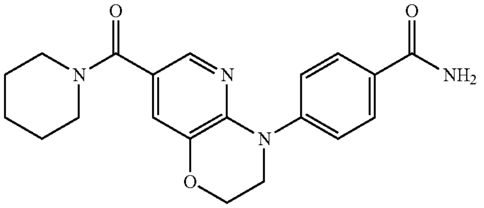 [SMILES: NC(=O)c1ccc(N2CCOc3cc(C(=O)N4CCCCC4)cnc32)cc1] | $^1$H NMR (400 MHz, DMSO-$d_6$) δ 1.41-1.63 (6H, m), 3.36-3.52 (4H, m), 3.94 (2H, t, J = 4.3 Hz), 4.34 (2H, t, J = 4.3 Hz), 7.14 (1H, d, J = 2.4 Hz), 7.26 (1H, s), 7.45-7.51 (2H, m), 7.69 (1H, d, J = 1.8 Hz), 7.82-7.93 (3H, m).<br>LRMS (ESI$^+$) 367 [M + H]$^+$. |
| 6-18 | 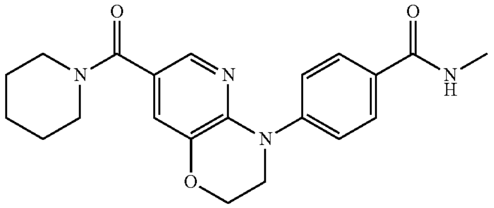 [SMILES: CNC(=O)c1ccc(N2CCOc3cc(C(=O)N4CCCCC4)cnc32)cc1] | $^1$H NMR (400 MHz, DMSO-$d_6$) δ 1.41-1.64 (6H, m), 2.77 (3H, d, J = 4.9 Hz), 3.36-3.52 (4H, m), 3.94 (2H, t, J = 4.3 Hz), 4.34 (2H, t, J = 4.3 Hz), 7.14 (1H, d, J = 1.8 Hz), 7.46-7.51 (2H, m), 7.69 (1H, d, J = 2.4 Hz), 7.79-7.84 (2H, m), 8.35 (1H, q, J = 4.9 Hz).<br>LRMS (ESI$^+$) 381 [M + H]$^+$. |

TABLE 117

| Example No. | Chemical Structural Formula | Spectrum Data |
|---|---|---|
| 6-19 | 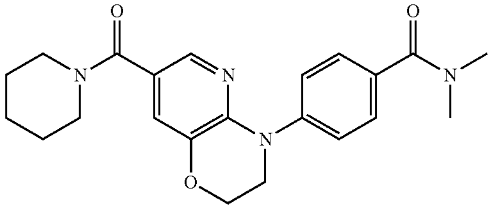 [SMILES: CN(C)C(=O)c1ccc(N2CCOc3cc(C(=O)N4CCCCC4)cnc32)cc1] | $^1$H NMR (400 MHz, DMSO-$d_6$) δ 1.41-1.65 (6H, m), 2.97 (6H, s), 3.37-3.50 (4H, m), 3.93 (2H, t, J = 4.0 Hz), 4.34 (2H, t, J = 4.0 Hz), 7.13 (1H, d, J = 1.8 Hz), 7.41 (2H, d, J = 8.6 Hz), 7.47 (2H, d, J = 7.9 Hz), 7.67-7.70 (1H, m).<br>LRMS (ESI$^+$) 395 [M + H]$^+$. |
| 6-20 | 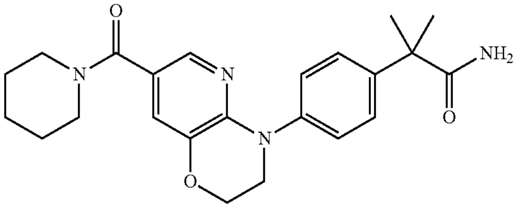 [SMILES: CC(C)(C(N)=O)c1ccc(N2CCOc3cc(C(=O)N4CCCCC4)cnc32)cc1] | $^1$H NMR (400 MHz, DMSO-$d_6$) δ 1.36-1.65 (12H, m), 3.38-3.49 (4H, m), 3.87 (2H, t, J = 4.5 Hz), 4.32 (2H, t, J = 4.2 Hz), 6.86-6.95 (2H, m), 7.08 (1H, d, J = 1.8 Hz), 7.29-7.36 (4H, m), 7.64 (1H, d, J = 1.8 Hz).<br>LRMS (ESI$^+$) 409 [M + H]$^+$. |

TABLE 117-continued

| Example No. | Chemical Structural Formula | Spectrum Data |
|---|---|---|
| 6-21 | 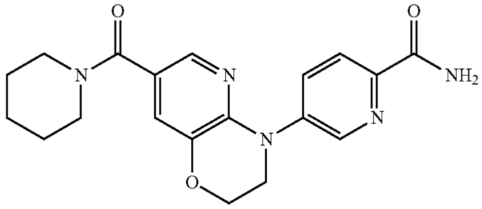 [SMILES: NC(=O)c1ccc(N2CCOc3cc(C(=O)N4CCCCC4)cnc32)cn1] | $^1$H NMR (400 MHz, DMSO-$d_6$) δ 1.41-1.64 (6H, m), 3.34-3.53 (4H, m), 4.00 (2H, t, J = 4.3 Hz), 4.38 (2H, t, J = 4.3 Hz), 7.19 (1H, d, J = 1.8 Hz), 7.50-7.55 (1H, m), 7.72 (1H, d, J = 1.8 Hz), 7.95 (1H, dd, J = 8.6, 2.4 Hz), 7.98-8.05 (2H, m), 8.80 (1H, d, J = 1.8 Hz). LRMS (ESI$^+$) 368 [M + H]$^+$. |
| 6-22 | 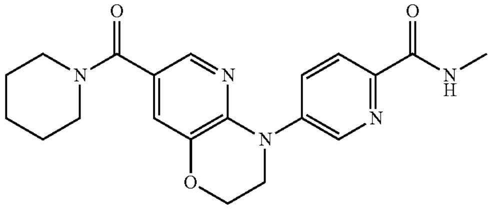 [SMILES: CNC(=O)c1ccc(N2CCOc3cc(C(=O)N4CCCCC4)cnc32)cn1] | $^1$H NMR (400 MHz, DMSO-$d_6$) δ 1.40-1.64 (6H, m), 2.81 (3H, d, J = 4.9 Hz), 3.37-3.51 (4H, m), 4.00 (2H, t, J = 4.3 Hz), 4.38 (2H, t, J = 4.3 Hz), 7.19 (1H, d, J = 1.8 Hz), 7.72 (1H, d, J = 1.8 Hz), 7.95 (1H, dd, J = 8.6, 1.8 Hz), 8.01 (1H, d, J = 8.6 Hz), 8.63-8.69 (1H, m), 8.80 (1H, d, J = 2.4 Hz). LRMS (ESI$^+$) 382 [M + H]$^+$. |

Example 7-1

[Formula 162]

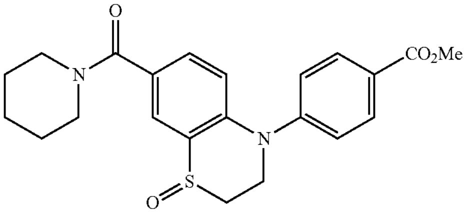

Methyl 4-(1-Oxide-7-(piperidine-1-carbonyl)-2,3-dihydro-4H-benzo[b][1,4]thiazin-4-yl)benzoate To a solution of methyl 4-(7-piperidine-1-carbonyl)-2,3-dihydro-4H-benzo[b][1,4]thiazin-4-yl)benzoate (90 mg) in dichloromethane (1.2 mL), 3-chloroperbenzoic acid (56.0 mg) was added at 0° C. The resultant reaction solution was heated to room temperature, stirred for 2 hours, and concentrated under reduced pressure. The thus obtained residue was purified by silica gel column chromatography (ethyl acetate) to obtain the title compound (88.1 mg).

$^1$H NMR (400 MHz, $CDCl_3$) δ 1.53-1.64 (4H, m), 1.64-1.73 (2H, m), 2.90-3.00 (1H, m), 3.19-3.27 (1H, m), 3.43-3.67 (4H, m), 3.87-3.94 (1H, m), 3.95 (3H, s), 4.38-4.48 (1H, m), 6.80 (1H, d, J=8.6 Hz), 7.31 (1H, dd, J=8.6, 2.4 Hz), 7.37 (2H, d, J=8.6 Hz), 7.74 (1H, d, J=2.4 Hz), 8.13 (2H, d, J=8.6 Hz).

LRMS (ESI$^+$) 413 [M+H]$^+$.

Compounds of the following Examples 7-2 to 7-10 were obtained in the same manner as in Example 7-1 by using corresponding starting materials and reactants. Their structures and spectrum data are shown in the following tables.

TABLE 118

| Reference Example No. | Chemical Structural Formula | Spectrum Data |
|---|---|---|
| 7-2 | 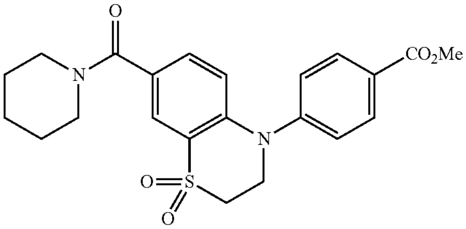 [SMILES: COC(=O)c1ccc(N2CCS(=O)(=O)c3cc(C(=O)N4CCCCC4)ccc32)cc1] | $^1$H NMR (400 MHz, $CDCl_3$) δ 1.54-1.65 (4H, m), 1.65-1.74 (2H, m), 3.46-3.53 (2H, m), 3.53-3.70 (4H, m), 3.95 (3H, s), 4.28-4.35 (2H, m), 6.65 (1H, d, J = 9.2 Hz), 7.30-7.38 (3H, m), 7.90 (1H, d, J = 2.4 Hz), 8.14 (2H, d, J = 8.6 Hz). LRMS (ESI$^+$) 429 [M + H]$^+$. |
| 7-3 | 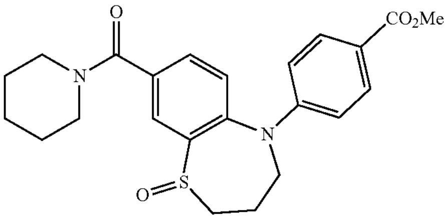 [SMILES: COC(=O)c1ccc(N2CCCS(=O)c3cc(C(=O)N4CCCCC4)ccc32)cc1] | $^1$H NMR (400 MHz, $CDCl_3$) δ 1.57-1.76 (6H, m), 2.00-2.12 (1H, m), 2.45-2.57 (1H, m), 2.94-3.03 (1H, m), 3.10-3.20 (1H, m), 3.33-3.50 (3H, m), 3.67-3.82 (211, m), 3.87 (3H, s), 4.08-4.17 (1H, m), 6.66 (2H, d, J = 9.1 Hz), 7.29 (1H, d, J = 7.9 Hz), 7.61 (1H, dd, J = 7.9, 1.8 Hz), 7.89 (2H, d, J = 9.1 Hz), 7.91 (1H, d, J = 1.8 Hz). LRMS (ESI$^+$) 427 [M + H]$^+$. |

TABLE 119

| Reference Example No. | Chemical Structural Formula | Spectrum Data |
|---|---|---|
| 7-4 | 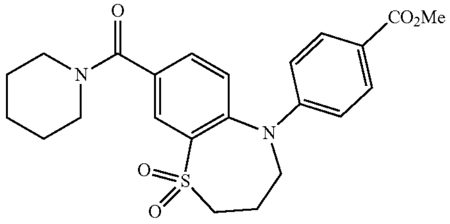 [SMILES: COC(=O)c1ccc(N2CCCS(=O)(=O)c3cc(C(=O)N4CCCCC4)ccc32)cc1] | $^1$H NMR (400 MHz, $CDCl_3$) δ 1.52-1.78 (6H, m), 2.25-2.36 (2H, m), 3.27-3.35 (2H, m), 3.37-3.48 (2H, m), 3.65-3.80 (2H, m), 3.86 (3H, s), 3.83-3.95 (2H, m), 6.72 (2H, d, J = 9.1 Hz), 7.44 (1H, d, J = 8.5 Hz), 7.70 (1H, dd, J = 8.5, 1.8 Hz), 7.90 (2H, d, J = 9.1 Hz), 8.18 (1H, d, J = 1.8 Hz). LRMS (ESI$^+$) 443 [M + H]$^+$. |
| 7-5 | 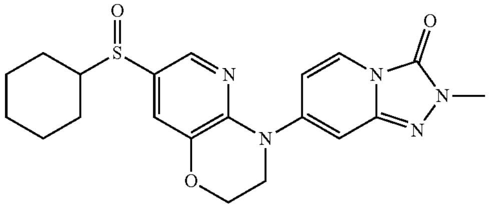 [SMILES: Cn1nc2cc(N3CCOc4cc(S(=O)C5CCCCC5)cnc43)ccn2c1=O] | $^1$H NMR (400 MHz, $CDCl_3$) δ 1.17-1.38 (4H, m), 1.39-1.52 (1H, m), 1.63-1.72 (1H, m), 1.75-1.94 (3H, m), 1.96-2.04 (1H, m), 2.57-2.67 (1H, m), 3.65 (3H, s), 3.93 (2H, dd, J = 6.1, 3.7 Hz), 4.42-4.47 (2H, m), 6.68 (1H, d, J = 1.8 Hz), 6.96 (1H, dd, J = 7.9, 1.8 Hz), 7.46 (1H, d, J = 1.8 Hz), 7.70 (1H, dd, J = 7.9, 1.2 Hz), 7.90 (1H, d, J = 1.8 Hz). LRMS (ESI$^+$) 414 [M + H]$^+$. |
| 7-6 | 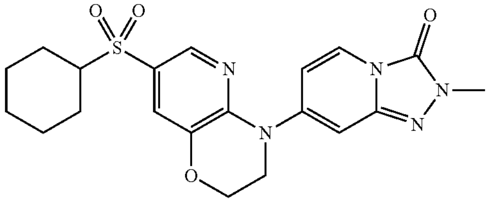 | $^1$H NMR (400 MHz, $CDCl_3$) δ 1.07-1.30 (3H, m), 1.33-1.46 (2H, m), 1.64-1.72 (1H, m), 1.83-1.92 (2H, m), 2.06-2.15 (2H, m), 2.83-2.92 (1H, m), 3.66 (3H, s), 3.96 (2H, t, J = 4.6 Hz), 4.45 (2H, t, J = 4.6 Hz), 6.72-6.75 (1H, m), 6.91 (1H, dd, J = 7.6, 2.1 Hz), 7.51 (1H, d, J = 1.8 Hz), 7.71 (1H, d, J = 8.6 Hz), 8.22 (1H, d, J = 1.8 Hz). LRMS (ESI$^+$) 430 [M + H]$^+$. |

TABLE 120

| Example No. | Chemical Structural Formula | Spectrum Data |
|---|---|---|
| 7-7 | 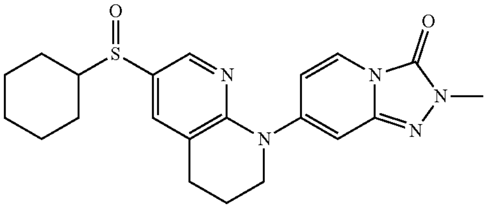 [SMILES: Cn1nc2cc(N3CCCc4cc(S(=O)C5CCCCC5)cnc43)ccn2c1=O] | $^1$H NMR (400 MHz, $CDCl_3$) δ 1.16-1.37 (4H, m), 1.39-1.52 (1H, m), 1.63-1.95 (4H, m), 1.99-2.08 (1H, m), 2.10-2.21 (2H, m), 2.56-2.67 (1H, m), 2.94 (2H, t, J = 6.1 Hz), 3.64 (3H, s), 3.85 (2H, t, J = 6.1 Hz), 6.71-6.76 (2H, m), 7.65 (1H, dd, J = 7.3, 1.2 Hz), 7.67-7.70 (1H, m), 8.08 (1H, d, J = 2.4 Hz). LRMS (ESI$^+$) 412 [M + H]$^+$. |
| 7-8 | 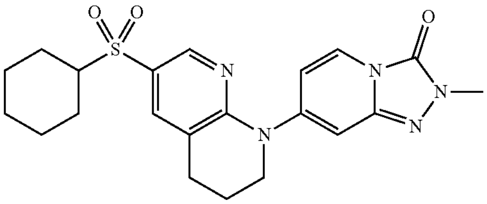 [SMILES: Cn1nc2cc(N3CCCc4cc(S(=O)(=O)C5CCCCC5)cnc43)ccn2c1=O] | $^1$H NMR (400 MHz, $CDCl_3$) δ 1.08-1.30 (3H, m), 1.33-1.46 (2H, m), 1.64-1.74 (1H, m), 1.83-1.93 (2H, m), 2.06-2.21 (4H, m), 2.86 (1H, tt, J = 12.2, 3.1 Hz), 2.94 (2H, t, J = 5.5 Hz), 3.65 (3H, s), 3.87 (2H, t, J = 5.5 Hz), 6.68 (1H, dd, J = 7.3, 1.8 Hz), 6.79 (1H, d, J = 1.2 Hz), 7.66-7.72 (2H, m), 8.39 (1H, d, J = 2.4 Hz). LRMS (ESI$^+$) 428 [M + H]$^+$. |
| 7-9 | 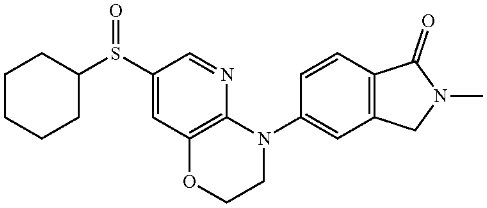 [SMILES: CN1Cc2cc(N3CCOc4cc(S(=O)C5CCCCC5)cnc43)ccc2C1=O] | $^1$H NMR (400 MHz, $CDCl_3$) δ 1.14-1.35 (4H, m), 1.38-1.51 (1H, m), 1.63-1.76 (2H, m), 1.78-1.95 (2H, m), 2.00-2.10 (1H, m), 2.57-2.67 (1H, m), 3.21 (3H, s), 3.93-4.05 (2H, m), 4.35-4.46 (4H, m), 7.39-7.44 (2H, m), 7.55 (1H, d, J = 1.2 Hz), 7.83 (1H, d, J = 1.8 Hz), 7.87 (1H, d, J = 8.6 Hz). LRMS (ESI$^+$) 412 [M + H]$^+$. |

TABLE 120-continued

| Example No. | Chemical Structural Formula | Spectrum Data |
|---|---|---|
| 7-10 | 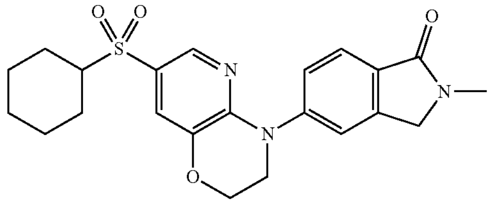 [SMILES: CN1Cc2cc(N3CCOc4cc(S(=O)(=O)C5CCCCC5)cnc43)ccc2C1=O] | $^1$H NMR (400 MHz, $CDCl_3$) δ 1.06-1.30 (3H, m), 1.32-1.45 (2H, m), 1.63-1.72 (1H, m), 1.82-1.91 (2H, m), 2.06-2.14 (2H, m), 2.85 (1H, tt, J = 12.2, 3.7 Hz), 3.21 (3H, s), 4.01 (2H, t, J = 4.3 Hz), 4.38-4.45 (4H, m), 7.41 (1H, dd, J = 8.6, 1.8 Hz), 7.45 (1H, d, J = 1.8 Hz), 7.55 (1H, d, J = 1.2 Hz), 7.89 (1H, d, J = 8.6 Hz), 8.14 (1H, d, J = 1.8 Hz). LRMS ($ESI^+$) 428 $[M + H]^+$. |

Example 8-1

[Formula 163]

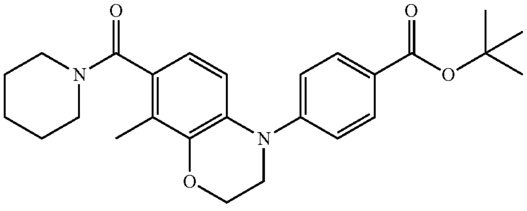

tert-Butyl 4-(8-Methyl-7-(piperidine-1-carbonyl)-2,3-dihydro-4H-benzo[b][1,4]oxazin-4-yl)benzoate To a solution of 4-(4-(tert-butoxycarbonyl)phenyl)-8-methyl-3,4-dihydro-2H-benzo[b] [1,4]oxazine-7-carboxylic acid (29.1 mg) in N, N-dimethyl formamide (0.8 mL), piperidine (8.6 μL) and diisopropylethylamine (29.4 μL) were added. To the resultant reaction solution, 1-[bis(dimethylamino)methylene]-1H-1,2,3-triazolo[4,5-b]pyridinium 3-oxide hexafluorophosphate (32.9 mg) was added, followed by stirring at room temperature for 2.5 hours. The resultant reaction solution was purified by silica gel column chromatography (methanol:water=5:95 to 65:35 to 90:10 to 100:0) to obtain the title compound (31.9 mg).

$^1$H NMR (400 MHz, $CDCl_3$) δ: 1.41-1.70 (15H, m), 2.17 (3H, s), 3.25 (2H, t, J=5.5 Hz), 3.67-3.81 (4H, m), 4.24-4.37 (2H, m), 6.60 (1H, d, J=7.9 Hz), 6.95 (1H, d, J=8.6 Hz), 7.17-7.23 (2H, m), 7.91-7.96 (2H, m).

LRMS ($ESI^+$) 437 $[M+H]^+$.

Compounds of the following Examples 8-2 to 8-231 were obtained in the same manner as in Example 8-1 by using corresponding starting materials and reactants. Their structures and spectrum data are shown in the following tables.

TABLE 121

| Example No. | Chemical Structural Formula | Spectrum Data |
|---|---|---|
| 8-2 | 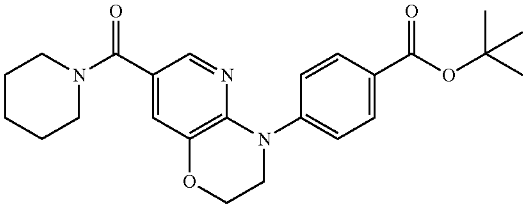 [SMILES: CC(C)(C)OC(=O)c1ccc(N2CCOc3cc(C(=O)N4CCCCC4)cnc32)cc1] | $^1$H NMR (400 MHz, $CDCl_3$) δ 1.44-1.72 (15H, m), 3.36-3.70 (4H, m), 3.94 (2H, t, J = 4.2 Hz), 4.37 (2H, t, J = 4.2 Hz), 7.22 (1H, d, J = 2.4 Hz), 7.41-7.46 (2H, m), 7.84 (1H, d, J = 1.8 Hz) , 7.99-8.03 (2H, m). LRMS ($ESI^+$) 424 $[M + H]^+$. |
| 8-3 | 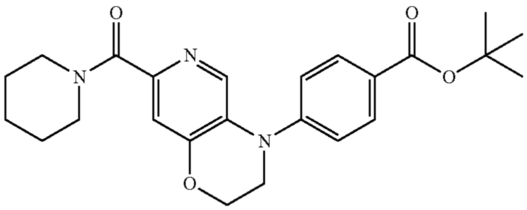 [SMILES: CC(C)(C)OC(=O)c1ccc(N2CCOc3cc(C(=O)N4CCCCC4)ncc32)cc1] | $^1$H NMR (400 MHz, $CDCl_3$) δ 1.47-1.71 (15H, m), 3.51-3.58 (2H, m), 3.67-3.73 (2H, m), 3.79 (2H, t, J = 4.2 Hz), 4.37 (2H, t, J = 4.2 Hz), 7.17-7.19 (1H, m), 7.21-7.28 (2H, m), 7.96-8.01 (2H, m), 8.29 (1H, s). LRMS ($ESI^+$) 424 $[M + H]^+$. |
| 8-4 | 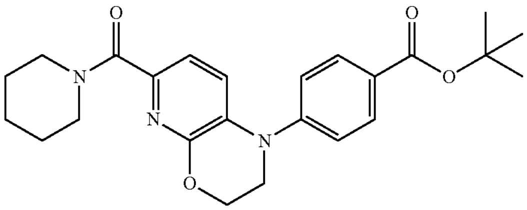 [SMILES: CC(C)(C)OC(=O)c1ccc(N2CCOc3nc(C(=O)N4CCCCC4)ccc32)cc1] | $^1$H NMR (400 MHz, DMSO-$d_6$) δ 1.42-1.64 (15H, m), 3.42-3.57 (4H, m), 3.80 (2H, t, J = 4.3 Hz), 4.44 (2H, t, J = 4.3 Hz), 7.04 (1H, d, J = 8.6 Hz), 7.35-7.39 (2H, m), 7.43 (1H, d, J = 7.9 Hz), 7.88-7.92 (2H, m). LRMS ($ESI^+$) 424 $[M + H]^+$. |

TABLE 121-continued

| Example No. | Chemical Structural Formula | Spectrum Data |
|---|---|---|
| 8-5 | 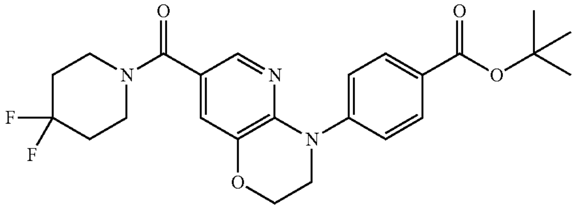 [SMILES: CC(C)(C)OC(=O)c1ccc(N2CCOc3cc(C(=O)N4CCC(F)(F)CC4)cnc32)cc1] | $^1$H NMR (400 MHz, $CDCl_3$) δ: 1.59 (9H, s), 1.94-2.08 (4H, m), 3.68-3.80 (4H, m), 3.96 (2H, t, J = 4.6 Hz), 4.38 (2H, t, J = 4.3 Hz), 7.21-7.25 (1H, m), 7.42-7.46 (2H, m), 7.85 (1 H, d, J = 1.8 Hz), 8.00-8.04 (2H, m). LRMS ($ESI^+$) 460 $[M + H]^+$. |
| 8-6 | 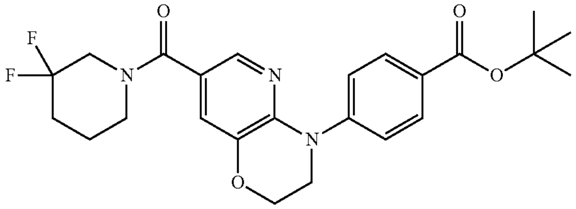 [SMILES: CC(C)(C)OC(=O)c1ccc(N2CCOc3cc(C(=O)N4CCCC(F)(F)C4)cnc32)cc1] | $^1$H NMR (400 MHz, $CDCl_3$) δ: 1.59 (9H, s), 1.78-1.87 (2H, m), 2.00-2.14 (2H, m), 3.56-3.85 (4H, m), 3.95 (2H, t, J = 4.6 Hz), 4.38 (2H, t, J = 4.6 Hz), 7.21-7.31 (1H, m), 7.42-7.46 (2H, m), 7.86 (1H, d, J = 1.8 Hz), 8.00-8.04 (2H, m). LRMS ($ESI^+$) 460 $[M + H]^+$. |
| 8-7 | 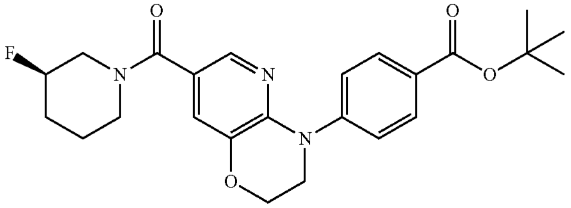 [SMILES: CC(C)(C)OC(=O)c1ccc(N2CCOc3cc(C(=O)N4CCC[C@@H](F)C4)cnc32)cc1] | $^1$H NMR (400 MHz, $CDCl_3$) δ: 1.39-2.11 (13H, m), 3.02-3.75 (3H, m), 3.84-4.01 (3H, m), 4.37 (2H, t, J = 4.0 Hz), 4.51-4.84 (1H, m), 7.25 (1H, s), 7.44 (2H, d, J = 8.6 Hz), 7.86 (1H, s), 8.01 (2H, d, J = 7.9 Hz). LRMS ($ESI^+$) 442 $[M + H]^+$. |

TABLE 122

| Example No. | Chemical Structural Formula | Spectrum Data |
|---|---|---|
| 8-8 | 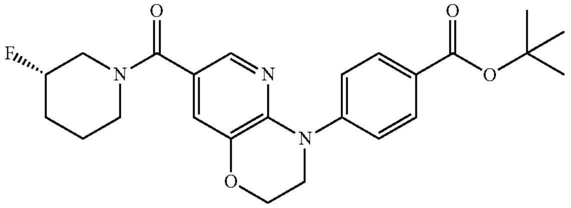 [SMILES: CC(C)(C)OC(=O)c1ccc(N2CCOc3cc(C(=O)N4CCC[C@H](F)C4)cnc32)cc1] | $^1$H NMR (400 MHz, $CDCl_3$) δ: 1.41-2.07 (13H, m), 3.17-4.04 (6H, m), 4.37 (2H, t, J = 4.3 Hz), 4.52-4.82 (1H, m), 7.25 (1H, d, J = 1.8 Hz), 7.41-7.46 (2H, m), 7.86 (1H, d, J = 2.4 Hz), 7.99-8.04 (2H, m). LRMS ($ESI^+$) 442 $[M + H]^+$. |
| 8-9 | 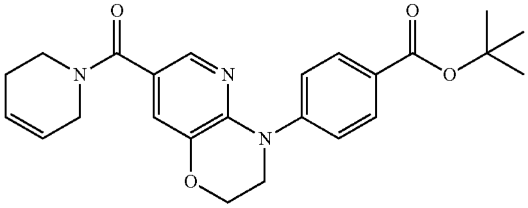 [SMILES: CC(C)(C)OC(=O)c1ccc(N2CCOc3cc(C(=O)N4CC=CCC4)cnc32)cc1] | $^1$H NMR (400 MHz, $CDCl_3$) δ: 1.59 (9H, s), 2.16-2.29 (2H, m), 3.47-3.84 (2H, m), 3.95 (2H, t, J = 4.6 Hz), 4.01-4.19 (2 H, m), 4.37 (2H, t, J = 4.3 Hz), 5.58-5.90 (2H, m), 7.21-7.32 (1H, m), 7.42-7.46 (2H, m), 7.87 (1H, d, J = 2.4 Hz), 7.99-8.03 (2H, m). LRMS ($ESI^+$) 422 $[M + H]^+$. |
| 8-10 | 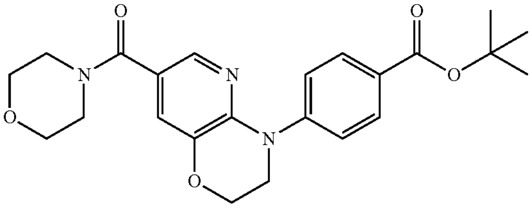 [SMILES: CC(C)(C)OC(=O)c1ccc(N2CCOc3cc(C(=O)N4CCOCC4)cnc32)cc1] | $^1$H NMR (400 MHz, $CDCl_3$) δ: 1.59 (9H, s), 3.47-3.81 (8H, m), 3.95 (2H, t, J = 4.6 Hz), 4.38 (2H, t, J = 4.3 Hz), 7.23 (1H, d, J = 2.4 Hz), 7.41-7.45 (2H, m), 7.84 (1H, d, J = 1.8 Hz), 7.99-8.04 (2H, m). LRMS ($ESI^+$) 426 $[M + H]^+$. |

TABLE 122-continued

| Example No. | Chemical Structural Formula | Spectrum Data |
|---|---|---|
| 8-11 | 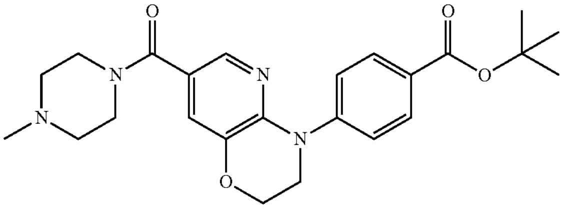 [SMILES: CN1CCN(C(=O)c2cnc3c(c2)OCCN3c2ccc(C(=O)OC(C)(C)C)cc2)CC1] | $^1$H NMR (400 MHz, $CDCl_3$) δ: 1.59 (9H, s), 2.32 (3H, s), 2.34-2.50 (4H, m), 3.50-3.78 (4H, m), 3.95 (2H, t, J = 4.6 Hz), 4.37 (2H, t, J = 4.6 Hz), 7.23 (1H, d, J = 1.8 Hz), 7.41-7.46 (2H, m), 7.85 (1H, d, J = 2.4 Hz), 7.99-8.03 (2H, m).<br>LRMS (ESI$^+$) 439 [M + H]$^+$. |
| 8-12 | 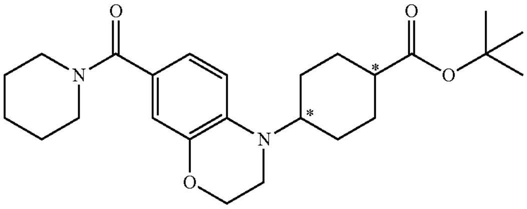 [SMILES: CC(C)(C)OC(=O)C1CCC(N2CCOc3cc(C(=O)N4CCCCC4)ccc32)CC1] | $^1$H NMR (400 MHz, $CDCl_3$) δ: 1.41-1.78 (21H, m), 2.21-2.30 (2H, m), 2.56-2.61 (1H, m), 3.27 (2H, t, J = 4.5 Hz), 3.42-3.68 (5H, m), 4.17 (2H, t, J = 4.5 Hz), 6.67 (1H, d, J = 9.1 Hz), 6.86 (1H, d, J = 2.4 Hz), 6.93 (1H, dd, J = 8.5, 2.4 Hz).<br>LRMS (ESI$^+$) 429 [M + H]$^+$. |
| 8-13 | 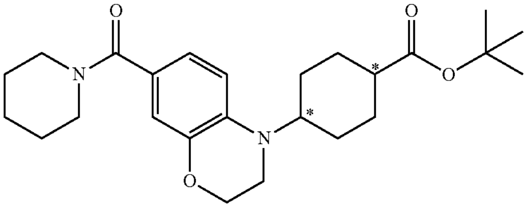 [SMILES: CC(C)(C)OC(=O)C1CCC(N2CCOc3cc(C(=O)N4CCCCC4)ccc32)CC1] | $^1$H NMR (400 MHz, $CDCl_3$) δ: 1.39-1.80 (19H, m), 1.85-1.93 (2H, m), 2.06-2.21 (31-1, m), 3.28 (2H, t, J = 4.5 Hz), 3.42-3.68 (5H, m), 4.19 (2H, t, J = 4.5 Hz), 6.67 (11-1, d, J = 8.5 Hz), 6.87 (1H, d, J = 1.8 Hz), 6.93 (1H, dd, J = 8.5, 1.8 Hz).<br>LRMS (ESI$^+$) 429 [M + H]$^+$. |

TABLE 123

| Example No. | Chemical Structural Formula | Spectrum Data |
|---|---|---|
| 8-14 | 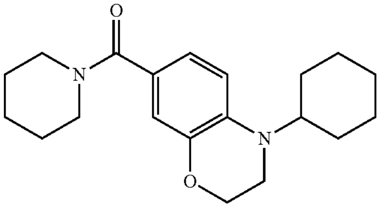 [SMILES: O=C(c1ccc2c(c1)OCCN2C1CCCCC1)N1CCCCC1] | $^1$H NMR (400 MHz, DMSO-$d_6$) δ: 1.05-1.19 (1H, m), 1.31-1.50 (8H, m), 1.55-1.81 (7H, m), 3.26 (2H, t, J = 4.5 Hz), 3.42 (4H, t, J = 4.8 Hz), 3.57-3.66 (1H, m), 4.11 (2H, t, J = 4.5 Hz), 6.67 (1H, d, J = 1.8 Hz), 6.76 (1H, d, J = 8.5 Hz), 6.81 (1H, dd, J = 8.5, 1.8 Hz).<br>LRMS (ESI$^+$) 329 [M + H]$^+$. |
| 8-15 | 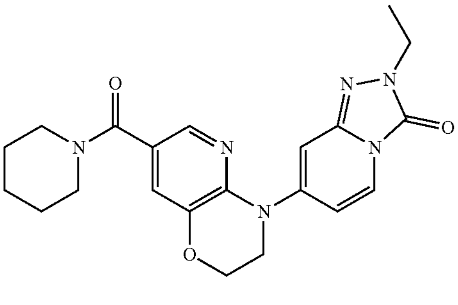 [SMILES: CCn1nc2cc(N3CCOc4cc(C(=O)N5CCCCC5)cnc43)ccn2c1=O] | $^1$H NMR (400 MHz, DMSO-$d_6$) δ: 1.28 (3H, t, J = 7.0 Hz), 1.41-1.64 (6H, m), 3.32-3.58 (4H, m), 3.83-3.95 (4H, m), 4.36 (2H, t, J = 4.3 Hz), 6.91 (1H, d, J = 1.2 Hz), 6.98 (1H, dd, J = 7.9, 1.8 Hz), 7.21 (1H, d, J = 1.8 Hz), 7.73-7.79 (2H, m).<br>LRMS (ESI$^+$) 409 [M + H]$^+$. |

TABLE 123-continued

| Example No. | Chemical Structural Formula | Spectrum Data |
| --- | --- | --- |
| 8-16 | 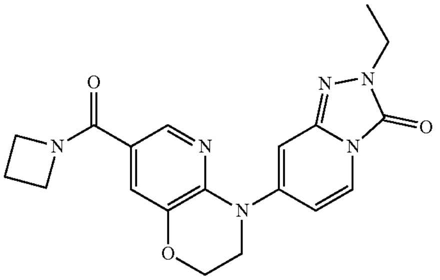 [SMILES: CCn1nc2cc(N3CCOc4cc(C(=O)N5CCC5)cnc43)ccn2c1=O] | $^1H$ NMR (400 MHz, DMSO-$d_6$) δ: 1.28 (3H, t, J = 7.0 Hz), 2.20-2.28 (2H, m), 3.88 (2H, q, J = 7.1 Hz), 3.94 (2H, t, J = 4.6 Hz), 3.98-4.06 (2H, m), 4.28-4.41 (4H, m), 6.93-6.97 ( 2H, m), 7.36 (1H, d, J = 1.8 Hz), 7.75-7.79 (1H, m), 8.00 ( 1H, d, J = 1.8 Hz). LRMS (ESI$^+$) 381 [M + H]$^+$. |
| 8-17 | 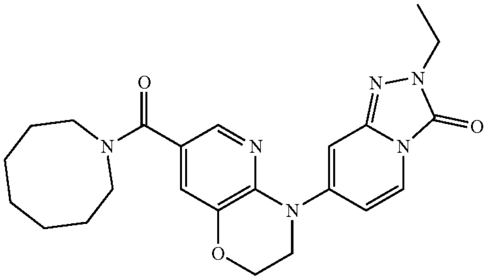 [SMILES: CCn1nc2cc(N3CCOc4cc(C(=O)N5CCCCCCC5)cnc43)ccn2c1=O] | $^1H$ NMR (400 MHz, DMSO-$d_6$) δ: 1.28 (3H, t, J = 7.0 Hz), 1.43-1.61 (8H, m), 1.64-1.75 (2H, m), 3.27-3.39 (2H, m), 3.50 (2H, t, J = 5.8 Hz), 3.87 (2H, q, J = 7.1 Hz), 3.93 (2H, t, J = 4.3 Hz), 4.36 (2H, t, J = 4.3 Hz), 6.90 (1H, d, J = 1.2 Hz), 6.98 (1H, dd, J = 7.6, 2.1 Hz), 7.19 (1H, d, J = 1.8 Hz), 7.73-7.78 (2H, m). LRMS (ESI$^+$) 437 [M + H]$^+$. |
| 8-18 | 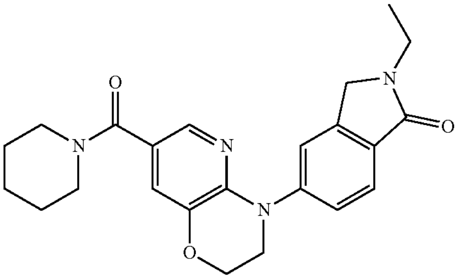 [SMILES: CCN1Cc2cc(N3CCOc4cc(C(=O)N5CCCCC5)cnc43)ccc2C1=O] | $^1H$ NMR (400 MHz, DMSO-$d_6$) δ: 1.16 (3H, t, J = 7.3 Hz), 1.40-1.65 (6H, m), 3.35-3.59 (6H, m), 3.96 (2H, t, J = 4.3 Hz), 4.35 (2H, t, J = 4.3 Hz), 4.45 (2H, s), 7.15 (1H, d, J = 1.8 Hz), 7.51 (1H, dd, J = 7.9, 1.8 Hz), 7.63 (2H, d, J = 8.6 Hz), 7.68 (1H, d, J = 1.8 Hz). LRMS (ESI$^+$) 407 [M + H]$^+$. |
| 8-19 | 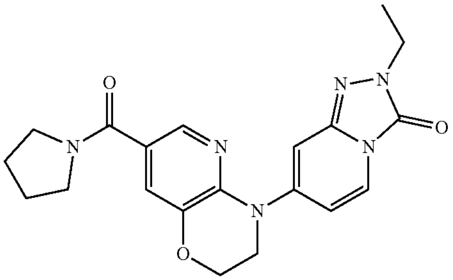 [SMILES: CCn1nc2cc(N3CCOc4cc(C(=O)N5CCCC5)cnc43)ccn2c1=O] | $^1H$ NMR (400 MHz, DMSO-$d_6$) δ 1.28 (3H, t, J = 7.0 Hz), 1.75-1.88 (4H, m), 3.38-3.51 (4H, m), 3.88 (2H, q, J = 7.1 Hz), 3.93 (2H, t, J = 4.6 Hz), 4.36 (2H, t, J = 4.3 Hz), 6.92 (1H, d, J = 1.2 Hz), 6.97 (1H, dd, J = 7.6, 2.1 Hz), 7.34 (1H, d, J = 1.8 Hz), 7.76 (1H, d, J = 7.3 Hz), 7.95 (1H, d, J = 1.8 Hz). LRMS (ESI$^+$) 395 [M + H]$^+$. |

TABLE 124

| Example No. | Chemical Structural Formula | Spectrum Data |
| --- | --- | --- |
| 8-20 | 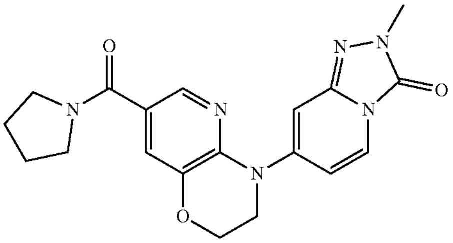 [SMILES: Cn1nc2cc(N3CCOc4cc(C(=O)N5CCCC5)cnc43)ccn2c1=O] | $^1H$ NMR (400 MHz, DMSO-$d_6$) δ 1.74-1.89 (4H, m), 3.38-3.54 (7H, m), 3.93 (2H, t, J = 4.3 Hz), 4.36 (2H, t, J = 4.3 Hz), 6.89 (1H, d, J = 1.8 Hz), 6.98 (1H, dd, J = 7.6, 2.1 Hz), 7.34 (1H, d, J = 1.8 Hz), 7.75 (1H, d, J = 7.3 Hz), 7.95 (1H, d, J = 1.8 Hz). LRMS (ESI$^+$) 381 [M + H]$^+$. |

TABLE 124-continued

| Example No. | Chemical Structural Formula | Spectrum Data |
| --- | --- | --- |
| 8-21 | 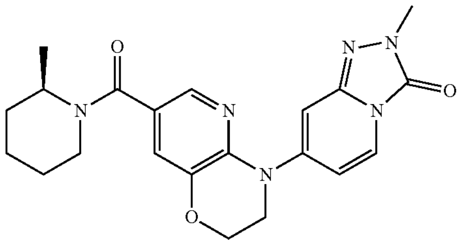 [SMILES: C[C@@H]1CCCCN1C(=O)c1cnc2c(c1)OCCN2c1ccn2c(=O)n(C)nc2c1] | $^1$H NMR (400 MHz, DMSO-$d_6$) δ 1.17 (3H, d, J = 7.3 Hz), 1.27-1.73 (6H, m), 2.90-3.04 (1H, m), 3.49 (3H, s), 3.77-4.05 (3H, m), 4.25-4.47 (3H, m), 6.88 (1H, d, J = 1.8 Hz), 6.98 (1H, dd, J = 7.3, 1.8 Hz), 7.19 (1H, d, J = 1.8 Hz), 7.73-7.77 (2H, m). LRMS (ESI$^+$) 409 [M + H]$^+$. |
| 8-22 | 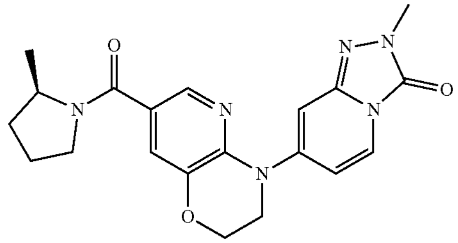 [SMILES: C[C@@H]1CCCN1C(=O)c1cnc2c(c1)OCCN2c1ccn2c(=O)n(C)nc2c1] | $^1$H NMR (400 MHz, DMSO-$d_6$) δ 0.73-1.32 (3H, m), 1.40-1.95 (3H, m), 1.99-2.12 (1H, m), 3.34-3.63 (5H, m), 3.93 (2H, t, J = 4.6 Hz), 4.01-4.16 (1H, m), 4.29-4.42 (2H, m), 6.89 (1H, d, J = 1.8 Hz), 6.98 (1H, dd, J = 7.9, 1.8 Hz), 7.31 (1H, d, J = 1.8 Hz), 7.75 (1H, d, J = 8.6 Hz), 7.85-7.97 (1H, m). LRMS (ESI$^+$) 395 [M + H]$^+$. |
| 8-23 | 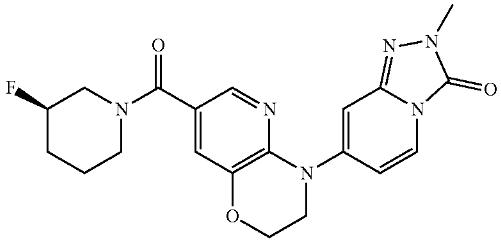 [SMILES: Cn1nc2cc(N3CCOc4cc(C(=O)N5CCC[C@@H](F)C5)cnc43)ccn2c1=O] | $^1$H NMR (400 MHz, DMSO-$d_6$) δ 1.43-1.95 (4H, m), 2.87-3.27 (1H, m), 3.38-3.60 (4H, m), 3.69-4.24 (4H, m), 4.37 (2H, t, J = 4.6 Hz), 4.75 (1H, d, J = 47.7 Hz), 6.89 (1H, d, J = 2.4 Hz), 6.98 (1H, dd, J = 7.6, 2.1 Hz), 7.20 (1H, d, J = 1.8 Hz), 7.75 (1H, d, J = 8.6 Hz), 7.78 (1H, d, J = 1.8 Hz). LRMS (ESI$^+$) 413 [M + H]$^+$. |
| 8-24 | 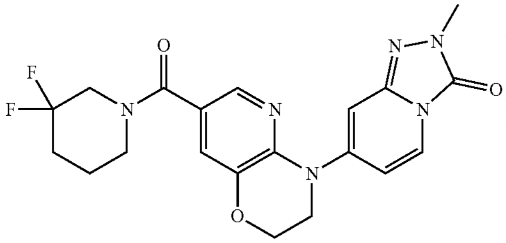 [SMILES: Cn1nc2cc(N3CCOc4cc(C(=O)N5CCCC(F)(F)C5)cnc43)ccn2c1=O] | $^1$H NMR (400 MHz, DMSO-$d_6$) δ 1.63-1.74 (2H, m), 2.02-2.16 (2H, m), 3.40-3.64 (5H, m), 3.71-3.90 (2H, m), 3.94 (2H, t, J = 4.3 Hz), 4.37 (2H, t, J = 4.3 Hz), 6.91 (1H, d, J = 1.2 Hz), 6.99 (1H, dd, J = 7.9, 1.8 Hz), 7.21 (1H, d, J = 1.8 Hz), 7.75 (1H, d, J = 8.6 Hz), 7.79 (1H, d, J = 1.8 Hz). LRMS (ESI$^+$) 431 [M + H]$^+$. |
| 8-25 | 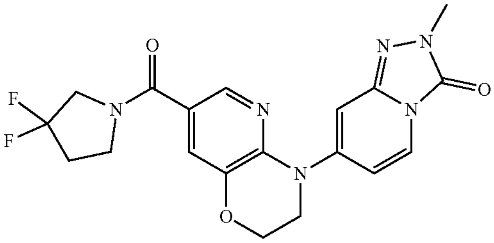 [SMILES: Cn1nc2cc(N3CCOc4cc(C(=O)N5CCC(F)(F)C5)cnc43)ccn2c1=O] | $^1$H NMR (400 MHz, DMSO-$d_6$) δ 2.35-2.52 (2H, m), 3.49 (3H, s), 3.61-4.09 (6H, m), 4.37 (2H, t, J = 4.3 Hz), 6.92 (1H, d, J = 1.2 Hz), 6.97 (1H, dd, J = 7.3, 1.8 Hz), 7.37 (1H, d, J = 1.8 Hz), 7.76 (1H, d, J = 7.9 Hz), 7.98 (1H, d, J = 1. 8 Hz). LRMS (ESI$^+$) 417 [M + H]$^+$. |

TABLE 125

| Example No. | Chemical Structural Formula | Spectrum Data |
|---|---|---|
| 8-26 | 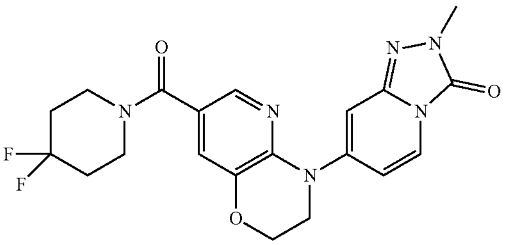 [SMILES: Cn1nc2cc(N3CCOc4cc(C(=O)N5CCC(F)(F)CC5)cnc43)ccn2c1=O] | $^{1}$H NMR (400 MHz, DMSO-$d_6$) δ 1.95-2.10 (4H, m), 3.49 (3 H, s), 3.51-3.69 (4H, m), 3.93 (2H, t, J = 4.3 Hz), 4.37 (2H, t, J = 4.3 Hz), 6.90 (1H, d, J = 1.2 Hz), 6.98 (1H, dd, J = 7.6, 2.1 Hz), 7.30 (1H, d, J = 1.8 Hz), 7.76 (1H, d, J = 6.7 Hz), 7.85 (1H, d, J = 1.8 Hz). LRMS (ESI$^+$) 431 [M + H]$^+$. |
| 8-27 | 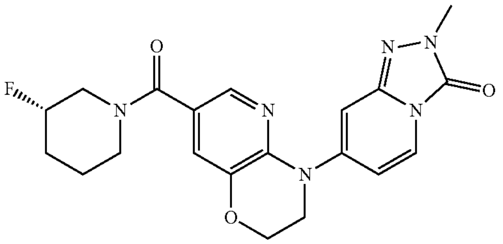 [SMILES: Cn1nc2cc(N3CCOc4cc(C(=O)N5CCC[C@H](F)C5)cnc43)ccn2c1=O] | $^{1}$H NMR (400 MHz, DMSO-$d_6$) δ 1.40-1.99 (4H, m), 2.93-3.28 (1H, m), 3.39-3.58 (4H, m), 3.68-4.24 (4H, m), 4.37 (2H, t, J = 4.6 Hz), 4.75 (1H, d, J = 47.1 Hz), 6.89 (1H, d, J = 2.4 Hz), 6.98 (1H, dd, J = 7.6, 2.1 Hz), 7.20 (1H, d, J = 1.8 Hz), 7.75 (1H, d, J = 7.9 Hz), 7.78 (1H, d, J = 1.8 Hz). LRMS (ESI$^+$) 413 [M + H]$^+$. |
| 8-28 | 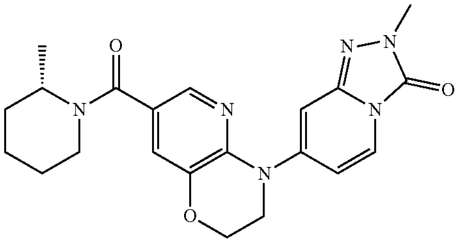 [SMILES: C[C@H]1CCCCN1C(=O)c1cnc2c(c1)OCCN2c1ccn2c(=O)n(C)nc2c1] | $^{1}$H NMR (400 MHz, DMSO-$d_6$) δ 1.17 (3H, d, J = 7.3 Hz), 1.27-1.76 (6H, m), 2.83-3.11 (1H, m), 3.49 (3H, s), 3.68-4.06 (3H, m), 4.15-4.58 (3H, m), 6.88 (1H, d, J = 1.2 Hz), 6.98 (1H, dd, J = 7.6, 2.1 Hz), 7.19 (1H, d, J = 1.8 Hz), 7.73-7.77 (2H, m). LRMS (ESI$^+$) 409 [M + H]$^+$. |
| 8-29 | 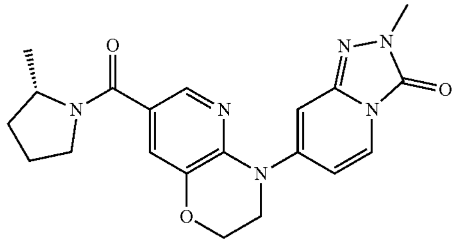 [SMILES: C[C@H]1CCCN1C(=O)c1cnc2c(c1)OCCN2c1ccn2c(=O)n(C)nc2c1] | $^{1}$H NMR (400 Mflz, DMSO-$d_6$) δ 0.73-1.29 (3H, m), 1.42-1.93 (3H, m), 1.99-2.11 (1H, m), 3.34-3.64 (5H, m), 3.93 (2H, t, J = 4.6 Hz), 4.02-4.15 (1H, m), 4.31-4.41 (2H, m), 6.89 H, d, J = 1.8 Hz), 6.98 (1H, dd, J = 7.9, 1.8 Hz), 7.31 (1H, d, J = 1.8 Hz), 7.75 (1H, d, J = 7.9 Hz), 7.85-7.96 (1H, m). LRMS (ESI$^+$) 395 [M + H]$^+$. |
| 8-30 | 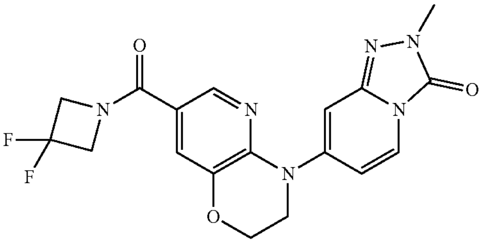 [SMILES: Cn1nc2cc(N3CCOc4cc(C(=O)N5CC(F)(F)C5)cnc43)ccn2c1=O] | $^{1}$H NMR (400 MHz, DMSO-$d_6$) δ 3.50 (3H, s), 3.95 (2H, t, J = 4.3 Hz), 4.27-5.02 (6H, m), 6.92-6.97 (2H, m), 7.43 (1H, d, J = 1.8 Hz), 7.78 (1H, dd, J = 6.7, 1.2 Hz), 8.08 (1H, d, J = 2.4 Hz). LRMS (ESI$^+$) 403 [M + H]$^+$. |
| 8-31 | 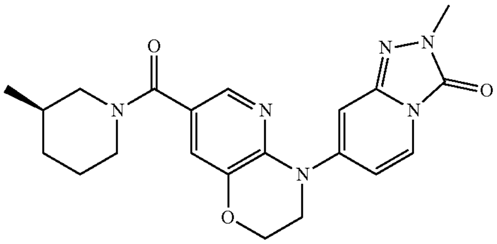 [SMILES: C[C@@H]1CCCN(C(=O)c2cnc3c(c2)OCCN3c2ccn3c(=O)n(C)nc3c2)C1] | $^{1}$H NMR (400 MHz, DMSO-$d_6$) δ 0.66-0.99 (3H, m), 1.06-1.20 (1H, m), 1.33-1.47 (1H, m), 1.48-1.69 (2H, m), 1.71-1.81 (1H, m), 2.56-3.07 (2H, m), 3.49 (3H, s), 3.51-3.76 (1H, m), 3.85-4.00 (2H, m), 4.04-4.40 (3H, m), 6.88 (1H, d, J = 1.8 Hz), 6.99 (1H, dd, J = 7.6, 2.1 Hz), 7.20 (1H, d, J = 1.8 Hz), 7.75 (1H, d, J = 8.6 Hz), 7.77 (1H, d, J = 2.4 Hz). LRMS (ESI$^+$) 409 [M + H]$^+$. |

TABLE 126

| Example No. | Chemical Structural Formula | Spectrum Data |
|---|---|---|
| 8-32 | 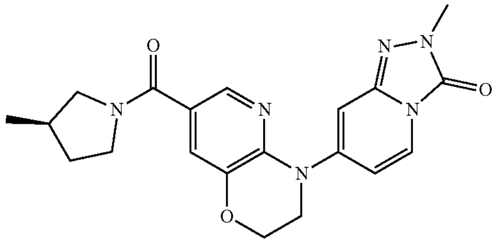 [SMILES: C[C@@H]1CCN(C(=O)c2cnc3c(c2)OCCN3c2ccn3c(=O)n(C)nc3c2)C1] | $^1$H NMR (400 MHz, DMSO-$d_6$) δ 0.91-1.06 (3H, m), 1.37-1.53 (1H, m), 1.88-2.04 (1H, m), 2.09-2.30 (1H, m), 2.91-3.15 (1H, m), 3.35-3.64 (6H, m), 3.93 (2H, t, J = 4.6 Hz), 4.36 (2H, t, J = 4.3 Hz), 6.89 (1H, d, J = 1.2 Hz), 6.95-7.01 (1H, m), 7.31-7.37 (1H, m), 7.75 (1H, d, J = 8.6 Hz), 7.92-7.98 (1H, m). LRMS (ESI$^+$) 395 [M + H]$^+$. |
| 8-33 | 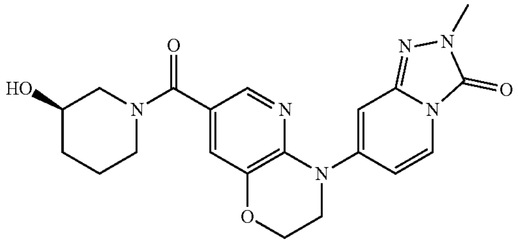 [SMILES: Cn1nc2cc(N3CCOc4cc(C(=O)N5CCC[C@@H](O)C5)cnc43)ccn2c1=O] | $^1$H NMR (400 MHz, DMSO-$d_6$) δ 1.26-1.51 (2H, m), 1.55-1.95 (2H, m), 2.63-3.74 (8H, m), 3.93 (2H, t, J = 4.6 Hz), 4.36 (2H, t, J = 4.3 Hz), 4.78-5.03 (1H, m), 6.88 (1H, d, J = 1.2 Hz), 6.98 (1H, dd, J = 7.6, 2.1 Hz), 7.18-7.28 (1H, m), 7.70-7.87 (2H, m). LRMS (ESI$^+$) 411 [M + H]$^+$. |
| 8-34 | 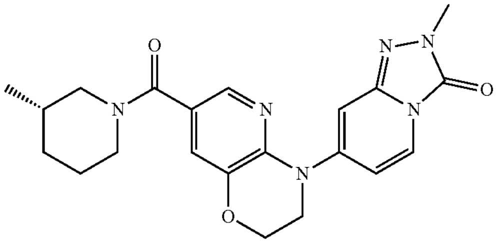 [SMILES: C[C@H]1CCCN(C(=O)c2cnc3c(c2)OCCN3c2ccn3c(=O)n(C)nc3c2)C1] | $^1$H NMR (400 MHz, DMSO-$d_6$) δ 0.75-0.93 (3H, m), 1.07-1.20 (1H, m), 1.32-1.47 (1H, m), 1.48-1.83 (3H, m), 2.59-3.12 (2H, m), 3.42-3.77 (4H, m), 3.85-4.00 (2H, m), 4.04-4.45 (3H, m), 6.88 (1H, d, J = 1.8 Hz), 6.99 (1H, dd, J = 7.3, 1.8 Hz), 7.20 (1H, d, J = 1.8 Hz), 7.73-7.79 (2H, m). LRMS (ESI$^+$) 409 [M + H]$^+$. |
| 8-35 | 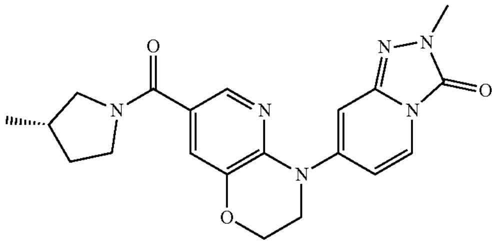 [SMILES: C[C@H]1CCN(C(=O)c2cnc3c(c2)OCCN3c2ccn3c(=O)n(C)nc3c2)C1] | $^1$H NMR (400 MHz, DMSO-$d_6$) δ 0.92-1.07 (3H, m), 1.38-1.55 (1H, m), 1.86-2.04 (1H, m), 2.10-2.29 (1H, m), 2.93-3.15 (1H, m), 3.34-3.63 (6H, m), 3.93 (2H, t, J = 4.6 Hz), 4.36 (2H, t, J = 4.3 Hz), 6.90 (1H, d, J = 1.2 Hz), 6.95-7.00 (1H, m), 7.32-7.36 (1H, m), 7.75 (1H, d, J = 7.3 Hz), 7.92-7.97 (1H, m). LRMS (ESI$^+$) 395 [M + H]$^+$. |
| 8-36 | 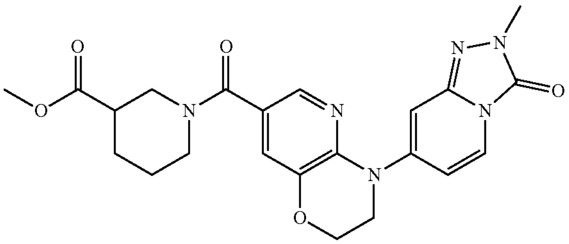 [SMILES: COC(=O)C1CCCN(C(=O)c2cnc3c(c2)OCCN3c2ccn3c(=O)n(C)nc3c2)C1] | $^1$H NMR (400 MHz, DMSO-$d_6$) δ 1.36-2.03 (4H, m), 2.52-2.68 (1H, m), 2.74-3.18 (2H, m), 3.49 (3H, s), 3.52-4.04 (7H, m), 4.12-4.44 (2H, m), 6.89 (1H, d, J = 1.2 Hz), 6.98 (1H, dd, J = 7.6, 2.1 Hz), 7.23 (1H, d, J = 1.8 Hz), 7.72-7.83 (2H, m). LRMS (ESI$^+$) 453 [M + H]$^+$. |
| 8-37 | 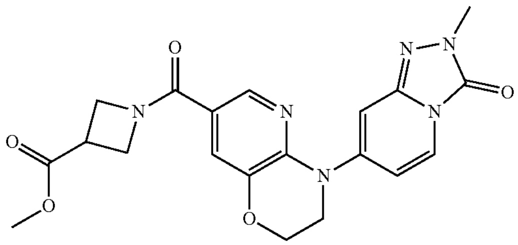 [SMILES: COC(=O)C1CN(C(=O)c2cnc3c(c2)OCCN3c2ccn3c(=O)n(C)nc3c2)C1] | $^1$H NMR (400 MHz, DMSO-$d_6$) δ 3.49 (3H, s), 3.51-3.60 (1H, m), 3.65 (3H, s), 3.91-3.98 (2H, m), 4.02-4.27 (2H, m), 4.30-4.46 (3H, m), 4.49-4.62 (1H, m), 6.91-6.98 (2H, m), 7.36 (1H, d, J = 1.8 Hz), 7.76 (1H, d, J = 6.7 Hz), 8.01 (1H, d, J = 1.8 Hz). LRMS (ESI$^+$) 425 [M + H]$^+$. |

TABLE 127

| Example No. | Chemical Structural Formula | Spectrum Data |
|---|---|---|
| 8-38 | 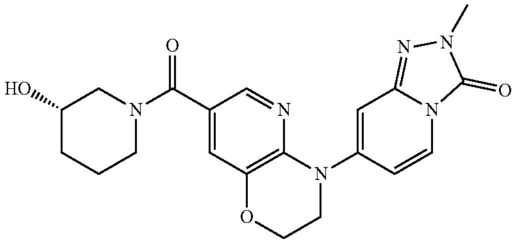 [SMILES: Cn1nc2cc(N3CCOc4cc(C(=O)N5CCC[C@H](O)C5)cnc43)ccn2c1=O] | $^1$H NMR (400 MHz, DMSO-$d_6$) δ 1.30-1.51 (2H, m), 1.56-1.94 (2H, m), 2.92-3.75 (8H, m), 3.93 (2H, t, J = 4.3 Hz), 4.36 (2H, t, J = 4.3 Hz), 4.77-5.02 (1H, m), 6.88 (1H, d, J = 1.8 Hz), 6.98 (1H, dd, J = 7.9, 1.8 Hz), 7.17-7.29 (1H, m), 7.71-7.84 (2H, m). LRMS (ESI$^+$) 411 [M + H]$^+$. |
| 8-39 | 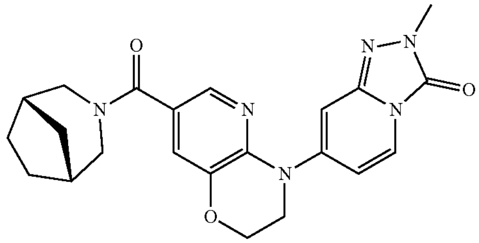 [SMILES: Cn1nc2cc(N3CCOc4cc(C(=O)N5C[C@@H]6CC[C@@H](C6)C5)cnc43)ccn2c1=O] | $^1$H NMR (400 MHz, DMSO-d6) δ 1.23-1.63 (6H, m), 2.01-2.30 (2H, m), 2.68-2.89 (1H, m), 3.05-3.54 (5H, m), 3.87-3.98 (2H, m), 4.14-4.44 (3H, m), 6.87 (1H, d, J = 1.2 Hz), 6.98 (1H, dd, J = 7.3, 1.8 Hz), 7.18 (1H, d, J = 1.8 Hz), 7.72-7.77 (2H, m). LRMS (ESI$^+$) 421 [M + H]$^+$. |
| 8-40 | 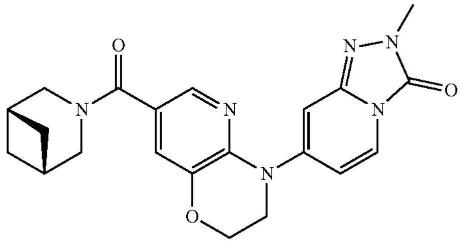 [SMILES: Cn1nc2cc(N3CCOc4cc(C(=O)N5C[C@H]6C[C@@H](C5)C6)cnc43)ccn2c1=O] | $^1$H NMR (400 MHz, DMSO-$d_6$) δ 1.29-1.39 (2H, m), 2.03-2.14 (2H, m), 2.30-2.39 (1H, m), 2.41-2.58 (1H, m), 3.49 (3H, s), 3.59-3.73 (4H, m), 3.92 (2H, t, J = 4.3 Hz), 4.36 (2H, t, J = 4.3 Hz), 6.88 (1H, d, J = 1.2 Hz), 6.98 (1H, dd, J = 7.3, 1.8 Hz), 7.33 (1H, d, J = 1.8 Hz), 7.75 (1H, d, J = 8.6 Hz), 7.87 (1H, d, J = 1.8 Hz). LRMS (ESI$^+$) 407 [M + H]$^+$. |
| 8-41 | 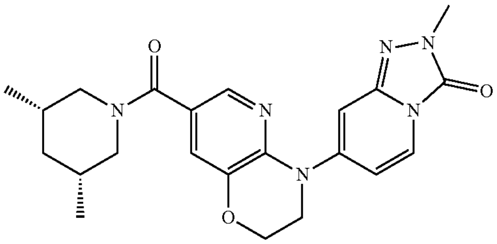 [SMILES: C[C@@H]1C[C@H](C)CN(C(=O)c2cnc3c(c2)OCCN3c2ccn3c(=O)n(C)nc3c2)C1] | $^1$H NMR (400 MHz, DMSO-$d_6$) δ 0.63-1.03 (7H, m), 1.49-1.64 (2H, m), 1.72-1.81 (1H, m), 2.09-2.70 (2H, m), 3.44-3.78 (4H, m), 3.93 (2H, t, J = 4.3 Hz), 4.28-4.48 (3H, m), 6.89 (1H, d, J = 1.2 Hz), 6.99 (1H, dd, J = 7.6, 2.1 Hz), 7.20 (1H, d, J = 2.4 Hz), 7.73-7.79 (2H, m). LRMS (ESI$^+$) 423 [M + H]$^+$. |
| 8-42 | 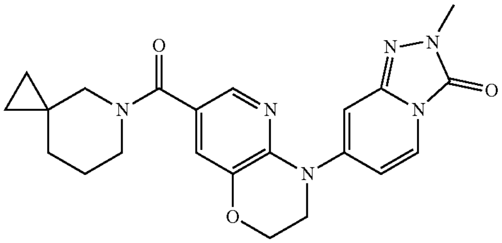 [SMILES: Cn1nc2cc(N3CCOc4cc(C(=O)N5CCCC6(CC6)C5)cnc43)ccn2c1=O] | $^1$H NMR (400 MHz, DMSO-$d_6$) δ 0.04-0.55 (4H, m), 1.38-1.49 (2H, m), 1.53-1.66 (2H, m), 3.09-3.68 (7H, m), 3.93 (2H, t, J = 4.3 Hz), 4.36 (2H, t, J = 4.3 Hz), 6.88 (1H, d, J = 1.2-Hz), 6.98 (1H, dd, J = 7.6, 2.1 Hz), 7.14-7.22 (1H, m), 7.71 7.81 (2H, m). LRMS (ESI$^+$) 421 [M + H]$^+$. |
| 8-43 | 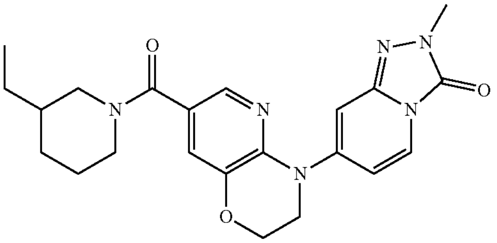 [SMILES: CCC1CCCN(C(=O)c2cnc3c(c2)OCCN3c2ccn3c(=O)n(C)nc3c2)C1] | $^1$H NMR (400 MHz, DMSO-$d_6$) δ 0.68-0.97 (3H, m), 1.00-1.47 (5H, m), 1.53-1.71 (1H, m), 1.77-1.88 (1H, m), 2.41-3.09 (2H, m), 3.38-3.77 (4H, m), 3.87-4.00 (2H, m), 4.12-4.42 (3H, m), 6.88 (1H, d, J = 1.8 Hz), 6.98 (1H, dd, J = 7.3, 1.8 Hz), 7.20 (1H, d, J = 1.8 Hz), 7.75 (1H, d, J = 7.9 Hz), 7.77 (1H, d, J = 1.8 Hz). LRMS (ESI$^+$) 423 [M + H]$^+$. |

TABLE 128

| Example No. | Chemical Structural Formula | Spectrum Data |
|---|---|---|
| 8-44 | 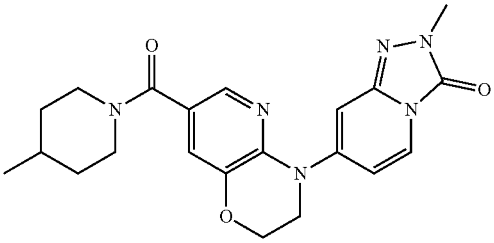 [SMILES: CC1CCN(C(=O)c2cnc3c(c2)OCCN3c2ccn3c(=O)n(C)nc3c2)CC1] | $^1$H NMR (400 MHz, DMSO-$d_6$) δ 0.90 (3H, d, J = 6.1 Hz), 0.96-1.12 (2H, m), 1.50-1.71 (3H, m), 2.62-3.10 (2H, m), 3.49 (3H, s), 3.59-4.02 (3H, m), 4.15-4.45 (3H, m), 6.88 (1H, d, J = 1.2 Hz), 6.98 (1H, dd, J = 7.6, 2.1 Hz), 7.21 (1H, d, J = 1.8 Hz), 7.75 (1H, d, J = 6.7 Hz), 7.77 (1H, d, J = 1.8 Hz). LRMS (ESI$^+$) 409 [M + H]$^+$. |
| 8-45 | 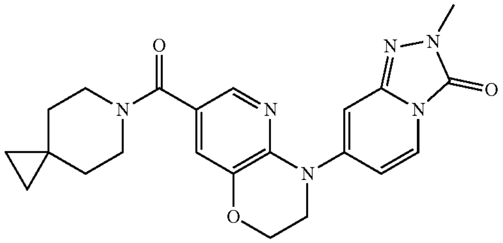 [SMILES: Cn1nc2cc(N3CCOc4cc(C(=O)N5CCC6(CC5)CC6)cnc43)ccn2c1=O] | $^1$H NMR (400 MHz, DMSO-$d_6$) δ 0.29-0.36 (4H, m), 1.28-1.39 (4H, m), 3.36-3.63 (7H, m), 3.93 (2H, t, J = 4.6 Hz), 4.36 (2H, t, J = 4.6 Hz), 6.88 (1H, d, J = 1.2 Hz), 6.98 (1H, d d, J = 7.6, 2.1 Hz), 7.23 (1H, d, J = 1.8 Hz), 7.75 (1H, d, J = 8.6 Hz), 7.80 (1H, d, J = 1.8 Hz). LRMS (ESI$^+$) 421 [M + H]$^+$. |
| 8-46 | 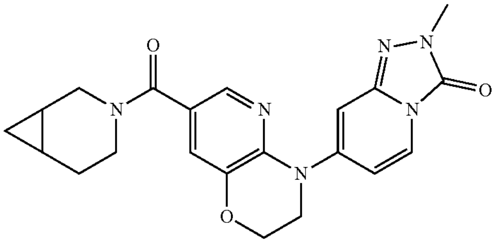 [SMILES: Cn1nc2cc(N3CCOc4cc(C(=O)N5CCC6CC6C5)cnc43)ccn2c1=O] | $^1$H NMR (400 MHz, DMSO-$d_6$) δ 0.03-0.33 (1H, m), 0.53-0.69 (1H, m), 0.88-1.20 (2H, m), 1.58-1.71 (1H, m), 1.89-2.00 (1H, m), 3.00-3.14 (1H, m), 3.49 (3H, s), 3.51-3.89 (3H, m), 3.93 (2H, t, J = 4.3 Hz), 4.36 (2H, t, J = 4.3 Hz), 6.88 (1H, d, J = 1.2 Hz), 6.98 (1H, dd, J = 7.9, 1.8 Hz), 7.19 (1H, d, J = 1.8 Hz), 7.73-7.79 (2H, m). LRMS (ESI$^+$) 407 [M + H]$^+$. |
| 8-47 | 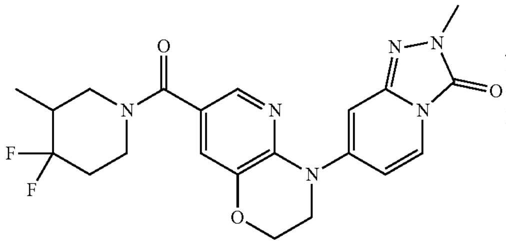 | $^1$H NMR (400 MHz, $CDCl_3$) δ 1.14-1.75 (4H, m), 1.84-2.10 (2H, m), 2.73-3.17 (2H, m), 3.64 (3H, s), 3.84-3.94 (3H, m), 4.29-4.68 (3H, m), 6.64 (1H, d, J = 1.2 Hz), 6.99 (1H, dd, J = 7.6, 2.1 Hz), 7.29 (1H, d, J = 1.8 Hz), 7.68 (1H, d, J = 7.3 Hz), 7.92 (1H, d, J = 1.8 Hz). LRMS (ESI$^+$) 445 [M + H]$^+$. |
| 8-48 | 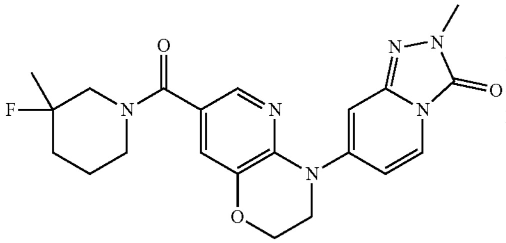 [SMILES: Cn1nc2cc(N3CCOc4cc(C(=O)N5CCCC(C)(F)C5)cnc43)ccn2c1=O] | $^1$H NMR (400 MHz, $CDCl_3$) δ 0.79-1.17 (4H, m), 1.75-2.24 (3H, m), 2.94-3.13 (1H, m), 3.29-3.42 (1H, m), 3.65 (3H, s), 3.73-4.60 (6H, m), 6.66 (1H, d, J = 1.2 Hz), 6.96 (1H, dd, J = 7.6, 2.1 Hz), 7.24-7.28 (1H, m), 7.69 (1H, d, J = 7.9 Hz), 7.89 (1H, d, J = 1.8 Hz). LRMS (ESI$^+$) 427 [M + H]$^+$. |
| 8-49 | 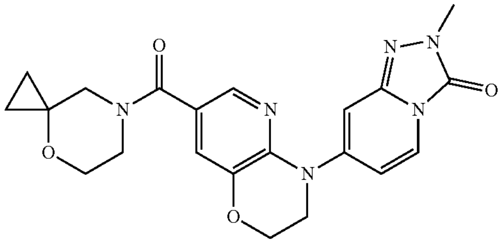 [SMILES: Cn1nc2cc(N3CCOc4cc(C(=O)N5CCOC6(CC6)C5)cnc43)ccn2c1=O] | $^1$H NMR (400 MHz, DMSO-$d_6$) δ 0.39-0.76 (4H, m), 3.43-3.70 (9H, m), 3.93 (2H, t, J = 4.6 Hz), 4.36 (2H, t, J = 4.3 Hz), 6.90 (1H, d, J = 1.2 Hz), 6.98 (1H, dd, J = 7.6, 2.1 Hz), 7.20-7.27 (1H, m), 7.75 (1H, d, J = 6.7 Hz), 7.78-7.85 (1H, m). LRMS (ESI$^+$) 423 [M + H]$^+$. |

TABLE 129

| Example No. | Chemical Structural Formula | Spectrum Data |
|---|---|---|
| 8-50 | 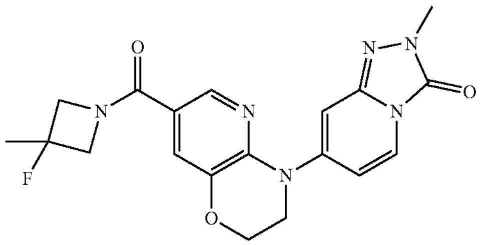 [SMILES: Cn1nc2cc(N3CCOc4cc(C(=O)N5CC(C)(F)C5)cnc43)ccn2c1=O] | $^1$H NMR (400 MHz, DMSO-d$_6$) δ 1.57 (3H, d, J = 22.0 Hz), 3.50 (3H, s), 3.94 (2H, t, J = 4.3 Hz), 3.99-4.22 (2H, m), 4.25-4.64 (4H, m), 6.93-6.97 (2H, m), 7.40 (1H, d, J = 1.8 Hz), 7.77 (1H dd, J = 7.0, 1.5 Hz), 8.04 (1H, d, J = 1.8 Hz).<br>LRMS (ESI$^+$) 399 [M + H]$^+$. |
| 8-51 | 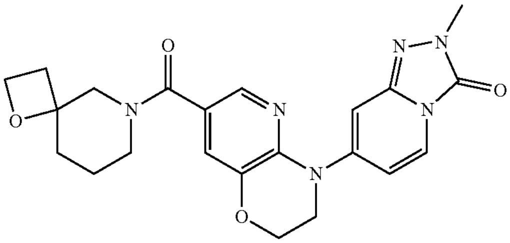 [SMILES: Cn1nc2cc(N3CCOc4cc(C(=O)N5CCCC6(CCO6)C5)cnc43)ccn2c1=O] | $^1$H NMR (400 MHz, DMSO-d$_6$) δ 1.37-1.64 (2H, m), 1.66-2.02 (2H, m), 2.08-2.38 (2H, m), 2.73-3.37 (2H, m), 3.49 (3H, s), 3.55-4.02 (3H, m), 4.06-4.47 (5H, m), 6.90 (1H, d, J = 1.2 Hz), 6.99 (1H, dd, J = 7.3, 1.8 Hz), 7.16-7.34 (1H, m), 7.72-7.88 (2H, m).<br>LRMS (ESI$^+$) 437 [M + H]$^+$. |
| 8-52 | 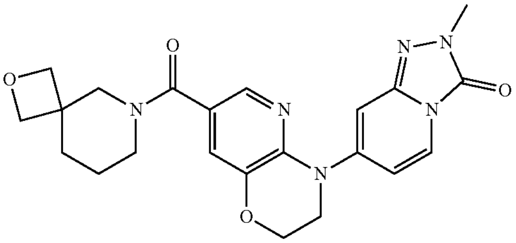 [SMILES: Cn1nc2cc(N3CCOc4cc(C(=O)N5CCCC6(COC6)C5)cnc43)ccn2c1=O] | $^1$H NMR (400 MHz, DMSO-d$_6$) δ 1.38-1.48 (2H, m), 1.82 (2H, t, J = 5.8 Hz), 3.25-3.47 (2H, m), 3.49 (3H, s), 3.58-3.84 (2H, m), 3.94 (2H, t, J = 4.3 Hz), 4.034.45 (6H, m), 6.89 (1H, d, J = 1.2 Hz), 7.00 (1H, dd, J = 7.6, 1.5 Hz), 7.23 (1H, d, J = 1.2 Hz), 7.72-7.83 (2H, m).<br>LRMS (ESI$^+$) 437 [M + H]$^+$. |
| 8-53 | 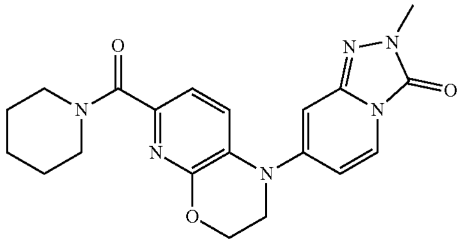 | $^1$H NMR (400 MHz, DMSO-d$_6$) δ 1.42-1.65 (6H, m), 3.38-3.59 (7H, m), 3.79 (2H, t, J = 4.3 Hz), 4.45 (2H, t, J = 4.6 Hz), 6.66 (1H, dd, J = 7.6, 2.1 Hz), 6.79 (1H, d, J = 1.2 Hz), 7.08 (1H, d, J = 7.9 Hz), 7.43 (1H, d, J = 7.9 Hz), 7.81 (1H, d, J = 7.3 Hz).<br>LRMS (ESI$^+$) 395 [M + H]$^+$. |
| 8-54 | 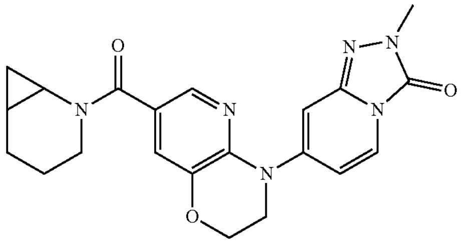 [SMILES: Cn1nc2cc(N3CCOc4cc(C(=O)N5CCCC6CC65)cnc43)ccn2c1=O] | $^1$H NMR (400 MHz, DMSO-d$_6$) δ 0.30-0.41 (0.3H, m), 0.52-0.59 (0.7H, m), 0.61-0.71 (0.7H, m), 0.77-0.91 (0.3H, m), 1.17-1.39 (2.0H, m), 1.44-1.67 (1.0H, m), 1.69-1.90 (2.0H, m), 2.44-2.57 (0.7H, m), 2.68-2.76 (0.7H, m), 2.87-3.02 (0.6H, m), 3.49 (3.0H, s), 3.89-4.05 (3.0H, m), 4.30-4.41 (2.0H, m), 6.88 (1.0H, s), 6.98 (1.0H, dd, J = 7.9, 1.8 Hz), 7.23 (0.3H, s), 7.41 (0.7H, d, J = 1.8 Hz), 7.75 (1.0H, d, J = 7.3 Hz), 7.79 (0.3H, s), 8.01 (0.7H, d, J = 1.8 Hz).<br>LRMS (ESI$^+$) 407 [M + H]$^+$. |
| 8-55 | 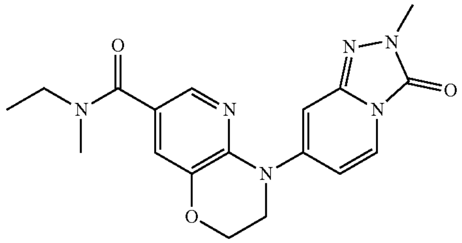 [SMILES: CCN(C)C(=O)c1cnc2c(c1)OCCN2c1ccn2c(=O)n(C)nc2c1] | $^1$H NMR (400 MHz, DMSO-d$_6$) δ 1.10 (3H, t, J = 7.0 Hz), 2.94 (3H, br s), 3.24-3.46 (2H, m), 3.50 (3H, s), 3.94 (2H, t, J = 4.2 Hz), 4.37 (2H, t, J = 4.5 Hz), 6.90 (1H, d, J = 1.2 Hz), 6.99 (1H, dd, J = 7.6, 2.1 Hz), 7.24 (1H, br s), 7.74-7.85 (2H, m).<br>LRMS (ESI$^+$) 369 [M + H]$^+$. |

TABLE 130

| Example No. | Chemical Structural Formula | Spectrum Data |
|---|---|---|
| 8-56 | 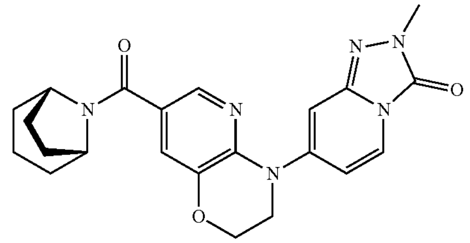 | $^1H$ NMR (400 MHz, DMSO-$d_6$) δ 1.37-2.04 (10H, m), 3.50 (3H, s), 3.95 (2H, t, J = 4.2 Hz), 4.08 (1H, br s), 4.38 (2H, t, J = 4.2 Hz), 4.54 (1H, br s), 6.91 (1H, d, J = 1.2 Hz), 7.00 (1H, dd, J = 7.6, 2.1 Hz), 7.27 (1H, d, J = 2.4 Hz), 7.76 (1H, d, J = 7.3 Hz), 7.87 (1H, d, J = 1.8 Hz). LRMS (ESI$^+$) 421 [M + H]$^+$. |
| 8-57 | 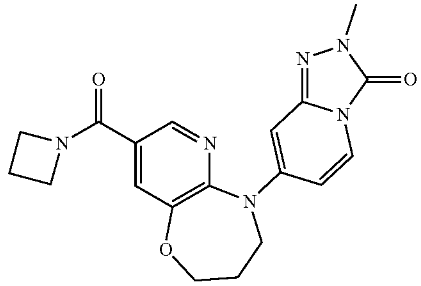 [SMILES: Cn1nc2cc(N3CCCOc4cc(C(=O)N5CCC5)cnc43)ccn2c1=O] | $^1H$ NMR (400 MHz, DMSO-$d_6$) δ 2.01-2.10 (2H, m), 2.22-2.31 (2H, m), 3.46 (3H, s), 3.97 (2H, t, J = 6.1 Hz), 4.05 (2H, t, J = 7.9 Hz), 4.22 (2H, t, J = 5.8 Hz), 4.37 (2H, t, J = 7.6 Hz), 6.45 (1H, dd, J = 7.9, 2.4 Hz), 6.69 (1H, d, J = 1.2 Hz), 7.56 (1H, d, J = 1.8 Hz), 7.66 (1H, d, J = 7.9 Hz), 8.25 (1H, d, J = 1.8 Hz). LRMS (ESI$^+$) 381 [M + H]$^+$. |
| 8-58 | 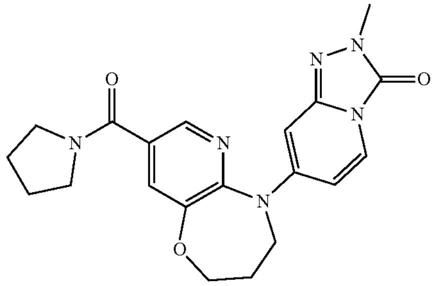 [SMILES: Cn1nc2cc(N3CCCOc4cc(C(=O)N5CCCC5)cnc43)ccn2c1=O] | $^1H$ NMR (400 MHz, DMSO-$d_6$) δ 1.76-1.92 (4H, m), 2.02-2.12 (2H, m), 3.42-3.53 (7H, m), 3.95 (2H, t, J = 6.1 Hz), 4.21 (2H, t, J = 5.8 Hz), 6.44 (1H, dd, J = 7.9, 1.8 Hz), 6.63 (1H, d, J = 1.8 Hz), 7.55 (1H, d, J = 2.4 Hz), 7.65 (1H, d, J = 7.9 Hz), 8.19 (1H, d, J = 1.8 Hz). LRMS (ESI$^+$) 395 [M + H]$^+$. |
| 8-59 | 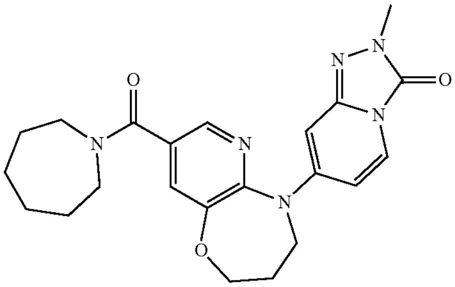 [SMILES: Cn1nc2cc(N3CCCOc4cc(C(=O)N5CCCCCC5)cnc43)ccn2c1=O] | $^1H$ NMR (400 MHz, DMSO-$d_6$) δ 1.46-1.65 (6H, m), 1.67-1.75 (2H, m), 2.03-2.11 (2H, m), 3.39 (2H, t, J = 5.8 Hz), 3.45 (3H, s), 3.54 (2H, t, J = 5.8 Hz), 3.95 (2H, t, J = 5.8 Hz), 4.21 (2H, t, J = 5.8 Hz), 6.46 (1H, dd, J = 7.9, 2.4 Hz), 6.61 (1H, d, J = 1.8 Hz), 7.42 (1H, d, J = 1.8 Hz), 7.65 (1H, d, J = 7.9 Hz), 8.04 (1H, d, J = 1.8 Hz). LRMS (ESI$^+$) 423 [M + H]$^+$. |
| 8-60 | 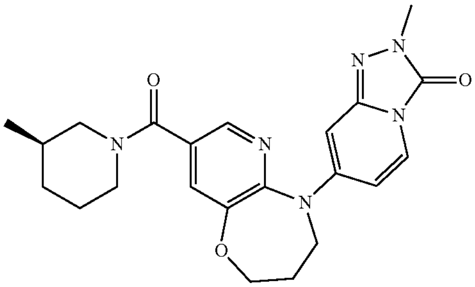 [SMILES: C[C@@H]1CCCN(C(=O)c2cnc3c(c2)OCCCN3c2ccn3c(=O)n(C)nc3c2)C1] | $^1H$ NMR (400 MHz, DMSO-$d_6$) δ 0.68-1.01 (3H, m), 1.10-1.26 (1H, m), 1.38-1.50 (1H, m), 1.53-1.84 (3H, m), 2.02-2.11 (2H, m), 2.72-3.12 (2H, m), 3.42-3.69 (4H, m), 3.96 (2H, t, J = 6.1 Hz), 4.15-4.37 (3H, m), 6.47 (1H, dd, J = 7.6, 2.1 Hz), 6.63 (1H, d, J = 1.8 Hz), 7.41 (1H, d, J = 1.8 Hz), 7.65 (1H, d, J = 7.9 Hz), 8.03 (1H, d, J = 1.8 Hz). LRMS (ESI$^+$) 423 [M + H]$^+$. |

TABLE 131

| Example No. | Chemical Structural Formula | Spectrum Data |
|---|---|---|
| 8-60 | 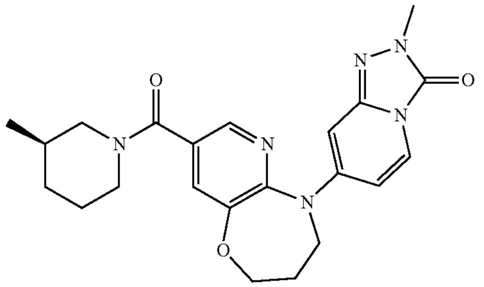 [SMILES: C[C@@H]1CCCN(C(=O)c2cnc3c(c2)OCCCN3c2ccn3c(=O)n(C)nc3c2)C1] | $^1$H NMR (400 MHz, DMSO-$d_6$) δ 0.68-1.01 (3H, m), 1.10-1.26 (1H, m), 1.38-1.50 (1H, m), 1.53-1.84 (3H, m), 2.02-2.11 (2H, m), 2.72-3.12 (2H, m), 3.42-3.69 (4H, m), 3.96 (2H, t, J = 6.1 Hz), 4.15-4.37 (3H, m), 6.47 (1H, dd, J = 7.6, 2.1 Hz), 6.63 (1H, d, J = 1.8 Hz), 7.41 (1H, d, J = 1.8 Hz), 7.65 (1H, d, J = 7.9 Hz), 8.03 (1H, d, J = 1.8 Hz). LRMS (ESI$^+$) 423 [M + H]$^+$. |
| 8-61 | 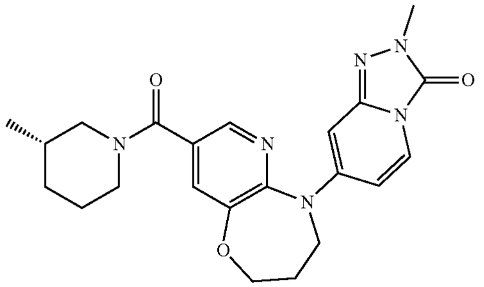 [SMILES: C[C@H]1CCCN(C(=O)c2cnc3c(c2)OCCCN3c2ccn3c(=O)n(C)nc3c2)C1] | $^1$H NMR (400 MHz, DMSO-$d_6$) δ 0.66-1.02 (3H, m), 1.09-1.26 (1H, m), 1.35-1.84 (4H, m), 2.01-2.13 (2H, m), 2.71-3.14 (2H, m), 3.40-3.66 (4H, m), 3.92-3.99 (2H, m), 4.15-4.36 (3H, m), 6.47 (1H, dd, J = 7.9, 2.4 Hz), 6.63 (1H, d, J = 1.8 Hz), 7.41 (1H, d, J = 1.8 Hz), 7.65 (1H, d, J = 7.9 Hz), 8.03 (1H, d, J = 1.8 Hz). LRMS (ESI$^+$) 423 [M + H]$^+$. |
| 8-62 | 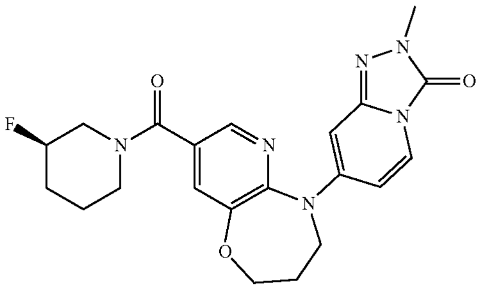 [SMILES: Cn1nc2cc(N3CCCOc4cc(C(=O)N5CCC[C@@H](F)C5)cnc43)ccn2c1=O] | $^1$H NMR (400 MHz, DMSO-$d_6$) δ 1.45-1.96 (4H, m), 2.01-2.12 (2H, m), 2.92-3.17 (1H, m), 3.42-3.84 (5H, m), 3.93-4.27 (5H, m), 4.79 (1H, d, J = 46.0 Hz), 6.49 (1H, dd, J = 7.9, 1.8 Hz), 6.64 (1H, d, J = 2.4 Hz), 7.39 (1H, d, J = 1.8 Hz), 7.66 (1H, d, J = 7.3 Hz), 8.03 (1H, d, J = 1.8 Hz). LRMS (ESI$^+$) 427 [M + H]$^+$. |
| 8-63 | 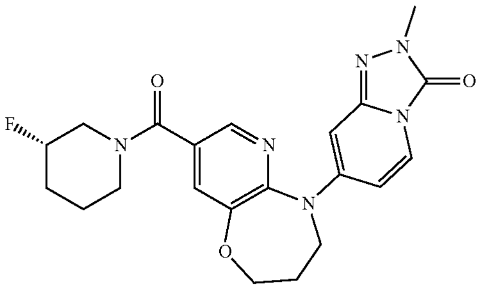 [SMILES: Cn1nc2cc(N3CCCOc4cc(C(=O)N5CCC[C@H](F)C5)cnc43)ccn2c1=O] | $^1$H NMR (400 MHz, DMSO-$d_6$) δ 1.46-1.97 (4H, m), 2.00-2.13 (2H, m), 2.86-3.17 (1H, m), 3.42-3.84 (5H, m), 3.89-4.27 (5H, m), 4.79 (1H, d, J = 47.2 Hz), 6.48 (1H, dd, J = 7.9, 2.4 Hz), 6.64 (1H, d, J = 1.8 Hz), 7.39 (1H, d, J = 1.8 Hz), 7.65 (1H, d, J = 7.9 Hz), 8.03 (1H, d, J = 1.8 Hz). LRMS (ESI$^+$) 427 [M + H]$^+$. |
| 8-64 | 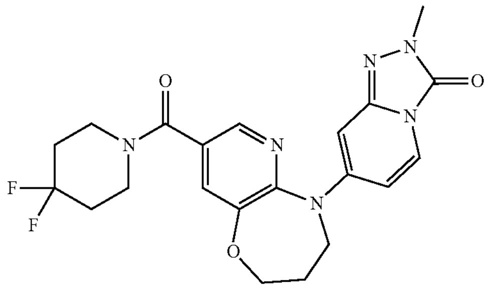 [SMILES: Cn1nc2cc(N3CCCOc4cc(C(=O)N5CCC(F)(F)CC5)cnc43)ccn2c1=O] | $^1$H NMR (400 MHz, DMSO-$d_6$) δ 1.99-2.14 (6H, m), 3.38-3.84 (7H, m), 3.96 (2H, t, J = 6.1 Hz), 4.22 (2H, t, J = 5.8 Hz), 6.48 (1H, dd, J = 7.9, 2.4 Hz), 6.64 (1H, d, J = 1.8 Hz), 7.51 (1H, d, J = 1.8 Hz), 7.66 (1H, d, J = 7.9 Hz), 8.10 (1H, d, J = 1.8 Hz). LRMS (ESI$^+$) 445 [M + H]$^+$. |

TABLE 131-continued

| Example No. | Chemical Structural Formula | Spectrum Data |
|---|---|---|
| 8-65 | 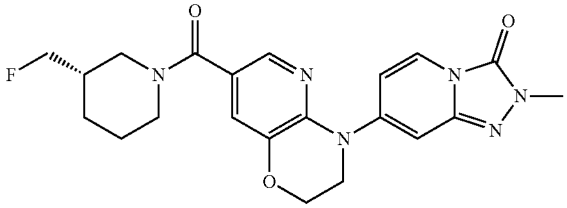 [SMILES: Cn1nc2cc(N3CCOc4cc(C(=O)N5CCC[C@H](CF)C5)cnc43)ccn2c1=O] | $^1$H NMR (400 MHz, $CDCl_3$) δ 1.35-2.06 (6H, m), 2.69-3.14 (2H, m), 3.64 (3H, s), 3.90 (2H, t, J = 4.6 Hz), 4.15-4.72 (5H, m), 6.64 (1H, d, J = 1.2 Hz), 6.97 (1H, dd, J = 7.9, 1.8 Hz), 7.25 (1H, d, J = 1.8 Hz), 7.68 (1H, d, J = 7.9 Hz), 7.89 (1H, d, J = 1.8 Hz). LRMS (ESI$^+$) 427 [M + H]$^+$. |

TABLE 132

| Example No. | Chemical Structural Formula | Spectrum Data |
|---|---|---|
| 8-66 | 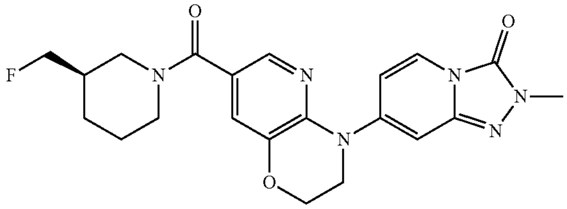 [SMILES: Cn1nc2cc(N3CCOc4cc(C(=O)N5CCC[C@@H](CF)C5)cnc43)ccn2c1=O] | $^1$H NMR (400 MHz, $CDCl_3$) δ 1.34-2.08 (6H, m), 2.72-3.14 (2H, m), 3.64 (3H, s), 3.90 (2H, t, J = 4.6 Hz), 4.13-4.71 (5H, m), 6.64 (1H, d, J = 1.2 Hz), 6.97 (1H, dd, J = 7.9, 1.8 Hz), 7.25 (1H, d, J = 1.8 Hz), 7.68 (1H, d, J = 6.7 Hz), 7.89 (1H, d, J = 1.8 Hz). LRMS (ESI$^+$) 427 [M + H]$^+$. |
| 8-67 | 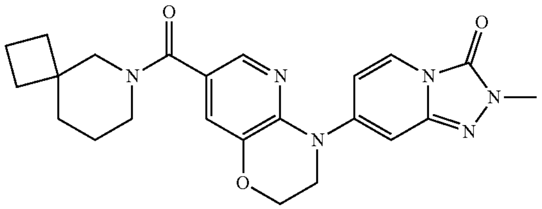 [SMILES: Cn1nc2cc(N3CCOc4cc(C(=O)N5CCCC6(CCC6)C5)cnc43)ccn2c1=O] | $^1$H NMR (400 MHz, $CDCl_3$) δ 1.46-1.97 (10H, m), 3.25-3.73 (7H, m), 3.91 (2H, t, J = 4.3 Hz), 4.41 (2H, t, J = 4.3 Hz), 6.64 (1H, d, J = 1.2 Hz), 6.99 (1H, dd, J = 7.3, 1.8 Hz), 7.25 (1H, d, J = 1.8 Hz), 7.69 (1H, d, J = 7.3 Hz), 7.88 (1H, d, J = 1.8 Hz). LRMS (ESI$^+$) 435 [M + H]$^+$. |

TABLE 133

| Example No. | Chemical Structural Formula | Spectrum Data |
|---|---|---|
| 8-68 | 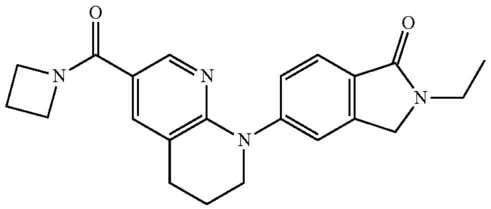 [SMILES: CCN1Cc2cc(N3CCCc4cc(C(=O)N5CCC5)cnc43)ccc2C1=O] | $^1$H NMR (400 MHz, $CDCl_3$) δ 1.26 (3H, t, J = 7.3 Hz), 2.07-2.15 (2H, m), 2.29-2.38 (2H, m), 2.91 (2H, t, J = 6.1 Hz), 3.67 (2H, q, J = 7.3 Hz), 3.84 (2H, t, J = 5.5 Hz), 4.14-4.37 (4H, m), 4.38 (2H, s), 7.37 (1H, dd, J = 8.6, 1.8 Hz), 7.44 (1H, s), 7.72 (1H, d, J = 1.8 Hz), 7.86 (1H, d, J = 7.9 Hz), 8.15 (1H, d, J = 1.8 Hz). LRMS (ESI$^+$) 377 [M + H]$^+$. |
| 8-69 | 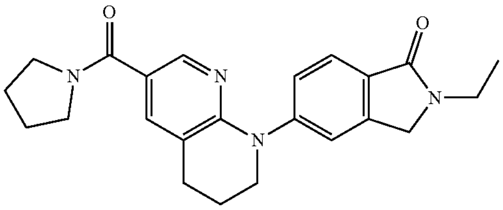 [SMILES: CCN1Cc2cc(N3CCCc4cc(C(=O)N5CCCC5)cnc43)ccc2C1=O] | $^1$H NMR (400 MHz, $CDCl_3$) δ 1.26 (3H, t, J = 7.3 Hz), 1.82-2.00 (4H, m), 2.07-2.15 (2H, m), 2.90 (2H, t, J = 6.1 Hz), 3.49-3.65 (4H, m), 3.68 (2H, t, J = 7.3 Hz), 3.84 (2H, t, J = 5.5 Hz), 4.38 (2H, s), 7.37 (1H, dd, J = 8.6, 1.8 Hz), 7.45 (1H, s), 7.59 (1H, d, J = 2.4 Hz), 7.85 (1H, d, J = 7.9 Hz), 8.14 (1H, d, J = 2.4 Hz). LRMS (ESI$^+$) 391 [M + H]$^+$. |

TABLE 133-continued

| Example No. | Chemical Structural Formula | Spectrum Data |
|---|---|---|
| 8-70 | 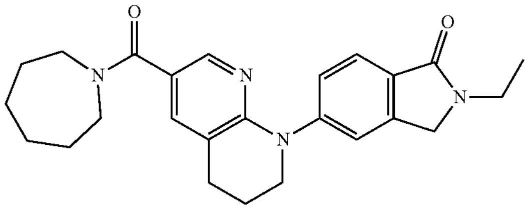 [SMILES: CCN1Cc2cc(N3CCCc4cc(C(=O)N5CCCCCC5)cnc43)ccc2C1=O] | $^1$H NMR (400 MHz, $CDCl_3$) δ 1.26 (3H, t, J = 7.3 Hz), 1.51-1.72 (6H, m), 1.76-1.87 (2H, m), 2.06-2.14 (2H, m), 2.90 (2H, t, J = 6.1 Hz), 3.44-3.71 (6H, m), 3.84 (2H, t, J = 5.5 Hz), 4.37 (2H, s), 7.36 (1H, dd, J = 8.6, 1.8 Hz), 7.41-7.43 (1H, m), 7.45 (1H, d, J = 1.2 Hz), 7.84 (1H, d, J = 7.9 Hz), 7.99 (1H, d, J = 1.8 Hz). LRMS (ESI$^+$) 419 [M + H]$^+$. |

TABLE 134

| Example No. | Chemical Structural Formula | Spectrum Data |
|---|---|---|
| 8-71 | 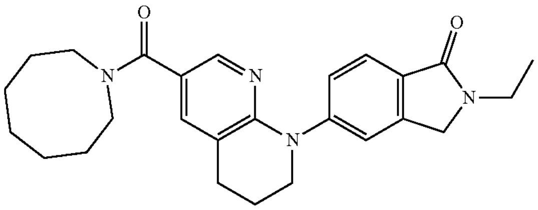 [SMILES: CCN1Cc2cc(N3CCCc4cc(C(=O)N5CCCCCCC5)cnc43)ccc2C1=O] | $^1$H NMR (400 MHz, $CDCl_3$) δ 1.26 (3H, t, J = 7.3 Hz), 1.53-1.70 (8H, m), 1.79-1.89 (2H, m), 2.06-2.15 (2H, m), 2.90 (2H, t, J = 6.1 Hz), 3.40-3.63 (4H, m), 3.67 (2H, q, J = 7.3 Hz), 3.84 (2H, t, J = 5.5 Hz), 4.37 (2H, s), 7.36 (1H, dd, J = 7.9, 1.8 Hz), 7.40 (1H, d, J = 1.8 Hz), 7.45 (1H, s), 7.84 (1H, d, J = 7.9 Hz), 7.99 (1H, d, J = 1.8 Hz). LRMS (ESI$^+$) 433 [M + H]$^+$. |
| 8-72 | 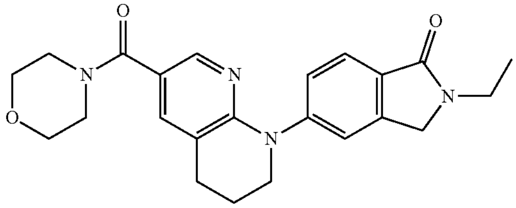 [SMILES: CCN1Cc2cc(N3CCCc4cc(C(=O)N5CCOCC5)cnc43)ccc2C1=O] | $^1$H NMR (400 MHz, $CDCl_3$) δ 1.26 (3H, t, J = 7.3 Hz), 2.07-2.16 (2H, m), 2.91 (2H, t, J = 6.1 Hz), 3.60-3.74 (10H, m), 3.84 (2H, t, J = 6.1 Hz), 4.38 (2H, s), 7.36 (1H, dd, J = 8.6, 1.8 Hz), 7.44 (1H, d, J = 1.2 Hz), 7.46 (1H, d, J = 1.8 Hz), 7.86 (1H, d, J = 8.6 Hz), 7.99 (1H, d, J = 2.4 Hz). LRMS (ESI$^+$) 407 [M + H]$^+$. |
| 8-73 | 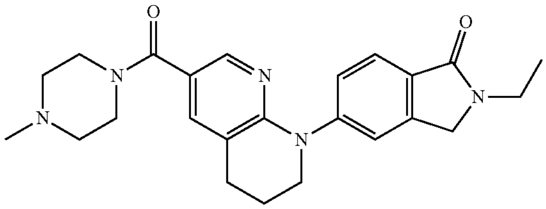 [SMILES: CCN1Cc2cc(N3CCCc4cc(C(=O)N5CCN(C)CC5)cnc43)ccc2C1=O] | $^1$H NMR (400 MHz, $CDCl_3$) δ 1.26 (3H, t, J = 7.3 Hz), 2.07-2.17 (2H, m), 2.32 (3H, s), 2.37-2.54 (4H, m), 2.91 (2H, t, J = 6.1 Hz), 3.58-3.74 (6H, m), 3.84 (2H, t, J = 5.5 Hz), 4.38 (2H, s), 7.36 (1H, dd, J = 7.9, 1.8 Hz), 7.43-7.48 (2H, m), 7.85 (1H, d, J = 7.9 Hz), 7.99 (1H, d, J = 2.4 Hz). LRMS (ESI$^+$) 420 [M + H]$^+$. |
| 8-74 | 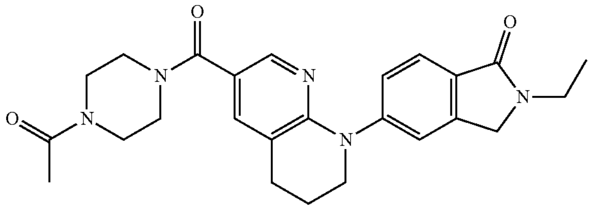 [SMILES: CCN1Cc2cc(N3CCCc4cc(C(=O)N5CCN(C(C)=O)CC5)cnc43)ccc2C1=O] | $^1$H NMR (400 MHz, $CDCl_3$) δ 1.26 (3H, t, J = 7.3 Hz), 2.08-2.16 (4H, m), 2.92 (2H, t, J = 6.1 Hz), 3.46-3.53 (2H, m), 3.57-3.72 (8H, m), 3.85 (2H, t, J = 6.1 Hz), 4.38 (2H, s), 7.37 (1H, dd, J = 7.9, 1.8 Hz), 7.44 (1H, s), 7.46 (2H, d, J = 1.8 Hz), 7.86 (1H, d, J = 8.6 Hz), 7.99 (1H, d, J = 2.4 Hz). LRMS (ESI$^+$) 448 [M + H]$^+$. |
| 8-75 | 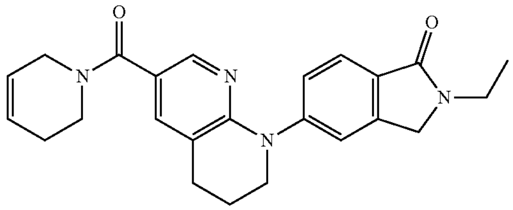 [SMILES: CCN1Cc2cc(N3CCCc4cc(C(=O)N5CC=CCC5)cnc43)ccc2C1=O] | $^1$H NMR (400 MHz, $CDCl_3$) δ 1.26 (3H, t, J = 7.3 Hz), 2.07-2.15 (2H, m), 2.17-2.26 (2H, m), 2.91 (2H, t, J = 6.1 Hz), 3.55-3.76 (4H, m), 3.84 (2H, t, J = 6.1 Hz), 4.03-4.16 (2H, m), 4.38 (2H, s), 5.58-5.77 (1H, m), 5.83-5.90 (1H, m), 7.37 (1H, dd, J = 1.8, 1.5 Hz), 7.45 (1H, d, J = 1.2 Hz), 7.48 (1H, d, J = 2.4 Hz), 7.85 (1H, d, J = 7.9 Hz), 8.01 (1H, d, J = 2.4 Hz). LRMS (ESI$^+$) 403 [M + H]$^+$. |

TABLE 135

| Example No. | Chemical Structural Formula | Spectrum Data |
|---|---|---|
| 8-76 | 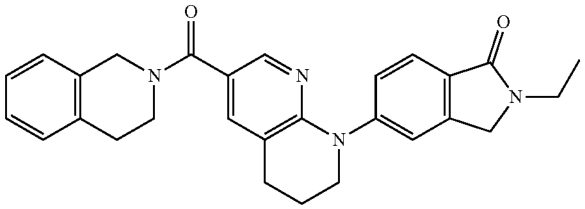 [SMILES: CCN1Cc2cc(N3CCCc4cc(C(=O)N5CCc6ccccc6C5)cnc43)ccc2C1=O] | $^1$H NMR (400 MHz, $CDCl_3$) δ 1.26 (3H, t, J = 7.3 Hz), 2.08-2.16 (2H, m), 2.88-2.95 (4H, m), 3.68 (2H, q, J = 7.3 Hz), 3.75-3.94 (4H, m), 4.39 (2H, s), 4.73-4.84 (2H, m), 7.02-7.22 (4H, m), 7.38 (1H, dd, J = 7.9, 1.8 Hz), 7.46 (1H, s), 7.51 (1H, d, J = 1.8 Hz), 7.86 (1H, d, J = 7.9 Hz), 8.07 (1H, d, J = 1.8 Hz).<br>LRMS (ESI$^+$) 453 [M + H]$^+$. |
| 8-77 | 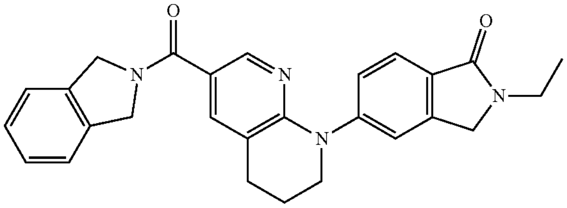 [SMILES: CCN1Cc2cc(N3CCCc4cc(C(=O)N5Cc6ccccc6C5)cnc43)ccc2C1=O] | $^1$H NMR (400 MHz, $CDCl_3$) δ 1.27 (3H, t, J = 7.3 Hz), 2.09-2.18 (2H, m), 2.93 (2H, t, J = 6.1 Hz), 3.68 (2H, q, J = 7.3 Hz), 3.86 (2H, t, J = 6.1 Hz), 4.39 (2H, s), 4.87-5.05 (4H, m), 7.12-7.20 (1H, m), 7.23-7.36 (3H, m), 7.40 (1H, dd, J = 7.9, 1.8 Hz), 7.48 (1H, d, J = 1.2 Hz), 7.60-7.64 (1H, m), 7.87 (1H, d, J = 7.9 Hz), 8.24 (1H, d, J = 1.8 Hz).<br>LRMS (ESI$^+$) 439 [M + H]$^+$. |
| 8-78 | 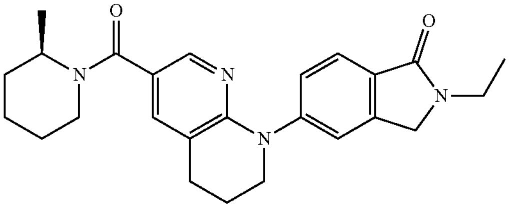 [SMILES: CCN1Cc2cc(N3CCCc4cc(C(=O)N5CCCC[C@H]5C)cnc43)ccc2C1=O] | $^1$H NMR (400 MHz, $CDCl_3$) δ 1.24 (3H, d, J = 7.3 Hz), 1.26 (3H, t, J = 7.3 Hz), 1.38-1.56 (2H, m), 1.62-1.75 (4H, m), 2.06-2.15 (2H, m), 2.90 (2H, t, J = 6.4 Hz), 2.96-3.07 (1H, m), 3.67 (2H, q, J = 7.3 Hz), 3.84 (2H, t, J = 5.5 Hz), 3.99-4.19 (1H, m), 4.37 (2H, s), 4.50-4.69 (1H, m), 7.36 (1H, dd, J = 8.6, 1.8 Hz), 7.42 (1H, d, J = 1.8 Hz), 7.45 (1H, d, J = 1.2 Hz), 7.84 (HI, d, J = 8.6 Hz), 7.97 (1H, d, J = 2.4 Hz).<br>LRMS (ESI$^+$) 419 [M + H]$^+$. |
| 8-79 | 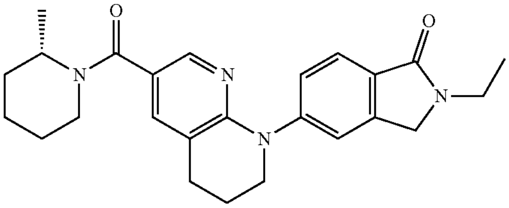 [SMILES: CCN1Cc2cc(N3CCCc4cc(C(=O)N5CCCC[C@@H]5C)cnc43)ccc2C1=O] | $^1$H NMR (400 MHz, $CDCl_3$) δ 1.24 (3H, d, J = 7.3 Hz), 1.26 (3H, t, J = 7.3 Hz), 1.37-1.57 (2H, m), 1.63-1.74 (4H, m), 2.06-2.15 (2H, m), 2.90 (2H, t, J = 6.4 Hz), 2.96-3.08 (1H, m), 3.67 (2H, q, J = 7.3 Hz), 3.84 (2H, t, J = 5.5 Hz), 4.01-4.18 (1H, m), 4.38 (2H, s), 4.51-4.67 (1H, m), 7.36 (1H, dd, J = 7.9, 1.8 Hz), 7.40-7.43 (1H, m), 7.45 (1H, d, J = 1.2 Hz), 7.85 (1H, d, J = 7.9 Hz), 7.97 (1H, d, J = 1.8 Hz).<br>LRMS (ESI$^+$) 419 [M + H]$^+$. |
| 8-80 | 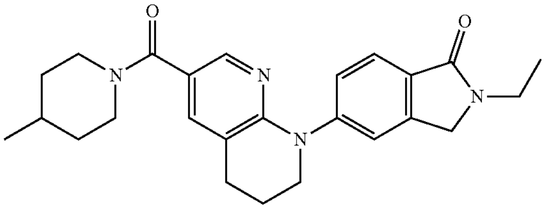 [SMILES: CCN1Cc2cc(N3CCCc4cc(C(=O)N5CCC(C)CC5)cnc43)ccc2C1=O] | $^1$H NMR (400 MHz, $CDCl_3$) δ 0.96 (3H, d, J = 6.7 Hz), 1.07-1.22 (2H, m), 1.26 (3H, t, J = 7.3 Hz), 1.61-1.74 (3H, m), 2.06-2.15 (2H, m), 2.67-3.06 (4H, m), 3.67 (2H, q, J = 7.3 Hz), 3.84 (2H, t, J = 5.5 Hz), 3.94-4.87 (4H, m), 7.36 (1H, dd, J = 7.9, 1.8 Hz), 7.43-7.46 (2H, m), 7.85 (1H, d, J = 7.9 Hz), 7.98 (1H, d, J = 1.8 Hz).<br>LRMS (ESI$^+$) 419 [M + H]$^+$. |

TABLE 136

| Example No. | Chemical Structural Formula | Spectrum Data |
|---|---|---|
| 8-81 | 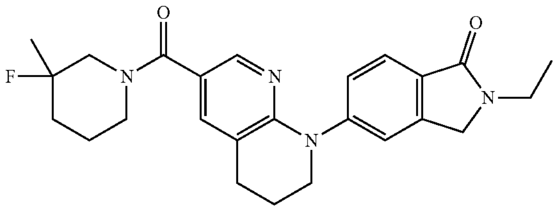 [SMILES: CCN1Cc2cc(N3CCCc4cc(C(=O)N5CCCC(C)(F)C5)cnc43)ccc2C1=O] | $^1$H NMR (400 MHz, $CDCl_3$) δ 1.26 (3H, t, J = 7.3 Hz), 1.29-1.41 (3H, m), 1.50-1.69 (2H, m), 1.82-1.97 (1H, m), 1.98-2.07 (1H, m), 2.07-2.15 (2H, m), 2.82-3.15 (4H, m), 3.67 (2H, q, J = 7.3 Hz), 3.84 (2H, dd, J = 6.1, 4.9 Hz), 3.91-4.61 (4H, m), 7.37 (1H, dd, J = 8.6, 1.8 Hz), 7.45 (1H, d, J = 1.2 Hz), 7.47 (1H, d, J = 1.8 Hz), 7.85 (1H, d, J = 7.9 Hz), 8.01 (1H, d, J = 2.4 Hz).<br>LRMS (ESI$^+$) 437 [M + H]$^+$. |

TABLE 136-continued

| Example No. | Chemical Structural Formula | Spectrum Data |
|---|---|---|
| 8-82 | 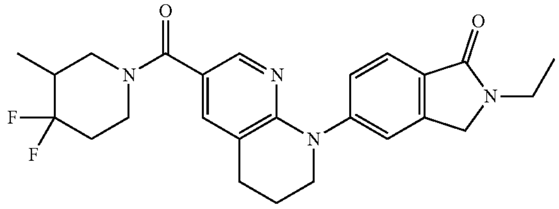 [SMILES: CCN1Cc2cc(N3CCCc4cc(C(=O)N5CCC(F)(F)C(C)C5)cnc43)ccc2C1=O] | $^1$H NMR (400 MHz, $CDCl_3$) δ 1.02 (3H, d, J = 6.1 Hz), 1.26 (3H, t, J = 7.3 Hz), 1.75-2.20 (5H, m), 2.91 (2H, t, J = 6.1 Hz), 2.96-3.10 (1H, m), 3.26-3.38 (1H, m), 3.67 (2H, q, J = 7.3 Hz), 3.85 (2H, t, J = 5.5 Hz), 3.94-4.31 (2H, m), 4.38 (2H, s), 7.37 (1H, dd, J = 7.9, 1.8 Hz), 7.43-7.48 (2H, m), 7.86 (1H, d, J = 8.6 Hz), 7.99 (1H, d, J = 2.4 Hz). LRMS (ESI$^+$) 455 [M + H]$^+$. |
| 8-83 | 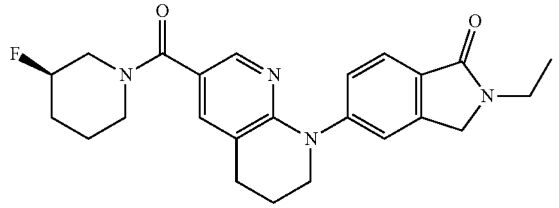 [SMILES: CCN1Cc2cc(N3CCCc4cc(C(=O)N5CCC[C@@H](F)C5)cnc43)ccc2C1=O] | $^1$H NMR (400 MHz, $CDCl_3$) δ 1.26 (3H, t, J = 7.3 Hz), 1.78-2.05 (4H, m), 2.07-2.15 (2H, m), 2.91 (2H, t, J = 6.1 Hz), 3.22-3.37 (1H, m), 3.45-3.63 (1H, m), 3.67 (2H, q, J = 7.3 Hz), 3.79-3.99 (4H, m), 4.38 (2H, s), 4.56-4.79 (1H, m), 7.36 (1H, dd, J = 8.6, 1.8 Hz), 7.43-7.48 (2H, m), 7.85 (1H, d, J = 7.9 Hz), 8.01 (1H, d, J = 2.4 Hz). LRMS (ESI$^+$) 423 [M + H]$^+$. |
| 8-84 | 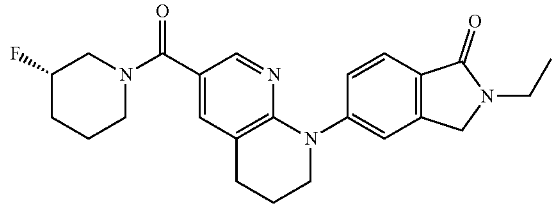 [SMILES: CCN1Cc2cc(N3CCCc4cc(C(=O)N5CCC[C@H](F)C5)cnc43)ccc2C1=O] | $^1$H NMR (400 MHz, $CDCl_3$) δ 1.26 (3H, t, J = 7.3 Hz), 1.76-2.05 (4H, m), 2.07-2.15 (2H, m), 2.91 (2H, t, J = 6.1 Hz), 3.23-3.37 (1H, m), 3.44-3.63 (1H, m), 3.67 (2H, q, J = 7.3 Hz), 3.80-4.00 (4H, m), 4.38 (2H, s), 4.56-4.77 (1H, m), 7.36 (1H, dd, J = 8.6, 1.8 Hz), 7.44-7.48 (2H, m), 7.85 (1H, d, J = 7.9 Hz), 8.01 (1H, d, J = 2.4 Hz). LRMS (ESI$^+$) 423 [M + H]$^+$. |
| 8-85 | 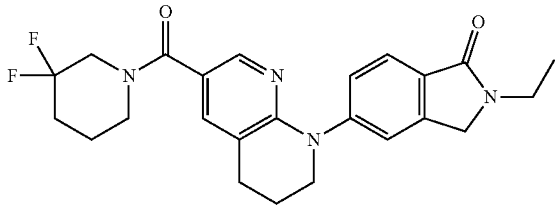 [SMILES: CCN1Cc2cc(N3CCCc4cc(C(=O)N5CCCC(F)(F)C5)cnc43)ccc2C1=O] | $^1$H NMR (400 MHz, $CDCl_3$) δ 1.26 (3H, t, J = 7.3 Hz), 1.78-1.88 (2H, m), 2.00-2.17 (4H, m), 2.91 (2H, t, J = 6.4 Hz), 3.57-3.72 (4H, m), 3.74-3.88 (4H, m), 4.38 (2H, s), 7.37 dd, J = 7.9, 1.8 Hz), 7.43-7.47 (2H, m), 7.86 (1H, d, J = 8.6 Hz), 8.00 (1H, d, J = 2.4 Hz). LRMS (ESI$^+$) 441 [M + H]$^+$. |

TABLE 137

| Example No. | Chemical Structural Formula | Spectrum Data |
|---|---|---|
| 8-86 | 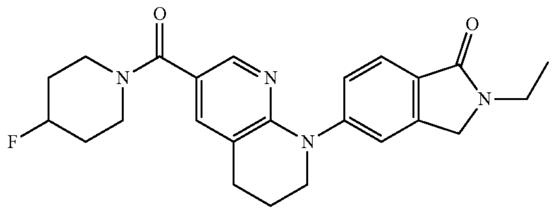 [SMILES: CCN1Cc2cc(N3CCCc4cc(C(=O)N5CCC(F)CC5)cnc43)ccc2C1=O] | $^1$H NMR (400 MHz, $CDCl_3$) δ 1.26 (3H, t, J = 7.3 Hz), 1.77-1.96 (4H, m), 2.07-2.16 (2H, m), 2.91 (2H, t, J = 6.1 Hz), 3.57-3.81 (6H, m), 3.84 (2H, t, J = 6.1 Hz), 4.38 (2H, s), 4.80-4.99 (1H, m), 7.37 (1H, dd, J = 7.9, 1.8 Hz), 7.43-7.47 (2H, m), 7.85 (1H, d, J = 8.5 Hz), 7.99 (1H, d, J = 1.8 Hz). LRMS (ESI$^+$) 423 [M + H]$^+$. |
| 8-87 | 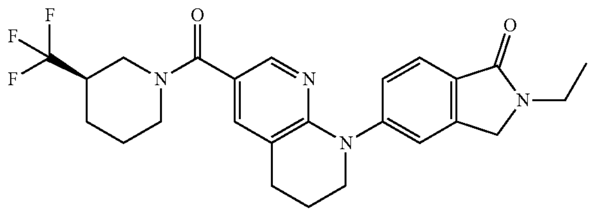 [SMILES: CCN1Cc2cc(N3CCCc4cc(C(=O)N5CCC[C@@H](C(F)(F)F)C5)cnc43)ccc2C1=O] | $^1$H NMR (400 MHz, $CDCl_3$) δ 1.26 (3H, t, J = 7.3 Hz), 1.41-1.57 (2H, m), 1.76-1.85 (1H, m), 2.06-2.16 (3H, m), 2.21-2.37 (1H, m), 2.83-3.01 (4H, m), 3.67 (2H, q, J = 7.3 Hz), 3.84 (2H, t, J = 5.8 Hz), 4.00-4.72 (4H, m), 7.37 (1H, dd, J = 7.9, 1.8 Hz), 7.42-7.47 (2H, m), 7.86 (1H, d, J = 7.9 Hz), 7.98 (1H, d, J = 1.8 Hz). LRMS (ESI$^+$) 473 [M + H]$^+$. |

TABLE 137-continued

| Example No. | Chemical Structural Formula | Spectrum Data |
|---|---|---|
| 8-88 | 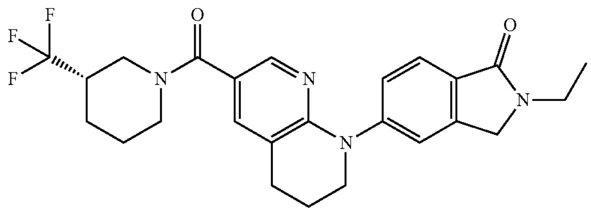 [SMILES: CCN1Cc2cc(N3CCCc4cc(C(=O)N5CCC[C@H](C(F)(F)F)C5)cnc43)ccc2C1=O] | $^1$H NMR (400 MHz, $CDCl_3$) δ 1.26 (3H, t, J = 7.3 Hz), 1.41-1.57 (2H, m), 1.76-1.87 (1H, m), 2.06-2.17 (3H, m), 2.23-2.38 (1H, m), 2.85-3.01 (4H, m), 3.67 (2H, q, J = 7.3 Hz), 3.85 (2H, t, J = 5.5 Hz), 4.00-4.72 (4H, m), 7.37 (1H, dd, J = 8.6, 1.8 Hz), 7.42-7.47 (2H, m), 7.86 (1H, d, J = 8.6 Hz), 7.98 (1H, d, J = 2.4 Hz). LRMS (ESI$^+$) 473 [M + H]$^+$. |
| 8-89 | 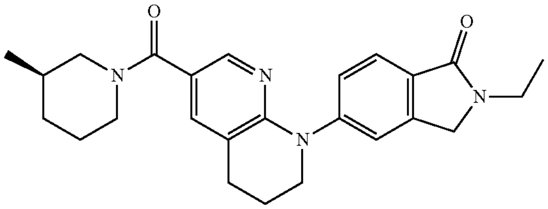 [SMILES: CCN1Cc2cc(N3CCCc4cc(C(=O)N5CCC[C@@H](C)C5)cnc43)ccc2C1=O] | $^1$H NMR (400 MHz, $CDCl_3$) δ 0.79-0.98 (3H, m), 1.08-1.21 (1H, m), 1.26 (3H, t, J = 7.3 Hz), 1.41-1.53 (2H, m), 1.63-1.76 (2H, m), 1.80-1.91 (1H, m), 2.06-2.15 (2H, m), 2.35-2.70 (1H, m), 2.82-2.97 (3H, m), 3.67 (2H, q, J = 7.3 Hz), 3.84 (2H, t, J = 5.5 Hz), 3.95-4.65 (3H, m), 7.36 (1H, dd, J = 7.9, 1.8 Hz), 7.41-7.46 (2H, m), 7.85 (1H, d, J = 8.6 Hz), 7.98 (1H, d, J = 2.4 Hz). LRMS (ESI$^+$) 419 [M + H]$^+$. |
| 8-90 | 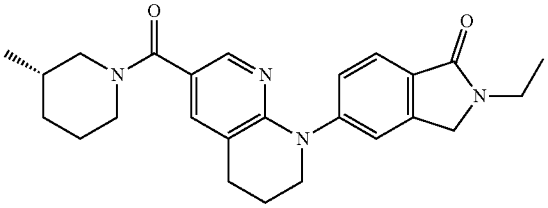 [SMILES: CCN1Cc2cc(N3CCCc4cc(C(=O)N5CCC[C@H](C)C5)cnc43)ccc2C1=O] | $^1$H NMR (400 MHz, $CDCl_3$) δ 0.75-1.00 (3H, m), 1.09-1.21 (1H, m), 1.26 (3H, t, J = 7.3 Hz), 1.41-1.54 (2H, m), 1.63-1.75 (2H, m), 1.80-1.90 (1H, m), 2.06-2.15 (2H, m), 2.38-2.70 (1H, m), 2.81-2.95 (3H, m), 3.67 (2H, q, J = 7.3 Hz), 3.84 (2H, t, J = 5.5 Hz), 4.09-4.67 (3H, m), 7.36 (1H, dd, J = 7.9, 1.8 Hz), 7.41-7.47 (2H, m), 7.85 (1H, d, J = 8.6 Hz), 7.98 (1H, d, J = 2.4 Hz). LRMS (ESI$^+$) 419 [M + H]$^+$. |

TABLE 138

| Example No. | Chemical Structural Formula | Spectrum Data |
|---|---|---|
| 8-91 | 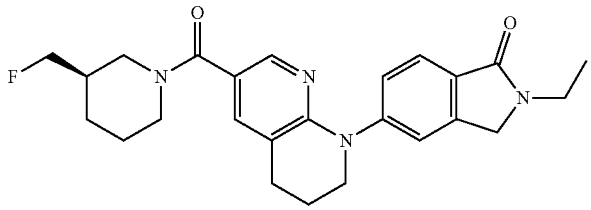 [SMILES: CCN1Cc2cc(N3CCCc4cc(C(=O)N5CCC[C@@H](CF)C5)cnc43)ccc2C1=O] | $^1$H NMR (400 MHz, $CDCl_3$) δ 1.26 (3H, t, J = 7.3 Hz), 1.34-1.51 (2H, m), 1.69-2.02 (3H, m), 2.06-2.16 (2H, m), 2.78-3.05 (4H, m), 3.67 (2H, q, J = 7.3 Hz), 3.84 (2H, t, J = 5.5 Hz), 3.96-4.45 (6H, m), 7.36 (1H, dd, J = 7.9, 1.8 Hz), 7.42-7.47 (2H, m), 7.85 (1H, d, J = 8.6 Hz), 7.99 (1H, d, J = 2.4 Hz). LRMS (ESI$^+$) 437 [M + H]$^+$. |
| 8-92 | 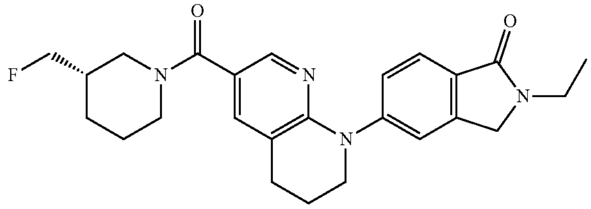 [SMILES: CCN1Cc2cc(N3CCCc4cc(C(=O)N5CCC[C@H](CF)C5)cnc43)ccc2C1=O] | $^1$H NMR (400 MHz, $CDCl_3$) δ 1.26 (3H, t, J = 7.3 Hz), 1.33-1.59 (2H, m), 1.69-2.04 (3H, m), 2.06-2.15 (2H, m), 2.73-3.07 (4H, m), 3.67 (2H, q, J = 7.3 Hz), 3.84 (2H, t, J = 5.4 Hz), 3.93-4.50 (6H, m), 7.36 (1H, dd, J = 7.9, 1.8 Hz), 7.42-7.47 (2H, m), 7.85 (1H, d, J = 8.5 Hz), 7.99 (1H, d, J = 2.4 Hz). LRMS (ESI$^+$) 437 [M + H]$^+$. |
| 8-93 | 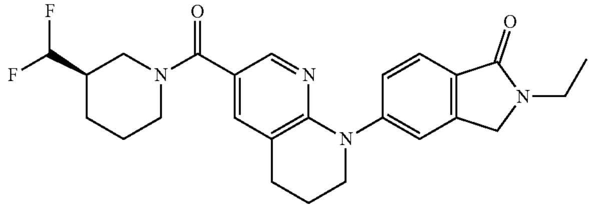 [SMILES: CCN1Cc2cc(N3CCCc4cc(C(=O)N5CCC[C@@H](C(F)F)C5)cnc43)ccc2C1=O] | $^1$H NMR (400 MHz, $CDCl_3$) δ 1.26 (3H, t, J = 7.3 Hz), 1.41-1.56 (2H, m), 1.72-1.84 (1H, m), 1.92-2.16 (4H, m), 2.83-3.06 (4H, m), 3.67 (2H, q, J = 7.3 Hz), 3.84 (2H, t, J = 5.8 Hz), 3.94-4.54 (4H, m), 5.67 (1H, t, J = 56.6 Hz), 7.37 (1H, dd, J = 8.5, 1.8 Hz), 7.41-7.47 (2H, m), 7.85 (1H, d, J = 7.9 Hz), 7.98 (1H, d, J = 2.4 Hz). LRMS (ESI$^+$) 455 [M + H]$^+$. |

TABLE 138-continued

| Example No. | Chemical Structural Formula | Spectrum Data |
|---|---|---|
| 8-94 | 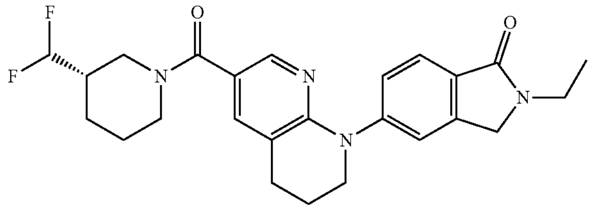 [SMILES: CCN1Cc2cc(N3CCCc4cc(C(=O)N5CCC[C@H](C(F)F)C5)cnc43)ccc2C1=O] | $^1$H NMR (400 MHz, $CDCl_3$) δ 1.26 (3H, t, J = 7.3 Hz), 1.41-1.56 (2H, m), 1.70-1.85 (1H, m), 1.92-2.16 (4H, m), 2.82-3.06 (4H, m), 3.67 (2H, q, J = 7.3 Hz), 3.84 (2H, t, J = 5.8 Hz), 3.95-4.56 (4H, m), 5.67 (1H, t, J = 52.7 Hz), 7.37 (1H, dd, J = 8.5, 1.8 Hz), 7.42-7.46 (2H, m), 7.85 (1H, d, J = 8.5 Hz), 7.98 (1H, d, J = 2.4 Hz). LRMS (ESI$^+$) 455 [M + H]$^+$. |
| 8-95 | 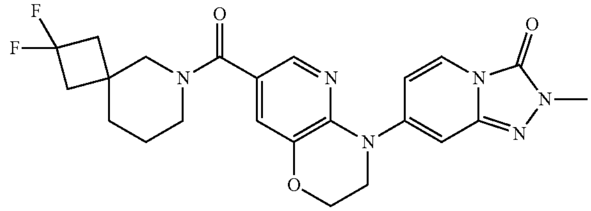 [SMILES: Cn1nc2cc(N3CCOc4cc(C(=O)N5CCCC6(C5)CC(F)(F)C6)cnc43)ccn2c1=O] | $^1$H NMR (400 MHz, $CDCl_3$) δ 1.62-1.83 (4H, m), 2.41 (4H, t, J = 12.5 Hz), 3.36-3.75 (7H, m), 3.90 (2H, t, J = 4.3 Hz), 4.41 (2H, t, J= 4.3 Hz), 6.65 (1H, d, J = 1.2 Hz), 6.96 (1H, dd, J = 7.9, 1.8 Hz), 7.25 (1H d, J = 1.8 Hz), 7.69 (1H d, J = 7.9 Hz), 7.88 (1H, d, J = 1.8 Hz). LRMS (ESI$^+$) 471 [M + H]$^+$. |

TABLE 139

| Example No. | Chemical Structural Formula | Spectrum Data |
|---|---|---|
| 8-96 | 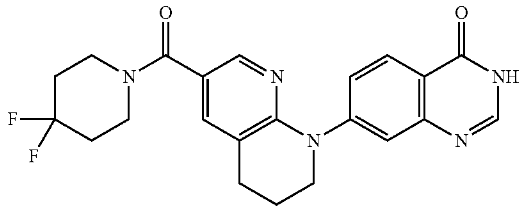 [SMILES: O=C(c1cnc2c(c1)CCCN2c1ccc2c(=O)[nH]cnc2c1)N1CCC(F)(F)CC1] | $^1$H NMR (400 MHz, $CDCl_3$) δ 1.93-2.09 (4H, m), 2.11-2.19 (2H, m), 2.93 (2H, t, J = 6.1 Hz), 3.70-3.82 (4H, m), 3.94 (2 H, t, J = 5.5 Hz), 7.52 (1H, d, J = 2.4 Hz), 7.60-7.65 (2H, m), 8.01 (1H, s), 8.05 (1H, d, J = 2.4 Hz), 8.25 (1H, dd, J = 7.9, 1.2 Hz), 9.85 (1H, br s). LRMS (ESI$^+$) 426 [M + H]$^+$. |
| 8-97 | 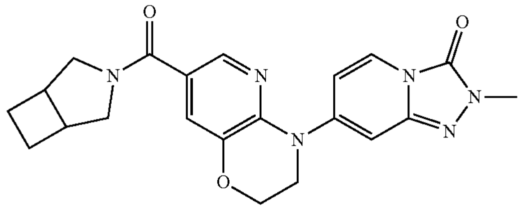 [SMILES: Cn1nc2cc(N3CCOc4cc(C(=O)N5CC6CCC6C5)cnc43)ccn2c1=O] | $^1$H NMR (400 MHz, $CDCl_3$) δ 1.62-1.80 (2H, m), 2.15-2.28 (2H, m), 2.92-3.00 (2H, m), 3.35-3.60 (3H, m), 3.64 (3H, s), 3.90 (2H, t, J = 4.6 Hz), 4.08-4.25 (1H, m), 4.41 (2H, t, J = 4.6 Hz), 6.64 (1H, d, J = 1.2 Hz), 6.99 (1H, dd, J = 7.6, 2.1 Hz), 7.40 (1H, d, J = 1.8 Hz), 7.69 (1H, d, J = 8.6 Hz), 8.03 (1H, d, J = 2.4 Hz). LRMS (ESI$^+$): 407 (M + H$^+$). |
| 8-98 | 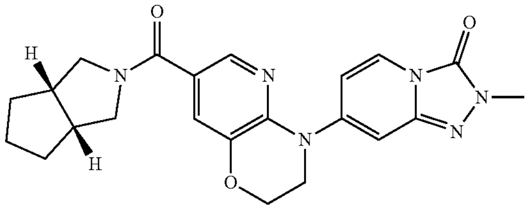 [SMILES: Cn1nc2cc(N3CCOc4cc(C(=O)N5C[C@H]6CCC[C@H]6C5)cnc43)ccn2c1=O] | $^1$H NMR (400 MHz, $CDCl_3$) δ 1.30-1.45 (1H, m), 1.61-1.91 (4H, m), 2.61-2.75 (2H, m), 3.22-3.58 (3H, m), 3.64 (3H, s), 3.67-3.87 (2H, m), 3.90 (2H, t, J = 4.5 Hz), 4.40 (2H, t, J = 4.5 Hz), 6.64 (1H, d, J = 1.2 Hz), 6.98 (1H, dd, J = 7.6, 2.1 Hz), 7.35 (1H, d, J = 1.8 Hz), 7.68 (1H, d, J = 7.6 Hz), 7.99 (1H, d, J = 1.8 Hz). LRMS (ESI$^+$): 421 (M + H$^+$). |
| 8-99 | 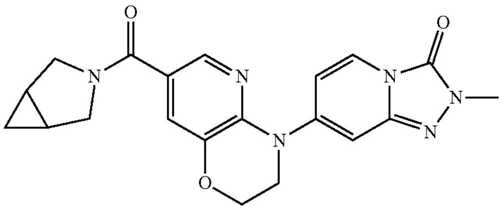 [SMILES: Cn1nc2cc(N3CCOc4cc(C(=O)N5CC6CC6C5)cnc43)ccn2c1=O] | $^1$H NMR (400 MHz, $CDCl_3$) δ 0.17 (1H, dd, J = 9.1, 4.2 Hz), 0.68-0.73 (1H, m), 1.47-1.58 (2H, m), 3.48 (1H, d, J = 10.3 Hz), 3.58 (1H, d, J = 10.3 Hz), 3.64 (3H, s), 3.67-3.76 (1H, m), 3.90 (2H 1, J = 4.5 Hz), 4.17 (1H, d, J = 12.1 Hz), 4.40 (2H, t, J = 4.5 Hz), 6.64 (1H, d, J = 1.8 Hz), 6.97 (1H, dd, J = 7.9, 1.8 Hz), 7.31 (1H, d, J = 1.8 Hz), 7.68 (1H, d, J = 7.9 Hz), 7.95 (1H, d, J = 2.4 Hz). LRMS (ESI$^+$): 393 (M + H$^+$). |

TABLE 139-continued

| Example No. | Chemical Structural Formula | Spectrum Data |
|---|---|---|
| 8-100 | 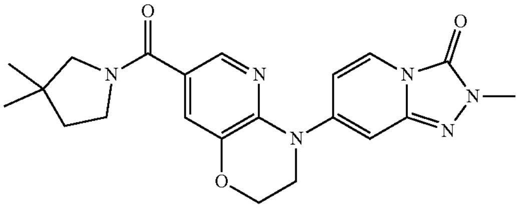 | $^1$H NMR (400 MHz, $CDCl_3$) δ 1.05 (4H, s), 1.15 (2H, s), 1.70-1.77 (2H, m), 3.26 (1.3H, s), 3.39 (0.7H, s), 3.61 (1H, t, J = 7.3 Hz), 3.64 (3H, s), 3.72 (1H, t, J = 7.3 Hz), 3.90 (2 H, t, J = 4.6 Hz), 4.41 (2H, t, J = 4.6 Hz), 6.64 (1H, s), 6.99 (1H, dd, J = 7.9, 1.8 Hz), 7.39 (1H, d, J = 1.8 Hz), 7.68 (1H, d, J = 7.9 Hz), 8.03 (1H, dd, J = 12.8, 1.8 Hz). LRMS ($ESI^+$): 409 (M + $H^+$). |

TABLE 140

| Example No. | Chemical Structural Formula | Spectrum Data |
|---|---|---|
| 8-101 | 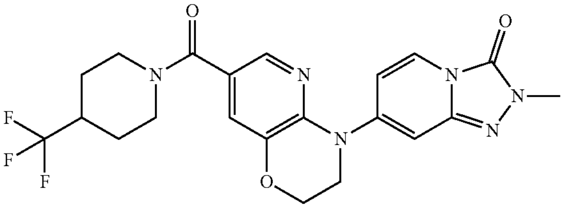 [SMILES: Cn1nc2cc(N3CCOc4cc(C(=O)N5CCC(C(F)(F)F)CC5)cnc43)ccn2c1=O] | $^1$H NMR (400 MHz, $CDCl_3$) δ 1.61-1.69 (2H, m), 1.87-2.02 (2H, m), 2.26-2.38 (1H, m), 2.72-3.14 (2H, m), 3.65 (3H, s), 3.91 (2H, t, J = 4.6 Hz), 4.04-4.98 (4H, m), 6.65 (1H, d, J = 1.2 Hz), 6.97 (1H, dd, J = 7.6, 2.1 Hz), 7.25-7.27 (1H, m), 7.69 (1H, d, J = 8.6 Hz), 7.89 (1H, d, J = 1.8 Hz). LRMS ($ESI^+$): 463 (M + $H^+$). |
| 8-102 | 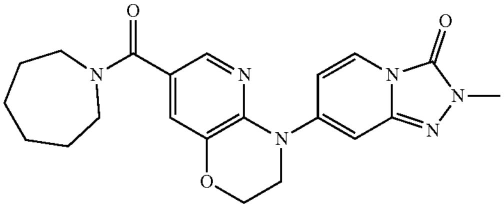 [SMILES: Cn1nc2cc(N3CCOc4cc(C(=O)N5CCCCCC5)cnc43)ccn2c1=O] | $^1$H NMR (400 MHz, $CDCl_3$) δ 1.60-1.72 (6H, m), 1.78-1.88 (2H, m), 3.47 (2H, t, J = 5.5 Hz), 3.60-3.70 (5H, m), 3.89 (2H, t, J = 4.6 Hz), 4.40 (2H, t, J = 4.6 Hz), 6.63 (1H, d, J = 1.2 Hz), 6.98 (1H, dd, J = 7.3, 1.8 Hz), 7.24 (1H, d, J = 1.8 Hz), 7.68 (1H, d, J = 6.7 Hz), 7.89 (1H, d, J = 1.8 Hz). LRMS ($ESI^+$): 409 (M + $H^+$). |
| 8-103 | 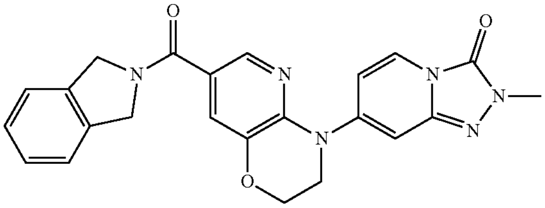 [SMILES: Cn1nc2cc(N3CCOc4cc(C(=O)N5Cc6ccccc6C5)cnc43)ccn2c1=O] | $^1$H NMR (400 MHz, $CDCl_3$) δ 3.65 (3H, s), 3.93 (2H, t, J = 4.5 Hz), 4.43 (2H, t, J = 4.5 Hz), 4.89 (2H, s), 5.02 (2H, s), 6.67 (1H, d, J = 1.8 Hz), 7.01 (1H, dd, J = 7.6, 2.1 Hz), 7.18 (1H, d, J = 7.6 Hz), 7.28-7.36 (3H, m), 7.44 (1H, d, J = 1.8 Hz), 7.70 (1H, d, J = 7.6 Hz), 8.13 (1H, d, J = 1.8 Hz). LRMS ($ESI^+$): 429 (M + $H^+$). |
| 8-104 | 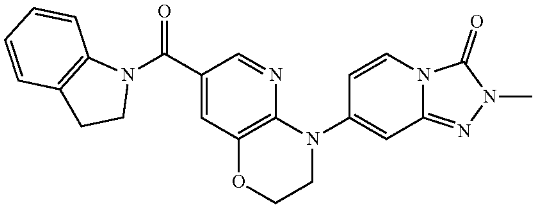 [SMILES: Cn1nc2cc(N3CCOc4cc(C(=O)N5CCc6ccccc65)cnc43)ccn2c1=O] | $^1$H NMR (400 MHz, $CDCl_3$) δ 3.14 (2H, t, J = 8.2 Hz), 3.65 (3H, s), 3.93 (2H, t, J = 4.5 Hz), 4.15 (2H, t, J = 8.2 Hz), 4.43 (2H, t, J = 4.5 Hz), 6.67 (1H, d, J = 1.8 Hz), 6.99 (1 H, dd, J = 7.9, 1.8 Hz), 7.05 (1H, d, J = 7.9 Hz), 7.14-7.23 (3H, m), 7.40 (1H, d, J = 1.8 Hz), 7.69 (1H, d, J = 7.9 Hz), 8.08 (1H, d, J = 1.8 Hz). LRMS ($ESI^+$): 429 (M + $H^+$). |
| 8-105 | 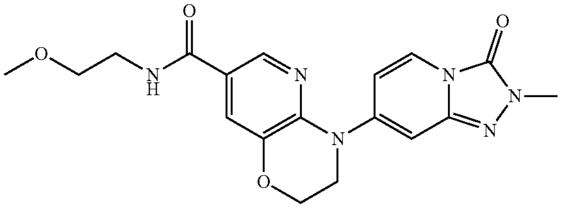 | $^1$H NMR (400 MHz, $CDCl_3$) δ 3.39 (3H, s), 3.55 (2H, t, J = 4.9 Hz), 3.62-3.66 (5H, m), 3.91 (2H, t, J = 4.6 Hz), 4.41 (2H, t, J = 4.6 Hz), 6.40 (1H, t, J = 5.2 Hz), 6.65 (1H, d, J = 1.6 Hz), 6.97 (1H, dd, J = 8.0, 2.4 Hz), 7.58 (1H, d, J = 1.6 Hz), 7.68 (1H, d, J = 8.0 Hz), 8.22 (1H, d, J = 2.4 Hz). LRMS ($ESI^+$): 385 (M + $H^+$). |

TABLE 140-continued

| Example No. | Chemical Structural Formula | Spectrum Data |
|---|---|---|
| 8-106 | 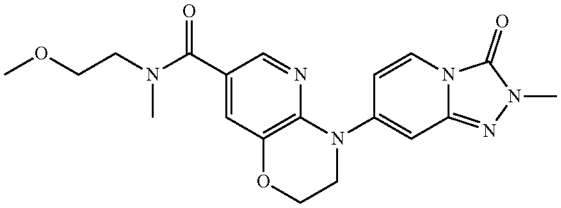 | $^1$H NMR (400 MHz, $CDCl_3$) δ 3.12 (3H, s), 3.30-3.41 (3H, m), 3.45-3.75 (7H, m), 3.90 (2H, t, J = 4.6 Hz), 4.40 (2H, t, J = 4.6 Hz), 6.63 (1H, d, J = 1.2 Hz), 6.98 (1H, dd, J = 7.6, 1.8 Hz), 7.30 (1H, d, J = 1.2 Hz), 7.68 (1H, d, J = 7.6 Hz), 7.94 (1H, d, J = 1.8 Hz). LRMS (ESI$^+$): 399 (M + H$^+$). |

TABLE 141

| Example No. | Chemical Structural Formula | Spectrum Data |
|---|---|---|
| 8-107 | 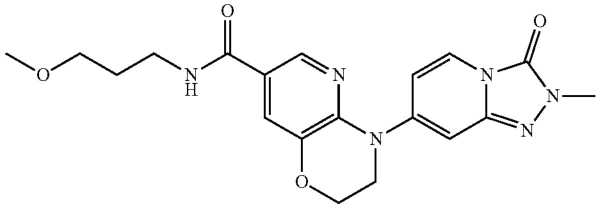 | $^1$H NMR (400 MHz, $CDCl_3$) δ 1.85-1.91 (2H, m), 3.39 (3H, s), 3.55-3.60 (4H, m), 3.64 (3H, s), 3.91 (2H, t, J = 4.5 Hz), 4.41 (2H, t, J = 4.5 Hz), 6.66 (1H, d, J = 1.8 Hz), 6.92 (1H, t, J = 4.8 Hz), 6.96 (1H, dd, J = 7.9, 1.8 Hz), 7.59 (1H, d, J = 2.4 Hz), 7.69 (1H, d, J = 7.9 Hz), 8.16 (1H, d, J = 1.8 Hz). LRMS (ESI$^+$): 399 (M + H$^+$). |
| 8-108 | 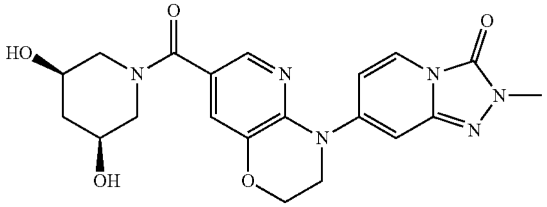 [SMILES: Cn1nc2cc(N3CCOc4cc(C(=O)N5C[C@H](O)C[C@H](O)C5)cnc43)ccn2c1=O] | $^1$H NMR (400 MHz, $CDCl_3$) δ 1.81 (1H, d, J = 14.5 Hz), 2.20 (1H, d, J = 14.5 Hz), 2.93-3.42 (3H, m), 3.64 (3H, s), 3.89-4.08 (5H, m), 4.18-4.36 (1H, m), 4.40 (2H, t, J = 4.5 Hz), 4.61-4.84 (1H, m), 6.64 (1H, d, J = 1.2 Hz), 6.98 (1H, dd, J = 8.3, 1.8 Hz), 7.41 (1H, d, J = 1.8 Hz), 7.68 (1H, d, J = 8.3 Hz), 8.01 (1H, d, J = 1.8 Hz). LRMS (ESI$^+$): 427 (M + H$^+$). |
| 8-109 | 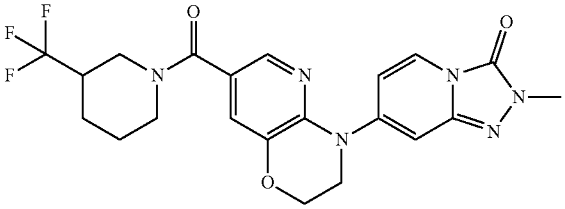 [SMILES: Cn1nc2cc(N3CCOc4cc(C(=O)N5CCCC(C(F)(F)F)C5)cnc43)ccn2c1=O] | $^1$H NMR (400 MHz, $CDCl_3$) δ 1.45-1.68 (2H, m), 1.78-1.89 (1H, m), 2.08-2.16 (1H, m), 2.23-2.40 (1H, m), 2.80-3.10 (2H, m), 3.65 (3H, s), 3.78-4.88 (6H, m), 6.66 (1H, d, J = 1.2 Hz), 6.96 (1H, dd, J = 7.6, 2.1 Hz), 7.25 (1H, d, J = 1.8 Hz), 7.69 (1H, d, J = 6.7 Hz), 7.88 (1H, d, J = 1.8 Hz). LRMS (ESI$^+$): 463 (M + H$^+$). |
| 8-110 | 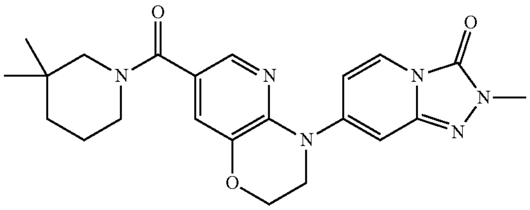 | $^1$H NMR (400 MHz, $CDCl_3$) δ 0.78-1.06 (6H, m), 1.41-1.48 (2H, m), 1.61-1.70 (2H, m), 3.03-3.68 (7H, m), 3.90 (2H, t, J = 4.3 Hz), 4.41 (2H, t, J = 4.6 Hz), 6.64 (1H, d, J = 1.2 Hz), 6.99 (1H, dd, J = 7.6, 2.1 Hz), 7.24 (1H, s), 7.68 (1H, d, J = 6.7 Hz), 7.88 (1H, s). LRMS (ESI$^+$): 423 (M + H$^+$). |
| 8-111 | 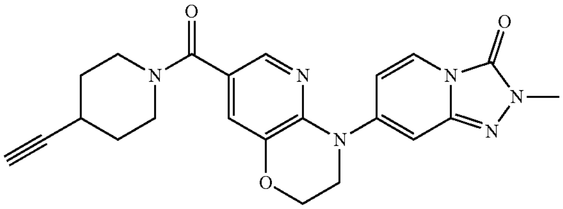 [SMILES: C#CC1CCN(C(=O)c2cnc3c(c2)OCCN3c2ccn3c(=O)n(C)nc3c2)CC1] | $^1$H NMR (400 MHz, $CDCl_3$) δ 1.62-1.97 (4H, m), 2.15 (1H, d, J = 2.4 Hz), 2.71-2.79 (1H, m), 3.30-3.60 (2H, m), 3.64 (3H, s), 3.70-4.01 (4H, m), 4.41 (2H, t, J = 4.3 Hz), 6.64 (1H, d, J = 1.8 Hz), 6.97 (1H, dd, J = 7.9, 1.8 Hz), 7.25 (1H, d, J = 1.8 Hz), 7.68 (1H, d, J = 6.7 Hz), 7.88 (1H, d, J =1.8 Hz). LRMS (ESI$^+$): 419 (M + H$^+$). |

TABLE 142

| Example No. | Chemical Structural Formula | Spectrum Data |
|---|---|---|
| 8-112 | 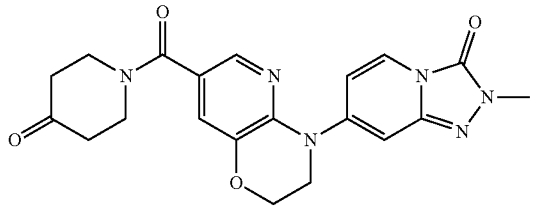 [SMILES: Cn1nc2cc(N3CCOc4cc(C(=O)N5CCC(=O)CC5)cnc43)ccn2c1=O] | $^1$H NMR (400 MHz, $CDCl_3$) δ 2.40-2.66 (4H, m), 3.65 (3H, s), 3.85-4.00 (6H, m), 4.43 (2H, t, J = 4.6 Hz), 6.67 (1H, t, J = 1.5 Hz), 6.96 (1H, dd, J = 7.6, 2.1 Hz), 7.32 (1H, d, J = 1.8 Hz), 7.70 (1H, d, J = 8.6 Hz), 7.97 (1H, d, J = 2.4 Hz). LRMS (ESI$^+$): 409 (M + H$^+$). |
| 8-113 | 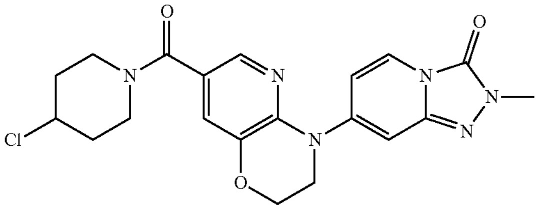 [SMILES: Cn1nc2cc(N3CCOc4cc(C(=O)N5CCC(Cl)CC5)cnc43)ccn2c1=O] | $^1$H NMR (400 MHz, $CDCl_3$) δ 1.82-1.99 (2H, m), 2.01-2.20 (2H, m), 3.41-3.89 (7H, m), 3.90 (2H, t, J = 4.6 Hz), 4.31-4.36 (1H, m), 4.41 (2H, t, J = 4.6 Hz), 6.65 (1H, d, J = 1.2 Hz), 6.96 (1H, dd, J = 7.3, 1.8 Hz), 7.26 (1H, t, J = 1.5 Hz), 7.69 (1H, d, J = 8.6 Hz), 7.89 (1H, d, J = 1.8 Hz). LRMS (ESI$^+$): 429 (M + H$^+$). |
| 8-114 | 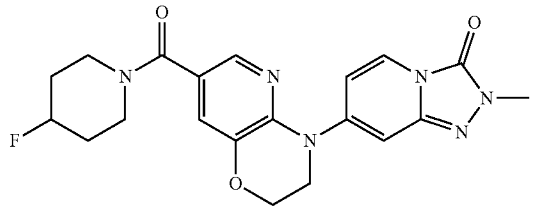 [SMILES: Cn1nc2cc(N3CCOc4cc(C(=O)N5CCC(F)CC5)cnc43)ccn2c1=O] | $^1$H NMR (400 MHz, $CDCl_3$) δ 1.76-2.01 (4H, m), 3.47-4.02 (9H, m), 4.41 (2H, t, J = 4.6 Hz), 4.84-5.00 (1H, m), 6.65 (1H, d, J = 1.8 Hz), 6.96 (1H, dd, J = 7.6, 2.1 Hz), 7.26 (1H, s), 7.69 (1H, d, J = 8.6 Hz), 7.90 (1H, d, J = 1.8 Hz). LRMS (ESI$^+$): 413 (M + H$^+$). |
| 8-115 | 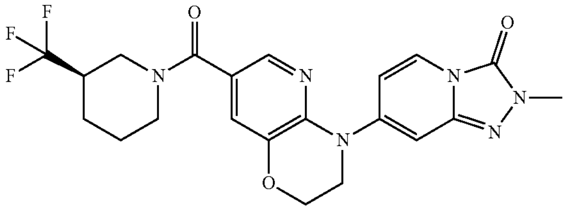 [SMILES: Cn1nc2cc(N3CCOc4cc(C(=O)N5CCC[C@@H](C(F)(F)F)C5)cnc43)ccn2c1=O] | $^1$H NMR (400 MHz, $CDCl_3$) δ 1.51-1.68 (2H, m), 1.77-1.91 (1H, m), 2.08-2.17 (1H, m), 2.23-2.41 (1H, m), 2.81-3.13 (2H, m), 3.64 (3H, s), 3.90-4.99 (6H, m), 6.66 (1H, d, J = 1.2 Hz), 6.96 (1H, dd, J = 7.9, 1.8 Hz), 7.25 (1H, d, J = 1.8 Hz), 7.69 (1H, d, J = 6.7 Hz), 7.88 (1H, d, J = 1.8 Hz). LRMS (ESI$^+$): 463 (M + H$^+$). |
| 8-116 | 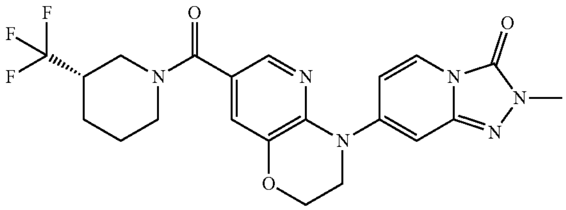 [SMILES: Cn1nc2cc(N3CCOc4cc(C(=O)N5CCC[C@H](C(F)(F)F)C5)cnc43)ccn2c1=O] | $^1$H NMR (400 MHz, $CDCl_3$) δ 1.46-1.68 (2H, m), 1.76-1.90 (1H, m), 2.08-2.17 (1H, m), 2.23-2.40 (1H, m), 2.78-3.12 (2H, m), 3.65 (3H, s), 3.90-4.96 (6H, m), 6.66 (1H, d, J = 1.8 Hz), 6.96 (1H, dd, J = 7.6, 2.1 Hz), 7.25 (1H, d, J = 2.4 Hz), 7.69 (1H, d, J = 8.6 Hz), 7.88 (1H, d, J = 2.4 Hz). LRMS (ESI$^+$): 463 (M + H$^+$). |
| 8-117 | 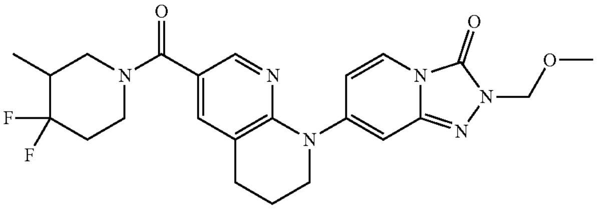 [SMILES: COCn1nc2cc(N3CCCc4cc(C(=O)N5CCC(F)(F)C(C)C5)cnc43)ccn2c1=O] | $^1$H NMR (400 MHz, $CDCl_3$) δ 0.96-1.12 (3H, m), 1.77-2.28 (5H, m), 2.90 (2H, t, J = 6.7 Hz), 2.96-3.14 (1H, m), 3.25-3.68, (6H, m), 3.84 (2H, t, J = 5.8 Hz), 5.30 (2H, s), 6.70 (1H, d, J = 1.8 Hz), 6.76 (1H, dd, J = 7.9, 1.8 Hz), 7.50-7.53 (1H, m), 7.65 (1H, d, J = 7.9 Hz), 8.10 (1H, d, J = 2.4 Hz). LRMS (ESI$^+$) 473 [M + H]$^+$. |

TABLE 143

| Example No. | Chemical Structural Formula | Spectrum Data |
| --- | --- | --- |
| 8-118 | 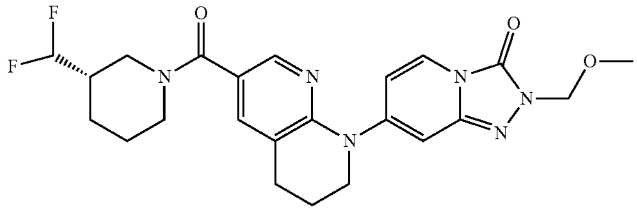 [SMILES: COCn1nc2cc(N3CCCc4cc(C(=O)N5CCC[C@H](C(F)F)C5)cnc43)ccn2c1=O] | $^1$H NMR (400 MHz, DMSO-$d_6$) δ 1.38-1.54 (2H, m), 1.62-1.78 (1H, m), 1.80-1.93 (1H, m), 1.94-2.15 (3H, m), 2.74-3.20 (6H, m), 3.28-3.37 (3H, m), 3.82 (2H, t, J = 5.8 Hz), 5.17 (2H, s), 6.02 (1H, t, J = 56.0 Hz), 6.79 (1H, dd, J = 7.6, 2.1 Hz), 6.90 (1H, d, J = 1.8 Hz), 7.53 (1H, d, J = 1.8 Hz), 7.72 (1H, d, J = 7.3 Hz), 8.03 (1H, d, J = 2.4 Hz). LRMS (ESI$^+$) 473 [M + H]$^+$. |
| 8-119 | 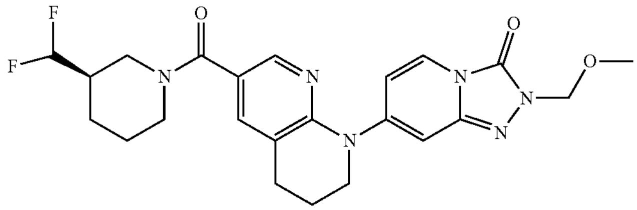 [SMILES: COCn1nc2cc(N3CCCc4cc(C(=O)N5CCC[C@@H](C(F)F)C5)cnc43)ccn2c1=O] | $^1$H NMR (400 MHz, DMSO-$d_6$) δ 1.37-1.55 (2H, m), 1.62-1.77 (1H, m), 1.80-1.92 (1H, m), 1.95-2.18 (3H, m), 2.72-3.19 (4H, m), 3.33 (3H, s), 3.53-4.58 (4H, m), 5.17 (2H, s), 6.02 (1H, t, J = 55.7 Hz), 6.79 (1H, dd, J = 7.6, 2.1 Hz), 6.90 (1H, d, J = 1.2 Hz), 7.53 (1H, d, J = 2.4 Hz), 7.72 (1H, d, J = 7.3 Hz.), 8.04 (1H, d, J = 2.4 Hz). LRMS (ESI$^+$) 473 [M + H]$^+$. |
| 8-120 | 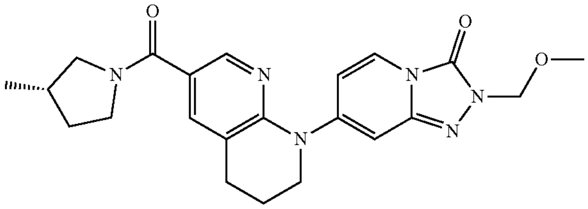 | $^1$H NMR (400 MHz, DMSO-$d_6$) δ 0.92-1.10 (3H, m), 1.39-1.60 (1H, m), 1.91-2.05 (3H, m), 2.12-2.30 (1H, m), 2.83 (2H, t, J = 6.7 Hz), 2.94-3.17 (1H, m), 3.27-3.36 (3H, m), 3.39-3.67 (3H, m), 3.81 (2H, t, J = 5.8 Hz), 5.17 (2H, s), 6.79 (1H, d, J = 8.5 Hz), 6.90 (1H, s), 7.65 (1H, s), 7.72 (1H, d, J = 7.9 Hz), 8.17 (1H, s). LRMS (ESI$^+$) 423 [M + H]$^+$. |
| 8-121 | 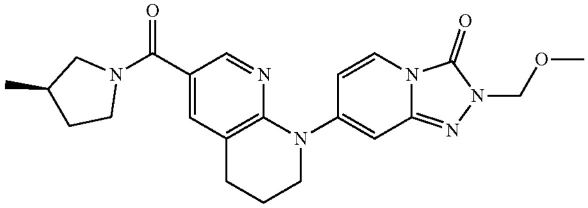 | $^1$H NMR (400 MHz, DMSO-$d_6$) δ 0.91-1.11 (3H, m), 1.40-1.57 (1H, m), 1.88-2.08 (3H, m), 2.13-2.30 (1H, m), 2.84 (2H, t, J = 6.1 Hz), 2.94-3.19 (1H, m), 3.27-3.36 (3H, m), 3.38-3.67 (3H, m), 3.82 (2H, t, J = 5.4 Hz), 5.17 (2H, s), 6.79 (1H, d, J = 7.9 Hz), 6.90 (1H, s), 7.65 (1H, s), 7.72 (1H, d, J = 7.3 Hz), 8.17 (1H, s). LRMS (ESI$^+$) 423 [M + H]$^+$. |
| 8-122 | 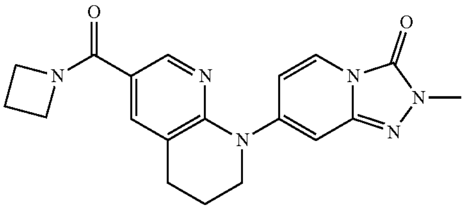 [SMILES: Cn1nc2cc(N3CCCc4cc(C(=O)N5CCC5)cnc43)ccn2c1=O] | $^1$H NMR (400 MHz, DMSO-$d_6$) δ 1.93-2.06 (2H, m), 2.19-2.31 (2H, m), 2.84 (2H, t, J = 6.4 Hz), 3.50 (3H, s), 3.81 (2H, t, J = 5.8 Hz), 3.92-4.12 (2H, m), 4.22-4.44 (2H, m), 6.74 (1H, dd, J = 7.3, 1.8 Hz), 6.93 (1H, d, J = 1.2 Hz), 7.66-7.74 (2H, m), 8.21 (1H, d, J = 1.8 Hz). LRMS (ESI$^+$) 365 [M + H]$^+$. |

TABLE 144

| Example No. | Chemical Structural Formula | Spectrum Data |
| --- | --- | --- |
| 8-123 | 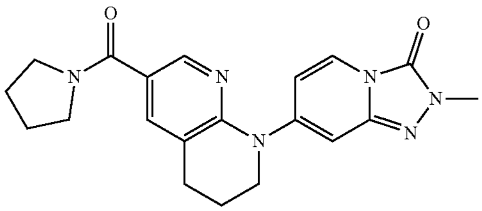 [SMILES: Cn1nc2cc(N3CCCc4cc(C(=O)N5CCCC5)cnc43)ccn2c1=O] | $^1$H NMR (400 MHz, DMSO-$d_6$) δ 1.76-1.90 (4H, m), 1.94-2.06 (2H, m), 2.83 (2H, t, J = 6.4 Hz), 3.38-3.56 (7H, m), 3.80 (2H, t, J = 5.8 Hz), 6.77 (1H, dd, J = 7.6, 2.1 Hz), 6.88-6.91 (1H, m), 7.62-7.66 (1H, m), 7.69 (1H, d, J = 7.9 Hz), 8.17 (1H, d, J = 2.4 Hz). LRMS (ESI$^+$) 379 [M + H]$^+$. |

TABLE 144-continued

| Example No. | Chemical Structural Formula | Spectrum Data |
|---|---|---|
| 8-124 | 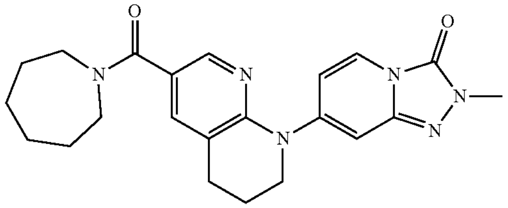 [SMILES: Cn1nc2cc(N3CCCc4cc(C(=O)N5CCCCCC5)cnc43)ccn2c1=O] | $^1$H NMR (400 MHz, DMSO-$d_6$) δ 1.43-1.76 (8H, m), 1.96-2.06 (2H, m), 2.83 (2H, t, J = 6.4 Hz), 3.37-3.59 (7H, m), 3.80 (2H, t, J = 5.8 Hz), 6.78 (1H, dd, J = 7.6, 2.1 Hz), 6.86-6.89 (1H, m), 7.48-7.53 (1H, m), 7.69 (1H, d, J = 7.3 Hz), 7.99 (1H, d, J = 1.8 Hz). LRMS (ESI$^+$) 407 [M + H]$^+$. |
| 8-125 | 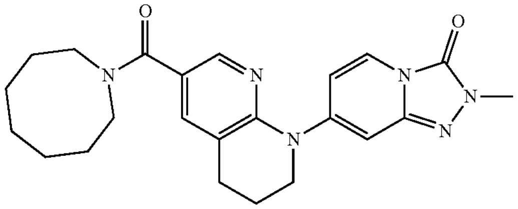 [SMILES: Cn1nc2cc(N3CCCc4cc(C(=O)N5CCCCCCC5)cnc43)ccn2c1=O] | $^1$H NMR (400 MHz, DMSO-$d_6$) δ 1.46-1.63 (8H, m), 1.65-1.78 (2H, m), 1.95-2.05 (2H, m), 2.83 (2H, t, J = 6.4 Hz), 3.34-3.42 (2H, m), 3.45-3.58 (5H, m), 3.80 (2H, t, J = 5.8 Hz), 6.78 (1H, dd, J = 7.6, 2.1 Hz), 6.88 (1H, d, J = 1.2 Hz), 7.46-7.50 (1H, m), 7.69 (1H, d, J = 8.5 Hz), 7.97 (1H, d, J = 2.4 Hz). LRMS (ESI$^+$) 421 [M + H]$^+$. |
| 8-126 | 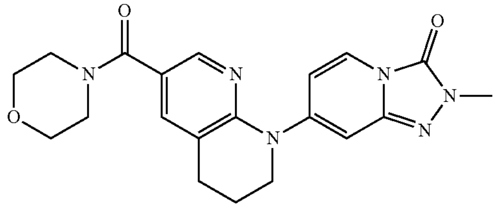 [SMILES: Cn1nc2cc(N3CCCc4cc(C(=O)N5CCOCC5)cnc43)ccn2c1=O] | $^1$H NMR (400 MHz, DMSO-$d_6$) δ 1.95-2.05 (2H, m), 2.83 (2H, t, J = 6.4 Hz), 3.44-3.65 (11H, m), 3.80 (2H, t, J = 5.8 Hz), 6.77 (1H, dd, J = 7.9, 1.8 Hz), 6.88-6.91 (1H, m), 7.51-7.56 (1H, m), 7.69 (1H, d, J = 8.5 Hz), 8.04 (1H, d, J = 2.4 Hz). LRMS (ESI$^+$) 395 [M + H]$^+$. |
| 8-127 | 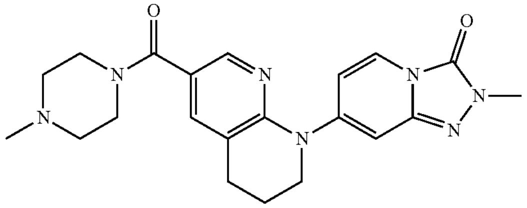 | $^1$H NMR (400 MHz, DMSO-$d_6$) δ 1.95-2.05 (2H, m), 2.19 (3H, s), 2.24-2.38 (4H, m), 2.83 (2H, t, J = 6.4 Hz), 3.39-3.61 (7H, m), 3.80 (2H, t, J = 5.8 Hz), 6.78 (1H, dd, J = 7.9, 1.8 Hz), 6.87-6.92 (1H, m), 7.49-7.53 (1H, m), 7.69 (1H, d, J = 8.5 Hz), 8.01 (1H, d, J = 2.4 Hz). LRMS (ESI$^+$) 408 [M + H]$^+$. |
| 8-128 | 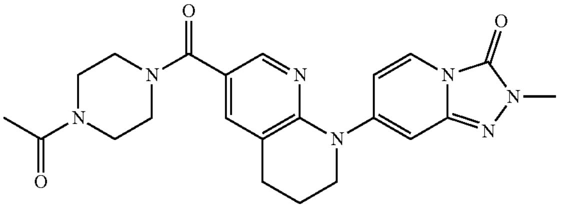 [SMILES: CC(=O)N1CCN(C(=O)c2cnc3c(c2)CCCN3c2ccn3c(=O)n(C)nc3c2)CC1] | $^1$H NMR (400 MHz, DMSO-$d_6$) δ 1.95-2.07 (5H, m), 2.84 (2H, t, J = 6.4 Hz), 3.44-3.61 (11H, m), 3.81 (2H, t, J = 5.8 Hz), 6.78 (1H, dd, J = 7.9, 1.8 Hz), 6.91 (1H, d, J = 1.2 Hz), 7.54 (1H, d, J = 1.8 Hz), 7.70 (1H, d, J = 7.3 Hz), 8.05 (1H, d, J = 2.4 Hz). LRMS (ESI$^+$) 436 [M + H]$^+$. |

TABLE 145

| Example No. | Chemical Structural Formula | Spectrum Data |
|---|---|---|
| 8-129 | 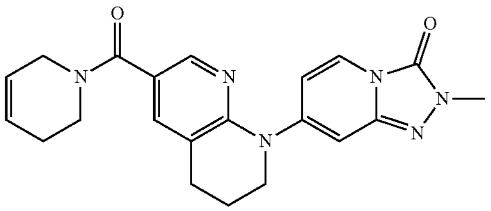 [SMILES: Cn1nc2cc(N3CCCc4cc(C(=O)N5CC=CCC5)cnc43)ccn2c1=O] | $^1$H NMR (400 MHz, DMSO-$d_6$) δ 1.95-2.06 (2H, m), 2.11-2.22 (2H, m), 2.84 (2H, t, J = 6.4 Hz), 3.41-3.70 (5H, m), 3.81 (2H, t, J = 5.8 Hz), 3.98-4.04 (2H, m), 5.59-5.78 (1H, m), 5.81-5.91 (1H, m), 6.78 (1H, dd, J = 7.6, 2.1 Hz), 6.90 (1H, d, J = 1.2 Hz), 7.53 (1H, d, J = 1.8 Hz), 7.69 (1H, d, J = 6.7 Hz), 8.03 (1H, d, J = 2.4 Hz). LRMS (ESI$^+$) 391 [M + H]$^+$. |

TABLE 145-continued

| Example No. | Chemical Structural Formula | Spectrum Data |
|---|---|---|
| 8-130 | 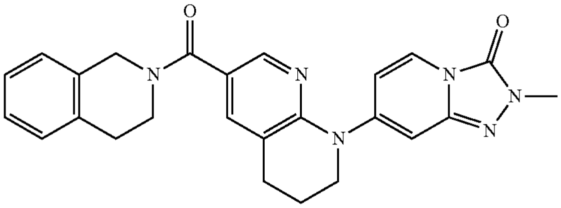 [SMILES: Cn1nc2cc(N3CCCc4cc(C(=O)N5CCc6ccccc6C5)cnc43)ccn2c1=O] | $^1$H NMR (400 MHz, DMSO-$d_6$) δ 1.95-2.08 (2H, m), 2.80-2.92 (4H, m), 3.50 (3H, s), 3.64-3.86 (4H, m), 4.71 (2H, s), 6.80 (1H, dd, J = 7.6, 2.1 Hz), 6.90-6.93 (1H, m), 7.12-7.26 (4H, m), 7.56-7.60 (1H, m), 7.70 (1H, d, J = 7.3 Hz), 8.09 (1H, d, J = 2.4 Hz). LRMS (ESI$^+$) 441 [M + H]$^+$. |
| 8-131 | 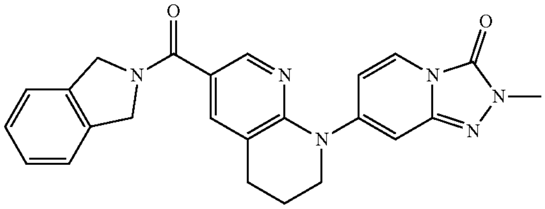 [SMILES: Cn1nc2cc(N3CCCc4cc(C(=O)N5Cc6ccccc6C5)cnc43)ccn2c1=O] | $^1$H NMR (400 MHz, DMSO-$d_6$) δ 1.96-2.09 (2H, m), 2.81-2.92 (2H, m), 3.51 (3H, s), 3.83 (2H, t, J = 5.8 Hz), 4.80-4.98 (4H, m), 6.80 (1H, dd, J = 7.9, 1.8 Hz), 6.93 (1H, d, J = 1.8 Hz), 7.23-7.34 (3H, m), 7.36-7.45 (1H, m), 7.69-7.78 (2H, m), 8.29 (1H, d, J = 2.4 Hz). LRMS (ESI$^+$) 427 [M + H]$^+$. |
| 8-132 | 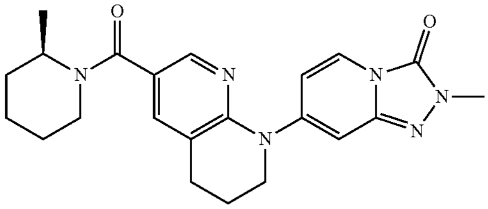 [SMILES: C[C@@H]1CCCCN1C(=O)c1cnc2c(c1)CCCN2c1ccn2c(=O)n(C)nc2c1] | $^1$H NMR (400 MHz, DMSO-$d_6$) δ 1.19 (3H, d, J = 7.3 Hz), 1.30-1.77 (6H, m), 1.93-2.07 (2H, m), 2.83 (2H, t, J = 6.4 Hz), 2.91-3.10 (1H, m), 3.50 (3H, s), 3.65-4.07 (3H, m), 4.22-4.58 (1H, m), 6.78 (1H, dd, J = 7.6, 2.1 Hz), 6.88 (1H, d, J = 1.8 Hz), 7.44-7.50 (1H, m), 7.69 (1H, d, J = 7.9 Hz), 7.97 (1H, d, J = 2.4 Hz). LRMS (ESI$^+$) 407 [M + H]$^+$. |
| 8-133 | 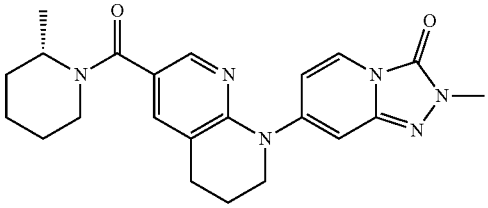 [SMILES: C[C@H]1CCCCN1C(=O)c1cnc2c(c1)CCCN2c1ccn2c(=O)n(C)nc2c1] | $^1$H NMR (400 MHz, DMSO-$d_6$) δ 1.19 (3H, d, J = 6.7 Hz), 1.30-1.75 (6H, m), 1.93-2.06 (2H, m), 2.83 (2H, t, J = 6.4 Hz), 2.90-3.10 (1H, m), 3.50 (3H, s), 3.65-4.06 (3H, m), 4.23-4.54 (1H, m), 6.78 (1H, dd, J = 7.6, 2.1 Hz), 6.88 (1H, d, J = 1.2 Hz), 7.46-7.49 (1H, m), 7.69 (1H, d, J = 7.9 Hz), 7.97 (1H, d, J = 2.4 Hz). LRMS (ESI$^+$) 407 [M + H]$^+$. |
| 8-134 | 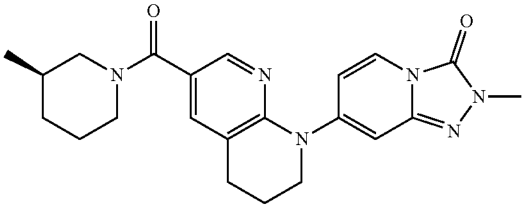 | $^1$H NMR (400 MHz, DMSO-$d_6$) δ 0.85 (3H, d, J = 6.7 Hz), 1.07-1.70 (4H, m), 1.73-1.85 (1H, m), 1.94-2.08 (2H, m), 2.54-2.70 (1H, m), 2.77-3.04 (3H, m), 3.49 (3H, s), 3.68-4.17 (4H, m), 6.77 (1H, dd, J = 7.6, 2.1 Hz), 6.85-6.88 (1H, m), 7.45-7.49 (1H, m), 7.66 (1H, d, J = 7.3 Hz), 7.98 (1H, d, J = 2.4 Hz). LRMS (ESI$^+$) 407 [M + H]$^+$. |

TABLE 146

| Example No. | Chemical Structural Formula | Spectrum Data |
|---|---|---|
| 8-135 | 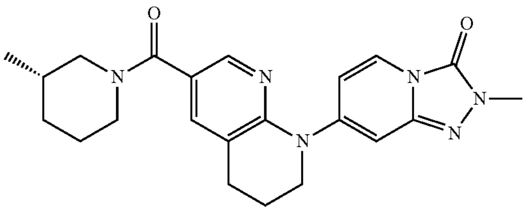 | $^1$H NMR (400 MHz, DMSO-$d_6$) δ 0.85 (3H, d, J = 6.7 Hz), 1.09-1.23 (1H, m), 1.34-1.70 (3H, m), 1.73-1.84 (1H, m), 1.95-2.08 (2H, m), 2.57-2.69 (1H, m), 2.83 (2H, t, J = 6.4 Hz), 2.88-3.01 (1H, m), 3.49 (3H, s), 3.72-4.12 (4H, m), 6.77 (1H, d d, J = 7.9, 1.8 Hz), 6.86 (1H, d, J = 1.8 Hz), 7.44-7.49 (1 H, m), 7.65 (1H, d, J = 7.9 Hz), 7.98 (1H, d, J = 1.8 Hz). LRMS (ESI$^+$) 407 [M + H]$^+$. |

TABLE 146-continued

| Example No. | Chemical Structural Formula | Spectrum Data |
|---|---|---|
| 8-136 | 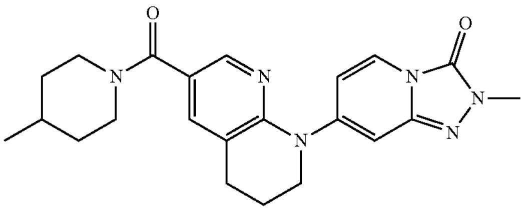 | $^1$H NMR (400 MHz, DMSO-$d_6$) δ 0.92 (3H, d, J = 6.1 Hz), 0.99-1.16 (2H, m), 1.48-1.75 (3H, m), 1.93-2.06 (2H, m), 2.72-3.19 (4H, m), 3.50 (3H, s), 3.58-4.54 (4H, m), 6.78 (1H, dd, J = 7.9, 1.8 Hz), 6.89 (1H, d, J = 1.2 Hz), 7.48-7.51 (1H, m), 7.69 (1H, d, J = 7.9 Hz), 7.99 (1H, d, J = 2.4 Hz). LRMS (ESI$^+$) 407 [M + H]$^+$. |
| 8-137 | 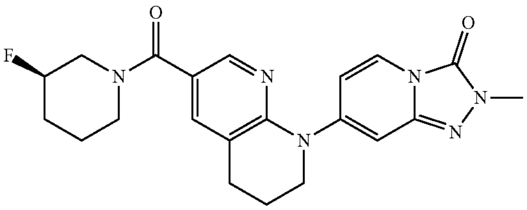 [SMILES: Cn1nc2cc(N3CCCc4cc(C(=O)N5CCC[C@@H](F)C5)cnc43)ccn2c1=O] | $^1$H NMR (400 MHz, DMSO-$d_6$) δ 1.44-1.58 (1H, m), 1.64-2.09 (5H, m), 2.83 (2H, t, J = 6.4 Hz), 2.95-3.26 (1H, m), 3.43-3.61 (4H, m), 3.70-4.18 (4H, m), 4.66-4.87 (1H, m), 6.78 (1H, dd, J = 7.9, 1.8 Hz), 6.90 (1H, d, J = 1.2 Hz), 7.47-7.52 (1 H, m), 7.69 (1H, d, J = 7.3 Hz), 7.99 (1H, d, J = 2.4 Hz). LRMS (ESI$^+$) 411 [M + H]$^+$. |
| 8-138 | 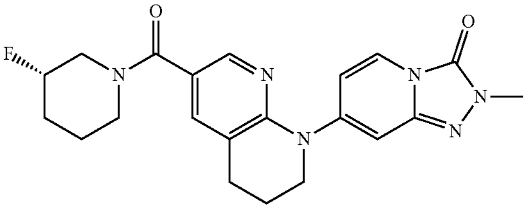 [SMILES: Cn1nc2cc(N3CCCc4cc(C(=O)N5CCC[C@H](F)C5)cnc43)ccn2c1=O] | $^1$H NMR (400 MHz, DMSO-$d_6$) δ 1.42-1.59 (1H, m), 1.62-1.94 (3H, m), 1.95-2.07 (2H, m), 2.83 (2H, t, J = 6.4 Hz), 2.94-3.27 (1H, m), 3.42-3.60 (4H, m), 3.66-4.19 (4H, m), 4.64-4.88 (1H, m), 6.78 (1H, dd, J = 7.6, 2.1 Hz), 6.90 (1H, d, J = 1.2 Hz), 7.48-7.51 (1H, m), 7.69 (1H, d, J = 7.9 Hz), 7.99 (1 H, d, J = 2.4 Hz). LRMS (ESI$^+$) 411 [M + H]$^+$. |
| 8-139 | 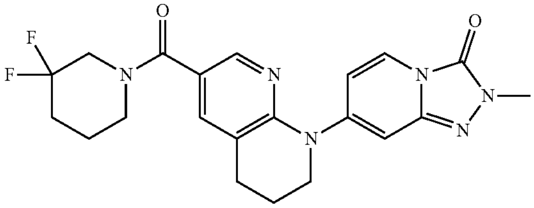 [SMILES: Cn1nc2cc(N3CCCc4cc(C(=O)N5CCCC(F)(F)C5)cnc43)ccn2c1=O] | $^1$H NMR (400 MHz, DMSO-$d_6$) δ 1.64-1.75 (2H, m), 1.94-2.18 (4H, m), 2.84 (2H, t, J = 6.1 Hz), 3.43-3.64 (5H, m), 3.73-3.92 (4H, m), 6.74-6.81 (1H, m), 6.88-6.94 (1H, m), 7.48-7.53 (1H, m), 7.69 (1H, d, J = 7.9 Hz), 7.98-8.03 (1H, m). LRMS (ESI$^+$) 429 [M + H]$^+$. |
| 8-140 | 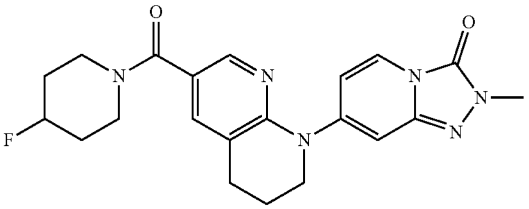 [SMILES: Cn1nc2cc(N3CCCc4cc(C(=O)N5CCC(F)CC5)cnc43)ccn2c1=O] | $^1$H NMR (400 MHz, DMSO-$d_6$) δ 1.64-1.80 (2H, m), 1.81-2.08 (4H, m), 2.83 (2H, t, J = 6.4 Hz), 3.37-3.70 (7H, m), 3.80 (2 H, t, J = 5.8 Hz), 4.80-5.03 (1H, m), 6.78 (1H, dd, J = 7.3, 1.8 Hz), 6.87-6.93 (1H, m), 7.51-7.56 (1H, m), 7.69 (1H, d, J = 7.9 Hz), 8.03 (1H, d, J = 2.4 Hz). LRMS (ESI$^+$) 411 [M + H]$^+$. |

TABLE 147

| Example No. | Chemical Structural Formula | Spectrum Data |
|---|---|---|
| 8-141 | 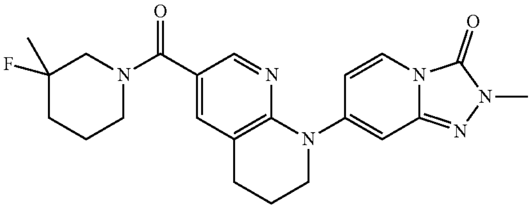 [SMILES: Cn1nc2cc(N3CCCc4cc(C(=O)N5CCCC(C)(F)C5)cnc43)ccn2c1=O] | $^1$H NMR (400 MHz, DMSO-$d_6$) δ 1.12-1.42 (3H, m), 1.47-1.80 (3H, m), 1.82-2.06 (3H, m), 2.72-3.27 (4H, m), 3.50 (3H, s), 3.57-4.53 (4H, m), 6.79 (1H, dd, J = 7.6, 2.1 Hz), 6.90 (1H, d, J = 1.2 Hz), 7.47-7.51 (1H, m), 7.69 (1H, d, J - 6.7 Hz), 7.99 (1H, d, J = 2.4 Hz). LRMS (ESI$^+$) 425 [M + H]$^+$. |

TABLE 147-continued

| Example No. | Chemical Structural Formula | Spectrum Data |
|---|---|---|
| 8-142 | 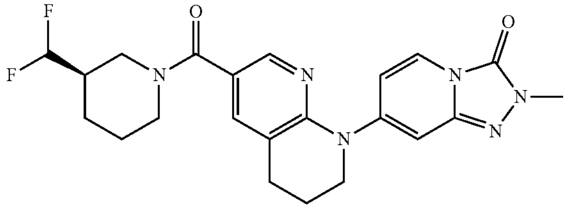 [SMILES: Cn1nc2cc(N3CCCc4cc(C(=O)N5CCC[C@@H](C(F)F)C5)cnc43)ccn2c1=O] | $^1$H NMR (400 MHz, DMSO-$d_6$) δ 1.36-1.55 (2H, m), 1.61-1.91 (2H, m), 1.93-2.17 (3H, m), 2.73-3.17 (4H, m), 3.50 (3H, s), 1.8 Hz), 6.90 (1H, d, J – 1.2 Hz), 7.52 (1H, d, J – 1.8 Hz), 7.69 (1H, d, J = 7.9 Hz), 8.02 (1H, d, J = 2.4 Hz). LRMS (ESI$^+$) 443 [M + H]$^+$. |
| 8-143 | 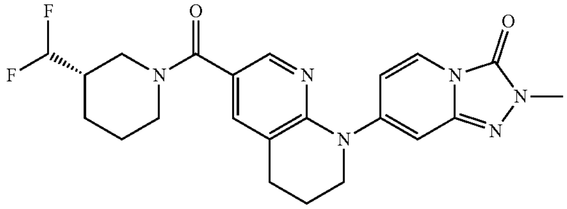 [SMILES: Cn1nc2cc(N3CCCc4cc(C(=O)N5CCC[C@H](C(F)F)C5)cnc43)ccn2c1=O] | $^1$H NMR (400 MHz, DMSO-$d_6$) δ 1.34-1.54 (2H, m), 1.62-1.91 (2H, m), 1.93-2.17 (3H, m), 2.73-3.17 (4H, m), 3.50 (3H, s), 2.1 Hz), 6.88-6.92 (1H, m), 7.49-7.54 (1H, m), 7.69 (1H, d, J = 7.3 Hz), 8.02 (1H, d, J = 1.8 Hz). LRMS (ESI$^+$) 443 [M + H]$^+$. |
| 8-144 | 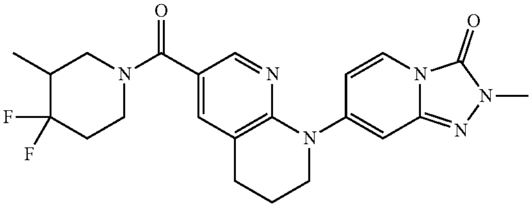 [SMILES: CC1CN(C(=O)c2cnc3c(c2)CCCN3c2ccn3c(=O)n(C)nc3c2)CCC1(F)F] | $^1$H NMR (400 MHz, DMSO-$d_6$) δ 0.85-1.05 (3H, m), 1.85-2.28 (5H, m), 2.78-3.14 (4H, m), 3.50 (3H, s), 3.67-4.20 (4H, m), 6.78 (1H, dd, J = 7.6, 2.1 Hz), 6.91 (1H, d, J = 1.2 Hz), 7.54-7.58 (1H, m), 7.70 (1H, d, J = 7.9 Hz), 8.29 (1H, d, J = 1.8 Hz). LRMS (ESI$^+$) 443 [M + H]$^+$. |
| 8-145 | 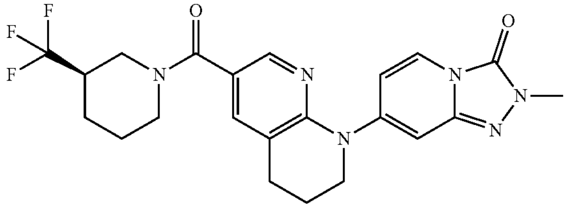 [SMILES: Cn1nc2cc(N3CCCc4cc(C(=O)N5CCC[C@@H](C(F)(F)F)C5)cnc43)ccn2c1=O] | $^1$H NMR (400 MHz, DMSO-$d_6$) δ 1.38-1.81 (3H, m), 1.92-2.08 (3H, m), 2.56-2.70 (1H, m), 2.74-3.20 (4H, m), 3.50 (3H, s), 3.62-4.70 (4H, m), 6.77 (1H, dd, J = 7.6, 2.1 Hz), 6.91 (1H d, J = 1.2 Hz), 7.50-7.55 (1H, m), 7.70 (1H, d, 7 = 7.3 Hz), 8.03 (1H, d, J = 2.4 Hz). LRMS (ESI$^+$) 461 [M + H]$^+$. |
| 8-146 | 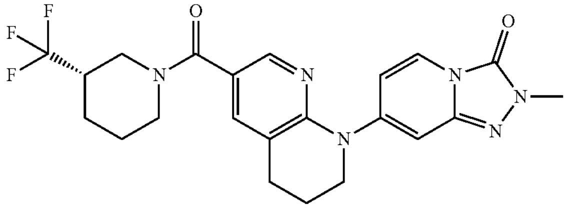 [SMILES: Cn1nc2cc(N3CCCc4cc(C(=O)N5CCC[C@H](C(F)(F)F)C5)cnc43)ccn2c1=O] | $^1$H NMR (400 MHz, DMSO-$d_6$) δ 1.39-1.81 (3H, m), 1.89-2.10 (3H, m), 2.55-2.71 (1H, m), 2.73-3.21 (4H, m), 3.50 (3H, s), 3.60-4.51 (4H, m), 6.77 (1H, dd, J = 7.6, 2.1 Hz), 6.91 (1H, d, J = 1.2 Hz), 7.49-7.54 (1H, m), 7.70 (1H, d, J = 7.3 Hz), 8.03 (1H, d, J = 2.4 Hz). LRMS (ESI$^+$) 461 [M + H]$^+$. |

TABLE 148

| Example No. | Chemical Structural Formula | Spectrum Data |
|---|---|---|
| 8-147 | 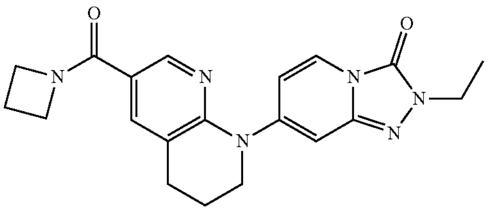 [SMILES: CCn1nc2cc(N3CCCc4cc(C(=O)N5CCC5)cnc43)ccn2c1=O] | $^1$H NMR (400 MHz, DMSO-$d_6$) δ 1.29 (3H, t, J = 7.3 Hz), 1.97-2.02 (2H, m), 2.19-2.31 (2H, m), 2.84 (2H, t, J = 6.4 Hz), 3.81 (2H, t, J = 5.8 Hz), 3.89 (2H, q, J = 7.3 Hz), 3.95-4.13 (2H, m), 4.20-4.53 (2H, m), 6.74 (1H, dd, J = 7.9, 1.8 Hz), 6.96 (1H, d, J = 1.2 Hz), 7.65-7.75 (2H, m), 8.20 (1H, d, J = 2.4 Hz). LRMS (ESI$^+$) 379 [M + H]$^+$. |

TABLE 148-continued

| Example No. | Chemical Structural Formula | Spectrum Data |
|---|---|---|
| 8-148 | 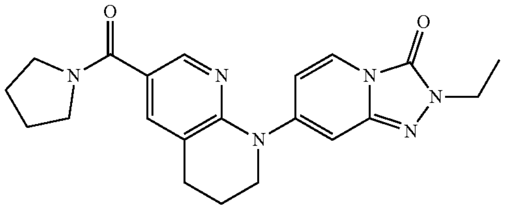 [SMILES: CCn1nc2cc(N3CCCc4cc(C(=O)N5CCCC5)cnc43)ccn2c1=O] | $^1$H NMR (400 MHz, DMSO-$d_6$) δ 1.28 (3H, t, J = 7.3 Hz), 1.75-1.89 (4H, m), 1.95-2.05 (2H, m), 2.82 (2H, t, J = 6.4 Hz), 3.39-3.54 (4H, m), 3.79 (2H, t, J = 5.8 Hz), 3.87 (2H, q, J = 7.1 Hz), 6.75 (1H, dd, J = 7.6, 2.1 Hz), 6.91 (1H, d, J = 2.4 Hz), 7.60-7.64 (1H, m), 7.69 (1H, d, J = 7.9 Hz), 8.15 (1H, d, J = 2.4 Hz). LRMS (ESI$^+$) 393 [M + H]$^+$. |
| 8-149 | 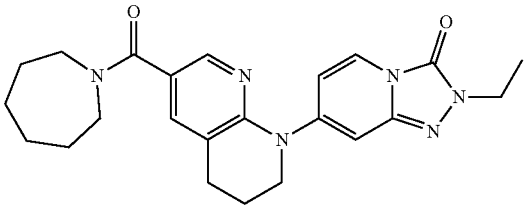 [SMILES: CCn1nc2cc(N3CCCc4cc(C(=O)N5CCCCCC5)cnc43)ccn2c1=O] | $^1$H NMR (400 MHz, DMSO-$d_6$) δ 1.29 (3H, t, J – 7.3 Hz), 1.42-1.78 (8H, m), 1.95-2.06 (2H, m), 2.83 (2H, t, J = 6.4 Hz), 3.36-3.60 (4H, m), 3.80 (2H, t, J = 5.8 Hz), 3.88 (2H, q, J = 7.1 Hz), 6.77 (1H, dd, J = 7.6, 2.1 Hz), 6.90 (1H, d, J = 1.8 Hz), 7.48-7.52 (1H, m), 7.69 (1H, d, J = 7.9 Hz), 7.99 (1H, d, J = 2.4 Hz). LRMS (ESI$^+$) 421 [M + H]$^+$. |
| 8-150 | 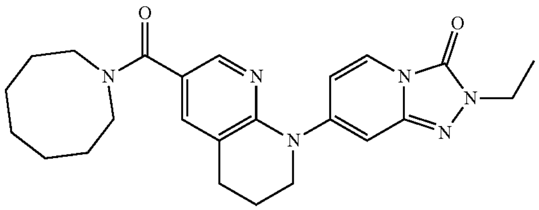 [SMILES: CCn1nc2cc(N3CCCc4cc(C(=O)N5CCCCCCC5)cnc43)ccn2c1=O] | $^1$H NMR (400 MHz, DMSO-$d_6$) δ 1.29 (3H, t, J = 7.3 Hz), 1.45-1.79 (10H, m), 1.95-2.05 (2H, m), 2.83 (2H, t, J = 6.4 Hz), 3.34-3.57 (4H, m), 3.80 (2H, t, J = 5.8 Hz), 3.88 (2H, q, J = 7.3 Hz), 6.78 (1H, dd, J = 7.6, 2.1 Hz), 6.90 (1H, d, J = 1.2 Hz), 7.45-7.50 (1H, m), 7.69 (1H, d, J = 7.3 Hz), 7.97 (1H, d, J = 2.4 Hz). LRMS (ESI$^+$) 435 [M + H]$^+$. |
| 8-151 | 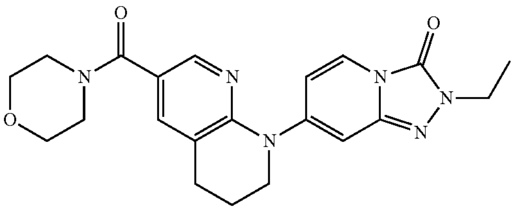 [SMILES: CCn1nc2cc(N3CCCc4cc(C(=O)N5CCOCC5)cnc43)ccn2c1=O] | $^1$H NMR (400 MHz, DMSO-$d_6$) δ 1.29 (3H, t, J = 7.3 Hz), 1.94-2.07 (2H, m), 2.83 (2H, t, J = 6.4 Hz), 3.42-3.68 (8H, m), 3.80 (2H, t, J = 5.8 Hz), 3.88 (2H, q, J = 7.3 Hz), 6.77 (1H, dd, J = 7.6, 2.1 Hz), 6.93 (1H, d, J = 1.2 Hz), 7.51-7.56 (1H, m), 7.70 (1H, d, J = 7.3 Hz), 8.03 (1H, d, J = 1.8 Hz). LRMS (ESI$^+$) 409 [M + H]$^+$. |

TABLE 149

| Example No. | Chemical Structural Formula | Spectrum Data |
|---|---|---|
| 8-152 | 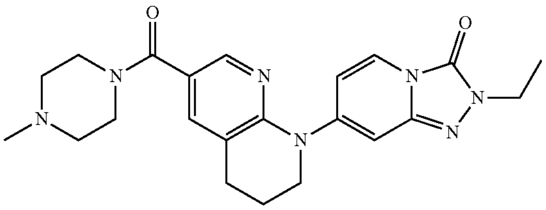 [SMILES: CCn1nc2cc(N3CCCc4cc(C(=O)N5CCN(C)CC5)cnc43)ccn2c1=O] | $^1$H NMR (400 MHz, DMSO-$d_6$) δ 1.29 (3H, t, J = 7.3 Hz), 1.95-2.06 (2H, m), 2.19 (3H, s), 2.24-2.40 (4H, m), 2.83 (2H, t, J = 6.4 Hz), 3.38-3.65 (4H, m), 3.80 (2H, t, J = 5.8 Hz), 3.88 (2H, q, J – 7.3 Hz), 6.77 (1H, dd, J – 7.6, 2.1 Hz), 6.92 (1H, d, J = 1.8 Hz), 7.49-7.53 (1H, m), 7.69 (1H, d, J = 7.9 Hz), 8.00 (1H, d, J = 1.8 Hz). LRMS (ESI$^+$) 422 [M + H]$^+$. |
| 8-153 | 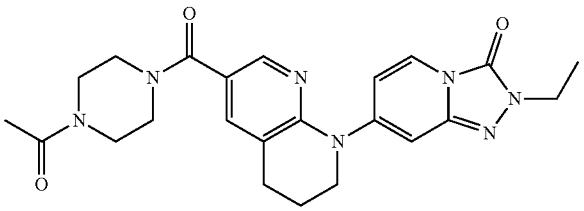 [SMILES: CCn1nc2cc(N3CCCc4cc(C(=O)N5CCN(C(C)=O)CC5)cnc43)ccn2c1=O] | $^1$H NMR (400 MHz, DMSO-$d_6$) δ 1.29 (3H, t, J = 7.3 Hz), 1.96-2.07 (5H, m), 2.84 (2H, t, J = 6.4 Hz), 3.40-3.61 (8H, m), 3.81 (2H, t, J – 5.8 Hz), 3.89 (2H, q, J – 7.1 Hz), 6.77 (1H, dd, J = 7.6, 2.1 Hz), 6.94 (1H, d, J = 1.2 Hz), 7.52-7.56 (1H, m), 7.71 (1H, d, J = 7.3 Hz), 8.05 (1H, d, J = 2.4 Hz). LRMS (ESI$^+$) 450 [M + H]$^+$. |

TABLE 149-continued

| Example No. | Chemical Structural Formula | Spectrum Data |
|---|---|---|
| 8-154 | 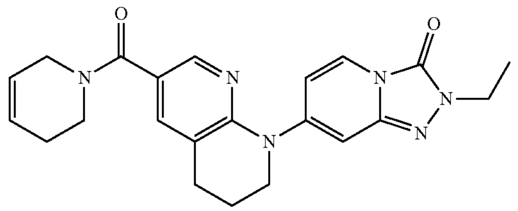 [SMILES: CCn1nc2cc(N3CCCc4cc(C(=O)N5CC=CCC5)cnc43)ccn2c1=O] | $^1$H NMR (400 MHz, DMSO-$d_6$) δ 1.29 (3H, t, J = 7.3 Hz), 1.95-2.06 (2H, m), 2.10-2.24 (2H, m), 2.84 (2H, t, J = 6.4 Hz), 3.41-3.71 (2H, m), 3.80 (2H, t, J = 5.8 Hz), 3.88 (2H, q, J = 7.3 Hz), 3.97-4.08 (2H, m), 5.58-5.93 (2H, m), 6.77 (1H, dd, J = 7.6, 2.1 Hz), 6.93 (1H, d, J = 1.2 Hz), 7.51-7.56 (1H, m), 7.70 (1H, d, J = 7.9 Hz), 8.01-8.06 (1H, m). LRMS (ESI$^+$) 405 [M + H]$^+$. |
| 8-155 | 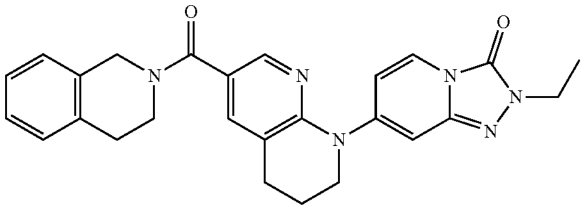 [SMILES: CCn1nc2cc(N3CCCc4cc(C(=O)N5CCc6ccccc6C5)cnc43)ccn2c1=O] | $^1$H NMR (400 MHz, DMSO-$d_6$) δ 1.29 (3H, t, J = 7.3 Hz), 1.97-2.08 (2H, m), 2.79-2.93 (4H, m), 3.59-3.94 (6H, m), 4.67-4.76 (2H, m), 6.80 (1H, dd, J = 7.9, 1.8 Hz), 6.94 (1H, d, J = 1.2 Hz), 7.09-7.29 (4H, m), 7.56-7.60 (1H, m), 7.71 (1H, d, J = 7.3 Hz), 8.09 (1H, d, J = 1.8 Hz). LRMS (ESI$^+$) 455 [M + H]$^+$. |
| 8-156 | 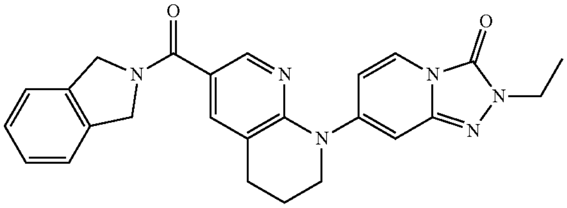 [SMILES: CCn1nc2cc(N3CCCc4cc(C(=O)N5Cc6ccccc6C5)cnc43)ccn2c1=O] | $^1$H NMR (400 MHz, DMSO-$d_6$) δ 1.30 (3H, t, J = 7.3 Hz), 1.96-2.09 (2H, m), 2.87 (2H, t, J = 6.4 Hz), 3.78-3.94 (4H, m), 4.80-4.97 (4H, m), 6.79 (1H, dd, J = 7.6, 2.1 Hz), 6.96 (1H, d, J = 1.2 Hz), 7.24-7.45 (4H, m), 7.69-7.78 (2H, m), 8.29 (1H, d, J = 2.4 Hz). LRMS (ESI$^+$) 441 [M + H]$^+$. |
| 8-157 | 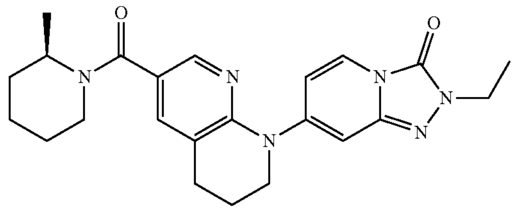 [SMILES: CCn1nc2cc(N3CCCc4cc(C(=O)N5CCCC[C@H]5C)cnc43)ccn2c1=O] | $^1$H NMR (400 MHz, DMSO-$d_6$) δ 1.19 (3H, d, J = 7.3 Hz), 1.29 (3H, t, J = 7.3 Hz), 1.33-1.75 (6H, m), 1.95-2.06 (2H, m), 2.83 (2H, t, J = 6.4 Hz), 2.91-3.09 (1H, m), 3.67-4.00 (5H, m), 4.27-4.58 (1H, m), 6.77 (1H, dd, J = 7.6, 2.1 Hz), 6.89-6.92 (1H, m), 7.45-7.49 (1H, m), 7.69 (1H, d, J = 6.7 Hz), 7.96 (1H, d, J = 2.4 Hz). LRMS (ESI$^+$) 421 [M + H]$^+$. |

TABLE 150

| Example No. | Chemical Structural Formula | Spectrum Data |
|---|---|---|
| 8-158 | 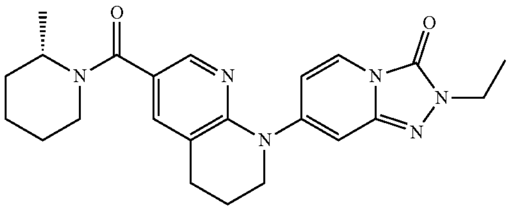 [SMILES: CCn1nc2cc(N3CCCc4cc(C(=O)N5CCCC[C@@H]5C)cnc43)ccn2c1=O] | $^1$H NMR (400 MHz, DMSO-$d_6$) δ 1.19 (3H, d, J = 7.3 Hz), 1.29 (3H, t, J = 7.3 Hz), 1.33-1.75 (6H, m), 1.95-2.05 (2H, m), 2.83 (2H, t, J = 6.4 Hz), 2.93-3.08 (1H, m), 3.72-3.98 (5H, m), 4.29-4.54 (1H, m), 6.77 (1H, dd, J = 7.6, 2.1 Hz), 6.89-6.92 (1H, m), 7.46-7.49 (1H, m), 7.69 (1H, d, J = 6.7 Hz), 7.96 (1H, d, J = 1.8 Hz). LRMS (ESI$^+$) 421 [M + H]$^+$. |
| 8-159 | 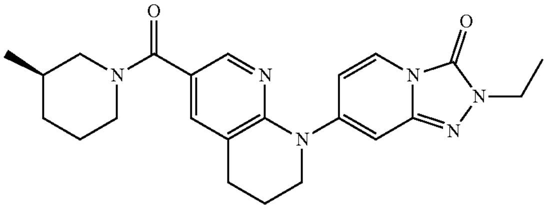 [SMILES: CCn1nc2cc(N3CCCc4cc(C(=O)N5CCC[C@@H](C)C5)cnc43)ccn2c1=O] | $^1$H NMR (400 MHz, DMSO-$d_6$) δ 0.68-0.98 (3H, m), 1.08-1.22 (1H, m), 1.29 (3H, t, J = 7.3 Hz), 1.34-1.69 (3H, m), 1.73-1.84 (1H, m), 1.94-2.06 (2H, m), 2.60-3.16 (4H, m), 3.46-4.61 (6H, m), 6.78 (1H, dd, J = 7.6, 2.1 Hz), 6.90-6.93 (1H, m), 7.46-7.51 (1H, m), 7.69 (1H, d, J = 6.7 Hz), 7.98 (1H, d, J = 2.4 Hz). LRMS (ESI$^+$) 421 [M + H]$^+$. |

TABLE 150-continued

| Example No. | Chemical Structural Formula | Spectrum Data |
|---|---|---|
| 8-160 | 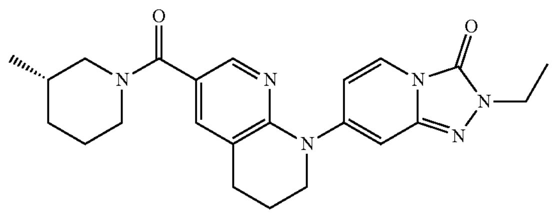 [SMILES: CCn1nc2cc(N3CCCc4cc(C(=O)N5CCC[C@H](C)C5)cnc43)ccn2c1=O] | $^1$H NMR (400 MHz, DMSO-$d_6$) δ 0.63-1.01 (3H, m), 1.06-1.22 (1H, m), 1.29 (3H, t, J = 7.3 Hz), 1.34-1.85 (4H, m), 1.92-2.08 (2H, m), 2.55-3.16 (4H, m), 3.46-4.46 (6H, m), 6.77 (1H, dd, J = 7.3, 1.8 Hz), 6.91 (1H, d, J = 1.2 Hz), 7.49 (1H, d, J = 1.8 Hz), 7.69 (1H, d, J = 7.9 Hz), 7.98 (1H, d, J = 2.4 Hz). LRMS (ESI$^+$) 421 [M + H]$^+$. |
| 8-161 | 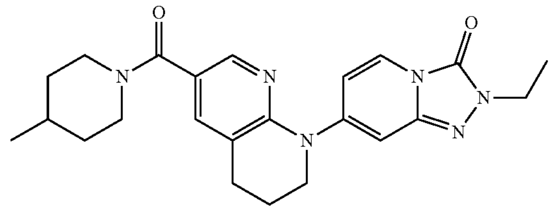 [SMILES: CCn1nc2cc(N3CCCc4cc(C(=O)N5CCC(C)CC5)cnc43)ccn2c1=O] | $^1$H NMR (400 MHz, DMSO-$d_6$) δ 0.92 (3H, d, J = 6.7 Hz), 0.99-1.15 (2H, m), 1.29 (3H, t, J = 7.3 Hz), 1.53-1.71 (3H, m), 1.95-2.06 (2H, m), 2.60-3.22 (4H, m), 3.46-4.74 (6H, m), 6.77 (1H, dd, J = 7.6, 2.1 Hz), 6.91 (1H, d, J = 1.2 Hz), 7.47-7.51 (1H, m), 7.69 (1H, d, J = 6.7 Hz), 7.99 (1H, d, J = 2.4 Hz). LRMS (ESI$^+$) 421 [M + H]$^+$. |
| 8-162 | 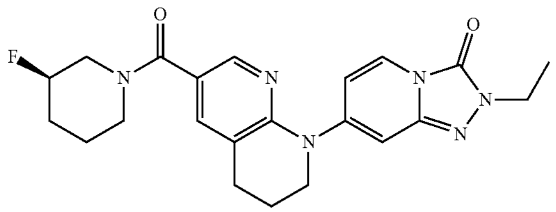 [SMILES: CCn1nc2cc(N3CCCc4cc(C(=O)N5CCC[C@@H](F)C5)cnc43)ccn2c1=O] | $^1$H NMR (400 MHz, DMSO-$d_6$) δ 1.29 (3H, t, J = 7.3 Hz), 1.41-1.59 (1H, m), 1.63-2.13 (5H, m), 2.83 (2H, t, J = 6.4 Hz), 2.95-3.27 (1H, m), 3.43-3.60 (1H, m), 3.64-4.31 (6H, m), 4.65-4.88 (1H, m), 6.77 (1H, dd, J = 7.6, 2.1 Hz), 6.92 (1H, d, J = 1.8 Hz), 7.47-7.52 (1H, m), 7.70 (1H, d, J = 6.7 Hz), 7.99 (1H, d, J = 2.4 Hz). LRMS (ESI$^+$) 425 [M + H]$^+$. |

TABLE 151

| Example No. | Chemical Structural Formula | Spectrum Data |
|---|---|---|
| 8-163 | 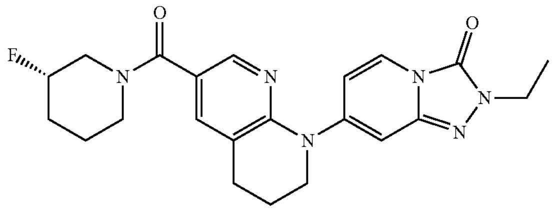 [SMILES: CCn1nc2cc(N3CCCc4cc(C(=O)N5CCC[C@H](F)C5)cnc43)ccn2c1=O] | $^1$H NMR (400 MHz, DMSO-$d_6$) δ 1.29 (3H, t, J = 7.3 Hz), 1.45-1.94 (4H, m), 1.96-2.08 (2H, m), 2.83 (2H, t, J = 6.4 Hz), 3.02-3.27 (1H, m), 3.42-3.60 (1H, m), 3.66-4.13 (6H, m), 4.66-4.88 (1H, m), 6.77 (1H, dd, J = 7.6, 2.1 Hz), 6.92 (1H, d, J = 1.8 Hz), 7.47-7.52 (1H, m), 7.70 (1H, d, J = 7.3 Hz), 7.99 (1H, d, J = 2.4 Hz). LRMS (ESI$^+$) 425 [M + H]$^+$. |
| 8-164 | 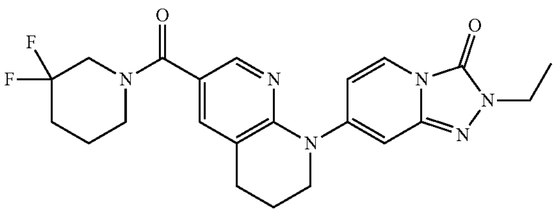 [SMILES: CCn1nc2cc(N3CCCc4cc(C(=O)N5CCCC(F)(F)C5)cnc43)ccn2c1=O] | $^1$H NMR (400 MHz, DMSO-$d_6$) δ 1.29 (3H, t, J = 7.3 Hz), 1.63-1.78 (2H, m), 1.94-2.20 (4H, m), 2.84 (2H, t, J = 6.4 Hz), 3.46-3.61 (2H, m), 3.72-3.95 (6H, m), 6.78 (1H, dd, J = 7.3, 1.8 Hz), 6.93-6.96 (1H, m), 7.48-7.53 (1H, m), 7.70 (1H, d, J = 7.3 Hz), 8.00 (1H, d, J = 1.8 Hz). LRMS (ESI$^+$) 443 [M + H]$^+$. |
| 8-165 | 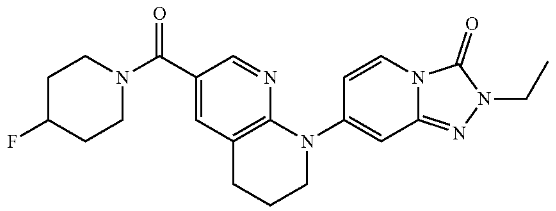 [SMILES: CCn1nc2cc(N3CCCc4cc(C(=O)N5CCC(F)CC5)cnc43)ccn2c1=O] | $^1$H NMR (400 MHz, DMSO-$d_6$) δ 1.29 (3H, t, J = 7.3 Hz), 1.63-2.06 (6H, m), 2.83 (2H, t, J = 6.4 Hz), 3.39-3.69 (4H, m), 3.80 (2H, t, J = 5.8 Hz), 3.88 (2H, q, J = 7.3 Hz), 4.80-5.03 (1H, m), 6.77 (1H, dd, J = 7.6, 2.1 Hz), 6.92 (1H, d, J = 1.2 Hz), 7.50-7.55 (1H, m), 7.70 (1H, d, J = 8.5 Hz), 8.03 (1H, d, J = 2.4 Hz). LRMS (ESI$^+$) 425 [M + H]$^+$. |

TABLE 151-continued

| Example No. | Chemical Structural Formula | Spectrum Data |
|---|---|---|
| 8-166 | 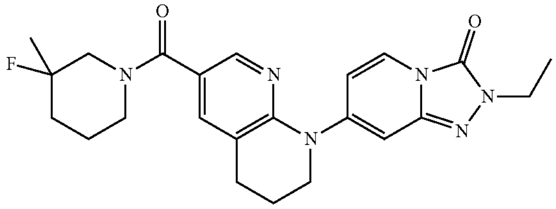 [SMILES: CCn1nc2cc(N3CCCc4cc(C(=O)N5CCCC(C)(F)C5)cnc43)ccn2c1=O] | $^1$H NMR (400 MHz, DMSO-$d_6$) δ 1.02-1.42 (6H, m), 1.49-1.78 (3H, m), 1.82-2.08 (3H, m), 2.64-3.28 (4H, m), 4.88-5.21 (6H, m), 6.78 (1H, dd, J = 7.6, 2.1 Hz), 6.90-6.95 (1H, m), 7.46-7.52 (1H, m), 7.69 (1H, d, J = 6.7 Hz), 7.98 (1H, d, J = 2.4 Hz).<br>LRMS (ESI$^+$) 439 [M + H]$^+$. |
| 8-167 | 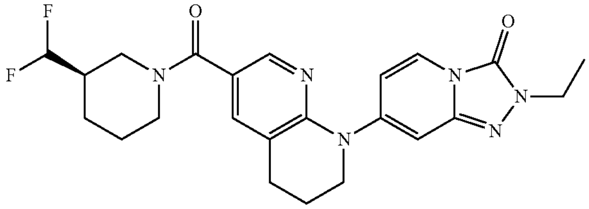 [SMILES: CCn1nc2cc(N3CCCc4cc(C(=O)N5CCC[C@@H](C(F)F)C5)cnc43)ccn2c1=O] | $^1$H NMR (400 MHz, DMSO-$d_6$) δ 1.29 (3H, t, J = 7.0 Hz), 1.37-1.54 (2H, m), 1.60-1.91 (2H, m), 1.95-2.21 (3H, m), 2.73-3.22 (4H, m), 3.53-5.30 (6H, m), 5.83-6.21 (1H, m), 6.77 (1H, dd, J = 7.9, 1.8 Hz), 6.92 (1H, d, J = 1.8 Hz), 7.52 (1H, d, J = 2.4 Hz), 7.70 (1H, d, J = 8.5 Hz), 8.02 (1H, d, J = 2.4 Hz).<br>LRMS (ESI$^+$) 457 [M + H]$^+$. |
| 8-168 | 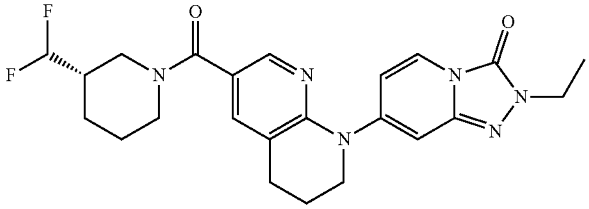 [SMILES: CCn1nc2cc(N3CCCc4cc(C(=O)N5CCC[C@H](C(F)F)C5)cnc43)ccn2c1=O] | $^1$H NMR (400 MHz, DMSO-$d_6$) δ 1.29 (3H, t, J = 7.0 Hz), 1.38-1.54 (2H, m), 1.63-1.92 (2H, m), 1.94-2.22 (3H, m), 2.74-3.21 (4H, m), 3.47-5.49 (6H, m), 5.82-6.22 (1H, m), 6.77 (1H, dd, J = 7.9, 1.8 Hz), 6.93 (1H, d, J = 1.2 Hz), 7.52 (1H, d, J = 2.4 Hz), 7.70 (1H, d, J = 7.9 Hz), 8.02 (1H, d, J = 2.4 Hz).<br>LRMS (ESI$^+$) 457 [M + H]$^+$. |

TABLE 152

| Example No. | Chemical Structural Formula | Spectrum Data |
|---|---|---|
| 8-169 | 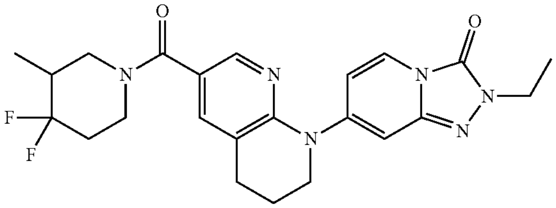 [SMILES: CCn1nc2cc(N3CCCc4cc(C(=O)N5CCC(F)(F)C(C)C5)cnc43)ccn2c1=O] | $^1$H NMR (400 MHz, DMSO-$d_6$) δ 0.84-1.05 (3H, m), 1.29 (3H, t, J = 7.3 Hz), 1.85-2.27 (5H, m), 2.84 (2H, t, J = 6.4 Hz), 2.90-3.07 (1H, m), 3.16-3.31 (1H, m), 3.64-4.29 (6H, m), 6.77 (1H, dd, J = 7.9, 1.8 Hz), 6.94 (1H, d, J = 1.2 Hz), 7.53-7.58 (1H, m), 7.70 (1H, d, J = 7.9 Hz), 8.06 (1H, d, J = 1.8 Hz).<br>LRMS (ESI$^+$) 457 [M + H]$^+$. |
| 8-170 | 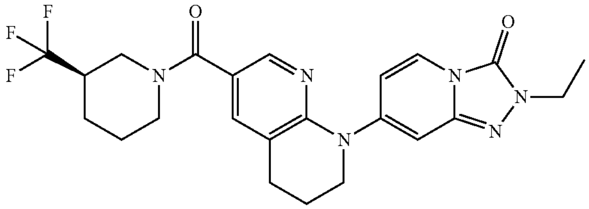 [SMILES: CCn1nc2cc(N3CCCc4cc(C(=O)N5CCC[C@@H](C(F)(F)F)C5)cnc43)ccn2c1=O] | $^1$H NMR (400 MHz, DMSO-$d_6$) δ 1.29 (3H, t, J = 7.0 Hz), 1.40-1.79 (3H, m), 1.93-2.06 (3H, m), 2.56-2.70 (1H, m), 2.77-3.20 (4H, m), 3.45-4.65 (6H, m), 6.76 (1H, dd, J = 7.6, 2.1 Hz), 6.93 (1H, d, J = 1.2 Hz), 7.50-7.54 (1H, m), 7.70 (1H, d, J = 7.3 Hz), 8.03 (1H, d, J = 1.8 Hz).<br>LRMS (ESI$^+$) 475 [M + H]$^+$. |
| 8-171 | 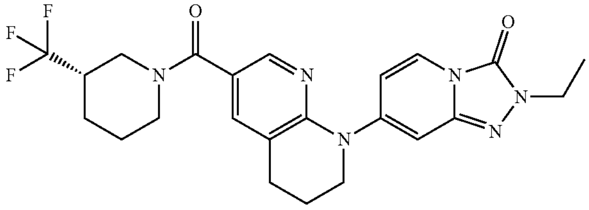 [SMILES: CCn1nc2cc(N3CCCc4cc(C(=O)N5CCC[C@H](C(F)(F)F)C5)cnc43)ccn2c1=O] | $^1$H NMR (400 MHz, DMSO-$d_6$) δ 1.29 (3H, t, J = 7.3 Hz), 1.39-1.81 (3H, m), 1.89-2.09 (3H, m), 2.57-2.71 (1H, m), 2.74-3.20 (4H, m), 3.45-4.70 (6H, m), 6.76 (1H, dd, J = 7.3, 1.8 Hz), 6.93 (1H, d, J = 1.2 Hz), 7.49-7.55 (1H, m), 7.70 (1H, d, J = 7.9 Hz), 8.03 (1H, d, J = 2.4 Hz).<br>LRMS (ESI$^+$) 475 [M + H]$^+$. |

TABLE 152-continued

| Example No. | Chemical Structural Formula | Spectrum Data |
|---|---|---|
| 8-172 | 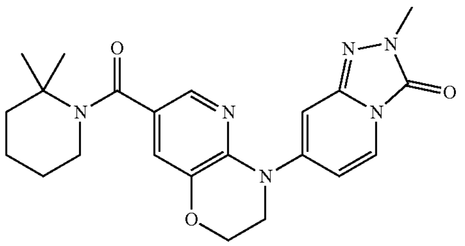 [SMILES: Cn1nc2cc(N3CCOc4cc(C(=O)N5CCCCC5(C)C)cnc43)ccn2c1=O] | $^1$H NMR (400 MHz, $CDCl_3$) δ 1.53 (6H, s), 1.61-1.69 (6H, m), 3.33 (2H, t, J = 5.4 Hz), 3.64 (3H, s), 3.89 (2H, t, J = 4.5 Hz), 4.39 (2H, t, J = 4.5 Hz), 6.63 (1H, d, J = 1.8 Hz), Hz), 6.97 (1H, dd, J = 7.6, 2.1 Hz), 7.30 (1H, d, J = 2.4 Hz), 7.68 Hz), (1H, d, J = 7.9 Hz), 7.94 (1H, d, J = 2.4 Hz). LRMS (ESI$^+$) 423 [M + H]$^+$. |
| 8-173 | 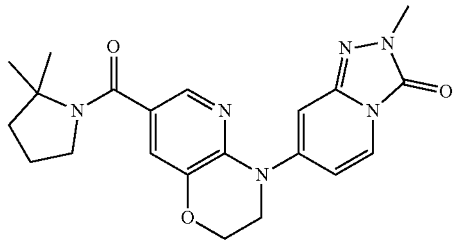 [SMILES: Cn1nc2cc(N3CCOc4cc(C(=O)N5CCCC5(C)C)cnc43)ccn2c1=O] | $^1$H NMR (400 MHz, $CDCl_3$) δ 1.57 (6H, s), 1.80-1.89 (4H, m), 3.47-3.54 (2H, m), 3.64 (3H, s), 3.89 (2H, t, J = 4.6 Hz), 4.39 (2H, t, J = 4.6 Hz), 6.62 (1H, d, J = 1.8 Hz), 6.98 (1H, dd, J = 7.9, 1.8 Hz), 7.29 (1H, s), 7.67 (1H, d, J = 7.9 Hz), 7.94 (1H, d, J = 1.8 Hz). LRMS (ESI$^+$): 409 [M + H]$^+$. |
| 8-174 | 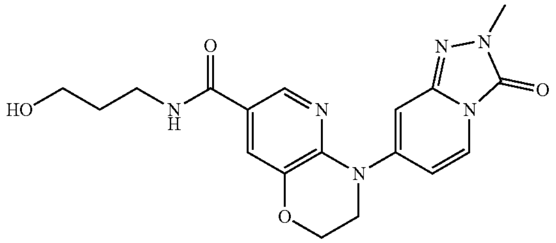 [SMILES: Cn1nc2cc(N3CCOc4cc(C(=O)NCCCO)cnc43)ccn2c1=O] | $^1$H NMR (400 MHz, $CDCl_3$) δ 1.78-1.84 (2H, m), 2.78 (1H, s), 3.61-3.67 (5H, m), 3.72-3.79 (2H, m), 3.91 (2H, t, J = 4.6 Hz), 4.41 (2H, t, J = 4.6 Hz), 6.61 (1H, t, J = 5.5 Hz), 6.67 (1H, d, J = 1.8 Hz), 6.95 (1H, dd, J = 7.3, 1.8 Hz), 7.59 (1H, d, J = 1.8 Hz), 7.68 (1H, d, J = 7.3 Hz), 8.19 (1H, d, J = 1.8 Hz). LRMS (ESI$^+$): 385 [M + H]$^+$. |

TABLE 153

| Example No. | Chemical Structural Formula | Spectrum Data |
|---|---|---|
| 8-175 | 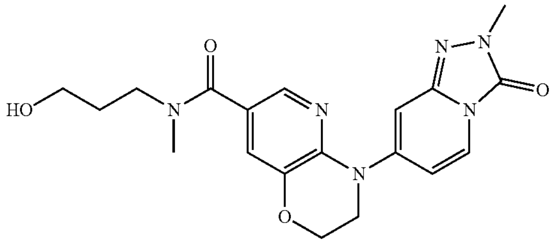 [SMILES: CN(CCCO)C(=O)c1cnc2c(c1)OCCN2c1ccn2c(=O)n(C)nc2c1] | $^1$H NMR (400 MHz, $CDCl_3$) δ 1.80-1.86 (2H, m), 3.06 (3H, s), 3.57-3.62 (2H, m), 3.65 (3H, s), 3.67-3.74 (2H, m), 3.75-3.83 (1H, m), 3.91 (2H, t, J = 4.6 Hz), 4.41 (2H, t, J = 4.6 Hz), 6.65 (1H, s), 6.97 (1H, dd, J = 7.9, 2.1 Hz), 7.29 (1H, s), 7.69 (1H, d, J = 7.9 Hz), 7.93 (1H, s). LRMS (ESI$^+$): 399 [M + H]$^+$. |
| 8-176 | 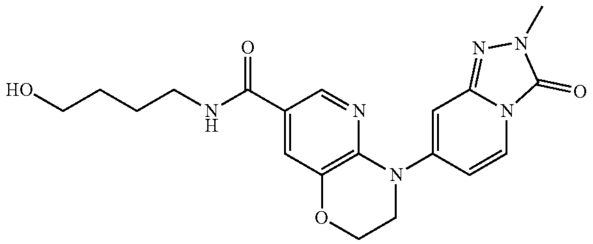 [SMILES: Cn1nc2cc(N3CCOc4cc(C(=O)NCCCCO)cnc43)ccn2c1=O] | $^1$H NMR (400 MHz, $CDCl_3$) δ 1.64-1.76 (5H, m), 3.50 (2H, q, J = 6.3 Hz), 3.65 (3H, s), 3.74 (2H, q, J = 5.1 Hz), 3.91 (2H, t, J = 4.3 Hz), 4.41 (2H, t, J = 4.3 Hz), 6.53 (1H, s), 6.66 (1H, d, J = 3.1 Hz), 6.96 (1H, dd, J = 7.9, 1.8 Hz), 7.60 (1H, d, J = 1.8 Hz), 7.68 (1H, dd, J = 7.9, 1.2 Hz), 8.20 (1H, d, J = 1.8 Hz). LRMS (ESI$^+$): 399 [M + H]$^+$. |

TABLE 153-continued

| Example No. | Chemical Structural Formula | Spectrum Data |
|---|---|---|
| 8-177 | 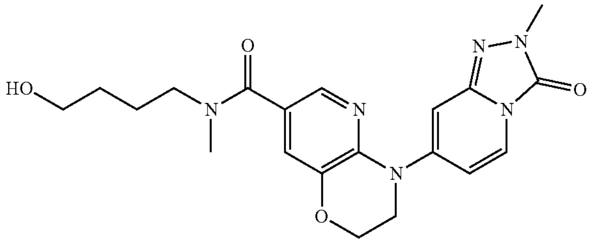 [SMILES: CN(CCCCO)C(=O)c1cnc2c(c1)OCCN2c1ccn2c(=O)n(C)nc2c1] | $^1$H NMR (400 MHz, $CDCl_3$) δ 1.30-1.86 (5H, m), 3.06 (3H, 3.35-3.72 (7H, m), 3.90 (2H, t, J = 4.6 Hz), 4.41 (2H, t, J = 4.6 Hz), 6.64 (1H, d, J = 1.8 Hz), 6.97 (1H, dd, J = 7.9, 1.8 Hz), 7.26 (1H, m), 7.68 (1H, d, J = 7.9 Hz), 7.90 (1H, s). LRMS (ESI$^+$): 413 [M + H]$^+$. |
| 8-178 | 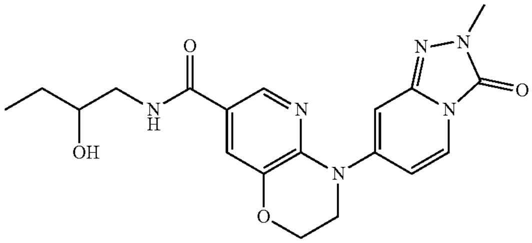 [SMILES: CCC(O)CNC(=O)c1cnc2c(c1)OCCN2c1ccn2c(=O)n(C)nc2c1] | $^1$H NMR (400 MHz, $CDCl_3$) δ 1.00 (3H, t, J = 7.3 Hz), 1.50-1.55 (1H, m), 1.58-1.61 (1H, m), 2.33 (1H, d, J = 4.3 Hz), 3.27-3.33 (1H, m), 3.65 (3H, s), 3.69-3.79 (2H, m), 3.91 (2H, t, J = 4.3 Hz), 4.41 (2H, t, J = 4.3 Hz), 6.49 (1H, s), 6.66 (1H, d, J = 1.2 Hz), 6.96 (1H, dd, J = 7.6, 2.1 Hz), 7.59 (1H, d, J = 2.4 Hz), 7.68 (1H, d, J = 6.7 Hz), 8.22 (1H, d, J = 1.8 Hz). LRMS (ESI$^+$): 399 [M + H]$^+$. |
| 8-179 | 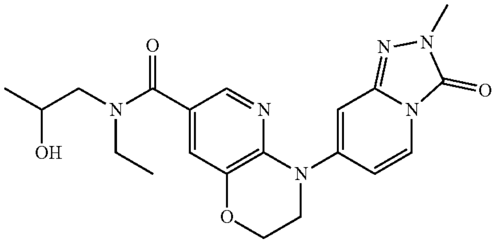 [SMILES: CCN(CC(C)O)C(=O)c1cnc2c(c1)OCCN2c1ccn2c(=O)n(C)nc2c1] | $^1$H NMR (400 MHz, $CDCl_3$) δ 1.19-1.28 (6H, m), 3.29 (1H, d, J = 13.9 Hz), 3.40-3.52 (2H, m), 3.64 (3H, s), 3.68-3.86 (2H, m), 3.91 (2H, t, J = 4.2 Hz), 4.06-4.18 (1H, m), 4.41 (2H, t, J = 4.2 Hz), 6.65 (1H, d, J = 1.8 Hz), 6.97 (1H, dd, J = 7.6, 2.1 Hz), 7.28 (1H, d, J = 1.8 Hz), 7.69 (1H, d, J = 7.9 Hz), 7.92 (1H, d, J = 2.4 Hz). LRMS (ESI$^+$): 413 [M + H]$^+$. |

TABLE 154

| Example No. | Chemical Structural Formula | Spectrum Data |
|---|---|---|
| 8-180 | 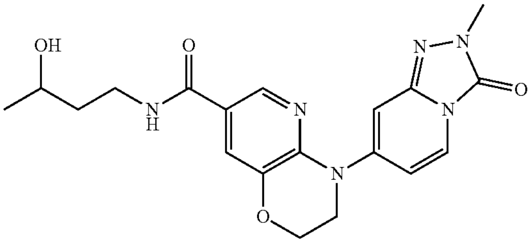 [SMILES: CC(O)CCNC(=O)c1cnc2c(c1)OCCN2c1ccn2c(=O)n(C)nc2c1] | $^1$H NMR (400 MHz, $CDCl_3$) δ 1.26 (3H, d, J = 6.1 Hz), 1.60-1.67 (1H, m), 1.73-1.80 (1H, m), 2.67 (1H, d, J = 3.0 Hz), 3.31-3.39 (1H, m), 3.64 (3H, s), 3.84-3.99 (4H, m), 4.41 (2 H, t, J = 4.5 Hz), 6.66 (1H, d, J = 1.2 Hz), 6.78 (1H, s), 6.95 (1H, dd, J = 7.6, 2.1 Hz), 7.59 (1H, d, J = 1.8 Hz), 7.68 (1H, d, J = 8.5 Hz), 8.19 (1H, d, J = 1.8 Hz). LRMS (ESI$^+$): 399 [M + H]$^+$. |
| 8-181 | 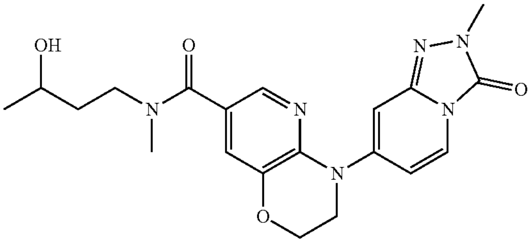 [SMILES: CC(O)CCN(C)C(=O)c1cnc2c(c1)OCCN2c1ccn2c(=O)n(C)nc2c1] | $^1$H NMR (400 MHz, $CDCl_3$) δ 1.24 (3H, d, J = 6.1 Hz), 1.50-1.88 (2H, m), 3.06 (3H, s), 3.08-3.19 (1H, m), 3.65 (3H, s), 3.69-3.78 (1H, m), 3.91 (2H, t, J = 4.3 Hz), 4.08 (1H, s), 4.17-4.29 (1H, m), 4.41 (2H, t, J = 4.3 Hz), 6.65 (1H, d, J = 1.8 Hz), 6.97 (1H, dd, J = 7.6, 2.1 Hz), 7.28 (1H, s), 7.68 (1H, d, J = 7.9 Hz), 7.93 (1H, d, J = 1.8 Hz). LRMS (ESI$^+$): 413 [M + H]$^+$. |

TABLE 154-continued

| Example No. | Chemical Structural Formula | Spectrum Data |
|---|---|---|
| 8-182 | 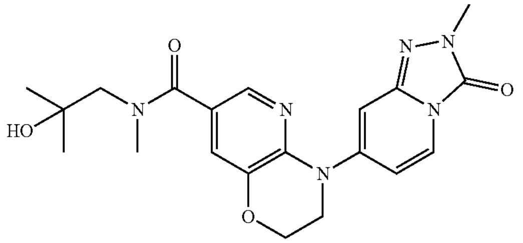 [SMILES: CN(CC(C)(C)O)C(=O)c1cnc2c(c1)OCCN2c1ccn2c(=O)n(C)nc2c1] | $^1$H NMR (400 MHz, $CDCl_3$) δ 1.30 (6H, s), 3.19 (3H, s), 3.59 (2H, s), 3.65 (3H, s), 3.91 (3H, t, J = 4.3 Hz), 4.42 (2H, t, J = 4.3 Hz), 6.65 (1H, d, J = 1.8 Hz), 6.97 (1H, dd, J = 8.6, 1.8 Hz), 7.31 (1H, s), 7.69 (1H, d, J = 8.6 Hz), 7.96 (1H, s). LRMS (ESI$^+$): 413 [M + H]$^+$. |
| 8-183 | 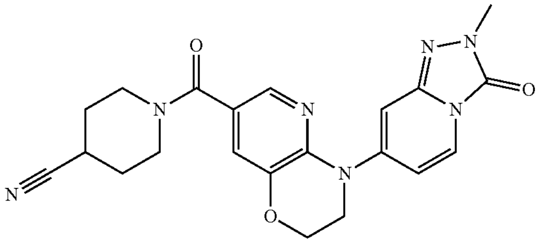 [SMILES: Cn1nc2cc(N3CCOc4cc(C(=O)N5CCC(C#N)CC5)cnc43)ccn2c1=O] | $^1$H NMR (400 MHz, $CDCl_3$) δ 1.85-2.03 (4H, m), 2.92-3.00 (1H, m), 3.55-3.86 (7H, m), 3.91 (2H, t, J = 4.9 Hz), 4.42 (2 H, dd, J = 4.9, 3.7 Hz), 6.66 (1H, d, J = 1.8 Hz), 6.95 (1H, dd, J = 7.6, 2.1 Hz), 7.25 (1H, d, J = 2.4 Hz), 7.69 (1H, d, J = 8.6 Hz), 7.88 (1H, d, J = 1.8 Hz). LRMS (ESI$^+$): 420 [M + H]$^+$. |
| 8-184 | 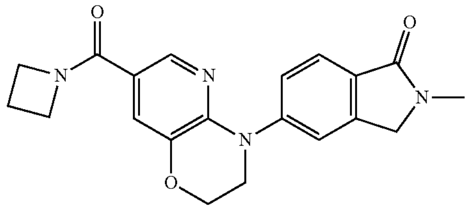 [SMILES: CN1Cc2cc(N3CCOc4cc(C(=O)N5CCC5)cnc43)ccc2C1=O] | $^1$H NMR (400 MHz, DMSO-$d_6$) δ 2.17-2.28 (2H, m), 3.06 (3H, s), 3.92-4.05 (4H, m), 4.25-4.39 (4H, m), 4.44 (2H, s), 7.31 (1H, d, J = 1.8 Hz), 7.51 (1H, dd, J = 8.5, 1.8 Hz), 7.60-7.66 (2H, m), 7.92 (1H, d, J = 1.8 Hz). LRMS (ESI$^+$) 365 [M + H]$^+$. |
| 8-185 | 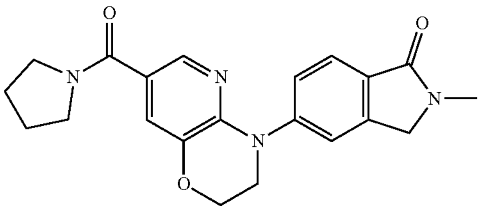 [SMILES: CN1Cc2cc(N3CCOc4cc(C(=O)N5CCCC5)cnc43)ccc2C1=O] | $^1$H NMR (400 MHz, DMSO-$d_6$) δ 1.73-1.91 (4H, m), 3.06 (3H, s), 3.37-3.55 (4H, m), 3.96 (2H, t, J = 4.5 Hz), 4.35 (2H, t, J = 4.2 Hz), 4.44 (2H, s), 7.29 (1H, d, J = 1.8 Hz), 7.51 (1H, dd, J = 7.9, 1.8 Hz), 7.60-7.65 (2H, m), 7.87 (1H, d, J = 1.8 Hz). LRMS (ESI$^+$) 379 [M + H]$^+$. |

TABLE 155

| Example No. | Chemical Structural Formula | Spectrum Data |
|---|---|---|
| 8-186 | 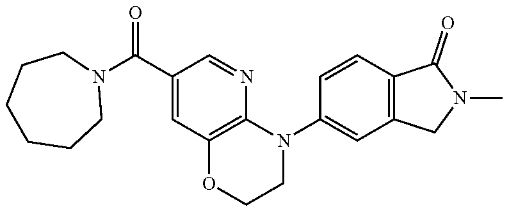 [SMILES: CN1Cc2cc(N3CCOc4cc(C(=O)N5CCCCCC5)cnc43)ccc2C1=O] | $^1$H NMR (400 MHz, DMSO-$d_6$) δ 1.40-1.76 (8H, m), 3.05 (3H, s), 3.34-3.56 (4H, m), 3.95 (2H, t, J = 4.6 Hz), 4.35 (2H, t, J = 4.3 Hz), 4.43 (2H, s), 7.16 (1H, d, J = 2.4 Hz), 7.51 (1H, dd, J = 7.9, 1.8 Hz), 7.59-7.65 (2H, m), 7.68 (1H, d, J = 2.4 Hz). LRMS (ESI$^+$) 407 [M + H]$^+$. |
| 8-187 | 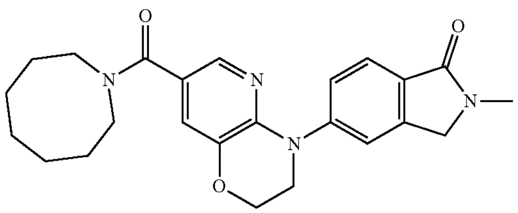 [SMILES: CN1Cc2cc(N3CCOc4cc(C(=O)N5CCCCCCC5)cnc43)ccc2C1=O] | $^1$H NMR (400 MHz, DMSO-$d_6$) δ 1.42-1.79 (10H, m), 3.06 (3H, s), 3.27-3.55 (4H, m), 3.96 (2H, t, J = 4.3 Hz), 4.35 (2H, t, J = 4.3 Hz), 4.43 (2H, s), 7.13 (1H, d, J = 2.4 Hz), 7.51 (1H, dd, J = 8.3, 2.1 Hz), 7.59-7.65 (2H, m), 7.67 (1H, d, J = 1.8 Hz). LRMS (ESI$^+$) 421 [M + H]$^+$. |

TABLE 155-continued

| Example No. | Chemical Structural Formula | Spectrum Data |
|---|---|---|
| 8-188 | 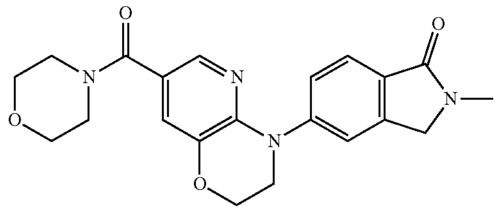 [SMILES: CN1Cc2cc(N3CCOc4cc(C(=O)N5CCOCC5)cnc43)ccc2C1=O] | $^1$H NMR (400 MHz, DMSO-$d_6$) δ 3.06 (3H, s), 3.40-3.65 (8H, m), 3.96 (2H, t, J = 4.2 Hz), 4.35 (2H, t, J = 4.2 Hz), 4.43 (2H, s), 7.20 (1H, d, J = 1.8 Hz), 7.51 (1H, dd, J = 8.5, 1.8 Hz), 7.59-7.65 (2H, m), 7.73 (1H, d, J = 1.8 Hz). LRMS (ESI$^+$) 395 [M + H]$^+$. |
| 8-189 | 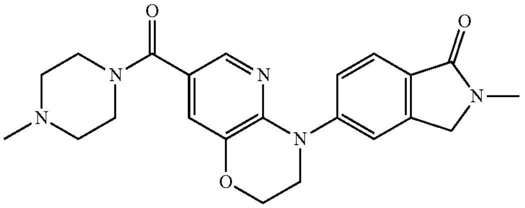 | $^1$H NMR (400 MHz, DMSO-$d_6$) δ 2.17 (3H, s), 2.24-2.34 (4H, m), 3.06 (3H, s), 3.41-3.56 (4H, m), 3.96 (2H, t, J = 4.6 Hz), 4.35 (2H, t, J = 4.3 Hz), 4.44 (2H, s), 7.16 (1H, d, J = 1.8 Hz), 7.51 (1H, dd, J = 8.6, 1.8 Hz), 7.60-7.65 (2H, m), 7.70 (1H, d, J = 1.8 Hz). LRMS (ESI$^+$) 408 [M + H]$^+$. |
| 8-190 | 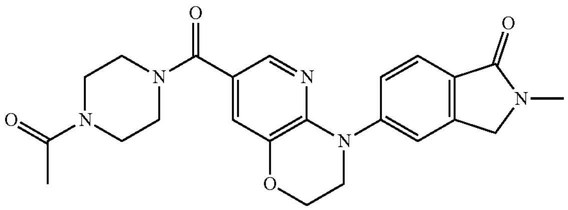 [SMILES: CC(=O)N1CCN(C(=O)c2cnc3c(c2)OCCN3c2ccc3c(c2)CN(C)C3=O)CC1] | $^1$H NMR (400 MHz, DMSO-$d_6$) δ 2.01 (3H, s), 3.06 (3H, s), 3.39-3.59 (8H, m), 3.97 (2H, t, J = 4.3 Hz), 4.36 (2H, t, J = 4.3 Hz), 4.44 (2H, s), 7.21 (1H, d, J = 1.8 Hz), 7.52 (1H, dcl, J = 8.6, 1.8 Hz), 7.60-7.66 (2H, m), 7.75 (1H, d, J = 2.4 Hz). LRMS (ESI$^+$) 436 [M + H]$^+$. |
| 8-191 | 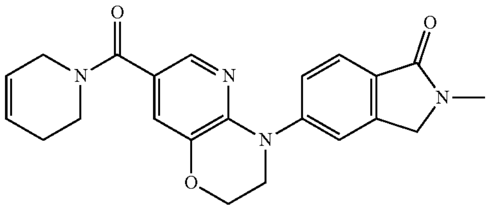 [SMILES: CN1Cc2cc(N3CCOc4cc(C(=O)N5CC=CCC5)cnc43)ccc2C1=O] | $^1$H NMR (400 MHz, DMSO-$d_6$) δ 2.07-2.20 (2H, m), 3.06 (3H, s), 3.41-3.68 (2H, m), 3.90-4.07(4H, m), 4.36 (2H, t, J = 4.3 Hz), 4.44 (2H, s), 5.59-5.77 (1H, m), 5.79-5.89 (1H, m), 7.19 (1H, d, J = 1.8 Hz), 7.52 (1H, dd, J = 8.6, 1.8 Hz), 7.60-7.66 (2H, m), 7.73 (1H, d, J = 1.8 Hz). LRMS (ESI$^+$) 391 [M + H]$^+$. |

TABLE 156

| Example No. | Chemical Structural Formula | Spectrum Data |
|---|---|---|
| 8-192 | 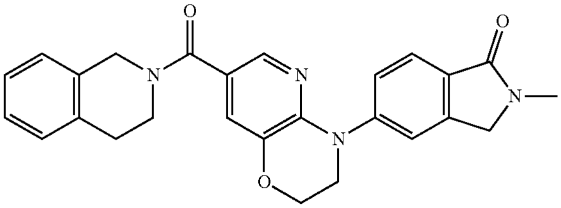 [SMILES: CN1Cc2cc(N3CCOc4cc(C(=O)N5CCc6ccccc6C5)cnc43)ccc2C1=O] | $^1$H NMR (400 MHz, DMSO-$d_6$) δ 2.85 (2H, t, J = 6.1 Hz), 3.06 (3H, s), 3.60-3.79 (2H, m), 3.98 (2H, t, J = 4.3 Hz), 4.37 (2H, t, J = 4.3 Hz), 4.44 (2H, s), 4.69 (2H, s), 7.11-7.22 (4H, m), 7.24 (1H, d, J = 2.4 Hz), 7.53 (1H, dd, J = 7.9, 1.8 Hz), 7.62-7.66 (2H, m), 7.79 (1H, d, J = 1.8 Hz). LRMS (ESI$^+$) 441 [M + H]$^+$. |
| 8-193 | 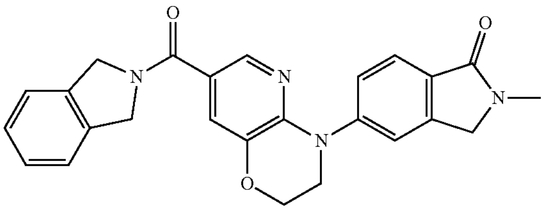 [SMILES: CN1Cc2cc(N3CCOc4cc(C(=O)N5Cc6ccccc6C5)cnc43)ccc2C1=O] | $^1$H NMR (400 MHz, DMSO-$d_6$) δ 3.06 (3H, s), 3.99 (2H, t, J = 4.6 Hz), 4.38 (2H, t, J = 4.3 Hz), 4.45 (2H, s), 4.84 (2H, s), 4.90 (2H, s), 7.25-7.32 (3H, m), 7.35-7.40 (1H, m), 7.42 (1H, d, J = 2.4 Hz), 7.54 (1H, dd, J = 7.9, 2.4 Hz), 7.62-7.67 (2H, m), 7.99 (1H, d, J = 2.4 Hz). LRMS (ESI$^+$) 427 [M + H]$^+$. |

TABLE 156-continued

| Example No. | Chemical Structural Formula | Spectrum Data |
|---|---|---|
| 8-194 | 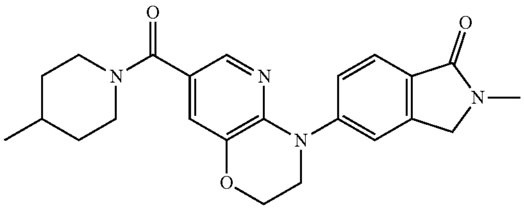 | $^1$H NMR (400 MHz, DMSO-$d_6$) δ 0.90 (3H, d, J = 6.1 Hz), 0.98-1.14 (2H, m), 1.52-1.67 (3H, m), 2.70-3.15 (5H, m), 3.54-4.61 (2H, m), 3.96 (2 H, t, J = 4.5 Hz), 4.35 (2H, t, J = 42 Hz), 4.43 (2H, s), 7.15 (1H, d, J = 1.8 Hz), 7.51 (1H, dd, J = 8.5, 1.8 Hz), 7.60-7.64 (2H, m), 7.68 (1H, d, J = 2.4 Hz). LRMS (ESI$^+$) 407 [M + H]$^+$. |
| 8-195 | 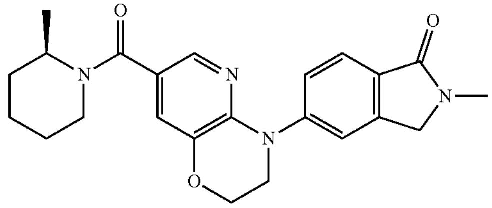 [SMILES: C[C@@H]1CCCCN1C(=O)c1cnc2c(c1)OCCN2c1ccc2c(c1)CN(C)C2=O] | $^1$H NMR (400 MHz, DMSO-$d_6$) δ 1.17 (3H, d, J = 7.3 Hz), 1.27-1.41 (1H, m), 1.42-1.69 (5H, m), 2.90-3.03 (1H, m), 3.06 (3H, s), 3.82-4.01 (3H, m), 4.29-4.46 (5H, m), 7.13 (1H, d, J = 2.4 Hz), 7.51 (1H, dd, J = 7.9, 1.8 Hz), 7.59-7.64 (2H, m), 7.66 (1H, d, J = 1.8 Hz). LRMS (ESI$^+$) 407 [M + H]$^+$. |
| 8-196 | 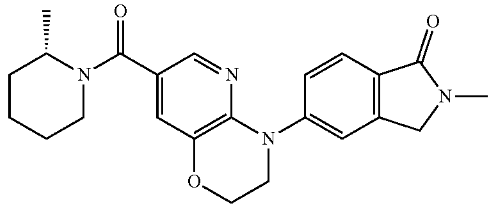 [SMILES: C[C@H]1CCCCN1C(=O)c1cnc2c(c1)OCCN2c1ccc2c(c1)CN(C)C2=O] | $^1$H NMR (400 MHz, DMSO-$d_6$) δ 1.17 (3H, d, J = 7.3 Hz), 1.27-1.42 (1H, m), 1.43-1.75 (5H, m), 2.90-3.03 (1H, m), 3.06 (3H, s), 3.72-4.05 (3H, m), 4.23-4.50 (5H, m), 7.13 (1H, d, J = 1.8 Hz), 7.51 (1H, dd, J = 8.3, 2.1 Hz), 7.59-7.64 (2H, m), 7.66 (1H, d, J = 1.8 Hz). LRMS (ESI$^+$) 407 [M + H]$^+$. |
| 8-197 | 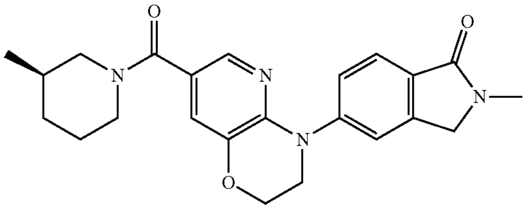 | $^1$H NMR (400 MHz, DMSO-$d_6$) δ 0.70-0.93 (3H, m), 1.06-1.20 (1H, m), 1.31-1.47 (1H, m), 1.48-1.68 (2H, m), 1.71-1.80 (1H, m), 2.36-3.01 (2H, m), 3.06 (3H, s), 3.48-3.90 (1H, m), 3.96 (2H, t, J = 4.3 Hz), 4.06-4.29 (1H, m), 4.35 (2H, t, J = 4.3 Hz), 4.44 (2H, s), 7.15 (1H, d, J = 1.8 Hz), 7.51 (1H, dd, J = 8.3, 2.1 Hz), 7.60-7.65 (2H, m), 7.68 (1H, d, J = 1.8 Hz). LRMS (ESI$^+$) 407 [M + H]$^+$. |
| 8-198 | 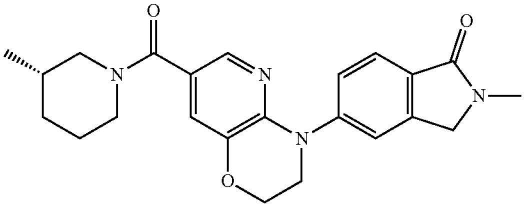 | $^1$H NMR (400 MHz, DMSO-$d_6$) δ 0.84 (3H, d, J = 6.7 Hz), 1.07-1.22 (1H, m), 1.33-1.49 (1H, m), 1.50-1.69 (2H, m), 1.71-1.85 (1H, m), 2.55-2.70 (1H, m), 2.85-2.99 (1H, m), 3.07 (3H, s), 3.80-4.04 (4H, m), 4.36 (2H, t, J = 4.3 Hz), 4.43 (2H, s), 7.13 (1H, d, J = 1.8 Hz), 7.52 (1H, dd, J = 8.3, 2.1 Hz), 7.59-7.65 (2H, m), 7.69 (1H, d, J = 1.8 Hz). LRMS (ESI$^+$) 407 [M + H]$^+$. |

TABLE 157

| Example No. | Chemical Structural Formula | Spectrum Data |
|---|---|---|
| 8-199 | 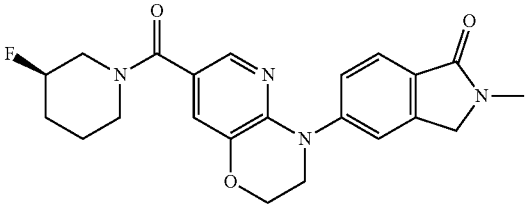 [SMILES: CN1Cc2cc(N3CCOc4cc(C(=O)N5CCC[C@@H](F)C5)cnc43)ccc2C1=O] | $^1$H NMR (400 MHz, DMSO-$d_6$) δ 1.42-1.96 (4H, m), 2.93-3.25 (4H, m), 3.41-3.57 (1H, m), 3.71-4.06 (4H, m), 4.36 (2H, t, J = 4.6 Hz), 4.44 (2H, s), 4.64-487 (1H, m), 7.14 (1H, d, J = 1.8 Hz), 7.51 (1H, dd, J = 7.9, 1.8 Hz), 7.59-7.65 (2H, m), 7.69 (1H, d, J = 1.8 Hz). LRMS (ESI$^+$) 411 [M + H]$^+$. |

TABLE 157-continued

| Example No. | Chemical Structural Formula | Spectrum Data |
|---|---|---|
| 8-200 | 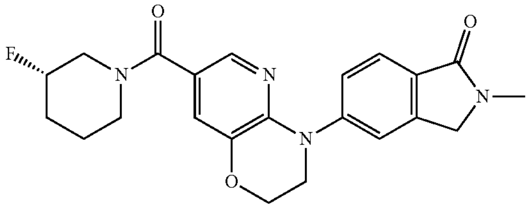 [SMILES: CN1Cc2cc(N3CCOc4cc(C(=O)N5CCC[C@H](F)C5)cnc43)ccc2C1=O] | $^1$H NMR (400 MHz, DMSO-$d_6$) δ 1.38-1.96 (4H, m), 2.97-3.24 (4H, m), 3.40-3.58 (1H, m), 3.74-4.05 (4H, m), 4.36 (2H, t, J = 4.3 Hz), 4.44 (2H, s), 4.654.85 (1H, m), 7.14 (1H, d, J = 1.8 Hz), 7.51 (1H, dd, J = 7.9, 1.8 Hz), 7.60-7.65 (2H, m), 7.69 (1H, d, J = 1.8 Hz). LRMS (ESI$^+$) 411 [M + H]$^+$. |
| 8-201 | 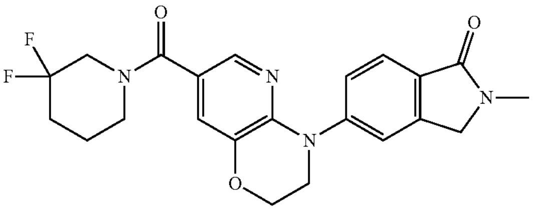 | $^1$H NMR (400 MHz, DMSO-$d_6$) δ 1.61-1.73 (2H, m), 2.00-2.16 (2H, m), 3.06 (3H, s), 3.41-3.59 (2H, m), 3.73-3.89 (2H, m), 3.97 (2H, t, J = 4.3 Hz), 4.36 (2H, t, J = 4.3 Hz), 4.44 (2H, s), 7.15 (1H, d, J = 1.8 Hz), 7.52 (1H, dd, J = 8.3, 2.1 1H), 7.61-7.65 (2H, m), 7.71 (1H, 4,5 = 2.4 Hz). LRMS (ESI$^+$) 429 [M + H]$^+$. |
| 8-202 | 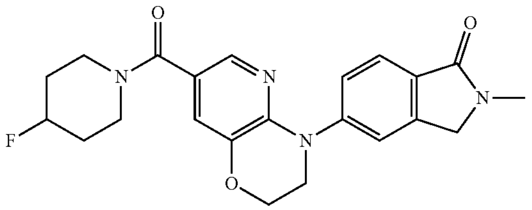 [SMILES: CN1Cc2cc(N3CCOc4cc(C(=O)N5CCC(F)CC5)cnc43)ccc2C1=O] | $^1$H NMR (400 MHz, DMSO-$d_6$) δ 1.62-1.78 (2H, m), 1.79-1.96 (2H, m), 3.06 (3H, s), 3.38-3.66 (4H, m), 3.96 (2H, t, J = 4.3 Hz), 4.36 (2H, t, J = 4.3 Hz), 4.44 (2H, s), 4.76-5.01 (1H, m), 7.19 (1H, d, J = 1.8 Hz), 7.51 (1H, dd, J = 7.9, 1.8 Hz), 7.59-7.66 (2H, m), 7.73 (1H, d, J = 1.8 Hz). LRMS (ESI$^+$) 411 [M + H]$^+$. |
| 8-203 | 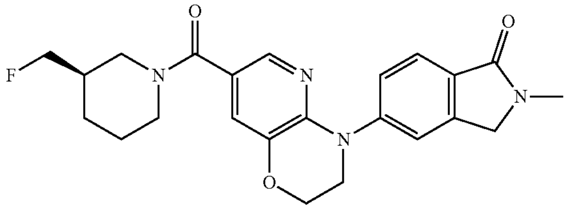 [SMILES: CN1Cc2cc(N3CCOc4cc(C(=O)N5CCC[C@@H](CF)C5)cnc43)ccc2C1=O] | $^1$H NMR (400 MHz, DMSO-$d_6$) δ 1.19-1.35 (1H, m), 1.36-1.51 (1H, m), 1.54-1.79 (2H, m), 1.81-1.99 (1H, m), 2.69-3.12 (5H, m), 3.64-4.50 (10H, m), 7.17 (1H, d, J = 1.8 Hz), 7.51 (1H, dd, J = 8.3, 2.1 Hz), 7.59-7.65 (2H, m), 7.71 (1H, d, J = 1.8 Hz). LRMS (ESI$^+$) 425 [M + H]$^+$. |
| 8-204 | 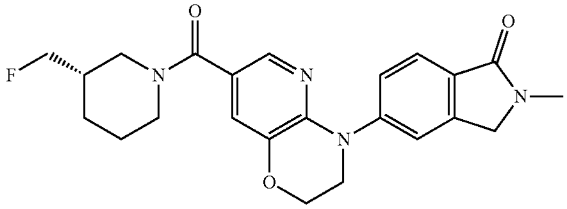 [SMILES: CN1Cc2cc(N3CCOc4cc(C(=O)N5CCC[C@H](CF)C5)cnc43)ccc2C1=O] | $^1$H NMR (400 MHz, DMSO-$d_6$) δ 120-1.36 (1H, m), 1.36-1.51 (1H, m), 1.54-1.79 (2H, m), 1.81-2.00 (1H, m), 2.68-3.11 (5H, m), 3.51-4.50 (10 H, m), 7.17 (1H, d, J = 1.8 Hz), 7.51 (1H, dd, J = 8.6, 1.8 Hz), 7.59-7.65 (2H, m), 7.71 (1H, d, J = 1.8 Hz). LRMS (ESI$^+$) 425 [M + H]$^+$. |
| 8-205 | 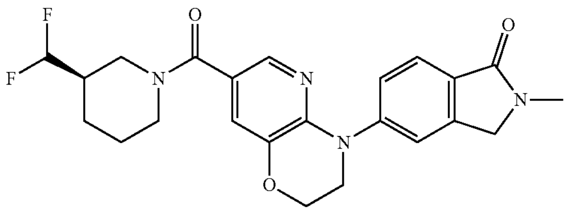 [SMILES: CN1Cc2cc(N3CCOc4cc(C(=O)N5CCC[C@@H](C(F)F)C5)cnc43)ccc2C1=O] | $^1$H NMR (400 MHz, DMSO-$d_6$) δ 1.35-1.51 (2H, m), 1.60-1.75 (1H, m), 1.77-1.92 (1H, m), 1.94-2.19 (1H, m), 2.76-3.12 (5H, m), 3.404.61 (8H, m), 5.90-6.11 (1H, m), 7.19 (1H, d, J = 2.4 Hz), 7.51 (1H, ad, J = 7.9, 1.8 Hz), 7.59-7.67 (2H, m), 7.72 (1H, d, J = 2.4 Hz). LRMS (ESI$^+$) 443 [M + H]$^+$. |

TABLE 158

| Example No. | Chemical Structural Formula | Spectrum Data |
|---|---|---|
| 8-206 | 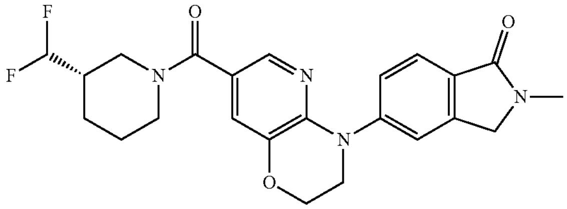 [SMILES: CN1Cc2cc(N3CCOc4cc(C(=O)N5CCC[C@H](C(F)F)C5)cnc43)ccc2C1=O] | $^1$H NMR (400 MHz, DMSO-d$_6$) δ 1.35-1.52 (2H, m), 1.60-1.75 (1H, m), 1.76-1.90 (1H, m), 1.95-2.14 (1H, m), 2.74-3.12 (5H, m), 3.57-4.49 (8H, m), 5.80-6.19 (1H, m), 7.19 (1H, d, J = 2.4 Hz), 7.51 (1H, dd, J = 7.9, 1.8 Hz), 7.59-7.66 (2H, m), 7.72 (1H, d, J = 2.4 Hz). LRMS (ESI$^+$) 443 [M + H]$^+$. |
| 8-207 | 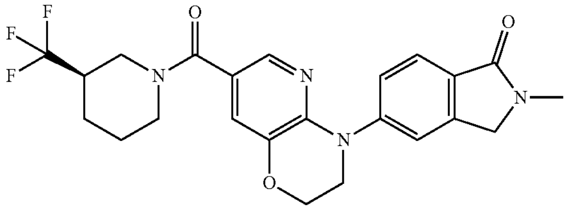 [SMILES: CN1Cc2cc(N3CCOc4cc(C(=O)N5CCC[C@@H](C(F)(F)F)C5)cnc43)ccc2C1=O] | $^1$H NMR (400 MHz, DMSO-d$_6$) δ 1.41-1.62 (2H, m), 1.63-1.77 (1H, m), 1.90-2.02 (1H, m), 2.55-2.71 (1H, m), 2.82-3.16 (5H, m), 3.68-4.04 (3H, m), 4.27-4.51 (5H, m), 7.19 (1H, d, J = 1.8 Hz), 7.52 (1H, dd, J = 8.3, 2.1 Hz), 7.60-7.65 (2H, m), 7.73 (1H, d, J = 1.8 Hz). LRMS (ESI$^+$) 461 [M + H]$^+$. |
| 8-208 | 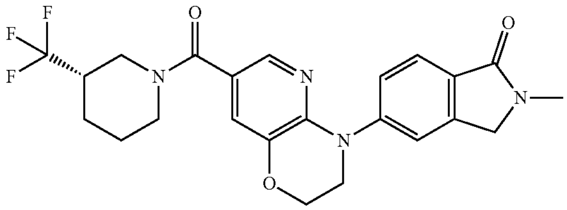 [SMILES: CN1Cc2cc(N3CCOc4cc(C(=O)N5CCC[C@H](C(F)(F)F)C5)cnc43)ccc2C1=O] | $^1$H NMR (400 MHz, DMSO-d$_6$) δ 1.40-1.63 (2H, m), 1.64-1.79 (1H, m), 1.88-2.05 (1H, m), 2.41-2.75 (1H, m), 2.86-3.25 (5H, m), 3.90-4.11 (3H, m), 4.27-4.63 (5H, m), 7.19 (1H, s), 7.52 (1H, d, J = 8.6 Hz), 7.60-7.67 (2H, m), 7.73 (1H, s). LRMS (ESI$^+$) 461 [M + H]$^+$. |
| 8-209 | 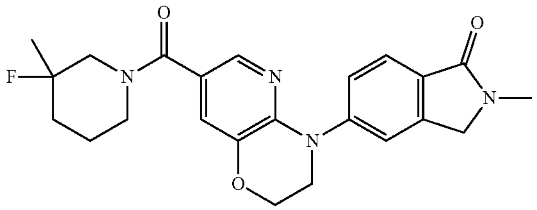 [SMILES: CN1Cc2cc(N3CCOc4cc(C(=O)N5CCCC(C)(F)C5)cnc43)ccc2C1=O] | $^1$H NMR (400 MHz, DMSO-d$_6$) δ 1.10-1.42 (3H, m), 1.47-1.78 (3H, m), 1.80-1.93 (1H, m), 2.66-3.02 (1H, m), 3.06 (3H, s), 3.08-3.30 (1H, m), 3.58-4.51 (8H, m), 7.13 (1H, d, J = 1.8 Hz), 7.52 (1H, dd, J = 7.9, 1.8 Hz), 7.60-7.65 (2H, m), 7.69 (1H, d, J = 1.8 Hz). LRMS (ESI$^+$) 425 [M + H]$^+$. |
| 8-210 | 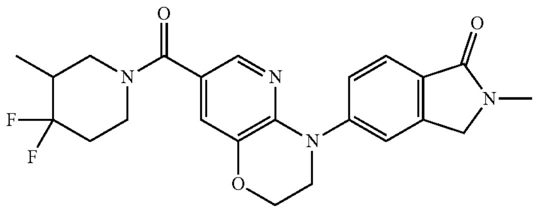 [SMILES: CC1CN(C(=O)c2cnc3c(c2)OCCN3c2ccc3c(c2)CN(C)C3=O)CCC1(F)F] | $^1$H NMR (400 MHz, DMSO-d$_6$) δ 0.92 (3H, d, J = 5.5 Hz), 1.86-2.25 (3H, m), 2.85-3.03 (1H, m), 3.06 (3H, s), 3.14-3.28 (1H, m), 3.60-4.12 (4 H, m), 4.36 (2H, t, J = 4.3 Hz), 4.44 (2H, s), 7.23 (1H, d, J = 1.8 Hz), 7.52 (1H, (Id, J = 8.3, 2.1 Hz), 7.59-7.67 (2H, m), 7.76 (1H, d, J = 1.8 Hz) LRMS (ESI$^+$) 443 [M + H]$^+$. |
| 8-211 | 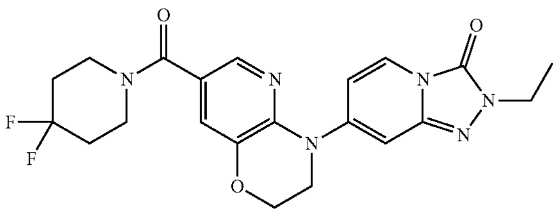 [SMILES: CCn1nc2cc(N3CCOc4cc(C(=O)N5CCC(F)(F)CC5)cnc43)ccn2c1=O] | $^1$H NMR (400 MHz, DMSO-d$_6$) δ 1.28 (3H, t, J = 7.0 Hz), 1.95-2.10 (4H, m), 3.58 (4H, s), 3.88 (2H, q, J = 7.1 Hz), 3.94 (2H, t, J = 4.3 Hz), 4.37 (2H, t, J = 4.6 Hz), 6.92 (1H, d, J = 1.2 Hz), 6.97 (1H, dd, J = 7.6, 2.1 Hz), 7.30 (1H, d, J = 1.8 Hz), 7.76 (1H, d, J = 8.6 Hz), 7.85 (1H, d, J = 1.8 Hz). LRMS (ESI$^+$) 445 [M + H]$^+$. |

TABLE 159

| Example No. | Chemical Structural Formula | Spectrum Data |
|---|---|---|
| 8-212 | 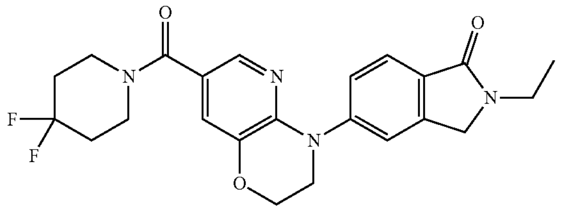 | $^1$H NMR (400 MHz, DMSO-$d_6$) δ 1.16 (3H, t, J = 7.3 Hz), 1.95-2.09 (4H, m), 3.46-3.68 (6H, m), 3.96 (2H, t, J = 4.3 Hz), 4.36 (2H, t, J = 4.3 Hz), 4.45 (2H, s), 7.24 (1H, d, J = 1.8 Hz), 7.51 (1H, dd, J = 8.3, 2.1 Hz), 7.60-7.66 (2H, m), 7.76 (1H, d, J = 1.8 Hz).<br>LRMS (ESI$^+$) 443 [M + H]$^+$. |
| 8-213 | 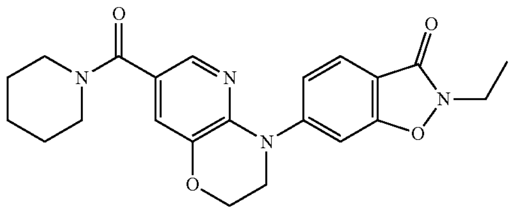 [SMILES: CCn1oc2cc(N3CCOc4cc(C(=O)N5CCCCC5)cnc43)ccc2c1=O] | $^1$H NMR (400 MHz, DMSO-$d_6$) δ 1.25 (3H, t, J = 7.0 Hz), 1.39-1.67 (6H, m), 3.44 (4H, s), 3.93-4.03 (4H, m), 4.36 (2H, t, J = 4.6 Hz), 7.20 (1H, d, J = 1.8 Hz), 7.44 (1H, dd, J = 8.6, 1.8 Hz), 7.52 (1H, d, J = 1.2 Hz), 7.70 (1H, d, J = 8.6 Hz), 7.74 (1H, d, J = 1.8 Hz).<br>LRMS (ESI$^+$) 409 [M + H]$^+$. |
| 8-214 | 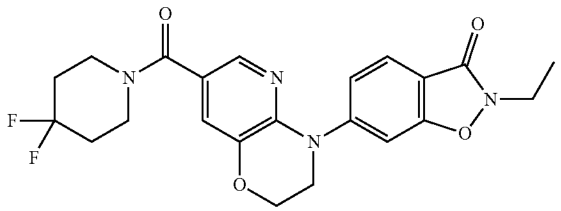 [SMILES: CCn1oc2cc(N3CCOc4cc(C(=O)N5CCC(F)(F)CC5)cnc43)ccc2c1=O] | $^1$H NMR (400 MHz, DMSO-$d_6$) δ 1.25 (3H, t, J = 7.0 Hz), 1.95-2.10 (4H, m), 3.50-3.66 (4H, m), 3.92-4.05 (4H, m), 4.37 (2H, t, J = 4.3 Hz), 7.28 (1H, d, J = 1.8 Hz), 7.45 (1H, d d, J = 8.6, 1.8 Hz), 7.52 (1H, d, J = 1.2 Hz), 7.71 (1H, d, J = 8.6 Hz), 7.82 (1H, d, J = 1.8 Hz).<br>LRMS (ESI$^+$) 445 [M + H]$^+$. |
| 8-215 | 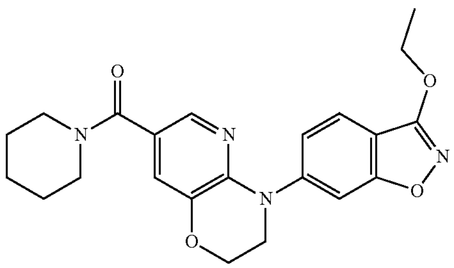 [SMILES: CCOc1noc2cc(N3CCOc4cc(C(=O)N5CCCCC5)cnc43)ccc12] | $^1$H NMR (400 MHz, DMSO-$d_6$) δ 1.40-1.64 (9H, m), 3.35-3.52 (4H, m), 3.99 (2H, t, J = 4.3 Hz), 4.36 (2H, t, J = 4.3 Hz), 4.44 (2H, q, J = 6.9 Hz), 7.17 (1H, d, J = 1.8 Hz), 7.49 (1H, dd, J = 8.6, 1.8 Hz), 7.62 (1H, d, J = 1.2 Hz), 7.65 (1H, d, J = 8.6 Hz), 7.71 (1H, d, J = 1.8 Hz).<br>LRMS (ESI$^+$) 409 [M + H]$^+$. |
| 8-216 | 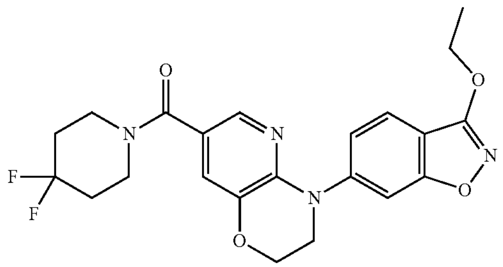 [SMILES: CCOc1noc2cc(N3CCOc4cc(C(=O)N5CCC(F)(F)CC5)cnc43)ccc12] | $^1$H NMR (400 MHz, DMSO-$d_6$) δ 1.44 (3H, t, J = 7.0 Hz), (4H, m), 3.52-3.64 (4H, m), 4.00 (2H, t, J = 4.3 Hz), 4.37 (2H, t, J = 4.3 Hz), 4.44 (2H, q, J = 6.9 Hz), 7.26 (1H, d, J = 1.8 Hz), 7.49 (1H, dd, J = 8.6, 1.8 Hz), 7.63 (1 H, d, J = 1.2 Hz), 7.65 (1H, d, J = 9.2 Hz), 7.79 (1H, d, J = 2.4 Hz).<br>LRMS (ESI$^+$) 445 [M + H]$^+$. |
| 8-217 | 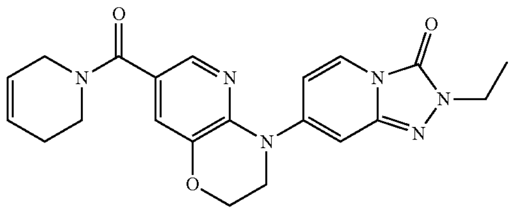 [SMILES: CCn1nc2cc(N3CCOc4cc(C(=O)N5CC=CCC5)cnc43)ccn2c1=O] | $^1$H NMR (400 MHz, DMSO-$d_6$) δ 1.28 (3H, t, J = 7.3 Hz), 2.14 (2H, s), 3.39-3.74 (2H, m), 3.81-4.07 (6H, m), 4.36 (2H, t, J = 4.3 Hz), 5.54-5.88 (2H, m), 6.92 (1H, d, J = 1.8 Hz), 6.98 (1H, dd, J = 7.6, 2.1 Hz), 7.24 (1H, d, J = 1.8 Hz), 7.76 (1H, d, J = 7.9 Hz), 7.82 (1H, d, J = 1.8 Hz).<br>LRMS (ESI$^+$) 407 [M + H]$^+$. |

TABLE 160

| Example No. | Chemical Structural Formula | Spectrum Data |
|---|---|---|
| 8-218 | 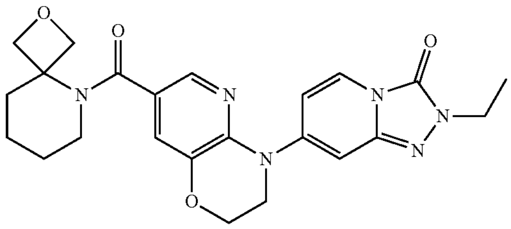 [SMILES: CCn1nc2cc(N3CCOc4cc(C(=O)N5CCCCC56COC6)cnc43)ccn2c1=O] | $^1$H NMR (400 MHz, DMSO-$d_6$) δ 1.17-1.25 (2H, m), 1.28 (3 H, t, J = 7.0 Hz), 1.60-1.69 (2H, m), 1.99 (2H, t, J = 5.5 Hz), 3.24 (2H, t, J = 5.2 Hz), 3.88 (2H, q, J = 7.1 Hz), 3.94 (2H, t, J = 4.3 Hz), 4.32 (2H, d, J = 7.3 Hz), 4.37 (2H, t, J = 4.6 Hz), 4.62 (2H, d, J = 6.7 Hz), 6.92-6.98 (2H, m), 7.30 (1H, d, J = 1.8 Hz), 7.76 (1H, d, J = 8.6 Hz), 7.91 (1H, d, J = 1.8 Hz).<br>LRMS (ESI$^+$) 451 [M + H]$^+$. |
| 8-219 | 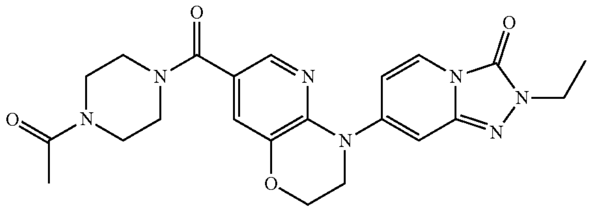 [SMILES: CCn1nc2cc(N3CCOc4cc(C(=O)N5CCN(C(C)=O)CC5)cnc43)ccn2c1=O] | $^1$H NMR (400 MHz, DMSO-$d_6$) δ 1.28 (3H, t, J = 7.0 Hz), 2.01 (3H, s), 3.39-3.62 (8H, m), 3.88 (2H, q, J = 7.1 Hz), 3.94 (2H, t, J = 4.6 Hz), 4.37 (2H, t, J = 4.6 Hz), 6.93 (1H, d, J = 1.2 Hz), 6.97 (1H, dd, J = 7.3, 1.8 Hz), 7.27 (1H, d, J = 2.4 Hz), 7.76 (1H, d, J = 6.7 Hz), 7.84 (1H, d, J = 1.8 Hz).<br>LRMS (ESI$^+$) 452 [M + H]$^+$. |
| 8-220 | 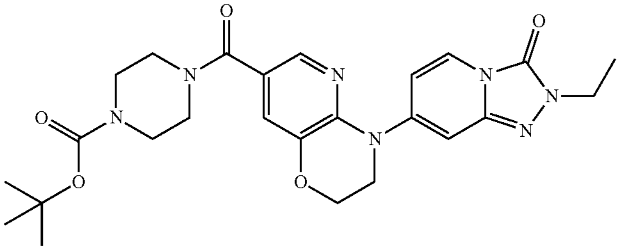 [SMILES: CCn1nc2cc(N3CCOc4cc(C(=O)N5CCN(C(=O)OC(C)(C)C)CC5)cnc43)ccn2c1=O] | $^1$H NMR (400 MHz, DMSO-$d_6$) δ 1.28 (3H, t, J = 7.0 Hz), 1.40 (9H, s), 3.36 (4H, s), 3.47 (4H, s), 3.88 (2H, q, J = 7.3 Hz), 3.93 (2H, t, J = 4.3 Hz), 4.37 (2H, t, J = 4.6 Hz), 6.93 (1H, d, J = 1.2 Hz), 6.97 (1H, dd, J = 7.9, 1.8 Hz), 7.25 (1H, d, J = 1.8 Hz), 7.76 (1H, d, J = 8.6 Hz), 7.82 (1H, d, J = 1.8 Hz).<br>LRMS (ESI$^+$) 510 [M + H]$^+$. |
| 8-221 | 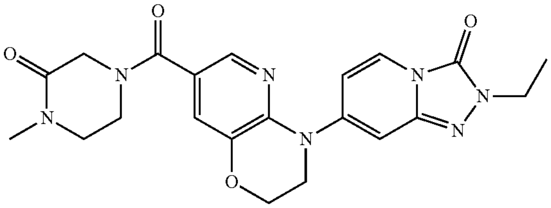 [SMILES: CCn1nc2cc(N3CCOc4cc(C(=O)N5CCN(C)C(=O)C5)cnc43)ccn2c1=O] | $^1$H NMR (400 MHz, DMSO-$d_6$) δ 1.28 (3H, t, J = 7.0 Hz), 2.85 (3H, s), 3.36 (2H, t, J = 5.5 Hz), 3.72 (2H, s), 3.88 (2H, q, J = 7.1 Hz), 3.94 (2H, t, J = 4.6 Hz), 4.08 (2H, s), 4.37 (2H, t, J = 4.3 Hz), 6.93 (1H, d, J = 1.8 Hz), 6.98 (1H, dd, J = 7.9, 1.8 Hz), 7.29 (1H, d, J = 1.8 Hz), 7.76 (1H, d, J = 7.9 Hz), 7.86 (1H, d, J = 2.4 Hz).<br>LRMS (ESI$^+$) 438 [M + H]$^+$. |
| 8-222 | 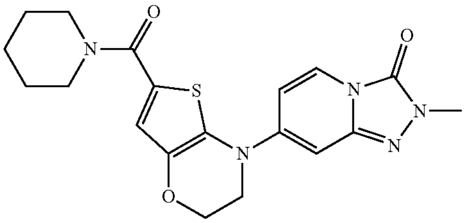 [SMILES: Cn1nc2cc(N3CCOc4cc(C(=O)N5CCCCC5)sc43)ccn2c1=O] | $^1$H NMR (400 MHz, DMSO-$d_6$) δ 1.47-1.66 (6H, m), 3.46 (3H, (4H, t, J = 5.2 Hz,), 3.80 (2H, t, J = 4.3 Hz), 4.30 (2H, t, J = 4.3 Hz), 6.73 (1H, d, J = 1.2 Hz), 6.82 (1H, dd, J = 7.9, 2.4 Hz), 7.06 (1H, s), 7.85 (1H, d, J = 7.9 Hz).<br>LRMS (ESI$^+$) 400 [M + H]$^+$. |

TABLE 161

| Example No. | Chemical Structural Formula | Spectrum Data |
|---|---|---|
| 8-223 | 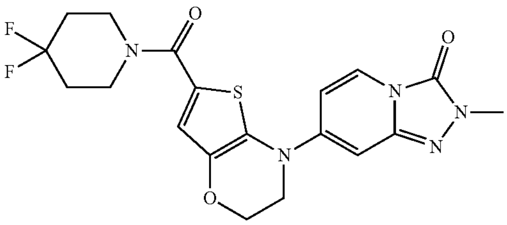 [SMILES: Cn1nc2cc(N3CCOc4cc(C(=O)N5CCC(F)(F)CC5)sc43)ccn2c1=O] | $^1$H NMR (400 MHz, DMSO-$d_6$) δ 1.97-2.12 (4H, m), 3.46 (3H, s), 3.72 (4H, t, J = 5.5 Hz), 3.81 (2H, t, J = 4.3 Hz), 4.31 (2H, t, J = 4.0 Hz), 6.75 (1H, d, J = 1.8 Hz), 6.82 (1H, dd, J = 7.9, 2.4 Hz), 7.19 (HI, s), 7.86 (1H d, J = 7.3 Hz).<br>LRMS (ESI$^+$) 436 [M + H]$^+$. |

TABLE 161-continued

| Example No. | Chemical Structural Formula | Spectrum Data |
|---|---|---|
| 8-224 | 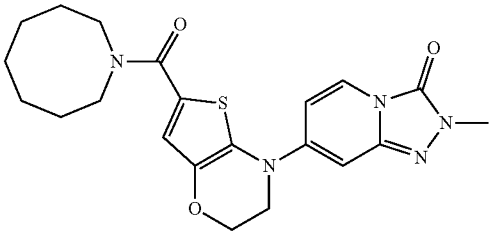 [SMILES: Cn1nc2cc(N3CCOc4cc(C(=O)N5CCCCCCC5)sc43)ccn2c1=O] | $^1$H NMR (400 MHz, DMSO-d$_6$) δ 1.36-1.59 (6H, m), 1.70 (4H, s), 3.46 (3H, s), 3.59 (4H, s), 3.80 (2H, t, J = 4.0 Hz), 4.30 (2H, t, J = 4.3 Hz), 6.73 (1H, d, J = 1.8 Hz), 6.83 (1H, dd, J = 7.6, 2.1 Hz), 7.08 (1H, s), 7.86 (1H, d, J = 7.3 Hz). LRMS (ESI$^+$) 428 [M + H]$^+$. |
| 8-225 | 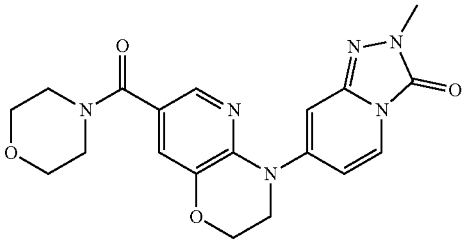 [SMILES: Cn1nc2cc(N3CCOc4cc(C(=O)N5CCOCC5)cnc43)ccn2c1=O] | $^1$H NMR (400 MHz, DMSO-d$_6$) δ 3.38-3.68 (11H, m), 3.93 (2H, t, J = 4.6 Hz), 4.36 (2H, t, J = 4.6 Hz), 6.89 (1H, d, J = 1.8 Hz), 6.98 (1H, dd, J = 7.9, 1.8 Hz), 7.25 (1H, d, J = 2.4 Hz), 7.75 (1H, d, J = 8.6 Hz), 7.82 (1H, d, J = 1.8 Hz). LRMS (ESI$^+$) 397 [M + H]$^+$. |
| 8-226 | 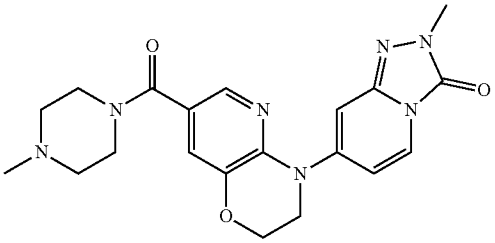 [SMILES: CN1CCN(C(=O)c2cnc3c(c2)OCCN3c2ccn3c(=O)n(C)nc3c2)CC1] | $^1$H NMR (400 MHz, DMSO-d$_6$) δ 2.17 (3H, s), 2.22-2.38 (4H, m), 3.35-3.65 (7H, m), 3.93 (2H, t, J = 4.6 Hz), 4.36 (2H, t, J = 4.6 Hz), 6.89 (1H, d, J = 1.2 Hz), 6.98 (1H, dd, J = 7.6, 2.1 Hz), 7.22 (1H, d, J = 1.8 Hz), 7.75 (1H, d, J = 7.9 Hz), 7.79 (1H, d, J = 1.8 Hz). LRMS (ESI$^+$) 410 [M + H]$^+$. |
| 8-227 | 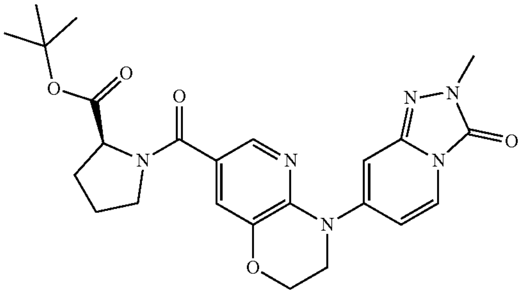 [SMILES: Cn1nc2cc(N3CCOc4cc(C(=O)N5CCC[C@H]5C(=O)OC(C)(C)C)cnc43)ccn2c1=O] | $^1$H NMR (400 MHz, DMSO-d$_6$) δ 1.23 (3H, s), 1.39 (6H, s), 1.72-1.95 (3H, m), 2.17-2.33 (1H, m), 3.44-3.66 (511, m), 3.87-4.00 (2H, m), 4.24-4.51 (3H, m), 6.86-7.01 (2H, m), 7.16-7.34 (1H, m), 7.76 (1H, d, J = 7.9 Hz), 7.80-7.99 (1H, m). LRMS (ESI$^+$) 481 [M + H]$^+$. |
| 8-228 | 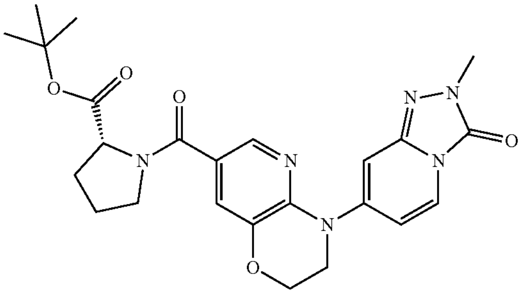 [SMILES: Cn1nc2cc(N3CCOc4cc(C(=O)N5CCC[C@@H]5C(=O)OC(C)(C)C)cnc43)ccn2c1=O] | $^1$H NMR (400 MHz, DMSO-d$_6$) δ 1.23 (3H, s), 1.39 (6H, s), 1.74-1.95 (3H, m), 2.15-2.30 (1H, m), 3.42-3.68 (5H, m), 3.85-4.00 (2H, m), 4.25-4.52 (3H, m), 6.86-7.00 (2H, m), 7.17-7.35 (1H, m), 7.76 (1H, d, J = 7.9 Hz), 7.79-7.99 (1H, m). LRMS (ESI$^+$) 481 [M + H]$^+$. |

TABLE 162

| Example No. | Chemical Structural Formula | Spectrum Data |
|---|---|---|
| 8-229 | 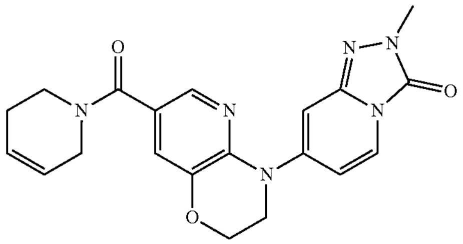 [SMILES: Cn1nc2cc(N3CCOc4cc(C(=O)N5CC=CCC5)cnc43)ccn2c1=O] | $^1$H NMR (400 MHz, DMSO-$d_6$) δ 2.12-2.18 (2H, m), 3.49 (3 H, s), 3.56 (2H, t, J = 5.8 Hz), 3.94 (2H, t, J = 4.2 Hz), 3.98-4.03 (2H, m), 4.37 (2H, t, J = 4.2 Hz), 5.66-5.73 (1H, m), 5.81-5.88 (1H, m), 6.90 (1H, d, J = 1.8 Hz), 6.97 (1H, dd, J = 7.3, 2.4 Hz), 7.21 (1H, d, J = 1.8 Hz), 7.70 (1H, d, J = 7.3 Hz), 7.82 (1H, d, J = 2.4 Hz). LRMS (ESI$^+$) 393 [M + H]$^+$. |
| 8-230 | 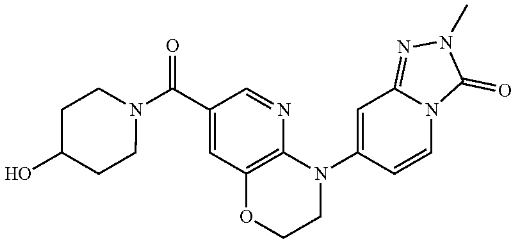 [SMILES: Cn1nc2cc(N3CCOc4cc(C(=O)N5CCC(O)CC5)cnc43)ccn2c1=O] | $^1$H NMR (400 MHz, DMSO-$d_6$) δ 1.27-1.42 (2H, m), 1.66-1.81 (2H, m), 3.14-3.25 (2H, m), 3.50 (3H, s), 3.56-4.02 (5H, 1H), 4.37 (2H, t, J = 1.8 Hz), 4.78 (1H, d, J = 4.2 Hz), 6.89 (1H, d, J = 1.2 Hz), 6.99 (1H, dd, J = 7.9, 1.8 Hz), 7.22 (1H, d, J = 1.8 Hz), 7.76 (1H, d, J = 7.9 Hz), 7.79 (1H, d, J = 1.8 Hz). LRMS (ESI$^+$) 411 [M + H]$^+$. |
| 8-231 | 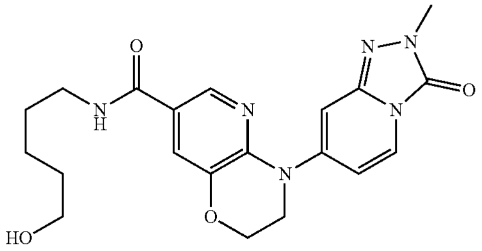 [SMILES: Cn1nc2cc(N3CCOc4cc(C(=O)NCCCCCO)cnc43)ccn2c1=O] | $^1$H NMR (400 MHz, DMSO-$d_6$) δ 1.26-1.36 (2H, m), 1.39-1.55 (4H, m), 3.19-3.26 (2H, m), 3.35-3.41 (2H, m), 3.51 (3H, s), 3.95 (2H, t, J = 4.2 Hz), 4.334.40 (3H, m), 6.92 (1H, d, J = 1.8 Hz), 6.97 (1H, dd, J = 7.9, 2.4 Hz), 7.61 (1H, d, J = 2.4 Hz), 7.77 (1H, d, J = 7.9 Hz), 8.24 (1H, d, J = 1.8 Hz), 8.36 (1H, t, J = 5.8 Hz). LRMS (ESI$^+$) 413 [M + H]$^+$. |

Example 9-1

[Formula 164]

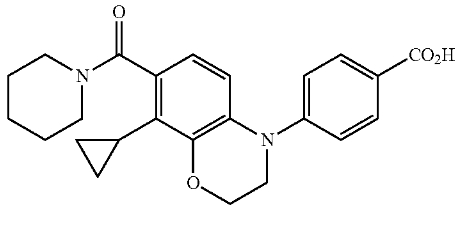

4-(8-Cyclopropyl-7-(piperidine-1-carbonyl)-2,3-dihydro-4H-benzo[b][1,4]oxazin-4-yl)benzoic Acid To a solution of methyl 4-(4-(tert-butoxycarbonyl)phenyl)-8-cyclopropyl-3,4-dihydro-2H-benzo[b][1,4]oxazine-7-carboxylate (31.4 mg) in tetrahydrofuran (1.0 mL), a 1 mol/L lithium hydroxide aqueous solution (0.23 mL) was added, followed by stirring at room temperature for 4 hours, at 65° C. for 3.5 hours, and at 70° C. for 9 hours. After adding a 1 mol/L lithium hydroxide aqueous solution (0.23 mL) thereto, the resultant reaction solution was heated to reflux for 10 hours. The resultant was stirred at room temperature for 5.5 days, a 1 mol/L hydrogen chloride aqueous solution (460 μL) was added to the reaction solution, the resultant was concentrated under reduced pressure, and the thus obtained residue was washed with water. The residue was dissolved in ethyl acetate, and dried over sodium sulfate. The resultant was filtered, and the thus obtained filtrate was concentrated under reduced pressure to obtain a crude product containing 4-(4-(tert-butoxycarbonyl)phenyl)-8-cyclopropyl-3,4-dihydro-2H-benzo[b][1,4]oxazine-7-carboxylic acid (17.1 mg).

To a solution, in N,N-dimethylformamide (0.5 mL), of the crude product (17.1 mg) containing 4-(4-(tert-butoxycarbonyl)phenyl)-8-cyclopropyl-3,4-dihydro-2H-benzo[b][1,4]oxazine-7-carboxylic acid, piperidine (6.4 μL) and diisopropylethylamine (22.1 μL) were added. To the resultant reaction solution, 1-[bis(dimethylamino)methylene]-1H-1,2,3-triazolo[4,5-b]pyridinium 3-oxide hexafluorophosphate (24.6 mg) was added, followed by stirring at room temperature for 2.5 hours. The resultant reaction solution was concentrated under reduced pressure, and the thus obtained residue was purified by silica gel column chromatography (ethyl acetate:hexane=5:95 to 30:70) to obtain a mixture containing tert-butyl 4-(8-cyclopropyl-7-(piperidine-1-carbonyl)-2,3-dihydro-4H-benzo[b][1,4]oxazin-4-yl)benzoate (12.5 mg).

To a solution, in dichloromethane (0.5 mL), of the mixture (12.5 mg) containing tert-butyl 4-(8-cyclopropyl-7-(piperidine-1-carbonyl)-2,3-dihydro-4H-benzo[b][1,4]oxazin-4-yl)benzoate, trifluoroacetic acid (0.25 mL) was added. After stirring at room temperature for 2.5 hours, the resultant reaction solution was concentrated under reduced pressure, and the thus obtained residue was purified by silica gel column chromatography (acetonitrile:water=5:95 to 60:40 to 80:20) to obtain the title compound (10.1 mg).

$^1$H NMR (400 MHz, DMSO-$d_6$) δ: 0.48-0.57 (1H, m), 0.73-0.76 (3H, m), 1.32-1.71 (7H, m), 3.17 (2H, t, J=5.5

Hz), 3.45-3.55 (1H, m), 3.59-3.68 (1H, m), 3.73-3.79 (2H, m), 4.23-4.29 (2H, m), 6.50 (1H, d, J=8.6 Hz), 6.91 (1H, d, J=7.9 Hz), 7.26 (2H, d, J=9.2 Hz), 7.87 (2H, d, J=8.6 Hz). (COOH peak missing)

LRMS ($ESI^+$) 407 $[M+H]^+$.

Example 10-1

[Formula 165]

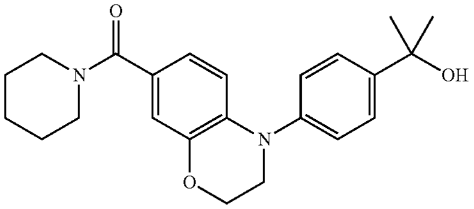

(4-(4-(2-Hydroxypropan-2-yl)phenyl)-3,4-dihydro-2H-benzo[b][1,4]oxazin-7-yl)(piperidin-1-yl)methanone To a solution of methyl 4-(7-(piperidine-1-carbonyl)-2,3-dihydro-4H-benzo[b][1,4]oxazin-4-yl)benzoate (46.2 mg) in tetrahydrofuran (1.2 mL), methylmagnesium bromide (100 μL; 3 mol/L diethyl ether solution) was added under ice cooling, followed by stirring for 50 minutes. After stirring at room temperature for 13.5 hours, methylmagnesium bromide (100 μL; 3 mol/L diethyl ether solution) was added thereto, followed by stirring at room temperature for 23.5 hours. To the resultant reaction solution, a saturated ammonium chloride aqueous solution (5 mL) and water (5 mL) were added, followed by extraction with ethyl acetate (10 mL×2). The resultant organic layers were combined, dried over anhydrous sodium sulfate, and filtered, and the resultant filtrate was concentrated under reduced pressure. The thus obtained residue was purified by silica gel column chromatography (ethyl acetate:hexane=10:90 to 80:20) to obtain the title compound (30.8 mg).

$^1H$ NMR (400 MHz, DMSO-$d_6$) δ1.40-1.51 (10H, m), 1.55-1.62 (2H, m), 3.38-3.46 (4H, m), 3.68 (2H, t, J=4.2 Hz), 4.27 (2H, t, J=4.2 Hz), 4.99 (1H, s), 6.69 (1H, d, J=8.5 Hz), 6.73 (1H, dd, J=8.5, 1.8 Hz), 6.80 (1H, d, J=1.2 Hz), 7.18-7.23 (2H, m), 7.46-7.51 (2H, m).

LRMS ($ESI^+$) 381 $[M+H]^+$.

Compounds of the following Examples 10-2 to 10-3 were obtained in the same manner as in Example 10-1 by using corresponding starting materials and reactants. Their structures and spectrum data are shown in the following table.

TABLE 163

| Example No. | Chemical Structural Formula | Spectrum Data |
|---|---|---|
| 10-2 | 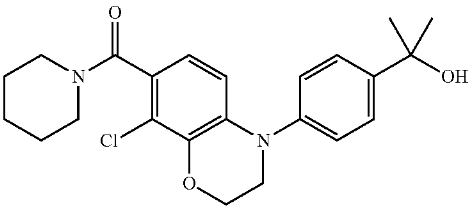 [SMILES: CC(C)(O)c1ccc(N2CCOc3c2ccc(C(=O)N2CCCCC2)c3Cl)cc1] | $^1H$ NMR (400 MHz, DMSO-$d_6$) δ 1.31-1.62 (12H, m), 3.06-3.18 (2H, m), 3.48-3.61 (2H, m), 3.70 (2H, t J = 4.3 Hz), 4.34-4.39 (2H, m), 5.00 (1H, s), 6.60 (1H, d, J = 8.6 Hz), 6.64 (1H, d, J = 8.6 Hz), 7.18-723 (2H, m), 7.46-7.51 (2H, m).<br>LRMS ($ESI^+$) 415 $[M + H]^+$. |
| 10-3 | 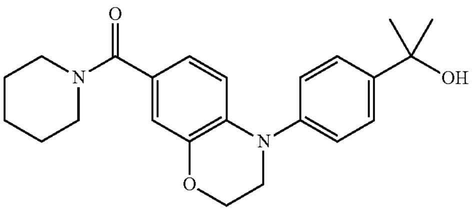 [SMILES: CC(C)(O)c1ccc(N2CCOc3cc(C(=O)N4CCCCC4)ccc32)cc1] | $^1H$ NMR (400 MHz, $CDCl_3$) δ 1.45-1.76 (12H, m), 3.40-3.70 (4H, m), 3.91 (2H, t, J = 4.6 Hz), 4.34 (2H, t, J = 4.3 Hz), 7.19 (1H, d, J = 1.8 Hz), 7.32-7.37 (2H, m), 7.50-7.55 (2H, m), 7.83 (1H, d, J = 1.8 Hz). (OH peak missing)<br>LRMS ($ESI^+$) 382 $[M + H]^+$. |

Example 11-1

[Formula 166]

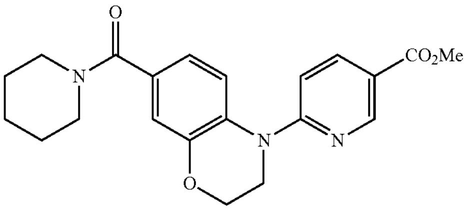

Methyl 6-(7-(Piperidine-1-carbonyl)-2,3-dihydro-4H-benzo[b][1,4]oxazin-4-yl)nicotinate A solution, in toluene (4.2 mL), of (3,4-dihydro-2H-benzo[b][1,4]oxazin-7-yl)(piperidin-1-yl)methanone (103 mg), methyl 6-bromonicotinate (108 mg; commercially available product), palladium (II) acetate (4.7 mg), 2-dicyclohexylphospino-2',4',6'-triisopropylbiphenyl (15.0 mg) and cesium carbonate (163 mg) was stirred at an external temperature of 105° C. for 3 hours, and then stirred under heating to reflux for 8 hours. The resultant reaction solution was concentrated under reduced pressure, and the thus obtained residue was purified by silica gel column chromatography (ethyl acetate:hexane=10:90 to 80:20 to 100:0) to obtain the title compound (35.7 mg).

$^1$H NMR (400 MHz, $CDCl_3$) δ 1.48-1.74 (6H, m), 3.32-3.78 (4H, m), 3.91 (3H, s), 4.22 (2H, t, J=4.5 Hz), 4.32 (2H, t, J=4.5 Hz), 6.93 (1H, dd, J=8.5, 1.8 Hz), 7.01 (1H, d, J=1.8 Hz), 7.29 (1H, s), 7.40 (1H, d, J=8.5 Hz), 8.08 (1H, dd, J=8.5, 2.4 Hz), 8.92 (1H, d, J=2.4 Hz).

LRMS ($ESI^+$) 382 $[M+H]^+$.

Compounds of the following Examples 11-2 to 11-7 were obtained in the same manner as in Example 11-1 by using corresponding starting materials and reactants. Their structures and spectrum data are shown in the following tables.

TABLE 164

| Example No. | Chemical Structural Formula | Spectrum Data |
|---|---|---|
| 11-2 | 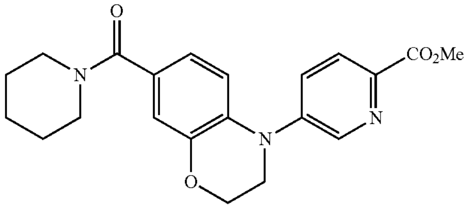 [SMILES: COC(=O)c1ccc(N2CCOc3cc(C(=O)N4CCCCC4)ccc32)cn1] | $^1$H NMR (400 MHz, $CDCl_3$) δ 1.45-1.72 (6H, m), 3.34-3.75 (4H, m), 3.82 (2H, t, J = 4.2 Hz), 4.00 (3H, s), 4.33 (2H, t, J = 4.2 Hz), 6.87 (1H, dd, J = 8.5, 1.8 Hz), 7.01 (1H, d, J = 2.4 Hz), 7.11 (1H, d, J = 8.5 Hz), 7.62 (1H, dd, J = 8.5, 2.4 Hz), 8.09 (1H, d, J = 8.5 Hz), 8.64 (HI, d, J = 3.0 Hz). LRMS ($ESI^+$) 382 $[M + H]^+$. |
| 11-3 | 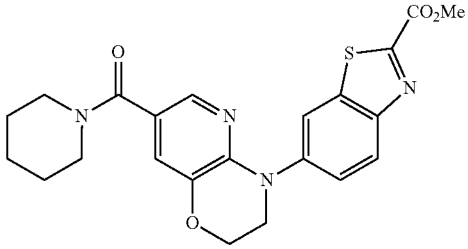 [SMILES: COC(=O)c1nc2ccc(N3CCOc4cc(C(=O)N5CCCCC5)cnc43)cc2s1] | $^1$H NMR (400 MHz, DMSO-$d_6$) δ: 1.36-1.69 (6H, m), 3.22-3.92 (4H, m), 3.97 (3H, s), 4.01 (2H, t, J = 4.3 Hz), 4.38 (2H, t, J = 4.3 Hz), 7.17 (1H, d, J = 1.8 Hz), 7.70 (1H, d, J = 1.8 Hz), 7.79 (1H, dd, J = 8.9, 2.1 Hz), 8.16 (1H, d, J = 9.2 Hz), 8.22 (1H, d, J = 2.4 Hz). LRMS ($ESI^+$) 439 $[M + H]^+$. |

TABLE 165

| Example No. | Chemical Structural Formula | Spectrum Data |
|---|---|---|
| 11-4 | 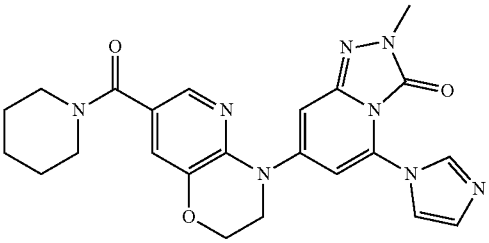 [SMILES: Cn1nc2cc(N3CCOc4cc(C(=O)N5CCCCC5)cnc43)cc(-n3ccnc3)n2c1=O] | $^1$H NMR (400 MHz, DMSO-$d_6$) δ 1.39-1.64 (6H, m), 3.17-3.58 (7H, m), 3.95 (2H, t, J = 4.3 Hz), 4.36 (2H, t, J = 4.6 Hz), 6.97-7.03 (3H, m), 7.21 (1H, d, J = 1.8 Hz), 7.50 (1H, t, J = 1.5 Hz), 779 (1H, d, J = 1.8 Hz), 7.97 (1H, s). LRMS ($ESI^+$) 461 $[M + H]^+$. |

TABLE 165-continued

| Example No. | Chemical Structural Formula | Spectrum Data |
| --- | --- | --- |
| 11-5 | 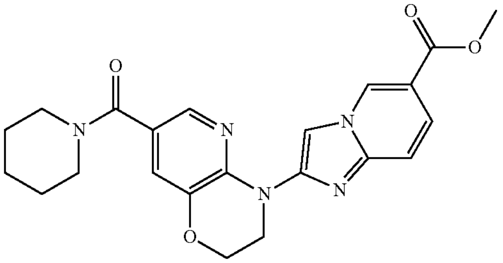 [SMILES: COC(=O)c1ccc2nc(N3CCOc4cc(C(=O)N5CCCCC5)cnc43)cn2c1] | $^1$H NMR (400 MHz, DMSO-$d_6$) δ 1.45-1.67 (6H, m), 3.38-3.56 (4H, m), 3.87 (3H, s), 4.37 (4H, s), 7.21 (1H, d, J = 1.8 Hz), 7.53 (1H, d, J = 9.2 Hz), 7.63 (1H, dd, J = 9.8, 1.8 Hz), 7.97 (1H, d, J = 1.8 Hz), 8.74 (1H, s), 9.36 (1H, d, J = 1.8 Hz). LRMS (ESI$^+$) 422 [M + H]$^+$. |
| 11-6 | 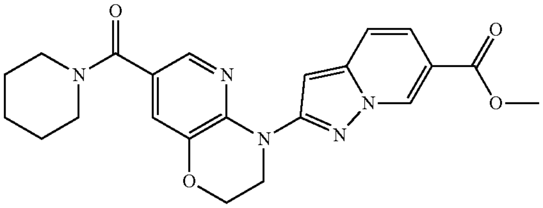 [SMILES: COC(=O)c1ccc2cc(N3CCOc4cc(C(=O)N5CCCCC5)cnc43)nn2c1] | $^1$H NMR (400 MHz, DMSO-$d_6$) δ 1.42-1.67 (6H, m), 3.37-3.58 (4H, m), 3.86 (3H, s), 4.27 (2H, t, J = 4.3 Hz), 4.38 (2H, t, J = 4.6 Hz), 7.24 (1H, d, J = 2.4 Hz), 7.47 (1H, d, J = 1.2 Hz), 7.56 (1H, dd, J = 9.2, 1.8 Hz), 7.66 (1H, dd, J = 9.2, 1.2 Hz), 7.95 (1H, d, J = 1.8 Hz), 9.06 (1H, s). LRMS (ESI$^+$) 422 [M + H]$^+$. |
| 11-7 | 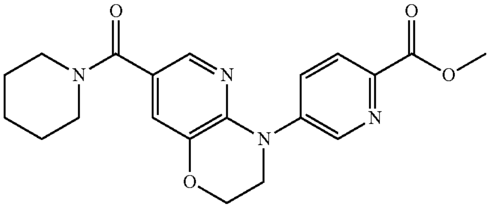 [SMILES: COC(=O)c1ccc(N2CCOc3cc(C(=O)N4CCCCC4)cnc32)cn1] | $^1$H NMR (400 MHz, $CDCl_3$) δ 1.42-1.79 (6H, m), 3.26-3.79 (4H, m), 3.94-4.04 (5H, m), 4.41 (2H, t, J = 4.3 Hz), 7.23-7.29 (1H, m), 7.84 (1H, t, J = 1.5 Hz), 7.94 (1H, dd, J = 8.6, 1.8 Hz), 8.15 (1H, dd, J = 8.6, 1.2 Hz), 8.85 (1H, d, J = 2.4 Hz). LRMS (ESI$^+$) 383 [M + H]$^+$. |

Example 12-1

[Formula 167]

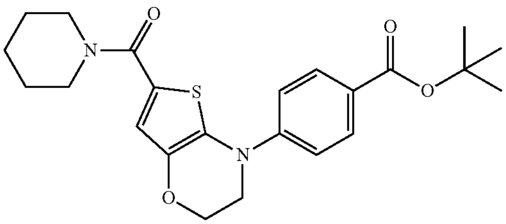

tert-Butyl 4-(6-(Piperidine-1-carbonyl)-2,3-dihydro-4H-thieno[3,2-b] [1,4]oxazin-4-yl)benzoate To a solution of ethyl 4-(4-(tert-butoxycarbonyl)phenyl)-3,4-dihydro-2H-thieno[3,2-b][1,4]oxazine-6-carboxylate (60.5 mg) in tetrahydrofuran (3.1 mL), a solution of lithium hydroxide (19.5 mg) in water (1 mL) was added, followed by stirring at room temperature for 2.5 hours, at 40° C. for 0.5 hours, at 65° C. for 3 hours and at 70° C. for 9 hours. To the resultant reaction solution, 1 mol/L hydrogen chloride aqueous solution (465 μL) was added, and the resultant was concentrated under reduced pressure to obtain a crude product (57.7 mg) containing 4-(4-(tert-butoxycarbonyl) phenyl)-3,4-dihydro-2H-thieno[3,2-b][1,4]oxazine-6-carboxylic acid.

To a solution, in N,N-dimethylformamide (0.8 mL), of the crude product (57.7 mg) containing 4-(4-(tert-butoxycarbonyl)phenyl)-3,4-dihydro-2H-thieno[3,2-b][1,4]oxazine-6-carboxylic acid, piperidine (16.8 μL) and diisopropylethylamine (57.8 (LL) were added. To the resultant reaction solution, 1-[bis(dimethylamino)methylene]-1H-1,2,3-triazolo[4,5-b]pyridinium 3-oxide hexafluorophosphate (64.6 mg) was added, followed by stirring for 0.5 hours. The resultant reaction solution was purified by silica gel column chromatography (methanol:water=5:95 to 60:40 to 100:0) to obtain the title compound (41.1 mg).

$^1$H NMR (400 MHz, $CDCl_3$) δ 1.46-1.72 (15H, m), 3.65-3.71 (4H, m), 3.78 (2H, t, J=4.3 Hz), 4.32 (2H, t, J=4.3 Hz), 6.88 (1H, s), 7.30-7.35 (2H, m), 7.93-7.97 (2H, m).

LRMS (ESI$^+$) 429 [M+H]$^+$.

Example 13-1

[Formula 168]

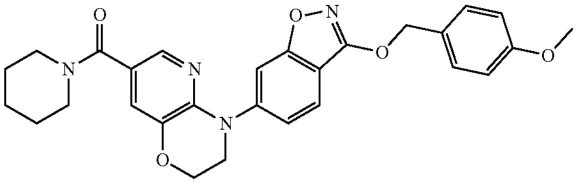

(4-(3-((4-Methoxybenzyl)oxy)benzo[d]isoxazol-6-yl)-3,4-dihydro-2H-pyrido[3,2-b][1,4]oxazin-7-yl) (piperidin-1-yl)methanone To a solution of methyl 2-hydroxy-4-iodobenzoate (7.75 g; commercially available product) in 1,4-dioxane (200 mL), hydroxylamine (50 mL) was added at room temperature. After stirring at room temperature for 3 days, water and ethyl acetate were added to the resultant reaction solution to separate an organic layer and an aqueous layer. The aqueous layer was prepared to be acidic by using concentrated hydrochloric acid. The resultant was extracted with ethyl acetate, washed with saturated saline, and dried over sodium sulfate. The resultant was filtered, and the obtained filtrate was concentrated under reduced pressure to obtain a crude product containing N,2-dihydroxy-4-iodobenzamide (11.8 g).

To a solution, in tetrahydrofuran (200 mL), of the crude product (11.8 g) containing N,-2-dihydroxy-4-iodobenzamide, 1,1'-carbonyldiimidazole (13.6 g) was added. The resultant reaction solution was heated to reflux for 1.5 hours, and water and ethyl acetate were added thereto to separate an organic layer and an aqueous layer. The aqueous layer was prepared to be acidic by using concentrated hydrochloric acid. The resultant was extracted with ethyl acetate, washed with water and saturated saline, and dried over magnesium sulfate. The resultant was filtered, and the obtained filtrate was concentrated under reduced pressure to obtain a crude product containing 6-iodobenzo[d]isoxazol-3 (2H)-one (4.08 g).

To a solution, in N,N-dimethylformamide (5.8 mL), of the crude product (300 mg) containing 6-iodobenzo[d]isoxazol-3 (2H)-one, 4-methoxybenzylchloride (235 μL) was added. To the resultant reaction solution, potassium carbonate (477 mg) was added at room temperature, followed by stirring at room temperature for 17 hours. Water was added to the reaction solution, followed by extraction with ethyl acetate. The resultant organic layers were combined, and dried over sodium sulfate. The resultant was filtered, the obtained filtrate was concentrated under reduced pressure, and the thus obtained residue was purified by silica gel column chromatography (ethyl acetate:hexane=0:100 to 30:70) to obtain a mixture containing 6-iodo-3-((4-methoxybenzyl)oxy)benzo[d]isoxazole (165 mg).

A solution, in toluene (0.8 mL), of (3,4-dihydro-2H-pyrido[3,2-b][1,4]oxazin-7-yl)(piperidin-1-yl)methanone (30.0 mg), the mixture (69.4 mg) containing 6-iodo-3-((4-methoxybenzyl)oxy)benzo[d]isoxazole, tris(dibenzylideneacetone)dipalladium (0) (11.0 mg), 4,5-bis(diphenylphosphino)-9,9-dimethylxanthene (Xantphos) (14.0 mg) and sodium tert-butoxide (23.3 mg) was stirred at 85° C. for 1 hour, and the resultant reaction solution was then filtered, and the obtained filtrate was concentrated under reduced pressure. The thus obtained residue was purified by silica gel column chromatography (ethyl acetate:hexane=5:95 to 100:0 to ethyl acetate:methanol=50:50) to obtain the title compound (62.4 mg).

$^1$H NMR (400 MHz, $CDCl_3$) δ: 1.50-1.75 (6H, m), 3.36-3.74 (4H, m), 3.84 (3H, s), 3.96 (2H, t, J=4.3 Hz), 4.38 (2H, t, J=4.3 Hz), 5.39 (2H, s), 6.92-6.98 (2H, m), 7.23 (1H, d, J=1.8 Hz), 7.36 (1H, dd, J=8.6, 1.8 Hz), 7.39-7.41 (1H, m), 7.43-7.49 (2H, m), 7.59 (1H, d, J=8.6 Hz), 7.83 (1H, d, J=1.8 Hz).

LRMS (ESI$^+$) 501 [M+H]$^+$.

Example 14-1

[Formula 169]

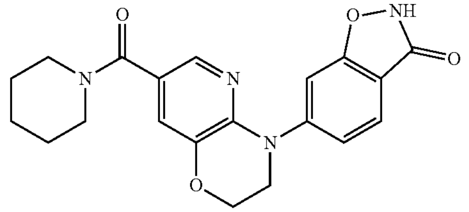

6-(7-Piperidine-1-carbonyl)-2,3-dihydro-4H-pyrido [3,2-b] [1,4]oxazin-4-yl)benzo[d]isoxazol-3 (2H)-one To a solution of (4-(3-((4-methoxybenzyl)oxy)benzo[d] isoxazol-6-yl)-3,4-dihydro-2H-pyrido[3,2-b][1,4]oxazin-7-yl)(piperidin-1-yl)methanone (60.6 mg) in dichloromethane (2.4 mL), trifluoroacetic acid (1.2 mL) was added at room temperature. After stirring at room temperature for 5 hours, the resultant reaction solution was concentrated under reduced pressure. The thus obtained residue was purified by silica gel column chromatography (methanol:water=10:90 to 30:70 to 100:0) to obtain the title compound (10.2 mg).

$^1$H NMR (400 Hz, DMSO-D6) δ: 1.40-1.63 (6H, m), 3.15-3.60 (4H, m), 3.95 (2H, t, J=4.2 Hz), 4.35 (2H, t, J=3.9 Hz), 7.13 (1H, d, J=1.8 Hz), 7.28 (1H, d, J=9.1 Hz), 7.39 (1H, s), 7.64 (1H, d, J=8.5 Hz), 7.68 (1H, d, J=1.8 Hz). (NH peak missing)

LRMS (ESI$^+$) 381 [M+H]$^+$.

Compounds of the following Examples 14-2 to 14-10 were obtained in the same manner as in Example 14-1 by using corresponding starting materials and reactants. Their structures and spectrum data are shown in the following tables.

TABLE 166

| Example No. | Chemical Structural Formula | Spectrum Data |
|---|---|---|
| 14-2 | 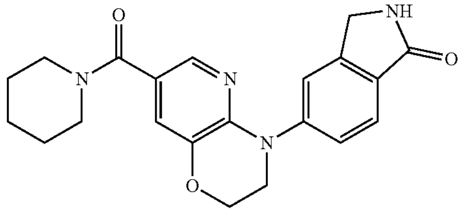 [SMILES: O=C1NCc2cc(N3CCOc4cc(C(=O)N5CCCCC5)cnc43)ccc21] | $^1$H NMR (400 MHz, DMSO-$d_6$) δ 1.41-1.65 (6H, m), 3.35-3.55 (4H, m), 3.92-3.99 (2H, m), 4.31-4.38 (4H, m), 7.15 (1H, d, J = 1.8 Hz), 7.51 (1H, dd, J = 8.6, 1.8 Hz), 7.59 (1H, d, J = 1.2 Hz), 7.63 (1H, d, J = 8.6 Hz), 7.68 (1H, d, J = 2.4 Hz), 8.44 (1H, s). LRMS (ESI$^+$) 379 [M + H]$^+$. |

TABLE 166-continued

| Example No. | Chemical Structural Formula | Spectrum Data |
|---|---|---|
| 14-3 | 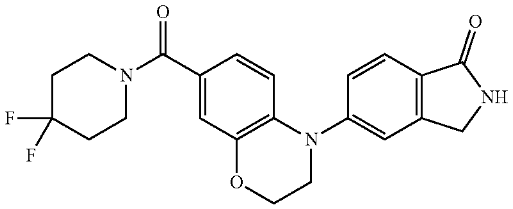 [SMILES: O=C1NCc2cc(N3CCOc4cc(C(=O)N5CCC(F)(F)CC5)ccc43)ccc21] | $^1$H NMR (400 MHz, $CDCl_3$) δ 1.93-2.10 (4H, m), 3.64-3.86 (6H, m), 4.34 (2H, t, J = 4.3 Hz), 4.44 (2H, s), 6.30 (1H, br s), 6.87 (1H, dd, J = 8.6, 2.4 Hz), 7.00 (1H, d, J = 2.4 Hz), 7.04 (1H, d, J = 8.6 Hz), 7.29-7.37 (2H, m), 7.85 (1H, d, J = 8.6 Hz). LRMS ($ESI^+$) 414 $[M + H]^+$. |
| 14-4 | 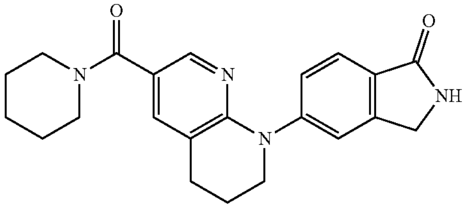 [SMILES: O=C1NCc2cc(N3CCCc4cc(C(=O)N5CCCCC5)cnc43)ccc21] | $^1$H NMR (400 MHz, DMSO-$d_6$) δ 1.39-1.67 (6H, m), 1.95-2.07 (2H, m), 2.87 (2H, t, J = 6.1 Hz), 3.38-3.57 (4H, m), 3.80 (2H, t, J = 5.4 Hz), 4.35 (2H, s), 7.38-7.45 (2H, m), 7.51 (1H, s), 7.63 (1H, d, J = 8.5 Hz), 7.84 (1H, d, J = 1.8 Hz), 8.45 (1H, s). LRMS ($ESI^+$) 377 $[M + H]^+$. |
| 14-5 | 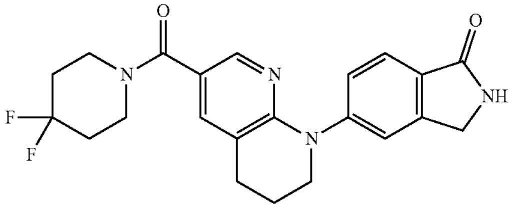 [SMILES: O=C1NCc2cc(N3CCCc4cc(C(=O)N5CCC(F)(F)CC5)cnc43)ccc21] | $^1$H NMR (400 MHz, DMSO-$d_6$) δ 1.94-2.11 (6H, m), 2.87 (2H, t, J = 6.4 Hz), 3.51-3.67 (4H, m), 3.81 (2H, t, J = 5.4 Hz), 4.35 (2H, s), 7.42 (1H, dd, J = 7.9, 1.8 Hz), 7.48 (1H, d, J = 2.4 Hz), 7.51 (1H, s), 7.64 (1H, d, J = 7.9 Hz), 7.92 (1H, d, J = 1.8 Hz), 8.46 (1H, s). .LRMS ($ESI^+$) 413 $[M + H]^+$. |

TABLE 167

| Example No. | Chemical Structural Formula | Spectrum Data |
|---|---|---|
| 14-6 | 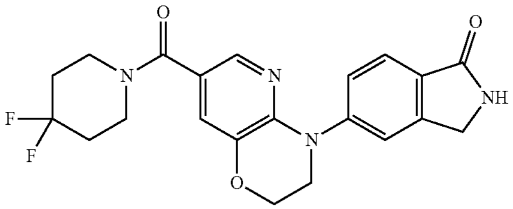 [SMILES: O=C1NCc2cc(N3CCOc4cc(C(=O)N5CCC(F)(F)CC5)cnc43)ccc21] | $^1$H NMR (400 MHz, $CDCl_3$) δ 1.99-2.07 (4H, m), 3.56-3.62 (4H, m), 3.97 (2H, t, J = 4.6 Hz), 4.36-4.38 (4H, m), 7.24 (1H, d, J = 1.9 Hz), 7.53 (1H, dd, J = 8.4, 1.9 Hz), 7.61 (1H, d, J = 1.1 Hz), 7.65 (1H, d, J = 8.0 Hz), 7.77 (1H, d, J = 1.9 Hz), 8.45 (1H, s). LRMS ($ESI^+$) 415 $[M + H]^+$. |
| 14-7 | 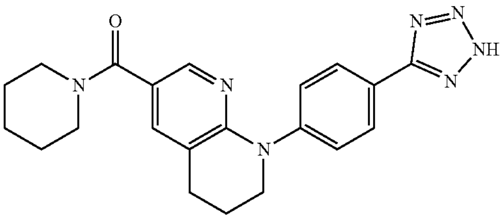 [SMILES: O=C(c1cnc2c(c1)CCCN2c1ccc(-c2nn[nH]n2)cc1)N1CCCCC1] | $^1$H NMR (400 MHz, $CDCl_3$) δ 1.42-1.69 (6H, m), 2.01-2.12 (2H, m), 2.91 (2H, t, J – 6.1 Hz), 3.34-3.55 (4H, m), 3.85 (2H, t, J – 5.8 Hz), 7.59-7.71 (3H, m), 7.79-7.85 (1H, m), 8.09-8.19 (2H, m). (NH peak missing) LRMS ($ESI^+$) 390 $[M + H]^+$. |
| 14-8 | 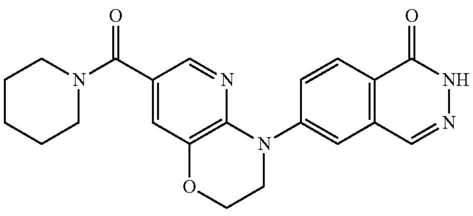 [SMILES: O=C(c1cnc2c(c1)OCCN2c1ccc2c(=O)[nH]ncc2c1)N1CCCCC1] | $^1$H NMR (400 MHz, DMSO-$d_6$) δ 1.39-1.70 (6H, m), 3.34-3.68 (4H, m), 4.04 (2H, t, J = 4.2 Hz), 4.39 (2H, t, J = 4.5 Hz), 7.22 (1H, d, J = 2.4 Hz), 7.75 (1H, d, J = 1.8 Hz), 7.86 (1H, d, J = 2.4 Hz), 7.99 (1H, dd, J = 8.8, 2.1 Hz), 8.15 (1H, d, J = 9.1 Hz), 8.29 (1H, s), 12.52 (1H, s). LRMS ($ESI^+$) 392 $[M + H]^+$. |

TABLE 167-continued

| Example No. | Chemical Structural Formula | Spectrum Data |
| --- | --- | --- |
| 14-9 | 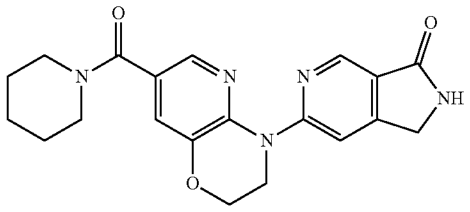 [SMILES: O=C1NCc2cc(N3CCOc4cc(C(=O)N5CCCCC5)cnc43)ncc21] | $^1$H NMR (400 MHz, DMSO-d$_6$) δ 1.41-1.65 (6H, m), 3.33-3.62 (4H, m), 4.23-4.30 (2H, m), 4.32-4.38 (2H, m), 4.41 (2H, s), 7.28 (1H, d, J = 1.8 Hz), 7.87 (1H, d, J = 2.4 Hz), 8.28 (1H, d, J = 12 Hz), 8.47-8.51 (1H, m), 8.64 (1H, d, J = 1.2 Hz). LRMS (ESI$^+$) 380 [M + H]$^+$. |
| 14-10 | 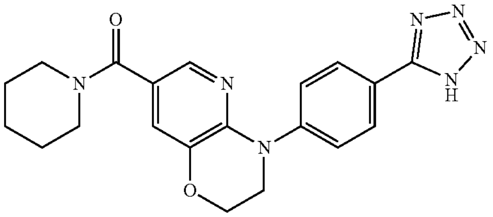 [SMILES: O=C(c1cnc2c(c1)OCCN2c1ccc(-c2nnn[nH]2)cc1)N1CCCCC1] | $^1$H NMR (400 MHz, DMSO-d$_6$) δ 1.43-1.66 (6H, m), 3.33-3.53 (4H, m), 3.98 (2H, t, J = 3.6 Hz), 4.37 (2H, t, J = 4.2 Hz), 7.17 (1H, d, J = 1.8 Hz), 7.63-7.69 (2H, m), 7.72 (1H, d, J = 1.8 Hz), 7.99-8.05 (2H, m). (NH peak missing) LRMS (ESI$^+$) 392 [M + H]$^+$. |

Example 15-1

[Formula 170]

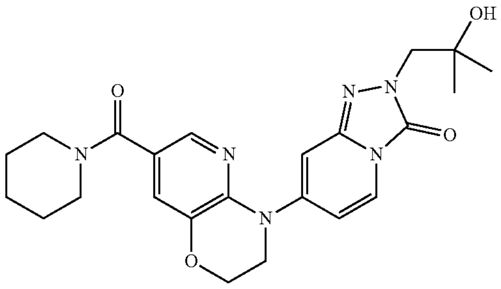

2-(2-Hydroxy-2-methylpropyl)-7-(7-(piperidine-1-carbonyl)-2,3-dihydro-4H-pyrido[3,2-b][1,4]oxazin-4-yl)-[1,2,4]triazolo[4,3-a]pyridin-3(2H)-one To a solution of 7-iodo-[1,2,4]triazolo[4,3-a]pyridin-3(2H)-one (183 mg; known compound described in literature, WO2011057757A1) in N,N-dimethylformamide (1.8 mL), potassium carbonate (193 mg) was added. To the resultant reaction solution, 2,2-dimethyloxirane (125 μL) was added at room temperature, followed by stirring at 120° C. for 40 minutes. The resultant was stirred at 120° C. for 30 minutes under microwave irradiation. To the resultant reaction solution, water was added, the resultant was extracted with ethyl acetate, and the resultant organic layers were combined and dried over sodium sulfate. The resultant was filtered, the obtained filtrate was concentrated under reduced pressure, and the thus obtained residue was purified by silica gel column chromatography (ethyl acetate:hexane=10:90 to 100:0 to ethyl acetate:methanol=90:10) to obtain a mixture containing 2-(2-hydroxy-2-methylpropyl)7-iodo-[1,2,4]triazolo[4,3-a]pyridin-3(2H)-one (34.7 mg).

A solution, in toluene (2 mL), of (3,4-dihydro-2H-pyrido[3,2-b][1,4]oxazin-7-yl)(piperidin-1-yl)methanone (24.7 mg), the mixture (34.7 mg) containing 2-(2-hydroxy-2-methylpropyl)-7-iodo-[1,2,4]triazolo[4,3-a]pyridin-3 (2H)-one, tris(dibenzylideneacetone)dipalladium (0) (4.6 mg), 4,5-bis(diphenylphosphino)-9,9-dimethylxanthene (Xantphos) (5.8 mg), and sodium tert-butoxide (19.2 mg) was stirred at 85° C. for 1.5 hours, the resultant reaction solution was filtered, and the obtained filtrate was concentrated under reduced pressure. The thus obtained residue was purified by silica gel column chromatography (ethyl acetate:hexane=30:70 to 100:0 to ethyl acetate:methanol=85:15) to obtain the title compound (35.9 mg).

$^1$H NMR (400 MHz, DMSO-d$_6$) δ: 1.14 (6H, s), 1.40-1.65 (6H, m), 3.15-3.57 (4H, m), 3.76 (2H, s), 3.93 (2H, t, J=4.6 Hz), 4.36 (2H, t, J=4.6 Hz), 4.66 (1H, s), 6.92 (1H, d, J=1.8 Hz), 6.97 (1H, dd, J=7.9, 1.8 Hz), 7.21 (1H, d, J=1.8 Hz), 7.73-7.79 (2H, m).

LRMS (ESI$^+$) 453 [M+H]$^+$.

Example 16-1

[Formula 171]

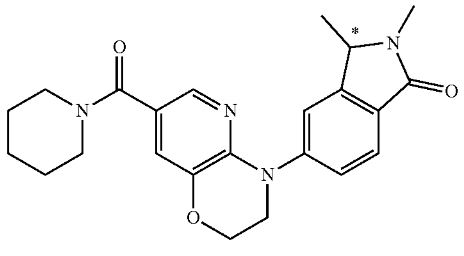

Isomer A:

2,3-Dimethyl-5-(7-piperidine-1-carbonyl)-2,3-dihydro-4H-pyrido[3,2-b] [1,4]oxazin-4-yl)isoindolin-1-one Isomer B:

2,3-Dimethyl-5-(7-(piperidine-1-carbonyl)-2,3-dihydro-4H-pyrido[3,2-b] [1,4]oxazin-4-yl)isoindolin-1-one To a solution of 2-methyl-5-(7-(piperidine-1-carbonyl)-2,3-dihydro-4H-pyrido[3,2-b][1,4]oxazin-4-yl)isoindolin-1- one (75.0 mg) in tetrahydrofuran (3.5 mL), methyl iodide (13.1 μL) was added. To the resultant reaction solution, sodium bis(trimethylsilyl)amide (229 μL; 1.0 M tetrahydrofuran solution) was added at −78° C., followed by stirring at −78° C. for 20 minutes, and then a saturated ammonium chloride aqueous solution was added to the resultant reaction solution. The resultant was extracted with dichloromethane (3 mL×3), and the resultant organic layers were combined and dried over sodium sulfate. The resultant was filtered, the obtained filtrate was concentrated under reduced pressure, and the thus obtained residue was purified by silica gel column chromatography (ethyl acetate:hexane=50:50 to 100:0 to ethyl acetate:methanol=90:10) to obtain a mixture (35.6 mg) of the title compound. The obtained mixture was purified by high-performance liquid chromatography (IPA, flow rate: 3 mL/min) using an optically active column (CHIRALPAK IA: Daicel Corporation) to obtain the isomer A (10.8 mg) with a retention time of analysis condition (flow rate: 0.3 mL/min) of 28.1 minutes and the isomer B (11.2 mg) with a retention time of 42.9 minutes.

Isomer A:

$^1$H NMR (400 MHz, $CDCl_3$) δ: 1.44-1.74 (9H, m), 3.12 (3H, s), 3.34-3.74 (4H, m), 3.89-4.05 (2H, m), 4.31-4.50 (3H, m), 7.23 (1H, d, J=1.8 Hz), 7.40 (1H, dd, J=8.6, 1.8 Hz), 7.49 (1H, d, J=1.8 Hz), 7.81-7.86 (2H, m).

LRMS ($ESI^+$) 407 $[M+H]^+$.

Isomer B:

$^1$H NMR (400 MHz, $CDCl_3$) δ: 1.40-1.75 (9H, m), 3.12 (3H, s), 3.34-3.74 (4H, m), 3.89-4.04 (2H, m), 4.32-4.50 (3H, m), 7.23 (1H, d, J=1.8 Hz), 7.40 (1H, dd, J=8.6, 1.8 Hz), 7.49 (1H, d, J=1.8 Hz), 7.80-7.88 (2H, m).

LRMS ($ESI^+$) 407 $[M+H]^+$.

Example 17-1

[Formula 172]

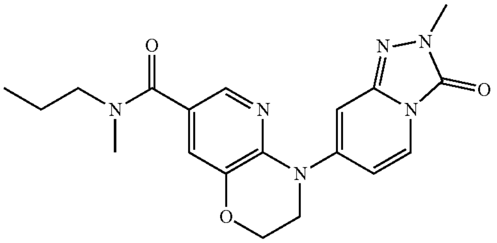

N-Methyl-4-(2-methyl-3-oxo-2,3-dihydro-[1,2,4]triazolo[4,3-a]pyridin-7-yl)-N-propyl-3,4-dihydro-2H-pyrido[3,2-b][1,4]oxazine-7-carboxamide To a solution of 4-(2-methyl-3-oxo-2,3-dihydro-[1,2,4]triazolo[4,3-a]pyridin-7-yl)-N-propyl-3,4-dihydro-2H-pyrido[3,2-b][1,4]oxazine-7-carboxamide (25.0 mg) in N,N-dimethylformamide (0.8 ml), sodium hydride (3.0 mg) and subsequently methyl iodide (8.5 μL) were added at room temperature. After stirring at room temperature for 3.5 hours, a saturated ammonium chloride aqueous solution was added to the resultant reaction solution. The resultant reaction solution was purified by silica gel column chromatography (methanol:water=5:95 to 100:0, further with another column, ethyl acetate:hexane=30:70 to 100:0, subsequently methanol:ethyl acetate=0:100 to 10:90) to obtain the title compound (19.8 mg).

$^1$H NMR (400 MHz, DMSO-$d_6$) δ0.64-0.96 (3H, m), 1.45-1.62 (2H, m), 2.93 (3H, s), 3.18-3.41 (2H, m), 3.49 (3H, s), 3.93 (2H, t, J=4.2 Hz), 4.36 (2H, t, J=4.5 Hz), 6.89 (1H, d, J=1.8 Hz), 6.99 (1H, dd, J=7.6, 2.1 Hz), 7.18-7.26 (1H, m), 7.73-7.86 (2H, m).

LRMS ($ESI^+$) 383 $[M+H]^+$.

Compounds of the following Examples 17-2 to 17-3 were obtained in the same manner as in Example 17-1 by using corresponding starting materials and reactants. Their structures and spectrum data are shown in the following table.

TABLE 168

| Example No. | Chemical Structural Formula | Spectrum Data |
|---|---|---|
| 17-2 | 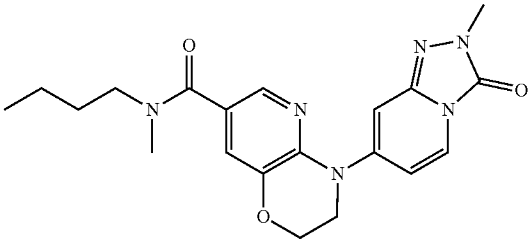 | $^1$H NMR (400 MHz, DMSO-$d_6$) δ 0.68-1.37 (5H, m), 1.42-1.60 (2H, m), 2.93 (3H, s), 3.19-3.44 (2H, m), 3.49 (3H, s), 3.93 (2H, t, J = 4.2 Hz), 4.36 (2H, t, J = 4.5 Hz), 6.89 (1H, d, J = 1.8 Hz), 6.98 (1H, dd, J = 7.9, 1.8 Hz), 7.18-7.27 (1H, m), 7.72-7.85 (2H, m). LRMS ($ESI^+$) 397 $[M + H]^+$. |
| 17-3 | 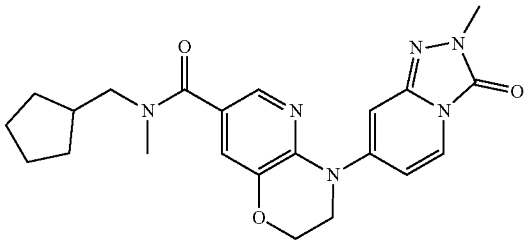 | $^1$H NMR (400 MHz, DMSO-$d_6$) δ 0.87-1.29 (2H, m), 1.31-1.81 (6H, m), 2.08-2.30 (1H, m), 2.94 (3H, s), 3.15-3.43 (2H, m), 3.49 (3H, s), 3.93 (2H, t, J = 4.3 Hz), 4.36 (2H, t, J = 4.3 Hz), 6.88 (1H, d, J = 1.2 Hz), 6.98 (1H, dd, J = 7.6, 2.1 Hz), 7.17-7.26 (1H, m), 7.71-7.85 (2H, m). LRMS ($ESI^+$) 423 $[M + H]^+$. |

Example 18-1

[Formula 173]

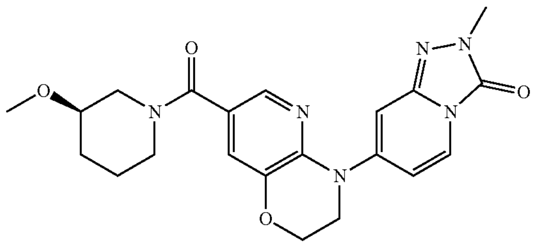

(R)-7-(7-(3-Methoxypiperidine-1-carbonyl)-2,3-dihydro-4H-pyrido[3,2-b] [1,4]oxazin-4-yl)-2-methyl-[1,2,4]triazolo[4,3-a]pyridin-3(2H)-one To a solution of (R)-7-(7-(3-hydroxypiperidine-1-carbonyl)-2,3-dihydro-4H-pyrido[3,2-b][1,4]oxazin-4-yl)-2-methyl-[1,2,4]triazolo[4,3-a]pyridin-3(2H)-one (36.3 mg) in N,N-dimethylformamide (1 mL), sodium hydride (3.9 mg) and subsequently methyl iodide (6.1 μL) were added at room temperature. After stirring at room temperature for 5.5 hours, the resultant reaction solution was purified by silica gel column chromatography (methanol:water=5:95 to 100:0) to obtain the title compound (27.0 mg).

$^1$H NMR (400 MHz, DMSO-$d_6$) δ1.30-2.02 (4H, m), 3.00-3.79 (11H, m), 3.93 (2H, t, J=4.3 Hz), 4.36 (2H, t, J=4.6 Hz), 6.89 (1H, d, J=1.2 Hz), 6.98 (1H, dd, J=7.3, 1.8 Hz), 7.18-7.24 (1H, m), 7.72-7.85 (2H, m).

LRMS (ESI$^+$) 425 [M+H]$^+$.

A compound of the following Example 18-2 was obtained in the same manner as in Example 18-1 by using corresponding starting material and reactant. Its structure and spectrum data are shown in the following table.

Example 19-1

[Formula 174]

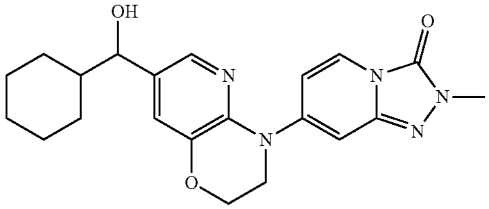

7-(7-(Cyclohexyl(hydroxy)methyl)-2,3-dihydro-4H-pyrido[3,2-b] [1,4]oxazin-4-yl)-2-methyl-[1,2,4]triazolo[4,3-a]pyridin-3 (2H)-one A suspension of 7-(7-(cyclohexanecarbonyl)-2,3-dihydro-4H-pyrido[3,2-b] [1,4]oxazin-4-yl)-2-methyl-[1,2,4]triazolo[4,3-a]pyridin-3(2H)-one (35.0 mg) in methanol (1 mL), sodium borohydride (6.8 mg) was added at room temperature. After stirring at room temperature for 1 hour, water was added to the resultant reaction solution, followed by stirring at room temperature for 1 hour. A residue obtained by concentrating the reaction solution under reduced pressure was purified by silica gel column chromatography (ethyl acetate) to obtain the title compound (35.0 mg).

$^1$H NMR (400 MHz, $CDCl_3$) δ 0.85-1.29 (5H, m), 1.38-1.46 (1H, m), 1.62-1.73 (2H, m), 1.74-1.82 (1H, m), 1.83 (1H, d, J=3.7 Hz), 1.94-2.02 (1H, m), 3.63 (3H, s), 3.86 (2H, dd, J=4.9, 3.7 Hz), 4.33 (1H, dd, J=7.3, 3.1 Hz), 4.39 (2H, dd, J=4.9, 3.7 Hz), 6.56 (1H, d, J=1.8 Hz), 7.04 (1H, dd, J=7.9, 1.8 Hz), 7.16 (1H, d, J=1.8 Hz), 7.65 (1H, d, J=8.6 Hz), 7.73 (1H, d, J=1.8 Hz).

LRMS (ESI$^+$) 396 [M+H]$^+$.

Compounds of the following Examples 19-2 to 19-4 were obtained in the same manner as in Example 19-1 by using corresponding starting materials and reactants. Their structures and spectrum data are shown in the following table.

TABLE 169

| Example No. | Chemical Structural Formula | Spectrum Data |
|---|---|---|
| 18-2 | 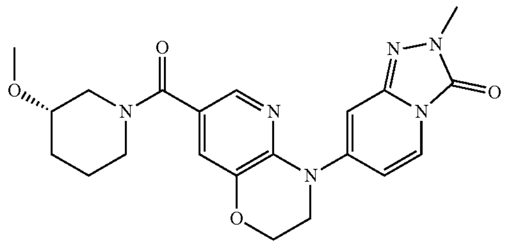 | $^1$H NMR (400 MHz, DMSO-$d_6$) δ 1.26-1.96 (4H, m), 3.06-3.45 (8H, m), 3.49 (3H, s), 3.93 (2H, t, J = 4.5 Hz), 4.36 (2H, t, J = 4.2 Hz), 6.89 (1H, d, J = 1.2 Hz), 6.98 (1H, dd, J = 7.9, 1.8 Hz), 7.20-7.23 (1H, m), 7.73-7.81 (2H, m). LRMS (ESI$^+$) 425 [M + H]$^+$. |

TABLE 170

| Example No. | Chemical Structural Formula | Spectrum Data |
|---|---|---|
| 19-2 | 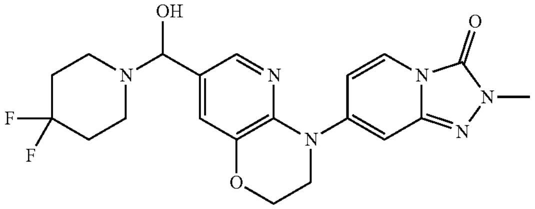 [SMILES: Cn1nc2cc(N3CCOc4cc(C(O)N5CCC(F)(F)CC5)cnc43)ccn2c1=O] | $^1$H NMR (400 MHz, $CDCl_3$) δ 1.17-1.53 (4H, m), 1.54-1.81 (2H, m), 1.98-2.22 (3H, m), 2.36 (1H, s), 3.61 (3H, s), 3.86 (2H, t, J = 4.9 Hz), 4.32-4.44 (3H, m), 6.52 (1H, d, J = 1.2 Hz), 7.01 (1H, dd, J = 7.9, 1.8 Hz), 7.15 (1H, d, J = 1.2 Hz), 7.60 (1H, d, J = 7.9 Hz), 7.72 (1H, d, J = 1.2 Hz). LRMS (ESI$^+$) 432 [M + H]$^+$. |
| 19-3 | 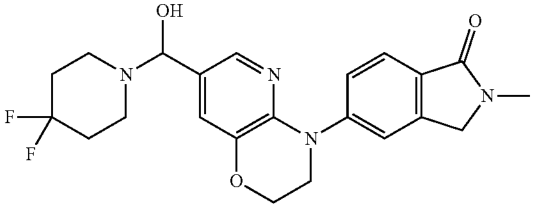 [SMILES: CN1Cc2cc(N3CCOc4cc(C(O)N5CCC(F)(F)CC5)cnc43)ccc2C1=O] | $^1$H NMR (400 MHz, $CDCl_3$) δ 1.17-1.53 (4H, m), 1.61-1.74 (2H, m), 1.82 (1H, d, J = 3.0 Hz), 1.97-2.21 (3H, m), 3.19 (3H, s), 3.94 (2H, dd, J = 5.4, 3.6 Hz), 4.32-4.40 (5H, m), 7.12 (1H, d, J = 1.8 Hz), 7.39 (1H, dd, J = 7.9, 1.8 Hz), 7.54 (1H, d, J = 1.2 Hz), 7.66 (1H, d, J = 1.8 Hz), 7.83 (1H, d, J = 8.5 Hz). LRMS (ESI$^+$) 430 [M + H]$^+$. |
| 19-4 | 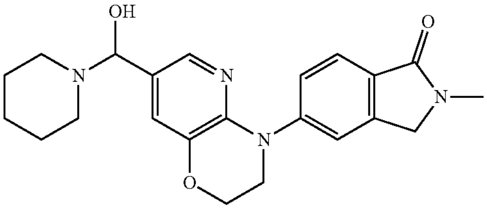 [SMILES: CN1Cc2cc(N3CCOc4cc(C(O)N5CCCCC5)cnc43)ccc2C1=O] | $^1$H NMR (400 MHz, $CDCl_3$) δ 0.80-1.32 (6H, m), 1.36-1.47 (1H, m), 1.52-1.73 (2H, m), 1.73-1.83 (1H, m), 1.86-1.95 (1H, m), 1.96-2.06 (1H, m), 3.19 (3H, s), 3.93 (2H, dd, J = 5.5, 3.7 Hz), 4.24-4.43 (5H, m), 7.13 (1H, d, J = 1.8 Hz), 7.38 (1H, dd, J = 8.6, 1.8 Hz), 7.55 (1H, s), 7.66 (1H, d, J = 1.8 Hz), 7.82 (1H, d, J = 8.6 Hz). LRMS (ESI$^+$) 394 [M + H]$^+$. |

Example 20-1

[Formula 175]

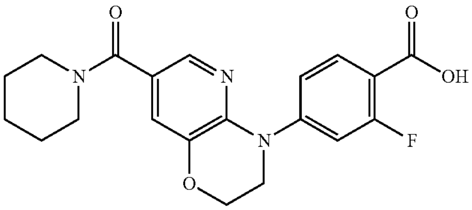

2-Fluoro-4-(7-(piperidine-1-carbonyl)-2,3-dihydro-4H-pyrido[3,2-b][1,4]oxazin-4-yl)benzoic Acid A solution, in N,N-dimethylformamide (3 mL), of (3,4-dihydro-2H-pyrido[3,2-b] [1,4]oxazin-7-yl) (piperidin-1-yl) methanone (100 mg), ethyl 2,4-difluorobenzoate (607 μL) and cesium carbonate (394 mg) was stirred under microwave irradiation at 80° C. for 3 hours and then at 130° C. for 2.5 hours, and the resultant reaction solution was then poured into water. After extraction with ethyl acetate, the resultant organic layers were combined and dried over anhydrous sodium sulfate. The resultant was filtered, the obtained filtrate was concentrated under reduced pressure, and the thus obtained residue was purified by silica gel column chromatography (ethyl acetate:hexane=5:95 to 60:40) to obtain a crude product (135 mg) of ethyl 2-fluoro-4-(7-piperidine-1-carbonyl)-2,3-dihydro-4H-pyrido[3,2-b][1,4]oxazin-4-yl)benzoate. To a solution, in tetrahydrofuran (5.3 mL), of the crude product of ethyl 2-fluoro-4-(7-piperidine-1-carbonyl)-2,3-dihydro-4H-pyrido[3,2-b][1,4]oxazin-4-yl)benzoate (135 mg), a 1 mol/L lithium hydroxide aqueous solution (1.96 mL) was added at room temperature. After stirring at room temperature for 17.3 hours, the resultant reaction solution was concentrated under reduced pressure. The thus obtained residue was washed with ethyl acetate, and a 1 mol/L hydrogen chloride aqueous solution (1.96 mL) was added thereto. After extraction with ethyl acetate, the resultant organic layers were combined and dried over anhydrous sodium sulfate. The resultant was filtered, the obtained filtrate was concentrated under reduced pressure, and the thus obtained residue was purified by silica gel column chromatography (methanol:water=5:95 to 100:0). The resultant was washed with ethyl acetate to obtain the title compound (27.9 mg).

$^1$H NMR (400 MHz, DMSO-$d_6$) δ1.41-1.64 (6H, m), 3.23-3.58 (4H, m), 3.97 (2H, t, J=4.3 Hz), 4.34 (2H, t, J=4.3 Hz), 7.20 (1H, d, J=2.4 Hz), 7.37 (1H, dd, J=8.9, 2.1 Hz), 7.44 (1H, dd, J=13.4, 1.8 Hz), 7.77 (1H, d, J=1.8 Hz), 7.83 (1H, t, J=8.9 Hz), 12.97 (1H, s).

LRMS (ESI$^+$) 386 [M+H]$^+$.

Example 21-1

[Formula 176]

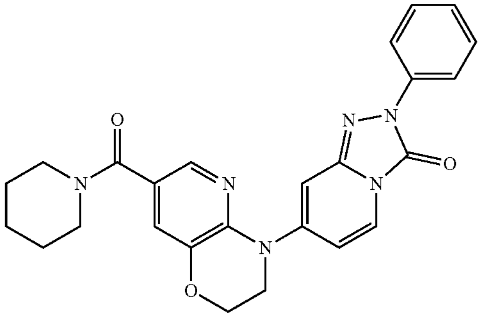

2-Phenyl-7-(7-(piperidine-1-carbonyl)-2,3-dihydro-4H-pyrido[3,2-b] [1,4]oxazin-4-yl)-[1,2,4]triazolo[4,3-a]pyridin-3 (2H)-one To a solution of 7-iodo-[1,2,4]triazolo[4,3-a]pyridin-3 (2H)-one (131 mg) in dichloromethane (20 mL), triethylamine (209 μL) was added. To the resultant reaction solution, methanol (4 mL), phenylboronic acid (91.4 mg) and copper (II) acetate (136 mg) were added at room temperature. The resultant was stirred at room temperature for 1.5 hours, and then heated to reflux for 13.5 hours. The resultant reaction solution was concentrated under reduced pressure, and the thus obtained residue was purified by silica gel column chromatography (ethyl acetate:hexane=5:95 to 100:0) to obtain a crude product of 7-iodo-2-phenyl-[1,2,4]triazolo[4,3-a]pyridin-3(2H)-one (3.5 mg). A solution, in 1,4-dioxane (1.0 mL), of the crude product (3.5 mg) of 7-iodo-2-phenyl-[1,2,4]triazolo[4,3-a]pyridin-3(2H)-one, (3,4-dihydro-2H-pyrido[3,2-b][1,4]oxazin-7-yl)(piperidin-1-yl)methanone (2.6 mg), tris(dibenzylideneacetone)dipalladium (0) (0.5 mg), 4,5-bis(diphenylphosphino)-9,9-dimethylxanthene (Xantphos) (0.6 mg) and sodium tert-butoxide (2.0 mg) was heated to reflux for 4.5 hours, and then concentrated under reduced pressure. The thus obtained residue was purified by silica gel column chromatography (ethyl acetate:hexane=30:70 to 100:0), and the resultant was washed with diethyl ether to obtain the title compound (3.1 mg).

$^1$H NMR (400 MHz, DMSO-$d_6$) δ1.39-1.69 (6H, m), 3.17-3.68 (4H, m), 3.97 (2H, t, J=4.3 Hz), 4.39 (2H, t, J=4.3 Hz), 6.99 (1H, d, J=1.8 Hz), 7.08 (1H, dd, J=7.9, 1.8 Hz), 7.24 (1H, d, J=1.8 Hz), 7.25-7.31 (1H, m), 7.51 (2H, t, J=8.3 Hz), 7.81 (1H, d, J=1.8 Hz), 7.86 (1H, d, J=7.9 Hz), 8.05 (2H, d, J=7.9 Hz).

LRMS (ESI$^+$) 457 [M+H]$^+$.

Example 22-L

[Formula 177]

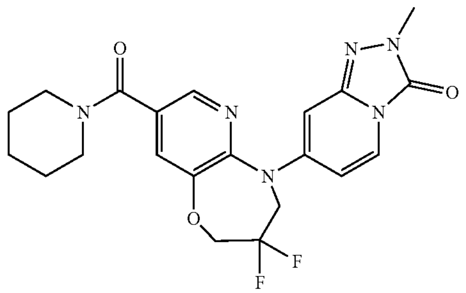

7-(3,3-Difluoro-8-(piperidine-1-carbonyl)-3,4-dihydropyrido[3,2-b][1,4]oxazepin-5(2H)-yl)-2-methyl-[1,2,4]triazolo[4,3-a]pyridin-3 (2H)-one To a solution of 2,4,6-trichlorophenyl 5-acetyl-3,3-difluoro-2,3,4,5-tetrahydropyrido[3,2-b][1,4]oxazepine-8-carboxylate (47.4 mg) in tetrahydrofuran (1 mL), triethylamine (24 μL), N,N-dimethyl-4-aminopyridine (0.7 mg) and piperidine (13.7 μL) were added. After stirring at 45° C. for 6 hours, methanol (0.6 mL) and an aqueous solution (0.6 mL) of potassium hydroxide (16.1 mg) were added to the resultant reaction solution at room temperature. After stirring at room temperature for 21.2 hours, a 1 mol/L hydrogen chloride aqueous solution (287 μL) was added thereto. The resultant reaction solution was concentrated under reduced pressure, and extracted with ethyl acetate, and the resultant organic layers were combined, washed with saturated saline and dried over anhydrous sodium sulfate. The resultant was concentrated under reduced pressure to obtain a crude product of (3,3-difluoro-2,3,4,5-tetrahydropyrido[3,2-b][1,4]oxazepin-8-yl)(piperidin-1-yl)methanone (40.3 mg).

A solution, in 1,4-dioxane (1.2 mL), of the crude product (40.3 mg) of (3,3-difluoro-2,3,4,5-tetrahydropyrido[3,2-b][1,4]oxazepin-8-yl)(piperidin-1-yl)methanone, 7-iodo-2-methyl-[1,2,4]triazolo[4,3-a]pyridin-3(2H)-one (38.0 mg), tris(dibenzylideneacetone)dipalladium (0) (5.3 mg), 4,5-bis(diphenylphosphino)-9,9-dimethylxanthene (Xantphos) (6.7 mg) and sodium tert-butoxide (22.1 mg) was stirred at 85° C. for 2 hours. The resultant reaction solution was concentrated under reduced pressure, and the thus obtained residue was purified by silica gel column chromatography (ethyl acetate:hexane=10:90 to 100:0, subsequently methanol: ethyl acetate=0:100 to 10:90) to obtain the title compound (18.8 mg).

$^1$H NMR (400 MHz, DMSO-$d_6$) δ 1.42-1.65 (6H, m), 3.26-3.63 (7H, m), 4.51-4.64 (4H, m), 6.62 (1H, dd, J=7.9, 1.8 Hz), 7.01 (1H, d, J=1.2 Hz), 7.46 (1H, d, J=2.4 Hz), 7.73 (1H, d, J=6.7 Hz), 7.99 (1H, d, J=1.8 Hz).

LRMS (ESI$^+$) 445 [M+H]$^+$.

Example 23-L

[Formula 178]

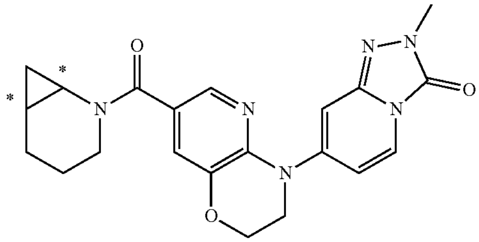

Isomer A 7-(7-(2-Azabicyclo[4,1,0]heptane-2-carbonyl)-2,3-dihydro-4H-pyrido[3,2-b][1,4]oxazin-4-yl)-2-methyl-[1,2,4]triazolo[4,3-a]pyridin-3(2H)-one Isomer B 7-(7-(2-Azabicyclo[4,1,0]heptane-2-carbonyl)-2,3-dihydro-4H-pyrido[3,2-b][1,4]oxazin-4-yl)-2-methyl-[1,2,4]triazolo[4,3-a]pyridin-3(2H)-one A racemic mixture of 7-(7-(2-azabicyclo[4,1,0]heptane-2-carbonyl)-2,3-dihydro-4H-pyrido[3,2-b] [1,4]oxazin-4- yl)-2-methyl-[1,2,4]triazolo[4,3-a]pyridin-3 (2H)-one (77.9 mg) was purified by high-performance liquid chromatography (ethanol:dichloromethane=5:95, flow rate: 7.5 mL/min) using an optically active column (CHIRALPAK IA: Daicel Corporation) to obtain the isomer A (21.0 mg) with a retention time of analysis condition (flow rate: 0.5 mL/min) of 11.8 minutes and the isomer B (17.0 mg) with a retention time of 13.9 minutes.

Isomer A:

$^1$H NMR (400 MHz, DMSO-d$_6$) δ0.37-0.58 (1H, m), 0.62-0.93 (1H, m), 1.20-1.40 (2H, m), 1.47-1.70 (1H, m), 1.73-1.87 (2H, m), 2.37-3.07 (2H, m), 3.49 (3H, s), 3.85-4.08 (3H, m), 4.33-4.39 (2H, m), 6.89 (1H, d, J=1.2 Hz), 6.98 (1H, dd, J=7.6, 2.1 Hz), 7.21-7.45 (1H, m), 7.72 (1H, d, J=8.6 Hz), 7.86-8.09 (1H, m).

LRMS (ESI$^+$) 407 [M+H]$^+$.

Isomer B:

$^1$H NMR (400 MHz, DMSO-d$_6$) δ0.28-0.59 (1H, m), 0.60-0.95 (1H, m), 1.19-1.43 (2H, m), 1.50-1.69 (1H, m), 1.73-1.89 (2H, m), 2.40-3.05 (2H, m), 3.49 (3H, s), 3.84-4.07 (3H, m), 4.31-4.42 (2H, m), 6.89 (1H, d, J=1.2 Hz), 6.98 (1H, dd, J=7.6, 2.1 Hz), 7.15-7.47 (1H, m), 7.72 (1H, d, J=8.6 Hz), 7.86-8.12 (1H, m).

LRMS (ESI$^+$) 407 [M+H]$^+$.

An isomer A and an isomer B of the following Example 23-2 were obtained in the same manner as in Example 23-1 by using corresponding starting materials and reactants. Their structures and spectrum data are shown in the following table.

Example 24-L

[Formula 179]

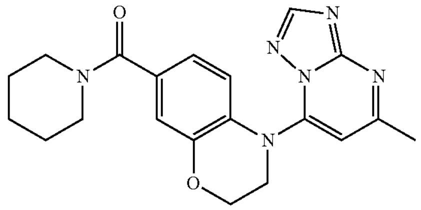

(4-(5-Methyl-[1,2,4]triazolo[1,5-a]pyrimidin-7-yl)-3,4-dihydro-2H-benzo[b][1,4]oxazin-7-yl)(piperidin-1-yl)methanone A solution, in ethanol (2 mL), of (3,4-dihydro-2H-benzo[b][1,4]oxazin-7-yl)(piperidin-1-yl)methanone (50.0 mg) and 7-chloro-5-methyl-[1,2,4]triazolo[1,5-a]pyrimidine (50.0 mg) was stirred at room temperature for 24 hours. The resultant reaction mixture was concentrated under reduced pressure, and the thus obtained residue was purified by silica gel column chromatography (ethyl acetate:methanol=9:1) to obtain the title compound (74.0 mg).

$^1$H NMR (400 MHz, $CDCl_3$) δ 1.48-1.76 (6H, m), 2.59 (3H, s), 3.29-3.83 (4H, m), 4.29 (2H, t, J=4.2 Hz), 4.36 (2H, t, J=4.2 Hz), 6.64 (1H, s), 6.97 (1H, dd, J=8.5, 1.8 Hz), 7.06 (1H, d, J=1.8 Hz), 7.16 (1H, d, J=8.5 Hz), 8.41 (1H, s).

LRMS (ESI$^+$) 379 [M+H]$^+$.

Compounds of the following Examples 24-2 to 24-3 were obtained in the same manner as in Example 24-1 by using corresponding starting materials and reactants. Their structures and spectrum data are shown in the following table.

TABLE 171

| Example No. | Chemical Structural Formula | Spectrum Data |
|---|---|---|
| 23-2 Isomer A | 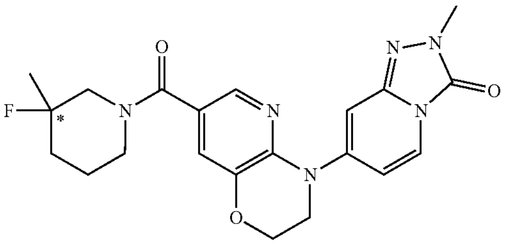 [SMILES: Cn1nc2cc(N3CCOc4cc(C(=O)N5CCCC(C)(F)C5)cnc43)ccn2c1=O] | $^1$H NMR (400 MHz, DMSO-d$_6$) δ 1.11-1.40 (3H, m), 1.42-1.78 (3H, m), 1.80-1.95 (1H, m), 2.58-3.30 (2H, m), 3.49 (3H, s), 3.55-4.58 (6H, m), 6.89 (1H, d, J = 1.8 Hz), 6.99 (1H, d d, J = 7.6, 2.1 Hz), 7.18 (1H, d, J = 2.4 Hz), 7.73-7.79 (2H, m). LRMS (ESI$^+$) 427 [M + H]$^+$. |
| 23-2 Isomer B | 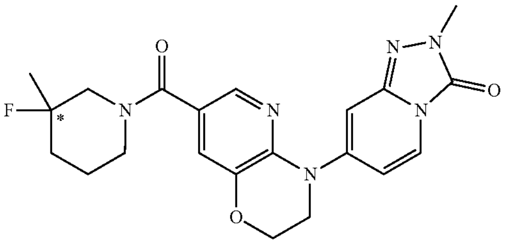 [SMILES: Cn1nc2cc(N3CCOc4cc(C(=O)N5CCCC(C)(F)C5)cnc43)ccn2c1=O] | $^1$H NMR (400 MHz, DMSO-d$_6$) δ 1.10-1.42 (3H, m), 1.43-1.78 (3H, m), 1.80-1.94 (1H, m), 2.62-3.36 (2H, m), 3.49 (3H, s), 3.55-4.47 (6H, m), 6.89 (1H, d, J = 1.2 Hz), 6.99 (1H, d d, J = 7.6, 2.1 Hz), 7.18 (1H, d, J = 2.4 Hz), 7.73-7.79 (2H, m). LRMS (ESI$^+$) 427 [M + H]$^+$. |

TABLE 172

| Example No. | Chemical Structural Formula | Spectrum Data |
|---|---|---|
| 24-2 | 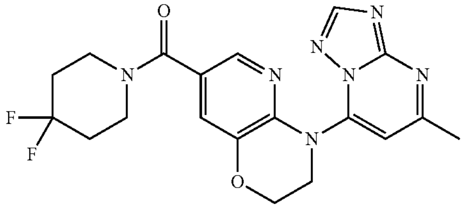 [SMILES: Cc1cc(N2CCOc3cc(C(=O)N4CCC(F)(F)CC4)cnc32)n2ncnc2n1] | $^1$H NMR (400 MHz, $CDCl_3$) δ 1.90-2.17 (4H, m), 2.60 (3H, s), 3.51-3.99 (4H, m), 4.28-4.39 (4H, m), 6.65 (1H, s), 6.98 (1H, dd, J = 8.5, 1.8 Hz), 7.08 (1H, d, J = 1.8 Hz), 7.17 (1H, d, J = 8.5Hz), 8.42 (1H, s). LRMS (ESI$^+$) 415 [M + H]$^+$. |
| 24-3 | 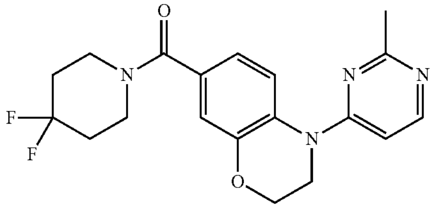 [SMILES: Cc1nccc(N2CCOc3cc(C(=O)N4CCC(F)(F)CC4)ccc32)n1] | $^1$H NMR (400 MHz, $CDCl_3$) δ 1.89-2.16 (4H, m), 2.61 (3H, s), 3.54-3.96 (4H, m), 4.23 (2H, t, J = 4.3 Hz), 4.32 (2H, t, J = 4.3 Hz), 6.96 (1H, dd, J = 8.6, 2.4 Hz), 6.99 (1H, d, J = 6.1 Hz), 7.02 (1H, d, J = 2.4 Hz), 7.45 (1H, d, J = 8.6 Hz), 8.27 (1H, d, J = 6.1 Hz). LRMS (ESI$^+$) 375 [M + H]$^+$. |

Example 25-1

[Formula 180]

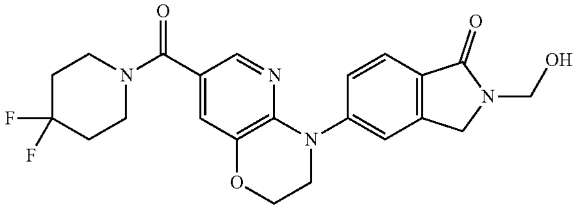

5-(7-(4,4-Difluoropiperidine-1-carbonyl)-2,3-dihydro-4H-pyrido[3,2-b]oxazin-4-yl)-2-(hydroxymethyl)isoindolin-1-one To a solution of 5-(7-(4,4-difluoropiperidine-1-carbonyl)-2,3-dihydro-4H-pyrido[3,2-b]oxazin-4-yl)isoindolin-1-one (141 mg) in tetrahydrofuran (2.0 mL), formaldehyde (37% aqueous solution, 30 μL) and potassium hydroxide (48% aqueous solution, 10 μL) were added at room temperature, followed by stirring for 1 hour. The resultant reaction mixture was poured into ice water, followed by extraction with ethyl acetate. The thus extracted organic layers were combined, washed with saturated saline, and dried over anhydrous sodium sulfate. The resultant reaction mixture was concentrated under reduced pressure, and the thus obtained residue was purified by silica gel column chromatography (ethyl acetate:methanol=10:1) to obtain the title compound (117 mg).

$^1$H NMR (400 MHz, $CDCl_3$) δ 1.98-2.04 (4H, m), 3.05 (1H, t, J=6.9 Hz), 3.72-3.77 (4H, m), 3.97 (2H, t, J=4.6 Hz), 4.39 (2H, t, J=4.6 Hz), 4.59 (2H, s), 5.14 (2H, d, J=6.5 Hz), 7.24 (1H, d, J=1.9 Hz), 7.44 (1H, dd, J=8.4, 1.9 Hz), 7.56 (1H, d, J=1.1 Hz), 7.85 (1H, d, J=1.9 Hz), 7.88 (1H, d, J=8.4 Hz).

LRMS (ESI$^+$) 445 [M+H]$^+$.

Example 26-1

[Formula 181]

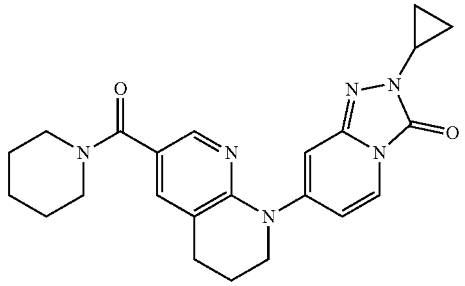

2-Cyclopropyl-7-(6-(piperidine-1-carbonyl)-3,4-dihydro-1,8-naphthylidin-1(2H)-yl)-[1,2,4]triazolo[4,3-a]pyridin-3(2H)-one To a suspension of 7-(6-(piperidine-1-carbonyl)-3,4-dihydro-1,8-naphthylidin-1(2H)-yl)-[1,2,4]triazolo[4,3-a]pyridin-3(2H)-one (41.0 mg) in toluene (540 μL), cyclopropylboronic acid (27.8 mg), copper acetate (39.2 mg), pyridine (72 μL) and triethylamine (72 μL) were added, and the resultant was stirred under microwave irradiation at 140° C. for 1 hour. The resultant reaction mixture was concentrated under reduced pressure, and the thus obtained residue was purified by silica gel column chromatography (ethyl acetate:hexane=40:60 to ethyl acetate:methanol=80:20) to obtain the title compound (10.1 mg).

$^1$H NMR (400 MHz, DMSO-$d_6$) δ0.91-1.06 (4H, m), 1.44-1.69 (6H, m), 1.94-2.05 (2H, m), 2.82 (2H, t, J=6.4 Hz), 3.35-3.58 (5H, m), 3.78 (2H, t, J=5.8 Hz), 6.76 (1H, dd, J=7.3, 1.8 Hz), 6.85-6.88 (1H, m), 7.47-7.51 (1H, m), 7.67 (1H, d, J=7.9 Hz), 7.98 (1H, d, J=2.4 Hz).

LRMS (ESI$^+$) 419 [M+H]$^+$.

A compound of the following Example 26-2 was obtained in the same manner as in Example 26-1 by using corresponding starting material and reactant. Its structure and spectrum data are shown in the following table.

TABLE 173

| Example No. | Chemical Structural Formula | Spectrum Data |
|---|---|---|
| 26-2 | 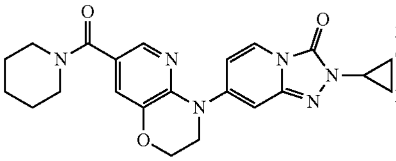 | $^1$H NMR (400 MHz, DMSO-$d_6$) δ 0.90-1.07 (4H, m), 1.41-1.65 (6H, m), 3.24-3.58 (5H, m), 3.91 (2H, t, J = 4.3 Hz), 4.35 (2H, t, J = 4.3 Hz), 6.86 (1H, d, J = 12 Hz), 6.96 (1H, dd, J = 7.3, 1.8 Hz), 7.20 (1H, d, J = 1.8 Hz), 7.73 (1H, d, J = 8.6 Hz), 7.77 (1H, d, J = 1.8 Hz). LRMS (ESI$^+$) 421 [M + H]$^+$. |

Example 27-1

[Formula 182]

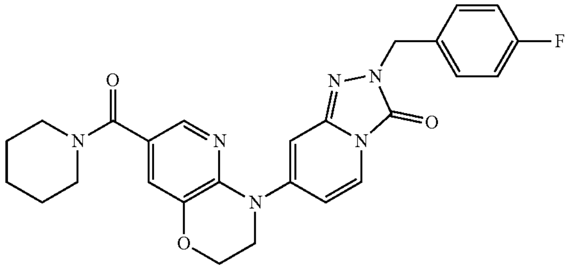

2-(4-Fluorobenzyl)-7-(7-piperidine-1-carbonyl)-2,3-dihydro-4H-pyrido[3,2-b] [1,4]oxazin-4-yl)-[1,2,4] triazolo[4,3-a]pyridin-3(2H)-one To a solution of 7-(7-(piperidine-1-carbonyl)-2,3-dihydro-4H-pyrido[3,2-b] [1,4]oxazin-4-yl)-[1,2,4]triazolo[4,3-a]pyridin-3 (2H)-one (41.8 mg) in N, N-dimethyl formamide (500 μL), 1-(bromomethyl)-4-fluorobenzene (22.9 mg) was added at room temperature, and sodium hydride (4.8 mg) was further added thereto, followed by stirring at room temperature for 22 hours. The resultant reaction mixture was purified by silica gel column chromatography (ethyl acetate: hexane=10:90 to 100:0) to obtain the title compound (29.7 mg).

$^1$H NMR (400 MHz, DMSO-$d_6$) δ 1.43-1.64 (6H, m), 3.28-3.57 (4H, m), 3.91 (2H, t, J=4.6 Hz), 4.35 (2H, t, J=4.3 Hz), 5.05 (2H, s), 6.88 (1H, d, J=1.8 Hz), 7.00 (1H, dd, J=7.9, 1.8 Hz), 7.13-7.22 (3H, m), 7.31-7.36 (2H, m), 7.76-7.81 (2H, m).

LRMS (ESI$^+$) 489 [M+H]$^+$.

Compounds of the following Examples 27-2 to 27-8 were obtained in the same manner as in Example 27-1 by using corresponding starting materials and reactants. Their structures and spectrum data are shown in the following tables.

TABLE 174

| Example No. | Chemical Structural Formula | Spectrum Data |
|---|---|---|
| 27-2 | 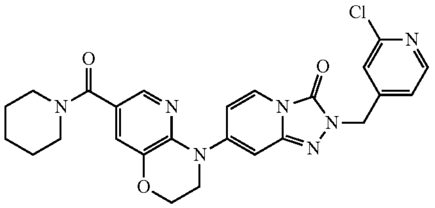 [SMILES: O=C(c1cnc2c(c1)OCCN2c1ccn2c(=O)n(Cc3ccnc(Cl)c3)nc2c1)N1CCCCC1] | $^1$H NMR (400 MHz, DMSO-$d_6$) δ 1.42-1.64 (6H, m), 3.27-3.62 (4H, m), 3.93 (2H, t, J = 4.6 Hz), 4.36 (2H, t, J = 4.3 Hz), 5.16 (2H, s), 6.90 (1H, d, J = 1.8 Hz), 7.03 (1H, dd, J = 7.6, 2.1 Hz), 7.21 (1H, d, J = 1.8 Hz), 7.28 (1H, dd, J = 5.2, 1.5 Hz), 7.42 (1H, s), 7.78 (1H, d, J = 2.4 Hz), 7.81 (1H, d, J = 8.6 Hz), 8.36 (1H d, J = 4.3 Hz). LRMS (ESI$^+$) 506 [M + H]$^+$. |
| 27-3 | 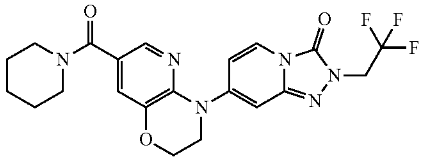 [SMILES: O=C(c1cnc2c(c1)OCCN2c1ccn2c(=O)n(CC(F)(F)F)nc2c1)N1CCCCC1] | $^1$H NMR (400 MHz, DMSO-$d_6$) δ 1.40-1.66 (6H, m), 3.22-3.63 (4H, m), 3.94 (2H, t, J = 4.3 Hz), 4.37 (2H, t, J = 4.3 Hz), 4.78 (2H, q, J = 9.0 Hz), 6.92 (1H, d, J = 1.8 Hz), 7.05 (1H, dd, J = 7.6, 2.1 Hz), 7.22 (1H, d, J = 1.8 Hz), 7.77-7.82 (2H, m). LRMS (ESI$^+$) 463 [M + H]$^+$. |
| 27-4 | 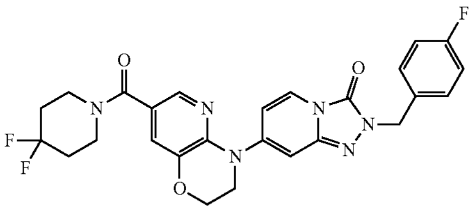 [SMILES: O=C(c1cnc2c(c1)OCCN2c1ccn2c(=O)n(Cc3ccc(F)cc3)nc2c1)N1CCC(F)(F)CC1] | $^1$H NMR (400 MHz, DMSO-$d_6$) δ 1.95-2.10 (4H, m), 3.49-3.67 (4H, m), 3.92 (2H, t, J = 4.3 Hz), 4.36 (2H, t, J = 4.3 Hz), 5.05 (2H, s), 6.90 (1H, d, J = 1.2 Hz), 6.99 (1H, dd, J = 7.3, 1.8 Hz), 7.13-7.20 (2H, m), 7.29 (1H, d, J = 2.4 Hz), 7.31-7.37 (2H, m), 7.80 (1H, d, J = 7.3 Hz), 7.85 (1H d, J = 1.8 Hz), LRMS (ESI$^+$) 525 [M + H]$^+$. |

TABLE 174-continued

| Example No. | Chemical Structural Formula | Spectrum Data |
|---|---|---|
| 27-5 | 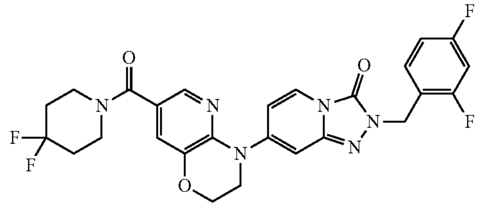 [SMILES: O=C(c1cnc2c(c1)OCCN2c1ccn2c(=O)n(Cc3ccc(F)cc3F)nc2c1)N1CCC(F)(F)CC1] | $^1$H NMR (400 MHz, DMSO-$d_6$) δ 1.95-2.10 (4H, m), 3.47-3.68 (4H, m), 3.91 (2H, t, J = 4.3 Hz), 4.35 (2H, t, J = 4.6 Hz), 5.08 (2H, s), 6.90 (1H, d, J = 1.8 Hz), 6.99 (1H, dd, J = 7.6, 2.1 Hz), 7.03-7.12 (1H, m), 7.22-7.31 (2H, m), 7.35-7.44 (1H, m), 7.79 (1H, d, J = 7.3 Hz), 7.85 (1H, d, J = 1.8 Hz). LRMS (ESI$^+$) 543 [M + H]$^+$. |

TABLE 175

| Example No. | Chemical Structural Formula | Spectrum Data |
|---|---|---|
| 27-6 | 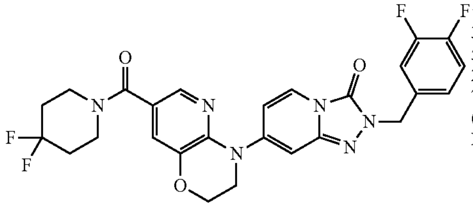 | $^1$H NMR (400 MHz, DMSO-$d_6$) δ 1.93-2.12 (4H, m), 3.45-3.69 (4H, m), 3.93 (2H, t, J = 4.3 Hz), 4.36 (2H, t, J = 4.3 Hz), 5.07 (2H, s), 6.90 (1H, d, J = 1.2 Hz), 7.00 (1H, dd, J = 7.6, 2.1 Hz), 7.11-7.17 (1H, m), 7.30 (1H, d, J = 1.8 Hz), 7.34-7.45 (2H m), 7.80 (1H, d, J = 7.3 Hz), 7.85 (1H, d, J = 1.8 Hz). LRMS (ESI$^+$) 543 [M + H]$^+$. |
| 27-7 | 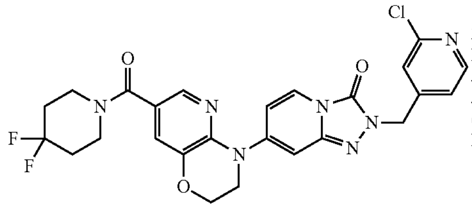 [SMILES: O=C(c1cnc2c(c1)OCCN2c1ccn2c(=O)n(Cc3ccc(F)c(F)c3)nc2c1)N1CCC(F)(F)CC1] | $^1$H NMR (400 MHz, DMSO-$d_6$) δ 1.96-2.10 (4H, m), 3.47-3.70 (4H, m), 3.94 (2H, t, J = 4.3 Hz), 4.37 (2H, t, J = 4.3 Hz), 5.16 (2H, s), 6.92 (1H, d, J = 1.2 Hz), 7.02 (1H, dd, J = 7.6, 2.1 Hz), 7.28 (1H, dd, J = 4.9, 1.2 Hz), 7.30 (1H, d, J = 1.8 Hz), 7.42 (1H, s), 7.82 (1H, d, ,T = 8.6 Hz), 7.86 (1H, d, J = 2.4 Hz), 8.37 (1H, d, J = 5.5 Hz). LRMS (ESI$^+$) 542 [M + H]$^+$. |
| 27-8 | 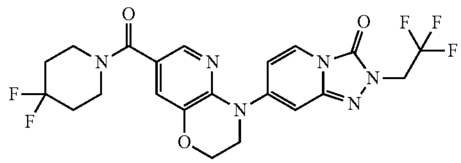 [SMILES: O=C(c1cnc2c(c1)OCCN2c1ccn2c(=O)n(CC(F)(F)F)nc2c1)N1CCC(F)(F)CC1] | $^1$H NMR (400 MHz, DMSO-$d_6$) δ 1.95-2.10 (4H, m), 3.45-3.70 (4H, m), 3.95 (2H, t, J = 4.6 Hz), 4.37 (2H, t, J = 4.3 Hz), 4.79 (2H, q, J = 9.0 Hz), 6.93 (1H, d, J = 1.8 Hz), 7.04 (1H, dd, J = 7.6, 2.1 Hz), 7.31 (1H, d, J = 1.8 Hz), 7.81 (1H, d, J = 8.6 Hz), 7.87 (1H, d, J = 1.8 Hz). LRMS (ESI$^+$) 499 [M + H]$^+$. |

Example 28-1

[Formula 183]

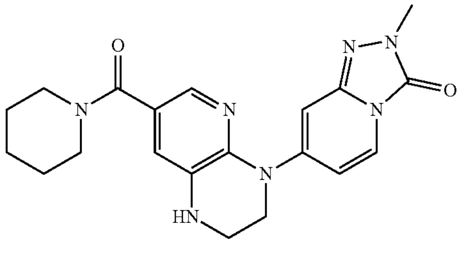

2-Methyl-7-(7-(piperidine-1-carbonyl)-2,3-dihydropyrido[2,3-b]pyrazin-4(1H)-yl)-[1,2,4]triazolo[4,3-a]pyridin-3(2H)-one To a mixed solution, in ethanol (70 mL) and N,N-dimethylacetamide (70 mL), of di-tert-butyl 7-bromo-2,3-dihydropyrido[2,3-b]pyrazine-1,4-dicarboxylate (2.69 g), [1,1'-bis(diphenylphosphino)ferrocene]palladium (II) dichloride dichloromethane adduct (795 mg) and triethylamine (3.62 mL) were added at room temperature, and the resultant mixture was stirred under heating to reflux for 3 hours under carbon monoxide atmosphere, followed by concentrating the resultant reaction solution under reduced pressure. The thus obtained residue was purified by silica gel column chromatography (ethyl acetate:hexane=0:100 to 100:0) to obtain a mixture containing 1-(tert-butyl) 7-ethyl 3,4-dihydropyrido[2,3-b]pyrazine-1,7 (2H)-dicarboxylate (1.51 g).

To a solution, in 1,4-dioxane (31 mL), of the mixture (1.51 g) containing 1-(tert-butyl) 7-ethyl 3,4-dihydropyrido[2,3-b]pyrazine-1,7 (2H)-dicarboxylate and 7-iodo-2- methyl-[1,2,4]triazolo[4,3-a]pyridin-3(2H)-one (946 mg), tris(dibenzylideneacetone)dipalladium (0) (143 mg), 4,5-bis (diphenylphosphino)-9,9-dimethylxanthene (Xantphos) (181 mg) and sodium tert-butoxide (1.50 g) were added, followed by stirring under heating to reflux for 1.5 hours. The resultant reaction solution was concentrated under reduced pressure and washed with dichloromethane, and a solid was collected by filtration. The thus obtained solid was washed with methanol, the resultant filtrate was concentrated under reduced pressure and washed with ethyl acetate to obtain a mixture containing 2-(2-methyl-3-oxo-2,3-dihydro-[1,2,4]triazolo[4,3-a]pyridin-7-yl)1,2,3,4-tetrahydropyrido[2,3-b]pyrazine-7-carboxylic acid sodium salt (1.62 g).

To a solution, in N,N-dimethylformamide (7.2 mL), of the mixture (469 mg) containing 2-(2-methyl-3-oxo-2,3-dihydro-[1,2,4]triazo[4,3-a]pyridin-7-yl)1,2,3,4-tetrahydropyrido[2,3-b]pyrazine-7-carboxylic acid sodium salt, piperidine (428 μL), diisopropylethylamine (1.22 mL) and 1-[bis (dimethylamino)methylene]-1H-1,2,3-triazolo[4,5-b] pyridinium 3-oxide hexafluorophosphate (658 mg) were added, the resultant was stirred at room temperature for 6 hours, and the resultant reaction solution was poured into water. After extraction with dichloromethane, the resultant organic layers were combined and dried over anhydrous sodium sulfate. The resultant was concentrated under reduced pressure, and the thus obtained residue was purified by silica gel column chromatography (ethyl acetate: hexane=10:90 to 100:0, methanol:ethyl acetate=0:100 to 20:80) to obtain the title compound (306 mg).

$^1$H NMR (400 MHz, DMSO-$d_6$) δ1.41-1.71 (6H, m), 3.12-3.27 (6H, m), 3.47 (3H, s), 3.76 (2H, t, J=4.9 Hz), 6.39 (1H, t, J=7.3 Hz), 6.71 (1H, d, J=1.2 Hz), 6.83-6.87 (2H, m), 7.40 (1H, d, J=2.4 Hz), 7.66 (1H, d, J=7.9 Hz).

LRMS (ESI$^+$) 394 [M+H]$^+$.

A compound of the following Example 28-2 was obtained in the same manner as in Example 28-1 by using corresponding starting material and reactant. Its structure and spectrum data are shown in the following table.

Example 29-1

[Formula 184]

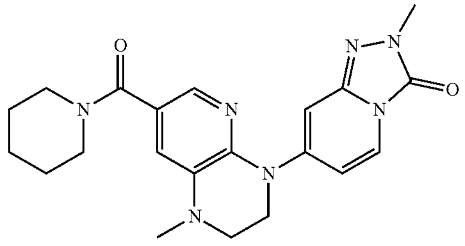

2-Methyl-7-(l-methyl-7-(piperidine-1-carbonyl)-2,3-dihydropyrido[2,3-b]pyrazin-4(1H)-yl)-[1,2,4]triazolo[4,3-a]pyridin-3(2H)-one To a solution of 2-methyl-7-(7-(piperidine-1-carbonyl)-2,3-dihydropyrido[2,3-b]pyrazin-4(1H)-yl)-[1,2,4]triazolo[4,3-a]pyridin-3(2H)-one (48.4 mg) in N,N-dimethylformamide (1 mL), sodium hydride (5.9 mg) and subsequently methyl iodide (15.3 μL) were added at room temperature. After stirring at room temperature for 4 days, the resultant reaction solution was purified by silica gel column chromatography (methanol:water=10:90 to 100:0) to obtain the title compound (10.4 mg).

$^1$H NMR (400 MHz, DMSO-$d_6$) δ1.42-1.65 (6H, m), 2.90 (3H, s), 3.36-3.54 (9H, m), 3.84-3.90 (2H, m), 6.77-6.79 (1H, m), 6.80-6.84 (2H, m), 7.44 (1H, d, J=1.8 Hz), 7.67 (1H, d, J=6.7 Hz).

LRMS (ESI$^+$) 408 [M+H]$^+$.

Compounds of the following Examples 29-2 to 29-5 were obtained in the same manner as in Example 29-1 by using corresponding starting materials and reactants. Their structures and spectrum data are shown in the following table.

TABLE 176

| Example No. | Chemical Structural Formula | Spectrum Data |
|---|---|---|
| 28-2 | 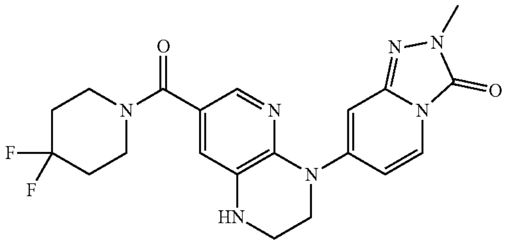 | $^1$H NMR (400 MHz, DMSO-$d_6$) δ 1.93-2.09 (4H, m), 3.38-3.44 (2H, m), 3.48 (3H, s), 3.50-3.64 (4H, m), 3.77 (2H, t, J = 4.6 Hz), 6.38-6.43 (1H, m), 6.73 (1H, d, J = 1.2 Hz), 6.85 (1H, dd, J = 7.6, 2.1 Hz), 6.90 (1H, d, J = 2.4 Hz), 7.49 (1H, d, J = 1.8 Hz), 7.67 (1H, d, J = 7.3 Hz). LRMS (ESI$^+$) 430 [M + H]$^+$. |

TABLE 177

| Example No. | Chemical Structural Formula | Spectrum Data |
|---|---|---|
| 29-2 | 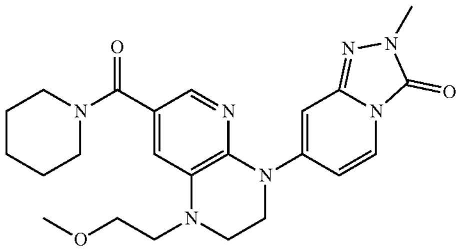 [SMILES: COCCN1CCN(c2ccn3c(=O)n(C)nc3c2)c2ncc(C(=O)N3CCCCC3)cc21] | $^1$H NMR (400 MHz, DMSO-$d_6$) δ 1.43-1.65 (6H, m), 3.25 (3H, s), 3.36-3.58 (13H, m), 3.79 (2H, t, J = 4.9 Hz), 6.72 (1H, d, J = 1.8 Hz), 6.81 (1H, dd, J = 7.6, 2.1 Hz), 6.91 (1H, d, J = 1.8 Hz), 7.40 (1H, d, J = 1.8 Hz), 7.65 (1H, d, J = 7.9 Hz). LRMS (ESI$^+$) 452 [M + H]$^+$. |
| 29-3 | 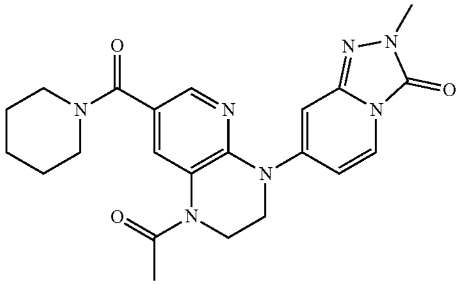 [SMILES: CC(=O)N1CCN(c2ccn3c(=O)n(C)nc3c2)c2ncc(C(=O)N3CCCCC3)cc21] | $^1$H NMR (400 MHz, DMSO-$d_6$) δ 1.41-1.67 (6H, m), 2.25 (3H, s), 3.34-3.63 (7H, m), 3.85-4.02 (4H, m), 6.81 (1H, dd, J = 7.6, 2.1 Hz), 7.00 (1H, s), 7.74 (1H, d, J = 7.3 Hz), 7.94 (1H, d, J = 1.2 Hz), 7.98-8.48 (1H, m). LRMS (ESI$^+$) 436 [M + H]$^+$. |
| 29-4 | 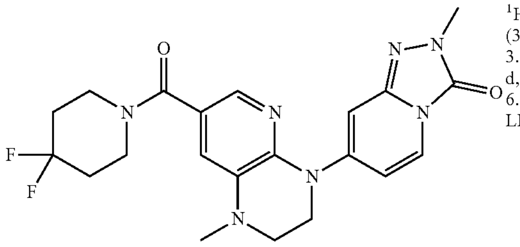 | $^1$H NMR (400 MHz, DMSO-$d_6$) δ 1.95-2.09 (4H, m), 2.91 (3H, s), 3.38-3.45 (2H, m), 3.48 (3H, s), 3.51-3.67 (4H, m), 3.85-3.91 (2H, m), 6.81 (2H, dq, J = 11.6, 3.1 Hz), 6.90 (1H, d, J = 1.8 Hz), 7.52 (1H, d, J = 1.8 Hz), 7.68 (1H, d, J = 6.7 Hz). LRMS (ESI$^+$) 444 [M + H]$^+$. |
| 29-5 | 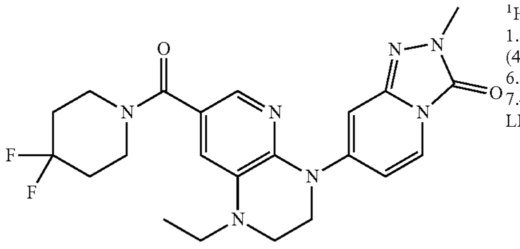 | $^1$H NMR (400 MHz, DMSO-$d_6$) δ 1.09 (3H, t, J = 7.0 Hz), 1.96-2.10 (4H, m), 3.35-3.47 (4H, m), 3.48 (3H, s), 3.50-3.68 (4H, m), 3.83 (2H, t, J = 4.9 Hz), 6.75 (1H, d, J = 1.2 Hz), 6.81 (1H, dd, J = 7.3, 1.8 Hz), 6.95 (1H, d, J = 1.8 Hz), 7.47 (1H, d, J = 1.8 Hz), 7.66 (1H, d, J = 7.9 Hz). LRMS (ESI$^+$) 458 [M + H]$^+$. |

Example 30-1

[Formula 185]

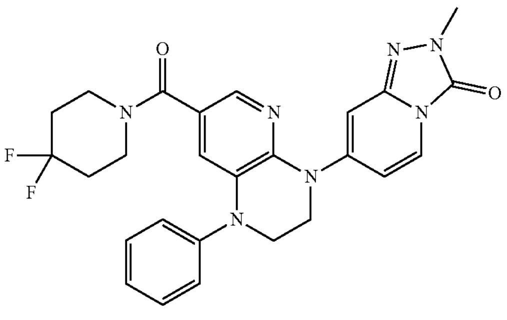

7-(7-(4,4-Difluoropiperidine-1-carbonyl)-1-phenyl-2,3-dihydropyrido[2,3-b]pyrazin-4(1H)-yl)-2-methyl-[1,2,4]triazolo[4,3-a]pyridin-3 (2H)-one A solution, in 1,4-dioxane (2 mL), of 7-(7-(4,4-difluoropiperidine-1-carbonyl)-2,3-dihydropyrido[2,3-b] pyrazin-4 (1H)-yl)-2-methyl-[1,2,4]triazolo[4,3-a]pyridin-3 (2H)-one (50.0 mg), bromobenzene (14.7 μL), tris (dibenzylideneacetone) dipalladium (0) (5.3 mg), 4,5-bis (diphenylphosphino)-9,9-dimethylxanthene (Xantphos) (6.7 mg) and cesium carbonate (113 mg) was stirred under heating to reflux for 7 hours, followed by concentration under reduced pressure. The thus obtained residue was purified by silica gel column chromatography (methanol: ethyl acetate=0:100 to 20:80) and the resultant was washed with ethanol to obtain the title compound (47.7 mg).

$^1$H NMR (400 MHz, DMSO-$d_6$) δ1.88-2.03 (4H, m), 3.43-3.63 (7H, m), 3.78-3.86 (2H, m), 3.94-4.02 (2H, m), 6.86-6.93 (3H, m), 7.23 (1H, t, J=7.3 Hz), 7.35 (2H, dd, J=8.6, 1.2 Hz), 7.43-7.50 (2H, m), 7.66 (1H, d, J=1.8 Hz), 7.71-7.76 (1H, m).

LRMS (ESI$^{+}$) 506 [M+H]$^{+}$.

Compounds of the following Examples 30-2 to 30-5 were obtained in the same manner as in Example 30-1 by using corresponding starting materials and reactants. Their structures and spectrum data are shown in the following table.

TABLE 178

| Example No. | Chemical Structural Formula | Spectrum Data |
|---|---|---|
| 30-2 | 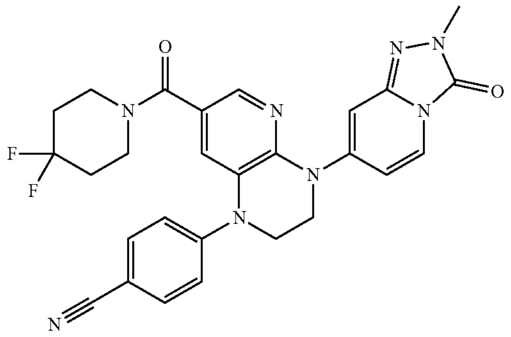 [SMILES: Cn1nc2cc(N3CCN(c4ccc(C#N)cc4)c4cc(C(=O)N5CCC(F)(F)CC5)cnc43)ccn2c1=O] | $^{1}H$ NMR (400 MHz, DMSO-$d_6$) δ 1.93-2.07 (4H, m), 3.47-3.65 (7H, m), 3.88-3.99 (4H, m), 6.86 (1H, dd, J = 7.6, 2.1 Hz), 6.96 (1H, d, J = 1.2 Hz), 7.38-7.47 (3H, m), 7.75 (1H, d, J = 8.6 Hz), 7.79-7.85 (3H, m). LRMS (ESI$^{+}$) 531 [M + H]$^{+}$. |
| 30-3 | 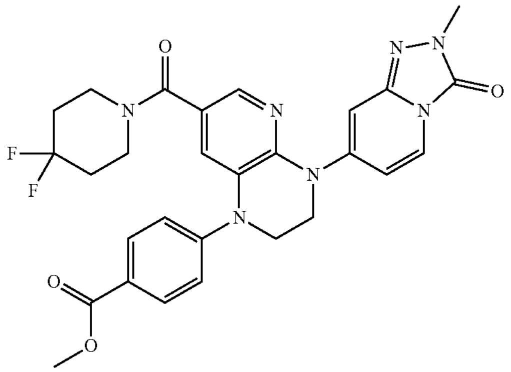 [SMILES: COC(=O)c1ccc(N2CCN(c3ccn4c(=O)n(C)nc4c3)c3ncc(C(=O)N4CCC(F)(F)CC4)cc32)cc1] | $^{1}H$ NMR (400 MHz, DMSO-$d_6$) δ 1.91-2.06 (4H, m), 3.50 (3H, s), 3.52-3.64 (4H, m), 3.83 (3H, s), 3.88-4.00 (4H, m), 6.87 (1H, dd, J = 7.6, 2.1 Hz), 6.95 (1H, d, J = 1.8 Hz), 7.34 (1H, d, J = 1.8 Hz), 7.37-7.43 (2H, m), 7.74 (1H, d, J = 7.9 Hz), 7.80 (1H, d, J = 1.8 Hz), 7.94-7.99 (2H, m). LRMS (ESI$^{+}$) 564 [M + H]$^{+}$. |
| 30-4 | 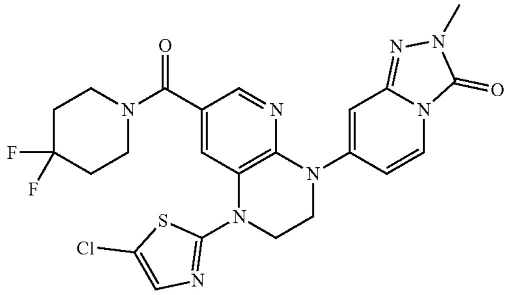 [SMILES: Cn1nc2cc(N3CCN(c4ncc(Cl)s4)c4cc(C(=O)N5CCC(F)(F)CC5)cnc43)ccn2c1=O] | $^{1}H$ NMR (400 MHz, DMSO-$d_6$) δ 1.98-2.13 (4H, m), 3.50 (3H, s), 3.54-3.69 (4H, m), 3.95-4.05 (4H, m), 6.81 (1H, dd, J = 7.9, 1.8 Hz), 6.96 (1H, d, J = 1.2 Hz), 7.48 (1H, s), 7.75 (1H, dd, J = 7.6, 0.9 Hz), 7.96 (1H, d, J = 1.8 Hz), 8.60 (1 H, d, J = 1.8 Hz). LRMS (ESI$^{+}$) 547 [M + H]$^{+}$. |
| 30-5 | 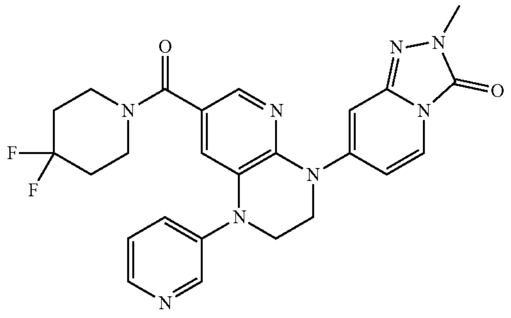 [SMILES: Cn1nc2cc(N3CCN(c4cccnc4)c4cc(C(=O)N5CCC(F)(F)CC5)cnc43)ccn2c1=O] | $^{1}H$ NMR (400 MHz, DMSO-$d_6$) δ 1.88-2.04 (4H, m), 3.45-3.62 (7H, m), 3.82-3.90 (2H, m), 3.95-4.02 (2H, m), 6.88 (1H, dd, J = 7.6, 2.1 Hz), 6.91-6.94 (1H, m), 6.98 (1H, d, J = 1.8 Hz), 7.48 (1H, dd, J = 8.6, 4.3 Hz), 7.71 (1H, d, J = 1.8 Hz), 7.74 (1H, d, J = 8.6 Hz), 7.78-7.82 (1H, m), 8.41 (1H, dd, J = 4.6, 1.5 Hz), 8.61 (1H, d, J = 2.4 Hz). LRMS (ESI$^{+}$) 507 [M + H]$^{+}$. |

Example 31-1

[Formula 186]

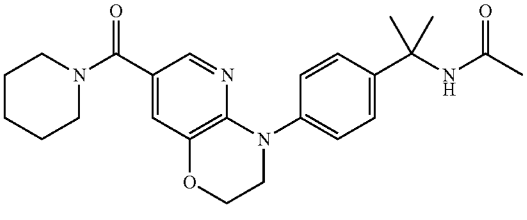

(N-(2-(4-(7-(Piperidine-1-carbonyl)-2,3-dihydro-4H-pyrido[3,2-b][1,4]oxazin-4-yl)phenyl)propan-2-yl) acetamide To a solution, in dichloromethane (1.0 mL), of (4-(4-(2-aminopropan-2-yl)phenyl)-3,4-dihydro-2H-pyrido[3,2-b][1,4]oxazin-7-yl)(piperidin-1-yl)methanone (38.0 mg) and triethylamine (41.8 μL), acetyl chloride (7.1 μL) was added at room temperature. The resultant reaction solution was purified by silica gel column chromatography (ethyl acetate: hexane=30:70 to 100:0 to ethyl acetate:methanol=80:20), and the resultant was washed with a mixture of diethyl ether and hexane to obtain the title compound (18.8 mg).

$^1$H NMR (400 MHz, DMSO-$d_6$) δ1.42-1.64 (12H, m), 1.82 (3H, s), 3.37-3.51 (4H, m), 3.86 (2H, t, J=4.3 Hz), 4.31 (2H, t, J=4.3 Hz), 7.07 (1H, d, J=1.8 Hz), 7.28 (4H, s), 7.64 (1H, d, J=1.8 Hz), 8.04 (1H, s).

LRMS (ESI$^+$) 423 [M+H]$^+$.

A compound of the following Example 31-2 was obtained in the same manner as in Example 31-1 by using corresponding starting material and reactant. Its structure and spectrum data are shown in the following table.

-continued

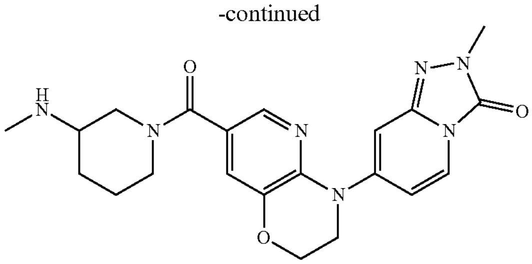

2-Methyl-7-(7-(3-(methylamino)piperidine-1-carbonyl)-2,3-dihydro-4H-pyrido[3,2-b][1,4]oxazin-4-yl)-[1,2,4]triazolo[4,3-a]pyridin-3(2H)-one Trifluoroacetate To a solution of tert-butyl methyl(1-(4-(2-methyl-3-oxo-2,3-dihydro-[1,2,4]triazolo[4,3-a]pyridin-7-yl)-3,4-dihydro-2H-pyrido[3,2-b] [1,4]oxazine-7-carbonyl)piperidin-3-yl) carbamate (165 mg) in dichloromethane (3.2 mL), trifluoroacetic acid (1.6 ml) was added at room temperature. After stirring at room temperature for 2.5 hours, the resultant reaction solution was concentrated under reduced pressure. The thus obtained residue was purified by silica gel column chromatography (ethyl acetate:hexane=50:50 to 100:0 to ethyl acetate:methanol=80:20) to obtain the title compound (133 mg).

$^1$H NMR (400 MHz, DMSO-$d_6$) δ1.40-1.54 (1H, m), 1.60-1.82 (2H, m), 2.00-2.11 (1H, m), 2.52-2.62 (3H, m), 3.10-3.26 (2H, m), 3.27-3.47 (2H, m), 3.49 (3H, s), 3.94 (2H, t, J=4.3 Hz), 3.98-4.08 (1H, m), 4.37 (2H, t, J=4.6 Hz), 6.91 (1H, d, J=1.2 Hz), 6.98 (1H, dd, J=7.6, 2.1 Hz), 7.29 (1H, d, J=1.8 Hz), 7.76 (1H, d, J=8.6 Hz), 7.85 (1H, d, J=1.8 Hz), 8.62-8.96 (2H, m).

LRMS (ESI$^+$) 424 [M+H]$^+$.

TABLE 179

| Example No. | Chemical Structural Formula | Spectrum Data |
|---|---|---|
| 31-2 | 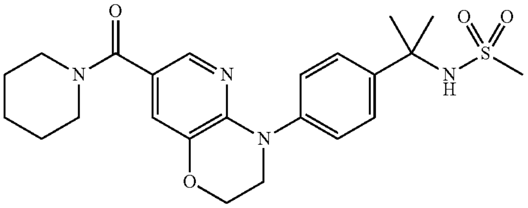 [SMILES: CC(C)(NS(C)(=O)=O)c1ccc(N2CCOc3cc(C(=O)N4CCCCC4)cnc32)cc1] | $^1$H NMR (400 MHz, DMSO-$d_6$) δ 1.40-1.68 (12H, m), 2.64 (3H, s), 3.35-3.54 (4H, m), 3.89 (2H, t, J = 4.3 Hz), 4.32 (2H, t, J = 4.3 Hz), 7.09 (1H, d, J = 1.8 Hz), 7.34-7.39 (2H, m), 7.45-7.51 (3H, m), 7.65 (1H, d, J = 2.4 Hz). LRMS (ESI$^+$) 459 [M + H]$^+$. |

Example 32-1

[Formula 187]

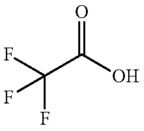

Example 33-1

[Formula 188]

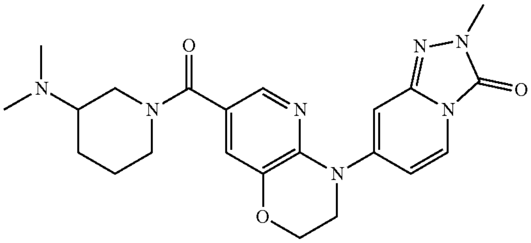

7-(7-(3-(Dimethylamino)piperidine-1-carbonyl)-2,3-dihydro-4H-pyrido[3,2-b] [1,4]oxazin-4-yl)-2-methyl-[1,2,4]triazolo[4,3-a]pyridin-3(2H)-one To a solution of 2-methyl-7-(7-(3-(methylamino)piperidine-1-carbonyl)-2,3-dihydro-4H-pyrido[3,2-b] [1,4]oxazin-4-yl)-[1,2,4]triazolo[4,3-a]pyridin-3(2H)-one trifluoroacetate (56.1 mg) in tetrahydrofuran (1.3 mL), paraformaldehyde (18.2 mg) was added at room temperature. After stirring at room temperature for 5 minutes, acetic acid (375 µL) was added thereto, followed by stirring at 65° C. for 3 hours. To the resultant reaction solution, sodium triacetoxyborohydride (140 mg) was added at room temperature. After stirring at 65° C. for 4 hours, a saturated sodium bicarbonate aqueous solution was added to the resultant reaction solution, and the reaction solution was concentrated under reduced pressure. The thus obtained residue was purified by silica gel column chromatography (methanol:water=5:95 to 100:0) to obtain the title compound (41.0 mg).

$^{1}H$ NMR (400 MHz, DMSO-$d_6$) δ1.31-1.48 (2H, m), 1.57-1.75 (1H, m), 1.83-1.93 (1H, m), 2.00-2.30 (6H, m), 2.62-3.70 (8H, m), 3.93 (2H, t, J=4.3 Hz), 4.36 (2H, t, J=4.3 Hz), 6.88 (1H, d, J=1.2 Hz), 6.98 (1H, dd, J=7.3, 1.8 Hz), 7.21 (1H, d, J=1.8 Hz), 7.72-7.80 (2H, m).

LRMS ($ESI^+$) 438 $[M+H]^+$.

Example 34-1

[Formula 189]

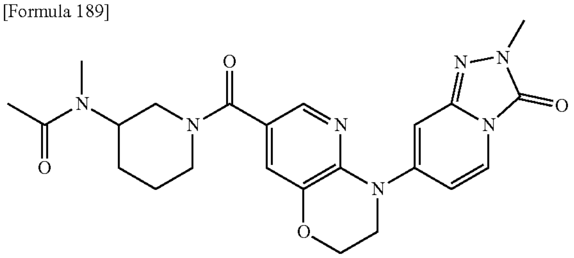

N-Methyl-N-(1-(4-(2-methyl-3-oxo-2,3-dihydro-[1,2,4]triazolo[4,3-a]pyridin-7-yl)-3,4-dihydro-2H-pyrido[3,2-b][1,4]oxazin-7-carbonyl)piperidin-3-yl)acetamide To a solution, in dichloromethane (1.0 mL), of 2-methyl-7-(7-(3-(metylamino)piperidine-1-carbonyl)-2,3-dihydro-4H-pyrido[3,2-b] [1,4]oxazin-4-yl)-[1,2,4]triazolo[4,3-a]pyridin-3(2H)-one trifluoroacetate (42.1 mg) and triethylamine (41.5 (XL), acetyl chloride (7.8 µL) was added at room temperature. After stirring at room temperature for 7 hours, the resultant reaction solution was concentrated under reduced pressure. The thus obtained residue was purified by silica gel column chromatography (methanol:water=5:95 to 100:0) to obtain the title compound (31.8 mg).

$^{1}H$ NMR (400 MHz, DMSO-$d_6$) δ1.38-1.86 (4H, m), 1.88-2.10 (3H, m), 2.29-2.53 (1H, m), 2.60-3.12 (5H, m), 3.49 (3H, s), 3.61-3.79 (1H, m), 3.86-3.99 (2H, m), 4.13-4.47 (3H, m), 6.89 (1H, d, J=1.2 Hz), 6.98 (1H, dd, J=7.3, 1.8 Hz), 7.25 (1H, dd, J=12.1, 1.8 Hz), 7.75 (1H, d, J=7.9 Hz), 7.81 (1H, dd, J=7.3, 2.4 Hz).

LRMS ($ESI^+$) 466 $[M+H]^+$.

Example 35-1

[Formula 190]

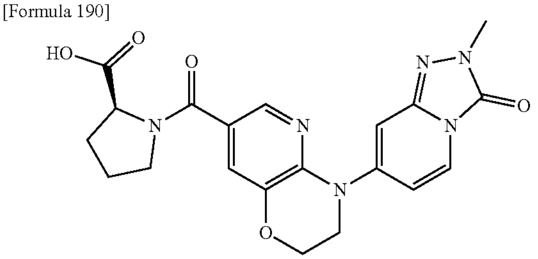

(4-(2-Methyl-3-oxo-2,3-dihydro-[1,2,4]triazolo[4,3-a]pyridin-7-yl)-3,4-dihydro-2H-pyrido[3,2-b][1,4]oxazine-7-carbonyl)-L-proline To a solution of tert-butyl (4-(2-methyl-3-oxo-2,3-dihydro-[1,2,4]triazolo[4,3-a]pyridin-7-yl)-3,4-dihydro-2H-pyrido[3,2-b][1,4]oxazine-7-carbonyl)-L-proline (167 mg) in dichloromethane (3 mL), trifluoroacetic acid (1.5 mL) was added at room temperature. After stirring at room temperature for 24 hours, the resultant reaction solution was concentrated under reduced pressure. The thus obtained residue was purified by silica gel column chromatography (methanol:water=5:95 to 100:0), and the resultant was washed with diethyl ether to obtain the title compound (104 mg).

$^{1}H$ NMR (400 MHz, DMSO-$d_6$) δ1.72-2.02 (3H, m), 2.16-2.30 (1H, m), 3.44-3.69 (5H, m), 3.86-4.14 (2H, m), 4.28-4.52 (3H, m), 6.85-7.01 (2H, m), 7.20 (0.2H, s), 7.33 (0.8H, d, J=1.8 Hz), 7.76 (1H, d, J=7.3 Hz), 7.81 (0.2H, s), 7.97 (0.8H, d, J=1.8 Hz), 12.34-12.97 (1H, m).

LRMS ($ESI^+$) 425 $[M+H]^+$.

A compound of the following Example 35-2 was obtained in the same manner as in Example 35-1 by using corresponding starting material and reactant. Its structure and spectrum data are shown in the following table.

TABLE 180

| Example No. | Chemical Structural Formula | Spectrum Data |
|---|---|---|
| 35-2 | 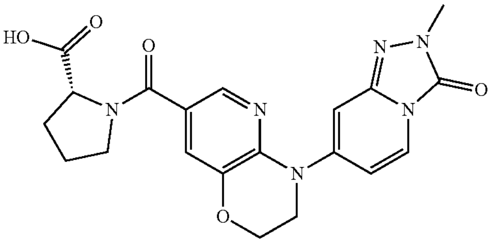 | $^{1}H$ NMR (400 MHz, DMSO-$d_6$) δ 1.75-2.01 (3H, m), 2.16-2.30 (1H, m), 3.45-3.68 (5H, m), 3.88-3.99 (2H, m), 4.29-4.53 (3H, 1,1.0 m), 6.86-7.01 (2H, m), 7.20 (0.2H, s), 7.33 (0.8H, d, J = 1.8 Hz), 7.76 (1H, d, J = 6.7 Hz), 7.81 (0.2H, s), 7.97 (0.8H, d, J = 1.8 Hz), 12.29-13.00 (1H, m).<br>LRMS ($ESI^+$) 425 [M + H]$^+$. |

Example 36-1

[Formula 191]

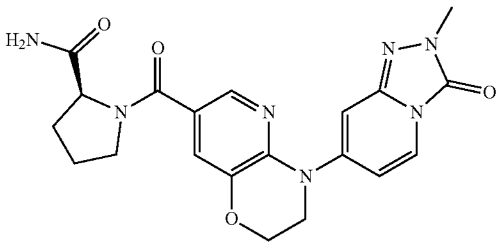

(S)-1-(4-(2-Methyl-3-oxo-2,3-dihydro-[1,2,4]triazolo[4,3-a]pyridin-7-yl)-3,4-dihydro-2H-pyrido[3,2-b][1,4]oxazine-7-carbonyl)pyrrolidine-2-carboxamide To a solution, in N,N-dimethylformamide (0.5 mL), of (4-(2-methyl-3-oxo-2,3-dihydro-[1,2,4]triazolo[4,3-a]pyridin-7-yl)-3,4-dihydro-2H-pyrido[3,2-b][1,4]oxazine-7-carbonyl)-L-proline (50.9 mg), ammonium chloride (12.8 mg) and diisopropylethylamine (102 μL), 1-[bis(dimethylamino)methylene]-1H-1,2,3-triazolo[4,5-b]pyridinium 3-oxide hexafluorophosphate (50.2 mg) was added, followed by stirring at room temperature for 4.5 hours. The resultant reaction mixture was purified by silica gel column chromatography (methanol:water=5:95 to 100:0) to obtain the title compound (5.7 mg).

$^1$H NMR (400 MHz, DMSO-$d_6$) δ1.69-1.95 (3H, m), 2.08-2.21 (1H, m), 3.44-3.70 (5H, m), 3.87-3.99 (2H, m), 4.23-4.41 (3H, m), 6.83-7.08 (3H, m), 7.13-7.21 (0.3H, m), 7.27-7.46 (1.7H, m), 7.72-7.82 (1.3H, m), 7.98-8.04 (0.7H, m).

LRMS (ESI$^+$) 424 [M+H]$^+$.

A compound of the following Example 36-2 was obtained in the same manner as in Example 36-1 by using corresponding starting material and reactant. Its structure and spectrum data are shown in the following table, Example 37-1

[Formula 192]

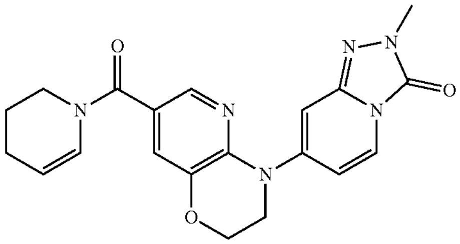

2-Methyl-7-(7-(1,2,3,4-tetrahydropyridine-1-carbonyl)-2,3-dihydro-4H-pyrido[3,2-b][1,4]oxazin-4-yl)-[1,2,4]triazolo[4,3-a]pyridin-3(2H)-one Dichloromethane (2.00 ml) and triethylamine (41.8 μL) were added to N-(5-hydroxypentyl)-4-(2-methyl-3-oxo-2,3-dihydro-[1,2,4]triazolo[4,3-a]pyridin-7-yl)-3,4-dihydro-2H-pyrido[3,2-b][1,4]oxazine-7-carboxamide (41.2 mg), and the resultant was cooled with ice. A solution of a sulfur trioxide pyridine complex (52.5 mg) in dimethylsulfoxide (1.20 mL) was added thereto under ice cooling, and the resultant was heated to room temperature and then stirred for 2 hours. The resultant reaction solution was concentrated under reduced pressure, and the thus obtained residue was purified by silica gel column chromatography (chloroform: methanol=100:0 to 90:10), the thus obtained residue was solidified by adding isopropyl ether (5 mL) and acetone (3 mL) thereto. The thus obtained solid was collected by filtration to obtain 4-(2-methyl-3-oxo-2,3-dihydro-[1,2,4]triazolo[4,3-a]pyridin-7-yl)-N-(5-oxopentyl)-3,4-dihydro-2H-pyrido[3,2-b] [1,4]oxazine-7-carboxamide (14.9 mg).

$^1$H NMR (400 MHz, DMSO-$d_6$): δ 1.42-1.60 (4H, m), 2.42-2.48 (2H, m), 3.17-3.28 (2H, m), 3.51 (3H, s), 3.95 (2H, t, J=4.8 Hz), 4.37 (2H, t, J=4.8 Hz), 6.92 (1H, d, J=2.4 Hz), 6.97 (1H, dd, J=7.9, 2.4 Hz), 7.60 (1H, d, J=2.4 Hz), 7.77 (1H, d, J=7.9 Hz), 8.24 (1H, d, J=2.4 Hz), 8.38 (1H, t, J=5.8 Hz), 9.67 (1H, t, J=1.8 Hz).

LRMS (ESI$^+$): 411 [M+H]$^+$.

To the thus obtained 4-(2-methyl-3-oxo-2,3-dihydro-[1,2,4]triazolo[4,3-a]pyridin-7-yl)-N-(5-oxopentyl)-3,4-dihydro-2H-pyrido[3,2-b][1,4]oxazine-7-carboxamide (20.5 mg), dichloromethane (1.00 mL) and trifluoroacetic acid (one drop) were added, followed by stirring under heating to

TABLE 181

| Example No. | Chemical Structural Formula | Spectrum Data |
|---|---|---|
| 36-2 | 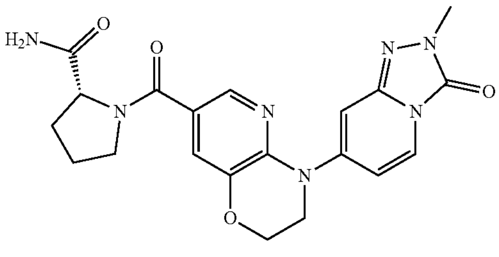 | $^1$H NMR (400 MHz, DMSO-$d_6$) δ 1.67-1.96 (3H, m), 2.09-2.21 (1H, m), 3.45-3.69 (5H, m), 3.88-3.98 (2H, m), 4.22-4.42 (3H, m), 6.87-7.06 (3H, m), 7.15-7.21 (0.3H, m), 7.31-7.47 (1.7H, m), 7.72-7.81 (1.3H, m), 7.97-8.04 (0.7H, m). LRMS (ESI$^+$) 424 [M + H]$^+$. |

reflux for 1 hour. The resultant reaction solution was purified by silica gel column chromatography (chloroform:methanol=100:0 to 90:10), and the thus obtained residue was solidified by adding isopropyl ether (5 mL) and acetone (3 mL) thereto. The thus obtained solid was collected by filtration to obtain the title compound (7.8 mg).

$^1$H NMR (400 MHz, DMSO-$d_6$) δ1.77-1.86 (2H, m), 2.03-2.10 (2H, m), 3.50 (3H, s), 3.64 (2H, t, J=5.8 Hz), 3.95 (2H, t, J=4.2 Hz), 4.37 (2H, t, J=4.2 Hz), 4.96-5.07 (1H, m), 6.65-6.83 (1H, m), 6.92 (1H, d, J=1.8 Hz), 6.97 (1H, dd, J=7.9, 1.8 Hz), 7.26 (1H, d, J=1.8 Hz), 7.73 (1H, d, J=7.9 Hz), 7.86 (1H, d, J=1.8 Hz).

LRMS (ESI$^+$) 393 [M+H]$^+$.

Next, results supporting the efficacy of the compound of the present invention are described with reference to test examples.

Test Example 1

15-PGDH Enzyme Inhibition Test

A test compound and 4 nM recombinant human 15-PGDH (R&D Systems) were added, in 50 mM Tris-HCl (pH 8.0) containing 0.01% TWEEN 20 (Sigma) and 0.01% bovine gamma globulin (Sigma), to a 384-well Flat Bottom Black plate (Corning, 3820), and the resultant was allowed to stand still at room temperature for 12 minutes, and 30 μM PGE2 (Cayman Chemical) and 1 mM NAD+ (Sigma) were added thereto to start the reaction. 60 minutes after starting the reaction, measurement was performed using Synergy 2 (BioTeck) at an excitation wavelength of 340 nm and a fluorescence wavelength of 440 nm. Assuming that a fluorescence signal obtained with an assay buffer added instead of the test compound and NAD+ was 100% and that a signal obtained with NAD+ added was 0%, a concentration corresponding to 50% inhibition plotted on a concentration-reaction curve of the test compound was defined as an $IC_{50}$ value. Incidentally, in the following tables, an $IC_{50}$ value smaller than 10 nM was shown as +++, an $IC_{50}$ value equal to or larger than 10 nM and smaller than 100 nM was shown as ++, and an $IC_{50}$ value equal to or larger than 100 nM was shown as +.

TABLE 182

| Test Compound (Example No.) | $IC_{50}$ Value |
|---|---|
| 1-7 | +++ |
| 1-17 | +++ |
| 1-18 | +++ |
| 1-19 | +++ |
| 1-20 | +++ |
| 1-21 | +++ |
| 1-22 | +++ |
| 1-23 | +++ |
| 1-24 | +++ |
| 1-25 | +++ |
| 1-26 | ++ |
| 1-27 | +++ |
| 1-28 | +++ |
| 1-29 | +++ |
| 1-30 | +++ |
| 1-31 | +++ |
| 1-32 | +++ |
| 1-33 | +++ |
| 1-34 | +++ |
| 1-35 | +++ |
| 1-36 | +++ |
| 1-37 | +++ |
| 1-38 | +++ |
| 1-39 | ++ |
| 1-40 | +++ |

TABLE 182-continued

| Test Compound (Example No.) | $IC_{50}$ Value |
|---|---|
| 1-41 | +++ |
| 1-42 | +++ |
| 1-43 | +++ |
| 1-44 | +++ |
| 1-45 | +++ |
| 1-46 | ++ |
| 1-47 | +++ |
| 1-48 | +++ |
| 1-49 | +++ |
| 1-50 | +++ |
| 1-51 | ++ |
| 1-52 | +++ |
| 1-53 | +++ |

TABLE 183

| Test Compound (Example No.) | $IC_{50}$ Value |
|---|---|
| 1-54 | +++ |
| 1-55 | +++ |
| 1-56 | ++ |
| 1-57 | +++ |
| 1-58 | +++ |
| 1-59 | +++ |
| 1-60 | +++ |
| 1-61 | +++ |
| 1-62 | +++ |
| 1-63 | +++ |
| 1-64 | +++ |
| 1-65 | +++ |
| 1-66 | +++ |
| 1-67 | +++ |
| 1-68 | +++ |
| 1-69 | +++ |
| 1-70 | +++ |
| 1-71 | +++ |
| 1-72 | ++ |
| 1-73 | ++ |
| 1-74 | ++ |
| 1-75 | +++ |
| 1-76 | +++ |
| 1-77 | +++ |
| 1-78 | +++ |
| 1-79 | +++ |
| 1-80 | +++ |
| 1-81 | +++ |
| 1-82 | +++ |
| 1-83 | +++ |
| 1-84 | +++ |
| 1-85 | ++ |
| 1-86 | ++ |
| 1-87 | +++ |
| 1-88 | +++ |
| 1-90 | ++ |
| 1-91 | ++ |
| 1-92 | +++ |
| 1-93 | +++ |

TABLE 184

| Test Compound (Example No.) | $IC_{50}$ Value |
|---|---|
| 1-94 | +++ |
| 1-95 | +++ |
| 1-96 | +++ |
| 1-97 | +++ |
| 1-98 | ++ |
| 1-99 | +++ |
| 1-100 | +++ |
| 1-101 | +++ |
| 1-102 | ++ |
| 1-103 | +++ |
| 1-104 | +++ |

TABLE 184-continued

| Test Compound (Example No.) | $IC_{50}$ Value |
|---|---|
| 1-105 | +++ |
| 1-106 | +++ |
| 1-107 | +++ |
| 1-108 | ++ |
| 1-109 | +++ |
| 1-110 | +++ |
| 1-111 | +++ |
| 1-112 | +++ |
| 1-113 | +++ |
| 1-114 | +++ |
| 1-115 | +++ |
| 1-116 | +++ |
| 1-117 | +++ |
| 1-118 | +++ |
| 1-119 | +++ |
| 1-120 | +++ |
| 1-121 | +++ |
| 1-122 | +++ |
| 1-123 | +++ |
| 1-124 | +++ |
| 1-125 | +++ |
| 1-126 | +++ |
| 1-127 | +++ |
| 1-128 | +++ |
| 1-129 | +++ |
| 2-1 | ++ |
| 2-2 | +++ |
| 2-3 | +++ |
| 2-4 | +++ |

TABLE 185

| Test Compound (Example No.) | $IC_{50}$ Value |
|---|---|
| 2-5 | +++ |
| 2-6 | +++ |
| 2-7 | +++ |
| 2-8 | +++ |
| 2-9 | +++ |
| 2-10 | +++ |
| 2-11 | +++ |
| 2-12 | +++ |
| 2-13 | +++ |
| 2-14 | +++ |
| 2-15 | +++ |
| 2-16 | ++ |
| 2-17 | ++ |
| 2-18 | +++ |
| 2-19 | + |
| 2-20 | + |
| 2-21 | +++ |
| 2-22 | +++ |
| 2-23 | +++ |
| 3-1 | +++ |
| 4-1 | +++ |
| 4-2 | +++ |
| 4-3 | ++ |
| 4-4 | +++ |
| 4-5 | +++ |
| 4-6 | +++ |
| 4-7 | +++ |
| 4-8 | +++ |
| 4-9 | +++ |
| 4-10 | ++ |
| 4-11 | ++ |
| 4-12 | +++ |
| 4-13 | ++ |
| 4-14 | +++ |
| 4-15 | ++ |
| 5-1 | +++ |
| 5-2 | +++ |
| 5-3 | +++ |
| 6-1 | +++ |

TABLE 186

| Test Compound (Example No.) | $IC_{50}$ Value |
|---|---|
| 6-2 | +++ |
| 6-3 | +++ |
| 6-4 | +++ |
| 6-5 | +++ |
| 6-6 | +++ |
| 6-7 | +++ |
| 6-8 | +++ |
| 6-11 | ++ |
| 7-5 | +++ |
| 8-7 | ++ |
| 8-14 | ++ |
| 8-15 | +++ |
| 8-16 | +++ |
| 8-17 | +++ |
| 8-18 | +++ |
| 8-19 | +++ |
| 8-20 | +++ |
| 8-21 | +++ |
| 8-22 | ++ |
| 8-23 | +++ |
| 8-24 | +++ |
| 8-25 | +++ |
| 8-26 | +++ |
| 8-27 | +++ |
| 8-28 | +++ |
| 8-29 | +++ |
| 8-30 | +++ |
| 8-31 | +++ |
| 8-32 | +++ |
| 8-33 | +++ |
| 8-34 | +++ |
| 8-35 | +++ |
| 8-36 | +++ |
| 8-37 | +++ |
| 8-38 | +++ |
| 8-39 | +++ |
| 8-40 | +++ |
| 8-41 | +++ |
| 8-42 | +++ |
| 8-43 | +++ |

TABLE 187

| Test Compound (Example No.) | $IC_{50}$ Value |
|---|---|
| 8-44 | +++ |
| 8-45 | +++ |
| 8-46 | +++ |
| 8-47 | +++ |
| 8-48 | +++ |
| 8-49 | +++ |
| 8-50 | +++ |
| 8-51 | ++ |
| 8-52 | ++ |
| 8-53 | +++ |
| 8-54 | +++ |
| 8-55 | +++ |
| 8-56 | +++ |
| 8-57 | +++ |
| 8-58 | +++ |
| 8-59 | +++ |
| 8-60 | +++ |
| 8-61 | +++ |
| 8-62 | +++ |
| 8-63 | +++ |
| 8-64 | +++ |
| 8-65 | +++ |
| 8-66 | +++ |
| 8-67 | +++ |
| 9-1 | +++ |
| 10-1 | +++ |
| 11-3 | +++ |
| 14-1 | +++ |
| 14-2 | +++ |
| 15-1 | +++ |

TABLE 187-continued

| Test Compound (Example No.) | $IC_{50}$ Value |
|---|---|
| 16-1 Isomer A | +++ |
| 16-1 Isomer B | +++ |
| 17-1 | +++ |
| 17-2 | +++ |
| 17-3 | +++ |
| 18-1 | +++ |
| 18-2 | +++ |
| 19-1 | +++ |
| 20-1 | +++ |
| 21-1 | +++ |

TABLE 188

| Test Compound (Example No.) | $IC_{50}$ Value |
|---|---|
| 22-1 | ++ |
| 23-1 Isomer A | +++ |
| 23-1 Isomer B | +++ |
| 23-2 Isomer A | +++ |
| 23-2 Isomer B | +++ |

TABLE 189

| Test Compound (Example No.) | $IC_{50}$ Value |
|---|---|
| 1-130 | +++ |
| 1-131 | +++ |
| 1-132 | +++ |
| 1-133 | +++ |
| 1-134 | +++ |
| 1-135 | ++ |
| 1-136 | ++ |
| 1-137 | + |
| 1-138 | + |
| 1-139 | +++ |
| 1-140 | +++ |
| 1-141 | +++ |
| 1-145 | +++ |
| 1-146 | +++ |
| 1-147 | +++ |
| 1-148 | +++ |
| 1-149 | +++ |
| 1-150 | +++ |
| 1-151 | +++ |
| 1-152 | +++ |
| 1-153 | +++ |
| 1-154 | +++ |
| 1-155 | +++ |
| 1-157 | +++ |
| 1-160 | +++ |
| 1-161 | +++ |
| 1-162 | +++ |
| 1-163 | +++ |
| 1-164 | ++ |
| 1-165 | +++ |
| 1-166 | +++ |
| 1-167 | ++ |
| 1-168 | ++ |
| 1-169 | +++ |

TABLE 190

| Test Compound (Example No.) | $IC_{50}$ Value |
|---|---|
| 1-171 | +++ |
| 1-172 | +++ |
| 1-173 | +++ |
| 1-174 | +++ |
| 1-175 | +++ |
| 1-176 | +++ |
| 1-177 | +++ |

TABLE 190-continued

| Test Compound (Example No.) | $IC_{50}$ Value |
|---|---|
| 1-178 | +++ |
| 1-180 | +++ |
| 1-181 | +++ |
| 1-182 | +++ |
| 1-183 | ++ |
| 1-184 | +++ |
| 1-185 | ++ |
| 1-186 | ++ |
| 1-188 | +++ |
| 1-189 | +++ |
| 1-190 | +++ |
| 1-191 | +++ |
| 1-192 | +++ |
| 1-193 | +++ |
| 1-194 | +++ |
| 1-195 | +++ |
| 1-196 | +++ |
| 1-197 | +++ |
| 1-198 | +++ |
| 1-199 | ++ |
| 1-200 | ++ |
| 1-201 | +++ |
| 1-202 | +++ |
| 1-203 | +++ |
| 1-204 | +++ |
| 1-205 | +++ |
| 1-207 | ++ |
| 1-209 | +++ |
| 1-210 | +++ |
| 1-211 | ++ |
| 1-212 | ++ |

TABLE 191

| Test Compound (Example No.) | $IC_{50}$ Value |
|---|---|
| 1-213 | +++ |
| 1-214 | ++ |
| 1-215 | +++ |
| 1-216 | +++ |
| 1-217 | +++ |
| 1-218 | +++ |
| 1-219 | +++ |
| 1-222 | +++ |
| 1-223 | +++ |
| 1-224 | +++ |
| 1-225 | ++ |
| 1-226 | +++ |
| 1-227 | +++ |
| 1-228 | + |
| 1-230 | ++ |
| 1-232 | ++ |
| 1-233 | ++ |
| 1-234 | ++ |
| 1-235 | + |
| 1-236 | + |
| 1-237 | +++ |
| 1-238 | + |
| 1-239 | ++ |
| 1-240 | ++ |
| 1-241 | +++ |
| 1-242 | ++ |
| 1-243 | ++ |
| 1-244 | ++ |
| 1-245 | ++ |
| 1-246 | + |
| 1-247 | + |
| 1-248 | + |
| 1-249 | + |
| 1-251 | +++ |
| 1-252 | +++ |
| 1-253 | ++ |
| 1-254 | ++ |
| 1-255 | ++ |

TABLE 192

| Test Compound (Example No.) | $IC_{50}$ Value |
|---|---|
| 1-257 | +++ |
| 1-258 | +++ |
| 1-259 | +++ |
| 1-260 | +++ |
| 1-261 | +++ |
| 1-262 | +++ |
| 1-263 | + |
| 1-264 | +++ |
| 1-265 | +++ |
| 1-266 | ++ |
| 1-267 | +++ |
| 1-268 | +++ |
| 1-269 | +++ |
| 1-270 | + |
| 2-26 | +++ |
| 2-27 | + |
| 2-28 | + |
| 2-29 | +++ |
| 2-30 | +++ |
| 2-31 | +++ |
| 2-32 | +++ |
| 2-33 | +++ |
| 2-34 | +++ |
| 2-35 | +++ |
| 2-36 | + |
| 2-37 | + |
| 2-38 | +++ |
| 4-16 | +++ |
| 4-17 | +++ |
| 4-18 | ++ |
| 4-19 | ++ |
| 4-20 | ++ |
| 4-21 | +++ |
| 6-10 | + |
| 6-12 | + |
| 6-13 | + |
| 6-14 | +++ |
| 6-15 | ++ |

TABLE 193

| Test Compound (Example No.) | $IC_{50}$ Value |
|---|---|
| 6-16 | ++ |
| 6-17 | +++ |
| 6-18 | +++ |
| 6-19 | +++ |
| 6-20 | + |
| 6-21 | +++ |
| 6-22 | +++ |
| 7-6 | + |
| 7-7 | +++ |
| 7-8 | + |
| 7-9 | +++ |
| 7-10 | ++ |
| 8-8 | + |
| 8-68 | +++ |
| 8-69 | +++ |
| 8-70 | +++ |
| 8-71 | +++ |
| 8-72 | +++ |
| 8-73 | +++ |
| 8-74 | + |
| 8-75 | +++ |
| 8-76 | +++ |
| 8-77 | +++ |
| 8-78 | +++ |
| 8-79 | +++ |
| 8-80 | +++ |
| 8-81 | +++ |
| 8-82 | +++ |
| 8-83 | +++ |
| 8-84 | +++ |
| 8-85 | +++ |
| 8-86 | +++ |

TABLE 193-continued

| Test Compound (Example No.) | $IC_{50}$ Value |
|---|---|
| 8-87 | +++ |
| 8-88 | +++ |
| 8-89 | +++ |
| 8-90 | +++ |
| 8-91 | +++ |
| 8-92 | +++ |

TABLE 194

| Test Compound (Example No.) | $IC_{50}$ Value |
|---|---|
| 8-93 | +++ |
| 8-94 | +++ |
| 8-95 | ++ |
| 8-96 | +++ |
| 8-97 | +++ |
| 8-98 | +++ |
| 8-99 | +++ |
| 8-100 | +++ |
| 8-101 | +++ |
| 8-102 | +++ |
| 8-103 | +++ |
| 8-104 | ++ |
| 8-105 | +++ |
| 8-106 | +++ |
| 8-107 | +++ |
| 8-108 | ++ |
| 8-109 | +++ |
| 8-110 | +++ |
| 8-111 | +++ |
| 8-112 | ++ |
| 8-113 | +++ |
| 8-114 | +++ |
| 8-115 | +++ |
| 8-116 | +++ |
| 8-117 | +++ |
| 8-118 | +++ |
| 8-119 | +++ |
| 8-120 | +++ |
| 8-121 | +++ |
| 8-122 | +++ |
| 8-123 | +++ |
| 8-124 | +++ |
| 8-125 | +++ |
| 8-126 | ++ |
| 8-127 | ++ |
| 8-128 | + |
| 8-129 | +++ |
| 8-130 | +++ |

TABLE 195

| Test Compound (Example No.) | $IC_{50}$ Value |
|---|---|
| 8-131 | +++ |
| 8-132 | +++ |
| 8-133 | +++ |
| 8-134 | +++ |
| 8-135 | +++ |
| 8-136 | +++ |
| 8-137 | +++ |
| 8-138 | +++ |
| 8-139 | +++ |
| 8-140 | +++ |
| 8-141 | +++ |
| 8-142 | +++ |
| 8-143 | +++ |
| 8-144 | +++ |
| 8-145 | ++ |
| 8-146 | +++ |
| 8-147 | +++ |
| 8-148 | +++ |
| 8-149 | +++ |

TABLE 195-continued

| Test Compound (Example No.) | $IC_{50}$ Value |
|---|---|
| 8-150 | +++ |
| 8-151 | ++ |
| 8-152 | ++ |
| 8-153 | + |
| 8-154 | +++ |
| 8-155 | +++ |
| 8-156 | +++ |
| 8-157 | ++ |
| 8-158 | +++ |
| 8-159 | +++ |
| 8-160 | +++ |
| 8-161 | +++ |
| 8-162 | +++ |
| 8-163 | +++ |
| 8-164 | +++ |
| 8-165 | +++ |
| 8-166 | +++ |
| 8-167 | +++ |
| 8-168 | +++ |

TABLE 196

| Test Compound (Example No.) | $IC_{50}$ Value |
|---|---|
| 8-169 | +++ |
| 8-170 | ++ |
| 8-171 | +++ |
| 8-172 | + |
| 8-173 | ++ |
| 8-174 | ++ |
| 8-175 | ++ |
| 8-176 | ++ |
| 8-177 | + |
| 8-178 | + |
| 8-179 | ++ |
| 8-180 | ++ |
| 8-181 | ++ |
| 8-182 | ++ |
| 8-183 | ++ |
| 8-184 | +++ |
| 8-185 | +++ |
| 8-186 | +++ |
| 8-187 | +++ |
| 8-188 | +++ |
| 8-189 | +++ |
| 8-190 | + |
| 8-191 | +++ |
| 8-192 | +++ |
| 8-193 | +++ |
| 8-194 | +++ |
| 8-195 | +++ |
| 8-196 | +++ |
| 8-197 | +++ |
| 8-198 | +++ |
| 8-199 | +++ |
| 8-200 | +++ |
| 8-201 | +++ |
| 8-202 | +++ |
| 8-203 | +++ |
| 8-204 | +++ |
| 8-205 | +++ |
| 8-206 | +++ |

TABLE 197

| Test Compound (Example No.) | $IC_{50}$ Value |
|---|---|
| 8-207 | +++ |
| 8-208 | +++ |
| 8-209 | +++ |
| 8-210 | +++ |
| 8-211 | +++ |
| 8-212 | +++ |

TABLE 197-continued

| Test Compound (Example No.) | $IC_{50}$ Value |
|---|---|
| 8-213 | +++ |
| 8-214 | +++ |
| 8-215 | +++ |
| 8-216 | +++ |
| 8-217 | +++ |
| 8-218 | + |
| 8-219 | + |
| 8-220 | + |
| 8-221 | + |
| 8-222 | +++ |
| 8-223 | ++ |
| 8-224 | ++ |
| 8-225 | ++ |
| 8-226 | ++ |
| 8-227 | + |
| 8-228 | + |
| 8-229 | +++ |
| 8-230 | +++ |
| 10-2 | +++ |
| 10-3 | ++ |
| 11-4 | ++ |
| 11-5 | + |
| 11-6 | +++ |
| 14-3 | +++ |
| 14-4 | +++ |
| 14-5 | +++ |
| 14-6 | +++ |
| 14-7 | +++ |
| 14-8 | +++ |
| 14-9 | +++ |
| 14-10 | +++ |
| 19-2 | ++ |

TABLE 198

| Test Compound (Example No.) | $IC_{50}$ Value |
|---|---|
| 19-3 | +++ |
| 19-4 | +++ |
| 24-1 | + |
| 24-2 | + |
| 24-3 | ++ |
| 25-1 | +++ |
| 26-1 | +++ |
| 26-2 | +++ |
| 27-1 | +++ |
| 27-2 | +++ |
| 27-3 | +++ |
| 27-4 | +++ |
| 27-5 | +++ |
| 27-6 | +++ |
| 27-7 | +++ |
| 27-8 | +++ |
| 28-2 | +++ |
| 29-1 | +++ |
| 29-2 | +++ |
| 29-3 | +++ |
| 29-4 | +++ |
| 29-5 | +++ |
| 30-1 | ++ |
| 30-2 | ++ |
| 30-3 | ++ |
| 30-4 | +++ |
| 30-5 | + |
| 31-1 | + |
| 31-2 | + |
| 32-1 | + |
| 33-1 | + |
| 34-1 | + |
| 35-1 | + |
| 35-2 | + |
| 36-1 | + |
| 36-2 | + |
| 37-1 | +++ |

As is understood from these tables, the compound (1) of the present invention or a pharmacologically acceptable salt thereof is found to exhibit strong 15-PGDH inhibitory effect.

Test Example 2

Disease Model Test

Material and Method

Animal

Nine-week old female $C_{57}BL/6J$ mice were purchased from Charles River Laboratories, and were used when they were 10 weeks old. The mice were maintained under environment controlled in temperature (standard range: 20 to 26° C.) and relative humidity (standard range: 30 to 70%) in a 12-hour light/dark cycle (lighted from 7:00 AM to 7:00 PM). The mice were allowed to free access to feed (CE-2; CLEA Japan) and drinking water. All the animal experiments employed in this test were performed according to the guideline of Institutional Animal Care and Use Committee of KYORIN Pharmaceutical Co., Ltd., WATARASE Research Center.

DSS-Induced Chronic Colitis Mouse Model

DSS [M.W. 36 to 50 kDa (591-18791, lot No. Q6182)] was purchased from MP Biomedicals. On a DSS administration day (day 1), a DSS powder was weighed to prepare a 3% DSS solution with autoclave sterile water. A water bottle of each cage was filled with 100 mL of the DSS solution, which was exchanged with a freshly prepared once every three days. The same amount of autoclaved sterile water not containing DSS was given to a DSS untreated group. In order to check after the recovery phase following acute colitis, the DSS solution was exchanged with usual drinking water on day 5, and was exchanged every 2 days (day 7, day 9 and day 11).

TABLE 199

Table of Groups

| Group | DSS | Administration | Dose of Compound (mg/kg/day) | Number of Animals |
|---|---|---|---|---|
| DSS Untreated Group | Autoclaved Sterile Water | Solvent (0.5% MC) | 0 | 8-10 |
| DSS Treated Control Group | 3% DSS Solution | Solvent (0.5% MC) | 0 | 8-10 |
| Compound Administration Group | 3% DSS Solution | Compound Suspension | 20 | 8-10 |

Administration of Compound

Compound was homogenously pulverized in a test tube containing five stainless steel beads (diameter: 3 mm) by ShakeMaster Auto ver. 2.0 (BMS-A20TP; Biomedical Science) at 1100 rpm for 5 minutes. Next, 0.5% methylcellulose (0.5% MC) was added to the pulverized compound for suspension using ShakeMaster at 1100 rpm for 5 minutes, and thus, a compound suspension in an appropriate concentration was prepared. After performing ultrasonication for 5 minutes, the resultant suspension was stored at 4° C. until use. A dose was set to 10 mL/kg. In the evening on day 5, the administration was started, and the compound suspension or a solvent was orally administered twice a day to each mouse.

Measurement of Disease Activity Index (DAI) Score

A DAI score was calculated as a sum of scores of three parameters (consistency of stool (diarrhea), bleeding (blood in stool) and a weight loss rate) obtained from day 10 to day 12.

The scores of the respective parameters were defined as follows:

Consistency of Stool: 0 (normal), 1 (loose stool), 2 (diarrhea), 3 (watery diarrhea)

Bleeding: 0 (no blood), 1 (bleeding on outer surface of stool), 2 (bleeding inside stool), 3 (rectal bleeding)

Weight Loss Rate: 0 (<5%), 1 (5 to 10%), 2 (10 to 15%), 3 (>15%)

(Each mouse was kept in an individual cage for 15 to 30 minutes to collect a stool sample)

Calculation of Improvement Rate

An improvement rate of the DAI score of each compound administration group was calculated in accordance with the following expression:

Improvement rate=100−((Score of compound administration group-Score average of DSS untreated group)/(Score average of DSS treated control group−Score average of DSS untreated group))×100

Incidentally, the improvement rate of 30% to 50% was shown as +, and that higher than 50% was shown as ++.

Each compounds used in the test had an improvement rate of + or ++.

As is understood from these tables, the compound (1) of the present invention or a pharmacologically acceptable salt thereof exhibits excellent therapeutic or preventive effect on the disease also when administered into a living body.

INDUSTRIAL APPLICABILITY

A compound of the present invention is useful, owing to its potent 15-PGDH inhibitory effect, as an agent for treatment or prevention of fibrosis (such as lung fibrosis (idiopathic pulmonary fibrosis or the like), liver fibrosis, kidney fibrosis, myocardial fibrosis, scleroderma and bone marrow fibrosis), inflammatory diseases (such as chronic obstructive pulmonary disease (COPD), acute lung injury, sepsis, exacerbation of asthma and lung disease, inflammatory bowel disease (such as ulcerative colitis and Crohn's disease), peptic ulcer (such as NSAID induced ulcer), autoinflammatory diseases (such as Behcet's disease), vasculitis syndrome, acute liver injury, acute kidney injury, non-alcoholic fatty liver (NASH), atopic dermatitis, psoriasis, interstitial cystitis, prostatitis syndrome (such as chronic prostatitis/chronic pelvic pain syndrome)), cardiovascular diseases (such as pulmonary hypertension, angina, myocardial infarction, heart failure, ischemic heart disease, chronic kidney disease, renal failure, cerebral apoplexy and peripheral circulatory disturbance), wounds (such as diabetic ulcer, burn, pressure ulcer, acute mucosal injury including Stevens-Johnson syndrome, mucosal injury (such as mucositis or stomatitis) related to an anticancer chemotherapy agent, mainly such as an alkylating agent, a DNA synthesis inhibitor, a DNA gyrase inhibitor or an antimetabolite, cellular or humoral immunotherapy or radioactive rays, or graft-versus-host disease), autoimmune diseases (such as multiple sclerosis or rheumatoid arthritis), graft-versus-host disease (GVHD), hair growth, osteoporosis, ear diseases (such as hearing loss, tinnitus, dizziness and dysequilibrium), eye diseases (such as glaucoma and dry eye), diabetes, underactive bladder, neutropenia, promotion of engraftment in stem cell or bone marrow transplantation or organ transplantation, neurodegenesis and nerve cell death (such as psycho-neurologic disease, neuropathy, neurotoxic disease, neuropathic pain and neurogenerative disease), muscle regeneration (such as muscular atrophy, muscular dystrophy and muscle damage), and cervical ripening.

The invention claimed is:

1. A compound of a formula selected from the group consisting of formula A1aa), formula A1ba), formula A2aa), formula A2ba), formula A2ca), formula A2da), formula A2ea), formula A3aa) and formula A3ba)

A1aa)

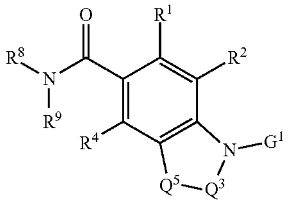

A1ba)

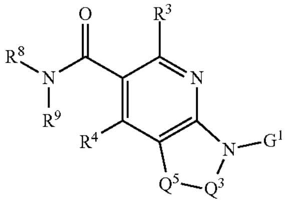

A2aa)

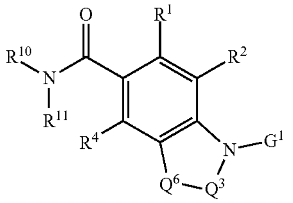

A2ba)

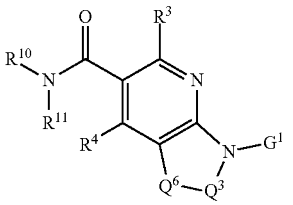

A2ca)

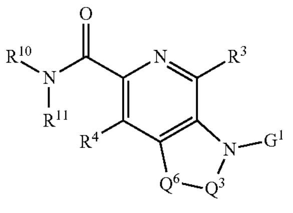

-continued

A2da)

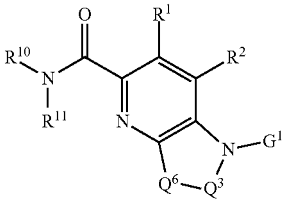

A2ea)

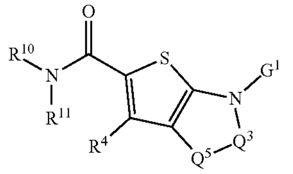

A3aa)

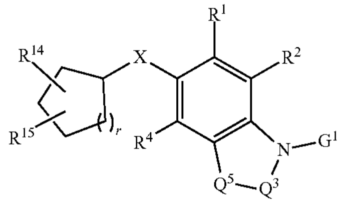

A3ba)

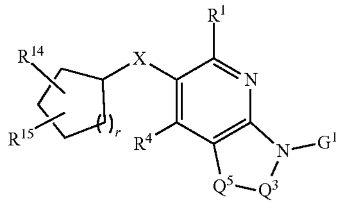

where $Q^3$ is $-(CH_2)_m-(CR^5R^6)_n-(CH_2)_p-$;

$Q^5$ is a methylene group, an oxygen atom, a sulfur atom or $NR^7$ group;

$Q^6$ is a single bond, a methylene group, an oxygen atom, a sulfur atom, a SO group, a $SO_2$ group, a methyleneoxy group or $NR^7$ group;

$R^1$ and $R^2$ are the same or different, and a hydrogen atom, a halogen atom, a $C_1$-$C_3$ alkyl group, a $C_1$-$C_3$ alkoxy group or a $C_3$-$C_8$ cycloalkyl group;

$R^3$ is a hydrogen atom, a $C_1$-$C_3$ alkyl group or a $C_1$-$C_3$ alkoxy group;

$R^4$ is a hydrogen atom, a halogen atom, a $C_1$-$C_3$ alkyl group, a $C_1$-$C_3$ alkoxy group or a $C_3$-$C_8$ cycloalkyl group;

$R^7$ is a hydrogen atom or a $C_1$-$C_3$ alkyl group;

$R^8$ and $R^9$ are the same or different, and a hydrogen atom or a $C_1$-$C_6$ alkyl group optionally having at least one substituent selected from group D1;

when one of $R^8$ and $R^9$ is a hydrogen atom, the other is a $C_1$-$C_6$ alkyl group having at least one substituent selected from group D1;

$R^5$ and $R^6$ are the same or different, and a hydrogen atom, a halogen atom, or a $C_1$-$C_3$ alkyl group or a $C_1$-$C_3$ alkoxy group, each optionally having at least one substituent selected from group D1;

$NR^{10}R^{11}$ in $-CONR^{10}R^{11}$ is a group selected from the group consisting of formulas B1) to B20),

B1)

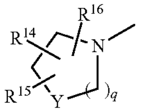

B2)

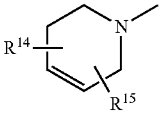

B3)

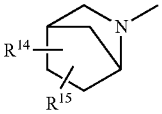

B4)

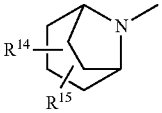

B5)

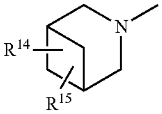

B6)

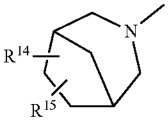

B7)

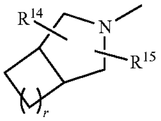

B8)

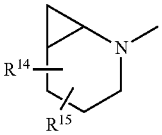

B9)

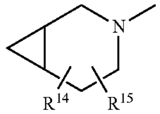

B10)

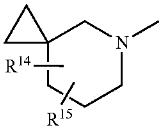

B11)

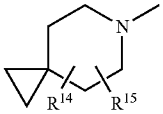

B12)

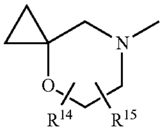

-continued

B13)

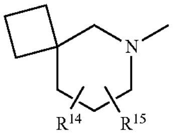

B14)

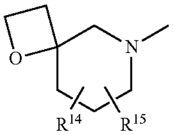

B15)

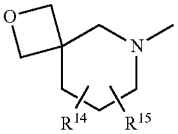

B16)

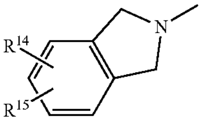

B17)

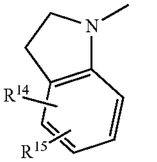

B18)

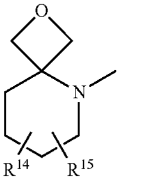

B19)

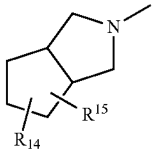

B20)

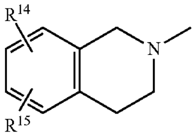

$R^{14}$, $R^{15}$ and $R^{16}$ are the same or different, and a hydrogen atom, a halogen atom, a hydroxy group, a carbonyl group, a carboxyl group, a $C_1$-$C_6$ alkyl group, a halo $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkylsulfonylamino group, an aminocarbonyl group optionally having one or two $C_1$-$C_6$ alkyl groups, or an amino group optionally having one or two $C_1$-$C_6$ alkyl groups;

$R^{14}$ and $R^{15}$ are substituted optionally in any ring in the formula;

Y is a methylene group, an oxygen atom, a sulfur atom or a N—$R^{17}$ group;

$R^{17}$ is a hydrogen atom or a $C_1$-$C_3$ alkyl group optionally having at least one substituent selected from group D;

each of m, n and p is 0, 1 or 2, and m+n+p is an integer of 2 to 5;

each of q and r is 0, 1, 2 or 3;

$G^1$ is a group selected from the group consisting of formula G1a), formula G1b), formula G1c), formula G1d), formula G1e), formula G1f), formula G1g), formula G1h), formula G1i), formula G1j), formula G1k), formula G1l), formula G1m), formula G1n), formula G1o), formula G1p), formula G1q), formula G1r), formula G1s), formula G1t), formula G1u), formula G1v), formula G1w), formula G1x), formula G1y), formula G1z), formula G1A), formula G1B), formula G1C), formula G1D), formula G1E), formula G1F), formula G1G), formula G1H), formula G1I), formula G1J), formula G1K), formula G1L), formula G1M), formula G1N), formula G1O), formula G1P), formula G1Q), formula G1R), formula G1S) and formula G1T), G1a)

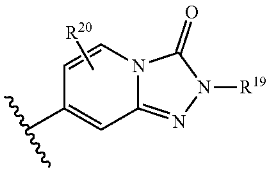

G1b)

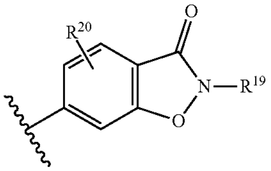

G1c)

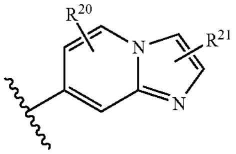

G1d)

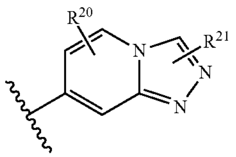

G1e)

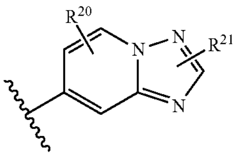

G1f)

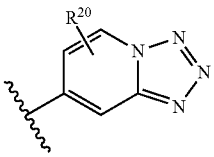

-continued

G1g)

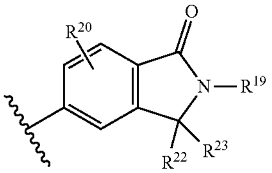

G1h)

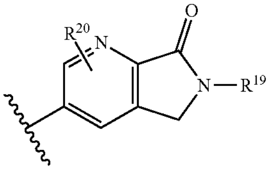

G1i)

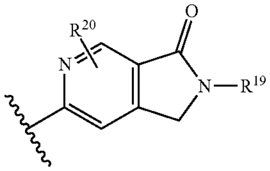

G1j)

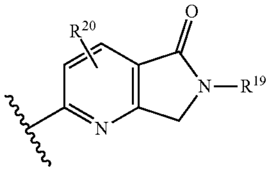

G1k)

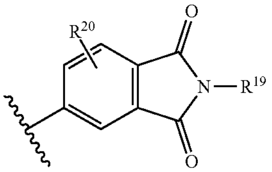

G1l)

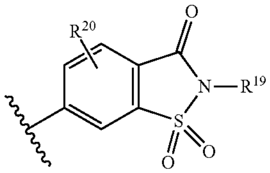

G1m)

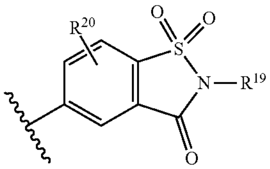

G1n)

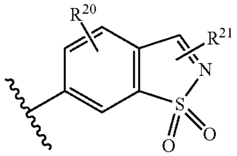

G1o)

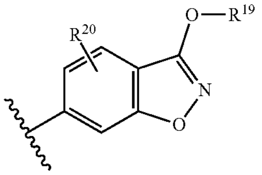

-continued
G1p)
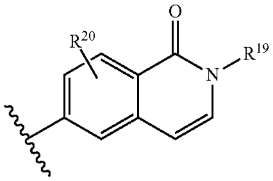
G1q)
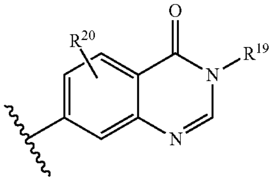
G1r)
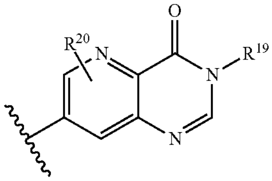
G1s)
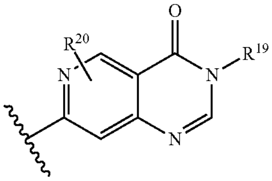
G1t)
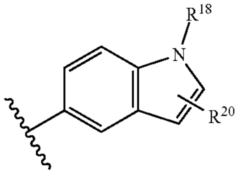
G1u)
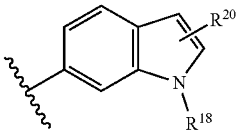
G1v)
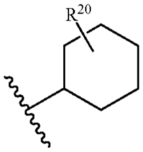
G1w)
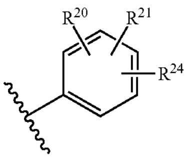
G1x)
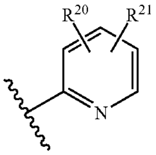
-continued
G1y)
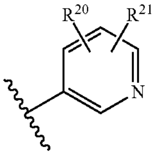
G1z)
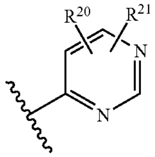
G1A)
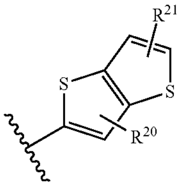
G1B)
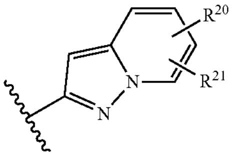
G1C)
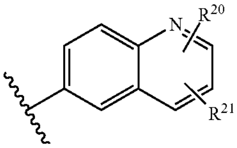
G1D)
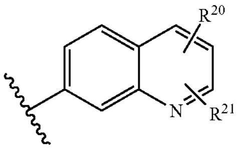
G1E)
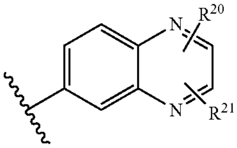
G1F)
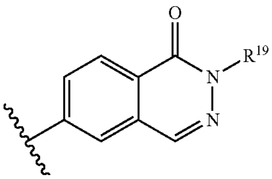
G1G)
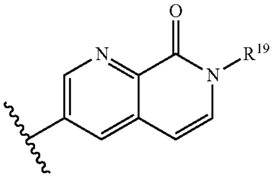

-continued

G1H)

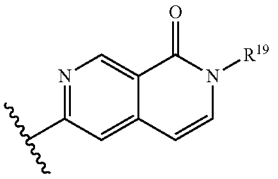

G1I)

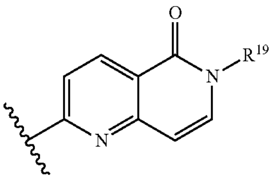

G1J)

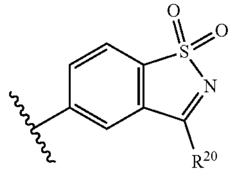

G1K)

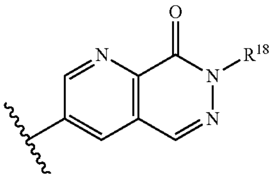

G1L)

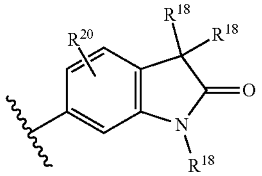

G1M)

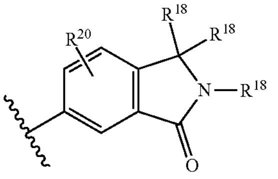

G1N)

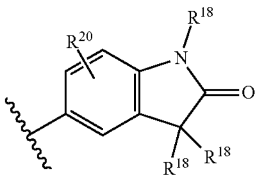

G1O)

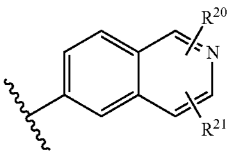

-continued

G1P)

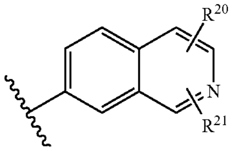

G1Q)

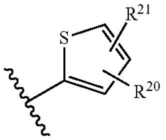

G1R)

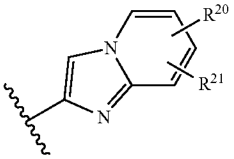

G1S)

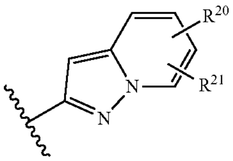

G1T)

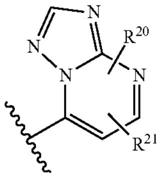

where $R^{18}$ is a hydrogen atom or a $C_1$-$C_3$ alkyl group;

$R^{19}$ is a hydrogen atom, a 3- to 8-membered heterocycloalkyl group containing an oxygen atom, or a $C_3$-$C_8$ cycloalkyl group, a hydroxyl $C_1$-$C_6$ alkyl group, a phenyl group, a phenyl $C_1$-$C_3$ alkyl group, a 6-membered aromatic heterocyclic group, a 6-membered aromatic heterocyclic $C_1$-$C_3$ alkyl group, a $C_1$-$C_3$ alkyl group, a halo $C_1$-$C_3$ alkyl group or a $C_1$-$C_3$ alkoxy $C_1$-$C_3$ alkyl group, each optionally having at least one substituent selected from group C;

$R^{20}$ is a hydrogen atom, a halogen atom, a hydroxy group, a nitrile group, a carboxyl group, a formyl group; or $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having at least one substituent selected from group A3; an aminocarbonyl group optionally having one or two $C_1$-$C_6$ alkyl groups optionally having at least one substituent selected from group B1; or a 5-membered aromatic heterocyclic group or a 6-membered aromatic heterocyclic group, each optionally having at least one substituent selected from group B1;

$R^{21}$ is a hydrogen atom, a halogen atom, a hydroxy group, a nitrile group, a carboxyl group, a formyl group; or a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having at least one substituent selected from group B1; an amino group or an aminocarbonyl group, each optionally having one or two $C_1$-$C_6$ alkyl groups optionally having, in an amino group, at least one substituent selected from group A3; or a 5-membered aromatic heterocyclic group or a 6-membered aromatic heterocyclic group, each optionally having at least one substituent selected from group B1;

$R^{20}$ and $R^{21}$ are substituted optionally in any ring in the formula;

$R^{22}$ and $R^{23}$ are the same or different, and a hydrogen atom, a halogen atom or a $C_1$-$C_3$ alkyl group;

$R^{24}$ is a hydrogen atom or a substituent selected from group B1;

X is —C(=O)—, —CH(OH)—, —S—, —SO— or —$SO_2$—;

group A3 consists of a halogen atom, a hydroxy group, a nitrile group, a carboxyl group, a formyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group and a $C_1$-$C_6$ alkylsulfonylamino group;

group B1 consists of a halogen atom, a hydroxy group, a carbonyl group, a carboxyl group, a $C_1$-$C_6$ alkyl group, a halo $C_1$-$C_6$ alkyl group, a $C_1$-$C_6$ alkylcarbonyl group, a $C_1$-$C_6$ alkoxy group, a halo $C_1$-$C_6$ alkoxy group, a $C_1$-$C_6$ alkoxycarbonyl group, a $C_1$-$C_6$ alkylsulfonylamino group, an aminocarbonyl group optionally having one or two $C_1$-$C_6$ alkyl groups, an amino group optionally having one or two $C_1$-$C_6$ alkyl groups, and a 3- to 8-membered heterocycloalkyl group;

group C consists of a halogen atom, a hydroxy group, a nitrile group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, an amino group optionally having one or two $C_1$-$C_6$ alkyl groups, and a 3- to 8-membered heterocycloalkyl group;

group D consists of a halogen atom, a hydroxy group, a carboxyl group, a $C_1$-$C_6$ alkylcarbonyl group, a $C_1$-$C_6$ alkoxy group, a $C_1$-$C_6$ alkoxycarbonyl group, an aminocarbonyl group optionally having one or two $C_1$-$C_6$ alkyl groups, a $C_1$-$C_6$ alkylsulfonyl group, an aminosulfonyl group optionally having one or two $C_1$-$C_6$ alkyl groups, a $C_1$-$C_6$ alkylsulfonylamino group, an amino group optionally having one or two $C_1$-$C_6$ alkyl groups, and a 3- to 8-membered heterocycloalkyl group; and group D1 consists of a halogen atom, a hydroxy group, a carboxyl group, a $C_1$-$C_6$ alkylcarbonyl group, a $C_1$-$C_6$ alkoxy group and a $C_1$-$C_6$ alkoxycarbonyl group, or a pharmacologically acceptable salt thereof.

2. The compound according to claim 1, or a pharmacologically acceptable salt thereof, wherein $G^1$ is a group selected from the group consisting of formula G1aa), formula G1ba), formula G1ca), formula G1fa), formula G1ga), formula G1ha), formula G1ia), formula G1la), formula G1oa), formula G1pa), formula G1qa), formula G1va), formula G1wa), formula G1xa), formula G1ya) and formula G1Aa), G1aa)

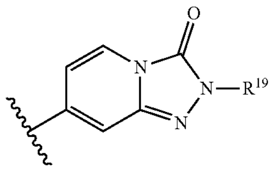

G1ba)

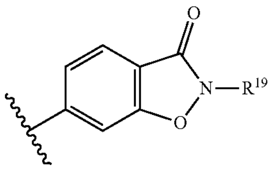

G1ca)

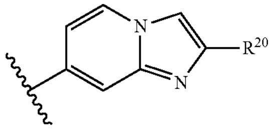

G1fa)

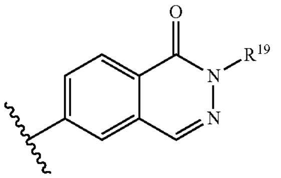

G1ga)

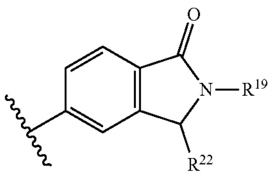

G1ha)

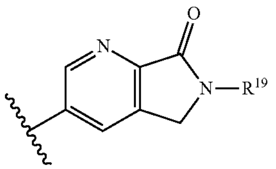

G1ia)

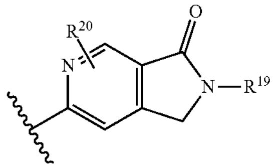

G1la)

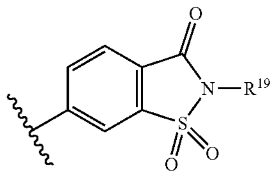

G1oa)

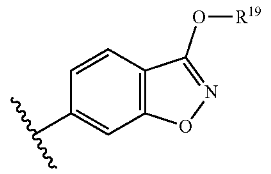

-continued

G1pa)

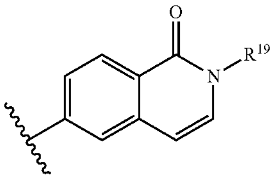

G1qa)

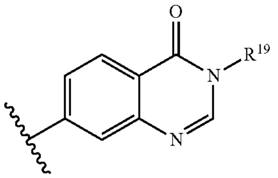

G1va)

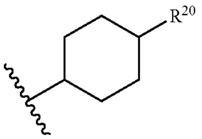

G1wa)

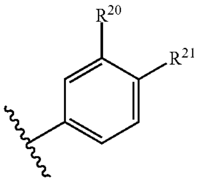

G1xa)

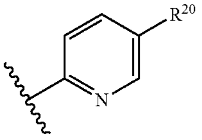

G1ya)

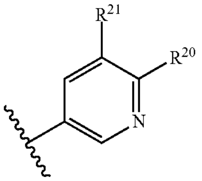

G1Aa)

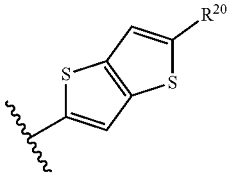

where $R^{19}$ is a hydrogen atom, a 3- to 8-membered heterocycloalkyl group containing an oxygen atom, or a $C_3$-$C_8$ cycloalkyl group, a hydroxyl $C_1$-$C_6$ alkyl group, a phenyl group, a phenyl $C_1$-$C_3$ alkyl group, a 6-membered aromatic heterocyclic group, a 6-membered aromatic heterocyclic $C_1$-$C_3$ alkyl group, a $C_1$-$C_3$ alkyl group, a halo $C_1$-$C_3$ alkyl group or a $C_1$-$C_3$ alkoxy $C_1$-$C_3$ alkyl group, each optionally having at least one substituent selected from group C;

$R^{20}$ is a hydrogen atom, a halogen atom, a hydroxy group, a nitrile group, a carboxyl group, a formyl group; or $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having at least one substituent selected from group A3; an aminocarbonyl group optionally having one or two $C_1$-$C_6$ alkyl groups optionally having at least one substituent selected from group B1; or a 5-membered aromatic heterocyclic group or a 6-membered aromatic heterocyclic group, each optionally having at least one substituent selected from group B1;

$R^{21}$ is a hydrogen atom, a halogen atom, a hydroxy group, a nitrile group, a carboxyl group, a formyl group; or a $C_1$-$C_6$ alkyl group, a $C_1$-$C_6$ alkylcarbonyl group, a $C_1$-$C_6$ alkoxy group, a $C_1$-$C_6$ alkoxycarbonyl group, a $C_1$-$C_6$ alkylsulfonylamino group, a $C_1$-$C_6$ alkylsulfonyl group, a $C_3$-$C_8$ cycloalkyl group, a 3- to 8-membered heterocycloalkylcarbonyl group, a 3- to 8-membered heterocycloalkylamino group or a 3- to 8-membered heterocycloalkylaminocarbonyl group, each optionally having at least one substituent selected from group B1; an amino group or an aminocarbonyl group, each optionally having one or two $C_1$-$C_6$ alkyl groups optionally having, in an amino group, at least one substituent selected from group A3; or a 5-membered aromatic heterocyclic group or a 6-membered aromatic heterocyclic group, each optionally having at least one substituent selected from group B1; and $R^{22}$ is a hydrogen atom, a halogen atom or a $C_1$-$C_3$ alkyl group.

3. The compound according to claim 2, or a pharmacologically acceptable salt thereof, wherein $NR^{10}R^{11}$ in —$CONR^{10}R^{11}$ is a group selected from the group consisting of formula B1a), formula B2a), formula B4a), formula B5a), formula B7a), formula B8a), formula B9a), formula B10a), formula B11a), formula B13a) and formula B16a), B1a)

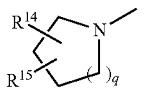

B2a)

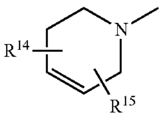

B4a)

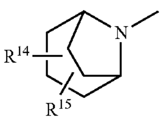

B5a)

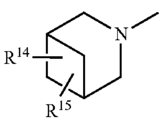

B7a)

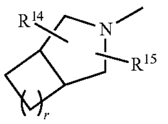

-continued

B8a)

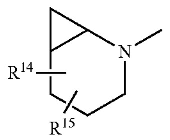

B9a)

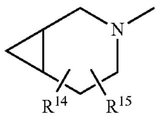

B10a)

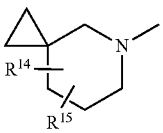

B11a)

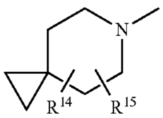

B13a)

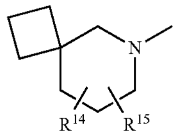

B16a)

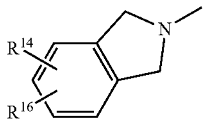

where $R^{14}$ and $R^{15}$ are the same or different, and a hydrogen atom, a halogen atom, a hydroxy group, a nitrile group, a carboxyl group, a $C_1$-$C_6$ alkyl group, a $C_1$-$C_6$ alkylcarbonyl group, a $C_1$-$C_6$ alkoxy group, a $C_1$-$C_6$ alkoxycarbonyl group or a halo $C_1$-$C_6$ alkyl group;

$R^{14}$ and $R^{15}$ are substituted optionally in any ring in the formula B1a), formula B2a), formula B4a), formula B5a), formula B7a), formula B8a), formula B9a), formula B10a), formula B11a), formula B13a) and formula B16a); and each of q and r is 0, 1, 2 or 3.

4. The compound according to claim 3, or a pharmacologically acceptable salt thereof, wherein the compound is a compound of a formula selected from the group consisting of formula A2aa), formula A2ba) and formula A3ba), A2aa)

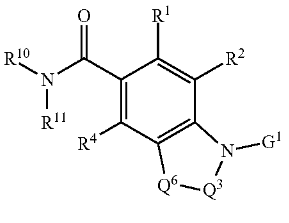

-continued

A2ba)

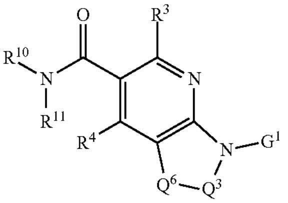

A3ba)

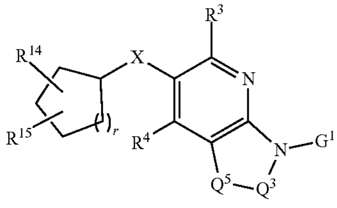

where $Q^6$ is a single bond, a methylene group, an oxygen atom, a methyleneoxy group or $NR^7$ group;

$Q^3$ is $-(CH_2)_m-(CR^5R^6)_n-(CH_2)_p-$;

$R^5$ and $R^6$ are the same or different, and a hydrogen atom, a halogen atom, a $C_1$-$C_3$ alkyl group, a $C_1$-$C_3$ alkoxy group or a halo $C_1$-$C_3$ alkyl group; and each of m, n and p is 0, 1 or 2, and m+n+p is an integer of 2 to 5.

5. The compound according to claim 4, or a pharmacologically acceptable salt thereof, wherein the compound is a compound of a formula selected from the group consisting of formula A2aaa), formula A2baa), formula A2caa) and formula A2daa), A2aaa)

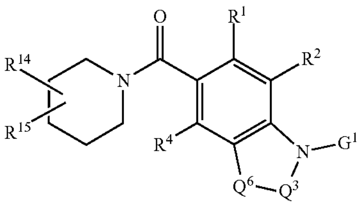

A2baa)

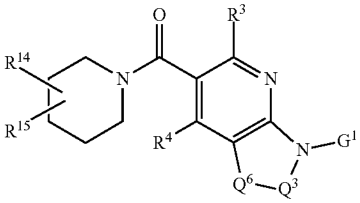

A2caa)

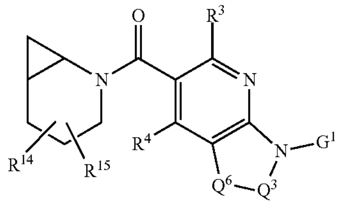

-continued

A2daa)

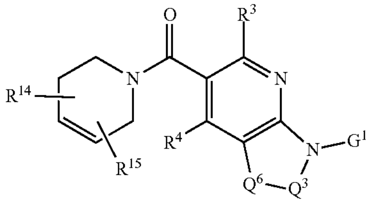

where $G^1$ is a group selected from the group consisting of formula G1aa), formula G1fa), formula G1ga), formula G1ia), formula G1pa), formula G1qa) and formula G1ya), G1aa)

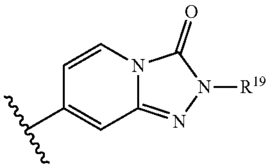

G1fa)

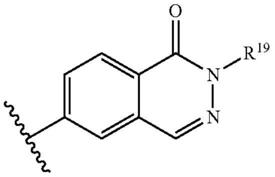

G1ga)

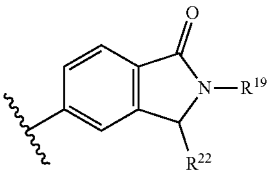

G1ia)

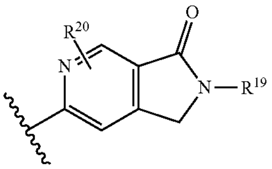

G1pa)

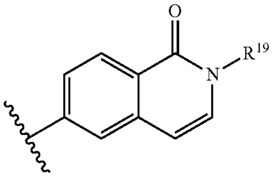

G1qa)

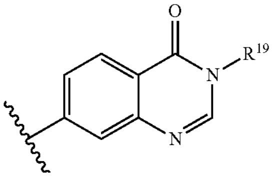

-continued

G1ya)

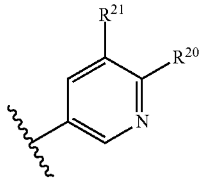

where $Q^3$ is $-(CH_2)_m-(CR^5R^6)_n-(CH_2)_p-$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^7$ is a hydrogen atom or a $C_1$-$C_3$ alkyl group;

$R^{19}$ is a hydrogen atom, a $C_1$-$C_3$ alkyl group, a $C_1$-$C_3$ alkoxy $C_1$-$C_3$ alkyl group, a $C_3$-$C_8$ cycloalkyl group, a hydroxyl $C_1$-$C_6$ alkyl group, a halo $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^{22}$ is a hydrogen atom or a $C_1$-$C_3$ alkyl group; and each of m, n and p is 0, 1 or 2, and m+n+p is an integer of 2 to 5.

6. A method for treating at least one of fibrosis, cardiovascular diseases, and autoimmune diseases, comprising:

administering the compound of claim 1 or a pharmacologically acceptable salt thereof to a patient in need thereof.

7. A method for treating at least one of fibrosis, cardiovascular diseases, and autoimmune diseases, comprising:

administering an effective amount of the compound of claim 2 or a pharmacologically acceptable salt thereof to a patient in need thereof.

8. The compound according to claim 1, or a pharmacologically acceptable salt thereof, wherein the compound is a compound having a structure selected from

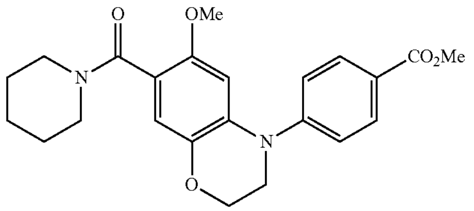

-continued
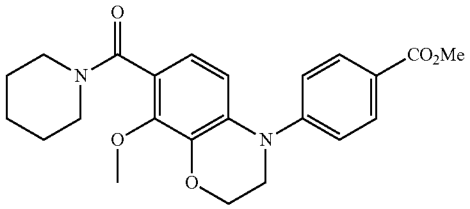
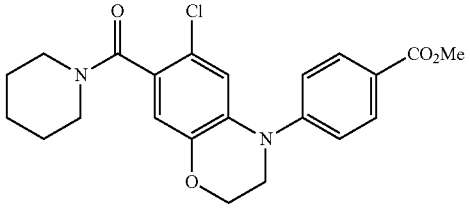
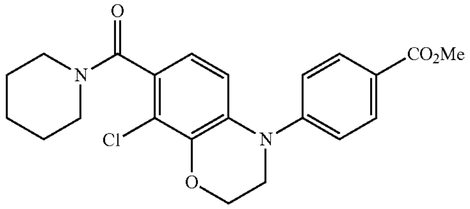
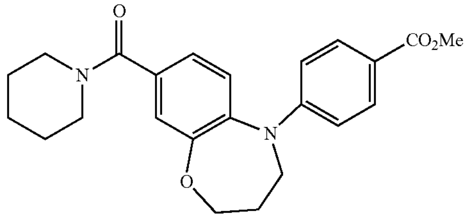
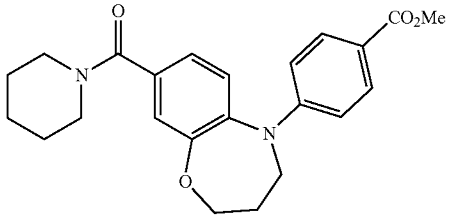
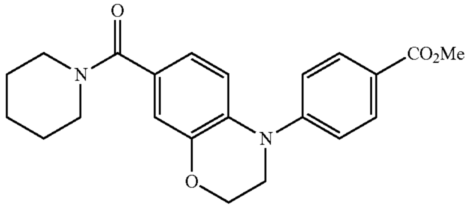
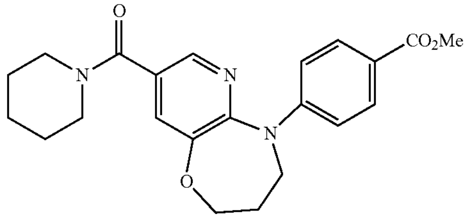
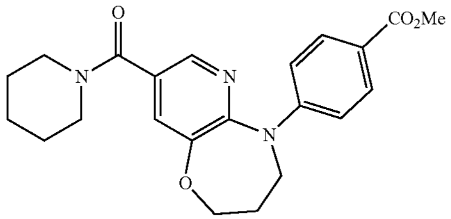
-continued
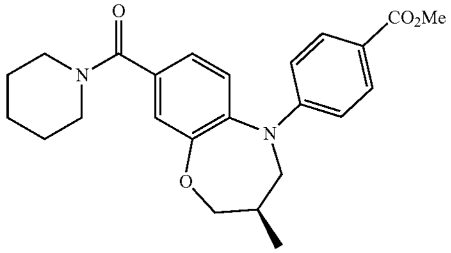
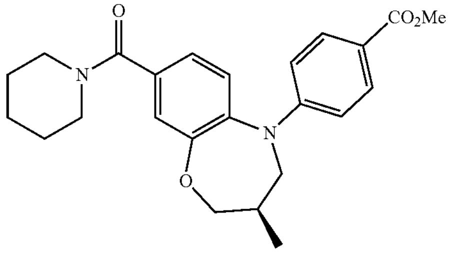
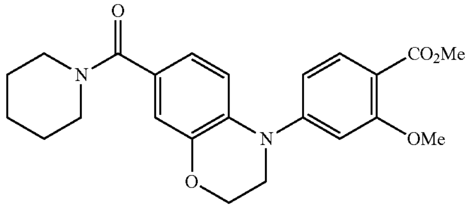
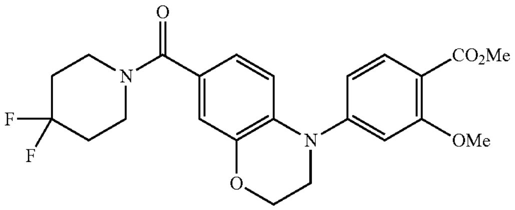
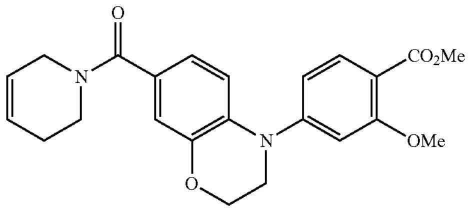
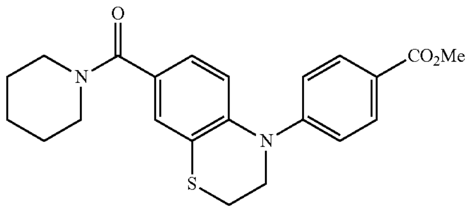
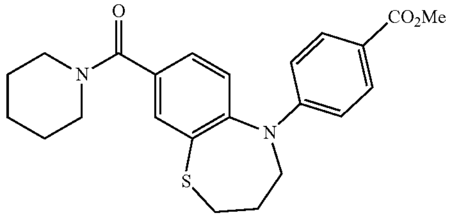

-continued
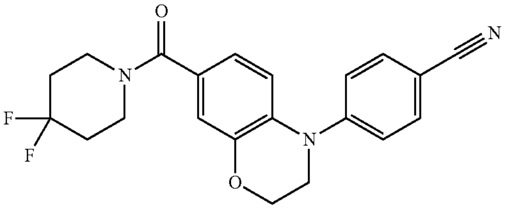
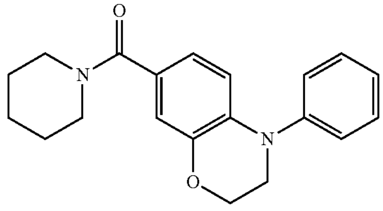
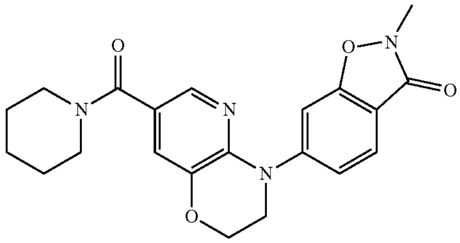
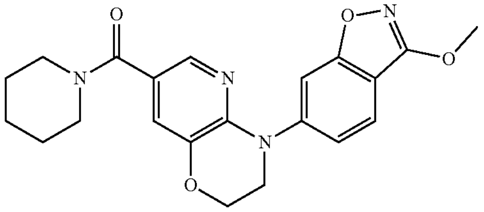
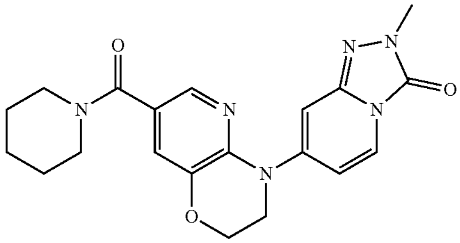
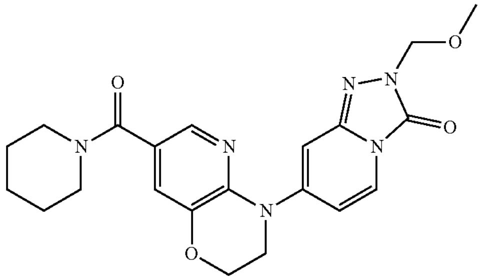
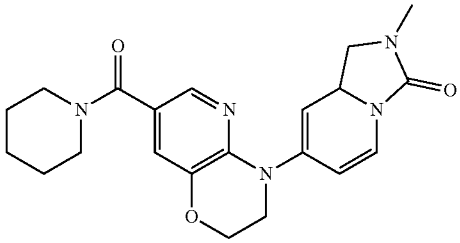
-continued
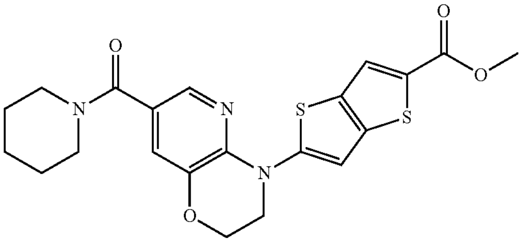
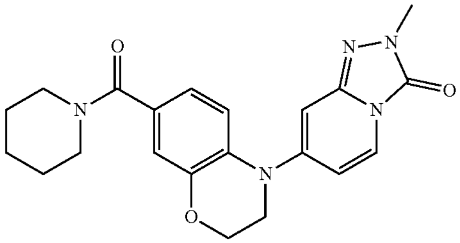
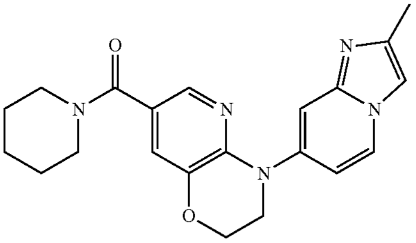
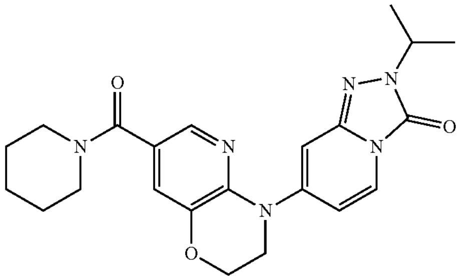
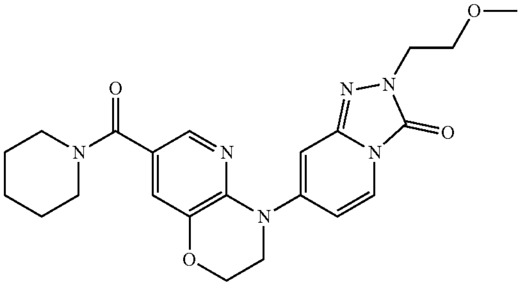
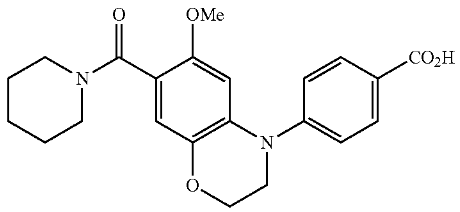
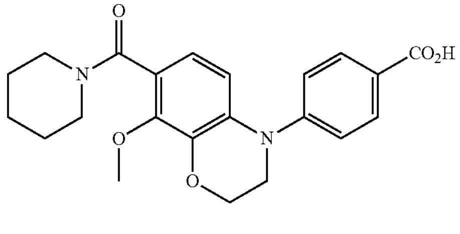

-continued
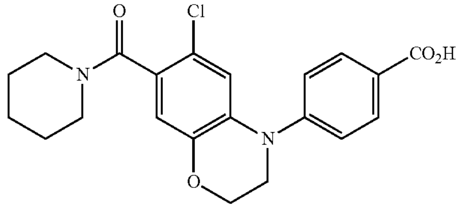
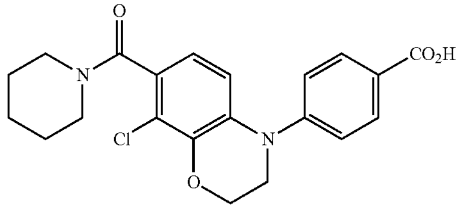
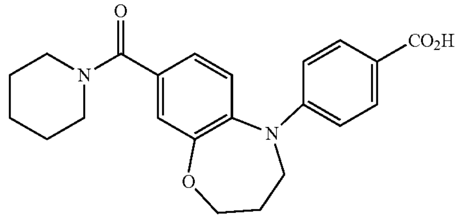
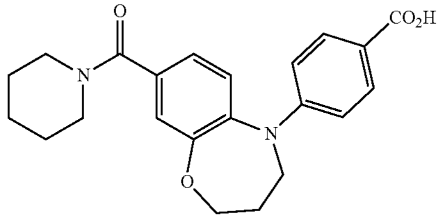
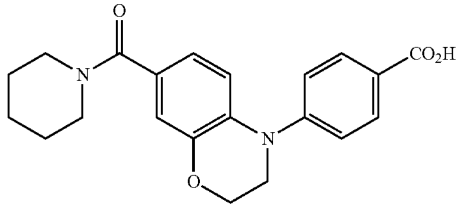
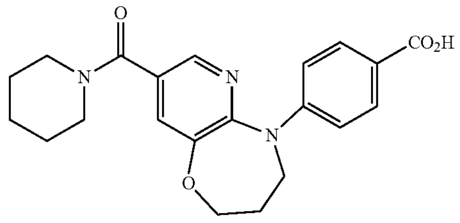
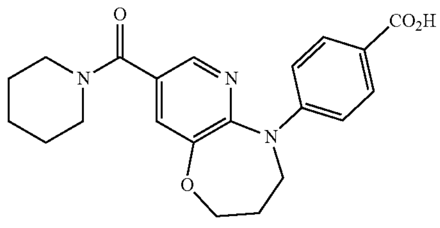
-continued
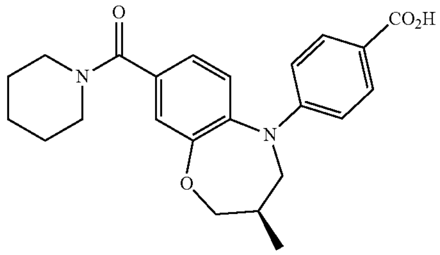
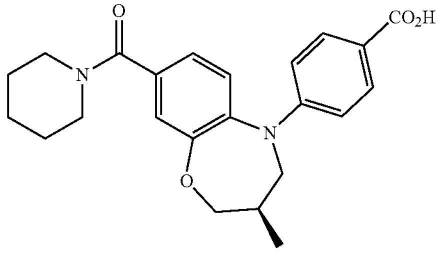
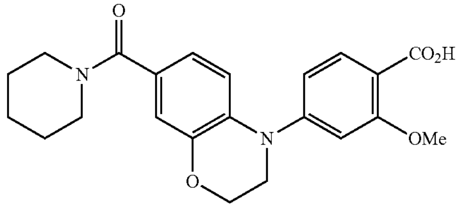
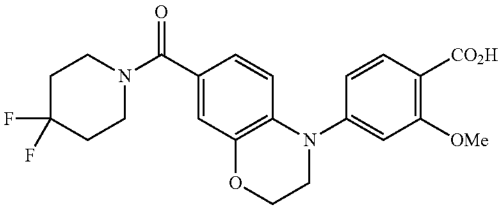
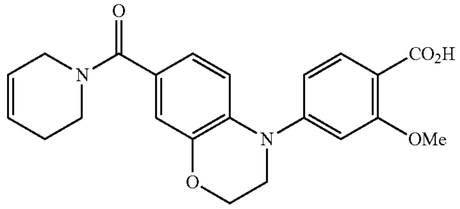
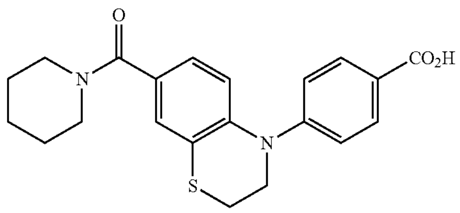
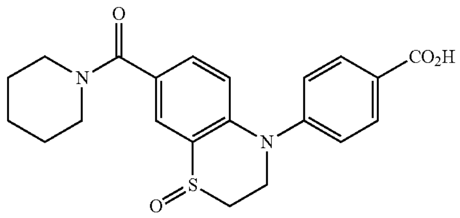

-continued
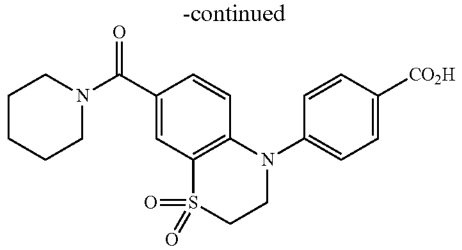
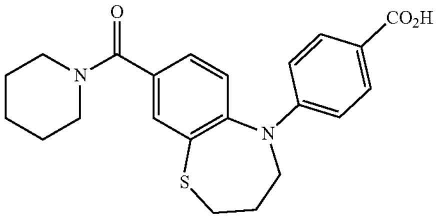
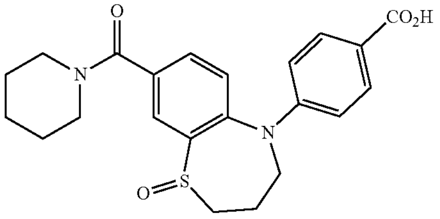
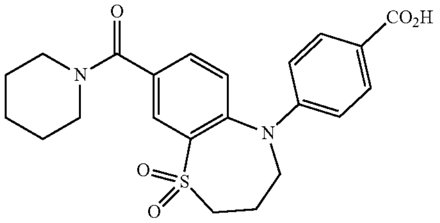
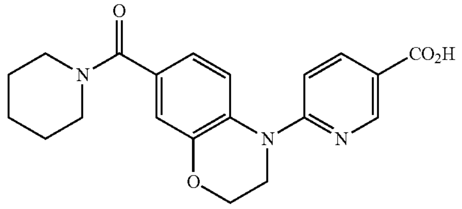
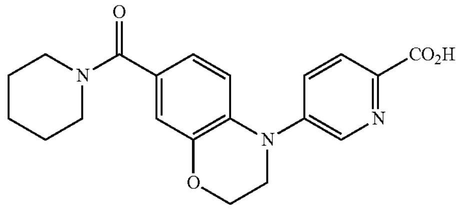
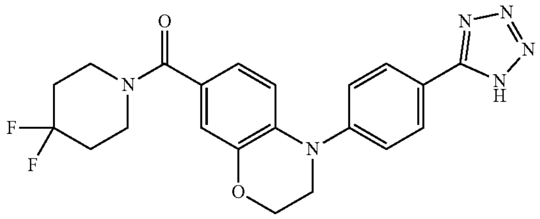
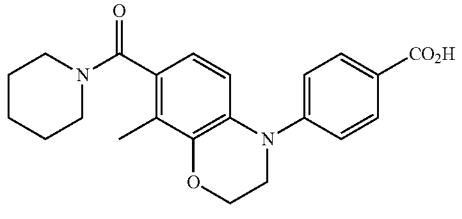
-continued
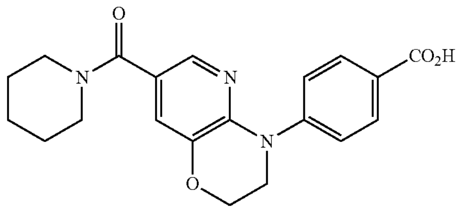
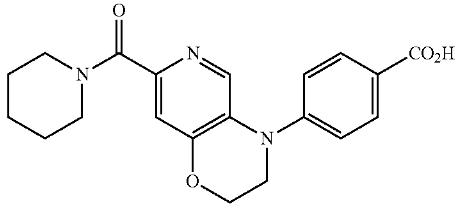
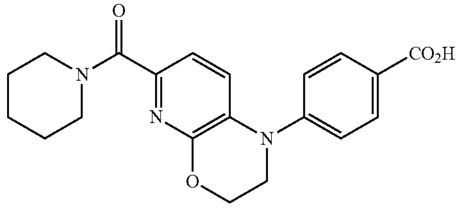
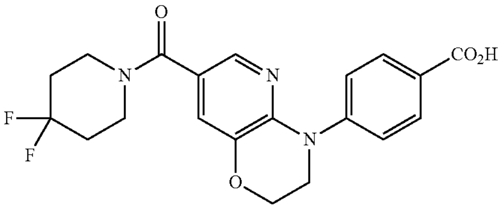
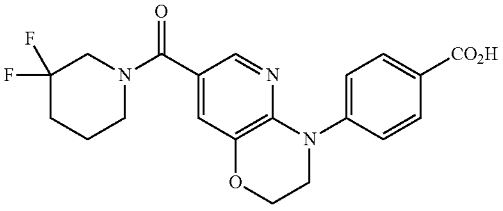
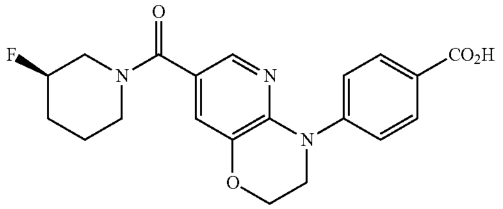
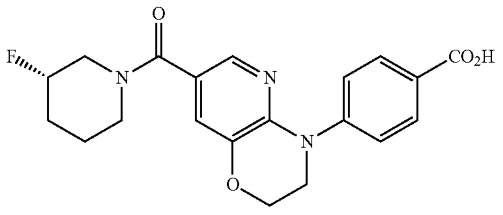
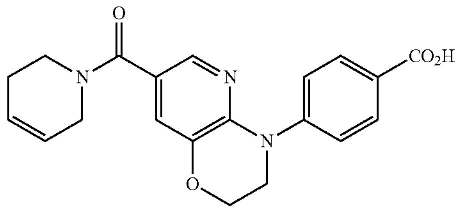

-continued
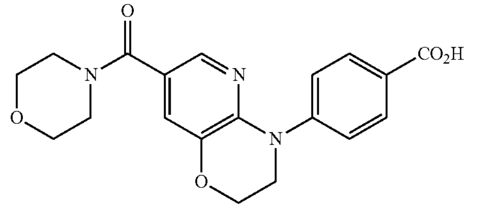
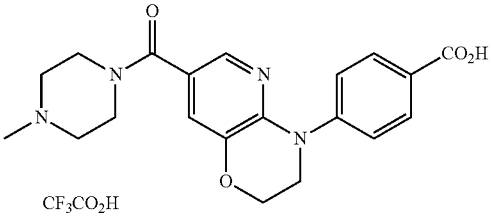
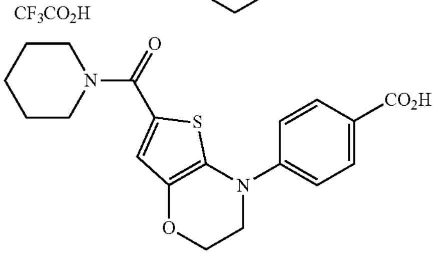
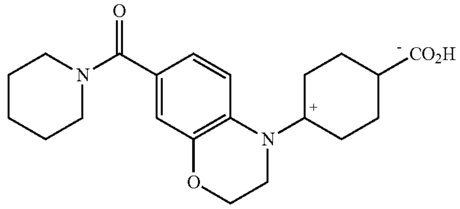
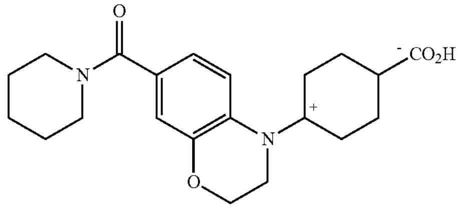
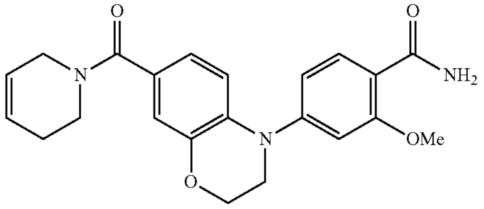
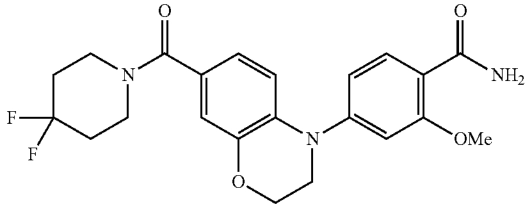
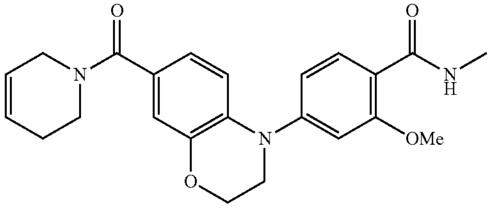
-continued
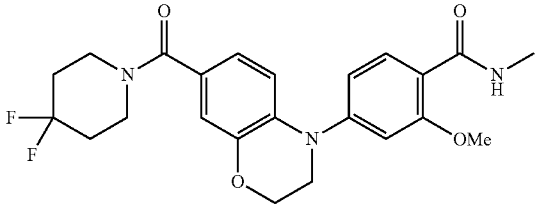
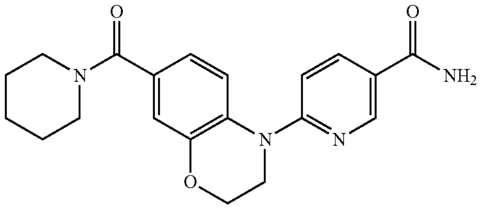
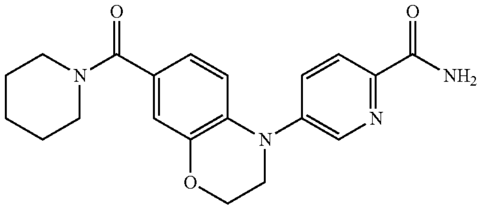
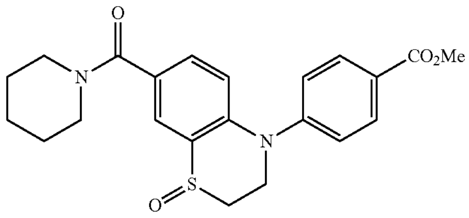
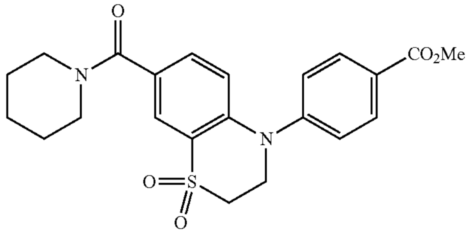
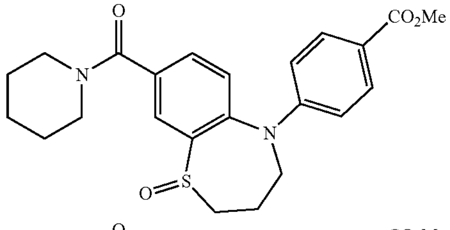
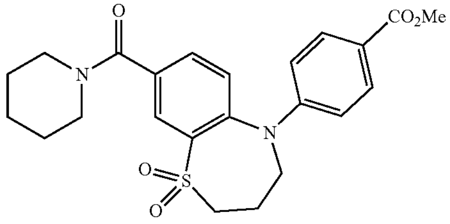
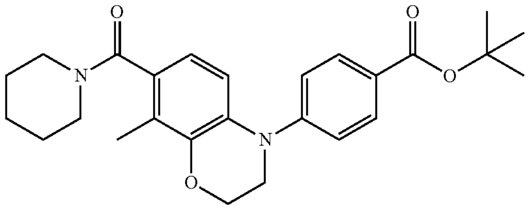

-continued
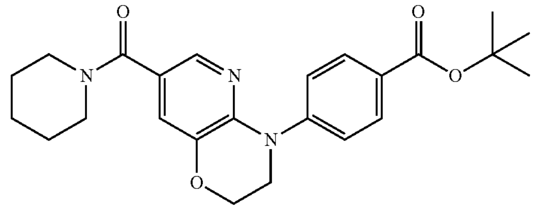
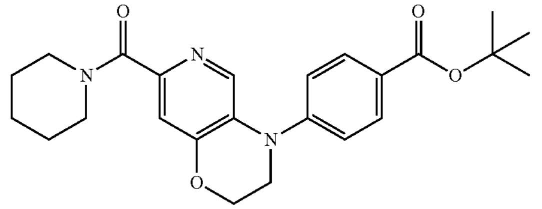
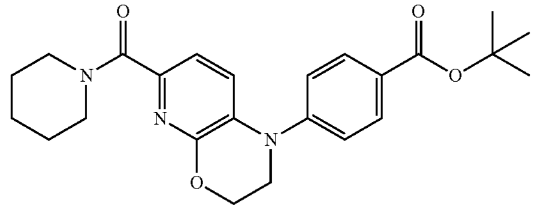
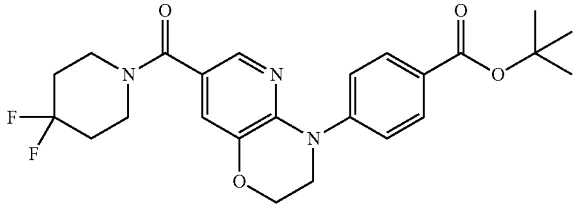
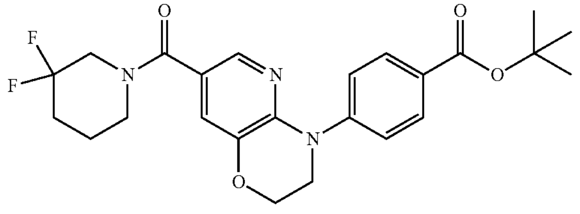
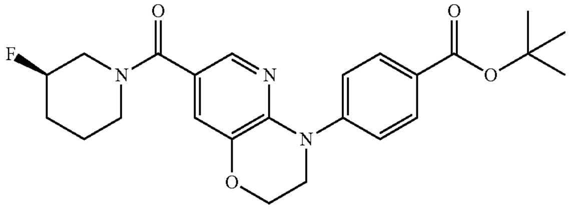
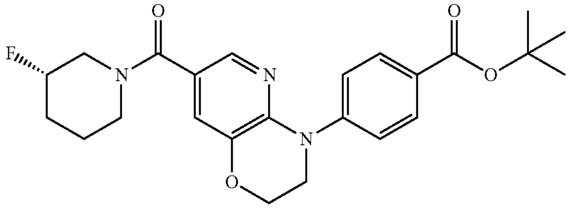
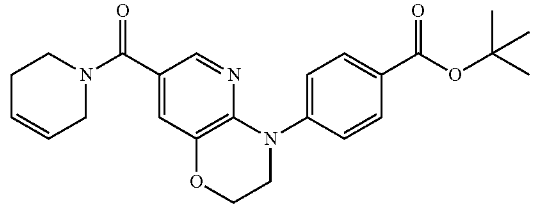
-continued
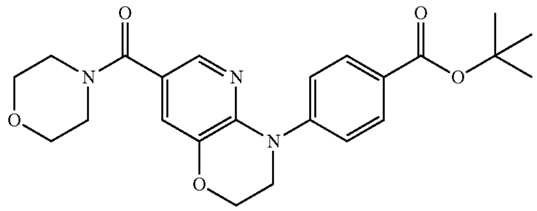
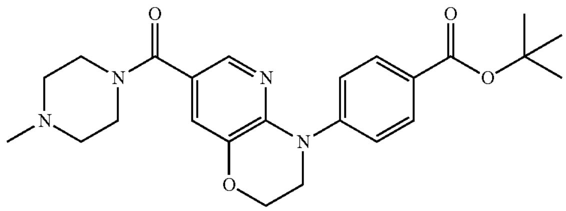
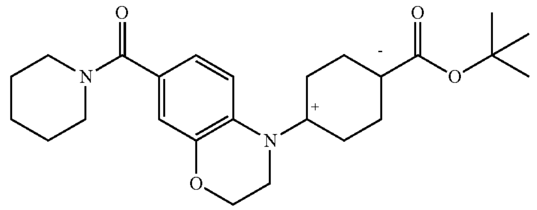
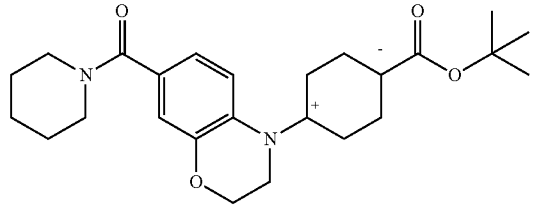
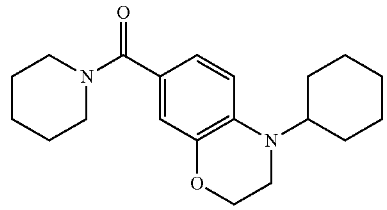
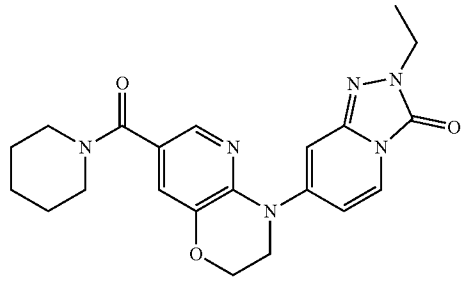
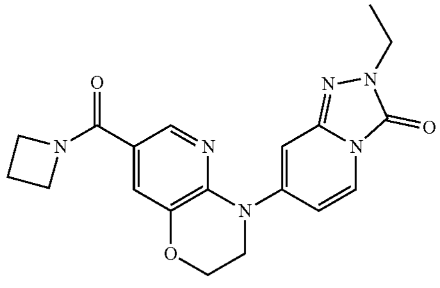

-continued
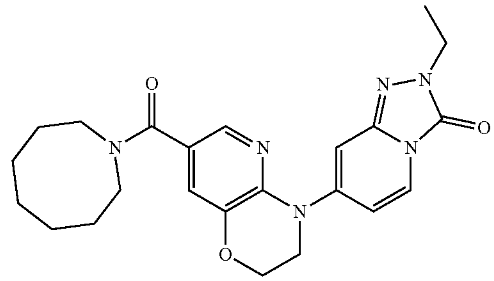
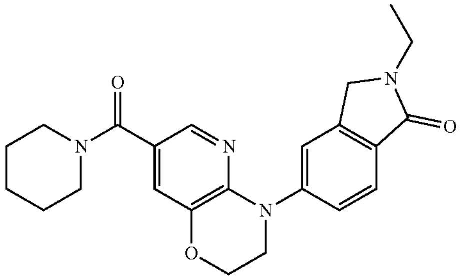
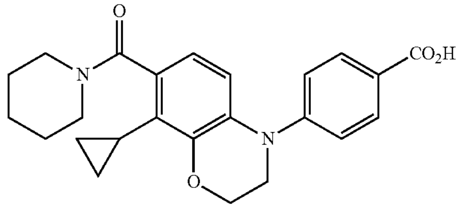
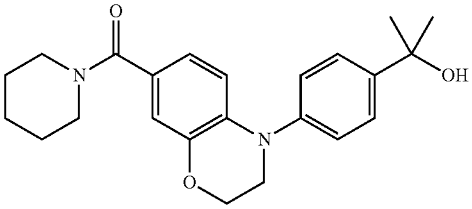
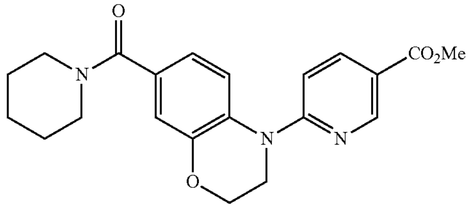
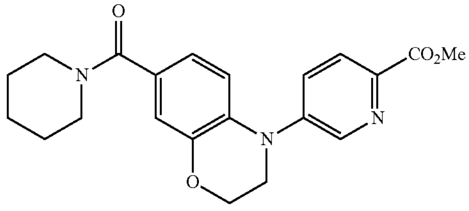
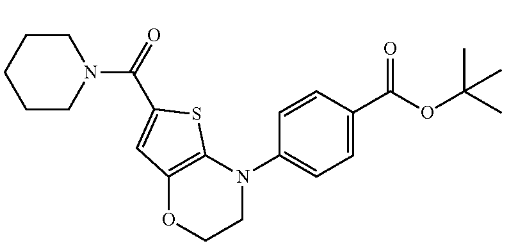
-continued
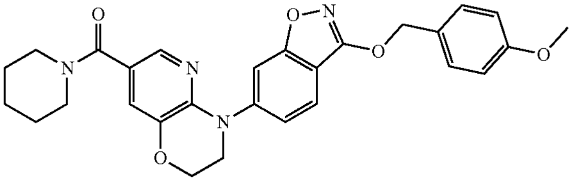
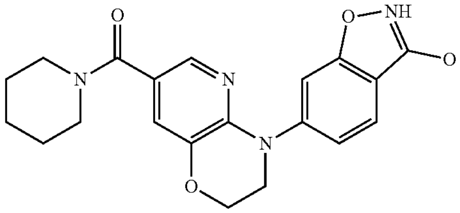
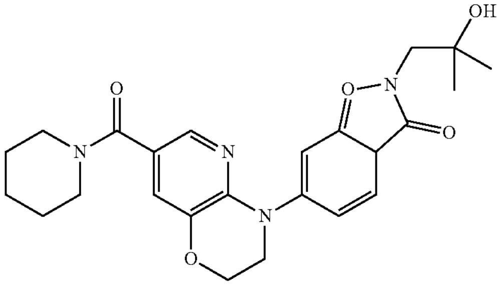
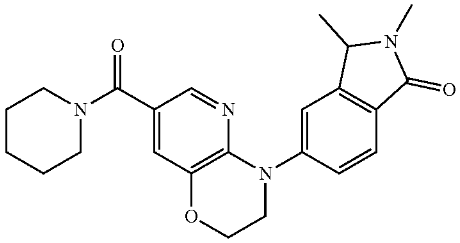
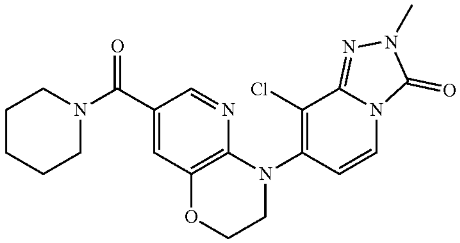
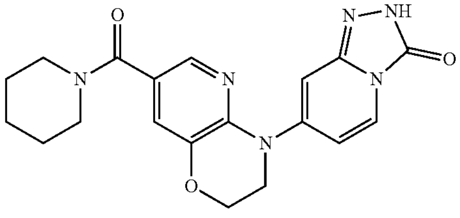
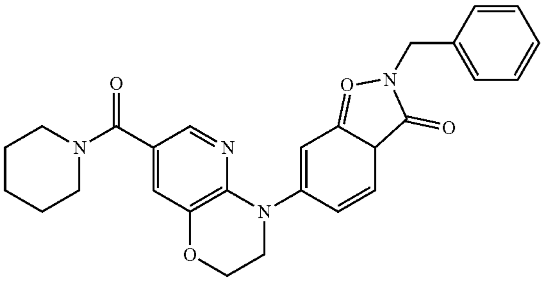

-continued
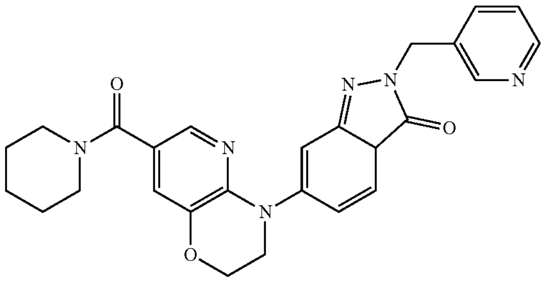
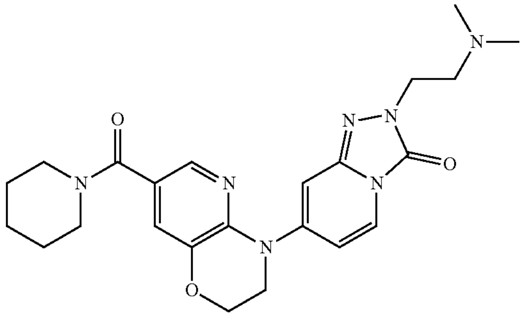
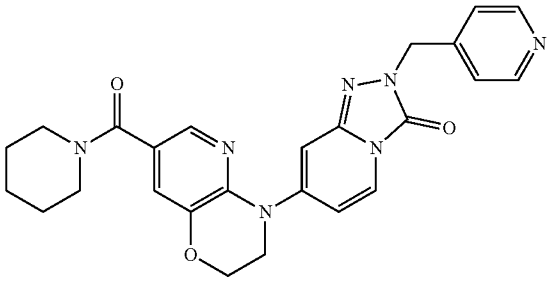
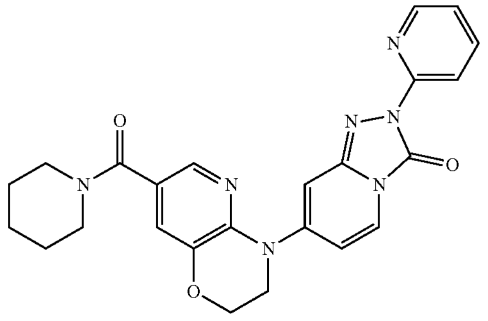
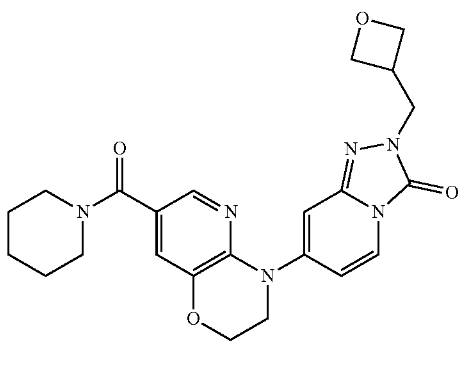
-continued
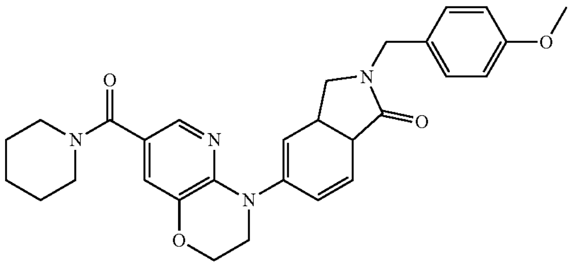
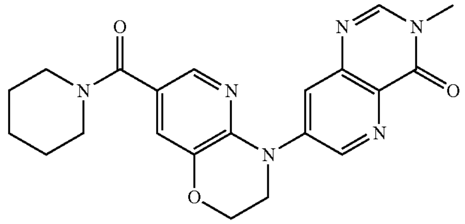
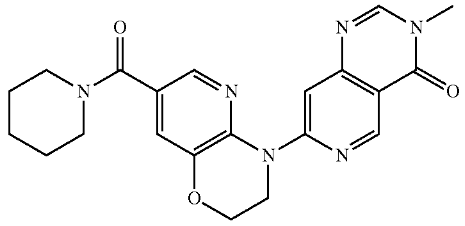
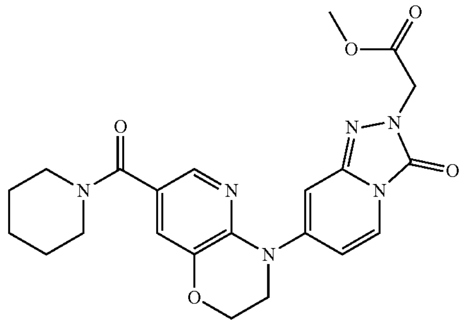
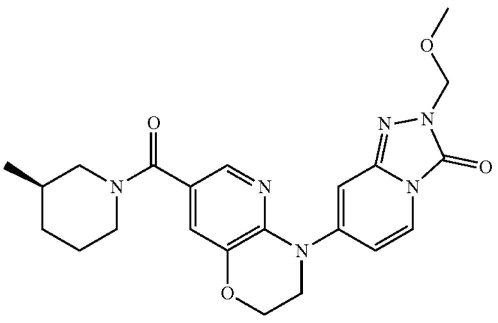
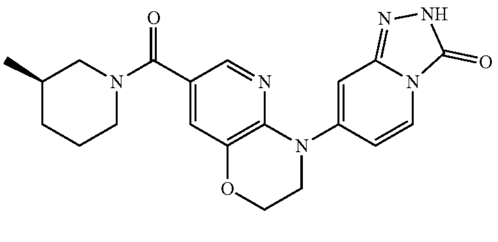

-continued
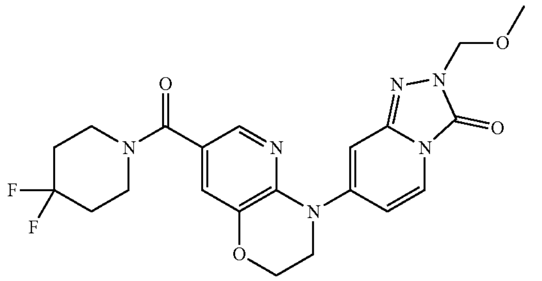
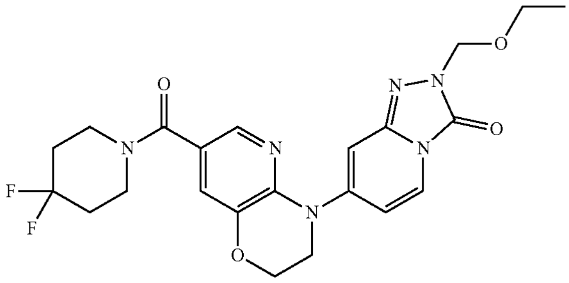
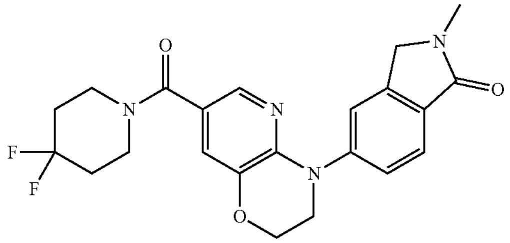
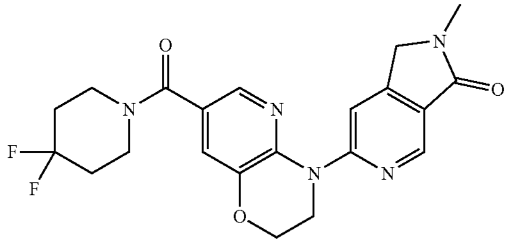
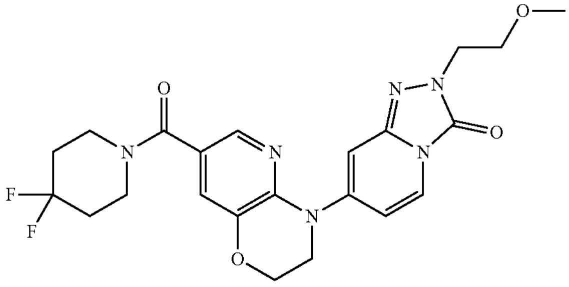
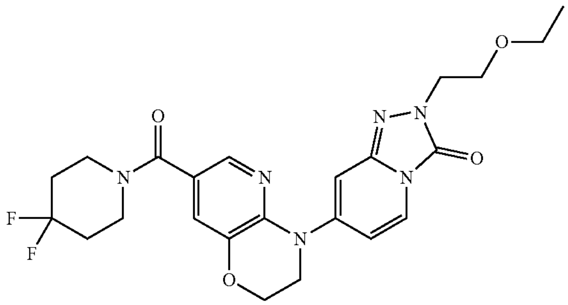
-continued
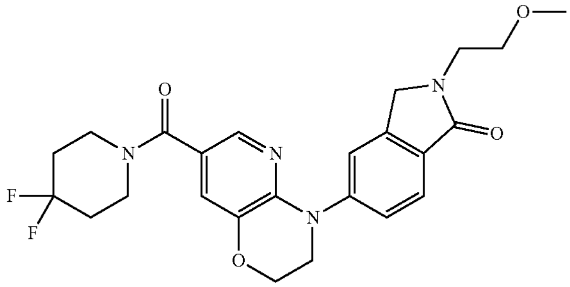
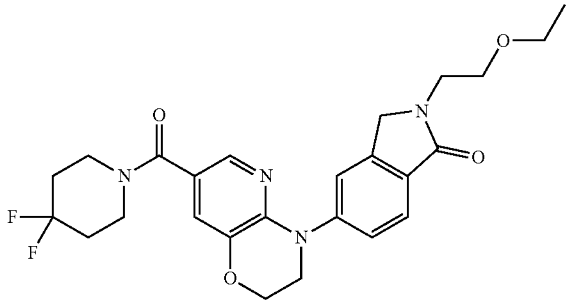
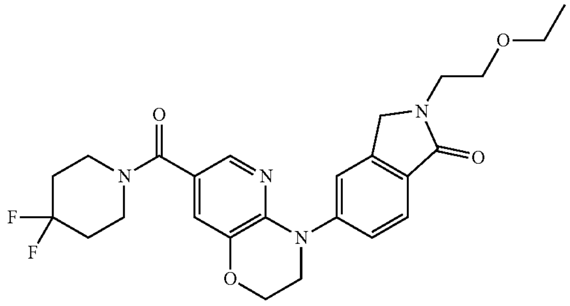
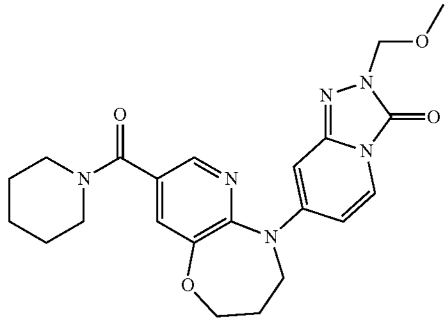
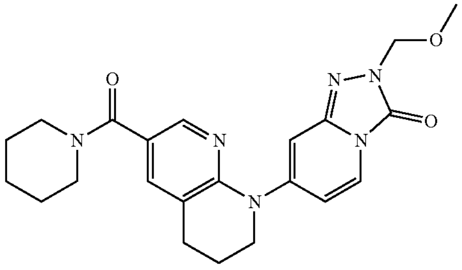
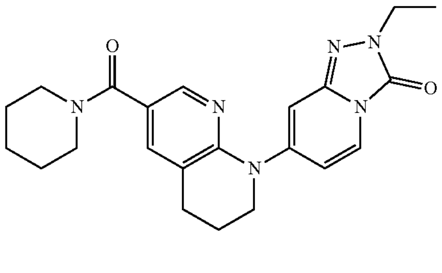

-continued
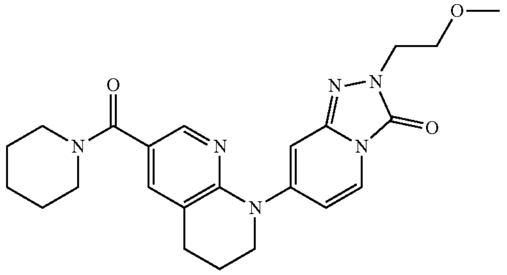
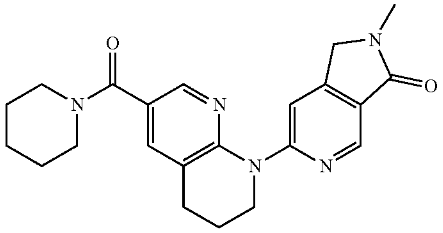
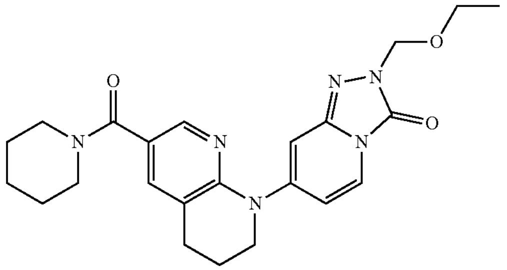
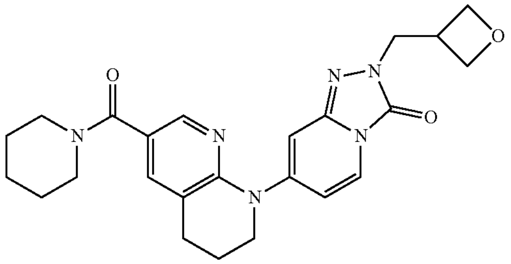
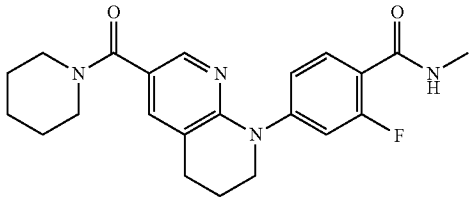
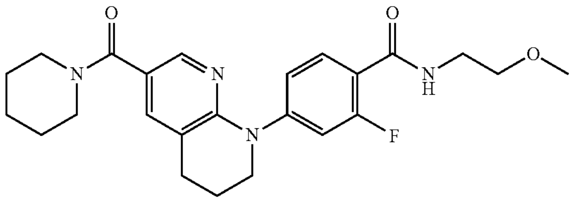
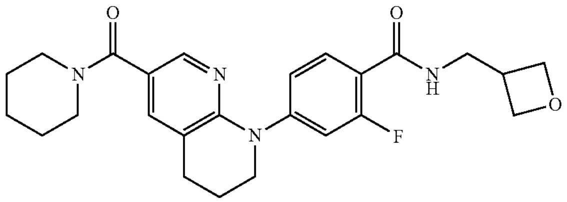
-continued
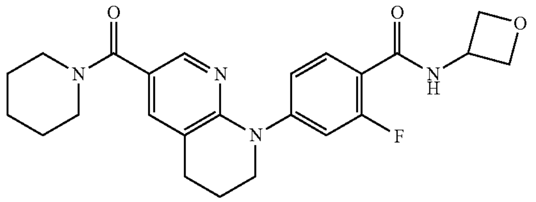
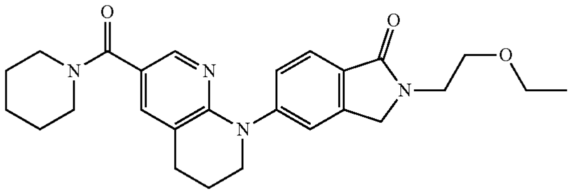
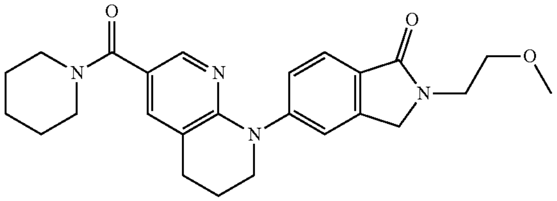
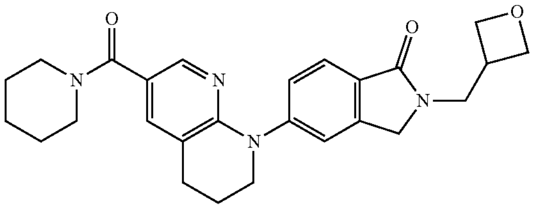
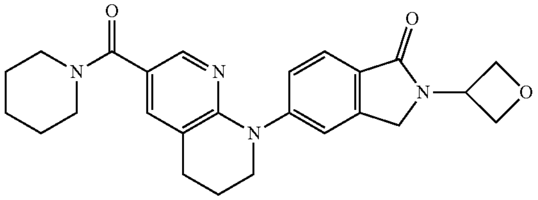
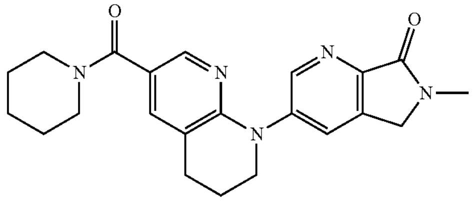
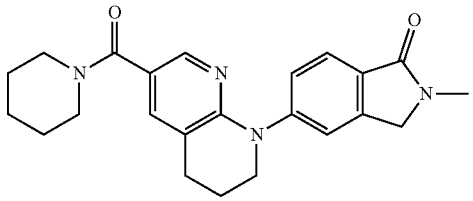
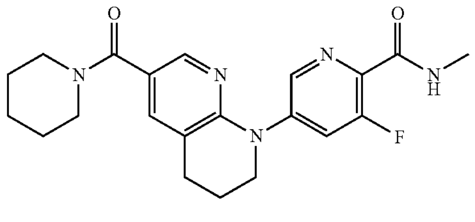

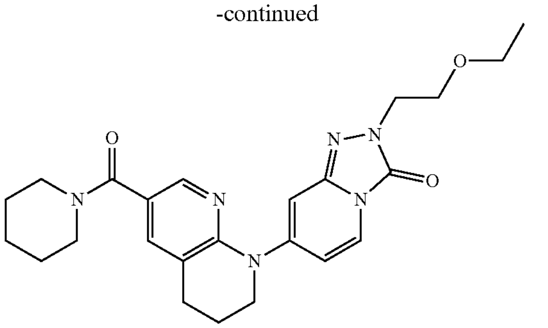
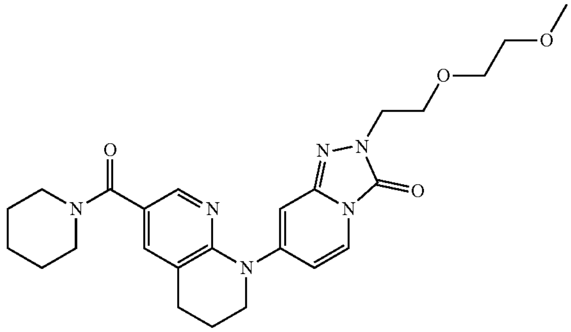
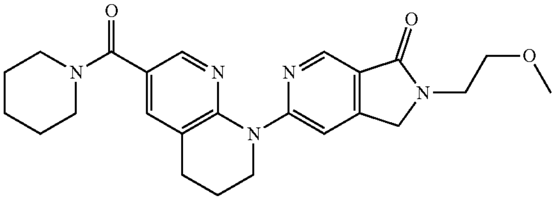
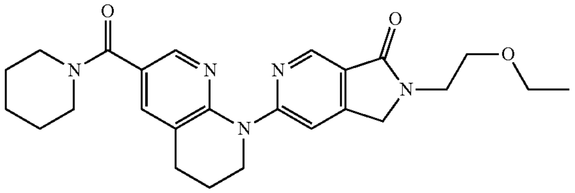
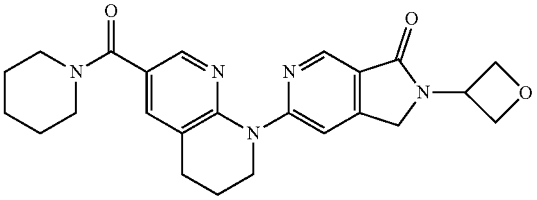
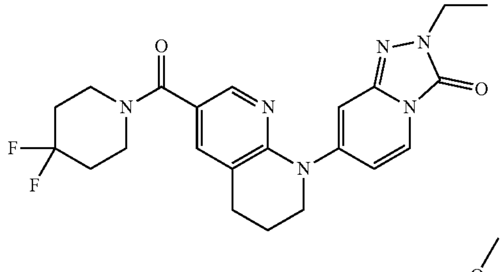
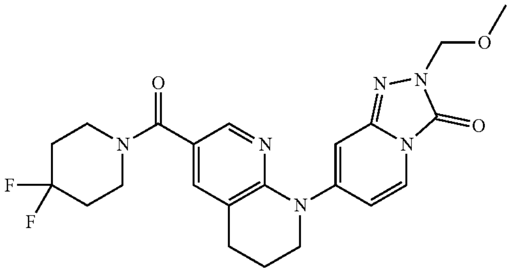
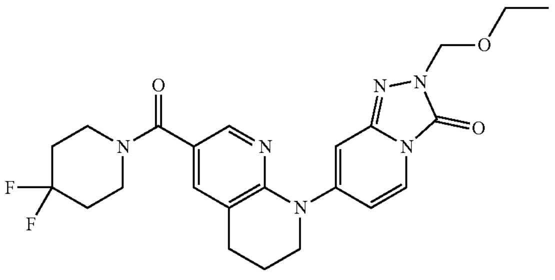
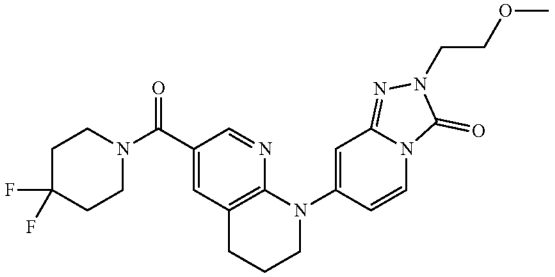
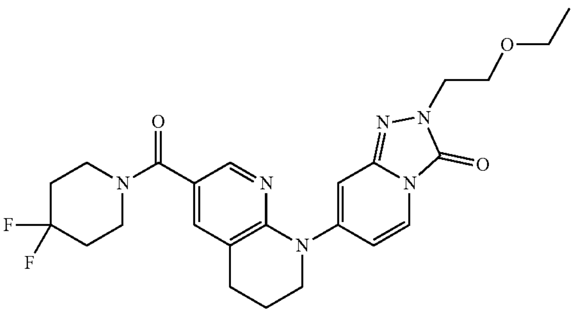
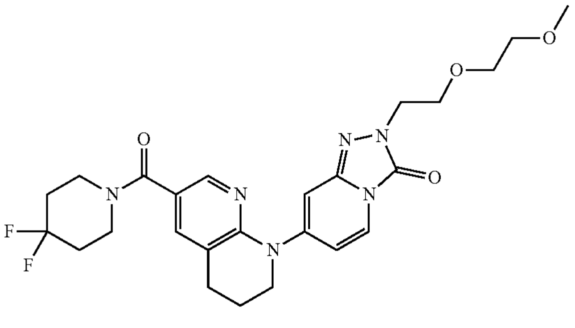
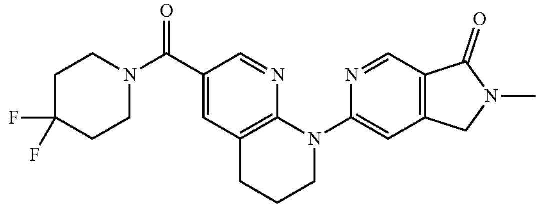
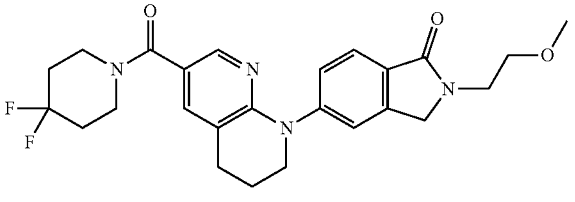

-continued
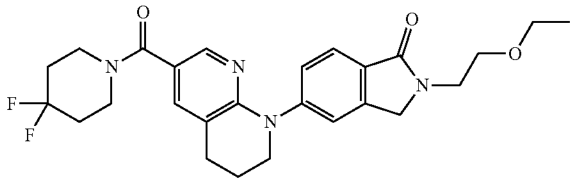
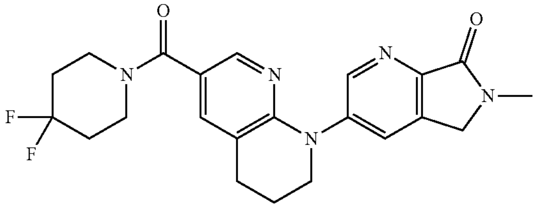
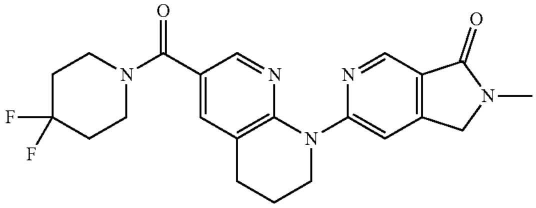
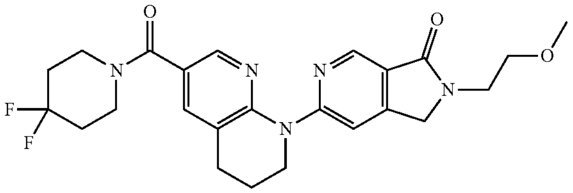
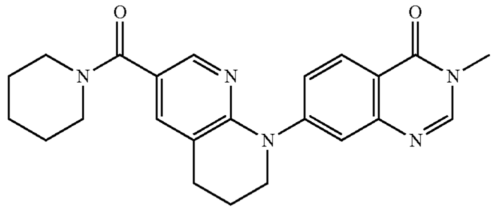
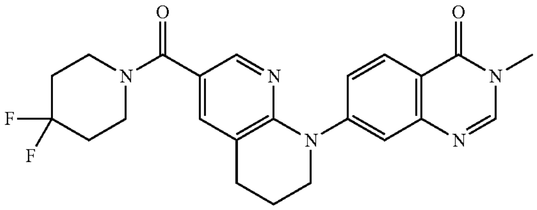
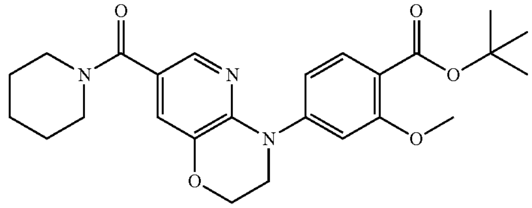
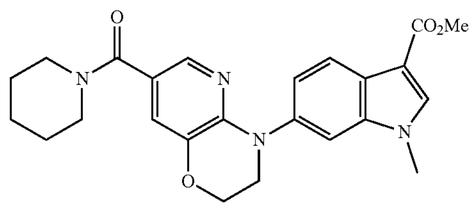
-continued
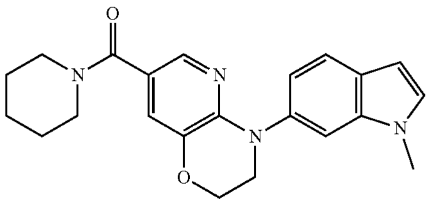
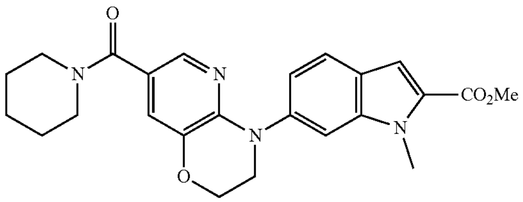
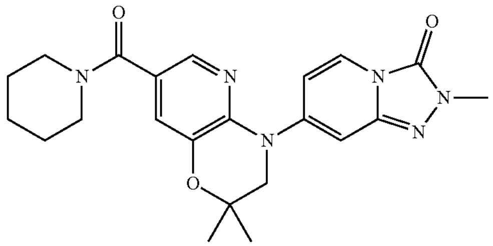
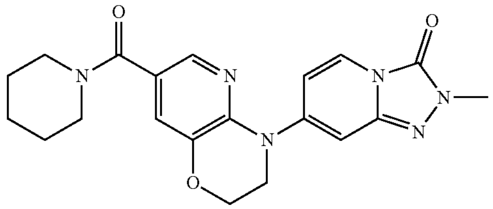
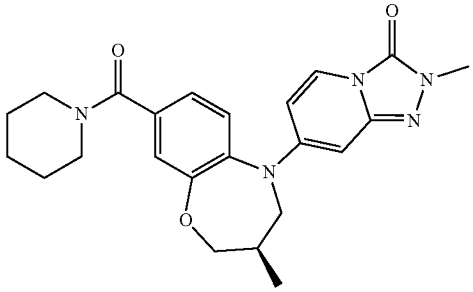
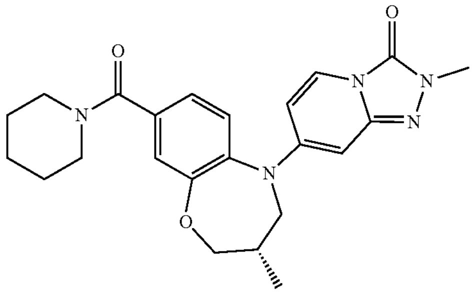
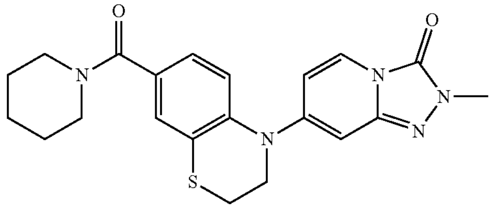

-continued
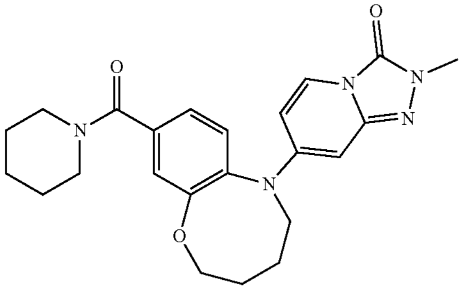
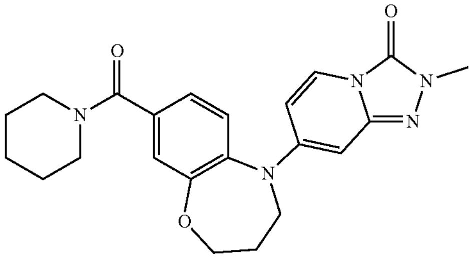
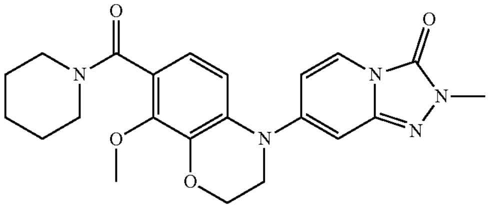
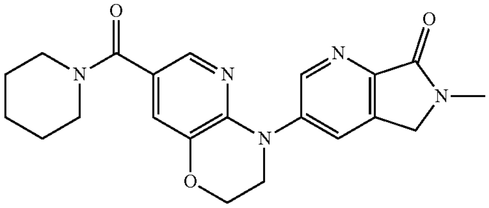
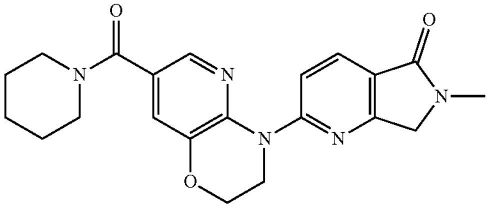
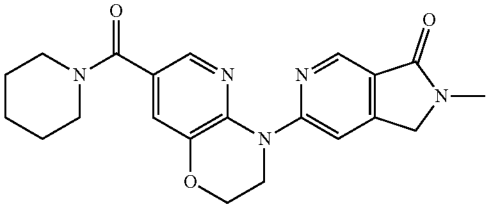
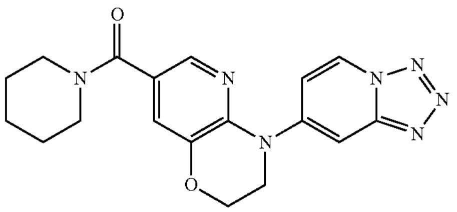
-continued
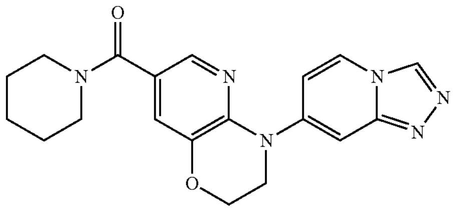
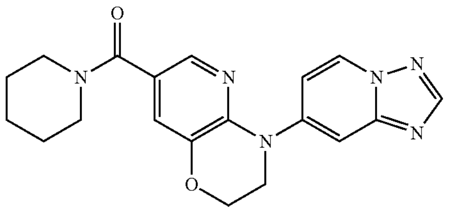
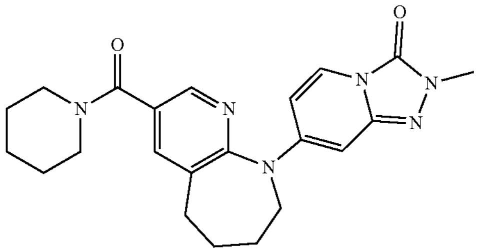
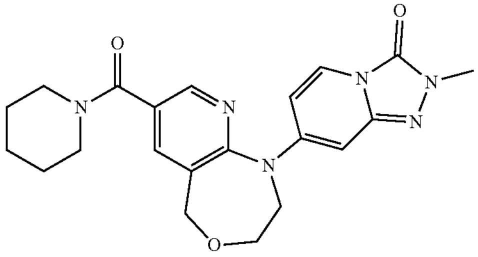
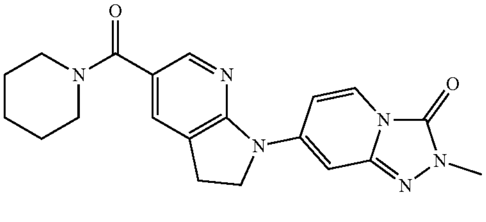
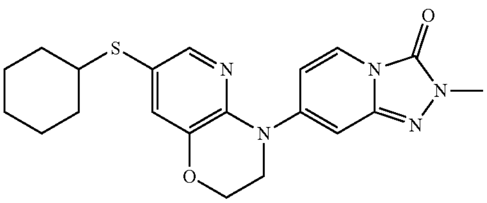
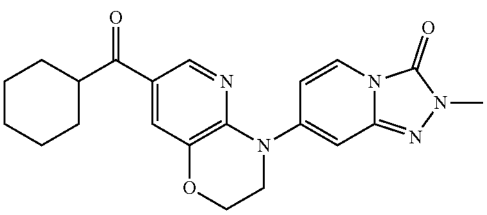

-continued
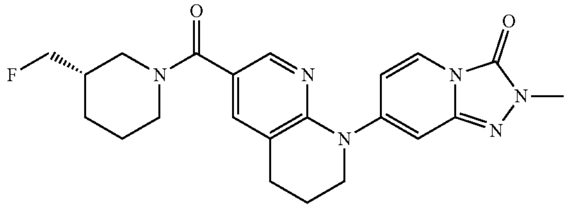
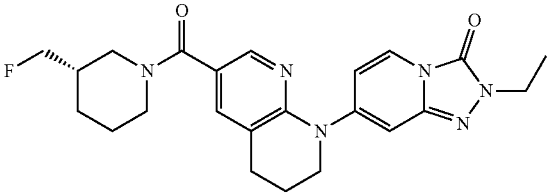
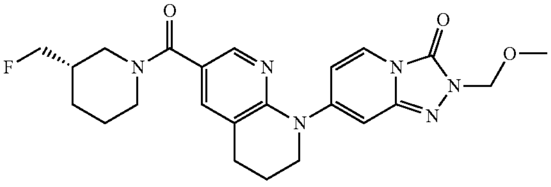
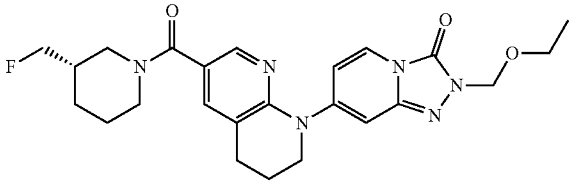
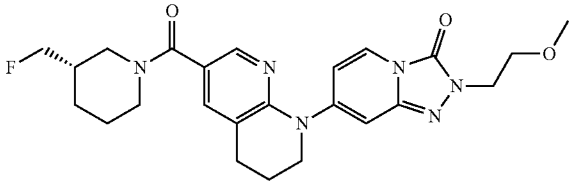
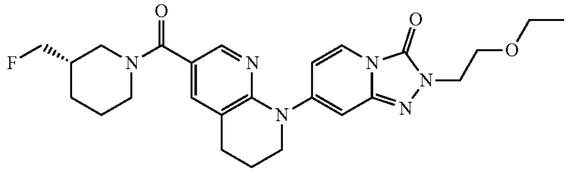
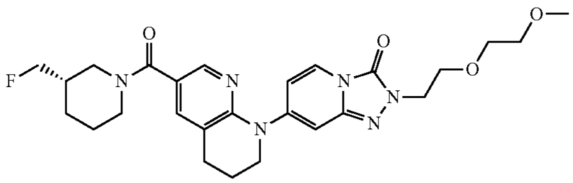
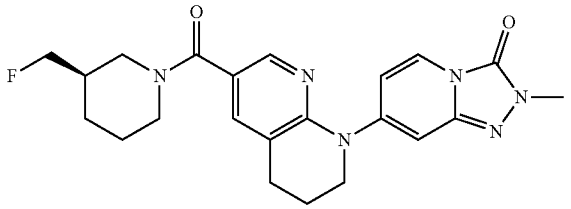
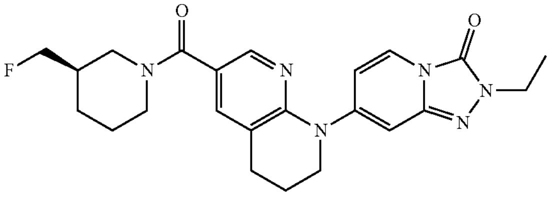
-continued
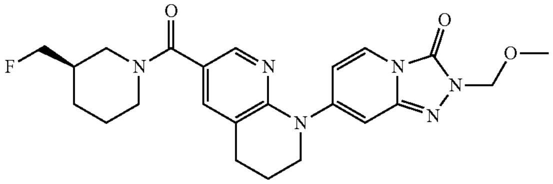
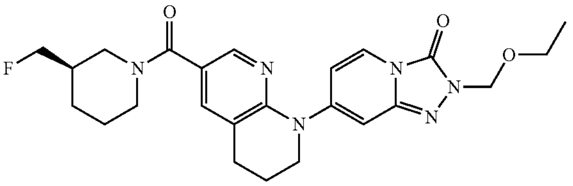
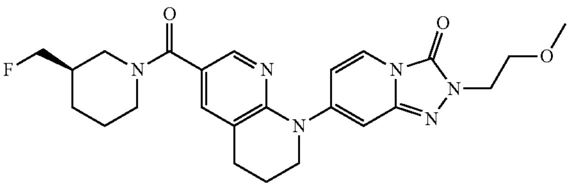
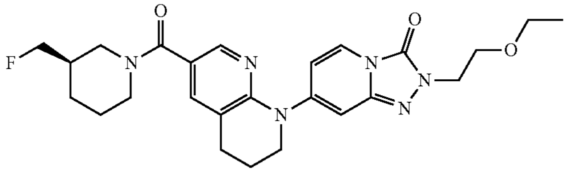
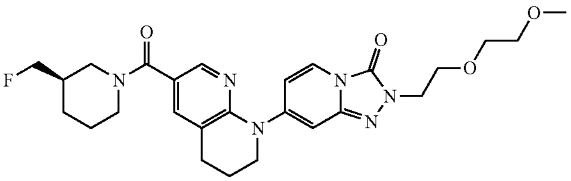
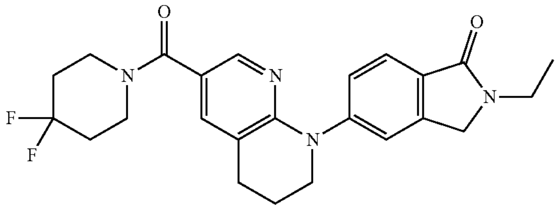
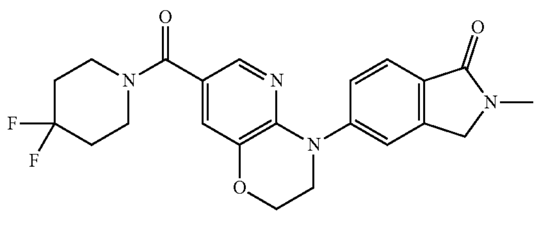
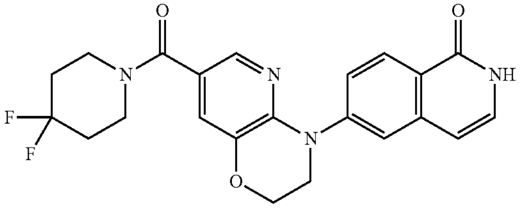

-continued
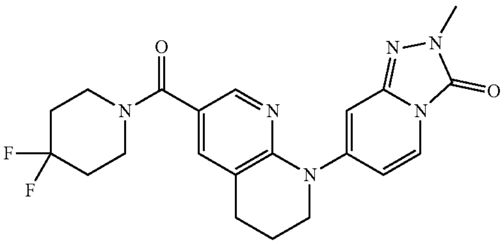
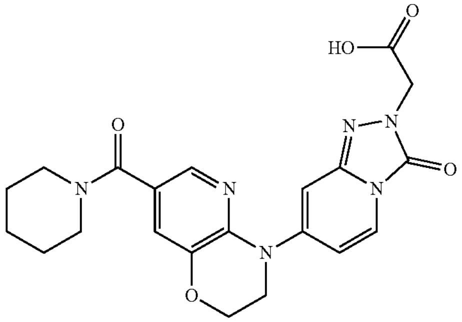
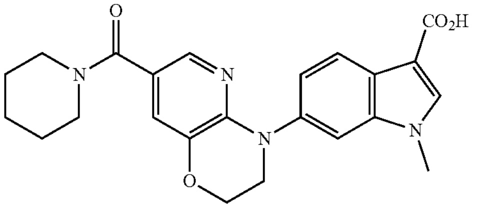
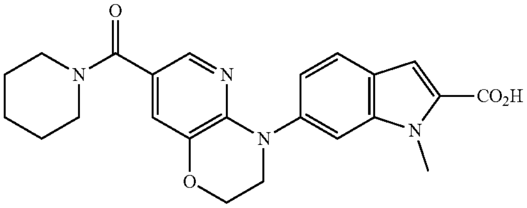
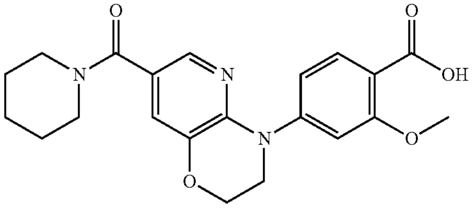
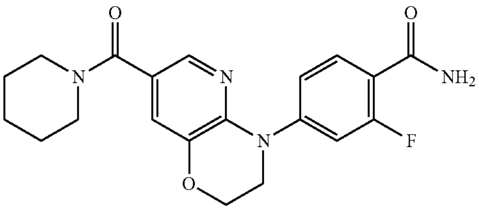
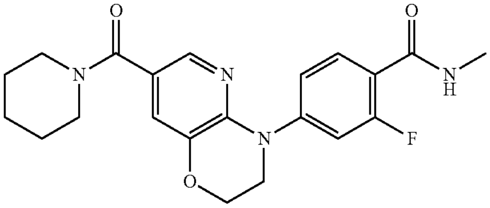
-continued
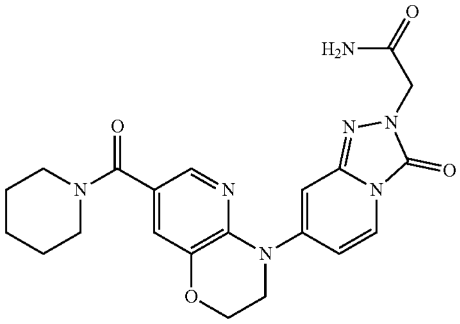
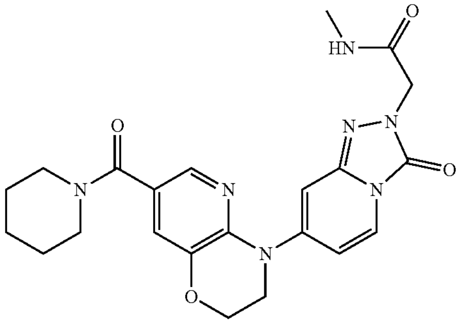
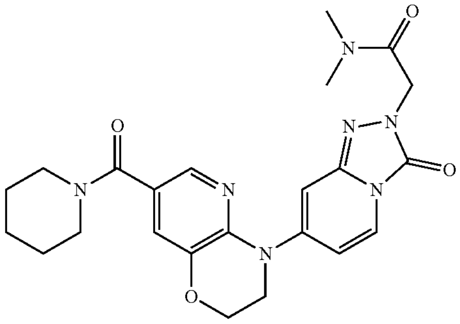
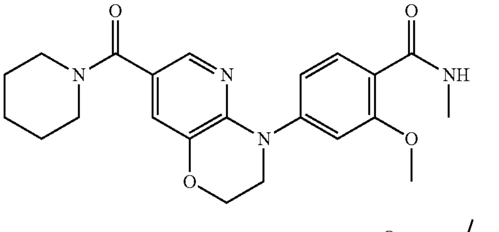
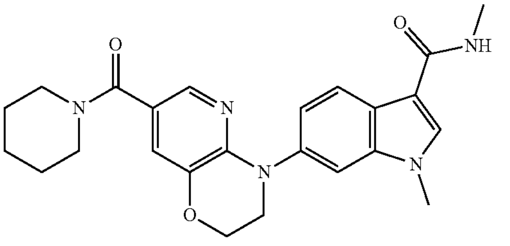
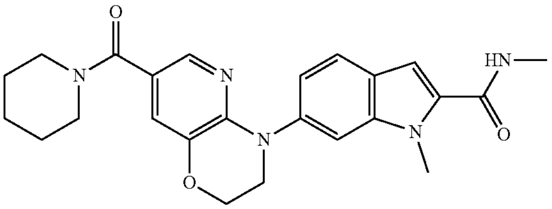

-continued
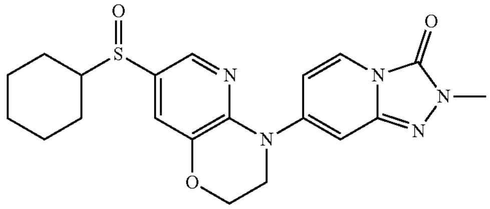
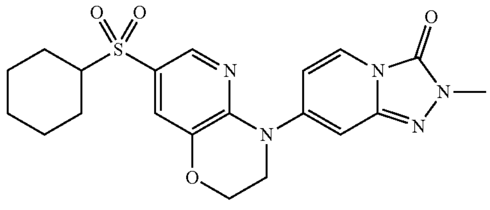
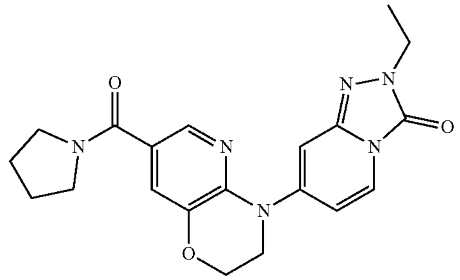
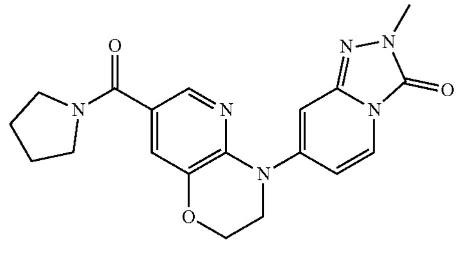
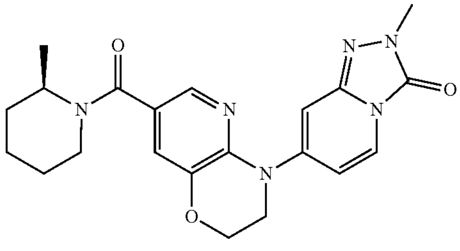
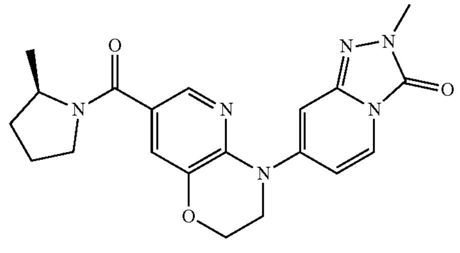
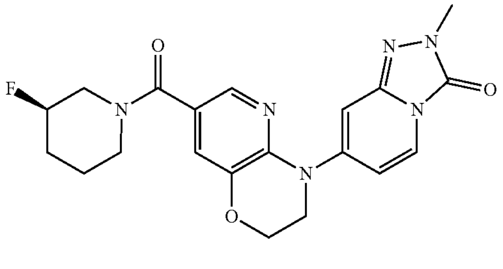
-continued
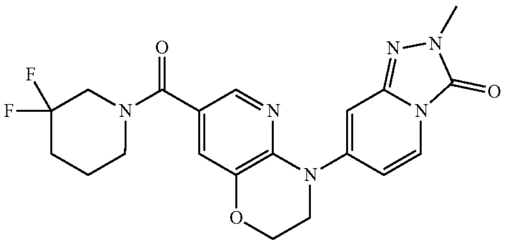
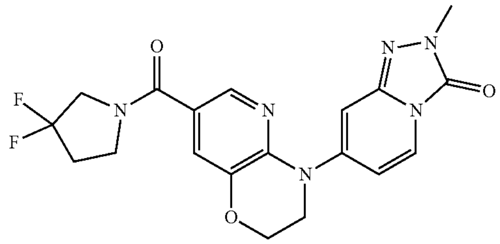
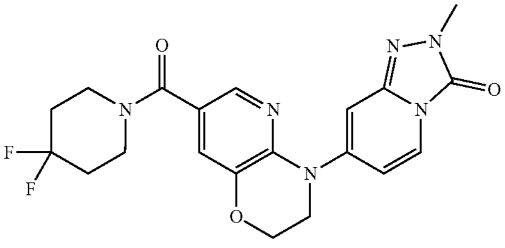
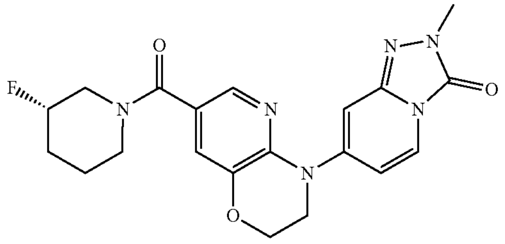
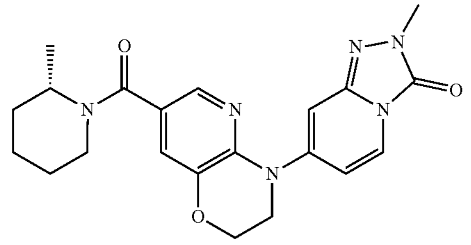
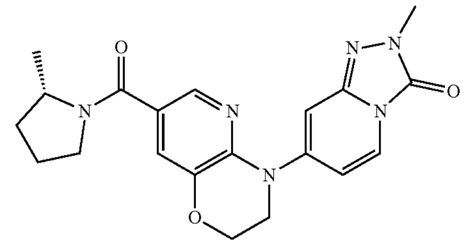
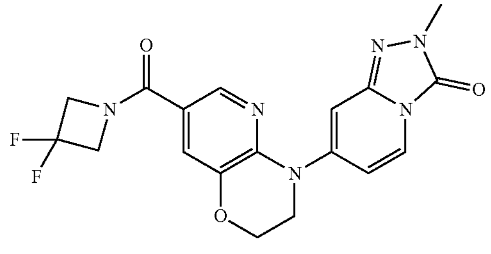

-continued
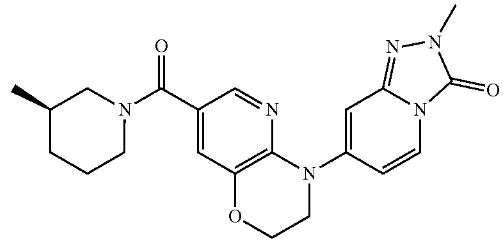
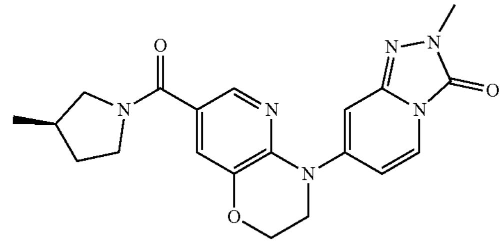
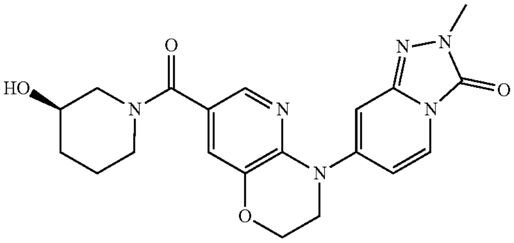
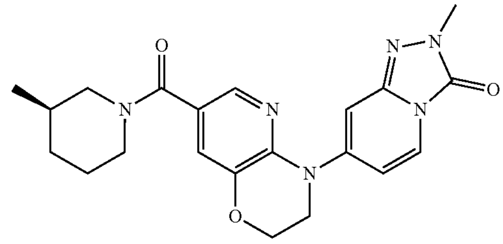
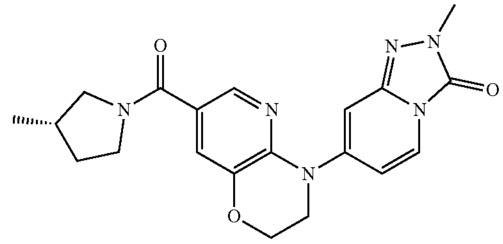
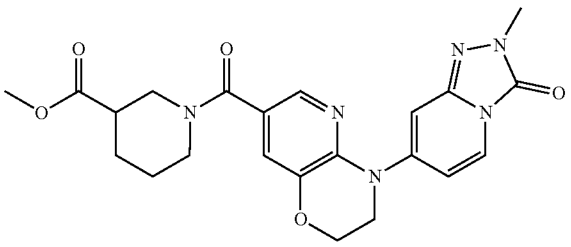
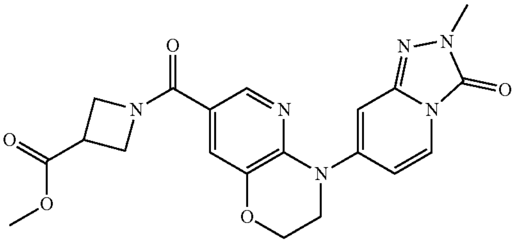
-continued
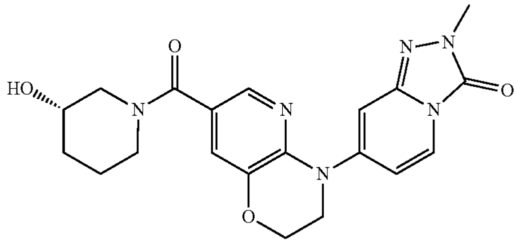
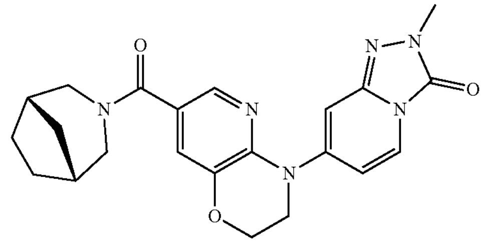
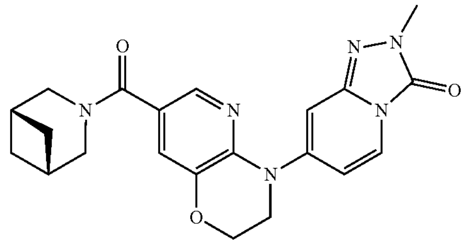
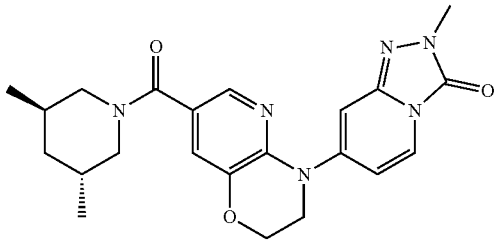
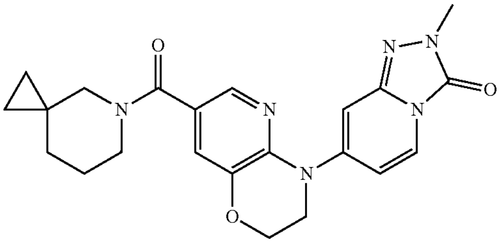
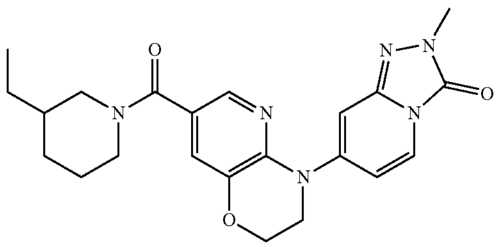
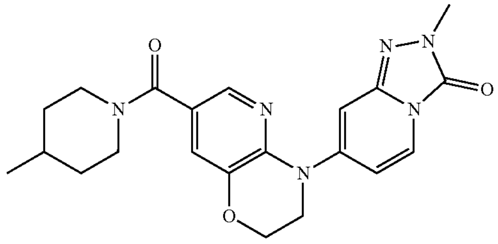

-continued
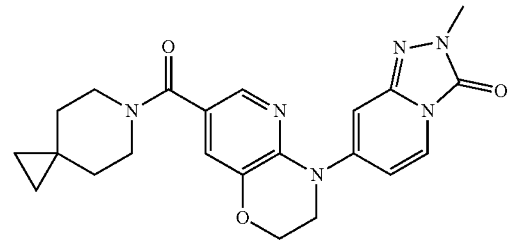
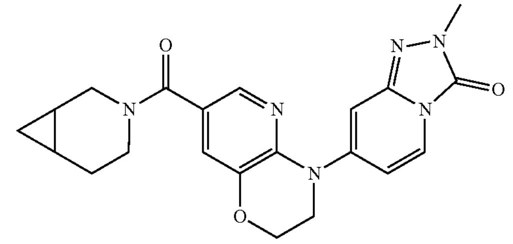
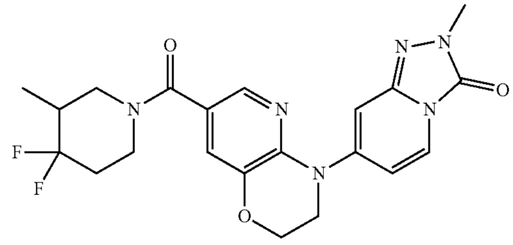
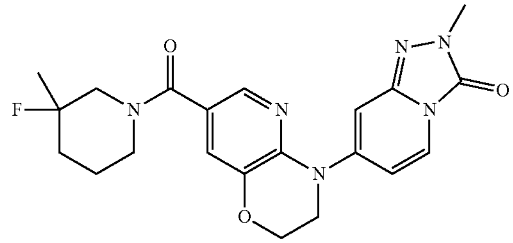
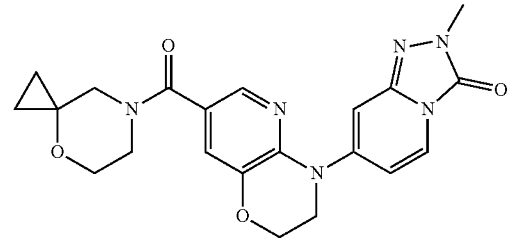
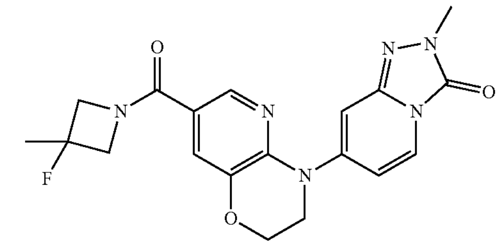
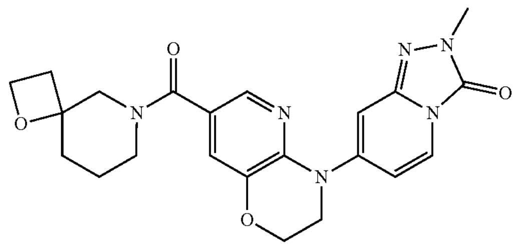
-continued
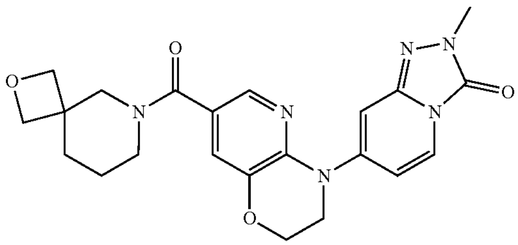
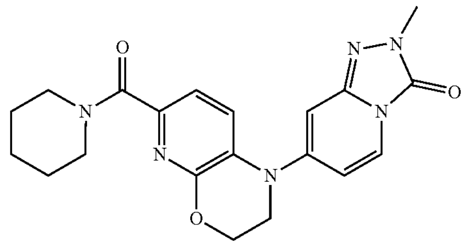
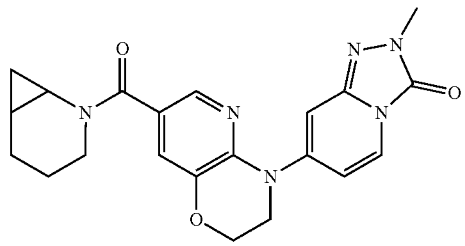
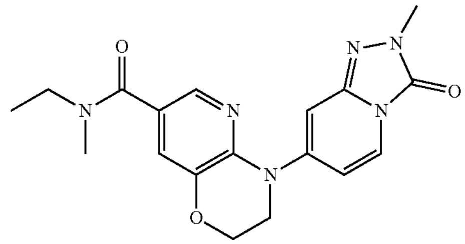
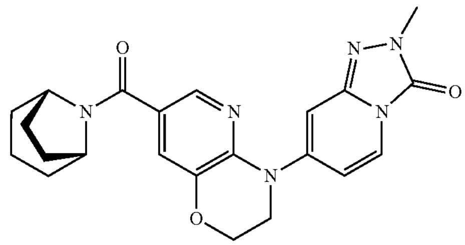
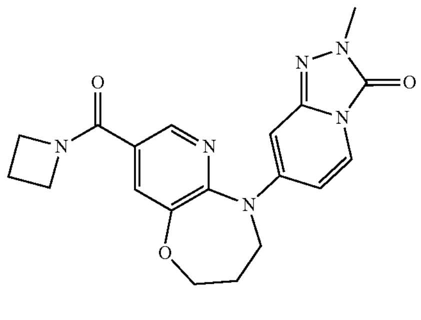

-continued
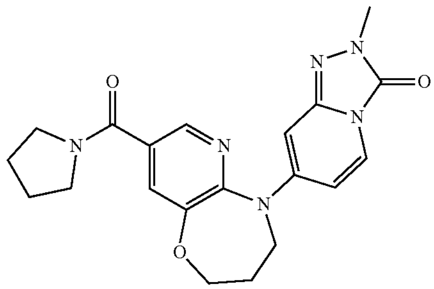
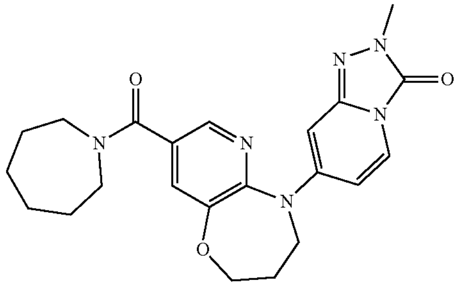
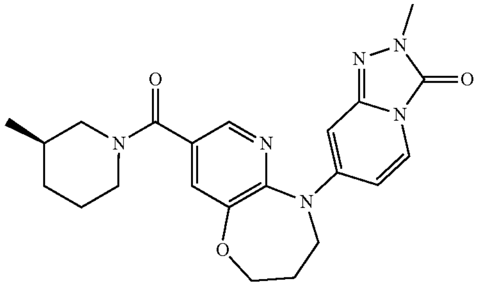
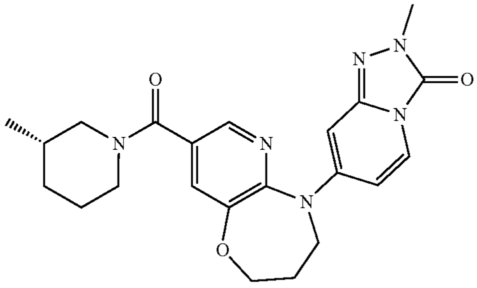
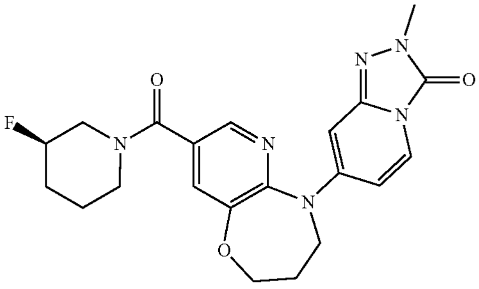
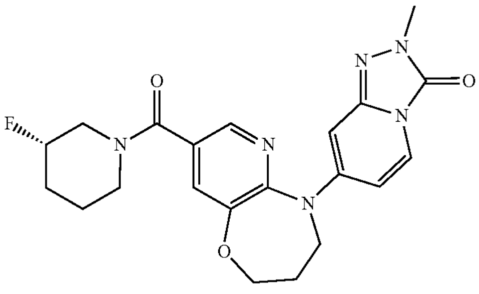
-continued
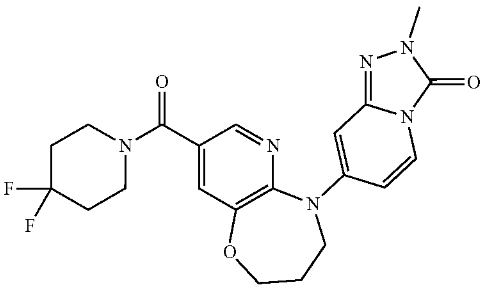
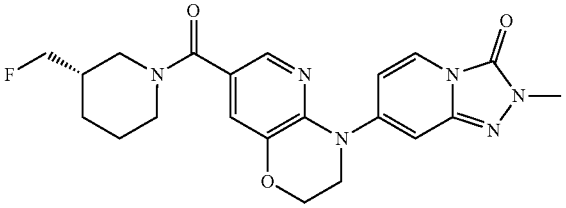
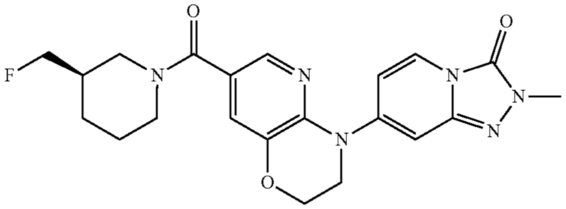
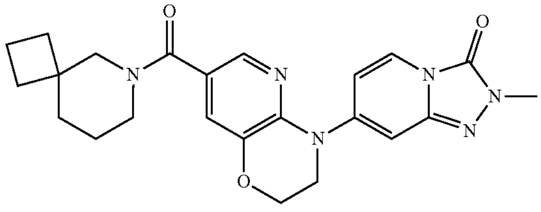
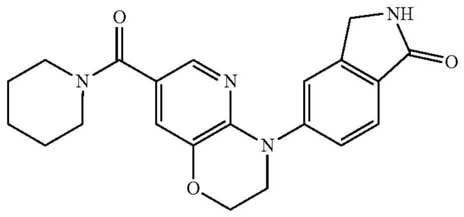
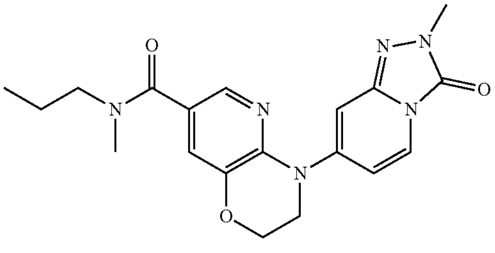
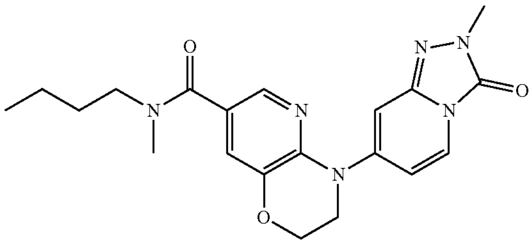

-continued
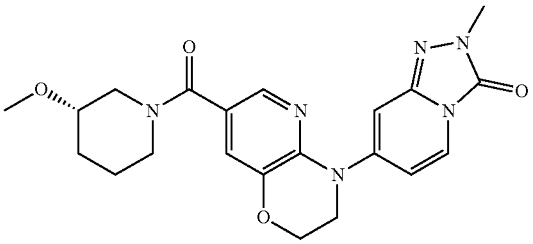
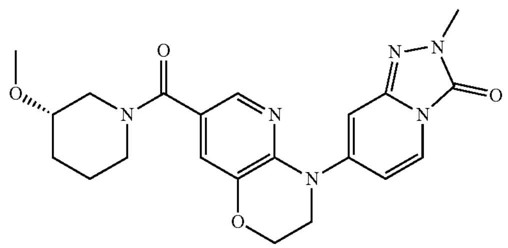
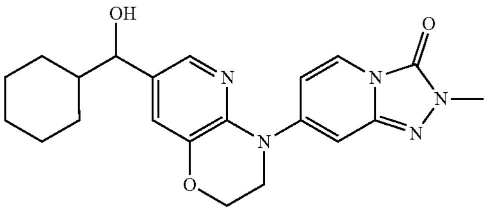
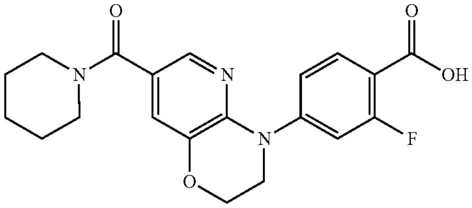
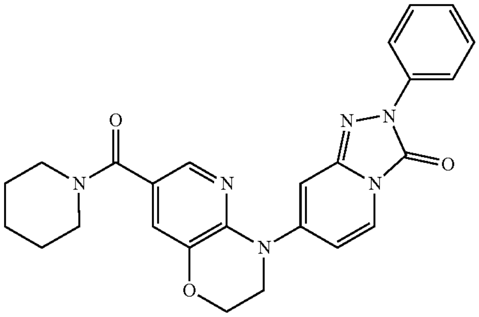
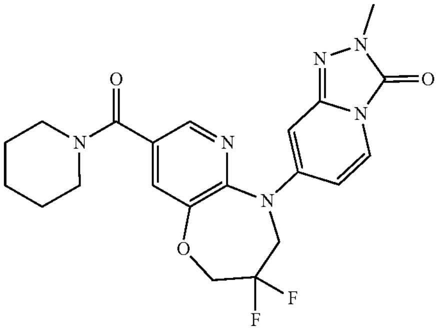
-continued
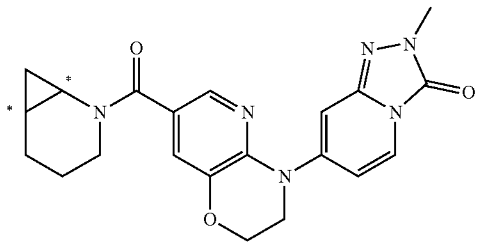
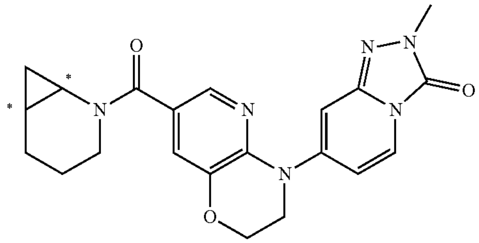
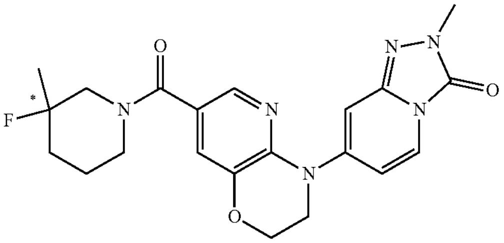
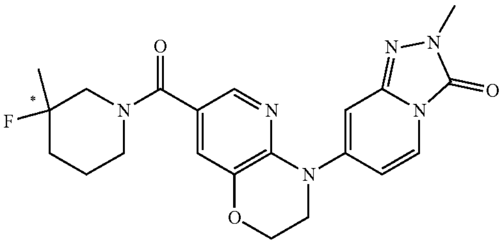
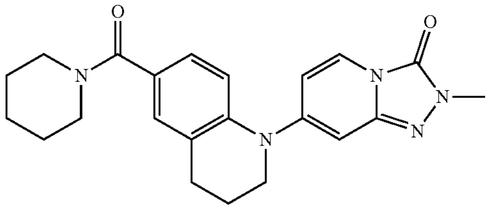
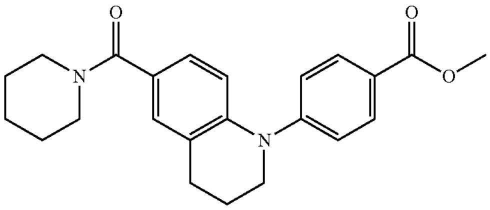
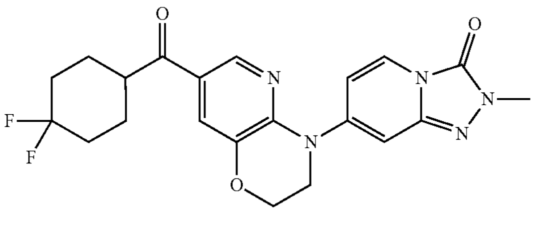

-continued
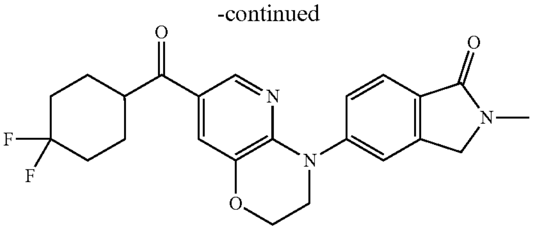
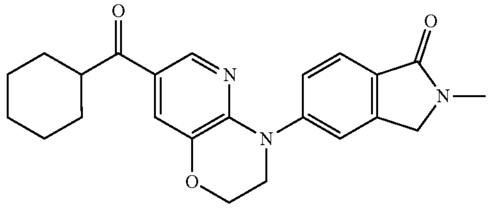
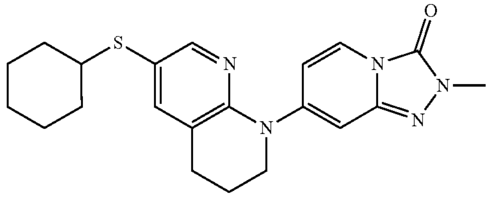
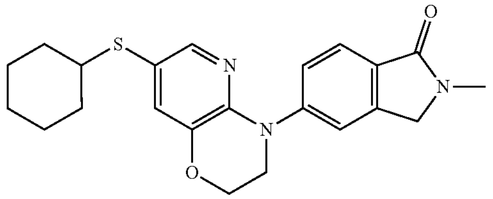
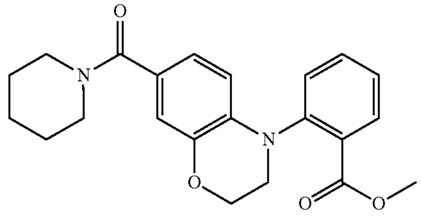
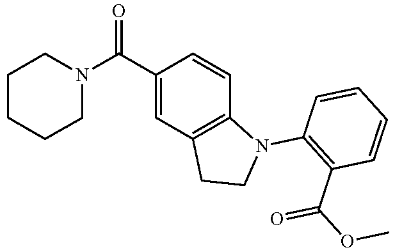
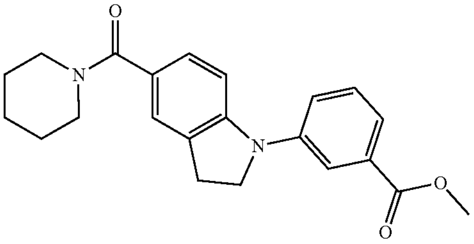
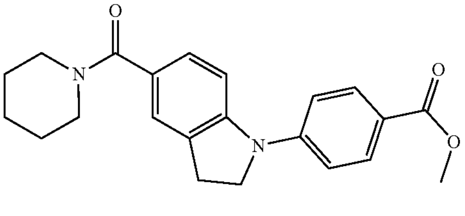
-continued
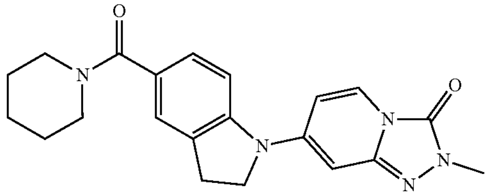
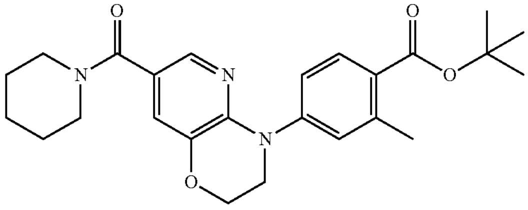
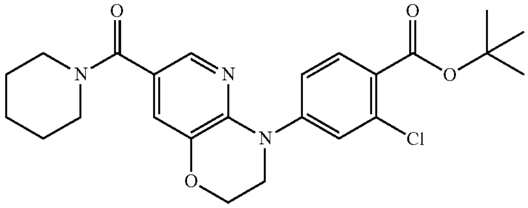
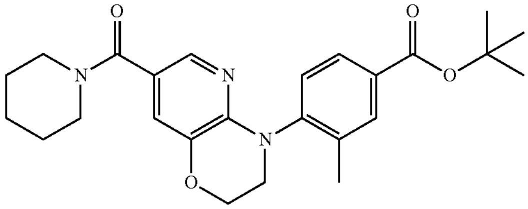
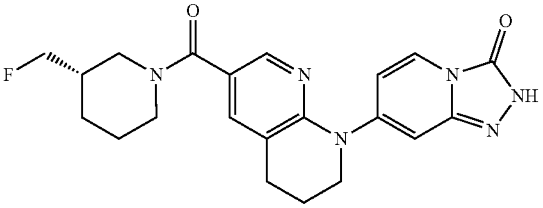
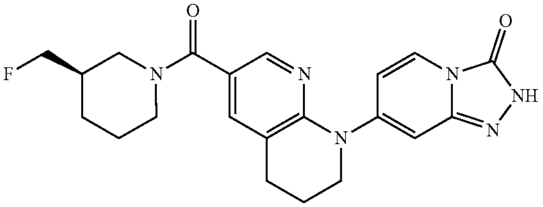
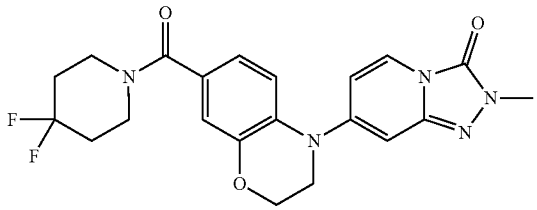
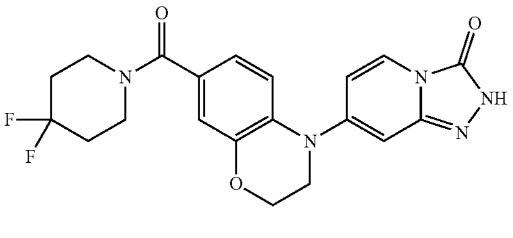

-continued
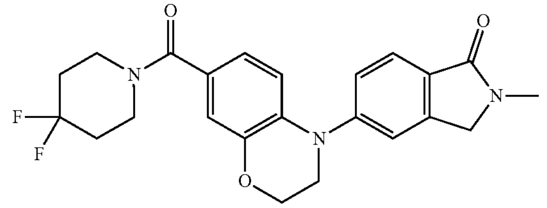
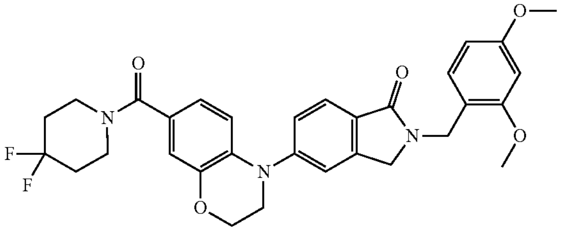
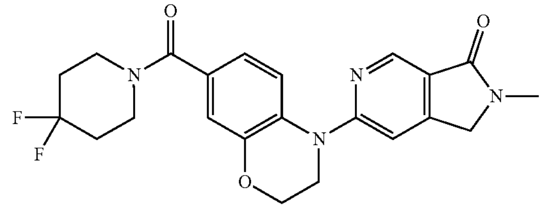
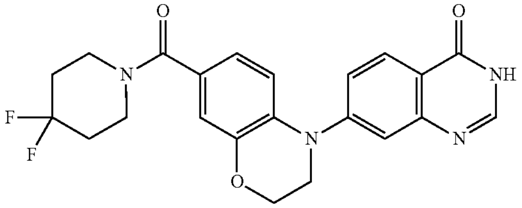
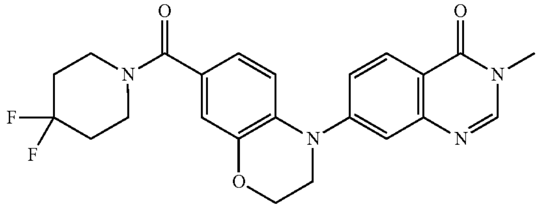
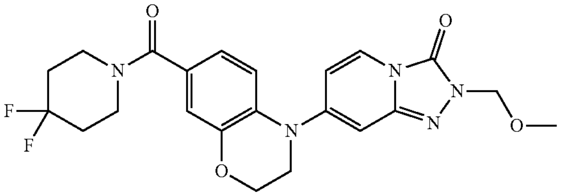
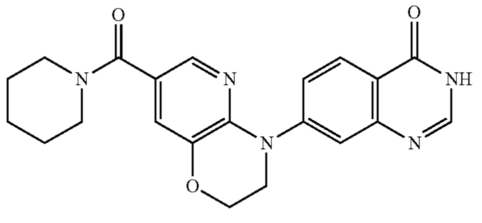
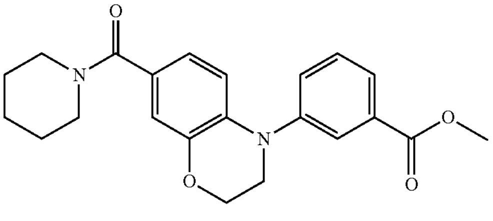
-continued
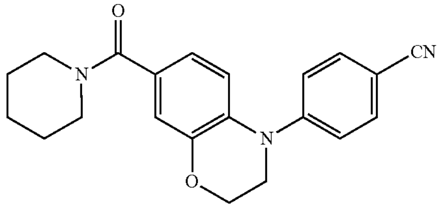
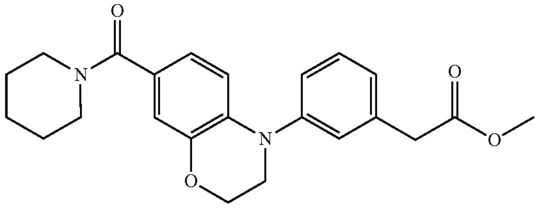
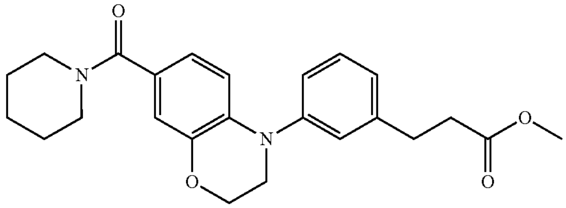
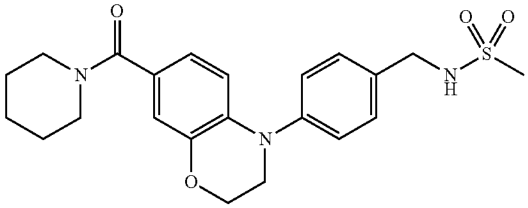
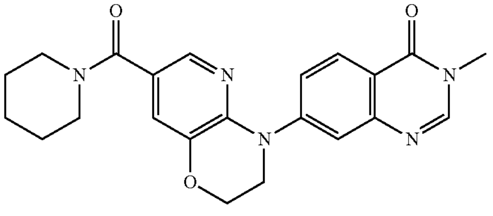
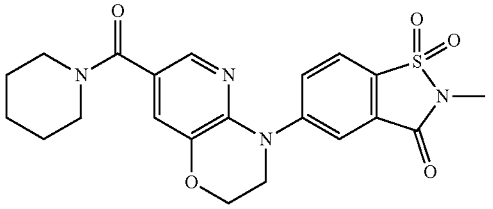
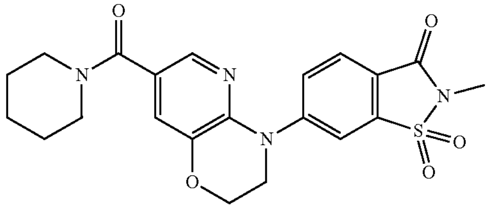
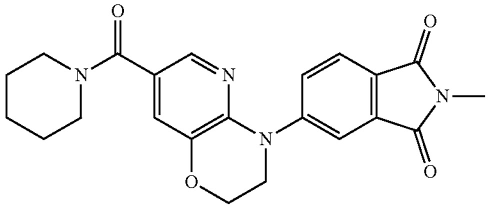

-continued
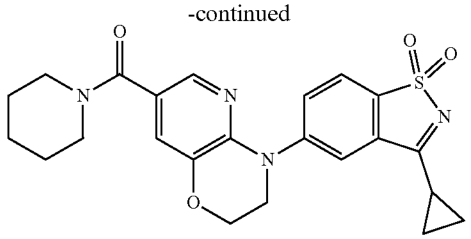
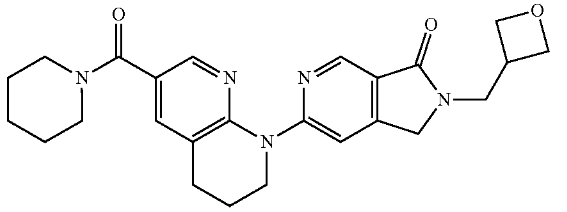
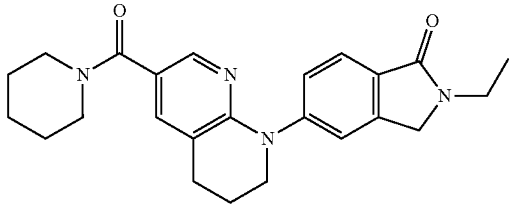
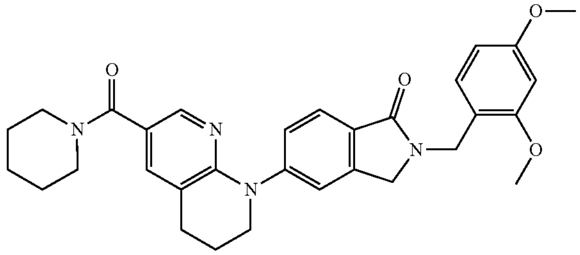
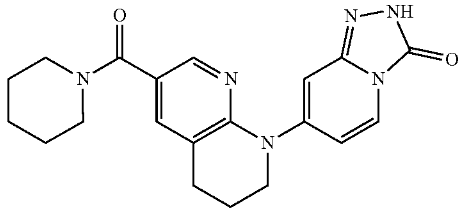
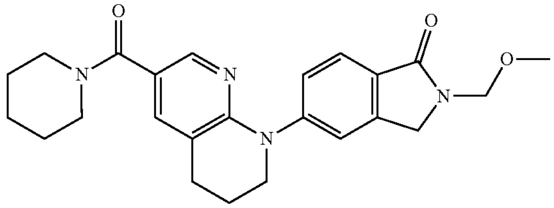
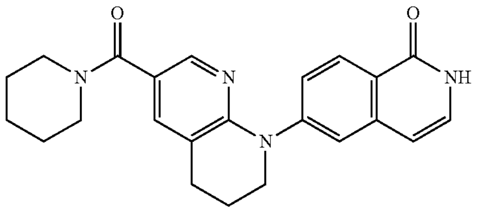
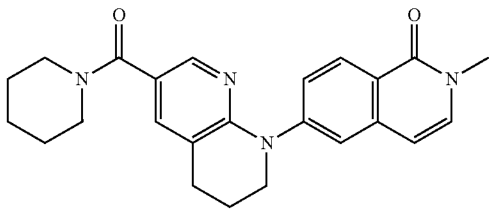
-continued
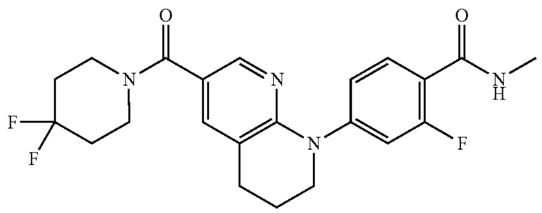
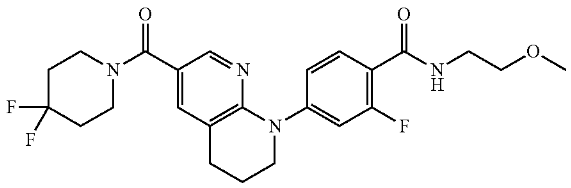
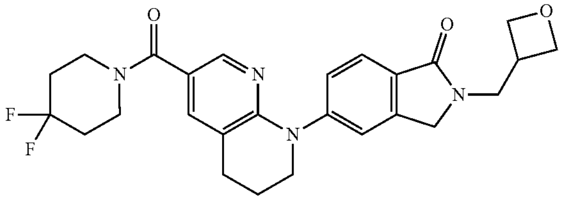
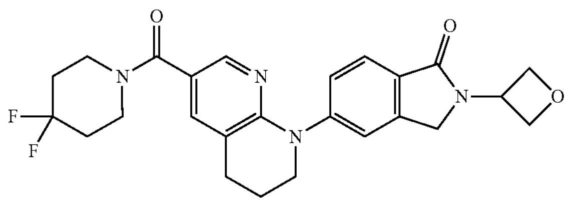
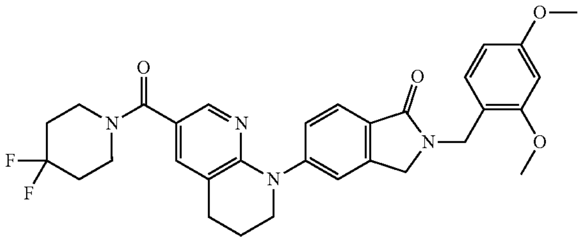
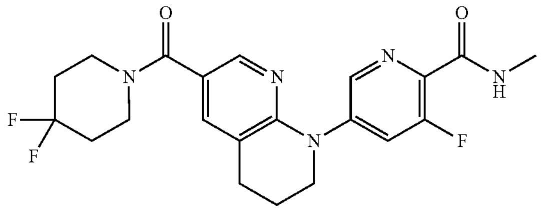
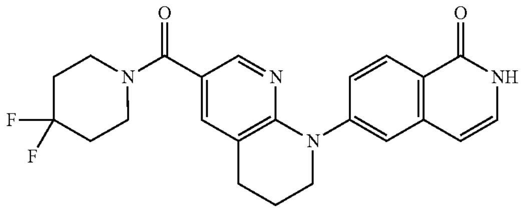
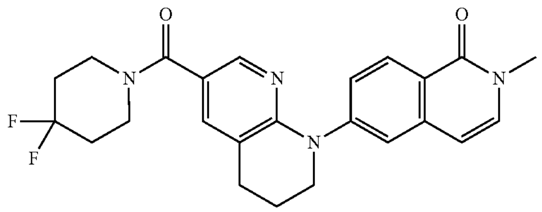

-continued
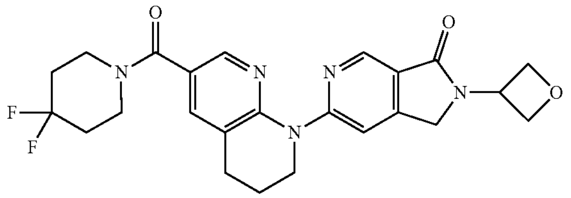
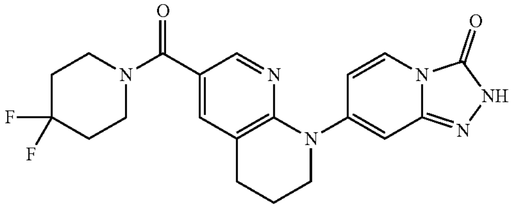
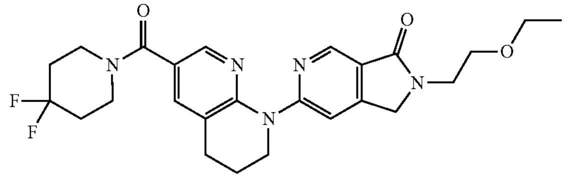
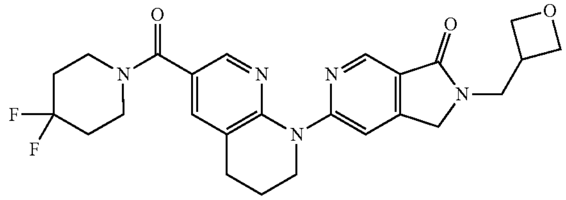
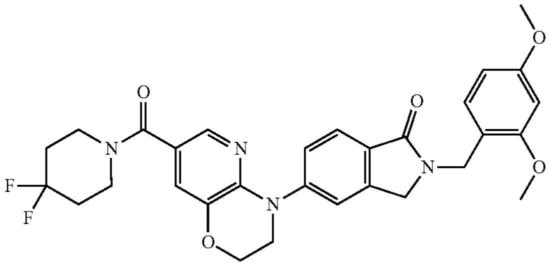
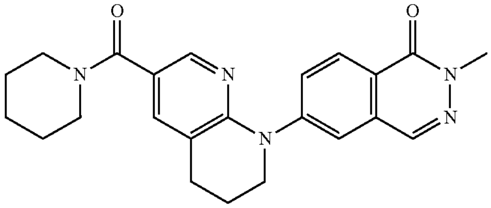
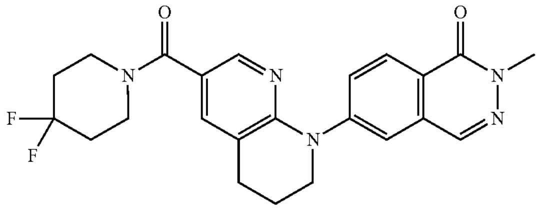
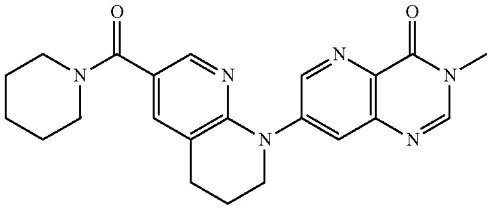
-continued
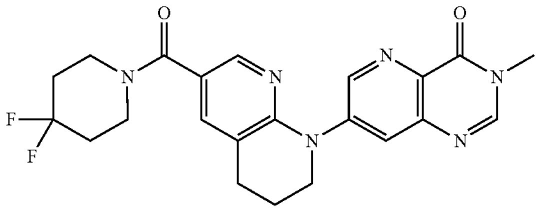
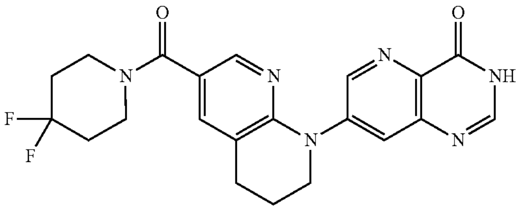
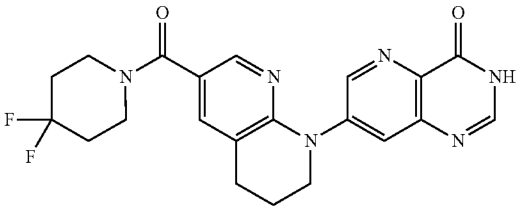
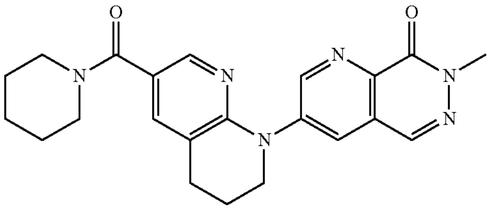
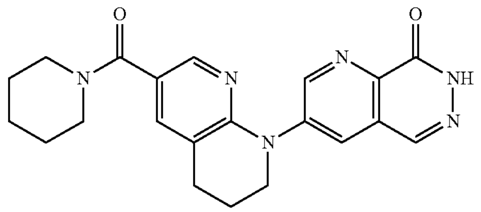
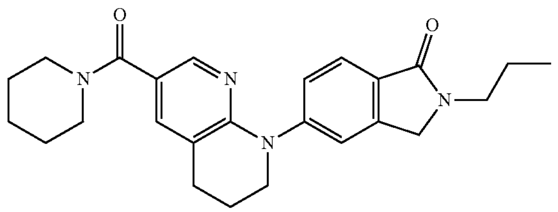
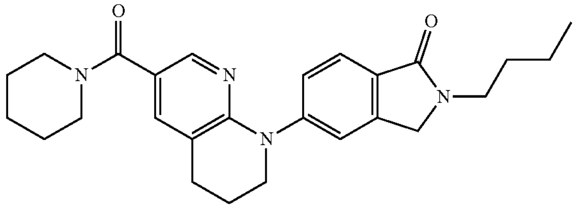
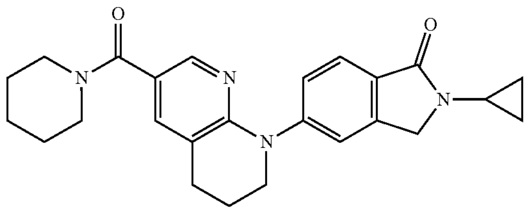

-continued
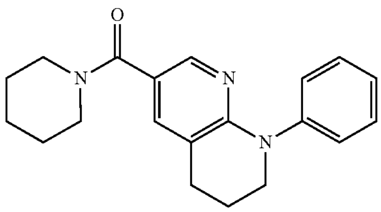
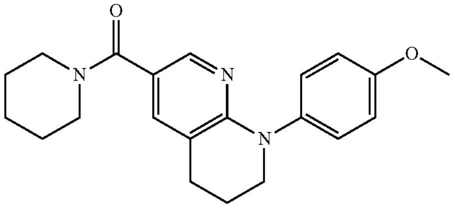
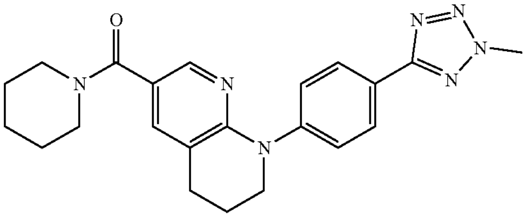
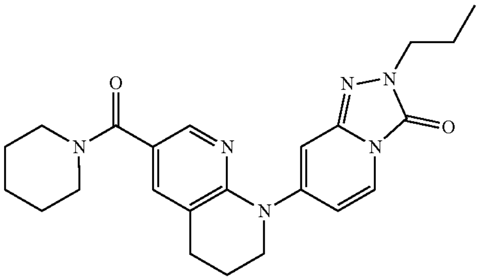
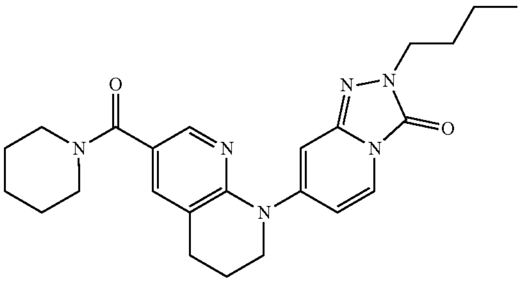
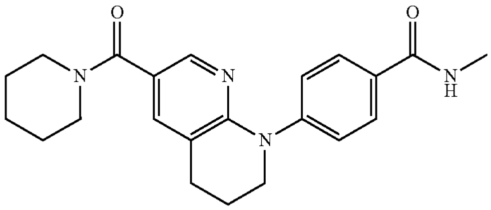
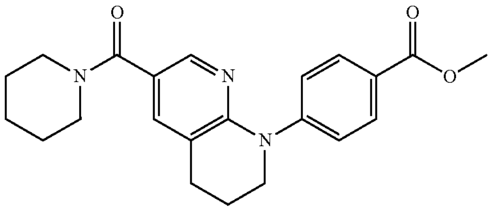
-continued
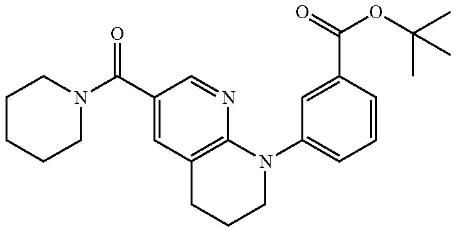
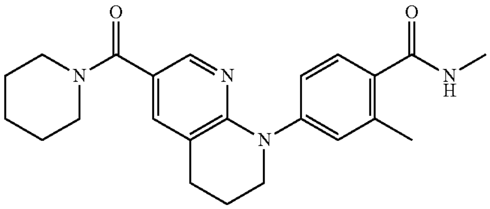
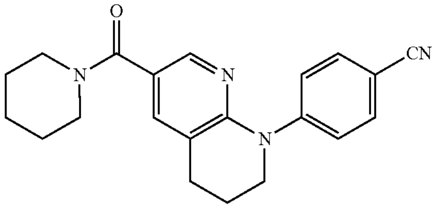
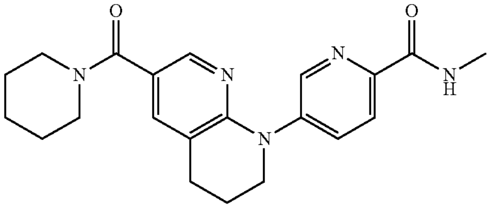
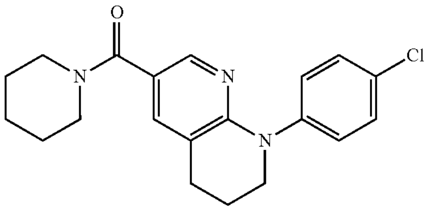
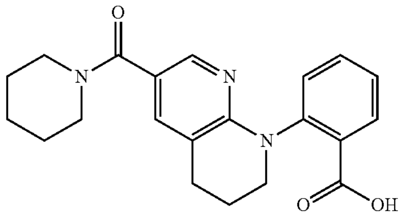
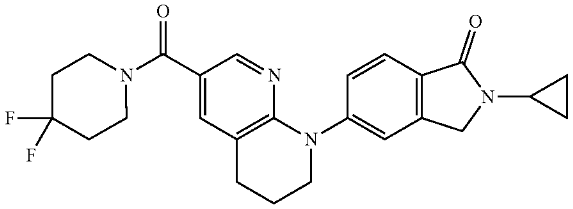
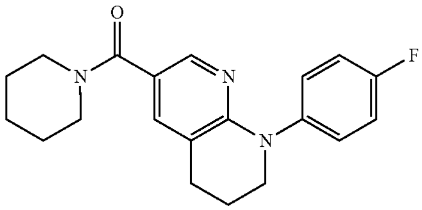

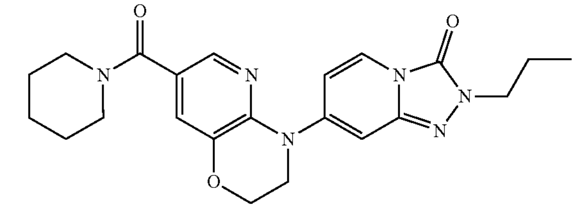
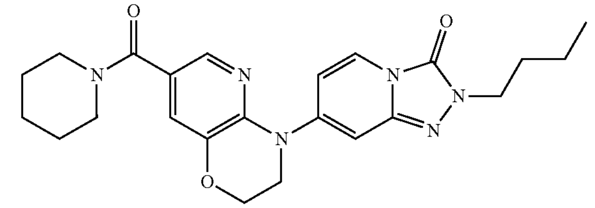
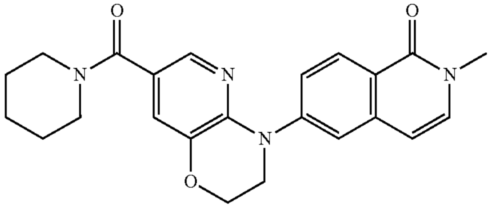
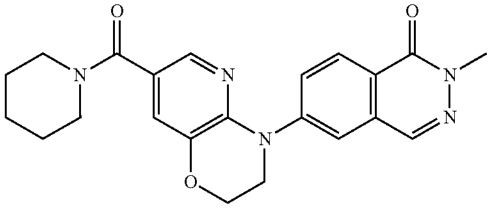
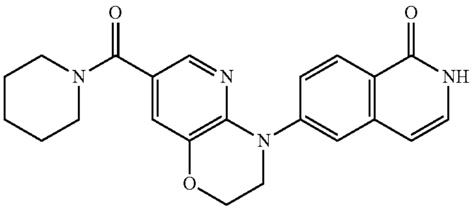
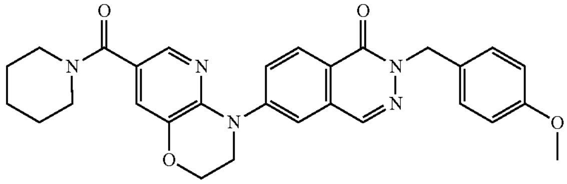
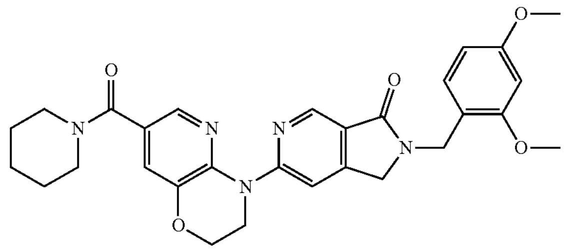
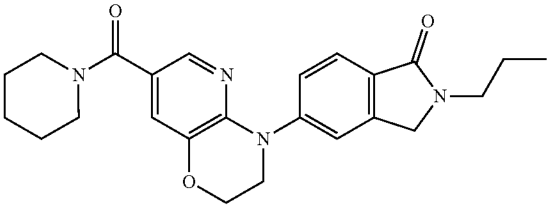
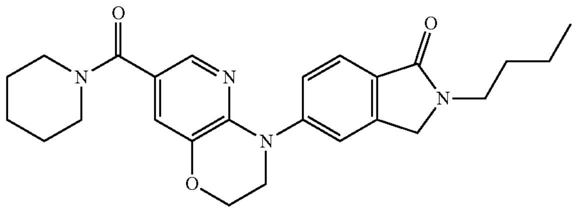
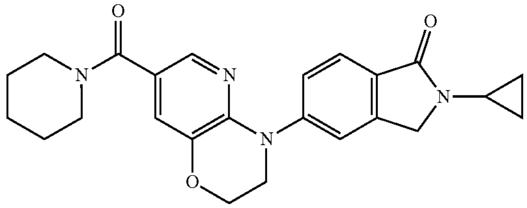
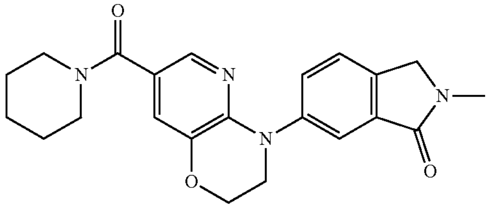
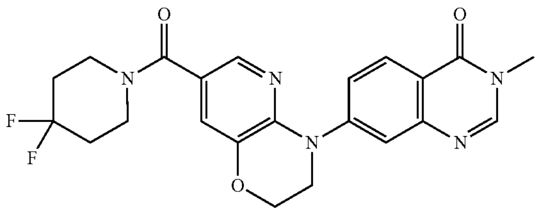
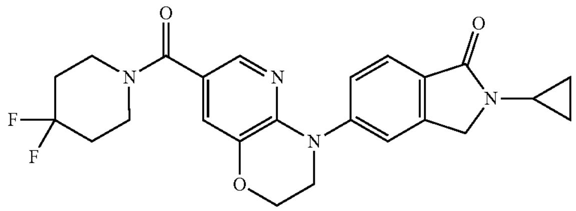
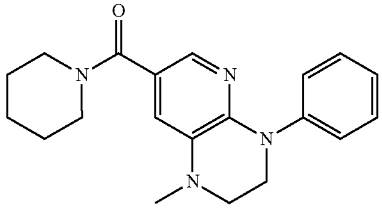
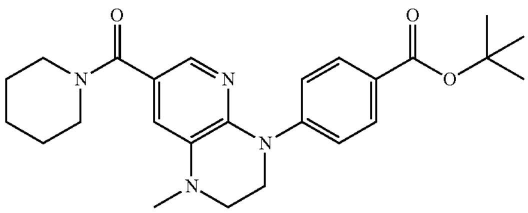

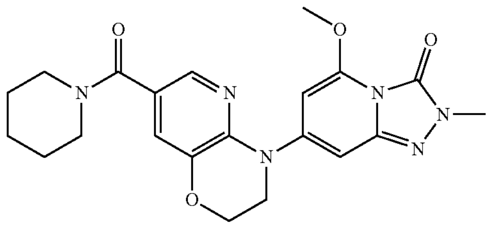
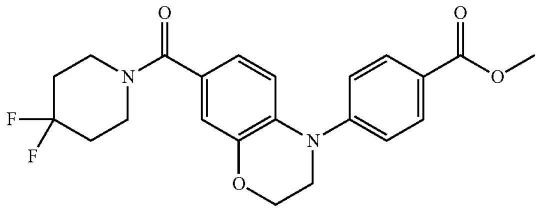
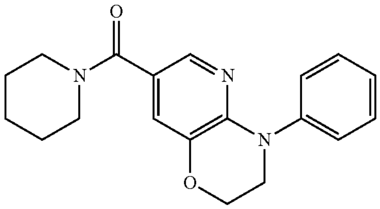
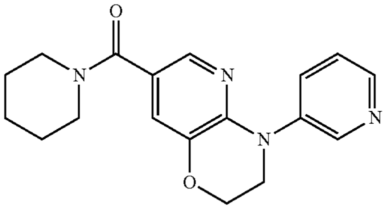
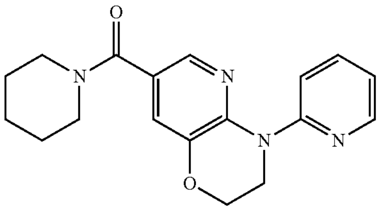
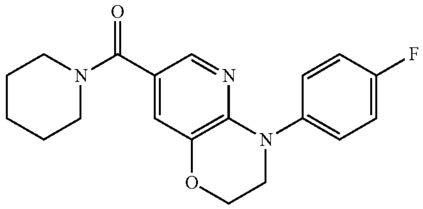
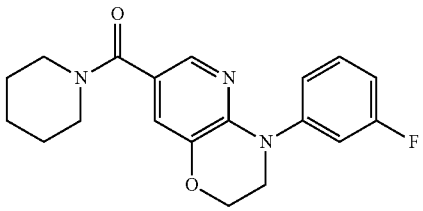
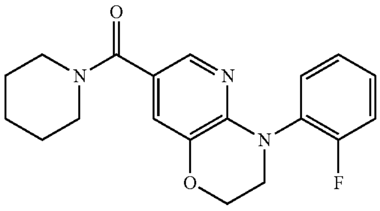
-continued
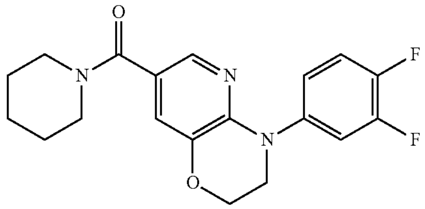
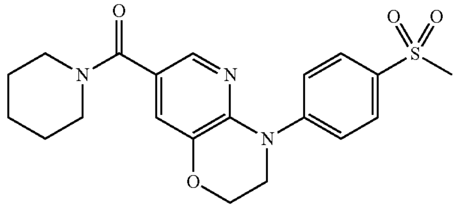
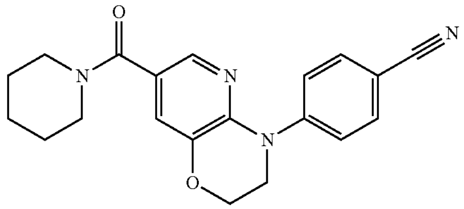
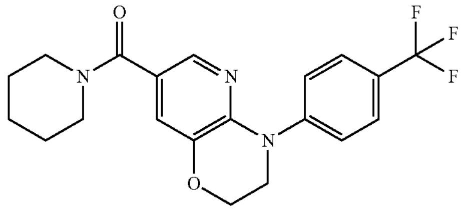
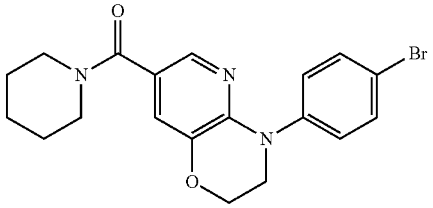
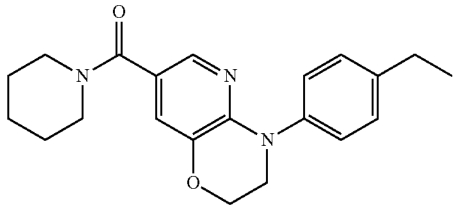
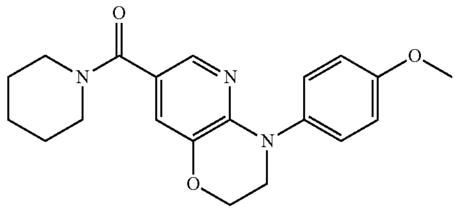
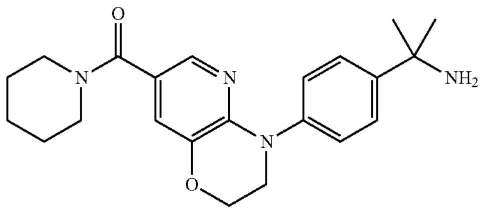

-continued
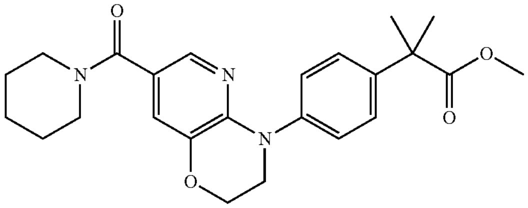
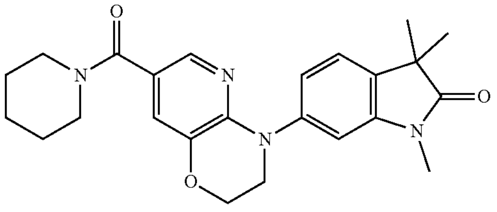
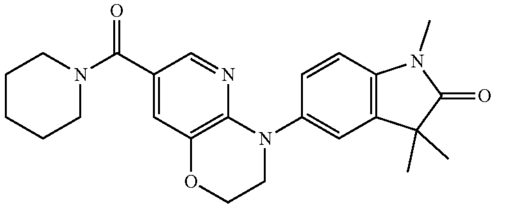
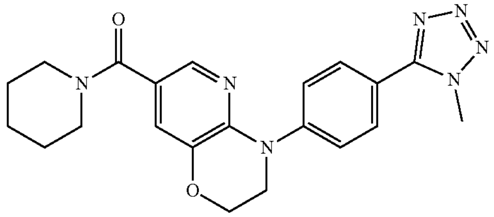
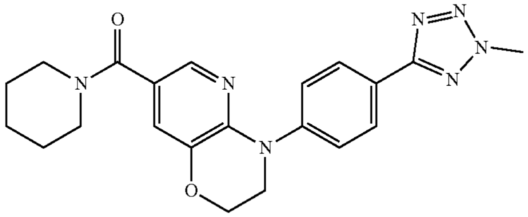
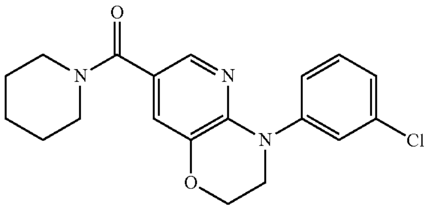
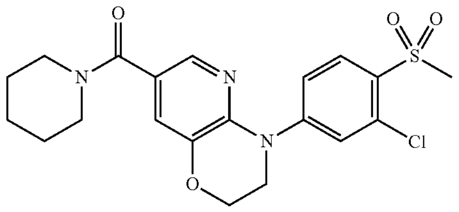
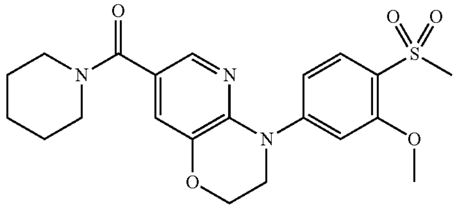
-continued
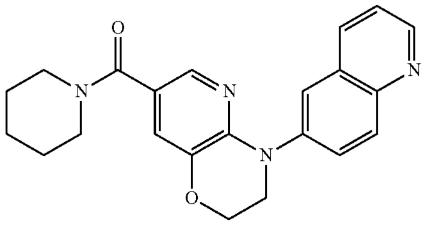
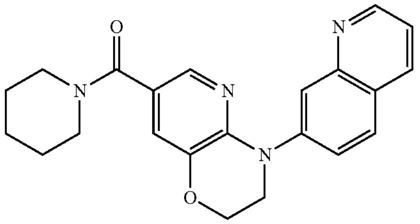
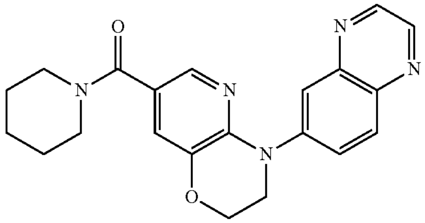
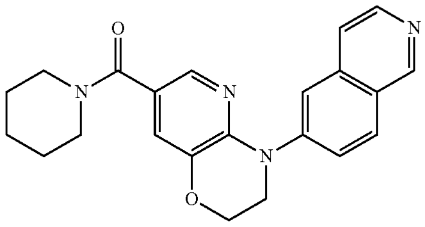
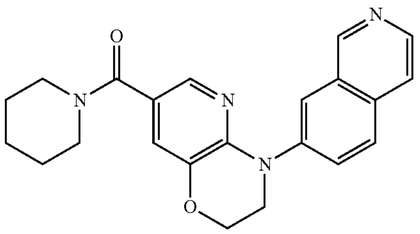
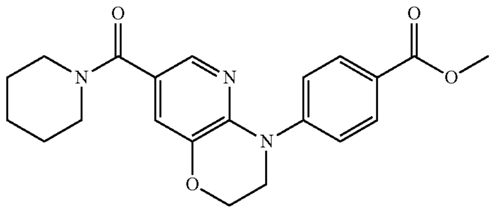
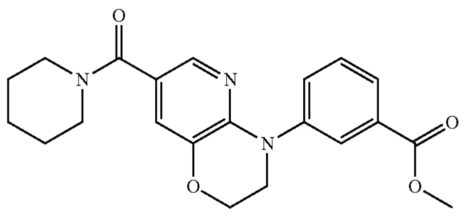

-continued
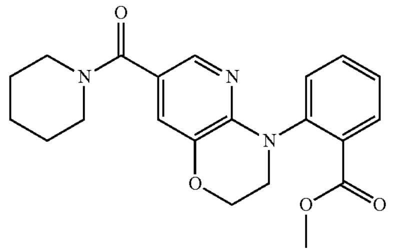
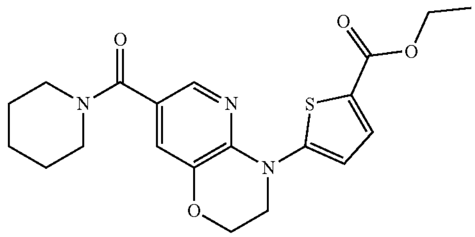
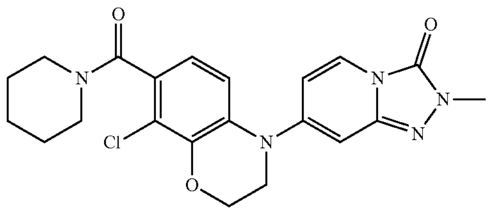
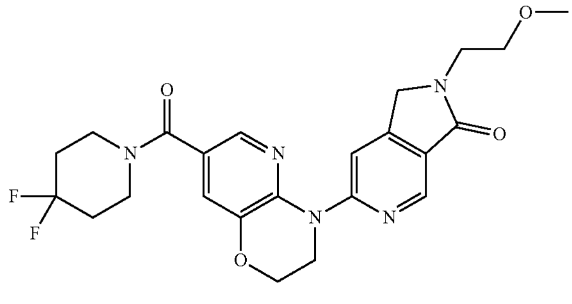
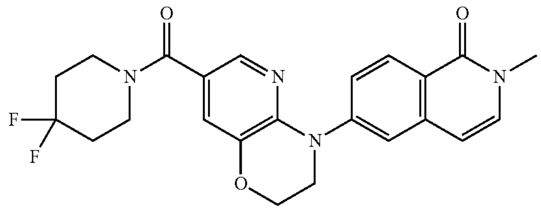
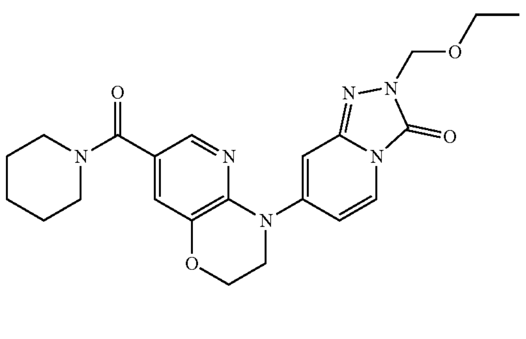
-continued
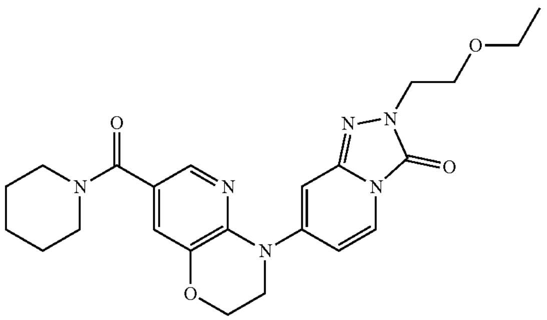
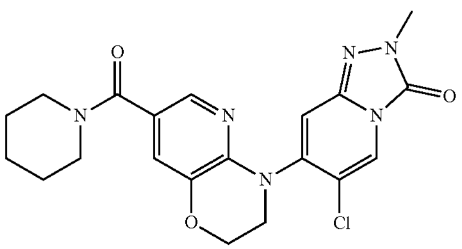
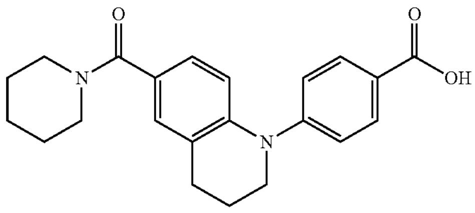
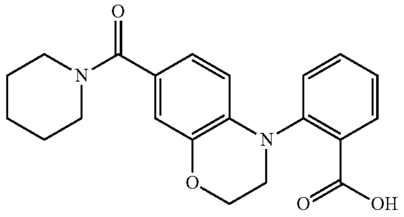
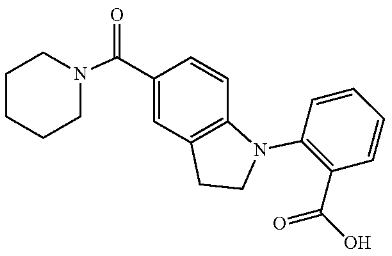
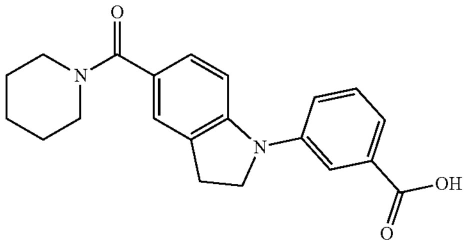
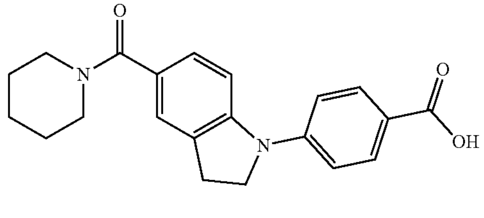

-continued
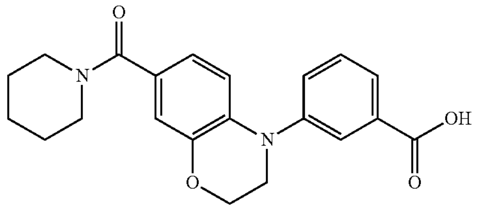
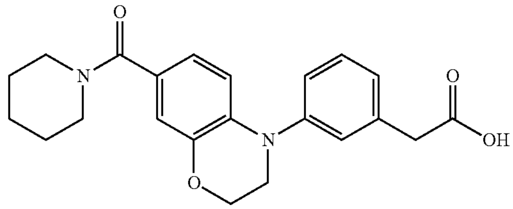
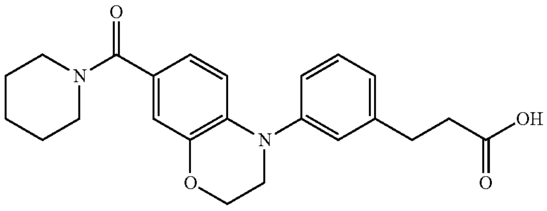
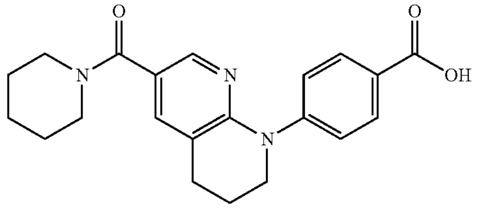
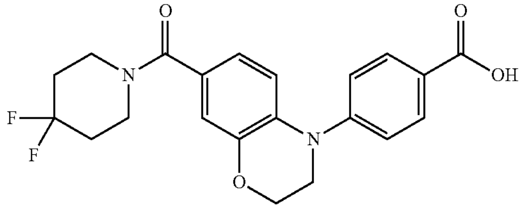
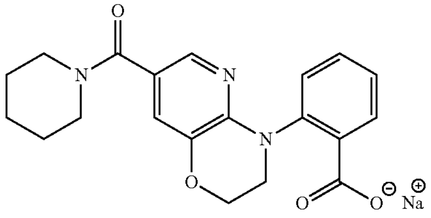
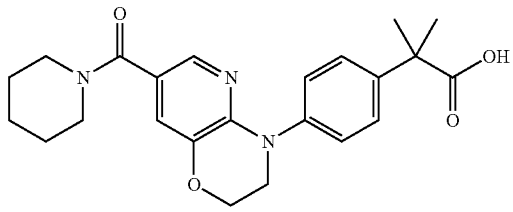
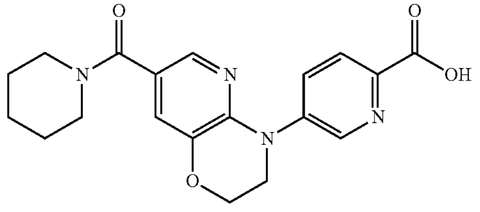
-continued
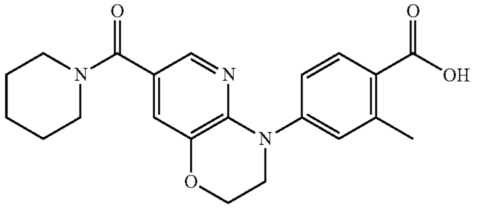
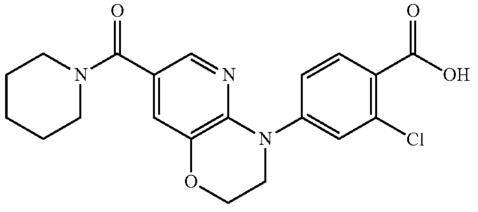
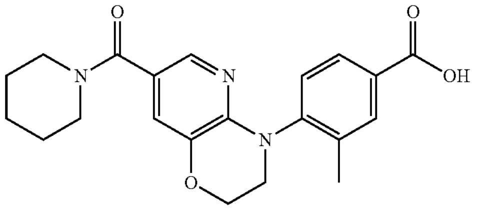
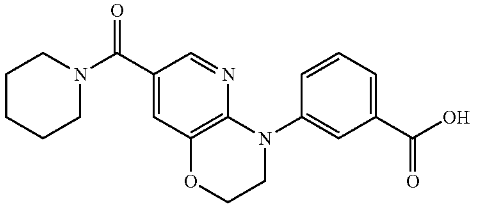
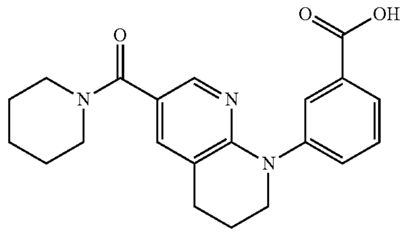
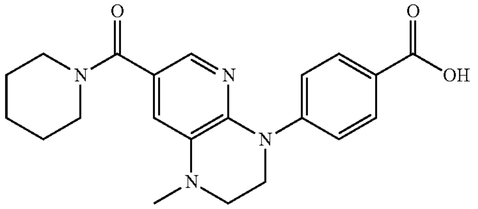
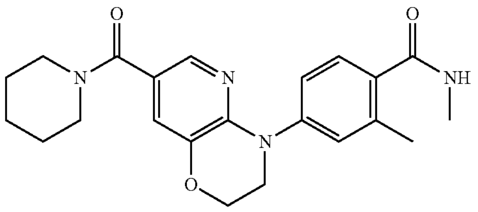
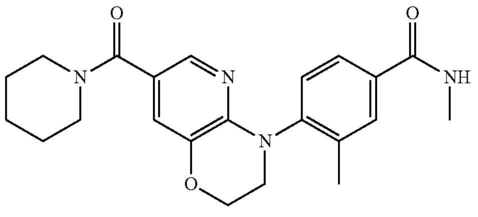

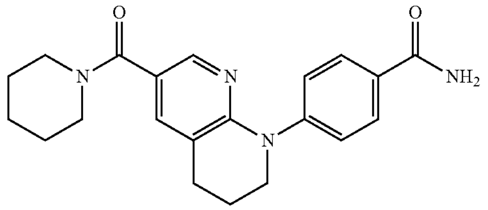
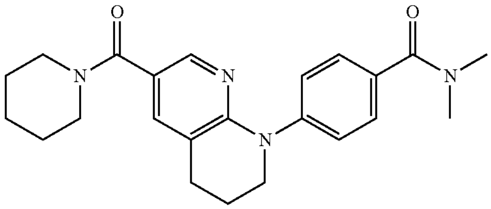
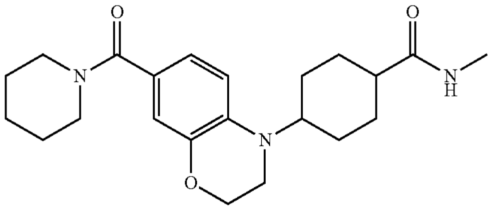
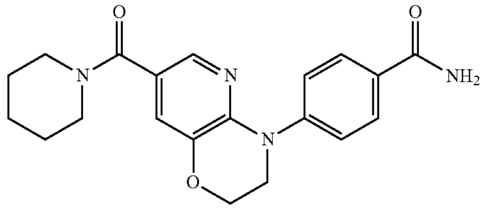
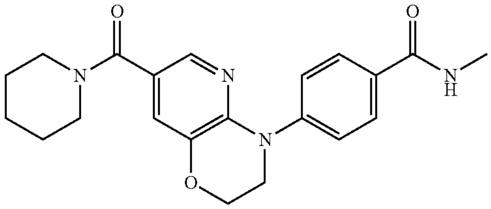
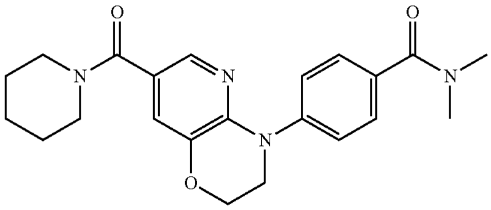
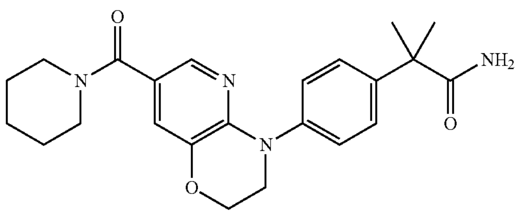
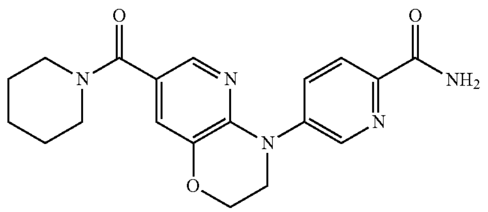
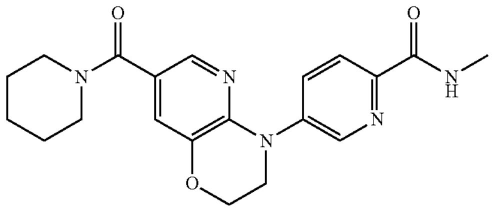
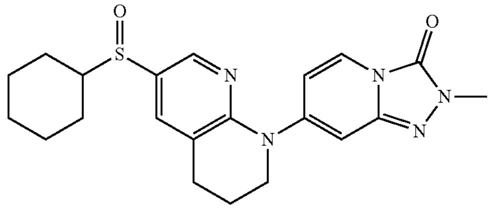
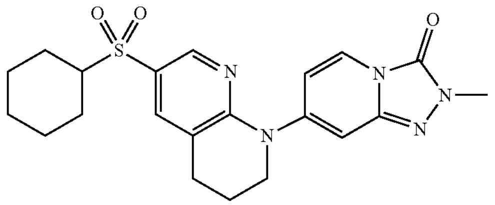
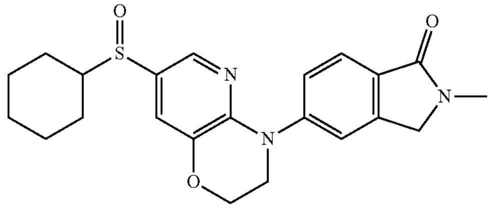
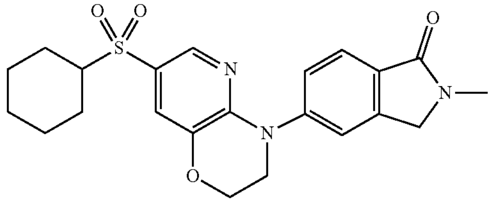
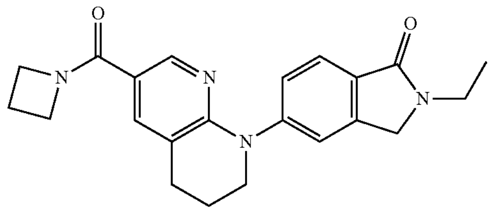
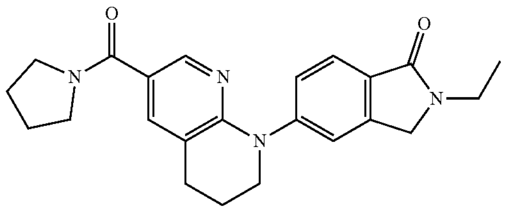
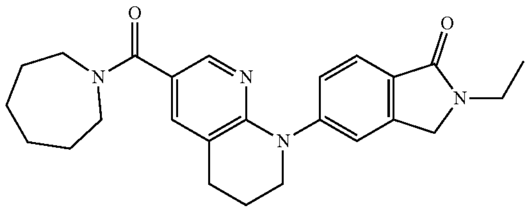

-continued
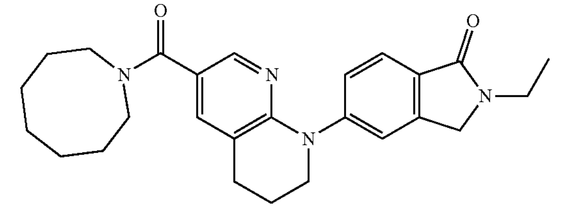
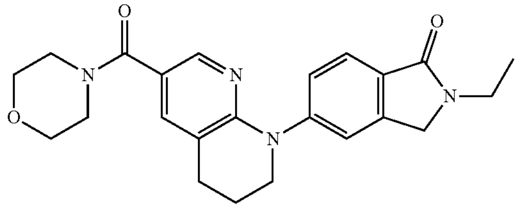
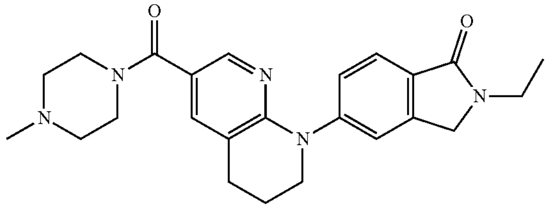
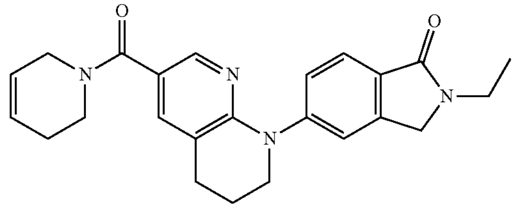
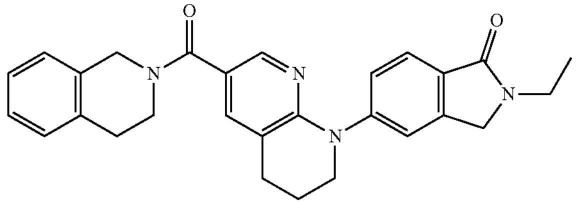
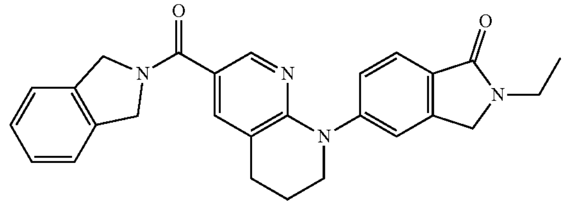
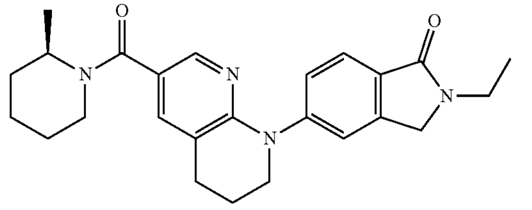
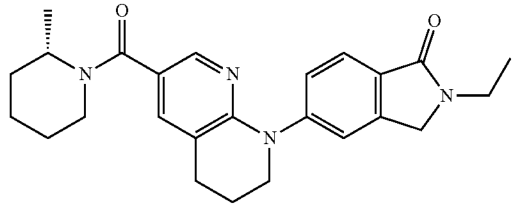
-continued
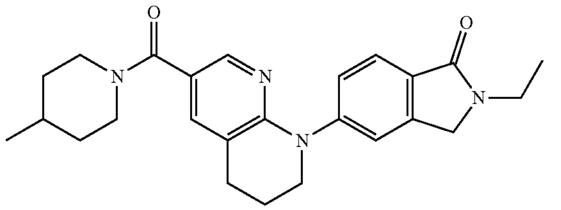
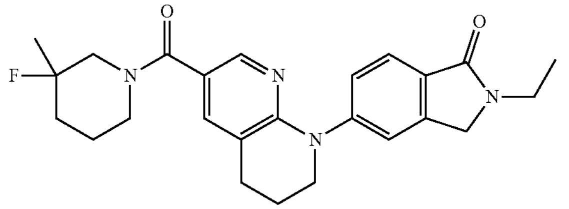
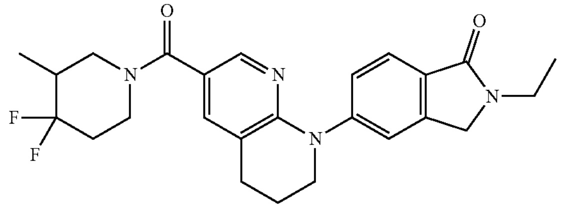
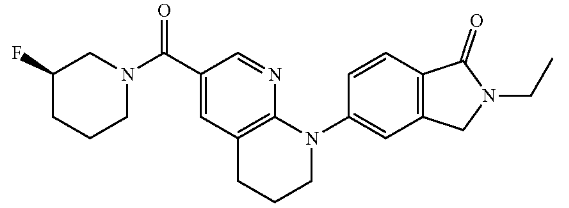
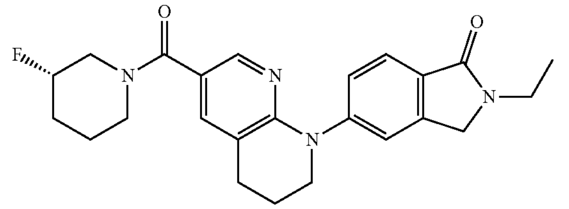
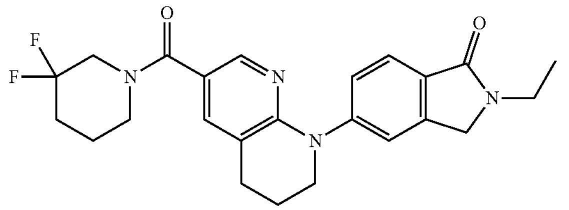
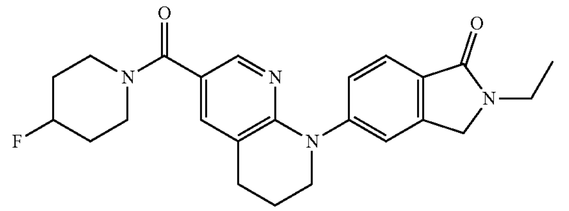
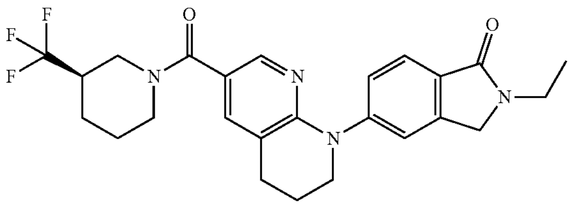

-continued
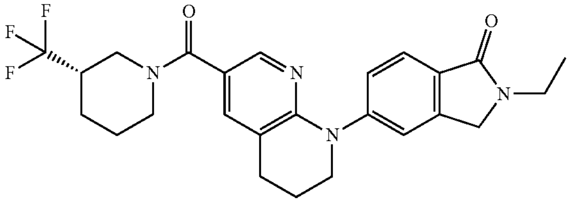
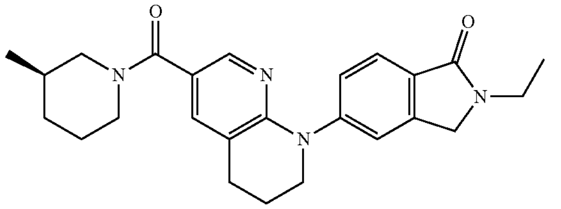
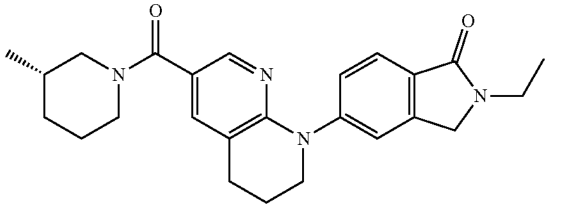
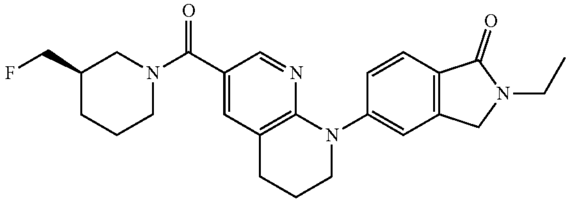
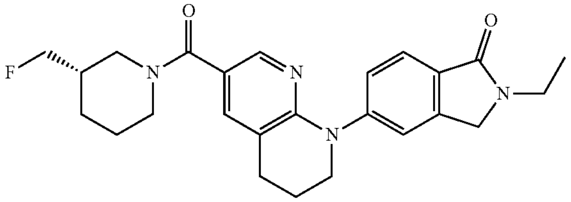
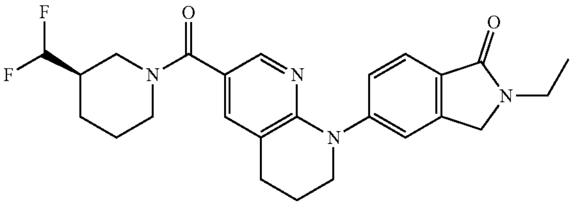
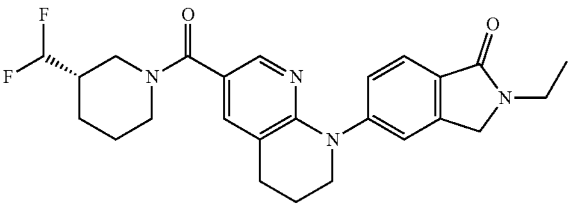
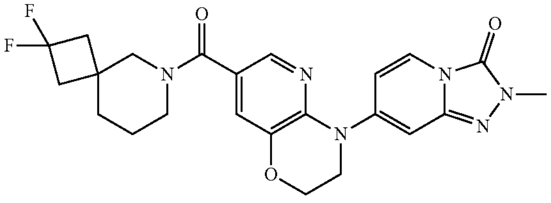
-continued
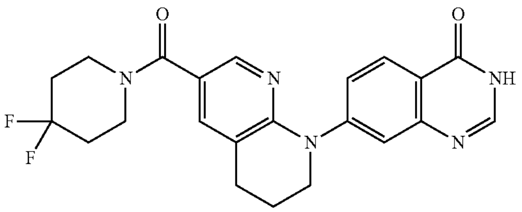
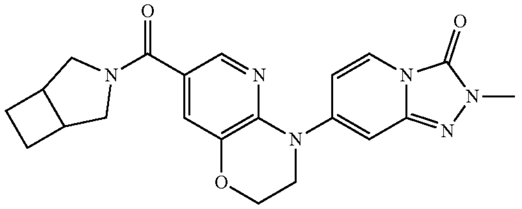
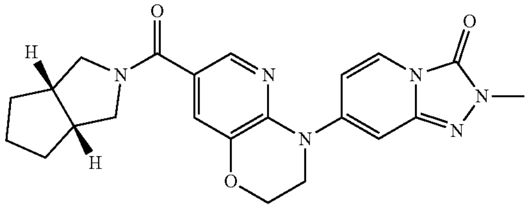
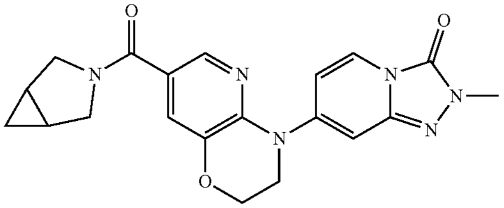
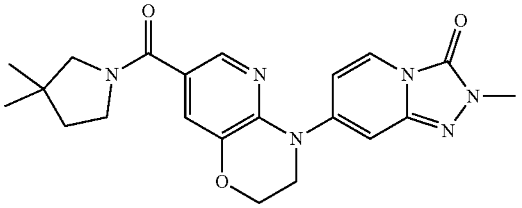
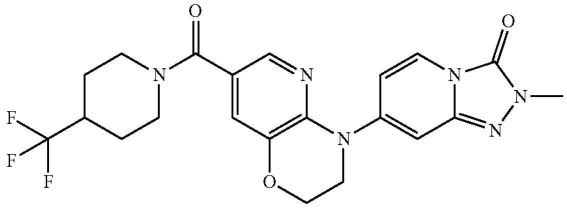
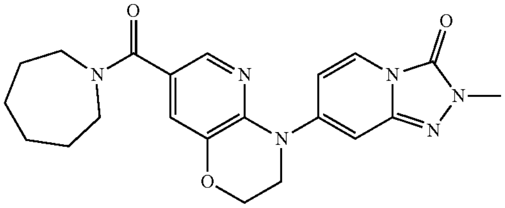
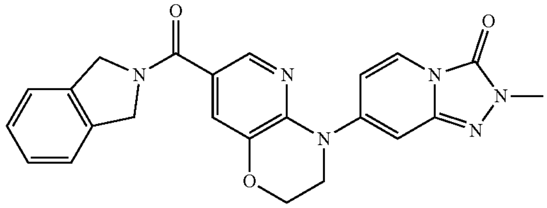

-continued
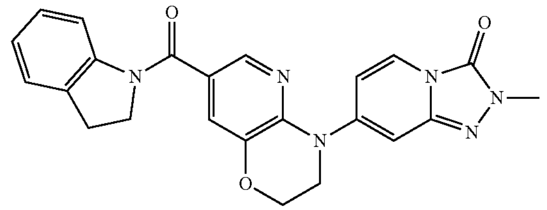
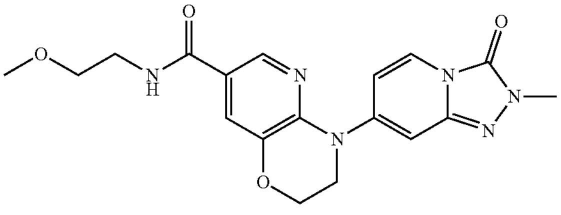
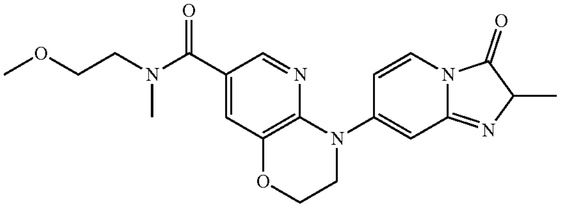
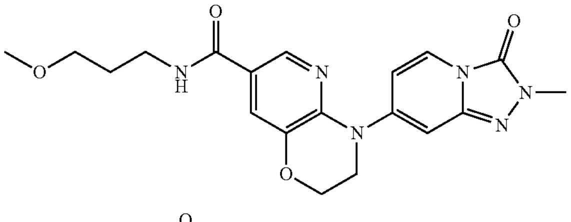
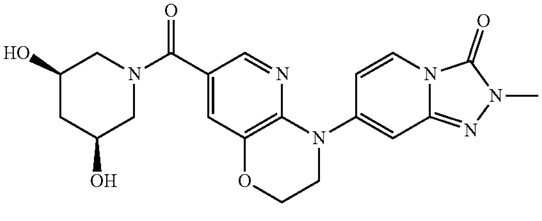
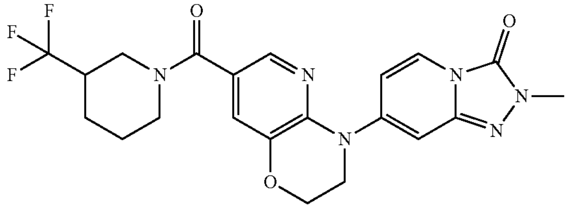
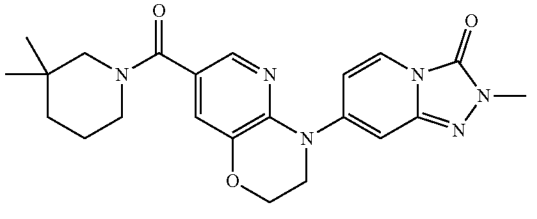
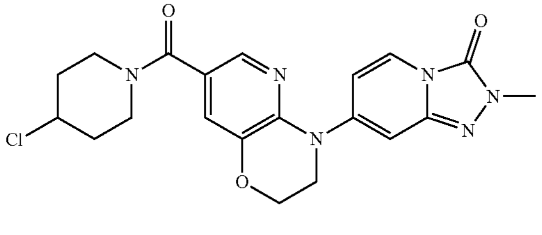
-continued
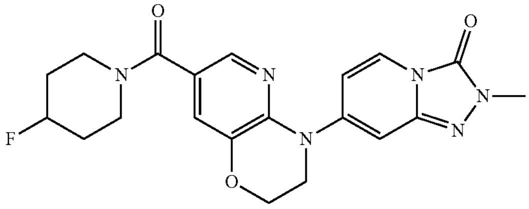
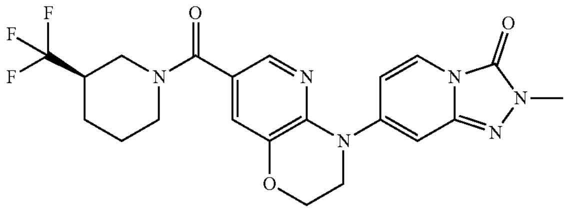
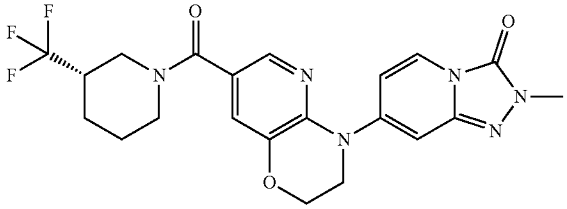
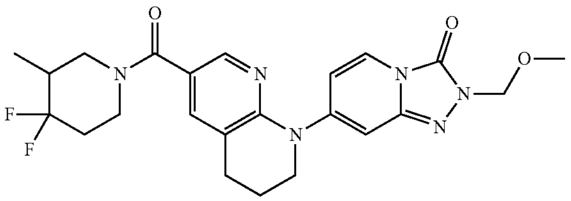
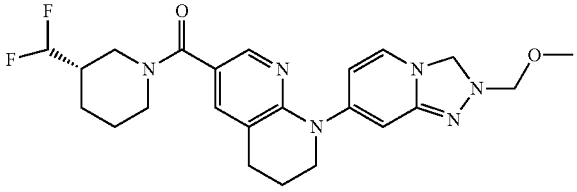
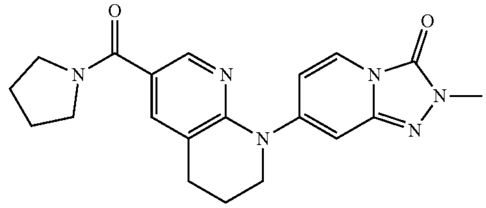
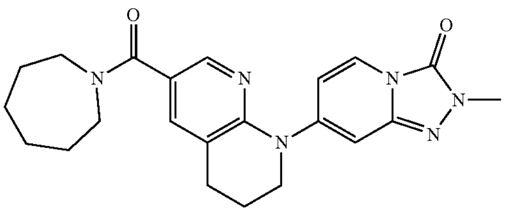
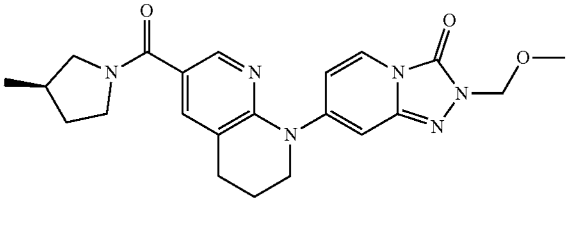

-continued
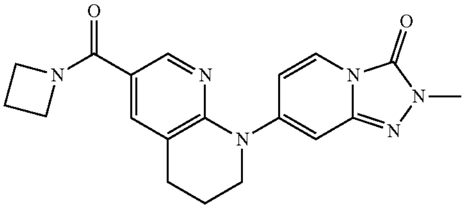
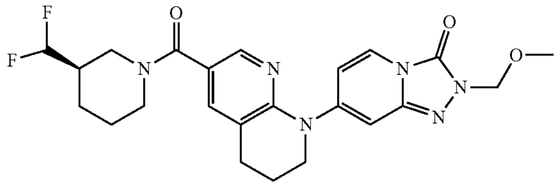
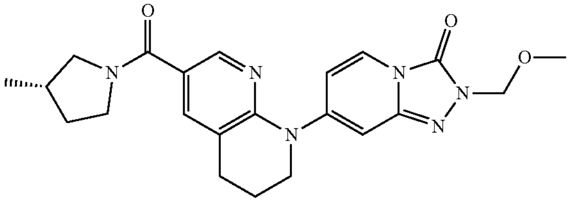
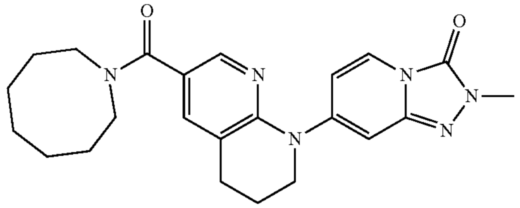
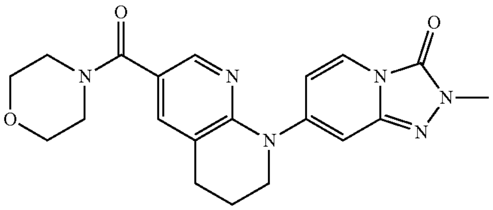
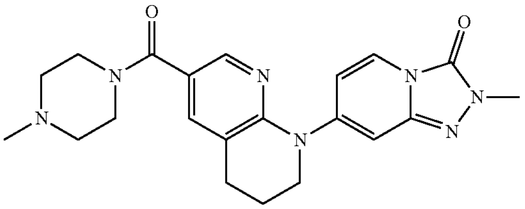
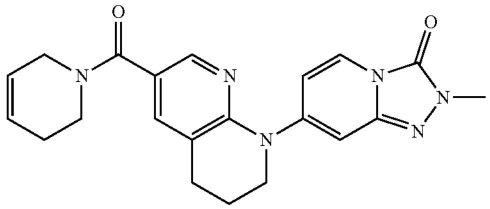
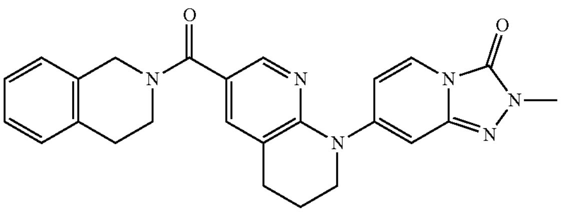
-continued
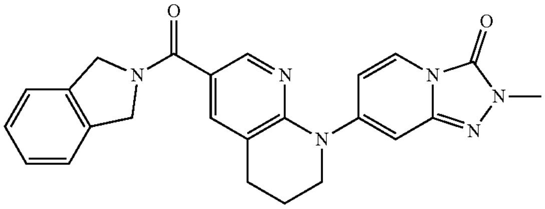
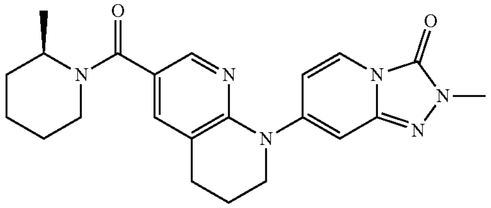
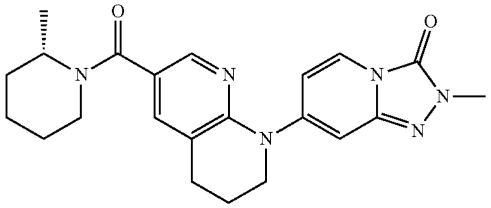
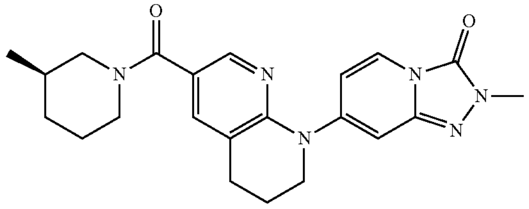
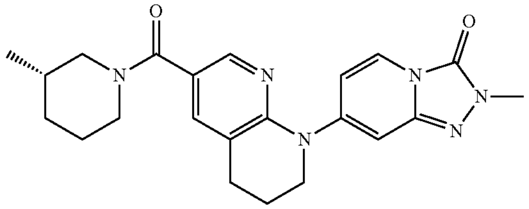
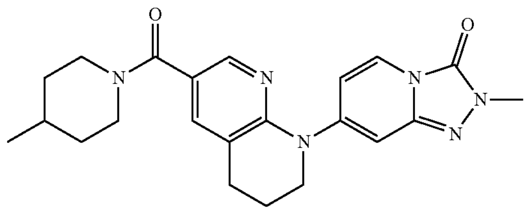
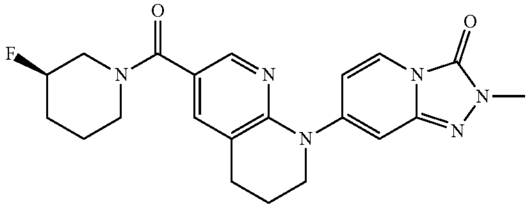

-continued
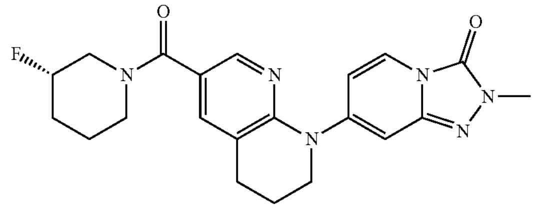
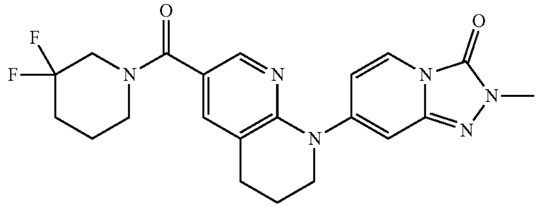
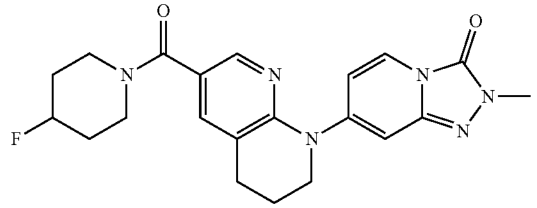
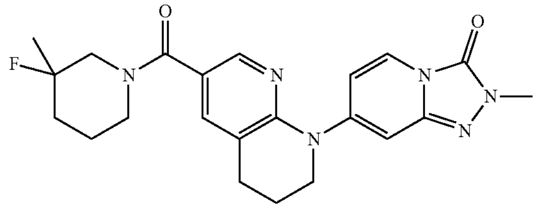
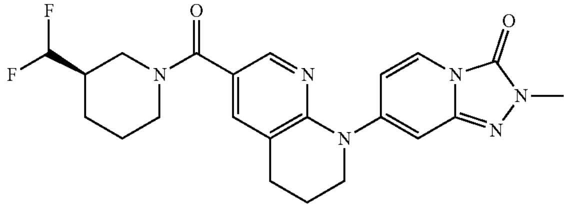
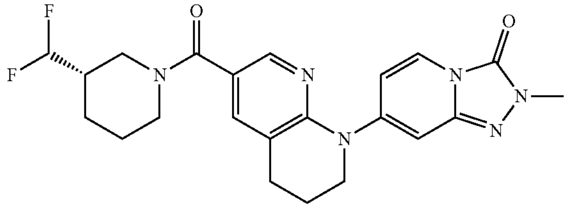
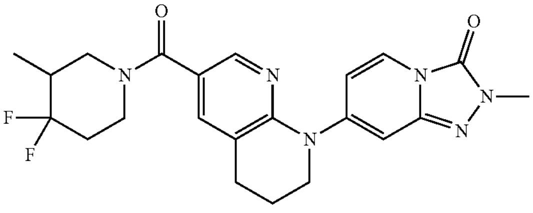
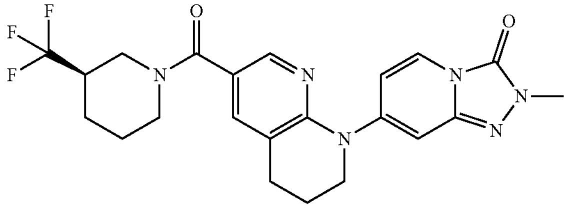
-continued
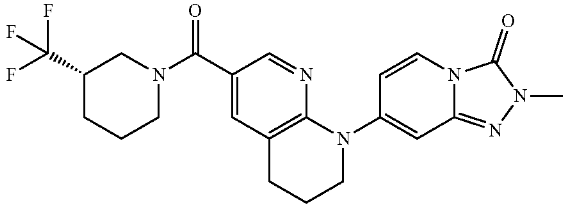
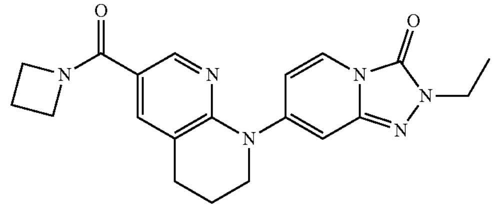
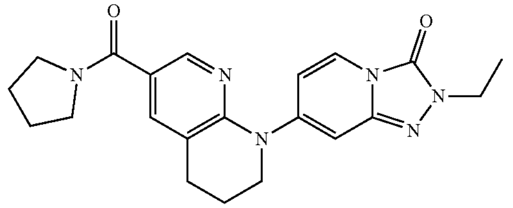
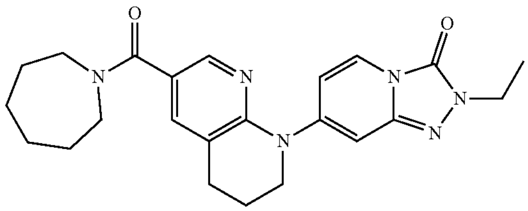
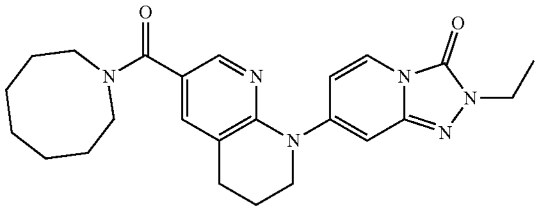
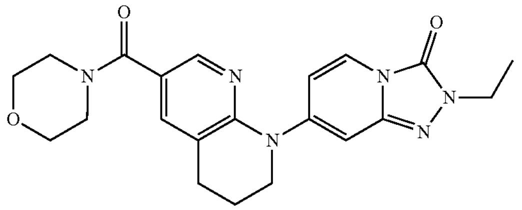
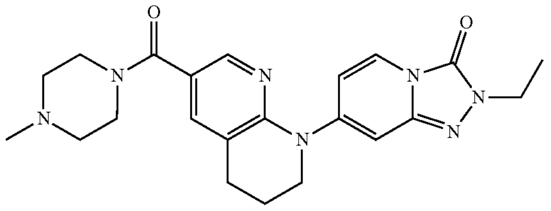
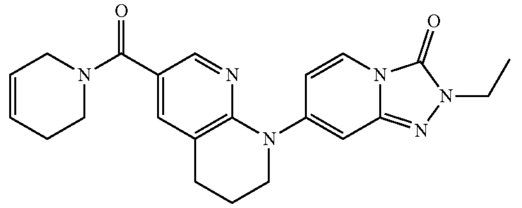

-continued
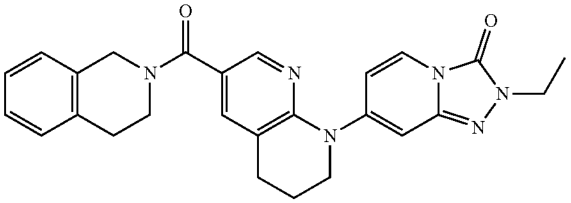
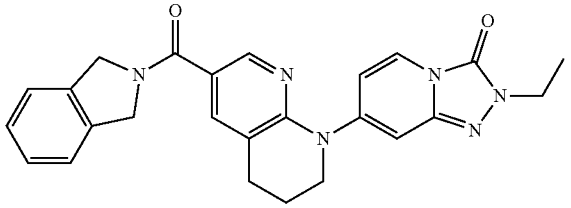
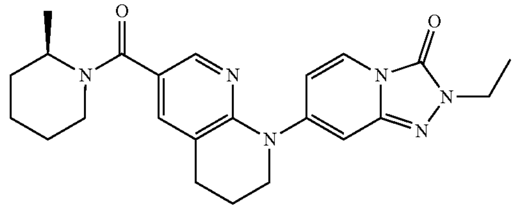
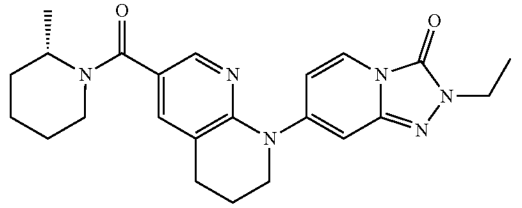
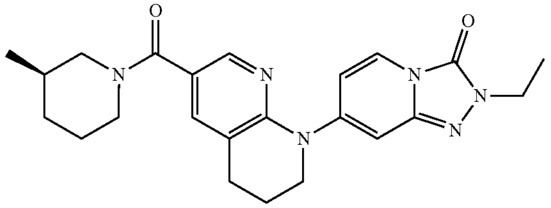
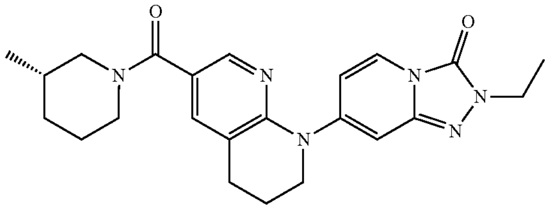
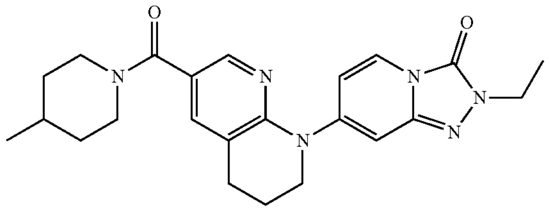
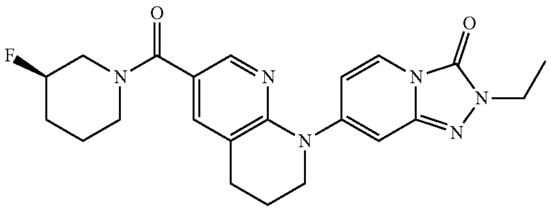
-continued
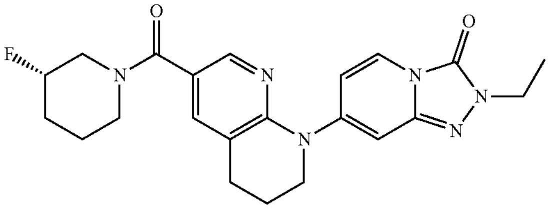
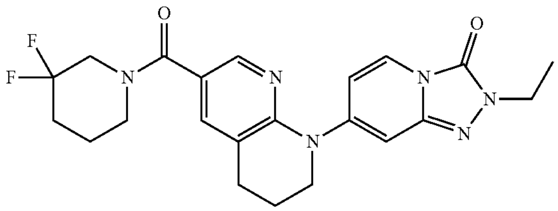
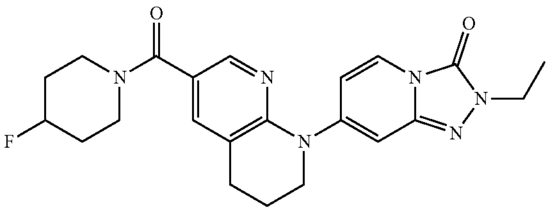
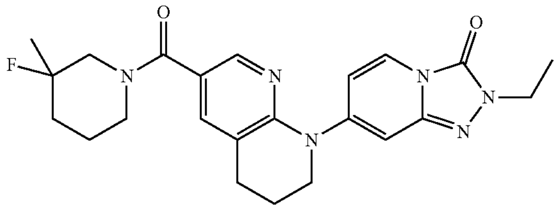
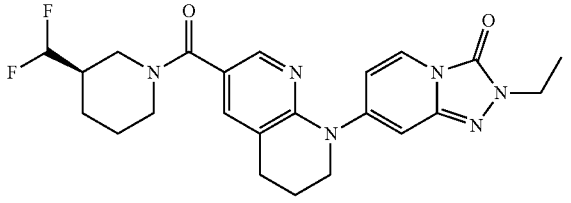
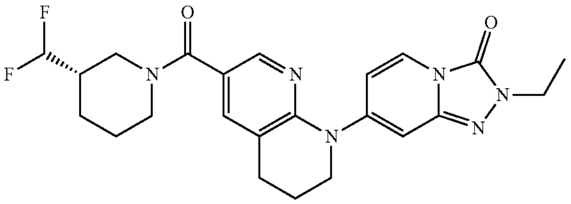
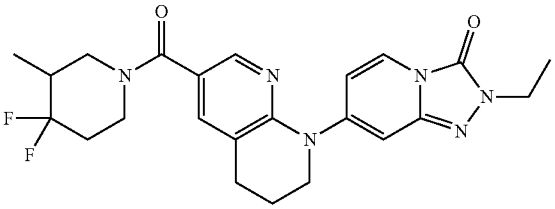
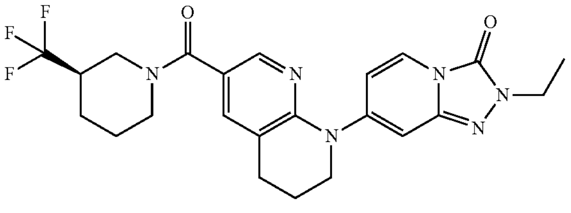

-continued
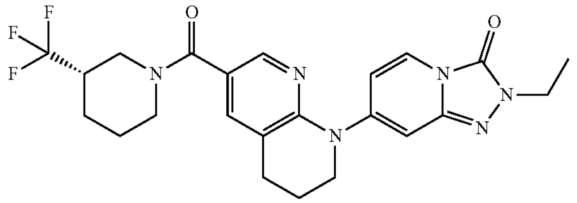
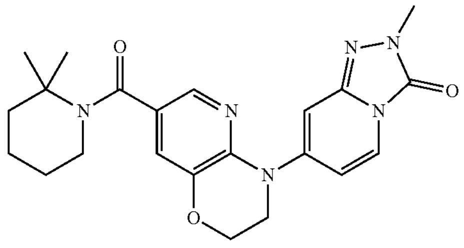
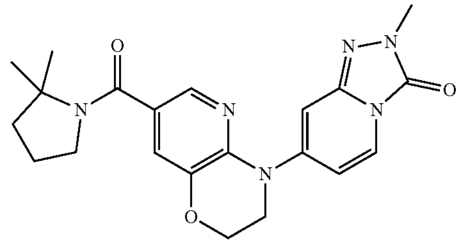
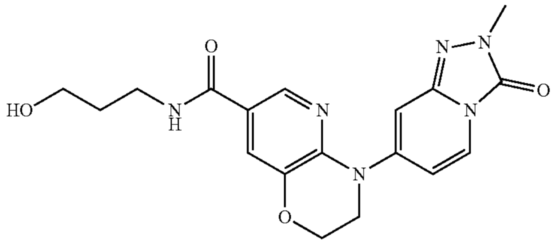
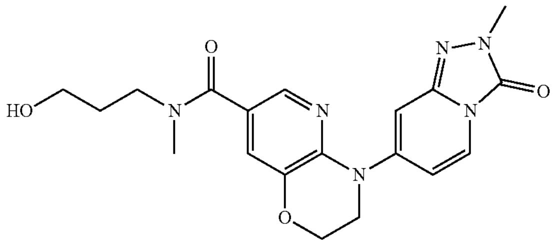
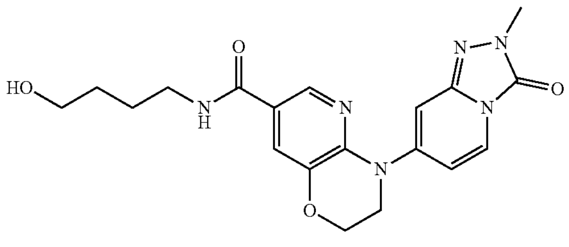
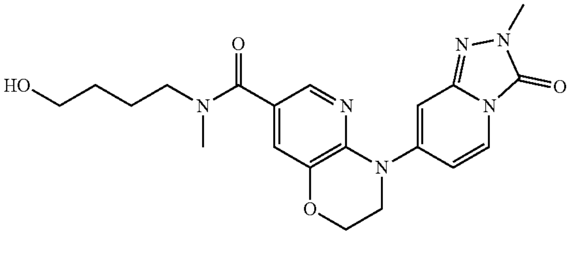
-continued
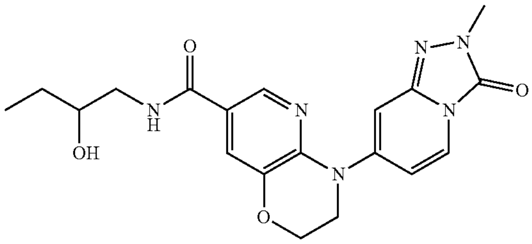
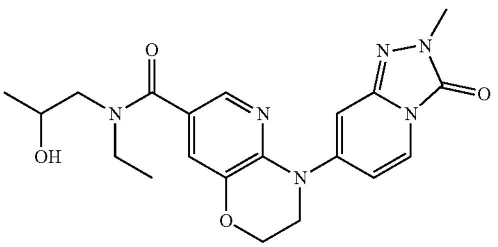
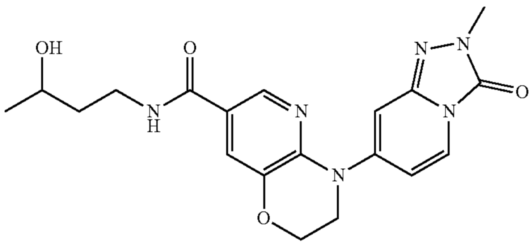
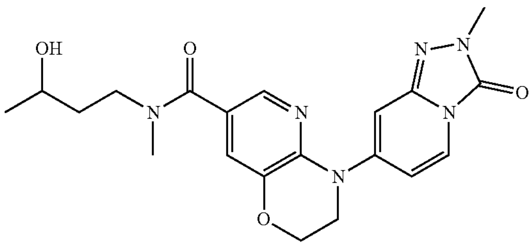
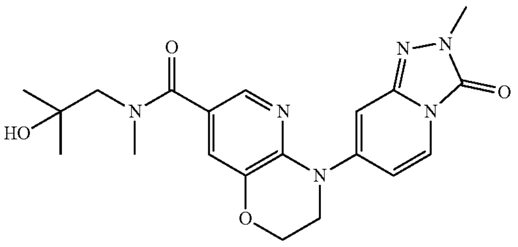
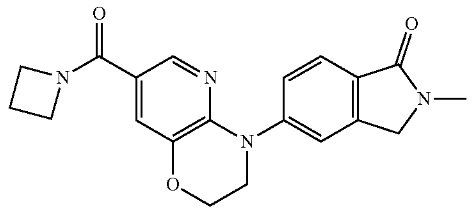
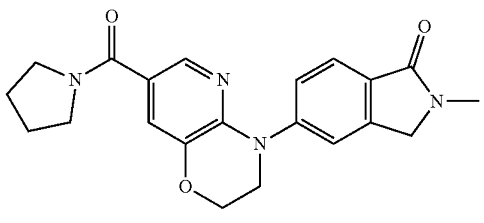

-continued
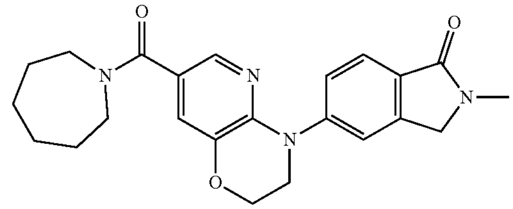
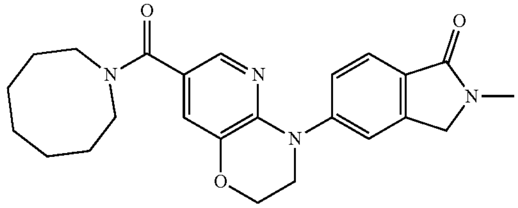
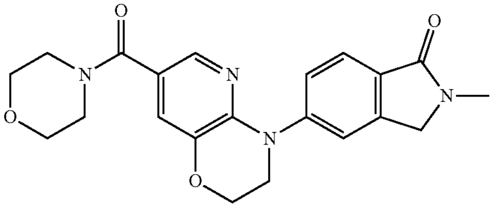
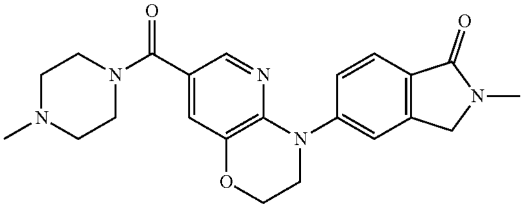
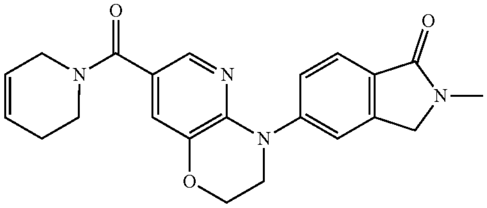
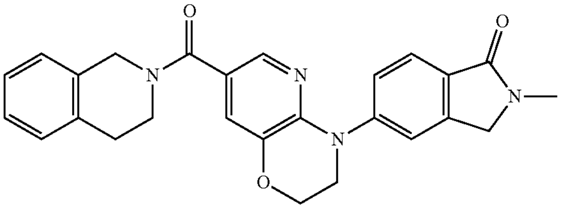
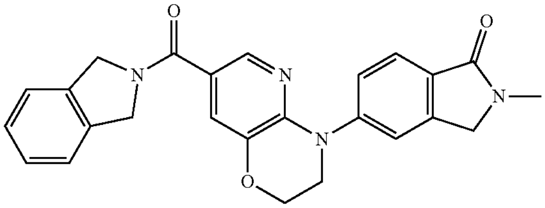
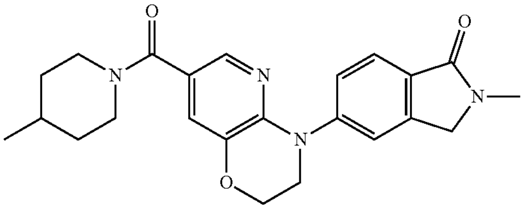
-continued
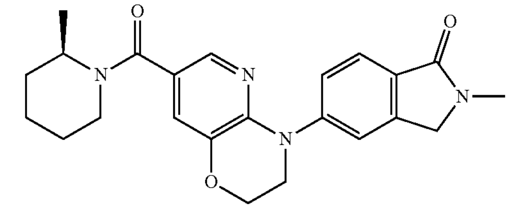
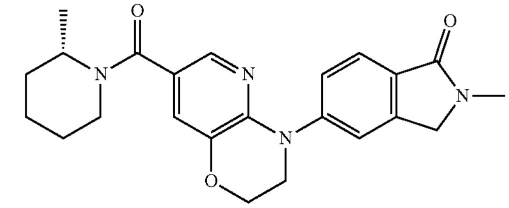
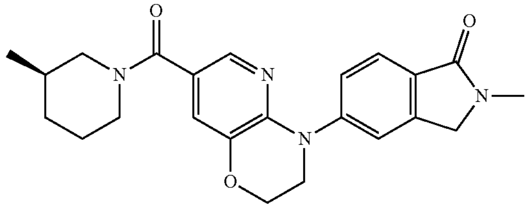
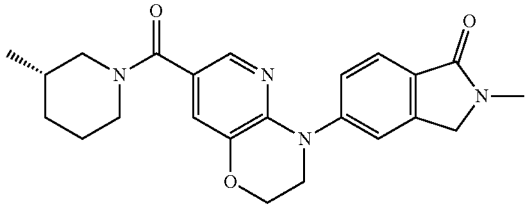
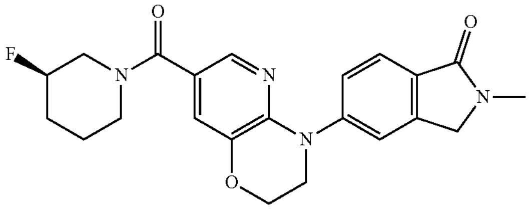
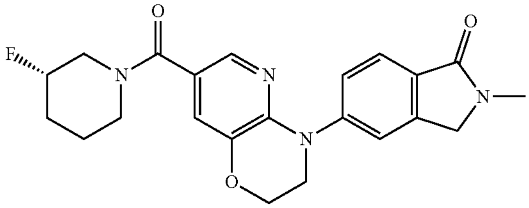
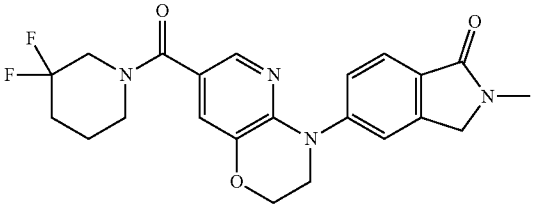
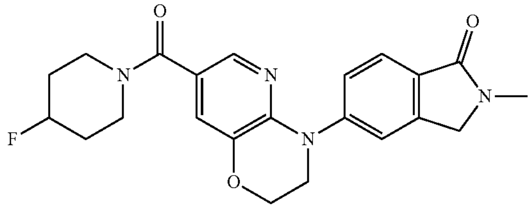

-continued
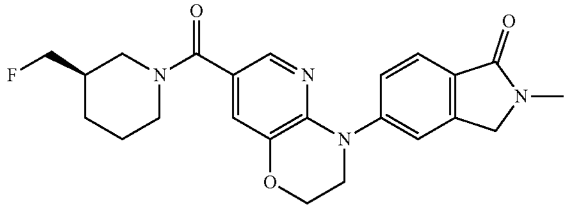
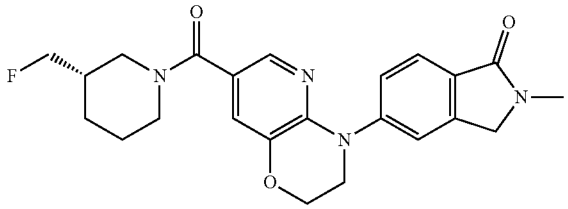
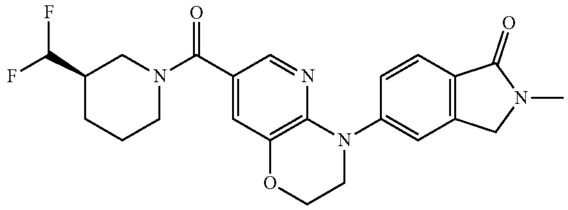
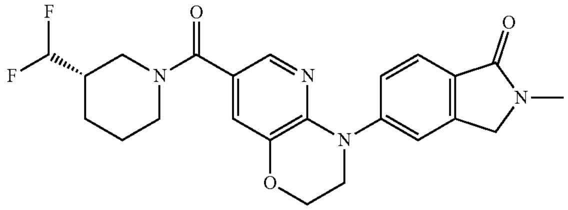
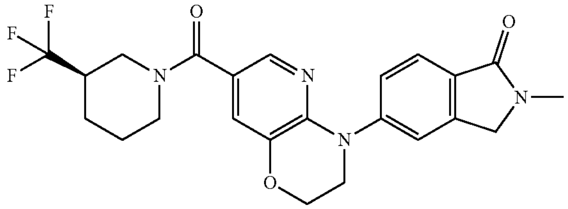
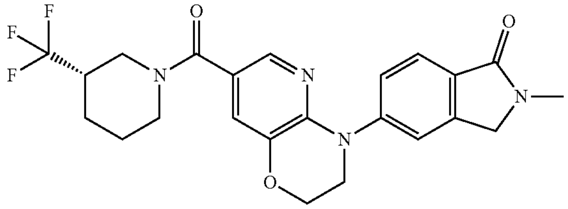
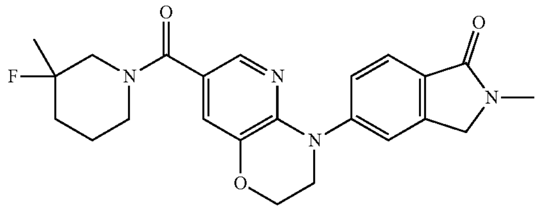
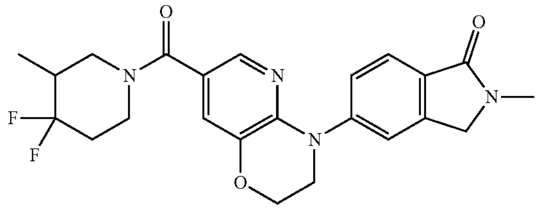
-continued
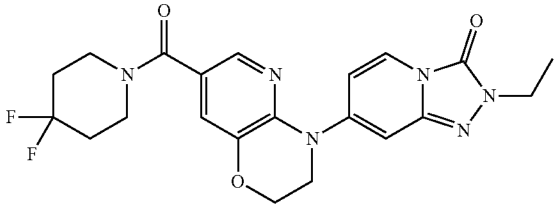
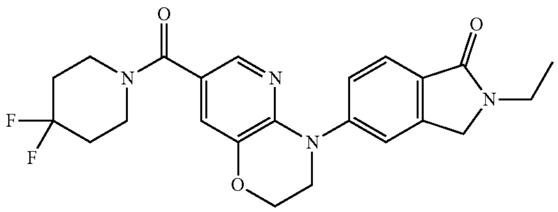
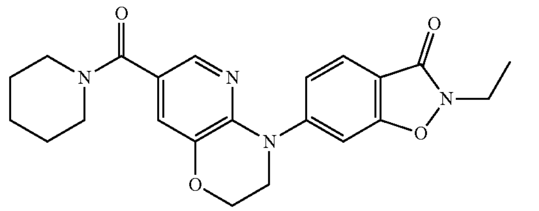
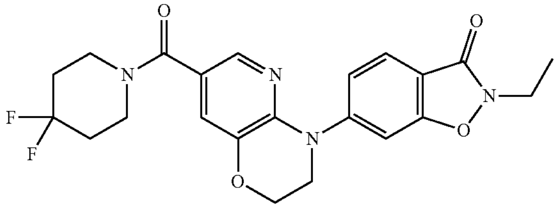
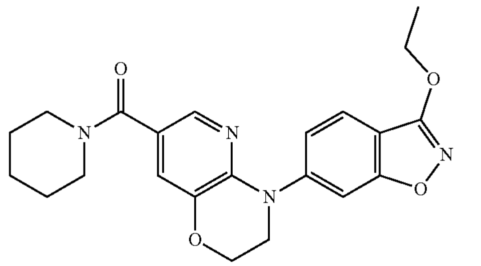
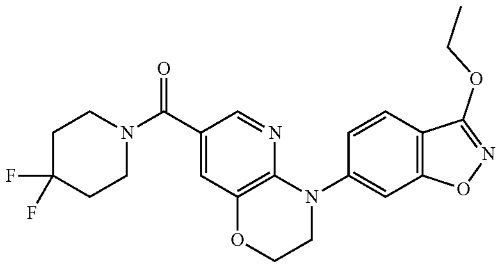
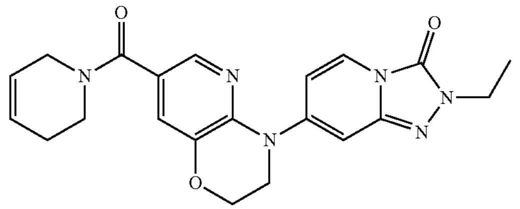

-continued
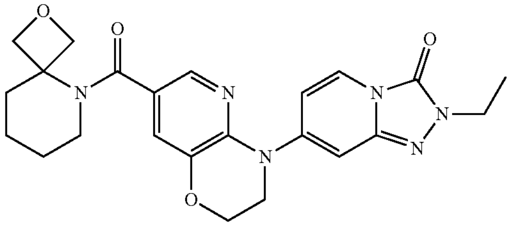
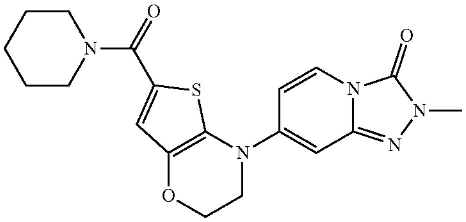
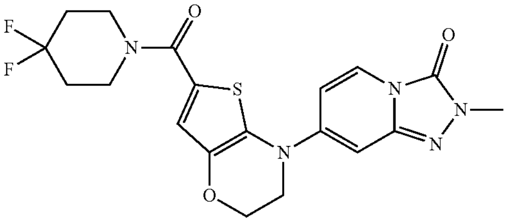
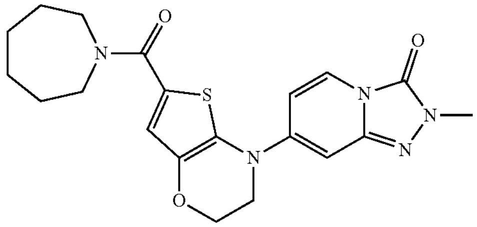
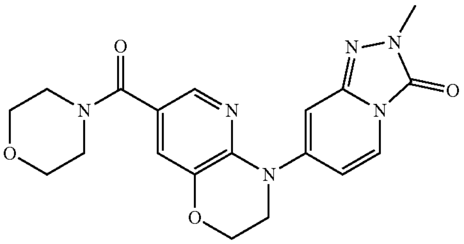
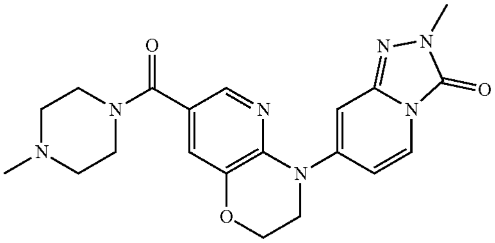
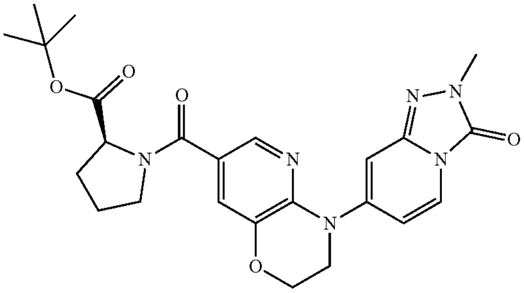
-continued
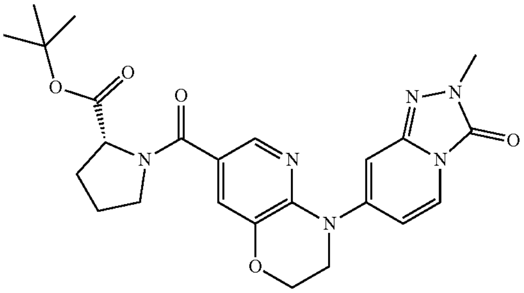
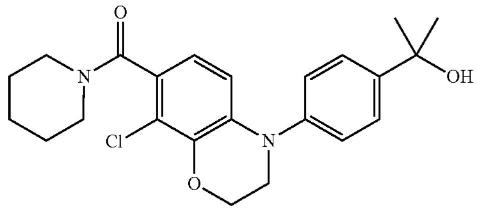
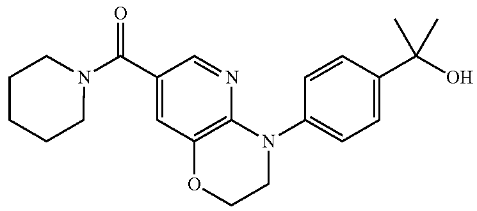
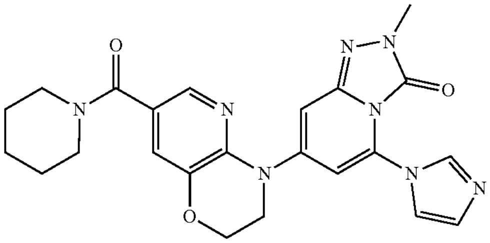
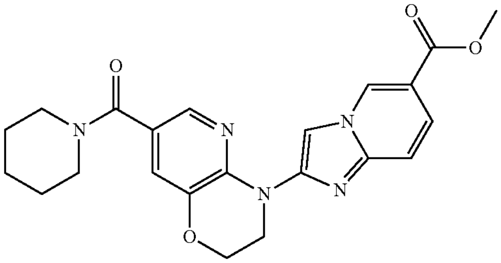
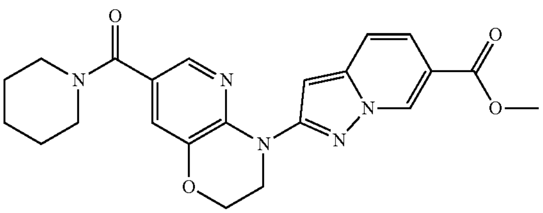
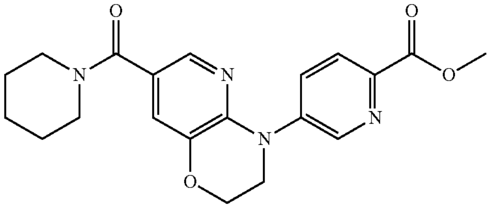

-continued
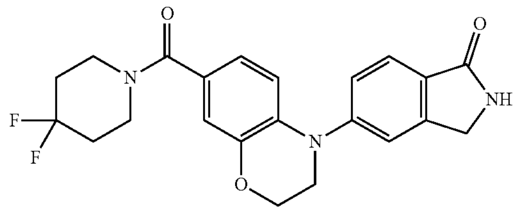
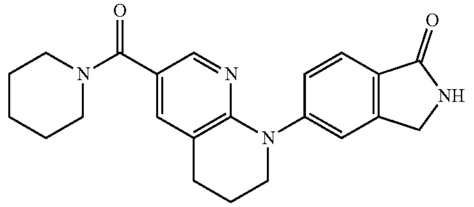
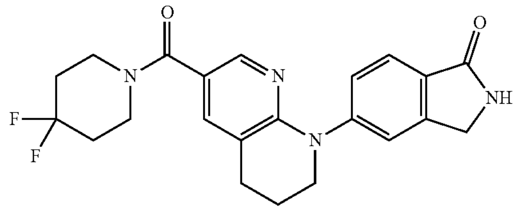
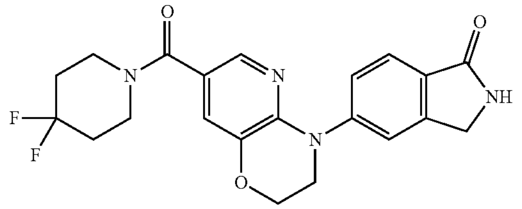
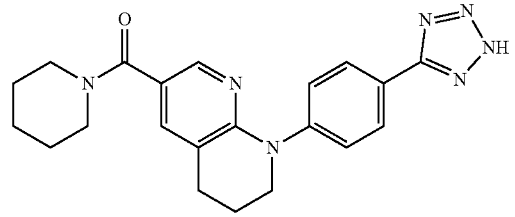
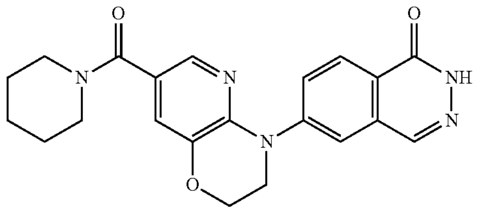
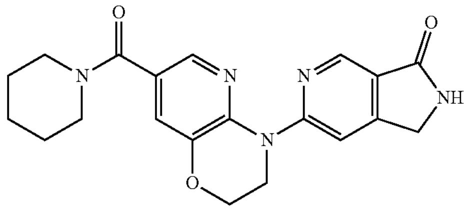
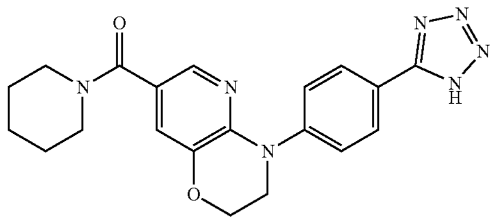
-continued
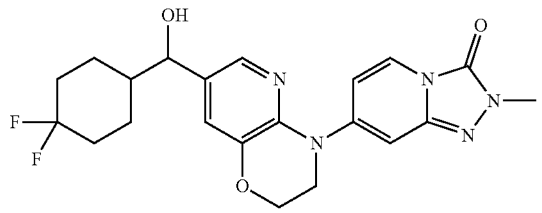
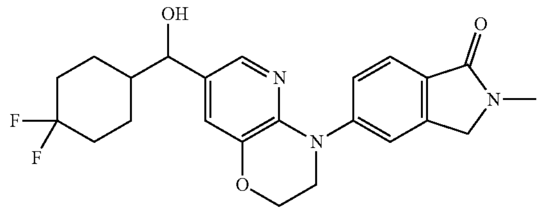
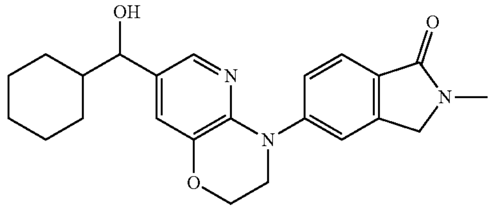
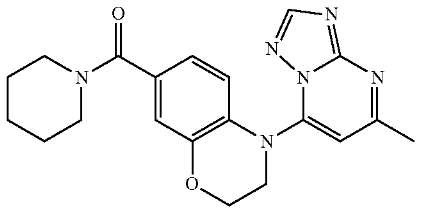
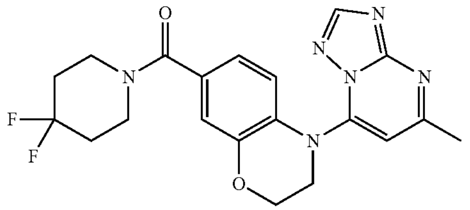
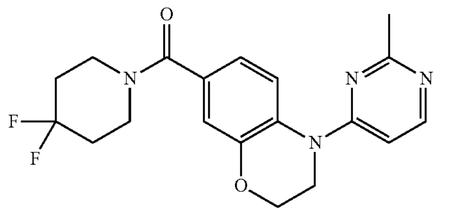
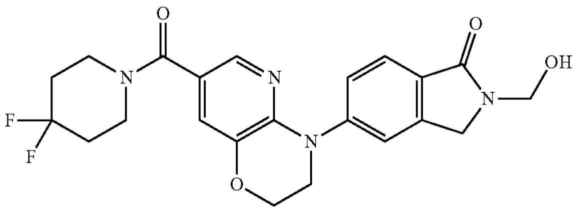

-continued
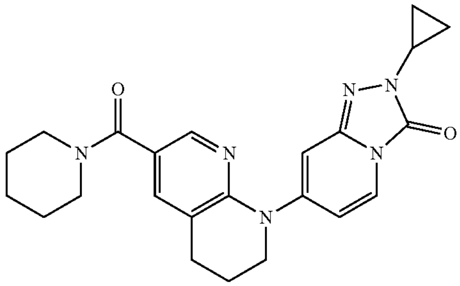
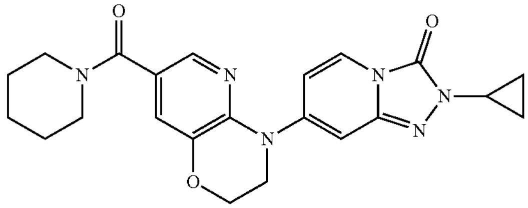
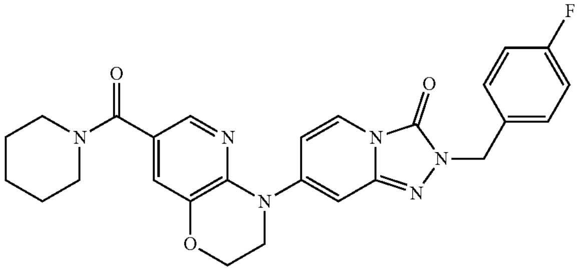
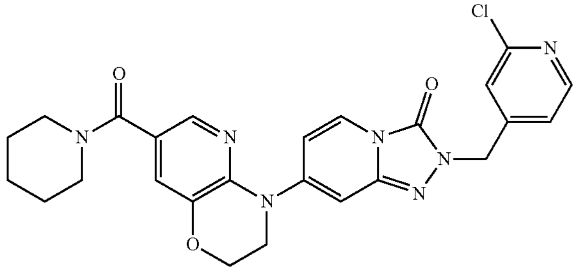
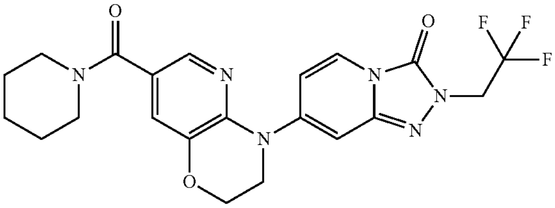
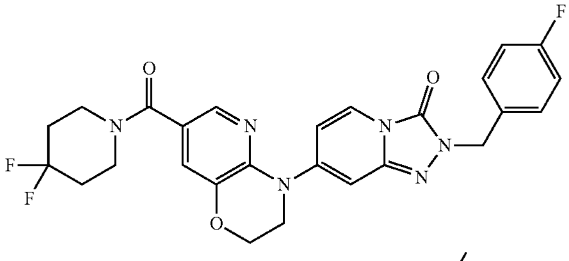
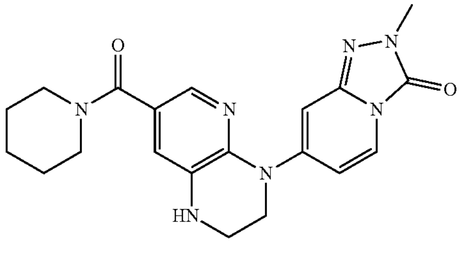
-continued
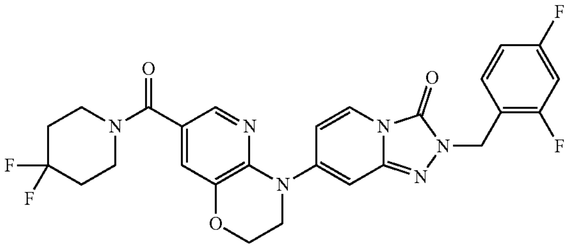
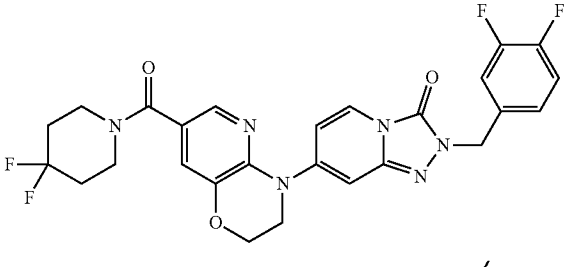
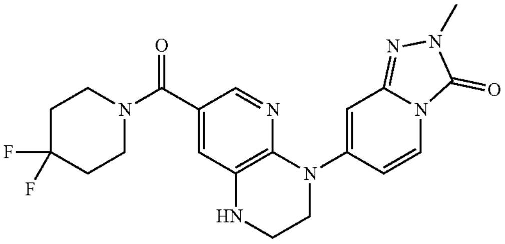
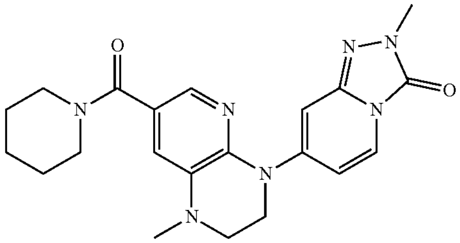
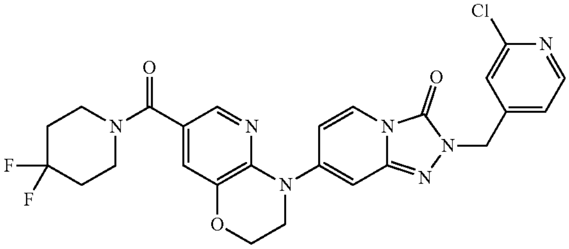
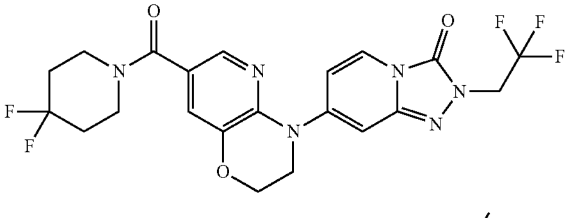
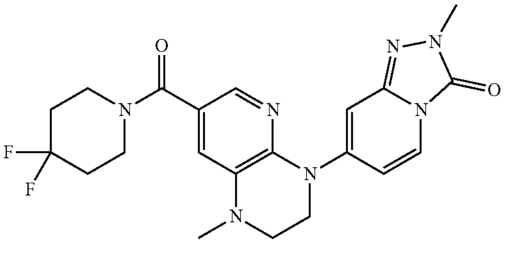

-continued

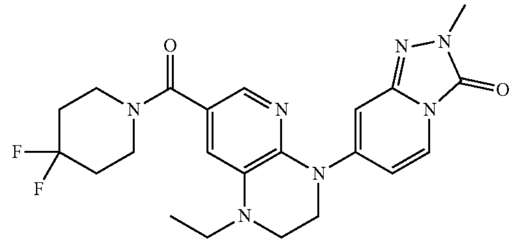

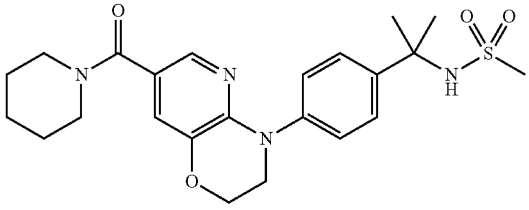

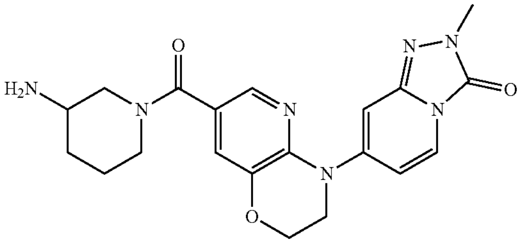

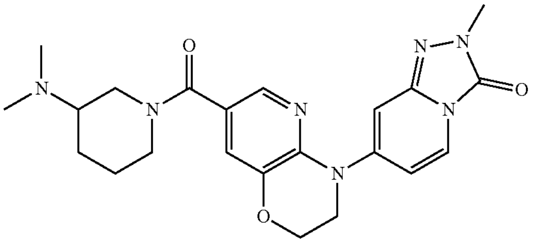

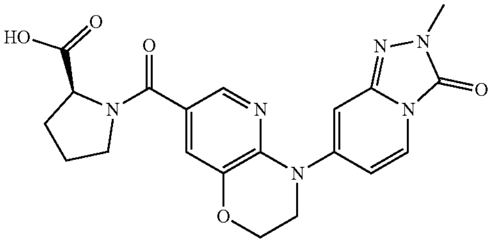

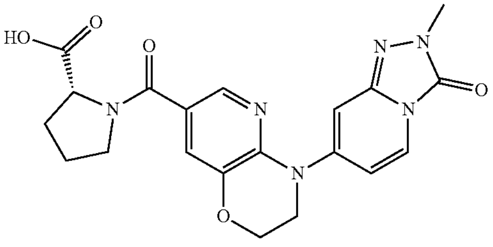 [SMILES: Cn1nc2cc(N3CCOc4cc(C(=O)N5CCC[C@@H]5C(=O)O)cnc43)ccn2c1=O]

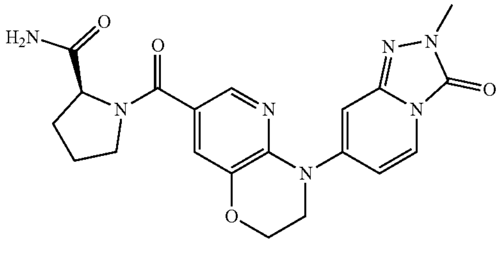 [SMILES: Cn1nc2cc(N3CCOc4cc(C(=O)N5CCC[C@@H]5C(N)=O)cnc43)ccn2c1=O]

-continued

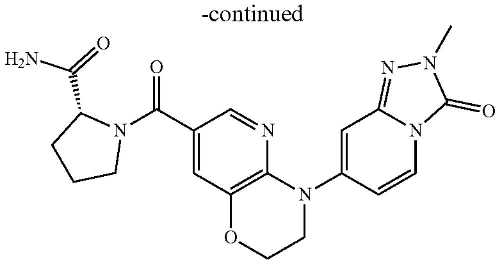

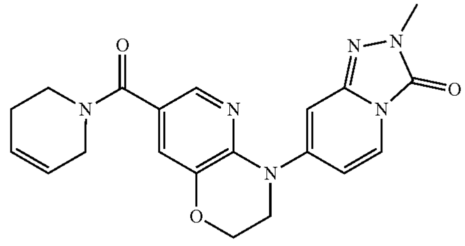

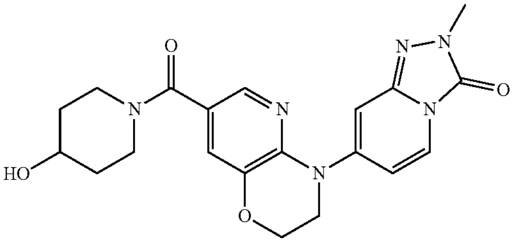

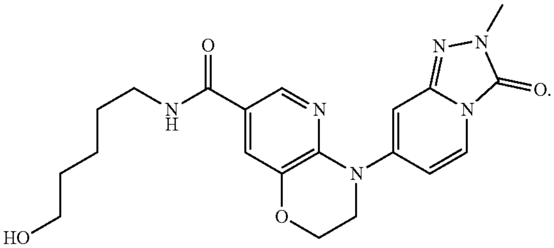

9. The compound according to claim 3, or a pharmacologically acceptable salt thereof, wherein the compound is a compound of formula A2aa), A2aa)

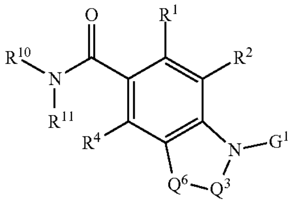

where $Q^6$ is a single bond, a methylene group, an oxygen atom, a methyleneoxy group or $NR^7$ group;

$Q^3$ is $-(CH_2)_m-(CR^5R^6)_n-(CH_2)_p-$;

$R^5$ and $R^6$ are the same or different, and a hydrogen atom, a halogen atom, a $C_1$-$C_3$ alkyl group, a $C_1$-$C_3$ alkoxy group or a halo $C_1$-$C_3$ alkyl group; and each of m, n and p is 0, 1 or 2, and m+n+p is an integer of 2 to 5.

10. The compound according to claim 3, or a pharmacologically acceptable salt thereof, wherein the compound is a compound of formula A2ba), A2ba)

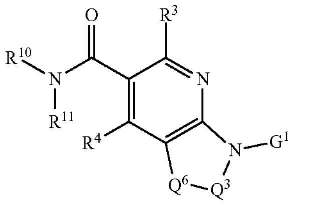

where $Q^6$ is a single bond, a methylene group, an oxygen atom, a methyleneoxy group or $NR^7$ group;

$Q^3$ is $—(CH_2)_m—(CR^5R^6)_n—(CH_2)_p—$;

$R^5$ and $R^6$ are the same or different, and a hydrogen atom, a halogen atom, a $C_1$-$C_3$ alkyl group, a $C_1$-$C_3$ alkoxy group or a halo $C_1$-$C_3$ alkyl group; and each of m, n and p is 0, 1 or 2, and m+n+p is an integer of 2 to 5.

11. The compound according to claim 4, or a pharmacologically acceptable salt thereof, wherein the compound is a compound of formula A2aaa), A2aaa)

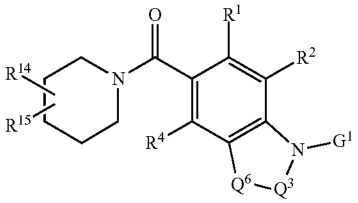

where $G^1$ is a group selected from the group consisting of formula G1aa), formula G1fa), formula G1ga), formula G1ia), formula G1pa), formula G1qa) and formula G1ya), G1aa)

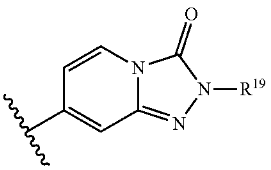

G1fa)

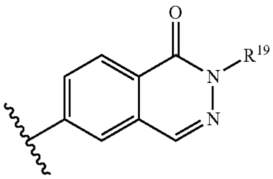

G1ga)

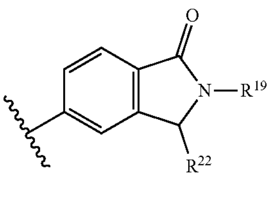

-continued

G1ia)

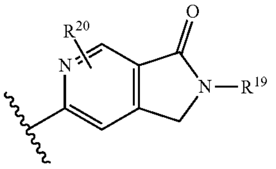

G1pa)

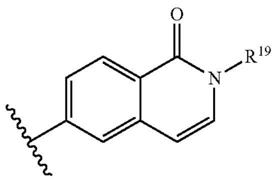

G1qa)

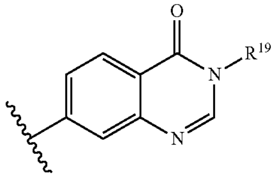

G1ya)

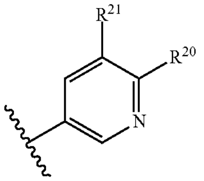

where $Q^3$ is $—(CH_2)_m—(CR^5R^6)_n—(CH_2)_p—$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^7$ is a hydrogen atom or a $C_1$-$C_3$ alkyl group;

$R^{19}$ is a hydrogen atom, a $C_1$-$C_3$ alkyl group, a $C_1$-$C_3$ alkoxy $C_1$-$C_3$ alkyl group, a $C_3$-$C_8$ cycloalkyl group, a hydroxyl $C_1$-$C_6$ alkyl group, a halo $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^2$ is a hydrogen atom or a $C_1$-$C_3$ alkyl group; and each of m, n and p is 0, 1 or 2, and m+n+p is an integer of 2 to 5.

12. The compound according to claim 4, or a pharmacologically acceptable salt thereof, wherein the compound is a compound of formula A2baa), A2baa)

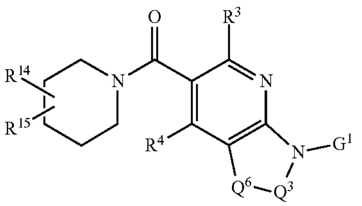

where $G^1$ is a group selected from the group consisting of formula G1aa), formula G1fa), formula G1ga), formula G1ia), formula G1pa), formula G1qa) and formula G1ya), G1aa)

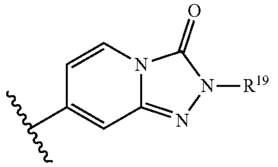

G1fa)

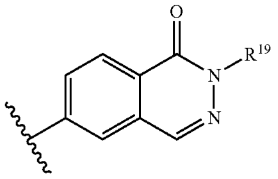

G1ga)

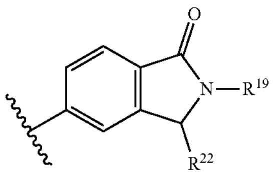

G1ia)

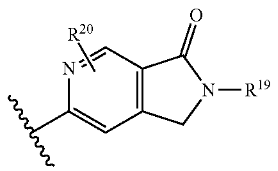

G1pa)

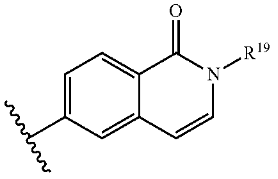

G1qa)

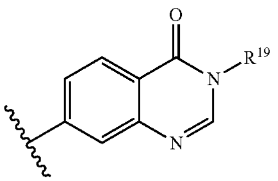

-continued

G1ya)

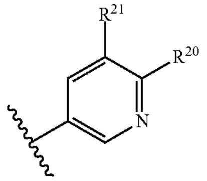

where $Q^3$ is $-(CH_2)_m-(CR^5R^6)_n-(CH_2)_p-$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^7$ is a hydrogen atom or a $C_1$-$C_3$ alkyl group;

$R^{19}$ is a hydrogen atom, a $C_1$-$C_3$ alkyl group, a $C_1$-$C_3$ alkoxy $C_1$-$C_3$ alkyl group, a $C_3$-$C_8$ cycloalkyl group, a hydroxyl $C_1$-$C_6$ alkyl group, a halo $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^{22}$ is a hydrogen atom or a $C_1$-$C_3$ alkyl group; and each of m, n and p is 0, 1 or 2, and m+n+p is an integer of 2 to 5.

13. The compound according to claim 4, or a pharmacologically acceptable salt thereof, wherein the compound is a compound of formula A2caa), A2caa)

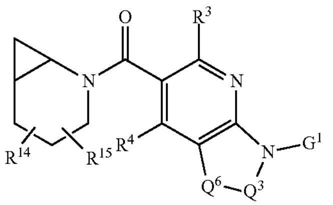

where $G^1$ is a group selected from the group consisting of formula G1 aa), formula G1fa), formula G1ga), formula G1ia), formula G1pa), formula G1qa) and formula G1ya), G1aa)

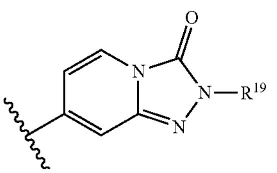

-continued

G1fa)

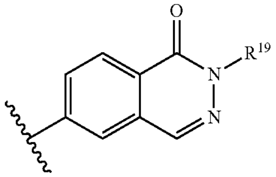

G1ga)

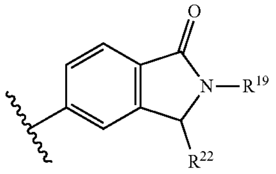

G1ia)

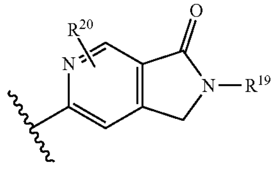

G1pa)

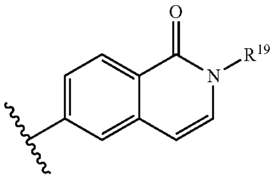

G1qa)

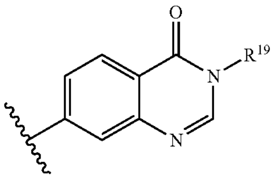

G1ya)

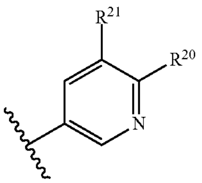

where $Q^3$ is $-(CH_2)_m-(CR^5R^6)_n-(CH_2)_p-$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^7$ is a hydrogen atom or a $C_1$-$C_3$ alkyl group;

$R^{19}$ is a hydrogen atom, a $C_1$-$C_3$ alkyl group, a $C_1$-$C_3$ alkoxy $C_1$-$C_3$ alkyl group, a $C_3$-$C_8$ cycloalkyl group, a hydroxyl $C_1$-$C_6$ alkyl group, a halo $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^{22}$ is a hydrogen atom or a $C_1$-$C_3$ alkyl group; and each of m, n and p is 0, 1 or 2, and m+n+p is an integer of 2 to 5.

14. The compound according to claim 4, or a pharmacologically acceptable salt thereof, wherein the compound is a compound of formula A2daa), A2daa)

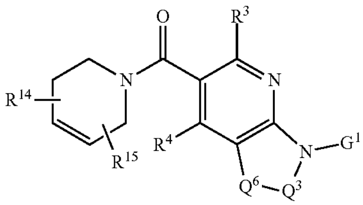

where $G^1$ is a group selected from the group consisting of formula G1aa), formula G1fa), formula G1ga), formula G1ia), formula G1pa), formula G1qa) and formula G1ya), G1aa)

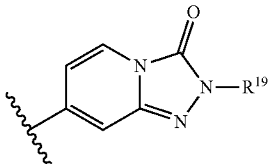

G1fa)

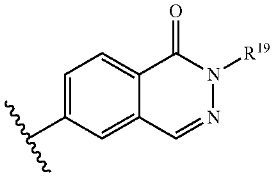

G1ga)

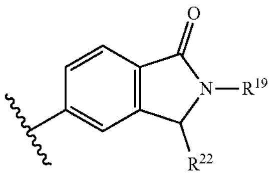

G1ia)

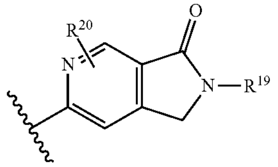

G1pa)

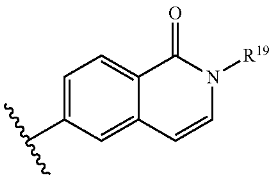

-continued

G1qa)

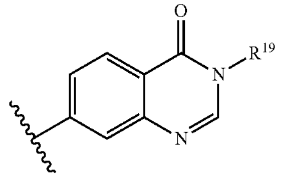

G1ya)

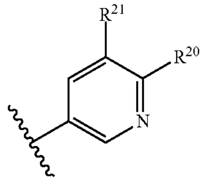

where $Q^3$ is $-(CH_2)_m-(CR^5R^6)_n-(CH_2)_p-$;

$Q^6$ is a single bond, a methylene group, an oxygen atom, or $NR^7$ group;

$R^1$ and $R^2$ are the same or different, and a hydrogen atom, a halogen atom or a $C_1$-$C_3$ alkyl group;

$R^3$ is a hydrogen atom or a $C_1$-$C_3$ alkyl group;

$R^4$ is a hydrogen atom, a halogen atom or a $C_1$-$C_3$ alkyl group;

$R^{14}$ and $R^{15}$ are the same or different, and a hydrogen atom, a fluorine atom, a chlorine atom, a $C_1$-$C_3$ alkyl group or a halo $C_1$-$C_3$ alkyl group;

$R^5$ and $R^6$ are the same or different, and a hydrogen atom, a halogen atom or a $C_1$-$C_3$ alkyl group;

$R^7$ is a hydrogen atom or a $C_1$-$C_3$ alkyl group;

$R^{19}$ is a hydrogen atom, a $C_1$-$C_3$ alkyl group, a $C_1$-$C_3$ alkoxy $C_1$-$C_3$ alkyl group, a $C_3$-$C_8$ cycloalkyl group, a hydroxyl $C_1$-$C_6$ alkyl group, a halo $C_1$-$C_3$ alkyl group, a $C_1$-$C_6$ alkoxycarbonyl $C_1$-$C_3$ alkyl group or a 3- to 8-membered heterocycloalkyl $C_1$-$C_3$ alkyl group;

$R^{20}$ is a hydrogen atom, a halogen atom, a nitrile group, a carboxyl group, formyl group, a hydroxy $C_1$-$C_6$ alkyl group, a $C_1$-$C_6$ alkoxycarbonyl group or a aminocarbonyl group optionally having one or two $C_1$-$C_6$ alkyl groups;

$R^{21}$ is a hydrogen atom or a halogen atom;

$R^{22}$ is a hydrogen atom or a $C_1$-$C_3$ alkyl group; and each of m, n and p is 0, 1 or 2, and m+n+p is an integer of 2 to 5.

15. A pharmaceutical composition for treating at least one of fibrosis, cardiovascular diseases, and autoimmune diseases, comprising:

the compound of claim 1 or a pharmacologically acceptable salt thereof; and a pharmacologically acceptable carrier.

16. A pharmaceutical composition for treating wounds, comprising:

the compound of claim 1 or a pharmacologically acceptable salt thereof; and a pharmacologically acceptable carrier.

17. A pharmaceutical composition for treating at least one of inflammatory diseases, graft-versus-host disease, hair growth, osteoporosis, hearing loss, tinnitus, dizziness, disequilibrium, glaucoma, dry eye, neutropenia, diabetes, underactive bladder, promotion of engraftment in stem cell or bone marrow transplantation or organ transplantation, neurogenesis and nerve cell death, muscle regeneration and cervical ripening, comprising:

the compound of claim 1 or a pharmacologically acceptable salt thereof; and a pharmacologically acceptable carrier.

18. A pharmaceutical composition for treating at least one of fibrosis, cardiovascular diseases and autoimmune diseases, comprising:

the compound of claim 2 or a pharmacologically acceptable salt thereof; and a pharmacologically acceptable carrier.

19. A pharmaceutical composition for treating wounds, comprising:

the compound of claim 2 or a pharmacologically acceptable salt thereof; and a pharmacologically acceptable carrier.

20. A pharmaceutical composition for treating at least one of inflammatory diseases, graft-versus-host disease, hair growth, osteoporosis, hearing loss, tinnitus, dizziness, disequilibrium, glaucoma, dry eye, neutropenia, diabetes, underactive bladder, promotion of engraftment in stem cell or bone marrow transplantation or organ transplantation, neurogenesis and nerve cell death, muscle regeneration and cervical ripening, comprising:

the compound of claim 2 or a pharmacologically acceptable salt thereof; and a pharmacologically acceptable carrier.

21. The compound according to claim 1, or a pharmacologically acceptable salt thereof, wherein the compound is a compound having a structure selected from the following structures:

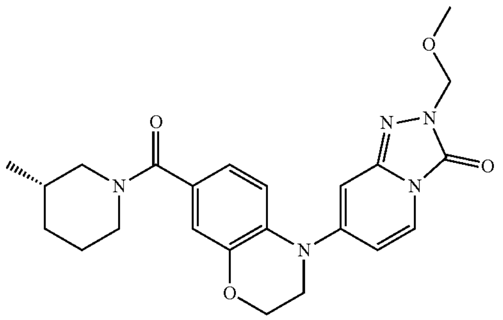

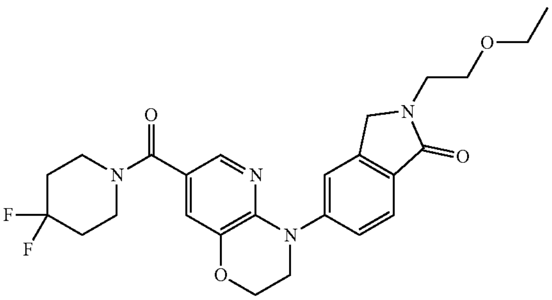

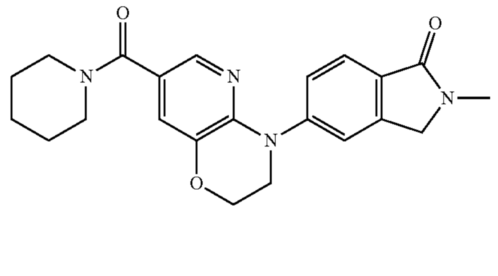

-continued
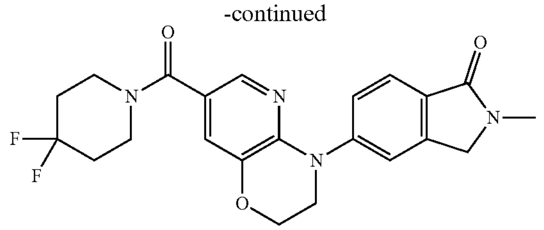
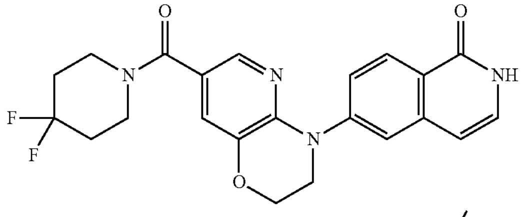
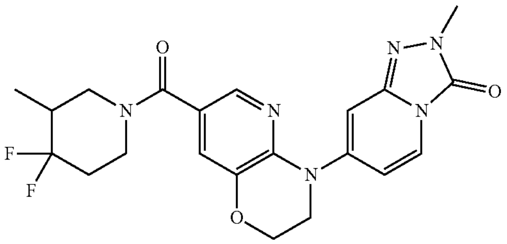
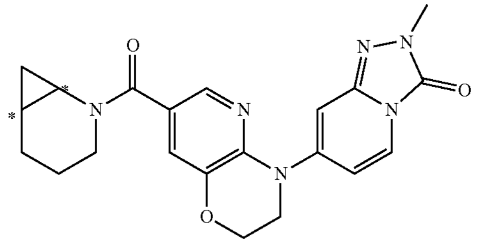
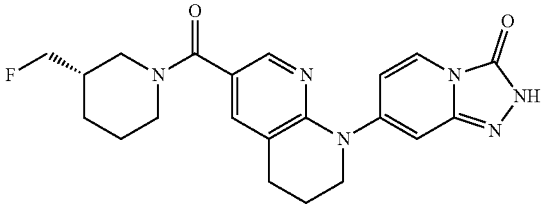
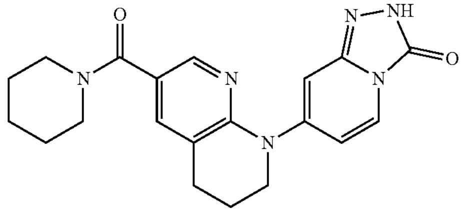
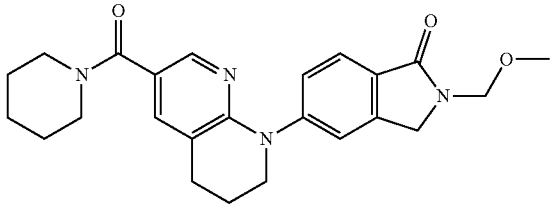
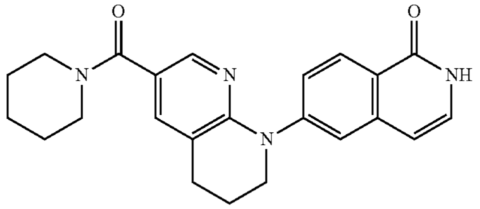
-continued
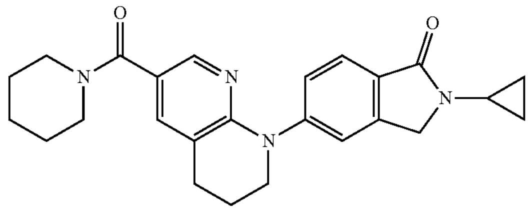
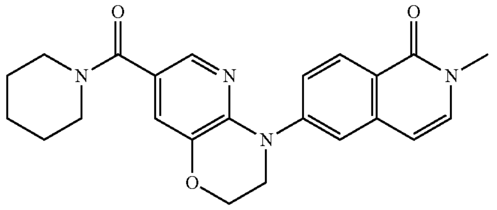
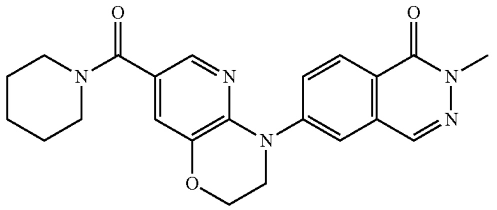
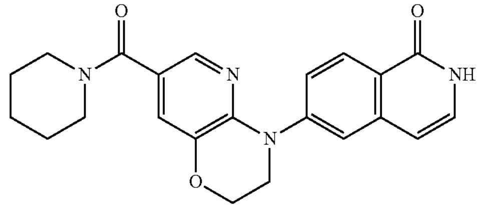
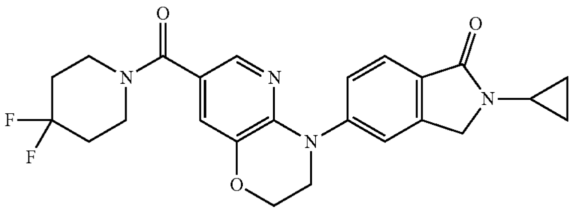
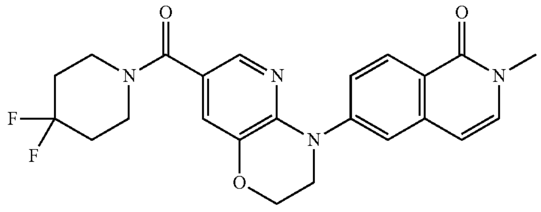
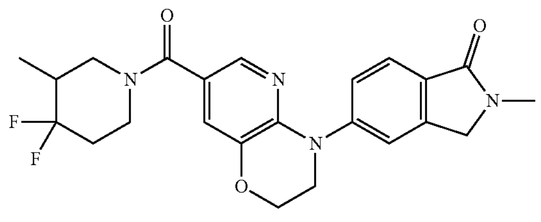
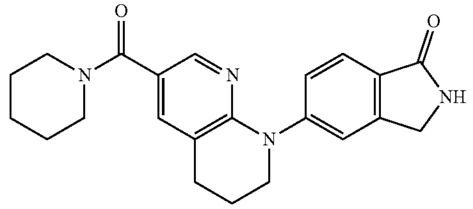

-continued

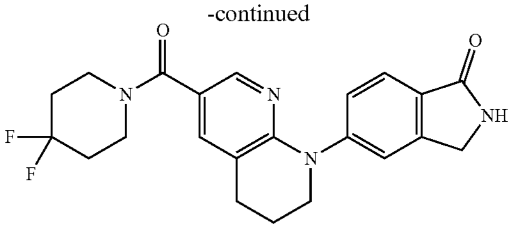

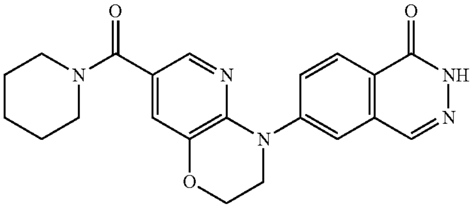

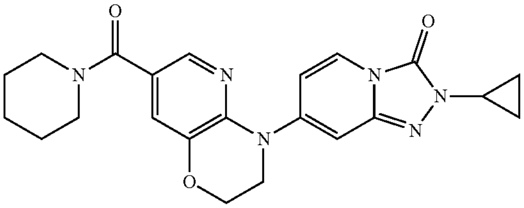

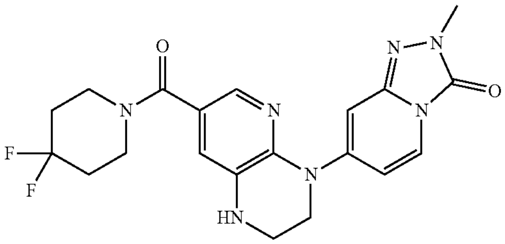

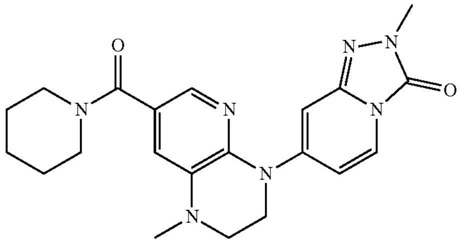

-continued

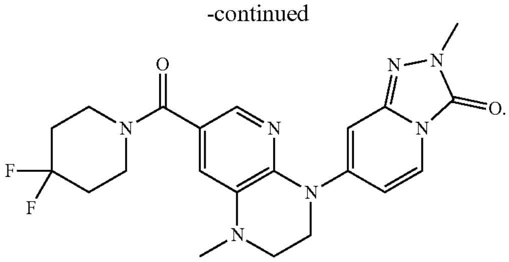

22. A pharmaceutical composition for treating at least one of fibrosis, cardiovascular diseases and autoimmune diseases, comprising:

the compound of claim 21 or a pharmacologically acceptable salt thereof; and a pharmacologically acceptable carrier.

23. A pharmaceutical composition for treating wounds, comprising:

the compound of claim 21 or a pharmacologically acceptable salt thereof; and a pharmacologically acceptable carrier.

24. A pharmaceutical composition for treating at least one of inflammatory diseases, graft-versus-host disease, hair growth, osteoporosis, hearing loss, tinnitus, dizziness, disequilibrium, glaucoma, dry eye, neutropenia, diabetes, underactive bladder, promotion of engraftment in stem cell or bone marrow transplantation or organ transplantation, neurogenesis and nerve cell death, muscle regeneration and cervical ripening, comprising:

the compound of claim 21 or a pharmacologically acceptable salt thereof; and a pharmacologically acceptable carrier.

* * * * *